(12) United States Patent
Adcock et al.

(10) Patent No.: US 11,192,877 B2
(45) Date of Patent: Dec. 7, 2021

(54) 3-(5-HYDROXY-1-OXOISOINDOLIN-2-YL) PIPERIDINE-2,6-DIONE DERIVATIVES AND USES THEREOF

(71) Applicant: Novartis AG, Basel (CH)

(72) Inventors: Claire Adcock, Arlington, MA (US); Simone Bonazzi, Cambridge, MA (US); Artiom Cernijenko, Cambridge, MA (US); Philip Lam, Somerville, MA (US); Kathryn Taylor Linkens, Brookline, MA (US); Hasnain Ahmed Malik, Boston, MA (US); Noel Marie-France Thomsen, Chelmsford, MA (US); Michael Scott Visser, Braintree, MA (US)

(73) Assignee: Novartis AG, Basel (CH)

(*) Notice: Subject to any disclaimer, the term of this patent is extended or adjusted under 35 U.S.C. 154(b) by 28 days.

(21) Appl. No.: 16/504,375

(22) Filed: Jul. 8, 2019

(65) Prior Publication Data
US 2020/0017461 A1 Jan. 16, 2020

Related U.S. Application Data

(60) Provisional application No. 62/695,920, filed on Jul. 10, 2018, provisional application No. 62/835,543, filed on Apr. 18, 2019.

(51) Int. Cl.
*C07D 401/04* (2006.01)
*C07D 407/14* (2006.01)

(52) U.S. Cl.
CPC ......... *C07D 401/04* (2013.01); *C07D 407/14* (2013.01)

(58) Field of Classification Search
CPC ..... A61P 35/00; C07D 401/14; C07D 407/14; C07D 401/04
USPC ........................................................ 546/201
See application file for complete search history.

(56) References Cited

U.S. PATENT DOCUMENTS

| 7,612,096 | B2 | 11/2009 | Zeldis et al. |
|---|---|---|---|
| 8,394,832 | B2 | 3/2013 | Xu et al. |
| 9,212,177 | B2 | 12/2015 | Kao et al. |
| 9,295,664 | B2 | 3/2016 | Adams et al. |
| 9,598,669 | B2 | 3/2017 | Edinger et al. |
| 2004/0087558 | A1 | 5/2004 | Zeldis et al. |
| 2005/0130265 | A1 | 6/2005 | Georgopoulos et al. |
| 2005/0203142 | A1 | 9/2005 | Zeldis et al. |
| 2006/0073126 | A1 | 4/2006 | Shiku et al. |
| 2007/0128636 | A1 | 6/2007 | Baker et al. |
| 2007/0161696 | A1 | 7/2007 | Zeldis et al. |
| 2007/0269827 | A1 | 11/2007 | Harley |
| 2010/0291679 | A1 | 11/2010 | Edinger et al. |
| 2012/0149715 | A1 | 6/2012 | Kao et al. |
| 2013/0149339 | A1 | 6/2013 | Honda et al. |
| 2013/0157363 | A1 | 6/2013 | Kim et al. |
| 2013/0281304 | A1 | 10/2013 | Feinberg et al. |
| 2013/0325429 | A1 | 12/2013 | Kao et al. |
| 2014/0341921 | A1 | 11/2014 | Honda et al. |
| 2014/0342946 | A1 | 11/2014 | Kuriakose et al. |
| 2015/0110733 | A1 | 4/2015 | Tchelet et al. |
| 2015/0110761 | A1 | 4/2015 | Tang et al. |
| 2015/0111771 | A1 | 4/2015 | Lindstedt et al. |
| 2015/0266959 | A1 | 9/2015 | Vignali et al. |
| 2015/0291562 | A1 | 10/2015 | Crew et al. |
| 2015/0307846 | A1 | 10/2015 | Chen et al. |
| 2016/0007893 | A1 | 1/2016 | Roberts |
| 2016/0032317 | A1 | 2/2016 | Rossi et al. |
| 2016/0058872 | A1 | 3/2016 | Crew et al. |
| 2016/0356778 | A1 | 12/2016 | Iha et al. |
| 2018/0009754 | A1 | 1/2018 | Long et al. |
| 2018/0099940 | A1 | 4/2018 | Crew et al. |
| 2018/0125821 | A1 | 5/2018 | Crew et al. |
| 2018/0155322 | A1* | 6/2018 | Crew ............... A61K 31/5386 |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |

(Continued)

FOREIGN PATENT DOCUMENTS

| CN | 106932576 A | 7/2017 |
|---|---|---|
| EP | 2177615 A1 | 4/2010 |

(Continued)

OTHER PUBLICATIONS

CAS Registry No. 2229724-87-0, entered Jun. 29, 2018.

(Continued)

*Primary Examiner* — Taylor V Oh
(74) *Attorney, Agent, or Firm* — Michelle Han

(57) ABSTRACT

The present disclosure provides a compound of Formula (I'):

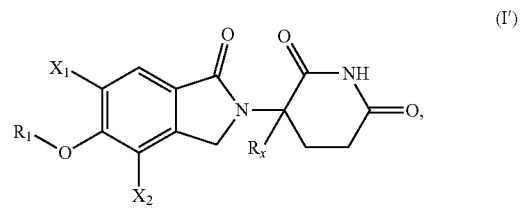

or a pharmaceutically acceptable salt, hydrate, solvate, prodrug, stereoisomer, or tautomer thereof, wherein $R_x$, $X_1$, $X_2$, and $R_1$ are as defined herein, and methods of making and using same.

16 Claims, No Drawings
Specification includes a Sequence Listing.

(56) References Cited

U.S. PATENT DOCUMENTS

| | | | |
|---|---|---|---|
| 2018/0228907 A1 | 8/2018 | Crew et al. |
| 2018/0237418 A1 | 8/2018 | Crew et al. |
| 2019/0076539 A1 | 3/2019 | Phillips et al. |
| 2020/0016143 A1 | 1/2020 | Beckwith et al. |

FOREIGN PATENT DOCUMENTS

| | | | |
|---|---|---|---|
| EP | 2682750 A1 | 1/2014 |
| EP | 3050570 A1 | 8/2016 |
| EP | 3061758 A1 | 8/2016 |
| EP | 3202461 A1 | 8/2017 |
| EP | 3214081 A1 | 9/2017 |
| GB | 2456390 A | 7/2009 |
| JP | 2009092508 | 4/2009 |
| KR | 2007120709 | 12/2007 |
| KR | 2009071808 | 7/2009 |
| WO | 2002044372 A2 | 6/2002 |
| WO | 2003014315 A2 | 2/2003 |
| WO | 2005044178 A2 | 5/2005 |
| WO | 2006028964 A1 | 3/2006 |
| WO | 2006060507 A2 | 6/2006 |
| WO | 2006061216 A2 | 6/2006 |
| WO | 2007079185 A2 | 7/2007 |
| WO | 2009068621 A1 | 6/2009 |
| WO | 2009094592 A2 | 7/2009 |
| WO | 2009117122 A2 | 9/2009 |
| WO | 2009137095 A2 | 11/2009 |
| WO | 2010053732 A1 | 5/2010 |
| WO | 2011015037 A1 | 2/2011 |
| WO | 2011056505 A1 | 5/2011 |
| WO | 2011142827 A2 | 11/2011 |
| WO | 2012054509 A2 | 4/2012 |
| WO | 2012175613 A1 | 12/2012 |
| WO | 2013006474 A2 | 1/2013 |
| WO | 2013037118 A1 | 3/2013 |
| WO | 2014039960 A1 | 3/2014 |
| WO | 2014151764 A2 | 9/2014 |
| WO | 2014200952 A2 | 12/2014 |
| WO | 2015035367 A1 | 3/2015 |
| WO | 2015050875 A1 | 4/2015 |
| WO | 2015107196 A1 | 7/2015 |
| WO | 2015109212 A1 | 7/2015 |
| WO | 2015160845 A2 | 10/2015 |
| WO | 2016090273 A1 | 6/2016 |
| WO | 2016097059 A1 | 6/2016 |
| WO | 2016103269 A1 | 6/2016 |
| WO | 2016118638 A1 | 7/2016 |
| WO | 2016140974 A1 | 9/2016 |
| WO | 2016191178 A1 | 12/2016 |
| WO | 2016196580 A1 | 12/2016 |
| WO | 2016196912 A1 | 12/2016 |
| WO | 2016197032 A1 | 12/2016 |
| WO | 2016209806 A1 | 12/2016 |
| WO | 2017042337 A1 | 3/2017 |
| WO | 2017044979 A2 | 3/2017 |
| WO | 2017058881 A1 | 4/2017 |
| WO | 2017059062 A1 | 4/2017 |
| WO | 2017075451 A1 | 5/2017 |
| WO | 2017075465 A1 | 5/2017 |
| WO | 2017075478 A2 | 5/2017 |
| WO | 2017095525 A1 | 6/2017 |
| WO | 2017161001 A1 | 9/2017 |
| WO | 2017176958 A1 | 10/2017 |
| WO | 2017191274 A2 | 11/2017 |
| WO | 2017197051 A1 | 11/2017 |
| WO | 2017197056 A1 | 11/2017 |
| WO | 2018071606 A1 | 4/2018 |
| WO | 2018102067 A2 | 6/2018 |
| WO | 2018102725 A1 | 6/2018 |
| WO | 2018118598 A1 | 6/2018 |
| WO | 2018119357 A1 | 6/2018 |
| WO | 2018119441 A1 | 6/2018 |
| WO | 2018119448 A1 | 6/2018 |
| WO | 2018140809 A1 | 8/2018 |
| WO | 2018144649 A1 | 8/2018 |
| WO | 2019038717 A1 | 2/2019 |
| WO | 2019079569 A1 | 4/2019 |
| WO | 2019191112 A1 | 10/2019 |

OTHER PUBLICATIONS

CAS Registry No. 2229724-85-8, entered Jun. 29, 2018.
CAS Registry No. 2229724-81-4, entered Jun. 29, 2018.
CAS Registry No. 2229724-59-6, entered Jun. 29, 2018.
CAS Registry No. 2229724-58-5, entered Jun. 29, 218.
CAS Registry No. 2229715-16-4, entered Jun. 29, 2018.
CAS Registry No. 2229715-15-3, entered Jun. 29, 2018.
CAS Registry No. 2229715-13-1, entered Jun. 29, 2018.
CAS Registry No. 2229712-98-3, entered Jun. 29, 2018.
CAS Registry No. 229712-87-0, entered Jun. 29, 2018.
CAS Registry No. 2229712-35-8, entered Jun. 29, 2018.
CAS Registry No. 2229711-92-4, entered Jun. 29, 2018.
CAS Registry No. 2229711-91-3, entered Jun. 29, 2018.
CAS Registry No. 2229711-82-2, entered Jun. 29, 2018.
CAS Registry No. 2229708-36-3, entered Jun. 29, 2018.
CAS Registry No. 2229708-28-3, entered Jun. 29, 2018.
CAS Registry No. 2229708-27-2, entered Jun. 29, 2018.
CAS Registry No. 2229708-26-1, entered Jun. 29, 2018.
CAS Registry No. 2226301-43-3, entered Jun. 1, 2018.
CAS Registry No. 2226300-66-7, entered Jun. 1, 2018.
CAS Registry No. 2226300-65-6, entered Jun. 1, 2018.
CAS Registry No. 2226300-15-6, entered Jun. 1, 2018.
CAS Registry No. 2226299-67-6, entered Jun. 1, 2018.
CAS Registry No. 2226297-14-7, entered Jun. 1, 2018.
CAS Registry No. 2226297-13-6, entered Jun. 1, 2018.
CAS Registry No. 2226296-63-3, entered Jun. 1, 2018.
CAS Registry No. 2226295-52-7, entered Jun. 1, 2018.
CAS Registry No. 2226295-42-5, entered Jun. 1, 2018.
CAS Registry No. 2226295-16-3, entered Jun. 1, 2018.
CAS Registry No. 2226295-05-0, entered Jun. 1, 2018.
CAS Registry No. 2226295-01-6, entered Jun. 1, 2018.
CAS Registry No. 2226294-99-9, entered Jun. 1, 2018.
CAS Registry No. 2226294-79-5, entered Jun. 1, 2018.
CAS Registry No. 2222117-01-1, entered May 2, 2018.
CAS Registry No. 2222116-12-1, entered May 2, 2018.
CAS Registry No. 2222116-11-0, entered May 2, 2018.
CAS Registry No. 2222116-10-9, entered May 2, 2018.
CAS Registry No. 2222116-09-6, entered May 2, 2018.
CAS Registry No. 2222115-94-6, entered May 2, 2018.
CAS Registry No. 2222115-85-5, entered May 2, 2018.
CAS Registry No. 2222115-84-4, entered May 2, 2018.
CAS Registry No. 2222115-82-2, entered May 2, 2019.
CAS Registry No. 2222115-81-1, entered May 2, 2018.
CAS Registry No. 2222115-80-0, entered May 2, 2018.
CAS Registry No. 2222111-80-8, entered May 2, 2018.
CAS Registry No. 2222111-16-0, entered May 2, 2018.
CAS Registry No. 2222111-07-9, entered May 2, 2018.
CAS Registry No. 2222110-65-6, entered May 2, 2018.
CAS Registry No. 2222110-33-8, entered May 2, 2018.
CAS Registry No. 2222110-32-7, entered May 2, 2018.
CAS Registry No. 2222110-08-7, entered May 2, 2018.
CAS Registry No. 2222110-06-5, entered May 2, 2018.
CAS Registry No. 2222109-95-5, entered May 2, 2018.
CAS Registry No. 2222109-84-2, entered May 2, 2018.
CAS Registry No. 2222109-83-1, entered May 2, 2018.
Woo, Ken et al., "Identification of a thalidomide derivative that selectively targets tumorigenic liver progenitor cells and comparing its effect with lenalidomide and sorafenib", European Journal of Medicinal Chemistry, 120:275-283. 2016.
Yeung, Sing Yee, et al., "Novel thalidomide analogues with potent NFkB and TNF expression inhibition", MedChemComm, 2(11):1073-1078. 2011.
Stewart, Scott G., et al., "New thalidomide analogues derived through Sonogashira or Suzuki reactions and their TNF expression inhibition profiles", Bioorganic & Medicinal Chemistry, 18(2):650-662. 2010.

(56) References Cited

OTHER PUBLICATIONS

Stewart, Scott G., et al., "Synthesis and TNF expression inhibitory properties of new thalidomide analogues derived via Heck cross coupling", Bioorganic & Medicinal Chemistry Letters, 17(21):5819-5824. 2007.
CAS Registry No. 2241326-47-4.
CAS Registry No. 2222115-39-9.
CAS Registry No. 1448326-82-6, entered Aug. 14, 2013.
CAS Registry No. 1384753-62-1, entered Jul. 27, 2012.
CAS Registry No. 1384753-63-2, entered Jul. 27, 2012.
CAS Registry No. 1384753-61-0, entered Jul. 27, 2012.
CAS Registry No. 1384753-60-9, entered Jul. 27, 2012.
CAS Registry No. 1384753-59-6, entered Jul. 27, 2012.
CAS Registry No. 1384753-58-5, entered Jul. 27, 2012.
CAS Registry No. 1384753-57-4, entered Jul. 27, 2012.
CAS Registry No. 1384753-56-3, entered Jul. 27, 2012.
CAS Registry No. 1384753-55-2, entered Jul. 27, 2012.
CAS Registry No. 1384753-54-1, entered Jul. 27, 2012.
CAS Registry No. 1384753-53-0, entered Jul. 27, 2012.
CAS Registry No. 1384753-52-9, entered Jul. 27, 2012.
CAS Registry No. 1384439-40-0, entered Jul. 26, 2012.
CAS Registry No. 1216805-57-0, entered Apr. 5, 2010.
CAS Registry No. 1216805-54-7, entered Apr. 5, 2010.
CAS Registry No. 1216805-53-6, entered Apr. 5, 2010.
CAS Registry No. 1216805-49-0, entered Apr. 5, 2010.
CAS Registry No. 1216805-28-5, entered Apr. 5, 2010.
CAS Registry No. 1216805-25-2, entered Apr. 5, 2010.
CAS Registry No. 1216805-51-4, entered Apr. 5, 2010.
CAS Registry No. 959150-76-6, entered Dec. 21, 2007.
Nakayama, et al., "Aiolos Overexpression in Systemic Lupus Erythematosus B Cell Subtypes and BAFF-Induced Memory B Cell Differentiation Are Reduced by CC-220 Modulation of Cereblon Activity," J. Immunol.,199(7), 2388-2407, (2017).
Hansen, et al., "Protein Degradation via CRL4CRBN Ubiquitin Ligase: Discovery and Structure-Activity Relationships of Novel Glutarimide Analogs That Promote Degradation of Aiolos and/or GSPT1," J. Med. Chem, 61(2), pp. 492-503, (2018).
Kroenke, et al., "IKZF1 expression is a prognostic marker in newly diagnosed standard-risk multiple myeloma treated with lenalidomide and intensive chemotherapy: a study of the German Myeloma Study Group (DSMM)", Leukemia vol. 31(5):1363-1367, (2017).
Harada, et. al., "Expansion of Th1-like Vgamma9Vdelta2T cells by new-generation IMiDs, lenalidomide and pomalidomide, in combination with zoledronic acid," Leukemia vol. 31, pp. 258-262, (2017).
Jones et. al., "Lenalidomide, Thalidomide, and Pomalidomide Reactivate the Epstein-Barr Virus Lytic Cycle through Phosphoinositide 3-Kinase Signaling and Ikaros Expression," Clin. Cancer Res., 22(19), 4901-4912, (2016).
CAS Registry No. 2154353-25-8, entered Dec. 8, 2017.
CAS Registry No. 2154353-21-4, entered Dec. 8, 2017.
CAS Registry No. 2154343-22-1, entered Dec. 8, 2017.
CAS Registry No. 2154342-61-5, entered Dec. 8, 2017.
CAS Registry No. 959150-73-3, entered Dec. 21, 2007.
Matyskiela, et al., "A Cereblon Modulator (CC-220) with Improved Degradation of Ikaros and Aiolos", Journal of Medicinal Chemistry, 61(2):535-542. 2018.
Chung, et al., "Thalidomide Pharmacokinetics and Metabolite Formation in Mice, Rabbits, and Multiple Myeloma Patients", Clinical Cancer Research, 10(17):5949-5956. 2004.
Lu, et al., "Thalidomide Metabolites in Mice and Patients with Multiple Myeloma", Clinical Cancer Research, 9(5):1680-1688. 2003.
CAS Registry No. 2329254-89-7, entered Jun. 11, 2019.
CAS Registry No. 2222119-82-4, entered May 2, 2018.
CAS Registry No. 2222119-81-3, entered May 2, 2018.
CAS Registry No. 2222113-59-7, entered May 2, 2018.
CAS Registry No. 2332556-93-9, entered Jun. 13, 2019.
CAS Registry No. 2241313-04-0, entered Aug. 21, 2018.
CAS Registry No. 2241306-92-1, entered Aug. 21, 2018.
CAS Registry No. 2230955-59-4, entered Jul. 18, 2018.
CAS Registry No. 2230955-58-3, entered Jul. 18, 2018.

* cited by examiner

3-(5-HYDROXY-1-OXOISOINDOLIN-2-YL) PIPERIDINE-2,6-DIONE DERIVATIVES AND USES THEREOF

RELATED APPLICATIONS

This application claims the benefit of and priority to U.S. Provisional application Nos. 62/695,920, filed Jul. 10, 2018, and 62/835,543, filed Apr. 18, 2019, the entire contents of each of which are incorporated herein by reference in their entireties.

FIELD OF THE DISCLOSURE

The present disclosure relates to 3-(5-hydroxy-1-oxoisoindolin-2-yl)piperidine-2,6-dione compounds and compositions and their use for the treatment of IKAROS Family Zinc Finger 2 (IKZF2)-dependent diseases or disorders or where reduction of IKZF2 or IKZF4 protein levels can ameliorate a disease or disorder.

BACKGROUND OF THE DISCLOSURE

IKAROS Family Zinc Finger 2 (IKZF2) (also known as Helios) is one of the five members of the Ikaros family of transcription factors found in mammals. IKZF2 contains four zinc finger domains near the N-terminus which are involved in DNA binding and two zinc finger domains at the C-terminus which are involved in protein dimerization. IKZF2 is about 50% identical with Ikaros family members, Ikaros (IKZF1), Aiolos (IKZF3), and Eos (IKZF4) with highest homology in the zinc finger regions (80%+ identity). These four Ikaros family transcription factors bind to the same DNA consensus site and can heterodimerize with each other when co-expressed in cells. The fifth Ikaros family protein, Pegasus (IKZF5), is only 25% identical to IKZF2, binds a different DNA site than other Ikaros family members and does not readily heterodimerize with the other Ikaros family proteins. IKZF2, IKZF1 and IKZF3 are expressed mainly in hematopoietic cells while IKZF4 and IKZF5 are expressed in a wide variety of tissues. (John, L. B., et al., (2011), Mol. Immunol. 48:1272-1278; Perdomo, J., et al., (2000), J. Biol. Chem. 275:38347-38354.)

IKZF2 is believed to have an important role in the function and stability of regulatory T cells (Tregs). IKZF2 is highly expressed at the mRNA and protein level by regulatory T-cell populations. Knockdown of IKZF2 by siRNA has been shown to result in downregulation of FoxP3 and to impair the ability of isolated human CD4+ CD25+ Tregs to block T-cell activation in vitro. Moreover, overexpression of IKZF2 in isolated murine Tregs has been shown to increase expression of Treg related markers such as CD103 and GITR and the IKZF2 overexpressing cells showed increased suppression of responder T-cells. IKZF2 has also been found to bind the promoter of FoxP3, the defining transcription factor of the regulatory T-cell lineage, and to affect FoxP3 expression.

Knockout of IKZF2 within FoxP3-expressing Tregs in mice has been shown to cause activated Tregs to lose their inhibitory properties, to express T-effector cytokines, and to take on T-effector functions. IKZF2 knockout mutant mice develop autoimmune disease by 6-8 months of age, with increased numbers of activated CD4 and CD8 T cells, follicular helper T cells, and germinal center B cells. This observed effect is believed to be cell intrinsic, as Rag2−/− mice given bone marrow from IKZF2 knockout mice, but not bone marrow from IKZF2+/+ develop autoimmune disease. Direct evidence that IKZF2 affects regulatory T-cell function has been shown in the analysis of mice in which IKZF2 was deleted only in FoxP3 expressing cells (FoxP3-YFP-Cre Heliosfl/fl). The results showed that the mice also develop autoimmune disease with similar features as observed in the whole animal IKZF2 knockout. Moreover, pathway analysis of a CHIP-SEQ experiment has also suggested that IKZF2 is affecting expression of genes in the STAT5/IL-2Ra pathway in regulatory T-cells. This effect of IKZF2 loss was shown to be more apparent after an immune challenge (viral infection or injection with sheep's blood), and it was noted that after immune stimulation, the IKZF2 negative regulatory T cells began to take on features of effector T cells. (Getnet, D., et al., Mol. Immunol. (2010), 47:1595-1600; Bin Dhuban, K., et al., (2015), J. Immunol. 194:3687-96; Kim, H-J., et al., (2015), Science 350:334-339; Nakawaga, H., et al., (2016) PNAS, 113: 6248-6253)

Overexpression of Ikaros isoforms which lack the DNA binding regions have been shown to be associated with multiple human haematological malignancies. Recently, mutations in the IKZF2 gene, which lead to abnormal splicing variants, have been identified in adult T-cell leukemias and low hypodiploid acute lymphoblastic leukemia. It has been proposed that these isoforms, which are capable of dimerization, have a dominant negative effect on Ikaros family transcription factors which primes the development of lymphomas. IKZF2 knockout mutants that survive into adulthood do not develop lymphomas, supporting this hypothesis (Asanuma, S., et al., (2013), Cancer Sci. 104: 1097-1106; Zhang, Z., et al., (2007), Blood 109:2190-2197; Kataoka, D., et al., (2015), Nature Genetics 47:1304-1315.)

Currently, anti-CTLA4 antibodies are used in the clinic to target Tregs in tumors. However, targeting CTLA4 often causes systemic activation of T-effector cells, resulting in excessive toxicity and limiting therapeutic utility. Up to ¾ of patients treated with a combination of anti-PD1 and anti-CTLA4 have reported grade 3 or higher adverse events (National Cancer Institute, Division of Cancer Treatment & diagnosis, Common Terminology for Adverse Events (CT-CAE), https://ctep.cancer.gov/protocolDevelopment/electronic_applications/ctc.htm). Thus, a strong need exists to provide compounds that target Tregs in tumors without causing systemic activation of T-effector cells.

An IKZF2-specific degrader has the potential to focus the enhanced immune response to areas within or near tumors providing a potentially more tolerable and less toxic therapeutic agent for the treatment of cancer.

SUMMARY OF THE DISCLOSURE

The compounds of the disclosure have use as therapeutic agents, particularly for cancers and related diseases. In one aspect, the compounds of the disclosure have IKZF2 degrader activity, preferably having such activity at or below the 50 µM level, and more preferably having such activity at or below the 10 µM level. In another aspect, the compounds of the disclosure have degrader activity for IKZF2 that is selective over one or more of IKZF1, IKZF3, IKZF4, and/or IKZF5. In another aspect, the compounds of the disclosure have degrader activity for both IKZF2 and IKZF4. The compounds of the disclosure have usefulness in treating cancer and other diseases for which such degrader activity would be beneficial for the patient. For example, while not intending to be bound by any theory, the inventors believe that reducing levels of IKZF2 in Tregs in a tumor may allow the patient immune system to more effectively attack the disease. In summary, the present disclosure provides novel IKZF2 degraders useful for the treatment of cancer and other diseases.

A first aspect of the present disclosure relates to compounds of Formula (I'):

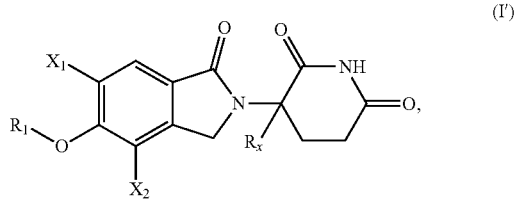

(I')

wherein:

$X_1$ and $X_2$ are each independently H, $(C_1-C_4)$alkyl, $(C_1-C_6)$alkoxy, $(C_1-C_4)$haloalkyl, $(C_1-C_6)$haloalkoxy, $(C_3-C_7)$cycloalkyl, halogen, —CN, —OH, or —NH$_2$;

$R_x$ is H or D;

$R_1$ is

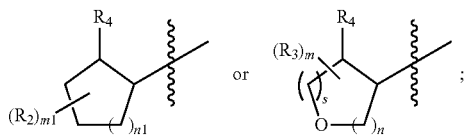

each $R_2$ is independently at each occurrence $(C_1-C_6)$alkyl, $(C_1-C_6)$alkoxy, $(C_1-C_6)$haloalkyl, $(C_1-C_6)$haloalkoxy, halogen, —CN, —OH, or —NH$_2$; or two $R_2$ together with the carbon atoms to which they are attached form a $(C_3-C_7)$cycloalkyl or a 4- to 7-membered heterocycloalkyl ring comprising 1-3 heteroatoms selected from O, N, and S; or two $R_2$ together when on adjacent carbon atoms form a phenyl or a 5- or 6-membered heteroaryl ring comprising 1-3 heteroatoms selected from O, N, and S; or $R_2$ and $R_6$ together with the carbon and nitrogen atoms to which they are attached form a 4- to 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_3$ is $(C_1-C_6)$alkyl, $(C_1-C_6)$alkoxy, $(C_1-C_6)$haloalkyl, $(C_1-C_6)$haloalkoxy, halogen, —OH, or —NH$_2$;

$R_4$ is —OR$_5$ or —NR$_6$R$_6$;

$R_5$ is H, $(C_1-C_6)$alkyl, $(C_1-C_6)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S;

$R_6$ and $R_6$' are each independently H, $(C_1-C_6)$alkyl, $(C_1-C_6)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$; or $R_6$ and $R_6$' together with the nitrogen atom to which they are attached form a 4- to 8-membered heterocycloalkyl ring optionally comprising 1-2 additional heteroatoms selected from O, N, and S, and optionally substituted with one to four $R_8$; or $R_2$ and $R_6$ together with the carbon and nitrogen atoms to which they are attached form a 4- to 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_7$ is $(C_3-C_7)$cycloalkyl, 4- to 7-membered heterocycloalkyl ring comprising 1-3 heteroatoms selected from O, N, and S, $(C_6-C_{10})$aryl, or 5- or 6-membered heteroaryl comprising 1-3 heteroatoms selected from O, N, and S, wherein the cycloalkyl, heterocycloalkyl, aryl, and heteroaryl are optionally substituted with one to four $R_9$;

each $R_8$ is independently at each occurrence halogen, $(C_1-C_6)$alkyl, $(C_1-C_6)$alkoxy, $(C_1-C_6)$haloalkyl, $(C_1-C_6)$haloalkoxy, —CN, —OH, —NR$_{13}$R$_{14}$, —NH$_2$, —O$(C_3-C_7)$cycloalkyl, —O-4- to 7-membered heterocycloalkyl ring comprising 1-3 heteroatoms selected from O, N, and S, —O$(C_6-C_{10})$aryl, or —O-5- or 6-membered heteroaryl comprising 1-3 heteroatoms selected from O, N, and S, wherein the alkoxy is optionally substituted with one to three $R_{10}$ and the cycloalkyl, heterocycloalkyl, aryl and heteroaryl are optionally substituted with one to three $R_{11}$; or two $R_8$ together with the atoms to which they are attached form a $(C_4-C_7)$cycloalkyl or a 4- to 7-membered heterocycloalkyl ring comprising 1-2 heteroatoms selected from O, N, and S optionally substituted with two $R_{15}$; or two $R_8$ when on adjacent atoms together with the atoms to which they are attached form a $(C_6-C_{10})$aryl, or 5- or 6-membered heteroaryl comprising 1-3 heteroatoms selected from O, N, and S; or two $R_8$ together with the same atom to which they are attached form a =(O);

each $R_9$ is independently at each occurrence $(C_1-C_6)$alkyl, $(C_1-C_6)$haloalkyl, $(C_1-C_6)$alkoxy, $(C_1-C_6)$haloalkoxy, halogen, $(C_3-C_6)$cycloalkyl, —OH, —CN, —NH$_2$, or —NR$_{13}$R$_{14}$; or two $R_9$ together with the atoms to which they are attached form a $(C_4-C_7)$cycloalkyl or a 5- to 7-membered heterocycloalkyl ring comprising 1-2 heteroatoms selected from O, N, and S optionally substituted with one or more substituents each independently selected from $(C_1-C_6)$alkyl, $(C_1-C_6)$haloalkyl, halogen, —OH, —CN, and —NH$_2$; or two $R_9$ when on adjacent atoms together with the atoms to which they are attached form a $(C_6-C_{10})$aryl, or 5- or 6-membered heteroaryl comprising 1-3 heteroatoms selected from O, N, and S;

each $R_{10}$ is independently at each occurrence selected from $(C_3-C_7)$cycloalkyl, 4- to 7-membered heterocycloalkyl ring comprising 1-3 heteroatoms selected from O, N, and S, $(C_6-C_{10})$aryl, and 5- or 6-membered heteroaryl comprising 1-3 heteroatoms selected from O, N, and S;

each $R_{11}$ is independently at each occurrence selected from $(C_1-C_6)$alkyl, $(C_1-C_6)$haloalkyl, $(C_1-C_6)$alkoxy, $(C_1-C_6)$haloalkoxy, halogen, —OH, —CN, and —NH$_2$;

each $R_{12}$ is independently at each occurrence $(C_1-C_6)$alkyl, $(C_1-C_6)$haloalkyl, $(C_1-C_6)$alkoxy, $(C_1-C_6)$haloalkoxy, halogen, —OH, —CN, or —NH$_2$;

two $R_{12}$ together with the atoms to which they are attached form a $(C_4\text{-}C_7)$cycloalkyl or a 4- to 7-membered heterocycloalkyl ring comprising 1-2 heteroatoms selected from O, N, and S;

$R_{13}$ and $R_{14}$ are each independently selected from $(C_1\text{-}C_6)$alkyl, $(C_1\text{-}C_6)$haloalkyl, $(C_3\text{-}C_7)$cycloalkyl, 4- to 7-membered heterocycloalkyl ring comprising 1-3 heteroatoms selected from O, N, and S, $(C_6\text{-}C_{10})$aryl, and 5- or 6-membered heteroaryl comprising 1-3 heteroatoms selected from O, N, and S;

two $R_{15}$ together with the atoms to which they are attached form a $(C_4\text{-}C_7)$cycloalkyl or a 4- to 7-membered heterocycloalkyl ring comprising 1-2 heteroatoms selected from O, N, and S;

m and m1 are each independently 0, 1 or 2;
n1 is 0, 1, 2, or 3; and
each s and n is independently 1, 2, or 3, wherein s+n is ≤4;
or pharmaceutically acceptable salts, hydrates, solvates, prodrugs, stereoisomers, and tautomers thereof.

In one embodiment, the present disclosure relates to compounds of Formula (I') having the structure of Formula (I):

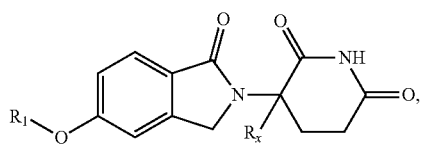

wherein:
$R_x$ is H or D;
$R_1$ is

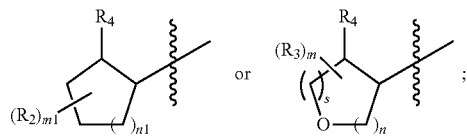

each $R_2$ is independently at each occurrence $(C_1\text{-}C_6)$alkyl, $(C_1\text{-}C_6)$alkoxy, $(C_1\text{-}C_6)$haloalkyl, $(C_1\text{-}C_6)$haloalkoxy, halogen, —CN, —OH, or —NH$_2$; or two $R_2$ together with the carbon atoms to which they are attached form a $(C_3\text{-}C_7)$cycloalkyl or a 4- to 7-membered heterocycloalkyl ring comprising 1-3 heteroatoms selected from O, N, and S; or two $R_2$ together when on adjacent carbon atoms form a phenyl or a 5- or 6-membered heteroaryl ring comprising 1-3 heteroatoms selected from O, N, and S; or $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1\text{-}C_6)$alkyl, $(C_1\text{-}C_6)$haloalkyl, halogen, —OH, —CN, and —NH$_2$;

each $R_3$ is $(C_1\text{-}C_6)$alkyl, $(C_1\text{-}C_6)$alkoxy, $(C_1\text{-}C_6)$haloalkyl, $(C_1\text{-}C_6)$haloalkoxy, halogen, —OH, or —NH$_2$;

$R_4$ is —OR$_5$ or —NR$_6$R$_6'$;

$R_5$ is H, $(C_1\text{-}C_6)$alkyl, $(C_1\text{-}C_6)$haloalkyl, $(C_3\text{-}C_7)$cycloalkyl, 5- or 6-membered heterocycloalkyl comprising 1-3 heteroatoms selected from O, N, and S, $(C_6\text{-}C_{10})$aryl, or 5- or 6-membered heteroaryl comprising 1-3 heteroatoms selected from O, N, and S, wherein the alkyl is optionally substituted with one to three substituents independently selected from $(C_6\text{-}C_{10})$aryl and 5- or 6-membered heteroaryl comprising 1-3 heteroatoms selected from O, N, and S;

$R_6$ and $R_6'$ are each independently H, $(C_1\text{-}C_6)$alkyl, $(C_1\text{-}C_6)$haloalkyl, $(C_3\text{-}C_7)$cycloalkyl, 5- or 6-membered heterocycloalkyl comprising 1-3 heteroatoms selected from O, N, and S, $(C_6\text{-}C_{10})$aryl, or 5- or 6-membered heteroaryl comprising 1-3 heteroatoms selected from O, N, and S, wherein the alkyl is optionally substituted with one to three $R_7$; or $R_6$ and $R_6'$ together with the nitrogen atom to which they are attached form a 4- to 7-membered heterocycloalkyl ring optionally comprising 1-2 additional heteroatoms selected from O, N, and S, and optionally substituted with one to four $R_8$; or $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1\text{-}C_6)$alkyl, $(C_1\text{-}C_6)$haloalkyl, halogen, —OH, —CN, and —NH$_2$;

each $R_7$ is $(C_3\text{-}C_7)$cycloalkyl, 4- to 7-membered heterocycloalkyl ring comprising 1-3 heteroatoms selected from O, N, and S, $(C_6\text{-}C_{10})$aryl, or 5- or 6-membered heteroaryl comprising 1-3 heteroatoms selected from O, N, and S, wherein the cycloalkyl, heterocycloalkyl, aryl, and heteroaryl are optionally substituted with one to four $R_9$;

each $R_8$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —CN, —OH, or —NH$_2$, wherein the alkoxy is optionally substituted with one to three substituents independently selected from $(C_3\text{-}C_7)$cycloalkyl, 4- to 7-membered heterocycloalkyl ring comprising 1-3 heteroatoms selected from O, N, and S, $(C_6\text{-}C_{10})$aryl, and 5- or 6-membered heteroaryl comprising 1-3 heteroatoms selected from O, N, and S; or two $R_8$ together with the atoms to which they are attached form a $(C_5\text{-}C_7)$cycloalkyl or a 4- to 7-membered heterocycloalkyl ring comprising 1-2 heteroatoms selected from O, N, and S;

each $R_9$ is independently at each occurrence $(C_1\text{-}C_6)$alkyl, $(C_1\text{-}C_6)$haloalkyl, halogen, —OH, —CN, or —NH$_2$; or two $R_9$ together with the atoms to which they are attached form a $(C_5\text{-}C_7)$cycloalkyl or a 5- to 7-membered heterocycloalkyl ring comprising 1-2 heteroatoms selected from O, N, and S optionally substituted with one or more substituents each independently selected from $(C_1\text{-}C_6)$alkyl, $(C_1\text{-}C_6)$haloalkyl, halogen, —OH, —CN, and —NH$_2$;

m and m1 are each independently 0, 1 or 2;
n1 is 0, 1, 2, or 3; and
each s and n is independently 1, 2, or 3, wherein s+n is ≤4;
or pharmaceutically acceptable salts, hydrates, solvates, prodrugs, stereoisomers, and tautomers thereof.

In another aspect, the present disclosure relates to compounds of Formula (I') or Formula (I') or Formula (I), wherein:
$R_x$ is H or D;
$R_1$ is

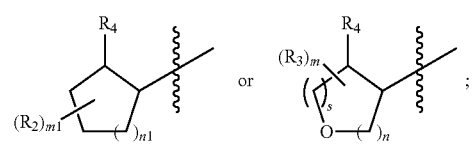

each $R_2$ is independently at each occurrence $(C_1-C_6)$alkyl, $(C_1-C_6)$alkoxy, $(C_1-C_6)$haloalkyl, $(C_1-C_6)$haloalkoxy, halogen, —CN, —OH, or —NH$_2$; or two $R_2$ together with the carbon atoms to which they are attached form a $(C_3-C_7)$cycloalkyl or a 4- to 7-membered heterocycloalkyl ring comprising 1-3 heteroatoms selected from O, N, and S; or two $R_2$ together when on adjacent carbon atoms form a phenyl or a 5- or 6-membered heteroaryl ring comprising 1-3 heteroatoms selected from O, N, and S; or $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_3$ is $(C_1-C_6)$alkyl, $(C_1-C_6)$alkoxy, $(C_1-C_6)$haloalkyl, $(C_1-C_6)$haloalkoxy, halogen, —OH, or —NH$_2$;

$R_4$ is —OR$_5$ or —NR$_6$R$_{6'}$;

$R_5$ is H, $(C_1-C_6)$alkyl, $(C_1-C_6)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S;

$R_6$ and $R_{6'}$ are each independently H, $(C_1-C_6)$alkyl, $(C_1-C_6)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$; or $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_7$ is $(C_3-C_7)$cycloalkyl, 4- to 7-membered heterocycloalkyl ring comprising 1-3 heteroatoms selected from O, N, and S, $(C_6-C_{10})$aryl, or 5- or 6-membered heteroaryl comprising 1-3 heteroatoms selected from O, N, and S, wherein the cycloalkyl, heterocycloalkyl, aryl, and heteroaryl are optionally substituted with one to four $R_9$;

each $R_8$ is independently at each occurrence halogen, $(C_1-C_6)$alkyl, $(C_1-C_6)$haloalkyl, halogen, —CN, —OH, or —NH$_2$; or two $R_8$ together with the atoms to which they are attached form a $(C_5-C_7)$cycloalkyl or a 4- to 7-membered heterocycloalkyl ring comprising 1-2 heteroatoms selected from O, N, and S;

each $R_9$ is independently at each occurrence $(C_1-C_6)$alkyl, $(C_1-C_6)$haloalkyl, halogen, —OH, —CN, or —NH$_2$; or two $R_9$ together with the atoms to which they are attached form a $(C_5-C_7)$cycloalkyl or a 5- to 7-membered heterocycloalkyl ring comprising 1-2 heteroatoms selected from O, N, and S optionally substituted with one or more substituents each independently selected from $(C_1-C_6)$alkyl, $(C_1-C_6)$haloalkyl, halogen, —OH, —CN, and —NH$_2$;

m and m1 are each independently 0, 1 or 2;

n1 is 0, 1, 2, or 3; and each s and n is independently 1, 2, or 3, wherein s+n is ≤4;

or pharmaceutically acceptable salts, hydrates, solvates, prodrugs, stereoisomers, and tautomers thereof.

In one aspect of the disclosure, the hydrogens in the compound of Formula (I') or Formula (I') are present in their normal isotopic abundances. In a preferred aspect of the disclosure, the hydrogens are isotopically enriched in deuterium (D), and in a particularly preferred aspect of the invention the hydrogen at position $R_x$ is enriched in D, as discussed in more detail concerning isotopes and isotopic enrichment below.

Another aspect of the present disclosure relates to a pharmaceutical composition comprising a therapeutically effective amount of a compound of Formula (I') or Formula (I') or Formula (I), or a pharmaceutically acceptable salt, hydrate, solvate, prodrug, stereoisomer, or tautomer thereof, and a pharmaceutically acceptable carrier or excipient. The pharmaceutical composition is useful in the treatment of IKZF2-dependent diseases or disorders. The pharmaceutical composition may further comprise at least one additional pharmaceutical agent.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient for use in the treatment of an IKZF2-dependent disease or disorder by reducing IKZF2 protein levels wherein reduction of IKZF2 protein levels treats the IKZF2-dependent disease or disorder. The pharmaceutical composition is useful in the treatment of IKZF2-dependent diseases or disorders. The pharmaceutical composition may further comprise at least one additional pharmaceutical agent.

Another aspect of the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient. The pharmaceutical composition is useful in the treatment of diseases or disorders affected by the reduction of IKZF2 protein levels. The pharmaceutical composition may further comprise at least one additional pharmaceutical agent.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient for use in the treatment of a disease or disorder affected by the reduction of IKZF2 protein levels wherein reduction of IKZF2 protein levels treats the disease or disorder. The pharmaceutical composition may further comprise at least one additional pharmaceutical agent.

In another aspect, the present disclosure relates to a method of degrading IKZF2. The method comprises administering to the patient in need thereof a compound of Formula (I') or Formula (I), or a pharmaceutically acceptable salt, hydrate, solvate, prodrug, stereoisomer, or tautomer thereof.

Another aspect of the present disclosure relates to a method of modulating IKZF2 protein levels. The method comprises administering to the patient in need thereof a compound of Formula (I') or Formula (I), or a pharmaceutically acceptable salt, hydrate, solvate, prodrug, stereoisomer, or tautomer thereof.

In another aspect, the present disclosure relates to a method of reducing IKZF2 protein levels. The method comprises administering to the patient in need thereof a compound of Formula (I') or Formula (I), or a pharmaceutically acceptable salt, hydrate, solvate, prodrug, stereoisomer, or tautomer thereof.

In another aspect, the present disclosure relates to a method of decreasing IKZF2 protein levels. The method comprises administering to the patient in need thereof a compound of Formula (I') or Formula (I), or a pharmaceutically acceptable salt, hydrate, solvate, prodrug, stereoisomer, or tautomer thereof.

Another aspect of the present disclosure relates to a method of reducing the proliferation of a cell. The method comprises administering to the patient in need thereof a compound of Formula (I') or Formula (I), or a pharmaceutically acceptable salt, hydrate, solvate, prodrug, stereoisomer, or tautomer thereof and reducing IKZF2 protein levels.

In another aspect, the present disclosure relates to a method of reducing IKZF2 protein levels. The method comprises administering to the patient in need thereof a compound of Formula (I') or Formula (I), or a pharmaceutically acceptable salt, hydrate, solvate, prodrug, stereoisomer, or tautomer thereof.

In another aspect, the present disclosure relates to a method of treating cancer. The method comprises administering to the patient in need thereof a compound of Formula (I') or Formula (I), or a pharmaceutically acceptable salt, hydrate, solvate, prodrug, stereoisomer, or tautomer thereof. In one embodiment, the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer and soft tissue sarcomas selected from rhabdomyosarcoma (RMS), synovial sarcoma, osteosarcoma, rhabdoid cancers, and Ewing's sarcoma. In another embodiment, the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In yet another embodiment, the cancer is selected from non-small cell lung cancer (NSCLC), melanoma, triple-negative breast cancer (TNBC), nasopharyngeal cancer (NPC), and microsatellite stable colorectal cancer (mssCRC). In another embodiment, the cancer is a cancer for which the immune response is deficient or an immunogenic cancer.

Another aspect of the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient for use in the treatment of an IKZF2-dependent disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient in the manufacture of a medicament for treating of an IKZF2-dependent disease or disorder.

Another aspect of the present disclosure relates to a method for treating an IKZF2-dependent disease or disorder comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, and a pharmaceutically acceptable carrier or excipient.

In another aspect, the present disclosure relates to a method for treating an IKZF2-dependent disease or disorder comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof.

Another aspect of the present disclosure relates to a compound of Formula (I') or Formula (I), or a pharmaceutically acceptable salt, hydrate, solvate, prodrug, stereoisomer, or tautomer thereof, for use in the treatment of an IKZF2-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating an IKZF2-dependent disease or disorder.

Another aspect of the present disclosure relates to a method for treating a disease or disorder that is affected by the modulation of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof.

In another aspect, the present disclosure relates to a method for treating a disease or disorder that is affected by a decrease in IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof.

Another aspect of the present disclosure relates to a method for treating a disease or disorder that is affected by the reduction of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the modulation of IKZF2 protein levels.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the reduction of IKZF2 protein levels.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by a decrease in IKZF2 protein levels.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the modulation of IKZF2 protein levels.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the reduction of IKZF2 protein levels.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by a decrease in IKZF2 protein levels.

In another aspect, the present disclosure relates to a method of treating cancer comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the cancer is a cancer for which the immune response is deficient or an immunogenic cancer.

Another aspect of the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease or disorder associated with the modulation of IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In another embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder associated with the modulation of IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In another embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease or disorder associated with the reduction of IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In another embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder associated with the reduction of IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In another embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease or disorder associated with a decrease in IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In another embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder associated with a decrease in IKZF2 protein levels. In one embodiment, the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In another embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to a method of treating cancer comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the cancer is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a compound of Formula (I') or Formula (I), or a pharmaceutically acceptable salt, hydrate, solvate, prodrug, stereoisomer, or tautomer thereof, for use in the treatment of cancer, wherein the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the cancer is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating cancer, wherein the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the cancer is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a method of treating a disease or disorder that is affected by the modulation of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to a method of treating a disease or disorder that is affected by the reduction of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a method of treating a disease or disorder that is affected by a decrease of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the modulation of IKZF2 protein levels wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the reduction of IKZF2 protein levels wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by a decrease of IKZF2 protein levels, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the modulation of IKZF2 levels, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the reduction of IKZF2 protein levels, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by a decrease in IKZF2 protein levels, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiforme, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC).

In another aspect, the present disclosure relates to a method of treating a disease or disorder that is affected by the modulation of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is a cancer for which the immune response is deficient or an immunogenic cancer.

Another aspect of the present disclosure relates to a method of treating a disease or disorder that is affected by the reduction of IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is a cancer for which the immune response is deficient or an immunogenic cancer.

In another aspect, the present disclosure relates to a method of treating a disease or disorder that is affected by a decrease in IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the disease or disorder is a cancer for which the immune response is deficient or an immunogenic cancer.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the modulation of IKZF2 protein levels, wherein the disease or disorder is a cancer for which the immune response is deficient or an immunogenic cancer.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by the reduction of IKZF2 protein levels, wherein the disease or disorder is a cancer for which the immune response is deficient or an immunogenic cancer.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder that is affected by a decrease in IKZF2 protein levels, wherein the disease or disorder is a cancer for which the immune response is deficient or an immunogenic cancer.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the modulation of IKZF2 protein levels wherein the disease or disorder is a cancer for which the immune response is deficient or an immunogenic cancer.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by the reduction of IKZF2 protein levels wherein the disease or disorder is a cancer for which the immune response is deficient or an immunogenic cancer.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder that is affected by a decrease in IKZF2 protein levels wherein the disease or disorder is a cancer for which the immune response is deficient or an immunogenic cancer.

In another aspect, the present disclosure relates to a method of treating cancer comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the cancer is a cancer for which the immune response is deficient or an immunogenic cancer.

Another aspect of the present disclosure relates to a compound of Formula (I') or Formula (I), or a pharmaceutically acceptable salt, hydrate, solvate, prodrug, stereoisomer, or tautomer thereof, for use in the treatment of a cancer for which the immune response is deficient or an immunogenic cancer.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a cancer for which the immune response is deficient or an immunogenic cancer.

Another aspect of the present disclosure relates to a method of treating an IKZF2-dependent disease or disorder by modulating IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein modulation of IKZF2 protein levels treats the IKZF2-dependent disease or disorder.

In another aspect, the present disclosure relates to a method of treating an IKZF2-dependent disease or disorder by reducing IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein reduction of IKZF2 protein levels treats the IKZF2-dependent disease or disorder.

Another aspect of the present disclosure relates to a method of treating an IKZF2-dependent disease or disorder by decreasing IKZF2 protein levels comprising the step of administering to a subject in need thereof a therapeutically effective amount of a compound of Formula (I') or Formula (I), or a pharmaceutically acceptable salt, hydrate, solvate, prodrug, stereoisomer, or tautomer thereof, wherein the decrease in IKZF2 protein levels treats the IKZF2-dependent disease or disorder.

Another aspect of the present disclosure relates to a method of treating an IKZF2-dependent disease or disorder by modulating IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein modulation of IKZF2 protein levels treats the IKZF2-dependent disease or disorder.

In another aspect, the present disclosure relates to a method of treating an IKZF2-dependent disease or disorder by reducing IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein reduction of IKZF2 protein levels treats the IKZF2-dependent disease or disorder.

Another aspect of the present disclosure relates to a method of treating an IKZF2-dependent disease or disorder by decreasing IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein the decrease in IKZF2 protein levels treats the IKZF2-dependent disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by reducing IKZF2 protein levels wherein reduction of IKZF2 protein levels treats the IKZF2-dependent disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of an IKZF2-dependent disease or disorder by reducing IKZF2 protein levels wherein reduction of IKZF2 protein levels treats the IKZF2-dependent disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by modulating IKZF2 protein levels wherein modulation of IKZF2 protein levels treats the IKZF2-dependent disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of an IKZF2-dependent disease or disorder by modulating IKZF2 protein levels wherein modulation of IKZF2 protein levels treats the IKZF2-dependent disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by decreasing IKZF2 protein levels wherein the decrease in IKZF2 protein levels treats the IKZF2-dependent disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of an IKZF2-dependent disease or disorder by decreasing IKZF2 protein levels wherein the decrease in IKZF2 protein levels treats the IKZF2-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the treatment of an IKZF2-dependent disease or disorder by reducing IKZF2 protein levels wherein reduction of IKZF2 protein levels treats the IKZF2-dependent disease or disorder.

Another aspect of the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the treatment of an IKZF2-dependent disease or disorder by reducing IKZF2 protein levels wherein reduction of IKZF2 protein levels treats the IKZF2-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the treatment of an IKZF2-dependent disease or disorder by modulating IKZF2 protein levels wherein modulation of IKZF2 protein levels treats the IKZF2-dependent disease or disorder.

Another aspect of the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the treatment of an IKZF2-dependent disease or disorder by modulating IKZF2 protein levels wherein modulation of IKZF2 protein levels treats the IKZF2-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the treatment of an IKZF2-dependent disease or disorder by decreasing IKZF2 protein levels wherein the decrease in IKZF2 protein levels treats the IKZF2-dependent disease or disorder.

Another aspect of the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the treatment of an IKZF2-dependent disease or disorder by decreasing IKZF2 protein levels wherein the decrease in IKZF2 protein levels treats the IKZF2-dependent disease or disorder.

Another aspect of the present disclosure relates to a method of treating a disease or disorder by reducing IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein reduction of IKZF2 protein levels treats the disease or disorder.

In another aspect, the present disclosure relates to a method of treating a disease or disorder by reducing IKZF2 protein levels comprising the step of administering to a subject in need thereof a compound of Formula (I') or Formula (I), or a pharmaceutically acceptable salt, hydrate, solvate, prodrug, stereoisomer, or tautomer thereof, wherein reduction of IKZF2 protein levels treats the disease or disorder.

Another aspect of the present disclosure relates to a method of treating a disease or disorder by modulating IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein modulation of IKZF2 protein levels treats the disease or disorder.

In another aspect, the present disclosure relates to a method of treating a disease or disorder by modulating IKZF2 protein levels comprising the step of administering to a subject in need thereof a compound of Formula (I') or Formula (I), or a pharmaceutically acceptable salt, hydrate, solvate, prodrug, stereoisomer, or tautomer thereof, wherein modulation of IKZF2 protein levels treats the disease or disorder.

Another aspect of the present disclosure relates to a method of treating a disease or disorder by decreasing IKZF2 protein levels comprising the step of administering to a subject in need thereof a pharmaceutical composition comprising a therapeutically effective amount of a compound of Formula (I') or Formula (I), or a pharmaceutically acceptable salt, hydrate, solvate, prodrug, stereoisomer, or tautomer thereof, wherein decreasing IKZF2 protein levels treats the disease or disorder.

In another aspect, the present disclosure relates to a method of treating a disease or disorder by decreasing IKZF2 protein levels comprising the step of administering to a subject in need thereof a compound of Formula (I') or Formula (I), or a pharmaceutically acceptable salt, hydrate, solvate, prodrug, stereoisomer, or tautomer thereof, wherein decreasing IKZF2 protein levels treats the disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of an IKZF2-dependent disease or disorder by reducing IKZF2 protein levels wherein reduction of IKZF2 protein levels treats the IKZF2-dependent disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by reducing IKZF2 protein levels wherein reduction of IKZF2 protein levels treats the IKZF2-dependent disease or disorder.

Another aspect of the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by modulating IKZF2 protein levels wherein modulation of IKZF2 protein levels treats the IKZF2-dependent disease or disorder.

In another aspect, the present disclosure relates a compound of Formula (I') or Formula (I), or a pharmaceutically acceptable salt, hydrate, solvate, prodrug, stereoisomer, or tautomer thereof, for use in the treatment of an IKZF2-dependent disease or disorder by modulating IKZF2 protein levels wherein modulation of IKZF2 protein levels treats the IKZF2-dependent disease or disorder.

Another aspect of the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of an IKZF2-dependent disease or disorder by decreasing IKZF2 protein levels wherein decreasing IKZF2 protein levels treats the IKZF2-dependent disease or disorder.

In another aspect, the present disclosure relates a compound of Formula (I') or Formula (I), or a pharmaceutically acceptable salt, hydrate, solvate, prodrug, stereoisomer, or tautomer thereof, for use in the treatment of an IKZF2-dependent disease or disorder by decreasing IKZF2 protein levels wherein decreasing IKZF2 protein levels treats the IKZF2-dependent disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder by reducing IKZF2 protein levels, wherein reduction of IKZF2 protein levels treats the disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of a disease or disorder by reducing IKZF2 protein levels wherein reduction of IKZF2 protein levels treats the disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder by modulating IKZF2 protein levels, wherein modulation of IKZF2 protein levels treats the disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of a disease or disorder by modulating IKZF2 protein levels wherein modulation of IKZF2 protein levels treats the disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder by decreasing IKZF2 protein levels, wherein decreasing IKZF2 protein levels treats the disease or disorder.

In another aspect, the present disclosure relates to a pharmaceutical composition comprising a therapeutically effective amount of a compound of Formula (I') or Formula (I), or a pharmaceutically acceptable salt, hydrate, solvate, prodrug, stereoisomer, or tautomer thereof, for use in the treatment of a disease or disorder by decreasing IKZF2 protein levels wherein decreasing IKZF2 protein levels treats the disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by reducing IKZF2 protein levels, wherein reduction of IKZF2 protein levels treats the IKZF2-dependent disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by reducing IKZF2 protein levels, wherein reduction of IKZF2 protein levels treats the IKZF2-dependent disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by modulating IKZF2 protein levels, wherein modulation of IKZF2 protein levels treats the IKZF2-dependent disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by modulating IKZF2 protein levels, wherein modulation of IKZF2 protein levels treats the IKZF2-dependent disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by decreasing IKZF2 protein levels, wherein decreasing IKZF2 protein levels treats the IKZF2-dependent disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a IKZF2-dependent disease or disorder by decreasing IKZF2 protein levels, wherein decreasing IKZF2 protein levels treats the IKZF2-dependent disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder by reducing IKZF2 protein levels, wherein reduction of IKZF2 protein levels treats the disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a disease or disorder by reducing IKZF2 protein levels, wherein reduction of IKZF2 protein levels treats the disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder by modulating IKZF2 protein levels, wherein modulation of IKZF2 protein levels treats the disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a disease or disorder by modulating IKZF2 protein levels, wherein modulation of IKZF2 protein levels treats the disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating a disease or disorder by decreasing IKZF2 protein levels, wherein decreasing IKZF2 protein levels treats the disease or disorder.

In another aspect, the present disclosure relates to the use of a pharmaceutical composition comprising a therapeutically effective amount of a compound of Formula (I') or Formula (I), or a pharmaceutically acceptable salt, hydrate, solvate, prodrug, stereoisomer, or tautomer thereof, in the manufacture of a medicament for treating a disease or disorder by decreasing IKZF2 protein levels, wherein decreasing IKZF2 protein levels treats the disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder by reducing IKZF2 protein levels wherein reduction of IKZF2 protein levels treats the disease or disorder.

In another aspect, the present disclosure relates to a compound of Formula (I') or Formula (I), or a pharmaceutically acceptable salt, hydrate, solvate, prodrug, stereoisomer, or tautomer thereof, for use in the treatment of a disease or disorder by modulating IKZF2 protein levels wherein modulation of IKZF2 protein levels treats the disease or disorder.

Another aspect of the present disclosure relates to a compound of Formula (I') or Formula (I), or a pharmaceutically acceptable salt, hydrate, solvate, prodrug, stereoisomer, or tautomer thereof, for use in the treatment of a disease or disorder by decreasing IKZF2 protein levels wherein decreasing IKZF2 protein levels treats the disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the treatment of a disease or disorder by reducing IKZF2 protein levels, wherein reduction of IKZF2 protein levels treats the disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the treatment of a disease or disorder by modulating IKZF2 protein levels, wherein modulation of IKZF2 protein levels treats the disease or disorder.

Another aspect of the present disclosure relates to the use of a compound of Formula (I') or Formula (I), or a pharmaceutically acceptable salt, hydrate, solvate, prodrug, stereoisomer, or tautomer thereof, in the treatment of a disease or disorder by decreasing IKZF2 protein levels, wherein decreasing of IKZF2 protein levels treats the disease or disorder.

In another aspect of the disclosure, the compounds according to the disclosure are formulated into pharmaceutical compositions comprising an effective amount, preferably a pharmaceutically effective amount, of a compound according to the disclosure or salt, hydrate, solvate, prodrug, stereoisomer, or tautomer thereof, and a pharmaceutically acceptable excipient or carrier.

Another aspect of the present disclosure relates to the use of a compound of Formula (I') or Formula (I), or a pharmaceutically acceptable salt, hydrate, solvate, prodrug, stereoisomer, or tautomer thereof, in the manufacture of a medicament for treating an IKZF2-dependent disease or disorder.

In another aspect, the present disclosure relates to a compound of Formula (I') or Formula (I), or a pharmaceutically acceptable salt, hydrate, solvate, prodrug, stereoisomer, or tautomer thereof, for use in the manufacture of a medicament for treating a disease associated with modulating IKZF2 protein levels.

Another aspect of the present disclosure relates to the use of a compound of Formula (I') or Formula (I), or a pharmaceutically acceptable salt, hydrate, solvate, prodrug, stereoisomer, or tautomer thereof, in the treatment of a disease associated with the modulation of IKZF2 protein levels.

In some embodiments of the methods disclosed herein, the administration of the compound of Formula (I') or Formula (I), or a pharmaceutically acceptable salt, hydrate, solvate, prodrug, stereoisomer, or tautomer thereof, is performed orally, parentally, subcutaneously, by injection, or by infusion.

The present disclosure provides degraders of IKZF2 that are therapeutic agents in the treatment of diseases such as cancer and metastasis, in the treatment of diseases affected by the modulation of IKZF2 protein levels, and in the treatment IKZF2-dependent diseases or disorders.

In one embodiment, the disease or disorder that can be treated by the compounds of the present disclosure is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, Ewing's sarcoma non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the disease or disorder is selected from non-small cell lung cancer (NSCLC), melanoma, triple-negative breast cancer (TNBC), nasopharyngeal cancer (NPC), and microsatellite stable colorectal cancer (mssCRC). In another embodiment, the IKZF2-dependent disease or disorder is a cancer for which the immune response is deficient or an immunogenic cancer.

The present disclosure provides agents with novel mechanisms of action toward IKZF2 proteins in the treatment of various types of diseases including cancer and metastasis, in the treatment of diseases affected by the modulation of IKZF2 protein levels, and in the treatment IKZF2-dependent diseases or disorders. Ultimately the present disclosure provides the medical community with a novel pharmacological strategy for the treatment of diseases and disorders associated with IKZF2 proteins.

DETAILED DESCRIPTION OF THE DISCLOSURE

The present disclosure relates to compounds and compositions that are capable of modulating IKZF2 protein levels. The disclosure features methods of treating, preventing, or ameliorating a disease or disorder in which IKZF2 plays a role by administering to a patient in need thereof a therapeutically effective amount of a compound of Formula (I') or Formula (I), or a pharmaceutically acceptable salt, hydrate, solvate, prodrug, stereoisomer, or tautomer thereof. The methods of the present disclosure can be used in the treatment of a variety of IKZF2-dependent diseases and disorders by modulating IKZF2 protein levels. Modulation of IKZF2 protein levels through degradation provides a novel approach to the treatment, prevention, or amelioration of diseases including, but not limited to, cancer and metathesis, and other IKZF2-dependent diseases or disorders.

In one aspect, the compounds of the disclosure have use as therapeutic agents, particularly for cancers and related diseases. In one aspect, the compounds of the disclosure have IKZF2 degradation activity, preferably having such activity at or below the 50 µM level, and more preferably having such activity at or below the 10 µM level. In another aspect, the compounds of the disclosure have degrader activity for IKZF2 that is selective over one or more of IKZF1, IKZF3, IKZF4, and/or IKZF5. In another aspect, the compounds of the disclosure have degrader activity for both IKZF2 and IKZF4. The compounds of the disclosure have usefulness in treating cancer and other diseases for which such degradation activity would be beneficial for the patient. For example, while not intending to be bound by any theory, the inventors believe that reducing levels of IKZF2 in Tregs in a tumor may allow the patient immune system to more effectively attack the disease. In summary, the present disclosure provides novel IKZF2 degraders useful for the treatment of cancer and other diseases.

In a first aspect of the disclosure, the compounds of Formula (I') are described:

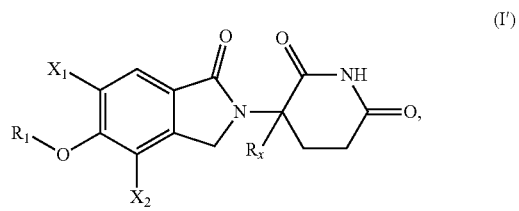

or pharmaceutically acceptable salts, hydrates, solvates, prodrugs, stereoisomers, and tautomers thereof, wherein $R_x$, $X_1$, $X_2$, and $R_1$ are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $(C_1-C_{10})$alkyl means an alkyl group or radical having 1 to 10 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-. Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" refer to one or more than one (e.g., to at least one) of the grammatical object of the article. By way of example, "an element" means one element or more than one element.

The term "and/or" means either "and" or "or" unless indicated otherwise.

The term "optionally substituted" means that a given chemical moiety (e.g., an alkyl group) can (but is not required to) be bonded other substituents (e.g., heteroatoms).

For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$)alkyl, ($C_1$-$C_6$)alkyl, ($C_1$-$C_6$)alkoxy, ($C_1$-$C_6$)haloalkyl, ($C_1$-$C_6$)haloalkoxy, —O—($C_2$-$C_6$)alkenyl, —O—($C_2$-$C_6$)alkynyl, ($C_2$-$C_6$)alkenyl, ($C_2$-$C_6$)alkynyl, —OH, —OP(O)(OH)$_2$, —OC(O)($C_1$-$C_6$)alkyl, —C(O)($C_1$-$C_6$)alkyl, —OC(O)O($C_1$-$C_6$)alkyl, —NH$_2$, —NH(($C_1$-$C_6$)alkyl), —N(($C_1$-$C_6$)alkyl)$_2$, —NHC(O)($C_1$-$C_6$)alkyl, —C(O)NH($C_1$-$C_6$)alkyl, —S(O)$_2$($C_1$-$C_6$)alkyl, —S(O)NH($C_1$-$C_6$)alkyl, and S(O)N(($C_1$-$C_6$)alkyl)$_2$. The substituents can themselves be optionally substituted. "Optionally substituted" as used herein also refers to substituted or unsubstituted whose meaning is described below.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

The term "unsubstituted" means that the specified group bears no substituents.

Unless otherwise specifically defined, "aryl" means a cyclic, aromatic hydrocarbon group having 1 to 3 aromatic rings, including monocyclic or bicyclic groups such as phenyl, biphenyl, or naphthyl. When containing two aromatic rings (bicyclic, etc.), the aromatic rings of the aryl group are optionally joined at a single point (e.g., biphenyl), or fused (e.g., naphthyl). The aryl group is optionally substituted by one or more substituents, e.g., 1 to 5 substituents, at any point of attachment. Exemplary substituents include, but are not limited to, —H, -halogen, —CN, —O—($C_1$-$C_6$)alkyl, ($C_1$-$C_6$)alkyl, —O—($C_2$-$C_6$)alkenyl, —O—($C_2$-$C_6$)alkynyl, ($C_2$-$C_6$)alkenyl, ($C_2$-$C_6$)alkynyl, —OH, —OP(O)(OH)$_2$, —OC(O)($C_1$-$C_6$)alkyl, —C(O)($C_1$-$C_6$)alkyl, —OC(O)O($C_1$-$C_6$)alkyl, —NH$_2$, —NH(($C_1$-$C_6$)alkyl), —N(($C_1$-$C_6$)alkyl)$_2$, —S(O)$_2$—($C_1$-$C_6$)alkyl, —S(O)NH($C_1$-$C_6$)alkyl, and S(O)N(($C_1$-$C_6$)alkyl)$_2$. The substituents are themselves optionally substituted. Furthermore, when containing two fused rings, the aryl groups optionally have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$\Delta^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4 d]thiazolyl, imidazo[2,1-b][1,3,4]thiadiazolyl, thieno[2,3-b]pyrrolyl, 3H-indolyl, and derivatives thereof. Furthermore, when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" mean fluorine, chlorine, bromine, or iodine.

"Alkyl" means a straight or branched chain saturated hydrocarbon containing 1-12 carbon atoms. Examples of a ($C_1$-$C_6$)alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" means a straight or branched chain saturated hydrocarbon containing 1-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

"Alkenyl" means a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted and may be straight or branched.

"Alkynyl" means a straight or branched chain unsaturated hydrocarbon containing 2-12 carbon atoms. The "alkynyl" group contains at least one triple bond in the chain. Examples of alkenyl groups include ethynyl, propargyl, n-butynyl, isobutynyl, pentynyl, or hexynyl. An alkynyl group can be unsubstituted or substituted.

"Cycloalkyl" or "carbocyclyl" means a monocyclic or polycyclic saturated carbon ring containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A ($C_3$-$C_5$)cycloalkyl is a cycloalkyl group containing between 3 and 8 carbon atoms. A cycloalkyl group can be fused (e.g., decalin) or bridged (e.g., norbomane).

"Heterocyclyl" or "heterocycloalkyl" means a saturated or partially saturated monocyclic or polycyclic ring containing carbon and at least one heteroatom selected from oxygen, nitrogen, or sulfur (O, N, or S) and wherein there is not delocalized n electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, imidazolinyl, dithiolanyl, and homotropanyl.

"Haloalkyl" means an alkyl group substituted with one or more halogens. Examples of haloalkyl groups include, but are not limited to, trifluoromethyl, difluoromethyl, pentafluoroethyl, trichloromethyl, etc.

"Haloalkoxy" means an alkoxy group substituted with one or more halogens. Examples of haloalkyl groups include, but are not limited to, trifluoromethoxy, difluoromethoxy, pentafluoroethoxy, trichloromethoxy, etc.

"Cyano" means a substituent having a carbon atom joined to a nitrogen atom by a triple bond, e.g., C≡N.

"Amino" means a substituent containing at least one nitrogen atom (e.g., —$NH_2$).

"Hydroxyalkyl" means an alkyl group substituted with one or more —OH groups. Examples of hydroxyalkyl groups include HO—$CH_2$—, HO—$CH_2CH_2$—, and $CH_2$—CH(OH)—.

"Spirocycloalkyl" or "spirocyclyl" means carbogenic bicyclic ring systems with both rings connected through a single atom. The rings can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. A ($C_3$-$C_{12}$)spirocycloalkyl is a spirocycle containing between 3 and 12 carbon atoms.

"Spiroheterocycloalkyl" or "spiroheterocyclyl" means a spirocycle wherein at least one of the rings is a heterocycle one or more of the carbon atoms can be substituted with a heteroatom (e.g., one or more of the carbon atoms can be substituted with a heteroatom in at least one of the rings). One or both of the rings in a spiroheterocycle can be fused to another ring carbocyclic, heterocyclic, aromatic, or heteroaromatic ring.

B. Salt, Prodrug, Derivative, and Solvate Terms and Conventions

"Prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

"Pharmaceutically acceptable prodrug" as used herein means a prodrug of a compound of the disclosure which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

"Salt" means an ionic form of the parent compound or the product of the reaction between the parent compound with a suitable acid or base to make the acid salt or base salt of the parent compound. Salts of the compounds of the present disclosure can be synthesized from the parent compounds, which contain a basic or acidic moiety, by conventional chemical methods. Generally, the salts are prepared by reacting the free base or acid parent compound with stoichiometric amounts or with an excess of the desired salt-forming inorganic or organic acid or base in a suitable solvent or various combinations of solvents.

"Pharmaceutically acceptable salt" means a salt of a compound of the disclosure which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present disclosure are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

"Pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamon acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

"Pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, TEA, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

"Solvate" means a complex of variable stoichiometry formed by a solute, for example, a compound of Formula (I') or Formula (I)) and solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, such solvents selected for the purpose of the disclosure do not interfere with the biological activity of the solute. Solvates encompasses both solution-phase and isolatable solvates. Representative solvates include hydrates, ethanolates, methanolates, and the like.

"Hydrate" means a solvate wherein the solvent molecule(s) is/are water.

The compounds of the present disclosure as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

"Isomers" means compounds having the same number and kind of atoms, and hence the same molecular weight, but differing with respect to the arrangement or configuration of the atoms in space. The term includes stereoisomers and geometric isomers.

"Stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure, which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

"Enantiomers" means a pair of stereoisomers that are non-superimposable mirror images of each other.

"Diastereoisomers" or "diastereomers" mean optical isomers which are not mirror images of each other.

"Racemic mixture" or "racemate" mean a mixture containing equal parts of individual enantiomers.

"Non-racemic mixture" means a mixture containing unequal parts of individual enantiomers.

"Geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the disclosure, the disclosure contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, Advanced Organic Chemistry: Reactions, Mechanisms, and Structure, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^1$H NMR, and $^{13}$C NMR.

Some of the compounds of the disclosure can exist in more than one tautomeric form. As mentioned above, the compounds of the disclosure include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the disclosure from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

D. Pharmaceutical Administration and Treatment Terms and Conventions

A "patient" or "subject" is a mammal, e.g., a human, mouse, rat, guinea pig, dog, cat, horse, cow, pig, or nonhuman primate, such as a monkey, chimpanzee, baboon or, rhesus. In certain embodiments, the subject is a primate. In yet other embodiments, the subject is a human.

An "effective amount" or "therapeutically effective amount" when used in connection with a compound means an amount of a compound of the present disclosure that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "pharmaceutically effective amount" or "therapeutically effective amount" means an amount of a compound according to the disclosure which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the disclosure which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the disclosure, and the age, body weight, general health, sex, and diet of the patient. Such a therapeutically effective amount can be determined routinely by one of ordinary skill in the art having regard to their own knowledge, the prior art, and this disclosure.

As used herein, the term "pharmaceutical composition" refers to a compound of the disclosure, or a pharmaceutically acceptable salt, hydrate, solvate, prodrug, stereoisomer, or tautomer thereof, together with at least one pharmaceutically acceptable carrier, in a form suitable for oral or parenteral administration.

"Carrier" encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

A subject is "in need of" a treatment if such subject would benefit biologically, medically, or in quality of life from such treatment (preferably, a human).

As used herein, the term "inhibit", "inhibition", or "inhibiting" refers to the reduction or suppression of a given condition, symptom, or disorder, or disease, or a significant decrease in the baseline activity of a biological activity or process.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder.

"Pharmaceutically acceptable" means that the substance or composition must be compatible chemically and/or toxicologically, with the other ingredients comprising a formulation, and/or the mammal being treated therewith.

"Disorder" means, and is used interchangeably with, the terms disease, condition, or illness, unless otherwise indicated.

"Administer", "administering", or "administration" means to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

"Prodrug" means a compound which is convertible in vivo by metabolic means (e.g., by hydrolysis) to a disclosed compound.

"Compounds of the present disclosure", "Compounds of Formula (I') or Formula (I)", "compounds of the disclosure", and equivalent expressions (unless specifically identified otherwise) refer to compounds of Formulae (I), (Ia), (Ib), (Ic), (Id), (Ie), (If), (Ig), (Ih), (Ii), (Ij), (Ik), (Il), (Im) (In), (Io), (Ip), (Iq), (Ir), (Is), and (It) as herein described including the tautomers, the prodrugs, salts particularly the pharmaceutically acceptable salts, and the solvates and hydrates thereof, where the context so permits thereof, as well as all stereoisomers (including diastereoisomers and enantiomers), rotamers, tautomers, and isotopically labelled compounds (including deuterium substitutions), as well as inherently formed moieties (e.g., polymorphs, solvates and/or hydrates). For purposes of this disclosure, solvates and hydrates are generally considered compositions. In general and preferably, the compounds of the disclosure and the formulas designating the compounds of the disclosure are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

"Stable compound" or "stable structure" means a compound that is sufficiently robust to survive isolation to a useful degree of purity from a reaction mixture, and formulation into an efficacious therapeutic or diagnostic agent. For example, a compound that would have a "dangling valency" or is a carbanion is not a compound contemplated by the disclosure.

In a specific embodiment, the term "about" or "approximately" means within 20%, preferably within 10%, and more preferably within 5% of a given value or range.

The yield of each of the reactions described herein is expressed as a percentage of the theoretical yield. "Cancer" means any cancer caused by the proliferation of malignant neoplastic cells, such as tumors, neoplasms, carcinomas, sarcomas, leukemias, lymphomas, and the like. For example, cancers include, but are not limited to, mesothelioma, leukemias, and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal, and esophageal), genitourinary cancers (e.g., prostate, bladder, renal, uterine, ovarian, testicular), lung cancer (e.g., small-cell and non-small cell), breast cancer (e.g., triple-negative breast cancer (TNBC)), pancreatic cancer, melanoma, and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating, and studying are, for example, colon carcinoma, familiary adenomatous polyposis carcinoma, and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing's sarcoma, plasmocytoma, non-small cell lung cancer (NSCLC), melanoma, triple-negative breast cancer (TNBC), nasopharyngeal cancer (NPC), microsatellite stable colorectal cancer (mss-CRC), thymoma, carcinoid, acute myelogenous leukemia, and gastrointestinal stromal tumor (GIST).

"Simultaneously" or "simultaneous" when referring to a method of treating or a therapeutic use means with a combination of a compound of Formula (I), or a pharmaceutically acceptable salt, hydrate, solvate, prodrug, stereoisomer, or tautomer thereof, and one or more second agent(s) means administration of the compound and the one or more second agent(s) by the same route and at the same time.

"Separately" or "separate" when referring to a method of treating or a therapeutic use means with a combination of a compound of Formula (I), or a pharmaceutically acceptable salt, hydrate, solvate, prodrug, stereoisomer, or tautomer thereof, and one or more second agent(s) means administration of the compound and the one or more second agent(s) by different routes and at approximately the same time.

By therapeutic administration "over a period of time" means, when referring to a method of treating or a therapeutic use with a combination of a compound of Formula (I), or a pharmaceutically acceptable salt, hydrate, solvate, prodrug, stereoisomer, or tautomer thereof, and one or more second agent(s), administration of the compound and the one or more second agent(s) by the same or different routes and at different times. In some embodiments, the administration of the compound or the one or more second agent(s) occurs before the administration of the other begins. In this way, it is possible to administer a one of the active ingredients (i.e., a compound of the Formula (I), or a pharmaceutically acceptable salt, hydrate, solvate, prodrug, stereoisomer, or tautomer thereof, or one or more second agent(s)) for several months before administering the other active ingredient or ingredients. In this case, no simultaneous administration occurs. Another therapeutic administration over a period of time consists of the administration over time of the two or more active ingredients of the combination using different frequencies of administration for each of the active ingredients, whereby at certain time points in time simultaneous administration of all of the active ingredients takes place whereas at other time points in time only a part of the active ingredients of the combination may be administered (e.g., for example. a compound of formula (I), or a pharmaceutically acceptable salt, hydrate, solvate, prodrug, stereoisomer, or tautomer thereof, and the one or more second agents the therapeutic administration over a period of time could be such that a compound of Formula (I), or a pharmaceutically acceptable salt, hydrate, solvate, prodrug, stereoisomer, or tautomer thereof, is administered once a day and the one or more second agent(s) is administered once every four weeks.)

The compounds can be administered simultaneously (as a single preparation or separate preparation), sequentially, separately, or over a period of time to the other drug therapy or treatment modality. In general, a combination therapy envisions administration of two or more drugs during a single cycle or course of therapy.

"IKZF2-dependent disease or disorder" means any disease or disorder which is directly or indirectly affected by the modulation of IKZF2 protein levels.

"IKZF4-dependent disease or disorder" means any disease or disorder which is directly or indirectly affected by the modulation of IKZF4 protein levels.

D. Specific Embodiments and Methods for Testing Compounds of Formula (I') or Formula (I)

The present disclosure relates to compounds or pharmaceutically acceptable salts, hydrates, solvates, prodrugs, stereoisomers, or tautomers thereof, capable of modulating IKZF2 protein levels, which are useful for the treatment of diseases and disorders associated with modulation of IKZF2 protein levels. The disclosure further relates to compounds, or pharmaceutically acceptable salts, hydrates, solvates, prodrugs, stereoisomers, or tautomers thereof, which are useful for reducing or decreasing IKZF2 protein levels.

In one embodiment, the compounds of Formula (I') or Formula (I) have the structure of Formula (Ia):

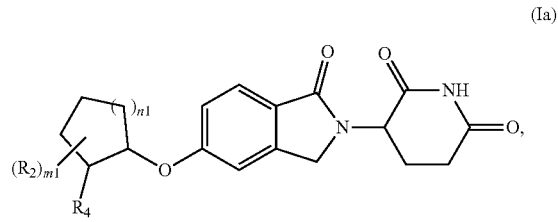

or pharmaceutically acceptable salts, hydrates, solvates, prodrugs, stereoisomers, and tautomers thereof.

In another embodiment, the compounds of Formula (I') or Formula (I) have the structure of Formula (Ib):

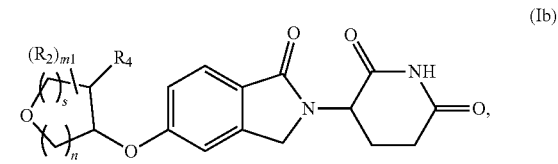

or pharmaceutically acceptable salts, hydrates, solvates, prodrugs, stereoisomers, and tautomers thereof.

In yet another embodiment, the compounds of Formula (I') or Formula (I) have the structure of Formula (Ic):

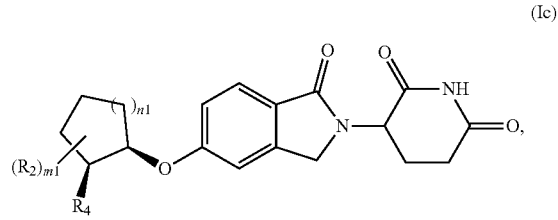

or pharmaceutically acceptable salts, hydrates, solvates, prodrugs, stereoisomers, and tautomers thereof.

In another embodiment, the compounds of Formula (I') or Formula (I) have the structure of Formula (Id):

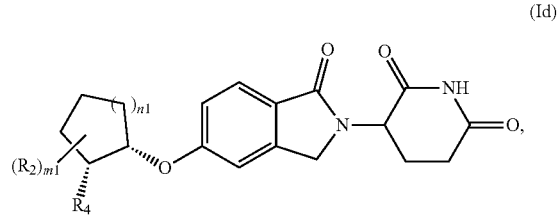

or pharmaceutically acceptable salts, hydrates, solvates, prodrugs, stereoisomers, and tautomers thereof.

In another embodiment, the compounds of Formula (I') or Formula (I) have the structure of Formula (Ie):

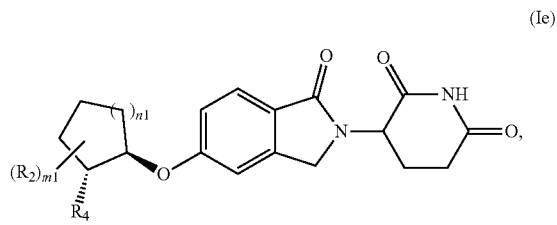

(Ie)

or pharmaceutically acceptable salts, hydrates, solvates, prodrugs, stereoisomers, and tautomers thereof.

In another embodiment, the compounds of Formula (I') or Formula (I) have the structure of Formula (If):

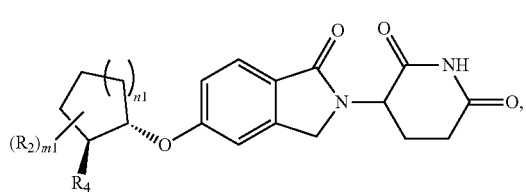

(If)

or pharmaceutically acceptable salts, hydrates, solvates, prodrugs, stereoisomers, and tautomers thereof.

In another embodiment, the compounds of Formula (I') or Formula (I) have the structure of Formula (Ig):

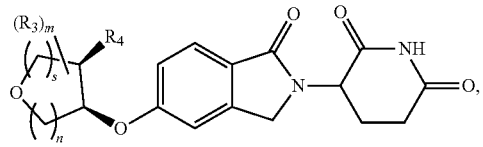

(Ig)

or pharmaceutically acceptable salts, hydrates, solvates, prodrugs, stereoisomers, and tautomers thereof.

In another embodiment, the compounds of Formula (I') or Formula (I) have the structure of Formula (Ih):

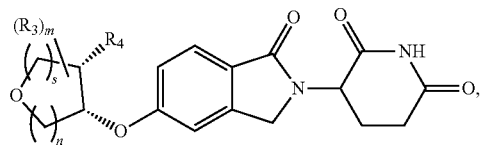

(Ih)

or pharmaceutically acceptable salts, hydrates, solvates, prodrugs, stereoisomers, and tautomers thereof.

In another embodiment, the compounds of Formula (I') or Formula (I) have the structure of Formula (Ii):

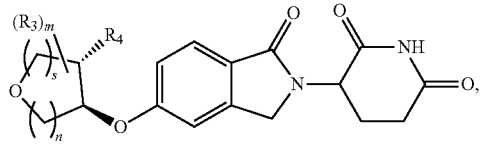

(Ii)

or pharmaceutically acceptable salts, hydrates, solvates, prodrugs, stereoisomers, and tautomers thereof.

In another embodiment, the compounds of Formula (I') or Formula (I) have the structure of Formula (Ij):

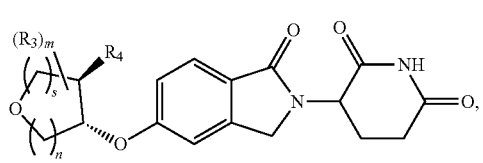

(Ij)

or pharmaceutically acceptable salts, hydrates, solvates, prodrugs, stereoisomers, and tautomers thereof.

In another embodiment, the compounds of Formula (I') or Formula (I) have the structure of Formula (Ik):

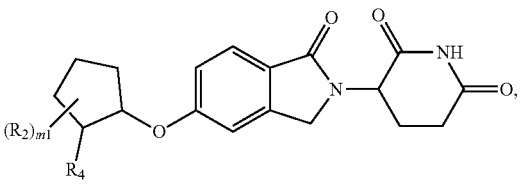

(Ik)

or pharmaceutically acceptable salts, hydrates, solvates, prodrugs, stereoisomers, and tautomers thereof.

In another embodiment, the compounds of Formula (I') or Formula (I) have the structure of Formula (Il):

(Il)

or pharmaceutically acceptable salts, hydrates, solvates, prodrugs, stereoisomers, and tautomers thereof.

In another embodiment, the compounds of Formula (I') or Formula (I) have the structure of Formula (Im):

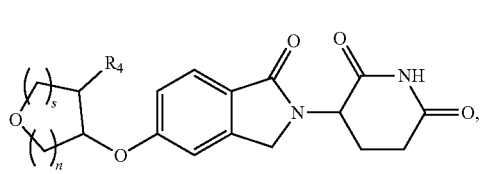

(Im)

or pharmaceutically acceptable salts, hydrates, solvates, prodrugs, stereoisomers, and tautomers thereof.

In another embodiment, the compounds of Formula (I') or Formula (I) have the structure of Formula (In):

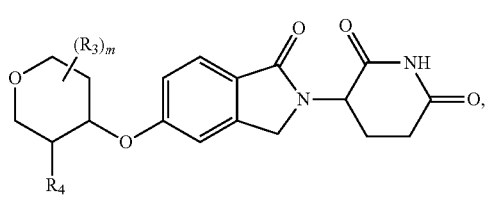

(In)

or pharmaceutically acceptable salts, hydrates, solvates, prodrugs, stereoisomers, and tautomers thereof.

In another embodiment, the compounds of Formula (I') or Formula (I) have the structure of Formula (Io):

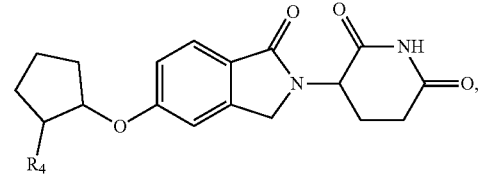

(Io)

or pharmaceutically acceptable salts, hydrates, solvates, prodrugs, stereoisomers, and tautomers thereof.

In another embodiment, the compounds of Formula (I') or Formula (I) have the structure of Formula (Ip):

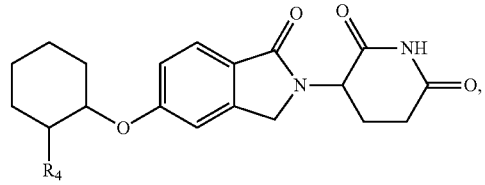

(Ip)

or pharmaceutically acceptable salts, hydrates, solvates, prodrugs, stereoisomers, and tautomers thereof.

In another embodiment, the compounds of Formula (I') or Formula (I) have the structure of Formula (Iq):

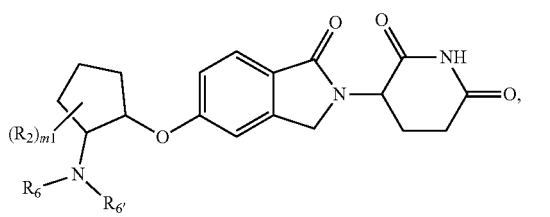

(Iq)

or pharmaceutically acceptable salts, hydrates, solvates, prodrugs, stereoisomers, and tautomers thereof.

In another embodiment, the compounds of Formula (I') or Formula (I) have the structure of Formula (Ir):

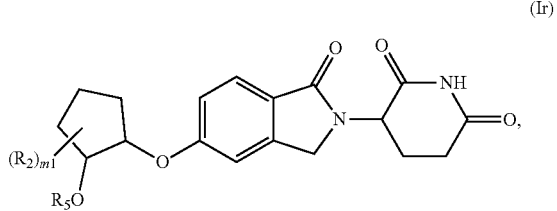

(Ir)

or pharmaceutically acceptable salts, hydrates, solvates, prodrugs, stereoisomers, and tautomers thereof.

In another embodiment, the compounds of Formula (I') or Formula (I) have the structure of Formula (Is):

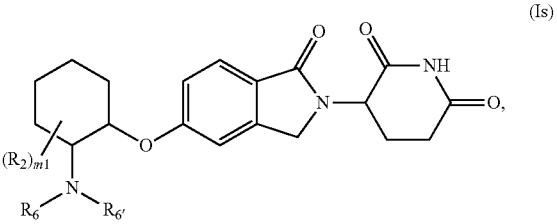

(Is)

or pharmaceutically acceptable salts, hydrates, solvates, prodrugs, stereoisomers, and tautomers thereof.

In another embodiment, the compounds of Formula (I') or Formula (I) have the structure of Formula (It):

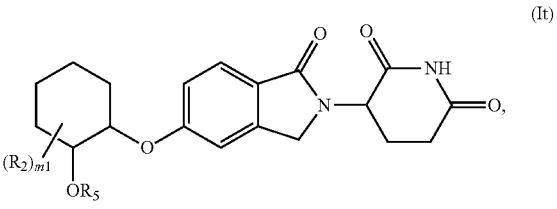

(It)

or pharmaceutically acceptable salts, hydrates, solvates, prodrugs, stereoisomers, and tautomers thereof.

In some embodiments of the formulae above (e.g., Formulae (I), (Ia), (Ib), (Ic), (Id), (Ie), (If), (Ig), (Ih), (Ii), (Ij), (Ik), (Il), (Im), (In), (Io), (p), (Iq), (Ir), (Is), and (It)), $R_1$ is In another embodiment, $R_1$ is

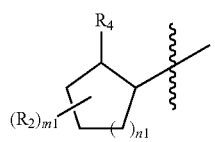

In another embodiment, $R_1$ is

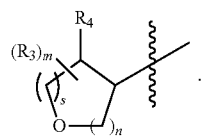

In some embodiments of the formulae above, $X_1$ is H, $(C_1-C_3)$alkyl, $(C_1-C_6)$alkoxy, $(C_1-C_3)$haloalkyl, $(C_1-C_6)$haloalkoxy, $(C_3-C_7)$cycloalkyl, halogen, —CN, —OH, or —NH$_2$. In another embodiment, $X_1$ is H, $(C_1-C_3)$alkyl, $(C_1-C_6)$alkoxy, $(C_1-C_3)$haloalkyl, $(C_1-C_3)$haloalkoxy, halogen, —CN, —OH, or —NH$_2$. In yet another embodiment, $X_1$ is H, $(C_1-C_4)$alkyl, $(C_1-C_6)$alkoxy, $(C_1-C_4)$haloalkyl, $(C_1-C_4)$haloalkoxy, $(C_3-C_7)$cycloalkyl, or halogen. In another embodiment, $X_1$ is H, $(C_1-C_4)$alkyl, $(C_1-C_6)$alkoxy, $(C_1-C_4)$haloalkyl, $(C_1-C_4)$haloalkoxy, or halogen. In yet another embodiment, $X_1$ is H, halogen, —CN, —OH, or —NH$_2$. In another embodiment, $X_1$ is H, $(C_1-C_4)$alkyl, $(C_1-C_4)$haloalkyl, halogen, —CN, —OH, or —NH$_2$. In yet another embodiment, $X_1$ is H, $(C_1-C_4)$alkyl, $(C_1-C_4)$haloalkyl, halogen, —OH, or —NH$_2$. In another embodiment, $X_1$ is H, $(C_1-C_4)$alkyl, halogen, —OH, or —NH$_2$. In yet another embodiment, $X_1$ is H, halogen, —OH, or —NH$_2$. In another embodiment, $X_1$ is H.

In some embodiments of the formulae above, $X_2$ is H, $(C_1-C_3)$alkyl, $(C_1-C_6)$alkoxy, $(C_1-C_3)$haloalkyl, $(C_1-C_6)$haloalkoxy, $(C_3-C_7)$cycloalkyl, halogen, —CN, —OH, or —NH$_2$. In another embodiment, $X_2$ is H, $(C_1-C_3)$alkyl, $(C_1-C_6)$alkoxy, $(C_1-C_3)$haloalkyl, $(C_1-C_3)$haloalkoxy, halogen, —CN, —OH, or —NH$_2$. In yet another embodiment, $X_2$ is H, $(C_1-C_4)$alkyl, $(C_1-C_6)$alkoxy, $(C_1-C_4)$haloalkyl, $(C_1-C_4)$haloalkoxy, $(C_3-C_7)$cycloalkyl, or halogen. In another embodiment, $X_2$ is H, $(C_1-C_4)$alkyl, $(C_1-C_6)$alkoxy, $(C_1-C_4)$haloalkyl, $(C_1-C_4)$haloalkoxy, or halogen. In yet another embodiment, $X_2$ is H, halogen, —CN, —OH, or —NH$_2$. In another embodiment, $X_2$ is H, $(C_1-C_4)$alkyl, $(C_1-C_4)$haloalkyl, halogen, —CN, —OH, or —NH$_2$. In yet another embodiment, $X_2$ is H, $(C_1-C_4)$alkyl, $(C_1-C_4)$haloalkyl, halogen, —OH, or —NH$_2$. In another embodiment, $X_2$ is H, $(C_1-C_4)$alkyl, halogen, —OH, or —NH$_2$. In yet another embodiment, $X_2$ is H, halogen, —OH, or —NH$_2$. In another embodiment, $X_2$ is H.

In some embodiments of the formulae above, $X_1$ is H and $X_2$ is $(C_1-C_3)$alkyl, $(C_1-C_6)$alkoxy, $(C_1-C_3)$haloalkyl, $(C_1-C_6)$haloalkoxy, $(C_3-C_7)$cycloalkyl, halogen, —CN, —OH, or —NH$_2$. In another embodiment, $X_1$ is $(C_1-C_3)$alkyl, $(C_1-C_6)$alkoxy, $(C_1-C_3)$haloalkyl, $(C_1-C_6)$haloalkoxy, $(C_3-C_7)$cycloalkyl, halogen, —CN, —OH, or —NH$_2$ and $X_2$ is H. In yet another embodiment, $X_1$ is H and $X_2$ is H.

In some embodiments of the formulae above, $R_x$ is D. In another embodiment, $R_x$ is H.

In some embodiments of the formulae above, each $R_2$ is independently at each occurrence $(C_1-C_3)$alkyl, $(C_1-C_3)$alkoxy, $(C_1-C_3)$haloalkyl, $(C_1-C_3)$haloalkoxy, halogen, —CN, —OH, or —NH$_2$. In another embodiment, $R_2$ is independently at each occurrence $(C_1-C_3)$alkyl, $(C_1-C_3)$alkoxy, $(C_1-C_3)$haloalkyl, $(C_1-C_3)$haloalkoxy, or halogen. In yet another embodiment, $R_2$ is independently at each occurrence halogen, —CN, —OH, or —NH$_2$. In another embodiment, $R_2$ is independently at each occurrence $(C_1-C_3)$alkyl, $(C_1-C_3)$alkoxy, $(C_1-C_3)$haloalkyl, or $(C_1-C_3)$haloalkoxy. In yet another embodiment, $R_2$ is independently at each occurrence $(C_1-C_3)$alkyl, $(C_1-C_3)$haloalkyl, halogen, —CN, —OH, or —NH$_2$. In another embodiment, $R_2$ is independently at each occurrence $(C_1-C_3)$alkyl, $(C_1-C_3)$haloalkyl, halogen, or —CN. In yet another embodiment, $R_2$ is independently at each occurrence $(C_1-C_3)$alkyl, halogen, or —CN. In another embodiment, $R_2$ is independently at each occurrence $(C_1-C_3)$alkyl or $(C_1-C_3)$haloalkyl. In yet another embodiment, $R_2$ is independently at each occurrence $(C_1-C_3)$alkyl or —CN. In another embodiment, $R_2$ is independently at each occurrence $(C_1-C_3)$alkyl. In yet another embodiment, $R_2$ is independently at each occurrence methyl, ethyl, n-propyl, or isopropyl.

In some embodiments of the formulae above, two $R_2$ together with the carbon atoms to which they are attached form a $(C_3-C_7)$cycloalkyl or a 4- to 7-membered heterocycloalkyl ring comprising 1-3 heteroatoms selected from O, N, and S; or two $R_2$ together when on adjacent carbon atoms form a phenyl or a 5- or 6-membered heteroaryl ring comprising 1-3 heteroatoms selected from O, N, and S. In another embodiment, two $R_2$ together with the carbon atoms to which they are attached form a $(C_3-C_7)$cycloalkyl or a 4- to 7-membered heterocycloalkyl ring comprising 1-3 heteroatoms selected from O, N, and S. In yet another embodiment, two $R_2$ together with the carbon atoms to which they are attached form a $(C_3-C_7)$cycloalkyl or a 5- to 7-membered heterocycloalkyl ring comprising 1-3 heteroatoms selected from O, N, and S. In another embodiment, two $R_2$ together with the carbon atoms to which they are attached form a $(C_3-C_7)$cycloalkyl or a 5- or 6-membered heterocycloalkyl ring comprising 1-3 heteroatoms selected from O, N, and S. In yet another embodiment, two $R_2$ together with the carbon atoms to which they are attached form a $(C_4-C_7)$cycloalkyl or a 5- or 6-membered heterocycloalkyl ring comprising 1-3 heteroatoms selected from O, N, and S. In another embodiment, two $R_2$ together with the carbon atoms to which they are attached form a $(C_5-C_7)$cycloalkyl or a 5- or 6-membered heterocycloalkyl ring comprising 1-3 heteroatoms selected from O, N, and S.

In another embodiment, two $R_2$ together with the carbon atoms to which they are attached form a $(C_3-C_7)$cycloalkyl. In another embodiment, two $R_2$ together with the carbon atoms to which they are attached form a $(C_4-C_7)$cycloalkyl. In yet another embodiment, two $R_2$ together with the carbon atoms to which they are attached form a $(C_5-C_7)$cycloalkyl. In another embodiment, two $R_2$ together with the carbon atoms to which they are attached form a 4- to 7-membered heterocycloalkyl ring comprising 1-3 heteroatoms selected from O, N, and S. In another embodiment, two $R_2$ together with the carbon atoms to which they are attached form a 5- to 7-membered heterocycloalkyl ring comprising 1-3 heteroatoms selected from O, N, and S. In another embodiment, two $R_2$ together with the carbon atoms to which they are attached form a 5- or 6-membered heterocycloalkyl ring comprising 1-3 heteroatoms selected from O, N, and S.

In another embodiment, two $R_2$ together when on adjacent carbon atoms form a phenyl or a 5- or 6-membered heteroaryl ring comprising 1-3 heteroatoms selected from O, N, and S. In another embodiment, two $R_2$ together when on adjacent carbon atoms form a phenyl or a 5-membered heteroaryl ring comprising 1-3 heteroatoms selected from O, N, and S. In yet another embodiment, two $R_2$ together when on adjacent carbon atoms form a phenyl or a 6-membered heteroaryl ring comprising 1-3 heteroatoms selected from O, N, and S. In another embodiment, two $R_2$ together when on adjacent carbon atoms form a phenyl. In yet another embodiment, two $R_2$ together when on adjacent carbon atoms form a 5- or 6-membered heteroaryl ring comprising 1-3 heteroatoms selected from O, N, and S. In another embodiment, two $R_2$ together when on adjacent carbon atoms form a 5-membered heteroaryl ring comprising 1-3 heteroatoms selected from O, N, and S. In yet another embodiment, two $R_2$ together when on adjacent carbon atoms form a 6-membered heteroaryl ring comprising 1-3 heteroatoms selected from O, N, and S.

In another embodiment, two $R_2$ together with the carbon atoms to which they are attached form a $(C_3-C_7)$cycloalkyl, or two $R_2$ together when on adjacent carbon atoms a phenyl or a 5- or 6-membered heteroaryl ring comprising 1-3 heteroatoms selected from O, N, and S. In yet another embodiment, two $R_2$ together with the carbon atoms to which they are attached form a 4- to 7-membered heterocycloalkyl ring comprising 1-3 heteroatoms selected from O, N, and S, or two $R_2$ together when on adjacent carbon atoms a phenyl or a 5- or 6-membered heteroaryl ring comprising 1-3 heteroatoms selected from O, N, and S. In another embodiment, two $R_2$ together with the carbon atoms to which they are attached form a $(C_3-C_7)$cycloalkyl or a 4- to 7-membered heterocycloalkyl ring comprising 1-3 heteroatoms selected from O, N, and S, or two $R_2$ together when on adjacent carbon atoms a phenyl. In yet another embodiment, two $R_2$ together with the carbon atoms to which they are attached form a $(C_3-C_7)$cycloalkyl or a 4- to 7-membered heterocycloalkyl ring comprising 1-3 heteroatoms selected from O, N, and S, or two $R_2$ together when on adjacent carbon atoms a 5- or 6-membered heteroaryl ring comprising 1-3 heteroatoms selected from O, N, and S.

In another embodiment, two $R_2$ together with the carbon atoms to which they are attached form a $(C_3-C_7)$cycloalkyl or two $R_2$ together when on adjacent carbon atoms form a phenyl. In another embodiment, two $R_2$ together with the carbon atoms to which they are attached form a $(C_4-C_7)$cycloalkyl or two $R_2$ together when on adjacent carbon atoms form a phenyl. In another embodiment, two $R_2$ together with the carbon atoms to which they are attached form a $(C_5-C_7)$cycloalkyl or two $R_2$ together when on adjacent carbon atoms form a phenyl.

In another embodiment, two $R_2$ together with the carbon atoms to which they are attached form a 4- to 7-membered heterocycloalkyl ring comprising 1-3 heteroatoms selected from O, N, and S or two $R_2$ together when on adjacent carbon atoms form a 5- or 6-membered heteroaryl ring comprising 1-3 heteroatoms selected from O, N, and S. In yet another embodiment, two $R_2$ together with the carbon atoms to which they are attached form a 5- to 7-membered heterocycloalkyl ring comprising 1-3 heteroatoms selected from O, N, and S or two $R_2$ together when on adjacent carbon atoms form a 5- or 6-membered heteroaryl ring comprising 1-3 heteroatoms selected from O, N, and S. In another embodiment, two $R_2$ together with the carbon atoms to which they are attached form a 5- or 6-membered heterocycloalkyl ring comprising 1-3 heteroatoms selected from O, N, and S or two $R_2$ together when on adjacent carbon atoms form a 5- or 6-membered heteroaryl ring comprising 1-3 heteroatoms selected from O, N, and S.

In some embodiments of the formulae above, $R_2$ and $R_6$ together with the carbon and nitrogen atoms to which they are attached form a 4- to 6-membered heterocycloalkyl ring optionally comprising 1-2 additional heteroatoms selected from O, N, and S, and optionally substituted with one to three substituents each independently selected from $(C_1-C_6)$alkyl, $(C_1-C_6)$haloalkyl, and halogen. In another embodiment, $R_2$ and $R_6$ together with the carbon and nitrogen atoms to which they are attached form a 4- or 5-membered heterocycloalkyl ring optionally comprising 1-2 additional heteroatoms selected from O, N, and S, and optionally substituted with one to three substituents each independently selected from $(C_1-C_6)$alkyl, $(C_1-C_6)$haloalkyl, and halogen. In another embodiment, $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to three substituents each independently selected from $(C_1-C_6)$alkyl, $(C_1-C_6)$haloalkyl, and halogen.

In another embodiment, $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, and halogen. In another embodiment, $R_2$ and $R_6$ together with the carbon and nitrogen atoms to which they are attached form a 5- or 6-membered heterocycloalkyl ring optionally comprising 1-2 additional heteroatoms selected from O, N, and S, substituted with one to four substituents each independently selected from $(C_1-C_6)$alkyl, $(C_1-C_6)$haloalkyl, and halogen. In another embodiment, $R_2$ and $R_6$ together with the carbon and nitrogen atoms to which they are attached form a 4- to 6-membered heterocycloalkyl ring optionally comprising 1-2 additional heteroatoms selected from O, N, and S. In another embodiment, $R_2$ and $R_6$ together with the carbon and nitrogen atoms to which they are attached form a 4- or 5-membered heterocycloalkyl ring optionally comprising 1-2 additional heteroatoms selected from O, N, and S. In another embodiment, $R_2$ and $R_6$ together with the carbon and nitrogen atoms to which they are attached form a 5- or 6-membered heterocycloalkyl ring optionally comprising 1-2 additional heteroatoms selected from O, N, and S.

In some embodiments of the formulae above, each $R_3$ is $(C_1-C_6)$alkyl, $(C_1-C_3)$alkoxy, $(C_1-C_3)$haloalkyl, $(C_1-C_3)$haloalkoxy, halogen, —OH, or —NH$_2$. In another embodiment, $R_3$ is $(C_1-C_6)$alkyl, $(C_1-C_3)$alkoxy, $(C_1-C_3)$haloalkyl, $(C_1-C_3)$haloalkoxy, or halogen. In another embodiment, $R_3$ is $(C_1-C_6)$alkyl, $(C_1-C_3)$alkoxy, $(C_1-C_3)$haloalkyl, or $(C_1-C_3)$haloalkoxy. In another embodiment, $R_3$ is $(C_1-C_6)$alkyl, $(C_1-C_3)$haloalkyl, or halogen. In another embodiment, $R_3$ is halogen, —OH, or —NH$_2$. In another embodiment, $R_3$ is $(C_1-C_6)$alkyl, $(C_1-C_3)$haloalkyl, halogen, —OH, or —NH$_2$. In another embodiment, $R_3$ is $(C_1-C_6)$alkyl, $(C_1-C_3)$haloalkyl, halogen, or —OH. In another embodiment, $R_3$ is $(C_1-C_6)$alkyl or $(C_1-C_3)$haloalkyl. In another embodiment, $R_3$ is $(C_1-C_6)$alkyl.

In some embodiments of the formulae above, $R_4$ is —OR$_5$. In another embodiment, $R_4$ is —NR$_6$R$_{6'}$.

In some embodiments of the formulae above, $R_5$ is H, $(C_1-C_3)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S. In another embodiment, $R_5$ is $(C_1-C_3)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S.

In another embodiment, $R_5$ is H, $(C_1-C_3)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is substituted with one to three substituents independently selected from $(C_6-C_{10})$aryl and 5- or 6-membered heteroaryl comprising 1-3 heteroatoms selected from O, N, and S. In yet another embodiment, $R_5$ is $(C_1-C_3)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is substituted with one to three substituents independently selected from $(C_6-C_{10})$aryl and 5- or 6-membered heteroaryl comprising 1-3 heteroatoms selected from O, N, and S.

In another embodiment, $R_5$ is H, $(C_1-C_3)$alkyl, or $(C_1-C_3)$haloalkyl, wherein the alkyl is optionally substituted with one to three substituents independently selected from $(C_6-C_{10})$aryl and 5- or 6-membered heteroaryl comprising 1-3 heteroatoms selected from O, N, and S. In yet another embodiment, $R_5$ is $(C_1-C_6)$alkyl, or $(C_1-C_3)$haloalkyl, wherein the alkyl is optionally substituted with one to three substituents independently selected from $(C_6-C_{10})$aryl and 5- or 6-membered heteroaryl comprising 1-3 heteroatoms selected from O, N, and S. In another embodiment, $R_5$ is $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S.

In another embodiment, $R_5$ is H, $(C_1-C_3)$alkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S. In yet another embodiment, $R_5$ is H, $(C_1-C_3)$alkyl, $(C_3-C_7)$cycloalkyl, or 5- or 6-membered heterocycloalkyl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S.

In another embodiment, $R_5$ is H, $(C_1-C_3)$alkyl, $(C_6-C_{10})$aryl, or 5- or 6-membered heteroaryl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S. In yet another embodiment, $R_5$ is H, $(C_1-C_3)$alkyl, $(C_3-C_7)$cycloalkyl, or $(C_6-C_{10})$aryl, wherein the alkyl is optionally substituted with one to three substituents independently selected from $(C_6-C_{10})$aryl and 5- or 6-membered heteroaryl comprising 1-3 heteroatoms selected from O, N, and S.

In another embodiment, $R_5$ is H, $(C_1-C_3)$alkyl, $(C_3-C_7)$cycloalkyl, or $(C_6-C_{10})$aryl, wherein the alkyl is optionally substituted with one to three substituents independently selected from $(C_6-C_{10})$aryl. In yet another embodiment, $R_5$ is H, $(C_1-C_3)$alkyl, 5- or 6-membered heterocycloalkyl comprising 1-3 heteroatoms selected from O, N, and S, or 5- or 6-membered heteroaryl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S. In another embodiment, $R_5$ is H, $(C_1-C_3)$alkyl, $(C_3-C_7)$cycloalkyl, or $(C_6-C_{10})$aryl, wherein the alkyl is optionally substituted with one to three $(C_6-C_{10})$aryl.

In some embodiments of the formulae above, $R_6$ is H, $(C_1-C_6)$alkyl, $(C_1-C_6)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$. In another embodiment, $R_6$ is H, $(C_1-C_6)$alkyl, $(C_1-C_3)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$. In yet another embodiment, $R_6$ is $(C_1-C_6)$alkyl, $(C_1-C_3)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$. In another embodiment, $R_6$ is H, $(C_1-C_6)$alkyl, $(C_1-C_3)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is substituted with one to three $R_7$ and wherein the cycloalkyl, heterocycloalkyl, aryl, and heteroaryl are optionally substituted with one to four $R_{12}$.

In another embodiment, $R_6$ is H, $(C_1-C_6)$alkyl, $(C_1-C_6)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$. In another embodiment, $R_6$ is H, $(C_1-C_6)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$. In yet another embodiment, $R_6$ is $(C_1-C_6)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$. In another embodiment, $R_6$ is H, $(C_1-C_6)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is substituted with one to three $R_7$.

In another embodiment, $R_6$ is $(C_1-C_6)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is substituted with one to three $R_7$ and wherein the cycloalkyl, heterocycloalkyl, aryl, and heteroaryl are optionally substituted with one to four $R_{12}$. In yet another embodiment, $R_6$ is H, $(C_1-C_6)$alkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$. In another embodiment, $R_6$ is H, $(C_1-C_6)$alkyl, $(C_3-C_7)$cycloalkyl, or 5- or 6-membered heterocycloalkyl comprising 1-3 heteroatoms selected from O, N, and S, wherein the alkyl is optionally substituted with one to three $R_7$ and wherein the cycloalkyl and heterocycloalkyl are optionally substituted with one to four $R_{12}$. In yet another embodiment, $R_6$ is H, $(C_1-C_6)$alkyl, $(C_6-C_{10})$aryl, or 5- or 6-membered heteroaryl comprising 1-3 heteroatoms selected from O, N, and S, wherein the alkyl is optionally substituted with one to three $R_7$ and wherein the aryl and heteroaryl are optionally substituted with one to four $R_{12}$.

In another embodiment, $R_6$ is $(C_1-C_6)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is substituted with one to three $R_7$. In yet another embodiment, $R_6$ is H, $(C_1-C_6)$alkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$. In another embodiment, $R_6$ is H, $(C_1-C_6)$alkyl, $(C_3-C_7)$cycloalkyl, or 5- or 6-membered heterocycloalkyl comprising 1-3 heteroatoms selected from O, N, and S, wherein the alkyl is optionally substituted with one to three $R_7$. In yet another embodiment, $R_6$ is H, $(C_1-C_6)$alkyl, $(C_6-C_{10})$aryl, or 5- or 6-membered heteroaryl comprising 1-3 heteroatoms selected from O, N, and S, wherein the alkyl is optionally substituted with one to three $R_7$.

In another embodiment, $R_6$ is H, $(C_1-C_6)$alkyl, $(C_2-C_6)$hydroxyalkyl, 5- or 6-membered heterocycloalkyl comprising 1-3 heteroatoms selected from O, N, and S, or 5- or 6-membered heteroaryl comprising 1-3 heteroatoms selected from O, N, and S, wherein the alkyl is optionally substituted with one to three $R_7$ and wherein the heterocycloalkyl and heteroaryl are optionally substituted with one to four $R_{12}$. In yet another embodiment, $R_6$ is H, $(C_1-C_6)$alkyl, $(C_1-C_3)$haloalkyl, $(C_2-C_6)$hydroxyalkyl, $(C_3-C_7)$cycloalkyl, or $(C_6-C_{10})$aryl, wherein the alkyl is optionally substituted with one to three $R_7$ and wherein the cycloalkyl and aryl are optionally substituted with one to four $R_{12}$. In another embodiment, $R_6$ is H, $(C_1-C_6)$alkyl, $(C_3-C_7)$cycloalkyl, or $(C_6-C_{10})$aryl, wherein the alkyl is optionally substituted with one to three $R_7$ and wherein the cycloalkyl and aryl are optionally substituted with one to four $R_{12}$.

In another embodiment, $R_6$ is H, $(C_1-C_6)$alkyl, 5- or 6-membered heterocycloalkyl comprising 1-3 heteroatoms selected from O, N, and S, or 5- or 6-membered heteroaryl comprising 1-3 heteroatoms selected from O, N, and S, wherein the alkyl is optionally substituted with one to three $R_7$. In yet another embodiment, $R_6$ is H, $(C_1-C_6)$alkyl, $(C_1-C_3)$haloalkyl, $(C_3-C_7)$cycloalkyl, or $(C_6-C_{10})$aryl, wherein the alkyl is optionally substituted with one to three $R_7$. In another embodiment, $R_6$ is H, $(C_1-C_6)$alkyl, $(C_3-C_7)$cycloalkyl, or $(C_6-C_{10})$aryl, wherein the alkyl is optionally substituted with one to three $R_7$.

In some embodiments of the formulae above, $R_{6'}$ is H, $(C_1-C_6)$alkyl, $(C_1-C_6)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$. In another embodiment, $R_{6'}$ is H, $(C_1-C_6)$alkyl, $(C_1-C_3)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$. In yet another embodiment, $R_{6'}$ is $(C_1-C_6)$alkyl, $(C_1-C_3)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$. In another embodiment, $R_{6'}$ is H, $(C_1-C_6)$alkyl, $(C_1-C_3)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is substituted with one to three $R_7$ and wherein the cycloalkyl, heterocycloalkyl, aryl, and heteroaryl are optionally substituted with one to four $R_{12}$.

In another embodiment, $R_{6'}$ is H, $(C_1-C_6)$alkyl, $(C_1-C_6)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$. In another embodiment, $R_{6'}$ is H, $(C_1-C_6)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$. In yet another embodiment, $R_{6'}$ is $(C_1-C_6)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$. In another embodiment, $R_{6'}$ is H, $(C_1-C_6)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is substituted with one to three $R_7$.

In another embodiment, $R_{6'}$ is $(C_1-C_6)$alkyl, $(C_1-C_3)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is substituted with one to three $R_7$ and wherein the cycloalkyl, heterocycloalkyl, aryl, and heteroaryl are optionally substituted with one to four $R_{12}$. In yet another embodiment, $R_{6'}$ is H, $(C_1-C_6)$alkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$. In another embodiment, $R_{6'}$ is H, $(C_1-C_6)$alkyl, $(C_2-C_6)$hydroxyalkyl, $(C_3-C_7)$cycloalkyl, or 5- or 6-membered heterocycloalkyl comprising 1-3 heteroatoms selected from O, N, and S, wherein the alkyl is optionally substituted with one to three $R_7$ and wherein the cycloalkyl and heterocycloalkyl are optionally substituted with one to four $R_{12}$. In yet another embodiment, $R_{6'}$ is H, $(C_1-C_6)$alkyl, $(C_2-C_6)$hydroxyalkyl, $(C_6-C_{10})$aryl, or 5- or 6-membered heteroaryl comprising 1-3 heteroatoms selected from O, N, and S, wherein the alkyl is optionally substituted with one to three $R_7$ and wherein the aryl and heteroaryl are optionally substituted with one to four $R_{12}$.

In another embodiment, $R_{6'}$ is $(C_1-C_6)$alkyl, $(C_1-C_3)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is substituted with one to three $R_7$. In yet another embodiment, $R_{6'}$ is H, $(C_1-C_6)$alkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$. In another embodiment, $R_6$ is H, $(C_1-C_6)$alkyl, $(C_3-C_7)$cycloalkyl, or 5- or 6-membered heterocycloalkyl comprising 1-3 heteroatoms selected from O, N, and S, wherein the alkyl is optionally substituted with one to three $R_7$. In yet another embodiment, $R_{6'}$ is H, $(C_1-C_6)$alkyl, $(C_6-C_{10})$aryl, or 5- or 6-membered heteroaryl comprising 1-3 heteroatoms selected from O, N, and S, wherein the alkyl is optionally substituted with one to three $R_7$.

In another embodiment, $R_{6'}$ is H, $(C_1-C_6)$alkyl, $(C_2-C_6)$hydroxyalkyl, 5- or 6-membered heterocycloalkyl comprising 1-3 heteroatoms selected from O, N, and S, or 5- or 6-membered heteroaryl comprising 1-3 heteroatoms selected from O, N, and S, wherein the alkyl is optionally substituted with one to three $R_7$ and wherein the heterocycloalkyl and heteroaryl are optionally substituted with one to four $R_{12}$. In yet another embodiment, $R_6$ is H, $(C_1-C_6)$alkyl, $(C_1-C_3)$haloalkyl, $(C_2-C_6)$hydroxyalkyl, $(C_3-C_7)$cycloalkyl, or $(C_6-C_{10})$aryl, wherein the alkyl is optionally substituted with one to three $R_7$ and wherein the cycloalkyl and aryl are optionally substituted with one to four $R_{12}$. In another embodiment, $R_{6'}$ is H, $(C_1-C_6)$alkyl, $(C_3-C_7)$cycloalkyl, or $(C_6-C_{10})$aryl, wherein the alkyl is optionally substituted with one to three $R_7$ and wherein the cycloalkyl and aryl are optionally substituted with one to four $R_{12}$. In yet another embodiment, $R_{6'}$ is H or $(C_1-C_6)$alkyl, wherein the alkyl is optionally substituted with one to three $R_7$. In another embodiment, $R_{6'}$ is H or $(C_1-C_6)$alkyl, wherein the alkyl is substituted with one to three $R_7$. In yet another embodiment, $R_{6'}$ is H or $(C_1-C_6)$alkyl.

In another embodiment, $R_{6'}$ is H, $(C_1-C_6)$alkyl, 5- or 6-membered heterocycloalkyl comprising 1-3 heteroatoms selected from O, N, and S, or 5- or 6-membered heteroaryl comprising 1-3 heteroatoms selected from O, N, and S, wherein the alkyl is optionally substituted with one to three $R_7$. In yet another embodiment, $R_{6'}$ is H, $(C_1-C_6)$alkyl, $(C_1-C_3)$haloalkyl, $(C_3-C_7)$cycloalkyl, or $(C_6-C_{10})$aryl, wherein the alkyl is optionally substituted with one to three $R_{11}$. In another embodiment, $R_{6'}$ is H, $(C_1-C_6)$alkyl, $(C_3-C_7)$cycloalkyl, or $(C_6-C_{10})$aryl, wherein the alkyl is optionally substituted with one to three $R_7$. In yet another embodiment, $R_{6'}$ is H or $(C_1-C_6)$alkyl, wherein the alkyl is optionally substituted with one to three $R_7$. In another embodiment, $R_{6'}$ is H or $(C_1-C_6)$alkyl, wherein the alkyl is substituted with one to three $R_7$. In yet another embodiment, $R_{6'}$ is H or $(C_1-C_6)$alkyl.

In some embodiments of the formulae above, $R_6$ and $R_{6'}$ together with the nitrogen atom to which they are attached form a 4- to 8-membered heterocycloalkyl ring optionally comprising 1-2 additional heteroatoms selected from O, N, and S, and optionally substituted with one to four $R_8$. In another embodiment, $R_6$ and $R_{6'}$ together with the nitrogen atom to which they are attached form a 5- to 8-membered heterocycloalkyl ring optionally comprising 1-2 additional heteroatoms selected from O, N, and S, and optionally substituted with one to four $R_8$. $R_6$ and $R_{6'}$ together with the nitrogen atom to which they are attached form a 6- to 8-membered heterocycloalkyl ring optionally comprising 1-2 additional heteroatoms selected from O, N, and S, and optionally substituted with one to four $R_8$. $R_6$ and $R_{6'}$ together with the nitrogen atom to which they are attached form a 7- or 8-membered heterocycloalkyl ring optionally comprising 1-2 additional heteroatoms selected from O, N, and S, and optionally substituted with one to four $R_8$.

In another embodiment, $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$. In another embodiment, $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to three $R_8$. In yet another embodiment, $R_6$ and $R_{6'}$ together with the nitrogen atom to which they are attached form a 5- to 7-membered heterocycloalkyl ring optionally comprising 1-2 additional heteroatoms selected from O, N, and S, and optionally substituted with one to three $R_8$. In another embodiment, $R_6$ and $R_{6'}$ together with the nitrogen atom to which they are attached form a 4- or 5-membered heterocycloalkyl ring optionally comprising 1-2 additional heteroatoms selected from O, N, and S, and optionally substituted with one to three $R_8$. In yet another embodiment, $R_6$ and $R_{6'}$ together with the nitrogen atom to which they are attached form a 5- or 6-membered heterocycloalkyl ring optionally comprising 1-2 additional heteroatoms selected from O, N, and S, and optionally substituted with one to three $R_8$.

In another embodiment, $R_6$ and $R_{6'}$ together with the nitrogen atom to which they are attached form a 6- or 7-membered heterocycloalkyl ring optionally comprising 1-2 additional heteroatoms selected from O, N, and S, and optionally substituted with one to three $R_8$. In yet another embodiment, $R_6$ and $R_{6'}$ together with the nitrogen atom to which they are attached form a 4-membered heterocycloalkyl ring optionally comprising 1-2 additional heteroatoms selected from O, N, and S, and optionally substituted with one to three $R_8$. In another embodiment, $R_6$ and $R_{6'}$ together with the nitrogen atom to which they are attached form a 5-membered heterocycloalkyl ring optionally comprising 1-2 additional heteroatoms selected from O, N, and S, and optionally substituted with one to three $R_8$. In yet another embodiment, $R_6$ and $R_{6'}$ together with the nitrogen atom to which they are attached form a 6-membered heterocycloalkyl ring optionally comprising 1-2 additional heteroatoms selected from O, N, and S, and optionally substituted with one to three $R_8$. In another embodiment, $R_6$ and $R_{6'}$ together with the nitrogen atom to which they are attached form a 7-membered heterocycloalkyl ring optionally comprising 1-2 additional heteroatoms selected from O, N, and S, and optionally substituted with one to three $R_8$.

In some embodiments of the formulae above, $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to three substituents each independently selected from $(C_1-C_6)$alkyl, $(C_1-C_6)$haloalkyl, halogen, —OH, —CN, and —$NH_2$. In another embodiment, $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to three substituents each independently selected from $(C_1-C_6)$alkyl, $(C_1-C_6)$haloalkyl, halogen, —OH, —CN, and —$NH_2$. In yet another embodiment, $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, and halogen. In another embodiment, $R_2$ and $R_6$ together with the carbon and nitrogen atoms to which they are attached form a 5- or 6-membered heterocycloalkyl ring optionally comprising 1-2 additional heteroatoms selected from O, N, and S, substituted with one to four substituents each independently selected from $(C_1-C_6)$alkyl, $(C_1-C_6)$haloalkyl, and halogen. In yet another embodiment, $R_2$ and $R_6$ together with the carbon and nitrogen atoms to which they are attached form a 5- or 6-membered heterocycloalkyl ring optionally comprising 1-2 additional heteroatoms selected from O, N, and S.

In another embodiment, $R_2$ and $R_6$ together with the carbon and nitrogen atoms to which they are attached form a 5-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, and halogen. In yet another embodiment, $R_2$ and $R_6$ together with the carbon and nitrogen atoms to which they are attached form a 5-membered heterocycloalkyl ring optionally comprising 1-2 additional heteroatoms selected from O, N, and S, substituted with one to four substituents each independently selected from $(C_1-C_6)$alkyl, $(C_1-C_6)$haloalkyl, and halogen. In another embodiment, $R_2$ and $R_6$ together with the carbon and nitrogen atoms to which they are attached form a 5-membered heterocycloalkyl ring optionally comprising 1-2 additional heteroatoms selected from O, N, and S.

In another embodiment, $R_2$ and $R_6$ together with the carbon and nitrogen atoms to which they are attached form a 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, and halogen. In yet another embodiment, $R_2$ and $R_6$ together with the carbon and nitrogen atoms to which they are attached form a 6-membered heterocycloalkyl ring optionally comprising 1-2 additional heteroatoms selected from O, N, and S, substituted with one to four substituents each independently selected from $(C_1-C_6)$alkyl, $(C_1-C_6)$haloalkyl, and halogen. In another embodiment, $R_2$ and $R_6$ together with the carbon and nitrogen atoms to which they are attached form a 6-membered heterocycloalkyl ring optionally comprising 1-2 additional heteroatoms selected from O, N, and S.

In some embodiments of the formulae above, each $R_7$ is $(C_3-C_7)$cycloalkyl, 4- to 7-membered heterocycloalkyl ring comprising 1-3 heteroatoms selected from O, N, and S, $(C_6-C_{10})$aryl, or 5- or 6-membered heteroaryl comprising 1-3 heteroatoms selected from O, N, and S, wherein the cycloalkyl, heterocycloalkyl, aryl, and heteroaryl are optionally substituted with one to three $R_9$. In another embodiment, each $R_7$ is $(C_3-C_7)$cycloalkyl or 4- to 7-membered heterocycloalkyl ring comprising 1-3 heteroatoms selected from O, N, and S, wherein the cycloalkyl and heterocycloalkyl are optionally substituted with one to three $R_9$. In yet another embodiment, each $R_7$ is $(C_6-C_{10})$aryl or 5- or 6-membered heteroaryl comprising 1-3 heteroatoms selected from O, N, and S, wherein the aryl and heteroaryl are optionally substituted with one to three $R_9$.

In another embodiment, each $R_7$ is $(C_3-C_7)$cycloalkyl or $(C_6-C_{10})$aryl, wherein the cycloalkyl and aryl are optionally substituted with one to three $R_9$. In yet another embodiment, each $R_7$ is 4- to 7-membered heterocycloalkyl ring comprising 1-3 heteroatoms selected from O, N, and S or 5- or 6-membered heteroaryl comprising 1-3 heteroatoms selected from O, N, and S, wherein the heterocycloalkyl and heteroaryl are optionally substituted with one to three $R_9$. In another embodiment, each $R_7$ is $(C_3-C_7)$cycloalkyl or 5- or 6-membered heteroaryl comprising 1-3 heteroatoms selected from O, N, and S, wherein the cycloalkyl and heteroaryl are optionally substituted with one to three $R_9$. In yet another embodiment, each $R_7$ is 4- to 7-membered heterocycloalkyl ring comprising 1-3 heteroatoms selected from O, N, and S or $(C_6-C_{10})$aryl, wherein the heterocycloalkyl and aryl are optionally substituted with one to three $R_9$.

In another embodiment, each $R_7$ is $(C_3-C_7)$cycloalkyl optionally substituted with one to three $R_9$. In yet another embodiment, each $R_7$ is $(C_3-C_7)$cycloalkyl substituted with one to three $R_9$. In another embodiment, each $R_7$ is $(C_3-C_7)$cycloalkyl. In yet another embodiment, each $R_7$ is $(C_6-C_{10})$aryl optionally substituted with one to three $R_9$. In another embodiment, each $R_7$ is $(C_6-C_{10})$aryl substituted with one to three $R_9$. In yet another embodiment, each $R_7$ is $(C_6-C_{10})$aryl.

In another embodiment, each $R_7$ is 4- to 7-membered heterocycloalkyl ring comprising 1-3 heteroatoms selected from O, N, and S, optionally substituted with one to three $R_9$. In yet another embodiment, each $R_7$ is 4- to 7-membered heterocycloalkyl ring comprising 1-3 heteroatoms selected from O, N, and S, substituted with one to three $R_9$. In another embodiment, each $R_7$ is 4- to 7-membered heterocycloalkyl ring comprising 1-3 heteroatoms selected from O, N, and S. In yet another embodiment, each $R_7$ is 5- or 6-membered heteroaryl comprising 1-3 heteroatoms selected from O, N, and S, optionally substituted with one to three $R_9$. In another embodiment, each $R_7$ is 5- or 6-membered heteroaryl comprising 1-3 heteroatoms selected from O, N, and S, substituted with one to three $R_9$. In yet another embodiment, each $R_7$ is 5- or 6-membered heteroaryl comprising 1-3 heteroatoms selected from O, N, and S.

In some embodiments of the formulae above, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, —CN, —OH, —NR$_{13}$R$_{14}$, —NH$_2$, —O(C$_3$-C$_7$)cycloalkyl, —O-4- to 7-membered heterocycloalkyl ring comprising 1-3 heteroatoms selected from O, N, and S, —O(C$_6$-C$_{10}$)aryl, or —O-5- or 6-membered heteroaryl comprising 1-3 heteroatoms selected from O, N, and S, wherein the alkoxy is optionally substituted with one to three $R_{10}$ and the cycloalkyl, heterocycloalkyl, aryl and heteroaryl are optionally substituted with one to three $R_{11}$. In another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, —CN, —OH, —NR$_{13}$R$_{14}$, and —NH$_2$. In another embodiment, each $R_8$ is independently at each occurrence —NR$_{13}$R$_{14}$, —NH$_2$, —O(C$_3$-C$_7$)cycloalkyl, —O-4- to 7-membered heterocycloalkyl ring comprising 1-3 heteroatoms selected from O, N, and S, —O(C$_6$-C$_{10}$)aryl, or —O-5- or 6-membered heteroaryl comprising 1-3 heteroatoms selected from O, N, and S. In another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, —CN, —OH, —NR$_{13}$R$_{14}$, —O(C$_3$-C$_7$)cycloalkyl, —O-4- to 7-membered heterocycloalkyl ring comprising 1-3 heteroatoms selected from O, N, and S, —O(C$_6$-C$_{10}$)aryl, or —O-5- or 6-membered heteroaryl comprising 1-3 heteroatoms selected from O, N, and S, wherein the alkoxy is optionally substituted with one or two $R_{10}$ and the cycloalkyl, heterocycloalkyl, aryl and heteroaryl are optionally substituted with one to three $R_1$.

In another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, —CN, —OH, or —NH$_2$, wherein the alkoxy is optionally substituted with one to three substituents independently selected from $(C_3-C_7)$cycloalkyl, 4- to 7-membered heterocycloalkyl ring comprising 1-3 heteroatoms selected from O, N, and S, $(C_6-C_{10})$aryl, and 5- or 6-membered heteroaryl comprising 1-3 heteroatoms selected from O, N, and S. In another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, —CN, or —OH, wherein the alkoxy is optionally substituted with one to three substituents independently selected from $(C_3-C_7)$cycloalkyl, 4- to 7-membered heterocycloalkyl ring comprising 1-3 heteroatoms selected from O, N, and S, $(C_6-C_{10})$aryl, and 5- or 6-membered heteroaryl comprising 1-3 heteroatoms selected from O, N, and S. In yet another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, halogen, —CN, or —OH, wherein the alkoxy is optionally substituted with $(C_3-C_7)$cycloalkyl, 4- to 7-membered heterocycloalkyl ring comprising 1-3 heteroatoms selected from O, N, and S, and $(C_6-C_{10})$aryl.

In another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, halogen, —CN, or —OH, wherein the alkoxy is optionally substituted with one to three substituents independently selected from $(C_3-C_7)$cycloalkyl, $(C_6-C_{10})$aryl, and 5- or 6-membered heteroaryl comprising 1-3 heteroatoms selected from O, N, and S. In another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, halogen, —CN, or —OH, wherein the alkoxy is optionally substituted with one to three substituents independently selected from 4- to 7-membered heterocycloalkyl ring comprising 1-3 heteroatoms selected from O, N, and S, $(C_6-C_{10})$aryl, and 5- or 6-membered heteroaryl comprising 1-3 heteroatoms selected from O, N, and S.

In another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, halogen, —CN, or —OH, wherein the alkoxy is optionally substituted with one to three substituents independently selected from $(C_3-C_7)$cycloalkyl and 4- to 7-membered heterocycloalkyl ring comprising 1-3 heteroatoms selected from O, N, and S. In another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, halogen, —CN, or —OH, wherein the alkoxy is optionally substituted with one to three substituents independently selected from $(C_6-C_{10})$aryl and 5- or 6-membered heteroaryl comprising 1-3 heteroatoms selected from O, N, and S.

In another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, halogen, —CN, or —OH, wherein the alkoxy is optionally substituted with one to three substituents independently selected from 4- to 7-membered heterocycloalkyl ring comprising 1-3 heteroatoms selected from O, N, and S and 5- or 6-membered heteroaryl comprising 1-3 heteroatoms selected from O, N, and S. In another embodiment, each $R_8$ is independently at each occurrence halogen, $(C_1-C_4)$alkyl, $(C_1-C_4)$alkoxy, $(C_1-C_4)$haloalkyl, $(C_1-C_4)$haloalkoxy, halogen, —CN, or —OH, wherein the alkoxy is optionally substituted with one to three substituents independently selected from $(C_3-C_7)$cycloalkyl and $(C_6-C_{10})$aryl.

In another embodiment, each $R_8$ is independently at each occurrence $(C_1-C_3)$alkyl, $(C_1-C_3)$haloalkyl, halogen, —CN, —OH, or —NH$_2$. In another embodiment, each $R_8$ is independently at each occurrence $(C_1-C_6)$alkyl, $(C_1-C_6)$haloalkyl, halogen, —CN, —OH, or —NH$_2$. In yet another embodiment, each $R_8$ is independently at each occurrence $(C_1-C_6)$alkyl, $(C_1-C_6)$haloalkyl, or halogen. In another embodiment, each $R_8$ is independently at each occurrence $(C_1-C_6)$alkyl, $(C_1-C_6)$haloalkyl, halogen, or —OH. In yet another embodiment, each $R_8$ is independently at each occurrence $(C_1-C_6)$alkyl, $(C_1-C_6)$haloalkyl, halogen, or —NH$_2$. In another embodiment, each $R_8$ is independently at each occurrence halogen, —CN, —OH, or —NH$_2$. In yet another embodiment, each $R_8$ is independently at each occurrence $(C_1-C_3)$alkyl, $(C_1-C_3)$haloalkyl, or halogen. In another embodiment, each $R_8$ is independently at each occurrence $(C_1-C_6)$alkyl or halogen. In another embodiment, each $R_8$ is independently at each occurrence $(C_1-C_6)$alkyl, halogen, or —CN. In yet another embodiment, each $R_8$ is independently at each occurrence halogen or —CN. In yet another embodiment, each $R_8$ is independently at each occurrence halogen.

In some embodiments of the formulae above, two $R_8$ together with the atoms to which they are attached form a $(C_4-C_7)$cycloalkyl or a 4- to 7-membered heterocycloalkyl ring comprising 1-2 heteroatoms selected from O, N, and S optionally substituted with two $R_{15}$. In another embodiment, two $R_8$ together with the atoms to which they are attached form a $(C_4-C_6)$cycloalkyl or a 4- to 7-membered heterocycloalkyl ring comprising 1-2 heteroatoms selected from O, N, and S optionally substituted with two $R_{15}$. In another embodiment, two $R_8$ together with the atoms to which they are attached form a $(C_4-C_5)$cycloalkyl or a 4- to 7-membered heterocycloalkyl ring comprising 1-2 heteroatoms selected from O, N, and S optionally substituted with two $R_{15}$. In another embodiment, two $R_8$ together with the atoms to which they are attached form a $(C_4-C_6)$cycloalkyl or a 5- to 7-membered heterocycloalkyl ring comprising 1-2 heteroatoms selected from O, N, and S optionally substituted with two $R_{15}$. In another embodiment, two $R_8$ together with the atoms to which they are attached form a $(C_4-C_5)$cycloalkyl or a 6- to 7-membered heterocycloalkyl ring comprising 1-2 heteroatoms selected from O, N, and S optionally substituted with two $R_{15}$. In another embodiment, two $R_8$ together with the atoms to which they are attached form a $(C_4-C_5)$cycloalkyl or a 4- to 5-membered heterocycloalkyl ring comprising 1-2 heteroatoms selected from O, N, and S optionally substituted with two $R_{15}$.

In another embodiment, two $R_8$ together with the atoms to which they are attached form a $(C_5-C_7)$cycloalkyl or a 4- to 7-membered heterocycloalkyl ring comprising 1-2 heteroatoms selected from O, N, and S. In another embodiment, two $R_8$ together with the atoms to which they are attached form a $(C_5-C_7)$cycloalkyl or a 5- to 7-membered heterocycloalkyl ring comprising 1-2 heteroatoms selected from O, N, and S. In another embodiment, two $R_8$ together with the atoms to which they are attached form a $(C_5-C_7)$cycloalkyl. In yet another embodiment, two $R_8$ together with the atoms to which they are attached form a $(C_5-C_6)$cycloalkyl. In another embodiment, two $R_8$ together with the atoms to which they are attached form a $(C_6-C_7)$cycloalkyl. In yet another embodiment, two $R_8$ together with the atoms to which they are attached form a $(C_5)$cycloalkyl. In another embodiment, two $R_8$ together with the atoms to which they are attached form a $(C_6)$cycloalkyl. In yet another embodiment, two $R_8$ together with the atoms to which they are attached form a $(C_7)$cycloalkyl.

In another embodiment, two $R_8$ together with the atoms to which they are attached form a $(C_4-C_7)$cycloalkyl optionally substituted with two $R_{15}$. In another embodiment, two $R_8$ together with the atoms to which they are attached form a $(C_5-C_7)$cycloalkyl optionally substituted with two $R_{15}$. In yet another embodiment, two $R_8$ together with the atoms to which they are attached form a $(C_5-C_6)$cycloalkyl optionally substituted with two $R_{15}$. In another embodiment, two $R_8$ together with the atoms to which they are attached form a $(C_6-C_7)$cycloalkyl optionally substituted with two $R_{15}$. In yet another embodiment, two $R_8$ together with the atoms to which they are attached form a $(C_5)$cycloalkyl optionally substituted with two $R_{15}$. In another embodiment, two $R_8$ together with the atoms to which they are attached form a $(C_6)$cycloalkyl optionally substituted with two $R_{15}$. In yet another embodiment, two $R_8$ together with the atoms to which they are attached form a $(C_7)$cycloalkyl optionally substituted with two $R_{15}$.

In another embodiment, two $R_8$ together with the atoms to which they are attached form a 4- to 6-membered heterocycloalkyl ring comprising 1-2 heteroatoms selected from O, N, and S. In yet another embodiment, two $R_8$ together with the atoms to which they are attached form a 4- or 5-membered heterocycloalkyl ring comprising 1-2 heteroatoms selected from O, N, and S. In another embodiment, two $R_8$ together with the atoms to which they are attached form a 5- to 7-membered heterocycloalkyl ring comprising 1-2 heteroatoms selected from O, N, and S. In yet another embodiment, two $R_8$ together with the atoms to which they are attached form a 5- or 6-membered heterocycloalkyl ring comprising 1-2 heteroatoms selected from O, N, and S. In another embodiment, two $R_8$ together with the atoms to which they are attached form a 6- or 7-membered heterocycloalkyl ring comprising 1-2 heteroatoms selected from O, N, and S. In yet another embodiment, two $R_8$ together with the atoms to which they are attached form a 5-membered heterocycloalkyl ring comprising 1-2 heteroatoms selected from O, N, and S. In another embodiment, two $R_8$ together with the atoms to which they are attached form a 6-membered heterocycloalkyl ring comprising 1-2 heteroatoms selected from O, N, and S. In yet another embodiment, two $R_8$ together with the atoms to which they are attached form a 7-membered heterocycloalkyl ring comprising 1-2 heteroatoms selected from O, N, and S.

In another embodiment, two $R_8$ together with the atoms to which they are attached form a 4- to 6-membered heterocycloalkyl ring comprising 1-2 heteroatoms selected from O, N, and S optionally substituted with two $R_{15}$. In yet another embodiment, two $R_8$ together with the atoms to which they are attached form a 4- or 5-membered heterocycloalkyl ring comprising 1-2 heteroatoms selected from O, N, and S optionally substituted with two $R_{15}$. In another embodiment, two $R_8$ together with the atoms to which they are attached form a 5- to 7-membered heterocycloalkyl ring comprising 1-2 heteroatoms selected from O, N, and S optionally substituted with two $R_{15}$. In yet another embodiment, two $R_8$ together with the atoms to which they are attached form a 5- or 6-membered heterocycloalkyl ring comprising 1-2 heteroatoms selected from O, N, and S optionally substituted with two $R_{15}$. In another embodiment, two $R_8$ together with the atoms to which they are attached form a 6- or 7-membered heterocycloalkyl ring comprising 1-2 heteroatoms selected from O, N, and S optionally substituted with two $R_{15}$. In yet another embodiment, two $R_8$ together with the atoms to which they are attached form a 5-membered heterocycloalkyl ring comprising 1-2 heteroatoms selected from O, N, and S optionally substituted with two $R_{15}$. In another embodiment, two $R_8$ together with the atoms to which they are attached form a 6-membered heterocycloalkyl ring comprising 1-2 heteroatoms selected from O, N, and S optionally substituted with two $R_{15}$. In yet another embodiment, two $R_8$ together with the atoms to which they are attached form a 7-membered heterocycloalkyl ring comprising 1-2 heteroatoms selected from O, N, and S optionally substituted with two $R_{15}$.

In another embodiment, two $R_8$ when on the same carbon atom together with the atoms to which they are attached form a $(C_4-C_7)$spirocycloalkyl or a 4- to 7-membered spiroheterocycloalkyl ring comprising 1-2 heteroatoms selected from O, N, and S optionally substituted with two $R_{15}$. In another embodiment, two $R_8$ when on adjacent atoms together with the atoms to which they are attached form a $(C_4-C_7)$cycloalkyl or a 4- to 7-membered heterocycloalkyl ring comprising 1-2 heteroatoms selected from O, N, and S optionally substituted with two $R_{15}$.

In another embodiment, two $R_8$ when on adjacent atoms together with the atoms to which they are attached form a $(C_6-C_{10})$aryl, or 5- or 6-membered heteroaryl comprising 1-3 heteroatoms selected from O, N, and S. In another embodiment, two $R_8$ when on adjacent atoms together with the atoms to which they are attached form a phenyl or 5- or 6-membered heteroaryl comprising 1-3 heteroatoms selected from O, N, and S. In another embodiment, two $R_8$ when on adjacent atoms together with the atoms to which they are attached form a $(C_6\text{-}C_{10})$aryl. In another embodiment, two $R_8$ when on adjacent atoms together with the atoms to which they are attached form a 5- or 6-membered heteroaryl comprising 1-3 heteroatoms selected from O, N, and S. In another embodiment, two $R_8$ when on adjacent atoms together with the atoms to which they are attached form a phenyl.

In another embodiment, two $R_8$ together with the same atom to which they are attached form a =(O).

In some embodiments of the formulae above, each $R_9$ is independently at each occurrence $(C_1\text{-}C_6)$alkyl, $(C_1\text{-}C_6)$haloalkyl, $(C_1\text{-}C_6)$alkoxy, $(C_1\text{-}C_6)$haloalkoxy, halogen, $(C_3\text{-}C_6)$cycloalkyl, —OH, —CN, —NH$_2$, or —NR$_{13}$R$_{14}$. In another embodiment, $R_9$ is independently at each occurrence $(C_1\text{-}C_6)$alkyl, $(C_1\text{-}C_6)$haloalkyl, halogen, $(C_3\text{-}C_6)$cycloalkyl, —OH, —CN, or NR$_{13}$R$_{14}$. In another embodiment, each $R_9$ is independently at each occurrence $(C_1\text{-}C_6)$alkyl, $(C_1\text{-}C_6)$haloalkyl, $(C_1\text{-}C_6)$alkoxy, $(C_1\text{-}C_6)$haloalkoxy, halogen, —OH, —CN, or —NH$_2$. In another embodiment, each $R_9$ is independently at each occurrence $(C_1\text{-}C_6)$alkyl, $(C_1\text{-}C_6)$haloalkyl, halogen, —OH, —CN, or —NH$_2$. In another embodiment, each $R_9$ is independently at each occurrence $(C_1\text{-}C_3)$alkyl, $(C_1\text{-}C_3)$haloalkyl, $(C_1\text{-}C_6)$alkoxy, $(C_1\text{-}C_6)$haloalkoxy, halogen, or —CN. In another embodiment, each $R_9$ is independently at each occurrence $(C_1\text{-}C_3)$alkyl, $(C_1\text{-}C_3)$haloalkyl, $(C_1\text{-}C_6)$alkoxy, halogen, or —CN. In another embodiment, each $R_9$ is independently at each occurrence $(C_1\text{-}C_3)$alkyl, $(C_1\text{-}C_3)$haloalkyl, halogen, or —CN. In yet another embodiment, each $R_9$ is independently at each occurrence halogen, —OH, —CN, or —NH$_2$. In another embodiment, each $R_9$ is independently at each occurrence $(C_1\text{-}C_3)$alkyl, $(C_1\text{-}C_3)$haloalkyl, $(C_1\text{-}C_6)$alkoxy, $(C_1\text{-}C_6)$haloalkoxy, or halogen. In another embodiment, each $R_9$ is independently at each occurrence $(C_1\text{-}C_3)$alkyl, $(C_1\text{-}C_3)$haloalkyl, $(C_1\text{-}C_6)$alkoxy, or halogen. In another embodiment, each $R_9$ is independently at each occurrence $(C_1\text{-}C_3)$alkyl, $(C_1\text{-}C_3)$haloalkyl, or halogen. In yet another embodiment, each $R_9$ is independently at each occurrence $(C_1\text{-}C_3)$alkyl, $(C_1\text{-}C_3)$haloalkyl, or —CN. In another embodiment, each $R_9$ is independently at each occurrence $(C_1\text{-}C_3)$alkyl or $(C_1\text{-}C_3)$haloalkyl. In yet another embodiment, each $R_9$ is independently at each occurrence halogen or —CN. In another embodiment, each $R_9$ is independently at each occurrence $(C_1\text{-}C_3)$alkyl or halogen. In yet another embodiment, each $R_9$ is independently at each occurrence $(C_1\text{-}C_3)$haloalkyl.

In some embodiments of the formulae above, two $R_9$ together with the atoms to which they are attached form a $(C_4\text{-}C_7)$cycloalkyl or a 5- to 7-membered heterocycloalkyl ring comprising 1-2 heteroatoms selected from O, N, and S optionally substituted with one to three substituents each independently selected from $(C_1\text{-}C_6)$alkyl, $(C_1\text{-}C_6)$haloalkyl, halogen, —OH, —CN, and —NH$_2$. In another embodiment, two $R_9$ together with the atoms to which they are attached form a $(C_5\text{-}C_7)$cycloalkyl or a 5- to 7-membered heterocycloalkyl ring comprising 1-2 heteroatoms selected from O, N, and S optionally substituted with one to three substituents each independently selected from $(C_1\text{-}C_6)$alkyl, $(C_1\text{-}C_6)$haloalkyl, halogen, —OH, —CN, and —NH$_2$. In another embodiment, two $R_9$ together with the atoms to which they are attached form a $(C_5\text{-}C_7)$cycloalkyl or a 5- to 7-membered heterocycloalkyl ring comprising 1-2 heteroatoms selected from O, N, and S optionally substituted with one to three substituents each independently selected from $(C_1\text{-}C_6)$alkyl, $(C_1\text{-}C_6)$haloalkyl, halogen, and —CN. In another embodiment, two $R_9$ together with the atoms to which they are attached form a $(C_5\text{-}C_7)$cycloalkyl or a 5- to 7-membered heterocycloalkyl ring comprising 1-2 heteroatoms selected from O, N, and S optionally substituted with one to three halogen. In yet another embodiment, two $R_9$ together with the atoms to which they are attached form a $(C_5\text{-}C_7)$cycloalkyl or a 5- to 7-membered heterocycloalkyl ring comprising 1-2 heteroatoms selected from O, N, and S. In another embodiment, two $R_9$ together with the atoms to which they are attached form a $(C_4\text{-}C_7)$cycloalkyl. In another embodiment, two $R_9$ together with the atoms to which they are attached form a $(C_5\text{-}C_7)$cycloalkyl. In another embodiment, two $R_9$ together with the atoms to which they are attached form a $(C_5\text{-}C_6)$cycloalkyl. In yet another embodiment, two $R_9$ together with the atoms to which they are attached form a $(C_6\text{-}C_7)$cycloalkyl. In another embodiment, two $R_9$ together with the atoms to which they are attached form a $(C_4)$cycloalkyl. In another embodiment, two $R_9$ together with the atoms to which they are attached form a $(C_5)$cycloalkyl. In yet another embodiment, two $R_9$ together with the atoms to which they are attached form a $(C_6)$cycloalkyl. In another embodiment, two $R_9$ together with the atoms to which they are attached form a $(C_7)$cycloalkyl.

In another embodiment, two $R_9$ together with the atoms to which they are attached form a 5- to 7-membered heterocycloalkyl ring comprising 1-2 heteroatoms selected from O, N, and S. In another embodiment, two $R_9$ together with the atoms to which they are attached form a 5- or 6-membered heterocycloalkyl ring comprising 1-2 heteroatoms selected from O, N, and S. In another embodiment, two $R_9$ together with the atoms to which they are attached form a 6- or 7-membered heterocycloalkyl ring comprising 1-2 heteroatoms selected from O, N, and S. In another embodiment, two $R_9$ together with the atoms to which they are attached form a 5-membered heterocycloalkyl ring comprising 1-2 heteroatoms selected from O, N, and S. In another embodiment, two $R_9$ together with the atoms to which they are attached form a 6-membered heterocycloalkyl ring comprising 1-2 heteroatoms selected from O, N, and S. In another embodiment, two $R_9$ together with the atoms to which they are attached form a 7-membered heterocycloalkyl ring comprising 1-2 heteroatoms selected from O, N, and S.

In another embodiment, two $R_9$ when on adjacent atoms together with the atoms to which they are attached form a $(C_6\text{-}C_{10})$aryl, or 5- or 6-membered heteroaryl comprising 1-3 heteroatoms selected from O, N, and S. In another embodiment, two $R_9$ when on adjacent atoms together with the atoms to which they are attached form a phenyl or 5- or 6-membered heteroaryl comprising 1-3 heteroatoms selected from O, N, and S. In another embodiment, two $R_9$ when on adjacent atoms together with the atoms to which they are attached form a $(C_6\text{-}C_{10})$aryl or 5-membered heteroaryl comprising 1-3 heteroatoms selected from O, N, and S. In another embodiment, two $R_9$ when on adjacent atoms together with the atoms to which they are attached form a $(C_6\text{-}C_{10})$aryl or 6-membered heteroaryl comprising 1-3 heteroatoms selected from O, N, and S. In another embodiment, two $R_9$ when on adjacent atoms together with the atoms to which they are attached form a phenyl or 5-membered heteroaryl comprising 1-3 heteroatoms selected from O, N, and S.

In another embodiment, two $R_9$ when on adjacent atoms together with the atoms to which they are attached form a phenyl or 6-membered heteroaryl comprising 1-3 heteroatoms selected from O, N, and S. In another embodiment, two $R_9$ when on adjacent atoms together with the atoms to which they are attached form a phenyl. In another embodiment, two $R_9$ when on adjacent atoms together with the atoms to which they are attached form a 5- or 6-membered heteroaryl comprising 1-3 heteroatoms selected from O, N, and S. In another embodiment, two $R_9$ when on adjacent atoms together with the atoms to which they are attached form a 5-membered heteroaryl comprising 1-3 heteroatoms selected from O, N, and S. In another embodiment, two $R_9$ when on adjacent atoms together with the atoms to which they are attached form a 6-membered heteroaryl comprising 1-3 heteroatoms selected from O, N, and S.

In some embodiments of the formulae above, each $R_{10}$ is $(C_3-C_7)$cycloalkyl, 4- to 7-membered heterocycloalkyl ring comprising 1-3 heteroatoms selected from O, N, and S, $(C_6-C_{10})$aryl, or 5- or 6-membered heteroaryl comprising 1-3 heteroatoms selected from O, N, and S. In another embodiment, each $R_{10}$ is $(C_3-C_7)$cycloalkyl or 4- to 7-membered heterocycloalkyl ring comprising 1-3 heteroatoms selected from O, N, and S. In yet another embodiment, each $R_{10}$ is $(C_6-C_{10})$aryl or 5- or 6-membered heteroaryl comprising 1-3 heteroatoms selected from O, N, and S In another embodiment, each $R_{10}$ is $(C_3-C_7)$cycloalkyl or $(C_6-C_{10})$aryl. In yet another embodiment, each $R_{10}$ is 4- to 7-membered heterocycloalkyl ring comprising 1-3 heteroatoms selected from O, N, and S or 5- or 6-membered heteroaryl comprising 1-3 heteroatoms selected from O, N, and S. In another embodiment, each $R_{10}$ is $(C_3-C_7)$cycloalkyl or 5- or 6-membered heteroaryl comprising 1-3 heteroatoms selected from O, N, and S. In yet another embodiment, each $R_{10}$ is 4- to 7-membered heterocycloalkyl ring comprising 1-3 heteroatoms selected from O, N, and S or $(C_6-C_{10})$aryl. In yet another embodiment, each $R_{10}$ is 4- to 7-membered heterocycloalkyl ring comprising 1-3 heteroatoms selected from O, N, and S. In another embodiment, each $R_{10}$ is 5- or 6-membered heteroaryl comprising 1-3 heteroatoms selected from O, N, and S. In another embodiment, each $R_{10}$ is $(C_3-C_7)$cycloalkyl. In yet another embodiment, each $R_{10}$ is $(C_6-C_{10})$aryl.

In some embodiments of the formulae above, each $R_{11}$ is independently at each occurrence $(C_1-C_6)$alkyl, $(C_1-C_6)$haloalkyl, $(C_1-C_6)$alkoxy, $(C_1-C_6)$haloalkoxy, halogen, —OH, —CN, or —NH$_2$. In another embodiment, each $R_{11}$ is independently at each occurrence $(C_1-C_6)$alkyl, $(C_1-C_6)$haloalkyl, halogen, —OH, —CN, or —NH$_2$. In another embodiment, each $R_{11}$ is independently at each occurrence $(C_1-C_3)$alkyl, $(C_1-C_3)$haloalkyl, $(C_1-C_6)$alkoxy, $(C_1-C_6)$haloalkoxy, halogen, or —CN. In another embodiment, each $R_{11}$ is independently at each occurrence $(C_1-C_3)$alkyl, $(C_1-C_3)$haloalkyl, $(C_1-C_6)$alkoxy, halogen, or —CN. In another embodiment, each $R_{11}$ is independently at each occurrence $(C_1-C_3)$alkyl, $(C_1-C_3)$haloalkyl, halogen, or —CN. In yet another embodiment, each $R_{11}$ is independently at each occurrence halogen, —OH, —CN, or —NH$_2$. In another embodiment, each $R_{11}$ is independently at each occurrence $(C_1-C_3)$alkyl, $(C_1-C_3)$haloalkyl, $(C_1-C_6)$alkoxy, $(C_1-C_6)$haloalkoxy, or halogen. In another embodiment, each $R_{11}$ is independently at each occurrence $(C_1-C_3)$alkyl, $(C_1-C_3)$haloalkyl, $(C_1-C_6)$alkoxy, or halogen. In another embodiment, each $R_{11}$ is independently at each occurrence $(C_1-C_3)$alkyl, $(C_1-C_3)$haloalkyl, or halogen. In yet another embodiment, each $R_{11}$ is independently at each occurrence $(C_1-C_3)$alkyl, $(C_1-C_3)$haloalkyl, or —CN. In another embodiment, each $R_{11}$ is independently at each occurrence $(C_1-C_3)$alkyl or $(C_1-C_3)$haloalkyl. In yet another embodiment, each $R_{11}$ is independently at each occurrence halogen or —CN. In another embodiment, each $R_{11}$ is independently at each occurrence $(C_1-C_3)$alkyl or halogen.

In some embodiments of the formulae above, each $R_{12}$ is independently at each occurrence $(C_1-C_6)$alkyl, $(C_1-C_6)$haloalkyl, $(C_1-C_6)$alkoxy, $(C_1-C_6)$haloalkoxy, halogen, —OH, —CN, or —NH$_2$. In another embodiment, each $R_{12}$ is independently at each occurrence $(C_1-C_6)$alkyl, $(C_1-C_6)$haloalkyl, halogen, —OH, —CN, or —NH$_2$. In another embodiment, each $R_{12}$ is independently at each occurrence $(C_1-C_3)$alkyl, $(C_1-C_3)$haloalkyl, $(C_1-C_6)$alkoxy, $(C_1-C_6)$haloalkoxy, halogen, or —CN. In another embodiment, each $R_{12}$ is independently at each occurrence $(C_1-C_3)$alkyl, $(C_1-C_3)$haloalkyl, $(C_1-C_6)$alkoxy, halogen, or —CN. In another embodiment, each $R_{12}$ is independently at each occurrence $(C_1-C_3)$alkyl, $(C_1-C_3)$haloalkyl, halogen, or —CN. In yet another embodiment, each $R_{12}$ is independently at each occurrence halogen, —OH, —CN, or —NH$_2$. In another embodiment, each $R_{12}$ is independently at each occurrence $(C_1-C_3)$alkyl, $(C_1-C_3)$haloalkyl, $(C_1-C_6)$alkoxy, $(C_1-C_6)$haloalkoxy, or halogen. In another embodiment, each $R_{12}$ is independently at each occurrence $(C_1-C_3)$alkyl, $(C_1-C_3)$haloalkyl, $(C_1-C_6)$alkoxy, or halogen. In another embodiment, each $R_{12}$ is independently at each occurrence $(C_1-C_3)$alkyl, $(C_1-C_3)$haloalkyl, or halogen. In yet another embodiment, each $R_{12}$ is independently at each occurrence $(C_1-C_3)$alkyl, $(C_1-C_3)$haloalkyl, or —CN. In another embodiment, each $R_{12}$ is independently at each occurrence $(C_1-C_3)$alkyl or $(C_1-C_3)$haloalkyl. In yet another embodiment, each $R_{12}$ is independently at each occurrence halogen or —CN. In another embodiment, each $R_{12}$ is independently at each occurrence $(C_1-C_3)$alkyl or halogen.

In some embodiments of the formulae above, two $R_{12}$ together with the atoms to which they are attached form a $(C_4-C_7)$cycloalkyl or a 4- to 7-membered heterocycloalkyl ring comprising 1-2 heteroatoms selected from O, N, and S. In another embodiment, two $R_{12}$ together with the atoms to which they are attached form a $(C_5-C_7)$cycloalkyl or a 4- to 7-membered heterocycloalkyl ring comprising 1-2 heteroatoms selected from O, N, and S. In another embodiment, two $R_{12}$ together with the atoms to which they are attached form a $(C_6-C_7)$cycloalkyl or a 4- to 7-membered heterocycloalkyl ring comprising 1-2 heteroatoms selected from O, N, and S. In another embodiment, two $R_{12}$ together with the atoms to which they are attached form a $(C_4-C_6)$cycloalkyl or a 4- to 7-membered heterocycloalkyl ring comprising 1-2 heteroatoms selected from O, N, and S. In another embodiment, two $R_{12}$ together with the atoms to which they are attached form a $(C_4-C_5)$cycloalkyl or a 4- to 7-membered heterocycloalkyl ring comprising 1-2 heteroatoms selected from O, N, and S.

In some embodiments of the formulae above, two $R_{12}$ together with the atoms to which they are attached form a $(C_4-C_7)$cycloalkyl or a 5- to 7-membered heterocycloalkyl ring comprising 1-2 heteroatoms selected from O, N, and S. In another embodiment, two $R_{12}$ together with the atoms to which they are attached form a $(C_4-C_7)$cycloalkyl or a 6- or 7-membered heterocycloalkyl ring comprising 1-2 heteroatoms selected from O, N, and S. In another embodiment, two $R_{12}$ together with the atoms to which they are attached form a $(C_4-C_7)$cycloalkyl or a 4- to 6-membered heterocycloalkyl ring comprising 1-2 heteroatoms selected from O, N, and S. In another embodiment, two $R_{12}$ together with the atoms to which they are attached form a $(C_4-C_7)$cycloalkyl or a 4- or 5-membered heterocycloalkyl ring comprising 1-2 heteroatoms selected from O, N, and S.

In another embodiment, two $R_{12}$ together with the atoms to which they are attached form a $(C_4-C_7)$cycloalkyl. In another embodiment, two $R_{12}$ together with the atoms to which they are attached form a $(C_5-C_7)$cycloalkyl. In another embodiment, two $R_{12}$ together with the atoms to which they are attached form a $(C_6-C_7)$cycloalkyl. In another embodiment, two $R_{12}$ together with the atoms to which they are attached form a $(C_4-C_6)$cycloalkyl. In another embodiment, two $R_{12}$ together with the atoms to which they are attached form a $(C_4-C_5)$cycloalkyl.

In another embodiment, two $R_{12}$ together with the atoms to which they are attached form a 4- to 7-membered heterocycloalkyl ring comprising 1-2 heteroatoms selected from O, N, and S. In another embodiment, two $R_{12}$ together with the atoms to which they are attached form a 5- to 7-membered heterocycloalkyl ring comprising 1-2 heteroatoms selected from O, N, and S. In another embodiment, two $R_{12}$ together with the atoms to which they are attached form a 6- or 7-membered heterocycloalkyl ring comprising 1-2 heteroatoms selected from O, N, and S. In another embodiment, two $R_{12}$ together with the atoms to which they are attached form a 4- to 6-membered heterocycloalkyl ring comprising 1-2 heteroatoms selected from O, N, and S. In another embodiment, two $R_{12}$ together with the atoms to which they are attached form a 4- or 5-membered heterocycloalkyl ring comprising 1-2 heteroatoms selected from O, N, and S.

In some embodiments of the formulae above, $R_{13}$ is selected from $(C_1-C_6)$alkyl, $(C_1-C_6)$haloalkyl, $(C_3-C_7)$cycloalkyl, 4- to 7-membered heterocycloalkyl ring comprising 1-3 heteroatoms selected from O, N, and S, $(C_6-C_{10})$aryl, and 5- or 6-membered heteroaryl comprising 1-3 heteroatoms selected from O, N, and S. In another embodiment, $R_{13}$ is selected from $(C_1-C_6)$alkyl and $(C_1-C_6)$haloalkyl. In another embodiment, $R_{13}$ is selected from $(C_3-C_7)$cycloalkyl, 4- to 7-membered heterocycloalkyl ring comprising 1-3 heteroatoms selected from O, N, and S, $(C_6-C_{10})$aryl, and 5- or 6-membered heteroaryl comprising 1-3 heteroatoms selected from O, N, and S. In another embodiment, $R_{13}$ is selected from $(C_3-C_7)$cycloalkyl and 4- to 7-membered heterocycloalkyl ring comprising 1-3 heteroatoms selected from O, N, and S. In yet another embodiment, each $R_{13}$ is selected from $(C_6-C_{10})$aryl and 5- or 6-membered heteroaryl comprising 1-3 heteroatoms selected from O, N, and S In another embodiment, $R_{13}$ is selected from $(C_3-C_7)$cycloalkyl and $(C_6-C_{10})$aryl. In yet another embodiment, $R_{13}$ is selected from 4- to 7-membered heterocycloalkyl ring comprising 1-3 heteroatoms selected from O, N, and S and 5- or 6-membered heteroaryl comprising 1-3 heteroatoms selected from O, N, and S. In another embodiment, $R_{13}$ is selected from $(C_3-C_7)$cycloalkyl and 5- or 6-membered heteroaryl comprising 1-3 heteroatoms selected from O, N, and S. In yet another embodiment, $R_{13}$ is selected from 4- to 7-membered heterocycloalkyl ring comprising 1-3 heteroatoms selected from O, N, and S and $(C_6-C_{10})$aryl. In yet another embodiment, $R_{13}$ is 4- to 7-membered heterocycloalkyl ring comprising 1-3 heteroatoms selected from O, N, and S. In another embodiment, $R_{13}$ is 5- or 6-membered heteroaryl comprising 1-3 heteroatoms selected from O, N, and S. In another embodiment, $R_{13}$ is $(C_3-C_7)$cycloalkyl. In yet another embodiment, each $R_{13}$ is $(C_6-C_{10})$aryl.

In some embodiments of the formulae above, $R_{14}$ is selected from $(C_1-C_6)$alkyl, $(C_1-C_6)$haloalkyl, $(C_3-C_7)$cycloalkyl, 4- to 7-membered heterocycloalkyl ring comprising 1-3 heteroatoms selected from O, N, and S, $(C_6-C_{10})$aryl, and 5- or 6-membered heteroaryl comprising 1-3 heteroatoms selected from O, N, and S. In another embodiment, $R_{14}$ is selected from $(C_1-C_6)$alkyl and $(C_1-C_6)$haloalkyl. In another embodiment, $R_{14}$ is selected from $(C_3-C_7)$cycloalkyl, 4- to 7-membered heterocycloalkyl ring comprising 1-3 heteroatoms selected from O, N, and S. In yet another embodiment, $R_{14}$ is selected from $(C_6-C_{10})$aryl and 5- or 6-membered heteroaryl comprising 1-3 heteroatoms selected from O, N, and S.

In another embodiment, $R_{14}$ is selected from $(C_3-C_7)$cycloalkyl and $(C_6-C_{10})$aryl. In yet another embodiment, $R_{14}$ is 4- to 7-membered heterocycloalkyl ring comprising 1-3 heteroatoms selected from O, N, and S and 5- or 6-membered heteroaryl comprising 1-3 heteroatoms selected from O, N, and S. In another embodiment, $R_{14}$ is selected from $(C_3-C_7)$cycloalkyl and 5- or 6-membered heteroaryl comprising 1-3 heteroatoms selected from O, N, and S. In yet another embodiment, $R_{14}$ is selected from 4- to 7-membered heterocycloalkyl ring comprising 1-3 heteroatoms selected from O, N, and S and $(C_6-C_{10})$aryl. In yet another embodiment, $R_{14}$ is 4- to 7-membered heterocycloalkyl ring comprising 1-3 heteroatoms selected from O, N, and S. In another embodiment, $R_{14}$ is 5- or 6-membered heteroaryl comprising 1-3 heteroatoms selected from O, N, and S. In another embodiment, $R_{14}$ is $(C_3-C_7)$cycloalkyl. In yet another embodiment, $R_{14}$ is $(C_6-C_{10})$aryl.

In some embodiments of the formulae above, two $R_{15}$ together with the atoms to which they are attached form a $(C_4-C_7)$cycloalkyl or a 4- to 7-membered heterocycloalkyl ring comprising 1-2 heteroatoms selected from O, N, and S. In another embodiment, two $R_{15}$ together with the atoms to which they are attached form a $(C_5-C_7)$cycloalkyl or a 4- to 7-membered heterocycloalkyl ring comprising 1-2 heteroatoms selected from O, N, and S. In another embodiment, two $R_{15}$ together with the atoms to which they are attached form a $(C_6-C_7)$cycloalkyl or a 4- to 7-membered heterocycloalkyl ring comprising 1-2 heteroatoms selected from O, N, and S. In another embodiment, two $R_{15}$ together with the atoms to which they are attached form a $(C_4-C_6)$cycloalkyl or a 4- to 7-membered heterocycloalkyl ring comprising 1-2 heteroatoms selected from O, N, and S. In another embodiment, two $R_{15}$ together with the atoms to which they are attached form a $(C_4-C_5)$cycloalkyl or a 4- to 7-membered heterocycloalkyl ring comprising 1-2 heteroatoms selected from O, N, and S.

In some embodiments of the formulae above, two $R_{15}$ together with the atoms to which they are attached form a $(C_4-C_7)$cycloalkyl or a 5- to 7-membered heterocycloalkyl ring comprising 1-2 heteroatoms selected from O, N, and S. In another embodiment, two $R_{15}$ together with the atoms to which they are attached form a $(C_4-C_7)$cycloalkyl or a 6- or 7-membered heterocycloalkyl ring comprising 1-2 heteroatoms selected from O, N, and S. In another embodiment, two $R_{15}$ together with the atoms to which they are attached form a $(C_4-C_7)$cycloalkyl or a 4- to 6-membered heterocycloalkyl ring comprising 1-2 heteroatoms selected from O, N, and S. In another embodiment, two $R_{15}$ together with the atoms to which they are attached form a $(C_4-C_7)$cycloalkyl or a 4- or 5-membered heterocycloalkyl ring comprising 1-2 heteroatoms selected from O, N, and S.

In another embodiment, two $R_{15}$ together with the atoms to which they are attached form a $(C_4-C_7)$cycloalkyl. In another embodiment, two $R_{15}$ together with the atoms to which they are attached form a $(C_5-C_7)$cycloalkyl. In another embodiment, two $R_{15}$ together with the atoms to which they are attached form a $(C_6-C_7)$cycloalkyl. In another embodiment, two $R_{15}$ together with the atoms to which they are attached form a $(C_4-C_6)$cycloalkyl. In another embodiment, two $R_{15}$ together with the atoms to which they are attached form a $(C_4\text{-}C_5)$cycloalkyl.

In another embodiment, two $R_{15}$ together with the atoms to which they are attached form a 4- to 7-membered heterocycloalkyl ring comprising 1-2 heteroatoms selected from O, N, and S. In another embodiment, two $R_{15}$ together with the atoms to which they are attached form a 5- to 7-membered heterocycloalkyl ring comprising 1-2 heteroatoms selected from O, N, and S. In another embodiment, two $R_{15}$ together with the atoms to which they are attached form a 6- or 7-membered heterocycloalkyl ring comprising 1-2 heteroatoms selected from O, N, and S. In another embodiment, two $R_{15}$ together with the atoms to which they are attached form a 4- to 6-membered heterocycloalkyl ring comprising 1-2 heteroatoms selected from O, N, and S. In another embodiment, two $R_{15}$ together with the atoms to which they are attached form a 4- or 5-membered heterocycloalkyl ring comprising 1-2 heteroatoms selected from O, N, and S.

In some embodiments of the formulae above, m is 0, 1, or 2. In another embodiment, m is 0 or 1. In yet another embodiment, m is 1 or 2. In another embodiment, m is 0. In yet another embodiment, m is 1. In another embodiment, m is 2.

In some embodiments of the formulae above, m1 is 0, 1, or 2. In another embodiment, m1 is 0 or 1. In yet another embodiment, m1 is 1 or 2. In another embodiment, m1 is 0. In yet another embodiment, m1 is 1. In another embodiment, m1 is 2.

In some embodiments of the formulae above, n1 is 0, 1, or 2. In another embodiment, n1 is 1, 2, or 3. In another embodiment, n1 is 0 or 1. In another embodiment, n1 is 1 or 2. In another embodiment, n1 is 2 or 3. In another embodiment, n1 is 0. In another embodiment, n1 is 1. In another embodiment, n1 is 2. In another embodiment, n1 is 3.

In some embodiments of the formulae above, each s and n is independently 1, 2, or 3, wherein s+n is ≤4. In another embodiment, each s and n is independently 1 or 2, wherein s+n is ≤4. In another embodiment, each s and n is independently 2 or 3, wherein s+n is ≤4. In another embodiment, s is 1 and n is 1. In another embodiment, s is 2 and n is 2. In another embodiment, s is 1 and n is 2. In another embodiment, s is 2 and n is 1. In another embodiment, s is 3 and n is 1. In another embodiment, s is 1 and n is 3.

In some embodiments of the formulae above, $R_1$ is

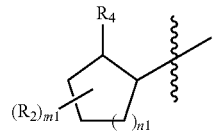

and $R_4$ is —$OR_5$.

In some embodiments of the formulae above, $R_1$ is

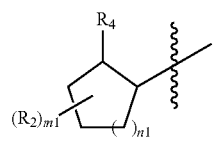

and $R_4$ is —$NR_6R_{6'}$.

In some embodiments of the formulae above, $R_1$ is

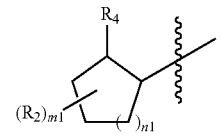

and n1 is 1 or 2.

In some embodiments of the formulae above, $R_1$ is

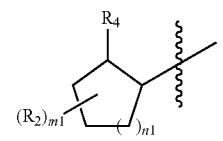

n is 1 or 2, and $R_4$ is —$OR_5$.

In some embodiments of the formulae above, $R_1$ is

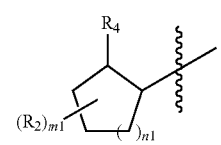

n1 is 1 or 2, and $R_4$ is —$NR_6R_{6'}$.

In some embodiments of the formulae above, n1 is 1 or 2 and $R_4$ is —$OR_5$.

In some embodiments of the formulae above, n1 is 1 or 2 and $R_4$ is —$NR_6R_{6'}$.

In some embodiments of the formulae above, $R_1$ is

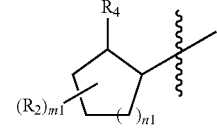

n1 is 1 or 2, and m1 is 0.

In some embodiments of the formulae above, $R_1$ is

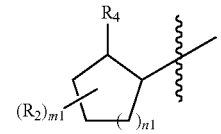

n1 is 1 or 2, m1 is 0, and $R_4$ is —$OR_5$.

In some embodiments of the formulae above, $R_1$ is

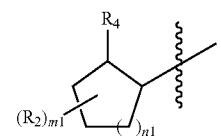

n1 is 1 or 2, m1 is 0, and $R_4$ is —$NR_6R_{6'}$.

In some embodiments of the formulae above, m1 is 0 and $R_4$ is $-NR_6R_{6'}$.

In some embodiments of the formulae above, m1 is 0 and $R_4$ is $-OR_5$.

In some embodiments of the formulae above, $R_1$ is

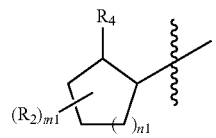

and m1 is 0.

In some embodiments of the formulae above, $R_1$ is

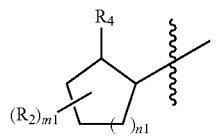

m1 is 0, and $R_4$ is $-OR_5$.

In some embodiments of the formulae above, $R_1$ is

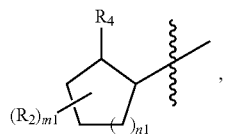

m1 is 0, and $R_4$ is $-NR_6R_{6'}$.

In some embodiments of the formulae above, n1 is 1 or 2 and m1 is 0.

In some embodiments of the formulae above, n1 is 1 or 2, m1 is 0, and $R_4$ is $-OR_5$.

In some embodiments of the formulae above, n1 is 1 or 2, m1 is 0, and $R_4$ is $-NR_6R_{6'}$.

In some embodiments of the formulae above, $R_1$ is

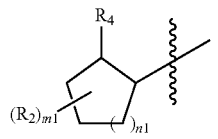

n1 is 1 or 2, and m1 is 2.

In some embodiments of the formulae above, $R_1$ is

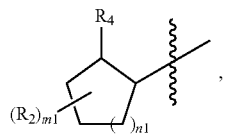

n1 is 1 or 2, m1 is 2, and $R_4$ is $-OR_5$.

In some embodiments of the formulae above, $R_1$ is

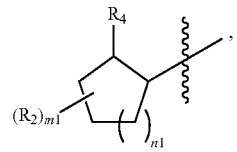

n1 is 1 or 2, m1 is 2, and $R_4$ is $-NR_6R_{6'}$.

In some embodiments of the formulae above, $R_1$ is

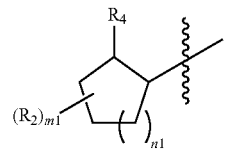

and m1 is 2.

In some embodiments of the formulae above, $R_1$ is

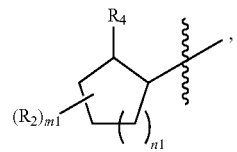

m1 is 2, and $R_4$ is $-OR_5$.

In some embodiments of the formulae above, $R_1$ is

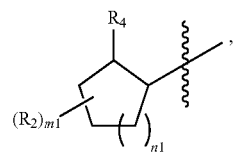

m1 is 2, and $R_4$ is $-NR_6R_{6'}$.

In some embodiments of the formulae above, n1 is 1 or 2 and m1 is 2.

In some embodiments of the formulae above, n1 is 1 or 2, m1 is 2, and $R_4$ is $-OR_5$.

In some embodiments of the formulae above, n1 is 1 or 2, m1 is 2, and $R_4$ is $-NR_6R_{6'}$.

In some embodiments of the formulae above, m1 is 2 and $R_4$ is $-OR_5$.

In some embodiments of the formulae above, m1 is 2 and $R_4$ is $-NR_6R_{6'}$.

In some embodiments of the formulae above, $R_1$ is

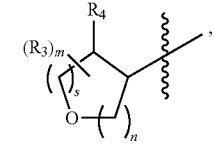

n is 2 and s is 1 or 2.

In some embodiments of the formulae above, $R_1$ is

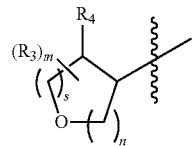

and $R_4$ is —$OR_5$.

In some embodiments of the formulae above, $R_1$ is

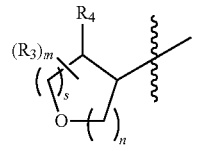

and $R_4$ is —$NR_6R_{6'}$.

In some embodiments of the formulae above, $R_1$ is

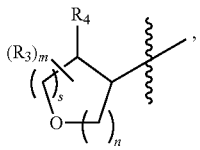

n is 2, s is 1 or 2, and m is 0 or 1.

In some embodiments of the formulae above, $R_1$ is

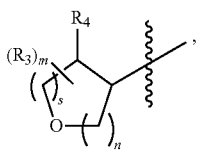

n is 2, s is 1 or 2, m is 0 or 1, and $R_4$ is —$OR_5$.

In some embodiments of the formulae above, $R_1$ is

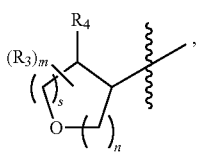

n is 2, s is 1 or 2, m is 0 or 1, and $R_4$ is —$NR_6R_{6'}$.

In some embodiments of the formulae above, $R_1$ is

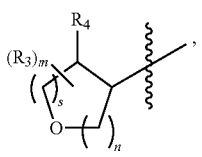

n is 2, s is 1 or 2, and $R_4$ is —$OR_5$.

In some embodiments of the formulae above, $R_1$ is

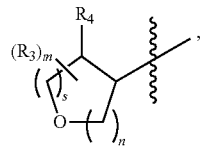

n is 2, s is 1 or 2, m is 0 or 1, and $R_4$ is —$NR_6R_{6'}$.

In some embodiments of the formulae above, $R_1$ is

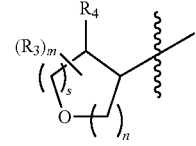

and m is 0 or 1.

In some embodiments of the formulae above, $R_1$ is

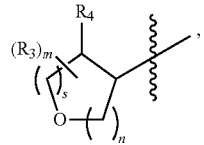

m is 0 or 1, and $R_4$ is —$OR_5$.

In some embodiments of the formulae above, $R_1$ is

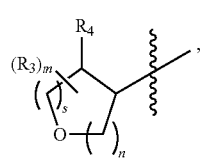

m is 0 or 1, and $R_4$ is —$NR_6R_{6'}$.

In some embodiments of the formulae above, $R_1$ is

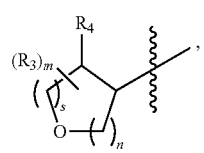

m is 0 or 1, and $R_4$ is —$OR_5$.

In some embodiments of the formulae above, $R_1$ is

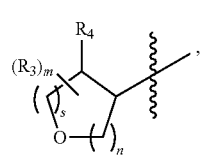

m is 0 or 1, and $R_4$ is —$NR_6R_{6'}$.

In some embodiments of the formulae above, n is 2, s is 1 or 2, and m is 0 or 1.

In some embodiments of the formulae above, n is 2, s is 1 or 2, m is 0 or 1, and $R_4$ is —$OR_5$.

In some embodiments of the formulae above, n is 2, s is 1 or 2, m is 0 or 1, and $R_4$ is —$NR_6R_{6'}$.

In some embodiments of the formulae above, n is 2, s is 1 or 2 and $R_4$ is —$OR_5$.

In some embodiments of the formulae above, n is 2, s is 1 or 2 and $R_4$ is —$NR_6R_{6'}$.

In some embodiments of the formulae above, m is 0 or 1, and $R_4$ is —$OR_5$.

In some embodiments of the formulae above, m is 0 or 1, and $R_4$ is —$NR_6R_{6'}$.

In some embodiments of the formulae above, $R_1$ is

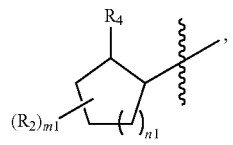

m1 is 0, $R_4$ is —$OR_5$, and $R_5$ is H, $(C_6-C_{10})$aryl, or $(C_1-C_6)$alkyl optionally substituted with one to three substituents each independently selected from $(C_6-C_{10})$aryl and 5- or 6-membered heteroaryl comprising 1-3 heteroatoms selected from O, N, and S. In another embodiment, $R_1$ is

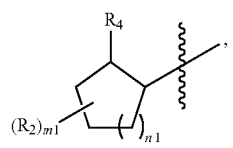

m1 is 0, $R_4$ is —$OR_5$, and $R_5$ is H, $(C_6-C_{10})$aryl, or $(C_1-C_6)$alkyl optionally substituted with one to three $(C_6-C_{10})$aryl.

In another embodiment, $R_1$ is

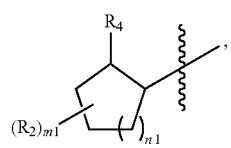

m1 is 0, $R_4$ is —$OR_5$, $R_5$ is H, $(C_6-C_{10})$aryl, or $(C_1-C_6)$alkyl optionally substituted with one to three substituents each independently selected from $(C_6-C_{10})$aryl and 5- or 6-membered heteroaryl comprising 1-3 heteroatoms selected from O, N, and S, and n1 is 0, 1, or 2. In another embodiment, $R_1$ is

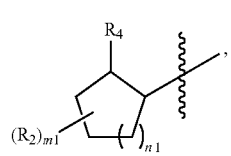

m1 is 0, $R_4$ is —$OR_5$, $R_5$ is H, $(C_6-C_{10})$aryl, or $(C_1-C_6)$alkyl optionally substituted with one to three substituents each independently selected from $(C_6-C_{10})$aryl and 5- or 6-membered heteroaryl comprising 1-3 heteroatoms selected from O, N, and S, and n1 is 1 or 2. In another embodiment, $R_1$ is

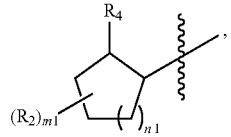

m1 is 0, $R_4$ is —$OR_5$, $R_5$ is H, $(C_6-C_{10})$aryl, or $(C_1-C_6)$alkyl optionally substituted with one to three substituents each independently selected from $(C_6-C_{10})$aryl and 5- or 6-membered heteroaryl comprising 1-3 heteroatoms selected from O, N, and S, and n1 is 0. In another embodiment, $R_1$ is

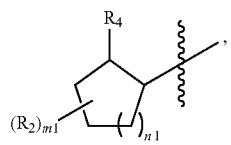

m1 is 0, $R_4$ is —$OR_5$, $R_5$ is H, $(C_6-C_{10})$aryl, or $(C_1-C_6)$alkyl optionally substituted with one to three substituents each independently selected from $(C_6-C_{10})$aryl and 5- or 6-membered heteroaryl comprising 1-3 heteroatoms selected from O, N, and S, and n1 is 1. In another embodiment, $R_1$ is

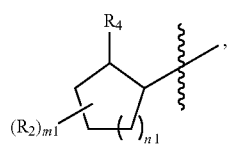

m1 is 0, $R_4$ is —$OR_5$, $R_5$ is H, $(C_6-C_{10})$aryl, or $(C_1-C_6)$alkyl optionally substituted with one to three substituents each independently selected from $(C_6-C_{10})$aryl and 5- or 6-membered heteroaryl comprising 1-3 heteroatoms selected from O, N, and S, and n1 is 2.

In another embodiment, $R_1$ is

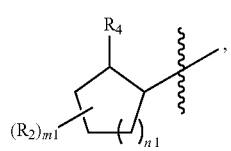

m1 is 0, $R_4$ is —$OR_5$, $R_5$ is H, $(C_6-C_{10})$aryl, or $(C_1-C_6)$alkyl optionally substituted with one to three $(C_6-C_{10})$aryl, and n1 is 0, 1, or 2. In another embodiment, $R_1$ is

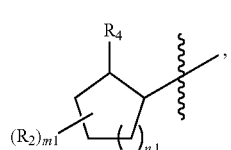

m1 is 0, $R_4$ is —$OR_5$, $R_5$ is H, $(C_6-C_{10})$aryl, or $(C_1-C_6)$alkyl optionally substituted with one to three $(C_6-C_{10})$aryl, and n1 is 1 or 2. In another embodiment, $R_1$ is

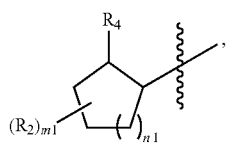

m1 is 0, R$_4$ is —OR$_5$, R$_5$ is H, (C$_6$-C$_{10}$)aryl, or (C$_1$-C$_6$)alkyl optionally substituted with one to three (C$_6$-C$_{10}$)aryl, and n1 is 0. In another embodiment, R$_1$ is

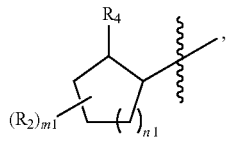

m1 is 0, R$_4$ is —OR$_5$, R$_8$ is H, (C$_6$-C$_{10}$)aryl, or (C$_1$-C$_6$)alkyl optionally substituted with one to three (C$_6$-C$_{10}$)aryl, and n1 is 1. In another embodiment, R$_1$ is

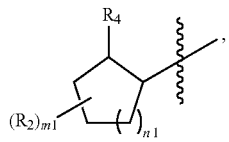

m1 is 0, R$_4$ is —OR$_5$, R$_5$ is H, (C$_6$-C$_{10}$)aryl, or (C$_1$-C$_6$)alkyl optionally substituted with one to three (C$_6$-C$_{10}$)aryl, and n1 is 2.

In some embodiments of the formulae above, R$_1$ is

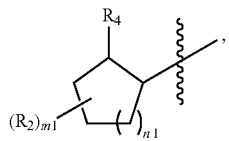

m1 is 0, R$_4$ is —OR$_5$, and R$_5$ is H or (C$_1$-C$_6$)alkyl optionally substituted with one to three substituents each independently selected from (C$_6$-C$_{10}$)aryl and 5- or 6-membered heteroaryl comprising 1-3 heteroatoms selected from O, N, and S. In another embodiment, R$_1$ is

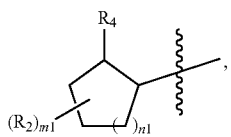

m1 is 0, R$_4$ is —OR$_5$, and R$_5$ is H or (C$_1$-C$_6$)alkyl optionally substituted with one to three (C$_6$-C$_{10}$)aryl.

In another embodiment, R$_1$ is

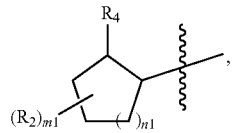

m1 is 0, R$_4$ is —OR$_5$, R$_5$ is H or (C$_1$-C$_6$)alkyl optionally substituted with one to three substituents each independently selected from (C$_6$-C$_{10}$)aryl and 5- or 6-membered heteroaryl comprising 1-3 heteroatoms selected from O, N, and S, and n1 is 0, 1, or 2. In another embodiment, R$_1$ is

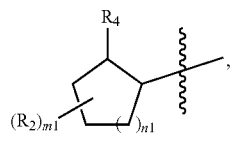

m1 is 0, R$_4$ is —OR$_5$, R$_5$ is H or (C$_1$-C$_6$)alkyl optionally substituted with one to three substituents each independently selected from (C$_6$-C$_{10}$)aryl and 5- or 6-membered heteroaryl comprising 1-3 heteroatoms selected from O, N, and S, and n1 is 1 or 2. In another embodiment, R$_1$ is

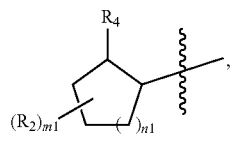

R$_1$ is 0, R$_4$ is —OR$_5$, R$_5$ is H or (C$_1$-C$_6$)alkyl optionally substituted with one to three substituents each independently selected from (C$_6$-C$_{10}$)aryl and 5- or 6-membered heteroaryl comprising 1-3 heteroatoms selected from O, N, and S, and n1 is 0. In another embodiment, R$_1$ is

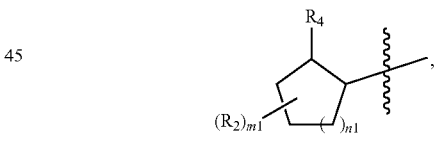

m1 is 0, R$_4$ is —OR$_5$, R$_5$ is H or (C$_1$-C$_6$)alkyl optionally substituted with one to three substituents each independently selected from (C$_6$-C$_{10}$)aryl and 5- or 6-membered heteroaryl comprising 1-3 heteroatoms selected from O, N, and S, and n1 is 1. In another embodiment, R$_1$ is

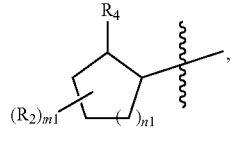

m1 is 0, R$_4$ is —OR$_5$, R$_5$ is H or (C$_1$-C$_6$)alkyl optionally substituted with one to three substituents each independently selected from (C$_6$-C$_{10}$)aryl and 5- or 6-membered heteroaryl comprising 1-3 heteroatoms selected from O, N, and S, and n1 is 2.

In another embodiment, $R_1$ is

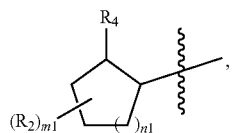

$m1$ is 0, $R_4$ is —$OR_5$, $R_5$ is H or $(C_1$-$C_6)$alkyl optionally substituted with one to three $(C_6$-$C_{10})$aryl, and $n1$ is 0, 1, or 2. In another embodiment, $R_1$ is

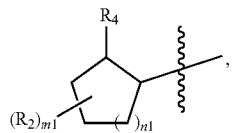

$m1$ is 0, $R_4$ is —$OR_5$, $R_5$ is H or $(C_1$-$C_6)$alkyl optionally substituted with one to three $(C_6$-$C_{10})$aryl, and $n1$ is 1 or 2. In another embodiment, $R_1$ is

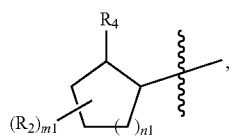

$m1$ is 0, $R_4$ is —$OR_5$, $R_5$ is H or $(C_1$-$C_6)$alkyl optionally substituted with one to three $(C_6$-$C_{10})$aryl, and $n1$ is 0. In another embodiment, $R_1$ is

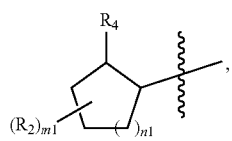

$m1$ is 0, $R_4$ is —$OR_5$, $R_5$ is H or $(C_1$-$C_6)$alkyl optionally substituted with one to three $(C_6$-$C_{10})$aryl, and $n1$ is 1. In another embodiment, $R_1$ is

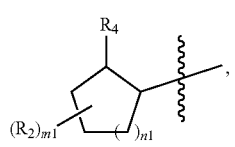

$m1$ is 0, $R_4$ is —$OR_5$, $R_8$ is H or $(C_1$-$C_6)$alkyl optionally substituted with one to three $(C_6$-$C_{10})$aryl, and $n1$ is 2.

In some embodiments of the formulae above, $R_1$ is

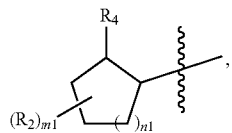

$m1$ is 0, $R_4$ is —$NR_6R_{6'}$, and $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$.

In another embodiment, $R_1$ is

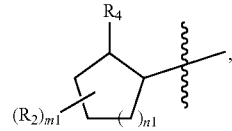

$m1$ is 0, $R_4$ is —$NR_6R_{6'}$, $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, and $n1$ is 0, 1, or 2. In another embodiment, $R_1$ is

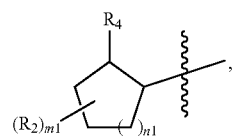

$m1$ is 0, $R_4$ is —$NR_6R_{6'}$, $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, and $n1$ is 1 or 2. In another embodiment, $R_1$ is

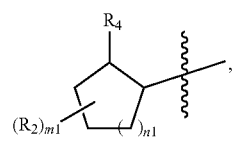

$m1$ is 0, $R_4$ is —$NR_6R_{6'}$, $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, and $n1$ is 0. In another embodiment, $R_1$ is

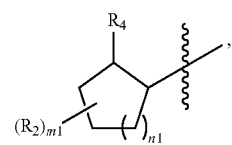

$m1$ is 0, $R_4$ is —$NR_6R_{6'}$, $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, and $n1$ is 1. In another embodiment, $R_1$ is

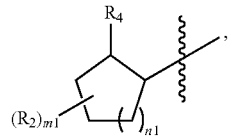

m1 is 0, R$_4$ is —NR$_6$R$_6$', R$_6$ and R$_6$' together with the nitrogen atom to which they are attached form a 4- to 7-membered heterocycloalkyl ring optionally comprising 1-2 additional heteroatoms selected from O, N, and S, and optionally substituted with one to four R$_8$, and n1 is 2.

In some embodiments of the formulae above, R$_1$ is

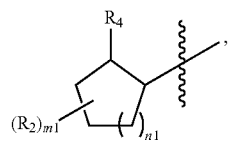

m1 is 0, R$_4$ is —NR$_6$R$_6$', and R$_6$ and R$_6$' are each independently H, (C$_1$-C$_6$)alkyl, or (C$_1$-C$_6$)haloalkyl, wherein the alkyl is optionally substituted with one to three R$_7$; or R$_6$ and R$_6$' together with the nitrogen atom to which they are attached form a 4- to 7-membered heterocycloalkyl ring optionally comprising 1-2 additional heteroatoms selected from O, N, and S, and optionally substituted with one to four R$_8$. In another embodiment, R is

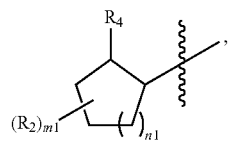

m1 is 0, R$_4$ is —NR$_6$R$_6$', R$_6$ and R$_6$' are each independently H, (C$_1$-C$_6$)alkyl, or (C$_1$-C$_6$)haloalkyl, wherein the alkyl is optionally substituted with one to three R$_7$; or R$_6$ and R$_6$' together with the nitrogen atom to which they are attached form a 4- to 7-membered heterocycloalkyl ring optionally comprising 1-2 additional heteroatoms selected from O, N, and S, and optionally substituted with one to four R$_8$, and R$_7$ is (C$_6$-C$_{10}$)aryl optionally substituted with one or two R$_9$.

In another embodiment, R$_1$ is

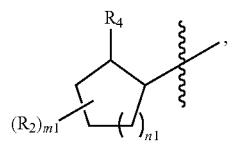

m1 is 0, R$_4$ is —NR$_6$R$_6$', R$_6$ and R$_6$' are each independently H, (C$_1$-C$_6$)alkyl, or (C$_1$-C$_6$)haloalkyl, wherein the alkyl is optionally substituted with one to three R$_7$; or R$_6$ and R$_6$' together with the nitrogen atom to which they are attached form a 4- to 7-membered heterocycloalkyl ring optionally comprising 1-2 additional heteroatoms selected from O, N, and S, and optionally substituted with one to four R$_8$, R$_7$ is (C$_6$-C$_{10}$)aryl optionally substituted with one or two R$_9$, and n1 is 0, 1, or 2. In another embodiment, R$_1$ is

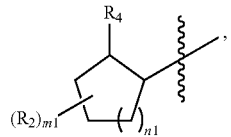

m1 is 0, R$_4$ is —NR$_6$R$_6$', R$_6$ and R$_6$' are each independently H, (C$_1$-C$_6$)alkyl, or (C$_1$-C$_6$)haloalkyl, wherein the alkyl is optionally substituted with one to three R$_7$; or R$_6$ and R$_6$' together with the nitrogen atom to which they are attached form a 4- to 7-membered heterocycloalkyl ring optionally comprising 1-2 additional heteroatoms selected from O, N, and S, and optionally substituted with one to four R$_8$, R$_7$ is (C$_6$-C$_{10}$)aryl optionally substituted with one or two R$_9$, and n1 is 1 or 2. In another embodiment, R$_1$ is

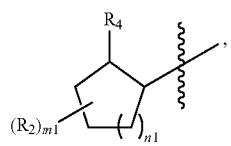

m1 is 0, R$_4$ is —NR$_6$R$_6$', R$_6$ and R$_6$' are each independently H, (C$_1$-C$_6$)alkyl, or (C$_1$-C$_6$)haloalkyl, wherein the alkyl is optionally substituted with one to three R$_7$; or R$_6$ and R$_6$' together with the nitrogen atom to which they are attached form a 4- to 7-membered heterocycloalkyl ring optionally comprising 1-2 additional heteroatoms selected from O, N, and S, and optionally substituted with one to four R$_8$, R$_7$ is (C$_6$-C$_{10}$)aryl optionally substituted with one or two R$_9$, and n1 is 0.

In another embodiment, R$_1$ is

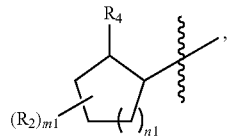

m1 is 0, R$_4$ is —NR$_6$R$_6$', R$_6$ and R$_6$' are each independently H, (C$_1$-C$_6$)alkyl, or (C$_1$-C$_6$)haloalkyl, wherein the alkyl is optionally substituted with one to three R$_7$; or R$_6$ and R$_6$' together with the nitrogen atom to which they are attached form a 4- to 7-membered heterocycloalkyl ring optionally comprising 1-2 additional heteroatoms selected from O, N, and S, and optionally substituted with one to four R$_8$, R$_7$ is (C$_6$-C$_{10}$)aryl optionally substituted with one or two R$_9$, and n1 is 1. In another embodiment, R$_1$ is

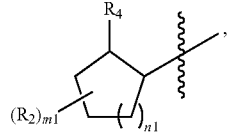

m1 is 0, R$_4$ is —NR$_6$R$_6$', R$_6$ and R$_6$' are each independently H, (C$_1$-C$_6$)alkyl, or (C$_1$-C$_6$)haloalkyl, wherein the alkyl is optionally substituted with one to three R$_7$; or R$_6$ and R$_6$' together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_6-C_{10})$aryl optionally substituted with one or two $R_9$, and n1 is 2.

In another embodiment, $R_1$ is

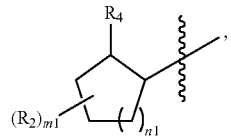

m1 is 0, $R_4$ is $-NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, and $R_7$ is $(C_3-C_7)$cycloalkyl or $(C_6-C_{10})$aryl, wherein the cycloalkyl and aryl are optionally substituted with one or two $R_9$.

In another embodiment, $R_1$ is

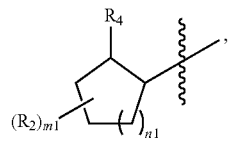

m1 is 0, $R_4$ is $-NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_3-C_7)$cycloalkyl or $(C_6-C_{10})$aryl, wherein the cycloalkyl and aryl are optionally substituted with one or two $R_9$, and n1 is 0, 1, or 2. In another embodiment, $R_1$ is

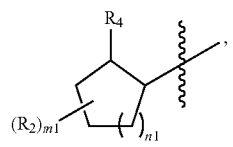

m1 is 0, $R_4$ is $-NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_3-C_7)$cycloalkyl or $(C_6-C_{10})$aryl, wherein the cycloalkyl and aryl are optionally substituted with one or two $R_9$, and n1 is 1 or 2. In another embodiment, $R_1$ is

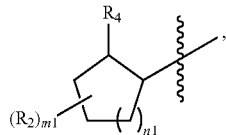

m1 is 0, $R_4$ is $-NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_3-C_7)$cycloalkyl or $(C_6-C_{10})$aryl, wherein the cycloalkyl and aryl are optionally substituted with one or two $R_9$, and n1 is 0.

In another embodiment, $R_1$ is

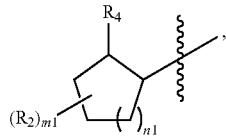

m1 is 0, $R_4$ is $-NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_3-C_7)$cycloalkyl or $(C_6-C_{10})$aryl, wherein the cycloalkyl and aryl are optionally substituted with one or two $R_9$, and n1 is 1. In another embodiment, $R_1$ is

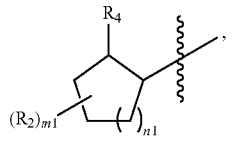

m1 is 0, $R_4$ is $-NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_3-C_7)$cycloalkyl or $(C_6-C_{10})$aryl, wherein the cycloalkyl and aryl are optionally substituted with one or two $R_9$, and n1 is 2.

In another embodiment, $R_1$ is

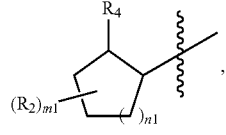

m1 is 0, $R_4$ is —$NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, and $R_7$ is $(C_6-C_{10})$aryl.

In another embodiment, $R_1$ is

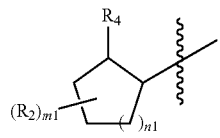

m1 is 0, $R_4$ is —$NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_6-C_{10})$aryl, and n1 is 0, 1, or 2.

In another embodiment, $R_1$ is

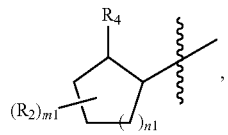

m1 is 0, $R_4$ is —$NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_6-C_{10})$aryl, and n1 is 1 or 2. In another embodiment, $R_1$ is

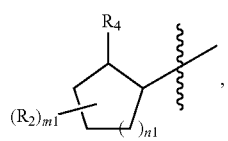

m1 is 0, $R_4$ is —$NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_6-C_{10})$aryl, and n1 is 0.

In another embodiment, $R_1$ is

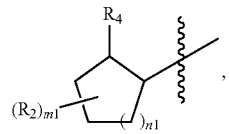

m1 is 0, $R_4$ is —$NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_6-C_{10})$aryl, and n1 is 1. In another embodiment, $R_1$ is

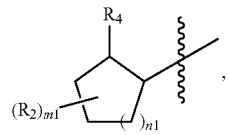

m1 is 0, $R_4$ is —$NR_6R_{6'}$, $R_6$ and $R_{6'}$ are each independently H, $(C_1-C_6)$alkyl, or $(C_1-C_6)$haloalkyl, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$, $R_7$ is $(C_6-C_{10})$aryl, and n1 is 2.

In some embodiments of the formulae above, $R_1$ is

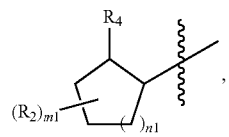

m1 is 0, $R_4$ is —$NR_6R_{6'}$, and $R_6$ is H, $(C_1-C_6)$haloalkyl, or $(C_1-C_6)$alkyl optionally substituted with one to three $R_7$. In another embodiment, $R_1$ is

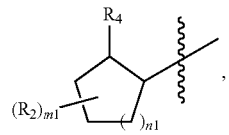

m1 is 0, $R_4$ is —$NR_6R_{6'}$, $R_6$ is H, $(C_1-C_6)$haloalkyl, or $(C_1-C_6)$alkyl optionally substituted with one to three $R_7$, and $R_{6'}$ is H, $(C_1-C_6)$haloalkyl, or $(C_1-C_6)$alkyl optionally substituted with one to three $R_7$.

In another embodiment, $R_1$ is

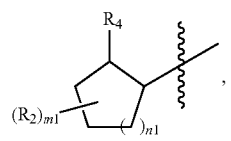

m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, and $R_7$ is $(C_3-C_7)$cycloalkyl or $(C_6-C_{10})$aryl, wherein the cycloalkyl and aryl are optionally substituted with one or two $R_9$.

In another embodiment, $R_1$ is

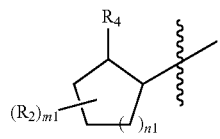, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, $R_7$ is $(C_3-C_7)$cycloalkyl or $(C_6-C_{10})$aryl, wherein the cycloalkyl and aryl are optionally substituted with one or two $R_9$, and n1 is 0, 1, or 2.

In another embodiment, $R_1$ is

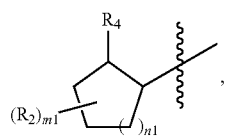, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, $R_7$ is $(C_3-C_7)$cycloalkyl or $(C_6-C_{10})$aryl, wherein the cycloalkyl and aryl are optionally substituted with one or two $R_9$, and n1 is 1 or 2. In another embodiment, $R_1$ is

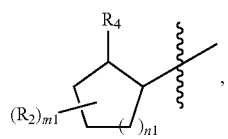, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, $R_7$ is $(C_3-C_7)$cycloalkyl or $(C_6-C_{10})$aryl, wherein the cycloalkyl and aryl are optionally substituted with one or two $R_9$, and n1 is 0.

In another embodiment, $R_1$ is

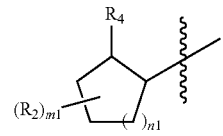, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H or $(C_1-C_6)$alkyl optionally substituted with one to three $R_7$, $R_7$ is $(C_3-C_7)$cycloalkyl or $(C_6-C_{10})$aryl, wherein the cycloalkyl and aryl are optionally substituted with one or two $R_9$, and n1 is 2.

In another embodiment, $R_1$ is

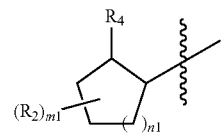, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, and $R_7$ is $(C_6-C_{10})$aryl optionally substituted with one or two $R_9$.

In another embodiment, $R_1$ is

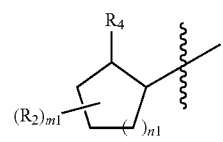, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, $R_7$ is $(C_6-C_{10})$aryl optionally substituted with one or two $R_9$, and n1 is 0, 1, or 2.

In another embodiment, $R_1$ is

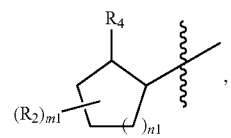, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, $R_7$ is $(C_6-C_{10})$aryl optionally substituted with one or two $R_9$, and n1 is 1 or 2. In another embodiment, $R_1$ is

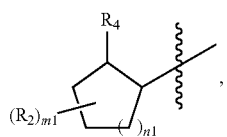, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, $R_7$ is $(C_6-C_{10})$aryl optionally substituted with one or two $R_9$, and n1 is 0.

In another embodiment, $R_1$ is

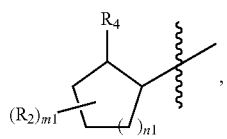, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, $R_7$ is $(C_6-C_{10})$aryl optionally substituted with one or two $R_9$, and n1 is 1. In another embodiment, $R_1$ is

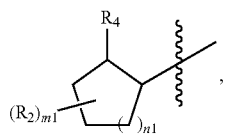, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H or $(C_1-C_6)$alkyl optionally substituted with one to three $R_7$, $R_7$ is $(C_6-C_{10})$aryl optionally substituted with one or two $R_9$, and n1 is 2.

In another embodiment, $R_1$ is

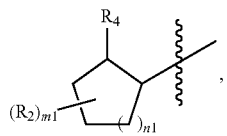, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, and $R_7$ is $(C_6-C_{10})$aryl. In another embodiment, $R_1$ is

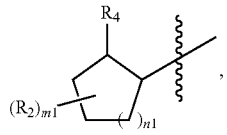, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, $R_7$ is $(C_6-C_{10})$aryl, and n1 is 1 or 2. In another embodiment, $R_1$ is

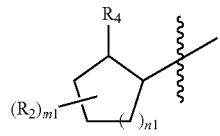, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, $R_7$ is $(C_6-C_{10})$aryl, and n1 is 1. In another embodiment, $R_1$ is

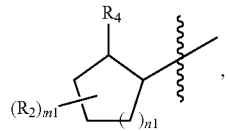, m1 is 0, $R_4$ is $-NR_6R_{6'}$, $R_6$ is H, $(C_1-C_6)$haloalkyl, or $(C_1-C_6)$alkyl optionally substituted with one to three $R_7$, $R_{6'}$ is H, $(C_1-C_6)$haloalkyl, or $(C_1-C_6)$alkyl optionally substituted with one to three $R_7$, $R_7$ is $(C_6-C_{10})$aryl, and n1 is 2.

In some embodiments of the formulae above, $R_1$ is

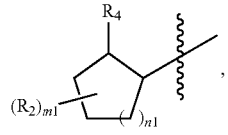, m1 is 0, $R_4$ is $-NR_6R_{6'}$, and $R_6$ is H or $(C_1-C_6)$alkyl optionally substituted with one to three $R_7$. In another embodiment, $R_1$ is

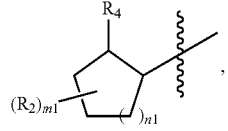, m1 is 0, $R_4$ is $-NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_3-C_7)$cycloalkyl or $(C_6-C_{10})$aryl, wherein the cycloalkyl and aryl are optionally substituted with one or two $R_9$.

In another embodiment, $R_1$ is

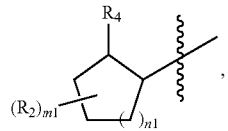, m1 is 0, $R_4$ is $-NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, $R_7$ is $(C_3-C_7)$ cycloalkyl or $(C_6-C_{10})$aryl, wherein the cycloalkyl and aryl are optionally substituted with one or two $R_9$, and n1 is 1 or 2. In another embodiment, $R_1$ is

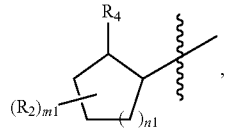, m1 is 0, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, $R_7$ is $(C_3-C_7)$ cycloalkyl or $(C_6-C_{10})$aryl, wherein the cycloalkyl and aryl are optionally substituted with one or two $R_9$, and n1 is 1. In another embodiment, $R_1$ is

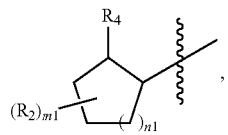, m1 is 0, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, $R_7$ is $(C_3-C_7)$ cycloalkyl or $(C_6-C_{10})$aryl, wherein the cycloalkyl and aryl are optionally substituted with one or two $R_9$, and n1 is 2. In another embodiment, $R_1$ is

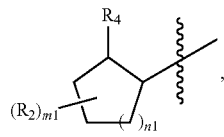, m1 is 0, $R_4$ is —$NR_6R_{6'}$, $R_6$ is H or $(C_1-C_6)$alkyl optionally substituted with one to three $R_7$, and $R_{6'}$ is H or $(C_1-C_6)$alkyl optionally substituted with one to three $R_7$. In another embodiment, $R_1$ is

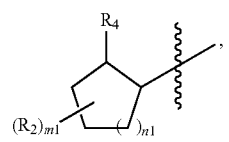, m1 is 0, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_6-C_{10})$aryl optionally substituted with one or two $R_9$. In another embodiment, $R_1$ is

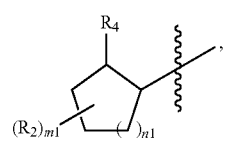, m1 is 0, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, $R_7$ is $(C_6-C_{10})$ aryl optionally substituted with one or two $R_9$, and n1 is 1 or 2. In another embodiment, $R_1$ is

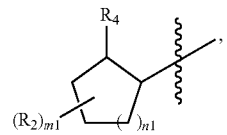, m1 is 0, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, $R_7$ is $(C_6-C_{10})$ aryl optionally substituted with one or two $R_9$, and n1 is 1. In another embodiment, $R_1$ is

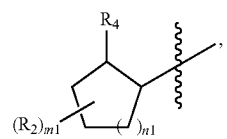, m1 is 0, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, $R_7$ is $(C_6-C_{10})$ aryl optionally substituted with one or two $R_9$, and n1 is 2. In another embodiment, $R_1$ is

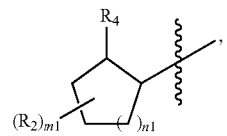, m1 is 0, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_6-C_{10})$aryl. In another embodiment, $R_1$ is

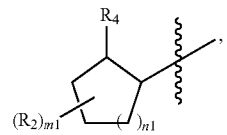, m1 is 0, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, $R_7$ is $(C_6-C_{10})$ aryl, and n1 is 1 or 2. In another embodiment, $R_1$ is

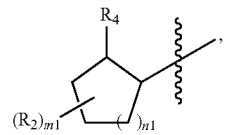, m1 is 0, $R_4$ is —$NR_6R_{6'}$, $R_6$ is H or $(C_1-C_6)$alkyl optionally substituted with one to three $R_7$, $R_6$ is H or $(C_1-C_6)$alkyl optionally substituted with one to three $R_7$, $R_7$ is $(C_6-C_{10})$ aryl, and n1 is 1. In another embodiment, $R_1$ is

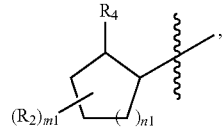

m1 is 0, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, $R_7$ is $(C_6-C_{10})$ aryl, and n1 is 2.

In some embodiments of the formulae above, $R_1$ is

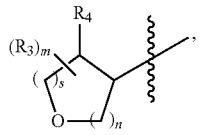

m is 0, n is 1, and s is 1. In another embodiment, $R_1$ is

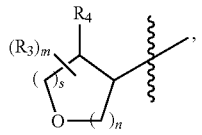

m is 0, n is 1, s is 1, and $R_4$ is —$OR_5$. In another embodiment, $R_1$ is

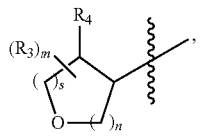

m is 0, n is 1, s is 1, $R_4$ is —$OR_5$, and $R_5$ is H, $(C_6-C_{10})$aryl, or $(C_1-C_6)$alkyl optionally substituted with one to three $(C_6-C_{10})$aryl. In another embodiment, $R_1$ is

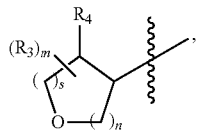

m is 0, n is 1, s is 1, $R_4$ is —$OR_5$, and $R_5$ is H or $(C_1-C_6)$alkyl optionally substituted with one to three $(C_6-C_{10})$aryl.

In some embodiments of the formulae above, $R_1$ is

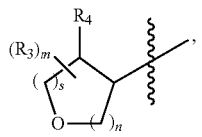

m is 0, n is 1, s is 1, and $R_4$ is —$NR_6R_{6'}$. In another embodiment, $R_1$ is

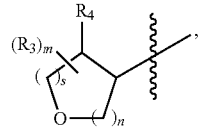

m is 0, n is 1, s is 1, $R_4$ is —$NR_6R_{6'}$, and $R_6$ is H or $(C_1-C_6)$alkyl optionally substituted with one to three $R_7$. In another embodiment, $R_1$ is

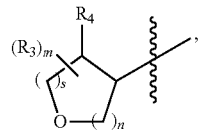

m is 0, n is 1, s is 1, $R_4$ is —$NR_6R_{6'}$, $R_6$ is H or $(C_1-C_6)$alkyl optionally substituted with one to three $R_7$, and $R_{6'}$ is H or $(C_1-C_6)$alkyl optionally substituted with one to three $R_7$. In another embodiment, $R_1$ is

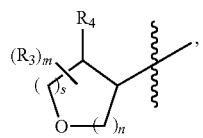

m is 0, n is 1, s is 1, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_3-C_7)$cycloalkyl or $(C_6-C_{10})$aryl, wherein the cycloalkyl and aryl are optionally substituted with one or two $R_9$.

In another embodiment, $R_1$ is

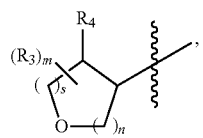

m is 0, n is 1, s is 1, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_6-C_{10})$aryl optionally substituted with one or more $R_9$.

In another embodiment, $R_1$ is

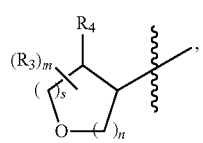

m is 0, n is 1, s is 1, $R_4$ is —$NR_6R_{6'}$, $R_6$ is H or ($C_1$-$C_6$)alkyl optionally substituted with one to three $R_7$, $R_{6'}$ is H or ($C_1$-$C_6$)alkyl optionally substituted with one to three $R_7$, and $R_7$ is ($C_6$-$C_{10}$)aryl.

In some embodiments of the formulae above, $R_1$ is

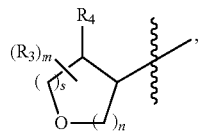

m is 0, n is 2, and s is 1. In another embodiment, R is

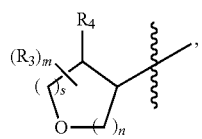

m is 0, n is 2, s is 1, and $R_4$ is —$OR_5$. In another embodiment, $R_1$ is

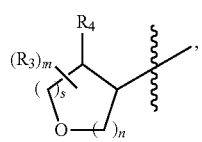

m is 0, n is 2, s is 1, $R_4$ is —$OR_5$, and $R_5$ is H or ($C_1$-$C_6$)alkyl optionally substituted with one to three ($C_6$-$C_{10}$)aryl.

In some embodiments of the formulae above, $R_1$ is

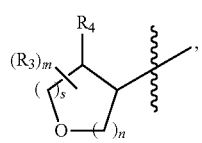

m is 0, n is 2, s is 1, and $R_4$ is —$NR_6R_{6'}$. In another embodiment, $R_1$ is

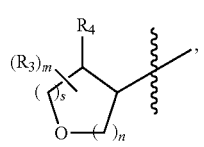

m is 0, n is 2, s is 1, $R_4$ is —$NR_6R_{6'}$, and $R_6$ is H or ($C_1$-$C_6$)alkyl optionally substituted with one to three $R_7$. In another embodiment, $R_1$ is

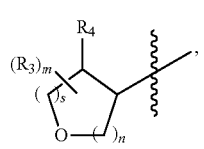

m is 0, n is 2, s is 1, $R_4$ is —$NR_6R_{6'}$, $R_6$ is H or ($C_1$-$C_6$)alkyl optionally substituted with one to three $R_7$, and $R_{6'}$ is H or ($C_1$-$C_6$)alkyl optionally substituted with one to three $R_7$. In another embodiment, $R_1$ is

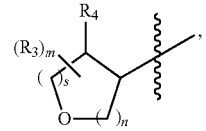

m is 0, n is 2, s is 1, $R_4$ is —$NR_6R_{6'}$, $R_6$ is H or ($C_1$-$C_6$)alkyl optionally substituted with one to three $R_7$, $R_{6'}$ is H or ($C_1$-$C_6$)alkyl optionally substituted with one to three $R_7$, and $R_7$ is ($C_3$-$C_7$)cycloalkyl or ($C_6$-$C_{10}$)aryl, wherein the cycloalkyl and aryl are optionally substituted with one or two $R_9$.

In another embodiment, $R_1$ is

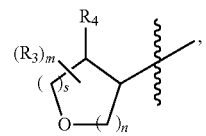

m is 0, n is 2, s is 1, $R_4$ is —$NR_6R_{6'}$, $R_6$ is H or ($C_1$-$C_6$)alkyl optionally substituted with one to three $R_7$, $R_{6'}$ is H or ($C_1$-$C_6$)alkyl optionally substituted with one to three $R_7$, and $R_7$ is ($C_6$-$C_{10}$)aryl optionally substituted with one or more $R_9$.

In another embodiment, $R_1$ is

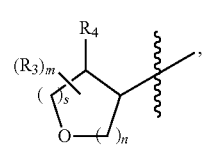

m is 0, n is 2, s is 1, $R_4$ is —$NR_6R_{6'}$, $R_6$ is H or ($C_1$-$C_6$)alkyl optionally substituted with one to three $R_7$, $R_{6'}$ is H or ($C_1$-$C_6$)alkyl optionally substituted with one to three $R_7$, and $R_7$ is ($C_6$-$C_{10}$)aryl.

In some embodiments of the formulae above, $R_1$ is

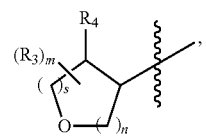

m is 0, n is 2, and s is 2. In another embodiment, R is

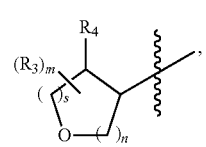

n is 2, s is 2, and $R_4$ is —$OR_5$. In another embodiment, $R_1$ is

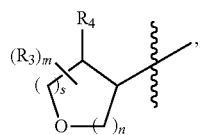

m is 0, n is 2, s is 2, $R_4$ is —$OR_5$, and $R_5$ is H or $(C_1-C_6)$alkyl optionally substituted with one to three $(C_6-C_{10})$aryl.

In some embodiments of the formulae above, $R_1$ is

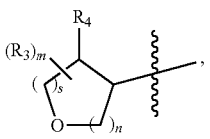

m is 0, n is 2, s is 2, and $R_4$ is —$NR_6R_{6'}$. In another embodiment, $R_1$ is

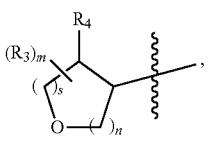

m is 0, n is 2, s is 2, $R_4$ is —$NR_6R_{6'}$, and $R_6$ is H or $(C_1-C_6)$alkyl optionally substituted with one to three $R_7$. In another embodiment, $R_1$ is

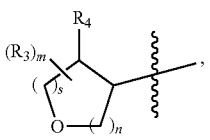

m is 0, n is 2, s is 2, $R_4$ is —$NR_6R_{6'}$, $R_6$ is H or $(C_1-C_6)$alkyl optionally substituted with one to three $R_7$, and $R_{6'}$ is H or $(C_1-C_6)$alkyl optionally substituted with one to three $R_7$. In another embodiment, $R_1$ is

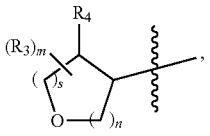

m is 0, n is 2, s is 2, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_3-C_7)$cycloalkyl or $(C_6-C_{10})$aryl, wherein the cycloalkyl and aryl are optionally substituted with one or two $R_9$.

In another embodiment, $R_1$ is

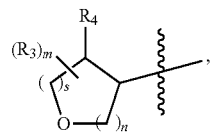

m is 0, n is 2, s is 2, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_6-C_{10})$aryl optionally substituted with one or more $R_9$.

In another embodiment, $R_1$ is

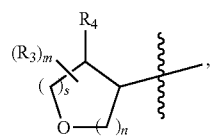

m is 0, n is 2, s is 2, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_6-C_{10})$aryl.

In some embodiments of the formulae above, $R_1$ is

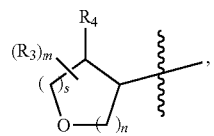

m is 0, n is 2, s is 1 or 2, and $R_4$ is —$OR_5$. In another embodiment, $R_1$ is

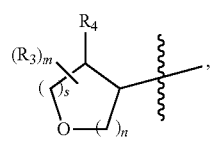

m is 0, n is 2, s is 1 or 2, $R_4$ is —$OR_5$ and $R_5$ is H or $(C_1-C_6)$alkyl optionally substituted with one to three $(C_6-C_{10})$aryl.

In some embodiments of the formulae above, $R_1$ is

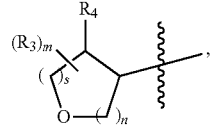

m is 0, n is 2, s is 1 or 2, and $R_4$ is —$NR_6R_{6'}$. In another embodiment, $R_1$ is In another embodiment, $R_1$ is

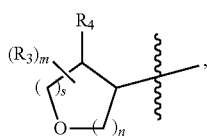

$m$ is 0, $n$ is 2, $s$ is 1 or 2, $R_4$ is —$NR_6R_{6'}$, and $R_6$ is H or $(C_1-C_6)$alkyl optionally substituted with one to three $R_7$. In another embodiment, $R_1$ is

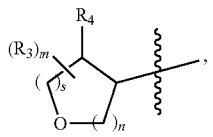

$m$ is 0, $n$ is 2, $s$ is 1 or 2, $R_4$ is —$NR_6R_{6'}$, $R_6$ is H or $(C_1-C_6)$alkyl optionally substituted with one to three $R_7$, and $R_{6'}$ is H or $(C_1-C_6)$alkyl optionally substituted with one to three $R_7$. In another embodiment, $R_1$ is

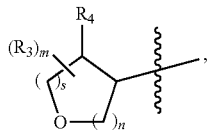

$m$ is 0, $n$ is 2, $s$ is 1 or 2, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_3-C_7)$cycloalkyl or $(C_6-C_{10})$aryl, wherein the cycloalkyl and aryl are optionally substituted with one or two $R_9$.

In another embodiment, $R_1$ is

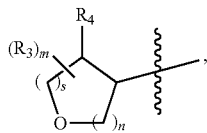

$m$ is 0, $n$ is 2, $s$ is 1 or 2, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_6-C_{10})$aryl optionally substituted with one or more $R_9$.

In another embodiment, $R_1$ is

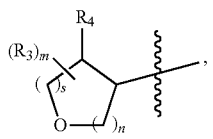

$m$ is 0, $n$ is 2, $s$ is 1 or 2, $R_4$ is —$NR_6R_{6'}$, $R_6$ is H or $(C_1-C_6)$alkyl optionally substituted with one to three $R_7$, $R_{6'}$ is H or $(C_1-C_6)$alkyl optionally substituted with one to three $R_7$, and $R_7$ is $(C_6-C_{10})$aryl.

In another embodiment, $R_1$ is

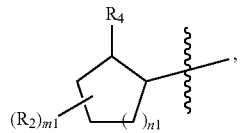

$m1$ is 0, $n1$ is 1, 2, or 3, $R_4$ is —$NR_6R_{6'}$, and $R_6$ is H or $(C_1-C_6)$alkyl optionally substituted with one to three $R_7$, $R_{6'}$ is H or $(C_1-C_6)$alkyl optionally substituted with one to three $R_7$, or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$. In another embodiment, R is

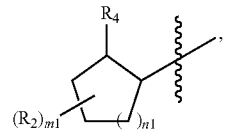

$m1$ is 0, $n1$ is 2 or 3, $R_4$ is —$NR_6R_{6'}$, and $R_6$ is H or $(C_1-C_6)$alkyl optionally substituted with one to three $R_7$, $R_{6'}$ is H or $(C_1-C_6)$alkyl optionally substituted with one to three $R_7$, or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$.

In another embodiment, $R_1$ is

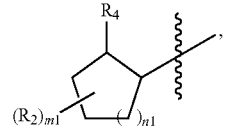

$m1$ is 0, $n1$ is 1 or 2, $R_4$ is —$NR_6R_{6'}$, and $R_6$ is H or $(C_1-C_6)$alkyl optionally substituted with one to three $R_7$, $R_{6'}$ is H or $(C_1-C_6)$alkyl optionally substituted with one to three $R_7$, or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$.

In another embodiment, $R_1$ is

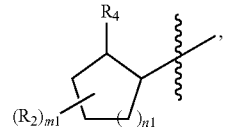

$m1$ is 0, $n1$ is 1, $R_4$ is —$NR_6R_{6'}$, and $R_6$ is H or $(C_1-C_6)$alkyl optionally substituted with one to three $R_7$, $R_{6'}$ is H or $(C_1-C_6)$alkyl optionally substituted with one to three $R_7$, or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$.

In another embodiment, $R_1$ is

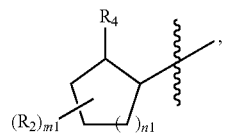

m1 is 0, n1 is 2, $R_4$ is —$NR_6R_{6'}$, and $R_6$ is H or ($C_1$-$C_6$)alkyl optionally substituted with one to three $R_7$, $R_{6'}$ is H or ($C_1$-$C_6$)alkyl optionally substituted with one to three $R_7$, or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$.

In another embodiment, $R_1$ is

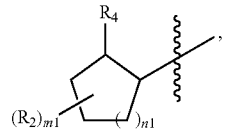

m1 is 0, n1 is 3, $R_4$ is —$NR_6R_{6'}$, and $R_6$ is H or ($C_1$-$C_6$)alkyl optionally substituted with one to three $R_7$, $R_{6'}$ is H or ($C_1$-$C_6$)alkyl optionally substituted with one to three $R_7$, or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$.

In another embodiment, $R_1$ is

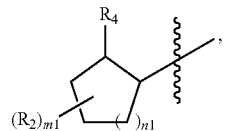

m1 is 0, n1 is 1, 2, or 3, $R_4$ is —$NR_6R_{6'}$, and $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$. In yet another embodiment, $R_1$ is

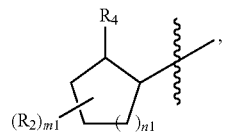

m1 is 0, n1 is 2 or 3, $R_4$ is —$NR_6R_{6'}$, and $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$.

In another embodiment, $R_1$ is

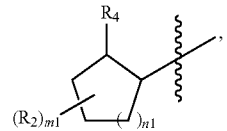

m1 is 0, n1 is 1 or 2, $R_4$ is —$NR_6R_{6'}$, and $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$. In yet another embodiment, $R_1$ is

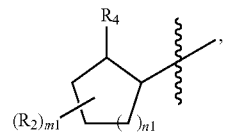

m1 is 0, n1 is 1, $R_4$ is —$NR_6R_{6'}$, and $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$.

In another embodiment, $R_1$ is

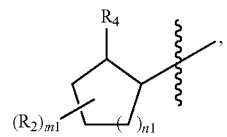

m1 is 0, n1 is 2, $R_4$ is —$NR_6R_{6'}$, and $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$. In yet another embodiment, $R_1$ is

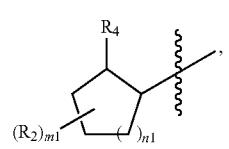

m1 is 0, n1 is 3, $R_4$ is —$NR_6R_{6'}$, and $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$.

Embodiment 1

A compound of Formula (I'), wherein:

$X_1$ and $X_2$ are each independently H, ($C_1$-$C_4$)alkyl, ($C_1$-$C_6$)alkoxy, ($C_1$-$C_4$)haloalkyl, ($C_1$-$C_6$)haloalkoxy, ($C_3$-$C_7$)cycloalkyl, halogen, —CN, —OH, or —$NH_2$;

$R_x$ is H or D;
$R_1$ is

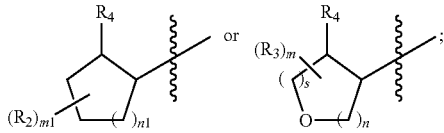

each $R_2$ is independently at each occurrence $(C_1-C_6)$alkyl, $(C_1-C_6)$alkoxy, $(C_1-C_6)$haloalkyl, $(C_1-C_6)$haloalkoxy, halogen, —CN, —OH, or —NH$_2$; or two $R_2$ together with the carbon atoms to which they are attached form a $(C_3-C_7)$cycloalkyl or a 4- to 7-membered heterocycloalkyl ring comprising 1-3 heteroatoms selected from O, N, and S; or two $R_2$ together when on adjacent carbon atoms form a phenyl or a 5- or 6-membered heteroaryl ring comprising 1-3 heteroatoms selected from O, N, and S; or $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_3$ is $(C_1-C_6)$alkyl, $(C_1-C_6)$alkoxy, $(C_1-C_6)$haloalkyl, $(C_1-C_6)$haloalkoxy, halogen, —OH, or —NH$_2$;

$R_4$ is —OR$_5$ or —NR$_6$R$_{6'}$;

$R_5$ is H, $(C_1-C_6)$alkyl, $(C_1-C_6)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S;

$R_6$ and $R_{6'}$ are each independently H, $(C_1-C_6)$alkyl, $(C_1-C_6)$haloalkyl, $(C_2-C_6)$hydroxyalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$; or $R_6$ and $R_{6'}$ together with the nitrogen atom to which they are attached form a 4- to 8-membered heterocycloalkyl ring optionally comprising 1-2 additional heteroatoms selected from O, N, and S, and optionally substituted with one to four $R_8$; or $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_7$ is $(C_3-C_7)$cycloalkyl, 4- to 7-membered heterocycloalkyl ring comprising 1-3 heteroatoms selected from O, N, and S, $(C_6-C_{10})$aryl, or 5- or 6-membered heteroaryl comprising 1-3 heteroatoms selected from O, N, and S, wherein the cycloalkyl, heterocycloalkyl, aryl and heteroaryl are optionally substituted with one to four $R_9$;

each $R_8$ is independently at each occurrence halogen, $(C_1-C_6)$alkyl, $(C_1-C_6)$alkoxy, $(C_1-C_6)$haloalkyl, $(C_1-C_6)$haloalkoxy, —CN, —OH, —NR$_{13}$R$_{14}$, —NH$_2$, —O(C$_3$-C$_7$)cycloalkyl, —O-4- to 7-membered heterocycloalkyl ring comprising 1-3 heteroatoms selected from O, N, and S, —O(C$_6$-C$_{10}$)aryl, or —O-5- or 6-membered heteroaryl comprising 1-3 heteroatoms selected from O, N, and S, wherein the alkoxy is optionally substituted with one to three $R_{10}$ and the cycloalkyl, heterocycloalkyl, aryl and heteroaryl are optionally substituted with one to three $R_1$; or two $R_8$ together with the atoms to which they are attached form a $(C_4-C_7)$cycloalkyl or a 4- to 7-membered heterocycloalkyl ring comprising 1-2 heteroatoms selected from O, N, and S optionally substituted with two $R_{15}$; or two $R_8$ when on adjacent atoms together with the atoms to which they are attached form a $(C_6-C_{10})$aryl, or 5- or 6-membered heteroaryl comprising 1-3 heteroatoms selected from O, N, and S; or two $R_8$ together with the same atom to which they are attached form a =(O);

each $R_9$ is independently at each occurrence $(C_1-C_6)$alkyl, $(C_1-C_6)$haloalkyl, $(C_1-C_6)$alkoxy, $(C_1-C_6)$haloalkoxy, halogen, —OH, —CN, or —NH$_2$; or two $R_9$ together with the atoms to which they are attached form a $(C_4-C_7)$cycloalkyl or a 5- to 7-membered heterocycloalkyl ring comprising 1-2 heteroatoms selected from O, N, and S optionally substituted with one or more substituents each independently selected from $(C_1-C_6)$alkyl, $(C_1-C_6)$haloalkyl, halogen, —OH, —CN, and —NH$_2$; or two $R_9$ when on adjacent atoms together with the atoms to which they are attached form a $(C_6-C_{10})$aryl, or 5- or 6-membered heteroaryl comprising 1-3 heteroatoms selected from O, N, and S;

each $R_{10}$ is independently at each occurrence selected from $(C_3-C_7)$cycloalkyl, 4- to 7-membered heterocycloalkyl ring comprising 1-3 heteroatoms selected from O, N, and S, $(C_6-C_{10})$aryl, and 5- or 6-membered heteroaryl comprising 1-3 heteroatoms selected from O, N, and S;

each $R_1$ is independently at each occurrence selected from $(C_1-C_6)$alkyl, $(C_1-C_6)$haloalkyl, $(C_1-C_6)$alkoxy, $(C_1-C_6)$haloalkoxy, halogen, —OH, —CN, and —NH$_2$;

each $R_{12}$ is independently at each occurrence $(C_1-C_6)$alkyl, $(C_1-C_6)$haloalkyl, $(C_1-C_6)$alkoxy, $(C_1-C_6)$haloalkoxy, halogen, —OH, —CN, or —NH$_2$;

two $R_{12}$ together with the atoms to which they are attached form a $(C_4-C_7)$cycloalkyl or a 4- to 7-membered heterocycloalkyl ring comprising 1-2 heteroatoms selected from O, N, and S;

$R_{13}$ and $R_{14}$ are each independently selected from $(C_1-C_6)$alkyl, $(C_1-C_6)$haloalkyl, $(C_3-C_7)$cycloalkyl, 4- to 7-membered heterocycloalkyl ring comprising 1-3 heteroatoms selected from O, N, and S, $(C_6-C_{10})$aryl, and 5- or 6-membered heteroaryl comprising 1-3 heteroatoms selected from O, N, and S;

two $R_{15}$ together with the atoms to which they are attached form a $(C_4-C_7)$cycloalkyl or a 4- to 7-membered heterocycloalkyl ring comprising 1-2 heteroatoms selected from O, N, and S;

m and m1 are each independently 0, 1 or 2;

n1 is 0, 1, 2, or 3; and each s and n is independently 1, 2, or 3, wherein s+n is ≤4;

or a pharmaceutically acceptable salt, hydrate, solvate, prodrug, stereoisomer, and tautomer thereof.

Embodiment 2

The compound of Embodiment 1, having a Formula (I), wherein:
$R_x$ is H or D;
$R_1$ is

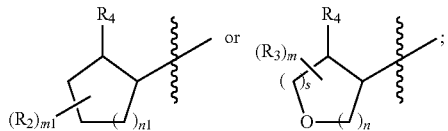

each $R_2$ is independently at each occurrence $(C_1-C_6)$alkyl, $(C_1-C_6)$alkoxy, $(C_1-C_6)$haloalkyl, $(C_1-C_6)$haloalkoxy, halogen, —CN, —OH, or —NH$_2$; or two $R_2$ together with the carbon atoms to which they are attached form a $(C_3-C_7)$cycloalkyl or a 4- to 7-membered heterocycloalkyl ring comprising 1-3 heteroatoms selected from O, N, and S; or two $R_2$ together when on adjacent carbon atoms form a phenyl or a 5- or 6-membered heteroaryl ring comprising 1-3 heteroatoms selected from O, N, and S; or $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_3$ is $(C_1-C_6)$alkyl, $(C_1-C_6)$alkoxy, $(C_1-C_6)$haloalkyl, $(C_1-C_6)$haloalkoxy, halogen, OH, or —NH$_2$;

$R_4$ is —OR$_5$ or —NR$_6$R$_{6'}$;

$R_5$ is H, $(C_1-C_6)$alkyl, $(C_1-C_6)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S;

$R_6$ and $R_{6'}$ are each independently H, $(C_1-C_6)$alkyl, $(C_1-C_6)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$; or $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_7$ is $(C_3-C_7)$cycloalkyl, 4- to 7-membered heterocycloalkyl ring comprising 1-3 heteroatoms selected from O, N, and S, $(C_6-C_{10})$aryl, or 5- or 6-membered heteroaryl comprising 1-3 heteroatoms selected from O, N, and S, wherein the cycloalkyl, heterocycloalkyl, aryl, and heteroaryl are optionally substituted with one to four $R_9$;

each $R_8$ is independently at each occurrence halogen, $(C_1-C_6)$alkyl, $(C_1-C_6)$alkoxy, $(C_1-C_6)$haloalkyl, $(C_1-C_6)$haloalkoxy, —CN, —OH, or —NH$_2$, wherein the alkoxy is optionally substituted with one to three substituents independently selected from $(C_3-C_7)$cycloalkyl, 4- to 7-membered heterocycloalkyl ring comprising 1-3 heteroatoms selected from O, N, and S, $(C_6-C_{10})$aryl, and 5- or 6-membered heteroaryl comprising 1-3 heteroatoms selected from O, N, and S; or two $R_8$ together with the atoms to which they are attached form a $(C_5-C_7)$cycloalkyl or a 4- to 7-membered heterocycloalkyl ring comprising 1-2 heteroatoms selected from O, N, and S;

each $R_9$ is independently at each occurrence $(C_1-C_6)$alkyl, $(C_1-C_6)$haloalkyl, halogen, —OH, —CN, or —NH$_2$; or two $R_9$ together with the atoms to which they are attached form a $(C_5-C_7)$cycloalkyl or a 5- to 7-membered heterocycloalkyl ring comprising 1-2 heteroatoms selected from O, N, and S optionally substituted with one or more substituents each independently selected from $(C_1-C_6)$alkyl, $(C_1-C_6)$haloalkyl, halogen, —OH, —CN, and —NH$_2$;

m and m1 are each independently 0, 1, or 2;
n1 is 0, 1, 2, or 3; and
each s and n is independently 1, 2, or 3, wherein s+n is ≤4;
or a pharmaceutically acceptable salt, hydrate, solvate, prodrug, stereoisomer, and tautomer thereof.

Embodiment 2A

The compound of Embodiment 1, having a Formula (I), wherein:
$R_x$ is H or D;
$R_1$ is

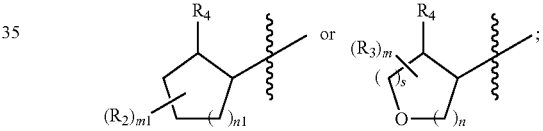

each $R_2$ is independently at each occurrence $(C_1-C_6)$alkyl, $(C_1-C_6)$alkoxy, $(C_1-C_6)$haloalkyl, $(C_1-C_6)$haloalkoxy, halogen, —CN, —OH, or —NH$_2$; or two $R_2$ together with the carbon atoms to which they are attached form a $(C_3-C_7)$cycloalkyl or a 4- to 7-membered heterocycloalkyl ring comprising 1-3 heteroatoms selected from O, N, and S; or two $R_2$ together when on adjacent carbon atoms form a phenyl or a 5- or 6-membered heteroaryl ring comprising 1-3 heteroatoms selected from O, N, and S; or $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_3$ is $(C_1-C_6)$alkyl, $(C_1-C_6)$alkoxy, $(C_1-C_6)$haloalkyl, $(C_1-C_6)$haloalkoxy, halogen, —OH, or —NH$_2$;

$R_4$ is —OR$_5$ or —NR$_6$R$_{6'}$;

$R_5$ is H, $(C_1-C_6)$alkyl, $(C_1-C_6)$haloalkyl, $(C_3-C_7)$cycloalkyl, 5- or 6-membered heterocycloalkyl comprising 1-3 heteroatoms selected from O, N, and S, $(C_6-C_{10})$aryl, or 5- or 6-membered heteroaryl comprising 1-3 heteroatoms selected from O, N, and S, wherein the alkyl is optionally substituted with one to three substituents independently selected from $(C_6-C_{10})$aryl and 5- or 6-membered heteroaryl comprising 1-3 heteroatoms selected from O, N, and S;

$R_6$ and $R_{6'}$ are each independently H, $(C_1$-$C_6)$alkyl, $(C_1$-$C_6)$haloalkyl, $(C_3$-$C_7)$cycloalkyl, 5- or 6-membered heterocycloalkyl comprising 1-3 heteroatoms selected from O, N, and S, $(C_6$-$C_{10})$aryl, or 5- or 6-membered heteroaryl comprising 1-3 heteroatoms selected from O, N, and S, wherein the alkyl is optionally substituted with one to three $R_7$; or $R_6$ and $R_{6'}$ together with the nitrogen atom to which they are attached form a 4- to 7-membered heterocycloalkyl ring optionally comprising 1-2 additional heteroatoms selected from O, N, and S, and optionally substituted with one to four $R_8$; or $R_2$ and $R_6$ together with the carbon and nitrogen atoms to which they are attached form a 5- or 6-membered heterocycloalkyl ring optionally comprising 1-2 additional heteroatoms selected from O, N, and S, and optionally substituted with one to four substituents each independently selected from $(C_1$-$C_6)$alkyl, $(C_1$-$C_6)$haloalkyl, halogen, —OH, —CN, and —NH$_2$;

each $R_7$ is $(C_3$-$C_7)$cycloalkyl, 4- to 7-membered heterocycloalkyl ring comprising 1-3 heteroatoms selected from O, N, and S, $(C_6$-$C_{10})$aryl, or 5- or 6-membered heteroaryl comprising 1-3 heteroatoms selected from O, N, and S, wherein the cycloalkyl, heterocycloalkyl, aryl, and heteroaryl are optionally substituted with one to four $R_9$;

each $R_8$ is independently at each occurrence halogen, $(C_1$-$C_6)$alkyl, $(C_1$-$C_6)$haloalkyl, halogen, —CN, —OH, or —NH$_2$; or two $R_8$ together with the atoms to which they are attached form a $(C_5$-$C_7)$cycloalkyl or a 4- to 7-membered heterocycloalkyl ring comprising 1-2 heteroatoms selected from O, N, and S;

each $R_9$ is independently at each occurrence $(C_1$-$C_6)$alkyl, $(C_1$-$C_6)$haloalkyl, halogen, —OH, —CN, or —NH$_2$; or two $R_9$ together with the atoms to which they are attached form a $(C_5$-$C_7)$cycloalkyl or a 5- to 7-membered heterocycloalkyl ring comprising 1-2 heteroatoms selected from O, N, and S optionally substituted with one or more substituents each independently selected from $(C_1$-$C_6)$alkyl, $(C_1$-$C_6)$haloalkyl, halogen, —OH, —CN, and —NH$_2$;

m and m1 are each independently 0, 1 or 2;

n1 is 0, 1, 2, or 3; and each s and n is independently 1, 2, or 3, wherein s+n is ≤4;

or pharmaceutically acceptable salts, hydrates, solvates, prodrugs, stereoisomers, and tautomers thereof.

Embodiment 3

The compound of any one of Embodiments 1, 2, and 2A, wherein $R_1$ is

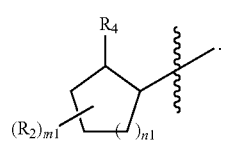

Embodiment 4

The compound of any one of Embodiments 1, 2, and 2A, wherein n1 is 0, 1, or 2.

Embodiment 5

The compound of any one of Embodiments 1 to 3 and 2A, wherein m is 0.

Embodiment 6

The compound of any one of Embodiments 1 to 3 and 2A, wherein m is 2.

Embodiment 7

The compound of any one of Embodiments 1, 2, and 2A, wherein $R_1$ is

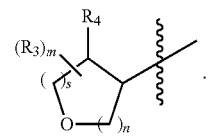

Embodiment 8

The compound of Embodiment 7, wherein n is 2 and s is 1 or 2.

Embodiment 9

The compound of Embodiment 7 or 8, wherein m is 0 or 1.

Embodiment 10

The compound of any one of Embodiments 1, 2, and 2A, having a Formula (Ia) or Formula (Ib), or a pharmaceutically acceptable salt, hydrate, solvate, prodrug, stereoisomer, and tautomer thereof.

Embodiment 11

The compound of any one of Embodiments 1, 2, and 2A, having a Formula (Ic), Formula (Id), Formula (Ie), Formula (If), Formula (Ig), Formula (Ih), Formula (Ii), or Formula (Ij), or a pharmaceutically acceptable salt, hydrate, solvate, prodrug, stereoisomer, and tautomer thereof.

Embodiment 12

The compound of any one of Embodiments 1, 2, and 2A, having a Formula (Ik), Formula (Il), Formula (Im), Formula (In), Formula (Io), or Formula (Ip), or a pharmaceutically acceptable salt, hydrate, solvate, prodrug, stereoisomer, and tautomer thereof.

Embodiment 13

The compound of any one of Embodiments 1 to 12 and 2A, wherein $R_4$ is —OR$_5$.

Embodiment 14

The compound of any one of Embodiments 1 to 12 and 2A, wherein $R_4$ is —NR$_6$R$_{6'}$.

Embodiment 15

The compound of any one of Embodiments 1, 2, and 2A, having a Formula (Iq), Formula (Ir), Formula (Is), or Formula (It), or a pharmaceutically acceptable salt, hydrate, solvate, prodrug, stereoisomer, and tautomer thereof.

Embodiment 16

The compound of Embodiment 1 selected from:

| Compound Structure/Compound Name |
|---|
| 3-(5-((((1S,2S)-2-((2,2-difluoroethyl)(ethyl)amino)cyclopentyl)oxy)-1-oxoisoindolin-2-yl)piperidine-2,6-dione |
| 3-(5-((((1S,2R)-2-((2,2-difluoroethyl)(ethyl)amino)cyclopentyl)oxy)-1-oxoisoindolin-2-yl)piperidine-2,6-dione |
| 3-(5-((((1R,2S)-2-((2,2-difluoroethyl)(ethyl)amino)cyclopentyl)oxy)-1-oxoisoindolin-2-yl)piperidine-2,6-dione |
| 3-(5-((((1R,2R)-2-((2,2-difluoroethyl)(ethyl)amino)cyclopentyl)oxy)-1-oxoisoindolin-2-yl)piperidine-2,6-dione |

-continued

| Compound Structure/Compound Name |
|---|
| 3-(5-((2-((2,2-difluoroethyl)(ethyl)amino)cyclopentyl)oxy)-1-oxoisoindolin-2-yl)piperidine-2,6-dione |
| 3-(5-((((1S,2R)-2-(benzylamino)cyclohexyl)oxy)-1-oxoisoindolin-2-yl)piperidine-2,6-dione |
| 3-(5-((((1S,2S)-2-(benzylamino)cyclohexyl)oxy)-1-oxoisoindolin-2-yl)piperidine-2,6-dione |
| 3-(5-((((1R,2S)-2-(benzylamino)cyclohexyl)oxy)-1-oxoisoindolin-2-yl)piperidine-2,6-dione |
| 3-(5-((((1R,2R)-2-(benzylamino)cyclohexyl)oxy)-1-oxoisoindolin-2-yl)piperidine-2,6-dione |

| Compound Structure/Compound Name | Compound Structure/Compound Name |
|---|---|
| 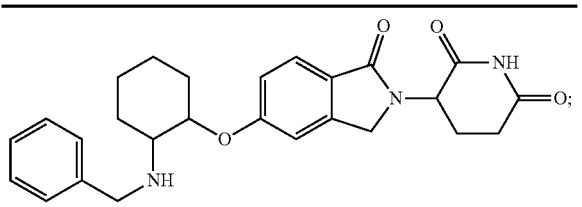<br>3-(5-((2-(benzylamino)cyclohexyl)oxy)-1-oxoisoindolin-2-yl)piperidine-2,6-dione | 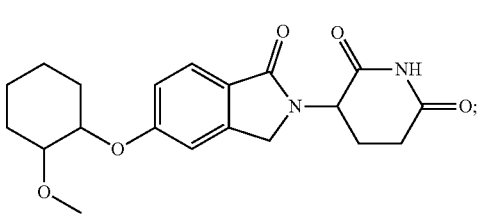<br>3-(5-((2-methoxycyclohexyl)oxy)-1-oxoisoindolin-2-yl)piperidine-2,6-dione |
| 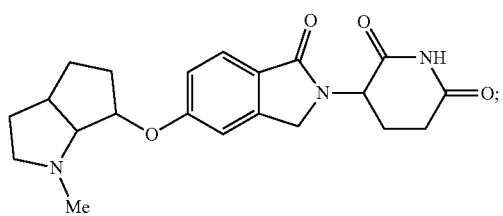<br>3-(5-((1-methyloctahydrocyclopenta[b]pyrrol-6-yl)oxy)-1-oxoisoindolin-2-yl)piperidine-2,6-dione | 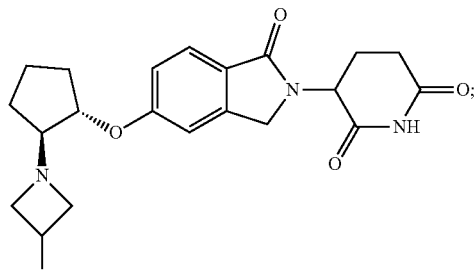<br>3-(5-(((1S,2S)-2-(3-hydroxyazetidin-1-yl)cyclopentyl)oxy)-1-oxoisoindolin-2-yl)piperidine-2,6-dione |
| 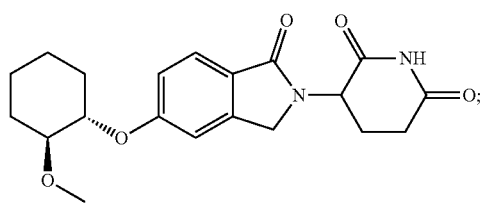<br>3-(5-(((1S,2S)-2-methoxycyclohexyl)oxy)-1-oxoisoindolin-2-yl)piperidine-2,6-dione | |
| 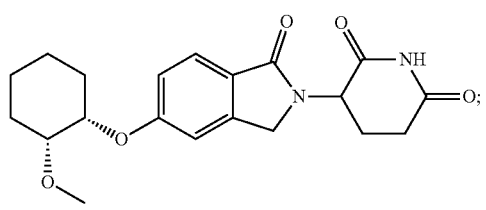<br>3-(5-(((1S,2R)-2-methoxycyclohexyl)oxy)-1-oxoisoindolin-2-yl)piperidine-2,6-dione | 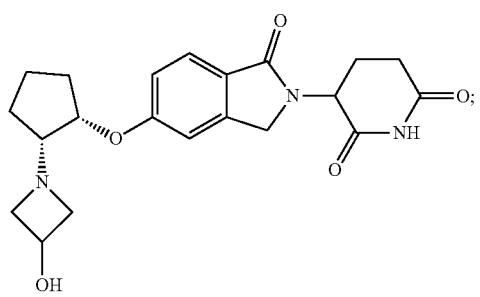<br>3-(5-(((1S,2R)-2-(3-hydroxyazetidin-1-yl)cyclopentyl)oxy)-1-oxoisoindolin-2-yl)piperidine-2,6-dione |
| 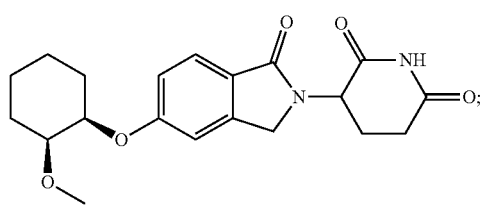<br>3-(5-(((1R,2S)-2-methoxycyclohexyl)oxy)-1-oxoisoindolin-2-yl)piperidine-2,6-dione | |
| 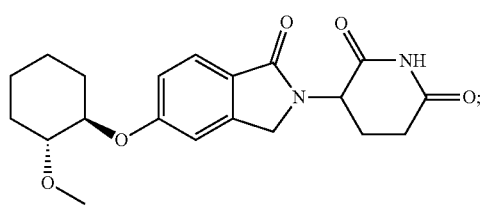<br>3-(5-(((1R,2R)-2-methoxycyclohexyl)oxy)-1-oxoisoindolin-2-yl)piperidine-2,6-dione | 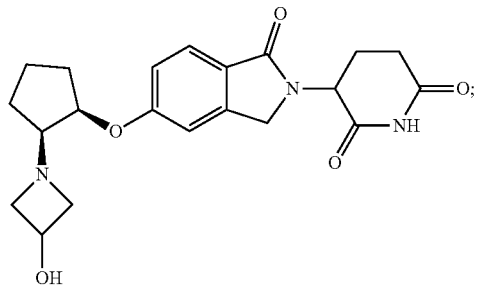<br>3-(5-(((1R,2S)-2-(3-hydroxyazetidin-1-yl)cyclopentyl)oxy)-1-oxoisoindolin-2-yl)piperidine-2,6-dione |

| Compound Structure/Compound Name |
|---|
| 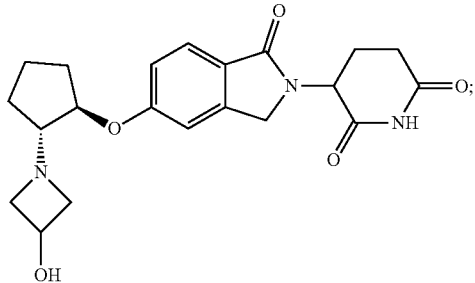<br>3-(5-(((1R,2R)-2-(3-hydroxyazetidin-1-yl)cyclopentyl)oxy)-1-oxoisoindolin-2-yl)piperidine-2,6-dione |
| 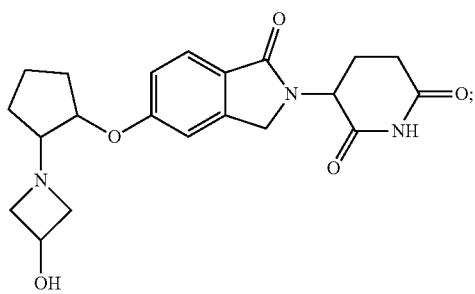<br>3-(5-((2-(3-hydroxyazetidin-1-yl)cyclopentyl)oxy)-1-oxoisoindolin-2-yl)piperidine-2,6-dione |
| 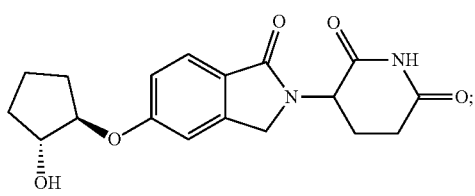<br>3-(5-(((1R,2R)-2-hydroxycyclopentyl)oxy)-1-oxoisoindolin-2-yl)piperidine-2,6-dione |
| 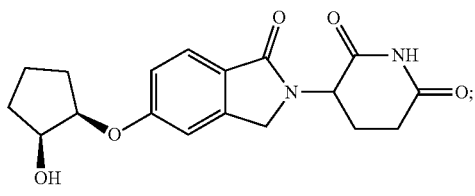<br>3-(5-(((1R,2S)-2-hydroxycyclopentyl)oxy)-1-oxoisoindolin-2-yl)piperidine-2,6-dione |
| 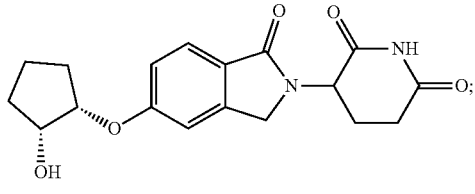<br>3-(5-(((1S,2R)-2-hydroxycyclopentyl)oxy)-1-oxoisoindolin-2-yl)piperidine-2,6-dione |

| Compound Structure/Compound Name |
|---|
| 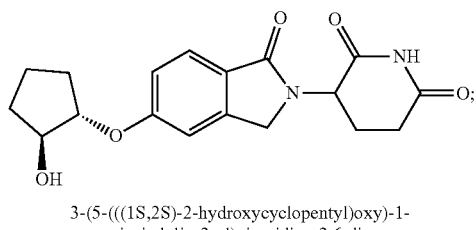<br>3-(5-(((1S,2S)-2-hydroxycyclopentyl)oxy)-1-oxoisoindolin-2-yl)piperidine-2,6-dione |
| 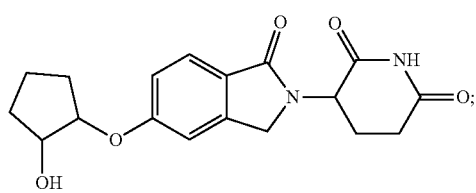<br>3-(5-((2-hydroxycyclopentyl)oxy)-1-oxoisoindolin-2-yl)piperidine-2,6-dione |
| 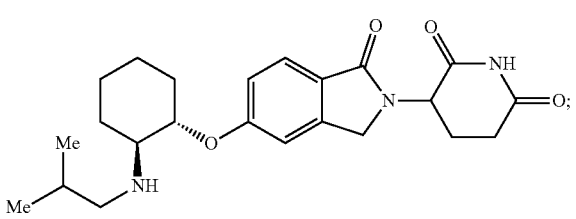<br>3-(5-(((1S,2S)-2-(isobutylamino)cyclohexyl)oxy)-1-oxoisoindolin-2-yl)piperidine-2,6-dione |
| 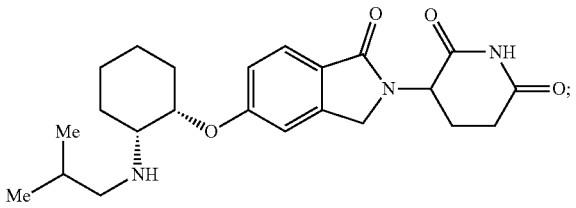<br>3-(5-(((1S,2R)-2-(isobutylamino)cyclohexyl)oxy)-1-oxoisoindolin-2-yl)piperidine-2,6-dione |
| 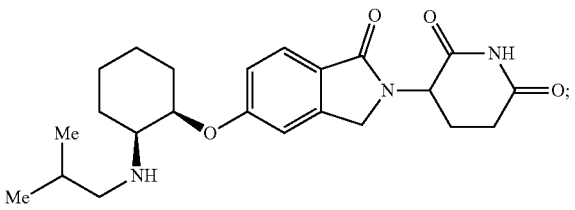<br>3-(5-(((1R,2S)-2-(isobutylamino)cyclohexyl)oxy)-1-oxoisoindolin-2-yl)piperidine-2,6-dione |
| 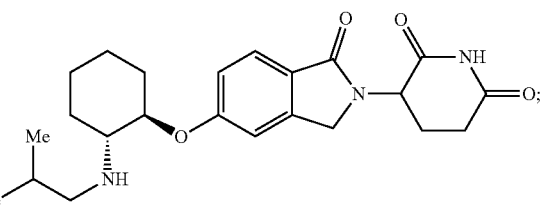<br>3-(5-(((1R,2R)-2-(isobutylamino)cyclohexyl)oxy)-1-oxoisoindolin-2-yl)piperidine-2,6-dione |

| Compound Structure/Compound Name |
|---|
| 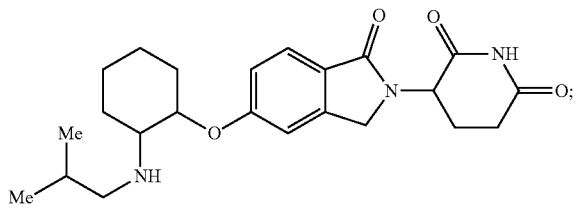<br>3-(5-((2-(isobutylamino)cyclohexyl)oxy)-1-oxoisoindolin-2-yl)piperidine-2,6-dione |
| 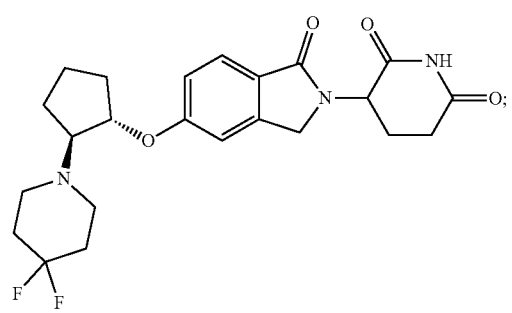<br>3-(5-(((1S,2S)-2-(4,4-difluoropiperidin-1-yl)cyclopentyl)oxy)-1-oxoisoindolin-2-yl)piperidine-2,6-dione |
| 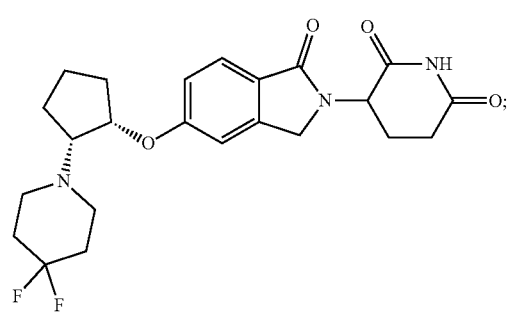<br>3-(5-(((1S,2S)-2-(4,4-difluoropiperidin-1-yl)cyclopentyl)oxy)-1-oxoisoindolin-2-yl)piperidine-2,6-dione |
| 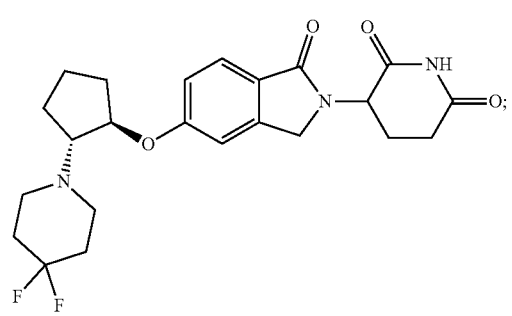<br>3-(5-(((1R,2R)-2-(4,4-difluoropiperidin-1-yl)cyclopentyl)oxy)-1-oxoisoindolin-2-yl)piperidine-2,6-dione |
| 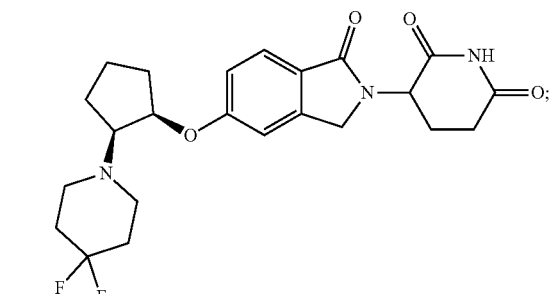<br>3-(5-(((1R,2S)-2-(4,4-difluoropiperidin-1-yl)cyclopentyl)oxy)-1-oxoisoindolin-2-yl)piperidine-2,6-dione |
| 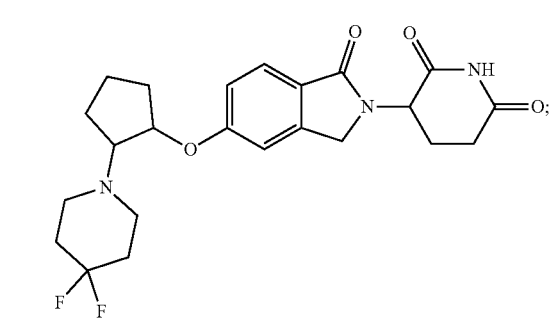<br>3-(5-((2-(4,4-difluoropiperidin-1-yl)cyclopentyl)oxy)-1-oxoisoindolin-2-yl)piperidine-2,6-dione |
| <br>3-(5-(((1S,2S)-2-(benzyloxy)cyclopentyl)oxy)-1-oxoisoindolin-2-yl)piperidine-2,6-dione |
| <br>3-(5-(((1S,2R)-2-(benzyloxy)cyclopentyl)oxy)-1-oxoisoindolin-2-yl)piperidine-2,6-dione |
| <br>3-(5-(((1R,2R)-2-(benzyloxy)cyclopentyl)oxy)-1-oxoisoindolin-2-yl)piperidine-2,6-dione |

| Compound Structure/Compound Name |
|---|
| 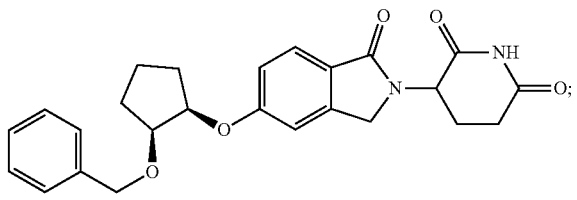 3-(5-((((1R,2S)-2-(benzyloxy)cyclopentyl)oxy)-1-oxoisoindolin-2-yl)piperidine-2,6-dione |
| 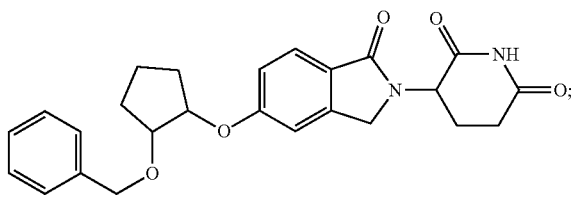 3-(5-((2-(benzyloxy)cyclopentyl)oxy)-1-oxoisoindolin-2-yl)piperidine-2,6-dione |
| 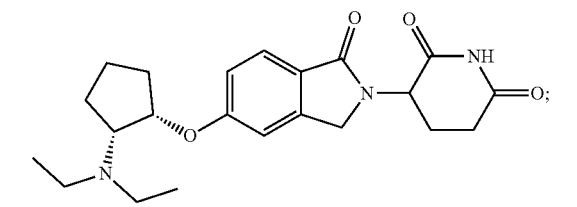 3-(5-((((1S,2R)-2-(diethylamino)cyclopentyl)oxy)-1-oxoisoindolin-2-yl)piperidine-2,6-dione |
| 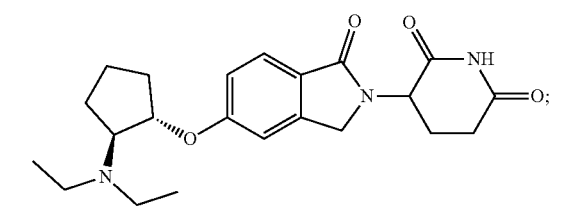 3-(5-((((1S,2S)-2-(diethylamino)cyclopentyl)oxy)-1-oxoisoindolin-2-yl)piperidine-2,6-dione |
| 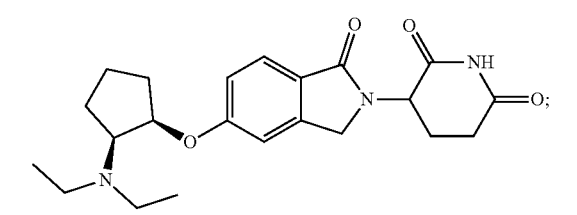 3-(5-((((1R,2S)-2-(diethylamino)cyclopentyl)oxy)-1-oxoisoindolin-2-yl)piperidine-2,6-dione |
| 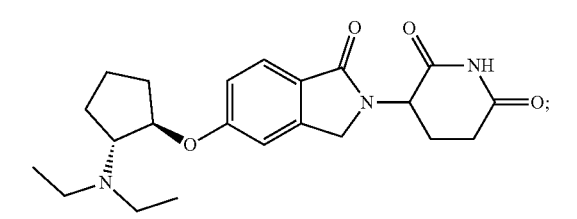 3-(5-((((1R,2R)-2-(diethylamino)cyclopentyl)oxy)-1-oxoisoindolin-2-yl)piperidine-2,6-dione |

| Compound Structure/Compound Name |
|---|
| 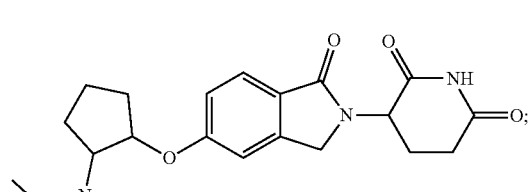 3-(5-((2-(diethylamino)cyclopentyl)oxy)-1-oxoisoindolin-2-yl)piperidine-2,6-dione |
| 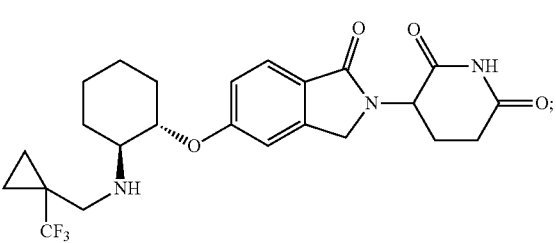 3-(1-oxo-5-((((1S,2S)-2-(((1-(trifluoromethyl)cyclopropyl)methyl)amino)cyclohexyl)oxy)isoindolin-2-yl)piperidine-2,6-dione |
| 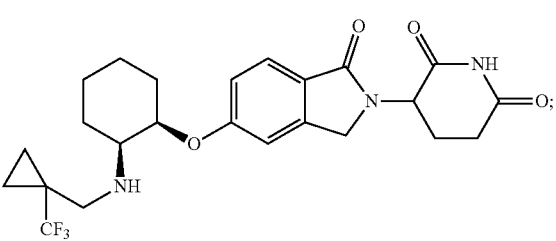 3-(1-oxo-5-((((1R,2S)-2-(((1-(trifluoromethyl)cyclopropyl)methyl)amino)cyclohexyl)oxy)isoindolin-2-yl)piperidine-2,6-dione |
| 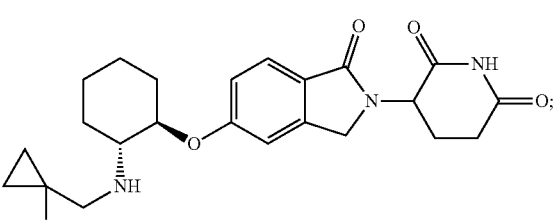 3-(1-oxo-5-((((1R,2R)-2-(((1-(trifluoromethyl)cyclopropyl)methyl)amino)cyclohexyl)oxy)isoindolin-2-yl)piperidine-2,6-dione |
| 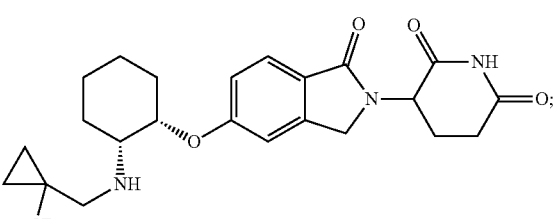 3-(1-oxo-5-((((1S,2R)-2-(((1-(trifluoromethyl)cyclopropyl)methyl)amino)cyclohexyl)oxy)isoindolin-2-yl)piperidine-2,6-dione |

| Compound Structure/Compound Name | Compound Structure/Compound Name |
|---|---|
| 3-(1-oxo-5-((2-(((1-(trifluoromethyl)cyclopropyl)methyl)amino)cyclohexyl)oxy)isoindolin-2-yl)piperidine-2,6-dione | 3-(5-(((1S,2S)-2-(diethylamino)cyclohexyl)oxy)-1-oxoisoindolin-2-yl)piperidine-2,6-dione |
| 3-(5-(((1S,2S)-2-aminocyclopentyl)oxy)-1-oxoisoindolin-2-yl)piperidine-2,6-dione | 3-(5-(((1S,2R)-2-(diethylamino)cyclohexyl)oxy)-1-oxoisoindolin-2-yl)piperidine-2,6-dione |
| 3-(5-(((1S,2R)-2-aminocyclopentyl)oxy)-1-oxoisoindolin-2-yl)piperidine-2,6-dione | 3-(5-(((1R,2R)-2-(diethylamino)cyclohexyl)oxy)-1-oxoisoindolin-2-yl)piperidine-2,6-dione |
| 3-(5-(((1R,2R)-2-aminocyclopentyl)oxy)-1-oxoisoindolin-2-yl)piperidine-2,6-dione | 3-(5-(((1R,2S)-2-(diethylamino)cyclohexyl)oxy)-1-oxoisoindolin-2-yl)piperidine-2,6-dione |
| 3-(5-(((1R,2S)-2-aminocyclopentyl)oxy)-1-oxoisoindolin-2-yl)piperidine-2,6-dione | |
| 3-(5-((2-aminocyclopentyl)oxy)-1-oxoisoindolin-2-yl)piperidine-2,6-dione | 3-(5-((2-(diethylamino)cyclohexyl)oxy)-1-oxoisoindoline-2-yl)piperidine-2,6-dione |

| Compound Structure/Compound Name | Compound Structure/Compound Name |
|---|---|
| 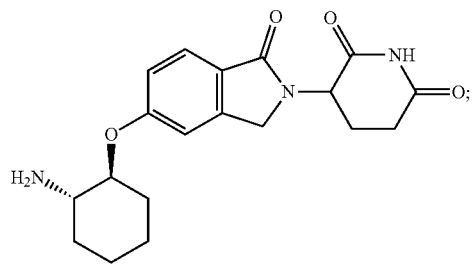<br>3-(5-(((1S,2S)-2-aminocyclohexyl)oxy)-1-oxoisoindolin-2-yl)piperidine-2,6-dione | 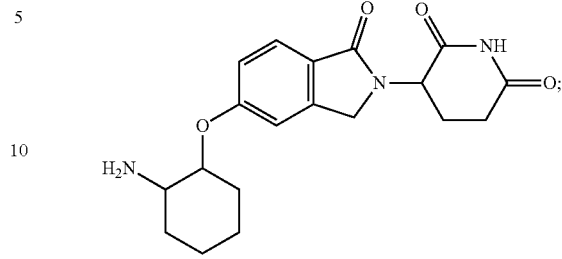<br>3-(5-((2-aminocyclohexyl)oxy)-1-oxoisoindolin-2-yl)piperidine-2,6-dione |
| <br>3-(5-(((1S,2R)-2-aminocyclohexyl)oxy)-1-oxoisoindolin-2-yl)piperidine-2,6-dione | 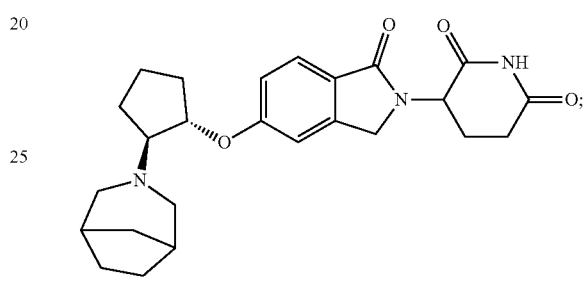<br>3-(5-(((1S,2S)-2-(3-azabicyclo[3.2.1]octan-3-yl)cyclopentyl)oxy)-1-oxoisoindolin-2-yl)piperidine-2,6-dione |
| 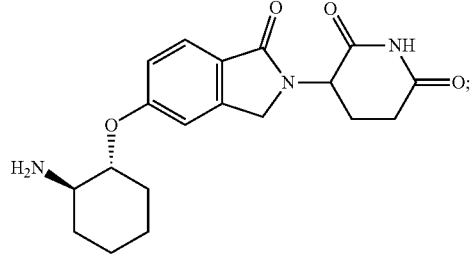<br>3-(5-(((1R,2R)-2-aminocyclohexyl)oxy)-1-oxoisoindolin-2-yl)piperidine-2,6-dione | 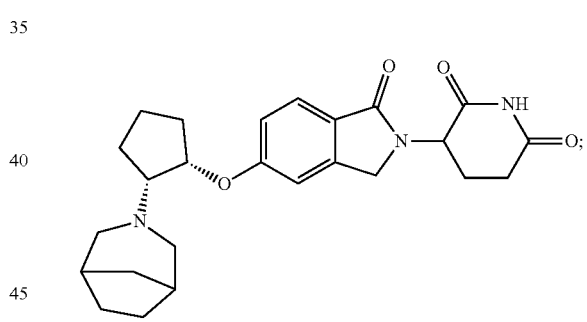<br>3-(5-(((1S,2R)-2-(3-azabicyclo[3.2.1]octan-3-yl)cyclopentyl)oxy)-1-oxoisoindolin-2-yl)piperidine-2,6-dione |
| 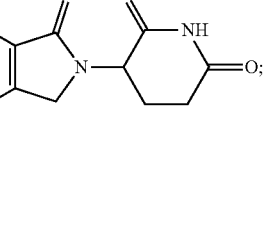<br>3-(5-(((1R,2S)-2-aminocyclohexyl)oxy)-1-oxoisoindolin-2-yl)piperidine-2,6-dione | 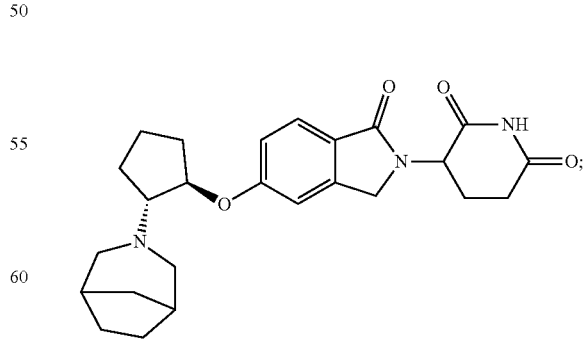<br>3-(5-(((1R,2R)-2-(3-azabicyclo[3.2.1]octan-3-yl)cyclopentyl)oxy)-1-oxoisoindolin-2-yl)piperidine-2,6-dione |

| Compound Structure/Compound Name |
|---|
| 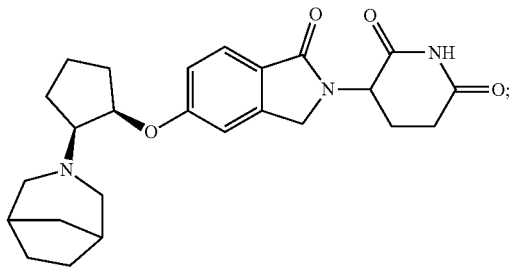<br>3-(5-(((1R,2S)-2-(3-azabicyclo[3.2.1]octan-3-yl)cyclopentyl)oxy)-1-oxoisoindolin-2-yl)piperidine-2,6-dione |
| 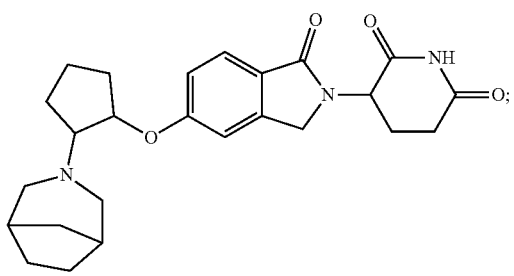<br>3-(5-((2-(3-azabicyclo[3.2.1]octan-3-yl)cyclopentyl)oxy)-1-oxoisoindolin-2-yl)piperidine-2,6-dione |
| 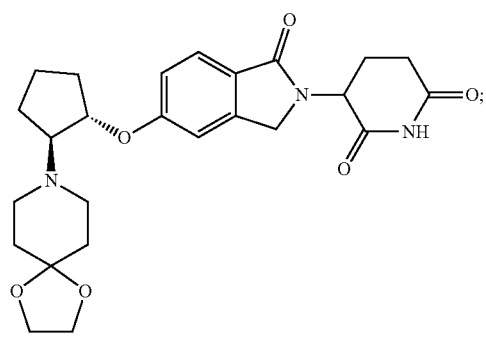<br>3-(5-(((1S,2S)-2-(1,4-dioxa-8-azaspiro[4.5]decan-8-yl)cyclopentyl)oxy)-1-oxoisoindolin-2-yl)piperidine-2,6-dione |
| 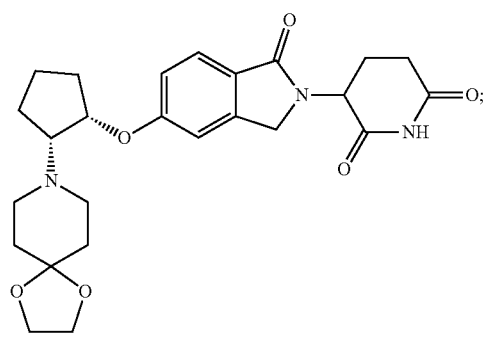<br>3-(5-(((1S,2R)-2-(1,4-dioxa-8-azaspiro[4.5]decan-8-yl)cyclopentyl)oxy)-1-oxoisoindolin-2-yl)piperidine-2,6-dione |

| Compound Structure/Compound Name |
|---|
| 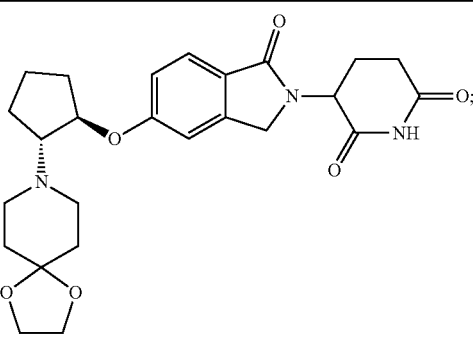<br>3-(5-(((1R,2R)-2-(1,4-dioxa-8-azaspiro[4.5]decan-8-yl)cyclopentyl)oxy)-1-oxoisoindolin-2-yl)piperidine-2,6-dione |
| 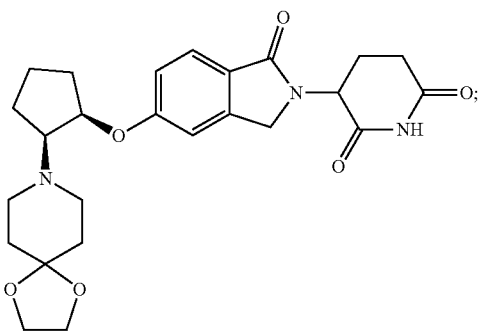<br>3-(5-(((1R,2S)-2-(1,4-dioxa-8-azaspiro[4.5]decan-8-yl)cyclopentyl)oxy)-1-oxoisoindolin-2-yl)piperidine-2,6-dione |
| 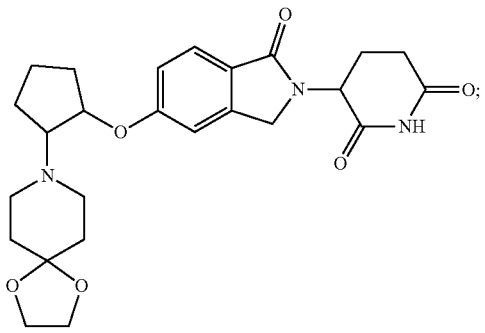<br>3-(5-((2-(1,4-dioxa-8-azaspiro[4.5]decan-8-yl)cyclopentyl)oxy)-1-oxoisoindolin-2-yl)piperidine-2,6-dione |
| 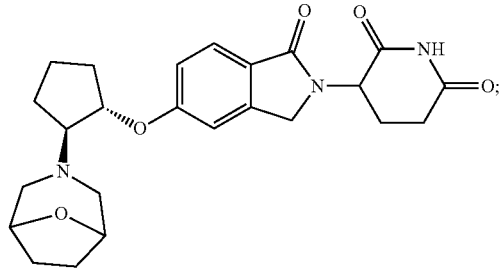<br>3-(5-(((1S,2S)-2-(8-oxa-3-azabicyclo[3.2.1]octan-3-yl)cyclopentyl)oxy)-1-oxoisoindolin-2-yl)piperidine-2,6-dione |

| Compound Structure/Compound Name | Compound Structure/Compound Name |
|---|---|
| 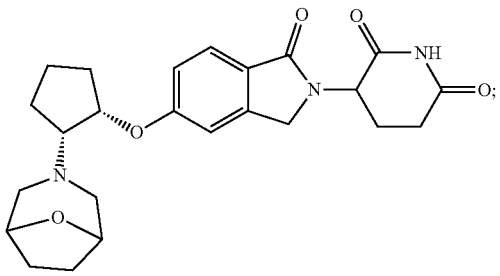<br>3-(5-(((1S,2R)-2-(8-oxa-3-azabicyclo[3.2.1]octan-3-yl)cyclopentyl)oxy)-1-oxoisoindolin-2-yl)piperidine-2,6-dione | 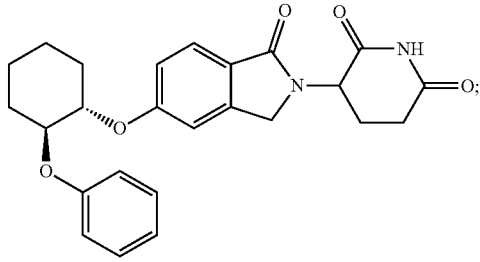<br>3-(1-oxo-5-(((1S,2S)-2-phenoxycyclohexyl)oxy)isoindolin-2-yl)piperidine-2,6-dione |
| 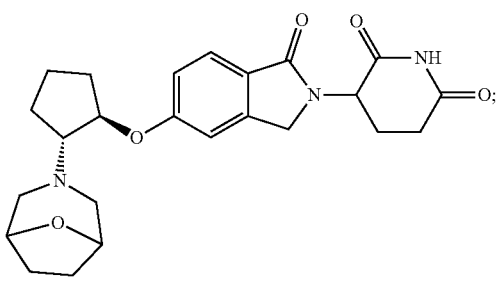<br>3-(5-(((1R,2R)-2-(8-oxa-3-azabicyclo[3.2.1]octan-3-yl)cyclopentyl)oxy)-1-oxoisoindolin-2-yl)piperidine-2,6-dione | 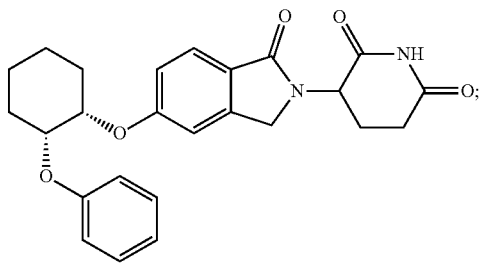<br>3-(1-oxo-5-(((1S,2R)-2-phenoxycyclohexyl)oxy)isoindolin-2-yl)piperidine-2,6-dione |
| 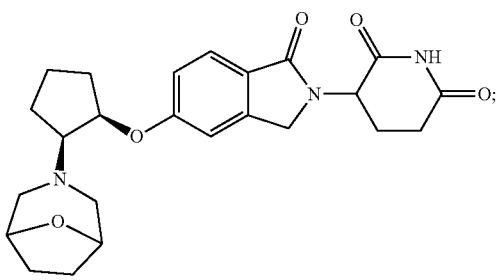<br>3-(5-(((1R,2S)-2-(8-oxa-3-azabicyclo[3.2.1]octan-3-yl)cyclopentyl)oxy)-1-oxoisoindolin-2-yl)piperidin-2,6-dione | 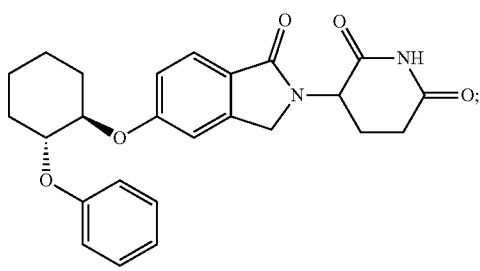<br>3-(1-oxo-5-(((1R,2R)-2-phenoxycyclohexyl)oxy)isoindolin-2-yl)piperidine-2,6-dione |
| 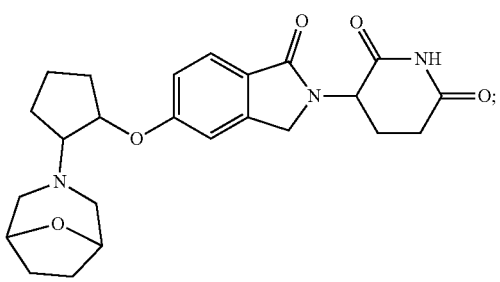<br>3-(5-((2-(8-oxa-3-azabicyclo[3.2.1]octan-3-yl)cyclopentyl)oxy)-1-oxoisoindolin-2-yl)piperidine-2,6-dione | 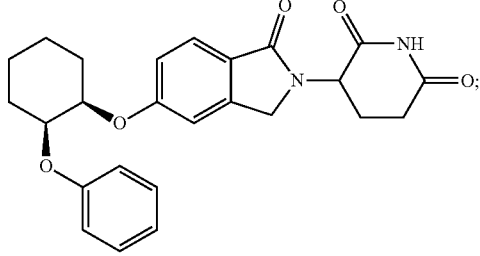<br>3-(1-oxo-5-(((1R,2S)-2-phenoxycyclohexyl)oxy)isoindolin-2-yl)piperidine-2,6-dione |

| Compound Structure/Compound Name |
|---|
| 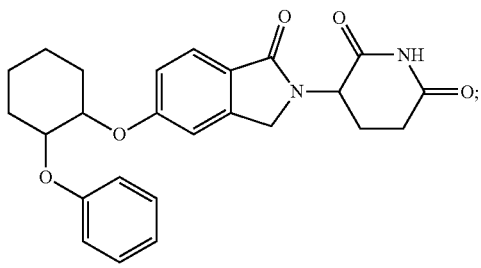<br>3-(1-oxo-5-((2-phenoxycyclohexyl)oxy)isoindolin-2-yl)piperidine-2,6-dione |
| 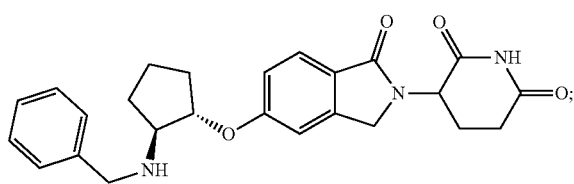<br>3-(5-(((1S,2S)-2-(benzylamino)cyclopentyl)oxy)-1-oxoisoindolin-2-yl)piperidine-2,6-dione |
| 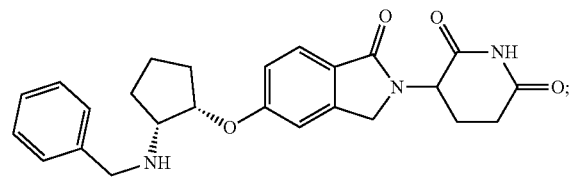<br>3-(5-(((1S,2R)-2-(benzylamino)cyclopentyl)oxy)-1-oxoisoindolin-2-yl)piperidine-2,6-dione |
| 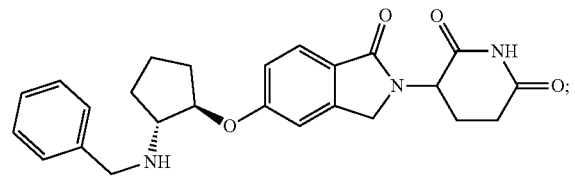<br>3-(5-(((1R,2R)-2-(benzylamino)cyclopentyl)oxy)-1-oxoisoindolin-2-yl)piperidine-2,6-dione |
| 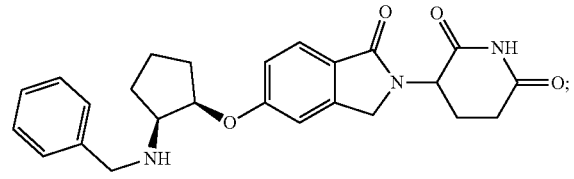<br>3-(5-(((1R,2S)-2-(benzylamino)cyclopentyl)oxy)-1-oxoisoindolin-2-yl)piperidine-2,6-dione |
| 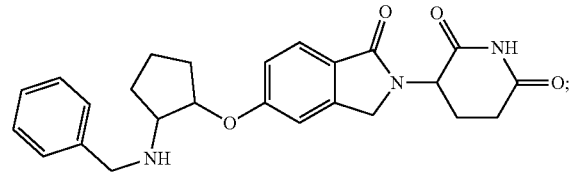<br>3-(5-((2-(benzylamino)cyclopentyl)oxy)-1-oxoisoindolin-2-yl)piperidine-2,6-dione |

| Compound Structure/Compound Name |
|---|
| 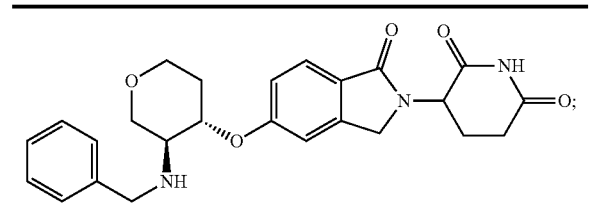<br>3-(5-(((3S,4S)-3-(benzylamino)tetrahydro-2H-pyran-4-yl)oxy)-1-oxoisoindolin-2-yl)piperidine-2,6-dione |
| 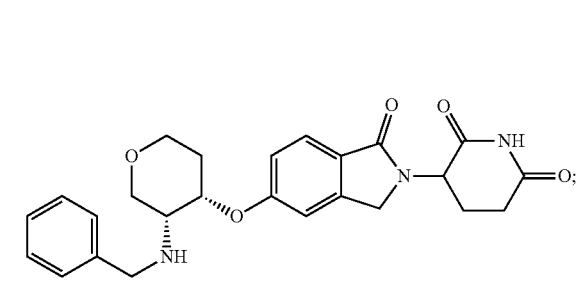<br>3-(5-(((3R,4S)-3-(benzylamino)tetrahydro-2H-pyran-4-yl)oxy)-1-oxoisoindolin-2-yl)piperidine-2,6-dione |
| 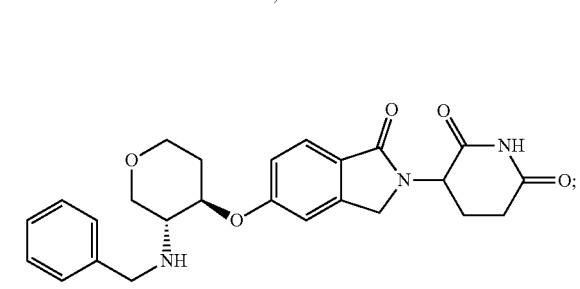<br>3-(5-(((3R,4R)-3-(benzylamino)tetrahydro-2H-pyran-4-yl)oxy)-1-oxoisoindolin-2-yl)piperidine-2,6-dione |
| 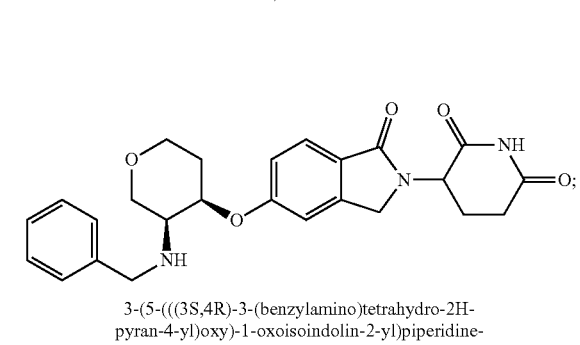<br>3-(5-(((3S,4R)-3-(benzylamino)tetrahydro-2H-pyran-4-yl)oxy)-1-oxoisoindolin-2-yl)piperidine-2,6-dione |
| 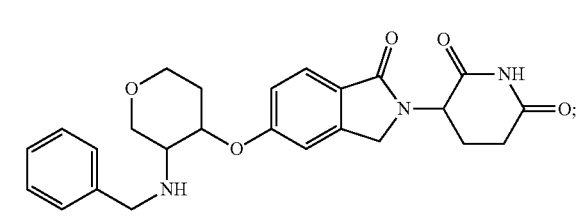<br>3-(5-((3-(benzylamino)tetrahydro-2H-pyran-4-yl)oxy)-1-oxoisoindolin-2-yl)piperidine-2,6-dione |

| Compound Structure/Compound Name | Compound Structure/Compound Name |
|---|---|
| 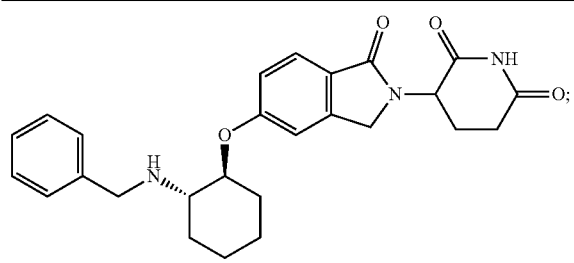<br>3-(5-(((1S,2S)-2-(benzylamino)cyclohexyl)oxy)-1-oxoisoindolin-2-yl)piperidine-2,6-dione | 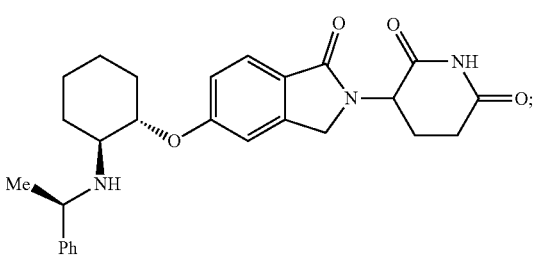<br>3-(1-oxo-5-(((1S,2S)-2-(((R)-1-phenylethyl)amino)cyclohexyl)oxy)isoindolin-2-yl)piperidine-2,6-dione |
| 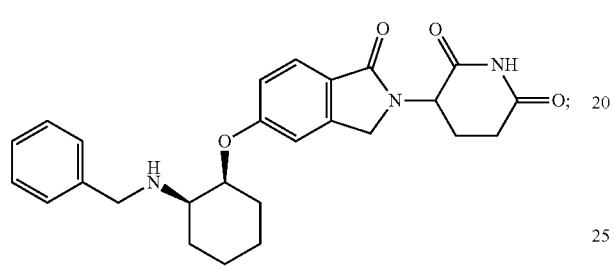<br>3-(5-(((1S,2R)-2-(benzylamino)cyclohexyl)oxy)-1-oxoisoindolin-2-yl)piperidine-2,6-dione | 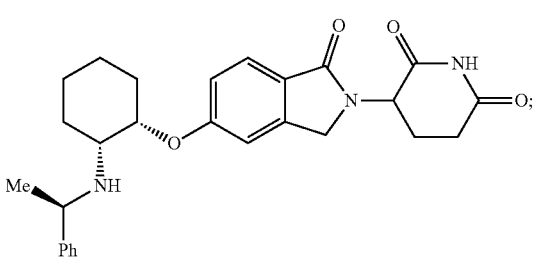<br>3-(1-oxo-5-(((1S,2R)-2-(((R)-1-phenylethyl)amino)cyclohexyl)oxy)isoindolin-2-yl)piperidine-2,6-dione |
| 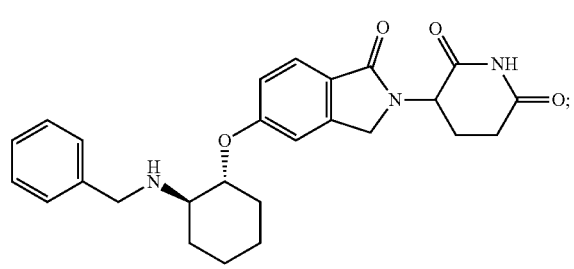<br>3-(5-(((1R,2R)-2-(benzylamino)cyclohexyl)oxy)-1-oxoisoindolin-2-yl)piperidine-2,6-dione | 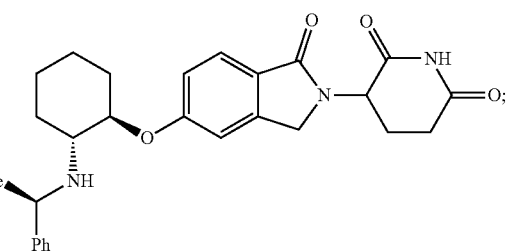<br>3-(1-oxo-5-(((1R,2R)-2-(((R)-1-phenylethyl)amino)cyclohexyl)oxy)isoindolin-2-yl)piperidine-2,6-dione |
| 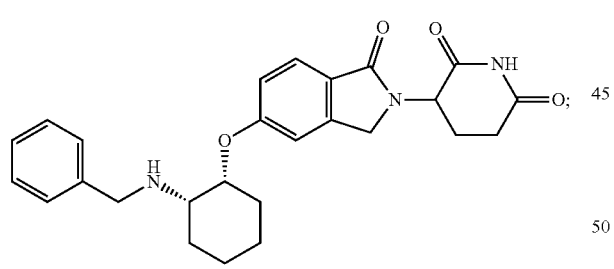<br>3-(5-(((1R,2S)-2-(benzylamino)cyclohexyl)oxy)-1-oxoisoindolin-2-yl)piperidine-2,6-dione | 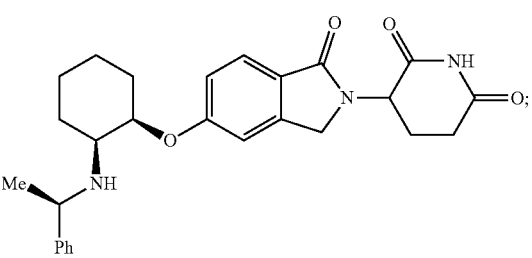<br>3-(1-oxo-5-(((1R,2S)-2-(((R)-1-phenylethyl)amino)cyclohexyl)oxy)isoindolin-2-yl)piperidine-2,6-dione |
| 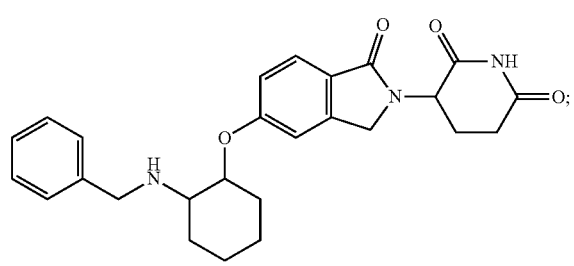<br>3-(5-((2-(benzylamino)cyclohexyl)oxy)-1-oxoisoindolin-2-yl)piperidine-2,6-dione | |

| Compound Structure/Compound Name | Compound Structure/Compound Name |
|---|---|
| 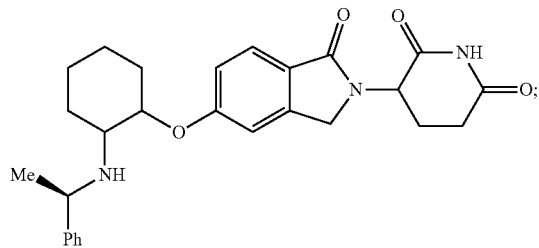<br>3-(1-oxo-5-((2-(((R)-1-phenylethyl)amino)cyclohexyl)oxy)isoindolin-2-yl)piperidine-2,6-dione | 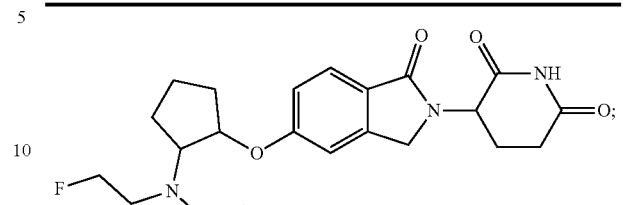<br>3-(5-((2-(ethyl(2-fluoroethyl)amino)cyclopentyl)oxy)-1-oxoisoindolin-2-yl)piperidine-2,6-dione |
| 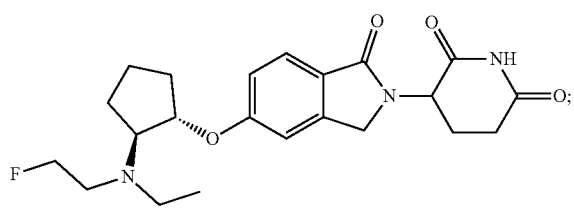<br>3-(5-(((1S,2S)-2-(ethyl(2-fluoroethyl)amino)cyclopentyl)oxy)-1-oxoisoindolin-2-yl)piperidine-2,6-dione | 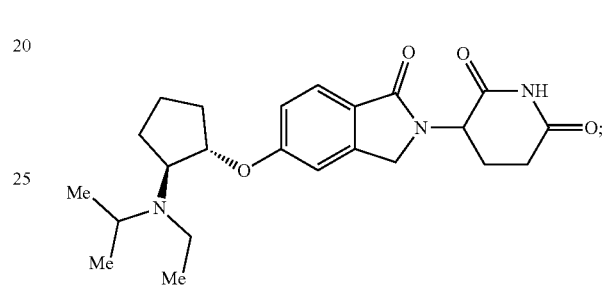<br>3-(5-(((1S,2S)-2-(ethyl(isopropyl)amino)cyclopentyl)oxy)-1-oxoisoindolin-2-yl)piperidine-2,6-dione |
| 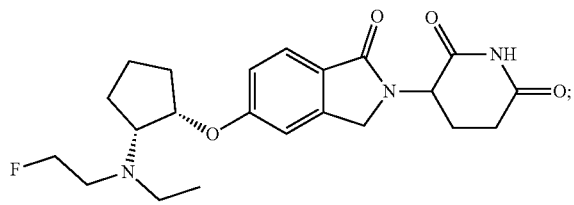<br>3-(5-(((1S,2R)-2-(ethyl(2-fluoroethyl)amino)cyclopentyl)oxy)-1-oxoisoindolin-2-yl)piperidine-2,6-dione | 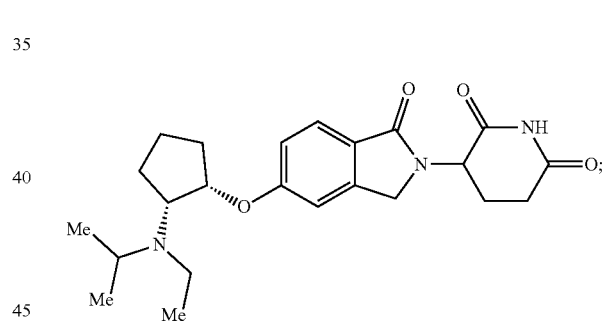<br>3-(5-(((1S,2R)-2-(ethyl(isopropyl)amino)cyclopentyl)oxy)-1-oxoisoindolin-2-yl)piperidine-2,6-dione |
| 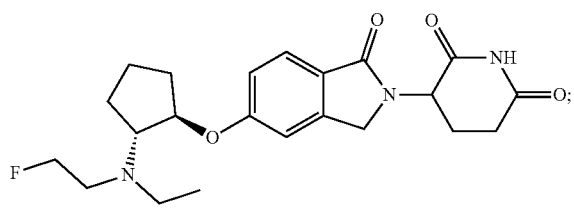<br>3-(5-(((1R,2R)-2-(ethyl(2-fluoroethyl)amino)cyclopentyl)oxy)-1-oxoisoindolin-2-yl)piperidine-2,6-dione | 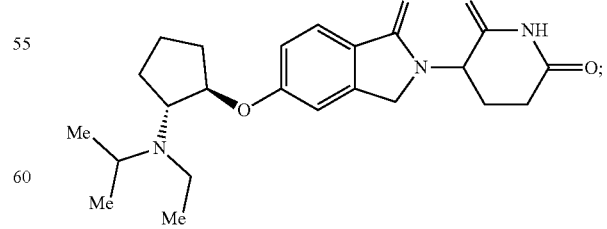<br>3-(5-(((1R,2R)-2-(ethyl(isopropyl)amino)cyclopentyl)oxy)-1-oxoisoindolin-2-yl)piperidine-2,6-dione |
| 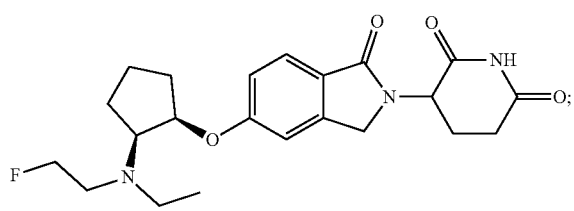<br>3-(5-(((1R,2S)-2-(ethyl(2-fluoroethyl)amino)cyclopentyl)oxy)-1-oxoisoindolin-2-yl)piperidine-2,6-dione | |

| Compound Structure/Compound Name |
|---|
| 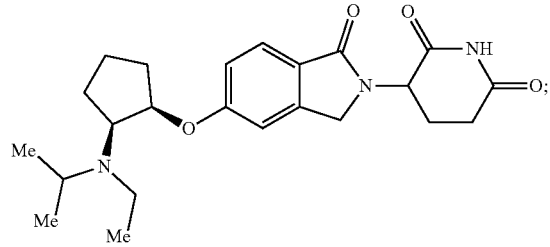<br>3-(5-(((1R,2S)-2-(ethyl(isopropyl)amino)cyclopentyl)oxy)-1-oxoisoindolin-2-yl)piperidine-2,6-dione |
| 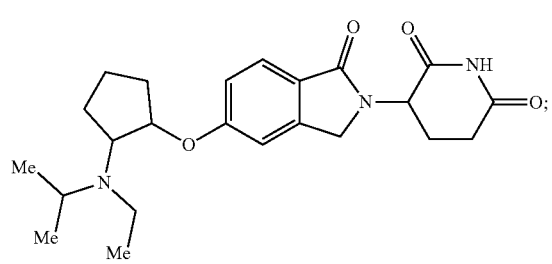<br>3-(5-((2-(ethyl(isopropyl)amino)cyclopentyl)oxy)-1-oxoisoindolin-2-yl)piperidine-2,6-dione |
| 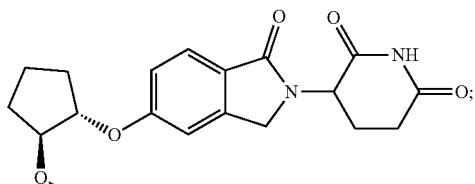<br>3-(5-(((1S,2S)-2-methoxycyclopentyl)oxy)-1-oxoisoindolin-2-yl)piperidine-2,6-dione |
| 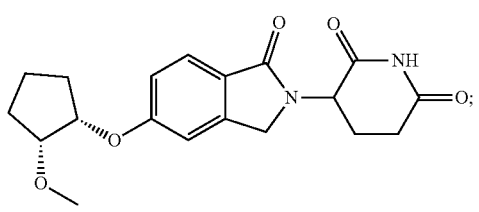<br>3-(5-(((1S,2R)-2-methoxycyclopentyl)oxy)-1-oxoisoindolin-2-yl)piperidine-2,6-dione |
| 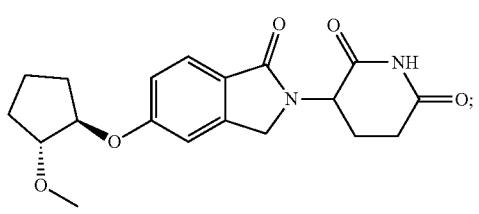<br>3-(5-(((1R,2R)-2-methoxycyclopentyl)oxy)-1-oxoisoindolin-2-yl)piperidine-2,6-dione |

| Compound Structure/Compound Name |
|---|
| 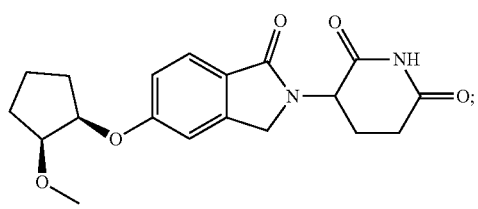<br>3-(5-(((1R,2S)-2-methoxycyclopentyl)oxy)-1-oxoisoindolin-2-yl)piperidine-2,6-dione |
| 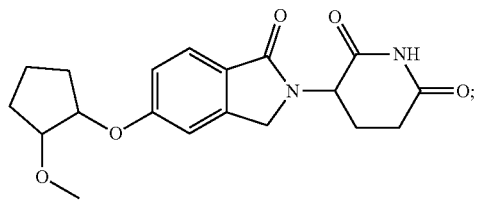<br>3-(5-((2-methoxycyclopentyl)oxy)-1-oxoisoindolin-2-yl)piperidine-2,6-dione |
| 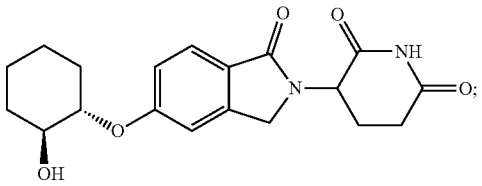<br>3-(5-(((1S,2S)-2-hydroxycyclohexyl)oxy)-1-oxoisoindolin-2-yl)piperidine-2,6-dione |
| 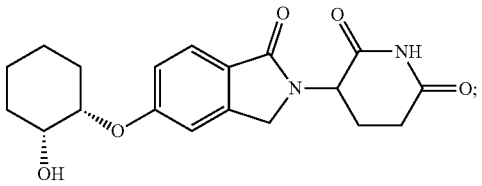<br>3-(5-(((1S,2R)-2-hydroxycyclohexyl)oxy)-1-oxoisoindolin-2-yl)piperidine-2,6-dione |
| 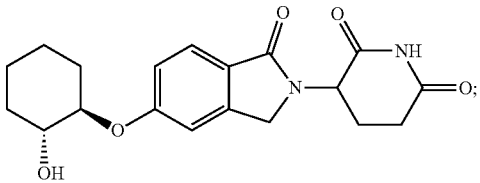<br>3-(5-(((1R,2R)-2-hydroxycyclohexyl)oxy)-1-oxoisoindolin-2-yl)piperidine-2,6-dione |
| 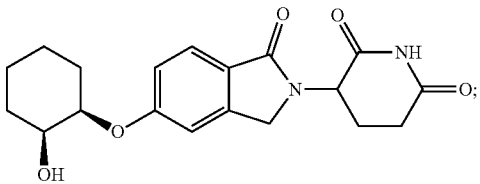<br>3-(5-(((1R,2S)-2-hydroxycyclohexyl)oxy)-1-oxoisoindolin-2-yl)piperidine-2,6-dione |

| Compound Structure/Compound Name | Compound Structure/Compound Name |
|---|---|
| 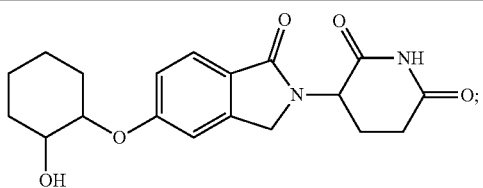<br>3-(5-((2-hydroxycyclohexyl)oxy)-1-oxoisoindolin-2-yl)piperidine-2,6-dione | 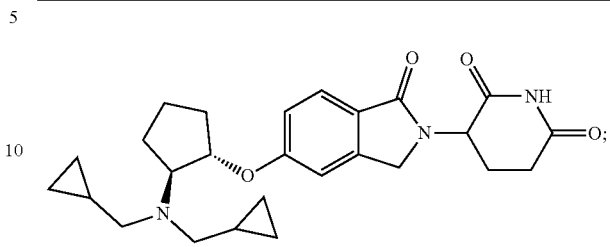<br>3-(5-(((1S,2S)-2-(bis(cyclopropylmethyl)amino)cyclopentyl)oxy)-1-oxoisoindolin-2-yl)piperidine-2,6-dione |
| 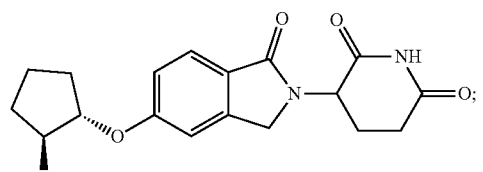<br>3-(5-(((1S,2S)-2-(ethylamino)cyclopentyl)oxy)-1-oxoisoindolin-2-yl)piperidine-2,6-dione | 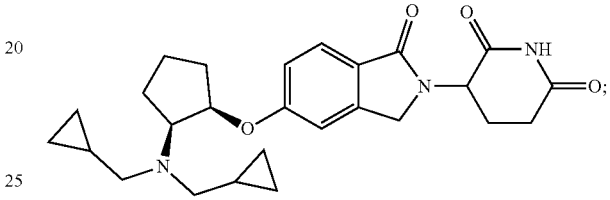<br>3-(5-(((1R,2S)-2-(bis(cyclopropylmethyl)amino)cyclopentyl)oxy)-1-oxoisoindolin-2-yl)piperidine-2,6-dione |
| 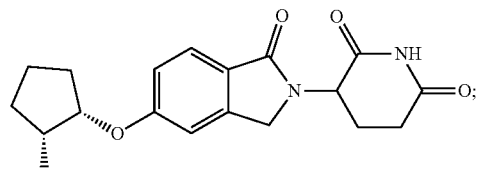<br>3-(5-(((1S,2R)-2-(ethylamino)cyclopentyl)oxy)-1-oxoisoindolin-2-yl)piperidine-2,6-dione | 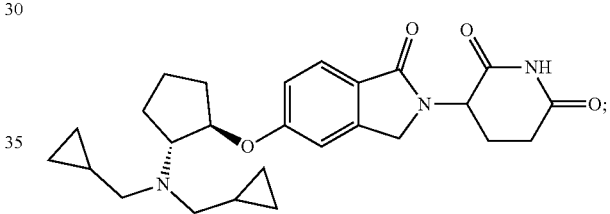<br>3-(5-(((1R,2R)-2-(bis(cyclopropylmethyl)amino)cyclopentyl)oxy)-1-oxoisoindolin-2-yl)piperidine-2,6-dione |
| 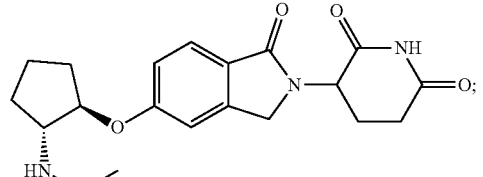<br>3-(5-(((1R,2R)-2-(ethylamino)cyclopentyl)oxy)-1-oxoisoindolin-2-yl)piperidine-2,6-dione | 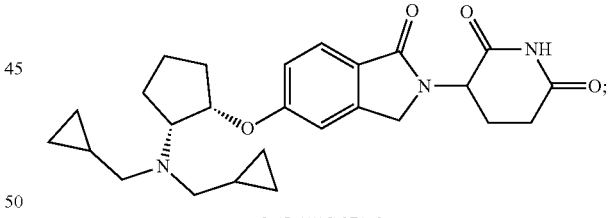<br>3-(5-(((1S,2R)-2-(bis(cyclopropylmethyl)amino)cyclopentyl)oxy)-1-oxoisoindolin-2-yl)piperidine-2,6-dione |
| 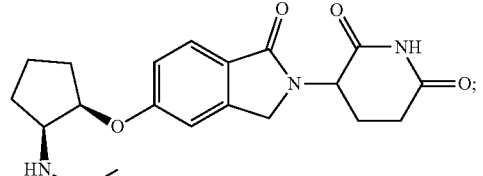<br>3-(5-(((1R,2S)-2-(ethylamino)cyclopentyl)oxy)-1-oxoisoindolin-2-yl)piperidine-2,6-dione | 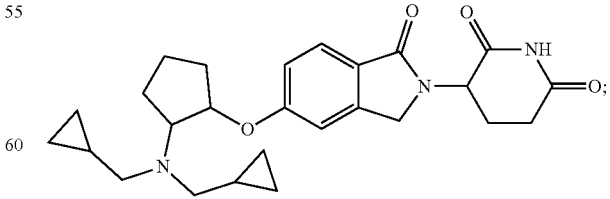<br>3-(5-((2-(bis(cyclopropylmethyl)amino)cyclopentyl)oxy)-1-oxoisoindolin-2-yl)piperidine-2,6-dione |
| 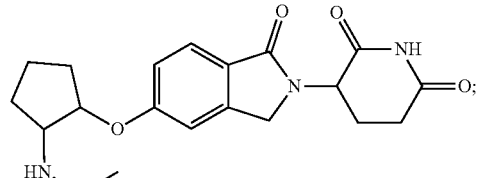<br>3-(5-((2-(ethylamino)cyclopentyl)oxy)-1-oxoisoindolin-2-yl)piperidine-2,6-dione | |

| Compound Structure/Compound Name | Compound Structure/Compound Name |
|---|---|
| 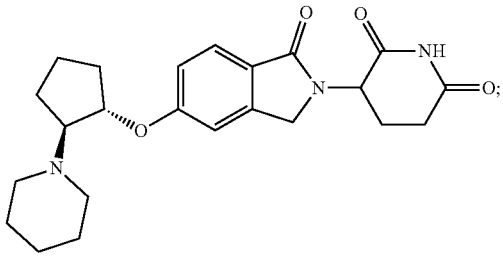<br>3-(1-oxo-5-((((1S,2S)-2-(piperidin-1-yl)cyclopentyl)oxy)isoindolin-2-yl)piperidine-2,6-dione | 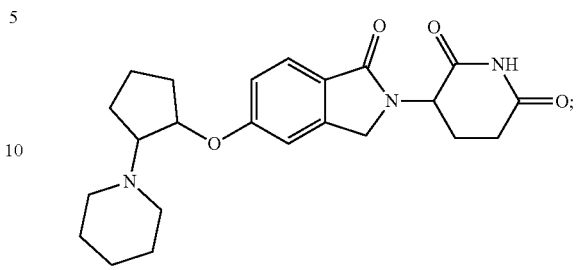<br>3-(1-oxo-5-((2-(piperidin-1-yl)cyclopentyl)oxy)isoindolin-2-yl)piperidine-2,6-dione |
| 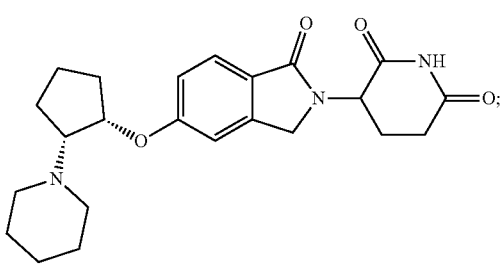<br>3-(1-oxo-5-((((1S,2R)-2-(piperidin-1-yl)cyclopentyl)oxy)isoindolin-2-yl)piperidine-2,6-dione | 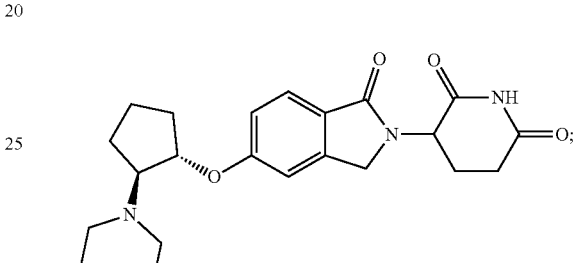<br>3-(5-((((1S,2S)-2-morpholinocyclopentyl)oxy)-1-oxoisoindolin-2-yl)piperidine-2,6-dione |
| 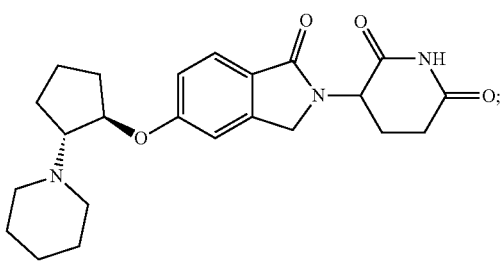<br>3-(1-oxo-5-((((1R,2R)-2-(piperidin-1-yl)cyclopentyl)oxy)isoindolin-2-yl)piperidine-2,6-dione | 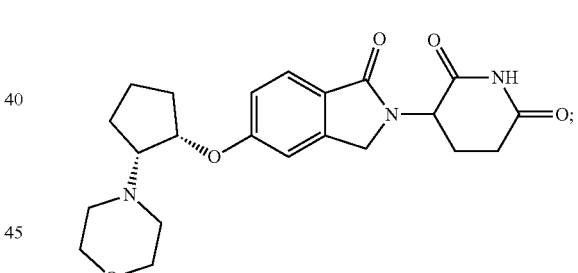<br>3-(5-((((1S,2R)-2-morpholinocyclopentyl)oxy)-1-oxoisoindolin-2-yl)piperidine-2,6-dione |
| 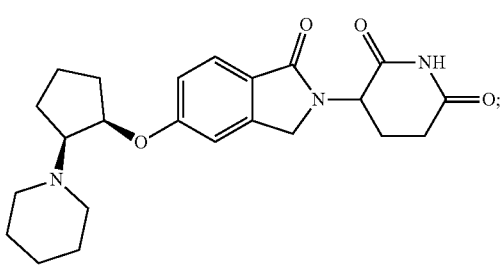<br>3-(1-oxo-5-((((1R,2S)-2-(piperidin-1-yl)cyclopentyl)oxy)isoindolin-2-yl)piperidine-2,6-dione | 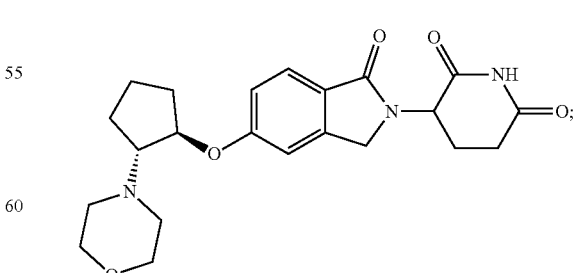<br>3-(5-((((1R,2R)-2-morpholinocyclopentyl)oxy)-1-oxoisoindolin-2-yl)piperidine-2,6-dione |

| Compound Structure/Compound Name |
|---|
| 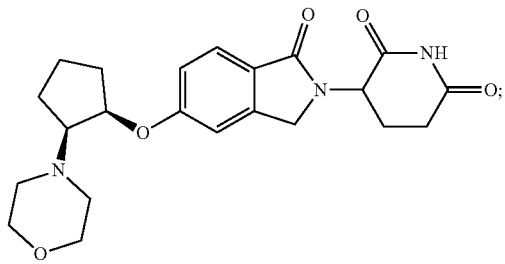 3-(5-(((1R,2S)-2-morpholinocyclopentyl)oxy)-1-oxoisoindolin-2-yl)piperidine-2,6-dione |
| 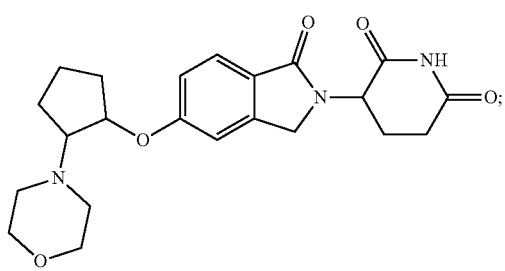 3-(5-((2-morpholinocyclopentyl)oxy)-1-oxoisoindolin-2-yl)piperidine-2,6-dione |
| 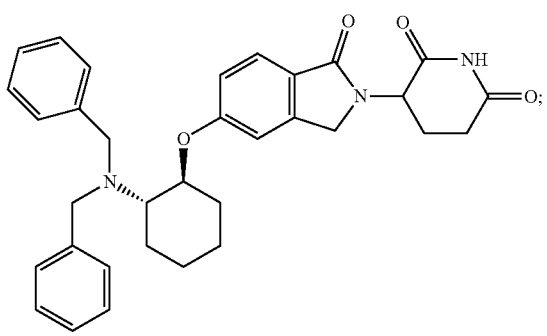 3-(5-(((1S,2S)-2-(dibenzylamino)cyclohexyl)oxy)-1-oxoisoindolin-2-yl)piperidine-2,6-dione |
| 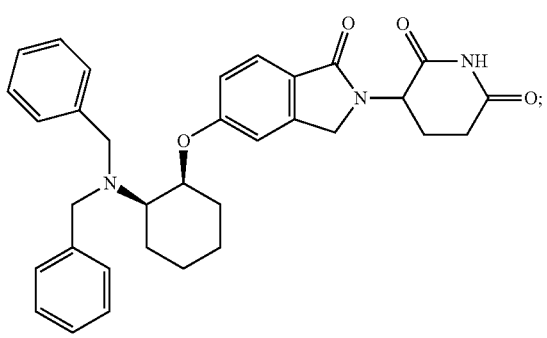 3-(5-(((1S,2R)-2-(dibenzylamino)cyclohexyl)oxy)-1-oxoisoindolin-2-yl)piperidine-2,6-dione |

| Compound Structure/Compound Name |
|---|
| 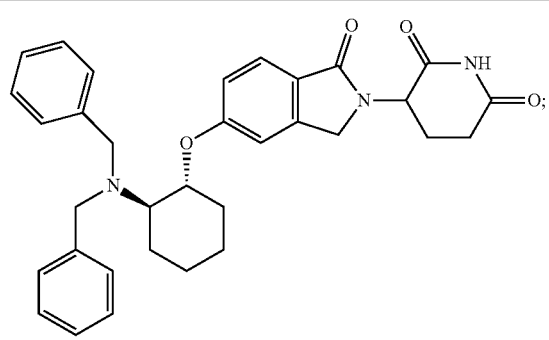 3-(5-(((1R,2R)-2-(dibenzylamino)cyclohexyl)oxy)-1-oxoisoindolin-2-yl)piperidine-2,6-dione |
| 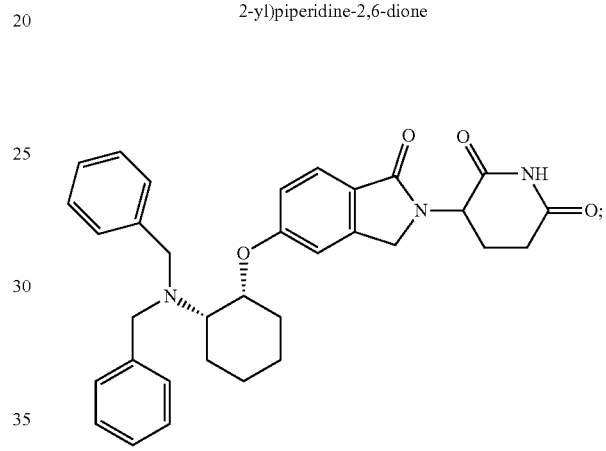 3-(5-(((1R,2S)-2-(dibenzylamino)cyclohexyl)oxy)-1-oxoisoindolin-2-yl)piperidine-2,6-dione |
| 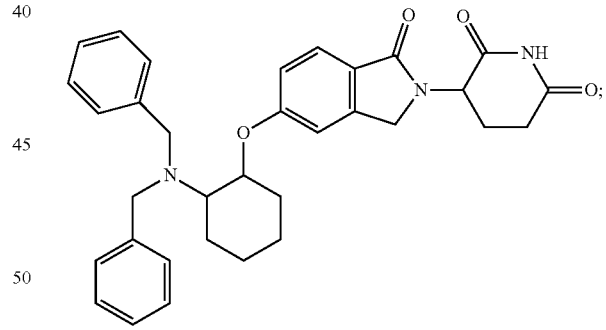 3-(5-((2-(dibenzylamino)cyclohexyl)oxy)-1-oxoisoindolin-2-yl)piperidine-2,6-dione |
| 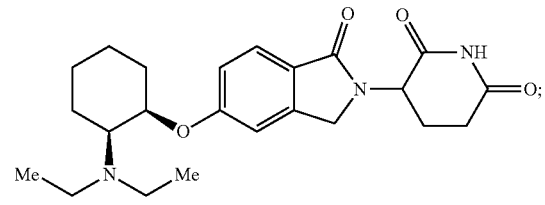 cis-3-(5-((2-(diethylamino)cyclohexyl)oxy)-1-oxoisoindolin-2-yl)piperidine-2,6-dione |

| Compound Structure/Compound Name |
|---|
| 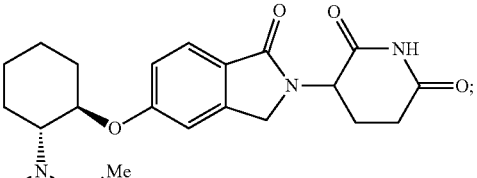<br>trans-3-(5-((2-(diethylamino)cyclohexyl)oxy)-1-oxoisoindolin-2-yl)piperidine-2,6-dione |
| 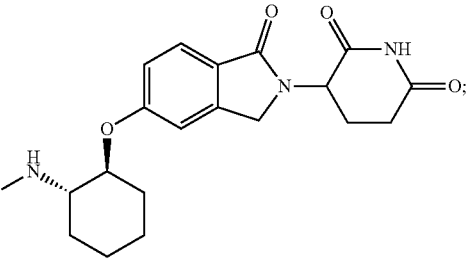<br>3-(5-(((1S,2S)-2-(methylamino)cyclohexyl)oxy)-1-oxoisoindolin-2-yl)piperidine-2,6-dione |
| 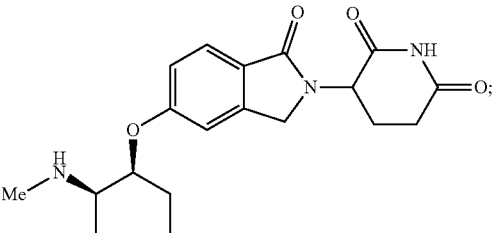<br>3-(5-(((1S,2R)-2-(methylamino)cyclohexyl)oxy)-1-oxoisoindolin-2-yl)piperidine-2,6-dione |
| 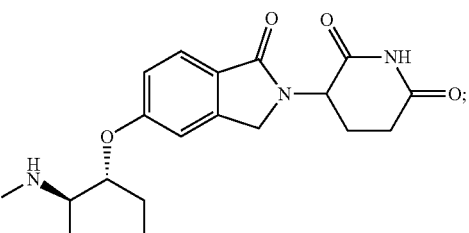<br>3-(5-(((1R,2R)-2-(methylamino)cyclohexyl)oxy)-1-oxoisoindolin-2-yl)piperidine-2,6-dione |
| 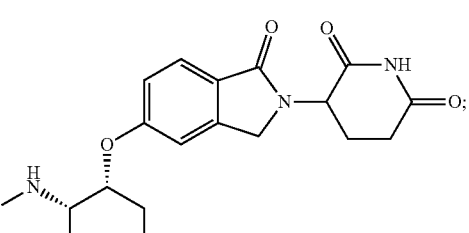<br>3-(5-(((1R,2S)-2-(methylamino)cyclohexyl)oxy)-1-oxoisoindolin-2-yl)piperidine-2,6-dione |

| Compound Structure/Compound Name |
|---|
| 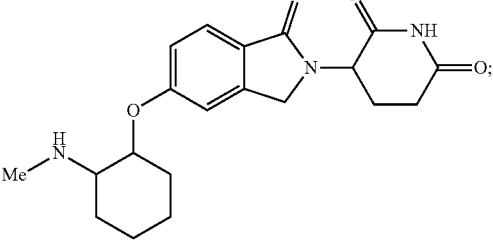<br>3-(5-((2-(methylamino)cyclohexyl)oxy)-1-oxoisoindolin-2-yl)piperidine-2,6-dione |
| 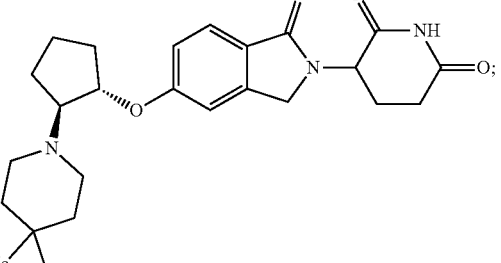<br>1-((1S,2S)-2-((2-(2,6-dioxopiperidin-3-yl)-1-oxoisoindolin-5-yl)oxy)cyclopentyl)-4-methylpiperidine-4-carbonitrile |
| 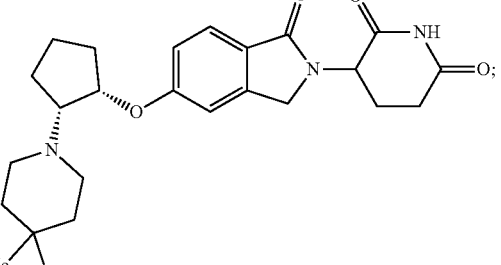<br>1-((1R,2S)-2-((2-(2,6-dioxopiperidin-3-yl)-1-oxoisoindolin-5-yl)oxy)cyclopentyl)-4-methylpiperidine-4-carbonitrile |
| 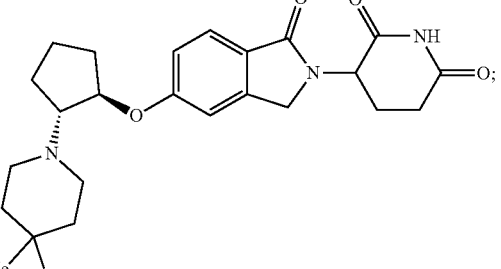<br>1-((1R,2R)-2-((2-(2,6-dioxopiperidin-3-yl)-1-oxoisoindolin-5-yl)oxy)cyclopentyl)-4-methylpiperidine-4-carbonitrile |

| Compound Structure/Compound Name |
|---|
| 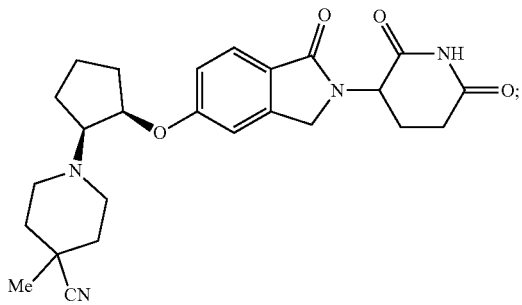<br>1-((1S,2R)-2-((2-(2,6-dioxopiperidin-3-yl)-1-oxoisoindolin-5-yl)oxy)cyclopentyl)-4-methylpiperidine-4-carbonitrile |
| 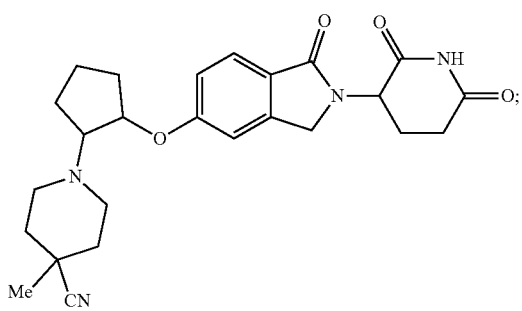<br>1-(2-((2-(2,6-dioxopiperidin-3-yl)-1-oxoisoindolin-5-yl)oxy)cyclopentyl)-4-methylpiperidine-4-carbonitrile |
| 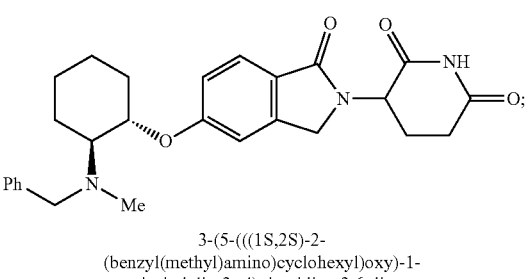<br>3-(5-(((1S,2S)-2-(benzyl(methyl)amino)cyclohexyl)oxy)-1-oxoisoindolin-2-yl)piperidine-2,6-dione |
| 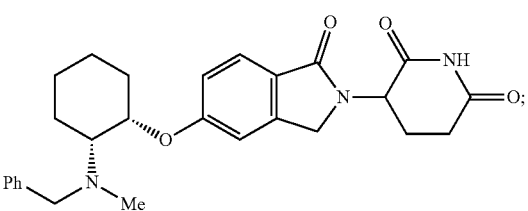<br>3-(5-(((1S,2R)-2-(benzyl(methyl)amino)cyclohexyl)oxy)-1-oxoisoindolin-2-yl)piperidine-2,6-dione |

| Compound Structure/Compound Name |
|---|
| 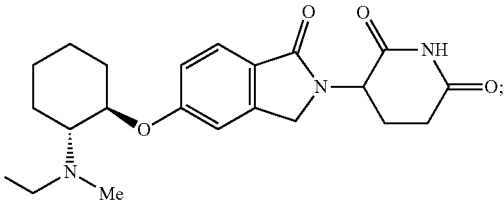<br>3-(5-(((1R,2S)-2-(benzyl(methyl)amino)cyclohexyl)oxy)-1-oxoisoindolin-2-yl)piperidine-2,6-dione |
| 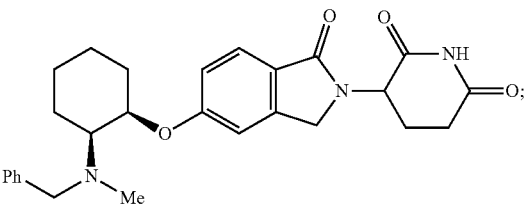<br>3-(5-(((1R,2S)-2-(benzyl(methyl)amino)cyclohexyl)oxy)-1-oxoisoindolin-2-yl)piperidine-2,6-dione |
| 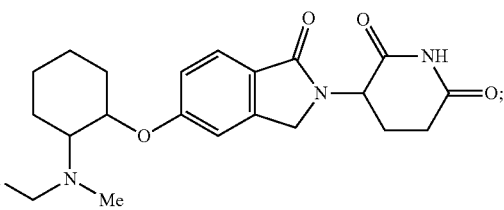<br>3-(5-((2-(benzyl(methyl)amino)cyclohexyl)oxy)-1-oxoisoindolin-2-yl)piperidine-2,6-dione |
| 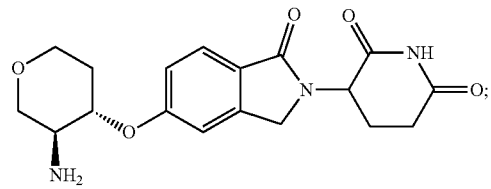<br>3-(5-(((3S,4S)-3-aminotetrahydro-2H-pyran-4-yl)oxy)-1-oxoisoindolin-2-yl)piperidine-2,6-dione |
| 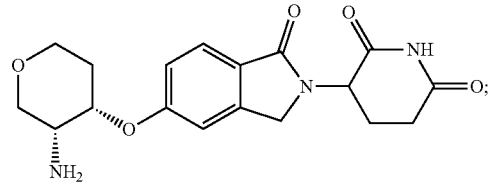<br>3-(5-(((3R,4S)-3-aminotetrahydro-2H-pyran-4-yl)oxy)-1-oxoisoindolin-2-yl)piperidine-2,6-dione |

| Compound Structure/Compound Name | Compound Structure/Compound Name |
|---|---|
| 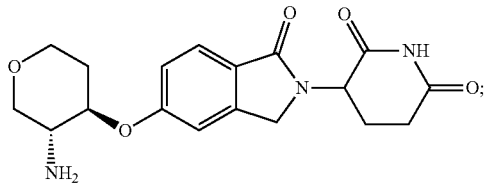<br>3-(5-(((3R,4R)-3-aminotetrahydro-2H-pyran-4-yl)oxy)-1-oxoisoindolin-2-yl)piperidine-2,6-dione | 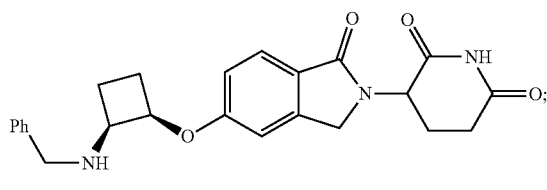<br>3-(5-((1R,2S)-2-(benzylamino)cyclobutoxy)-1-oxoisoindolin-2-yl)piperidine-2,6-dione |
| 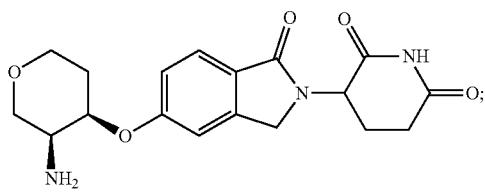<br>3-(5-(((3S,4R)-3-aminotetrahydro-2H-pyran-4-yl)oxy)-1-oxoisoindolin-2-yl)piperidine-2,6-dione | 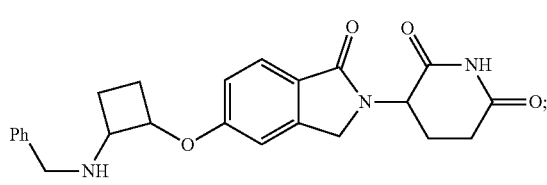<br>3-(5-(2-(benzylamino)cyclobutoxy)-1-oxoisoindolin-2-yl)piperidine-2,6-dione |
| 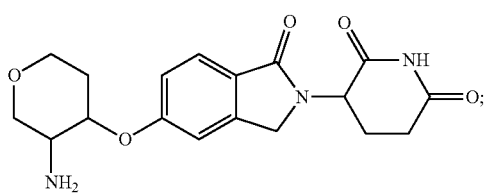<br>3-(5-((3-aminotetrahydro-2H-pyran-4-yl)oxy)-1-oxoisoindolin-2-yl)piperidine-2,6-dione | 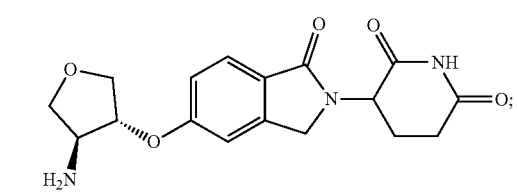<br>3-(5-(((3R,4S)-4-aminotetrahydrofuran-3-yl)oxy)-1-oxoisoindolin-2-yl)piperidine-2,6-dione |
| <br>3-(5-((1S,2S)-2-(benzylamino)cyclobutoxy)-1-oxoisoindolin-2-yl)piperidine-2,6-dione | 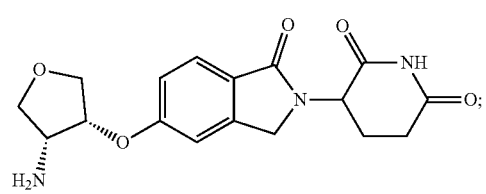<br>3-(5-(((3R,4R)-4-aminotetrahydrofuran-3-yl)oxy)-1-oxoisoindolin-2-yl)piperidine-2,6-dione |
| 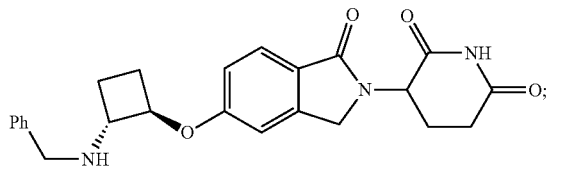<br>3-(5-((1R,2R)-2-(benzylamino)cyclobutoxy)-1-oxoisoindolin-2-yl)piperidine-2,6-dione | 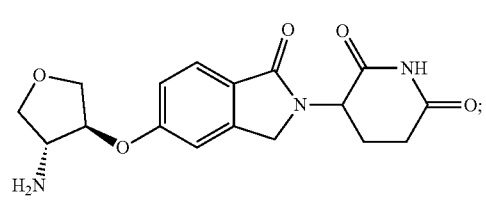<br>3-(5-(((3S,4R)-4-aminotetrahydrofuran-3-yl)oxy)-1-oxoisoindolin-2-yl)piperidine-2,6-dione |
| 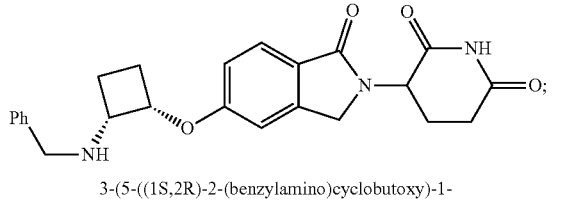<br>3-(5-((1S,2R)-2-(benzylamino)cyclobutoxy)-1-oxoisoindolin-2-yl)piperidine-2,6-dione | 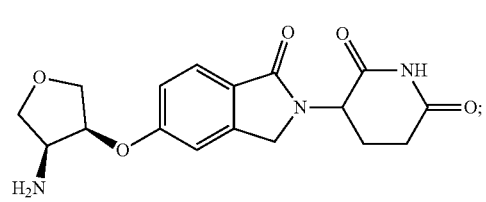<br>3-(5-(((3S,4S)-4-aminotetrahydrofuran-3-yl)oxy)-1-oxoisoindolin-2-yl)piperidine-2,6-dione |

| Compound Structure/Compound Name | Compound Structure/Compound Name |
|---|---|
| 3-(5-((4-aminotetrahydrofuran-3-yl)oxy)-1-oxoisoindolin-2-yl)piperidine-2,6-dione | 3-(5-(((1S,2S)-2-(ethylamino)cyclohexyl)oxy)-1-oxoisoindolin-2-yl)piperidine-2,6-dione |
| 3-(5-(((3R,4S)-4-(diethylamino)tetrahydrofuran-3-yl)oxy)-1-oxoisoindolin-2-yl)piperidine-2,6-dione | 3-(5-(((1S,2R)-2-(ethylamino)cyclohexyl)oxy)-1-oxoisoindolin-2-yl)piperidine-2,6-dione |
| 3-(5-(((3R,4R)-4-(diethylamino)tetrahydrofuran-3-yl)oxy)-1-oxoisoindolin-2-yl)piperidine-2,6-dione | 3-(5-(((1R,2R)-2-(ethylamino)cyclohexyl)oxy)-1-oxoisoindolin-2-yl)piperidine-2,6-dione |
| 3-(5-(((3S,4R)-4-(diethylamino)tetrahydrofuran-3-yl)oxy)-1-oxoisoindolin-2-yl)piperidine-2,6-dione | 3-(5-(((1R,2S)-2-(ethylamino)cyclohexyl)oxy)-1-oxoisoindolin-2-yl)piperidine-2,6-dione |
| 3-(5-(((3S,4S)-4-(diethylamino)tetrahydrofuran-3-yl)oxy)-1-oxoisoindolin-2-yl)piperidine-2,6-dione | 3-(5-((2-(ethylamino)cyclohexyl)oxy)-1-oxoisoindolin-2-yl)piperidine-2,6-dione |
| 3-(5-((4-(diethylamino)tetrahydrofuran-3-yl)oxy)-1-oxoisoindolin-2-yl)piperidine-2,6-dione | |

| Compound Structure/Compound Name |
|---|
| 4-((((1S,2S)-2-((2-(2,6-dioxopiperidin-3-yl)-1-oxoisoindolin-5-yl)oxy)cyclohexyl)amino)methyl)benzonitrile |
| 4-((((1R,2S)-2-((2-(2,6-dioxopiperidin-3-yl)-1-oxoisoindolin-5-yl)oxy)cyclohexyl)amino)methyl)benzonitrile |
| 4-((((1R,2R)-2-((2-(2,6-dioxopiperidin-3-yl)-1-oxoisoindolin-5-yl)oxy)cyclohexyl)amino)methyl)benzonitrile |
| 4-((((1S,2R)-2-((2-(2,6-dioxopiperidin-3-yl)-1-oxoisoindolin-5-yl)oxy)cyclohexyl)amino)methyl)benzonitrile |
| 4-(((2-((2-(2,6-dioxopiperidin-3-yl)-1-oxoisoindolin-5-yl)oxy)cyclohexyl)amino)methyl)benzonitrile |
| 3-(5-(((1S,2S)-2-(diethylamino)cyclobutoxy)-1-oxoisoindolin-2-yl)piperidine-2,6-dione |

| Compound Structure/Compound Name |
|---|
| 3-(5-(((1R,2S)-2-(diethylamino)cyclobutoxy)-1-oxoisoindolin-2-yl)piperidine-2,6-dione |
| 3-(5-(((1R,2S)-2-(diethylamino)cyclobutoxy)-1-oxoisoindolin-2-yl)piperidine-2,6-dione |
| 3-(5-(((1S,2R)-2-(diethylamino)cyclobutoxy)-1-oxoisoindolin-2-yl)piperidine-2,6-dione |
| 3-(5-(2-(diethylamino)cyclobutoxy)-1-oxoisoindolin-2-yl)piperidine-2,6-dione |
| 3-(5-(((1S,2S)-2-(ethyl((3-fluorobicyclo[1.1.1]pentan-1-yl)methyl)amino)cyclopentyl)oxy)-1-oxoisoindolin-2-yl)piperidine-2,6-dione |

| Compound Structure/Compound Name |
|---|
| 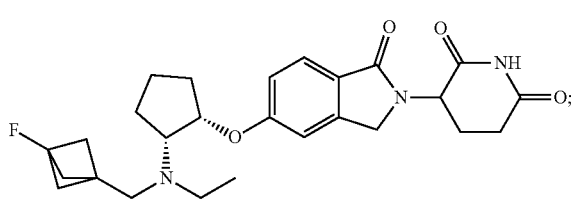<br>3-(5-((((1S,2R)-2-(ethyl((3-fluorobicyclo[1.1.1]pentan-1-yl)methyl)amino)cyclopentyl)oxy)-1-oxoisoindolin-2-yl)piperidine-2,6-dione |
| 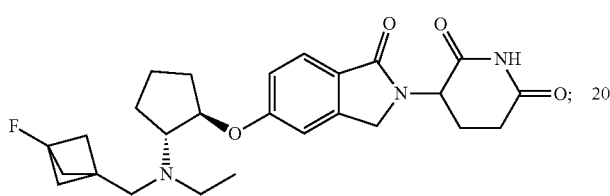<br>3-(5-((((1R,2R)-2-(ethyl((3-fluorobicyclo[1.1.1]pentan-1-yl)methyl)amino)cyclopentyl)oxy)-1-oxoisoindolin-2-yl)piperidine-2,6-dione |
| 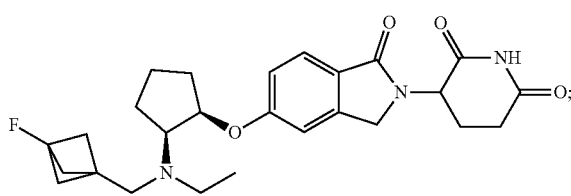<br>3-(5-((((1R,2S)-2-(ethyl((3-fluorobicyclo[1.1.1]pentan-1-yl)methyl)amino)cyclopentyl)oxy)-1-oxoisoindolin-2-yl)piperidine-2,6-dione |
| 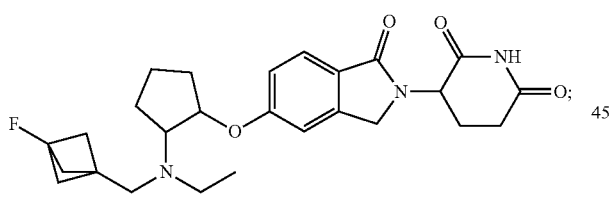<br>3-(5-((2-(ethyl((3-fluorobicyclo[1.1.1]pentan-1-yl)methyl)amino)cyclopentyl)oxy)-1-oxoisoindolin-2-yl)piperidine-2,6-dione |
| 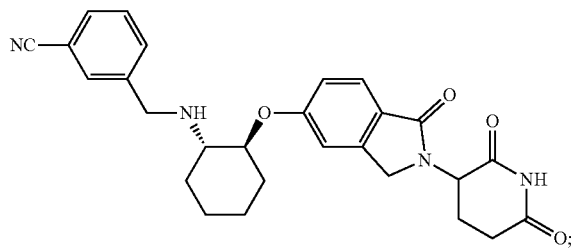<br>3-(((((1S,2S)-2-((2-(2,6-dioxopiperidin-3-yl)-1-oxoisoindolin-5-yl)oxy)cyclohexyl)amino)methyl)benzonitrile |
| 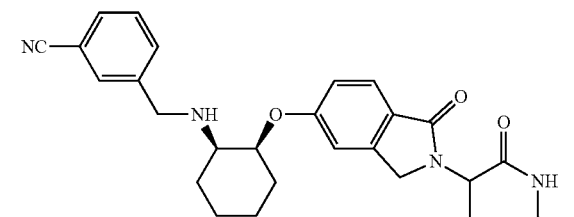<br>3-(((((1R,2S)-2-((2-(2,6-dioxopiperidin-3-yl)-1-oxoisoindolin-5-yl)oxy)cyclohexyl)amino)methyl)benzonitrile |
| <br>3-(((((1R,2R)-2-((2-(2,6-dioxopiperidin-3-yl)-1-oxoisoindolin-5-yl)oxy)cyclohexyl)amino)methyl)benzonitrile |
| 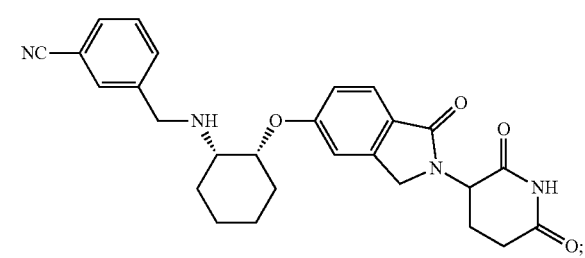<br>3-(((((1S,2R)-2-((2-(2,6-dioxopiperidin-3-yl)-1-oxoisoindolin-5-yl)oxy)cyclohexyl)amino)methyl)benzonitrile |
| 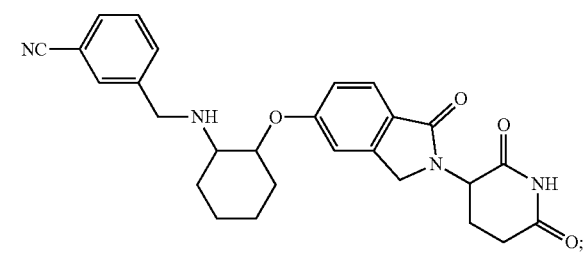<br>3-(((2-((2-(2,6-dioxopiperidin-3-yl)-1-oxoisoindolin-5-yl)oxy)cyclohexyl)amino)methyl)benzonitrile |

| Compound Structure/Compound Name | Compound Structure/Compound Name |
|---|---|
| 3-(5-(((1S,2S)-2-(isopropylamino)cyclohexyl)oxy)-1-oxoisoindolin-2-yl)piperidine-2,6-dione | 2-(((((1S,2S)-2-((2-(2,6-dioxopiperidin-3-yl)-1-oxoisoindolin-5-yl)oxy)cyclohexyl)amino)methyl)benzonitrile |
| 3-(5-(((1S,2R)-2-(isopropylamino)cyclohexyl)oxy)-1-oxoisoindolin-2-yl)piperidine-2,6-dione | 2-(((((1R,2S)-2-((2-(2,6-dioxopiperidin-3-yl)-1-oxoisoindolin-5-yl)oxy)cyclohexyl)amino)methyl)benzonitrile |
| 3-(5-(((1R,2S)-2-(isopropylamino)cyclohexyl)oxy)-1-oxoisoindolin-2-yl)piperidine-2,6-dione | 2-(((((1R,2R)-2-((2-(2,6-dioxopiperidin-3-yl)-1-oxoisoindolin-5-yl)oxy)cyclohexyl)amino)methyl)benzonitrile |
| 3-(5-(((1R,2R)-2-(isopropylamino)cyclohexyl)oxy)-1-oxoisoindolin-2-yl)piperidine-2,6-dione | 2-(((((1S,2R)-2-((2-(2,6-dioxopiperidin-3-yl)-1-oxoisoindolin-5-yl)oxy)cyclohexyl)amino)methyl)benzonitrile |
| 3-(5-((2-(isopropylamino)cyclohexyl)oxy)-1-oxoisoindolin-2-yl)piperidine-2,6-dione | |

| Compound Structure/Compound Name |
|---|
| 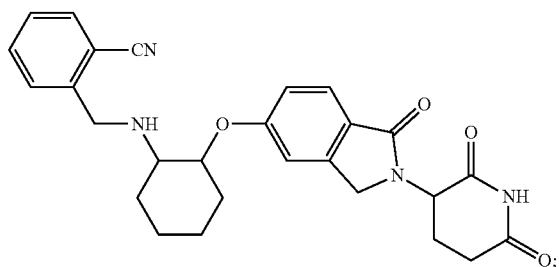<br>2-(((2-((2-(2,6-dioxopiperidin-3-yl)-1-oxoisoindolin-5-yl)oxy)cyclohexyl)amino)methyl)benzonitrile |
| 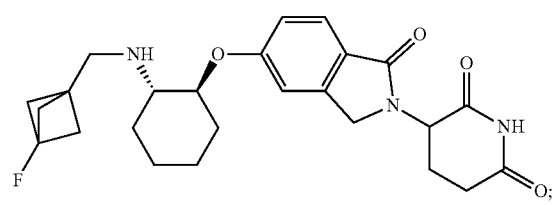<br>3-(5-(((1S,2S)-2-(((3-fluorobicyclo[1.1.1]pentan-1-yl)methyl)amino)cyclohexyl)oxy)-1-oxoisoindolin-2-yl)piperidine-2,6-dione |
| 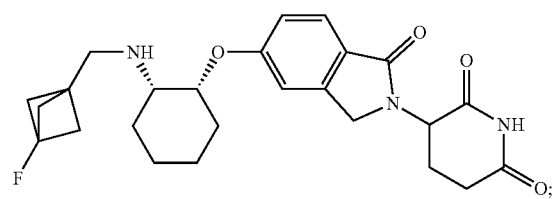<br>3-(5-(((1R,2S)-2-(((3-fluorobicyclo[1.1.1]pentan-1-yl)methyl)amino)cyclohexyl)oxy)-1-oxoisoindolin-2-yl)piperidine-2,6-dione |
| 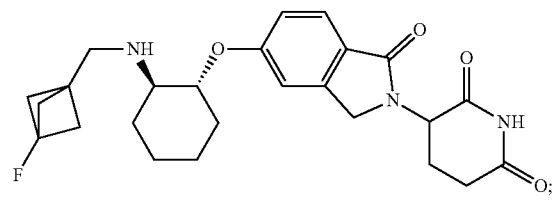<br>3-(5-(((1R,2R)-2-(((3-fluorobicyclo[1.1.1]pentan-1-yl)methyl)amino)cyclohexyl)oxy)-1-oxoisoindolin-2-yl)piperidine-2,6-dione |
| 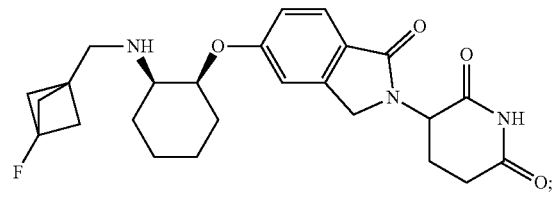<br>3-(5-(((1S,2R)-2-(((3-fluorobicyclo[1.1.1]pentan-1-yl)methyl)amino)cyclohexyl)oxy)-1-oxoisoindolin-2-yl)piperidine-2,6-dione |

| Compound Structure/Compound Name |
|---|
| 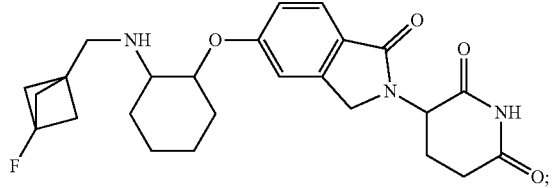<br>3-(5-((2-(((3-fluorobicyclo[1.1.1]pentan-1-yl)methyl)amino)cyclohexyl)oxy)-1-oxoisoindolin-2-yl)piperidine-2,6-dione |
| 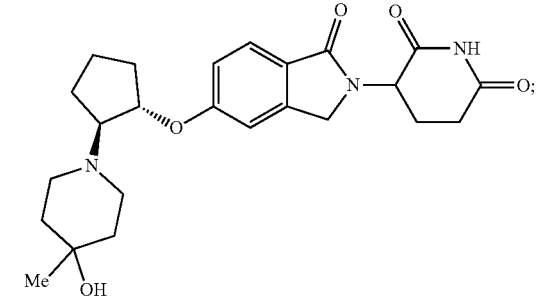<br>3-(5-(((1S,2S)-2-(4-hydroxy-4-methylpiperidin-1-yl)cyclopentyl)oxy)-1-oxoisoindolin-2-yl)piperidine-2,6-dione |
| 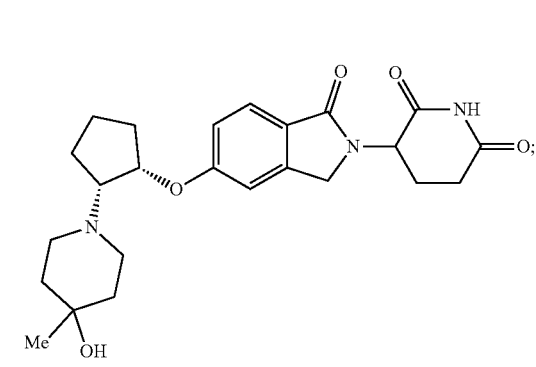<br>3-(5-(((1S,2R)-2-(4-hydroxy-4-methylpiperidin-1-yl)cyclopentyl)oxy)-1-oxoisoindolin-2-yl)piperidine-2,6-dione |
| 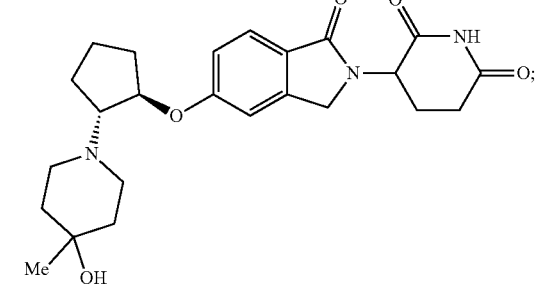<br>3-(5-(((1R,2R)-2-(4-hydroxy-4-methylpiperidin-1-yl)cyclopentyl)oxy)-1-oxoisoindolin-2-yl)piperidine-2,6-dione |

| Compound Structure/Compound Name | Compound Structure/Compound Name |
|---|---|
| 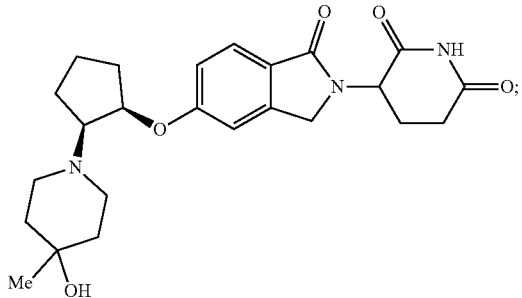<br>3-(5-((((1R,2S)-2-(4-hydroxy-4-methylpiperidin-1-yl)cyclopentyl)oxy)-1-oxoisoindolin-2-yl)piperidine-2,6-dione | 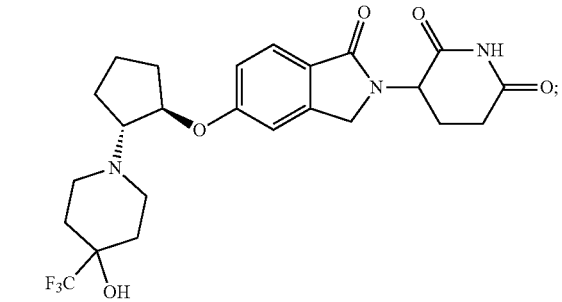<br>3-(5-((((1R,2R)-2-(4-hydroxy-4-(trifluoromethyl)piperidin-1-yl)cyclopentyl)oxy)-1-oxoisoindolin-2-yl)piperidine-2,6-dione |
| 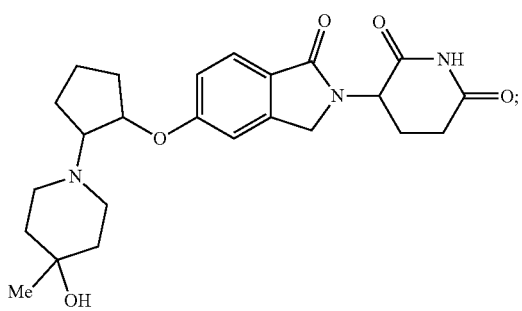<br>3-(5-((2-(4-hydroxy-4-methylpiperidin-1-yl)cyclopentyl)oxy)-1-oxoisoindolin-2-yl)piperidine-2,6-dione | 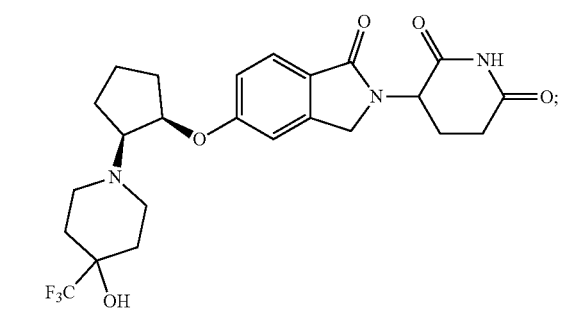<br>3-(5-((((1R,2S)-2-(4-hydroxy-4-(trifluoromethyl)piperidin-1-yl)cyclopentyl)oxy)-1-oxoisoindolin-2-yl)piperidine-2,6-dione |
| 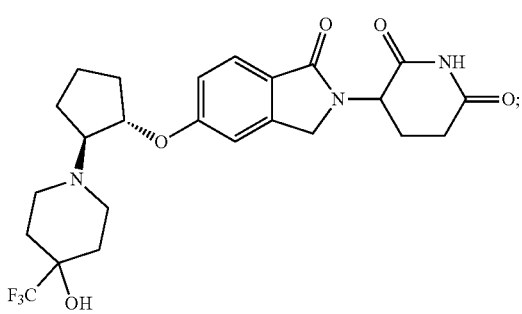<br>3-(5-((((1S,2S)-2-(4-hydroxy-4-(trifluoromethyl)piperidin-1-yl)cyclopentyl)oxy)-1-oxoisoindolin-2-yl)piperidine-2,6-dione | 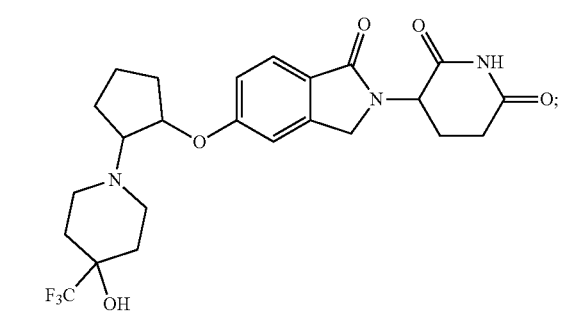<br>3-(5-((2-(4-hydroxy-4-(trifluoromethyl)pyridin-1-yl)cyclopentyl)oxy)-1-oxoisoindolin-2-yl)piperidine-2,6-dione |
| 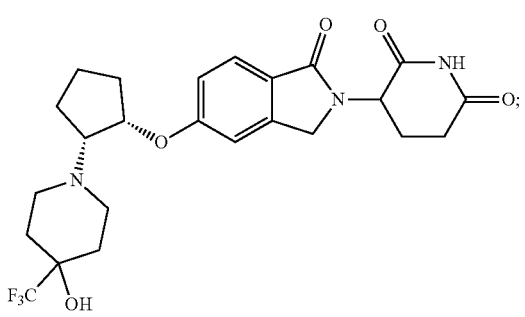<br>3-(5-((((1S,2R)-2-(4-hydroxy-4-(trifluoromethyl)piperidin-1-yl)cyclopentyl)oxy)-1-oxoisoindolin-2-yl)piperidine-2,6-dione | 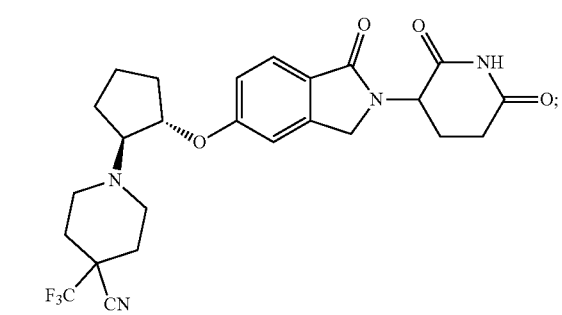<br>1-(((1S,2S)-2-((2-(2,6-dioxopiperidin-3-yl)-1-oxoisoindolin-5-yl)oxy)cyclopentyl)-4-(trifluoromethyl)piperidine-4-carbonitrile |

| Compound Structure/Compound Name |
|---|
| 1-((1R,2S)-2-((2-(2,6-dioxopiperidin-3-yl)-1-oxoisoindolin-5-yl)oxy)cyclopentyl)-4-(trifluoromethyl)piperidine-2,6-dione |
| 1-((1R,2R)-2-((2-(2,6-dioxopiperidin-3-yl)-1-oxoisoindolin-5-yl)oxy)cyclopentyl)-4-(trifluoromethyl)piperidine-4-carbonitrile |
| 1-((2S,2R)-2-((2-(2,6-dioxopiperidin-3-yl)-1-oxoisoindolin-5-yl)oxy)cyclopentyl)-4-(trifluoromethyl)piperidine-4-carbonitrile |
| 1-(2-((2-(2,6-dioxopiperidin-3-yl)-1-oxoisoindolin-5-yl)oxy)cyclopentyl)-4-(trifluoromethyl)piperidine-4-carbonitrile |
| 3-(5-(((1S,2S)-2-(2-oxa-7-azaspiro[3.5]nonan-7-yl)cyclopentyl)oxy)-1-oxoisoindolin-2-yl)piperidine-2,6-dione |
| 3-(5-(((1S,2R)-2-(2-oxa-7-azaspiro[3.5]nonan-7-yl)cyclopentyl)oxy)-1-oxoisoindolin-2-yl)piperidine-2,6-dione |
| 3-(5-(((1R,2R)-2-(2-oxa-7-azaspiro[3.5]nonan-7-yl)cyclopentyl)oxy)-1-oxoisoindolin-2-yl)piperidine-2,6-dione |
| 3-(5-(((1R,2S)-2-(2-oxa-7-azaspiro[3.5]nonan-7-yl)cyclopentyl)oxy)-1-oxoisoindolin-2-yl)piperidine-2,6-dione |

| Compound Structure/Compound Name | Compound Structure/Compound Name |
|---|---|
| 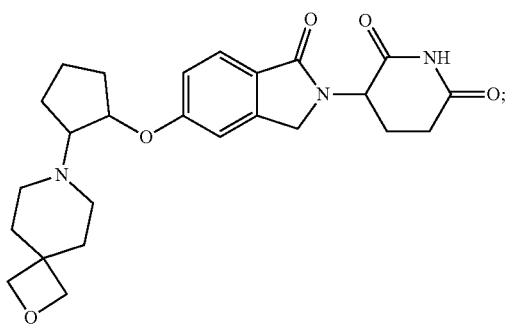<br>3-(5-((2-(2-oxa-7-azaspiro[3.5]nonan-7-yl)cyclopentyl)oxy)-1-oxoisoindolin-2-yl)piperidine-2,6-dione | 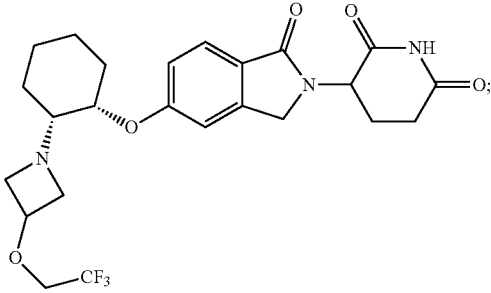<br>3-(1-oxo-5-(((1S,2R)-2-(3-(2,2,2-trifluoroethoxy)azetidin-1-yl)cyclohexyl)oxy)isoindolin-2-yl)piperidine-2,6-dione |
| 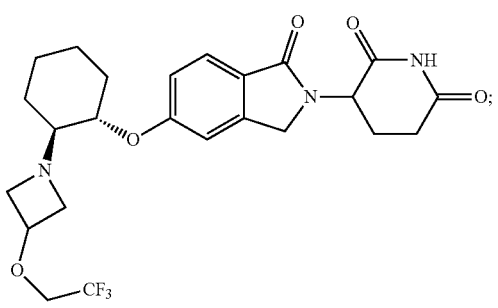<br>3-(1-oxo-5-(((1S,2S)-2-(3-(2,2,2-trifluoroethoxy)azetidin-1-yl)cyclohexyl)oxy)isoindolin-2-yl)piperidine-2,6-dione | 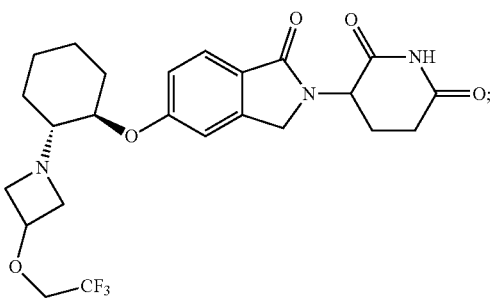<br>3-(1-oxo-5-(((1R,2R)-2-(3-(2,2,2-trifluoroethoxy)azetidin-1-yl)cyclohexyl)oxy)isoindolin-2-yl)piperidine-2,6-dione |
| 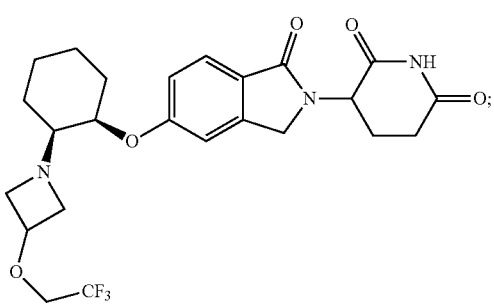<br>3-(1-oxo-5-(((1R,2S)-2-(3-(2,2,2-trifluoroethoxy)azetidin-1-yl)cyclohexyl)oxy)isoindolin-2-yl)piperidine-2,6-dione | 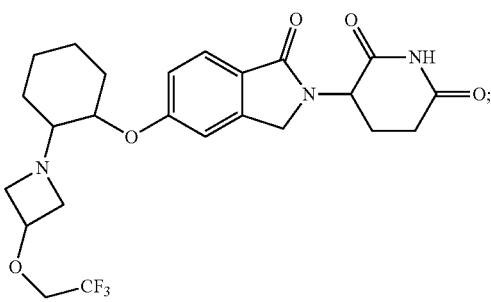<br>3-(1-oxo-5-((2-(3-(2,2,2-trifluoroethoxy)azetidin-1-yl)cyclohexyl)oxy)isoindolin-2-yl)piperidine-2,6-dione |
| | 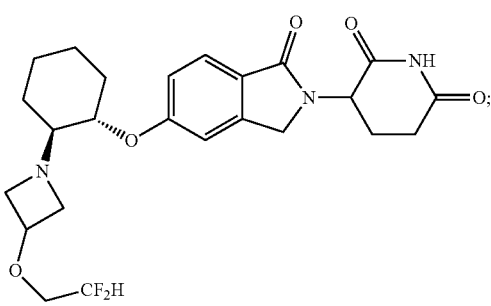<br>3-(5-(((1S,2S)-2-(3-(2,2-difluoroethoxy)azetidin-1-yl)cyclohexyl)oxy)-1-oxoisoindolin-2-yl)piperidine-2,6-dione |

| Compound Structure/Compound Name |
|---|
| 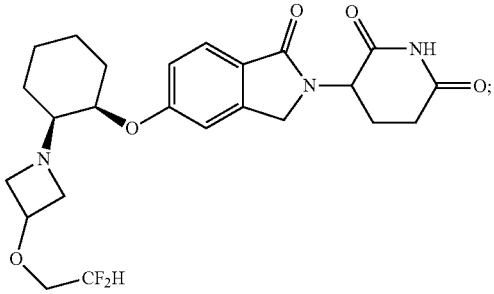<br>3-(5-(((1R,2S)-2-(3-(2,2-difluoroethoxy)azetidin-1-yl)cyclohexyl)oxy)-1-oxoisoindolin-2-yl)piperidine-2,6-dione |
| 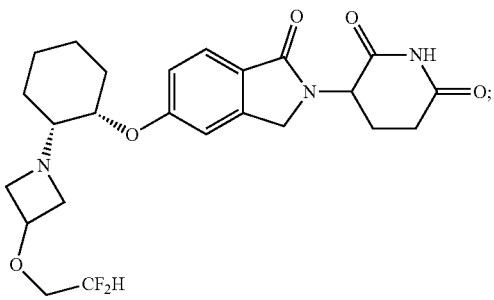<br>3-(5-(((1S,2R)-2-(3-(2,2-difluoroethoxy)azetidin-1-yl)cyclohexyl)oxy)-1-oxoisoindolin-2-yl)piperidine-2,6-dione |
| 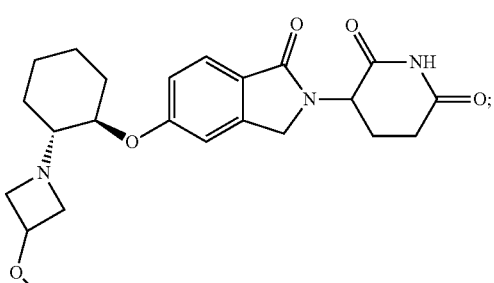<br>3-(5-(((1R,2R)-2-(3-(2,2-difluoroethoxy)azetidin-1-yl)cyclohexyl)oxy)-1-oxoisoindolin-2-yl)piperidine-2,6-dione |
| 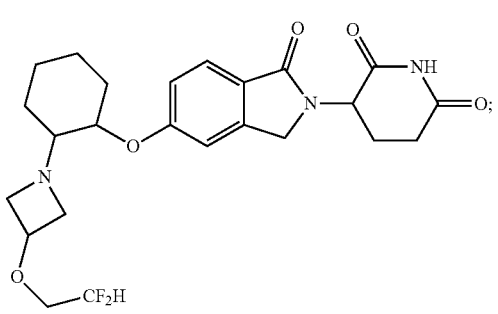<br>3-(5-((2-(3-(2,2-difluoroethoxy)azetidin-1-yl)cyclohexyl)oxy)-1-oxoisoindolin-2-yl)piperidine-2,6-dione |

| Compound Structure/Compound Name |
|---|
| 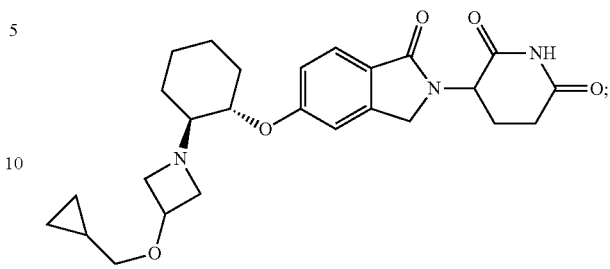<br>3-(5-(((1S,2S)-2-(3-(cyclopropylmethoxy)azetidin-1-yl)cyclohexyl)oxy)-1-oxoisoindolin-2-yl)piperidine-2,6-dione |
| 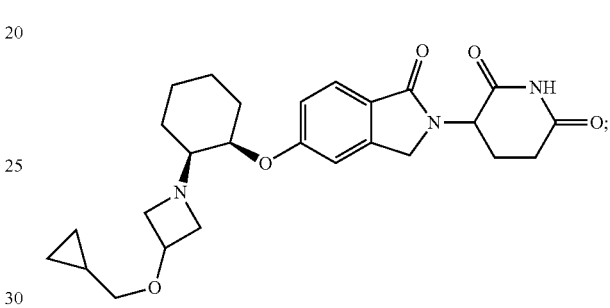<br>3-(5-(((1R,2S)-2-(3-(cyclopropylmethoxy)azetidin-1-yl)cyclohexyl)oxy)-1-oxoisoindolin-2-yl)piperidine-2,6-dione |
| 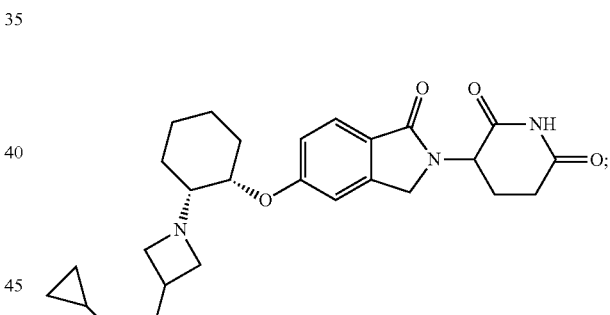<br>3-(5-(((1S,2R)-2-(3-(cyclopropylmethoxy)azetidin-1-yl)cyclohexyl)oxy)-1-oxoisoindolin-2-yl)piperidine-2,6-dione |
| 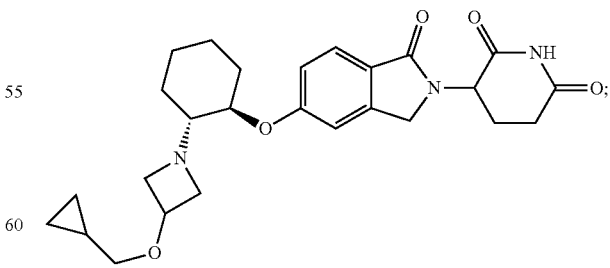<br>3-(5-(((1R,2R)-2-(3-(cyclopropylmethoxy)azetidin-1-yl)cyclohexyl)oxy)-1-oxoisoindolin-2-yl)piperidine-2,6-dione |

| Compound Structure/Compound Name | Compound Structure/Compound Name |
|---|---|
| 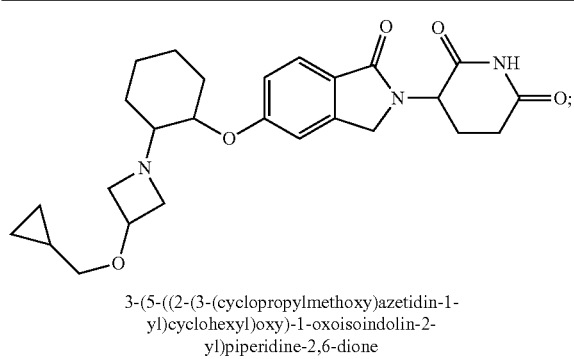<br>3-(5-((2-(3-(cyclopropylmethoxy)azetidin-1-yl)cyclohexyl)oxy)-1-oxoisoindolin-2-yl)piperidine-2,6-dione | 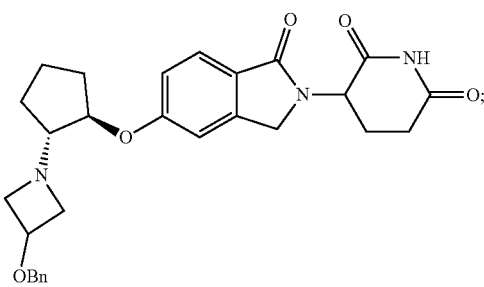<br>3-(5-(((1R,2R)-2-(3-(benzyloxy)azetidin-1-yl)cyclopentyl)oxy)-1-oxoisoindolin-2-yl)piperidine-2,6-dione |
| 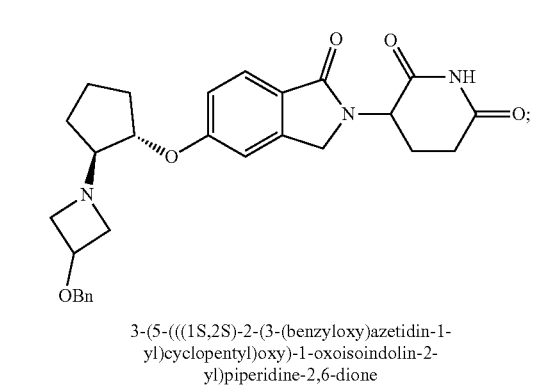<br>3-(5-(((1S,2S)-2-(3-(benzyloxy)azetidin-1-yl)cyclopentyl)oxy)-1-oxoisoindolin-2-yl)piperidine-2,6-dione | 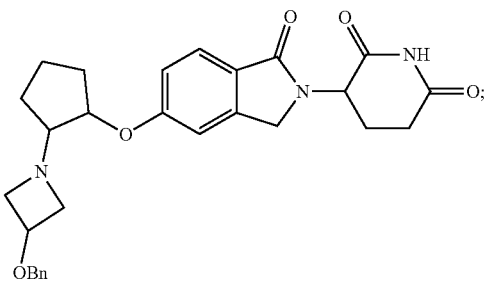<br>3-(5-((2-(3-(benzyloxy)azetidin-1-yl)cyclopentyl)oxy)-1-oxoisoindolin-2-yl)piperidine-2,6-dione |
| 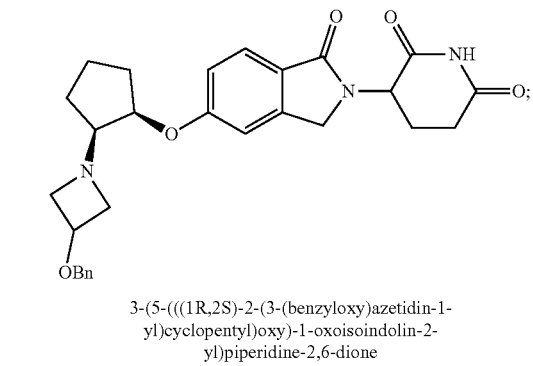<br>3-(5-(((1R,2S)-2-(3-(benzyloxy)azetidin-1-yl)cyclopentyl)oxy)-1-oxoisoindolin-2-yl)piperidine-2,6-dione | 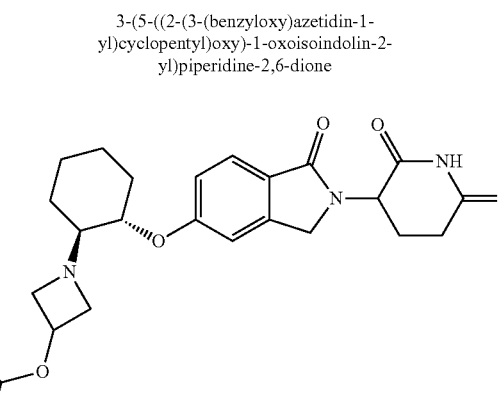<br>3-(5-(((1S,2S)-2-(3-isopropoxyazetidin-1-yl)cyclohexyl)oxy)-1-oxoisoindolin-2-yl)piperidine-2,6-dione |
| 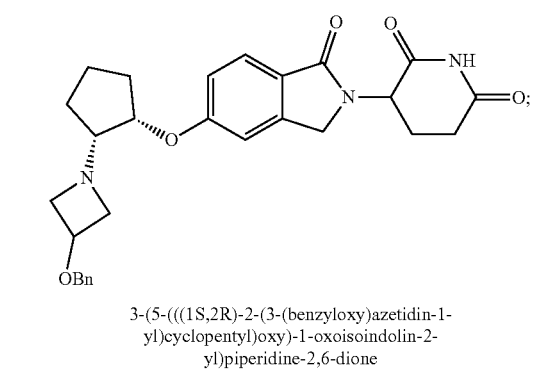<br>3-(5-(((1S,2R)-2-(3-(benzyloxy)azetidin-1-yl)cyclopentyl)oxy)-1-oxoisoindolin-2-yl)piperidine-2,6-dione | 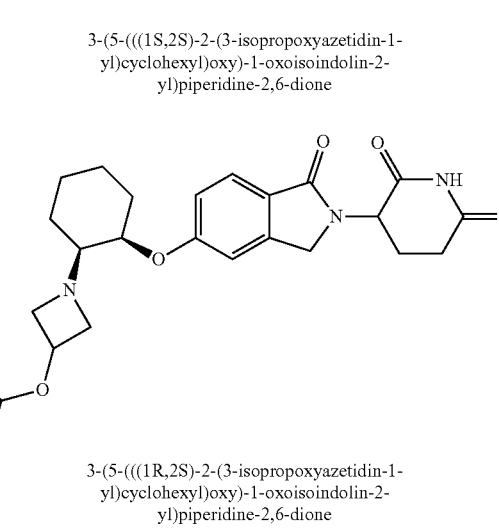<br>3-(5-(((1R,2S)-2-3-isopropoxyazetidin-1-yl)cyclohexyl)oxy)-1-oxoisoindolin-2-yl)piperidine-2,6-dione |

| Compound Structure/Compound Name | Compound Structure/Compound Name |
|---|---|
| 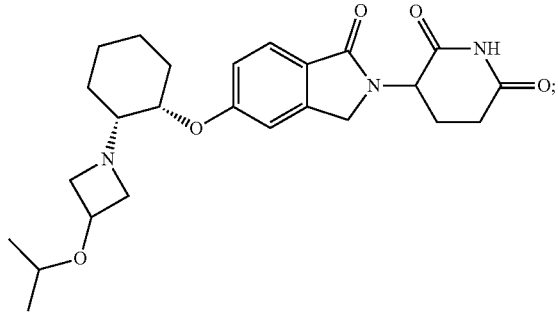<br>3-(5-((((1S,2R)-2-(3-isopropoxyazetidin-1-yl)cyclohexyl)oxy)-1-oxoisoindolin-2-yl)piperidine-2,6-dione | 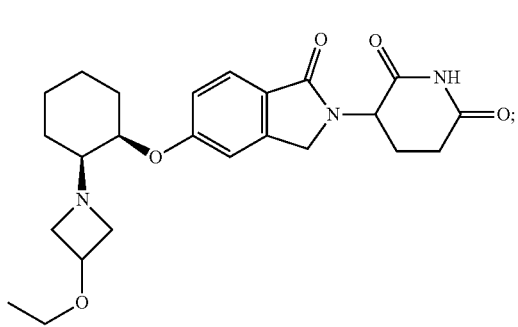<br>3-(5-((((1R,2S)-2-(3-ethoxyazetidin-1-yl)cyclohexyl)oxy)-1-oxoisoindolin-2-yl)piperidine-2,6-dione |
| 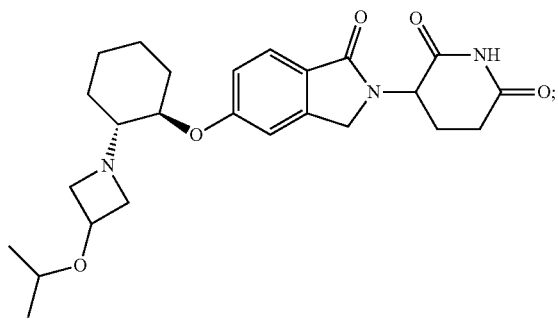<br>3-(5-((((1R,2R)-2-(3-isopropoxyazetidin-1-yl)cyclohexyl)oxy)-1-oxoisoindolin-2-yl)piperidine-2,6-dione | 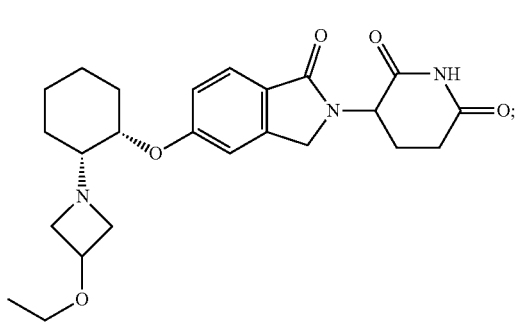<br>3-(5-((((1S,2R)-2-(3-ethoxyazetidin-1-yl)cyclohexyl)oxy)-1-oxoisoindolin-2-yl)piperidine-2,6-dione |
| 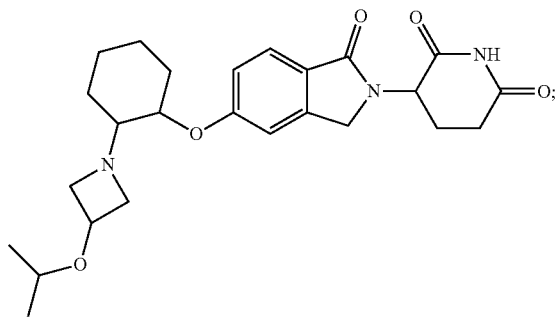<br>3-(5-((2-(3-isopropoxyazetidin-1-yl)cyclohexyl)oxy)-1-oxoisoindolin-2-yl)piperidine-2,6-dione | 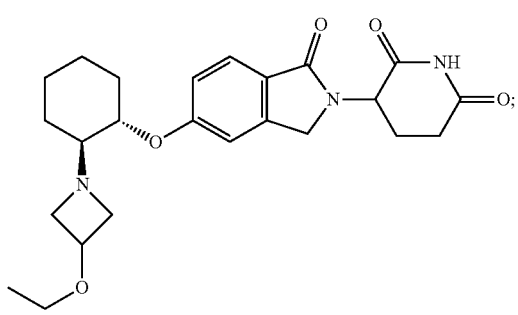<br>3-(5-((((1S,2S)-2-(3-ethoxyazetidin-1-yl)cyclohexyl)oxy)-1-oxoisoindolin-2-yl)piperidine-2,6-dione |
| 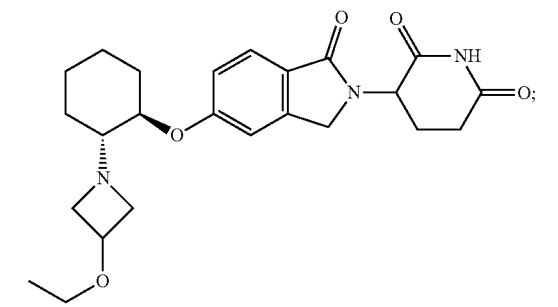<br>3-(5-((((1R,2R)-2-(3-ethoxyazetidin-1-yl)cyclohexyl)oxy)-1-oxoisoindolin-2-yl)piperidine-2,6-dione | 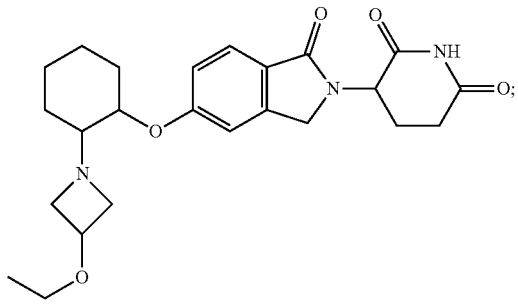<br>3-(5-((2-(3-ethoxyazetidin-1-yl)cyclohexyl)oxy)-1-oxoisoindolin-2-yl)piperidine-2,6-dione |

| Compound Structure/Compound Name | Compound Structure/Compound Name |
|---|---|
| 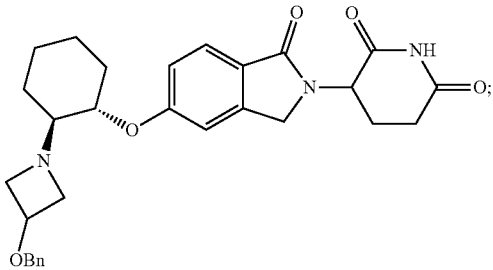<br>3-(5-((((1S,2S)-2-(3-(benzyloxy)azetidin-1-yl)cyclohexyl)oxy)-1-oxoisoindolin-2-yl)piperidine-2,6-dione | 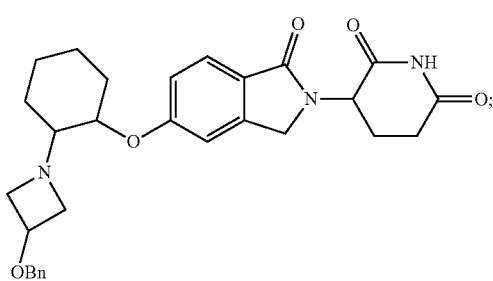<br>3-(5-((2-(3-(benzyloxy)azetidin-1-yl)cyclohexyl)oxy)-1-oxoisoindolin-2-yl)piperidine-2,6-dione |
| 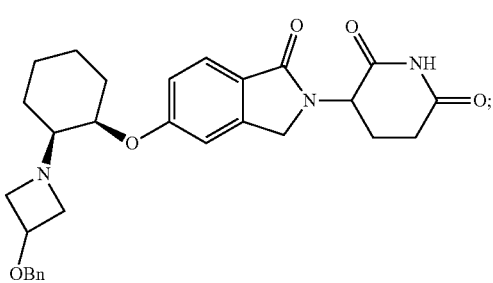<br>3-(5-((((1R,2S)-2-(3-(benzyloxy)azetidin-1-yl)cyclohexyl)oxy)-1-oxoisoindolin-2-yl)piperidine-2,6-dione | 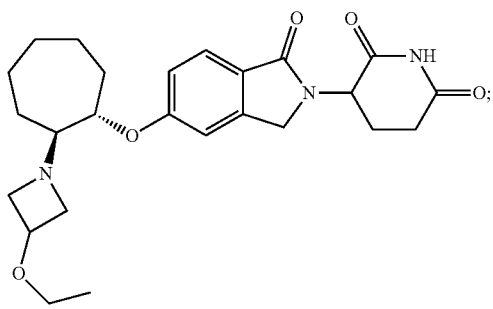<br>3-(5-((((1S,2S)-2-(3-ethoxyazetidin-1-yl)cycloheptyl)oxy)-1-oxoisoindolin-2-yl)piperidine-2,6-dione |
| <br>3-(5-((((1S,2R)-2-(3-(benzyloxy)azetidin-1-yl)cyclohexyl)oxy)-1-oxoisoindolin-2-yl)piperidine-2,6-dione | 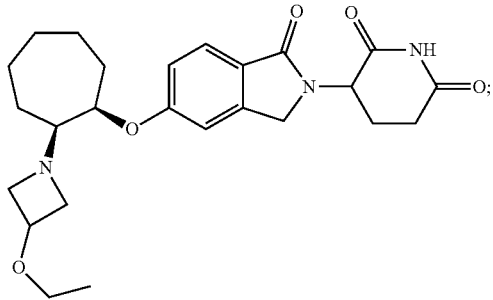<br>3-(5-((((1R,2S)-2-(3-ethoxyazetidin-1-yl)cycloheptyl)oxy)-1-oxoisoindolin-2-yl)piperidine-2,6-dione |
| 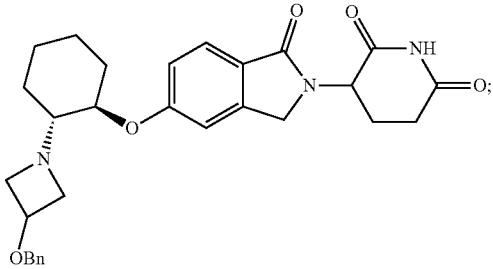<br>3-(5-((((1R,2R)-2-(3-(benzyloxy)azetidin-1-yl)cyclohexyl)oxy)-1-oxoisoindolin-2-yl)piperidine-2,6-dione | 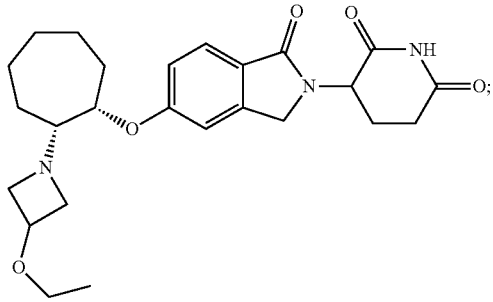<br>3-(5-((((1S,2R)-2-(3-ethoxyazetidin-1-yl)cycloheptyl)oxy)-1-oxoisoindolin-2-yl)piperidine-2,6-dione |

| Compound Structure/Compound Name | Compound Structure/Compound Name |
|---|---|
| 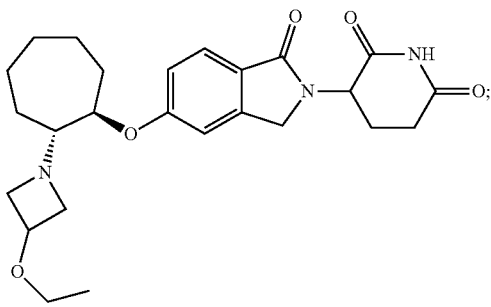<br>3-(5-(((1R,2R)-2-(3-ethoxyazetidin-1-yl)cycloheptyl)oxy)-1-oxoisoindolin-2-yl)piperidine-2,6-dione | 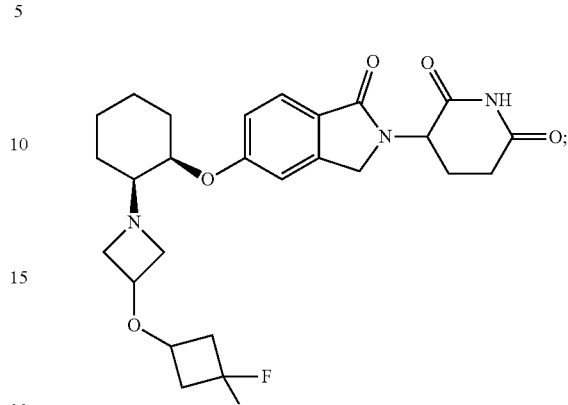<br>3-(5-(((1R,2S)-2-(3-(3,3-difluorocyclobutoxy)azetidin-1-yl)cyclohexyl)oxy)-1-oxoisoindolin-2-yl)piperidine-2,6-dione |
| 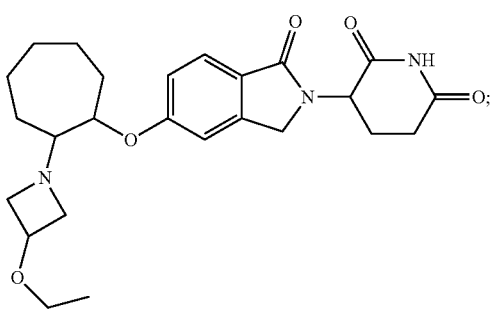<br>3-(5-((2-(3-ethoxyazetidin-1-yl)cycloheptyl)oxy)-1-oxoisoindolin-2-yl)piperidine-2,6-dione | 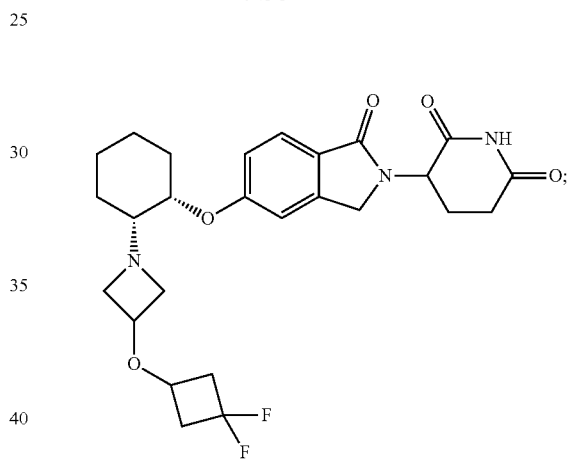<br>3-(5-(((1S,2R)-2-(3-(3,3-difluorocyclobutoxy)azetidin-1-yl)cyclohexyl)oxy)-1-oxoisoindolin-2-yl)piperidine-2,6-dione |
| 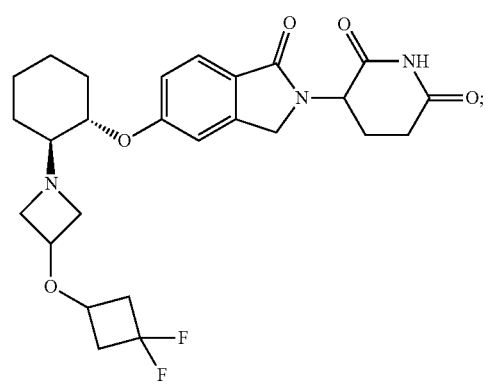<br>3-(5-(((1S,2S)-2-(3-(3,3-difluorocyclobutoxy)azetidin-1-yl)cyclohexyl)oxy)-1-oxoisoindolin-1-yl)piperidine-2,6-dione | 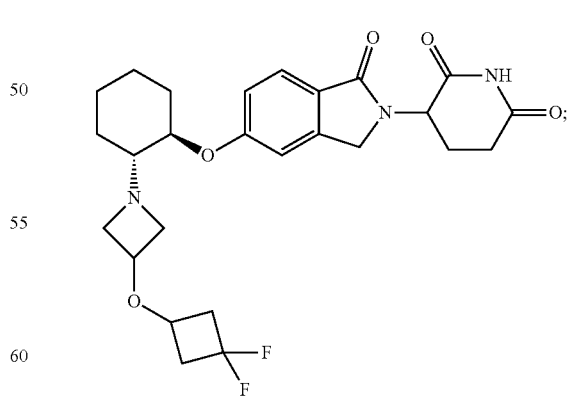<br>3-(5-(((1R,2R)-2-(3-(3,3-difluorocyclobutoxy)azetidin-1-yl)cyclohexyl)oxy)-1-oxoisoindolin-2-yl)piperidine-2,6-dione |

| Compound Structure/Compound Name | Compound Structure/Compound Name |
|---|---|
| 3-(5-((2-(3-(3,3-difluorocyclobutoxy)azetidin-1-yl)cyclohexyl)oxy)-1-oxoisoindolin-2-yl)piperidine-2,6-dione | 3-(5-((((1R,2R)-2-(4-hydroxypiperidin-1-yl)cyclopentyl)oxy)-1-oxoisoindolin-2-yl)piperidine-2,6-dione |
| 3-(5-((((1S,2S)-2-(4-hydroxypiperidin-1-yl)cyclopentyl)oxy)-1-oxoisoindolin-2-yl)piperidine-2,6-dione | 3-(5-((((1R,2S)-2-(4-hydroxypiperidin-1-yl)cyclopentyl)oxy)-1-oxoisoindolin-2-yl)piperidine-2,6-dione |
| | 3-(5-((2-(4-hydroxypiperidin-1-yl)cyclopentyl)oxy)-1-oxoisoindolin-2-yl)piperidine-2,6-dione |
| 3-(5-((((1S,2R)-2-(4-hydroxypiperidin-1-yl)cyclopentyl)oxy)-1-oxoisoindolin-2-yl)piperidine-2,6-dione | 3-(1-oxo-5-((((1S,2S)-2-(4-oxopiperidin-1-yl)cyclopentyl)oxy)isoindolin-2-yl)piperidine-2,6-dione |

| Compound Structure/Compound Name | Compound Structure/Compound Name |
|---|---|
| 3-(5-(((1S,2S)-2-(3-hydroxypyrrolidin-1-yl)cyclopentyl)oxy)-1-oxoisoindolin-2-yl)piperidine-2,6-dione | 3-(5-((2-(3-hydroxypyrrolidin-1-yl)cyclopentyl)oxy)-1-oxoisoindolin-2-yl)piperidine-2,6-dione |
| 3-(5-(((1S,2R)-2-(3-hydroxypyrrolidin-1-yl)cyclopentyl)oxy)-1-oxoisoindolin-2-yl)piperidine-2,6-dione | 3-(5-(((1S,2S)-2-(3-hydroxy-3-methylazetidin-1-yl)cyclopentyl)oxy)-1-oxoisoindolin-2-yl)piperidine-2,6-dione |
| 3-(5-(((1R,2R)-2-(3-hydroxypyrrolidin-1-yl)cyclopentyl)oxy)-1-oxoisoindolin-2-yl)piperidine-2,6-dione | 3-(5-(((1S,2R)-2-(3-hydroxy-3-methylazetidin-1-yl)cyclopentyl)oxy)-1-oxoisoindolin-2-yl)piperidine-2,6-dione |
| 3-(5-(((1R,2S)-2-(3-hydroxypyrrolidin-1-yl)cyclopentyl)oxy)-1-oxoisoindolin-2-yl)piperidine-2,6-dione | 3-(5-(((1R,2R)-2-(3-hydroxy-3-methylazetidin-1-yl)cyclopentyl)oxy)-1-oxoisoindolin-2-yl)piperidine-2,6-dione |

| Compound Structure/Compound Name | Compound Structure/Compound Name |
|---|---|
| 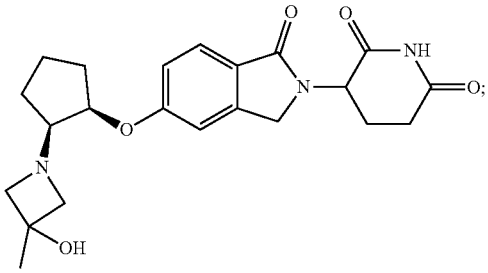<br>3-(5-(((1R,2S)-2-(3-hydroxy-3-methylazetidin-1-yl)cyclopentyl)oxy)-1-oxoisoindolin-2-yl)piperidine-2,6-dione | 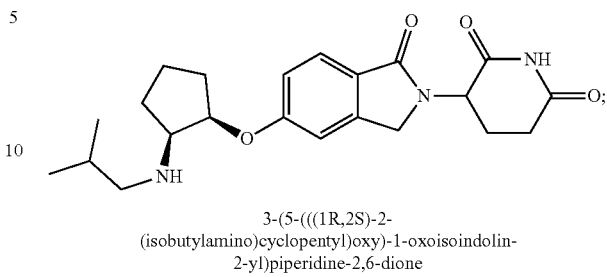<br>3-(5-((((1R,2S)-2-(isobutylamino)cyclopentyl)oxy)-1-oxoisoindolin-2-yl)piperidine-2,6-dione |
| 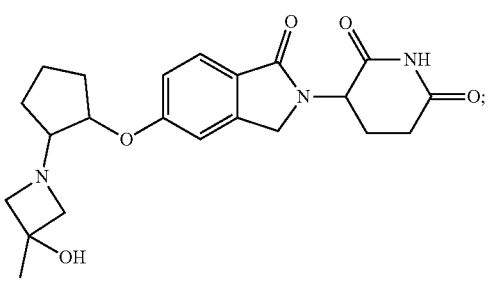<br>3-(5-((2-(3-hydroxy-3-methylazetidin-1-yl)cyclopentyl)oxy)-1-oxoisoindolin-2-yl)piperidine-2,6-dione | 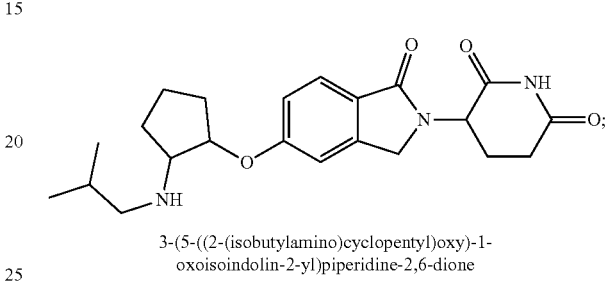<br>3-(5-((2-(isobutylamino)cyclopentyl)oxy)-1-oxoisoindolin-2-yl)piperidine-2,6-dione |
| 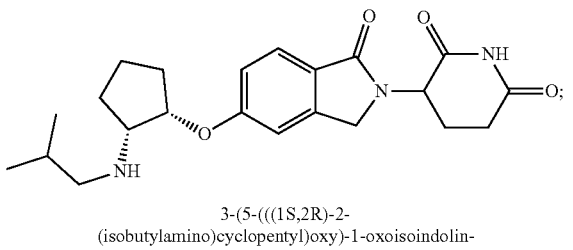<br>3-(5-((((1S,2R)-2-(isobutylamino)cyclopentyl)oxy)-1-oxoisoindolin-2-yl)piperidine-2,6-dione | 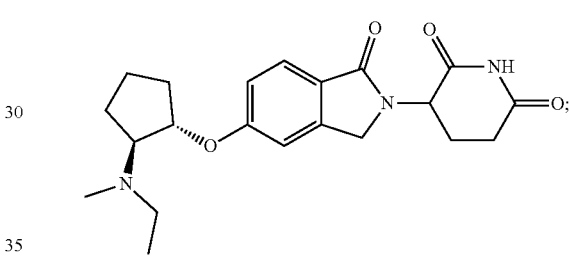<br>3-(5-((((1S,2S)-2-(ethyl(methyl)amino)cyclopentyl)oxy)-1-oxoisoindolin-2-yl)piperidine-2,6-dione |
| 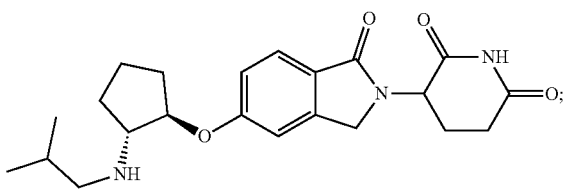<br>3-(5-((((1R,2R)-2-(isobutylamino)cyclopentyl)oxy)-1-oxoisoindolin-2-yl)piperidine-2,6-dione | 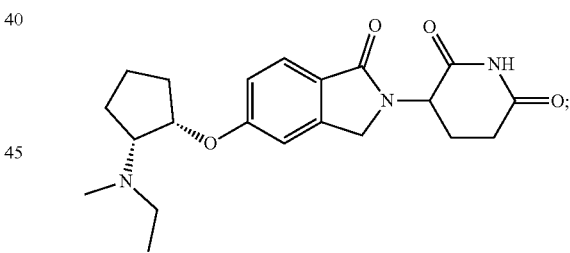<br>3-(5-((((1S,2R)-2-(ethyl(methyl)amino)cyclopentyl)oxy)-1-oxoisoindolin-2-yl)piperidine-2,6-dione |
| 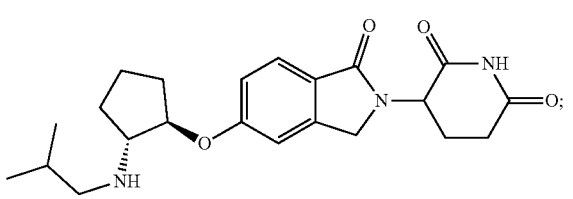<br>3-(5-((((1R,2R)-2-(isobutylamino)cyclopentyl)oxy)-1-oxoisoindolin-2-yl)piperidine-2,6-dione | 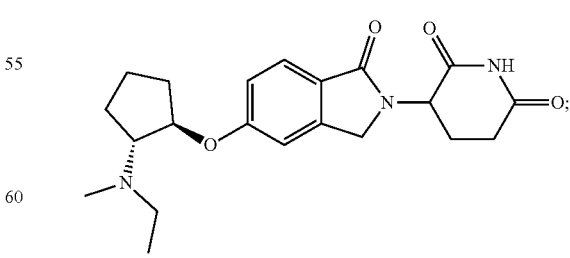<br>3-(5-((((1R,2R)-2-(ethyl(methyl)amino)cyclopentyl)oxy)-1-oxoisoindolin-2-yl)piperidine-2,6-dione |

| Compound Structure/Compound Name | Compound Structure/Compound Name |
|---|---|
| 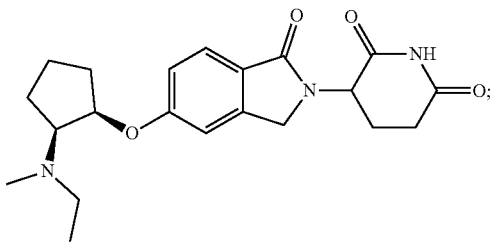<br>3-(5-(((1R,2S)-2-(ethyl(methyl)amino)cyclopentyl)oxy)-1-oxoisoindolin-2-yl)piperidine-2,6-dione | 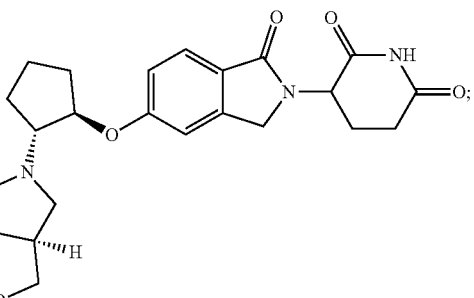<br>3-(1-oxo-5-(((1R,2R)-2-((3aR,6aS)-tetrahydro-1H-furo[3,4-c]pyrrol-5(3H)-yl)cyclopentyl)oxy)isoindolin-2-yl)piperidine-2,6-dione |
| 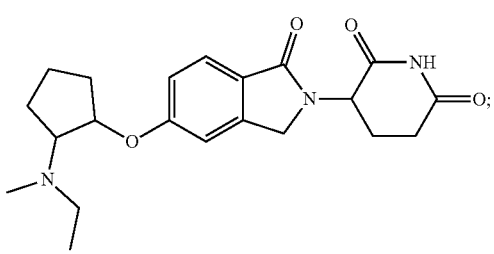<br>3-(5-((2-(ethyl(methyl)amino)cyclopentyl)oxy)-1-oxoisoindolin-2-yl)piperidine-2,6-dione | 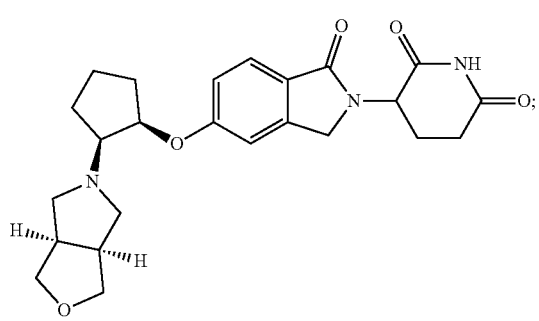<br>3-(1-oxo-5-(((1R,2S)-2-((3aR,6aS)-tetrahydro-1H-furo[3,4-c]pyrrol-5(3H)-yl)cyclopentyl)oxy)isoindolin-2-yl)piperidine-2,6-dione |
| 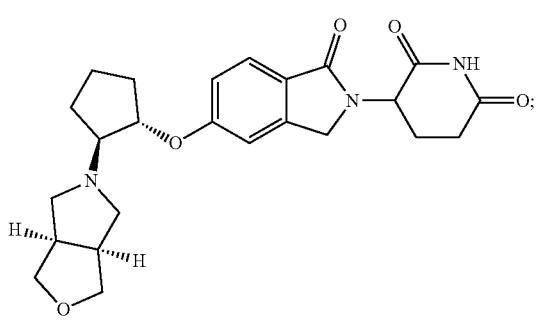<br>3-(1-oxo-5-(((1S,2S)-2-((3aR,6aS)-tetrahydro-1H-furo[3,4-c]pyrrol-5(3H)-yl)cyclopentyl)oxy)isoindolin-2-yl)piperidine-2,6-dione | 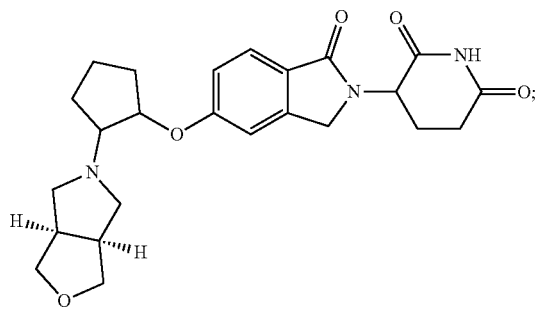<br>3-(1-oxo-5-((2-((3aR,6aS)-tetrahydro-1H-furo[3,4-c]pyrrol-5(3H)-yl)cyclopentyl)oxy)isoindolin-2-yl)piperidine-2,6-dione |
| 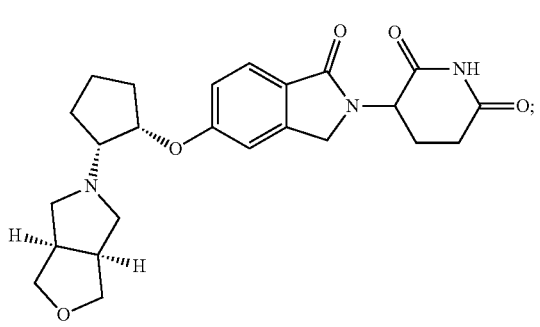<br>3-(1-oxo-5-(((1S,2R)-2-((3aR,6aS)-tetrahydro-1H-furo[3,4-c]pyrrol-5(3H)-yl)cyclopentyl)oxy)isoindolin-2-yl)piperidine-2,6-dione | 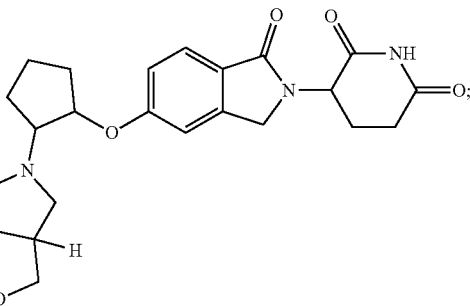<br>3-(1-oxo-5-((2-(tetrahydro-1H-furo[3,4-c]pyrrol-5(3H)-yl)cyclopentyl)oxy)isoindolin-2-yl)piperidine-2,6-dione |

| Compound Structure/Compound Name | Compound Structure/Compound Name |
|---|---|
| 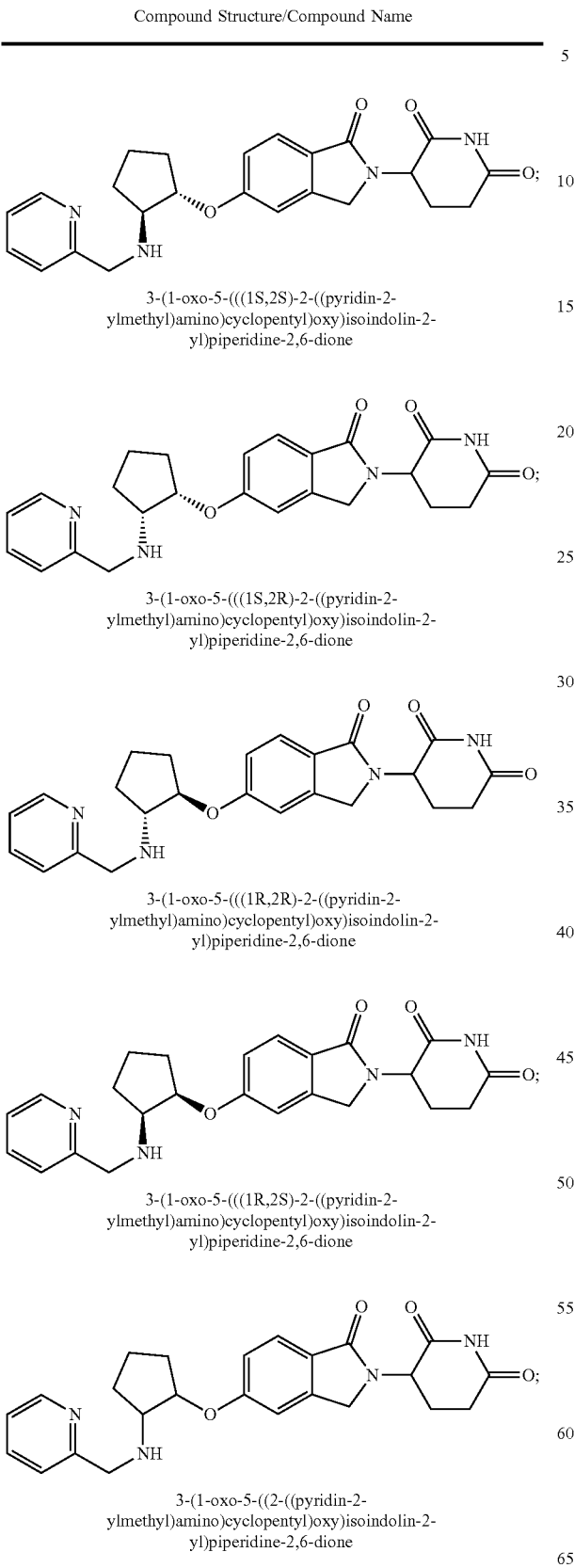 3-(1-oxo-5-((((1S,2S)-2-((pyridin-2-ylmethyl)amino)cyclopentyl)oxy)isoindolin-2-yl)piperidine-2,6-dione<br><br>3-(1-oxo-5-((((1S,2R)-2-((pyridin-2-ylmethyl)amino)cyclopentyl)oxy)isoindolin-2-yl)piperidine-2,6-dione<br><br>3-(1-oxo-5-((((1R,2R)-2-((pyridin-2-ylmethyl)amino)cyclopentyl)oxy)isoindolin-2-yl)piperidine-2,6-dione<br><br>3-(1-oxo-5-((((1R,2S)-2-((pyridin-2-ylmethyl)amino)cyclopentyl)oxy)isoindolin-2-yl)piperidine-2,6-dione<br><br>3-(1-oxo-5-((2-((pyridin-2-ylmethyl)amino)cyclopentyl)oxy)isoindolin-2-yl)piperidine-2,6-dione | 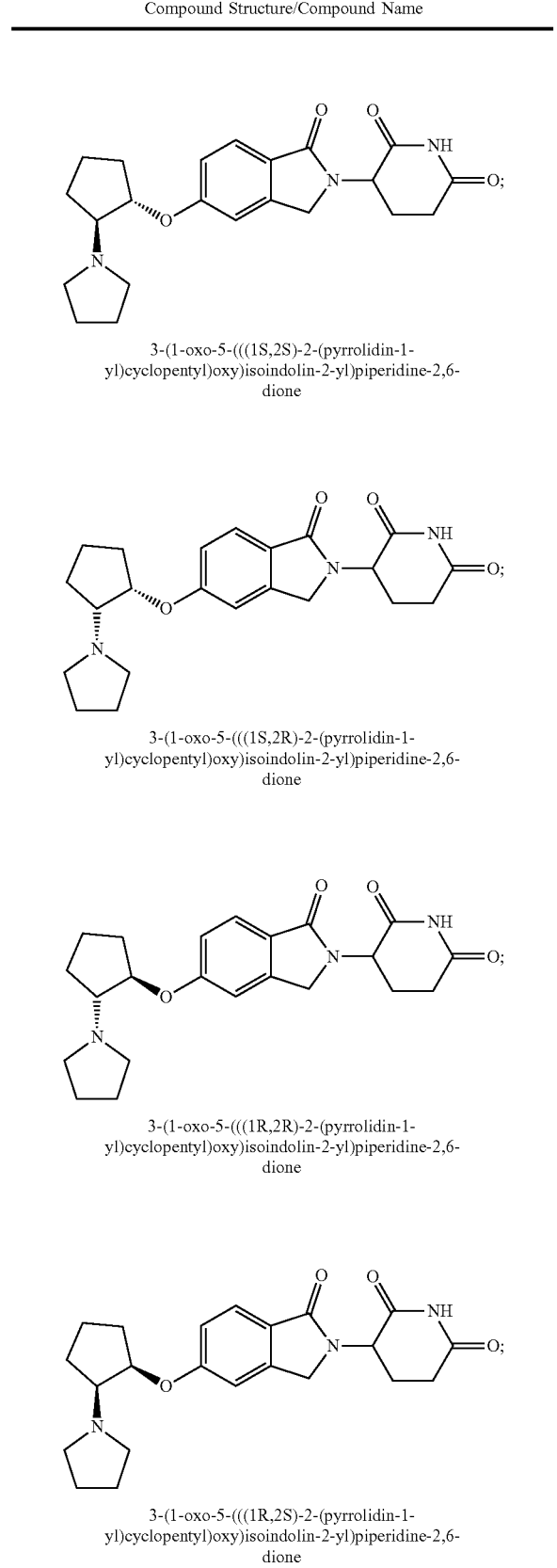 3-(1-oxo-5-((((1S,2S)-2-(pyrrolidin-1-yl)cyclopentyl)oxy)isoindolin-2-yl)piperidine-2,6-dione<br><br>3-(1-oxo-5-((((1S,2R)-2-(pyrrolidin-1-yl)cyclopentyl)oxy)isoindolin-2-yl)piperidine-2,6-dione<br><br>3-(1-oxo-5-((((1R,2R)-2-(pyrrolidin-1-yl)cyclopentyl)oxy)isoindolin-2-yl)piperidine-2,6-dione<br><br>3-(1-oxo-5-((((1R,2S)-2-(pyrrolidin-1-yl)cyclopentyl)oxy)isoindolin-2-yl)piperidine-2,6-dione |

| Compound Structure/Compound Name | Compound Structure/Compound Name |
|---|---|
| 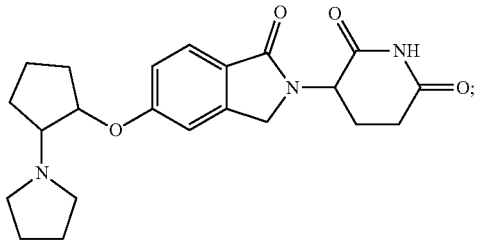<br>3-(1-oxo-5-((2-(pyrrolidin-1-yl)cyclopentyl)oxy)isoindolin-2-yl)piperidine-2,6-dione; | 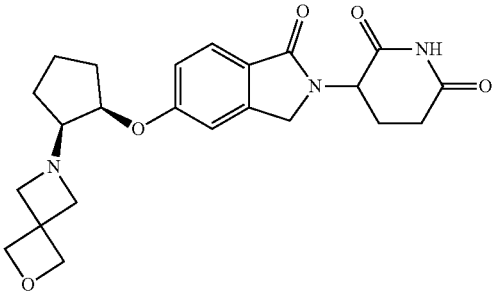<br>3-(5-(((1R,2S)-2-(2-oxa-6-azaspiro[3.3]heptan-6-yl)cyclopentyl)oxy)-1-oxoisoindolin-2-yl)piperidine-2,6-dione |
| 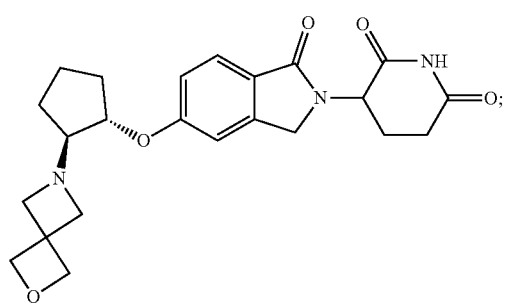<br>3-(5-(((1S,2S)-2-(2-oxa-6-azaspiro[3.3]heptan-6-yl)cyclopentyl)oxy)-1-oxoisoindolin-2-yl)piperidine-2,6-dione; | 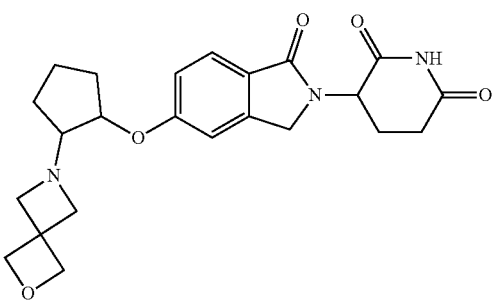<br>3-(5-((2-(2-oxa-6-azaspiro[3.3]heptan-6-yl)cyclopentyl)oxy)-1-oxoisoindolin-2-yl)piperidine-2,6-dione |
| 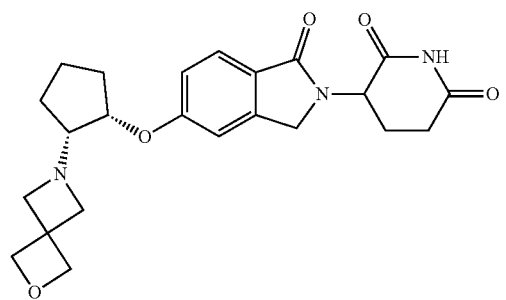<br>3-(5-(((1S,2R)-2-(2-oxa-6-azaspiro[3.3]heptan-6-yl)cyclopentyl)oxy)-1-oxoisoindolin-2-yl)piperidine-2,6-dione | 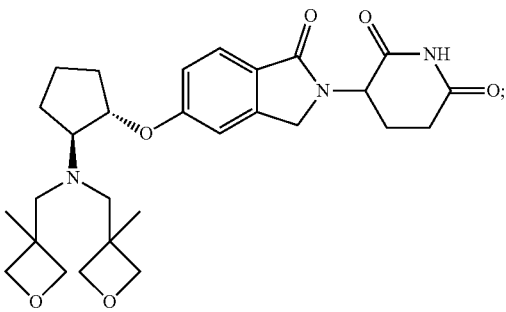<br>3-(5-(((1S,2S)-2-(bis((3-methyloxetan-3-yl)methyl)amino)cyclopentyl)oxy)-1-oxoisoindolin-2-yl)piperidine-2,6-dione; |
| 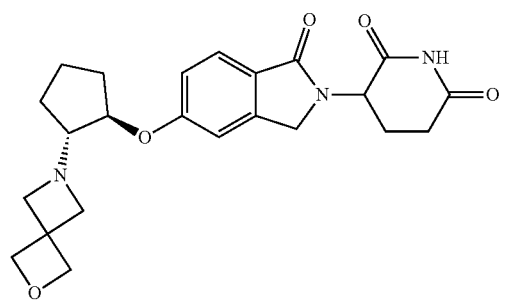<br>3-(5-(((1R,2R)-2-(2-oxa-6-azaspiro[3.3]heptan-6-yl)cyclopentyl)oxy)-1-oxoisoindolin-2-yl)piperidine-2,6-dione | 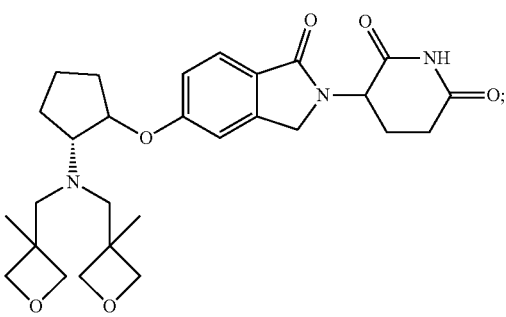<br>3-(5-(((1S,2R)-2-(bis((3-methyloxetan-3-yl)methyl)amino)cyclopentyl)oxy)-1-oxoisoindolin-2-yl)piperidine-2,6-dione; |

| Compound Structure/Compound Name | Compound Structure/Compound Name |
|---|---|
| 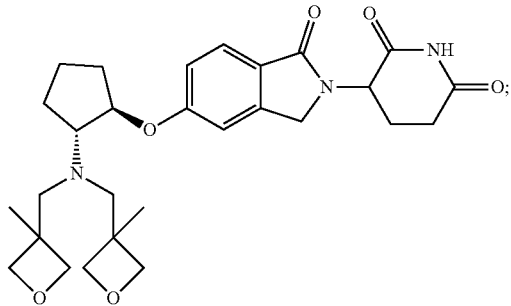 3-(5-(((1R,2R)-2-(bis((3-methyloxetan-3-yl)methyl)amino)cyclopentyl)oxy)-1-oxoisoindolin-2-yl)piperidine-2,6-dione | 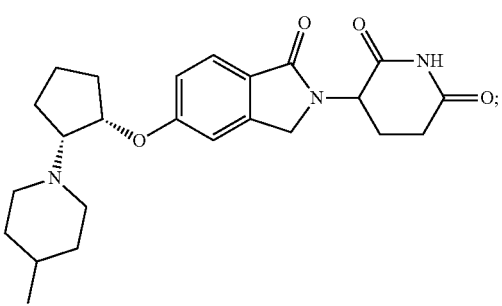 3-(5-(((1S,2R)-2-(4-methylpiperidin-1-yl)cyclopentyl)oxy)-1-oxoisoindolin-2-yl)piperidine-2,6-dione |
| 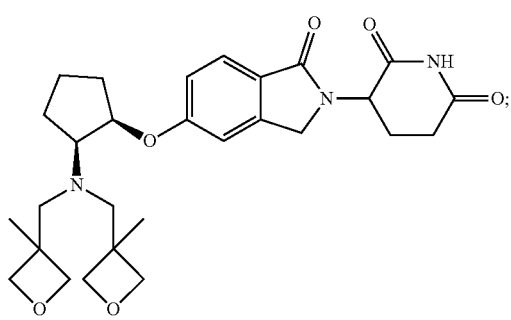 3-(5-(((1R,2S)-2-(bis((3-methyloxetan-3-yl)methyl)amino)cyclopentyl)oxy)-1-oxoisoindolin-2-yl)piperidine-2,6-dione | 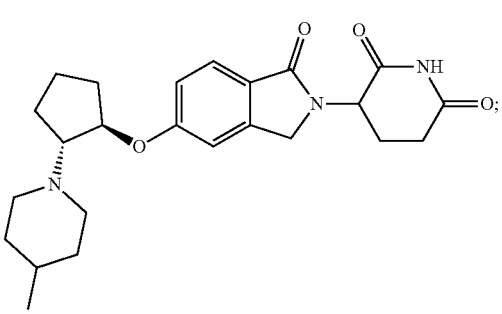 3-(5-(((1R,2R)-2-(4-methylpiperidin-1-yl)cyclopentyl)oxy)-1-oxoisoindolin-2-yl)piperidine-2,6-dione |
| 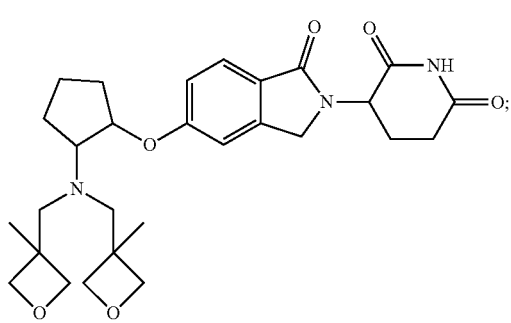 3-(5-((2-(bis((3-methyloxetan-3-yl)methyl)amino)cyclopentyl)oxy)-1-oxoisoindolin-2-yl)piperidine-2,6-dione | 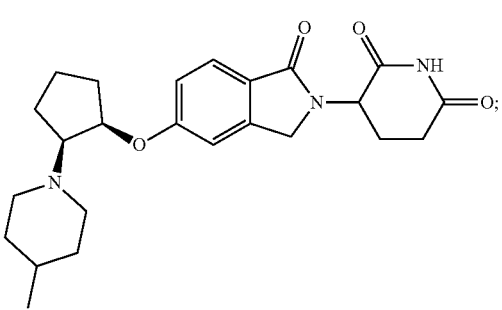 3-(5-(((1R,2S)-2-(4-methylpiperidin-1-yl)cyclopentyl)oxy)-1-oxoisoindolin-2-yl)piperidine-2,6-dione |
| 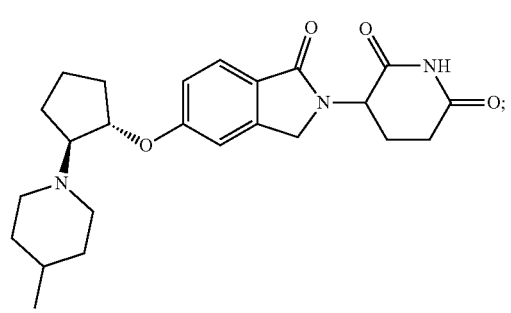 3-(5-(((1S,2S)-2-(4-methylpiperidin-1-yl)cyclopentyl)oxy)-1-oxoisoindolin-2-yl)piperidine-2,6-dione | 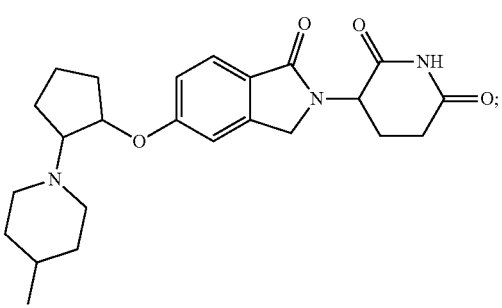 3-(5-((2-(4-methylpiperidin-1-yl)cyclopentyl)oxy)-1-oxoisoindolin-2-yl)piperidine-2,6-dione |

| Compound Structure/Compound Name | Compound Structure/Compound Name |
|---|---|
| 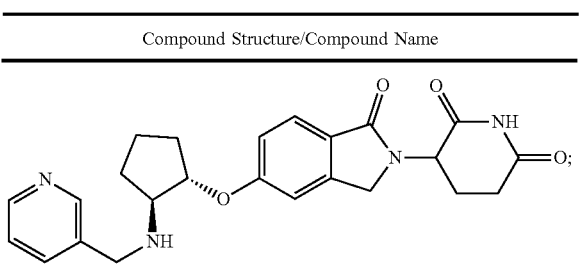<br>3-(1-oxo-5-(((1S,2S)-2-((pyridin-3-ylmethyl)amino)cyclopentyl)oxy)isoindolin-2-yl)piperidine-2,6-dione | 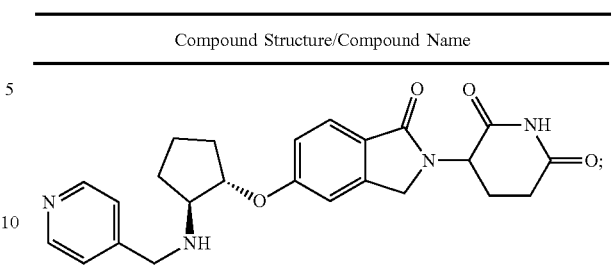<br>3-(1-oxo-5-(((1S,2S)-2-((pyridin-4-ylmethyl)amino)cyclopentyl)oxy)isoindolin-2-yl)piperidine-2,6-dione |
| 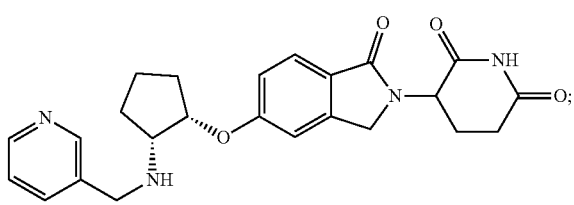<br>3-(1-oxo-5-(((1S,2R)-2-((pyridin-3-ylmethyl)amino)cyclopentyl)oxy)isoindolin-2-yl)piperidine-2,6-dione | 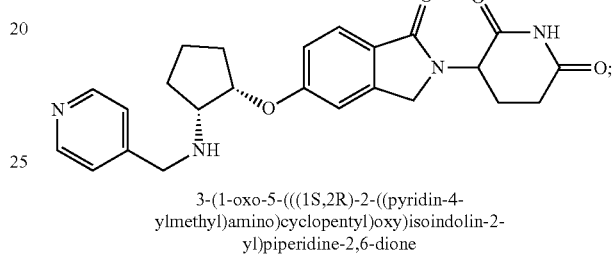<br>3-(1-oxo-5-(((1S,2R)-2-((pyridin-4-ylmethyl)amino)cyclopentyl)oxy)isoindolin-2-yl)piperidine-2,6-dione |
| 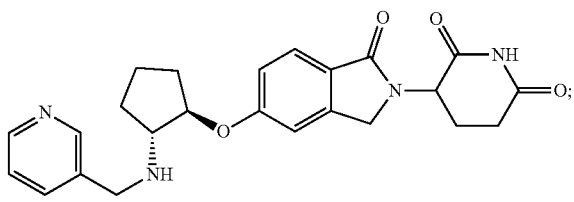<br>3-(1-oxo-5-(((1R,2R)-2-((pyridin-3-ylmethyl)amino)cyclopentyl)oxy)isoindolin-2-yl)piperidine-2,6-dione | 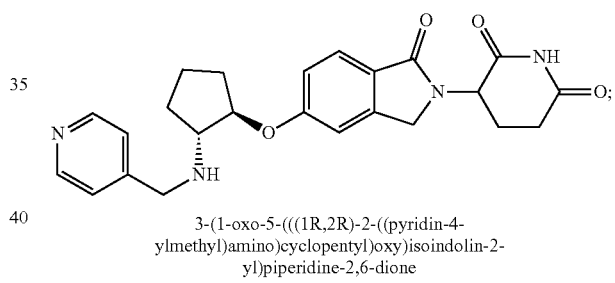<br>3-(1-oxo-5-(((1R,2R)-2-((pyridin-4-ylmethyl)amino)cyclopentyl)oxy)isoindolin-2-yl)piperidine-2,6-dione |
| 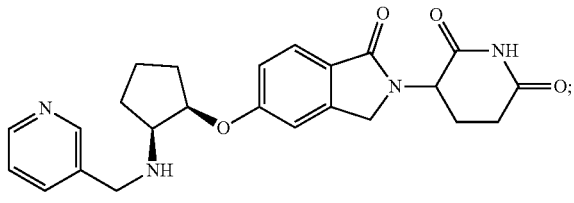<br>3-(1-oxo-5-(((1R,2S)-2-((pyridin-3-ylmethyl)amino)cyclopentyl)oxy)isoindolin-2-yl)piperidine-2,6-dione | 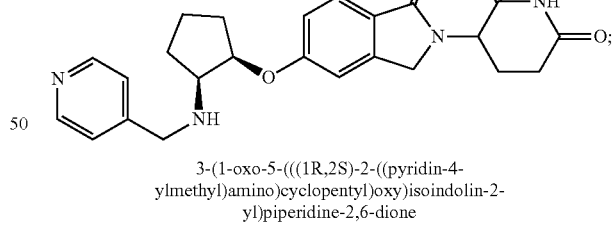<br>3-(1-oxo-5-(((1R,2S)-2-((pyridin-4-ylmethyl)amino)cyclopentyl)oxy)isoindolin-2-yl)piperidine-2,6-dione |
| 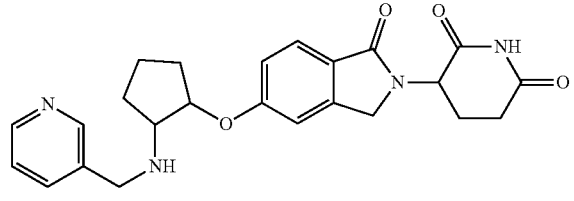<br>3-(1-oxo-5-((2-((pyridin-3-ylmethyl)amino)cyclopentyl)oxy)isoindolin-2-yl)piperidine-2,6-dione | 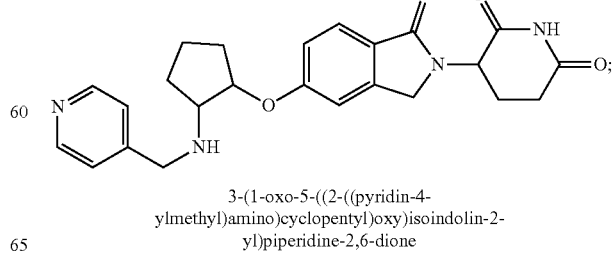<br>3-(1-oxo-5-((2-((pyridin-4-ylmethyl)amino)cyclopentyl)oxy)isoindolin-2-yl)piperidine-2,6-dione |

| Compound Structure/Compound Name |
|---|
| 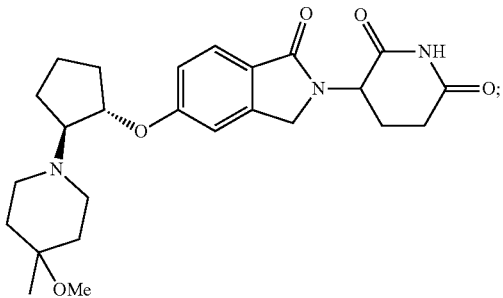 3-(5-(((1S,2S)-2-(4-methoxy-4-methylpiperidin-1-yl)cyclopentyl)oxy)-1-oxoisoindolin-2-yl)piperidine-2,6-dione |
| 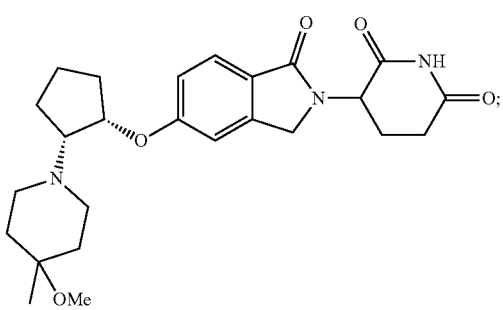 3-(5-(((1S,2R)-2-(4-methoxy-4-methylpiperidin-1-yl)cyclopentyl)oxy)-1-oxoisoindolin-2-yl)piperidine-2,6-dione |
| 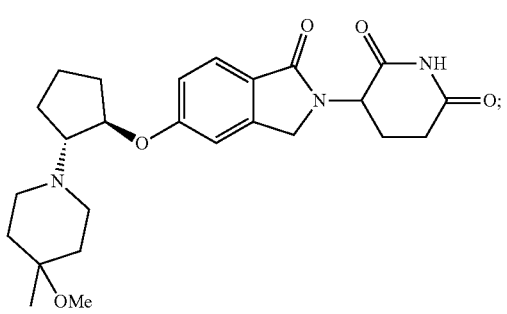 3-(5-(((1R,2R)-2-(4-methoxy-4-methylpiperidin-1-yl)cyclopentyl)oxy)-1-oxoisoindolin-2-yl)piperidine-2,6-dione |
| 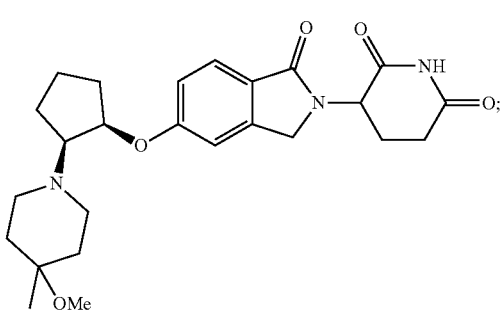 3-(5-(((1R,2S)-2-(4-methoxy-4-methylpiperidin-1-yl)cyclopentyl)oxy)-1-oxoisoindolin-2-yl)piperidine-2,6-dione |

| Compound Structure/Compound Name |
|---|
| 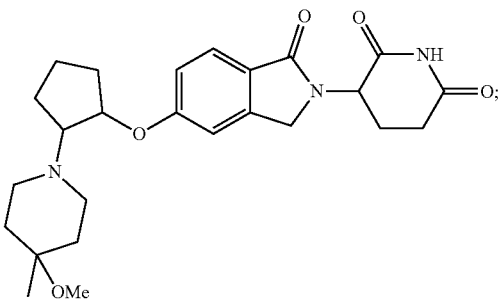 3-(5-((2-(4-methoxy-4-methylpiperidin-1-yl)cyclopentyl)oxy)-1-oxoisoindolin-2-yl)piperidine-2,6-dione |
| 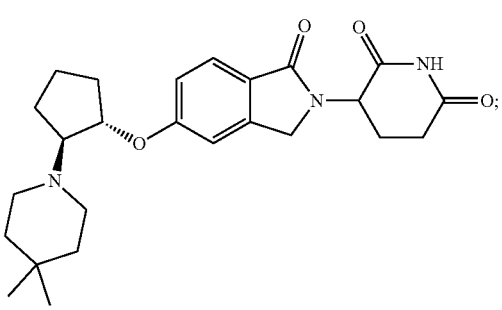 3-(5-(((1S,2S)-2-(4,4-dimethylpiperidin-1-yl)cyclopentyl)oxy)-1-oxoisoindolin-2-yl)piperidine-2,6-dione |
| 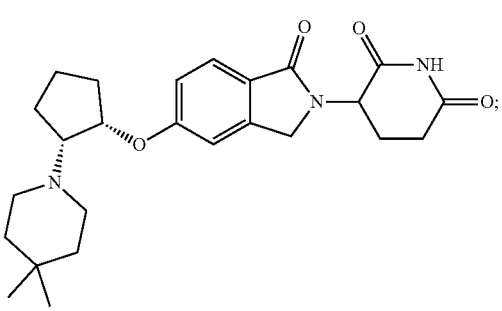 3-(5-(((1S,2R)-2-(4,4-dimethylpiperidin-1-yl)cyclopentyl)oxy)-1-oxoisoindolin-2-yl)piperidine-2,6-dione |
| 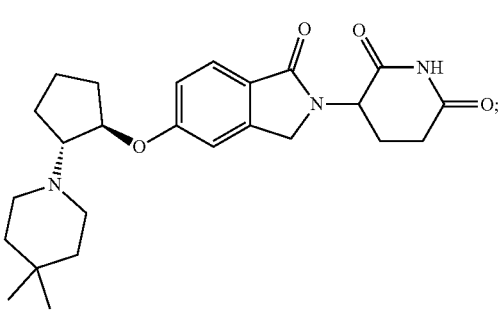 3-(5-(((1R,2R)-2-(4,4-dimethylpiperidin-1-yl)cyclopentyl)oxy)-1-oxoisoindolin-2-yl)piperidine-2,6-dione |

| Compound Structure/Compound Name |
|---|
| 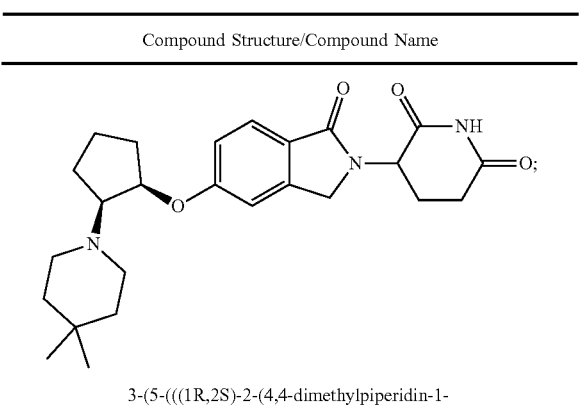<br>3-(5-((((1R,2S)-2-(4,4-dimethylpiperidin-1-yl)cyclopentyl)oxy)-1-oxoisoindolin-2-yl)piperidine-2,6-dione |
| 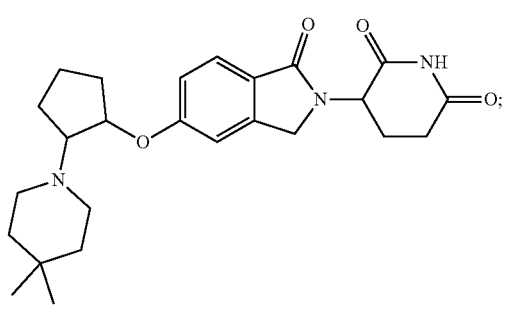<br>3-(5-((2-(4,4-dimethylpiperidin-1-yl)cyclopentyl)oxy)-1-oxoisoindolin-2-yl)piperidine-2,6-dione |
| 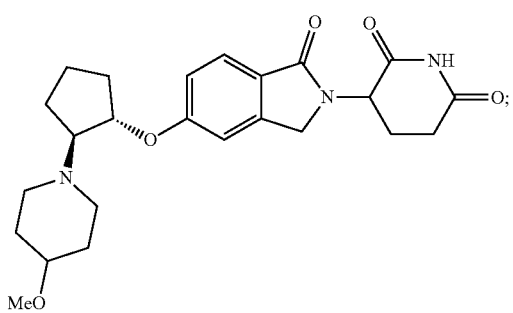<br>3-(5-((((1S,2S)-2-(4-methoxypiperidin-1-yl)cyclopentyl)oxy)-1-oxoisoindolin-2-yl)piperidine-2,6-dione |
| 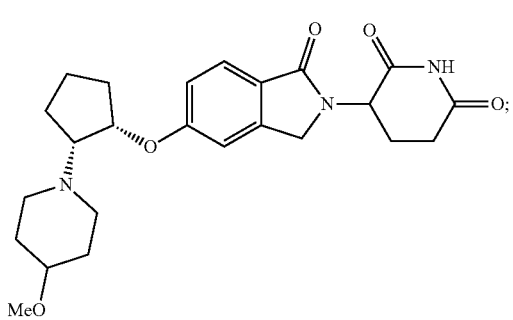<br>3-(5-((((1S,2R)-2-(4-methoxypiperidin-1-yl)cyclopentyl)oxy)-1-oxoisoindolin-2-yl)piperidine-2,6-dione |

| Compound Structure/Compound Name |
|---|
| 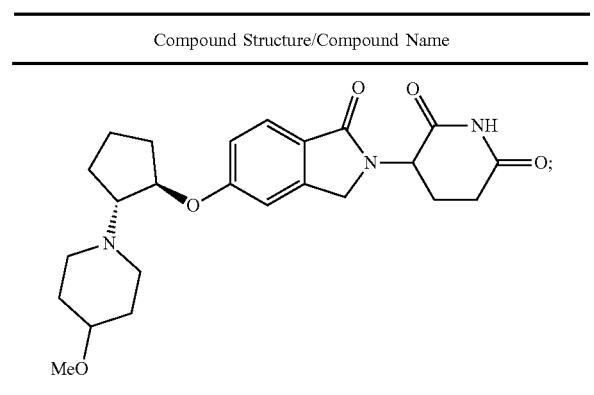<br>3-(5-((((1R,2R)-2-(4-methoxypiperidin-1-yl)cyclopentyl)oxy)-1-oxoisoindolin-2-yl)piperidine-2,6-dione |
| 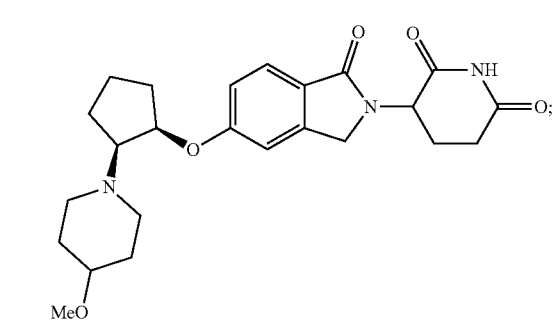<br>3-(5-((((1R,2S)-2-(4-methoxypiperidin-1-yl)cyclopentyl)oxy)-1-oxoisoindolin-2-yl)piperidine-2,6-dione |
| 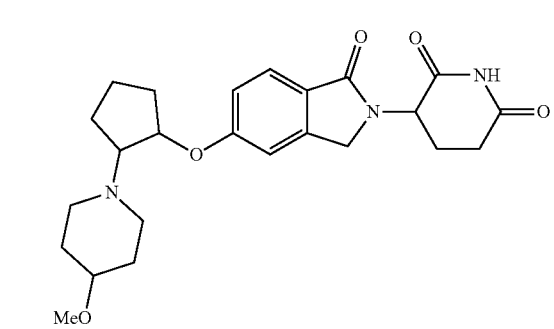<br>3-(5-((2-(4-methoxypiperidin-1-yl)cyclopentyl)oxy)-1-oxoisoindolin-2-yl)piperidine-2,6-dione |
| 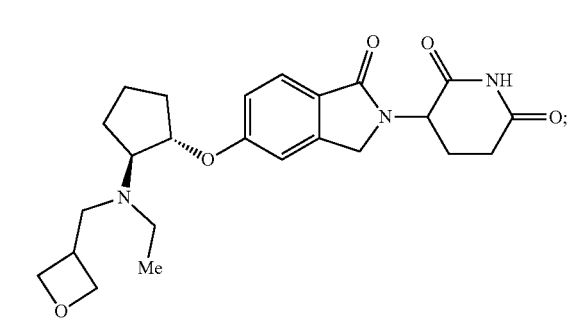<br>3-(5-((((1S,2S)-2-(ethyl(oxetan-3-ylmethyl)amino)cyclopentyl)oxy)-1-oxoisoindolin-2-yl)piperidine-2,6-dione |

| Compound Structure/Compound Name | Compound Structure/Compound Name |
|---|---|
| 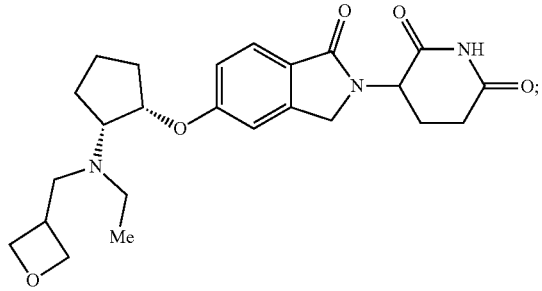<br>3-(5-(((1S,2R)-2-(ethyl(oxetan-3-ylmethyl)amino)cyclopentyl)oxy)-1-oxoisoindolin-2-yl)piperidine-2,6-dione | 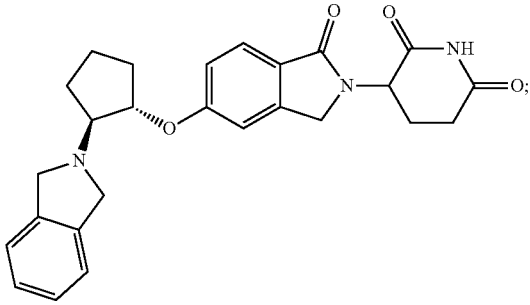<br>3-(5-(((1S,2S)-2-(isoindolin-2-yl)cyclopentyl)oxy)-1-oxoisoindolin-2-yl)piperidine-2,6-dione |
| 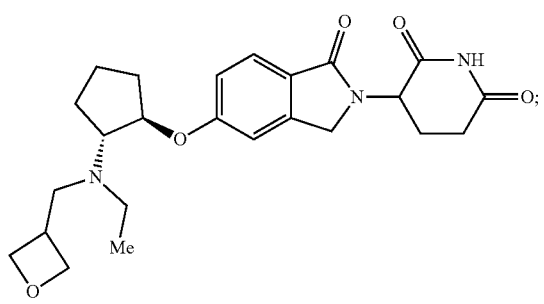<br>3-(5-(((1R,2R)-2-(ethyl(oxetan-3-ylmethyl)amino)cyclopentyl)oxy)-1-oxoisoindolin-2-yl)piperidine-2,6-dione | 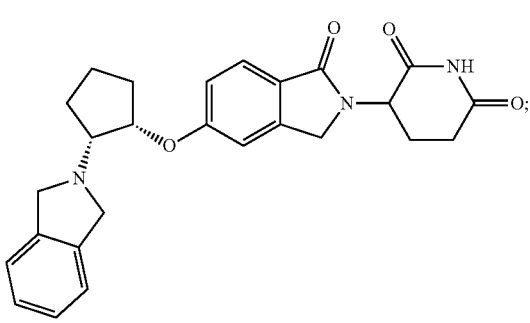<br>3-(5-(((1S,2R)-2-(isoindolin-2-yl)cyclopentyl)oxy)-1-oxoisoindolin-2-yl)piperidine-2,6-dione |
| 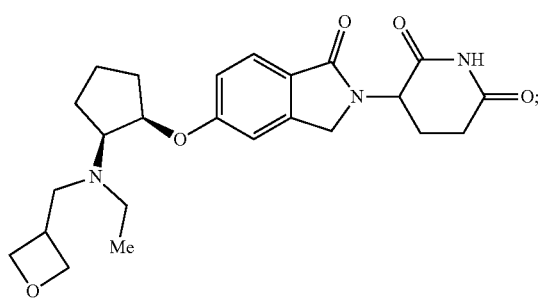<br>3-(5-(((1R,2S)-2-(ethyl(oxetan-3-ylmethyl)amino)cyclopentyl)oxy)-1-oxoisoindolin-2-yl)piperidine-2,6-dione | 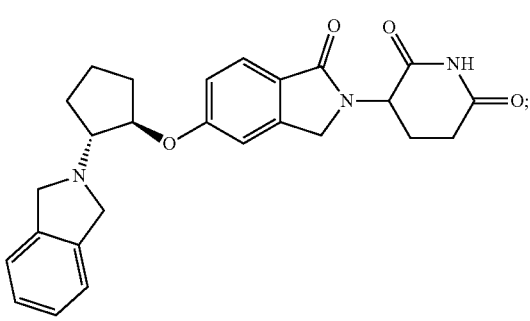<br>3-(5-(((1R,2R)-2-(isoindolin-2-yl)cyclopentyl)oxy)-1-oxoisoindolin-2-yl)piperidine-2,6-dione |
| 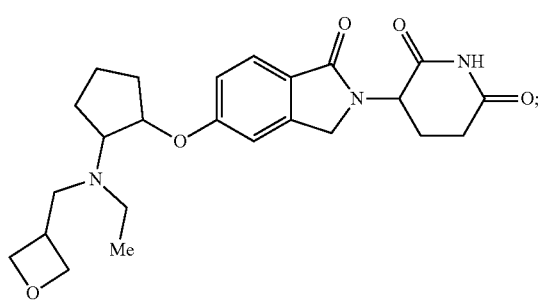<br>3-(5-((2-(ethyl(oxetan-3-ylmethyl)amino)cyclopentyl)oxy)-1-oxoisoindolin-2-yl)piperidine-2,6-dione | 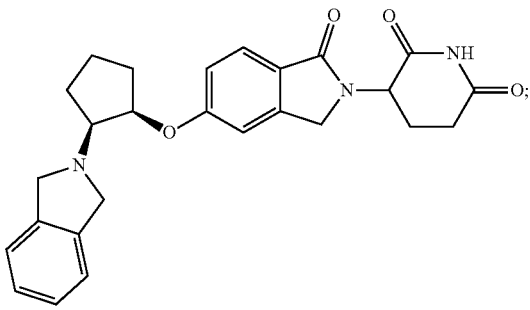<br>3-(5-(((1R,2S)-2-(isoindolin-2-yl)cyclopentyl)oxy)-1-oxoisoindolin-2-yl)piperidine-2,6-dione |

| Compound Structure/Compound Name |
|---|
| 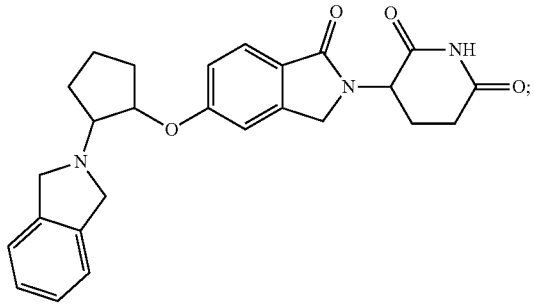<br>3-(5-((2-(isoindolin-2-yl)cyclopentyl)oxy)-1-oxoisoindolin-2-yl)piperidine-2,6-dione |
| 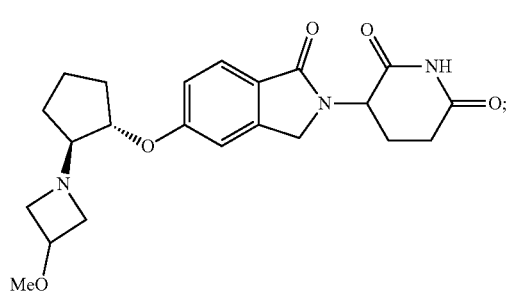<br>3-(5-(((1S,2S)-2-(3-methoxyazetidin-1-yl)cyclopentyl)oxy)-1-oxoisoindolin-2-yl)piperidine-2,6-dione |
| 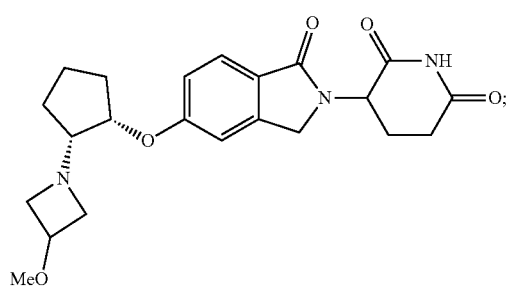<br>3-(5-(((1S,2R)-2-(3-methoxyazetidin-1-yl)cyclopentyl)oxy)-1-oxoisoindolin-2-yl)piperidine-2,6-dione |
| 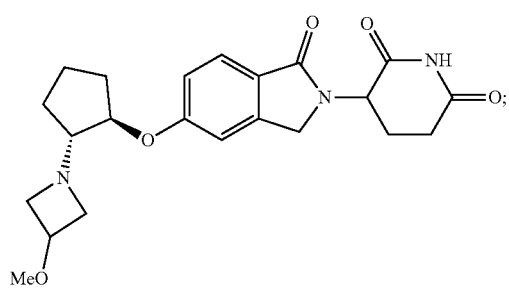<br>3-(5-(((1R,2R)-2-(3-methoxyazetidin-1-yl)cyclopentyl)oxy)-1-oxoisoindolin-2-yl)piperidine-2,6-dione |

| Compound Structure/Compound Name |
|---|
| 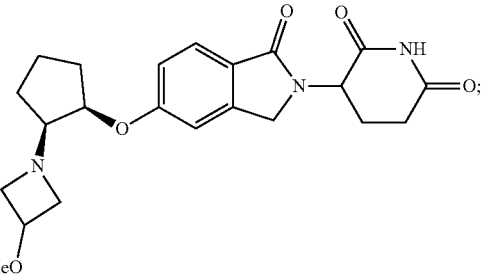<br>3-(5-((((1R,2S)-2-(3-methoxyazetidin-1-yl)cyclopentyl)oxy)-1-oxoisoindolin-2-yl)piperidine-2,6-dione |
| 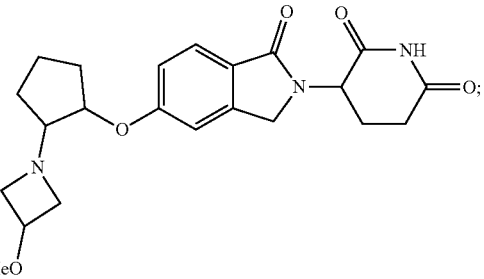<br>3-(5-((2-(3-methoxyazetidin-1-yl)cyclopentyl)oxy)-1-oxoisoindolin-2-yl)piperidine-2,6-dione |
| 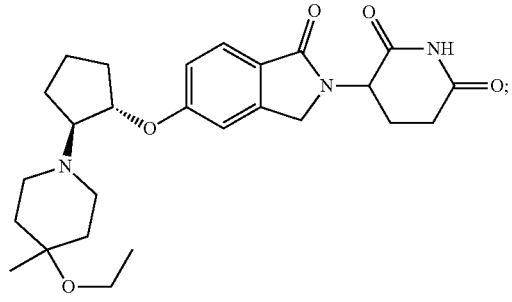<br>3-(5-(((1S,2S)-2-(4-ethoxy-4-methylpiperidin-1-yl)cyclopentyl)oxy)-1-oxoisoindolin-2-yl)piperidine-2,6-dione |
| 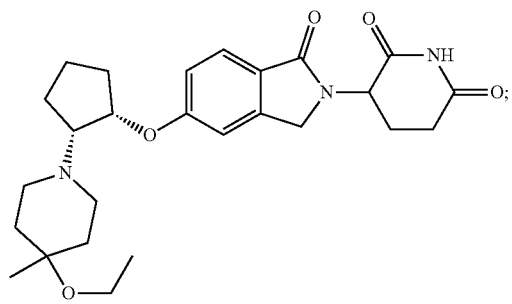<br>3-(5-(((1S,2R)-2-(4-ethoxy-4-methylpiperidin-1-yl)cyclopentyl)oxy)-1-oxoisoindolin-2-yl)piperidine-2,6-dione |

| Compound Structure/Compound Name | Compound Structure/Compound Name |
|---|---|
| 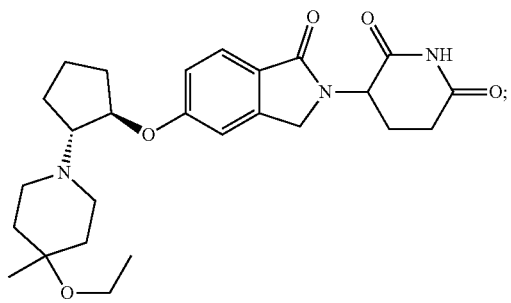<br>3-(5-((((1R,2R)-2-(4-ethoxy-4-methylpiperidin-1-yl)cyclopentyl)oxy)-1-oxoisoindolin-2-yl)piperidine-2,6-dione | 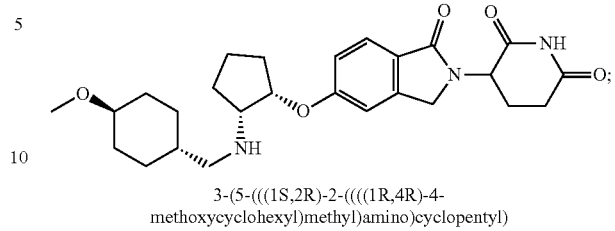<br>3-(5-((((1S,2R)-2-((((1R,4R)-4-methoxycyclohexyl)methyl)amino)cyclopentyl)oxy)-1-oxoisoindolin-2-yl)piperidine-2,6-dione |
| 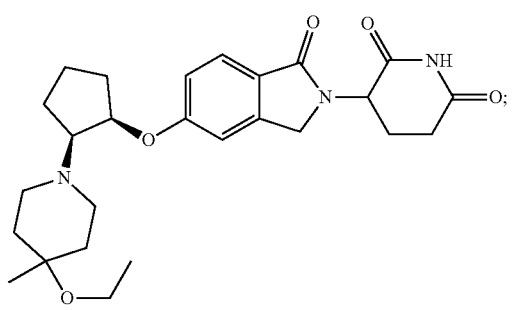<br>3-(5-((((1R,2S)-2-(4-ethoxy-4-methylpiperidin-1-yl)cyclopentyl)oxy)-1-oxoisoindolin-2-yl)piperidine-2,6-dione | 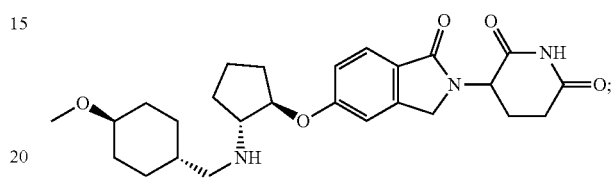<br>3-(5-((((1R,2R)-2-((((1R,4R)-4-methoxycyclohexyl)methyl)amino)cyclopentyl)oxy)-1-oxoisoindolin-2-yl)piperidine-2,6-dione |
| 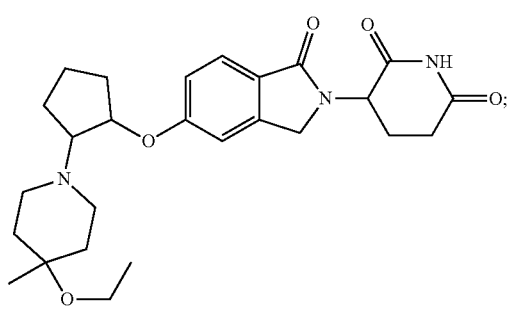<br>3-(5-((2-(4-ethoxy-4-methylpiperidin-1-yl)cyclopentyl)oxy)-1-oxoisoindolin-2-yl)piperidine-2,6-dione | 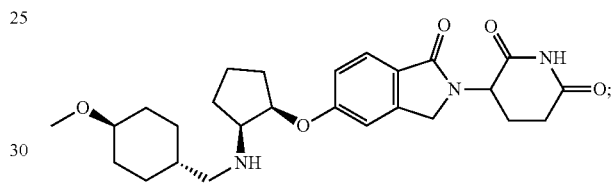<br>3-(5-((((1R,2S)-2-((((1R,4S)-4-methoxycyclohexyl)methyl)amino)cyclopentyl)oxy)-1-oxoisoindolin-2-yl)piperidine-2,6-dione |
| 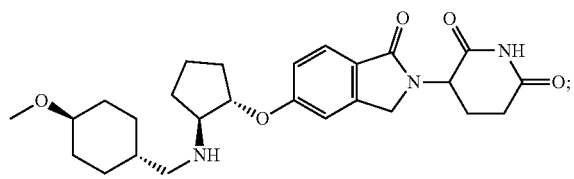<br>3-(5-((((1S,2S)-2-((((1R,4S)-4-methoxycyclohexyl)methyl)amino)cyclopentyl)oxy)-1-oxoisoindolin-2-yl)piperidine-2,6-dione | 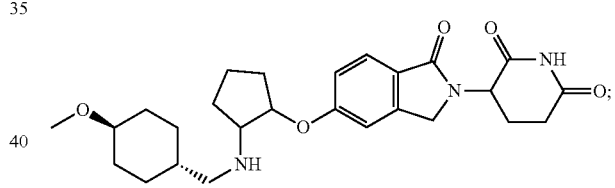<br>3-(5-((2-(((((1R,4R)-4-methoxycyclohexyl)methyl)amino)cyclopentyl)oxy)-1-oxoisoindolin-2-yl)piperidine-2,6-dione |
| | 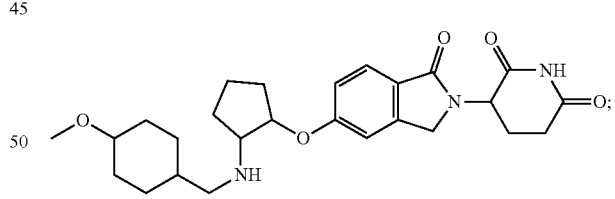<br>3-(5-((2-(((4-methoxycyclohexyl)methyl)amino)cyclopentyl)oxy)-1-oxoisoindolin-2-yl)piperidine-2,6-dione |
| | 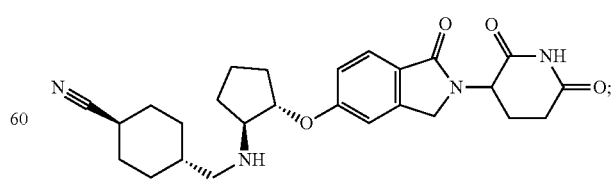<br>(1S,4R)-4-((((1S,2S)-2-((2-(2,6-dioxopiperidin-3-yl)-1-oxoisoindolin-5-yl)oxy)cyclopentyl)amino)methyl)cyclohexane-1-carbonitrile |

| Compound Structure/Compound Name | Compound Structure/Compound Name |
|---|---|
| 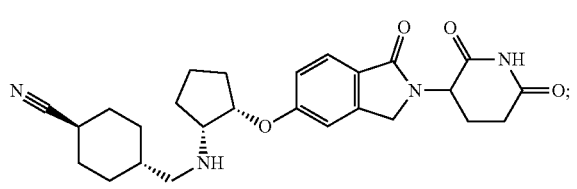      (1R,4r)-4-(((((1R,2S)-2-((2-(2,6-dioxopiperidin-3-yl)-1-oxoisoindolin-5-yl)oxy)cyclopentyl)amino)methyl)cyclohexane-1-carbonitrile | 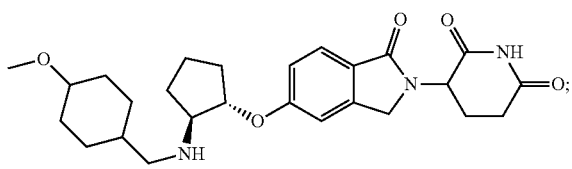      3-(5-((((1S,2S)-2-(((4-methoxycyclohexyl)methyl)amino)cyclopentyl)oxy)-1-oxoisoindolin-2-yl)piperidine-2,6-dione |
| 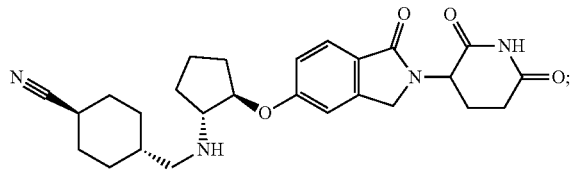      (1R,4r)-4-(((((1R,2R)-2-((2-(2,6-dioxopiperidin-3-yl)-1-oxoisoindolin-5-yl)oxy)cyclopentyl)amino)methyl)cyclohexane-1-carbonitrile | 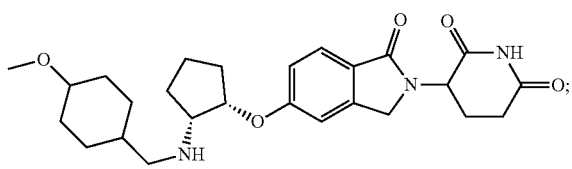      3-(5-((((1S,2R)-2-(((4-methoxycyclohexyl)methyl)amino)cyclopentyl)oxy)-1-oxoisoindolin-2-yl)piperidine-2,6-dione |
| 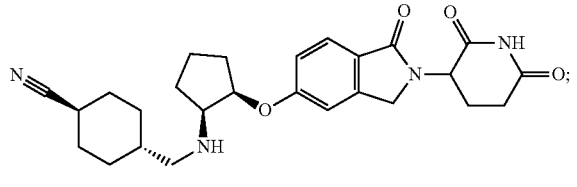      (1S,4r)-4-(((((1S,2R)-2-((2-(2,6-dioxopiperidin-3-yl)-1-oxoisoindolin-5-yl)oxy)cyclopentyl)amino)methyl)cyclohexane-1-carbonitrile | 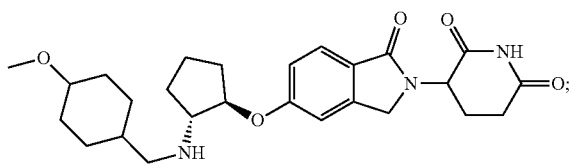      3-(5-((((1R,2R)-2-(((4-methoxycyclohexyl)methyl)amino)cyclopentyl)oxy)-1-oxoisoindolin-2-yl)piperidine-2,6-dione |
| 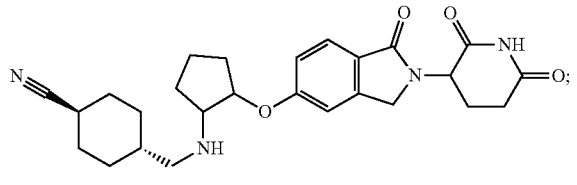      (1r,4r)-4-(((2-((2-(2,6-dioxopiperidin-3-yl)-1-oxoisoindolin-5-yl)oxy)cyclopentyl)amino)methyl)cyclohexane-1-carbonitrile | 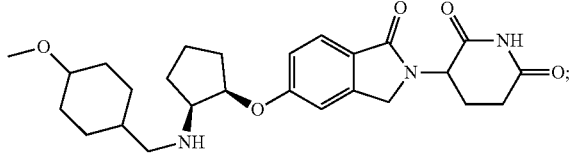      3-(5-((((1R,2S)-2-(((4-methoxycyclohexyl)methyl)amino)cyclopentyl)oxy)-1-oxoisoindolin-2-yl)piperidine-2,6-dione |
| 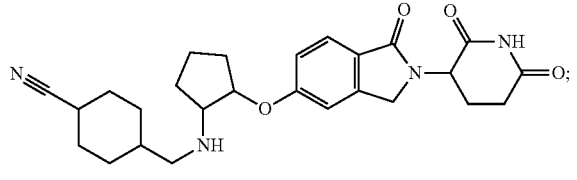      4-(((2-((2-(2,6-dioxopiperidin-3-yl)-1-oxoisoindolin-5-yl)oxy)cyclopentyl)amino)methyl)cyclohexane-1-carbonitrile | 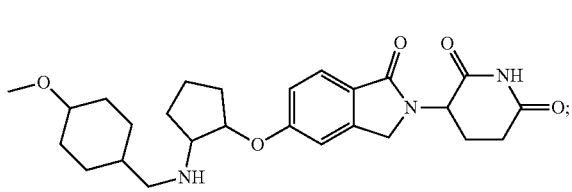      3-(5-((2-(((4-methoxycyclohexyl)methyl)amino)cyclopentyl)oxy)-1-oxoisoindolin-2-yl)piperidine-2,6-dione |

| Compound Structure/Compound Name | Compound Structure/Compound Name |
|---|---|
| 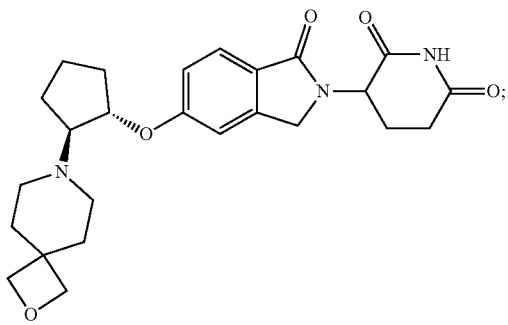 3-(5-(((1S,2S)-2-(2-oxa-7-azaspiro[3.5]nonan-7-yl)cyclopentyl)oxy)-1-oxoisoindolin-2-yl)piperidine-2,6-dione | 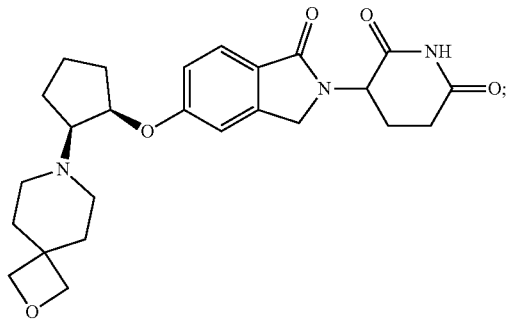 3-(5-(((1R,2S)-2-(2-oxa-7-azaspiro[3.5]nonan-7-yl)cyclopentyl)oxy)-1-oxoisoindolin-2-yl)piperidine-2,6-dione |
| 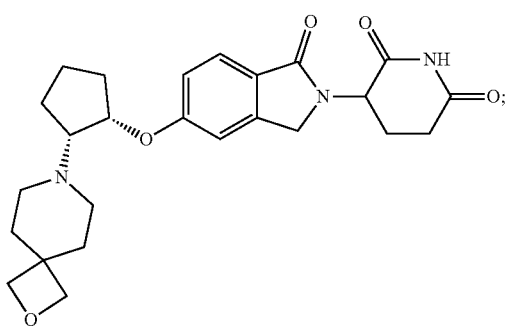 3-(5-(((1S,2R)-2-(2-oxa-7-azaspiro[3.5]nonan-7-yl)cyclopentyl)oxy)-1-oxoisoindolin-2-yl)piperidine-2,6-dione | 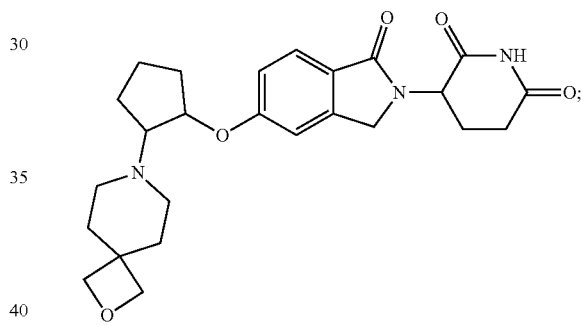 3-(5-((2-(2-oxa-7-azaspiro[3.5]nonan-7-yl)cyclopentyl)oxy)-1-oxoisoindolin-2-yl)piperidine-2,6-dione |
| 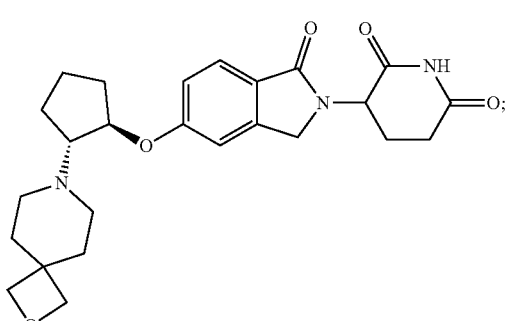 3-(5-(((1R,2R)-2-(2-oxa-7-azaspiro[3.5]nonan-7-yl)cyclopentyl)oxy)-1-oxoisoindolin-2-yl)piperidine-2,6-dione | 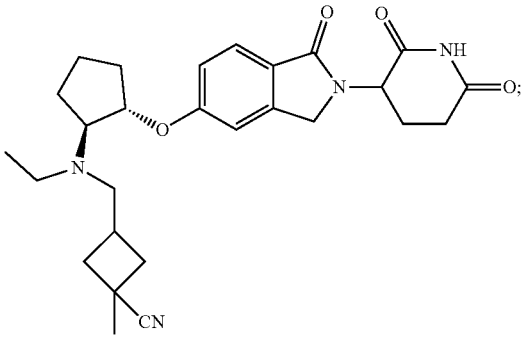 3-((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile |

| Compound Structure/Compound Name | Compound Structure/Compound Name |
|---|---|
| 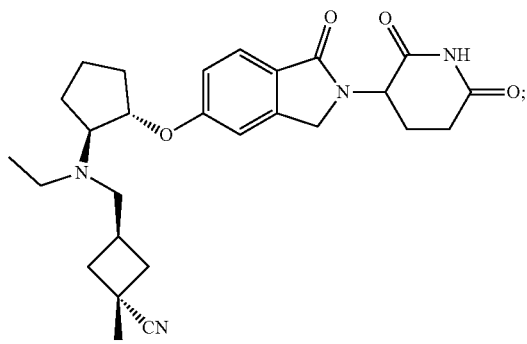<br>(1S,3R)-3-((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile | 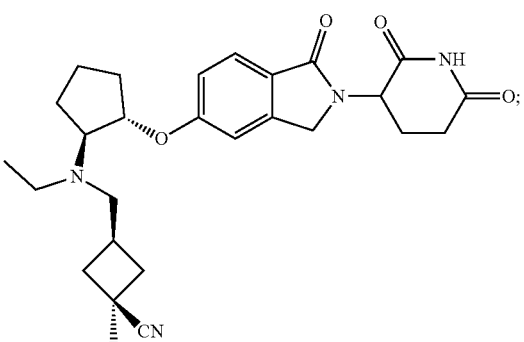<br>cis-3-(((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile |
| 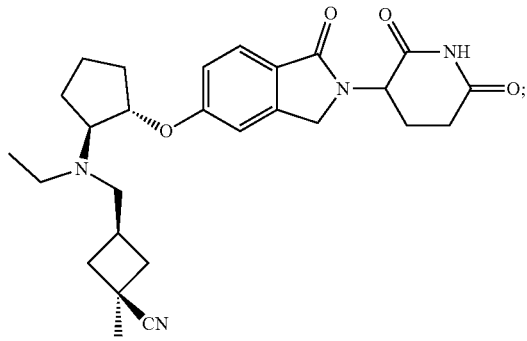<br>(1R,3S)-3-((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile | 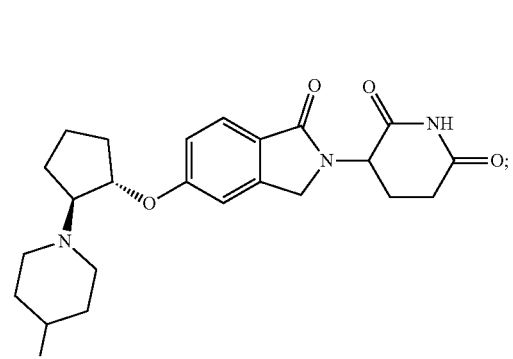<br>3-(5-(((1S,2S)-2-(4-fluoropiperidin-1-yl)cyclopentyl)oxy)-1-oxoisoindolin-2-yl)piperidine-2,6-dione |
| 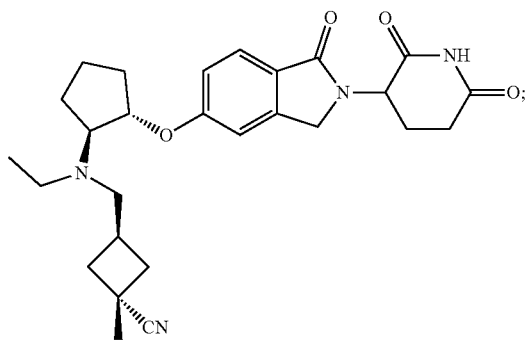<br>trans-3-((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile | 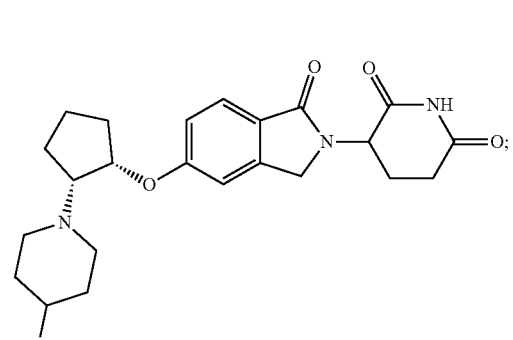<br>3-(5-(((1S,2R)-2-(4-fluoropiperidin-1-yl)cyclopentyl)oxy)-1-oxoisoindolin-2-yl)piperidine-2,6-dione |

| Compound Structure/Compound Name | Compound Structure/Compound Name |
|---|---|
| 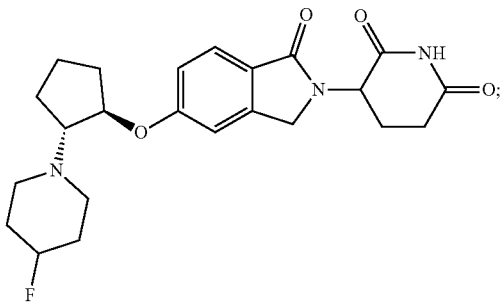 3-(5-((((1R,2R)-2-(4-fluoropiperidin-1-yl)cyclopentyl)oxy)-1-oxoisoindolin-2-yl)piperidine-2,6-dione | 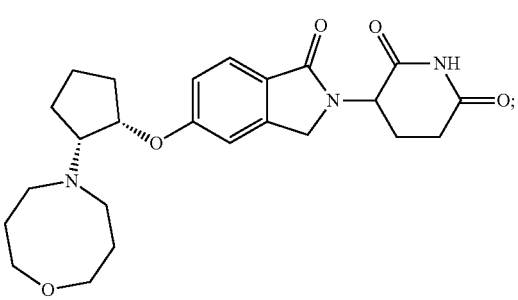 3-(5-((((1S,2R)-2-(1,5-oxazocan-5-yl)cyclopentyl)oxy)-1-oxoisoindolin-2-yl)piperidine-2,6-dione |
| 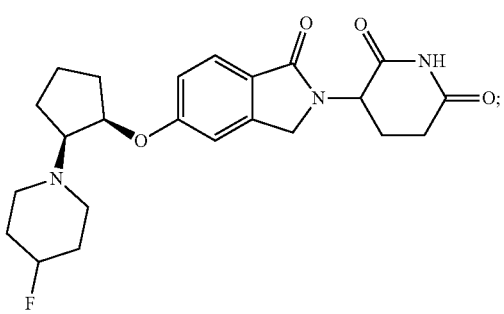 3-(5-((((1R,2S)-2-(4-fluoropiperidin-1-yl)cyclopentyl)oxy)-1-oxoisoindolin-2-yl)piperidine-2,6-dione | 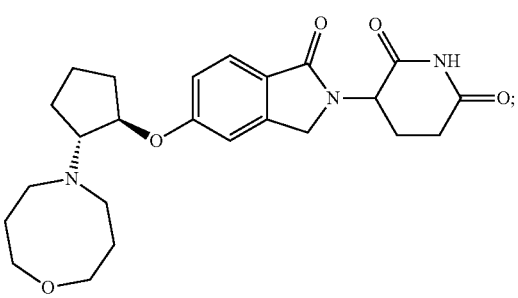 3-(5-((((1R,2R)-2-(1,5-oxazocan-5-yl)cyclopentyl)oxy)-1-oxoisoindolin-2-yl)piperidine-2,6-dione |
| 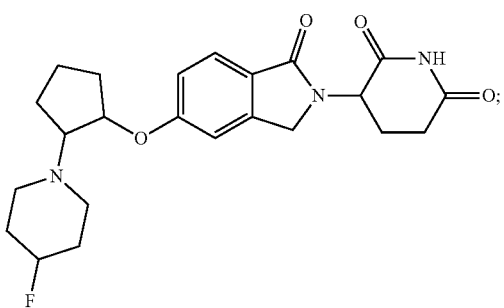 3-(5-((2-(4-fluoropiperidin-1-yl)cyclopentyl)oxy)-1-oxoisoindolin-2-yl)piperidine-2,6-dione | 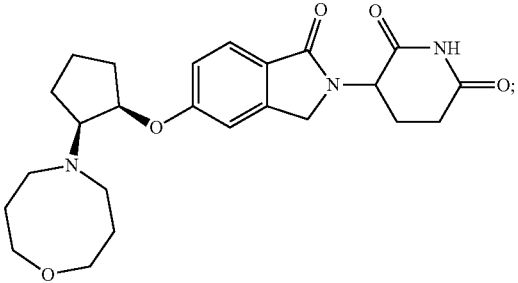 3-(5-((((1R,2S)-2-(1,5-oxazocan-5-yl)cyclopentyl)oxy)-1-oxoisoindolin-2-yl)piperidine-2,6-dione |
| 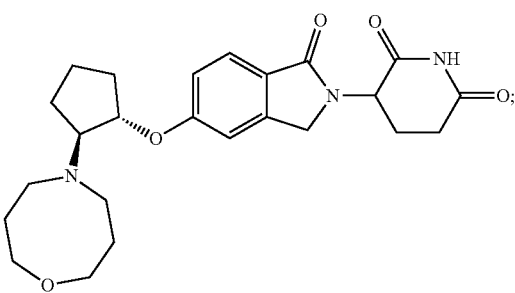 3-(5-((((1S,2S)-2-(1,5-oxazocan-5-yl)cyclopentyl)oxy)-1-oxoisoindolin-2-yl)piperidine-2,6-dione | 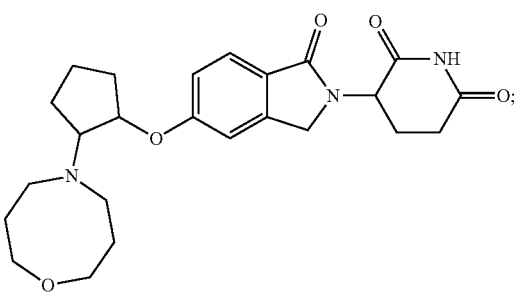 3-(5-((2-(1,5-oxazocan-5-yl)cyclopentyl)oxy)-1-oxoisoindolin-2-yl)piperidine-2,6-dione |

| Compound Structure/Compound Name |
|---|
| 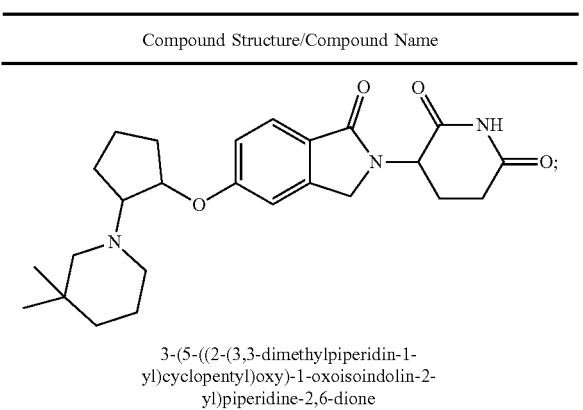 |
| 3-(5-((2-(3,3-dimethylpiperidin-1-yl)cyclopentyl)oxy)-1-oxoisoindolin-2-yl)piperidine-2,6-dione |
| 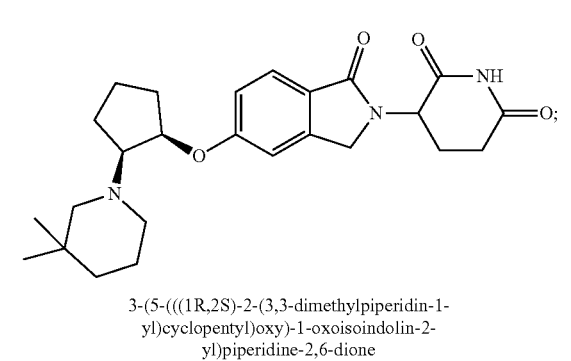 |
| 3-(5-(((1R,2S)-2-(3,3-dimethylpiperidin-1-yl)cyclopentyl)oxy)-1-oxoisoindolin-2-yl)piperidine-2,6-dione |
| 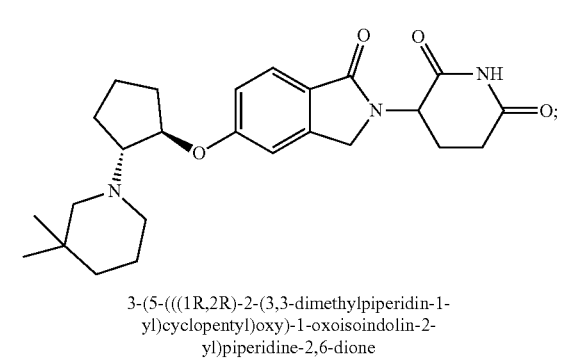 |
| 3-(5-(((1R,2R)-2-(3,3-dimethylpiperidin-1-yl)cyclopentyl)oxy)-1-oxoisoindolin-2-yl)piperidine-2,6-dione |
| 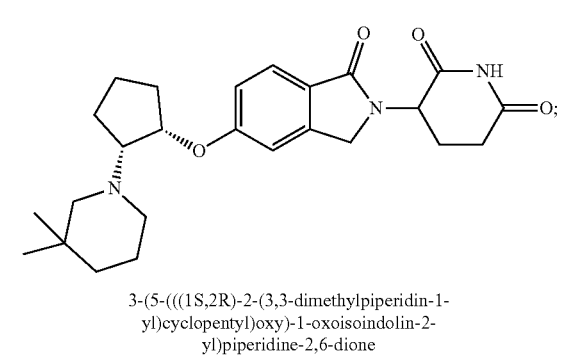 |
| 3-(5-(((1S,2R)-2-(3,3-dimethylpiperidin-1-yl)cyclopentyl)oxy)-1-oxoisoindolin-2-yl)piperidine-2,6-dione |
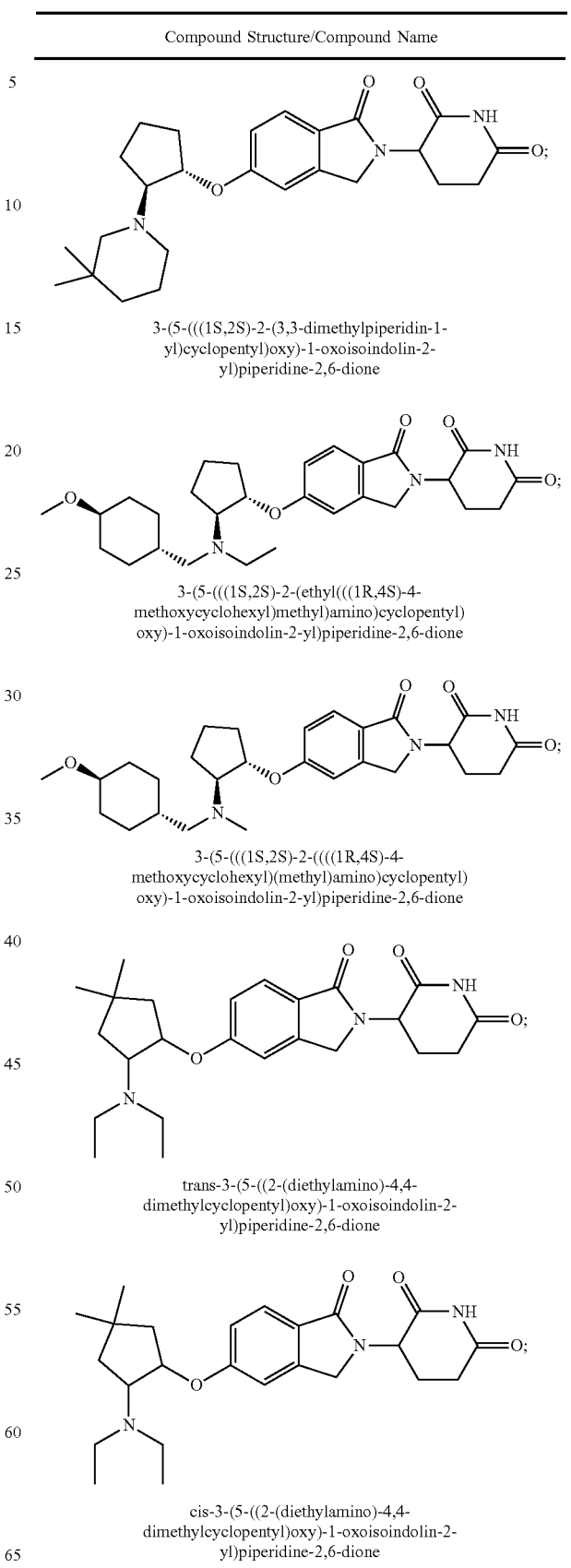

| Compound Structure/Compound Name | Compound Structure/Compound Name |
|---|---|
| 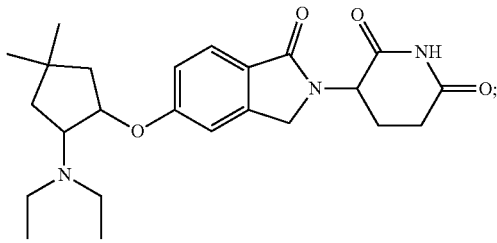 3-(5-((2-(diethylamino)-4,4-dimethylcyclopentyl)oxy)-1-oxoisoindolin-2-yl)piperidine-2,6-dione | 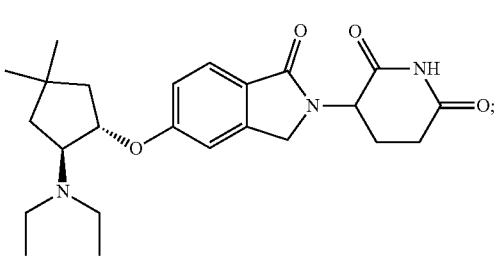 3-(5-(((1S,2S)-2-(diethylamino)-4,4-dimethylcyclopentyl)oxy)-1-oxoisoindolin-2-yl)piperidine-2,6-dione |
| 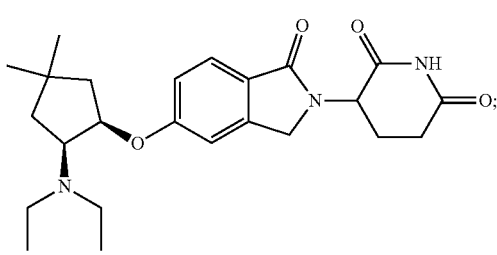 3-(5-(((1R,2S)-2-(diethylamino)-4,4-dimethylcyclopentyl)oxy)-1-oxoisoindolin-2-yl)piperidine-2,6-dione | 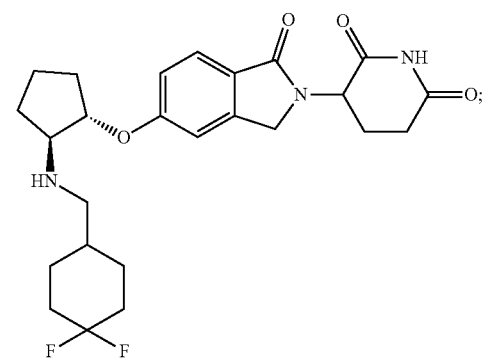 3-(5-(((1S,2S)-2-(((4,4-difluorocyclohexyl)methyl)amino)cyclopentyl)oxy)-1-oxoisoindolin-2-yl)piperidine-2,6-dione |
| 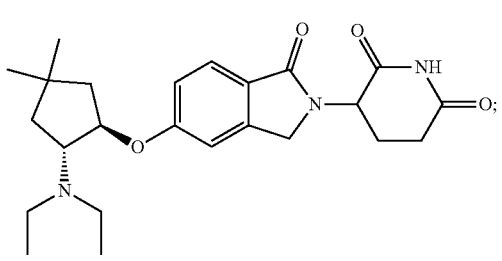 3-(5-(((1R,2R)-2-(diethylamino)-4,4-dimethylcyclopentyl)oxy)-1-oxoisoindolin-2-yl)piperidine-2,6-dione | |
| 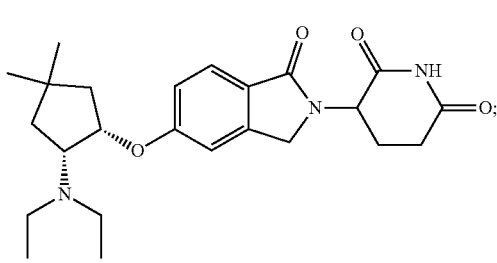 3-(5-(((1S,2R)-2-(diethylamino)-4,4-dimethylcyclopentyl)oxy)-1-oxoisoindolin-2-yl)piperidine-2,6-dione | 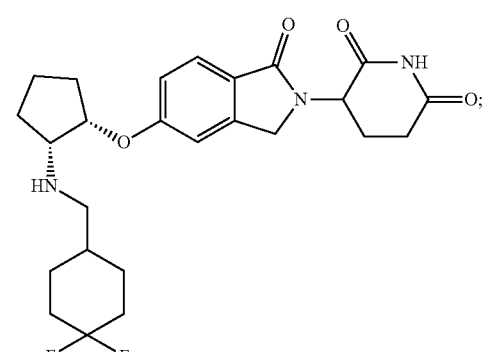 3-(5-(((1S,2R)-2-(((4,4-difluorocyclohexyl)methyl)amino)cyclopentyl)oxy)-1-oxoisoindolin-2-yl)piperidine-2,6-dione |

| Compound Structure/Compound Name |
|---|
| 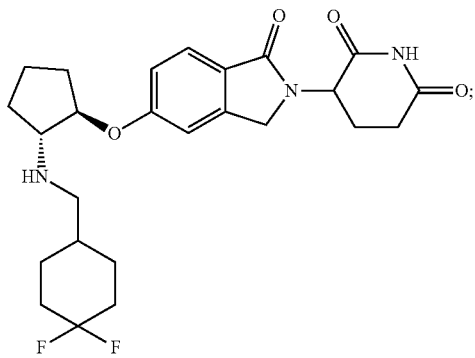<br>3-(5-(((1R,2R)-2-(((4,4-difluorocyclohexyl)methyl)amino)cyclopentyl)oxy)-1-oxoisoindolin-2-yl)piperidine-2,6-dione |
| 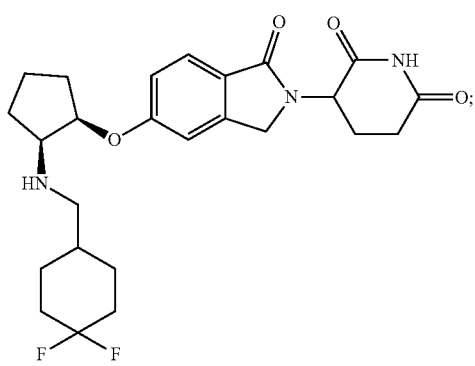<br>3-(5-(((1R,2S)-2-(((4,4-difluorocyclohexyl)methyl)amino)cyclopentyl)oxy)-1-oxoisoindolin-2-yl)piperidine-2,6-dione |
| 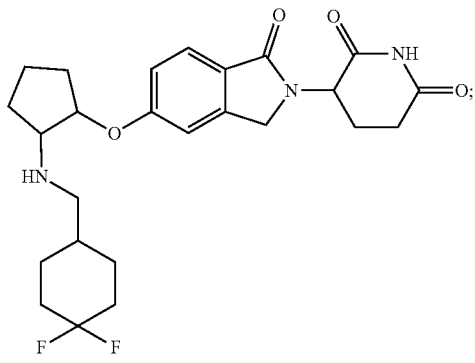<br>3-(5-((2-(((4,4-difluorocyclohexyl)methyl)amino)cyclopentyl)oxy)-1-oxoisoindolin-2-yl)piperidine-2,6-dione |
| 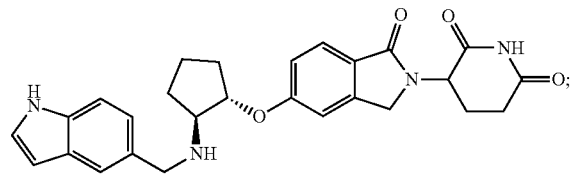<br>3-(5-(((1S,2S)-2-(((1H-indol-5-yl)methyl)amino)cyclopentyl)oxy)-1-oxoisoindolin-2-yl)piperidine-2,6-dione |

| Compound Structure/Compound Name |
|---|
| 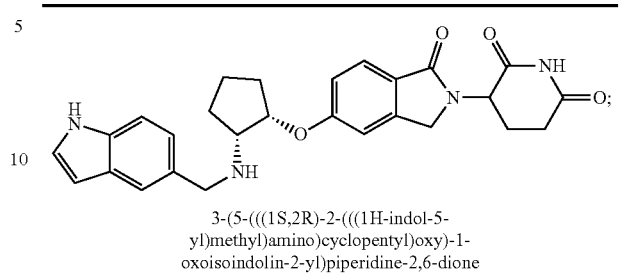<br>3-(5-(((1S,2R)-2-(((1H-indol-5-yl)methyl)amino)cyclopentyl)oxy)-1-oxoisoindolin-2-yl)piperidine-2,6-dione |
| 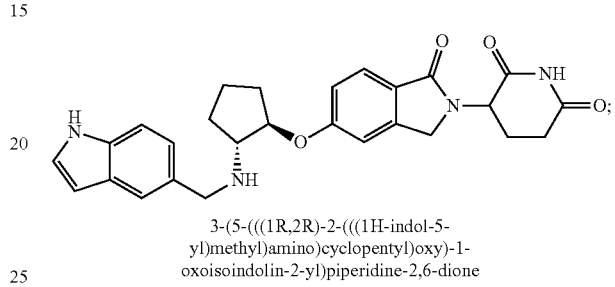<br>3-(5-(((1R,2R)-2-(((1H-indol-5-yl)methyl)amino)cyclopentyl)oxy)-1-oxoisoindolin-2-yl)piperidine-2,6-dione |
| 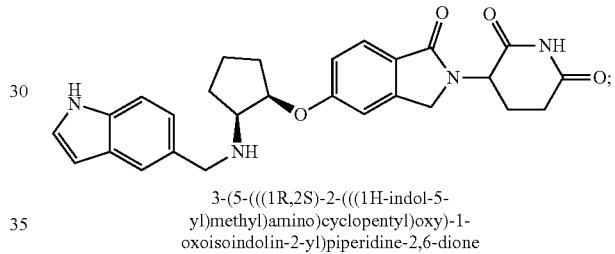<br>3-(5-(((1R,2S)-2-(((1H-indol-5-yl)methyl)amino)cyclopentyl)oxy)-1-oxoisoindolin-2-yl)piperidine-2,6-dione |
| 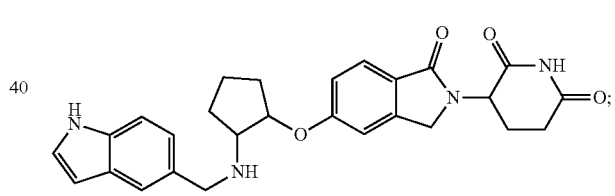<br>3-(5-((2-(((1H-indol-5-yl)methyl)amino)cyclopentyl)oxy)-1-oxoisoindolin-2-yl)piperidine-2,6-dione |
| 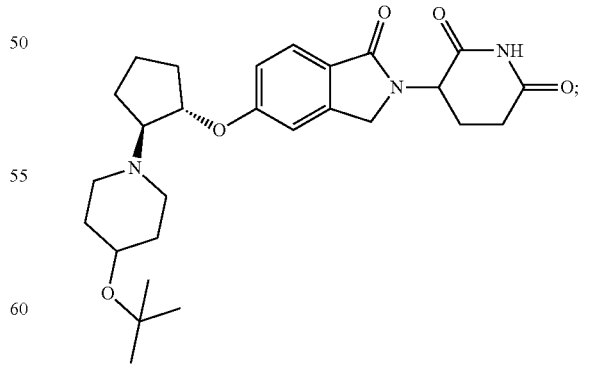<br>3-(5-(((1S,2S)-2-(4-(tert-butoxy)piperidin-1-yl)cyclopentyl)oxy)-1-oxoisoindolin-2-yl)piperidine-2,6-dione |

| Compound Structure/Compound Name | Compound Structure/Compound Name |
|---|---|
| 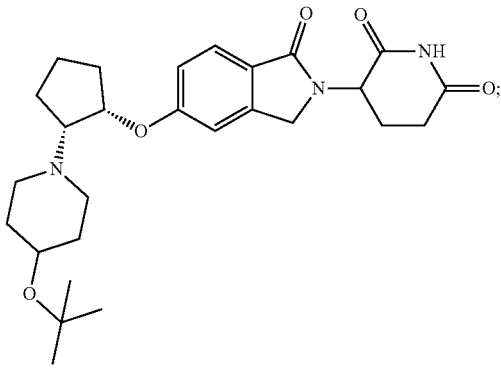<br>3-(5-(((1S,2R)-2-(4-(tert-butoxy)piperidin-1-yl)cyclopentyl)oxy)-1-oxoisoindolin-2-yl)piperidine-2,6-dione | 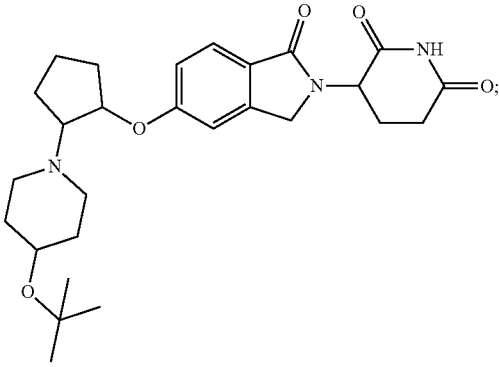<br>3-(5-((2-(4-tert-butoxy)piperidin-1-yl)cyclopentyl)oxy)-1-oxoisoindolin-2-yl)piperidine-2,6-dione |
| 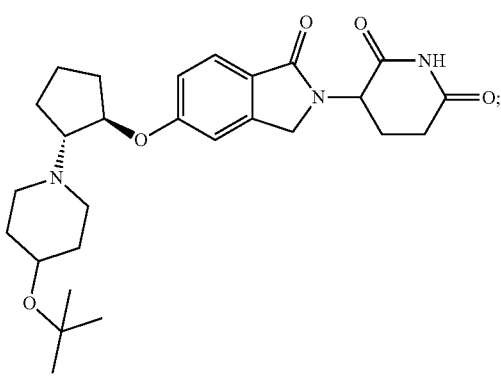<br>3-(5-(((1R,2R)-2-(4-(tert-butoxy)piperidin-1-yl)cyclopentyl)oxy)-1-oxoisoindolin-2-yl)piperidine-2,6-dione | 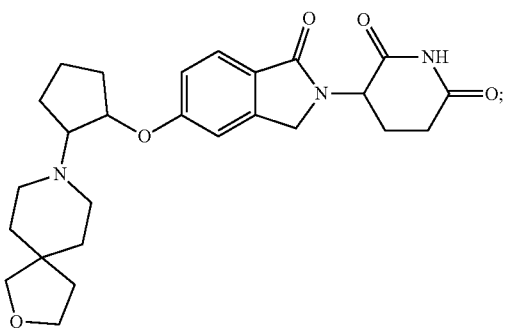<br>3-(5-((2-(2-oxa-8-azaspiro[4.5]decan-8-yl)cyclopentyl)oxy)-1-oxoisoindolin-2-yl)piperidine-2,6-dione |
| 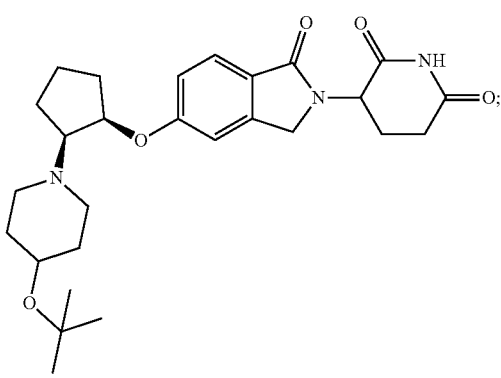<br>3-(5-(((1R,2S)-2-(4-(tert-butoxy)piperidin-1-yl)cyclopentyl)oxy)-1-oxoisoindolin-2-yl)piperidine-2,6-dione | 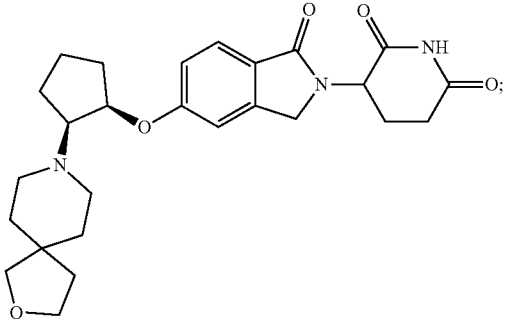<br>3-(5-(((1R,2S)-2-(2-oxa-8-azaspiro[4.5]decan-8-yl)cyclopentyl)oxy)-1-oxoisoindolin-2-yl)piperidine-2,6-dione |

| Compound Structure/Compound Name | Compound Structure/Compound Name |
|---|---|
| 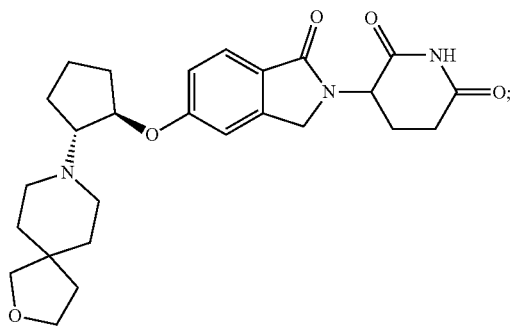<br>3-(5-((((1R,2R)-2-(2-oxa-8-azaspiro[4.5]decan-8-yl)cyclopentyl)oxy)-1-oxoisoindolin-2-yl)piperidine-2,6-dione | 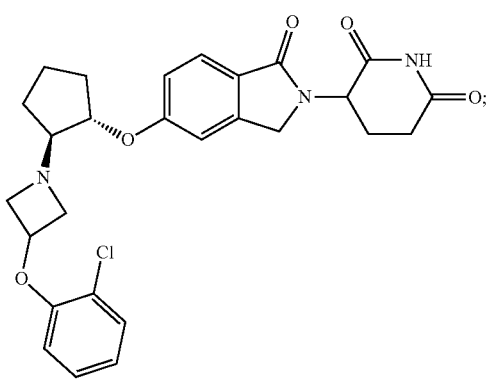<br>3-(5-((((1S,2S)-2-(3-(2-chlorophenoxy)azetidin-1-yl)cyclopentyl)oxy)-1-oxoisoindolin-2-yl)piperidine-2,6-dione |
| 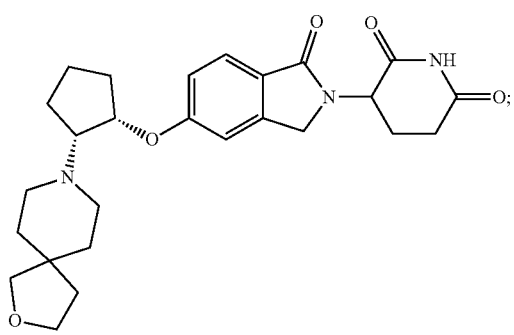<br>3-(5-((((1S,2R)-2-(2-oxa-8-azaspiro[4.5]decan-8-yl)cyclopentyl)oxy)-1-oxoisoindolin-2-yl)piperidine-2,6-dione | 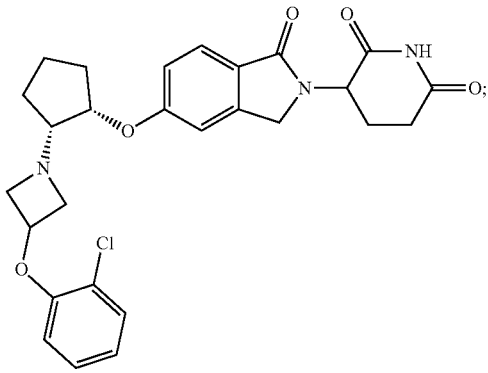<br>3-(5-((((1S,2R)-2-(3-(2-chlorophenoxy)azetidin-1-yl)cyclopentyl)oxy)-1-oxoisoindolin-2-yl)piperidine-2,6-dione |
| 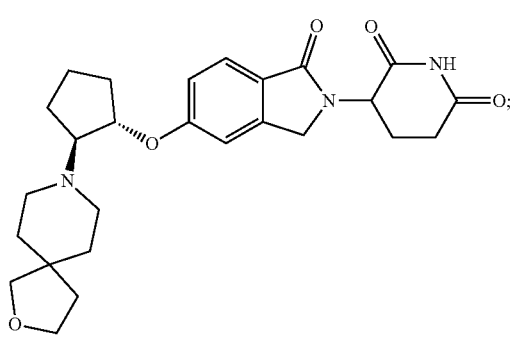<br>3-(5-((((1S,2S)-2-(2-oxa-8-azaspiro[4.5]decan-8-yl)cyclopentyl)oxy)-1-oxoisoindolin-2-yl)piperidine-2,6-dione | 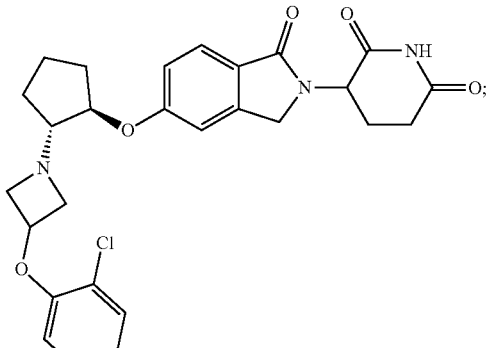<br>3-(5-((((1R,2R)-2-(3-(2-chlorophenoxy)azetidin-1-yl)cyclopentyl)oxy)-1-oxoisoindolin-2-yl)piperidine-2,6-dione |

| 215 -continued | 216 -continued |
|---|---|
| Compound Structure/Compound Name | Compound Structure/Compound Name |
| 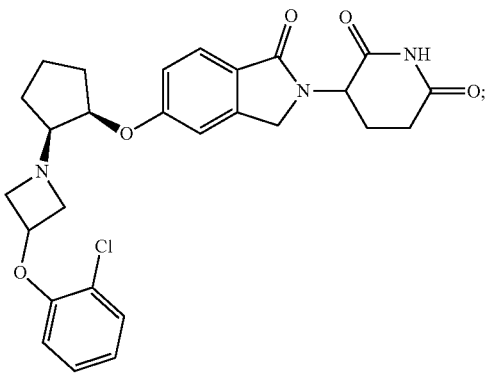　3-(5-(((1R,2S)-2-(3-(2-chlorophenoxy)azetidin-1-yl)cyclopentyl)oxy)-1-oxoisoindolin-2-yl)piperidine-2,6-dione | 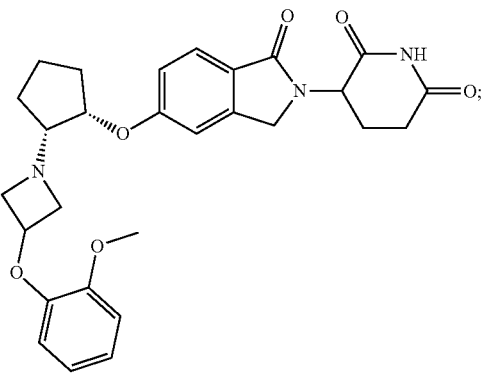　3-(5-(((1S,2R)-2-(3-(2-methoxyphenoxy)azetidin-1-yl)cyclopentyl)oxy)-1-oxoisoindolin-2-yl)piperidine-2,6-dione |
| 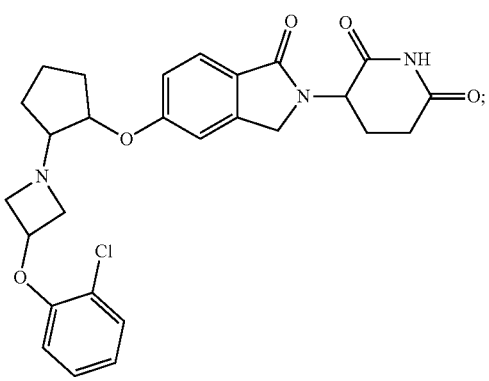　3-(5-((2-(3-(2-chlorophenoxy)azetidin-1-yl)cyclopentyl)oxy)-1-oxoisoindolin-2-yl)piperidine-2,6-dione | 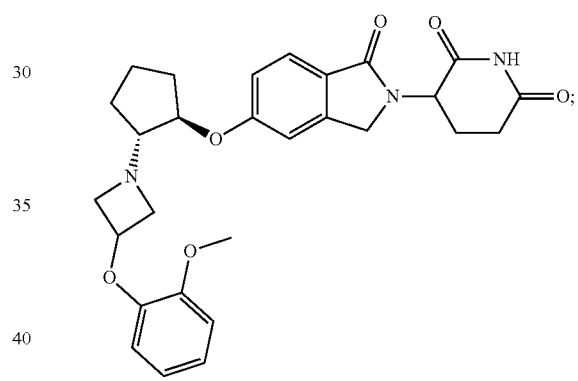　3-(5-(((1R,2R)-2-(3-(2-methoxyphenoxy)azetidin-1-yl)cyclopentyl)oxy)-1-oxoisoindolin-2-yl)piperidine-2,6-dione |
| 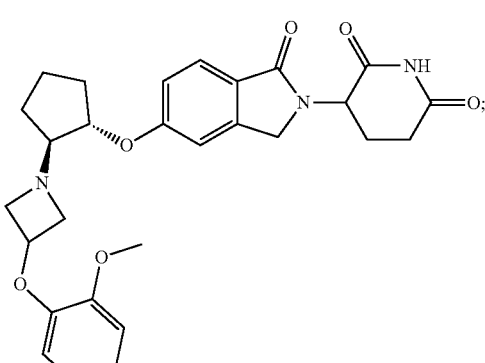　3-(5-(((1S,2S)-2-(3-(2-methoxyphenoxy)azetidin-1-yl)cyclopentyl)oxy)-1-oxoisoindolin-2-yl)piperidine-2,6-dione | 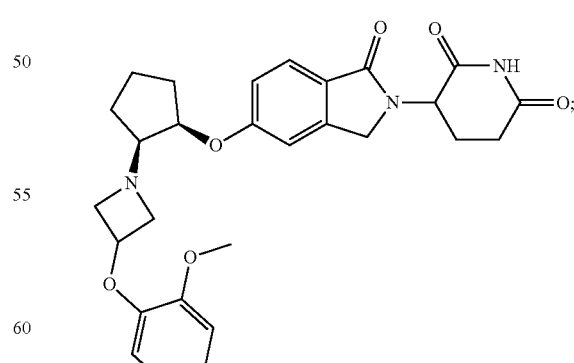　3-(5-(((1R,2S)-2-(3-(2-methoxyphenoxy)azetidin-1-yl)cyclopentyl)oxy)-1-oxoisoindolin-2-yl)piperidine-2,6-dione |

| Compound Structure/Compound Name |
|---|
| 3-(5-((2-(3-(2-methoxyphenoxy)azetidin-1-yl)cyclopentyl)oxy)-1-oxoisoindolin-2-yl)piperidine-2,6-dione |
| 3-(5-((2-(6-azaspiro[3.5]nonan-6-yl)cyclopentyl)oxy)-1-oxoisoindolin-2-yl)piperidine-2,6-dione |
| 3-(5-(((1S,2R)-2-(6-azaspiro[3.5]nonan-6-yl)cyclopentyl)oxy)-1-oxoisoindolin-2-yl)piperidine-2,6-dione |
| 3-(5-(((1R,2R)-2-(6-azaspiro[3.5]nonan-6-yl)cyclopentyl)oxy)-1-oxoisoindolin-2-yl)piperidine-2,6-dione |

| Compound Structure/Compound Name |
|---|
| 3-(5-(((1R,2S)-2-(6-azaspiro[3.5]nonan-6-yl)cyclopentyl)oxy)-1-oxoisoindolin-2-yl)piperidine-2,6-dione |
| 3-(5-(((1S,2S)-2-(6-azaspiro[3.5]nonan-6-yl)cyclopentyl)oxy)-1-oxoisoindolin-2-yl)piperidine-2,6-dione |
| 3-(5-(((1S,2S)-2-(ethyl(((1S,3R)-3-methoxycyclobutyl)methyl)amino)cyclopentyl)oxy)-1-oxoisoindolin-2-yl)piperidine-2,6-dione |
| 3-(5-(((1S,2R)-2-(ethyl(((1s,3S)-3-methoxycyclobutyl)methyl)amino)cyclopentyl)oxy)-1-oxoisoindolin-2-yl)piperidine-2,6-dione |

| Compound Structure/Compound Name | Compound Structure/Compound Name |
|---|---|
| 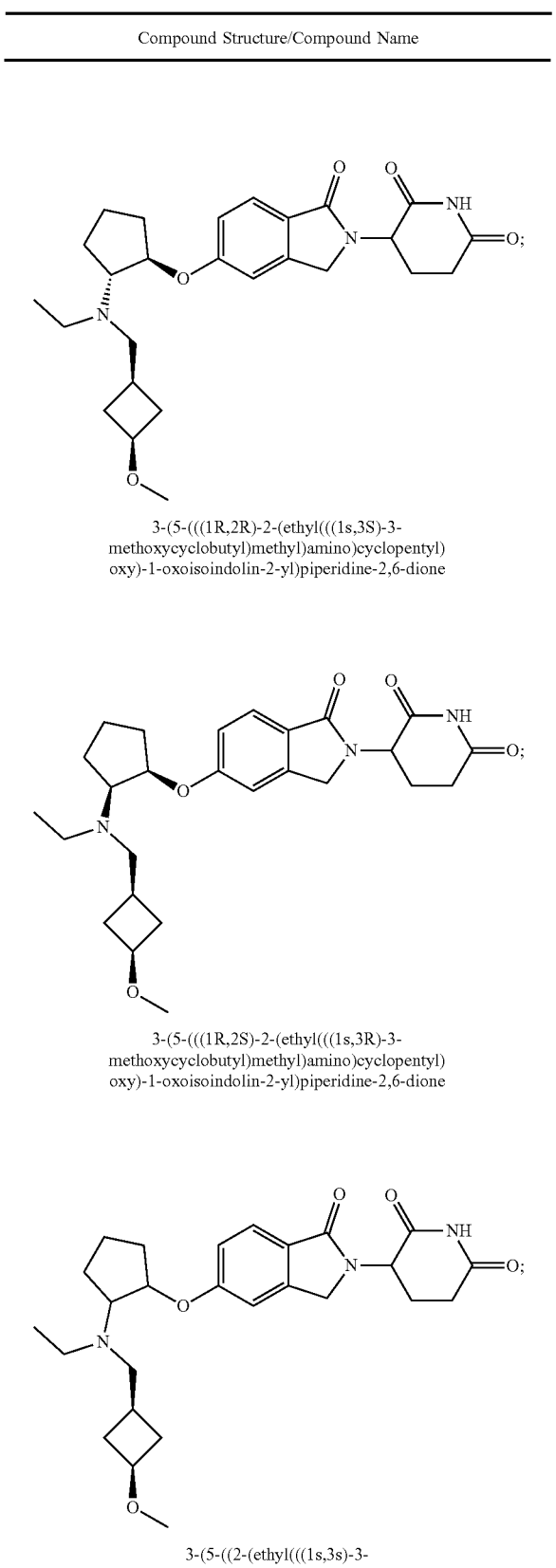 3-(5-((((1R,2R)-2-(ethyl(((1s,3S)-3-methoxycyclobutyl)methyl)amino)cyclopentyl)oxy)-1-oxoisoindolin-2-yl)piperidine-2,6-dione<br><br>3-(5-((((1R,2S)-2-(ethyl(((1s,3R)-3-methoxycyclobutyl)methyl)amino)cyclopentyl)oxy)-1-oxoisoindolin-2-yl)piperidine-2,6-dione<br><br>3-(5-((2-(ethyl(((1s,3s)-3-methoxycyclobutyl)methyl)amino)cyclopentyl)oxy)-1-oxoisoindolin-2-yl)piperidine-2,6-dione | 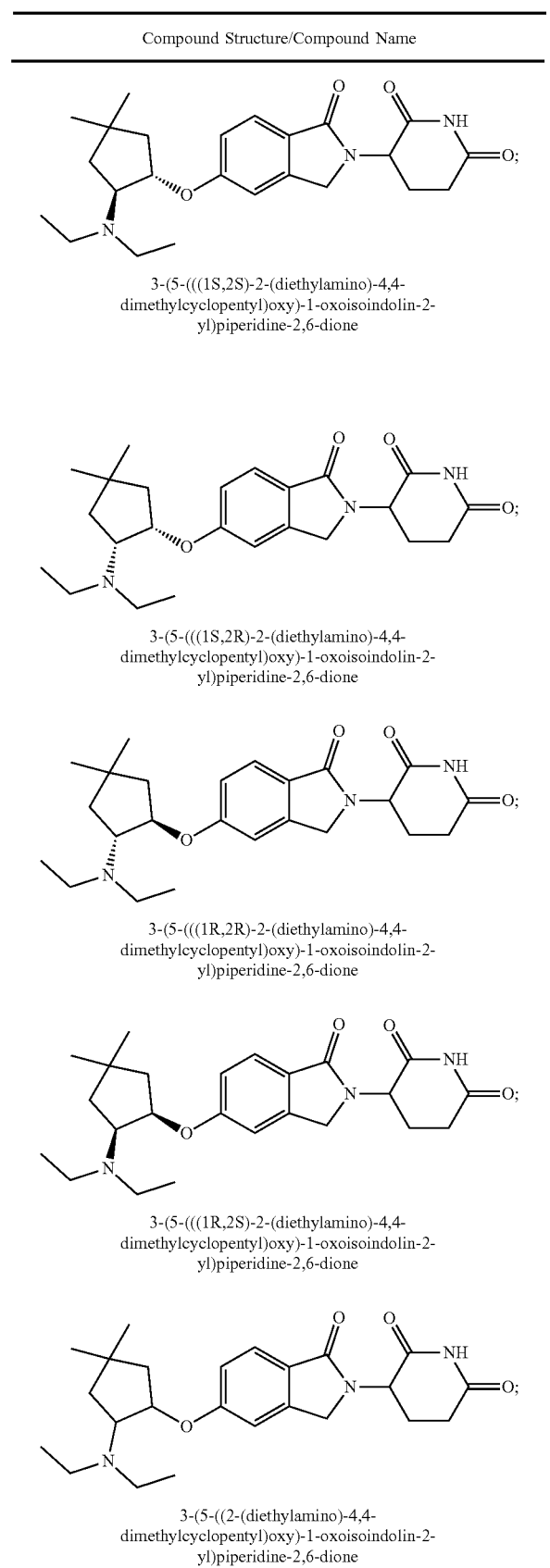 3-(5-((((1S,2S)-2-(diethylamino)-4,4-dimethylcyclopentyl)oxy)-1-oxoisoindolin-2-yl)piperidine-2,6-dione<br><br>3-(5-((((1S,2R)-2-(diethylamino)-4,4-dimethylcyclopentyl)oxy)-1-oxoisoindolin-2-yl)piperidine-2,6-dione<br><br>3-(5-((((1R,2R)-2-(diethylamino)-4,4-dimethylcyclopentyl)oxy)-1-oxoisoindolin-2-yl)piperidine-2,6-dione<br><br>3-(5-((((1R,2S)-2-(diethylamino)-4,4-dimethylcyclopentyl)oxy)-1-oxoisoindolin-2-yl)piperidine-2,6-dione<br><br>3-(5-((2-(diethylamino)-4,4-dimethylcyclopentyl)oxy)-1-oxoisoindolin-2-yl)piperidine-2,6-dione |

| Compound Structure/Compound Name |
|---|
| 3-(5-((((1S,2S)-2-(ethyl(((1R,3S)-3-methoxycyclobutyl)methyl)amino)cyclopentyl)oxy)-1-oxoisoindolin-2-yl)piperidine-2,6-dione |
| 3-(5-((((1S,2R)-2-(ethyl(((1r,3R)-3-methoxycyclobutyl)methyl)amino)cyclopentyl)oxy)-1-oxoisoindolin-2-yl)piperidine-2,6-dione |
| 3-(5-((((1R,2R)-2-(ethyl(((1r,3R)-3-methoxycyclobutyl)methyl)amino)cyclopentyl)oxy)-1-oxoisoindolin-2-yl)piperidine-2,6-dione |
| 3-(5-((((1R,2S)-2-(ethyl(((1r,3S)-3-methoxycyclobutyl)methyl)amino)cyclopentyl)oxy)-1-oxoisoindolin-2-yl)piperidine-2,6-dione |
| 3-(5-((2-(ethyl(((1r,3r)-3-methoxycyclobutyl)methyl)amino)cyclopentyl)oxy)-1-oxoisoindolin-2-yl)piperidine-2,6-dione |
| 3-(5-((2-(8-oxa-2-azaspiro[4.5]decan-2-yl)cyclopentyl)oxy)-1-oxoisoindolin-2-yl)piperidine-2,6-dione |

| Compound Structure/Compound Name | Compound Structure/Compound Name |
|---|---|
| 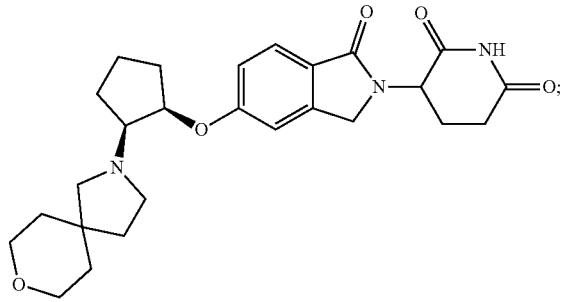<br>3-(5-(((1R,2S)-2-(8-oxa-2-azaspiro[4.5]decan-2-yl)cyclopentyl)oxy)-1-oxoisoindolin-2-yl)piperidine-2,6-dione | 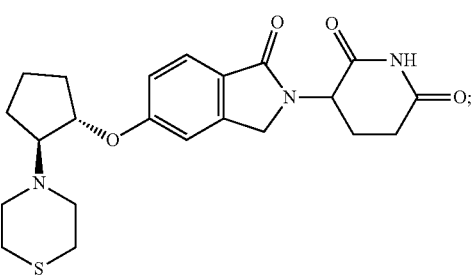<br>3-(1-oxo-5-(((1S,2S)-2-thiomorpholinocyclopentyl)oxy)isoindolin-2-yl)piperidine-2,6-dione |
| 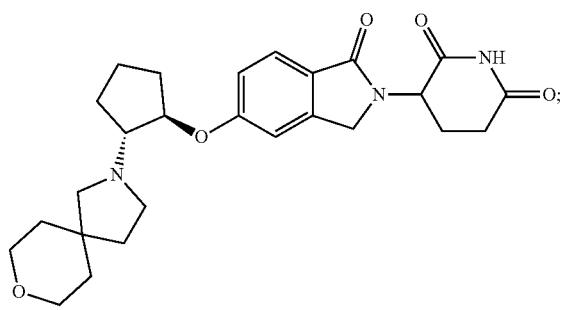<br>3-(5-(((1R,2R)-2-(8-oxa-2-azaspiro[4.5]decan-2-yl)cyclopentyl)oxy)-1-oxoisoindolin-2-yl)piperidine-2,6-dione | 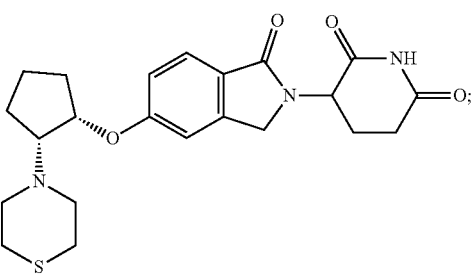<br>3-(1-oxo-5-(((1S,2R)-2-thiomorpholinocyclopentyl)oxy)isoindolin-2-yl)piperidine-2,6-dione |
| 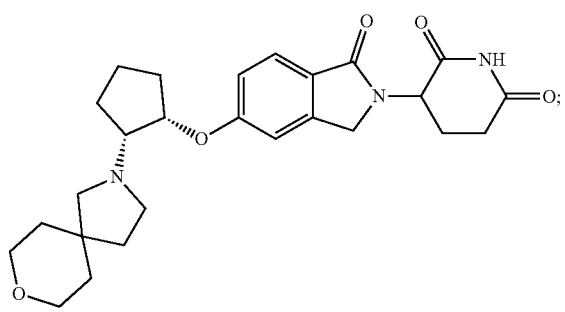<br>3-(5-(((1S,2R)-2-(8-oxa-2-azaspiro[4.5]decan-2-yl)cyclopentyl)oxy)-1-oxoisoindolin-2-yl)piperidine-2,6-dione | 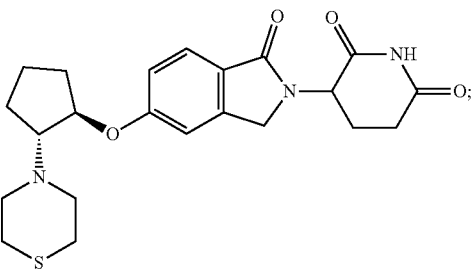<br>3-(1-oxo-5-(((1R,2R)-2-thiomorpholinocyclopentyl)oxy)isoindolin-2-yl)piperidine-2,6-dione |
| 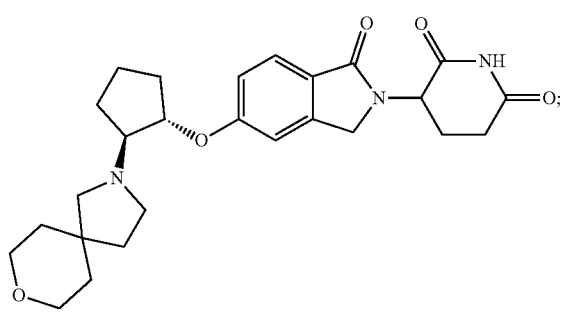<br>3-(5-(((1S,2S)-2-(8-oxa-2-azaspiro[4.5]decan-2-yl)cyclopentyl)oxy)-1-oxoisoindolin-2-yl)piperidine-2,6-dione | 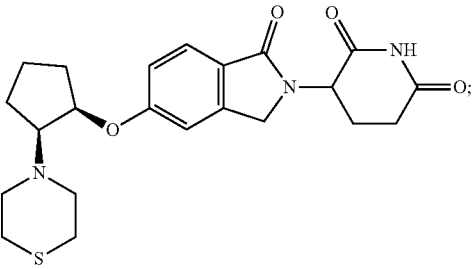<br>3-(1-oxo-5-(((1R,2S)-2-thiomorpholinocyclopentyl)oxy)isoindolin-2-yl)piperidine-2,6-dione |

TABLE-continued

| Compound Structure/Compound Name |
|---|
| 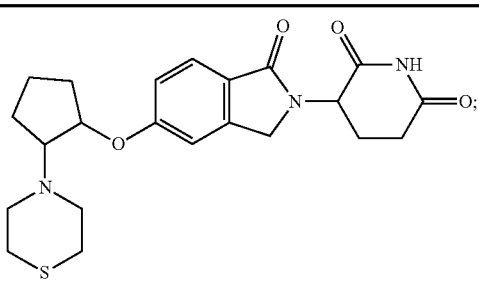<br>3-(1-oxo-5-((2-thiomorpholinocyclopentyl)oxy)isoindolin-2-yl)piperidine-2,6-dione |
| 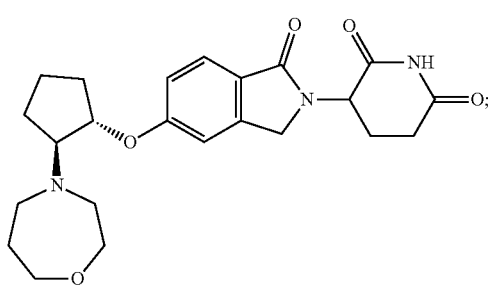<br>3-(5-(((1S,2S)-2-(1,4-oxazepan-4-yl)cyclopentyl)oxy)-1-oxoisoindolin-2-yl)piperidine-2,6-dione |
| 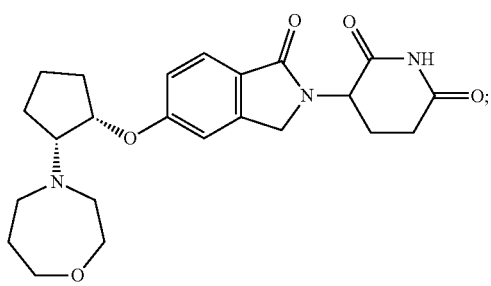<br>3-(5-(((1S,2R)-2-(1,4-oxazepan-4-yl)cyclopentyl)oxy)-1-oxoisoindolin-2-yl)piperidine-2,6-dione |
| 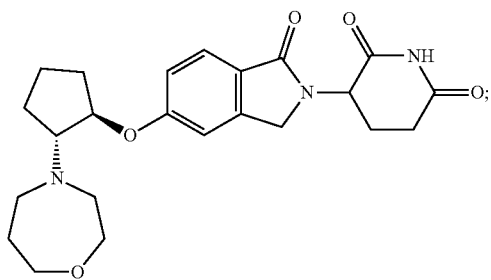<br>3-(5-(((1R,2R)-2-(1,4-oxazepan-4-yl)cyclopentyl)oxy)-1-oxoisoindolin-2-yl)piperidine-2,6-dione |

TABLE-continued

| Compound Structure/Compound Name |
|---|
| 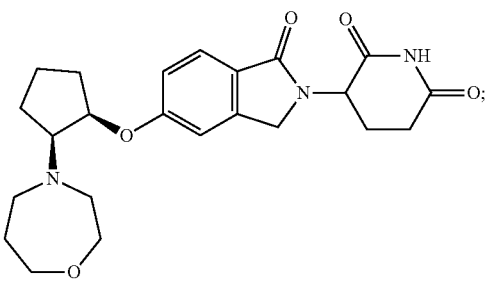<br>3-(5-(((1R,2S)-2-(1,4-oxazepan-4-yl)cyclopentyl)oxy)-1-oxoisoindolin-2-yl)piperidine-2,6-dione |
| 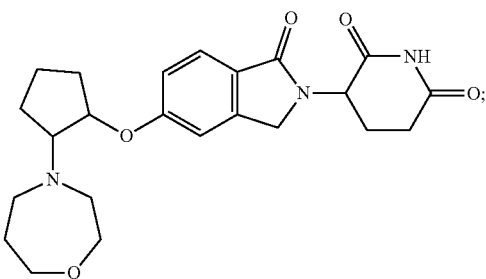<br>3-(5-((2-(1,4-oxazepan-4-yl)cyclopentyl)oxy)-1-oxoisoindolin-2-yl)piperidine-2,6-dione |
| 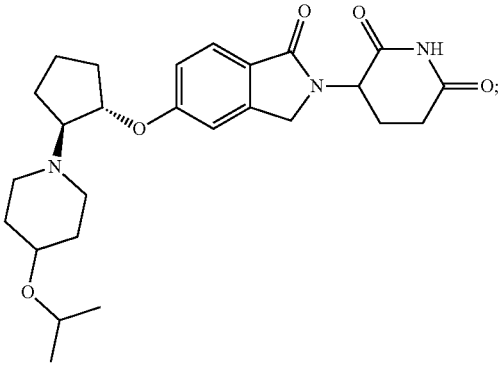<br>3-(5-(((1S,2S)-2-(4-isopropoxypiperidin-1-yl)cyclopentyl)oxy)-1-oxoisoindolin-2-yl)piperidine-2,6-dione |
| 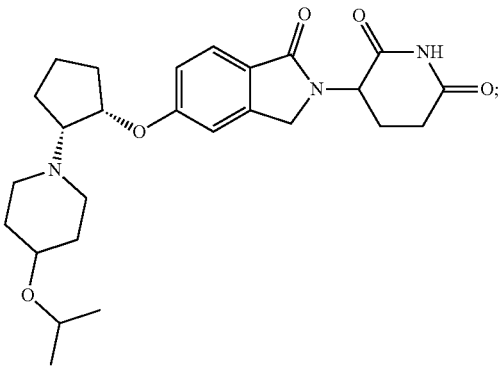<br>3-(5-(((1S,2R)-2-(4-isopropoxypiperidin-1-yl)cyclopentyl)oxy)-1-oxoisoindolin-2-yl)piperidine-2,6-dione |

| Compound Structure/Compound Name | Compound Structure/Compound Name |
|---|---|
| 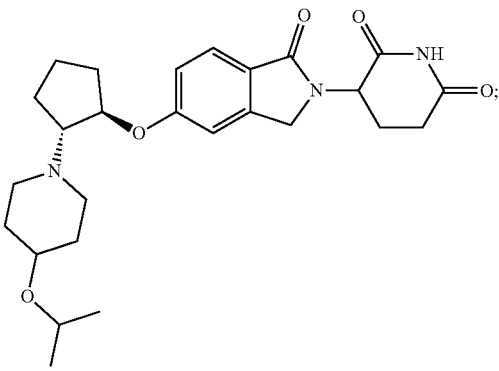<br>3-(5-(((1R,2R)-2-(4-isopropoxypiperidin-1-yl)cyclopentyl)oxy)-1-oxoisoindolin-2-yl)piperidine-2,6-dione | 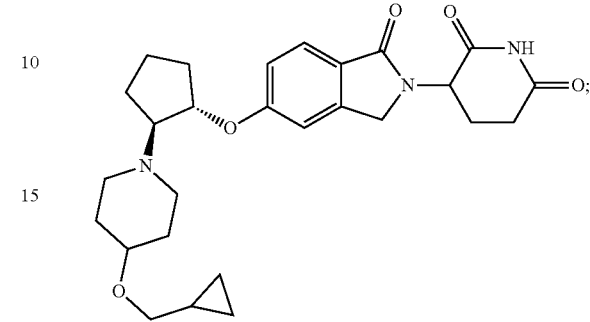<br>3-(5-(((1S,2S)-2-(4-(cyclopropylmethoxy)piperidin-1-yl)cyclopentyl)oxy)-1-oxoisoindolin-2-yl)piperidine-2,6-dione |
| 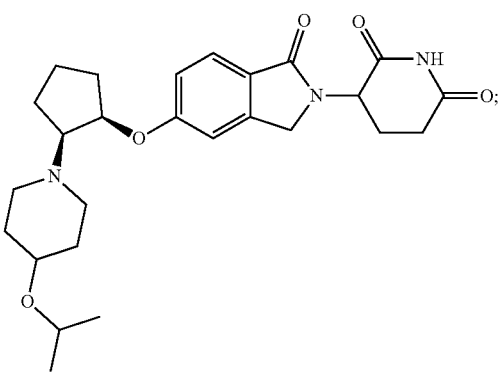<br>3-(5-(((1R,2S)-2-(4-isopropoxypiperidin-1-yl)cyclopentyl)oxy)-1-oxoisoindolin-2-yl)piperidine-2,6-dione | 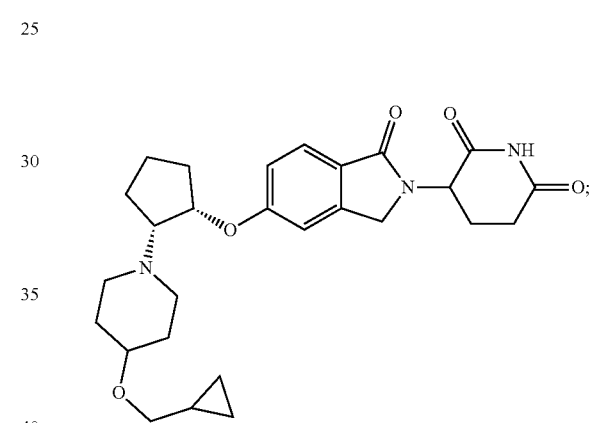<br>3-(5-(((1S,2R)-2-(4-(cyclopropylmethoxy)piperidin-1-yl)cyclopentyl)oxy)-1-oxoisoindolin-2-yl)piperidine-2,6-dione |
| 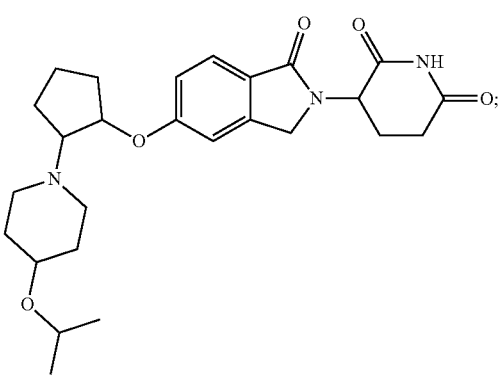<br>3-(5-((2-(4-isopropoxypiperidin-1-yl)cyclopentyl)oxy)-1-oxoisoindolin-2-yl)piperidine-2,6-dione | 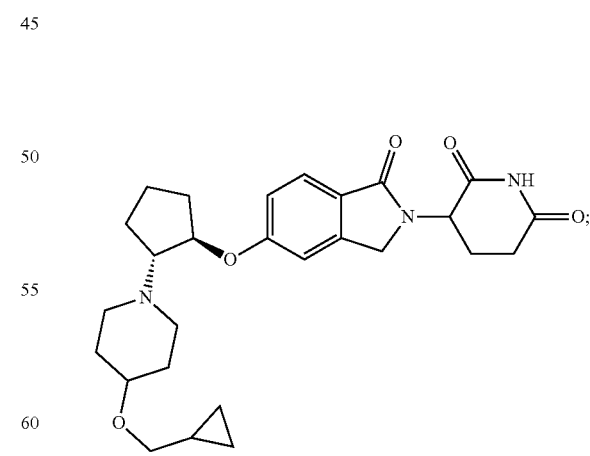<br>3-(5-(((1R,2R)-2-(4-(cyclopropylmethoxy)piperidin-1-yl)cyclopentyl)oxy)-1-oxoisoindolin-2-yl)piperidine-2,6-dione |

TABLE-continued

| Compound Structure/Compound Name |
|---|
| 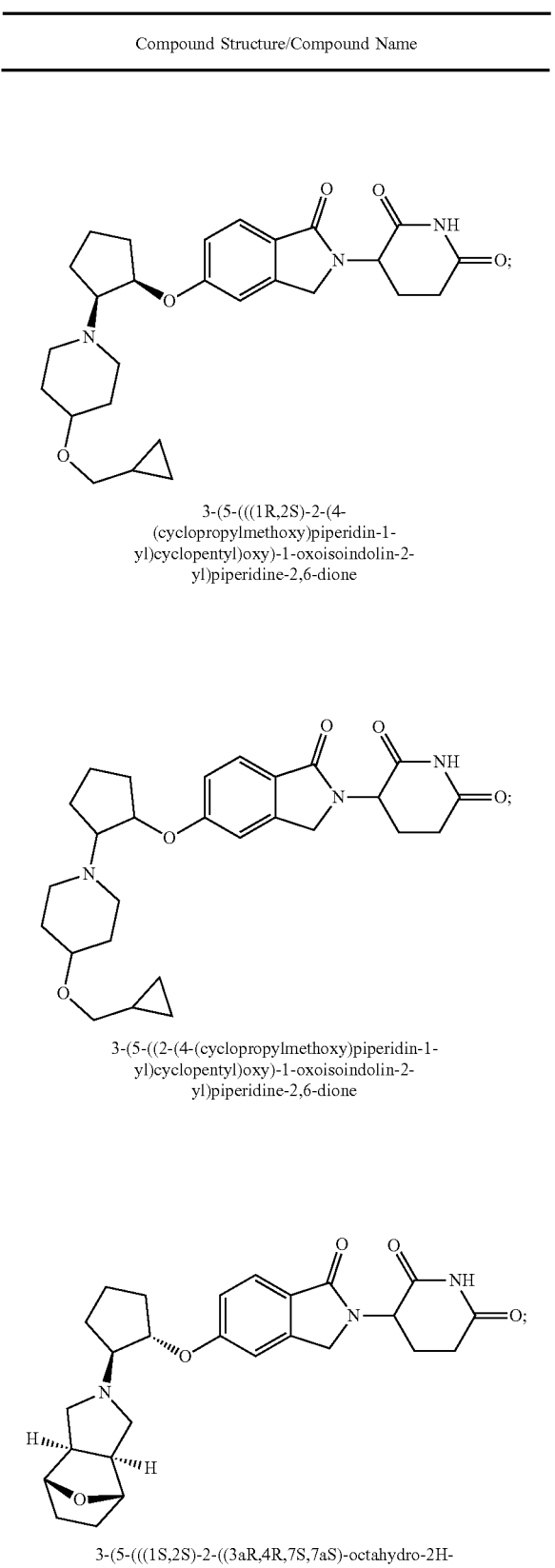
3-(5-(((1R,2S)-2-(4-(cyclopropylmethoxy)piperidin-1-yl)cyclopentyl)oxy)-1-oxoisoindolin-2-yl)piperidine-2,6-dione 3-(5-((2-(4-(cyclopropylmethoxy)piperidin-1-yl)cyclopentyl)oxy)-1-oxoisoindolin-2-yl)piperidine-2,6-dione 3-(5-(((1S,2S)-2-((3aR,4R,7S,7aS)-octahydro-2H-4,7-epoxyisoindol-2-yl)cyclopentyl)oxy)-1-oxoisoindolin-2-yl)piperidine-2,6-dione |

| Compound Structure/Compound Name |
|---|
| 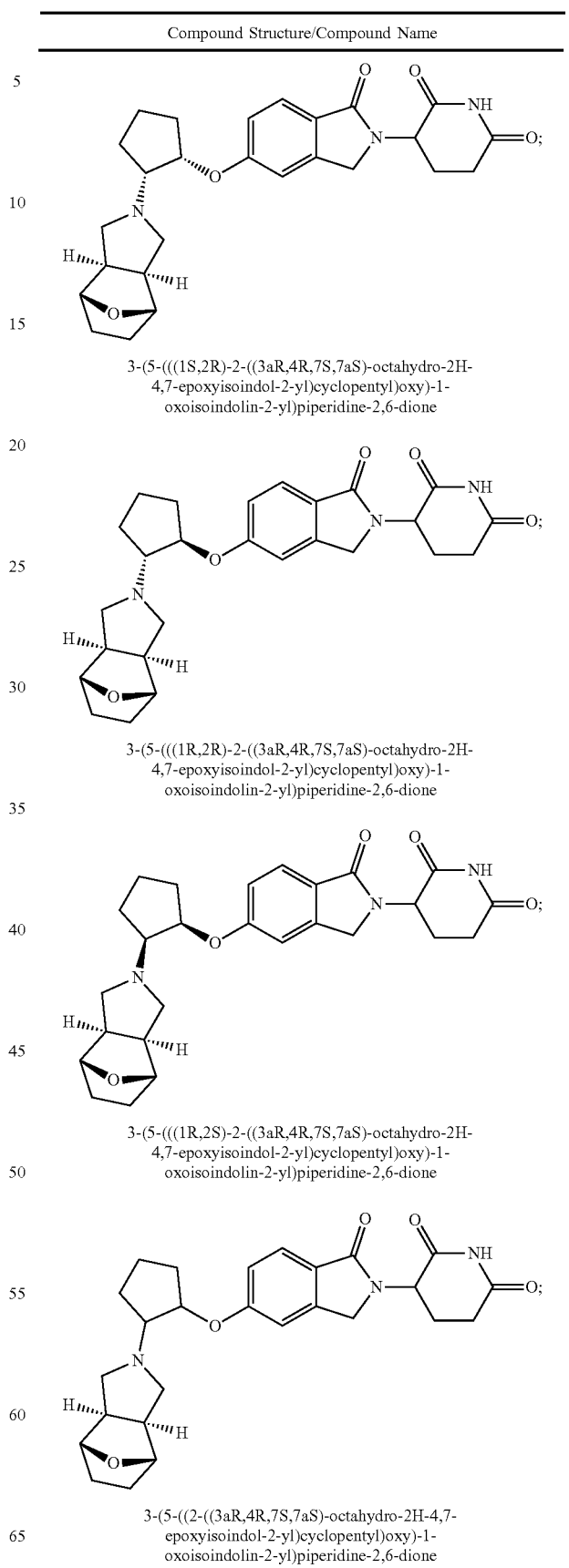
3-(5-(((1S,2R)-2-((3aR,4R,7S,7aS)-octahydro-2H-4,7-epoxyisoindol-2-yl)cyclopentyl)oxy)-1-oxoisoindolin-2-yl)piperidine-2,6-dione 3-(5-(((1R,2R)-2-((3aR,4R,7S,7aS)-octahydro-2H-4,7-epoxyisoindol-2-yl)cyclopentyl)oxy)-1-oxoisoindolin-2-yl)piperidine-2,6-dione 3-(5-(((1R,2S)-2-((3aR,4R,7S,7aS)-octahydro-2H-4,7-epoxyisoindol-2-yl)cyclopentyl)oxy)-1-oxoisoindolin-2-yl)piperidine-2,6-dione 3-(5-((2-((3aR,4R,7S,7aS)-octahydro-2H-4,7-epoxyisoindol-2-yl)cyclopentyl)oxy)-1-oxoisoindolin-2-yl)piperidine-2,6-dione |

| Compound Structure/Compound Name | Compound Structure/Compound Name |
|---|---|
| 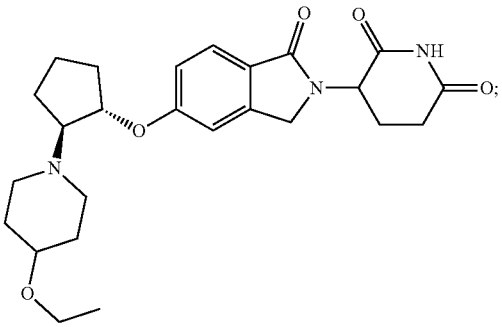<br>3-(5-(((1S,2S)-2-(4-ethoxypiperidin-1-yl)cyclopentyl)oxy)-1-oxoisoindolin-2-yl)piperidine-2,6-dione | 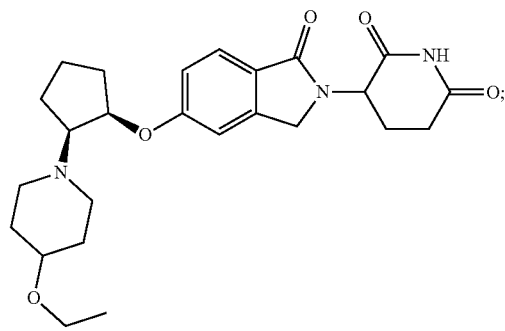<br>3-(5-(((1R,2S)-2-(4-ethoxypiperidin-1-yl)cyclopentyl)oxy)-1-oxoisoindolin-2-yl)piperidine-2,6-dione |
| 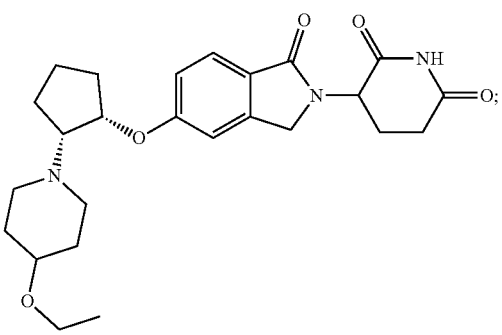<br>3-(5-(((1S,2R)-2-(4-ethoxypiperidin-1-yl)cyclopentyl)oxy)-1-oxoisoindolin-2-yl)piperidine-2,6-dione | 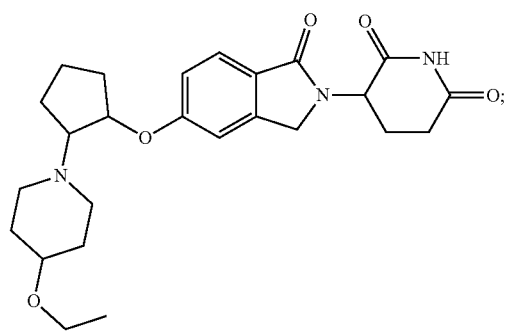<br>3-(5-((2-(4-ethoxypiperidin-1-yl)cyclopentyl)oxy)-1-oxoisoindolin-2-yl)piperidine-2,6-dione |
| 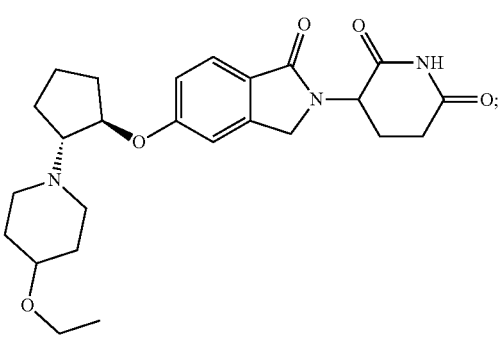<br>3-(5-(((1R,2R)-2-(4-ethoxypiperidin-1-yl)cyclopentyl)oxy)-1-oxoisoindolin-2-yl)piperidine-2,6-dione | 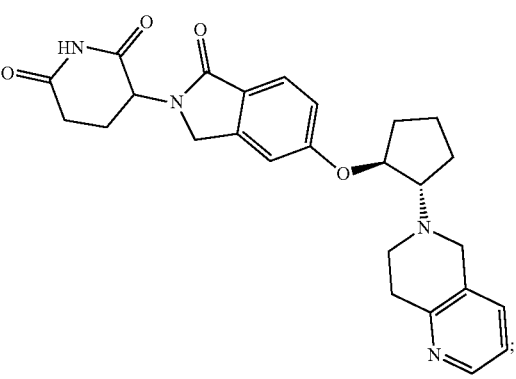<br>3-(5-(((1S,2S)-2-(7,8-dihydro-1,6-naphthyridin-6(5H)-yl)cyclopentyl)oxy)-1-oxoisoindolin-2-yl)piperidine-2,6-dione |

| Compound Structure/Compound Name | Compound Structure/Compound Name |
|---|---|
| 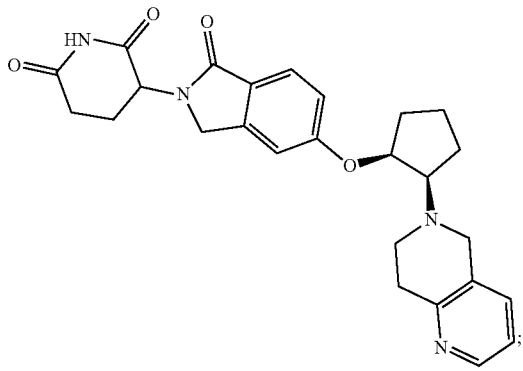 3-(5-((((1S,2R)-2-(7,8-dihydro-1,6-naphthyridin-6(5H)-yl)cyclopentyl)oxy)-1-oxoisoindolin-2-yl)piperidine-2,6-dione | 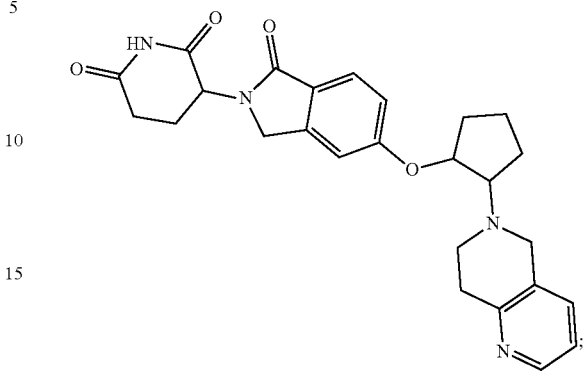 3-(5-((2-(7,8-dihydro-1,6-naphthyridin-6(5H)-yl)cyclopentyl)oxy)-1-oxoisoindolin-2-yl)piperidine-2,6-dione |
| 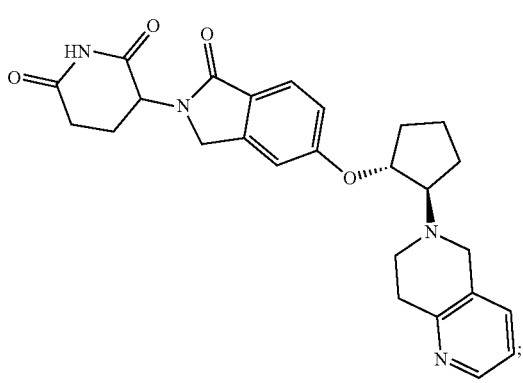 3-(5-((((1R,2R)-2-(7,8-dihydro-1,6-naphthyridin-6(5H)-yl)cyclopentyl)oxy)-1-oxoisoindolin-2-yl)piperidine-2,6-dione | 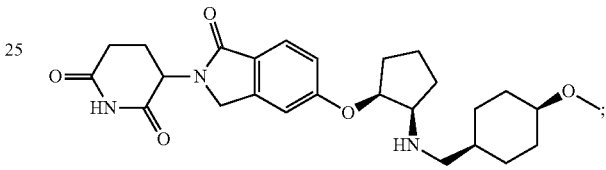 3-(5-(((1S,2R)-2-(((((1s,4S)-4-methoxycyclohexyl)methyl)amino)cyclopentyl)oxy)-1-oxoisoindolin-2-yl)piperidine-2,6-dione |
|  | 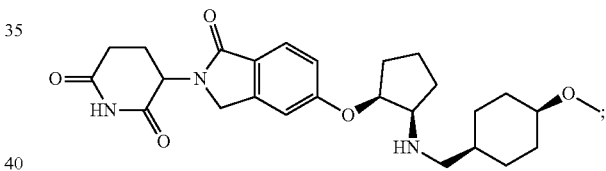 3-(5-(((1S,2R)-2-(((((1s,4S)-4-methoxycyclohexyl)methyl)amino)cyclopentyl)oxy)-1-oxoisoindolin-2-yl)piperidine-2,6-dione |
| 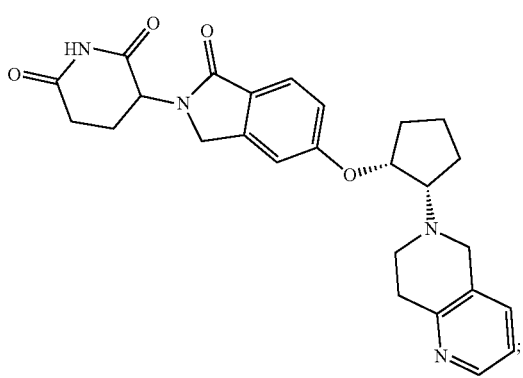 3-(5-((((1R,2S)-2-(7,8-dihydro-1,6-naphthyridin-6(5H)-yl)cyclopentyl)oxy)-1-oxoisoindolin-2-yl)piperidine-2,6-dione | 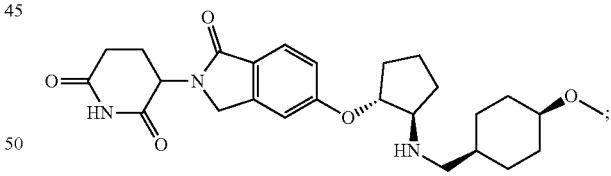 3-(5-(((1R,2R)-2-(((((1s,4S)-4-methoxycyclohexyl)methyl)amino)cyclopentyl)oxy)-1-oxoisoindolin-2-yl)piperidine-2,6-dione |
|  | 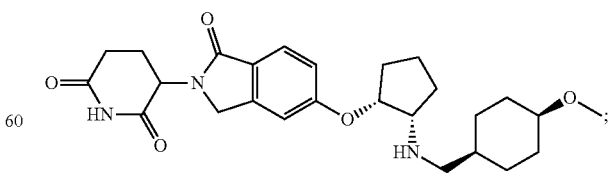 3-(5-(((1R,2S)-2-(((((1s,4R)-4-methoxycyclohexyl)methyl)amino)cyclopentyl)oxy)-1-oxoisoindolin-2-yl)piperidine-2,6-dione |

| Compound Structure/Compound Name | Compound Structure/Compound Name |
|---|---|
| 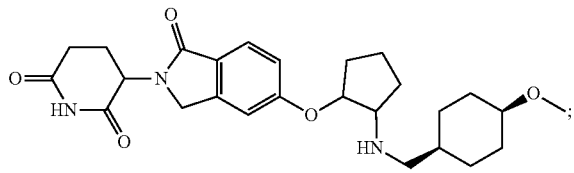<br>3-(5-((2-(((((1s,4s)-4-methoxycyclohexyl)methyl)amino)cyclopentyl)oxy)-1-oxoisoindolin-2-yl)piperidine-2,6-dione | 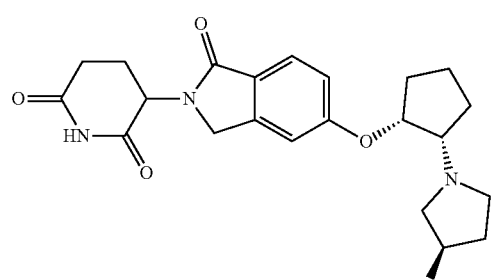<br>3-(5-((((1R,2S)-2-((R)-3-methoxypyrrolidin-1-yl)cyclopentyl)oxy)-1-oxoisoindolin-2-yl)piperidine-2,6-dione |
| 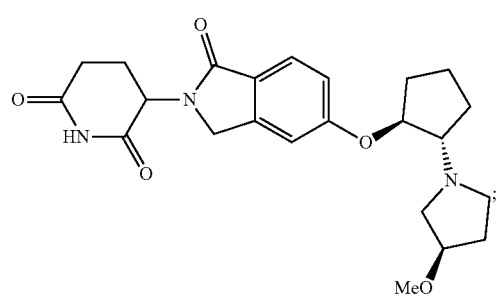<br>3-(5-((((1S,2S)-((R)-3-methoxypyrrolidin-1-yl)cyclopentyl)oxy)-1-oxoisoindolin-2-yl)piperidine-2,6-dione | 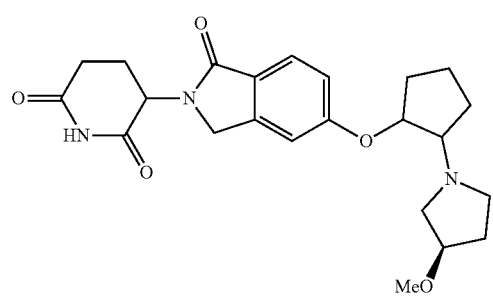<br>3-(5-((2-((R)-3-methoxypyrrolidin-1-yl)cyclopentyl)oxy)-1-oxoisoindolin-2-yl)piperidine-2,6-dione |
| 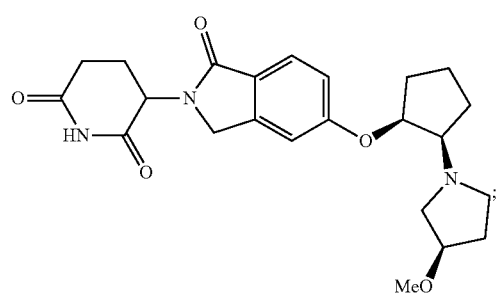<br>3-(5-((((1S,2R)-2-((R)-3-methoxypyrrolidin-1-yl)cyclopentyl)oxy)-1-oxoisoindolin-2-yl)piperidine-2,6-dione | 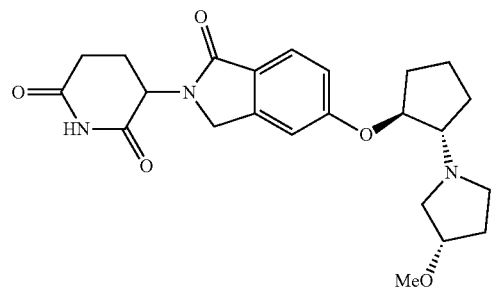<br>3-(5-((((1S,2S)-2-((S)-3-methoxypyrrolidin-1-yl)cyclopentyl)oxy)-1-oxoisoindolin-2-yl)piperidine-2,6-dione |
| 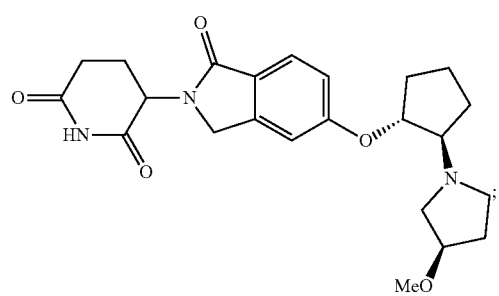<br>3-(5-((((1R,2R)-2-((R)-3-methoxypyrrolidin-1-yl)cyclopentyl)oxy)-1-oxoisoindolin-2-yl)piperidine-2,6-dione | 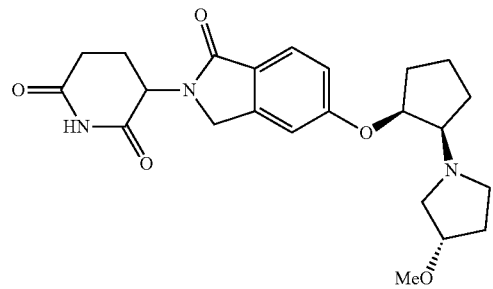<br>3-(5-((((1S,2R)-2-((S)-3-methoxypyrrolidin-1-yl)cyclopentyl)oxy)-1-oxoisoindolin-2-yl)piperidine-2,6-dione |

| Compound Structure/Compound Name |
|---|
| 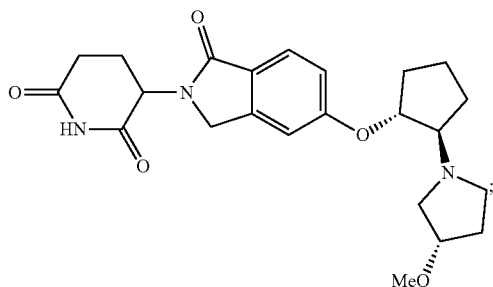<br>3-(5-(((1R,2R)-2-((S)-3-methoxypyrrolidin-1-yl)cyclopentyl)oxy)-1-oxoisoindolin-2-yl)piperidine-2,6-dione |
| 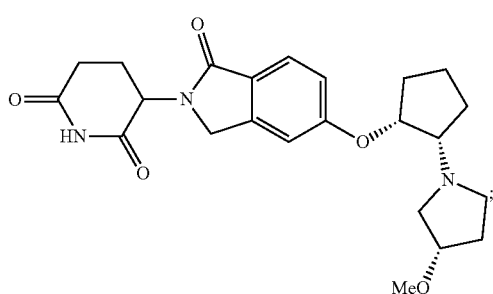<br>3-(5-(((1R,2S)-2-((S)-3-methoxypyrrolidin-1-yl)cyclopentyl)oxy)-1-oxoisoindolin-2-yl)piperidine-2,6-dione |
| 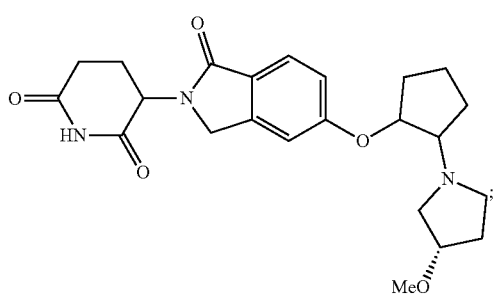<br>3-(5-((2-((S)-3-methoxypyrrolidin-1-yl)cyclopentyl)oxy)-1-oxoisoindolin-2-yl)piperidine-2,6-dione |
| 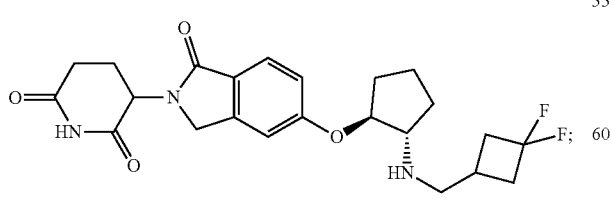<br>3-(5-(((1S,2S)-2-(((3,3-difluorocyclobutyl)methyl)amino)cyclopentyl)oxy)-1-oxoisoindolin-2-yl)piperidine-2,6-dione |

| Compound Structure/Compound Name |
|---|
| <br>3-(5-(((1S,2R)-2-(((3,3-difluorocyclobutyl)methyl)amino)cyclopentyl)oxy)-1-oxoisoindolin-2-yl)piperidine-2,6-dione |
| <br>3-(5-(((1R,2R)-2-(((3,3-difluorocyclobutyl)methyl)amino)cyclopentyl)oxy)-1-oxoisoindolin-2-yl)piperidine-2,6-dione |
| 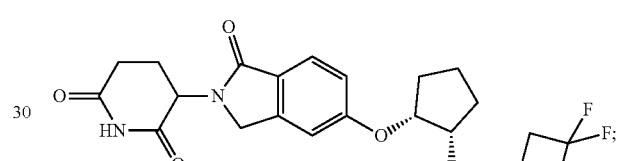<br>3-(5-(((1R,2S)-2-(((3,3-difluorocyclobutyl)methyl)amino)cyclopentyl)oxy)-1-oxoisoindolin-2-yl)piperidine-2,6-dione |
| 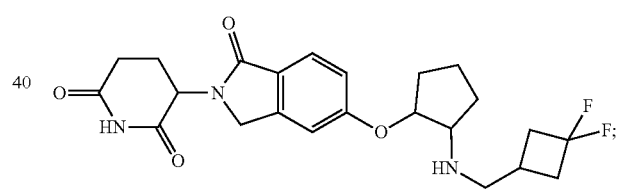<br>3-(5-((2-(((3,3-difluorocyclobutyl)methyl)amino)cyclopentyl)oxy)-1-oxoisoindolin-2-yl)piperidine-2,6-dione |
| 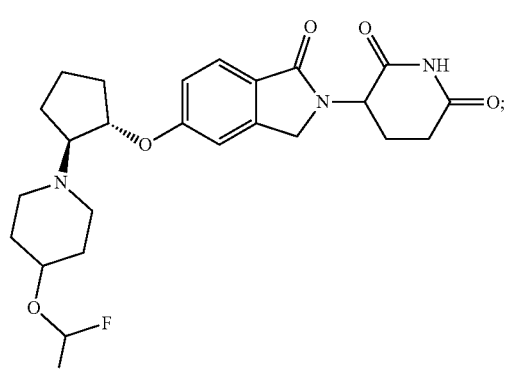<br>3-(5-(((1S,2S)-2-(4-(difluoromethoxy)piperidin-1-yl)cyclopentyl)oxy)-1-oxoisoindolin-2-yl)piperidine-2,6-dione |

| Compound Structure/Compound Name | Compound Structure/Compound Name |
|---|---|
| 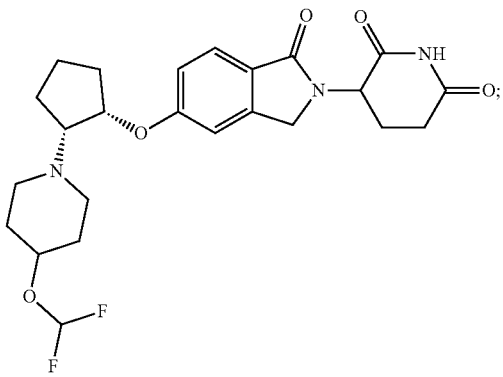<br>3-(5-(((1S,2R)-2-(4-(difluoromethoxy)piperidin-1-yl)cyclopentyl)oxy)-1-oxoisoindolin-2-yl)piperidine-2,6-dione | 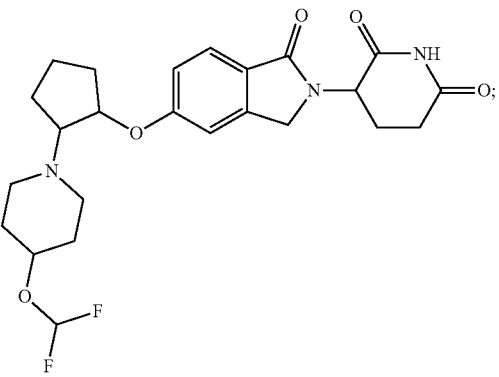<br>3-(5-((2-(4-(difluoromethoxy)piperidin-1-yl)cyclopentyl)oxy)-1-oxoisoindolin-2-yl)piperidine-2,6-dione |
| 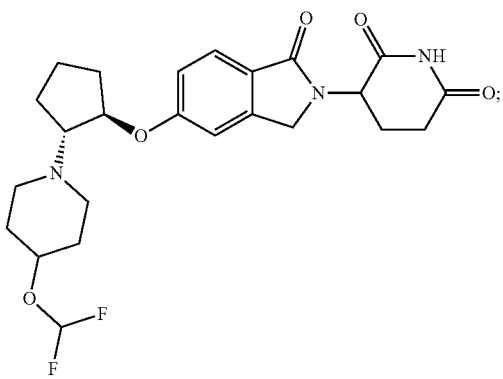<br>3-(5-(((1R,2R)-2-(4-(difluoromethoxy)piperidin-1-yl)cyclopentyl)oxy)-1-oxoisoindolin-2-yl)piperidine-2,6-dione | 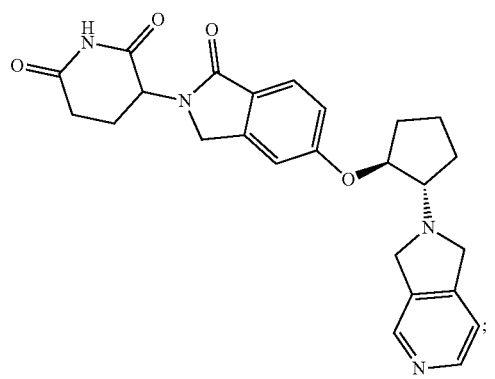<br>3-(5-(((1S,2S)-2-(1,3-dihydro-2H-pyrrolo[3,4-c]pyridin-2-yl)cyclopentyl)oxy)-1-oxoisoindolin-2-yl)piperidine-2,6-dione |
| 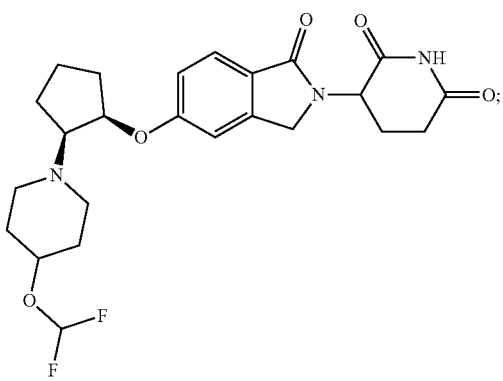<br>3-(5-(((1R,2S)-2-(4-(difluoromethoxy)piperidin-1-yl)cyclopentyl)oxy)-1-oxoisoindolin-2-yl)piperidine-2,6-dione | 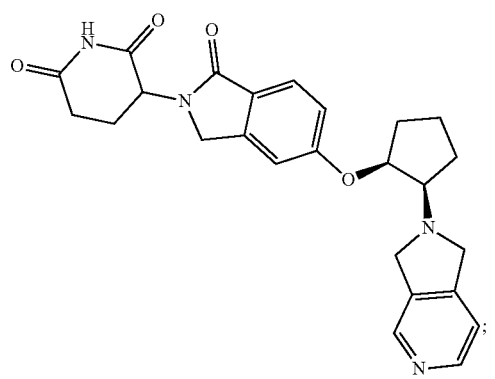<br>3-(5-(((1S,2R)-2-(1,3-dihydro-2H-pyrrolo[3,4-c]pyridin-2-yl)cyclopentyl)oxy)-1-oxoisoindolin-2-yl)pipeidine-2,6-dione |

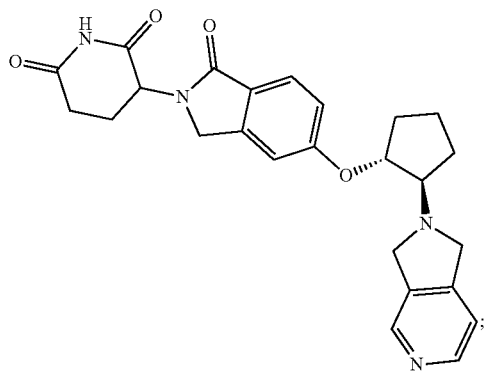

3-(5-(((1R,2R)-2-(1,3-dihydro-2H-pyrrolo[3,4-c]pyridin-2-yl)cyclopentyl)oxy)-1-oxoisoindolin-2-yl)piperidine-2,6-dione

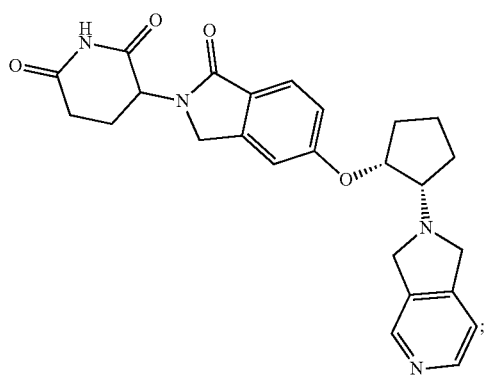

3-(5-(((1R,2S)-2-(1,3-dihydro-2H-pyrrolo[3,4-c]pyridin-2-yl)cyclopentyl)oxy)-1-oxoisoindolin-2-yl)piperidine-2,6-dione

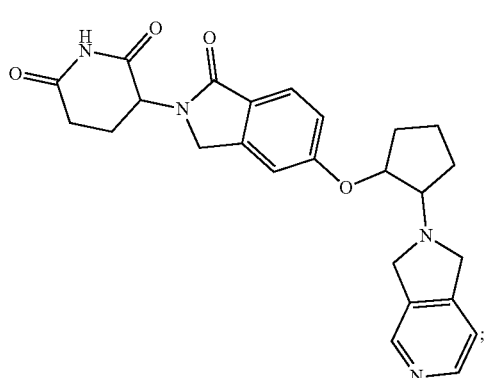

3-(5-((2-(1,3-dihydro-2H-pyrrolo[3,4-c]pyridin-2-yl)cyclopentyl)oxy)-1-oxoisoindolin-2-yl)piperidine-2,6-dione

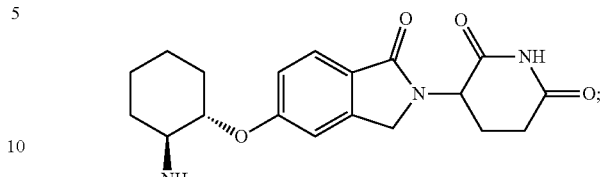

3-(1-oxo-5-(((1S,2S)-2-(propylamino)cyclohexyl)oxy)isoindolin-2-yl)piperidine-2,6-dione

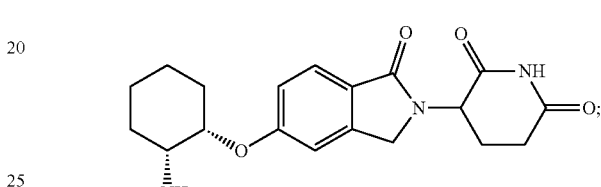

3-(1-oxo-5-(((1S,2R)-2-(propylamino)cyclohexyl)oxy)isoindolin-2-yl)piperidine-2,6-dione

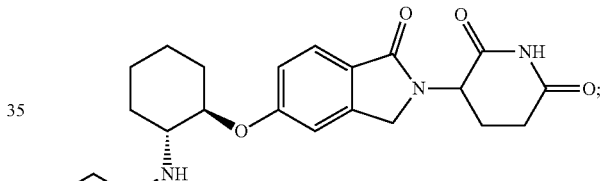

3-(1-oxo-5-(((1R,2R)-2-(propylamino)cyclohexyl)oxy)isoindolin-2-yl)piperidine-2,6-dione

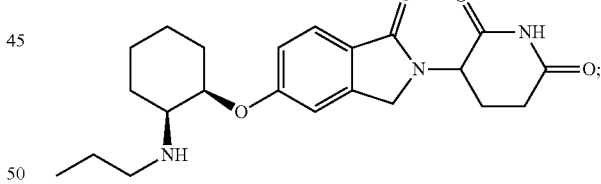

3-(1-oxo-5-(((1R,2S)-2-(propylamino)cyclohexyl)oxy)isoindolin-2-yl)piperidine-2,6-dione

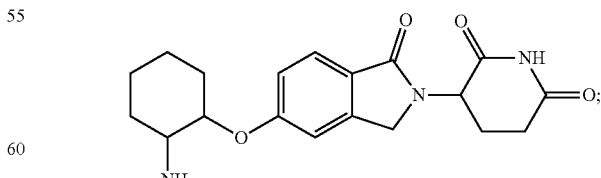

3-(1-oxo-5-((2-(propylamino)cyclohexyl)oxy)isoindolin-2-yl)piperidine-2,6-dione

| Compound Structure/Compound Name | Compound Structure/Compound Name |
|---|---|
| 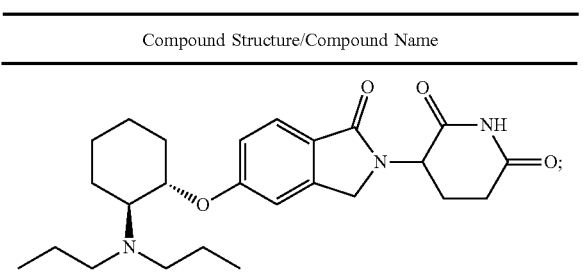<br>3-(5-(((1S,2S)-2-(dipropylamino)cyclohexyl)oxy)-1-oxoisoindolin-2-yl)piperidine-2,6-dione | 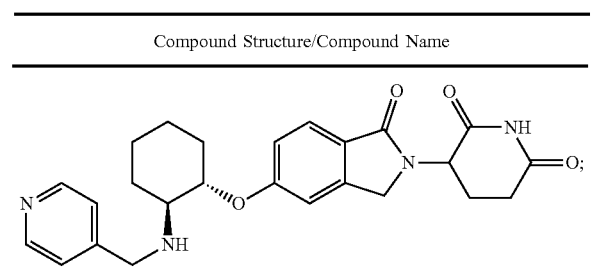<br>3-(1-oxo-5-(((1S,2S)-2-((pyridin-4-ylmethyl)amino)cyclohexyl)oxy)isoindolin-2-yl)piperidin-2,6-dione |
| 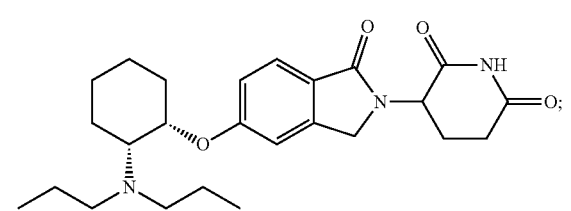<br>3-(5-(((1S,2R)-2-(dipropylamino)cyclohexyl)oxy)-1-oxoisoindolin-2-yl)piperidine-2,6-dione | 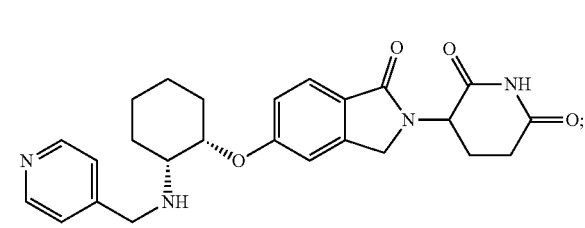<br>3-(1-oxo-5-(((1S,2R)-2-((pyridin-4-ylmethyl)amino)cyclohexyl)oxy)isoindolin-2-yl)piperidine-2,6-dione |
| 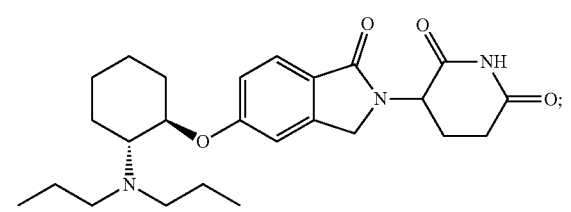<br>3-(5-(((1R,2R)-2-(dipropylamino)cyclohexyl)oxy)-1-oxoisoindolin-2-yl)piperidine-2,6-dione | 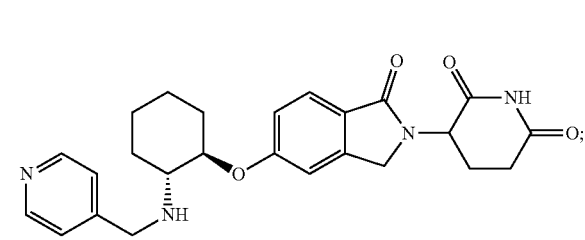<br>3-(1-oxo-5-(((1R,2R)-2-((pyridin-4-ylmethyl)amino)cyclohexyl)oxy)isoindolin-2-yl)piperidine-2,6-dione |
| 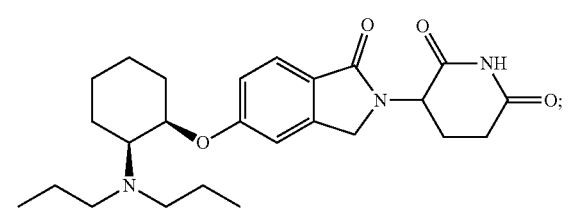<br>3-(5-(((1R,2S)-2-(dipropylamino)cyclohexyl)oxy)-1-oxoisoindolin-2-yl)piperidine-2,6-dione | 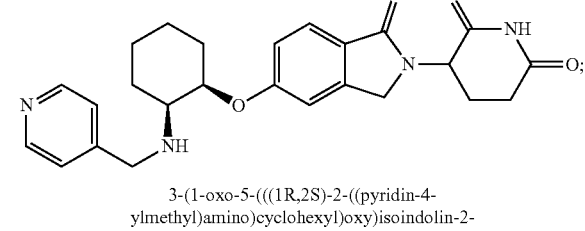<br>3-(1-oxo-5-(((1R,2S)-2-((pyridin-4-ylmethyl)amino)cyclohexyl)oxy)isoindolin-2-yl)piperidine-2,6-dione |
| 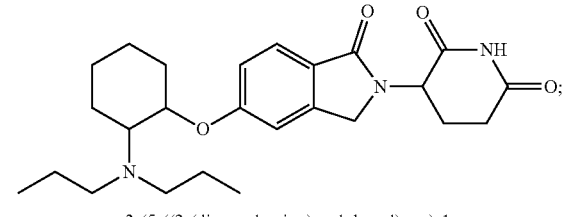<br>3-(5-((2-(dipropylamino)cyclohexyl)oxy)-1-oxoisoindolin-2-yl)piperidine-2,6-dione | 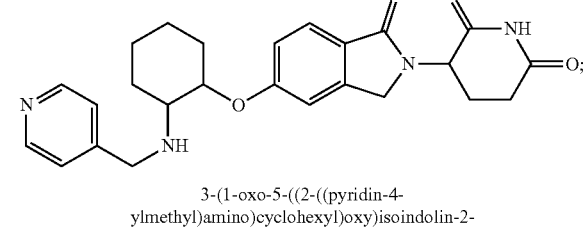<br>3-(1-oxo-5-((2-((pyridin-4-ylmethyl)amino)cyclohexyl)oxy)isoindolin-2-yl)piperidine-2,6-dione |

| Compound Structure/Compound Name | Compound Structure/Compound Name |
|---|---|
| 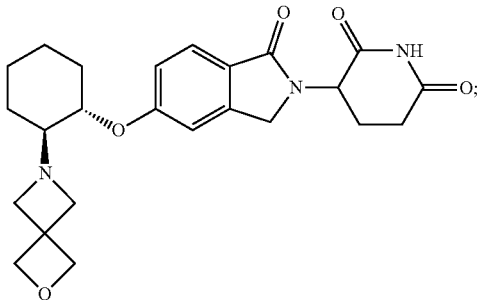<br>3-(5-(((1S,2S)-2-(2-oxa-6-azaspiro[3.3]heptan-6-yl)cyclohexyl)oxy)-1-oxoisoindolin-2-yl)piperidine-2,6-dione | 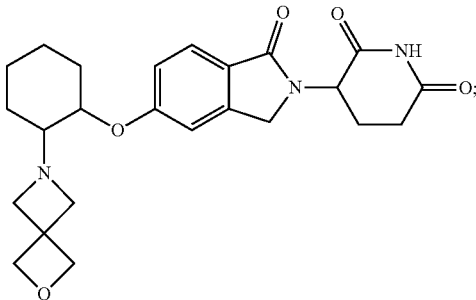<br>3-(5-((2-(2-oxa-6-azaspiro[3.3]heptan-6-yl)cyclohexyl)oxy)-1-oxoisoindolin-2-yl)piperidine-2,6-dione |
| 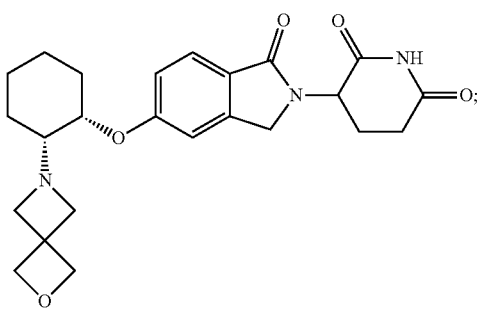<br>3-(5-(((1S,2R)-2-(2-oxa-6-azaspiro[3.3]heptan-6-yl)cyclohexyl)oxy)-1-oxoisoindolin-2-yl)piperidine-2,6-dione | 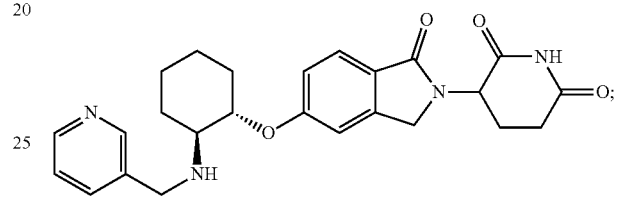<br>3-(1-oxo-5-(((1S,2S)-2-((pyridin-3-ylmethyl)amino)cyclohexyl)oxy)isoindolin-2-yl)piperidine-2,6-dione |
| 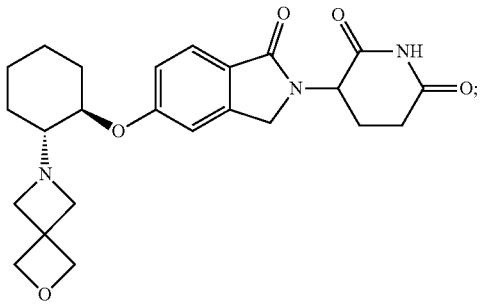<br>3-(5-(((1R,2R)-2-(2-oxa-6-azaspiro[3.3]heptan-6-yl)cyclohexyl)oxy)-1-oxoisoindolin-2-yl)piperidine-2,6-dione | 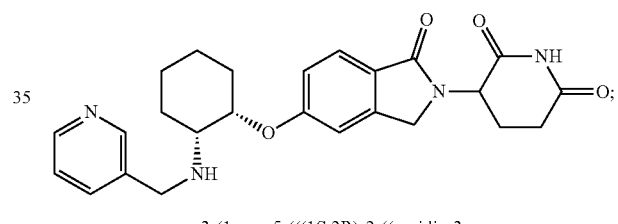<br>3-(1-oxo-5-(((1S,2R)-2-((pyridin-3-ylmethyl)amino)cyclohexyl)oxy)isoindolin-2-yl)piperidine-2,6-dione |
| | 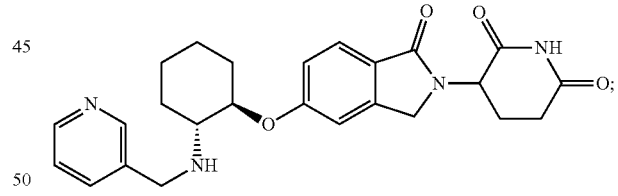<br>3-(1-oxo-5-(((1R,2R)-2-((pyridin-3-ylmethyl)amino)cyclohexyl)oxy)isoindolin-2-yl)piperidine-2,6-dione |
| 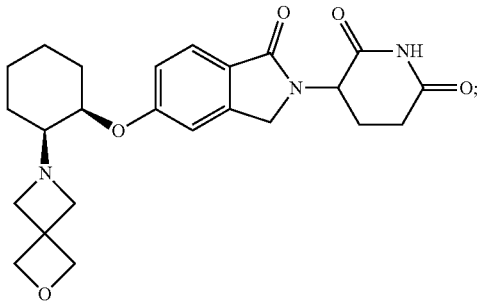<br>3-(5-(((1R,2S)-2-(2-oxa-6-azaspiro[3.3]heptan-6-yl)cyclohexyl)oxy)-1-oxoisoindolin-2-yl)piperidine-2,6-dione | 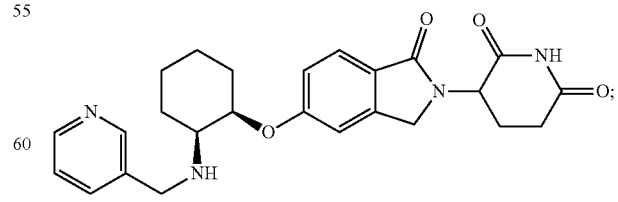<br>3-(1-oxo-5-(((1R,2S)-2-((pyridin-3-ylmethyl)amino)cyclohexyl)oxy)isoindolin-2-yl)piperidine-2,6-dione |

| Compound Structure/Compound Name | Compound Structure/Compound Name |
|---|---|
| 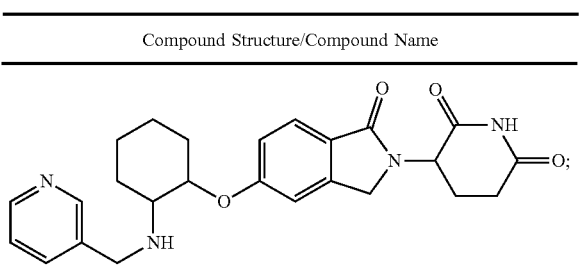<br>3-(1-oxo-5-((2-((pyridin-3-ylmethyl)amino)cyclohexyl)oxy)isoindolin-2-yl)piperidine-2,6-dione | 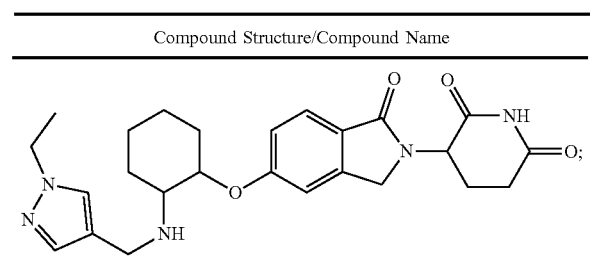<br>3-(5-((2-(((1-ethyl-1H-pyrazol-4-yl)methyl)amino)cyclohexyl)oxy)-1-oxoisoindolin-2-yl)piperidine-2,6-dione |
| 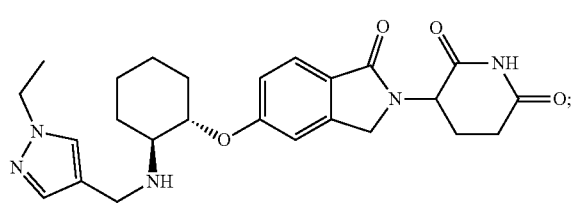<br>3-(5-(((1S,2S)-2-(((1-ethyl-1H-pyrazol-4-yl)methyl)amino)cyclohexyl)oxy)-1-oxoisoindolin-2-yl)piperidine-2,6-dione | 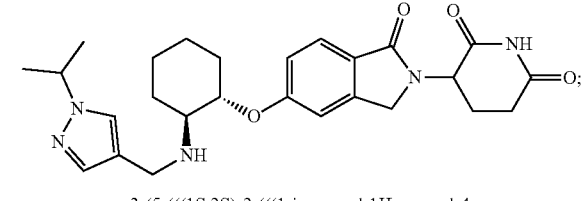<br>3-(5-(((1S,2S)-2-(((1-isopropyl-1H-pyrazol-4-yl)methyl)amino)cyclohexyl)oxy)-1-oxoisoindolin-2-yl)piperidine-2,6-dione |
| 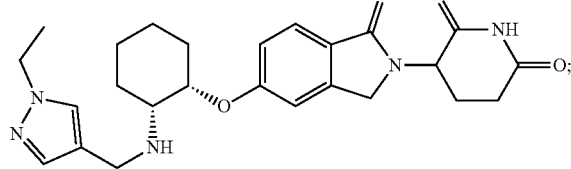<br>3-(5-(((1S,2R)-2-(((1-ethyl-1H-pyrazol-4-yl)methyl)amino)cyclohexyl)oxy)-1-oxoisoindolin-2-yl)piperidine-2,6-dione | 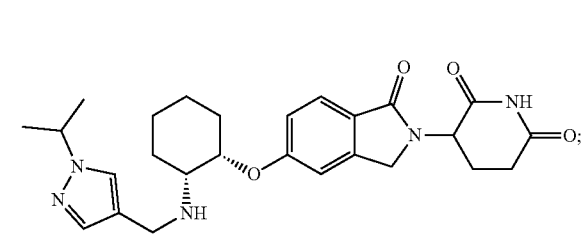<br>3-(5-(((1S,2R)-2-(((1-isopropyl-1H-pyrazol-4-yl)methyl)amino)cyclohexyl)oxy)-1-oxoisoindolin-2-yl)piperidine-2,6-dione |
| 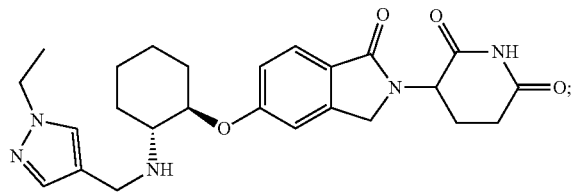<br>3-(5-(((1R,2R)-2-(((1-ethyl-1H-pyrazol-4-yl)methyl)amino)cyclohexyl)oxy)-1-oxoisoindolin-2-yl)piperidine-2,6-dione | 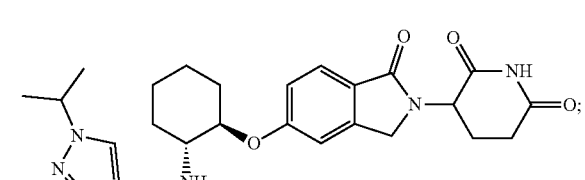<br>3-(5-(((1R,2R)-2-(((1-isopropyl-1H-pyrazol-4-yl)methyl)amino)cyclohexyl)oxy)-1-oxoisoindolin-2-yl)piperidine-2,6-dione |
| 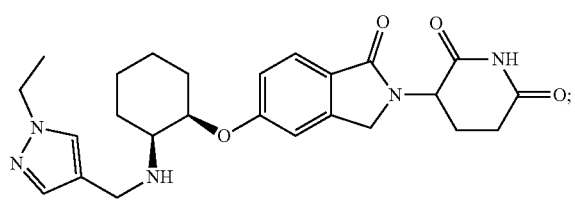<br>3-(5-(((1R,2S)-2-(((1-ethyl-1H-pyrazol-4-yl)methyl)amino)cyclohexyl)oxy)-1-oxoisoindolin-2-yl)piperidine-2,6-dione | 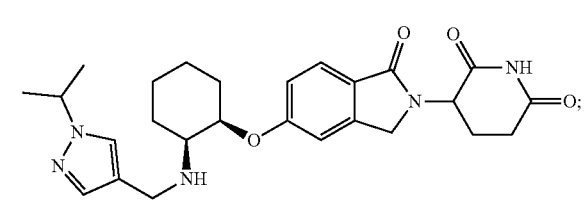<br>3-(5-(((1R,2S)-2-(((1-isopropyl-1H-pyrazol-4-yl)methyl)amino)cyclohexyl)oxy)-1-oxoisoindolin-2-yl)piperidine-2,6-dione |

| Compound Structure/Compound Name | Compound Structure/Compound Name |
|---|---|
| 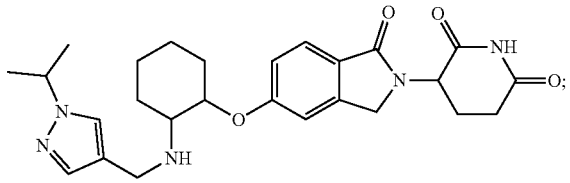<br>3-(5-((2-(((1-isopropyl-1H-pyrazol-4-yl)methyl)amino)cyclohexyl)oxy)-1-oxoisoindolin-2-yl)piperidine-2,6-dione | 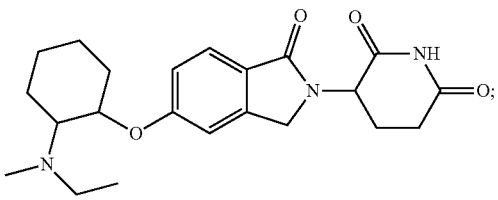<br>3-(5-((2-(ethyl(methyl)amino)cyclohexyl)oxy)-1-oxoisoindolin-2-yl)piperidin-2,6-dione |
| 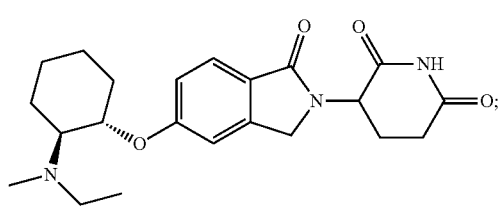<br>3-(5-(((1S,2S)-2-(ethyl(methyl)amino)cyclohexyl)oxy)-1-oxoisoindolin-2-yl)piperidine-2,6-dione | 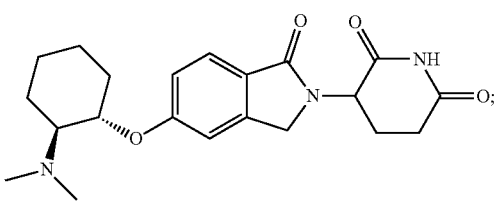<br>3-(5-(((1S,2S)-2-(dimethylamino)cyclohexyl)oxy)-1-oxoisoindolin-2-yl)piperidine-2,6-dione |
| 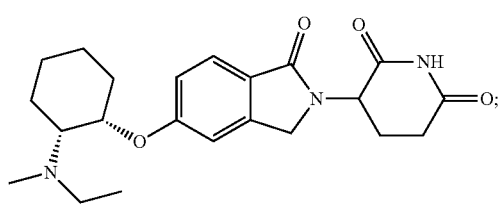<br>3-(5-(((1S,2R)-2-(ethyl(methyl)amino)cyclohexyl)oxy)-1-oxoisoindolin-2-yl)piperidine-2,6-dione | 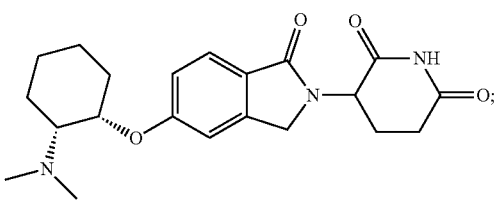<br>3-(5-(((1S,2R)-2-(dimethylamino)cyclohexyl)oxy)-1-oxoisoindolin-2-yl)piperidine-2,6-dione |
| 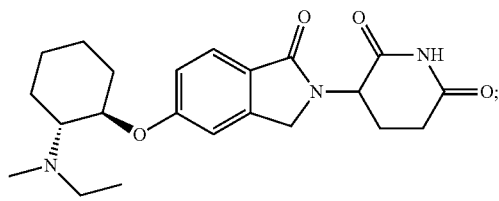<br>3-(5-(((1R,2R)-2-(ethyl(methyl)amino)cyclohexyl)oxy)-1-oxoisoindolin-2-yl)piperidine-2,6-dione | 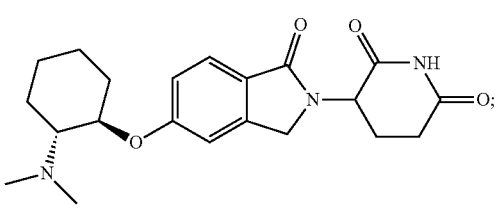<br>3-(5-(((1R,2R)-2-(dimethylamino)cyclohexyl)oxy)-1-oxoisoindolin-2-yl)piperidine-2,6-dione |
| 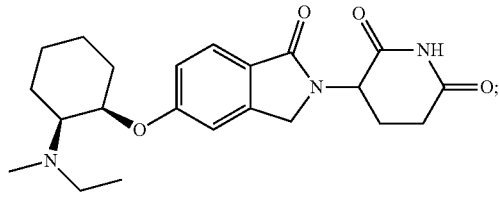<br>3-(5-(((1R,2S)-2-(ethyl(methyl)amino)cyclohexyl)oxy)-1-oxoisoindolin-2-yl)piperidine-2,6-dione | 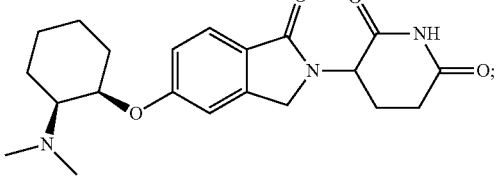<br>3-(5-(((1R,2S)-2-(dimethylamino)cyclohexyl)oxy)-1-oxoisoindolin-2-yl)piperidine-2,6-dione |

| Compound Structure/Compound Name | Compound Structure/Compound Name |
|---|---|
| 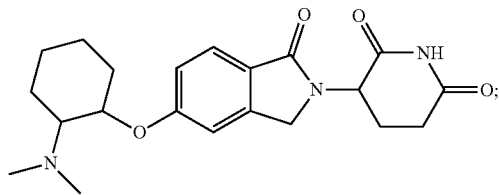<br>3-(5-((2-(dimethylamino)cyclohexyl)oxy)-1-oxoisoindolin-2-yl)piperidine-2,6-dione | 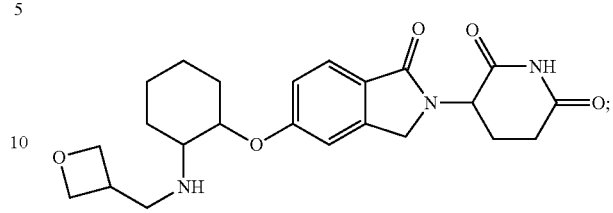<br>3-(5-((2-((oxetan-3-ylmethyl)amino)cyclohexyl)oxy)-1-oxoisoindolin-2-yl)piperidine-2,6-dione |
| 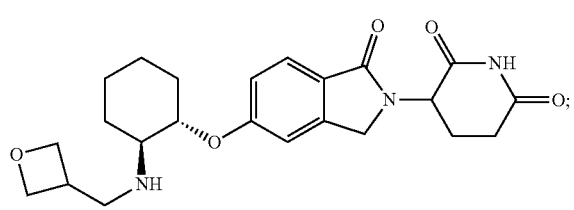<br>3-(5-(((1S,2S)-2-((oxetan-3-ylmethyl)amino)cyclohexyl)oxy)-1-oxoisoindolin-2-yl)piperidine-2,6-dione | 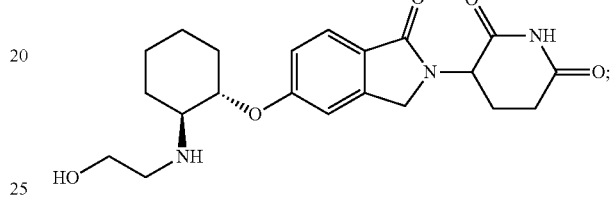<br>3-(5-(((1S,2S)-2-((2-hydroxyethyl)amino)cyclohexyl)oxy)-1-oxoisoindolin-2-yl)piperidine-2,6-dione |
| 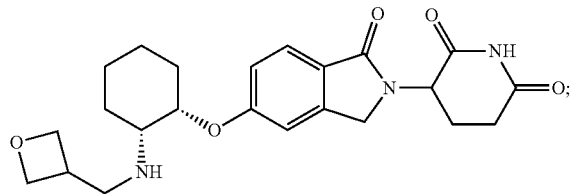<br>3-(5-(((1S,2R)-2-((oxetan-3-ylmethyl)amino)cyclohexyl)oxy)-1-oxoisoindolin-2-yl)piperidine-2,6-dione | 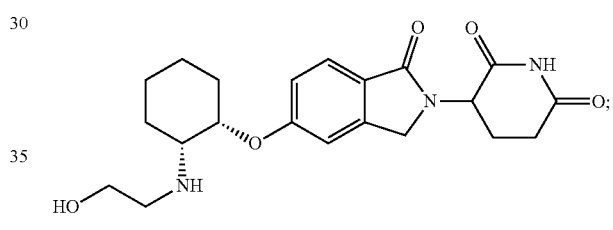<br>3-(5-(((1S,2R)-2-((2-hydroxyethyl)amino)cyclohexyl)oxy)-1-oxoisoindolin-2-yl)piperidine-2,6-dione |
| 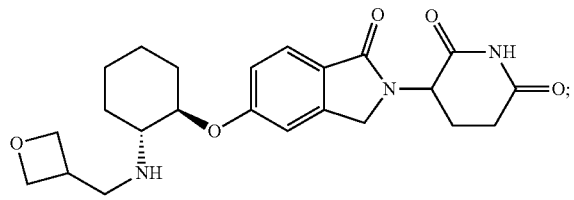<br>3-(5-(((1R,2R)-2-((oxetan-3-ylmethyl)amino)cyclohexyl)oxy)-1-oxoisoindolin-2-yl)piperidine-2,6-dione | 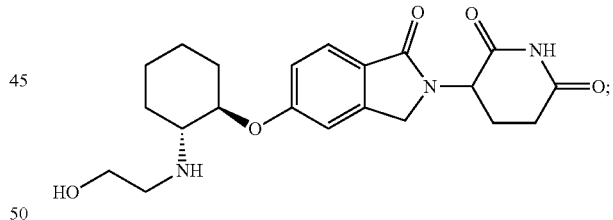<br>3-(5-(((1R,2R)-2-((2-hydroxyethyl)amino)cyclohexyl)oxy)-1-oxoisoindolin-2-yl)piperidine-2,6-dione |
| 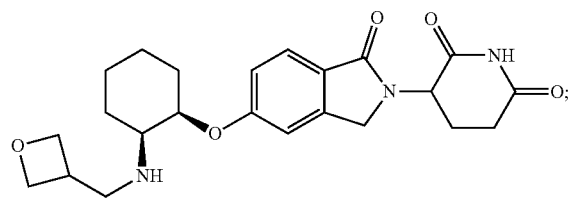<br>3-(5-(((1R,2S)-2-((oxetan-3-ylmethyl)amino)cyclohexyl)oxy)-1-oxoisoindolin-2-yl)piperidine-2,6-dione | 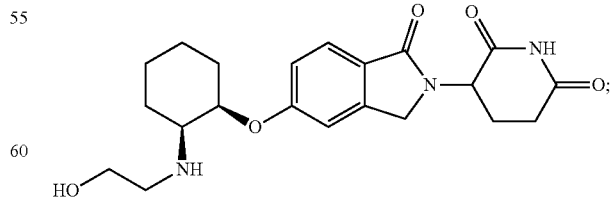<br>3-(5-(((1R,2S)-2-((2-hydroxyethyl)amino)cyclohexyl)oxy)-1-oxoisoindolin-2-yl)piperidine-2,6-dione |

253
-continued

| Compound Structure/Compound Name |
|---|
| 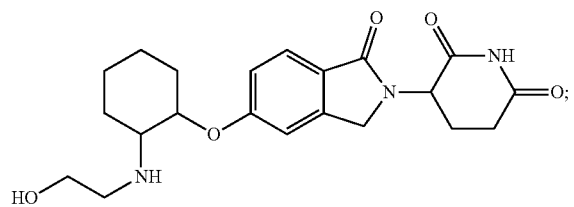
3-(5-((2-((2-hydroxyethyl)amino)cyclohexyl)oxy)-1-oxoisoindolin-2-yl)piperidine-2,6-dione |
| 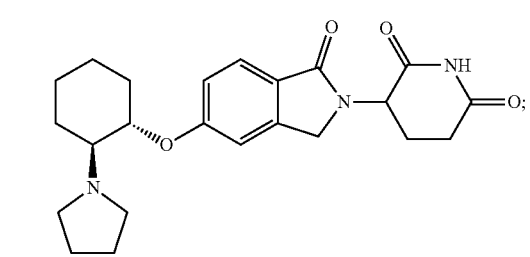
3-(1-oxo-5-(((1S,2S)-2-(pyrrolidin-1-yl)cyclohexyl)oxy)isoindolin-2-yl)piperidine-2,6-dione |
| 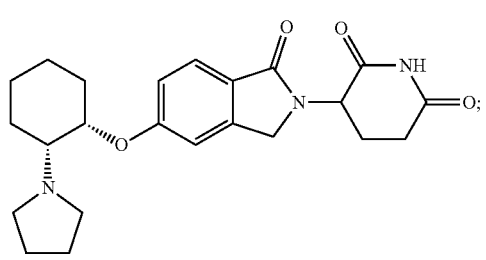
3-(1-oxo-5-(((1S,2R)-2-(pyrrolidin-1-yl)cyclohexyl)oxy)isoindolin-2-yl)piperidine-2,6-dione |
| 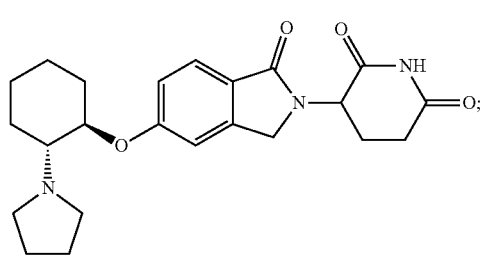
3-(1-oxo-5-(((1R,2R)-2-(pyrrolidin-1-yl)cyclohexyl)oxy)isoindolin-2-yl)piperidine-2,6-dione |
| 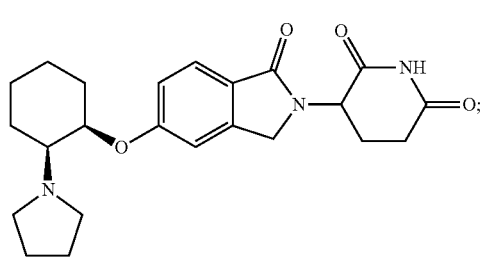
3-(1-oxo-5-(((1R,2S)-2-(pyrrolidin-1-yl)cyclohexyl)oxy)isoindolin-2-yl)piperidine-2,6-dione |

254
-continued

| Compound Structure/Compound Name |
|---|
| 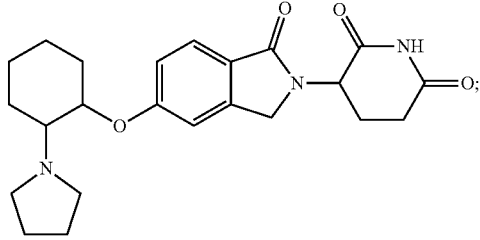
3-(1-oxo-5-((2-(pyrrolidin-1-yl)cyclohexyl)oxy)isoindolin-2-yl)piperidine-2,6-dione |
| 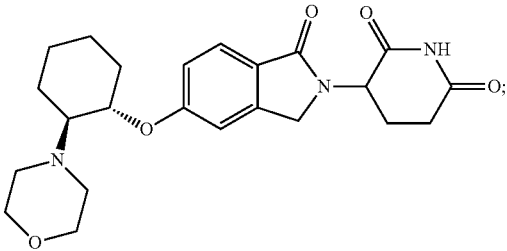
3-(5-(((1S,2S)-2-morpholinocyclohexyl)oxy)-1-oxoisoindolin-2-yl)piperidine-2,6-dione |
| 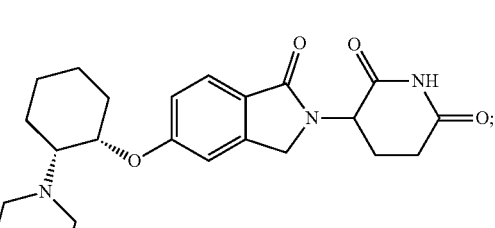
3-(5-(((1S,2R)-2-morpholinocyclohexyl)oxy)-1-oxoisoindolin-2-yl)piperidine-2,6-dione |
| 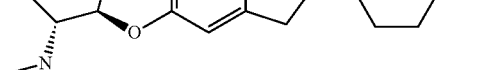
3-(5-(((1R,2R)-2-morpholinocyclohexyl)oxy)-1-oxoisoindolin-2-yl)piperidine-2,6-dione |

| Compound Structure/Compound Name | Compound Structure/Compound Name |
|---|---|
| 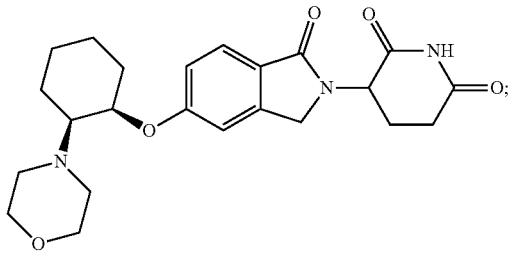<br>3-(5-(((1R,2S)-2-morpholinocyclohexyl)oxy)-1-oxoisoindolin-2-yl)piperidine-2,6-dione | 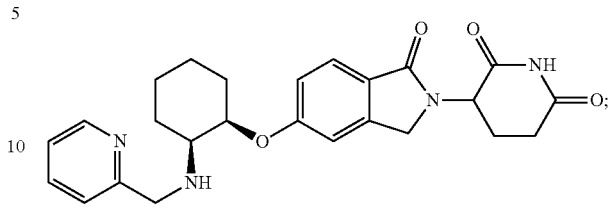<br>3-(1-oxo-5-(((1R,2S)-2-((pyridin-2-ylmethyl)amino)cyclohexyl)oxy)isoindolin-2-yl)piperidine-2,6-dione |
| 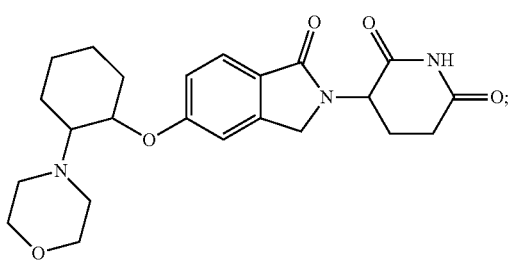<br>3-(5-((2-morpholinocyclohexyl)oxy)-1-oxoisoindolin-2-yl)piperidine-2,6-dione | 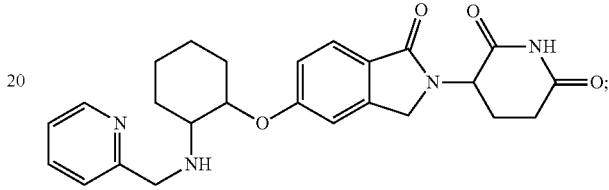<br>3-(1-oxo-5-((2-((pyridin-2-ylmethyl)amino)cyclohexyl)oxy)isoindolin-2-yl)piperidine-2,6-dione |
| 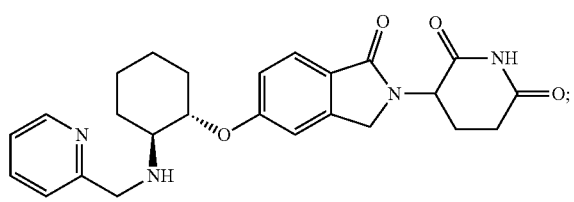<br>3-(1-oxo-5-(((1S,2S)-2-((pyridin-2-ylmethyl)amino)cyclohexyl)oxy)isoindolin-2-yl)piperidine-2,6-dione | 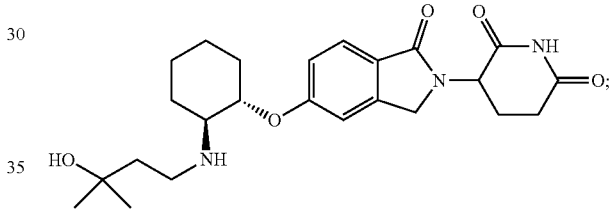<br>3-(5-(((1S,2S)-2-((3-hydroxy-3-methylbutyl)amino)cyclohexyl)oxy)-1-oxoisoindolin-2-yl)piperidine-2,6-dione |
| 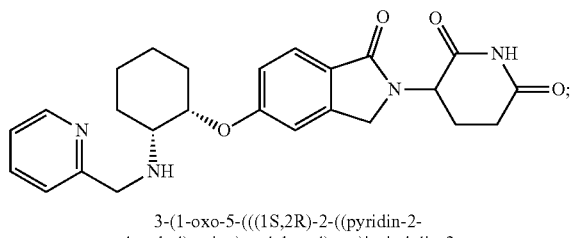<br>3-(1-oxo-5-(((1S,2R)-2-((pyridin-2-ylmethyl)amino)cyclohexyl)oxy)isoindolin-2-yl)piperidine-2,6-dione | 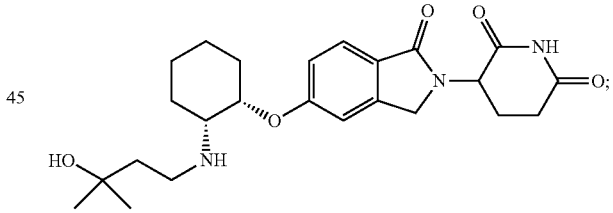<br>3-(5-(((1S,2R)-2-((3-hydroxy-3-methylbutyl)amino)cyclohexyl)oxy)-1-oxoisoindolin-2-yl)piperidine-2,6-dione |
| 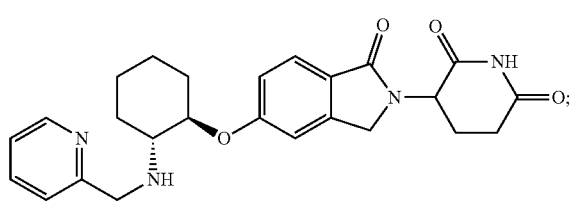<br>3-(1-oxo-5-(((1R,2R)-2-((pyridin-2-ylmethyl)amino)cyclohexyl)oxy)isoindolin-2-yl)piperidine-2,6-dione | 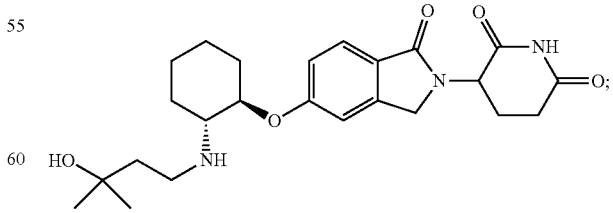<br>3-(5-(((1R,2R)-2-((3-hydroxy-3-methylbutyl)amino)cyclohexyl)oxy)-1-oxoisoindolin-2-yl)piperidine-2,6-dione |

| Compound Structure/Compound Name | Compound Structure/Compound Name |
|---|---|
| 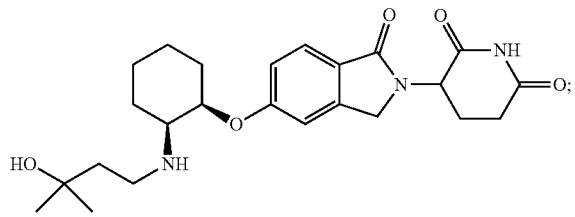<br>3-(5-(((1R,2S)-2-((3-hydroxy-3-methylbutyl)amino)cyclohexyl)oxy)-1-oxoisoindolin-2-yl)piperidine-2,6-dione | 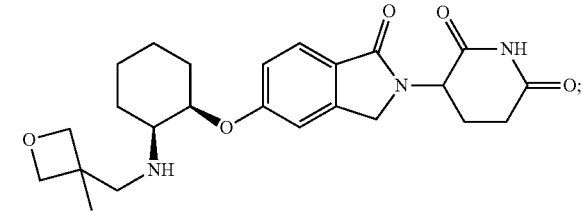<br>3-(5-(((1R,2S)-2-(((3-methyloxetan-3-yl)methyl)amino)cyclohexyl)oxy)-1-oxoisoindolin-2-yl)piperidine-2,6-dione |
| 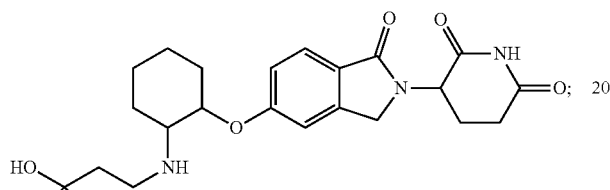<br>3-(5-((2-((3-hydroxy-3-methylbutyl)amino)cyclohexyl)oxy)-1-oxoisoindolin-2-yl)piperidine-2,6-dione | 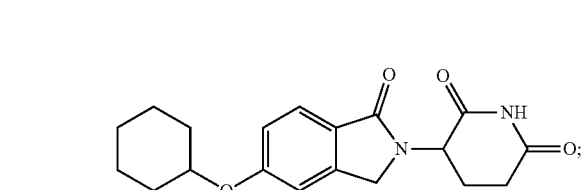<br>3-(5-((2-(((3-methyloxetan-3-yl)methyl)amino)cyclohexyl)oxy)-1-oxoisoindolin-2-yl)piperidine-2,6-dione |
| 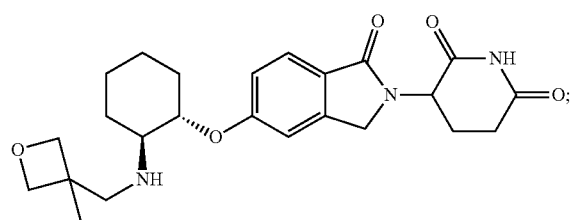<br>3-(5-(((1S,2S)-2-(((3-methyloxetan-3-yl)methyl)amino)cyclohexyl)oxy)-1-oxoisoindolin-2-yl)piperidine-2,6-dione | 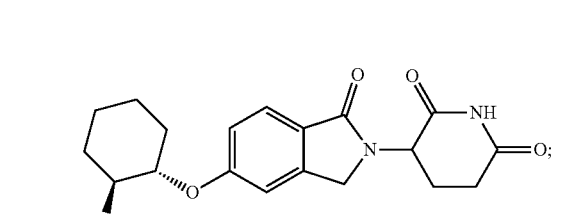<br>3-(5-(((1S,2S)-2-(4-methoxy-4-methylpiperidin-1-yl)cyclohexyl)oxy)-1-oxoisoindolin-2-yl)piperidine-2,6-dione |
| 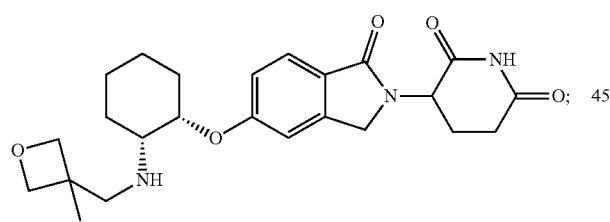<br>3-(5-(((1S,2R)-2-(((3-methyloxetan-3-yl)methyl)amino)cyclohexyl)oxy)-1-oxoisoindolin-2-yl)piperidine-2,6-dione | 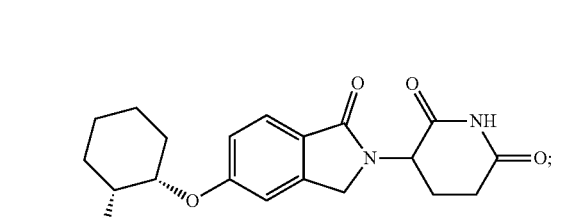<br>3-(5-(((1S,2R)-2-(4-methoxy-4-methylpiperidin-1-yl)cyclohexyl)oxy)-1-oxoisoindolin-2-yl)piperidine-2,6-dione |
| 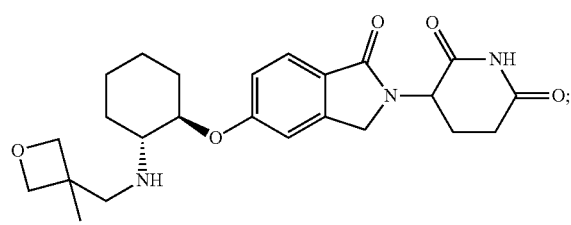<br>3-(5-(((1R,2R)-2-(((3-methyloxetan-3-yl)methyl)amino)cyclohexyl)oxy)-1-oxoisoindolin-2-yl)piperidine-2,6-dione | |

| Compound Structure/Compound Name | Compound Structure/Compound Name |
|---|---|
| 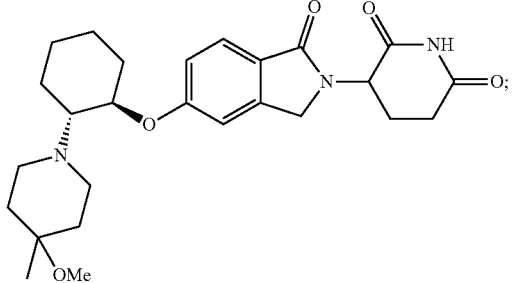<br>3-(5-(((1R,2R)-2-(4-methoxy-4-methylpiperidin-1-yl)cyclohexyl)oxy)-1-oxoisoindolin-2-yl)piperidine-2,6-dione | 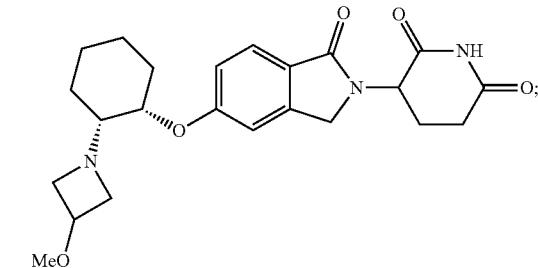<br>3-(5-(((1S,2R)-2-(3-methoxyazetidin-1-yl)cyclohexyl)oxy)-1-oxoisoindolin-2-yl)piperidine-2,6-dione |
| 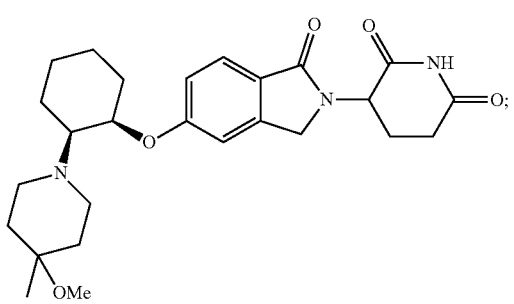<br>3-(5-(((1R,2S)-2-(4-methoxy-4-methylpiperidin-1-yl)cyclohexyl)oxy)-1-oxoisoindolin-2-yl)piperidine-2,6-dione | 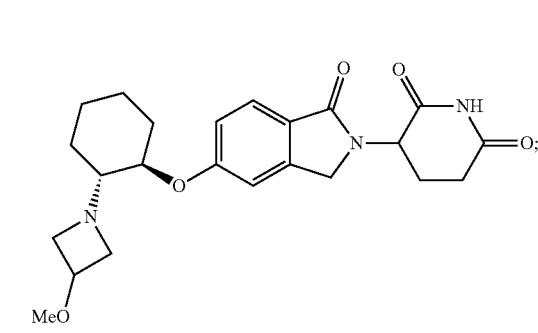<br>3-(5-(((1R,2R)-2-(3-methoxyazetidin-1-yl)cyclohexyl)oxy)-1-oxoisoindolin-2-yl)piperidine-2,6-dione |
| 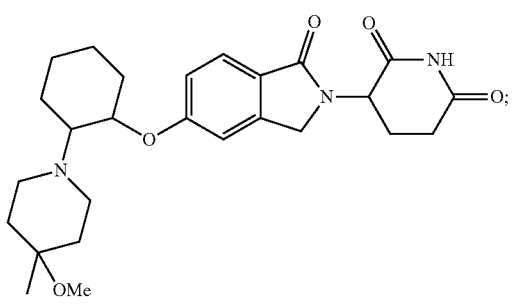<br>3-(5-((2-(4-methoxy-4-methylpiperidin-1-yl)cyclohexyl)oxy)-1-oxoisoindolin-2-yl)piperidine-2,6-dione | 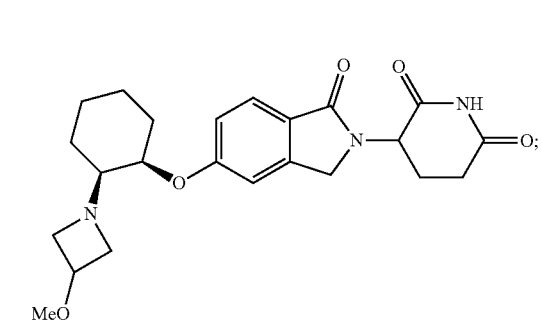<br>3-(5-(((1R,2S)-2-(3-methoxyazetidin-1-yl)cyclohexyl)oxy)-1-oxoisoindolin-2-yl)piperidine-2,6-dione |
| 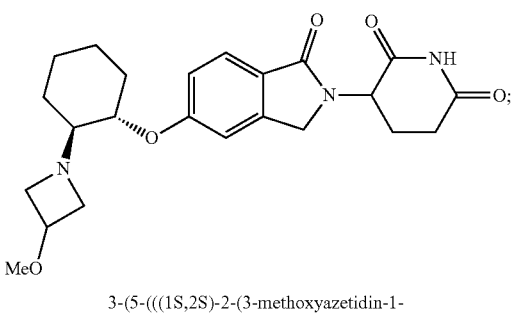<br>3-(5-(((1S,2S)-2-(3-methoxyazetidin-1-yl)cyclohexyl)oxy)-1-oxoisoindolin-2-yl)piperidine-2,6-dione | 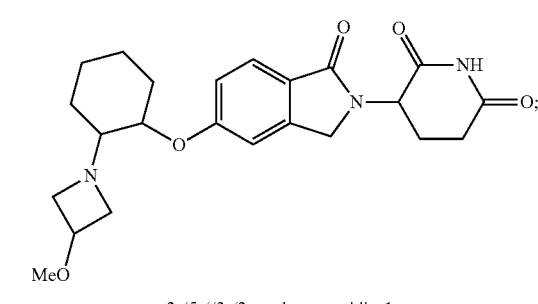<br>3-(5-((2-(3-methoxyazetidin-1-yl)cyclohexyl)oxy)-1-oxoisoindolin-2-yl)piperidine-2,6-dione |

| Compound Structure/Compound Name |
| --- |
| 3-(5-((((1S,2S)-2-(((6-methylpyridin-2-yl)methyl)amino)cyclohexyl)oxy)-1-oxoisoindolin-2-yl)piperidine-2,6-dione |
| 3-(5-((((1S,2R)-2-(((6-methylpyridin-2-yl)methyl)amino)cyclohexyl)oxy)-1-oxoisoindolin-2-yl)piperidine-2,6-dione |
| 3-(5-((((1R,2R)-2-(((6-methylpyridin-2-yl)methyl)amino)cyclohexyl)oxy)-1-oxoisoindolin-2-yl)piperidine-2,6-dione |
| 3-(5-((((1R,2S)-2-(((6-methylpyridin-2-yl)methyl)amino)cyclohexyl)oxy)-1-oxoisoindolin-2-yl)piperidine-2,6-dione |
| 3-(5-((2-(((6-methylpyridin-2-yl)methyl)amino)cyclohexyl)oxy)-1-oxoisoindolin-2-yl)piperidine-2,6-dione |

| Compound Structure/Compound Name |
| --- |
| 3-(5-((((1S,2S)-2-(((5-methoxypyridin-2-yl)methyl)amino)cyclohexyl)oxy)-1-oxoisoindolin-2-yl)piperidine-2,6-dione |
| 3-(5-((((1S,2R)-2-(((5-methoxypyridin-2-yl)methyl)amino)cyclohexyl)oxy)-1-oxoisoindolin-2-yl)piperidine-2,6-dione |
| 3-(5-((((1R,2R)-2-(((5-methoxypyridin-2-yl)methyl)amino)cyclohexyl)oxy)-1-oxoisoindolin-2-yl)piperidine-2,6-dione |
| 3-(5-((((1R,2S)-2-(((5-methoxypyridin-2-yl)methyl)amino)cyclohexyl)oxy)-1-oxoisoindolin-2-yl)piperidine-2,6-dione |
| 3-(5-((2-(((5-methoxypyridin-2-yl)methyl)amino)cyclohexyl)oxy)-1-oxoisoindolin-2-yl)piperidine-2,6-dione |
| 3-(5-((((1S,2S)-2-(((6-methoxypyridin-3-yl)methyl)amino)cyclohexyl)oxy)-1-oxoisoindolin-2-yl)piperidine-2,6-dione |

| Compound Structure/Compound Name | Compound Structure/Compound Name |
|---|---|
| 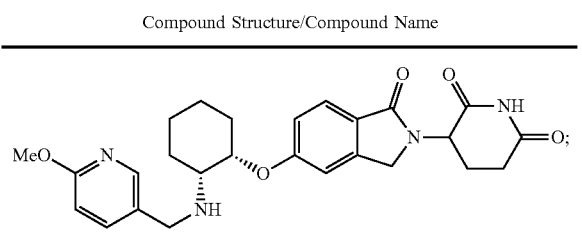<br>3-(5-(((1S,2R)-2-(((6-methoxypyridin-3-yl)methyl)amino)cyclohexyl)oxy)-1-oxoisoindolin-2-yl)piperidine-2,6-dione | 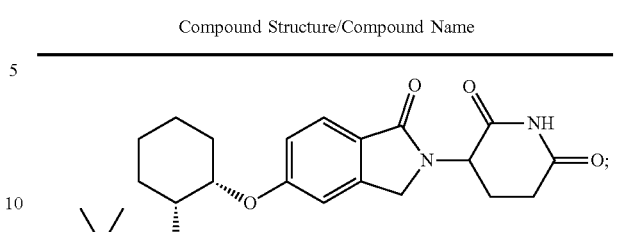<br>3-(5-(((1S,2R)-2-((2-hydroxy-2-methylpropyl)amino)cyclohexyl)oxy)-1-oxoisoindolin-2-yl)piperidine-2,6-dione |
| 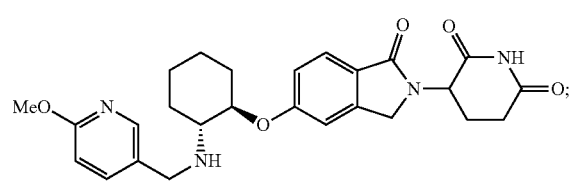<br>3-(5-(((1R,2R)-2-(((6-methoxypyridin-3-yl)methyl)amino)cyclohexyl)oxy)-1-oxoisoindolin-2-yl)piperidine-2,6-dione | 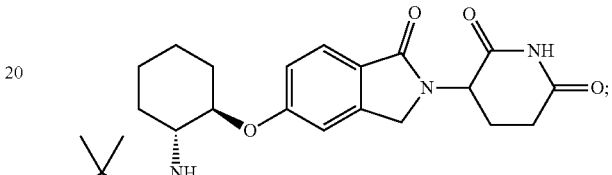<br>3-(5-(((1R,2R)-2-((2-hydroxy-2-methylpropyl)amino)cyclohexyl)oxy)-1-oxoisoindolin-2-yl)piperidine-2,6-dione |
| 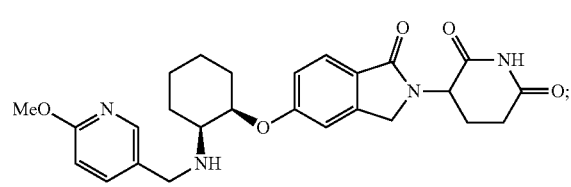<br>3-(5-(((1R,2S)-2-(((6-methoxypyridin-3-yl)methyl)amino)cyclohexyl)oxy)-1-oxoisoindolin-2-yl)piperidine-2,6-dione | 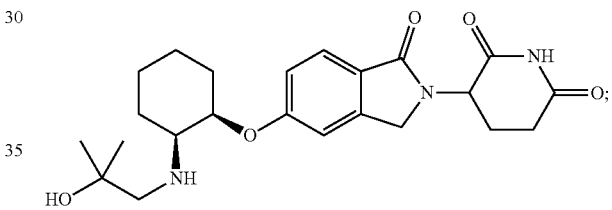<br>3-(5-(((1R,2S)-2-((2-hydroxy-2-methylpropyl)amino)cyclohexyl)oxy)-1-oxoisoindolin-2-yl)piperidine-2,6-dione |
| 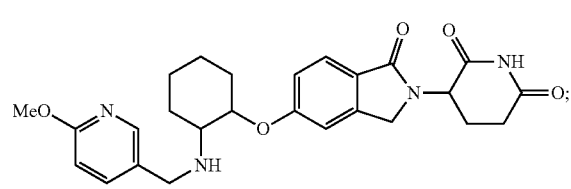<br>3-(5-((2-(((6-methoxypyridin-3-yl)methyl)amino)cyclohexyl)oxy)-1-oxoisoindolin-2-yl)piperidine-2,6-dione | 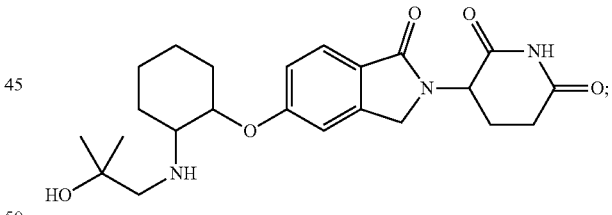<br>3-(5-((2-((2-hydroxy-2-methylpropyl)amino)cyclohexyl)oxy)-1-oxoisoindolin-2-yl)piperidine-2,6-dione |
| 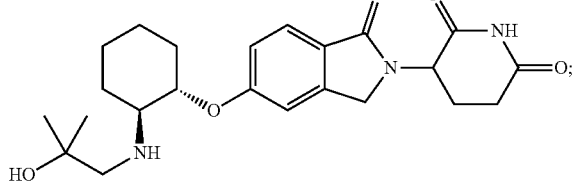<br>3-(5-(((1S,2S)-2-((2-hydroxy-2-methylpropyl)amino)cyclohexyl)oxy)-1-oxoisoindolin-2-yl)piperidine-2,6-dione | 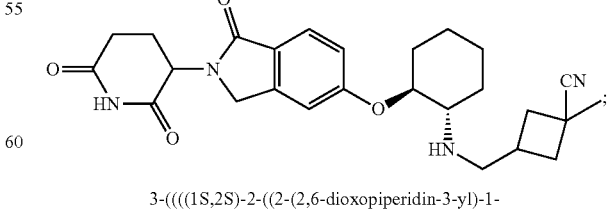<br>3-((((1S,2S)-2-((2-(2,6-dioxopiperidin-3-yl)-1-oxoisoindolin-5-yl)oxy)cyclohexyl)amino)methyl)-1-methylcyclobutane-1-carbonitrile |

| Compound Structure/Compound Name | Compound Structure/Compound Name |
|---|---|
| 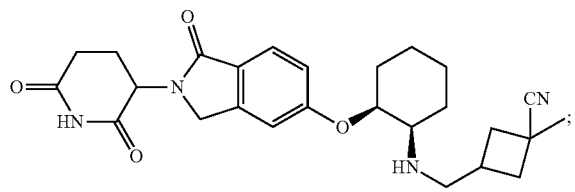<br>3-((((1R,2S)-2-((2-(2,6-dioxopiperidin-3-yl)-1-oxoisoindolin-5-yl)oxy)cyclohexyl)amino)methyl)-1-methylcyclobutane-1-carbonitrile | 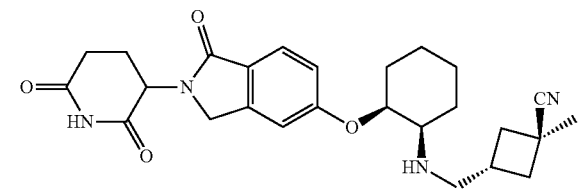<br>(1R,3R)-3-((((1R,2S)-2-((2-(2,6-dioxopiperidin-3-yl)-1-oxoisoindolin-5-yl)oxy)cyclohexyl)amino)methyl)-1-methylcyclobutane-1-carbonitrile |
| 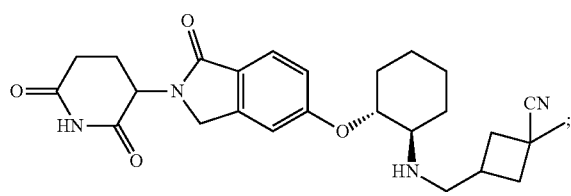<br>3-((((1R,2R)-2-((2-(2,6-dioxopiperidin-3-yl)-1-oxoisoindolin-5-yl)oxy)cyclohexyl)amino)methyl)-1-methylcyclobutane-1-carbonitrile | 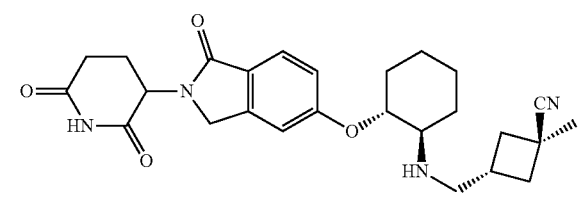<br>(1R,3R)-3-((((1R,2R)-2-((2-(2,6-dioxopiperidin-3-yl)-1-oxoisoindolin-5-yl)oxy)cyclohexyl)amino)methyl)-1-methylcyclobutane-1-carbonitrile |
| 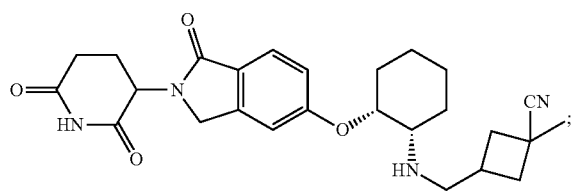<br>3-((((1S,2R)-2-((2-(2,6-dioxopiperidin-3-yl)-1-oxoisoindolin-5-yl)oxy)cyclohexyl)amino)methyl)-1-methylcyclobutane-1-carbonitrile | 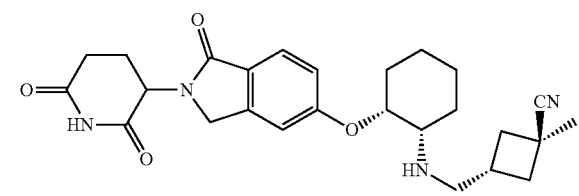<br>(1S,3r)-3-((((1S,2R)-2-((2-(2,6-dioxopiperidin-3-yl)-1-oxoisoindolin-5-yl)oxy)cyclohexyl)amino)methyl)-1-methylcyclobutane-1-carbonitrile |
| 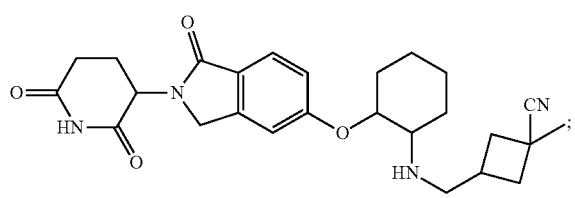<br>3-(((2-((2-(2,6-dioxopiperidin-3-yl)-1-oxoisoindolin-5-yl)oxy)cyclohexyl)amino)methyl)-1-methylcyclobutane-1-carbonitrile | 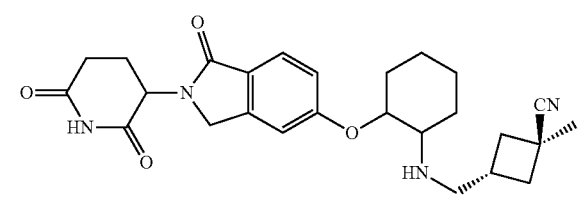<br>(1r,3r)-3-(((2-((2-(2,6-dioxopiperidin-3-yl)-1-oxoisoindolin-5-yl)oxy)cyclohexyl)amino)methyl)-1-methylcyclobutane-1-carbonitrile |
| 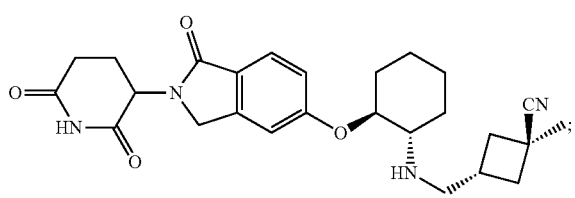<br>(1S,3R)-3-((((1S,2S)-2-((2-(2,6-dioxopiperidin-3-yl)-1-oxoisoindolin-5-yl)oxy)cyclohexyl)amino)methyl)-1-methylcyclobutane-1-carbonitrile | 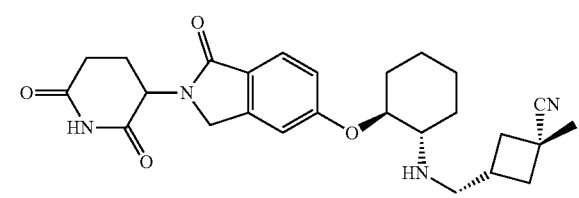<br>(1R,3S)-3-((((1S,2S)-2-((2-(2,6-dioxopiperidin-3-yl)-1-oxoisoindolin-5-yl)oxy)cyclohexyl)amino)methyl)-1-methylcyclobutane-1-carbonitrile |

| Compound Structure/Compound Name | Compound Structure/Compound Name |
|---|---|
| 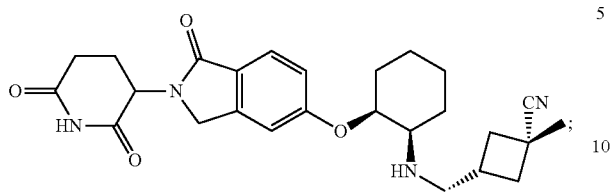<br>(1S,3s)-3-((((1R,2S)-2-((2-(2,6-dioxopiperidin-3-yl)-1-oxoisoindolin-5-yl)oxy)cyclohexyl)amino)methyl)-1-methylcyclobutane-1-carbonitrile | 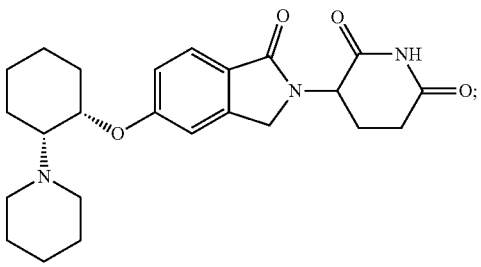<br>3-(1-oxo-5-(((1S,2R)-2-(piperidin-1-yl)cyclohexyl)oxy)isoindolin-2-yl)piperidine-2,6-dione |
| 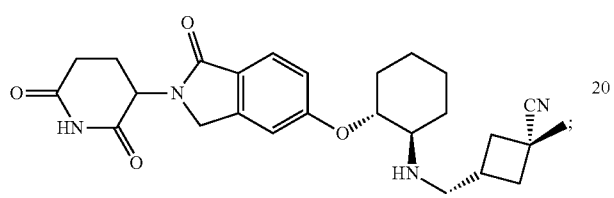<br>(1S,3s)-3-((((1R,2R)-2-((2-(2,6-dioxopiperidin-3-yl)-1-oxoisoindolin-5-yl)oxy)cyclohexyl)amino)methyl)-1-methylcyclobutane-1-carbonitrile | 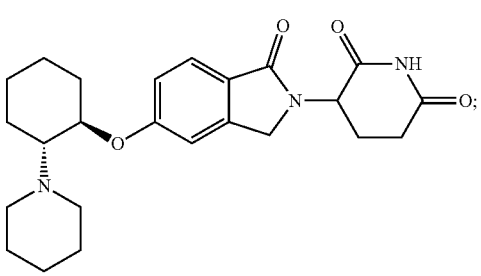<br>3-(1-oxo-5-(((1R,2R)-2-(piperidin-1-yl)cyclohexyl)oxy)isoindolin-2-yl)piperidine-2,6-dione |
| 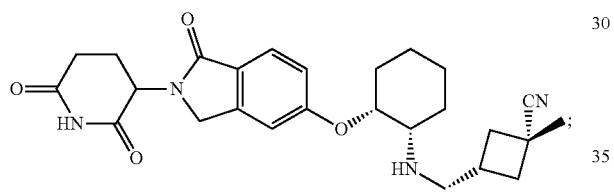<br>(1R,3s)-3-((((1S,2R)-2-((2-(2,6-dioxopiperidin-3-yl)-1-oxoisoindolin-5-yl)oxy)cyclohexyl)amino)methyl)-1-methylcyclobutane-1-carbonitrile | 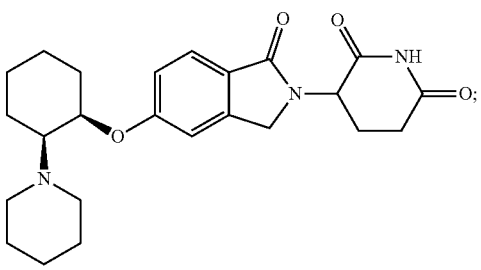<br>3-(1-oxo-5-(((1R,2S)-2-(piperidin-1-yl)cyclohexyl)oxy)isoindolin-2-yl)piperidine-2,6-dione |
| 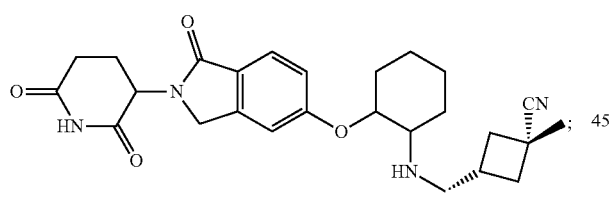<br>(1s,3s)-3-(((2-((2-(2,6-dioxopiperidin-3-yl)-1-oxoisoindolin-5-yl)oxy)cyclohexyl)amino)methyl)-1-methylcyclobutane-1-carbonitrile | 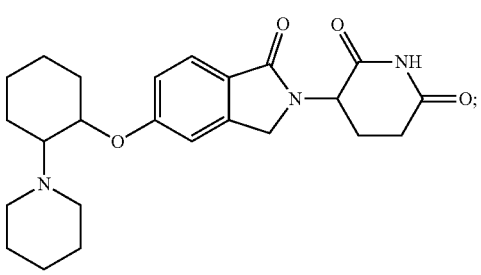<br>3-(1-oxo-5-((2-(piperidin-1-yl)cyclohexyl)oxy)isoindolin-2-yl)piperidine-2,6-dione |
| 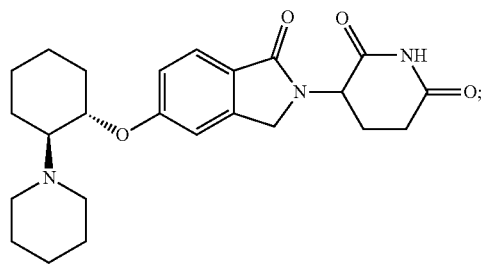<br>3-(1-oxo-5-(((1S,2S)-2-(piperidin-1-yl)cyclohexyl)oxy)isoindolin-2-yl)piperidine-2,6-dione | |

| Compound Structure/Compound Name | Compound Structure/Compound Name |
|---|---|
| 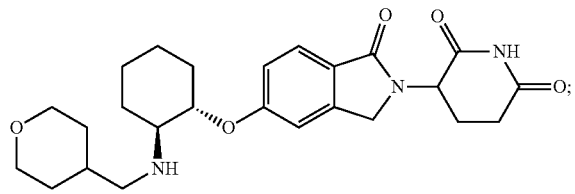<br>3-(1-oxo-5-(((1S,2S)-2-(((tetrahyro-2H-pyran-4-yl)methyl)amino)cyclohexyl)oxy)isoindolin-2-yl)piperidine-2,6-dione | 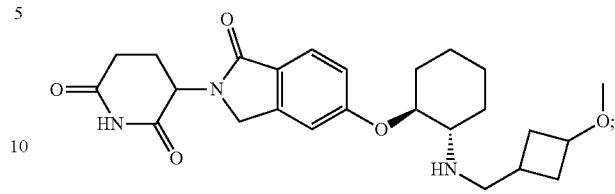<br>3-(5-(((1S,2S)-2-(((3-methoxycyclobutyl)methyl)amino)cyclohexyl)oxy)-1-oxoisoindolin-2-yl)piperidine-2,6-dione |
| 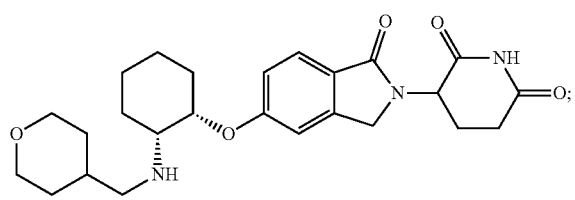<br>3-(1-oxo-5-(((1S,2R)-2-(((tetrahydro-2H-pyran-4-yl)methyl)amino)cyclohexyl)oxy)isoindolin-2-yl)piperidine-2,6-dione | 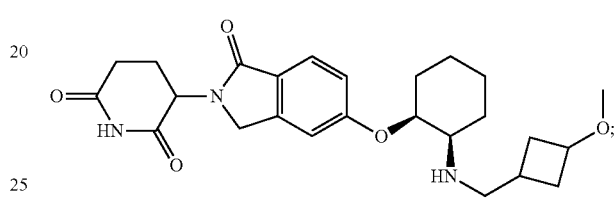<br>3-(5-(((1S,2R)-2-(((3-methoxycyclobutyl)methyl)amino)cyclohexyl)oxy)-1-oxoisoindolin-2-yl)piperidine-2,6-dione |
| 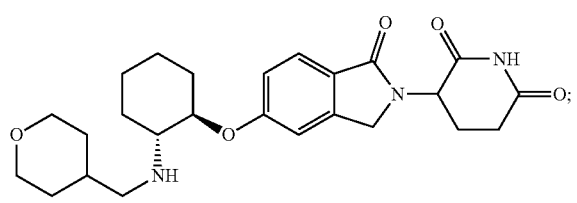<br>3-(1-oxo-5-(((1R,2R)-2-(((tetrahydro-2H-pyran-4-yl)methyl)amino)cyclohexyl)oxy)isoindolin-2-yl)piperidine-2,6-dione | 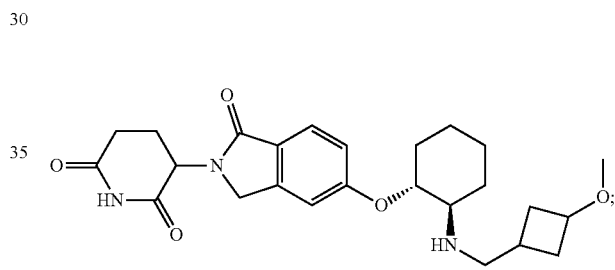<br>3-(5-(((1R,2R)-2-(((3-methoxycyclobutyl)methyl)amino)cyclohexyl)oxy)-1-oxoisoindolin-2-yl)piperidine-2,6-dione |
| 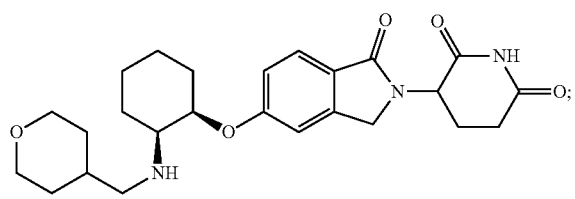<br>3-(1-oxo-5-(((1R,2S)-2-(((tetrahydro-2H-pyran-4-yl)methyl)amino)cyclohexyl)oxy)isoindolin-2-yl)piperidine-2,6-dione | 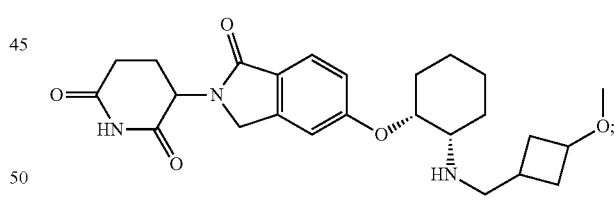<br>3-(5-(((1R,2S)-2-(((3-methoxycyclobutyl)methyl)amino)cyclohexyl)oxy)-1-oxoisoindolin-2-yl)piperidine-2,6-dione |
| 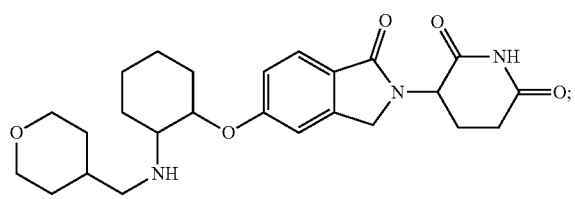<br>3-(1-oxo-5-((2-(((tetrahydro-2H-pyran-4-yl)methyl)amino)cyclohexyl)oxy)isoindolin-2-yl)piperidine-2,6-dione | 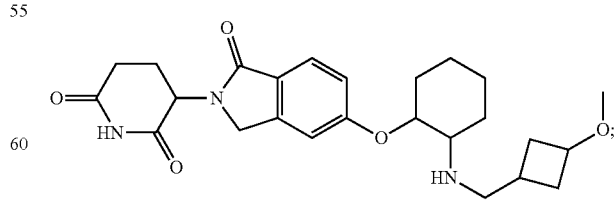<br>3-(5-((2-(((3-methoxycyclobutyl)methyl)amino)cyclohexyl)oxy)-1-oxoisoindolin-2-yl)piperidine-2,6-dione |

| Compound Structure/Compound Name | Compound Structure/Compound Name |
|---|---|
| 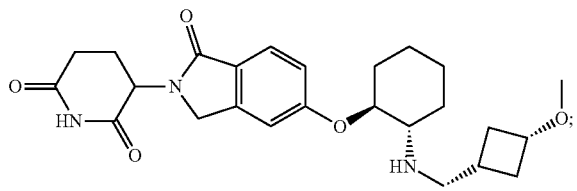<br>3-(5-((((1S,2S)-2-(((((1S,3R)-3-methoxycyclobutyl)methyl)amino)cyclohexyl)oxy)-1-oxoisoindolin-2-yl)piperidine-2,6-dione | 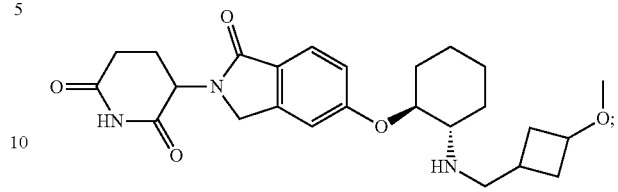<br>3-(5-((((1S,2S)-2-(((cis-3-methoxycyclobutyl)methyl)amino)cyclohexyl)oxy)-1-oxoisoindolin-2-yl)piperidine-2,6-dione |
| 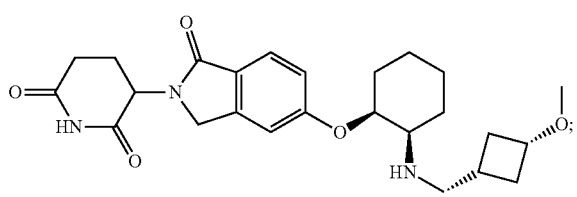<br>3-(5-((((1S,2R)-2-(((((1s,3S)-3-methoxycyclobutyl)methyl)amino)cyclohexyl)oxy)-1-oxoisoindolin-2-yl)piperidine-2,6-dione | 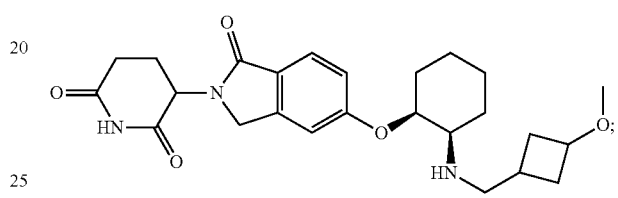<br>3-(5-((((1S,2R)-2-(((cis-3-methoxycyclobutyl)methyl)amino)cyclohexyl)oxy)-1-oxoisoindolin-2-yl)piperidine-2,6-dione |
| 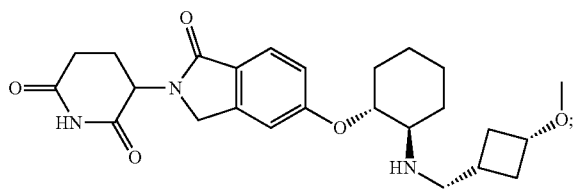<br>3-(5-((((1R,2R)-2-(((((1s,3S)-3-methoxycyclobutyl)methyl)amino)cyclohexyl)oxy)-1-oxoisoindolin-2-yl)piperidine-2,6-dione | 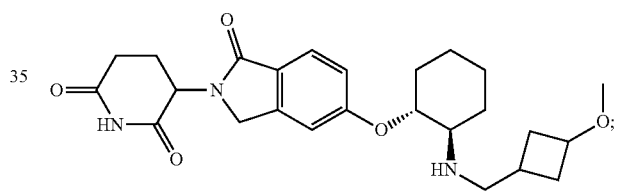<br>3-(5-((((1R,2R)-2-(((cis-3-methoxycyclobutyl)methyl)amino)cyclohexyl)oxy)-1-oxoisoindolin-2-yl)piperidine-2,6-dione |
| 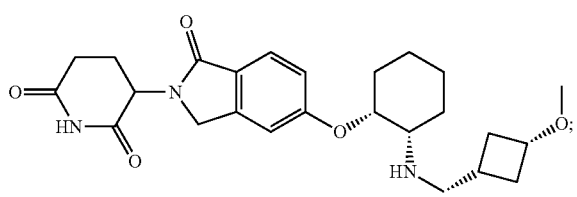<br>3-(5-((((1R,2S)-2-(((((1s,3R)-3-methoxycyclobutyl)methyl)amino)cyclohexyl)oxy)-1-oxoisoindolin-2-yl)piperidine-2,6-dione | 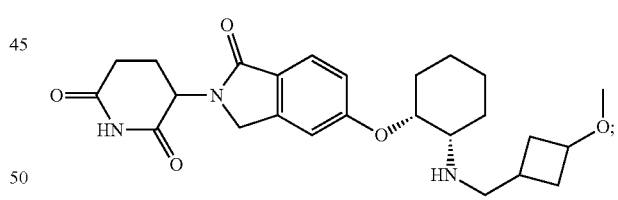<br>3-(5-((((1R,2S)-2-(((cis-3-methoxycyclobutyl)methyl)amino)cyclohexyl)oxy)-1-oxoisoindolin-2-yl)piperidine-2,6-dione |
| 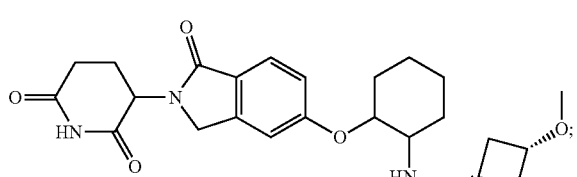<br>3-(5-((2-(((((1s,3s)-3-methoxycyclobutyl)methyl)amino)cyclohexyl)oxy)-1-oxoisoindolin-2-yl)piperidine-2,6-dione | 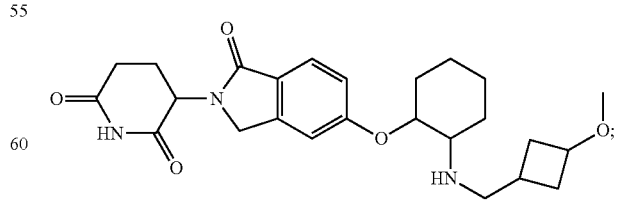<br>3-(5-((2-(((cis-3-methoxycyclobutyl)methyl)amino)cyclohexyl)oxy)-1-oxoisoindolin-2-yl)piperidine-2,6-dione |

| Compound Structure/Compound Name | Compound Structure/Compound Name |
|---|---|
| 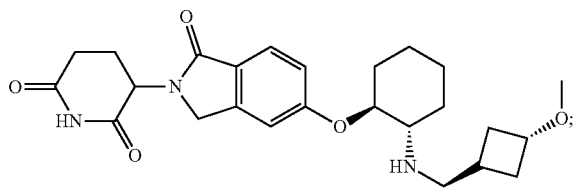<br>3-(5-((((1S,2S)-2-((((1R,3S)-3-methoxycyclobutyl)methyl)amino)cyclohexyl)oxy)-1-oxoisoindolin-2-yl)piperidine-2,6-dione | 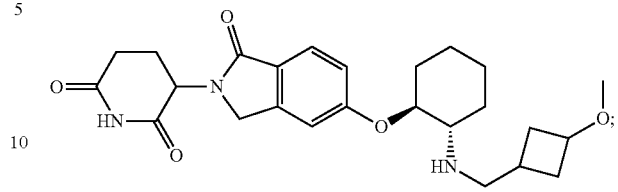<br>3-(5-((((1S,2S)-2-(((trans-3-methoxycyclobutyl)methyl)amino)cyclohexyl)oxy)-1-oxoisoindolin-2-yl)piperidine-2,6-dione |
| 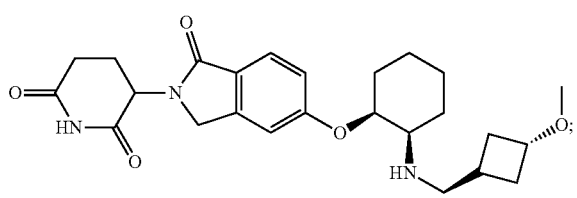<br>3-(5-((((1S,2R)-2-((((1s,3S)-3-methoxycyclobutyl)methyl)amino)cyclohexyl)oxy)-1-oxoisoindolin-2-yl)piperidine-2,6-dione | 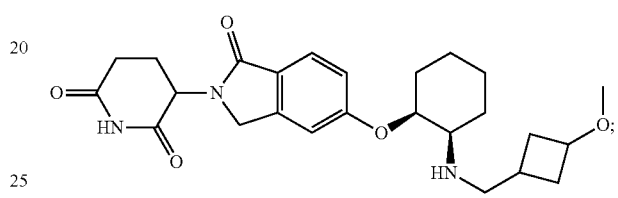<br>3-(5-((((1S,2R)-2-(((trans-3-methoxycyclobutyl)methyl)amino)cyclohexyl)oxy)-1-oxoisoindolin-2-yl)piperidine-2,6-dione |
| 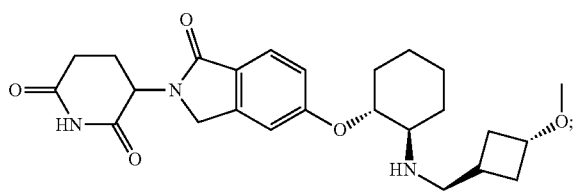<br>3-(5-((((1R,2R)-2-((((1s,3S)-3-methoxycyclobutyl)methyl)amino)cyclohexyl)oxy)-1-oxoisoindolin-2-yl)piperidine-2,6-dione | 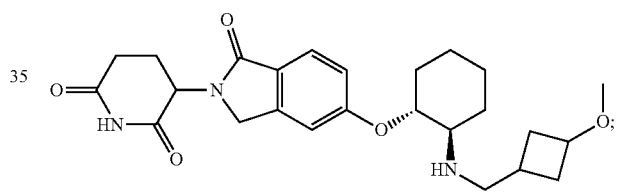<br>3-(5-((((1R,2R)-2-(((trans-3-methoxycyclobutyl)methyl)amino)cyclohexyl)oxy)-1-oxoisoindolin-2-yl)piperidine-2,6-dione |
| 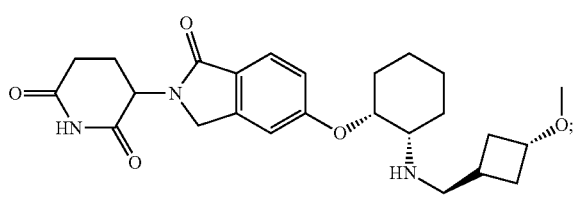<br>3-(5-((((1R,2S)-2-((((1s,3R)-3-methoxycyclobutyl)methyl)amino)cyclohexyl)oxy)-1-oxoisoindolin-2-yl)piperidine-2,6-dione | 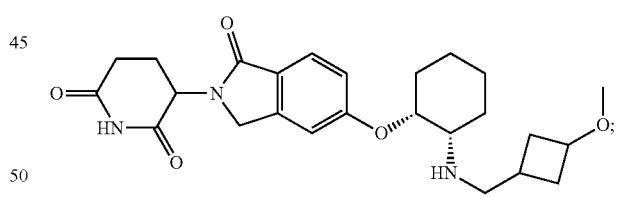<br>3-(5-((((1R,2S)-2-(((trans-3-methoxycyclobutyl)methyl)amino)cyclohexyl)oxy)-1-oxoisoindolin-2-yl)piperidine-2,6-dione |
| 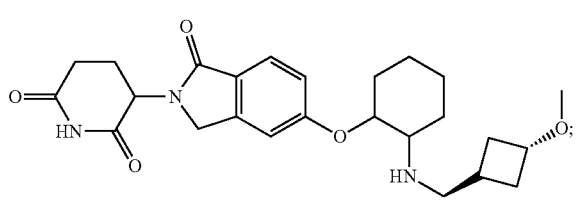<br>3-(5-((2-(((((1s,3s)-3-methoxycyclobutyl)methyl)amino)cyclohexyl)oxy)-1-oxoisoindolin-2-yl)piperidine-2,6-dione | 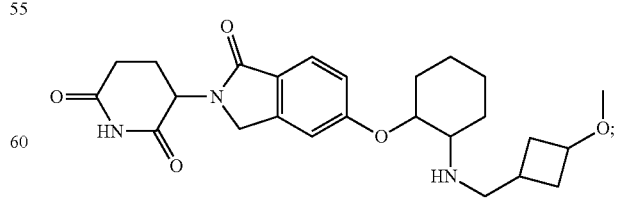<br>3-(5-((2-(((trans-3-methoxycyclobutyl)methyl)amino)cyclohexyl)oxy)-1-oxoisoindolin-2-yl)piperidine-2,6-dione |

| Compound Structure/Compound Name | Compound Structure/Compound Name |
|---|---|
| 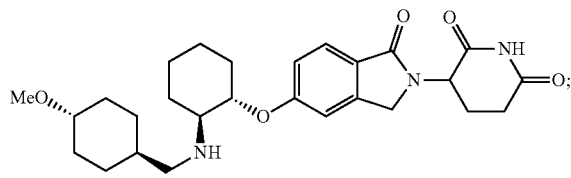<br>3-(5-((((1S,2S)-2-(((((1r,4S)-4-methoxycyclohexyl)methyl)amino)cyclohexyl)oxy)-1-oxoisoindolin-2-yl)piperidine-2,6-dione | 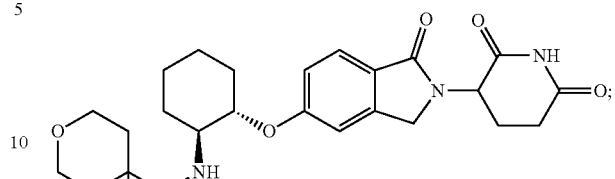<br>3-(5-((((1S,2S)-2-(((4-methyltetrahydro-2H-pyran-4-yl)methyl)amino)cyclohexyl)oxy)-1-oxoisoindolin-2-yl)piperidine-2,6-dione |
| 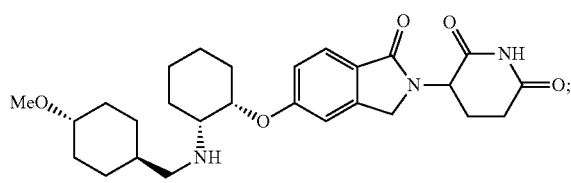<br>3-(5-((((1S,2R)-2-(((((1r,4R)-4-methoxycyclohexyl)methyl)amino)cyclohexyl)oxy)-1-oxoisoindolin-2-yl)piperidine-2,6-dione | 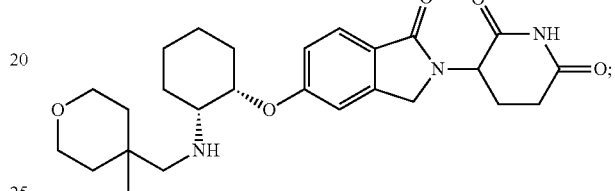<br>3-(5-((((1S,2R)-2-(((4-methyltetrahydro-2H-pyran-4-yl)methyl)amino)cyclohexyl)oxy)-1-oxoisoindolin-2-yl)piperidine-2,6-dione |
| 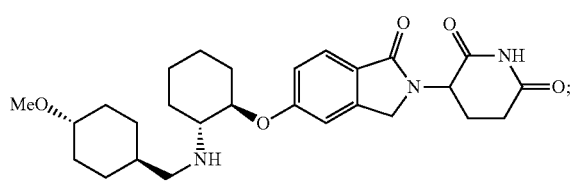<br>3-(5-((((1R,2R)-2-(((((1r,4R)-4-methoxycyclohexyl)methyl)amino)cyclohexyl)oxy)-1-oxoisoindolin-2-yl)piperidine-2,6-dione | 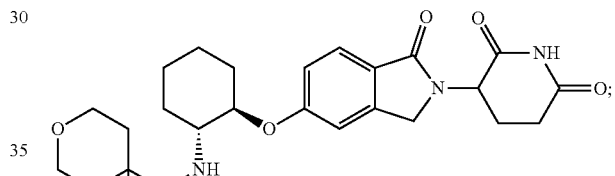<br>3-(5-((((1R,2R)-2-(((4-methyltetrahydro-2H-pyran-4-yl)methyl)amino)cyclohexyl)oxy)-1-oxoisoindolin-2-yl)piperidine-2,6-dione |
| 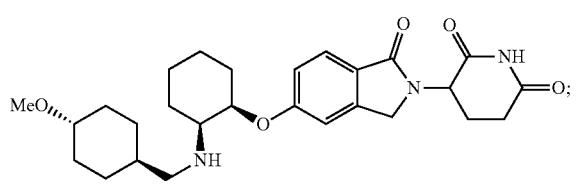<br>3-(5-((((1R,2S)-2-(((((1r,4S)-4-methoxycyclohexyl)methyl)amino)cyclohexyl)oxy)-1-oxoisoindolin-2-yl)piperidine-2,6-dione | 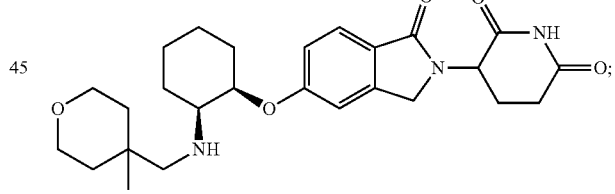<br>3-(5-((((1R,2S)-2-(((4-methyltetrahydro-2H-pyran-4-yl)methyl)amino)cyclohexyl)oxy)-1-oxoisoindolin-2-yl)piperidine-2,6-dione |
| 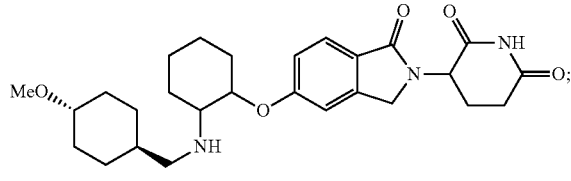<br>3-(5-((2-(((((1r,4r)-4-methoxycyclohexyl)methyl)amino)cyclohexyl)oxy)-1-oxoisoindolin-2-yl)piperidine-2,6-dione | 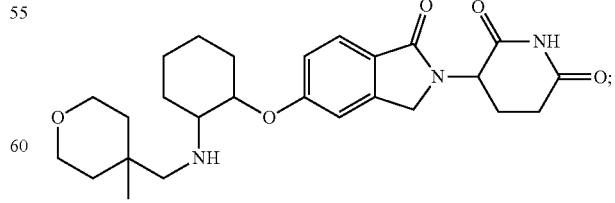<br>3-(5-((2-(((4-methyltetrahydro-2H-pyran-4-yl)methyl)amino)cyclohexyl)oxy)-1-oxoisoindolin-2-yl)piperidine-2,6-dione |

| Compound Structure/Compound Name | Compound Structure/Compound Name |
|---|---|
| 3-(1-oxo-5-((((1S,2S)-2-((pyrimidin-5-ylmethyl)amino)cyclohexyl)oxy)isoindolin-2-yl)piperidine-2,6-dione | 3-(1-oxo-5-((((1S,2S)-2-((2-(tetrahydro-2H-pyran-4-yl)ethyl)amino)cyclohexyl)oxy)isoindolin-2-yl)piperidine-2,6-dione |
| 3-(1-oxo-5-((((1S,2R)-2-((pyrimidin-5-ylmethyl)amino)cyclohexyl)oxy)isoindolin-2-yl)piperidine-2,6-dione | 3-(1-oxo-5-((((1S,2R)-2-((2-(tetrahydro-2H-pyran-4-yl)ethyl)amino)cyclohexyl)oxy)isoindolin-2-yl)piperidine-2,6-dione |
| 3-(1-oxo-5-((((1R,2R)-2-((pyrimidin-5-ylmethyl)amino)cyclohexyl)oxy)isoindolin-2-yl)piperidine-2,6-dione | 3-(1-oxo-5-((((1R,2R)-2-((2-(tetrahydro-2H-pyran-4-yl)ethyl)amino)cyclohexyl)oxy)isoindolin-2-yl)piperidine-2,6-dione |
| 3-(1-oxo-5-((((1R,2S)-2-((pyrimidin-5-ylmethyl)amino)cyclohexyl)oxy)isoindolin-2-yl)piperidine-2,6-dione | 3-(1-oxo-5-((((1R,2S)-2-((2-(tetrahydro-2H-pyran-4-yl)ethyl)amino)cyclohexyl)oxy)isoindolin-2-yl)piperidine-2,6-dione |
| 3-(1-oxo-5-((2-((pyrimidin-5-ylmethyl)amino)cyclohexyl)oxy)isoindolin-2-yl)piperidine-2,6-dione | |

| Compound Structure/Compound Name |
|---|
| 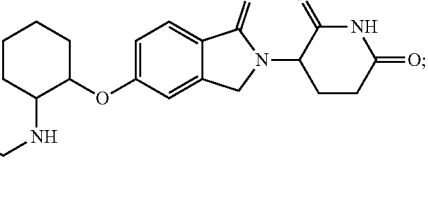<br>3-(1-oxo-5-((2-((2-(tetrahydro-2H-pyran-4-yl)ethyl)amino)cyclohexyl)oxy)isoindolin-2-yl)piperidine-2,6-dione |
| 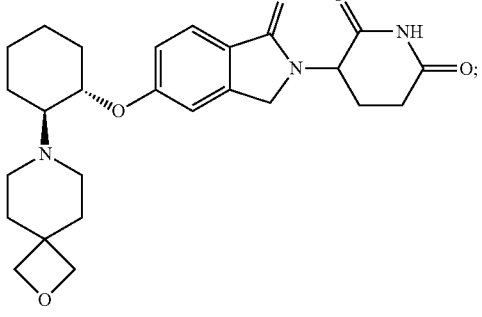<br>3-(5-(((1S,2S)-2-(2-oxa-7-azaspiro[3.5]nonan-7-yl)cyclohexyl)oxy)-1-oxoisoindolin-2-yl)piperidine-2,6-dione |
| 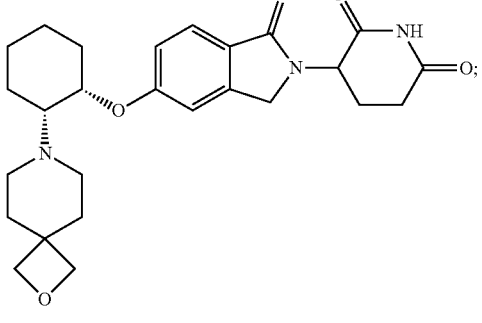<br>3-(5-(((1S,2R)-2-(2-oxa-7-azaspiro[3.5]nonan-7-yl)cyclohexyl)oxy)-1-oxoisoindolin-2-yl)piperidine-2,6-dione |
| 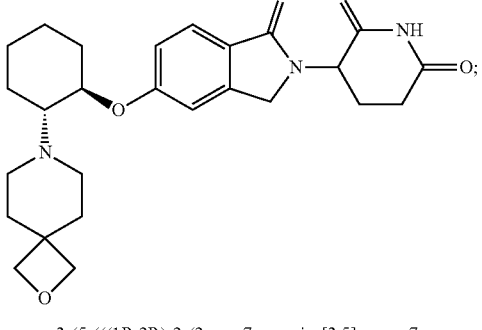<br>3-(5-(((1R,2R)-2-(2-oxa-7-azaspiro[3.5]nonan-7-yl)cyclohexyl)oxy)-1-oxoisoindolin-2-yl)piperidine-2,6-dione |

| Compound Structure/Compound Name |
|---|
| 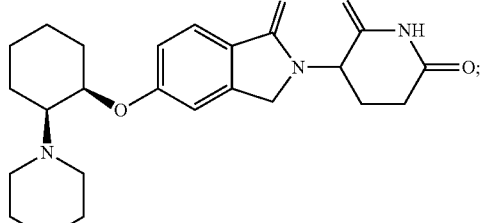<br>3-(5-(((1R,2S)-2-(2-oxa-7-azaspiro[3.5]nonan-7-yl)cyclohexyl)oxy)-1-oxoisoindolin-2-yl)piperidine-2,6-dione |
| 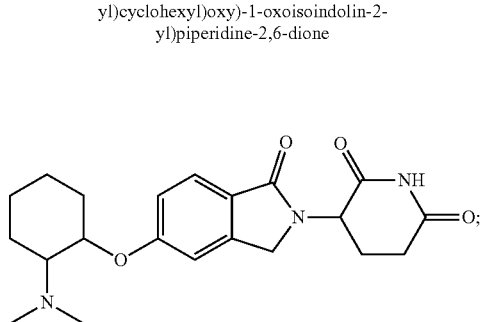<br>3-(5-((2-(2-oxa-7-azaspiro[3.5]nonan-7-yl)cyclohexyl)oxy)-1-oxoisoindolin-2-yl)piperidine-2,6-dione |
| 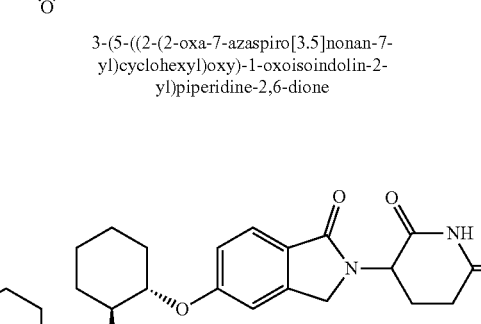<br>3-(5-(((1S,2S)-2-(((4-methoxytetrahydro-2H-pyran-4-yl)methyl)amino)cyclohexyl)oxy)-1-oxoisoindolin-2-yl)piperidine-2,6-dione |
| 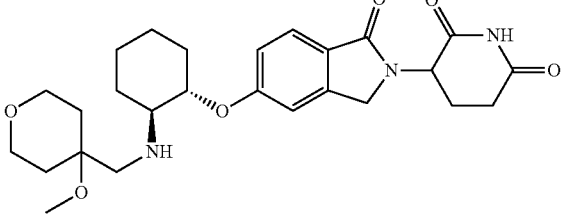<br>3-(5-(((1S,2R)-2-(((4-methoxytetrahydro-2H-pyran-4-yl)methyl)amino)cyclohexyl)oxy)-1-oxoisoindolin-2-yl)piperidine-2,6-dione |

| Compound Structure/Compound Name | Compound Structure/Compound Name |
|---|---|
| 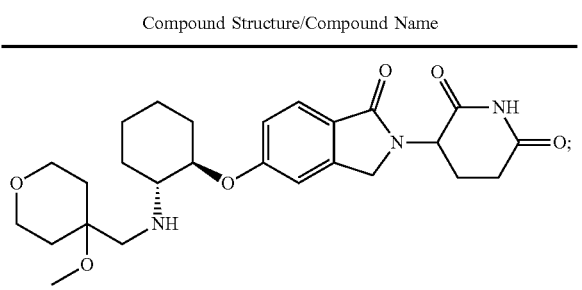 3-(5-(((1R,2R)-2-(((4-methoxytetrahydro-2H-pyran-4-yl)methyl)amino)cyclohexyl)oxy)-1-oxoisoindolin-2-yl)piperidine-2,6-dione | 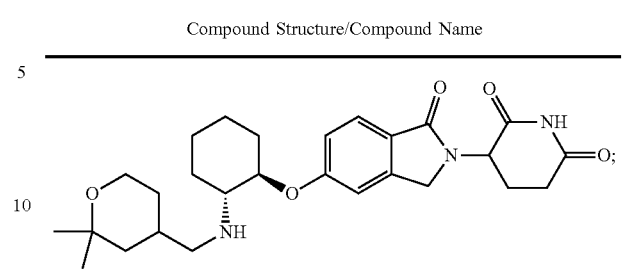 3-(5-(((1R,2R)-2-(((2,2-dimethyltetrahydro-2H-pyran-4-yl)methyl)amino)cyclohexyl)oxy)-1-oxoisoindolin-2-yl)piperidine-2,6-dione |
| 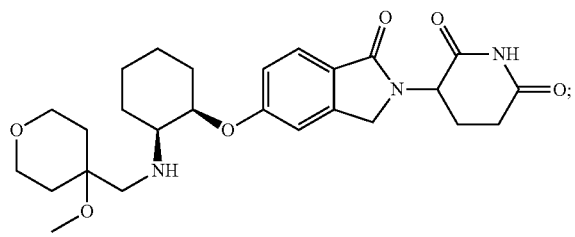 3-(5-(((1R,2S)-2-(((4-methoxytetrahydro-2H-pyran-4-yl)methyl)amino)cyclohexyl)oxy)-1-oxoisoindolin-2-yl)piperidine-2,6-dione | 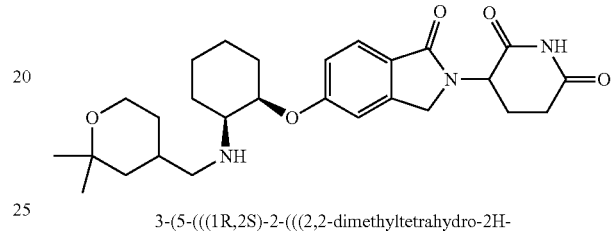 3-(5-(((1R,2S)-2-(((2,2-dimethyltetrahydro-2H-pyran-4-yl)methyl)amino)cyclohexyl)oxy)-1-oxoisoindolin-2-yl)piperidine-2,6-dione |
| 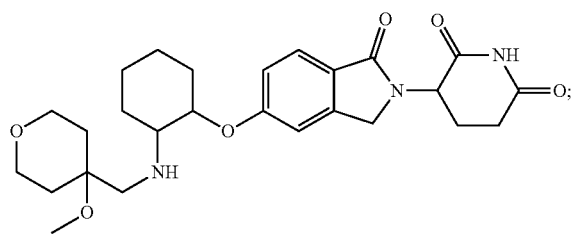 3-(5-((2-(((4-methoxytetrahydro-2H-pyran-4-yl)methyl)amino)cyclohexyl)oxy)-1-oxoisoindolin-2-yl)piperidine-2,6-dione | 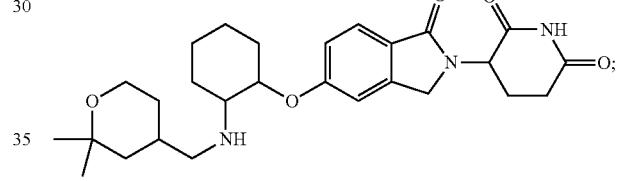 3-(5-((2-(((2,2-dimethyltetrahydro-2H-pyran-4-yl)methyl)amino)cyclohexyl)oxy)-1-oxoisoindolin-2-yl)piperidine-2,6-dione |
| 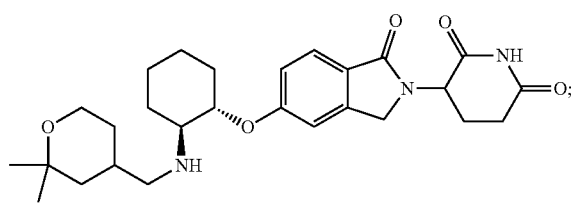 3-(5-(((1S,2S)-2-(((2,2-dimethyltetrahydro-2H-pyran-4-yl)methyl)amino)cyclohexyl)oxy)-1-oxoisoindolin-2-yl)piperidine-2,6-dione | 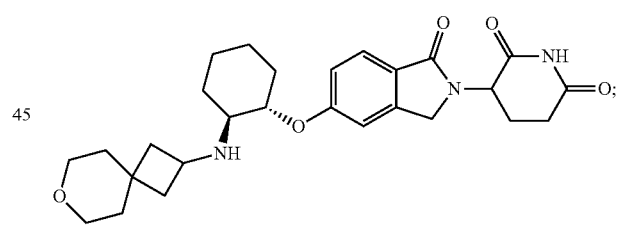 3-(5-(((1S,2S)-2-((7-oxaspiro[3.5]nonan-2-yl)amino)cyclohexyl)oxy)-1-oxoisoindolin-2-yl)piperidine-2,6-dione |
| 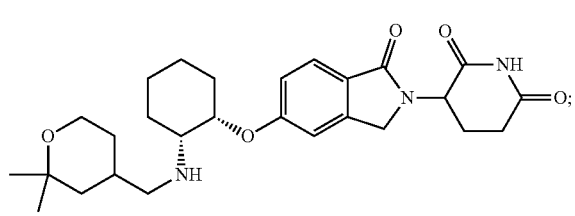 3-(5-(((1S,2R)-2-(((2,2-dimethyltetrahydro-2H-pyran-4-yl)methyl)amino)cyclohexyl)oxy)-1-oxoisoindolin-2-yl)piperidine-2,6-dione | 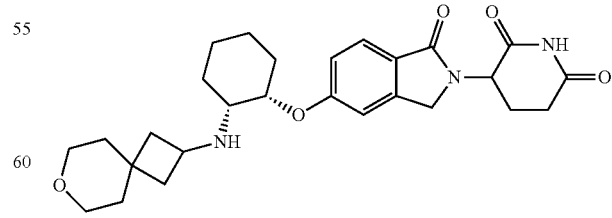 3-(5-(((1S,2R)-2-((7-oxaspiro[3.5]nonan-2-yl)amino)cyclohexyl)oxy)-1-oxoisoindolin-2-yl)piperidine-2,6-dione |

| Compound Structure/Compound Name | Compound Structure/Compound Name |
|---|---|
| 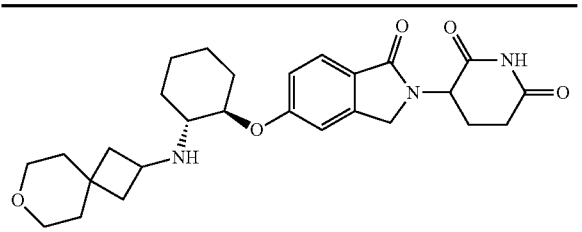<br>3-(5-((((1R,2R)-2-((7-oxaspiro[3.5]nonan-2-yl)amino)cyclohexyl)oxy)-1-oxoisoindolin-2-yl)piperidine-2,6-dione | 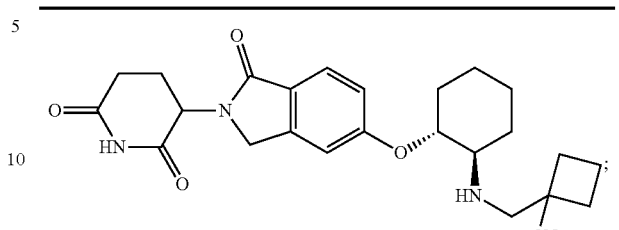<br>1-(((((1R,2R)-2-((2-(2,6-dioxopiperidin-3-yl)-1-oxoisoindolin-5-yl)oxy)cyclohexyl)amino)methyl)cyclobutane-1-carbonitrile |
| 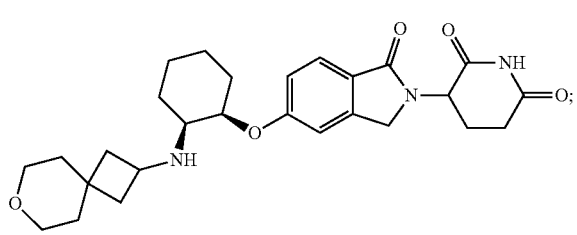<br>3-(5-((((1R,2S)-2-((7-oxaspiro[3.5]nonan-2-yl)amino)cyclohexyl)oxy)-1-oxoisoindolin-2-yl)piperidine-2,6-dione | 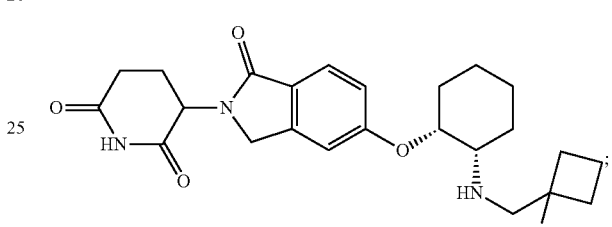<br>1-(((((1S,2R)-2-((2-(2,6-dioxopiperidin-3-yl)-1-oxoisoindolin-5-yl)oxy)cyclohexyl)amino)methyl)cyclobutane-1-carbonitrile |
| 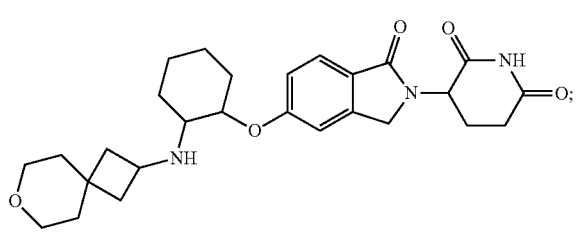<br>3-(5-((2-((7-oxaspiro[3.5]nonan-2-yl)amino)cyclohexyl)oxy)-1-oxoisoindolin-2-yl)piperidine-2,6-dione | 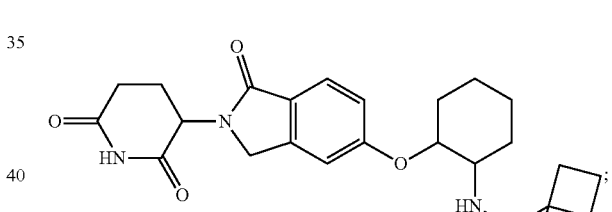<br>1-(((2-((2-(2,6-dioxopiperidin-3-yl)-1-oxoisoindolin-5-yl)oxy)cyclohexyl)amino)methyl)cyclobutane-1-carbonitrile |
| 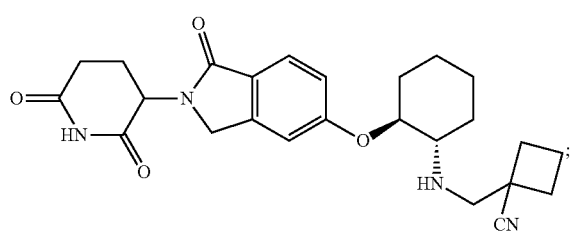<br>1-(((((1S,2S)-2-((2-(2,6-dioxopiperidin-3-yl)-1-oxoisoindolin-5-yl)oxy)cyclohexyl)amino)methyl)cyclobutane-1-carbonitrile | 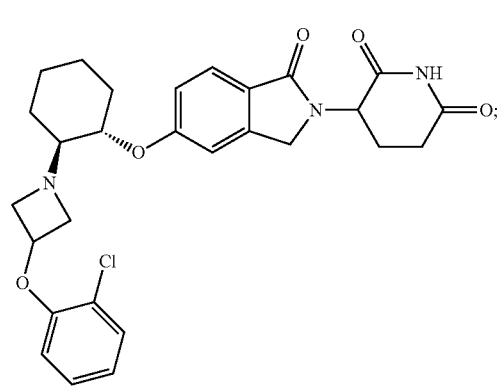<br>3-(5-(((1S,2S)-2-(3-(2-chlorophenoxy)azetidin-1-yl)cyclohexyl)oxy)-1-oxoisoindolin-2-yl)piperidine-2,6-dione |
| 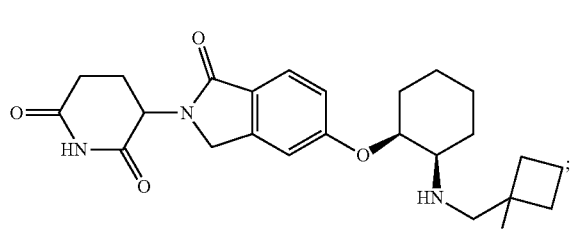<br>1-(((((1R,2S)-2-((2-(2,6-dioxopiperidin-3-yl)-1-oxoisoindolin-5-yl)oxy)cyclohexyl)amino)methyl)cyclobutane-1-carbonitrile | |

| Compound Structure/Compound Name | Compound Structure/Compound Name |
|---|---|
| 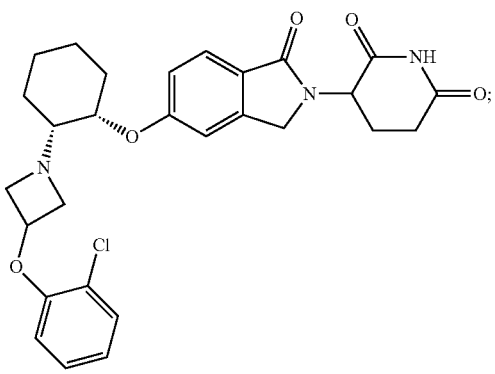<br>3-(5-(((1S,2R)-2-(3-(2-chlorophenoxy)azetidin-1-yl)cyclohexyl)oxy)-1-oxoisoindolin-2-yl)piperidine-2,6-dione | 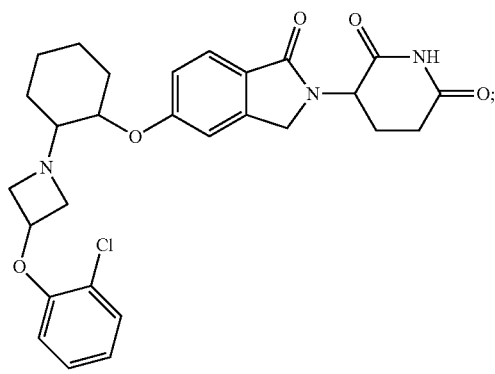<br>3-(5-((2-(3-(2-chlorophenoxy)azetidin-1-yl)cyclohexyl)oxy)-1-oxoisoindolin-2-yl)piperidine-2,6-dione |
| 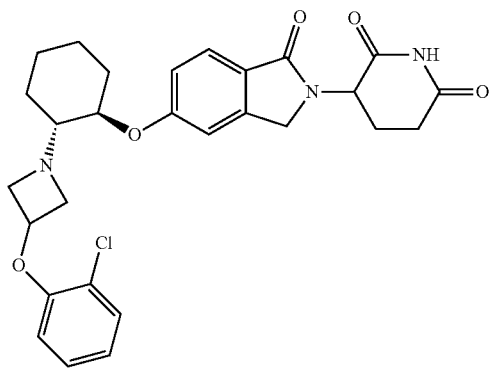<br>3-(5-(((1R,2R)-2-(3-(2-chlorophenoxy)azetidin-1-yl)cyclohexyl)oxy)-1-oxoisoindolin-2-yl)piperidine-2,6-dione | 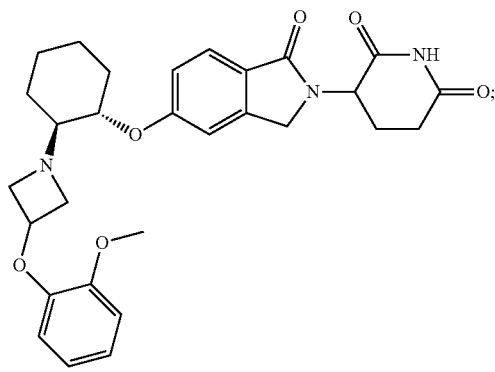<br>3-(5-(((1S,2S)-2-(3-(2-methoxyphenoxy)azetidin-1-yl)cyclohexyl)oxy)-1-oxoisoindolin-2-yl)piperidine-2,6-dione |
| 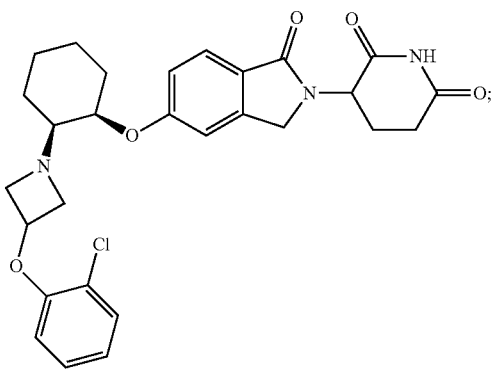<br>3-(5-(((1R,2S)-2-(3-(2-chlorophenoxy)azetidin-1-yl)cyclohexyl)oxy)-1-oxoisoindolin-2-yl)piperidine-2,6-dione | 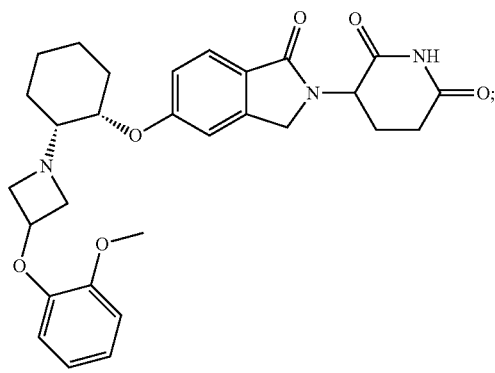<br>3-(5-(((1S,2R)-2-(3-(2-methoxyphenoxy)azetidin-1-yl)cyclohexyl)oxy)-1-oxoisoindolin-2-yl)piperidine-2,6-dione |

| Compound Structure/Compound Name | Compound Structure/Compound Name |
|---|---|
| 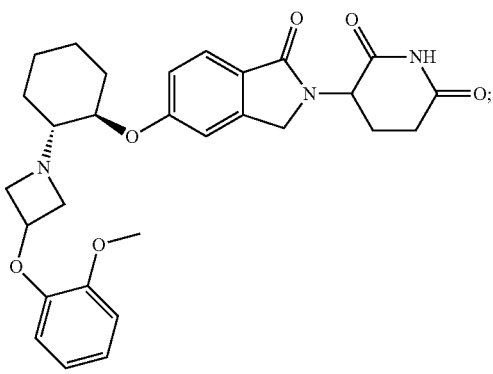

3-(5-(((1R,2R)-2-(3-(2-methoxyphenoxy)azetidin-1-yl)cyclohexyl)oxy)-1-oxoisoindolin-2-yl)piperidine-2,6-dione | 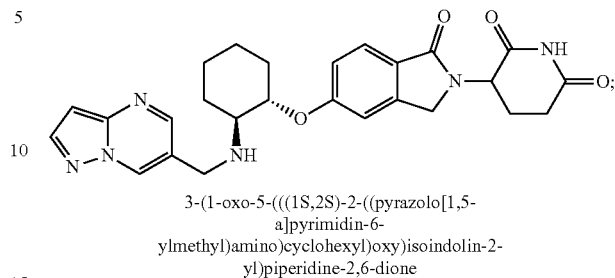

3-(1-oxo-5-(((1S,2S)-2-((pyrazolo[1,5-a]pyrimidin-6-ylmethyl)amino)cyclohexyl)oxy)isoindolin-2-yl)piperidine-2,6-dione |
| 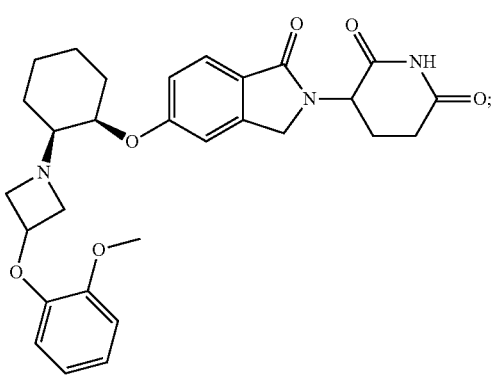

3-(5-(((1R,2S)-2-(3-(2-methoxyphenoxy)azetidin-1-yl)cyclohexyl)oxy)-1-oxoisoindolin-2-yl)piperidine-2,6-dione | 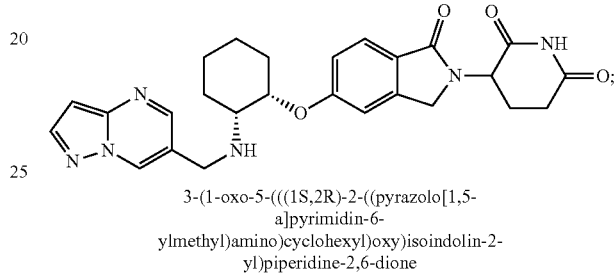

3-(1-oxo-5-(((1S,2R)-2-((pyrazolo[1,5-a]pyrimidin-6-ylmethyl)amino)cyclohexyl)oxy)isoindolin-2-yl)piperidine-2,6-dione |
| | 3-(1-oxo-5-(((1R,2R)-2-((pyrazolo[1,5-a]pyrimidin-6-ylmethyl)amino)cyclohexyl)oxy)isoindolin-2-yl)piperidine-2,6-dione |
| 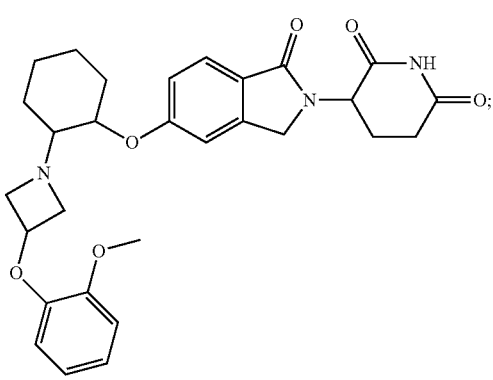

3-(5-((2-(3-(2-methoxyphenoxy)azetidin-1-yl)cyclohexyl)oxy)-1-oxoisoindolin-2-yl)piperidine-2,6-dione | 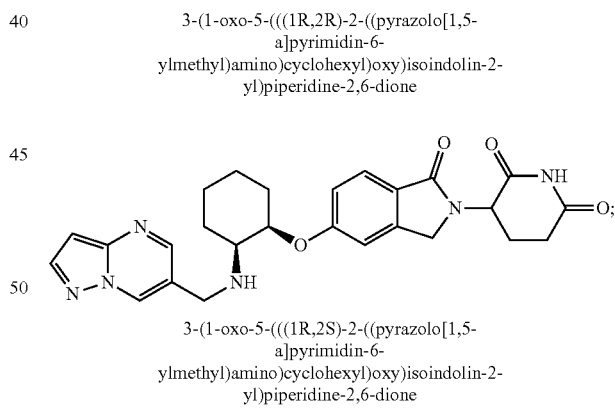

3-(1-oxo-5-(((1R,2S)-2-((pyrazolo[1,5-a]pyrimidin-6-ylmethyl)amino)cyclohexyl)oxy)isoindolin-2-yl)piperidine-2,6-dione |
| | 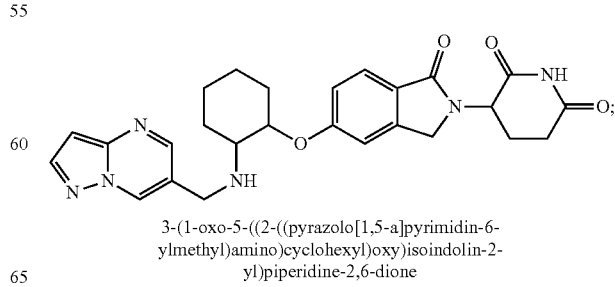

3-(1-oxo-5-((2-((pyrazolo[1,5-a]pyrimidin-6-ylmethyl)amino)cyclohexyl)oxy)isoindolin-2-yl)piperidine-2,6-dione |

| Compound Structure/Compound Name | Compound Structure/Compound Name |
|---|---|
| 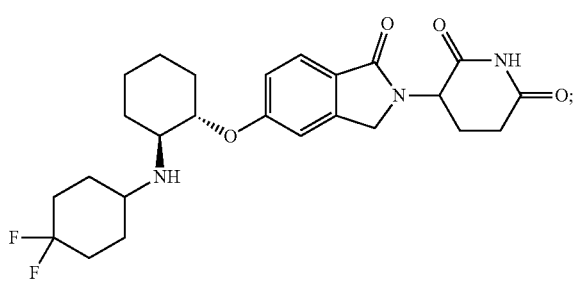<br>3-(5-(((1S,2S)-2-((4,4-difluorocyclohexyl)amino)cyclohexyl)oxy)-1-oxoisoindolin-2-yl)piperidine-2,6-dione | 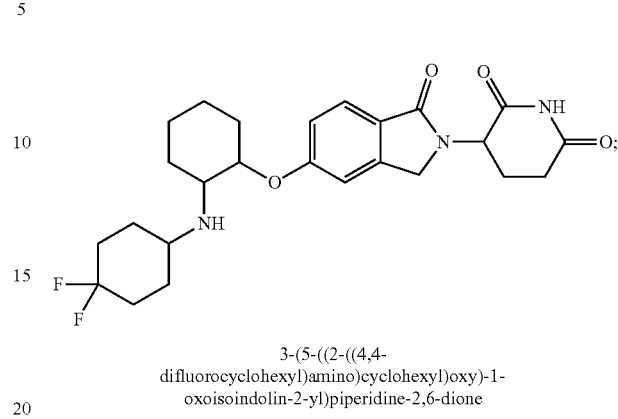<br>3-(5-((2-((4,4-difluorocyclohexyl)amino)cyclohexyl)oxy)-1-oxoisoindolin-2-yl)piperidine-2,6-dione |
| 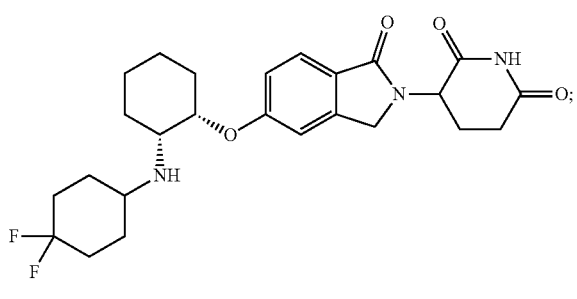<br>3-(5-(((1S,2R)-2-((4,4-difluorocyclohexyl)amino)cyclohexyl)oxy)-1-oxoisoindoline-2-yl)piperidine-2,6-dione | 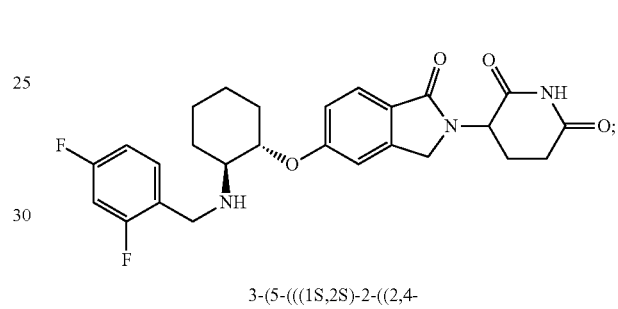<br>3-(5-(((1S,2S)-2-((2,4-difluorobenzyl)amino)cyclohexyl)oxy)-1-oxoisoindolin-2-yl)piperidine-2,6-dione |
| 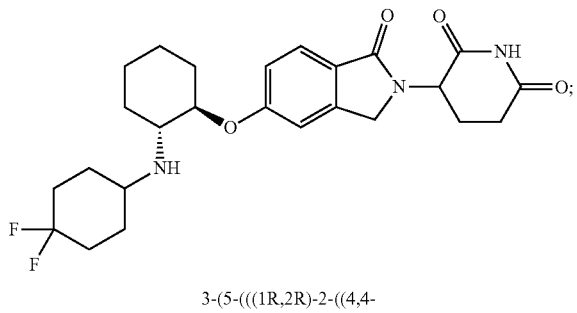<br>3-(5-(((1R,2R)-2-((4,4-difluorocyclohexyl)amino)cyclohexyl)oxy)-1-oxoisoindolin-2-yl)piperidine-2,6-dione | 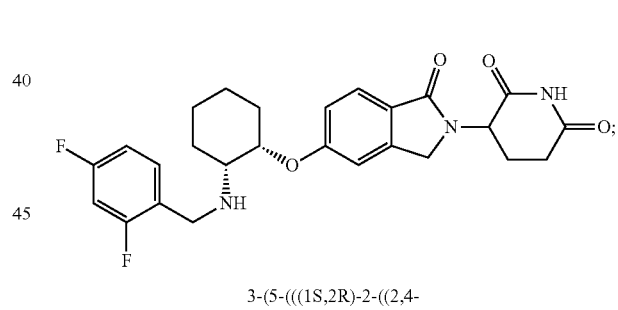<br>3-(5-(((1S,2R)-2-((2,4-difluorobenzyl)amino)cyclohexyl)oxy)-1-oxoisoindolin-2-yl)piperidine-2,6-dione |
| 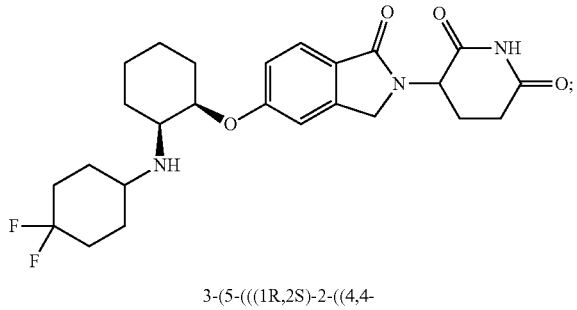<br>3-(5-(((1R,2S)-2-((4,4-difluorocyclohexyl)amino)cyclohexyl)oxy)-1-oxoisoindolidin-2-yl)piperidine-2,6-dione | 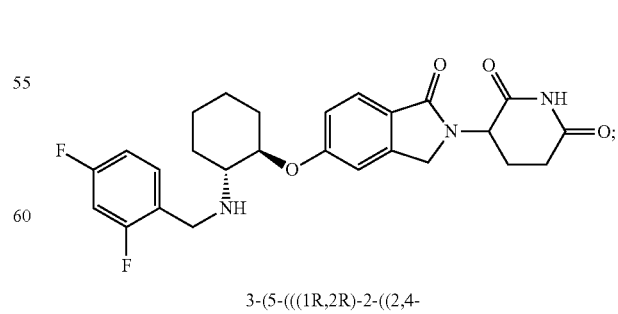<br>3-(5-(((1R,2R)-2-((2,4-difluorobenzyl)amino)cyclohexyl)oxy)-1-oxoisoindolin-2-yl)piperidine-2,6-dione |

| Compound Structure/Compound Name |
|---|
| 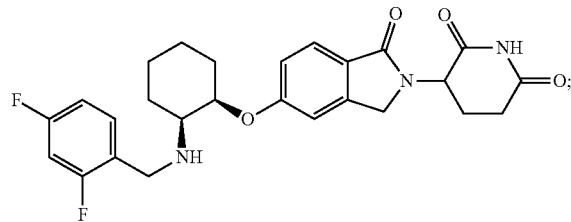 3-(5-(((1R,2S)-2-((2,4-difluorobenzyl)amino)cyclohexyl)oxy)-1-oxoisoindolin-2-yl)piperidine-2,6-dione |
| 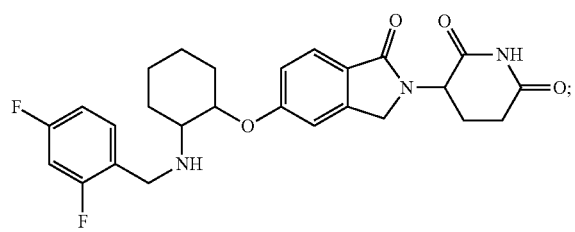 3-(5-((2-((2,4-difluorobenzyl)amino)cyclohexyl)oxy)-1-oxoisoindolin-2-yl)piperidine-2,6-dione |
| 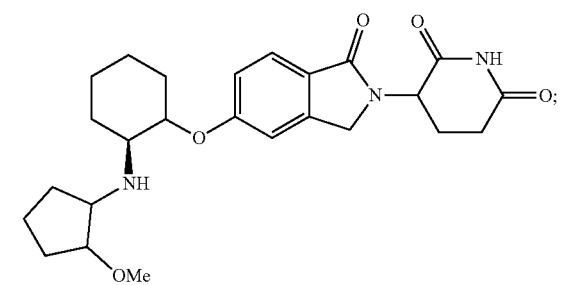 3-(5-(((1S,2S)-2-((2-methoxycyclopentyl)amino)cyclohexyl)oxy)-1-oxoisoindolin-2-yl)piperidine-2,6-dione |
| 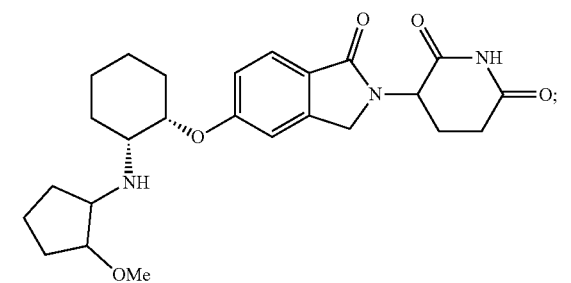 3-(5-(((1S,2R)-2-((2-methoxycyclopentyl)amino)cyclohexyl)oxy)-1-oxoisoindolin-2-yl)piperidine-2,6-dione |

| Compound Structure/Compound Name |
|---|
| 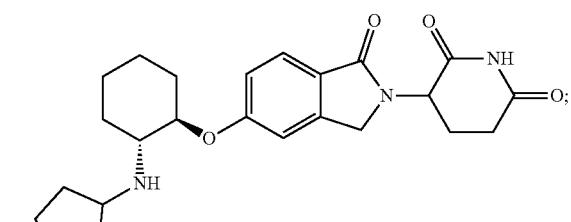 3-(5-(((1R,2R)-2-((2-methoxycyclopentyl)amino)cyclohexyl)oxy)-1-oxoisoindolin-2-yl)piperidine-2,6-dione |
| 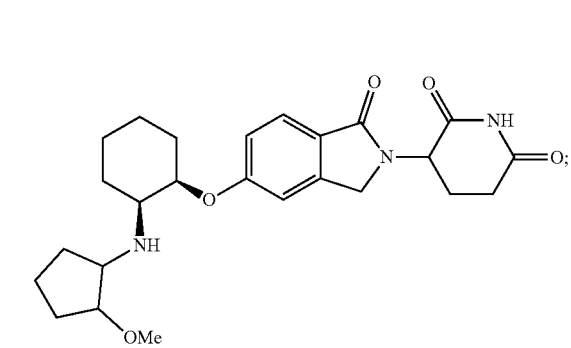 3-(5-(((1R,2S)-2-((2-methoxycyclopentyl)amino)cyclohexyl)oxy)-1-oxoisoindolin-2-yl)piperidine-2,6-dione |
| 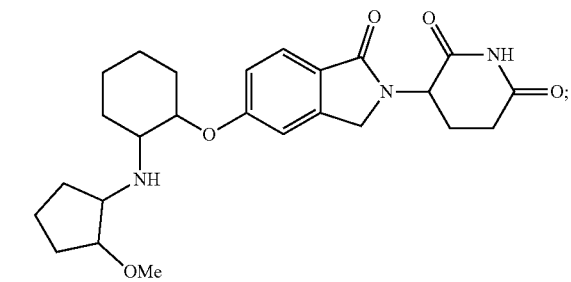 3-(5-((2-((2-methoxycyclopentyl)amino)cyclohexyl)oxy)-1-oxoisoindolin-2-yl)piperidine-2,6-dione |
| 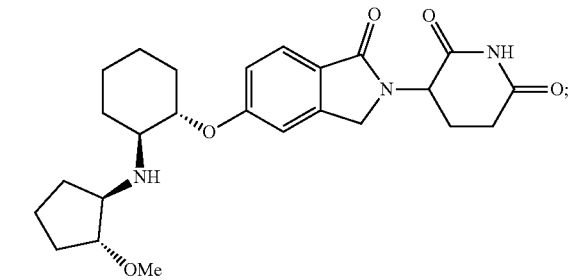 3-(5-(((1S,2S)-2-(((1R,2R)-2-methoxycyclopentyl)amino)cyclohexyl)oxy)-1-oxoisoindolin-2-yl)piperidine-2,6-dione |

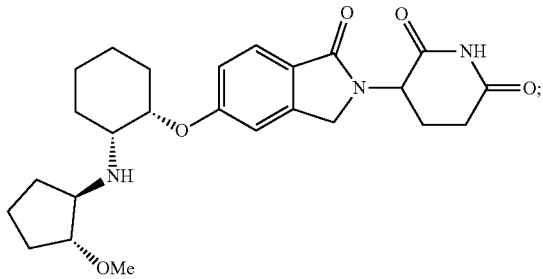

3-(5-(((1S,2R)-2-(((1R,2R)-2-methoxycyclopentyl)amino)cyclohexyl)oxy)-1-oxoisoindolin-2-yl)piperidine-2,6-dione

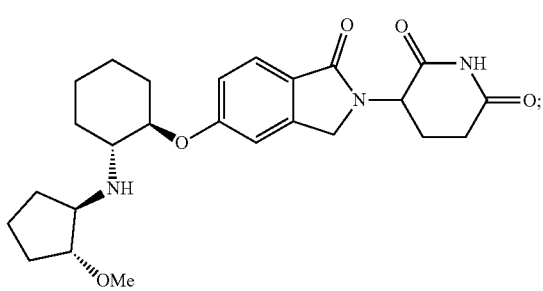

3-(5-(((1R,2R)-2-(((1R,2R)-2-methoxycyclopentyl)amino)cyclohexyl)oxy)-1-oxoisoindolin-2-yl)piperidine-2,6-dione

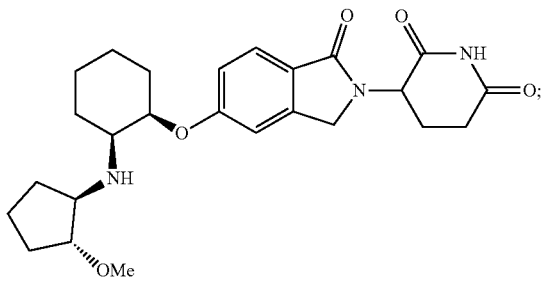

3-(5-(((1R,2S)-2-(((1R,2R)-2-methoxycyclopentyl)amino)cyclohexyl)oxy)-1-oxoisoindolin-2-yl)piperidine-2,6-dione

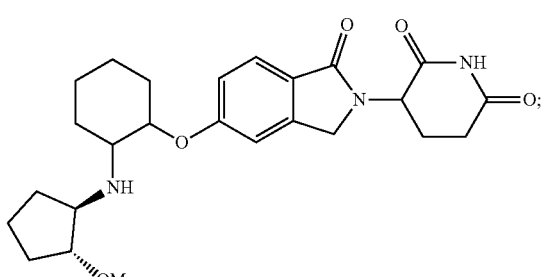

3-(5-((2-(((1R,2R)-2-methoxycyclopentyl)amino)cyclohexyl)oxy)-1-oxoisoindolin-2-yl)piperidine-2,6-dione

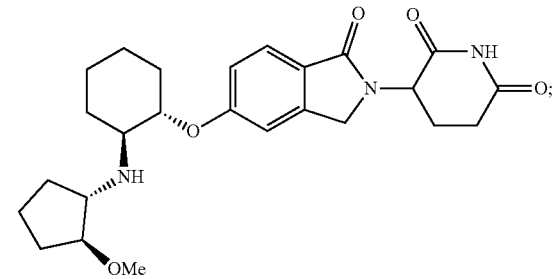

3-(5-((((1S,2S)-2-(((1S,2S)-2-methoxycyclopentyl)amino)cyclohexyl)oxy)-1-oxoisoindolin-2-yl)piperidine-2,6-dione

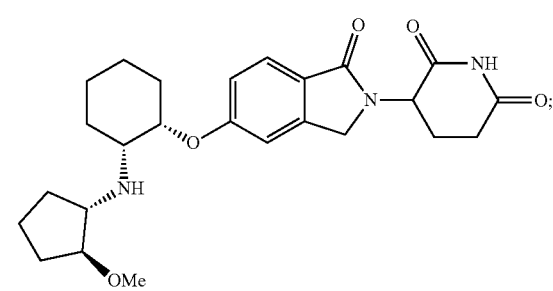

3-(5-((((1S,2R)-2-(((1S,2S)-2-methoxycyclopentyl)amino)cyclohexyl)oxy)-1-oxoisoindolin-2-yl)piperidine-2,6-dione

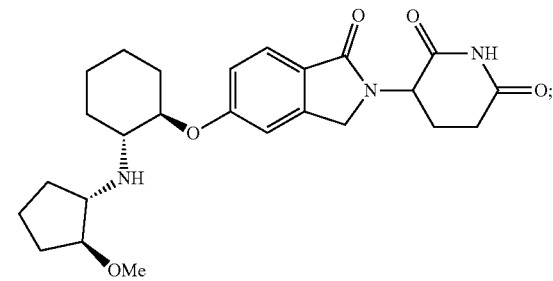

3-(5-(((1R,2R)-2-(((1S,2S)-2-methoxycyclopentyl)amino)cyclohexyl)oxy)-1-oxoisoindolin-2-yl)piperidine-2,6-dione

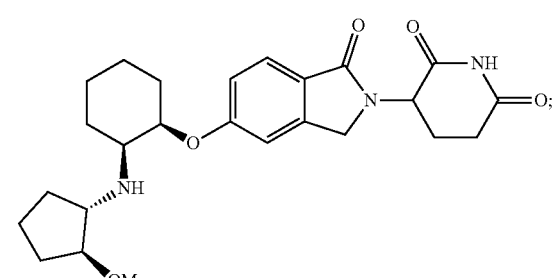

3-(5-(((1R,2S)-2-(((1S,2S)-2-methoxycyclopentyl)amino)cyclohexyl)oxy)-1-oxoisoindolin-2-yl)piperidine-2,6-dione

| Compound Structure/Compound Name |
|---|
| 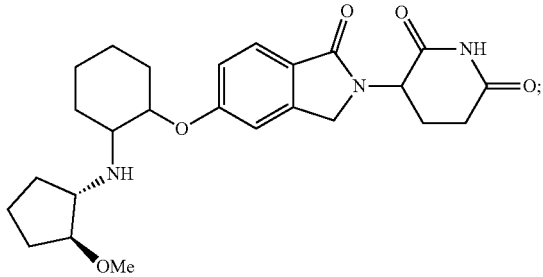<br>3-(5-((2-(((1S,2S)-2-methoxycyclopentyl)amino)cyclohexyl)oxy)-1-oxoisoindolin-2-yl)piperidine-2,6-dione |
| 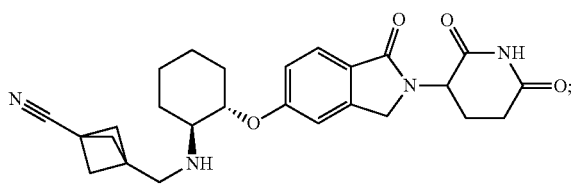<br>3-(((((1S,2S)-2-((2-(2,6-dioxopiperidin-3-yl)-1-oxoisoindolin-5-yl)oxy)cyclohexyl)amino)methyl)bicyclo[1.1.1]pentane-1-carbonitrile |
| 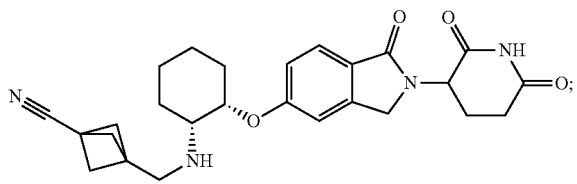<br>3-(((((1R,2S)-2-((2-(2,6-dioxopiperidin-3-yl)-1-oxoisoindolin-5-yl)oxy)cyclohexyl)amino)methyl)bicyclo[1.1.1]pentane-1-carbonitrile |
| 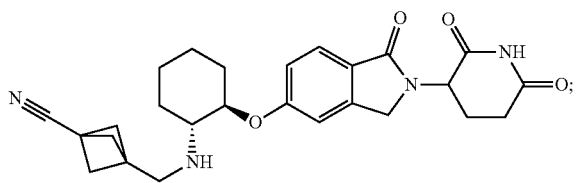<br>3-(((((1R,2S)-2-((2-(2,6-dioxopiperidin-3-yl)-1-oxoisoindolin-5-yl)oxy)cyclohexyl)amino)methyl)bicyclo[1.1.1]pentane-1-carbonitrile |
| 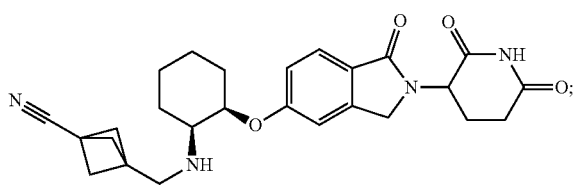<br>3-(((((1S,2R)-2-((2-(2,6-dioxopiperidin-3-yl)-1-oxoisoindolin-5-yl)oxy)cyclohexyl)amino)methyl)bicyclo[1.1.1]pentane-1-carbonitrile |

| Compound Structure/Compound Name |
|---|
| 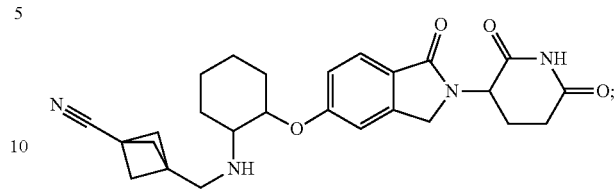<br>3-(((2-((2-(2,6-dioxopiperidin-3-yl)-1-oxoisoindolin-5-yl)oxy)cyclohexyl)amino)methyl)bicyclo[1.1.1]pentane-1-carbonitrile |
| 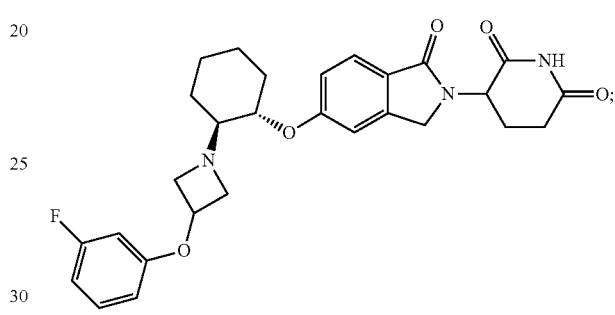<br>3-(5-(((1S,2S)-2-(3-(3-fluorophenoxy)azetidin-1-yl)cyclohexyl)oxy)-1-oxoisoindolin-2-yl)piperidine-2,6-dione |
| 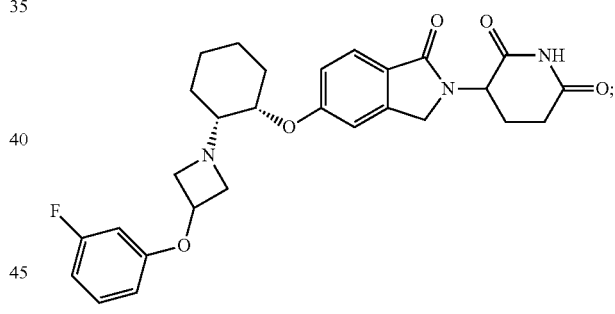<br>3-(5-(((1S,2R)-2-(3-(3-fluorophenoxy)azetidin-1-yl)cyclohexyl)oxy)-1-oxoisoindolin-2-yl)piperidine-2,6-dione |
| 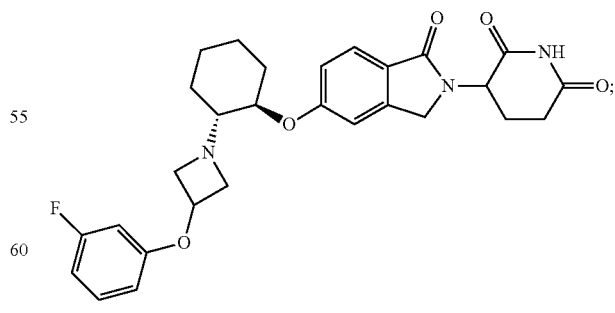<br>3-(5-(((1R,2R)-2-(3-(3-fluorophenoxy)azetidin-1-yl)cyclohexyl)oxy)-1-oxoisoindolin-2-yl)piperidine-2,6-dione; |

| Compound Structure/Compound Name | Compound Structure/Compound Name |
|---|---|
| 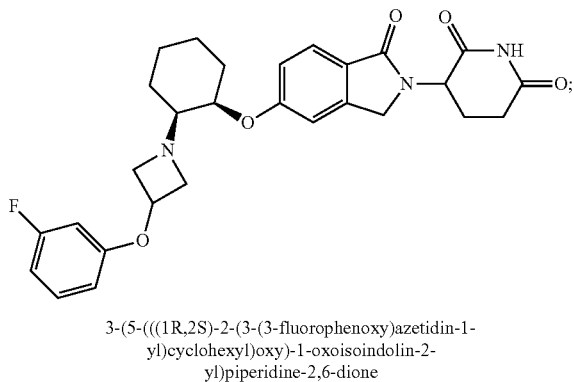<br>3-(5-(((1R,2S)-2-(3-(3-fluorophenoxy)azetidin-1-yl)cyclohexyl)oxy)-1-oxoisoindolin-2-yl)piperidine-2,6-dione | 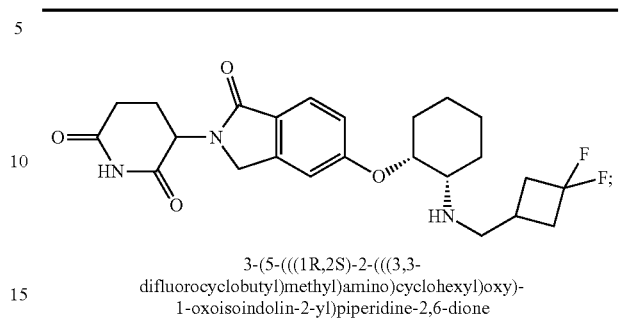<br>3-(5-(((1R,2S)-2-(((3,3-difluorocyclobutyl)methyl)amino)cyclohexyl)oxy)-1-oxoisoindolin-2-yl)piperidine-2,6-dione |
| 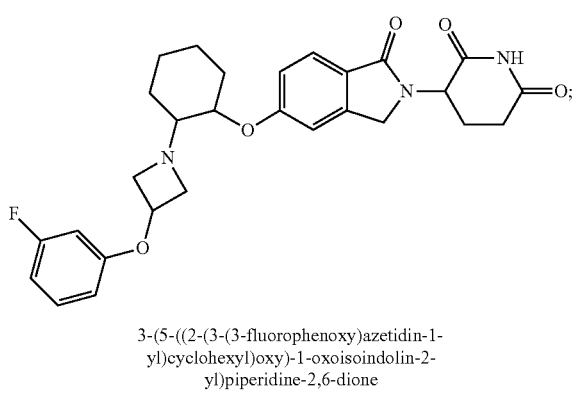<br>3-(5-((2-(3-(3-fluorophenoxy)azetidin-1-yl)cyclohexyl)oxy)-1-oxoisoindolin-2-yl)piperidine-2,6-dione | 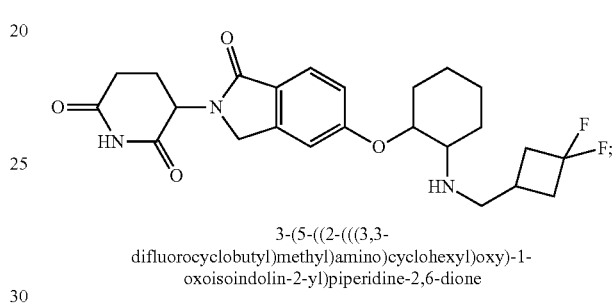<br>3-(5-((2-(((3,3-difluorocyclobutyl)methyl)amino)cyclohexyl)oxy)-1-oxoisoindolin-2-yl)piperidine-2,6-dione |
| 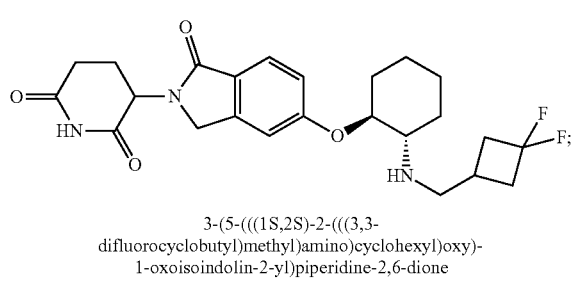<br>3-(5-(((1S,2S)-2-(((3,3-difluorocyclobutyl)methyl)amino)cyclohexyl)oxy)-1-oxoisoindolin-2-yl)piperidine-2,6-dione | 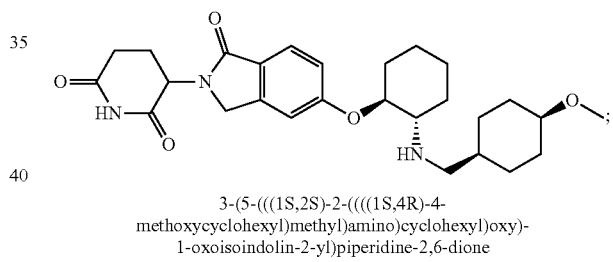<br>3-(5-(((1S,2S)-2-((((1S,4R)-4-methoxycyclohexyl)methyl)amino)cyclohexyl)oxy)-1-oxoisoindolin-2-yl)piperidine-2,6-dione |
| 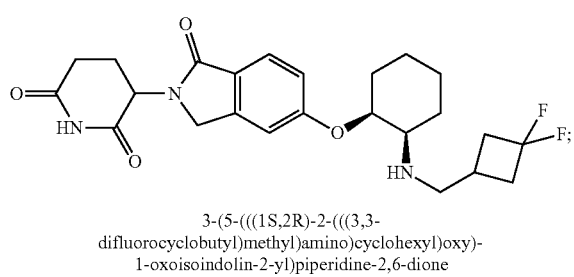<br>3-(5-(((1S,2R)-2-(((3,3-difluorocyclobutyl)methyl)amino)cyclohexyl)oxy)-1-oxoisoindolin-2-yl)piperidine-2,6-dione | 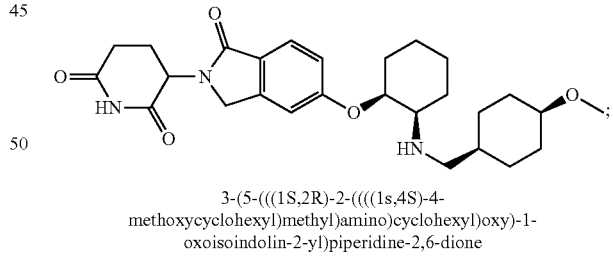<br>3-(5-(((1S,2R)-2-((((1s,4S)-4-methoxycyclohexyl)methyl)amino)cyclohexyl)oxy)-1-oxoisoindolin-2-yl)piperidine-2,6-dione |
| 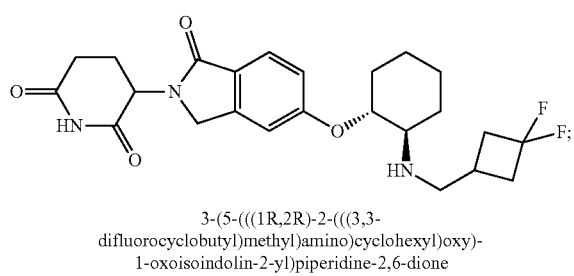<br>3-(5-(((1R,2R)-2-(((3,3-difluorocyclobutyl)methyl)amino)cyclohexyl)oxy)-1-oxoisoindolin-2-yl)piperidine-2,6-dione | 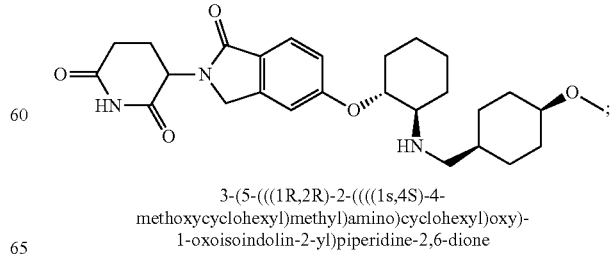<br>3-(5-(((1R,2R)-2-((((1s,4S)-4-methoxycyclohexyl)methyl)amino)cyclohexyl)oxy)-1-oxoisoindolin-2-yl)piperidine-2,6-dione |

| Compound Structure/Compound Name |
|---|
| 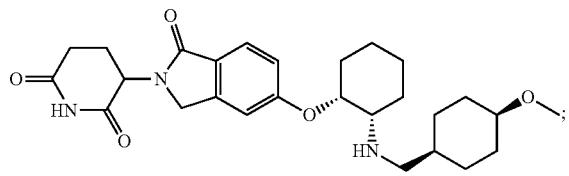<br>3-(5-(((1R,2S)-2-((((1s,4R)-4-methoxycyclohexyl)methyl)amino)cyclohexyl)oxy)-1-oxoisoindolin-2-yl)piperidine-2,6-dione |
| 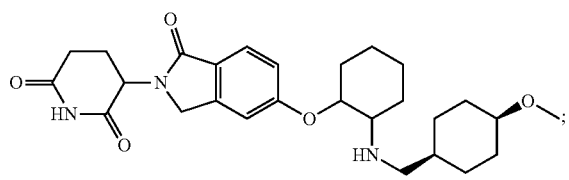<br>3-(5-((2-(((((1s,4s)-4-methoxycyclohexyl)methyl)amino)cyclohexyl)oxy)-1-oxoisoindolin-2-yl)piperidine-2,6-dione |
| 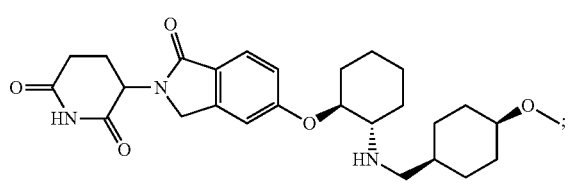<br>3-(5-(((1S,2S)-2-(((4-methoxycyclohexyl)methyl)amino)cyclohexyl)oxy)-1-oxoisoindolin-2-yl)piperidine-2,6-dione |
| 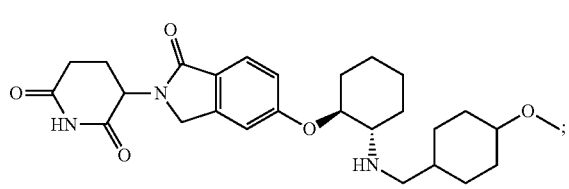<br>3-(5-(((1S,2S)-2-(((cis-4-methoxycyclohexyl)methyl)amino)cyclohexyl)oxy)-1-oxoisoindolin-2-yl)piperidine-2,6-dione |
| 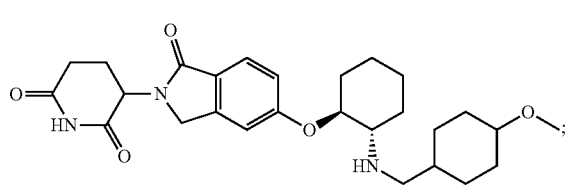<br>3-(5-(((1S,2S)-2-(((trans-4-methoxycyclohexyl)methyl)amino)cyclohexyl)oxy)-1-oxoisoindolin-2-yl)piperidine-2,6-dione |
| 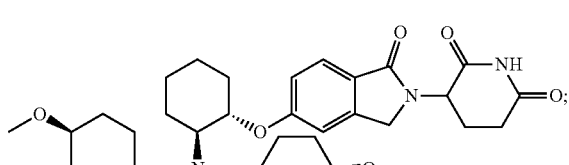<br>3-(5-(((1S,2S)-2-(bis(((1R,4S)-4-methoxycyclohexyl)methyl)amino)cyclohexyl)oxy)-1-oxoisoindolin-2-yl)piperidine-2,6-dione |
| 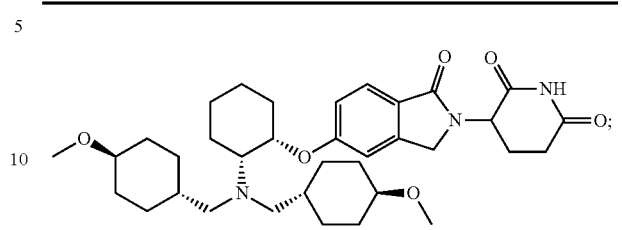<br>3-(5-(((1S,2R)-2-(bis(((1r,4R)-4-methoxycyclohexyl)methyl)amino)cyclohexyl)oxy)-1-oxoisoindolin-2-yl)piperidine-2,6-dione |
| 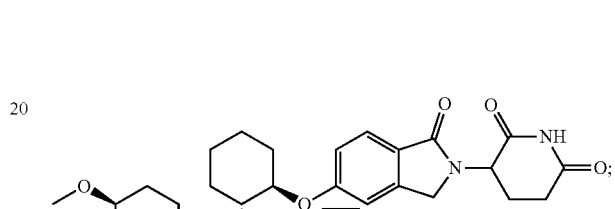<br>3-(5-(((1R,2R)-2-(bis(((1r,4R)-4-methoxycyclohexyl)methyl)amino)cyclohexyl)oxy)-1-oxoisoindolin-2-yl)piperidine-2,6-dione |
| 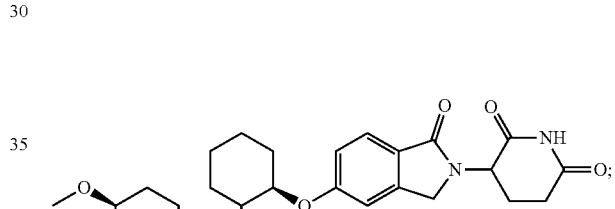<br>3-(5-(((1R,2S)-2-(bis(((1r,4S)-4-methoxycyclohexyl)methyl)amino)cyclohexyl)oxy)-1-oxoisoindolin-2-yl)piperidine-2,6-dione |
| 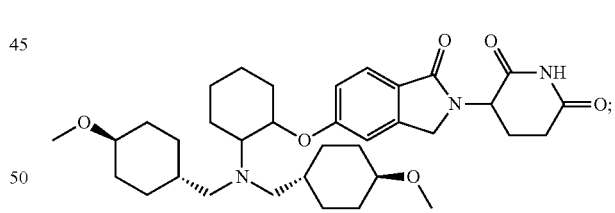<br>3-(5-((2-(bis(((1r,4R)-4-methoxycyclohexyl)methyl)amino)cyclohexyl)oxy)-1-oxoisoindolin-2-yl)piperidine-2,6-dione |
| 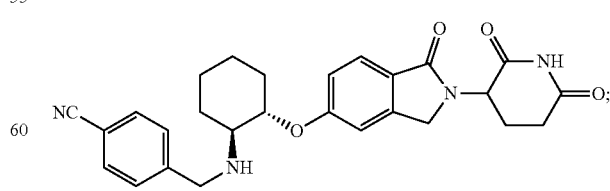<br>4-((((1S,2S)-2-((2-(2,6-dioxopiperidin-3-yl)-1-oxoisoindolin-5-yl)oxy)cyclohexyl)amino)methyl)benzonitrile |

| Compound Structure/Compound Name | Compound Structure/Compound Name |
|---|---|
| 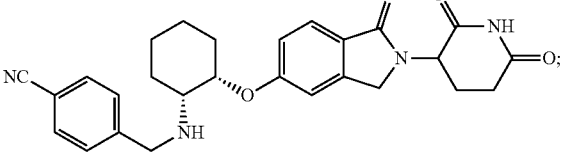<br>4-((((1R,2S)-2-((2-(2,6-dioxopiperidin-3-yl)-1-oxoisoindolin-5-yl)oxy)cyclohexyl)amino)methyl)benzonitrile | 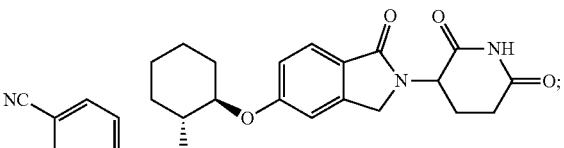<br>4-((((1R,2R)-2-((2-(2,6-dioxopiperidin-3-yl)-1-oxoisoindolin-5-yl)oxy)cyclohexyl)(methyl)amino)methyl)benzonitrile |
| 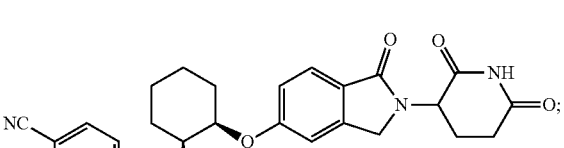<br>4-((((1R,2R)-2-((2-(2,6-dioxopiperidin-3-yl)-1-oxoisoindolin-5-yl)oxy)cyclohexyl)amino)methyl)benzonitrile | 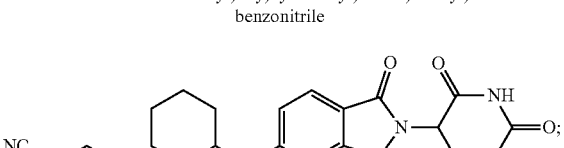<br>4-((((1S,2R)-2-((2-(2,6-dioxopiperidin-3-yl)-1-oxoisoindolin-5-yl)oxy)cyclohexyl)(methyl)amino)methyl)benzonitrile |
| 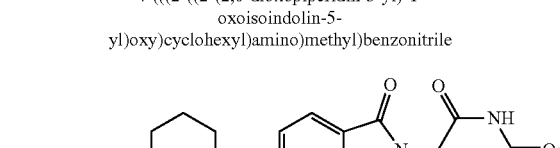<br>4-((((1S,2R)-2-((2-(2,6-dioxopiperidin-3-yl)-1-oxoisoindolin-5-yl)oxy)cyclohexyl)amino)methyl)benzonitrile | 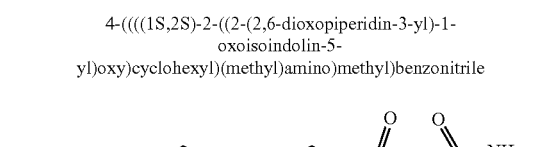<br>4-(((2-((2-(2,6-dioxopiperidin-3-yl)-1-oxoisoindolin-5-yl)oxy)cyclohexyl)(methyl)amino)methyl)benzonitrile |
| 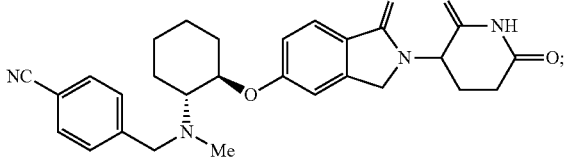<br>4-(((2-((2-(2,6-dioxopiperidin-3-yl)-1-oxoisoindolin-5-yl)oxy)cyclohexyl)amino)methyl)benzonitrile | 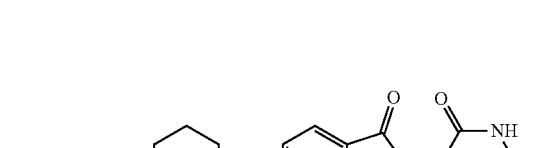<br>3-(5-(((1S,2S)-2-(((3-fluorobicyclo[1.1.1]pentan-1-yl)methyl)amino)cyclohexyl)oxy)-1-oxoisoindolin-2-yl)piperidine-2,6-dione |
| 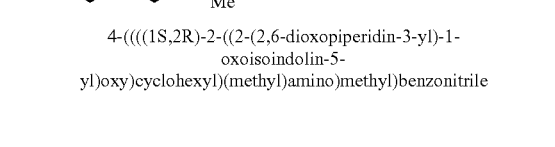<br>4-((((1S,2S)-2-((2-(2,6-dioxopiperidin-3-yl)-1-oxoisoindolin-5-yl)oxy)cyclohexyl)(methyl)amino)methyl)benzonitrile | 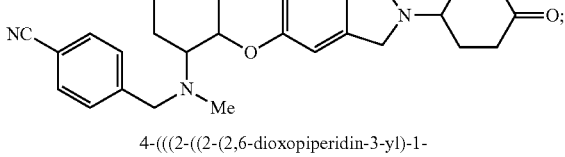<br>3-(5-(((1S,2R)-2-(((3-fluorobicyclo[1.1.1]pentan-1-yl)methyl)amino)cyclohexyl)oxy)-1-oxoisoindolin-2-yl)piperidine-2,6-dione |
| 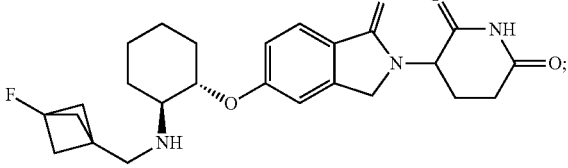<br>4-((((1R,2S)-2-((2-(2,6-dioxopiperidin-3-yl)-1-oxoisoindolin-5-yl)oxy)cyclohexyl)(methyl)amino)methyl)benzonitrile | |

| Compound Structure/Compound Name |
|---|
| 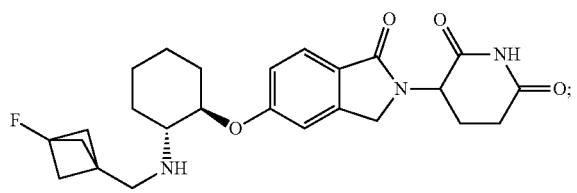<br>3-(5-(((1R,2R)-2-(((3-fluorobicyclo[1.1.1]pentan-1-yl)methyl)amino)cyclohexyl)oxy)-1-oxoisoindolin-2-yl)piperidine-2,6-dione |
| 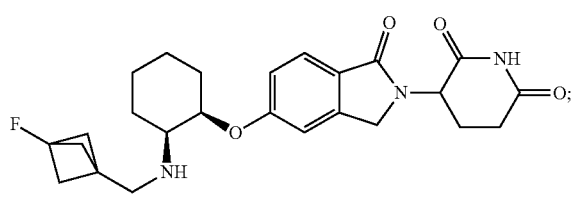<br>3-(5-(((1R,2S)-2-(((3-fluorobicyclo[1.1.1]pentan-1-yl)methyl)amino)cyclohexyl)oxy)-1-oxoisoindolin-2-yl)piperidine-2,6-dione |
| 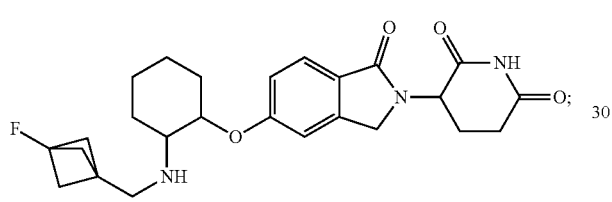<br>3-(5-((2-(((3-fluorobicyclo[1.1.1]pentan-1-yl)methyl)amino)cyclohexyl)oxy)-1-oxoisoindolin-2-yl)piperidine-2,6-dione |
| 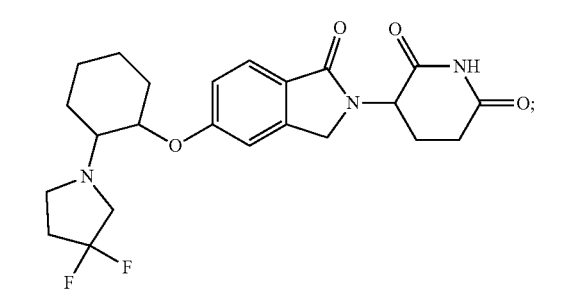<br>3-(5-((2-(3,3-difluoropyrrolidin-1-yl)cyclohexyl)oxy)-1-oxoisoindolin-2-yl)piperidine-2,6-dione |
| 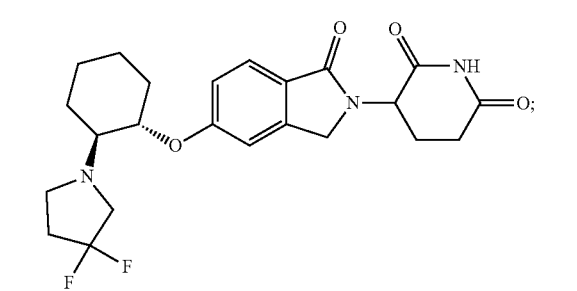<br>3-(5-(((1S,2S)-2-(3,3-difluoropyrrolidin-1-yl)cyclohexyl)oxy)-1-oxoisoindolin-2-yl)piperidine-2,6-dione |

| Compound Structure/Compound Name |
|---|
| 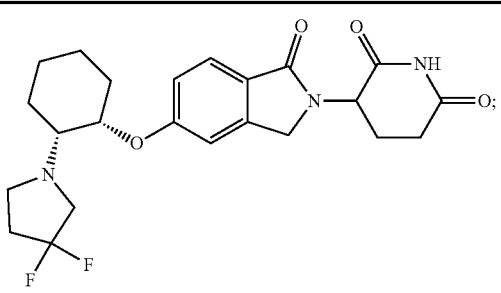<br>3-(5-(((1S,2R)-2-(3,3-difluoropyrrolidin-1-yl)cyclohexyl)oxy)-1-oxoisoindolin-2-yl)piperidine-2,6-dione |
| 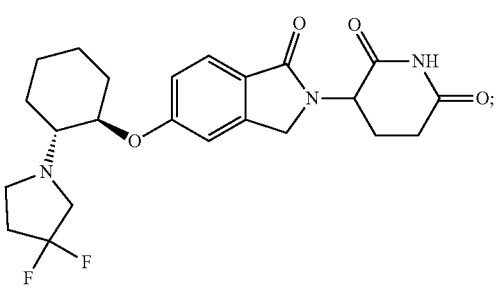<br>3-(5-(((1R,2R)-2-(3,3-difluoropyrrolidin-1-yl)cyclohexyl)oxy)-1-oxoisoindolin-2-yl)piperidine-2,6-dione |
| 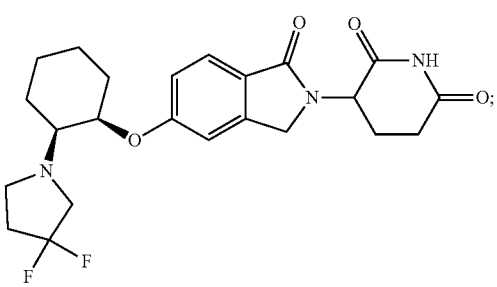<br>3-(5-(((1R,2S)-2-(3,3-difluoropyrrolidin-1-yl)cyclohexyl)oxy)-1-oxoisoindolin-2-yl)piperidine-2,6-dione |
| 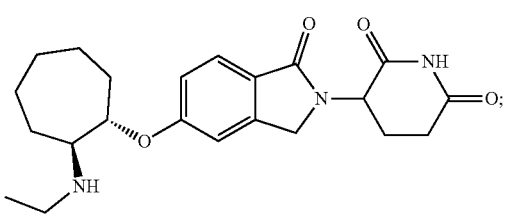<br>3-(5-(((1S,2S)-2-(ethylamino)cycloheptyl)oxy)-1-oxoisoindolin-2-yl)piperidine-2,6-dione |

| Compound Structure/Compound Name | Compound Structure/Compound Name |
|---|---|
| 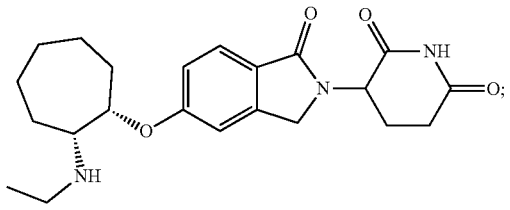 3-(5-(((1S,2R)-2-(ethylamino)cycloheptyl)oxy)-1-oxoisoindolin-2-yl)piperidine-2,6-dione | 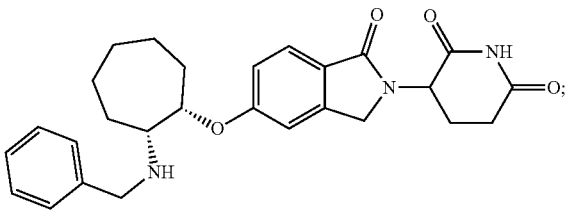 3-(5-(((1S,2R)-2-(benzylamino)cycloheptyl)oxy)-1-oxoisoindolin-2-yl)piperidine-2,6-dione |
| 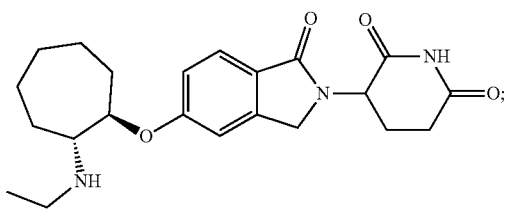 3-(5-(((1R,2R)-2-(ethylamino)cycloheptyl)oxy)-1-oxoisoindolin-2-yl)piperidine-2,6-dione | 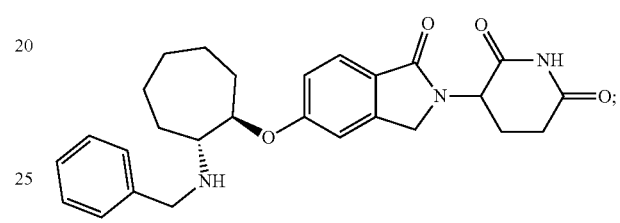 3-(5-(((1R,2R)-2-(benzylamino)cycloheptyl)oxy)-1-oxoisoindolin-2-yl)piperidine-2,6-dione |
| 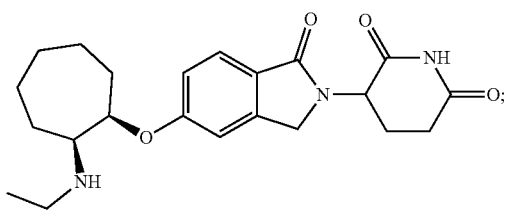 3-(5-(((1R,2S)-2-(ethylamino)cycloheptyl)oxy)-1-oxoisoindolin-2-yl)piperidine-2,6-dione | 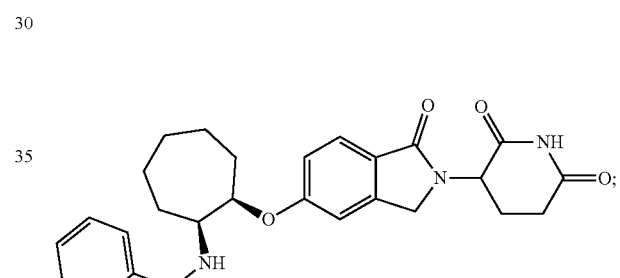 3-(5-(((1R,2S)-2-(benzylamino)cycloheptyl)oxy)-1-oxoisoindolin-2-yl)piperidine-2,6-dione |
| 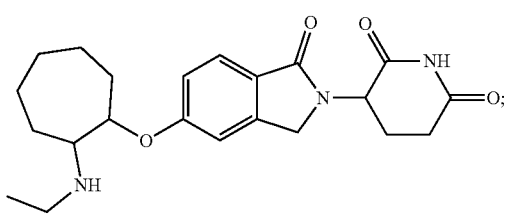 3-(5-((2-(ethylamino)cycloheptyl)oxy)-1-oxoisoindolin-2-yl)piperidine-2,6-dione | 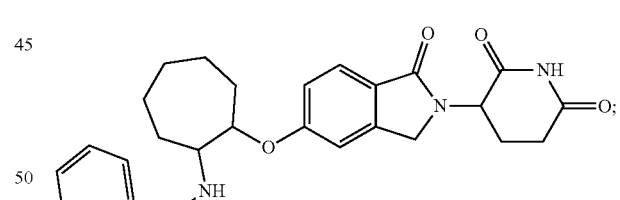 3-(5-((2-(benzylamino)cycloheptyl)oxy)-1-oxoisoindolin-2-yl)piperidine-2,6-dione |
| 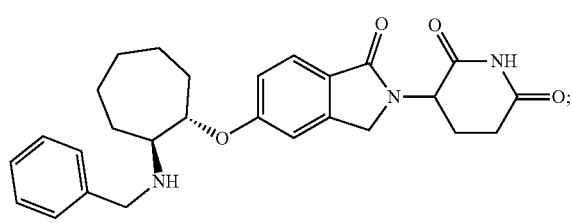 3-(5-(((1S,2S)-2-(benzylamino)cycloheptyl)oxy)-1-oxoisoindolin-2-yl)piperidine-2,6-dione | 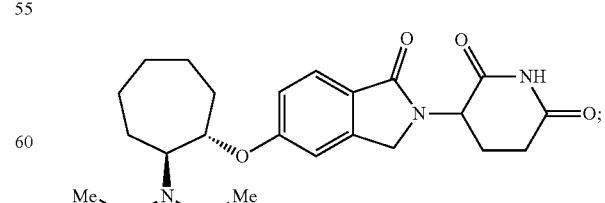 3-(5-(((1S,2S)-2-(diethylamino)cycloheptyl)oxy)-1-oxoisoindolin-2-yl)piperidine-2,6-dione |

| Compound Structure/Compound Name |
|---|
| 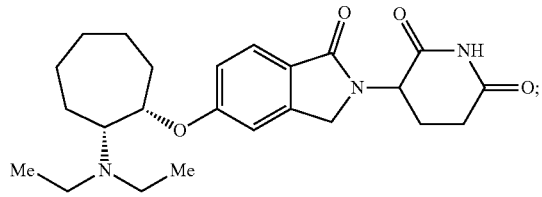<br>3-(5-(((1S,2R)-2-(diethylamino)cycloheptyl)oxy)-1-oxoisoindolin-2-yl)piperidine-2,6-dione |
| 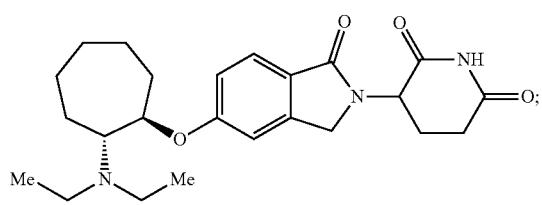<br>3-(5-(((1R,2R)-2-(diethylamino)cycloheptyl)oxy)-1-oxoisoindolin-2-yl)piperidine-2,6-dione |
| 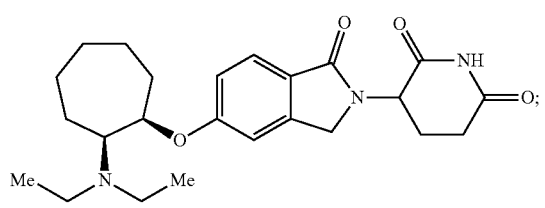<br>3-(5-(((1R,2S)-2-(diethylamino)cycloheptyl)oxy)-1-oxoisoindolin-2-yl)piperidine-2,6-dione |
| 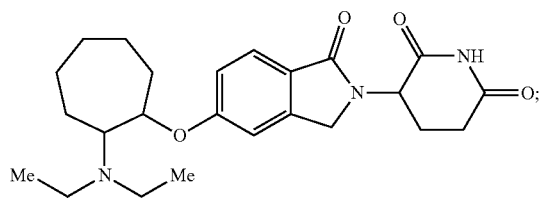<br>3-(5-((2-(diethylamino)cycloheptyl)oxy)-1-oxoisoindolin-2-yl)piperidine-2,6-dione |
| 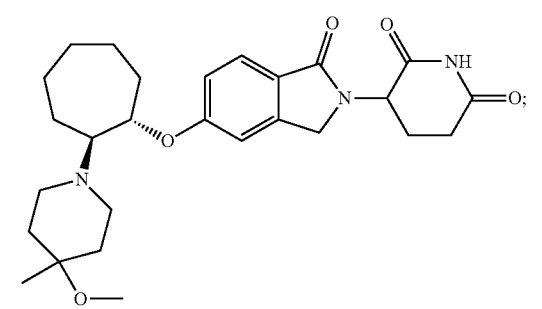<br>3-(5-(((1S,2S)-2-(4-methoxy-4-methylpiperidin-1-yl)cycloheptyl)oxy)-1-oxoisoindolin-2-yl)piperidine-2,6-dione |

| Compound Structure/Compound Name |
|---|
| 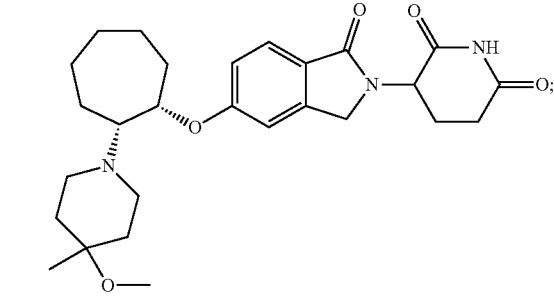<br>3-(5-(((1S,2R)-2-(4-methoxy-4-methylpiperidin-1-yl)cycloheptyl)oxy)-1-oxoisoindolin-2-yl)piperidine-2,6-dione |
| 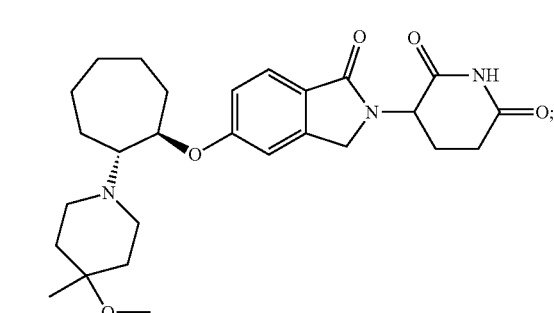<br>3-(5-(((1R,2R)-2-(4-methoxy-4-methylpiperidin-1-yl)cycloheptyl)oxy)-1-oxoisoindolin-2-yl)piperidine-2,6-dione |
| 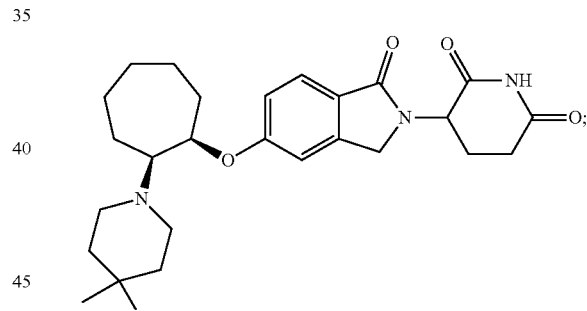<br>3-(5-(((1R,2S)-2-(4-methoxy-4-methylpiperidin-1-yl)cycloheptyl)oxy)-1-oxoisoindolin-2-yl)piperidine-2,6-dione |
| 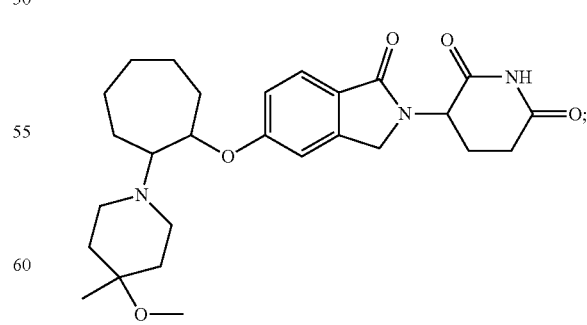<br>3-(5-((2-(4-methoxy-4-methylpiperidin-1-yl)cycloheptyl)oxy)-1-oxoisoindolin-2-yl)piperidine-2,6-dione |

| Compound Structure/Compound Name | Compound Structure/Compound Name |
|---|---|
| 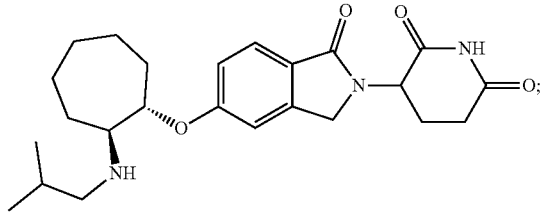<br>3-(5-(((1S,2S)-2-(isobutylamino)cycloheptyl)oxy)-1-oxoisoindolin-2-yl)piperidine-2,6-dione | 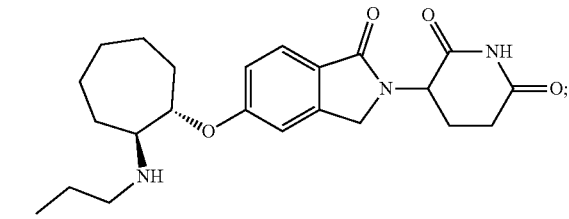<br>3-(1-oxo-5-(((1S,2S)-2-(propylamino)cycloheptyl)oxy)isoindolin-2-yl)piperidine-2,6-dione |
| 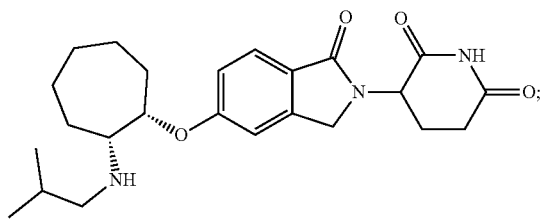<br>3-(5-(((1S,2R)-2-(isobutylamino)cycloheptyl)oxy)-1-oxoisoindolin-2-yl)piperidine-2,6-dione | 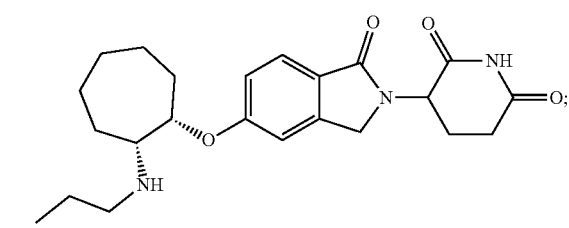<br>3-(1-oxo-5-(((1S,2R)-2-(propylamino)cycloheptyl)oxy)isoindolin-2-yl)piperidine-2,6-dione |
| 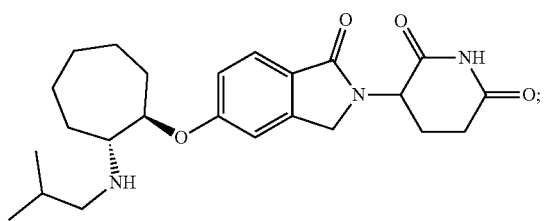<br>3-(5-(((1R,2R)-2-(isobutylamino)cycloheptyl)oxy)-1-oxoisoindolin-2-yl)piperidine-2,6-dione | 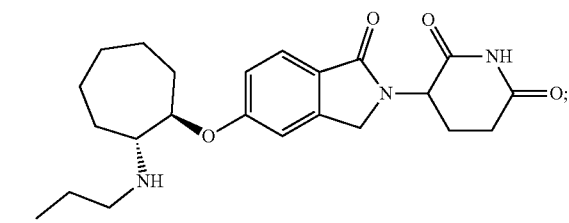<br>3-(1-oxo-5-(((1R,2R)-2-(propylamino)cycloheptyl)oxy)isoindolin-2-yl)piperidine-2,6-dione |
| 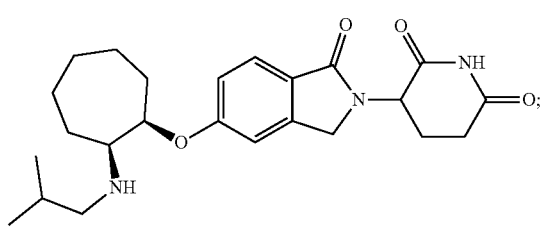<br>3-(5-(((1R,2S)-2-(isobutylamino)cycloheptyl)oxy)-1-oxoisoindolin-2-yl)piperidine-2,6-dione | 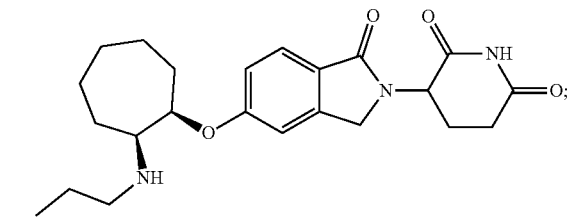<br>3-(1-oxo-5-(((1R,2S)-2-(propylamino)cycloheptyl)oxy)isoindolin-2-yl)piperidine-2,6-dione |
| 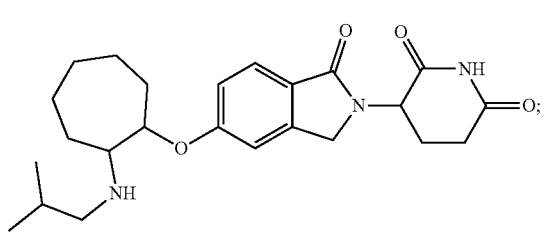<br>3-(5-((2-(isobutylamino)cycloheptyl)oxy)-1-oxoisoindolin-2-yl)piperidine-2,6-dione | 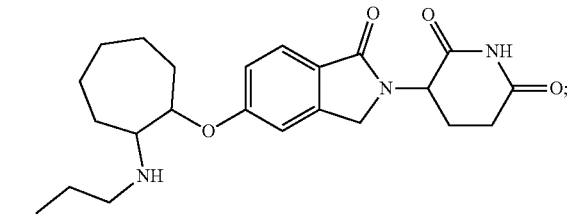<br>3-(1-oxo-5-((2-(propylamino)cycloheptyl)oxy)isoindolin-2-yl)piperidine-2,6-dione |

| Compound Structure/Compound Name |
|---|
| 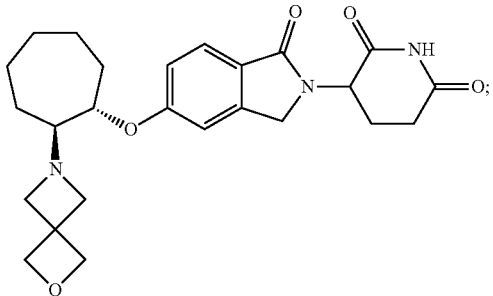<br>3-(5-((((1S,2S)-2-(2-oxa-6-azaspiro[3.3]heptan-6-yl)cycloheptyl)oxy)-1-oxoisoindolin-2-yl)piperidine-2,6-dione |
| 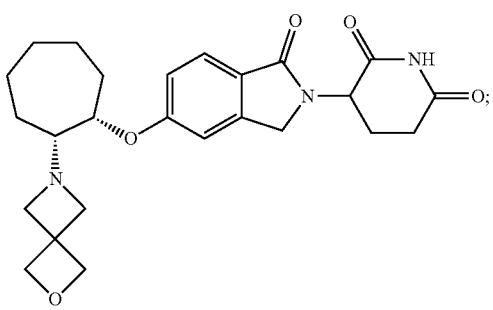<br>3-(5-((((1S,2R)-2-(2-oxa-6-azaspiro[3.3]heptan-6-yl)cycloheptyl)oxy)-1-oxoisoindolin-2-yl)piperidine-2,6-dione |
| 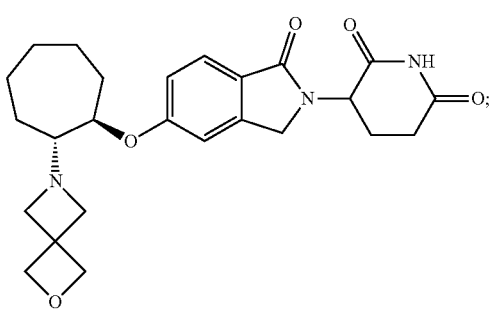<br>3-(5-((((1R,2R)-2-(2-oxa-6-azaspiro[3.3]heptan-6-yl)cycloheptyl)oxy)-1-oxoisoindolin-2-yl)piperidine-2,6-dione |
| 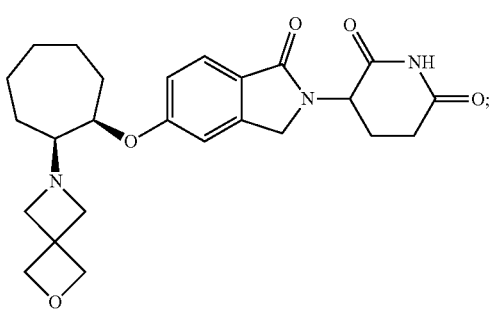<br>3-(5-((((1R,2S)-2-(2-oxa-6-azaspiro[3.3]heptan-6-yl)cycloheptyl)oxy)-1-oxoisoindolin-2-yl)piperidine-2,6-dione |

| Compound Structure/Compound Name |
|---|
| 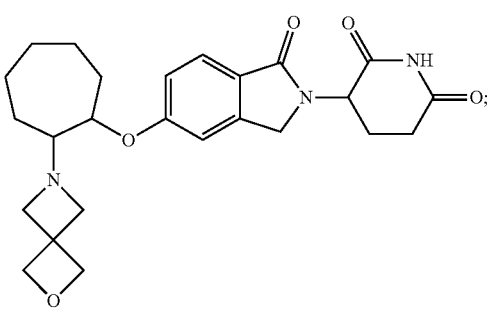<br>3-(5-((2-(2-oxa-6-azaspiro[3.3]heptan-6-yl)cycloheptyl)oxy)-1-oxoisoindolin-2-yl)piperidine-2,6-dione |
| 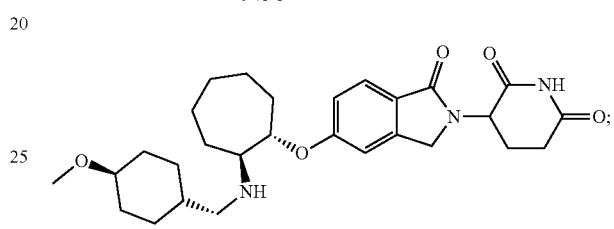<br>3-(5-((((1S,2S)-2-(((((1R,4S)-4-methoxycyclohexyl)methyl)amino)cycloheptyl)oxy)-1-oxoisoindolin-2-yl)piperidine-2,6-dione |
| 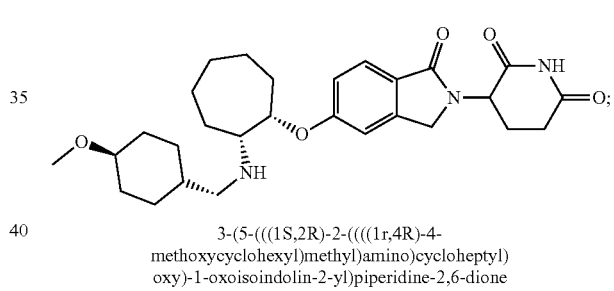<br>3-(5-((((1S,2R)-2-(((((1r,4R)-4-methoxycyclohexyl)methyl)amino)cycloheptyl)oxy)-1-oxoisoindolin-2-yl)piperidine-2,6-dione |
| 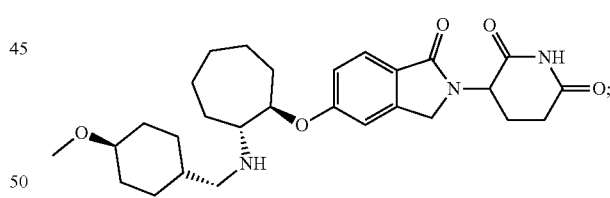<br>3-(5-((((1R,2R)-2-(((((1r,4R)-4-methoxycyclohexyl)methyl)amino)cycloheptyl)oxy)-1-oxoisoindolin-2-yl)piperidine-2,6-dione |
| 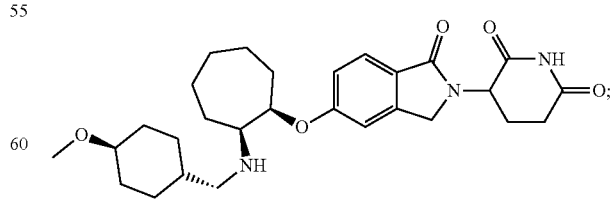<br>3-(5-((((1R,2S)-2-(((((1r,4S)-4-methoxycyclohexyl)methyl)amino)cycloheptyl)oxy)-1-oxoisoindolin-2-yl)piperidine-2,6-dione |

| Compound Structure/Compound Name |
|---|
| 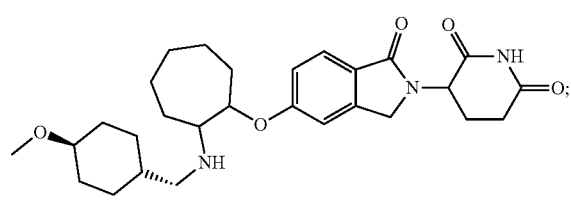 3-(5-((2-((((1r,4r)-4-methoxycyclohexyl)methyl)amino)cycloheptyl)oxy)-1-oxoisoindolin-2-yl)piperidine-2,6-dione |
| 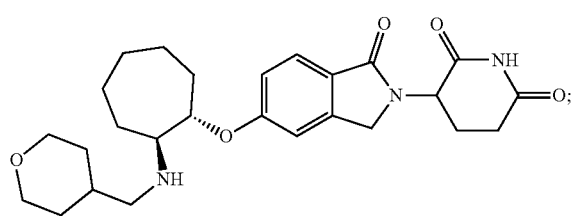 3-(1-oxo-5-(((1S,2S)-2-(((tetrahydro-2H-pyran-4-yl)methyl)amino)cycloheptyl)oxy)isoindolin-2-yl)piperidine-2,6-dione |
| 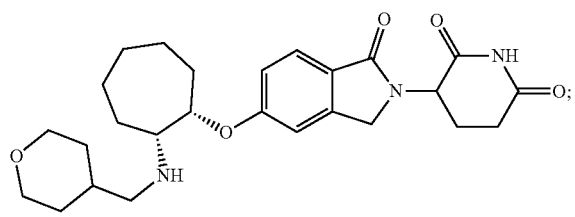 3-(1-oxo-5-(((1S,2R)-2-(((tetrahydro-2H-pyran-4-yl)methyl)amino)cycloheptyl)oxy)isoindolin-2-yl)piperidine-2,6-dione |
| 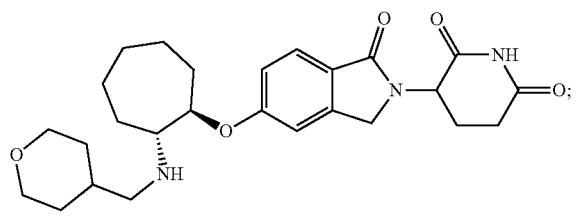 3-(1-oxo-5-(((1R,2R)-2-(((tetrahydro-2H-pyran-4-yl)methyl)amino)cycloheptyl)oxy)isoindolin-2-yl)piperidine-2,6-dione |
| 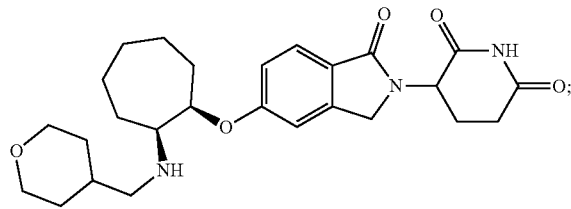 3-(1-oxo-5-(((1R,2S)-2-(((tetrahydro-2H-pyran-4-yl)methyl)amino)cycloheptyl)oxy)isoindolin-2-yl)piperidine-2,6-dione |

| Compound Structure/Compound Name |
|---|
| 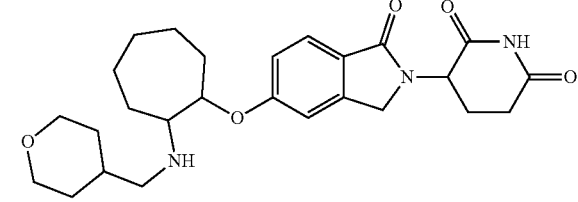 3-(1-oxo-5-((2-(((tetrahydro-2H-pyran-4-yl)methyl)amino)cycloheptyl)oxy)isoindolin-2-yl)piperidine-2,6-dione |
| 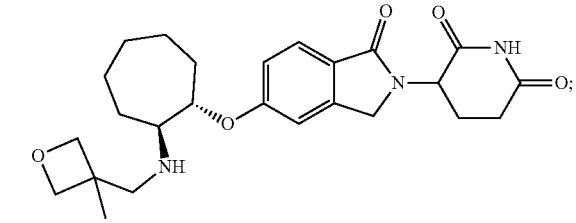 3-(5-(((1S,2S)-2-(((3-methyloxetan-3-yl)methyl)amino)cycloheptyl)oxy)-1-oxoisoindolin-2-yl)piperidine-2,6-dione |
| 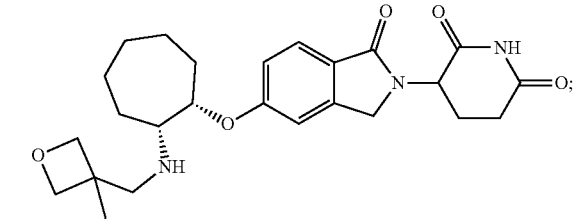 3-(5-(((1S,2R)-2-(((3-methyloxetan-3-yl)methyl)amino)cycloheptyl)oxy)-1-oxoisoindolin-2-yl)piperidine-2,6-dione |
| 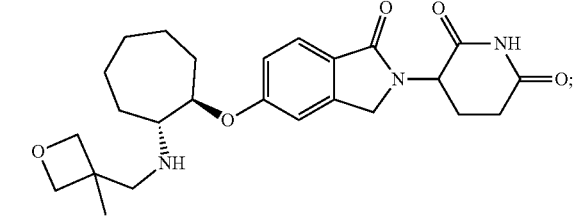 3-(5-(((1R,2R)-2-(((3-methyloxetan-3-yl)methyl)amino)cycloheptyl)oxy)-1-oxoisoindolin-2-yl)piperidine-2,6-dione |
| 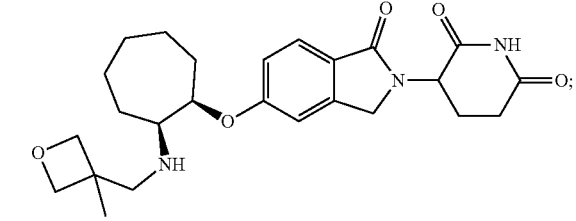 3-(5-(((1R,2S)-2-(((3-methyloxetan-3-yl)methyl)amino)cycloheptyl)oxy)-1-oxoisoindolin-2-yl)piperidine-2,6-dione |

| Compound Structure/Compound Name | Compound Structure/Compound Name |
|---|---|
| <br>3-(5-((2-(((3-methyloxetan-3-yl)methyl)amino)cycloheptyl)oxy)-1-oxoisoindolin-2-yl)piperidine-2,6-dione | 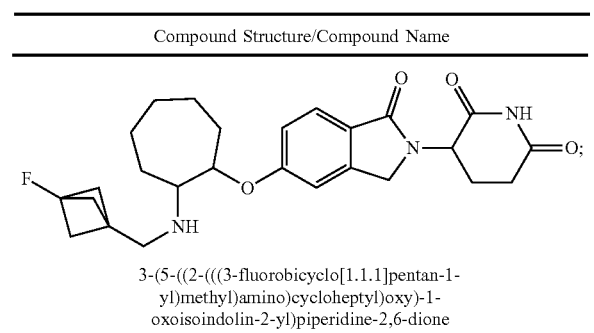<br>3-(5-((2-(((3-fluorobicyclo[1.1.1]pentan-1-yl)methyl)amino)cycloheptyl)oxy)-1-oxoisoindolin-2-yl)piperidine-2,6-dione |
| 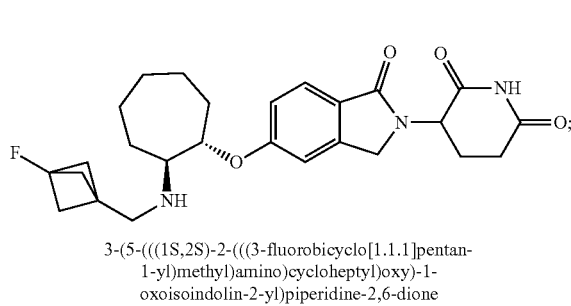<br>3-(5-(((1S,2S)-2-(((3-fluorobicyclo[1.1.1]pentan-1-yl)methyl)amino)cycloheptyl)oxy)-1-oxoisoindolin-2-yl)piperidine-2,6-dione | 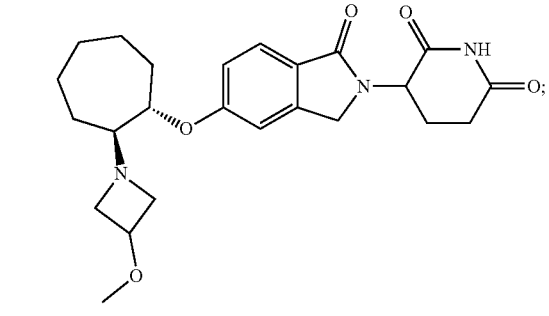<br>3-(5-(((1S,2S)-2-(3-methoxyazetidin-1-yl)cycloheptyl)oxy)-1-oxoisoindolin-2-yl)piperidine-2,6-dione |
| 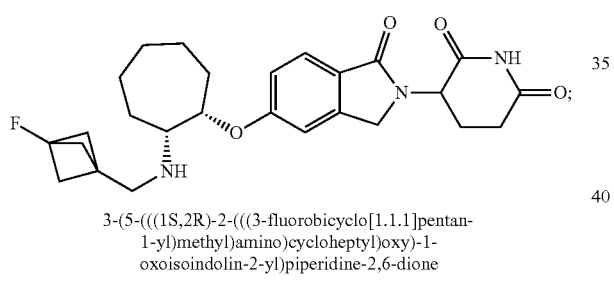<br>3-(5-(((1S,2R)-2-(((3-fluorobicyclo[1.1.1]pentan-1-yl)methyl)amino)cycloheptyl)oxy)-1-oxoisoindolin-2-yl)piperidine-2,6-dione | 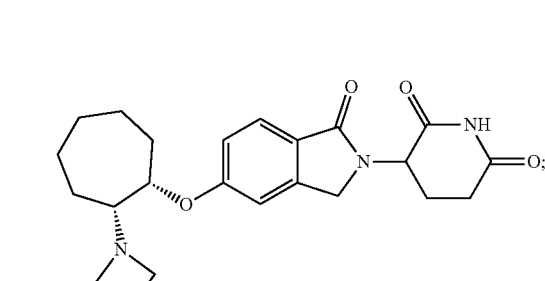<br>3-(5-(((1S,2R)-2-(3-methoxyazetidin-1-yl)cycloheptyl)oxy)-1-oxoisoindolin-2-yl)piperidine-2,6-dione |
| 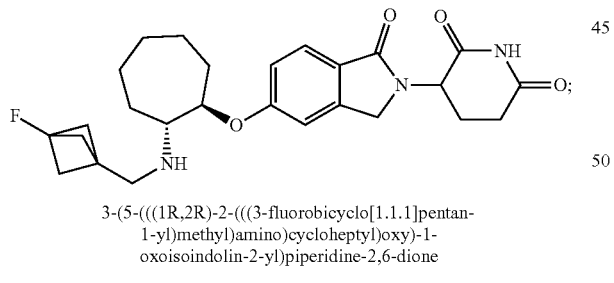<br>3-(5-(((1R,2R)-2-(((3-fluorobicyclo[1.1.1]pentan-1-yl)methyl)amino)cycloheptyl)oxy)-1-oxoisoindolin-2-yl)piperidine-2,6-dione | 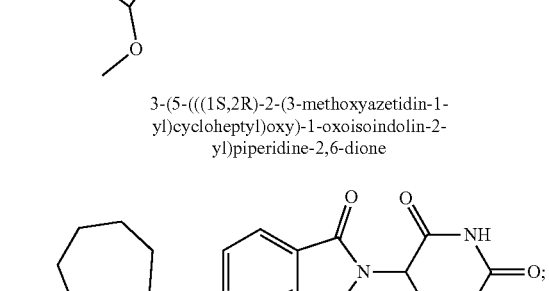 |
| 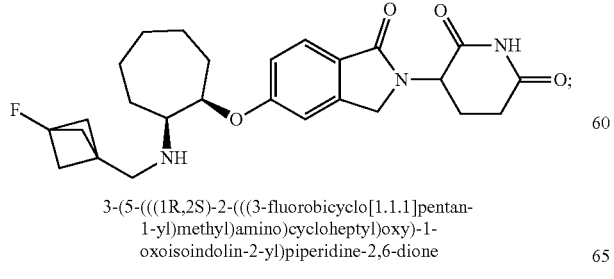<br>3-(5-(((1R,2S)-2-(((3-fluorobicyclo[1.1.1]pentan-1-yl)methyl)amino)cycloheptyl)oxy)-1-oxoisoindolin-2-yl)piperidine-2,6-dione | 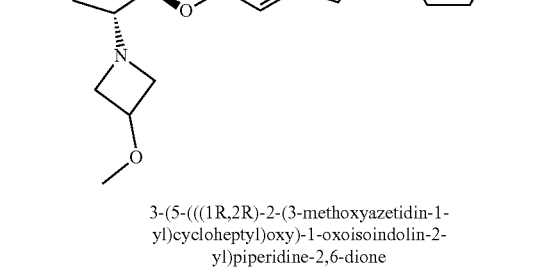<br>3-(5-(((1R,2R)-2-(3-methoxyazetidin-1-yl)cycloheptyl)oxy)-1-oxoisoindolin-2-yl)piperidine-2,6-dione |

| Compound Structure/Compound Name |
|---|
| 3-(5-(((1R,2S)-2-(3-methoxyazetidin-1-yl)cycloheptyl)oxy)-1-oxoisoindolin-2-yl)piperidine-2,6-dione |
| 3-(5-((2-(3-methoxyazetidin-1-yl)cycloheptyl)oxy)-1-oxoisoindolin-2-yl)piperidine-2,6-dione |
| 3-(5-(((1S,2S)-2-(((3,3-difluorocyclobutyl)methyl)amino)cycloheptyl)oxy)-1-oxoisoindolin-2-yl)piperidine-2,6-dione |
| 3-(5-(((1S,2R)-2-(((3,3-difluorocyclobutyl)methyl)amino)cycloheptyl)oxy)-1-oxoisoindolin-2-yl)piperidine-2,6-dione |

| Compound Structure/Compound Name |
|---|
| 3-(5-(((1R,2R)-2-(((3,3-difluorocyclobutyl)methyl)amino)cycloheptyl)oxy)-1-oxoisoindolin-2-yl)piperidine-2,6-dione |
| 3-(5-(((1R,2S)-2-(((3,3-difluorocyclobutyl)methyl)amino)cycloheptyl)oxy)-1-oxoisoindolin-2-yl)piperidine-2,6-dione |
| 3-(5-((2-(((3,3-difluorocyclobutyl)methyl)amino)cycloheptyl)oxy)-1-oxoisoindolin-2-yl)piperidine-2,6-dione |
| 3-(5-((2-(diethylamino)-3-methylcyclopentyl)oxy)-1-oxoisoindolin-2-yl)piperidine-2,6-dione |
| 3-(5-(((1S,2S)-2-(diethylamino)-3-methylcyclopentyl)oxy)-1-oxoisoindoline-2-yl)piperidine-2,6-dione |

| Compound Structure/Compound Name | Compound Structure/Compound Name |
|---|---|
| 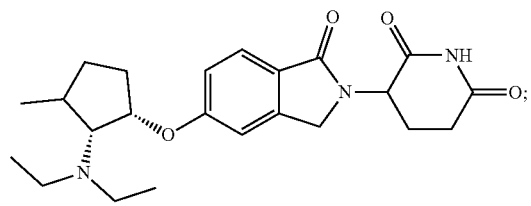<br>3-(5-(((1S,2R)-2-(diethylamino)-3-methylcyclopentyl)oxy)-1-oxoisoindolin-2-yl)piperidine-2,6-dione | 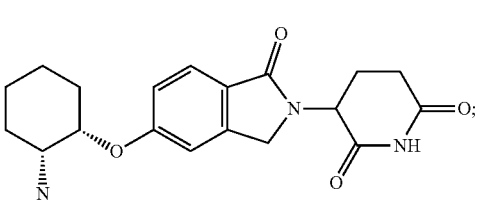<br>3-(1-oxo-5-(((1S,2R)-2-(3-(pyridazin-3-yloxy)azetidin-1-yl)cyclohexyl)oxy)isoindolin-2-yl)piperidine-2,6-dione |
| <br>3-(5-(((1R,2R)-2-(diethylamino)-3-methylcyclopentyl)oxy)-1-oxoisoindolin-2-yl)piperidine-2,6-dione | 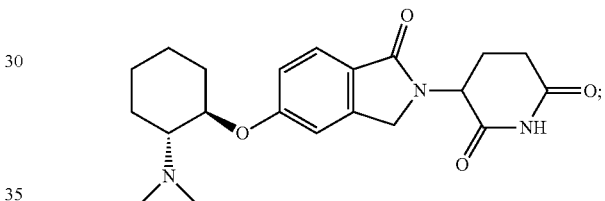<br>3-(1-oxo-5-(((1R,2R)-2-(3-(pyridazin-3-yloxy)azetidin-1-yl)cyclohexyl)oxy)isoindolin-2-yl)piperidine-2,6-dione |
| 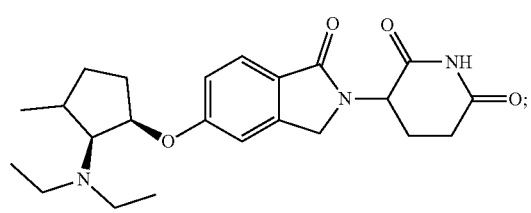<br>3-(5-(((1R,2S)-2-(diethylamino)-3-methylcyclopentyl)oxy)-1-oxoisoindolin-2-yl)piperidine-2,6-dione | 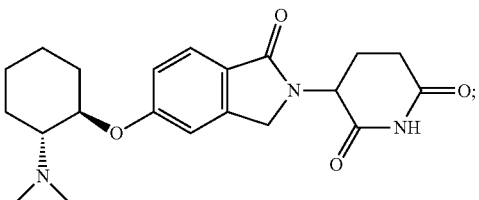<br>3-(1-oxo-5-(((1R,2S)-2-(3-(pyridazin-3-yloxy)azetidin-1-yl)cyclohexyl)oxy)isoindolin-2-yl)piperidine-2,6-dione |
| 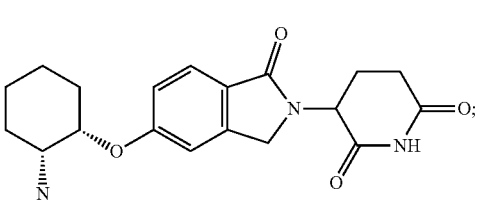<br>3-(1-oxo-5-(((1S,2S)-2-(3-(pyridazin-3-yloxy)azetidin-1-yl)cyclohexyl)oxy)isoindolin-2-yl)piperidine-2,6-dione | |

| Compound Structure/Compound Name | Compound Structure/Compound Name |
|---|---|
| 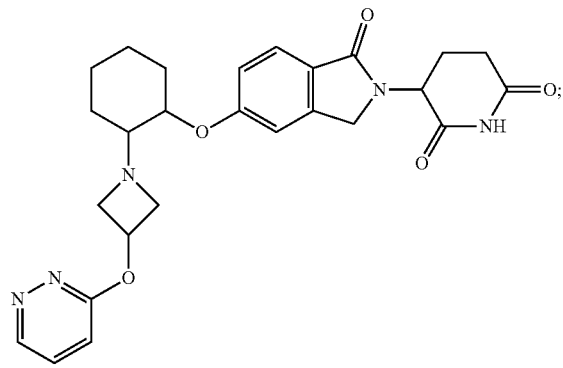<br>3-(1-oxo-5-((2-(3-(pyridazin-3-yloxy)azetidin-1-yl)cyclohexyl)oxy)isoindolin-2-yl)piperidine-2,6-dione | 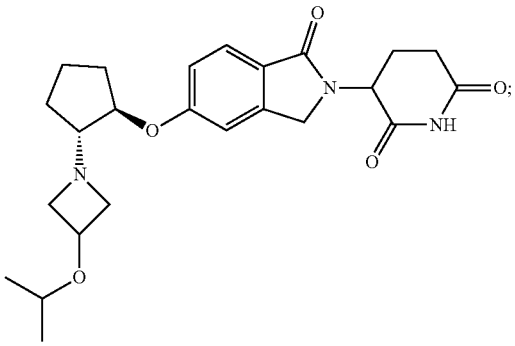<br>3-(5-(((1R,2R)-2-(3-isopropoxyazetidin-1-yl)cyclopentyl)oxy)-1-oxoisoindolin-2-yl)piperidine-2,6-dione |
| 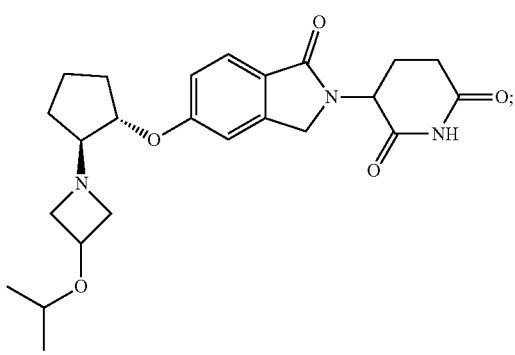<br>3-(5-(((1S,2S)-2-(3-isopropoxyazetidin-1-yl)cyclopentyl)oxy)-1-oxoisoindolin-2-yl)piperidine-2,6-dione | 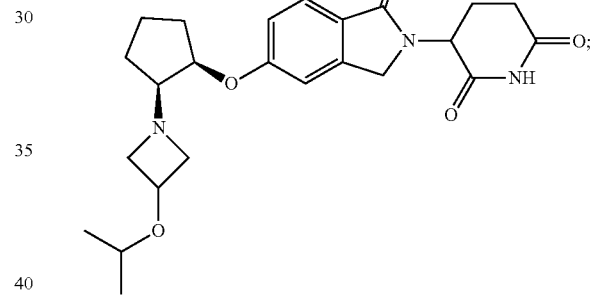<br>3-(5-(((1R,2S)-2-(3-isopropoxyazetidin-1-yl)cyclopentyl)oxy)-1-oxoisoindolin-2-yl)piperidine-2,6-dione |
| 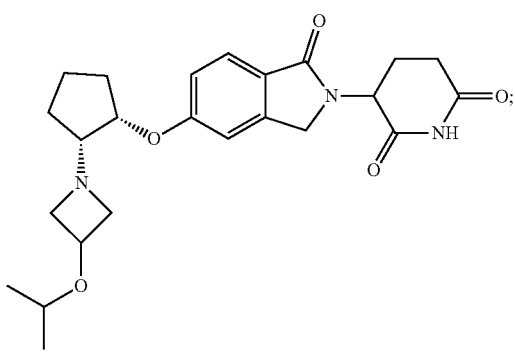<br>3-(5-(((1S,2R)-2-(3-isopropoxyazetidin-1-yl)cyclopentyl)oxy)-1-oxoisoindolin-2-yl)piperidine-2,6-dione | 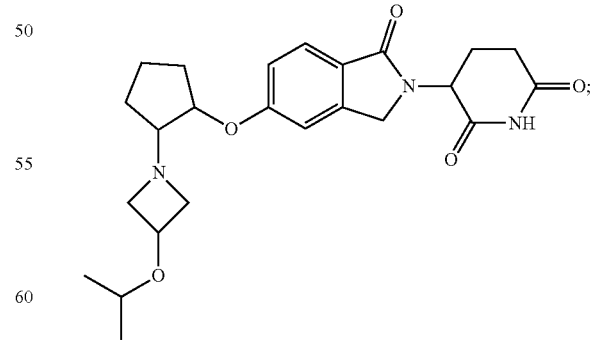<br>3-(5-((2-(3-isopropoxyazetidin-1-yl)cyclopentyl)oxy)-1-oxoisoindolin-2-yl)piperidine-2,6-dione |

| Compound Structure/Compound Name | Compound Structure/Compound Name |
|---|---|
| 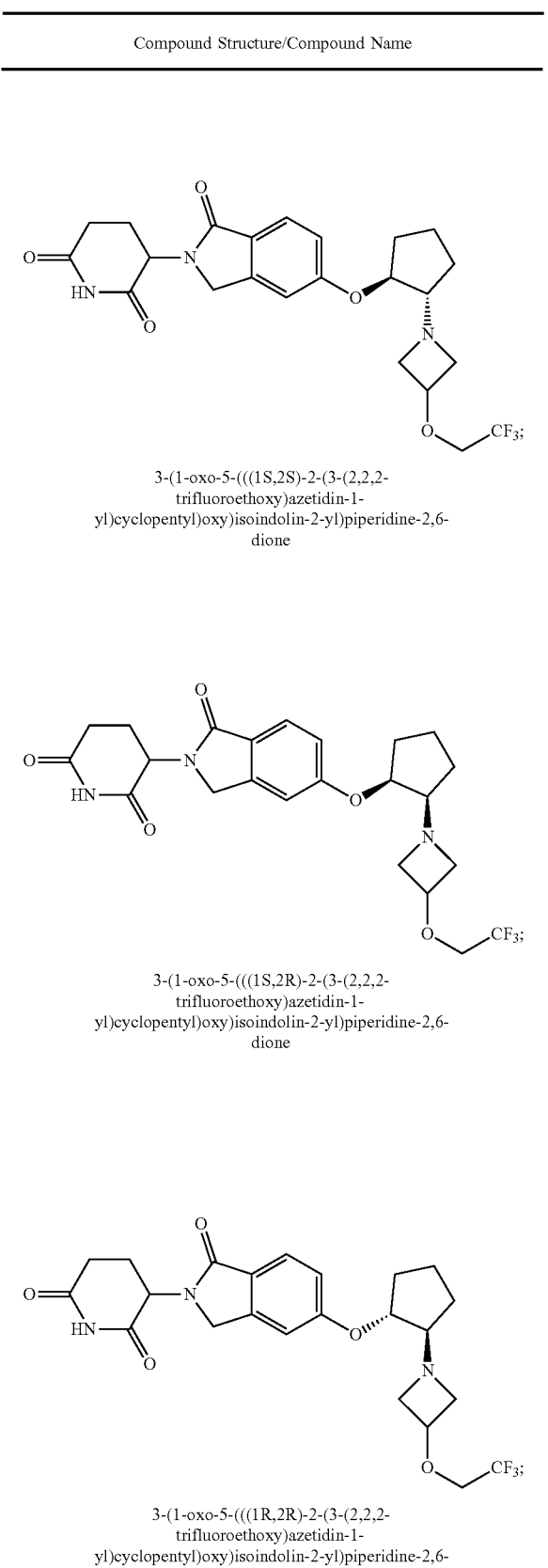<br>3-(1-oxo-5-(((1S,2S)-2-(3-(2,2,2-trifluoroethoxy)azetidin-1-yl)cyclopentyl)oxy)isoindolin-2-yl)piperidine-2,6-dione<br><br>3-(1-oxo-5-(((1S,2R)-2-(3-(2,2,2-trifluoroethoxy)azetidin-1-yl)cyclopentyl)oxy)isoindolin-2-yl)piperidine-2,6-dione<br><br>3-(1-oxo-5-(((1R,2R)-2-(3-(2,2,2-trifluoroethoxy)azetidin-1-yl)cyclopentyl)oxy)isoindolin-2-yl)piperidine-2,6-dione | 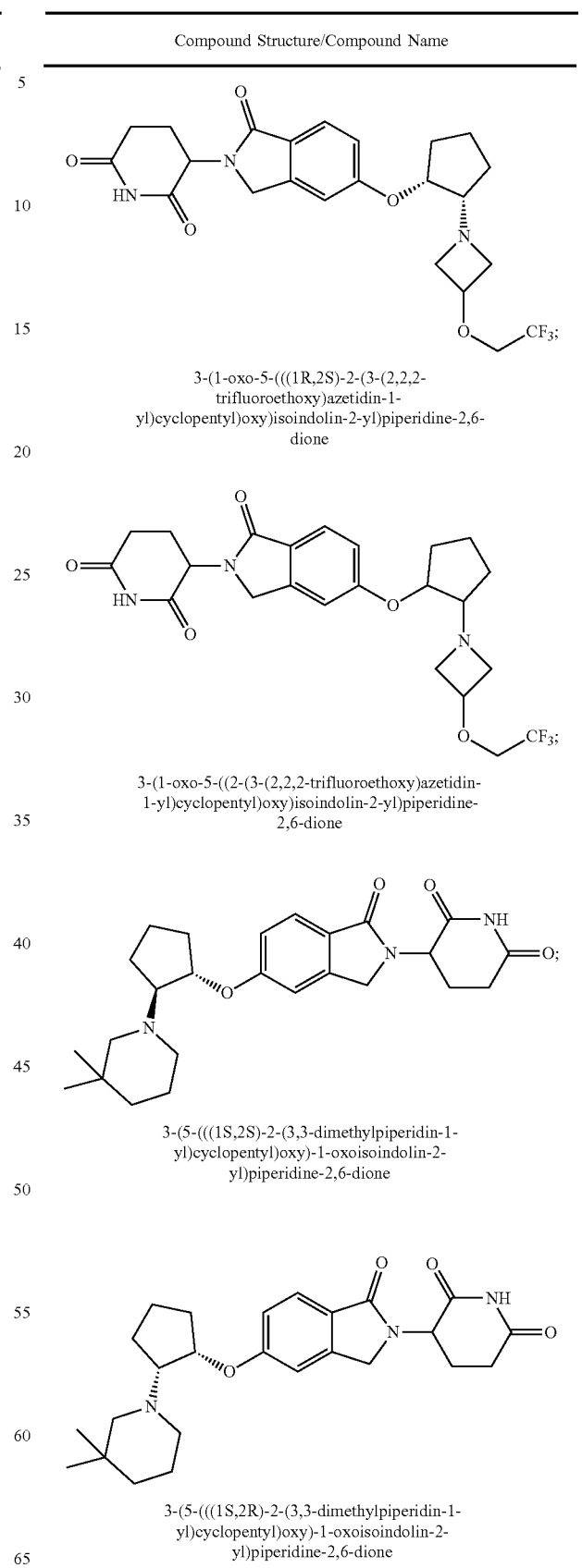<br>3-(1-oxo-5-(((1R,2S)-2-(3-(2,2,2-trifluoroethoxy)azetidin-1-yl)cyclopentyl)oxy)isoindolin-2-yl)piperidine-2,6-dione<br><br>3-(1-oxo-5-((2-(3-(2,2,2-trifluoroethoxy)azetidin-1-yl)cyclopentyl)oxy)isoindolin-2-yl)piperidine-2,6-dione<br><br>3-(5-(((1S,2S)-2-(3,3-dimethylpiperidin-1-yl)cyclopentyl)oxy)-1-oxoisoindolin-2-yl)piperidine-2,6-dione<br><br>3-(5-(((1S,2R)-2-(3,3-dimethylpiperidin-1-yl)cyclopentyl)oxy)-1-oxoisoindolin-2-yl)piperidine-2,6-dione |

| Compound Structure/Compound Name | Compound Structure/Compound Name |
|---|---|
| 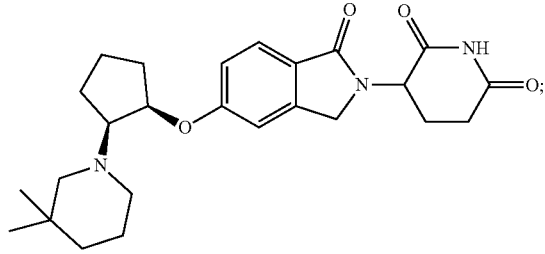<br>3-(5-(((1R,2S)-2-(3,3-dimethylpiperidin-1-yl)cyclopentyl)oxy)-1-oxoisoindolin-2-yl)piperidine-2,6-dione | 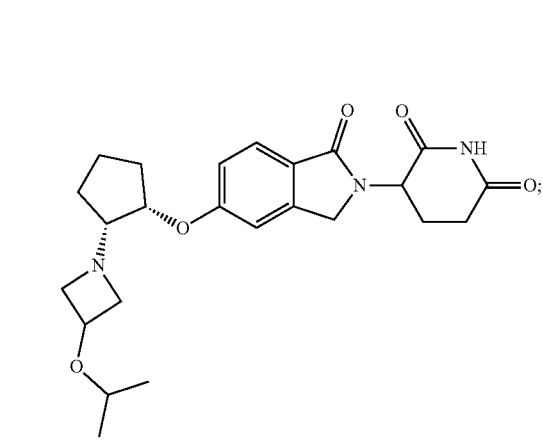<br>3-(5-(((1S,2R)-2-(3-isopropoxyazetidin-1-yl)cyclopentyl)oxy)-1-oxoisoindolin-2-yl)piperidine-2,6-dione |
| 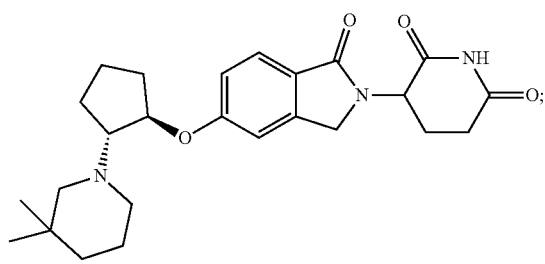<br>3-(5-(((1R,2R)-2-(3,3-dimethylpiperidin-1-yl)cyclopentyl)oxy)-1-oxoisoindolin-2-yl)piperidine-2,6-dione | 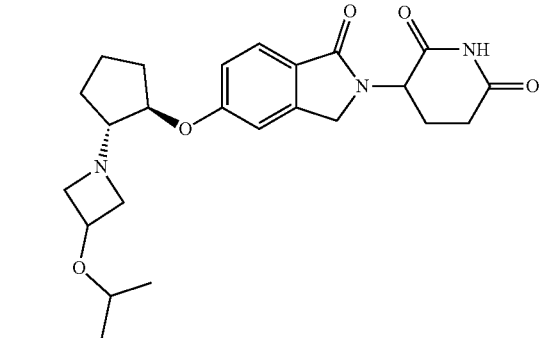<br>3-(5-(((1R,2R)-2-(3-isopropoxyazetidin-1-yl)cyclopentyl)oxy)-1-oxoisoindolin-2-yl)piperidine-2,6-dione; |
| 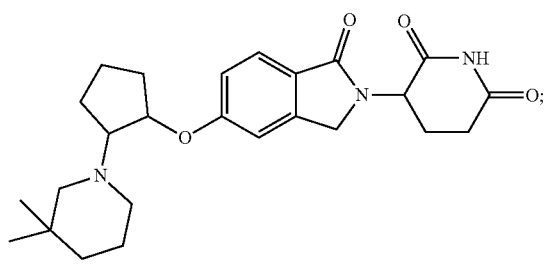<br>3-(5-((2-(3,3-dimethylpiperidin-1-yl)cyclopentyl)oxy)-1-oxoisoindolin-2-yl)piperidine-2,6-dione | |
| 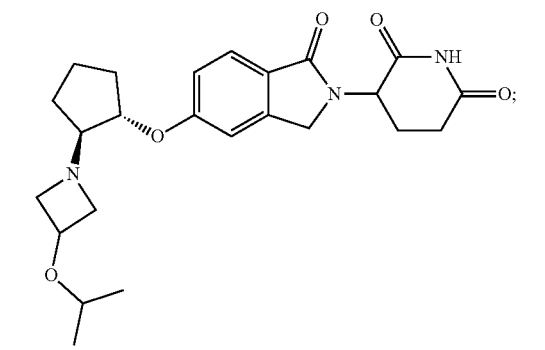<br>3-(5-(((1S,2S)-2-(3-isopropoxyazetidin-1-yl)cyclopentyl)oxy)-1-oxoisoindolin-2-yl)piperidine-2,6-dione | 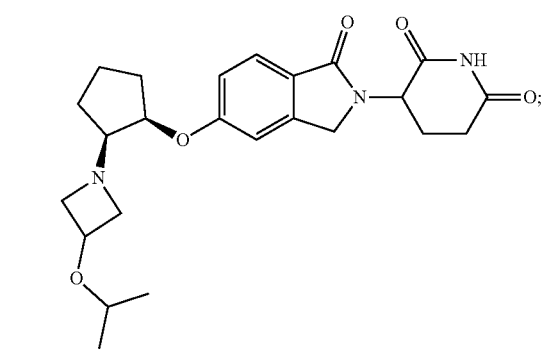<br>3-(5-(((1R,2S)-2-(3-isopropoxyazetidin-1-yl)cyclopentyl)oxy)-1-oxoisoindolin-2-yl)piperidine-2,6-dione |

| Compound Structure/Compound Name |
|---|
| 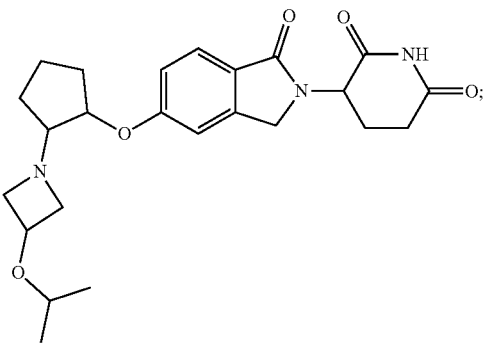<br>3-(5-((2-(3-isopropoxyazetidin-1-yl)cyclopentyl)oxy)-1-oxoisoindolin-2-yl)piperidine-2,6-dione |
| 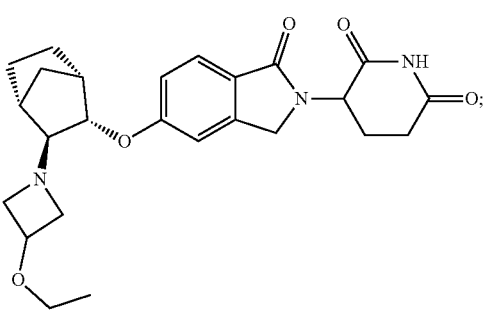<br>3-(5-(((1S,2S,3S,4R)-3-(3-ethoxyazetidin-1-yl)bicyclo[2.2.1]heptan-2-yl)oxy)-1-oxoisoindolin-2-yl)piperidine-2,6-dione |
| 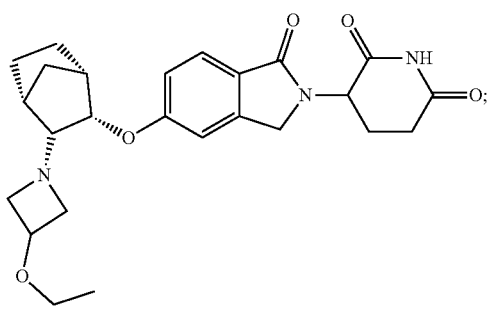<br>3-(5-(((1S,2S,3R,4R)-3-(3-ethoxyazetidin-1-yl)bicyclo[2.2.1]heptan-2-yl)oxy)-1-oxoisoindolin-2-yl)piperidine-2,6-dione |
| 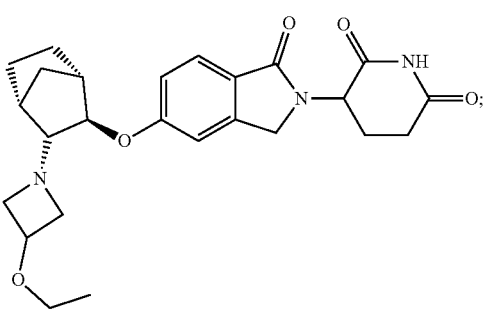<br>3-(5-(((1S,2R,3R,4R)-3-(3-ethoxyazetidin-1-yl)bicyclo[2.2.1]heptan-2-yl)oxy)-1-oxoisoindolin-2-yl)piperidine-2,6-dione |

| Compound Structure/Compound Name |
|---|
| 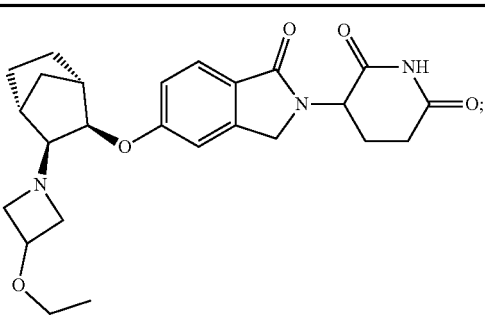<br>3-(5-(((1S,2R,3S,4R)-3-(3-ethoxyazetidin-1-yl)bicyclo[2.2.1]heptan-2-yl)oxy)-1-oxoisoindolin-2-yl)piperidine-2,6-dione |
| 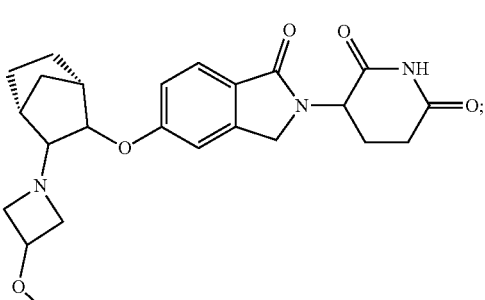<br>3-(5-(((1S,4R)-3-(3-ethoxyazetidin-1-yl)bicyclo[2.2.1]heptan-2-yl)oxy)-1-oxoisoindolin-2-yl)piperidine-2,6-dione |
| 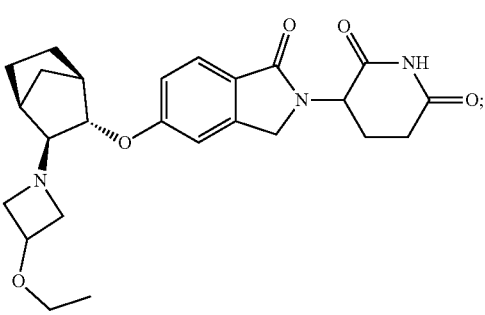<br>3-(5-(((1R,2S,3S,4S)-3-(3-ethoxyazetidin-1-yl)bicyclo[2.2.1]heptan-2-yl)oxy)-1-oxoisoindolin-2-yl)piperidine-2,6-dione |
| 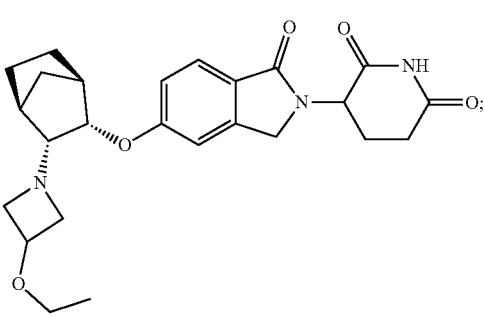<br>3-(5-(((1R,2S,3R,4S)-3-(3-ethoxyazetidin-1-yl)bicyclo[2.2.1]heptan-2-yl)oxy)-1-oxoisoindolin-2-yl)piperidine-2,6-dione |

| Compound Structure/Compound Name |
|---|
| 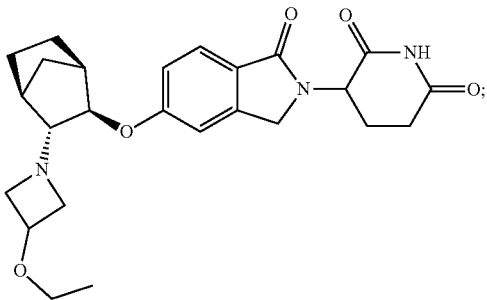 3-(5-(((1R,2R,3R,4S)-3-(3-ethoxyazetidin-1-yl)bicyclo[2.2.1]heptan-2-yl)oxy)-1-oxoisoindolin-2-yl)piperidine-2,6-dione |
| 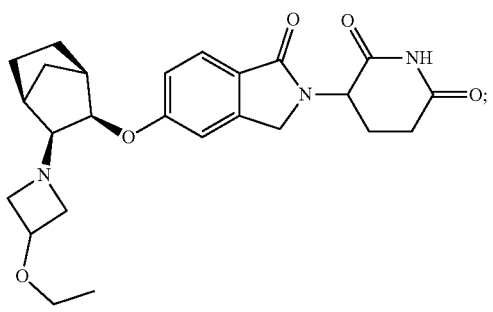 3-(5-(((1R,2R,3S,4S)-3-(3-ethoxyazetidin-1-yl)bicyclo[2.2.1]heptan-2-yl)oxy)-1-oxoisoindolin-2-yl)piperidine-2,6-dione |
| 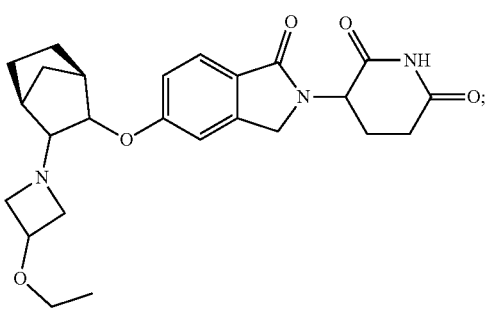 3-(5-(((1R,4S)-3-(3-ethoxyazetidin-1-yl)bicyclo[2.2.1]heptan-2-yl)oxy)-1-oxoisoindolin-2-yl)piperidine-2,6-dione |
| 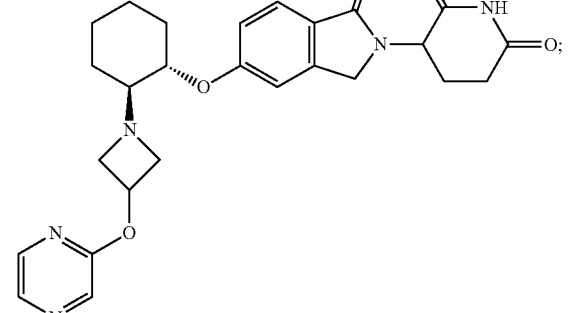 3-(1-oxo-5-(((1S,2S)-2-(3-(pyrazin-2-yloxy)azetidin-1-yl)cyclohexyl)oxy)isoindolin-2-yl)piperidine-2,6-dione |

| Compound Structure/Compound Name |
|---|
| 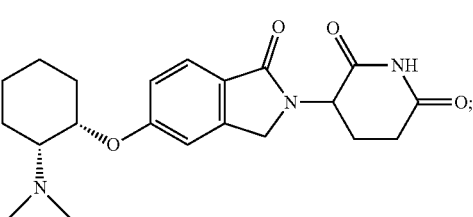 3-(1-oxo-5-(((1S,2R)-2-(3-(pyrazin-2-yloxy)azetidin-1-yl)cyclohexyl)oxy)isoindolin-2-yl)piperidine-2,6-dione |
| 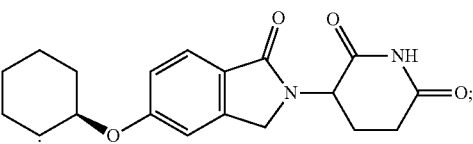 3-(1-oxo-5-(((1R,2R)-2-(3-(pyrazin-2-yloxy)azetidin-1-yl)cyclohexyl)oxy)isoindolin-2-yl)piperidine-2,6-dione |
| 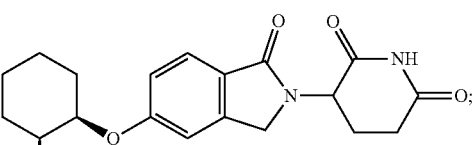 3-(1-oxo-5-(((1R,2S)-2-(3-(pyrazin-2-yloxy)azetidin-1-yl)cyclohexyl)oxy)isoindolin-2-yl)piperidine-2,6-dione |

| Compound Structure/Compound Name | Compound Structure/Compound Name |
|---|---|
| 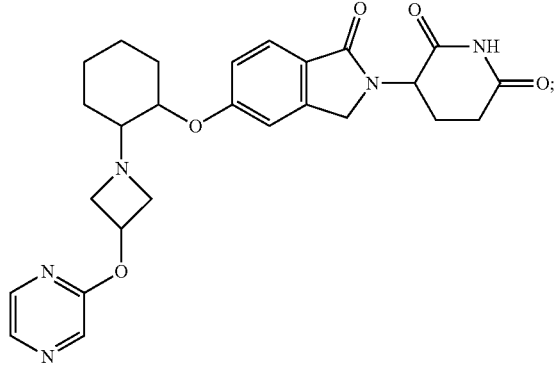<br>3-(1-oxo-5-((2-(3-(pyrazin-2-yloxy)azetidin-1-yl)cyclohexyl)oxy)isoindolin-2-yl)piperidine-2,6-dione | 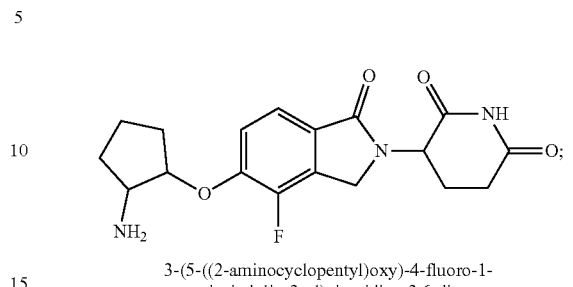<br>3-(5-((2-aminocyclopentyl)oxy)-4-fluoro-1-oxoisoindolin-2-yl)piperidine-2,6-dione |
| 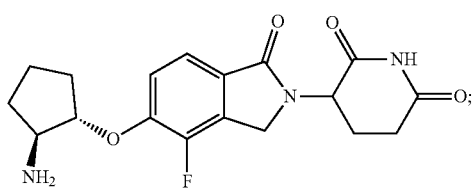<br>3-(5-(((1S,2S)-2-aminocyclopentyl)oxy)-4-fluoro-1-oxoisoindolin-2-yl)piperidine-2,6-dione | 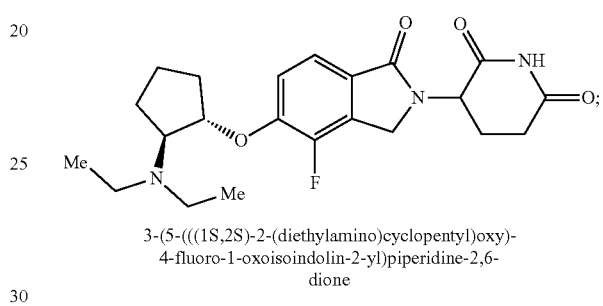<br>3-(5-(((1S,2S)-2-(diethylamino)cyclopentyl)oxy)-4-fluoro-1-oxoisoindolin-2-yl)piperidine-2,6-dione |
| 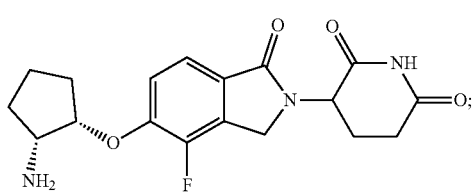<br>3-(5-(((1S,2R)-2-aminocyclopentyl)oxy)-4-fluoro-1-oxoisoindolin-2-yl)piperidine-2,6-dione | 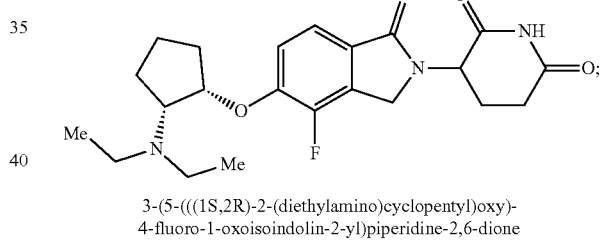<br>3-(5-(((1S,2R)-2-(diethylamino)cyclopentyl)oxy)-4-fluoro-1-oxoisoindolin-2-yl)piperidine-2,6-dione |
| 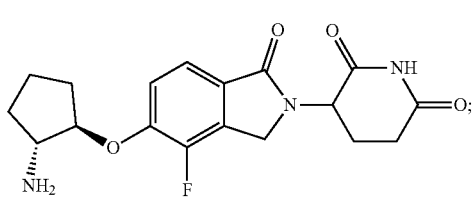<br>3-(5-(((1R,2R)-2-aminocyclopentyl)oxy)-4-fluoro-1-oxoisoindolin-2-yl)piperidine-2,6-dione | 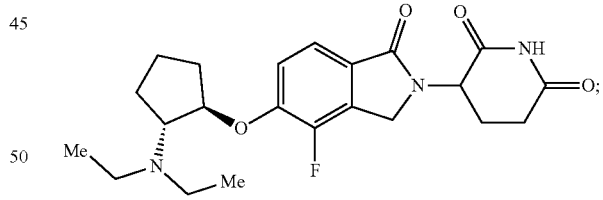<br>3-(5-(((1R,2R)-2-(diethylamino)cyclopentyl)oxy)-4-fluoro-1-oxoisoindolin-2-yl)piperidine-2,6-dione |
| 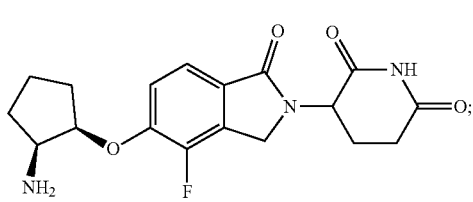<br>3-(5-(((1R,2S)-2-aminocyclopentyl)oxy)-4-fluoro-1-oxoisoindolin-2-yl)piperidine-2,6-dione | 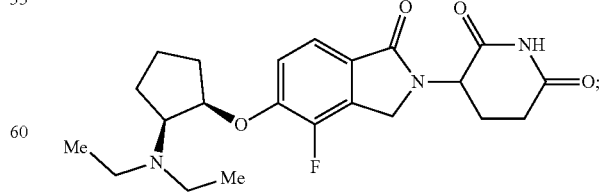<br>3-(5-(((1R,2S)-2-(diethylamino)cyclopentyl)oxy)-4-fluoro-1-oxoisoindolin-2-yl)piperidine-2,6-dione |

| Compound Structure/Compound Name |
|---|
| 3-(5-((2-(diethylamino)cyclopentyl)oxy)-4-fluoro-1-oxoisoindolin-2-yl)piperidine-2,6-dione |
| 3-(5-(((1S,2S)-2-aminocyclopentyl)oxy)-6-fluoro-1-oxoisoindolin-2-yl)piperidine-2,6-dione |
| 3-(5-(((1S,2R)-2-aminocyclopentyl)oxy)-6-fluoro-1-oxoisoindolin-2-yl)piperidine-2,6-dione |
| 3-(5-(((1R,2R)-2-aminocyclopentyl)oxy)-6-fluoro-1-oxoisoindolin-2-yl)piperidine-2,6-dione |
| 3-(5-(((1R,2S)-2-aminocyclopentyl)oxy)-6-fluoro-1-oxoisoindolin-2-yl)piperidine-2,6-dione |
| 3-(5-((2-aminocyclopentyl)oxy)-6-fluoro-1-oxoisoindolin-2-yl)piperidine-2,6-dione |
| 3-(5-(((1S,2S)-2-(diethylamino)cyclopentyl)oxy)-6-fluoro-1-oxoisoindolin-2-yl)piperidine-2,6-dione |
| 3-(5-(((1S,2R)-2-(diethylamino)cyclopentyl)oxy)-6-fluoro-1-oxoisoindolin-2-yl)piperidine-2,6-dione |
| 3-(5-(((1R,2R)-2-(diethylamino)cyclopentyl)oxy)-6-fluoro-1-oxoisoindolin-2-yl)piperidine-2,6-dione |
| 3-(5-(((1R,2S)-2-(diethylamino)cyclopentyl)oxy)-6-fluoro-1-oxoisoindolin-2-yl)piperidine-2,6-dione; and |
| 3-(5-((2-(diethylamino)cyclopentyl)oxy)-6-fluoro-1-oxoisoindolin-2-yl)piperidine-2,6-dione. | or a pharmaceutically acceptable salt, hydrate, solvate, prodrug, stereoisomer, or tautomer thereof.

Embodiment 17

A pharmaceutical composition comprising a therapeutically effective amount of a compound according to any one of Embodiments 1-16 and 2A, or a pharmaceutically acceptable salt thereof, and a pharmaceutically acceptable carrier or excipient.

Embodiment 18

The pharmaceutical composition of Embodiment 17 further comprising at least one additional pharmaceutical agent.

Embodiment 19

The pharmaceutical composition of Embodiment 17 or Embodiment 18 for use in the treatment of a disease or disorder that is affected by the reduction of IKZF2 protein levels.

Embodiment 20

A method of degrading IKZF2 comprising administering to the patient in need thereof a compound of any one of Embodiments 1-16 and 2A, or a pharmaceutically acceptable salt, hydrate, solvate, prodrug, stereoisomer, or tautomer thereof.

Embodiment 21

A method of treating a disease or disorder that is affected by the modulation of IKZF2 protein levels comprising administering to the patient in need thereof a compound of any one of Embodiments 1-16 and 2A, or a pharmaceutically acceptable salt, hydrate, solvate, prodrug, stereoisomer, or tautomer thereof.

Embodiment 22

A method of modulating IKZF2 protein levels comprising administering to the patient in need thereof a compound of any one of Embodiments 1-16 and 2A, or a pharmaceutically acceptable salt, hydrate, solvate, prodrug, stereoisomer, or tautomer thereof.

Embodiment 23

A method of reducing the proliferation of a cell the method comprising, contacting the cell with a compound of any one of Embodiments 1-16 and 2A, or a pharmaceutically acceptable salt, hydrate, solvate, prodrug, stereoisomer, or tautomer thereof, and reducing IKZF2 protein levels.

Embodiment 24

A method of treating cancer comprising administering to the patient in need thereof a compound of any one of Embodiments 1-15 and 2A, or a pharmaceutically acceptable salt, hydrate, solvate, prodrug, stereoisomer, or tautomer thereof.

Embodiment 25

The method of Embodiment 24, wherein the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer and soft tissue sarcomas selected from rhabdomyosarcoma (RMS), synovial sarcoma, osteosarcoma, rhabdoid cancers, and Ewing's sarcoma.

Embodiment 26

The method of Embodiment 24, wherein the cancer is a cancer for which the immune response is deficient or an immunogenic cancer.

Embodiment 27

A method for reducing IKZF2 protein levels in a subject comprising the step of administering to a subject in need thereof a therapeutically effective amount of a compound according to any one of Embodiments 1-16 and 2A, or a pharmaceutically acceptable salt.

Embodiment 28

The method of Embodiments any one of 20-27, wherein administering is performed orally, parentally, subcutaneously, by injection, or by infusion.

Embodiment 29

A compound according to any one of Embodiments 1-16 and 2A, or a pharmaceutically acceptable salt, hydrate, solvate, prodrug, stereoisomer, or tautomer thereof, for use in the treatment of a disease or disorder that is affected by the reduction of IKZF2 protein levels.

Embodiment 30

Use of a compound according to any one of Embodiments 1-16 and 2A, or a pharmaceutically acceptable salt, hydrate, solvate, prodrug, stereoisomer, or tautomer thereof, in the manufacture of a medicament for treating a disease or disorder that is affected by the reduction of IKZF2 protein levels.

Embodiment 31

A compound according to any one of Embodiments 1-16 and 2A, or a pharmaceutically acceptable salt, hydrate, solvate, prodrug, stereoisomer, or tautomer thereof, for use in the manufacture of a medicament for treating a disease or disorder associated with the reduction of IKZF2 protein levels.

Embodiment 32

The compound of Embodiment 31, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

Embodiment 33

Use of a compound according to any one of Embodiments 1-16 and 2A, or a pharmaceutically acceptable salt, hydrate, solvate, prodrug, stereoisomer, or tautomer thereof, in the treatment of a disease or disorder associated with the reduction of IKZF2 protein levels.

Embodiment 34

The use of Embodiment 33, wherein the disease or disorder is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, and Ewing's sarcoma.

Embodiment 35

The method of Embodiment 24, wherein the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST).

Embodiment 36

The compound of Embodiment 31, wherein the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST).

Embodiment 37

The use of Embodiment 33, wherein the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST).

In another embodiment of the disclosure, the compounds of the present disclosure are enantiomers. In some embodiments the compounds are the (S)-enantiomer. In other embodiments, the compounds are the (R)-enantiomer. In yet other embodiments, the compounds of the present disclosure may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Compounds of the disclosure, and pharmaceutically acceptable salts, hydrates, solvates, stereoisomers, and prodrugs thereof may exist in their tautomeric form (for example, as an amide or imino ether). All such tautomeric forms are contemplated herein as part of the present disclosure.

The compounds of the disclosure may contain asymmetric or chiral centers and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure and chemical structures and names. Also, for example, all keto-enol and imine-enamine forms of the compounds are included in the disclosure.

All stereoisomers (for example, geometric isomers, optical isomers, and the like) of the present compounds (including those of the salts, solvates, esters, and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I') or Formula (I) incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or is admixed, for example, as racemates or with all other, or other selected, stereoisomers.

The chiral centers of the compounds of the disclosure can have the S or R configuration as defined by the IUPAC 1974 Recommendations. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

The use of the terms "salt", "solvate", "ester," "prodrug", and the like, is intended to equally apply to the salt, solvate, ester, and prodrug of enantiomers, stereoisomers, rotamers, tautomers, positional isomers, racemates, or prodrugs of the inventive compounds.

The compounds of the disclosure may form salts which are also within the scope of this disclosure. Reference to a compound of the Formula herein is generally understood to include reference to salts thereof, unless otherwise indicated.

The compounds and intermediates may be isolated and used as the compound per se. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, and, such as $^2H$, $^3H$, $^{11}C$, $^{13}C$, $^{14}C$, $^{15}N$, $^{18}F$, $^{31}P$, $^{32}P$, respectively. The disclosure includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$, $^{11}C$ or labeled compound may be particularly desirable for PET or SPECT studies.

Further, substitution with heavier isotopes, particularly deuterium (i.e., $^2H$ or D) may afford certain therapeutic advantages resulting from greater metabolic stability, for example, increased in vivo half-life, reduced dosage requirements, reduced CYP450 inhibition (competitive or time dependent) or an improvement in therapeutic index. For example, substitution with deuterium may modulate undesirable side effects of the undeuterated compound, such as competitive CYP450 inhibition, time dependent CYP450 inactivation, etc. It is understood that deuterium in this context is regarded as a substituent in compounds of the present disclosure. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present disclosure can generally be prepared by conventional techniques known to those skilled in the art or by carrying out the procedures disclosed in the schemes or in the examples and preparations described below using an appropriate isotopically-labeled reagent in place of the non-isotopically labeled reagent.

Pharmaceutically acceptable solvates in accordance with the disclosure include those wherein the solvent of crystallization may be isotopically substituted, e.g., $D_2O$, $d_6$-acetone, $d_6$-DMSO.

The present disclosure relates to compounds which are modulators of IKZF2 protein levels. In one embodiment, the compounds of the present disclosure decrease IKZF2 protein levels. In yet one embodiment, the compounds of the present disclosure reduce IKZF2 protein levels. In another embodiment, the compounds of the present disclosure are degraders of IKZF2.

The present disclosure relates to compounds which are modulators of IKZF2 and IKZF4 protein levels. In one embodiment, the compounds of the present disclosure decrease IKZF2 and IKZF4 protein levels. In yet one embodiment, the compounds of the present disclosure reduce IKZF2 and IKZF4 protein levels. In another embodiment, the compounds of the present disclosure are degraders of IKZF2.

In some embodiments, the compounds of the disclosure are selective over other proteins. As used herein "selective modulator", "selective degrader", or "selective compound" means, for example, a compound of the disclosure, that effectively modulates, decreases, or reduces the levels of a specific protein or degrades a specific protein to a greater extent than any other protein. A "selective modulator", "selective degrader", or "selective compound" can be identified, for example, by comparing the ability of a compound to modulate, decrease, or reduce the levels of or to degrade a specific protein to its ability to modulate, decrease, or reduce the levels of or to degrade other proteins. In some embodiments, the selectivity can be identified by measuring the $EC_{50}$ or $IC_{50}$ of the compounds.

In some embodiments, the compounds of the present application are selective IKZF2 modulators. As used herein "selective IKZF2 modulator", "selective IKZF2 degrader", or "selective IKZF2 compound" refers to a compound of the application, for example, that effectively modulates, decrease, or reduces the levels of IKZF2 protein or degrades IKZF2 protein to a greater extent than any other protein, particularly any protein (transcription factor) from the Ikaros protein family (e.g., IKZF1, IKZF3, IKZF4, and IKZF5).

A "selective IKZF2 modulator", "selective IKZF2 degrader", or "selective IKZF2 compound" can be identified, for example, by comparing the ability of a compound to modulate IKZF2 protein levels to its ability to modulate levels of other members of the Ikaros protein family or other proteins. For example, a substance may be assayed for its ability to modulate IKZF2 protein levels, as well as IKZF1, IKZF3, IKZF4, IKZF5, and other proteins. In some embodiments, the selectivity can be identified by measuring the $EC_{50}$ of the compounds. In some embodiments, a selective IKZF2 degrader is identified by comparing the ability of a compound to degrade IKZF2 to its ability to degrade other members of the Ikaros protein family or other proteins.

In certain embodiments, the compounds of the application are IKZF2 degraders that exhibit at least 2-fold, 3-fold, 5-fold, 10-fold, 25-fold, 50-fold, or 100-fold selectivity for the degradation of IKZF2 over other proteins (e.g., IKZF1, IKZF3, IKZF4, and IKZF5). In various embodiments, the compounds of the application exhibit up to 1000-fold selectivity for the degradation of IKZF2 over other proteins.

In certain embodiments, the compounds of the application exhibit at least 2-fold, 3-fold, 5-fold, 10-fold, 25-fold, 50-fold, or 100-fold selectivity for the degradation of IKZF2 over the other members of the Ikaros protein family (e.g., IKZF1, IKZF3, IKZF4, and IKZF5). In various embodiments, the compounds of the application exhibit up to 1000-fold selectivity for the degradation of IKZF2 over the other members of the Ikaros protein family (e.g., IKZF1, IKZF3, IKZF4, and IKZF5).

In certain embodiments, the compounds of the application exhibit at least 2-fold, 3-fold, 5-fold, 10-fold, 25-fold, 50-fold, or 100-fold selectivity for the degradation of IKZF2 over IKZF1. In various embodiments, the compounds of the application exhibit up to 1000-fold selectivity for the degradation of IKZF2 over IKZF1.

In certain embodiments, the compounds of the application exhibit at least 2-fold, 3-fold, 5-fold, 10-fold, 25-fold, 50-fold, or 100-fold selectivity for the degradation of IKZF2 over IKZF3. In various embodiments, the compounds of the application exhibit up to 1000-fold selectivity for the degradation of IKZF2 over IKZF3.

In certain embodiments, the compounds of the application exhibit at least 2-fold, 3-fold, 5-fold, 10-fold, 25-fold, 50-fold, or 100-fold selectivity for the degradation of IKZF2 over IKZF4. In various embodiments, the compounds of the application exhibit up to 1000-fold selectivity for the degradation of IKZF2 over IKZF4.

In certain embodiments, the compounds of the application exhibit at least 2-fold, 3-fold, 5-fold, 10-fold, 25-fold, 50-fold, or 100-fold selectivity for the degradation of IKZF2 over IKZF5. In various embodiments, the compounds of the application exhibit up to 1000-fold selectivity for the degradation of IKZF2 over IKZF5.

In certain embodiments, the compounds of the application exhibit at least 2-fold, 3-fold, 5-fold, 10-fold, 25-fold, 50-fold, or 100-fold selectivity for the degradation of IKZF2 and IKZF4 over the other members of the Ikaros protein family (e.g., IKZF1, IKZF3, and IKZF5). In various embodiments, the compounds of the application exhibit up to 1000-fold selectivity for the degradation of IKZF2 and IKZF4 over the other members of the Ikaros protein family (e.g., IKZF1, IKZF3, and IKZF5).

In certain embodiments, the compounds of the application exhibit at least 2-fold, 3-fold, 5-fold, 10-fold, 25-fold, 50-fold, or 100-fold selectivity for the degradation of IKZF2 and IKZF4 over IKZF1. In various embodiments, the compounds of the application exhibit up to 1000-fold selectivity for the degradation of IKZF2 and IKZF4 over IKZF1.

In certain embodiments, the compounds of the application exhibit at least 2-fold, 3-fold, 5-fold, 10-fold, 25-fold, 50-fold, or 100-fold selectivity for the degradation of IKZF2 and IKZF4 over IKZF3. In various embodiments, the compounds of the application exhibit up to 1000-fold selectivity for the degradation of IKZF2 and IKZF4 over IKZF3.

In certain embodiments, the compounds of the application exhibit at least 2-fold, 3-fold, 5-fold, 10-fold, 25-fold, 50-fold, or 100-fold selectivity for the degradation of IKZF2 and IKZF4 over IKZF5. In various embodiments, the compounds of the application exhibit up to 1000-fold selectivity for the degradation of IKZF2 and IKZF4 over IKZF5.

In some embodiments, the degradation of IKZF2 is measured by $EC_{50}$.

Potency of can be determined by $EC_{50}$ value. A compound with a lower $EC_{50}$ value, as determined under substantially similar degradation conditions, is a more potent degrader relative to a compound with a higher $EC_{50}$ value. In some embodiments, the substantially similar conditions comprise determining degradation of protein levels in cells expressing the specific protein, or a fragment of any thereof.

The disclosure is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

E. Methods of Synthesizing Compounds of Formula (I') or Formula (I)

The compounds of the present disclosure may be made by a variety of methods, including standard chemistry. Suitable synthetic routes are depicted in the Schemes given below.

The compounds of the present disclosure may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I') or Formula (I).

Those skilled in the art will recognize if a stereocenter exists in the compounds of the present disclosure. Accordingly, the present disclosure includes all possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. Preferred methods include but are not limited to those methods described below.

Compounds of the present disclosure can be synthesized by following the steps outlined in General Schemes I, II, III, IV, and V which comprise different sequences of assembling intermediates I-a, I-b, I-c, I-d, I-e, I-f, II-a, II-b, II-c, III-a, III-b, IV-a, IV-b, IV-c, IV-d1, IV-d2, IV-e1, IV-e2, IV-f, V-a, V-b, V-c1, V-c2, V-d1, and V-d2. Starting materials are either commercially available or made by known procedures in the reported literature or as illustrated.

General Scheme I

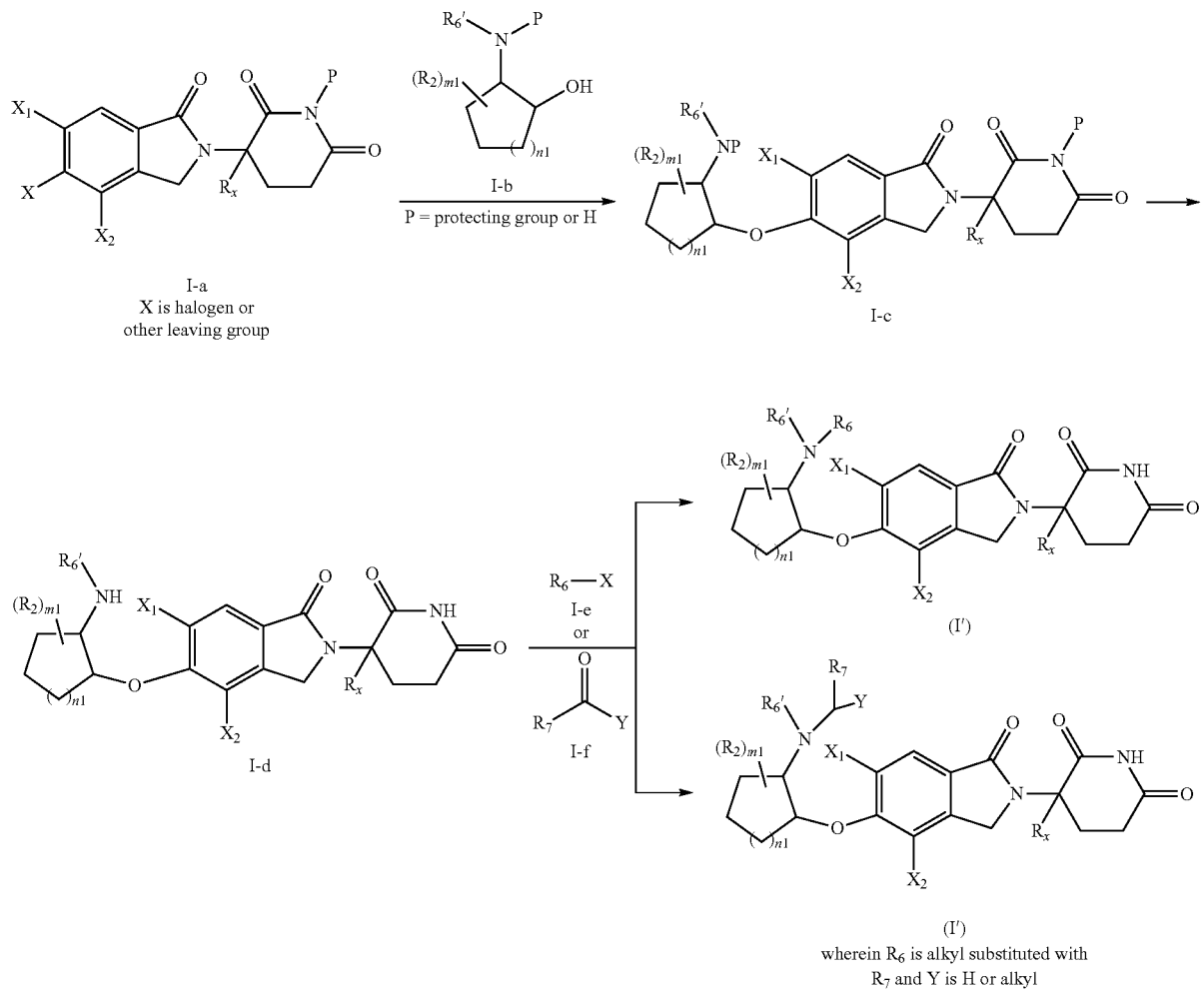

wherein $R_x$, $R_2$, $R_{6'}$, $R_7$, $X_1$, $X_2$, m1, and n1 are as defined in Formula (I').

The general way of preparing compounds of Formula (I') wherein $R_1$ is

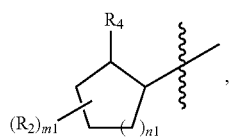

$R_4$ is —$NR_6R_{6'}$, and $R_6$ is alkyl substituted with $R_7$ or optionally substituted alkyl using intermediates I-a, I-b, I-c, I-d, I-e, and I-f is outlined in General Scheme I. Coupling of I-a with 1,2-aminoalcohol I-b using a catalyst (e.g., Ni(g-lyme)Cl$_2$ with 4,4-di-tert-butyl-2,2'-dipyridyl (dtbbpy)) and photocatalyst (e.g., 4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III)hexafluorophosphate (Ir [(dF(CF$_3$)ppy)$_2$dtbbpy]PF$_6$)), a base (e.g., 2,2,6,6-tetramethylpiperidine (TMP), quinuclidine or potassium carbonate (K$_2$CO$_3$)), and in a solvent, (e.g., acetonitrile (MeCN)), under irradiation of blue LED light yields I-c. When P is a protecting group (e.g. tert-butyloxycarbonyl (Boc) or 2-(trimethylsilyl)ethoxymethyl (SEM)), intermediate I-c is deprotected using a strong acid such as trifluoroacetic acid (TFA), methanesulfonic acid (MsOH), or hydrochloric acid (HCl) in a solvent (e.g., tetrahydrofuran (THF), MeCN, or dichloromethane (DCM)) optionally at elevated temperature to provide I-d. Reductive amination of I-d with aldehyde or ketone I-f provides compounds of Formula (I') where $R_6$ is a substituted alkyl. Alternatively, compounds of Formula (I') wherein $R_6$ is an optionally substituted alkyl can be obtained by alkylation of I-d with alkyl halide, tosylate or mesylate I-e in the presence of a base (e.g., triethylamine (Et$_3$N), N,N-diisopropylethylamine (i-Pr$_2$NEt), cesium carbonate (Cs$_2$CO$_3$), etc.), in a solvent (e.g., MeCN, N,N-dimethylformamide (DMF), etc.), and optionally at elevated temperature.

General Scheme II

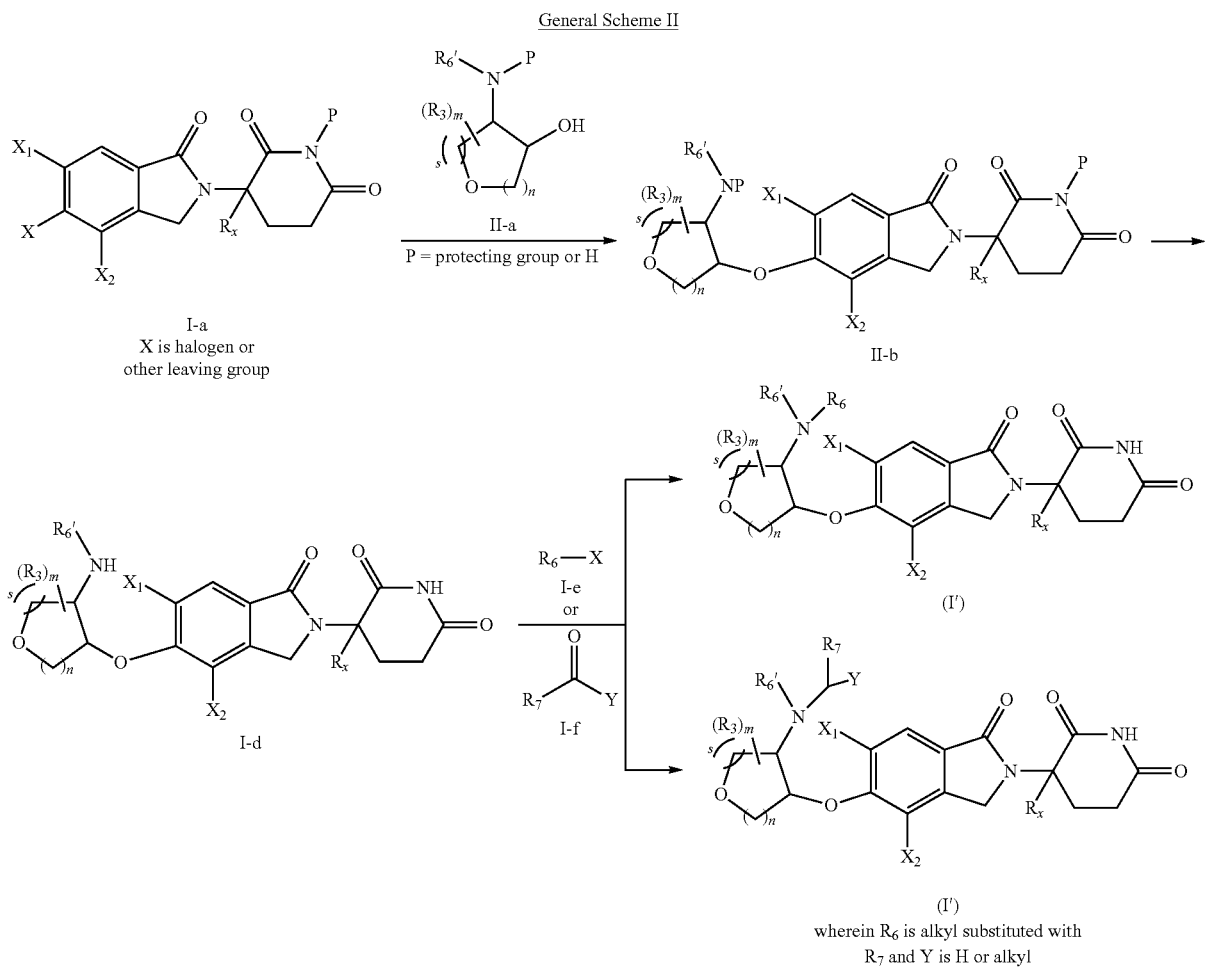

wherein $R_x$, $R_2$, $R_{6'}$, $R_7$, $X_1$, $X_2$, m, n, and s are as defined in Formula (I').

The general way of preparing compounds of Formula (I') wherein $R_1$ is

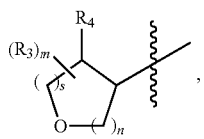

$R_4$ is —$NR_6R_{6'}$, and $R_6$ is alkyl substituted with $R_7$ or optionally substituted alkyl using intermediates I-a, II-a, II-b, II-c, I-e, and I-f is outlined in General Scheme II. Coupling of I-a with 1,2-aminoalcohol II-a using a catalyst (e.g., Ni(glyme)Cl$_2$ with 4,4-di-tert-butyl-2,2'-dipyridyl (dtbbpy)) and a photocatalyst (e.g., 4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate(Ir[(dF(CF$_3$)ppy)$_2$dtbbpy]PF$_6$)), a base (e.g., TMP, quinuclidine or K$_2$CO$_3$), and in a solvent, (e.g., MeCN), under irradiation of blue LED light yields II-b. When P is a protecting group (e.g., Boc or SEM), intermediate II-b is deprotected using a strong acid such as TFA, MsOH, or HCl in a solvent (e.g., THF, MeCN, or DCM) optionally at elevated temperature to provide II-c. Reductive amination of II-c with aldehyde or ketone I-f provides compounds of Formula (I') where $R_6$ is a substituted alkyl. Alternatively, compounds of Formula (I') wherein $R_6$ is an optionally substituted alkyl can be obtained by alkylation of II-c with alkyl halide, tosylate or mesylate I-e in the presence of a base (e.g., Et$_3$N, i-Pr$_2$NEt, Cs$_2$CO$_3$, etc.), in a solvent (e.g., MeCN, DMF, etc.), and optionally at elevated temperature.

General Scheme III

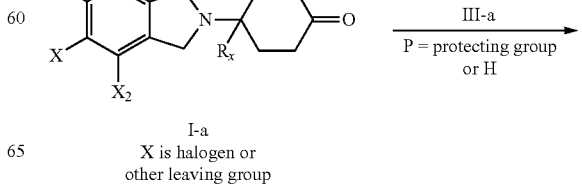

-continued

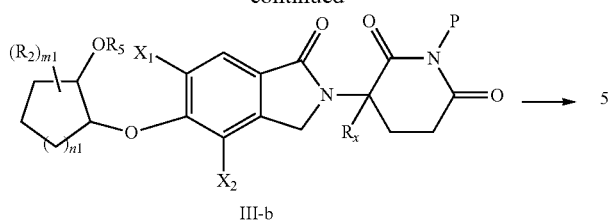

III-b

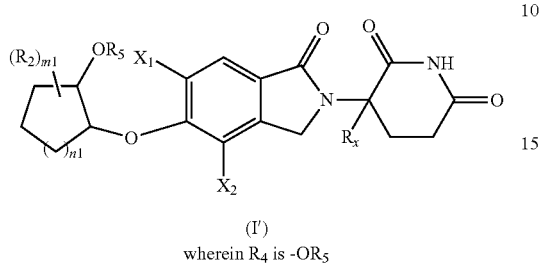

(I')
wherein R₄ is -OR₅ wherein $R_x$, $R_2$, $R_5$, $X_1$, $X_2$, m1, and n1 are as defined in Formula (I').

The general way of preparing compounds of Formula (I') wherein $R_1$ is

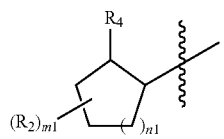

and $R_4$ is —OR₅, using intermediates I-a, III-a, and III-b is outlined in General Scheme III. Coupling of I-a with 1,2-diols or 1,2-etheralcohols III-a using a catalyst (e.g., Ni(glyme)Cl₂ with 4,4-di-tert-butyl-2,2'-dipyridyl (dtbbpy)) and a photocatalyst (e.g., 4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III)hexafluorophosphate (Ir[(dF(CF₃)ppy)₂dtbbpy]PF₆)), a base (e.g., TMP, quinuclidine or K₂CO₃), and in a solvent, (e.g., MeCN), under irradiation of blue LED light yields III-b. When P is a protecting group (e.g., SEM), intermediate III-b is deprotected using a strong acid such as TFA, MsOH, or HCl in a solvent (e.g., THF, MeCN, or DCM) optionally at elevated temperature to provide the desired compounds of Formula (I') wherein R₅ is H or substituted alkyl.

General Scheme IV

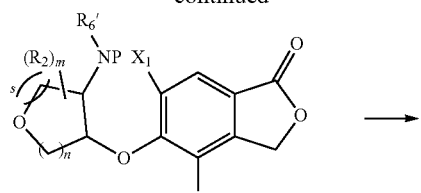

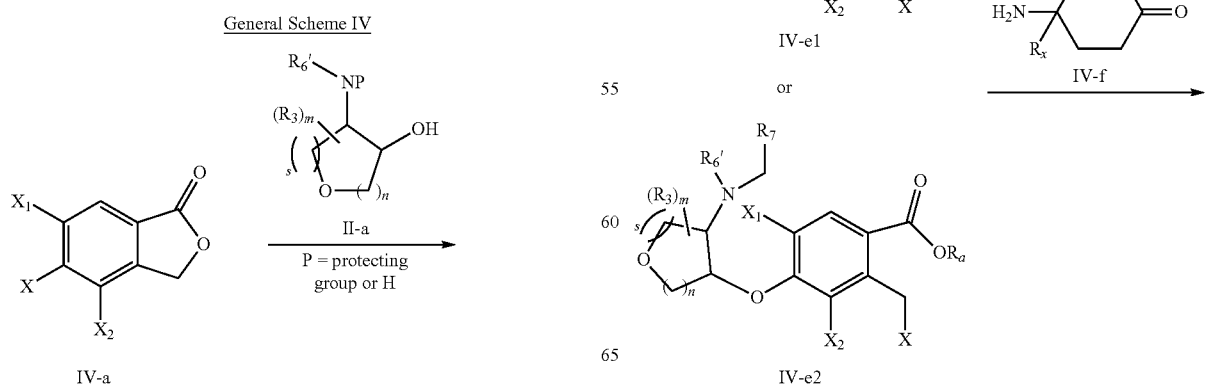

$R_a$ = alkyl, aryl, heteroaryl, haloalkyl
X is halogen or other leaving group

-continued

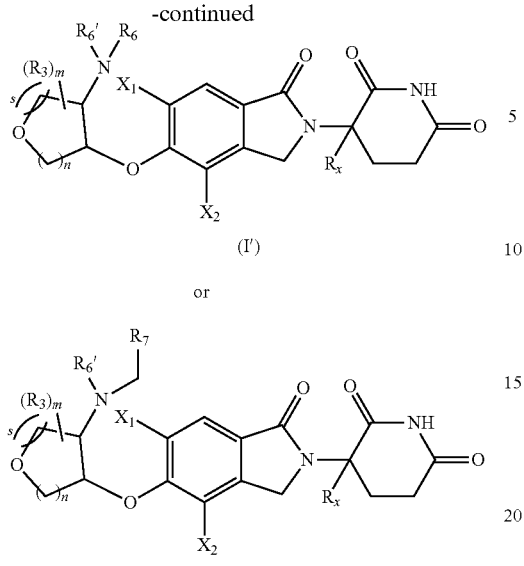

(I')

or

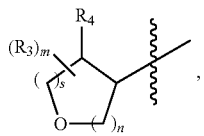

(I')

wherein R$_6$ is alkyl substituted with R$_7$
R$_7$ and Y are H or alykl wherein R$_x$, R$_3$, R$_6'$, R$_7$, X$_1$, X$_2$, m, n, and s are as defined in Formula (I').

The general way of preparing compounds of Formula (I') wherein R$_1$ is

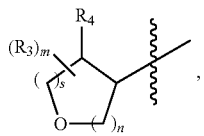,

R$_4$ is —NR$_6$R$_6'$, and R$_6$ is alkyl substituted with R$_7$ or optionally substituted alkyl using intermediates IV-a, IV-b, IV-c, IV-d1, IV-d2, IV-e1, IV-e2, IV-f, I-e, and I-f is outlined in General Scheme IV. Coupling of IV-a with 1,2-aminoalcohol II-a using a catalyst (e.g., Ni(glyme)Cl$_2$ with 4,4-di-tert-butyl-2,2'-dipyridyl (dtbbpy)) and a photocatalyst, (e.g., 4,4'-bis(1,1-dimethylethyl)-2,2'-bipyridine-N1,N1']bis[3,5-difluoro-2-[5-(trifluoromethyl)-2-pyridinyl-N]phenyl-C] Iridium(III) hexafluorophosphate(Ir[(dF(CF$_3$)ppy)$_2$dtbbpy] PF$_6$)), a base (e.g., TMP, quinuclidine, or K$_2$CO$_3$), and in a solvent, (e.g., MeCN), under irradiation of blue LED light yields IV-b. When P is a protecting group (e.g., Boc), intermediate IV-b is deprotected using a strong acid such as TFA or HCl in a solvent (e.g. THF or DCM) optionally at elevated temperature yields IV-c. Reductive amination of IV-c with aldehyde or ketone I-f provides IV-d. Alternatively, compounds IV-d can be obtained by alkylation of IV-c with an alkyl halide, tosylate or mesylate I-e in the presence of a base (e.g., Et$_3$N, i-Pr$_2$NEt, Cs$_2$CO$_3$, etc.), in a solvent (e.g., MeCN, DMF, etc.), and optionally at elevated temperature. Intermediate IV-d can then be converted to the corresponding haloester intermediate IV-e using SOCl$_2$ in a solvent (e.g., EtOH) at elevated temperatures. Cyclization of IV-e with 3-aminopiperidine-2,6-dione IV-f (or its HCl or CF$_3$CO$_2$H salt) with base (e.g., i-Pr$_2$NEt) in a solvent (e.g., DMF) at elevated temperature provides compounds of Formula (I') wherein R$_6$ is a substituted alkyl.

General Scheme V:

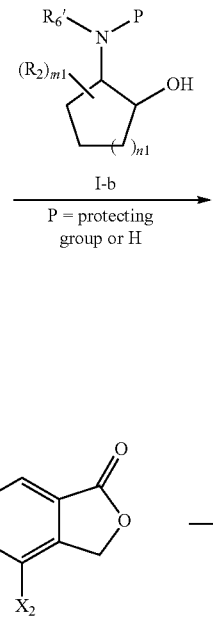

IV-a

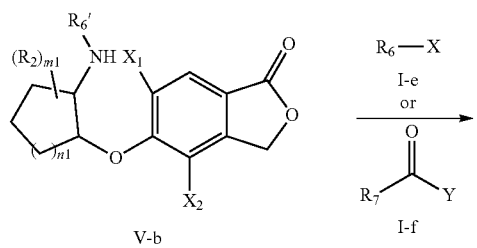

V-a

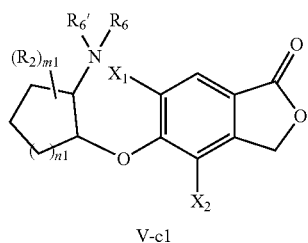

V-b

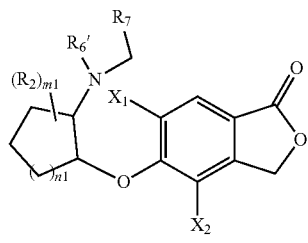

V-c1 or

V-c2

R$_a$ = alkyl, aryl, heteroaryl, haloalkyl
X is halogen or other leaving group

-continued

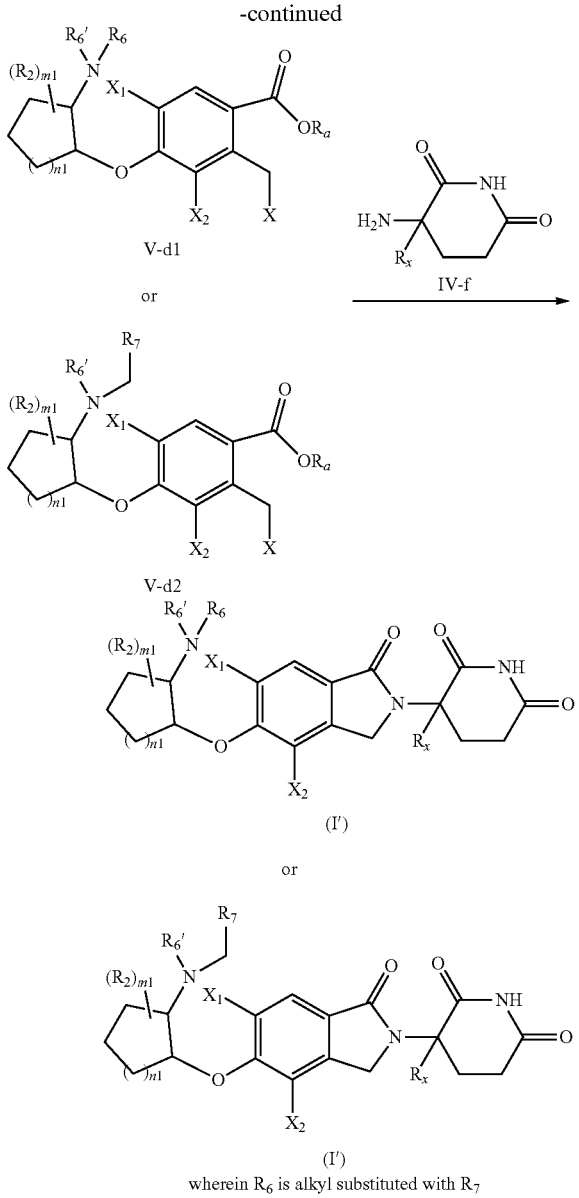

wherein R₆ is alkyl substituted with R₇
R₇ and Y are H or alykl wherein $R_x$, $R_3$, $R_{6'}$, $R_7$, $X_1$, $X_2$, m, n, and s are as defined in Formula (I').

The general way of preparing compounds of Formula (I') wherein $R_1$ is

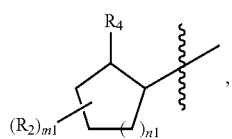

$R_4$ is —$NR_6R_{6'}$, and $R_6$ is alkyl substituted with $R_7$ or optionally substituted alkyl using intermediates IV-a, IV-f, V-a, V-b, V-c1, V-c2, V-d1, V-d2, I-b, I-e, and I-f is outlined in General Scheme V. Coupling of IV-a with 1,2-aminoalcohol I-b using a catalyst (e.g., Ni(glyme)Cl₂ with 4,4-di-tert-butyl-2,2'-dipyridyl (dtbbpy)) and a photocatalyst, (e.g., 4,4'-bis(1,1-dimethylethyl)-2,2'-bipyridine-N1,N1']bis[3,5-difluoro-2-[5-(trifluoromethyl)-2-pyridinyl-N]phenyl-C] Iridium(III)hexafluorophosphate (Ir[(dF(CF₃)ppy)₂dtbbpy] PF₆)), a base (e.g., TMP, quinuclidine, or K₂CO₃), and in a solvent, (e.g., MeCN), under irradiation of blue LED light yields V-a. When P is a protecting group (e.g., Boc), intermediate V-a is deprotected using a strong acid such as TFA or HCl in a solvent (e.g., THF or DCM) optionally at elevated temperature yields V-b. Reductive amination of V-b with aldehyde or ketone I-f provides V-c2. V-c1 can be obtained by alkylation of V-b with an alkyl halide, tosylate or mesylate I-e in the presence of a base (e.g., Et₃N, i-Pr₂NEt, Cs₂CO₃, etc.), in a solvent (e.g., MeCN, DMF, etc.), and optionally at elevated temperature. Intermediates V-c1 and V-c2 can then be converted to the corresponding haloester intermediate V-d1 and Vd2 using SOCl₂ in a solvent (e.g., EtOH) and optionally at elevated temperatures. Cyclization of V-d1 or Vd2 with 3-aminopiperidine-2,6-dione IV-f (or its HCl or CF₃CO₂H salt) using a base (e.g., i-Pr₂NEt) in a solvent (e.g., DMF) and optionally at elevated temperature provides compounds of Formula (I') wherein $R_6$ is a substituted alkyl or an optionally substituted alkyl.

A mixture of enantiomers, diastereomers, and cis/trans isomers resulting from the process described above can be separated into their single components by chiral salt technique, chromatography using normal phase, reverse phase or chiral column, depending on the nature of the separation.

Any resulting racemates of compounds of the present disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid, or camphor-10-sulfonic acid. Racemic compounds of the present disclosure or racemic intermediates can also be resolved by chiral chromatography, e.g., high pressure liquid chromatography (HPLC) using a chiral adsorbent.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

It should be understood that in the description and formula shown above, the various groups $R_x$, $R_2$, $R_3$, $R_5$, $R_{6'}$, $R_7$, $X_1$, $X_2$, m, m1, n, n1, and s and other variables are as defined above, except where otherwise indicated. Furthermore, for synthetic purposes, the compounds of General Schemes I, II, III, IV, and V are merely representative with elected radicals to illustrate the general synthetic methodology of the compounds of Formula (I') as defined herein.

F. Methods of Using Compounds of Formula (I') or Formula (I)

Another aspect of the disclosure relates to a method of treating, preventing, inhibiting, or eliminating a disease or disorder in a patient associated with modulation of IKZF2 protein levels. The method comprises administering to a patient in need of a treatment for diseases or disorders associated with modulation of IKZF2 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the disclosure relates to a method of treating, preventing, inhibiting, or eliminating a disease or disorder that is affected by the modulation of IKZF2 protein levels. The method comprises administering to a patient in need of a treatment for diseases or disorders affected by the modulation of IKZF2 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the disclosure relates to a method of treating, preventing, inhibiting, or eliminating a disease or disorder that is affected by the reduction of IKZF2 protein levels. The method comprises administering to a patient in need of a treatment for diseases or disorders affected by the reduction of IKZF2 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the disclosure relates to a method of treating, preventing, inhibiting, or eliminating a disease or disorder that is affected by a decrease in IKZF2 protein levels. The method comprises administering to a patient in need of a treatment for diseases or disorders affected by the reduction or decrease of IKZF2 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for the treatment, prevention, inhibition or elimination of a disease or disorder that is affected by the modulation of IKZF2 protein levels.

In another aspect, the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for the treatment, prevention, inhibition or elimination of a disease or disorder that is affected by the reduction of or a decrease in IKZF2 protein levels.

Another aspect of the disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder that is affected by the modulation of IKZF2 protein levels.

Another aspect of the disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder that is affected by the reduction of or a decrease in IKZF2 protein levels.

In another aspect, the present disclosure is directed to a method of modulating IKZF2 protein levels. The method involves administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 protein levels are modulated through degradation of the IKZF2 protein. In other embodiments, IKZF2 protein levels are modulated through degradation of the IKZF2 protein mediated by an E3 ligase.

Another aspect of the present disclosure relates to a method of treating, preventing, inhibiting, or eliminating a disease or disorder in a patient associated with the reduction of or decrease in IKZF2 protein levels, the method comprising administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

The present disclosure also relates to the use of a degrader of IKZF2 for the preparation of a medicament used in the treatment, prevention, inhibition or elimination of a IKZF2-dependent disease or disorder, wherein the medicament comprises a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to a method for treating, preventing, inhibiting, or eliminating a IKZF2-dependent disease or disorder, wherein the medicament comprises a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to a method for the manufacture of a medicament for treating, preventing, inhibiting, or eliminating a IKZF2-dependent disease or disorder mediated, wherein the medicament comprises a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease or disorder associated with the modulation of IKZF2 protein levels. In some embodiments, IKZF2 levels are modulated through degradation of the IKZF2 protein. In some embodiments, IKZF2 protein levels are modulated through degradation of the IKZF2 protein mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with the modulation of IKZF2 protein levels. In some embodiments, IKZF2 levels are modulated through degradation of the IKZF2 protein. In some embodiments, IKZF2 protein levels are modulated through degradation of the IKZF2 protein mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of a disease associated with the modulation of IKZF2 protein levels. In some embodiments, IKZF2 protein levels are modulated through degradation of the IKZF2 protein. In some embodiments, IKZF2 protein levels are modulated through degradation of the IKZF2 protein mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease or disorder associated with the reduction of IKZF2 protein levels. In some embodiments, IKZF2 levels are reduced through degradation of the IKZF2 protein. In some embodiments, IKZF2 levels are reduced through degradation of the IKZF2 protein mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with the reduction of IKZF2 protein levels. In some embodiments, IKZF2 levels are reduced through degradation of the IKZF2 protein. In some embodiments, IKZF2 levels are reduced through degradation of the IKZF2 protein mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of a disease associated with the reduction of IKZF2 protein levels. In some embodiments, IKZF2 protein levels are reduced through degradation of the IKZF2 protein. In some embodiments, IKZF2 levels are reduced through degradation of the IKZF2 protein mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease or disorder associated with a decrease in IKZF2 protein levels. In some embodiments, IKZF2 levels are decreased through degradation of the IKZF2 protein. In some embodiments, IKZF2 protein levels are decreased through degradation of the IKZF2 protein mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with a decrease in IKZF2 protein levels. In some embodiments, IKZF2 levels are decreased through degradation of the IKZF2 protein. In some embodiments, IKZF2 protein levels are decreased through degradation of the IKZF2 protein mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of a disease associated with a decrease in IKZF2 protein levels. In some embodiments, IKZF2 protein levels are reduced through degradation of the IKZF2 protein. In some embodiments, IKZF2 protein levels are decreased through degradation of the IKZF2 protein mediated by an E3 ligase.

In another aspect, the present disclosure relates to a method of inhibiting IKZF2 activity through degradation of IKZF2. In some embodiments, IKZF2 and IKZF4 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for inhibiting IKZF2 activity through degradation of IKZF2. In some embodiments, IKZF2 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the inhibition of IKZF2 activity through degradation of IKZF2. In some embodiments, IKZF2 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for inhibiting IKZF2 activity through degradation of IKZF2. In some embodiments, IKZF2 protein degradation is mediated by an E3 ligase.

In another aspect, the present disclosure relates to a method of inhibiting IKZF2 and IKZF4 activity through degradation of IKZF2 and IKZF4. In some embodiments, IKZF2 and IKZF4 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for inhibiting IKZF2 and IKZF4 activity through degradation of IKZF2 and IKZF4. In some embodiments, IKZF2 and IKZF4 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the inhibition of IKZF2 and IKZF4 activity through degradation of IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for inhibiting IKZF2 and IKZF4 activity through degradation of IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for inhibiting IKZF2 and IKZF4 activity through degradation of IKZF2 and IKZF4. In some embodiments, IKZF2 and IKZF4 protein degradation is mediated by an E3 ligase.

Another aspect of the disclosure relates to a method of treating, preventing, inhibiting, or eliminating a disease or disorder associated with modulation of IKZF2 and IKZF4 protein levels. The method comprises administering to a patient in need of a treatment for diseases or disorders associated with modulation of IKZF2 and IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure is directed to a method of modulating IKZF2 and IKZF4 protein levels. The method involves administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 and IKZF4 protein levels are modulated through degradation of the IKZF2 and IKZF4 proteins. In other embodiments, IKZF2 and IKZF4 protein levels are modulated through degradation of the IKZF2 and IKZF4 proteins mediated by an E3 ligase.

Another aspect of the disclosure relates to a method of treating, preventing, inhibiting, or eliminating a disease or disorder associated with modulation of, reduction of, or a decrease in IKZF4 protein levels. The method comprises administering to a patient in need of a treatment for diseases or disorders associated with modulation of, reduction of, or decrease in IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF4 protein levels are modulated, reduced, or decreased through degradation of the IKZF4 proteins. In some embodiments, IKZF4 protein levels are modulated, reduced, or decreased through degradation of the IKZF4 protein mediated by an E3 ligase.

In another aspect, the present disclosure is directed to a method of modulating, reducing or decreasing IKZF4 protein levels. The method involves administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF4 protein levels are modulated, reduced, or decreased through degradation of the IKZF4 proteins. In other embodiments, IKZF4 protein levels are modulated, reduced, or decreased through degradation of the IKZF4 protein mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for treating, preventing, inhibiting, or eliminating a disease or disorder associated with modulation of, reduction of, or a decrease in IKZF4 protein levels. In some embodiments, IKZF4 protein levels are modulated, reduced, or decreased through degradation of the IKZF4 proteins. In some embodiments, IKZF4 protein levels are modulated, reduced, or decreased through degradation of the IKZF4 protein mediated by an E3 ligase.

Another aspect of the disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for use in treating, preventing, inhibiting, or eliminating a disease or disorder associated with modulation of, reduction of, or a decrease in IKZF4 protein levels. In some embodiments, IKZF4 protein levels are modulated, reduced, or decreased through degradation of the IKZF4 proteins. In some embodiments, IKZF4 protein levels are modulated, reduced, or decreased through degradation of the IKZF4 protein mediated by an E3 ligase.

In another aspect, the present disclosure is directed to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder associated with modulation of, reduction of, or a decrease in IKZF4 protein levels. In some embodiments, IKZF4 protein levels are modulated, reduced, or decreased through degradation of the IKZF4 proteins. In some embodiments, IKZF4 protein levels are modulated, reduced, or decreased through degradation of the IKZF4 protein mediated by an E3 ligase.

Another aspect of the disclosure relates to a method of treating, preventing, inhibiting, or eliminating a disease or disorder associated with the reduction of IKZF2 and IKZF4 protein levels. The method comprises administering to a patient in need of a treatment for diseases or disorders associated with reduction of IKZF2 and IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure is directed to a method of reducing IKZF2 and IKZF4 protein levels. The method involves administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

Another aspect of the disclosure relates to a method of treating, preventing, inhibiting, or eliminating a disease or disorder associated with a decrease in IKZF2 and IKZF4 protein levels. The method comprises administering to a patient in need of a treatment for diseases or disorders associated with a decrease of IKZF2 and IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure is directed to a method of decreasing IKZF2 and IKZF4 protein levels. The method involves administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 and IKZF4 protein levels are decreased through degradation of the IKZF2 and IKZF4 proteins. In some embodiments, IKZF2 and IKZF4 protein levels are decreased through degradation of the IKZF2 and IKZF4 proteins mediated by an E3 ligase.

Another aspect of the present disclosure relates to a method of treating, preventing, inhibiting, or eliminating a disease or disorder in a patient associated with the modulation of IKZF2 and IKZF4 protein levels, the method comprising administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In one embodiment, the disease or disorder is selected from the group consisting of cancer and metastasis.

In another aspect, the present disclosure relates to a method of treating, preventing, inhibiting, or eliminating a disease or disorder in a patient associated with the reduction of IKZF2 and IKZF4 protein levels, the method comprising administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In one embodiment, the disease or disorder is selected from the group consisting of cancer and metastasis.

Another aspect of the present disclosure relates to a method of treating, preventing, inhibiting, or eliminating a disease or disorder in a patient associated with a decrease in IKZF2 and IKZF4 protein levels, the method comprising administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In one embodiment, the disease or disorder is selected from the group consisting of cancer and metastasis.

The present disclosure also relates to the use of a modulator of IKZF2 and IKZF4 protein levels for the preparation of a medicament used in the treatment, prevention, inhibition or elimination of a IKZF2 and IKZF4-dependent disease or disorder, wherein the medicament comprises a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In another aspect, the present disclosure relates to a method for the manufacture of a medicament for treating, preventing, inhibiting, or eliminating a IKZF2 and IKZF4-dependent disease or disorder, wherein the medicament comprises a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease associated with the modulation of IKZF2 and IKZF4 protein levels. In some embodiments, IKZF2 and IKZF4 protein levels are modulated through degradation of the IKZF2 and IKZF4 proteins. In other embodiments, IKZF2 and IKZF4 protein levels are modulated through degradation of the IKZF2 and IKZF4 proteins mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with the modulation of IKZF2 and IKZF4 protein levels. In some embodiments, IKZF2 and IKZF4 protein levels are modulated through degradation of the IKZF2 and IKZF4 proteins. In other embodiments, IKZF2 and IKZF4 protein levels are modulated through degradation of the IKZF2 and IKZF4 proteins mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease associated with the reduction of IKZF2 and IKZF4 protein levels. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with the reduction of IKZF2 and IKZF4 protein levels. In some embodiments, IKZF2 and IKZF4 are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

Another aspect of the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a disease associated with a decrease in IKZF2 and IKZF4 protein levels. In some embodiments, IKZF2 and IKZF4 protein levels are decreased through degradation of the IKZF2 and IKZF4 proteins. In some embodiments, IKZF2 and IKZF4 protein levels are decreased through degradation of the IKZF2 and IKZF4 proteins mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating a disease associated with a decrease in IKZF2 and IKZF4 protein levels. In some embodiments, IKZF2 and IKZF4 are decreased through degradation of the IKZF2 and IKZF4 proteins. In some embodiments, IKZF2 and IKZF4 protein levels are decreased through degradation of the IKZF2 and IKZF4 proteins mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of a disease associated with the modulation of IKZF2 and IKZF4 protein levels. In some embodiments, IKZF2 and IKZF4 protein levels are modulated through degradation of the IKZF2 and IKZF4 proteins. In other embodiments, IKZF2 and IKZF4 protein levels are modulated through degradation of the IKZF2 and IKZF4 proteins mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2-dependent disease or disorder by reducing or decreasing IKZF2 protein levels, wherein reduction or decrease of IKZF2 protein levels treats the IKZF2-dependent disease or disorder.

In another aspect, the present disclosure the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of an IKZF2-dependent disease or disorder by reducing or decreasing IKZF2 protein levels wherein reduction of or decrease in IKZF2 protein levels treats the IKZF2-dependent disease or disorder.

In another aspect, the present disclosure the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for treating an IKZF2-dependent disease or disorder by reducing or decreasing IKZF2 protein levels wherein reduction of or decrease in IKZF2 protein levels treats the IKZF2-dependent disease or disorder.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2 and IKZF4-dependent disease or disorder by reducing or decreasing IKZF2 and IKZF4 protein levels wherein the reduction of or decrease in IKZF2 and IKZF4 protein levels treats the IKZF2 and IKZF4-dependent disease or disorder.

In another aspect, the present disclosure the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of an IKZF2 and IKZF4-dependent disease or disorder by reducing or decreasing IKZF2 and IKZF4 protein levels wherein the reduction of or decrease in IKZF2 and IKZF4 protein levels treats the IKZF2 and IKZF4-dependent disease or disorder.

In another aspect, the present disclosure the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for treating an IKZF2 and IKZF4-dependent disease or disorder by reducing or decreasing IKZF2 and IKZF4 protein levels wherein the reduction of or decrease in IKZF2 and IKZF4 protein levels treats the IKZF2 and IKZF4-dependent disease or disorder.

Another aspect of the disclosure relates to a method of treating cancer. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of treating cancer.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating cancer.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of cancer.

Another aspect of the disclosure relates to a method of treating an IKZF2-dependent cancer. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of treating an IKZF2-dependent cancer.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent cancer.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2-dependent cancer.

Another aspect of the disclosure relates to a method of treating an IKZF2-dependent and IKZF4-dependent cancer. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of treating an IKZF2-dependent and IKZF4-dependent cancer.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent and IKZF4-dependent cancer.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2-dependent and IKZF4-dependent cancer.

Another aspect of the disclosure relates to a method of treating a cancer affected by the modulation of, the reduction of, or a decrease in IKZF2 protein levels. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of treating a cancer affected by the modulation of, the reduction of, or a decrease in IKZF2 protein levels Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a cancer affected by the modulation of, the reduction of, or a decrease in IKZF2 protein levels.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of a cancer affected by the modulation of, the reduction of, or a decrease in IKZF2 protein levels.

Another aspect of the disclosure relates to a method of treating a cancer affected by the modulation of, the reduction of, or a decrease in IKZF2 and IKZF4 protein levels. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the treatment of treating a cancer affected by the modulation of, the reduction of, or a decrease in IKZF2 and IKZF4 protein levels.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating a cancer affected by the modulation of, the reduction of, or a decrease in IKZF2 and IKZF4 protein levels.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of a cancer affected by the modulation of, the reduction of, or a decrease in IKZF2 and IKZF4 protein levels.

Another aspect of the disclosure relates to a method of degrading IKZF2. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 protein degradation is mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for degrading IKZF2. In some embodiments, IKZF2 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the degradation IKZF2. In some embodiments, IKZF2 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for degrading IKZF2. In some embodiments, IKZF2 protein degradation is mediated by an E3 ligase.

In another aspect, the present disclosure relates to a method of modulating IKZF2 protein levels through degradation of IKZF2. In some embodiments, IKZF2 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for modulating IKZF2 protein levels through degradation of IKZF2. In some embodiments, IKZF2 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the modulation IKZF2 protein levels through degradation of IKZF2. In some embodiments, IKZF2 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for modulating IKZF2 protein levels through degradation of IKZF2. In some embodiments, IKZF2 protein degradation is mediated by an E3 ligase.

Another aspect of the disclosure relates to a method of treating an IKZF2-dependent disease or disorder in a patient in need thereof by modulating IKZF2 protein levels through the degradation of IKZF2. In some embodiments, IKZF2 protein degradation is mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for treating an IKZF2-dependent disease or disorder in a patient in need thereof by modulating IKZF2 protein levels through the degradation of IKZF2. In some embodiments, IKZF2 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating an IKZF2-dependent disease or disorder in a patient in need thereof, by modulating IKZF2 protein levels through the degradation of IKZF2. In some embodiments, IKZF2 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent disease or disorder in a patient in need thereof by modulating IKZF2 protein levels through the degradation of IKZF2. In some embodiments, IKZF2 protein degradation is mediated by an E3 ligase.

In another aspect, the present disclosure relates to a method of degrading IKZF2. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, for degrading IKZF2. In some embodiments, IKZF2 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in degrading IKZF2. In some embodiments, IKZF2 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for degrading IKZF2. In some embodiments, IKZF2 protein degradation is mediated by an E3 ligase.

Another aspect of the disclosure relates to a method of reducing the proliferation of a cell, the method comprising contacting the cell with a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, that reduces IKZF2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

In another aspect, the present disclosure relates to the use a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for reducing the proliferation of a cell by reducing IKZF2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in reducing the proliferation of a cell by IKZF2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for reducing the proliferation of a cell by reducing IKZF2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

In another aspect, the disclosure relates to a method of treating, preventing, inhibiting, or eliminating a disease or disorder that is affected by the modulation of IKZF2 and IKZF4 protein levels. The method comprises administering to a patient in need of a treatment for diseases or disorders affected by the modulation of IKZF2 and IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the disclosure relates to a method of treating, preventing, inhibiting, or eliminating a disease or disorder that is affected by the reduction of or a decrease in IKZF2 and IKZF4 protein levels. The method comprises administering to a patient in need of a treatment for diseases or disorders affected by the reduction or decrease of IKZF2 and IKZF4 protein levels an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for the treatment, prevention, inhibition or elimination of a disease or disorder that is affected by the modulation of IKZF2 and IKZF4 protein levels.

Another aspect of the disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder that is affected by the modulation of IKZF2 and IKZF4 protein levels.

In another aspect, the disclosure relates to the use a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for the treatment, prevention, inhibition or elimination of a disease or disorder that is affected by the reduction of or a decrease in IKZF2 and IKZF4 protein levels.

Another aspect of the disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder that is affected by the reduction of or a decrease in IKZF2 and IKZF4 protein levels.

Another aspect of the disclosure relates to a method of degrading IKZF2 and IKZF4. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 and IKZF4 protein degradation is mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for degrading IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the degradation IKZF2 and IKZF4. In some embodiments, IKZF2 and IKZF4 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for degrading IKZF2 and IKZF4. In some embodiments, IKZF2 and IKZF4 protein degradation is mediated by an E3 ligase.

In another aspect, the present disclosure relates to a method of modulating IKZF2 and IKZF4 protein levels through degradation of IKZF2 and IKZF4. In some embodiments, IKZF2 and IKZF4 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for modulating IKZF2 and IKZF4 protein levels through degradation of IKZF2 and IKZF4. In some embodiments, IKZF2 and IKZF4 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the modulation of IKZF2 and IKZF4 protein levels through degradation of IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for modulating IKZF2 and IKZF4 protein levels through degradation of IKZF2 and IKZF4. In some embodiments, IKZF2 and IKZF4 protein degradation is mediated by an E3 ligase.

Another aspect of the disclosure relates to a method of treating an IKZF2-dependent and IKZF4-dependent disease or disorder in a patient in need thereof by modulating IKZF2 and IKZF4 protein levels through the degradation of IKZF2 and IKZF4. In some embodiments, IKZF2 and IKZF4 protein degradation is mediated by an E3 ligase.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for treating an IKZF2-dependent and IKZF4-dependent disease or disorder in a patient in need thereof by modulating IKZF2 and IKZF4 protein levels through the degradation of IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in treating an IKZF2-dependent and IKZF4-dependent disease or disorder in a patient in need thereof by modulating IKZF2 and IKZF4 protein levels through the degradation of IKZF2 and IKZF4. In some embodiments, IKZF2 and IKZF4 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent or IKZF4-dependent disease or disorder in a patient in need thereof by modulating IKZF2 and IKZF4 protein levels through the degradation of IKZF2 and IKZF4. In some embodiments, IKZF2 and IKZF4 protein degradation is mediated by an E3 ligase.

In another aspect, the present disclosure relates to a method of degrading IKZF2 and IKZF4. The method comprises administering to a patient in need thereof an effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof. In some embodiments, IKZF2 and IKZF4 protein degradation is mediated by an E3 ligase.

Another aspect of the disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for degrading IKZF2 and IKZF4. In some embodiments, IKZF2 and IKZF4 protein degradation is mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in degrading IKZF2 and IKZF4. In some embodiments, IKZF2 and IKZF4 protein degradation is mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for degrading IKZF2 and IKZF4. In some embodiments, IKZF2 and IKZF4 protein degradation is mediated by an E3 ligase.

Another aspect of the disclosure relates to a method of reducing the proliferation of a cell, the method comprising contacting the cell with a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, and reducing IKZF2 and IKZF4 protein levels. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

In another aspect, the present disclosure relates to the use a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for reducing the proliferation of a cell by reducing IKZF2 and IKZF4 protein levels. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in reducing the proliferation of a cell by reducing IKZF2 and IKZF4 protein levels. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

In another aspect, the present disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for reducing the proliferation of a cell by reducing IKZF2 and IKZF4 protein levels. In some embodiments, IKZF2 and IKZF4 protein levels are reduced through degradation of the IKZF2 and IKZF4 proteins. In other embodiments, IKZF2 and IKZF4 protein levels are reduced through degradation of the IKZF2 and IKZF4 proteins mediated by an E3 ligase.

In another aspect, the present disclosure relates to a method for treating an IKZF2-dependent disease or disorder. The method comprises the step of administering to a subject in need thereof a therapeutically effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, in the manufacture of a medicament for treating an IKZF2-dependent disease or disorder.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent disease or disorder.

In another aspect, the present disclosure relates to a method for treating an IKZF2-dependent and IKZF4-dependent disease or disorder. The method comprises the step of administering to a subject in need thereof a therapeutically effective amount of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the treatment of an IKZF2-dependent and IKZF4-dependent disease or disorder.

In another aspect, the present disclosure relates to the use of a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, in the manufacture of a medicament for treating an IKZF2-dependent and IKZF4-dependent disease or disorder.

Another aspect of the disclosure relates to a compound of Formula (I') or Formula (I), or a pharmaceutically acceptable salt, hydrate, solvate, prodrug, stereoisomer, or tautomer thereof, or a composition comprising a compound of Formula (I') or Formula (I), or a pharmaceutically acceptable salt, hydrate, solvate, prodrug, stereoisomer, or tautomer thereof, for use in the manufacture of a medicament for treating an IKZF2-dependent and IKZF4-dependent disease or disorder.

In another aspect, the present disclosure relates to a method of reducing IKZF2 protein levels. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the present disclosure relates to a method of reducing IKZF2 and IKZF4 protein levels. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the reduction of IKZF2 protein levels.

Another aspect of the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the reduction of IKZF2 and IKZF4 protein levels.

In another aspect, the present disclosure relates to the use of a compound of Formula (I') or Formula (I), or a pharmaceutically acceptable salt, hydrate, solvate, prodrug, stereoisomer, or tautomer thereof or a composition, in the manufacture of a medicament for reducing IKZF2 protein levels.

Another aspect of the present disclosure relates to the use of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, in the manufacture of a medicament for reducing IKZF2 and IKZF4 protein levels.

In another aspect, the present disclosure relates to a method of reducing IKZF2 protein levels, wherein reduction of IKZF2 protein levels treats or ameliorates the disease or disorder. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the present disclosure relates to a method of reducing IKZF2 and IKZF4 protein levels, wherein reduction of IKZF2 and IKZF4 protein levels treats or ameliorates the disease or disorder. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the reduction of IKZF2 protein levels, wherein reduction of IKZF2 protein levels treats or ameliorates the disease or disorder.

Another aspect of the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the reduction of IKZF2 and IKZF4 protein levels, wherein reduction of IKZF2 and IKZF4 protein levels treats or ameliorates the disease or disorder.

In another aspect, the present disclosure relates to the use of a compound of Formula (I') or Formula (I), or a pharmaceutically acceptable salt, hydrate, solvate, prodrug, stereoisomer, or tautomer thereof or a composition, in the manufacture of a medicament for reducing IKZF2 protein levels, wherein reduction of IKZF2 protein levels treats or ameliorates the disease or disorder.

Another aspect of the present disclosure relates to the use of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, in the manufacture of a medicament for reducing IKZF2 and IKZF4 protein levels, wherein reduction of IKZF2 and IKZF4 protein levels treats or ameliorates the disease or disorder.

In another aspect, the present disclosure relates to a method of treating a disease or disorder by reducing IKZF2 protein levels, wherein reduction of IKZF2 protein levels treats or ameliorates the disease or disorder. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

Another aspect of the present disclosure relates to a method of treating a disease or disorder by reducing IKZF2 and IKZF4 protein levels, wherein reduction of IKZF2 and IKZF4 protein levels treats or ameliorates the disease or disorder. The method comprises administering to the patient in need thereof a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof.

In another aspect, the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the treatment of a disease or disorder by reducing IKZF2 protein levels, wherein reduction of IKZF2 protein levels treats or ameliorates the disease or disorder.

Another aspect of the present disclosure relates to a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof for use in the treatment of a disease or disorder by reducing IKZF2 and IKZF4 protein levels, wherein reduction of IKZF2 and IKZF4 protein levels treats or ameliorates the disease or disorder.

In another aspect, the present disclosure relates to the use of a compound of Formula (I') or Formula (I), or a pharmaceutically acceptable salt, hydrate, solvate, prodrug, stereoisomer, or tautomer thereof or a composition, in the manufacture of a medicament for treating a disease or disorder by reducing IKZF2 protein levels, wherein reduction of IKZF2 protein levels treats or ameliorates the disease or disorder.

Another aspect of the present disclosure relates to the use of a compound of Formula (I') or Formula (I), or a pharmaceutically acceptable salt, hydrate, solvate, prodrug, stereoisomer, or tautomer thereof or a composition comprising a compound of Formula (I') or Formula (I), or a pharmaceutically acceptable salt, hydrate, solvate, prodrug, stereoisomer, or tautomer thereof, in the manufacture of a medicament for treating a disease or disorder by reducing IKZF2 and IKZF4 protein levels, wherein reduction of IKZF2 and IKZF4 protein levels treats or ameliorates the disease or disorder.

The compounds of the present disclosure present disclosure can be used for the treatment, of cancers including, but not limited to, liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid, or vaginal cancer or Epstein-Barr Virus-associated nasopharyngeal carcinoma, gastric cancer, rectal cancer, thyroid cancer, Hodgkin lymphoma or diffuse large B-cell lymphoma. In one embodiment, the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, cancer for which the immune response is deficient, an immunogenic cancer, Ewing's sarcoma, non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST).

In some embodiments of the methods above, the IKZF2-dependent disease or disorder is a disease or disorder including, but not limited to, liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid, or vaginal cancer or Epstein-Barr Virus-associated nasopharyngeal carcinoma, gastric cancer, rectal cancer, thyroid cancer, Hodgkin lymphoma or diffuse large B-cell lymphoma. In one embodiment, the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer and soft tissue sarcomas selected from rhabdomyosarcoma (RMS), synovial sarcoma, osteosarcoma, rhabdoid cancers, cancer for which the immune response is deficient, an immunogenic cancer, Ewing's sarcoma, non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST).

In some embodiments of the methods above, the disease or disorder affected by the modulation, reduction or decrease of IKZF2 and/or IKZF4 protein levels is a disease or disorder including, but not limited to, liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid, or vaginal cancer or Epstein-Barr Virus-associated nasopharyngeal carcinoma, gastric cancer, rectal cancer, thyroid cancer, Hodgkin lymphoma or diffuse large B-cell lymphoma. In one embodiment, the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, cancer for which the immune response is deficient, an immunogenic cancer, Ewing's sarcoma, non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST).

In some embodiments of the methods above, the IKZF2-dependent cancer and IKZF2-dependent and IKZF4-dependent cancer is a cancer selected from liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid, or vaginal cancer or Epstein-Barr Virus-associated nasopharyngeal carcinoma, gastric cancer, rectal cancer, thyroid cancer, Hodgkin lymphoma or diffuse large B-cell lymphoma. In one embodiment, the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, and soft tissue sarcomas selected from rhabdomyosarcoma (RMS), synovial sarcoma, osteosarcoma, rhabdoid cancers, cancer for which the immune response is deficient, an immunogenic cancer, Ewing's sarcoma, non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST).

In some embodiments of the methods above, IKZF2 protein levels are modulated by degradation of IKZF2. In some embodiments of the methods above, IKZF2 protein levels are reduced by degradation of IKZF2. In some embodiments of the methods above, IKZF2 protein levels are decreased by degradation of IKZF2.

In some embodiments of the methods above, IKZF2 and IKZF4 protein levels are modulated by degradation of IKZF2 and IKZF4. In some embodiments of the methods above, IKZF2 and IKZF4 protein levels are reduced by degradation of IKZF2 and IKZF4. In some embodiments of the methods above, IKZF2 protein levels are decreased by degradation of IKZF2 and IKZF4.

One therapeutic use of the compounds or compositions of the present disclosure, which modulate IKZF2 and/or IKZF4 protein levels by degradation of IKZF2 and/or IKZF4, is to provide treatment to patients or subjects suffering from cancer and metastasis.

The disclosed compounds of the disclosure can be administered in effective amounts to treat or prevent a disorder and/or prevent the development thereof in subjects.

Compounds of the application can be administered in therapeutically effective amounts in a combinational therapy with one or more therapeutic agents (pharmaceutical combinations) or modalities, e.g., non-drug therapies. For example, synergistic effects can occur with other anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent or a second agent that targets Helios or another cancer target) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

G. Administration, Pharmaceutical Compositions, and Dosing of Compounds of Formula (I') or Formula (I)

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride, and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes, and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles, and multilamellar vesicles. Liposomes can be formed from a variety of phospholipids, containing cholesterol, stearylamine or phosphatidylcholines.

In some embodiments, a film of lipid components is hydrated with an aqueous solution of drug to a form lipid layer encapsulating the drug, as described in U.S. Pat. No. 5,262,564, which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure is directed to pharmaceutical compositions comprising a compound of Formula (I') or Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

In one embodiment, the disclosure provides a kit comprising two or more separate pharmaceutical compositions, at least one of which contains a compound of the present disclosure. In one embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

The dosage regimen utilizing the disclosed compound is selected in accordance with a variety of factors including type, species, age, weight, sex, and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

H. Combination Therapy

The compounds of the disclosure can be administered in therapeutically effective amounts in a combinational therapy with one or more therapeutic agents (pharmaceutical combinations) or modalities, e.g., non-drug therapies. For example, synergistic effects can occur with other cancer agents. Where the compounds of the application are administered in conjunction with other therapies, dosages of the co-administered compounds will of course vary depending on the type of co-drug employed, on the specific drug employed, on the condition being treated and so forth.

The compounds can be administered simultaneously (as a single preparation or separate preparation), sequentially, separately, or over a period of time to the other drug therapy or treatment modality. In general, a combination therapy envisions administration of two or more drugs during a single cycle or course of therapy. A therapeutic agent is, for example, a chemical compound, peptide, antibody, antibody fragment or nucleic acid, which is therapeutically active or enhances the therapeutic activity when administered to a patient in combination with a compound of the present disclosure.

In one aspect, a compound of Formula (I') or Formula (I), or a pharmaceutically acceptable salt, hydrate, solvate, prodrug, stereoisomer, or tautomer thereof, of the present disclosure can be combined with other therapeutic agents, such as other anti-cancer agents, anti-allergic agents, anti-nausea agents (or anti-emetics), pain relievers, cytoprotective agents, and combinations thereof.

In some embodiments, the compounds of Formula (I') or Formula (I), or a pharmaceutically acceptable salt, hydrate, solvate, prodrug, stereoisomer, or tautomer thereof of the present disclosure are administered in combination with one or more second agent(s) selected from a PD-1 inhibitor, a PD-L1 inhibitor, a LAG-3 inhibitor, a cytokine, an A2A antagonist, a GITR agonist, a TIM-3 inhibitor, a STING agonist, and a TLR7 agonist, to treat a disease, e.g., cancer.

In another embodiment, one or more chemotherapeutic agents are used in combination with the compounds of Formula (I') or Formula (I), or a pharmaceutically acceptable salt, hydrate, solvate, prodrug, stereoisomer, or tautomer thereof, for treating a disease, e.g., cancer, wherein said chemotherapeutic agents include, but are not limited to, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), epirubicin (Ellence®), oxaliplatin (Eloxatin®), exemestane (Aromasin®), letrozole (Femara®), and fulvestrant (Faslodex®).

In other embodiments, the compounds of Formula (I') or Formula (I), or a pharmaceutically acceptable salt, hydrate, solvate, prodrug, stereoisomer, or tautomer thereof, of the present disclosure are used in combination with one or more other anti-HER2 antibodies, e.g., trastuzumab, pertuzumab, margetuximab, or HT-19 described above, or with other anti-HER2 conjugates, e.g., ado-trastuzumab emtansine (also known as Kadcyla®, or T-DM1).

In other embodiments, the compounds of Formula (I') or Formula (I), or a pharmaceutically acceptable salt, hydrate, solvate, prodrug, stereoisomer, or tautomer thereof, of the present disclosure are used in combination with one or more tyrosine kinase inhibitors, including but not limited to, EGFR inhibitors, Her3 inhibitors, IGFR inhibitors, and Met inhibitors, for treating a disease, e.g., cancer.

For example, tyrosine kinase inhibitors include but are not limited to, Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2, 4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); and Imatinib or Imatinib mesylate (Gilvec® and Gleevec®).

Epidermal growth factor receptor (EGFR) inhibitors include but are not limited to, Erlotinib hydrochloride (Tarceva®), Gefitinib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (Gilotrif®); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS187724-61-4).

EGFR antibodies include but are not limited to, Cetuximab (Erbitux®); Panitumumab (Vectibix®); Matuzumab (EMD-72000); Nimotuzumab (hR3); Zalutumumab; TheraCIM h-R3; MDX0447 (CAS 339151-96-1); and ch806 (mAb-806, CAS 946414-09-1).

Other HER2 inhibitors include but are not limited to, Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo[2,1-f][1,2,4]triazin-5-yl)methyl)piperidin-3-ol (BMS690514); (2E)-N-[4-[(3-Chloro-4-fluorophenyl)amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β,6aα)-octahydro-2- methylcyclopenta[c]pyrrol-5-yl]methoxy]-4-quinazolinamine (XL647, CAS 781613-23-8).

HER3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxy quinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU11271); (3Z)—N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU11274); (3Z)—N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1Hpyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin 3-yl]thio]-quinoline (SGX523, CAS 1022150-57-7); and (3Z)-5-[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGFR inhibitors include but are not limited to, BMS-754807, XL-228, OSI-906, GSK0904529A, A-928605, AXL1717, KW-2450, MK0646, AMG479, IMCA12, MEDI-573, and B1836845. See e.g., Yee, JNCI, 104; 975 (2012) for review.

In another embodiment, the compounds of Formula (I') or Formula (I) of the present disclosure are used in combination with one or more proliferation signalling pathway inhibitors, including but not limited to, MEK inhibitors, BRAF inhibitors, PI3K/Akt inhibitors, SHP2 inhibitors, and also mTOR inhibitors, and CDK inhibitors, for treating a disease, e.g., cancer.

For example, mitogen-activated protein kinase (MEK) inhibitors include but are not limited to, XL-518 (also known as GDC-0973, CAS No. 1029872-29-4, available from ACC Corp.); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); and Trametinib dimethyl sulfoxide (GSK-1120212, CAS 1204531-25-80).

BRAF inhibitors include, but are not limited to, Vemurafenib (or Zelboraf®), GDC-0879, PLX-4720 (available from Symansis), Dabrafenib (or GSK2118436), LGX 818, CEP-32496, UI-152, RAF 265, Regorafenib (BAY 73-4506), CCT239065, or Sorafenib (or Sorafenib Tosylate, or Nexavar®), or Ipilimumab (or MDX-010, MDX-101, or Yervoy).

Phosphoinositide 3-kinase (PI3K) inhibitors include, but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC0941, RG7321, GNE0941, Pictrelisib, or Pictilisib; and described in PCT Publication Nos. WO 09/036082 and WO 09/055730); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethylcyclopenta[5,6]naphtho[1,2-c]pyran-2,7,10(1H)-trione (PX866, CAS 502632-66-8); 8-Phenyl-2-(morpholin-4-yl)-chromen-4-one (LY294002, CAS 154447-36-6); (S)—N1-(4-methyl-5-(2-(1,1,1-trifluoro-2-methylpropan-2-yl)pyridin-4-yl)thiazol-2-yl)pyrrolidine-1,2-dicarboxamide (also known as BYL719 or Alpelisib); 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide (also known as GDC0032, RG7604, or Taselisib).

mTOR inhibitors include but are not limited to, Temsirolimus (Torisel®); Ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.04,9]hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N²-[1,4-dioxo-4-[[4-(4-oxo-8-phenyl-4H-1-benzopyran-2-yl)morpholinium-4-yl]methoxy]butyl]-L-arginylglycyl-L-□-aspartylL-serine-, inner salt (SF1126, CAS 936487-67-1).

CDK inhibitors include but are not limited to, Palbociclib (also known as PD-0332991, Ibrance®, 6-Acetyl-8-cyclopentyl-5-methyl-2-{[5-(1-piperazinyl)-2-pyridinyl]amino}pyrido[2,3-d]pyrimidin-7(8H)-one).

In yet another embodiment, the compounds of Formula (I') or Formula (I), or a pharmaceutically acceptable salt, hydrate, solvate, prodrug, stereoisomer, or tautomer thereof, of the present disclosure are used in combination with one or more pro-apoptotics, including but not limited to, IAP inhibitors, BCL2 inhibitors, MCL1 inhibitors, TRAIL agents, CHK inhibitors, for treating a disease, e.g., cancer.

For examples, IAP inhibitors include but are not limited to, LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and WO08/134679, all of which are incorporated herein by reference.

BCL-2 inhibitors include but are not limited to, 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386); Tetrocarcin A; Antimycin; Gossypol ((−)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); 4-[4-[(4'-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide (ABT-737, CAS 852808-04-9); and Navitoclax (ABT-263, CAS 923564-51-6).

Proapoptotic receptor agonists (PARAs) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab(CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinylpyrazolo[1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQRRRLYRSPAMPENL (SEQ ID NO: 33)), and CBP501 ((d-Bpa)sws(d-Phe-F5)(d-Cha)rrrqrr).

In a further embodiment, the compounds of Formula (I') or Formula (I), or a pharmaceutically acceptable salt, hydrate, solvate, prodrug, stereoisomer, or tautomer thereof, of the present disclosure are used in combination with one or more immunomodulators (e.g., one or more of an activator of a costimulatory molecule or an inhibitor of an immune checkpoint molecule), for treating a disease, e.g., cancer.

In certain embodiments, the immunomodulator is an activator of a costimulatory molecule. In one embodiment, the agonist of the costimulatory molecule is selected from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

GITR Agonists

In some embodiments, a GITR agonist is used in combination with a compound of Formula (I') or Formula (I), or a pharmaceutically acceptable salt, hydrate, solvate, prodrug, stereoisomer, or tautomer thereof, for treating a disease, e.g., cancer. In some embodiments, the GITR agonist is GWN323 (Novartis), BMS-986156, MK-4166 or MK-1248 (Merck), TRX518 (Leap Therapeutics), INCAGN1876 (Incyte/Agenus), AMG 228 (Amgen) or INBRX-110 (Inhibrx).

Exemplary GITR Agonists

In one embodiment, the GITR agonist is an anti-GITR antibody molecule. In one embodiment, the GITR agonist is an anti-GITR antibody molecule as described in WO 2016/057846, published on Apr. 14, 2016, entitled "Compositions and Methods of Use for Augmented Immune Response and Cancer Therapy," incorporated by reference in its entirety.

In one embodiment, the anti-GITR antibody molecule comprises at least one, two, three, four, five or six complementarity determining regions (CDRs) (or collectively all of the CDRs) from a heavy and light chain variable region comprising an amino acid sequence shown in Table 1 (e.g., from the heavy and light chain variable region sequences of MAB7 disclosed in Table 1), or encoded by a nucleotide sequence shown in Table 1. In some embodiments, the CDRs are according to the Kabat definition (e.g., as set out in Table 1). In some embodiments, the CDRs are according to the Chothia definition (e.g., as set out in Table 1). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 1, or encoded by a nucleotide sequence shown in Table 1.

In one embodiment, the anti-GITR antibody molecule comprises a heavy chain variable region (VH) comprising a VHCDR1 amino acid sequence of SEQ ID NO: 9, a VHCDR2 amino acid sequence of SEQ ID NO: 11, and a VHCDR3 amino acid sequence of SEQ ID NO: 13; and a light chain variable region (VL) comprising a VLCDR1 amino acid sequence of SEQ ID NO: 14, a VLCDR2 amino acid sequence of SEQ ID NO: 16, and a VLCDR3 amino acid sequence of SEQ ID NO: 18, each disclosed in Table 1.

In one embodiment, the anti-GITR antibody molecule comprises a VH comprising the amino acid sequence of SEQ ID NO: 1, or an amino acid sequence at least 85%, 90%, 95%, or 99% identical or higher to SEQ ID NO: 1. In one embodiment, the anti-GITR antibody molecule comprises a VL comprising the amino acid sequence of SEQ ID NO: 2, or an amino acid sequence at least 85%, 90%, 95%, or 99% identical or higher to SEQ ID NO: 2. In one embodiment, the anti-GITR antibody molecule comprises a VH comprising the amino acid sequence of SEQ ID NO: 1 and a VL comprising the amino acid sequence of SEQ ID NO: 2.

In one embodiment, the antibody molecule comprises a VH encoded by the nucleotide sequence of SEQ ID NO: 5, or a nucleotide sequence at least 85%, 90%, 95%, or 99% identical or higher to SEQ ID NO: 5. In one embodiment, the antibody molecule comprises a VL encoded by the nucleotide sequence of SEQ ID NO: 6, or a nucleotide sequence at least 85%, 90%, 95%, or 99% identical or higher to SEQ ID NO: 6. In one embodiment, the antibody molecule comprises a VH encoded by the nucleotide sequence of SEQ ID NO: 5 and a VL encoded by the nucleotide sequence of SEQ ID NO: 6.

In one embodiment, the anti-GITR antibody molecule comprises a heavy chain comprising the amino acid sequence of SEQ ID NO: 3, or an amino acid sequence at least 85%, 90%, 95%, or 99% identical or higher to SEQ ID NO: 3. In one embodiment, the anti-GITR antibody molecule comprises a light chain comprising the amino acid sequence of SEQ ID NO: 4, or an amino acid sequence at least 85%, 90%, 95%, or 99% identical or higher to SEQ ID NO: 4. In one embodiment, the anti-GITR antibody molecule comprises a heavy chain comprising the amino acid sequence of SEQ ID NO: 3 and a light chain comprising the amino acid sequence of SEQ ID NO: 4.

In one embodiment, the antibody molecule comprises a heavy chain encoded by the nucleotide sequence of SEQ ID NO: 7, or a nucleotide sequence at least 85%, 90%, 95%, or 99% identical or higher to SEQ ID NO: 7. In one embodiment, the antibody molecule comprises a light chain encoded by the nucleotide sequence of SEQ ID NO: 8, or a nucleotide sequence at least 85%, 90%, 95%, or 99% identical or higher to SEQ ID NO: 8. In one embodiment, the antibody molecule comprises a heavy chain encoded by the nucleotide sequence of SEQ ID NO: 7 and a light chain encoded by the nucleotide sequence of SEQ ID NO: 8.

The antibody molecules described herein can be made by vectors, host cells, and methods described in WO 2016/057846, incorporated by reference in its entirety.

TABLE 1

Amino acid and nucleotide sequences of exemplary anti-GITR antibody molecule

MAB7

| SEQ ID NO: 1 | VH | EVQLVESGGGLVQSGGSLRLSCAASGFSLSSYGVDWVRQAPGKG LEWVGVIWGGGGTYYASSLMGRFTISRDNSKNTLYLQMNSLRAE DTAVYYCARHAYGHDGGFAMDYWGQGTLVTVSS |
| --- | --- | --- |
| SEQ ID NO: 2 | VL | EIVMTQSPATLSVSPGERATLSCRASESVSSNVAWYQQRPGQAPR LLIYGASNRATGIPARFSGSGSGTDFTLTISRLEPEDFAVYYCGQSY SYPFTFGQGTKLEIK |
| SEQ ID NO: 3 | Heavy Chain | EVQLVESGGGLVQSGGSLRLSCAASGFSLSSYGVDWVRQAPGKG LEWVGVIWGGGGTYYASSLMGRFTISRDNSKNTLYLQMNSLRAE DTAVYYCARHAYGHDGGFAMDYWGQGTLVTVSSASTKGPSVFP LAPSSKSTSGGTAALGCLVKDYFPEPVTVSWNSGALTSGVHTFPA VLQSSGLYSLSSVVTVPSSSLGTQTYICNVNHKPSNTKVDKRVEP KSCDKTHTCPPCPAPELLGGPSVFLFPPKPKDTLMISRTPEVTCVV VDVSHEDPEVKFNWYVDGVEVHNAKTKPREEQYNSTYRVVSVL TVLHQDWLNGKEYKCKVSNKALPAPIEKTISKAKGQPREPQVYT LPPSREEMTKNQVSLTCLVKGFYPSDIAVEWESNGQPENNYKTTP PVLDSDGSFFLYSKLTVDKSRWQQGNVFSCSVMHEALHNHYTQK SLSLSPGK |
| SEQ ID NO: 4 | Light Chain | EIVMTQSPATLSVSPGERATLSCRASESVSSNVAWYQQRPGQAPR LLIYGASNRATGIPARFSGSGSGTDFTLTISRLEPEDFAVYYCGQSY SYPFTFGQGTKLEIKRTVAAPSVFIFPPSDEQLKSGTASVVCLLNNF YPREAKVQWKVDNALQSGNSQESVTEQDSKDSTYSLSSTLTLSK ADYEKHKVYACEVTHQGLSSPVTKSFNRGEC |
| SEQ ID NO: 5 | DNA VH | GAGGTGCAGCTGGTGGAATCTGGCGGCGGACTGGTGCAGTCCG GCGGCTCTCTGAGACTGTCTTGCGCTGCCTCCGGCTTCTCCCTG TCCTCTTACGGCGTGGACTGGGTGCGACAGGCCCCTGGCAAGG GCCTGGAATGGGTGGGAGTGATCTGGGGCGGAGGCGGCACCT ACTACGCCTCTTCCCTGATGGGCCGGTTCACCATCTCCCGGGAC AACTCCAAGAACACCCTGTACCTGCAGATGAACTCCCTGCGGG CCGAGGACACCGCCGTGTACTACTGCGCCAGACACGCCTACGG CCACGACGGCGGCTTCGCCATGGATTATTGGGGCCAGGGCACC CTGGTGACAGTGTCCTCC |
| SEQ ID NO: 6 | DNA VL | GAGATCGTGATGACCCAGTCCCCCGCCACCCTGTCTGTGTCTCC CGGCGAGAGAGCCACCCTGAGCTGCAGAGCCTCCGAGTCCGTG TCCTCCAACGTGGCCTGGTATCAGCAGAGACCTGGTCAGGCCC CTCGGCTGCTGATCTACGGCGCCTCTAACCGGGCCACCGGCAT CCCTGCCAGATTCTCCGGCTCCGGCAGCGGCACCGACTTCACC CTGACCATCTCCCGGCTGGAACCCGAGGACTTCGCCGTGTACT ACTGCGGCCAGTCCTACTCATACCCCTTCACCTTCGGCCAGGG CACCAAGCTGGAAATCAAG |
| SEQ ID NO: 7 | DNA Heavy Chain | GAGGTGCAGCTGGTGGAATCTGGCGGCGGACTGGTGCAGTCCG GCGGCTCTCTGAGACTGTCTTGCGCTGCCTCCGGCTTCTCCCTG TCCTCTTACGGCGTGGACTGGGTGCGACAGGCCCCTGGCAAGG GCCTGGAATGGGTGGGAGTGATCTGGGGCGGAGGCGGCACCT ACTACGCCTCTTCCCTGATGGGCCGGTTCACCATCTCCCGGGAC AACTCCAAGAACACCCTGTACCTGCAGATGAACTCCCTGCGGG CCGAGGACACCGCCGTGTACTACTGCGCCAGACACGCCTACGG CCACGACGGCGGCTTCGCCATGGATTATTGGGGCCAGGGCACC CTGGTGACAGTGTCCTCCGCTAGCACCAAGGGCCCAAGTGTGT TCCCCCTGGCCCCCAGCAGCAAGTCTACTTCCGGCGGAACTGC TGCCCTGGGTTGCCTGGTGAAGGACTACTTCCCCGAGCCCGTG ACAGTGTCCTGGAACTCTGGGGCTCTGACTTCCGGCGTGCACA CCTTCCCCGCCGTGCTGCAGAGCAGCGGCCTGTACAGCCTGAG CAGCGTGGTGACAGTGCCCTCCAGCTCTCTGGGAACCCAGACC |

TABLE 1-continued

Amino acid and nucleotide sequences of
exemplary anti-GITR antibody molecule

|  |  |  |
|---|---|---|
|  |  | TATATCTGCAACGTGAACCACAAGCCCAGCAACACCAAGGTGG<br>ACAAGAGAGTGGAGCCCAAGAGCTGCGACAAGACCCACACCT<br>GCCCCCCCTGCCCAGCTCCAGAACTGCTGGGAGGGCCTTCCGT<br>GTTCCTGTTCCCCCCCAAGCCCAAGGACACCCTGATGATCAGC<br>AGGACCCCCGAGGTGACCTGCGTGGTGGTGGACGTGTCCCACG<br>AGGACCCAGAGGTGAAGTTCAACTGGTACGTGGACGGCGTGG<br>AGGTGCACAACGCCAAGACCAAGCCCAGAGAGGAGCAGTACA<br>ACAGCACCTACAGGGTGGTGTCCGTGCTGACCGTGCTGCACCA<br>GGACTGGCTGAACGGCAAAGAATACAAGTGCAAAGTCTCCAA<br>CAAGGCCCTGCCAGCCCCAATCGAAAAGACAATCAGCAAGGC<br>CAAGGGCCAGCCACGGGAGCCCCAGGTGTACACCCTGCCCCCC<br>AGCCGGGAGGAGATGACCAAGAACCAGGTGTCCCTGACCTGT<br>CTGGTGAAGGGCTTCTACCCCAGCGATATCGCCGTGGAGTGGG<br>AGAGCAACGGCCAGCCCGAGAACAACTACAAGACCACCCCCC<br>CAGTGCTGGACAGCGACGGCAGCTTCTTCCTGTACAGCAAGCT<br>GACCGTGGACAAGTCCAGGTGGCAGCAGGGCAACGTGTTCAG<br>CTGCAGCGTGATGCACGAGGCCCTGCACAACCACTACACCCAG<br>AAGTCCCTGAGCCTGAGCCCCGGCAAG |
| SEQ ID NO: 8 | DNA<br>Light<br>Chain | GAGATCGTGATGACCCAGTCCCCCGCCACCCTGTCTGTGTCTCC<br>CGGCGAGAGAGCCACCCTGAGCTGCAGAGCCTCCGAGTCCGTG<br>TCCTCCAACGTGGCCTGGTATCAGCAGAAGACCTGGTCAGGCCC<br>CTCGGCTGCTGATCTACGGCGCCTCTAACCGGGCCACCGGCAT<br>CCCTGCCAGATTCTCCGGCTCCGGCAGCGGCACCGACTTCACC<br>CTGACCATCTCCCGGCTGGAACCCGAGGACTTCGCCGTGTACT<br>ACTGCGGCCAGTCCTACTCATACCCCTTCACCTTCGGCCAGGG<br>CACCAAGCTGGAAATCAAGCGTACGGTGGCCGCTCCCAGCGTG<br>TTCATCTTCCCCCCCAGCGACGAGCAGCTGAAGAGCGGCACCG<br>CCAGCGTGGTGTGCCTGCTGAACAACTTCTACCCCCGGGAGGC<br>CAAGGTGCAGTGGAAGGTGGACAACGCCCTGCAGAGCGGCAA<br>CAGCCAGGAGAGCGTCACCGAGCAGGACAGCAAGGACTCCAC<br>CTACAGCCTGAGCAGCACCCTGACCCTGAGCAAGGCCGACTAC<br>GAGAAGCATAAGGTGTACGCCTGCGAGGTGACCCACCAGGGC<br>CTGTCCAGCCCCGTGACCAAGAGCTTCAACAGGGGCGAGTGC |
| SEQ ID NO: 9 HCDR1<br>(KABAT) | | SYGVD |
| SEQ ID NO: 10 HCDR1<br>(CHOTHIA) | | GFSLSSY |
| SEQ ID NO: 11 HCDR2<br>(KABAT) | | VIWGGGGTYYASSLMG |
| SEQ ID NO: 12 HCDR2<br>(CHOTHIA) | | WGGGG |
| SEQ ID NO: 13 HCDR3<br>(KABAT) | | HAYGHDGGFAMDY |
| SEQ ID NO: 13 HCDR3<br>(CHOTHIA) | | HAYGHDGGFAMDY |
| SEQ ID NO: 14 LCDR1<br>(KABAT) | | RASESVSSNVA |
| SEQ ID NO: 15 LCDR1<br>(CHOTHIA) | | SESVSSN |
| SEQ ID NO: 16 LCDR2<br>(KABAT) | | GASNRAT |
| SEQ ID NO: 17 LCDR2<br>(CHOTHIA) | | GAS |
| SEQ ID NO: 18 LCDR3<br>(KABAT) | | GQSYSYPFT |
| SEQ ID NO: 19 LCDR3<br>(CHOTHIA) | | SYSYPF |

Other Exemplary GITR Agonists

In one embodiment, the anti-GITR antibody molecule is BMS-986156 (Bristol-Myers Squibb), also known as BMS 986156 or BMS986156. BMS-986156 and other anti-GITR antibodies are disclosed, e.g., in U.S. Pat. No. 9,228,016 and WO 2016/196792, incorporated by reference in their entirety. In one embodiment, the anti-GITR antibody molecule comprises one or more of the CDR sequences (or collectively all of the CDR sequences), the heavy chain or light chain variable region sequence, or the heavy chain or light chain sequence of BMS-986156, e.g., as disclosed in Table 2.

In one embodiment, the anti-GITR antibody molecule is MK-4166 or MK-1248 (Merck). MK-4166, MK-1248, and other anti-GITR antibodies are disclosed, e.g., in U.S. Pat. No. 8,709,424, WO 2011/028683, WO 2015/026684, and Mahne et al. *Cancer Res.* 2017; 77(5): 1108-1118, incorporated by reference in their entirety. In one embodiment, the anti-GITR antibody molecule comprises one or more of the CDR sequences (or collectively all of the CDR sequences), the heavy chain or light chain variable region sequence, or the heavy chain or light chain sequence of MK-4166 or MK-1248.

In one embodiment, the anti-GITR antibody molecule is TRX518 (Leap Therapeutics). TRX518 and other anti-GITR antibodies are disclosed, e.g., in U.S. Pat. Nos. 7,812,135, 8,388,967, 9,028,823, WO 2006/105021, and Ponte J et al. (2010) *Clinical Immunology;* 135:S96, incorporated by reference in their entirety. In one embodiment, the anti-GITR antibody molecule comprises one or more of the CDR sequences (or collectively all of the CDR sequences), the heavy chain or light chain variable region sequence, or the heavy chain or light chain sequence of TRX518.

In one embodiment, the anti-GITR antibody molecule is INCAGN1876 (Incyte/Agenus). INCAGN1876 and other anti-GITR antibodies are disclosed, e.g., in US 2015/0368349 and WO 2015/184099, incorporated by reference in their entirety. In one embodiment, the anti-GITR antibody molecule comprises one or more of the CDR sequences (or collectively all of the CDR sequences), the heavy chain or light chain variable region sequence, or the heavy chain or light chain sequence of INCAGN1876.

In one embodiment, the anti-GITR antibody molecule is AMG 228 (Amgen). AMG 228 and other anti-GITR antibodies are disclosed, e.g., in U.S. Pat. No. 9,464,139 and WO 2015/031667, incorporated by reference in their entirety. In one embodiment, the anti-GITR antibody molecule comprises one or more of the CDR sequences (or collectively all of the CDR sequences), the heavy chain or light chain variable region sequence, or the heavy chain or light chain sequence of AMG 228.

In one embodiment, the anti-GITR antibody molecule is INBRX-110 (Inhibrx). INBRX-110 and other anti-GITR antibodies are disclosed, e.g., in US 2017/0022284 and WO 2017/015623, incorporated by reference in their entirety. In one embodiment, the GITR agonist comprises one or more of the CDR sequences (or collectively all of the CDR sequences), the heavy chain or light chain variable region sequence, or the heavy chain or light chain sequence of INBRX-110.

In one embodiment, the GITR agonist (e.g., a fusion protein) is MEDI 1873 (MedImmune), also known as MEDI1873. MEDI 1873 and other GITR agonists are disclosed, e.g., in US 2017/0073386, WO 2017/025610, and Ross et al. *Cancer Res* 2016; 76(14 Suppl): Abstract nr 561, incorporated by reference in their entirety. In one embodiment, the GITR agonist comprises one or more of an IgG Fc domain, a functional multimerization domain, and a receptor binding domain of a glucocorticoid-induced TNF receptor ligand (GITRL) of MEDI 1873.

Further known GITR agonists (e.g., anti-GITR antibodies) include those described, e.g., in WO 2016/054638, incorporated by reference in its entirety.

In one embodiment, the anti-GITR antibody is an antibody that competes for binding with, and/or binds to the same epitope on GITR as, one of the anti-GITR antibodies described herein.

In one embodiment, the GITR agonist is a peptide that activates the GITR signalling pathway. In one embodiment, the GITR agonist is an immunoadhesin binding fragment (e.g., an immunoadhesin binding fragment comprising an extracellular or GITR binding portion of GITRL) fused to a constant region (e.g., an Fc region of an immunoglobulin sequence).

TABLE 2

Amino acid sequence of other exemplary anti-GITR antibody molecules

BMS-986156

| | | |
|---|---|---|
| SEQ ID NO: 20 | VH | QVQLVESGGGVVQPGRSLRLSCAASGFTFSSYGMHWVRQAPGKG LEWVAVIWYEGSNKYYADSVKGRFTISRDNSKNTLYLQMNSLRAE DTAVYYCARGGSMVRGDYYYGMDVWGQGTTVTVSS |
| SEQ ID NO: 21 | VL | AIQLTQSPSSLSASVGDRVTITCRASQGISSALAWYQQKPGKAPKLL IYDASSLESGVPSRFSGSGSGTDFTLTISSLQPEDFATYYCQQFNSYP YTFGQGTKLEIK |

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFRbeta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40%, 50% or more is included by this term. Thus, inhibition need not be 100%.

Inhibition of an inhibitory molecule can be performed at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, VISTA, BTLA, TIGIT, LAIR1, CD160, 2B4 and/or TGFR beta, or a combination thereof.

In one embodiment, the antibody molecule is a full antibody or fragment thereof (e.g., a Fab, F(ab')2, Fv, or a single chain Fv fragment (scFv)). In yet other embodiments, the antibody molecule has a heavy chain constant region (Fc) selected from, e.g., the heavy chain constant regions of IgG1, IgG2, IgG3, IgG4, IgM, IgA1, IgA2, IgD, and IgE; particularly, selected from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of Fc receptor binding, antibody glycosylation, the number of cysteine residues, effector cell function, or complement function).

In certain embodiments, the antibody molecule is in the form of a bispecific or multispecific antibody molecule. In one embodiment, the bispecific antibody molecule has a first binding specificity to PD-1 or PD-L1 and a second binding specificity, e.g., a second binding specificity to TIM-3, LAG-3, or PD-L2. In one embodiment, the bispecific antibody molecule binds to PD-1 or PD-L1 and TIM-3. In another embodiment, the bispecific antibody molecule binds to PD-1 or PD-L1 and LAG-3. In another embodiment, the bispecific antibody molecule binds to PD-1 and PD-L1. In yet another embodiment, the bispecific antibody molecule binds to PD-1 and PD-L2. In another embodiment, the bispecific antibody molecule binds to TIM-3 and LAG-3. Any combination of the aforesaid molecules can be made in a multispecific antibody molecule, e.g., a trispecific antibody that includes a first binding specificity to PD-1 or PD-1, and a second and third binding specificities to two or more of TIM-3, LAG-3, or PD-L2.

In certain embodiments, the immunomodulator is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immunomodulators, e.g., in combination with an inhibitor of LAG-3, TIM-3 or CTLA4. In an exemplary embodiment, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule.

Other combinations of immunomodulators with a PD-1 inhibitor (e.g., one or more of PD-L2, CTLA4, TIM3, LAG3, VISTA, BTLA, TIGIT, LAIR1, CD160, 2B4 and/or TGFR) are also within the present disclosure. Any of the antibody molecules known in the art or disclosed herein can be used in the aforesaid combinations of inhibitors of checkpoint molecule.

PD-1 Inhibitors

In some embodiments, the compounds of Formula (I') or Formula (I), or a pharmaceutically acceptable salt, hydrate, solvate, prodrug, stereoisomer, or tautomer thereof, of the present disclosure are used in combination with a PD-1 inhibitor to treat a disease, e.g., cancer. In some embodiments, the PD-1 inhibitor is selected from PDR001 (Novartis), Nivolumab (Bristol-Myers Squibb), Pembrolizumab (Merck & Co), Pidilizumab (CureTech), MEDI0680 (Medimmune), REGN2810 (Regeneron), TSR-042 (Tesaro), PF-06801591 (Pfizer), BGB-A317 (Beigene), BGB-108 (Beigene), INCSHR1210 (Incyte), or AMP-224 (Amplimmune).

Exemplary PD-1 Inhibitors

In one embodiment, the PD-1 inhibitor is an anti-PD-1 antibody molecule. In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety.

In one embodiment, the anti-PD-1 antibody molecule comprises at least one, two, three, four, five or six complementarity determining regions (CDRs) (or collectively all of the CDRs) from a heavy and light chain variable region comprising an amino acid sequence shown in Table 3 (e.g., from the heavy and light chain variable region sequences of BAP049-Clone-E or BAP049-Clone-B disclosed in Table 3), or encoded by a nucleotide sequence shown in Table 3. In some embodiments, the CDRs are according to the Kabat definition (e.g., as set out in Table 3). In some embodiments, the CDRs are according to the Chothia definition (e.g., as set out in Table 3). In some embodiments, the CDRs are according to the combined CDR definitions of both Kabat and Chothia (e.g., as set out in Table 3). In one embodiment, the combination of Kabat and Chothia CDR of VH CDR1 comprises the amino acid sequence GYTFTTYWMH (SEQ ID NO: 213). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 3, or encoded by a nucleotide sequence shown in Table 3.

In one embodiment, the anti-PD-1 antibody molecule comprises a heavy chain variable region (VH) comprising a VHCDR1 amino acid sequence of SEQ ID NO: 22, a VHCDR2 amino acid sequence of SEQ ID NO: 23, and a VHCDR3 amino acid sequence of SEQ ID NO: 24; and a light chain variable region (VL) comprising a VLCDR1 amino acid sequence of SEQ ID NO: 31, a VLCDR2 amino acid sequence of SEQ ID NO: 32, and a VLCDR3 amino acid sequence of SEQ ID NO: 286, each disclosed in Table 3.

In one embodiment, the antibody molecule comprises a VH comprising a VHCDR1 encoded by the nucleotide sequence of SEQ ID NO: 45, a VHCDR2 encoded by the nucleotide sequence of SEQ ID NO: 46, and a VHCDR3 encoded by the nucleotide sequence of SEQ ID NO: 47; and a VL comprising a VLCDR1 encoded by the nucleotide sequence of SEQ ID NO: 50, a VLCDR2 encoded by the nucleotide sequence of SEQ ID NO: 51, and a VLCDR3 encoded by the nucleotide sequence of SEQ ID NO: 52, each disclosed in Table 3.

In one embodiment, the anti-PD-1 antibody molecule comprises a VH comprising the amino acid sequence of SEQ ID NO: 27, or an amino acid sequence at least 85%, 90%, 95%, or 99% identical or higher to SEQ ID NO: 27. In one embodiment, the anti-PD-1 antibody molecule comprises a VL comprising the amino acid sequence of SEQ ID NO: 41, or an amino acid sequence at least 85%, 90%, 95% or 99% identical or higher to SEQ ID NO: 41. In one embodiment, the anti-PD-1 antibody molecule comprises a VL comprising the amino acid sequence of SEQ ID NO: 37, or an amino acid sequence at least 85%, 90%, 95%, or 99% identical or higher to SEQ ID NO: 37. In one embodiment, the anti-PD-1 antibody molecule comprises a VH comprising the amino acid sequence of SEQ ID NO: 27 and a VL comprising the amino acid sequence of SEQ ID NO: 41. In one embodiment, the anti-PD-1 antibody molecule comprises a VH comprising the amino acid sequence of SEQ ID NO: 27 and a VL comprising the amino acid sequence of SEQ ID NO: 37.

In one embodiment, the antibody molecule comprises a VH encoded by the nucleotide sequence of SEQ ID NO: 28, or a nucleotide sequence at least 85%, 90%, 95%, or 99% identical or higher to SEQ ID NO: 28. In one embodiment, the antibody molecule comprises a VL encoded by the nucleotide sequence of SEQ ID NO: 42 or 38, or a nucleotide sequence at least 85%, 90%, 95%, or 99% identical or higher to SEQ ID NO: 42 or 38. In one embodiment, the antibody molecule comprises a VH encoded by the nucleotide sequence of SEQ ID NO: 28 and a VL encoded by the nucleotide sequence of SEQ ID NO: 42 or 38.

In one embodiment, the anti-PD-1 antibody molecule comprises a heavy chain comprising the amino acid sequence of SEQ ID NO: 29, or an amino acid sequence at least 85%, 90%, 95%, or 99% identical or higher to SEQ ID NO: 29. In one embodiment, the anti-PD-1 antibody molecule comprises a light chain comprising the amino acid sequence of SEQ ID NO: 43, or an amino acid sequence at least 85%, 90%, 95%, or 99% identical or higher to SEQ ID NO: 43. In one embodiment, the anti-PD-1 antibody molecule comprises a light chain comprising the amino acid sequence of SEQ ID NO: 39, or an amino acid sequence at least 85%, 90%, 95%, or 99% identical or higher to SEQ ID NO: 39. In one embodiment, the anti-PD-1 antibody molecule comprises a heavy chain comprising the amino acid sequence of SEQ ID NO: 29 and a light chain comprising the amino acid sequence of SEQ ID NO: 43. In one embodiment, the anti-PD-1 antibody molecule comprises a heavy chain comprising the amino acid sequence of SEQ ID NO: 29 and a light chain comprising the amino acid sequence of SEQ ID NO: 39.

In one embodiment, the antibody molecule comprises a heavy chain encoded by the nucleotide sequence of SEQ ID NO: 30, or a nucleotide sequence at least 85%, 90%, 95%, or 99% identical or higher to SEQ ID NO: 30. In one embodiment, the antibody molecule comprises a light chain encoded by the nucleotide sequence of SEQ ID NO: 44 or 40, or a nucleotide sequence at least 85%, 90%, 95%, or 99% identical or higher to SEQ ID NO: 44 or 40. In one embodiment, the antibody molecule comprises a heavy chain encoded by the nucleotide sequence of SEQ ID NO: 30 and a light chain encoded by the nucleotide sequence of SEQ ID NO: 44 or 40.

The antibody molecules described herein can be made by vectors, host cells, and methods described in US 2015/0210769, incorporated by reference in its entirety.

TABLE 3

Amino acid and nucleotide sequences of exemplary anti-PD-1 antibody molecules

BAP049-Clone-B HC

| | | |
|---|---|---|
| SEQ ID NO: 22 (Kabat) | HCDR1 | TYWMH |
| SEQ ID NO: 23 (Kabat) | HCDR2 | NIYPGTGGSNFDEKFKN |
| SEQ ID NO: 24 (Kabat) | HCDR3 | WTTGTGAY |
| SEQ ID NO: 25 (Chothia) | HCDR1 | GYTFTTY |
| SEQ ID NO: 26 (Chothia) | HCDR2 | YPGTGG |
| SEQ ID NO: 24 (Chothia) | HCDR3 | WTTGTGAY |
| SEQ ID NO: 27 | VH | EVQLVQSGAEVKKPGESLRISCKGSGYTFTTYWMHWVRQAT GQGLEWMGNIYPGTGGSNFDEKFKNRVTITADKSTSTAYME LSSLRSEDTAVYYCTRWTTGTGAYWGQGTTVTVSS |
| SEQ ID NO: 28 | DNA VH | GAGGTGCAGCTGGTGCAGTCAGGCGCCGAAGTGAAGAAG CCCGGCGAGTCACTGAGAATTAGCTGTAAAGGTTCAGGCT ACACCTTCACTACCTACTGGATGCACTGGGTCCGCCAGGC TACCGGTCAAGGCCTCGAGTGGATGGGTAATATCTACCCC GGCACCGGCGGCTCTAACTTCGACGAGAAGTTTAAGAATA GAGTGACTATCACCGCCGATAAGTCTACTAGCACCGCCTA TATGGAACTGTCTAGCCTGAGATCAGAGGACACCGCCGTC TACTACTGCACTAGGTGGACTACCGGCACAGGCGCCTACT GGGGTCAAGGCACTACCGTGACCGTGTCTAGC |
| SEQ ID NO: 29 | Heavy chain | EVQLVQSGAEVKKPGESLRISCKGSGYTFTTYWMHWVRQAT GQGLEWMGNIYPGTGGSNFDEKFKNRVTITADKSTSTAYME LSSLRSEDTAVYYCTRWTTGTGAYWGQGTTVTVSSASTKGP SVFPLAPCSRSTSESTAALGCLVKDYFPEPVTVSWNSGALTSG VHTFPAVLQSSGLYSLSSVVTVPSSSLGTKTYTCNVDHKPSNT KVDKRVESKYGPPCPPCPAPEFLGGPSVFLFPPKPKDTLMISR TPEVTCVVVDVSQEDPEVQFNWYVDGVEVHNAKTKPREEQF NSTYRVVSVLTVLHQDWLNGKEYKCKVSNKGLPSSIEKTISK |

TABLE 3-continued

Amino acid and nucleotide sequences of exemplary anti-PD-1 antibody molecules

|  |  |  |
|---|---|---|
|  |  | AKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLG |
| SEQ ID NO: 30 | DNA heavy chain | GAGGTGCAGCTGGTGCAGTCAGGCGCCGAAGTGAAGAAG CCCGGCGAGTCACTGAGAATTAGCTGTAAAGGTTCAGGCT ACACCTTCACTACCTACTGGATGCACTGGGTCCGCCAGGC TACCGGTCAAGGCCTCGAGTGGATGGGTAATATCTACCCC GGCACCGGCGGCTCTAACTTCGACGAGAAGTTTAAGAATA GAGTGACTATCACCGCCGATAAGTCTACTAGCACCGCCTA TATGGAACTGTCTAGCCTGAGATCAGAGGACACCGCCGTC TACTACTGCACTAGGTGGACTACCGGCACAGGCGCCTACT GGGGTCAAGGCACTACCGTGACCGTGTCTAGCGCTAGCAC TAAGGGCCCGTCCGTGTTCCCCCTGGCACCTTGTAGCCGG AGCACTAGCGAATCCACCGCTGCCCTCGGCTGCCTGGTCA AGGATTACTTCCCGGAGCCCGTGACCGTGTCCTGGAACAG CGGAGCCCTGACCTCCGGAGTGCACACCTTCCCCGCTGTG CTGCAGAGCTCCGGGCTGTACTCGCTGTCGTCGGTGGTCA CGGTGCCTTCATCTAGCCTGGGTACCAAGACCTACACTTGC AACGTGGACCACAAGCCTTCCAACACTAAGGTGGACAAGC GCGTCGAATCGAAGTACGGCCCACCGTGCCCGCCTTGTCC CGCGCCGGAGTTCCTCGGCGGTCCCTCGGTCTTTCTGTTCC CACCGAAGCCCAAGGACACTTTGATGATTTCCCGCACCCC TGAAGTGACATGCGTGGTCGTGGACGTGTCACAGGAAGAT CCGGAGGTGCAGTTCAATTGGTACGTGGATGGCGTCGAGG TGCACAACGCCAAAACCAAGCCGAGGGAGGAGCAGTTCA ACTCCACTTACCGCGTCGTGTCCGTGCTGACGGTGCTGCAT CAGGACTGGCTGAACGGGAAGGAGTACAAGTGCAAAGTG TCCAACAAGGGACTTCCTAGCTCAATCGAAAAGACCATCT CGAAAGCCAAGGGACAGCCCCGGGAACCCCAAGTGTATA CCCTGCCACCGAGCCAGGAAGAAATGACTAAGAACCAAG TCTCATTGACTTGCCTTGTGAAGGGCTTCTACCCATCGGAT ATCGCCGTGGAATGGGAGTCCAACGGCCAGCCGGAAAAC AACTACAAGACCACCCCTCCGGTGCTGGACTCAGACGGAT CCTTCTTCCTCTACTCGCGGCTGACCGTGGATAAGAGCAG ATGGCAGGAGGGAAATGTGTTCAGCTGTTCTGTGATGCAT GAAGCCCTGCACAACCACTACACTCAGAAGTCCCTGTCCC TCTCCCTGGGA |

BAP049-Clone-B LC

| SEQ ID NO: 31 (Kabat) | LCDR1 | KSSQSLLDSGNQKNFLT |
| SEQ ID NO: 32 (Kabat) | LCDR2 | WASTRES |
| SEQ ID NO: 286 (Kabat) | LCDR3 | QNDYSYPYT |
| SEQ ID NO: 34 (Chothia) | LCDR1 | SQSLLDSGNQKNF |
| SEQ ID NO: 35 (Chothia) | LCDR2 | WAS |
| SEQ ID NO: 36 (Chothia) | LCDR3 | DYSYPY |
| SEQ ID NO: 37 | VL | EIVLTQSPATLSLSPGERATLSCKSSQSLLDSGNQKNFLTWYQ QKPGKAPKLLIYWASTRESGVPSRFSGSGSGTDFTFTISSLQPE DIATYYCQNDYSYPYTFGQGTKVEIK |
| SEQ ID NO: 38 | DNA VL | GAGATCGTCCTGACTCAGTCACCCGCTACCCTGAGCCTGA GCCCTGGCGAGCGGGCTACACTGAGCTGTAAATCTAGTCA GTCACTGCTGGATAGCGGTAATCAGAAGAACTTCCTGACC TGGTATCAGCAGAAGCCCGGTAAAGCCCCTAAGCTGCTGA TCTACTGGGCCTCTACTAGAGAATCAGGCGTGCCCTCTAG GTTTAGCGGTAGCGGTAGTGGCACCGACTTCACCTTCACT ATCTCTAGCCTGCAGCCCGAGGATATCGCTACCTACTACTG TCAGAACGACTATAGCTACCCCTACACCTTCGGTCAAGGC ACTAAGGTCGAGATTAAG |
| SEQ ID NO: 39 | Light chain | EIVLTQSPATLSLSPGERATLSCKSSQSLLDSGNQKNFLTWYQ QKPGKAPKLLIYWASTRESGVPSRFSGSGSGTDFTFTISSLQPE DIATYYCQNDYSYPYTFGQGTKVEIKRTVAAPSVFIFPPSDEQ |

TABLE 3-continued

Amino acid and nucleotide sequences of exemplary anti-PD-1 antibody molecules

| | | |
|---|---|---|
| | | LKSGTASVVCLLNNFYPREAKVQWKVDNALQSGNSQESVTE QDSKDSTYSLSSTLTLSKADYEKHKVYACEVTHQGLSSPVTK SFNRGEC |
| SEQ ID NO: 40 | DNA light chain | GAGATCGTCCTGACTCAGTCACCCGCTACCCTGAGCCTGA GCCCTGGCGAGCGGGCTACACTGAGCTGTAAATCTAGTCA GTCACTGCTGGATAGCGGTAATCAGAAGAACTTCCTGACC TGGTATCAGCAGAAGCCCGGTAAAGCCCCTAAGCTGCTGA TCTACTGGGCCTCTACTAGAGAATCAGGCGTGCCCTCTAG GTTTAGCGGTAGCGGTAGTGGCACCGACTTCACCTTCACT ATCTCTAGCCTGCAGCCCGAGGATATCGCTACCTACTACTG TCAGAACGACTATAGCTACCCCTACACCTTCGGTCAAGGC ACTAAGGTCGAGATTAAGCGTACGGTGGCCGCTCCCAGCG TGTTCATCTTCCCCCCCAGCGACGAGCAGCTGAAGAGCGG CACCGCCAGCGTGGTGTGCCTGCTGAACAACTTCTACCCC CGGGAGGCCAAGGTGCAGTGGAAGGTGGACAACGCCCTG CAGAGCGGCAACAGCCAGGAGAGCGTCACCGAGCAGGAC AGCAAGGACTCCACCTACAGCCTGAGCAGCACCCTGACCC TGAGCAAGGCCGACTACGAGAAGCATAAGGTGTACGCCTG CGAGGTGACCCACCAGGGCCTGTCCAGCCCCGTGACCAAG AGCTTCAACAGGGGCGAGTGC |
| BAP049-Clone-E HC | | |
| SEQ ID NO: 22 (Kabat) | HCDR1 | TYWMH |
| SEQ ID NO: 23 (Kabat) | HCDR2 | NIYPGTGGSNFDEKFKN |
| SEQ ID NO: 24 (Kabat) | HCDR3 | WTTGTGAY |
| SEQ ID NO: 25 (Chothia) | HCDR1 | GYTFTTY |
| SEQ ID NO: 26 (Chothia) | HCDR2 | YPGTGG |
| SEQ ID NO: 24 (Chothia) | HCDR3 | WTTGTGAY |
| SEQ ID NO: 27 | VH | EVQLVQSGAEVKKPGESLRISCKGSGYTFTTYWMHWVRQAT GQGLEWMGNIYPGTGGSNFDEKFKNRVTITADKSTSTAYME LSSLRSEDTAVYYCTRWTTGTGAYWGQGTTVTVSS |
| SEQ ID NO: 28 | DNA VH | GAGGTGCAGCTGGTGCAGTCAGGCGCCGAAGTGAAGAAG CCCGGCGAGTCACTGAGAATTAGCTGTAAAGGTTCAGGCT ACACCTTCACTACCTACTGGATGCACTGGGTCCGCCAGGC TACCGGTCAAGGCCTCGAGTGGATGGGTAATATCTACCCC GGCACCGGCGGCTCTAACTTCGACGAGAAGTTTAAGAATA GAGTGACTATCACCGCCGATAAGTCTACTAGCACCGCCTA TATGGAACTGTCTAGCCTGAGATCAGAGGACACCGCCGTC TACTACTGCACTAGGTGGACTACCGGCACAGGCGCCTACT GGGGTCAAGGCACTACCGTGACCGTGTCTAGC |
| SEQ ID NO: 29 | Heavy chain | EVQLVQSGAEVKKPGESLRISCKGSGYTFTTYWMHWVRQAT GQGLEWMGNIYPGTGGSNFDEKFKNRVTITADKSTSTAYME LSSLRSEDTAVYYCTRWTTGTGAYWGQGTTVTVSSASTKGP SVFPLAPCSRSTSESTAALGCLVKDYFPEPVTVSWNSGALTSG VHTFPAVLQSSGLYSLSSVVTVPSSSLGTKTYTCNVDHKPSNT KVDKRVESKYGPPCPPCPAPEFLGGPSVFLFPPKPKDTLMISR TPEVTCVVVDVSQEDPEVQFNWYVDGVEVHNAKTKPREEQF NSTYRVVSVLTVLHQDWLNGKEYKCKVSNKGLPSSIEKTISK AKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLG |
| SEQ ID NO: 30 | DNA heavy chain | GAGGTGCAGCTGGTGCAGTCAGGCGCCGAAGTGAAGAAG CCCGGCGAGTCACTGAGAATTAGCTGTAAAGGTTCAGGCT ACACCTTCACTACCTACTGGATGCACTGGGTCCGCCAGGC TACCGGTCAAGGCCTCGAGTGGATGGGTAATATCTACCCC GGCACCGGCGGCTCTAACTTCGACGAGAAGTTTAAGAATA GAGTGACTATCACCGCCGATAAGTCTACTAGCACCGCCTA TATGGAACTGTCTAGCCTGAGATCAGAGGACACCGCCGTC TACTACTGCACTAGGTGGACTACCGGCACAGGCGCCTACT GGGGTCAAGGCACTACCGTGACCGTGTCTAGCGCTAGCAC |

TABLE 3-continued

Amino acid and nucleotide sequences of exemplary anti-PD-1 antibody molecules

```
                    TAAGGGCCCGTCCGTGTTCCCCCTGGCACCTTGTAGCCGG
                    AGCACTAGCGAATCCACCGCTGCCCTCGGCTGCCTGGTCA
                    AGGATTACTTCCCGGAGCCCGTGACCGTGTCCTGGAACAG
                    CGGAGCCCTGACCTCCGGAGTGCACACCTTCCCCGCTGTG
                    CTGCAGAGCTCCGGGCTGTACTCGCTGTCGTCGGTGGTCA
                    CGGTGCCTTCATCTAGCCTGGGTACCAAGACCTACACTTGC
                    AACGTGGACCACAAGCCTTCCAACACTAAGGTGGACAAGC
                    GCGTCGAATCGAAGTACGGCCCACCGTGCCCGCCTTGTCC
                    CGCGCCGGAGTTCCTCGGCGGTCCCTCGGTCTTTCTGTTCC
                    CACCGAAGCCCAAGGACACTTTGATGATTTCCCGCACCCC
                    TGAAGTGACATGCGTGGTCGTGGACGTGTCACAGGAAGAT
                    CCGGAGGTGCAGTTCAATTGGTACGTGGATGGCGTCGAGG
                    TGCACAACGCCAAAACCAAGCCGAGGGAGGAGCAGTTCA
                    ACTCCACTTACCGCGTCGTGTCCGTGCTGACGGTGCTGCAT
                    CAGGACTGGCTGAACGGGAAGGAGTACAAGTGCAAAGTG
                    TCCAACAAGGGACTTCCTAGCTCAATCGAAAAGACCATCT
                    CGAAAGCCAAGGGACAGCCCCGGGAACCCCAAGTGTATA
                    CCCTGCCACCGAGCCAGGAAGAAATGACTAAGAACCAAG
                    TCTCATTGACTTGCCTTGTGAAGGGCTTCTACCCATCGGAT
                    ATCGCCGTGGAATGGGAGTCCAACGGCCAGCGGAAAAC
                    AACTACAAGACCACCCCTCCGGTGCTGGACTCAGACGGAT
                    CCTTCTTCCTCTACTCGCGGCTGACCGTGATAAGAGCAG
                    ATGGCAGGAGGGAAATGTGTTCAGCTGTTCTGTGATGCAT
                    GAAGCCCTGCACAACCACTACACTCAGAAGTCCCTGTCCC
                    TCTCCCTGGGA

BAP049-Clone-E LC

SEQ ID NO: 31      LCDR1   KSSQSLLDSGNQKNFLT
(Kabat)

SEQ ID NO: 32      LCDR2   WASTRES
(Kabat)

SEQ ID NO: 286     LCDR3   QNDYSYPYT
(Kabat)

SEQ ID NO: 34      LCDR1   SQSLLDSGNQKNF
(Chothia)

SEQ ID NO: 35      LCDR2   WAS
(Chothia)

SEQ ID NO: 36      LCDR3   DYSYPY
(Chothia)

SEQ ID NO: 41      VL      EIVLTQSPATLSLSPGERATLSCKSSQSLLDSGNQKNFLTWYQ
                           QKPGQAPRLLIYWASTRESGVPSRFSGSGSGTDFTFTISSLEAE
                           DAATYYCQNDYSYPYTFGQGTKVEIK

SEQ ID NO: 42      DNA     GAGATCGTCCTGACTCAGTCACCCGCTACCCTGAGCCTGA
                   VL      GCCCTGGCGAGCGGGCTACACTGAGCTGTAAATCTAGTCA
                           GTCACTGCTGGATAGCGGTAATCAGAAGAACTTCCTGACC
                           TGGTATCAGCAGAAGCCCGGTCAAGCCCCTAGACTGCTGA
                           TCTACTGGGCCTCTACTAGAGAATCAGGCGTGCCCTCTAG
                           GTTTAGCGGTAGCGGTAGTGGCACCGACTTCACCTTCACT
                           ATCTCTAGCCTGGAAGCCGAGGACGCCGCTACCTACTACT
                           GTCAGAACGACTATAGCTACCCCTACACCTTCGGTCAAGG
                           CACTAAGGTCGAGATTAAG

SEQ ID NO: 43      Light   EIVLTQSPATLSLSPGERATLSCKSSQSLLDSGNQKNFLTWYQ
                   chain   QKPGQAPRLLIYWASTRESGVPSRFSGSGSGTDFTFTISSLEAE
                           DAATYYCQNDYSYPYTFGQGTKVEIKRTVAAPSVFIFPPSDE
                           QLKSGTASVVCLLNNFYPREAKVQWKVDNALQSGNSQESVT
                           EQDSKDSTYSLSSTLTLSKADYEKHKVYACEVTHQGLSSPVT
                           KSFNRGEC SEQ ID NO: 44      DNA     GAGATCGTCCTGACTCAGTCACCCGCTACCCTGAGCCTGA
                   light   GCCCTGGCGAGCGGGCTACACTGAGCTGTAAATCTAGTCA
                   chain   GTCACTGCTGGATAGCGGTAATCAGAAGAACTTCCTGACC
                           TGGTATCAGCAGAAGCCCGGTCAAGCCCCTAGACTGCTGA
                           TCTACTGGGCCTCTACTAGAGAATCAGGCGTGCCCTCTAG
                           GTTTAGCGGTAGCGGTAGTGGCACCGACTTCACCTTCACT
                           ATCTCTAGCCTGGAAGCCGAGGACGCCGCTACCTACTACT
                           GTCAGAACGACTATAGCTACCCCTACACCTTCGGTCAAGG
                           CACTAAGGTCGAGATTAAGCGTACGGTGGCCGCTCCCAGC
                           GTGTTCATCTTCCCCCCCAGCGACGAGCAGCTGAAGAGCG
```

TABLE 3-continued

Amino acid and nucleotide sequences of exemplary anti-PD-1 antibody molecules

```
                            GCACCGCCAGCGTGGTGTGCCTGCTGAACAACTTCTACCC
                            CCGGGAGGCCAAGGTGCAGTGGAAGGTGGACAACGCCCT
                            GCAGAGCGGCAACAGCCAGGAGAGCGTCACCGAGCAGGA
                            CAGCAAGGACTCCACCTACAGCCTGAGCAGCACCCTGACC
                            CTGAGCAAGGCCGACTACGAGAAGCATAAGGTGTACGCCT
                            GCGAGGTGACCCACCAGGGCCTGTCCAGCCCCGTGACCAA
                            GAGCTTCAACAGGGGCGAGTGC
```

BAP049-Clone-B HC

SEQ ID NO: 45    HCDR1    ACCTACTGGATGCAC
(Kabat)

SEQ ID NO: 46    HCDR2    AATATCTACCCCGGCACCGGCGGCTCTAACTTCGACGAGA
(Kabat)                   AGTTTAAGAAT SEQ ID NO: 47    HCDR3    TGGACTACCGGCACAGGCGCCTAC
(Kabat)

SEQ ID NO: 48    HCDR1    GGCTACACCTTCACTACCTAC
(Chothia)

SEQ ID NO: 49    HCDR2    TACCCCGGCACCGGCGGC
(Chothia)

SEQ ID NO: 47    HCDR3    TGGACTACCGGCACAGGCGCCTAC
(Chothia)

BAP049-Clone-B LC

SEQ ID NO: 50    LCDR1    AAATCTAGTCAGTCACTGCTGGATAGCGGTAATCAGAAGA
(Kabat)                   ACTTCCTGACC SEQ ID NO: 51    LCDR2    TGGGCCTCTACTAGAGAATCA
(Kabat)

SEQ ID NO: 52    LCDR3    CAGAACGACTATAGCTACCCCTACACC
(Kabat)

SEQ ID NO: 53    LCDR1    AGTCAGTCACTGCTGGATAGCGGTAATCAGAAGAACTTC
(Chothia)

SEQ ID NO: 54    LCDR2    TGGGCCTCT
(Chothia)

SEQ ID NO: 55    LCDR3    GACTATAGCTACCCCTAC
(Chothia)

BAP049-Clone-E HC

SEQ ID NO: 45    HCDR1    ACCTACTGGATGCAC
(Kabat)

SEQ ID NO: 46    HCDR2    AATATCTACCCCGGCACCGGCGGCTCTAACTTCGACGAGA
(Kabat)                   AGTTTAAGAAT SEQ ID NO: 47    HCDR3    TGGACTACCGGCACAGGCGCCTAC
(Kabat)

SEQ ID NO: 48    HCDR1    GGCTACACCTTCACTACCTAC
(Chothia)

SEQ ID NO: 49    HCDR2    TACCCCGGCACCGGCGGC
(Chothia)

SEQ ID NO: 47    HCDR3    TGGACTACCGGCACAGGCGCCTAC
(Chothia)

BAP049-Clone-E LC

SEQ ID NO: 50    LCDR1    AAATCTAGTCAGTCACTGCTGGATAGCGGTAATCAGAAGA
(Kabat)                   ACTTCCTGACC SEQ ID NO: 51    LCDR2    TGGGCCTCTACTAGAGAATCA
(Kabat)

TABLE 3-continued

Amino acid and nucleotide sequences of exemplary anti-PD-1 antibody molecules

| | | |
|---|---|---|
| SEQ ID NO: 52 (Kabat) | LCDR3 | CAGAACGACTATAGCTACCCCTACACC |
| SEQ ID NO: 53 (Chothia) | LCDR1 | AGTCAGTCACTGCTGGATAGCGGTAATCAGAAGAACTTC |
| SEQ ID NO: 54 (Chothia) | LCDR2 | TGGGCCTCT |
| SEQ ID NO: 55 (Chothia) | LCDR3 | GACTATAGCTACCCCTAC |

Other Exemplary PD-1 Inhibitors

In some embodiments, the anti-PD-1 antibody is Nivolumab (CAS Registry Number: 946414-94-4). Alternative names for Nivolumab include MDX-1106, MDX-1106-04, ONO-4538, BMS-936558 or OPDIVO®. Nivolumab is a fully human IgG4 monoclonal antibody, which specifically blocks PD1. Nivolumab (clone 5C4) and other human monoclonal antibodies that specifically bind to PD1 are disclosed in U.S. Pat. No. 8,008,449 and PCT Publication No. WO2006/121168, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Nivolumab, e.g., as disclosed in Table 4.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) *New England Journal of Medicine* 369 (2): 134-44, PCT Publication No. WO2009/114335, and U.S. Pat. No. 8,354,509, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pembrolizumab, e.g., as disclosed in Table 4.

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in PCT Publication No. WO2009/101611, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pidilizumab, e.g., as disclosed in Table 4.

Other anti-PD1 antibodies are disclosed in U.S. Pat. No. 8,609,089, US Publication No. 2010028330, and/or US Publication No. 20120114649, incorporated by reference in their entirety. Other anti-PD1 antibodies include AMP 514 (Amplimmune).

In one embodiment, the anti-PD-1 antibody molecule is MEDI0680 (Medimmune), also known as AMP-514. MEDI0680 and other anti-PD-1 antibodies are disclosed in U.S. Pat. No. 9,205,148 and WO 2012/145493, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of MEDI0680.

In one embodiment, the anti-PD-1 antibody molecule is REGN2810 (Regeneron). In one embodiment, the anti-PD-1 antibody molecule comprises one or more of the CDR sequences (or collectively all of the CDR sequences), the heavy chain or light chain variable region sequence, or the heavy chain or light chain sequence of REGN2810.

In one embodiment, the anti-PD-1 antibody molecule is PF-06801591 (Pfizer). In one embodiment, the anti-PD-1 antibody molecule comprises one or more of the CDR sequences (or collectively all of the CDR sequences), the heavy chain or light chain variable region sequence, or the heavy chain or light chain sequence of PF-06801591.

In one embodiment, the anti-PD-1 antibody molecule is BGB-A317 or BGB-108 (Beigene). In one embodiment, the anti-PD-1 antibody molecule comprises one or more of the CDR sequences (or collectively all of the CDR sequences), the heavy chain or light chain variable region sequence, or the heavy chain or light chain sequence of BGB-A317 or BGB-108.

In one embodiment, the anti-PD-1 antibody molecule is INCSHR1210 (Incyte), also known as INCSHR01210 or SHR-1210. In one embodiment, the anti-PD-1 antibody molecule comprises one or more of the CDR sequences (or collectively all of the CDR sequences), the heavy chain or light chain variable region sequence, or the heavy chain or light chain sequence of INCSHR1210.

In one embodiment, the anti-PD-1 antibody molecule is TSR-042 (Tesaro), also known as ANB011. In one embodiment, the anti-PD-1 antibody molecule comprises one or more of the CDR sequences (or collectively all of the CDR sequences), the heavy chain or light chain variable region sequence, or the heavy chain or light chain sequence of TSR-042.

Further known anti-PD-1 antibodies include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety.

In one embodiment, the anti-PD-1 antibody is an antibody that competes for binding with, and/or binds to the same epitope on PD-1 as, one of the anti-PD-1 antibodies described herein.

In one embodiment, the PD-1 inhibitor is a peptide that inhibits the PD-1 signalling pathway, e.g., as described in U.S. Pat. No. 8,907,053, incorporated by reference in its entirety. In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DCIg (Amplimmune), e.g., disclosed in WO 2010/027827 and WO 2011/066342, incorporated by reference in their entirety).

ments, the PD-L1 inhibitor is selected from FAZ053 (Novartis), Atezolizumab (Genentech/Roche), Avelumab (Merck Serono and Pfizer), Durvalumab (MedImmune/AstraZeneca), or BMS-936559 (Bristol-Myers Squibb).

Exemplary PD-L1 Inhibitors

In one embodiment, the PD-L1 inhibitor is an anti-PD-L1 antibody molecule. In one embodiment, the PD-L1 inhibitor is an anti-PD-L1 antibody molecule as disclosed in US

TABLE 4

Amino acid sequences of other exemplary anti-PD-1 antibody molecules

Nivolumab

SEQ ID NO: 56 Heavy chain
QVQLVESGGGVVQPGRSLRLDCKASGITFSNSGMHWVRQAPGKGL
EWVAVIWYDGSKRYYADSVKGRFTISRDNSKNTLFLQMNSLRAED
TAVYYCATNDDYWGQGTLVTVSSASTKGPSVFPLAPCSRSTSESTA
ALGCLVKDYFPEPVTVSWNSGALTSGVHTFPAVLQSSGLYSLSSVV
TVPSSSLGTKTYTCNVDHKPSNTKVDKRVESKYGPPCPPCPAPEFLG
GPSVFLFPPKPKDTLMISRTPEVTCVVVDVSQEDPEVQFNWYVDGV
EVHNAKTKPREEQFNSTYRVVSVLTVLHQDWLNGKEYKCKVSNKG
LPSSIEKTISKAKGQPREPQVYTLPPSQEEMTKNQVSLTCLVKGFYPS
DIAVEWESNGQPENNYKTTPPVLDSDGSFFLYSRLTVDKSRWQEGN
VFSCSVMHEALHNHYTQKSLSLSLGK SEQ ID NO: 57 Light chain
EIVLTQSPATLSLSPGERATLSCRASQSVSSYLAWYQQKPGQAPRLLI
YDASNRATGIPARFSGSGSGTDFTLTISSLEPEDFAVYYCQQSSNWP
RTFGQGTKVEIKRTVAAPSVFIFPPSDEQLKSGTASVVCLLNNFYPRE
AKVQWKVDNALQSGNSQESVTEQDSKDSTYSLSSTLTLSKADYEK
HKVYACEVTHQGLSSPVTKSFNRGEC Pembrolizumab SEQ ID NO: 58 Heavy chain
QVQLVQSGVEVKKPGASVKVSCKASGYTFTNYYMYWVRQAPGQG
LEWMGGINPSNGGTNFNEKFKNRVTLTTDSSTTTAYMELKSLQFDD
TAVYYCARRDYRFDMGFDYWGQGTTVTVSSASTKGPSVFPLAPCS
RSTSESTAALGCLVKDYFPEPVTVSWNSGALTSGVHTFPAVLQSSGL
YSLSSVVTVPSSSLGTKTYTCNVDHKPSNTKVDKRVESKYGPPCPPC
PAPEFLGGPSVFLFPPKPKDTLMISRTPEVTCVVVDVSQEDPEVQFN
WYVDGVEVHNAKTKPREEQFNSTYRVVSVLTVLHQDWLNGKEYK
CKVSNKGLPSSIEKTISKAKGQPREPQVYTLPPSQEEMTKNQVSLTC
LVKGFYPSDIAVEWESNGQPENNYKTTPPVLDSDGSFFLYSRLTVDK
SRWQEGNVFSCSVMHEALHNHYTQKSLSLSLGK SEQ ID NO: 59 Light chain
EIVLTQSPATLSLSPGERATLSCRASKGVSTSGYSYLHWYQQKPGQA
PRLLIYLASYLESGVPARFSGSGSGTDFTLTISSLEPEDFAVYYCQHS
RDLPLTFGGGTKVEIKRTVAAPSVFIFPPSDEQLKSGTASVVCLLNNF
YPREAKVQWKVDNALQSGNSQESVTEQDSKDSTYSLSSTLTLSKAD
YEKHKVYACEVTHQGLSSPVTKSFNRGEC Pidilizumab SEQ ID NO: 60 Heavy chain
QVQLVQSGSELKKPGASVKISCKASGYTFTNYGMNWVRQAPGQGL
QWMGWINTDSGESTYAEEFKGRFVFSLDTSVNTAYLQITSLTAEDT
GMYFCVRVGYDALDYWGQGTLVTVSSASTKGPSVFPLAPSSKSTSG
GTAALGCLVKDYFPEPVTVSWNSGALTSGVHTFPAVLQSSGLYSLS
SVVTVPSSSLGTQTYICNVNHKPSNTKVDKRVEPKSCDKTHTCPPCP
APELLGGPSVFLFPPKPKDTLMISRTPEVTCVVVDVSHEDPEVKFNW
YVDGVEVHNAKTKPREEQYNSTYRVVSVLTVLHQDWLNGKEYKC
KVSNKALPAPIEKTISKAKGQPREPQVYTLPPSREEMTKNQVSLTCL
VKGFYPSDIAVEWESNGQPENNYKTTPPVLDSDGSFFLYSKLTVDKS
RWQQGNVFSCSVMHEALHNHYTQKSLSLSPGK SEQ ID NO: 61 Light chain
EIVLTQSPSSLSASVGDRVTITCSARSSVSYMHWFQQKPGKAPKLWI
YRTSNLASGVPSRFSGSGSGTSYCLTINSLQPEDFATYYCQQRSSFPL
TFGGGTKLEIKRTVAAPSVFIFPPSDEQLKSGTASVVCLLNNFYPREA
KVQWKVDNALQSGNSQESVTEQDSKDSTYSLSSTLTLSKADYEKH
KVYACEVTHQGLSSPVTKSFNRGEC PD-L1 Inhibitors In some embodiments, the compounds of Formula (I') or Formula (I), or a pharmaceutically acceptable salt, hydrate, solvate, prodrug, stereoisomer, or tautomer thereof, of the present disclosure are used in combination with a PD-L1 inhibitor for treating a disease, e.g., cancer. In some embodi- 2016/0108123, published on Apr. 21, 2016, entitled "Antibody Molecules to PD-L1 and Uses Thereof," incorporated by reference in its entirety.

In one embodiment, the anti-PD-L1 antibody molecule comprises at least one, two, three, four, five or six complementarity determining regions (CDRs) (or collectively all of the CDRs) from a heavy and light chain variable region comprising an amino acid sequence shown in Table 5 (e.g., from the heavy and light chain variable region sequences of BAP058-Clone O or BAP058-Clone N disclosed in Table 5), or encoded by a nucleotide sequence shown in Table 5. In some embodiments, the CDRs are according to the Kabat definition (e.g., as set out in Table 5). In some embodiments, the CDRs are according to the Chothia definition (e.g., as set out in Table 5). In some embodiments, the CDRs are according to the combined CDR definitions of both Kabat and Chothia (e.g., as set out in Table 5). In one embodiment, the combination of Kabat and Chothia CDR of VH CDR1 comprises the amino acid sequence GYTFTSYWMY (SEQ ID NO: 214). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 5, or encoded by a nucleotide sequence shown in Table 5.

In one embodiment, the anti-PD-L1 antibody molecule comprises a heavy chain variable region (VH) comprising a VHCDR1 amino acid sequence of SEQ ID NO: 62, a VHCDR2 amino acid sequence of SEQ ID NO: 63, and a VHCDR3 amino acid sequence of SEQ ID NO: 64; and a light chain variable region (VL) comprising a VLCDR1 amino acid sequence of SEQ ID NO: 70, a VLCDR2 amino acid sequence of SEQ ID NO: 71, and a VLCDR3 amino acid sequence of SEQ ID NO: 72, each disclosed in Table 5.

In one embodiment, the anti-PD-L1 antibody molecule comprises a VH comprising a VHCDR1 encoded by the nucleotide sequence of SEQ ID NO: 89, a VHCDR2 encoded by the nucleotide sequence of SEQ ID NO: 90, and a VHCDR3 encoded by the nucleotide sequence of SEQ ID NO: 91; and a VL comprising a VLCDR1 encoded by the nucleotide sequence of SEQ ID NO: 94, a VLCDR2 encoded by the nucleotide sequence of SEQ ID NO: 95, and a VLCDR3 encoded by the nucleotide sequence of SEQ ID NO: 96, each disclosed in Table 5.

In one embodiment, the anti-PD-L1 antibody molecule comprises a VH comprising the amino acid sequence of SEQ ID NO: 67, or an amino acid sequence at least 85%, 90%, 95%, or 99% identical or higher to SEQ ID NO: 67. In one embodiment, the anti-PD-L1 antibody molecule comprises a VL comprising the amino acid sequence of SEQ ID NO: 77, or an amino acid sequence at least 85%, 90%, 95%, or 99% identical or higher to SEQ ID NO: 77. In one embodiment, the anti-PD-L1 antibody molecule comprises a VH comprising the amino acid sequence of SEQ ID NO: 81, or an amino acid sequence at least 85%, 90%, 95%, or 99% identical or higher to SEQ ID NO: 81. In one embodiment, the anti-PD-L1 antibody molecule comprises a VL comprising the amino acid sequence of SEQ ID NO: 85, or an amino acid sequence at least 85%, 90%, 95%, or 99% identical or higher to SEQ ID NO: 85. In one embodiment, the anti-PD-L1 antibody molecule comprises a VH comprising the amino acid sequence of SEQ ID NO: 67 and a VL comprising the amino acid sequence of SEQ ID NO: 77. In one embodiment, the anti-PD-L1 antibody molecule comprises a VH comprising the amino acid sequence of SEQ ID NO: 81 and a VL comprising the amino acid sequence of SEQ ID NO: 85.

In one embodiment, the antibody molecule comprises a VH encoded by the nucleotide sequence of SEQ ID NO: 68, or a nucleotide sequence at least 85%, 90%, 95%, or 99% identical or higher to SEQ ID NO: 68. In one embodiment, the antibody molecule comprises a VL encoded by the nucleotide sequence of SEQ ID NO: 78, or a nucleotide sequence at least 85%, 90%, 95%, or 99% identical or higher to SEQ ID NO: 78. In one embodiment, the antibody molecule comprises a VH encoded by the nucleotide sequence of SEQ ID NO: 82, or a nucleotide sequence at least 85%, 90%, 95%, or 99% identical or higher to SEQ ID NO: 82. In one embodiment, the antibody molecule comprises a VL encoded by the nucleotide sequence of SEQ ID NO: 86, or a nucleotide sequence at least 85%, 90%, 95%, or 99% identical or higher to SEQ ID NO: 86. In one embodiment, the antibody molecule comprises a VH encoded by the nucleotide sequence of SEQ ID NO: 68 and a VL encoded by the nucleotide sequence of SEQ ID NO: 78. In one embodiment, the antibody molecule comprises a VH encoded by the nucleotide sequence of SEQ ID NO: 82 and a VL encoded by the nucleotide sequence of SEQ ID NO: 86.

In one embodiment, the anti-PD-L1 antibody molecule comprises a heavy chain comprising the amino acid sequence of SEQ ID NO: 69, or an amino acid sequence at least 85%, 90%, 95%, or 99% identical or higher to SEQ ID NO: 69. In one embodiment, the anti-PD-L1 antibody molecule comprises a light chain comprising the amino acid sequence of SEQ ID NO: 79, or an amino acid sequence at least 85%, 90%, 95%, or 99% identical or higher to SEQ ID NO: 79. In one embodiment, the anti-PD-L1 antibody molecule comprises a heavy chain comprising the amino acid sequence of SEQ ID NO: 83, or an amino acid sequence at least 85%, 90%, 95%, or 99% identical or higher to SEQ ID NO: 83. In one embodiment, the anti-PD-L1 antibody molecule comprises a light chain comprising the amino acid sequence of SEQ ID NO: 87, or an amino acid sequence at least 85%, 90%, 95%, or 99% identical or higher to SEQ ID NO: 87. In one embodiment, the anti-PD-L1 antibody molecule comprises a heavy chain comprising the amino acid sequence of SEQ ID NO: 69 and a light chain comprising the amino acid sequence of SEQ ID NO: 79. In one embodiment, the anti-PD-L1 antibody molecule comprises a heavy chain comprising the amino acid sequence of SEQ ID NO: 83 and a light chain comprising the amino acid sequence of SEQ ID NO: 87.

In one embodiment, the antibody molecule comprises a heavy chain encoded by the nucleotide sequence of SEQ ID NO: 76, or a nucleotide sequence at least 85%, 90%, 95%, or 99% identical or higher to SEQ ID NO: 76. In one embodiment, the antibody molecule comprises a light chain encoded by the nucleotide sequence of SEQ ID NO: 80, or a nucleotide sequence at least 85%, 90%, 95%, or 99% identical or higher to SEQ ID NO: 80. In one embodiment, the antibody molecule comprises a heavy chain encoded by the nucleotide sequence of SEQ ID NO: 84, or a nucleotide sequence at least 85%, 90%, 95%, or 99% identical or higher to SEQ ID NO: 84. In one embodiment, the antibody molecule comprises a light chain encoded by the nucleotide sequence of SEQ ID NO: 88, or a nucleotide sequence at least 85%, 90%, 95%, or 99% identical or higher to SEQ ID NO: 88. In one embodiment, the antibody molecule comprises a heavy chain encoded by the nucleotide sequence of SEQ ID NO: 76 and a light chain encoded by the nucleotide sequence of SEQ ID NO: 80. In one embodiment, the antibody molecule comprises a heavy chain encoded by the nucleotide sequence of SEQ ID NO: 84 and a light chain encoded by the nucleotide sequence of SEQ ID NO: 88.

The antibody molecules described herein can be made by vectors, host cells, and methods described in US 2016/0108123, incorporated by reference in its entirety.

TABLE 5

Amino acid and nucleotide sequences of exemplary anti-PD-L1 antibody molecules

BAP058-Clone O HC

| SEQ ID NO: 62 (Kabat) | HCDR1 | SYWMY |
|---|---|---|
| SEQ ID NO: 63 (Kabat) | HCDR2 | RIDPNSGSTKYNEKFKN |
| SEQ ID NO: 64 (Kabat) | HCDR3 | DYRKGLYAMDY |
| SEQ ID NO: 65 (Chothia) | HCDR1 | GYTFTSY |
| SEQ ID NO: 66 (Chothia) | HCDR2 | DPNSGS |
| SEQ ID NO: 64 (Chothia) | HCDR3 | DYRKGLYAMDY |
| SEQ ID NO: 67 | VH | EVQLVQSGAEVKKPGATVKISCKVSGYTFTSYWMYWVR QARGQRLEWIGRIDPNSGSTKYNEKFKNRFTISRDNSKNTL YLQMNSLRAEDTAVYYCARDYRKGLYAMDYWGQGTTV TVSS |
| SEQ ID NO: 68 | DNA VH | GAAGTGCAGCTGGTGCAGTCAGGCGCCGAAGTGAAGAA ACCCGGCGCTACCGTGAAGATTAGCTGTAAAGTCTCAG GCTACACCTTCACTAGCTACTGGATGTACTGGGTCCGAC AGGCTAGAGGGCAAAGACTGGAGTGGATCGGTAGAATC GACCCTAATAGCGGCTCTACTAAGTATAACGAGAAGTT TAAGAATAGGTTCACTATTAGTAGGGATAACTCTAAGA ACACCCTGTACCTGCAGATGAATAGCCTGAGAGCCGAG GACACCGCCGTCTACTACTGCGCTAGAGACTATAGAAA GGGCCTGTACGCTATGGACTACTGGGGTCAAGGCACTA CCGTGACCGTGTCTTCA |
| SEQ ID NO: 69 | Heavy chain | EVQLVQSGAEVKKPGATVKISCKVSGYTFTSYWMYWVR QARGQRLEWIGRIDPNSGSTKYNEKFKNRFTISRDNSKNTL YLQMNSLRAEDTAVYYCARDYRKGLYAMDYWGQGTTV TVSSASTKGPSVFPLAPCSRSTSESTAALGCLVKDYFPEPV TVSWNSGALTSGVHTFPAVLQSSGLYSLSSVVTVPSSSLGT KTYTCNVDHKPSNTKVDKRVESKYGPPCPPCPAPEFLGGP SVFLFPPKPKDTLMISRTPEVTCVVVDVSQEDPEVQFNWY VDGVEVHNAKTKPREEQFNSTYRVVSVLTVLHQDWLNG KEYKCKVSNKGLPSSIEKTISKAKGQPREPQVYTLPPSQEE MTKNQVSLTCLVKGFYPSDIAVEWESNGQPENNYKTTPPV LDSDGSFFLYSRLTVDKSRWQEGNVFSCSVMHEALHNHY TQKSLSLSLG |
| SEQ ID NO: 76 | DNA heavy chain | GAAGTGCAGCTGGTGCAGTCAGGCGCCGAAGTGAAGAA ACCCGGCGCTACCGTGAAGATTAGCTGTAAAGTCTCAG GCTACACCTTCACTAGCTACTGGATGTACTGGGTCCGAC AGGCTAGAGGGCAAAGACTGGAGTGGATCGGTAGAATC GACCCTAATAGCGGCTCTACTAAGTATAACGAGAAGTT TAAGAATAGGTTCACTATTAGTAGGGATAACTCTAAGA ACACCCTGTACCTGCAGATGAATAGCCTGAGAGCCGAG GACACCGCCGTCTACTACTGCGCTAGAGACTATAGAAA GGGCCTGTACGCTATGGACTACTGGGGTCAAGGCACTA CCGTGACCGTGTCTTCAGCTAGCACTAAGGGCCCGTCCG TGTTCCCCCTGGCACCTTGTAGCCGGAGCACTAGCGAAT CCACCGCTGCCCTCGGCTGCCTGGTCAAGGATTACTTCC CGGAGCCCGTGACCGTGTCCTGGAACAGCGGAGCCCTG ACCTCCGGAGTGCACACCTTCCCCGCTGTGCTGCAGAGC TCCGGGCTGTACTCGCTGTCGTCGGTGGTCACGGTGCCT TCATCTAGCCTGGGTACCAAGACCTACACTTGCAACGTG GACCACAAGCCTTCCAACACTAAGGTGGACAAGCGCGT CGAATCGAAGTACGGCCCCACCGTGCCCGCCTTGTCCCG CGCCGGAGTTCCTCGGCGGTCCCTCGGTCTTTCTGTTCC CACCGAAGCCCAAGGACACTTTGATGATTTCCCGCACC CCTGAAGTGACATGCGTGGTCGTGGACGTGTCACAGGA AGATCCGGAGGTGCAGTTCAATTGGTACGTGGATGGCG TCGAGGTGCACAACGCCAAAACCAAGCCGAGGGAGGA GCAGTTCAACTCCACTTACCGCGTCGTGTCCGTGCTGAC GGTGCTGCATCAGGACTGGCTGAACGGGAAGGAGTACA AGTGCAAAGTGTCCAACAAGGGACTTCCTAGCTCAATC GAAAAGACCATCTCGAAAGCCAAGGGACAGCCCCGGG AACCCCAAGTGTATACCCTGCCACCGAGCCAGGAAGAA ATGACTAAGAACCAAGTCTCATTGACTTGCCTTGTGAAG GGCTTCTACCCATCGGATATCGCCGTGGAATGGGAGTC CAACGGCCAGCCGGAAAACAACTACAAGACCACCCCTC |

TABLE 5-continued

Amino acid and nucleotide sequences of exemplary anti-PD-L1 antibody molecules

```
CGGTGCTGGACTCAGACGGATCCTTCTTCCTCTACTCGC
GGCTGACCGTGGATAAGAGCAGATGGCAGGAGGGAAA
TGTGTTCAGCTGTTCTGTGATGCATGAAGCCCTGCACAA
CCACTACACTCAGAAGTCCCTGTCCCTCTCCCTGGGA
```

BAP058-Clone O LC

| | | | |
|---|---|---|---|
| SEQ ID NO: 70 (Kabat) | | LCDR1 | KASQDVGTAVA |
| SEQ ID NO: 71 (Kabat) | | LCDR2 | WASTRHT |
| SEQ ID NO: 72 (Kabat) | | LCDR3 | QQYNSYPLT |
| SEQ ID NO: 73 (Chothia) | | LCDR1 | SQDVGTA |
| SEQ ID NO: 74 (Chothia) | | LCDR2 | WAS |
| SEQ ID NO: 75 (Chothia) | | LCDR3 | YNSYPL |
| SEQ ID NO: 77 | | VL | AIQLTQSPSSLSASVGDRVTITCKASQDVGTAVAWYLQKP GQSPQLLIYWASTRHTGVPSRFSGSGSGTDFTFTISSLEAED AATYYCQQYNSYPLTFGQGTKVEIK |
| SEQ ID NO: 78 | | DNA VL | GCTATTCAGCTGACTCAGTCACCTAGTAGCCTGAGCGCT AGTGTGGGCGATAGAGTGACTATCACCTGTAAAGCCTC TCAGGACGTGGGCACCGCCGTGGCCTGGTATCTGCAGA AGCCTGGTCAATCACCTCAGCTGCTGATCTACTGGGCCT CTACTAGACACACCGGCGTGCCCTCTAGGTTTAGCGGTA GCGGTAGTGGCACCGACTTCACCTTCACTATCTCTTCAC TGGAAGCCGAGGACGCCGCTACCTACTACTGTCAGCAG TATAATAGCTACCCCCTGACCTTCGGTCAAGGCACTAAG GTCGAGATTAAG |
| SEQ ID NO: 79 | | Light chain | AIQLTQSPSSLSASVGDRVTITCKASQDVGTAVAWYLQKP GQSPQLLIYWASTRHTGVPSRFSGSGSGTDFTFTISSLEAED AATYYCQQYNSYPLTFGQGTKVEIKRTVAAPSVFIFPPSDE QLKSGTASVVCLLNNFYPREAKVQWKVDNALQSGNSQES VTEQDSKDSTYSLSSTLTLSKADYEKHKVYACEVTHQGLS SPVTKSFNRGEC |
| SEQ ID NO: 80 | | DNA light chain | GCTATTCAGCTGACTCAGTCACCTAGTAGCCTGAGCGCT AGTGTGGGCGATAGAGTGACTATCACCTGTAAAGCCTC TCAGGACGTGGGCACCGCCGTGGCCTGGTATCTGCAGA AGCCTGGTCAATCACCTCAGCTGCTGATCTACTGGGCCT CTACTAGACACACCGGCGTGCCCTCTAGGTTTAGCGGTA GCGGTAGTGGCACCGACTTCACCTTCACTATCTCTTCAC TGGAAGCCGAGGACGCCGCTACCTACTACTGTCAGCAG TATAATAGCTACCCCCTGACCTTCGGTCAAGGCACTAAG GTCGAGATTAAGCGTACGGTGGCCGCTCCCAGCGTGTT CATCTTCCCCCCCAGCGACGAGCAGCTGAAGAGCGGCA CCGCCAGCGTGGTGTGCCTGCTGAACAACTTCTACCCCC GGGAGGCCAAGGTGCAGTGGAAGGTGGACAACGCCCT GCAGAGCGGCAACAGCCAGGAGAGCGTCACCGAGCAG GACAGCAAGGACTCCACCTACAGCCTGAGCAGCACCCT GACCCTGAGCAAGGCCGACTACGAGAAGCATAAGGTGT ACGCCTGCGAGGTGACCCACCAGGGCCTGTCCAGCCCC GTGACCAAGAGCTTCAACAGGGGCGAGTGC |

BAP058-Clone N HC

| | | | |
|---|---|---|---|
| SEQ ID NO: 62 (Kabat) | | HCDR1 | SYWMY |
| SEQ ID NO: 63 (Kabat) | | HCDR2 | RIDPNSGSTKYNEKFKN |
| SEQ ID NO: 64 (Kabat) | | HCDR3 | DYRKGLYAMDY |
| SEQ ID NO: 65 (Chothia) | | HCDR1 | GYTFTSY |
| SEQ ID NO: 66 (Chothia) | | HCDR2 | DPNSGS |
| SEQ ID NO: 64 (Chothia) | | HCDR3 | DYRKGLYAMDY |

TABLE 5-continued

Amino acid and nucleotide sequences of exemplary anti-PD-L1 antibody molecules

| | | |
|---|---|---|
| SEQ ID NO: 81 | VH | EVQLVQSGAEVKKPGATVKISCKVSGYTFTSYWMYWVR QATGQGLEWMGRIDPNSGSTKYNEKFKNRVTITADKSTST AYMELSSLRSEDTAVYYCARDYRKGLYAMDYWGQGTTV TVSS |
| SEQ ID NO: 82 | DNA VH | GAAGTGCAGCTGGTGCAGTCAGGCGCCGAAGTGAAGAA ACCCGGCGCTACCGTGAAGATTAGCTGTAAAGTCTCAG GCTACACCTTCACTAGCTACTGGATGTACTGGGTCCGAC AGGCTACCGGTCAAGGCCTGGAGTGGATGGGTAGAATC GACCCTAATAGCGGCTCTACTAAGTATAACGAGAAGTT TAAGAATAGAGTGACTATCACCGCCGATAAGTCTACTA GCACCGCCTATATGGAACTGTCTAGCCTGAGATCAGAG GACACCGCCGTCTACTACTGCGCTAGAGACTATAGAAA GGGCCTGTACGCTATGGACTACTGGGGTCAAGGCACTA CCGTGACCGTGTCTTCA |
| SEQ ID NO: 83 | Heavy chain | EVQLVQSGAEVKKPGATVKISCKVSGYTFTSYWMYWVR QATGQGLEWMGRIDPNSGSTKYNEKFKNRVTITADKSTST AYMELSSLRSEDTAVYYCARDYRKGLYAMDYWGQGTTV TVSSASTKGPSVFPLAPCSRSTSESTAALGCLVKDYFPEPV TVSWNSGALTSGVHTFPAVLQSSGLYSLSSVVTVPSSSLGT KTYTCNVDHKPSNTKVDKRVESKYGPPCPPCPAPEFLGGP SVFLFPPKPKDTLMISRTPEVTCVVVDVSQEDPEVQFNWY VDGVEVHNAKTKPREEQFNSTYRVVSVLTVLHQDWLNG KEYKCKVSNKGLPSSIEKTISKAKGQPREPQVYTLPPSQEE MTKNQVSLTCLVKGFYPSDIAVEWESNGQPENNYKTTPPV LDSDGSFFLYSRLTVDKSRWQEGNVFSCSVMHEALHNHY TQKSLSLSLG |
| SEQ ID NO: 84 | DNA heavy chain | GAAGTGCAGCTGGTGCAGTCAGGCGCCGAAGTGAAGAA ACCCGGCGCTACCGTGAAGATTAGCTGTAAAGTCTCAG GCTACACCTTCACTAGCTACTGGATGTACTGGGTCCGAC AGGCTACCGGTCAAGGCCTGGAGTGGATGGGTAGAATC GACCCTAATAGCGGCTCTACTAAGTATAACGAGAAGTT TAAGAATAGAGTGACTATCACCGCCGATAAGTCTACTA GCACCGCCTATATGGAACTGTCTAGCCTGAGATCAGAG GACACCGCCGTCTACTACTGCGCTAGAGACTATAGAAA GGGCCTGTACGCTATGGACTACTGGGGTCAAGGCACTA CCGTGACCGTGTCTTCAGCTAGCACTAAGGGCCCGTCCG TGTTCCCCCTGGCACCTTGTAGCCGGAGCACTAGCGAAT CCACCGCTGCCCTCGGCTGCCTGGTCAAGGATTACTTCC CGGAGCCCGTGACCGTGTCCTGGAACAGCGGAGCCCTG ACCTCCGGAGTGCACACCTTCCCCGCTGTGCTGCAGAGC TCCGGGCTGTACTCGCTGTCGTCGGTGGTCACGGTGCCT TCATCTAGCCTGGGTACCAAGACCTACACTTGCAACGTG GACCACAAGCCTTCCAACACTAAGGTGGACAAGCGCGT CGAATCGAAGTACGGCCCACCGTGCCCGCCTTGTCCCG CGCCGGAGTTCCTCGGCGGTCCCTCGGTCTTTCTGTTCC CACCGAAGCCCAAGGACACTTTGATGATTTCCCGCACC CCTGAAGTGACATGCGTGGTCGTGGACGTGTCACAGGA AGATCCGGAGGTGCAGTTCAATTGGTACGTGGATGGCG TCGAGGTGCACAACGCCAAAACCAAGCCGAGGGAGGA GCAGTTCAACTCCACTTACCGCGTCGTGTCCGTGCTGAC GGTGCTGCATCAGGACTGGCTGAACGGGAAGGAGTACA AGTGCAAAGTGTCCAACAAGGGACTTCCTAGCTCAATC GAAAAGACCATCTCGAAAGCCAAGGGACAGCCCCGGG AACCCCAAGTGTATACCCTGCCACCGAGCCAGGAAGAA ATGACTAAGAACCAAGTCTCATTGACTTGCCTTGTGAAG GGCTTCTACCCATCGGATATCGCCGTGGAATGGGAGTC CAACGGCCAGCCGGAAAAACTACAAGACCACCCCCTC CGGTGCTGGACTCAGACGGATCCTTCTTCCTCTACTCGC GGCTGACCGTGGATAAGAGCAGATGGCAGGAGGGAAA TGTGTTCAGCTGTTCTGTGATGCATAAGCCCTGCACAA CCACTACACTCAGAAGTCCCTGTCCCTCTCCCTGGGA |

BAP058-Clone N LC

| | | |
|---|---|---|
| SEQ ID NO: 70 (Kabat) | LCDR1 | KASQDVGTAVA |
| SEQ ID NO: 71 (Kabat) | LCDR2 | WASTRHT |
| SEQ ID NO: 72 (Kabat) | LCDR3 | QQYNSYPLT |
| SEQ ID NO: 73 (Chothia) | LCDR1 | SQDVGTA |

TABLE 5-continued

Amino acid and nucleotide sequences of exemplary anti-PD-L1 antibody molecules

| | | |
|---|---|---|
| SEQ ID NO: 74 (Chothia) | LCDR2 | WAS |
| SEQ ID NO: 75 (Chothia) | LCDR3 | YNSYPL |
| SEQ ID NO: 85 | VL | DVVMTQSPLSLPVTLGQPASISCKASQDVGTAVAWYQQK PGQAPRLLIYWASTRHTGVPSRFSGSGSGTEFTLTISSLQPD DFATYYCQQYNSYPLTFGQGTKVEIK |
| SEQ ID NO: 86 | DNA VL | GACGTCGTGATGACTCAGTCACCCCTGAGCCTGCCCGTG ACCCTGGGGCAGCCCGCCTCTATTAGCTGTAAAGCCTCT CAGGACGTGGGCACCGCCGTGGCCTGGTATCAGCAGAA GCCAGGGCAAGCCCCTAGACTGCTGATCTACTGGGCCT CTACTAGACACACCGGCGTGCCCTCTAGGTTTAGCGGTA GCGGTAGTGGCACCGAGTTCACCCTGACTATCTCTTCAC TGCAGCCCGACGACTTCGCTACCTACTACTGTCAGCAGT ATAATAGCTACCCCCTGACCTTCGGTCAAGGCACTAAG GTCGAGATTAAG |
| SEQ ID NO: 87 | Light chain | DVVMTQSPLSLPVTLGQPASISCKASQDVGTAVAWYQQK PGQAPRLLIYWASTRHTGVPSRFSGSGSGTEFTLTISSLQPD DFATYYCQQYNSYPLTFGQGTKVEIKRTVAAPSVFIFPPSD EQLKSGTASVVCLLNNFYPREAKVQWKVDNALQSGNSQE SVTEQDSKDSTYSLSSTLTLSKADYEKHKVYACEVTHQGL SSPVTKSFNRGEC |
| SEQ ID NO: 88 | DNA light chain | GACGTCGTGATGACTCAGTCACCCCTGAGCCTGCCCGTG ACCCTGGGGCAGCCCGCCTCTATTAGCTGTAAAGCCTCT CAGGACGTGGGCACCGCCGTGGCCTGGTATCAGCAGAA GCCAGGGCAAGCCCCTAGACTGCTGATCTACTGGGCCT CTACTAGACACACCGGCGTGCCCTCTAGGTTTAGCGGTA GCGGTAGTGGCACCGAGTTCACCCTGACTATCTCTTCAC TGCAGCCCGACGACTTCGCTACCTACTACTGTCAGCAGT ATAATAGCTACCCCCTGACCTTCGGTCAAGGCACTAAG GTCGAGATTAAGCGTACGGTGGCCGCTCCCAGCGTGTT CATCTTCCCCCCAGCGACGAGCAGCTGAAGAGCGGCA CCGCCAGCGTGGTGTGCCTGCTGAACAACTTCTACCCCC GGGAGGCCAAGGTGCAGTGGAAGGTGGACAACGCCCT GCAGAGCGGCAACAGCCAGGAGAGCGTCACCGAGCAG GACAGCAAGGACTCCACCTACAGCCTGAGCAGCACCCT GACCCTGAGCAAGGCCGACTACGAGAAGCATAAGGTGT ACGCCTGCGAGGTGACCCACCAGGGCCTGTCCAGCCCC GTGACCAAGAGCTTCAACAGGGGCGAGTGC |

BAP058-Clone O HC

| | | |
|---|---|---|
| SEQ ID NO: 89 (Kabat) | HCDR1 | agctactggatgtac |
| SEQ ID NO: 90 (Kabat) | HCDR2 | agaatcgaccctaatagcggctctactaagtataacgagaagtttaagaat |
| SEQ ID NO: 91 (Kabat) | HCDR3 | gactatagaaagggcctgtacgctatggactac |
| SEQ ID NO: 92 (Chothia) | HCDR1 | ggctacaccttcactagctac |
| SEQ ID NO: 93 (Chothia) | HCDR2 | gaccctaatagcggctct |
| SEQ ID NO: 91 (Chothia) | HCDR3 | gactatagaaagggcctgtacgctatggactac |

BAP058-Clone O LC

| | | |
|---|---|---|
| SEQ ID NO: 94 (Kabat) | LCDR1 | aaagcctctcaggacgtgggcaccgccgtggcc |
| SEQ ID NO: 95 (Kabat) | LCDR2 | tgggcctctactagacacacc |
| SEQ ID NO: 96 (Kabat) | LCDR3 | cagcagtataatagctacccctgacc |
| SEQ ID NO: 97 (Chothia) | LCDR1 | tctcaggacgtgggcaccgcc |

TABLE 5-continued

Amino acid and nucleotide sequences of exemplary anti-PD-L1 antibody molecules

| | | | |
|---|---|---|---|
| SEQ ID NO: 98 (Chothia) | | LCDR2 | tgggcctct |
| SEQ ID NO: 99 (Chothia) | | LCDR3 | tataatagctaccccctg |

BAP058-Clone N HC

| | | | |
|---|---|---|---|
| SEQ ID NO: 89 | (Kabat) | HCDR1 | agctactggatgtac |
| SEQ ID NO: 90 | (Kabat) | HCDR2 | agaatcgaccctaatagcggctctactaagtataacgagaagtttaagaat |
| SEQ ID NO: 91 | (Kabat) | HCDR3 | gactatagaaagggcctgtacgctatggactac |
| SEQ ID NO: 92 (Chothia) | | HCDR1 | ggctacaccttcactagctac |
| SEQ ID NO: 93 (Chothia) | | HCDR2 | gaccctaatagcggctct |
| SEQ ID NO: 91 (Chothia) | | HCDR3 | gactatagaaagggcctgtacgctatggactac |

BAP058-Clone N LC

| | | | |
|---|---|---|---|
| SEQ ID NO: 94 | (Kabat) | LCDR1 | aaagcctctcaggacgtgggcaccgccgtggcc |
| SEQ ID NO: 95 | (Kabat) | LCDR2 | tgggcctctactagacacacc |
| SEQ ID NO: 96 | (Kabat) | LCDR3 | cagcagtataatagctaccccctgacc |
| SEQ ID NO: 97 (Chothia) | | LCDR1 | tctcaggacgtgggcaccgcc |
| SEQ ID NO: 98 (Chothia) | | LCDR2 | tgggcctct |
| SEQ ID NO: 99 (Chothia) | | LCDR3 | tataatagctaccccctg |

Other Exemplary PD-L1 Inhibitors

In some embodiments, the PD-L1 inhibitor is anti-PD-L1 antibody. In some embodiments, the anti-PD-L1 inhibitor is selected from YW243.55.S70, MPDL3280A, MEDI-4736, or MDX-1105MSB-0010718C (also referred to as A09-246-2) disclosed in, e.g., WO 2013/0179174, and having a sequence disclosed herein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in PCT Publication No. WO 2007/005874.

In one embodiment, the PD-L1 inhibitor is YW243.55.S70. The YW243.55.S70 antibody is an anti-PD-L1 described in PCT Publication No. WO 2010/077634.

In one embodiment, the PD-L1 inhibitor is MDPL3280A (Genentech/Roche) also known as Atezolizumabm, RG7446, RO5541267, YW243.55.S70, or TECENTRIQ™. MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906 incorporated by reference in its entirety. In one embodiment, the anti-PD-L1 antibody molecule comprises one or more of the CDR sequences (or collectively all of the CDR sequences), the heavy chain or light chain variable region sequence, or the heavy chain or light chain sequence of Atezolizumab, e.g., as disclosed in Table 6.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in PCT Publication Nos. WO2010/027827 and WO2011/066342).

In one embodiment, the PD-L1 inhibitor is an anti-PD-L1 antibody molecule. In one embodiment, the anti-PD-L1 antibody molecule is Avelumab (Merck Serono and Pfizer), also known as MSB0010718C. Avelumab and other anti-PD-L1 antibodies are disclosed in WO 2013/079174, incorporated by reference in its entirety. In one embodiment, the anti-PD-L1 antibody molecule comprises one or more of the CDR sequences (or collectively all of the CDR sequences), the heavy chain or light chain variable region sequence, or the heavy chain or light chain sequence of Avelumab, e.g., as disclosed in Table 6.

In one embodiment, the anti-PD-L1 antibody molecule is Durvalumab (MedImmune/AstraZeneca), also known as MEDI4736. Durvalumab and other anti-PD-L1 antibodies are disclosed in U.S. Pat. No. 8,779,108, incorporated by reference in its entirety. In one embodiment, the anti-PD-L1 antibody molecule comprises one or more of the CDR sequences (or collectively all of the CDR sequences), the heavy chain or light chain variable region sequence, or the heavy chain or light chain sequence of Durvalumab, e.g., as disclosed in Table 6.

In one embodiment, the anti-PD-L1 antibody molecule is BMS-936559 (Bristol-Myers Squibb), also known as MDX- 1105 or 12A4. BMS-936559 and other anti-PD-L1 antibodies are disclosed in U.S. Pat. No. 7,943,743 and WO 2015/081158, incorporated by reference in their entirety. In one embodiment, the anti-PD-L1 antibody molecule comprises one or more of the CDR sequences (or collectively all of the CDR sequences), the heavy chain or light chain variable region sequence, or the heavy chain or light chain sequence of BMS-936559, e.g., as disclosed in Table 6.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entirety.

In one embodiment, the anti-PD-L1 antibody is an antibody that competes for binding with, and/or binds to the same epitope on PD-L1 as, one of the anti-PD-L1 antibodies described herein.

TABLE 6

Amino acid sequences of other exemplary anti-PD-L1 antibody molecules

Atezolizumab

| SEQ ID NO: 100 | Heavy chain | EVQLVESGGGLVQPGGSLRLSCAASGFTFSDSWIHWVRQAPGKGLE WVAWISPYGGSTYYADSVKGRFTISADTSKNTAYLQMNSLRAEDTA VYYCARRHWPGGFDYWGQGTLVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKVEPKSCDKTHTCPPCPA PELLGGPSVFLFPPKPKDTLMISRTPEVTCVVVDVSHEDPEVKFNWY VDGVEVHNAKTKPREEQYASTYRVVSVLTVLHQDWLNGKEYKCK VSNKALPAPIEKTISKAKGQPREPQVYTLPPSREEMTKNQVSLTCLVK GFYPSDIAVEWESNGQPENNYKTTPPVLDSDGSFFLYSKLTVDKSRW QQGNVFSCSVMHEALHNHYTQKSLSLSPGK |
|---|---|---|
| SEQ ID NO: 101 | Light chain | DIQMTQSPSSLSASVGDRVTITCRASQDVSTAVAWYQQKPGKAPKL LIYSASFLYSGVPSRFSGSGSGTDFTLTISSLQPEDFATYYCQQYLYHP ATFGQGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |

Avelumab

| SEQ ID NO: 102 | Heavy chain | EVQLLESGGGLVQPGGSLRLSCAASGFTFSSYIMMWVRQAPGKGLE WVSSIYPSGGITFYADTVKGRFTISRDNSKNTLYLQMNSLRAEDTAV YYCARIKLGTVTTVDYWGQGTLVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKVEPKSCDKTHTCPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCK VSNKALPAPIEKTISKAKGQPREPQVYTLPPSRDELTKNQVSLTCLVK GFYPSDIAVEWESNGQPENNYKTTPPVLDSDGSFFLYSKLTVDKSRW QQGNVFSCSVMHEALHNHYTQKSLSLSPGK |
|---|---|---|
| SEQ ID NO: 103 | Light chain | QSALTQPASVSGSPGQSITISCTGTSSDVGGYNYVSWYQQHPGKAPK LMIYDVSNRPSGVSNRFSGSKSGNTASLTISGLQAEDEADYYCSSYTS SSTRVFGTGTKVTVLGQPKANPTVTLFPPSSEELQANKATLVCLISDF YPGAVTVAWKADGSPVKAGVETTKPSKQSNNKYAASSYLSLTPEQ WKSHRSYSCQVTHEGSTVEKTVAPTECS |

Durvalumab

| SEQ ID NO: 104 | Heavy chain | EVQLVESGGGLVQPGGSLRLSCAASGFTFSRYWMSWVRQAPGKGL EWVANIKQDGSEKYYVDSVKGRFTISRDNAKNSLYLQMNSLRAEDT AVYYCAREGGWFGELAFDYWGQGTLVTVSSASTKGPSVFPLAPSSK STSGGTAALGCLVKDYFPEPVTVSWNSGALTSGVHTFPAVLQSSGLY SLSSVVTVPSSSLGTQTYICNVNHKPSNTKVDKRVEPKSCDKTHTCPP CPAPEFEGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPASIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPGK |
|---|---|---|
| SEQ ID NO: 105 | Light chain | EIVLTQSPGTLSLSPGERATLSCRASQRVSSSYLAWYQQKPGQAPRLL IYDASSRATGIPDRFSGSGSGTDFTLTISRLEPEDFAVYYCQQYGSLP WTFGQGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |

BMS-936559

| SEQ ID NO: 106 | VH | QVQLVQSGAEVKKPGSSVKVSCKTSGDTFSTYAISWVRQAPGQGLE WMGGIIPIFGKAHYAQKFQGRVTITADESTSTAYMELSSLRSEDTAV YFCARKFHFVSGSPFGMDVWGQGTTVTVSS |
|---|---|---|

TABLE 6-continued

Amino acid sequences of other exemplary anti-PD-L1 antibody molecules

| SEQ ID NO: 107 | VL | EIVLTQSPATLSLSPGERATLSCRASQSVSSYLAWYQQKPGQAPRLLI YDASNRATGIPARFSGSGSGTDFTLTISSLEPEDFAVYYCQQRSNWPT FGQGTKVEIK |
|---|---|---|

LAG-3 Inhibitors

In some embodiments, the compounds of Formula (I') or Formula (I), or a pharmaceutically acceptable salt, hydrate, solvate, prodrug, stereoisomer, or tautomer thereof, of the present disclosure are used in combination with a LAG-3 inhibitor to treat a disease, e.g., cancer. In some embodiments, the LAG-3 inhibitor is selected from LAG525 (Novartis), BMS-986016 (Bristol-Myers Squibb), or TSR-033 (Tesaro).

Exemplary LAG-3 Inhibitors

In one embodiment, the LAG-3 inhibitor is an anti-LAG-3 antibody molecule. In one embodiment, the LAG-3 inhibitor is an anti-LAG-3 antibody molecule as disclosed in US 2015/0259420, published on Sep. 17, 2015, entitled "Antibody Molecules to LAG-3 and Uses Thereof," incorporated by reference in its entirety.

In one embodiment, the anti-LAG-3 antibody molecule comprises at least one, two, three, four, five or six complementarity determining regions (CDRs) (or collectively all of the CDRs) from a heavy and light chain variable region comprising an amino acid sequence shown in Table 7 (e.g., from the heavy and light chain variable region sequences of BAP050-Clone I or BAP050-Clone J disclosed in Table 7), or encoded by a nucleotide sequence shown in Table 7. In some embodiments, the CDRs are according to the Kabat definition (e.g., as set out in Table 7). In some embodiments, the CDRs are according to the Chothia definition (e.g., as set out in Table 7). In some embodiments, the CDRs are according to the combined CDR definitions of both Kabat and Chothia (e.g., as set out in Table 7). In one embodiment, the combination of Kabat and Chothia CDR of VH CDR1 comprises the amino acid sequence GFTLTNYGMN (SEQ ID NO: 173). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 7, or encoded by a nucleotide sequence shown in Table 7.

In one embodiment, the anti-LAG-3 antibody molecule comprises a heavy chain variable region (VH) comprising a VHCDR1 amino acid sequence of SEQ ID NO: 108, a VHCDR2 amino acid sequence of SEQ ID NO: 109, and a VHCDR3 amino acid sequence of SEQ ID NO: 110; and a light chain variable region (VL) comprising a VLCDR1 amino acid sequence of SEQ ID NO: 117, a VLCDR2 amino acid sequence of SEQ ID NO: 118, and a VLCDR3 amino acid sequence of SEQ ID NO: 119, each disclosed in Table 7.

In one embodiment, the anti-LAG-3 antibody molecule comprises a VH comprising a VHCDR1 encoded by the nucleotide sequence of SEQ ID NO: 143 or 144, a VHCDR2 encoded by the nucleotide sequence of SEQ ID NO: 145 or 146, and a VHCDR3 encoded by the nucleotide sequence of SEQ ID NO: 147 or 148; and a VL comprising a VLCDR1 encoded by the nucleotide sequence of SEQ ID NO: 153 or 154, a VLCDR2 encoded by the nucleotide sequence of SEQ ID NO: 155 or 156, and a VLCDR3 encoded by the nucleotide sequence of SEQ ID NO: 157 or 158, each disclosed in Table 7. In one embodiment, the anti-LAG-3 antibody molecule comprises a VH comprising a VHCDR1 encoded by the nucleotide sequence of SEQ ID NO: 165 or 144, a VHCDR2 encoded by the nucleotide sequence of SEQ ID NO: 166 or 146, and a VHCDR3 encoded by the nucleotide sequence of SEQ ID NO: 167 or 148; and a VL comprising a VLCDR1 encoded by the nucleotide sequence of SEQ ID NO: 153 or 154, a VLCDR2 encoded by the nucleotide sequence of SEQ ID NO: 155 or 156, and a VLCDR3 encoded by the nucleotide sequence of SEQ ID NO: 157 or 158, each disclosed in Table 7.

In one embodiment, the anti-LAG-3 antibody molecule comprises a VH comprising the amino acid sequence of SEQ ID NO: 113, or an amino acid sequence at least 85%, 90%, 95%, or 99% identical or higher to SEQ ID NO: 113. In one embodiment, the anti-LAG-3 antibody molecule comprises a VL comprising the amino acid sequence of SEQ ID NO: 125, or an amino acid sequence at least 85%, 90%, 95%, or 99% identical or higher to SEQ ID NO: 125. In one embodiment, the anti-LAG-3 antibody molecule comprises a VH comprising the amino acid sequence of SEQ ID NO: 131, or an amino acid sequence at least 85%, 90%, 95%, or 99% identical or higher to SEQ ID NO: 131. In one embodiment, the anti-LAG-3 antibody molecule comprises a VL comprising the amino acid sequence of SEQ ID NO: 137, or an amino acid sequence at least 85%, 90%, 95%, or 99% identical or higher to SEQ ID NO: 137. In one embodiment, the anti-LAG-3 antibody molecule comprises a VH comprising the amino acid sequence of SEQ ID NO: 113 and a VL comprising the amino acid sequence of SEQ ID NO: 125. In one embodiment, the anti-LAG-3 antibody molecule comprises a VH comprising the amino acid sequence of SEQ ID NO: 131 and a VL comprising the amino acid sequence of SEQ ID NO: 137.

In one embodiment, the antibody molecule comprises a VH encoded by the nucleotide sequence of SEQ ID NO: 114 or 115, or a nucleotide sequence at least 85%, 90%, 95%, or 99% identical or higher to SEQ ID NO: 114 or 115. In one embodiment, the antibody molecule comprises a VL encoded by the nucleotide sequence of SEQ ID NO: 126 or 127, or a nucleotide sequence at least 85%, 90%, 95%, or 99% identical or higher to SEQ ID NO: 126 or 127. In one embodiment, the antibody molecule comprises a VH encoded by the nucleotide sequence of SEQ ID NO: 132 or 133, or a nucleotide sequence at least 85%, 90%, 95%, or 99% identical or higher to SEQ ID NO: 132 or 133. In one embodiment, the antibody molecule comprises a VL encoded by the nucleotide sequence of SEQ ID NO: 138 or 139, or a nucleotide sequence at least 85%, 90%, 95%, or 99% identical or higher to SEQ ID NO: 138 or 139. In one embodiment, the antibody molecule comprises a VH encoded by the nucleotide sequence of SEQ ID NO: 114 or 115 and a VL encoded by the nucleotide sequence of SEQ ID NO: 126 or 127. In one embodiment, the antibody molecule comprises a VH encoded by the nucleotide sequence of SEQ ID NO: 132 or 133 and a VL encoded by the nucleotide sequence of SEQ ID NO: 138 or 139.

In one embodiment, the anti-LAG-3 antibody molecule comprises a heavy chain comprising the amino acid sequence of SEQ ID NO: 116, or an amino acid sequence at least 85%, 90%, 95%, or 99% identical or higher to SEQ ID NO: 116. In one embodiment, the anti-LAG-3 antibody molecule comprises a light chain comprising the amino acid sequence of SEQ ID NO: 128, or an amino acid sequence at least 85%, 90%, 95%, or 99% identical or higher to SEQ ID NO: 128. In one embodiment, the anti-LAG-3 antibody molecule comprises a heavy chain comprising the amino acid sequence of SEQ ID NO: 134, or an amino acid sequence at least 85%, 90%, 95%, or 99% identical or higher to SEQ ID NO: 134. In one embodiment, the anti-LAG-3 antibody molecule comprises a light chain comprising the amino acid sequence of SEQ ID NO: 140, or an amino acid sequence at least 85%, 90%, 95%, or 99% identical or higher to SEQ ID NO: 140. In one embodiment, the anti-LAG-3 antibody molecule comprises a heavy chain comprising the amino acid sequence of SEQ ID NO: 116 and a light chain comprising the amino acid sequence of SEQ ID NO: 128. In one embodiment, the anti-LAG-3 antibody molecule comprises a heavy chain comprising the amino acid sequence of SEQ ID NO: 134 and a light chain comprising the amino acid sequence of SEQ ID NO: 140.

In one embodiment, the antibody molecule comprises a heavy chain encoded by the nucleotide sequence of SEQ ID NO: 123 or 124, or a nucleotide sequence at least 85%, 90%, 95%, or 99% identical or higher to SEQ ID NO: 123 or 124. In one embodiment, the antibody molecule comprises a light chain encoded by the nucleotide sequence of SEQ ID NO: 129 or 130, or a nucleotide sequence at least 85%, 90%, 95%, or 99% identical or higher to SEQ ID NO: 129 or 130. In one embodiment, the antibody molecule comprises a heavy chain encoded by the nucleotide sequence of SEQ ID NO: 135 or 136, or a nucleotide sequence at least 85%, 90%, 95%, or 99% identical or higher to SEQ ID NO: 135 or 136. In one embodiment, the antibody molecule comprises a light chain encoded by the nucleotide sequence of SEQ ID NO: 141 or 142, or a nucleotide sequence at least 85%, 90%, 95%, or 99% identical or higher to SEQ ID NO: 141 or 142. In one embodiment, the antibody molecule comprises a heavy chain encoded by the nucleotide sequence of SEQ ID NO: 123 or 124 and a light chain encoded by the nucleotide sequence of SEQ ID NO: 129 or 130. In one embodiment, the antibody molecule comprises a heavy chain encoded by the nucleotide sequence of SEQ ID NO: 135 or 136 and a light chain encoded by the nucleotide sequence of SEQ ID NO: 141 or 142.

The antibody molecules described herein can be made by vectors, host cells, and methods described in US 2015/0259420, incorporated by reference in its entirety.

TABLE 7

Amino acid and nucleotide sequences of exemplary anti-LAG-3 antibody molecules

BAP050-Clone I HC

| | | |
|---|---|---|
| SEQ ID NO: 108 (Kabat) | HCDR1 | NYGMN |
| SEQ ID NO: 109 (Kabat) | HCDR2 | WINTDTGEPTYADDFKG |
| SEQ ID NO: 110 (Kabat) | HCDR3 | NPPYYYGTNNAEAMDY |
| SEQ ID NO: 111 (Chothia) | HCDR1 | GFTLTNY |
| SEQ ID NO: 112 (Chothia) | HCDR2 | NTDTGE |
| SEQ ID NO: 110 (Chothia) | HCDR3 | NPPYYYGTNNAEAMDY |
| SEQ ID NO: 113 | VH | QVQLVQSGAEVKKPGASVKVSCKASGFTLTNYGMNWVRQAR GQRLEWIGWINTDTGEPTYADDFKGRFVFSLDTSVSTAYLQISS LKAEDTAVYYCARNPPYYYGTNNAEAMDYWGQGTTVTVSS |
| SEQ ID NO: 114 | DNA VH | CAAGTGCAGCTGGTGCAGTCGGGAGCCGAAGTGAAGAAGCC TGGAGCCTCGGTGAAGGTGTCGTGCAAGGCATCCGGATTCA CCCTCACCAATTACGGGATGAACTGGGTCAGACAGGCCCGG GGTCAACGGCTGGAGTGGATCGGATGGATTAACACCGACAC CGGGGAGCCTACCTACGCGGACGATTTCAAGGGACGGTTCG TGTTCTCCCTCGACACCTCCGTGTCCACCGCCTACCTCCAAA TCTCCTCACTGAAAGCGGAGGACACCGCCGTGTACTATTGC GCGAGGAACCCGCCCTACTACTACGGAACCAACAACGCCGA AGCCATGGACTACTGGGGCCAGGGCACCACTGTGACTGTGT CCAGC |
| SEQ ID NO: 115 | DNA VH | CAGGTGCAGCTGGTGCAGTCTGGCGCCGAAGTGAAGAAACC TGGCGCCTCCGTGAAGGTGTCCTGCAAGGCCTCTGGCTTCAC CCTGACCAACTACGGCATGAACTGGGTGCGACAGGCCAGGG GCCAGCGGCTGGAATGGATCGGCTGGATCAACACCGACACC GGCGAGCCTACCTACGCCGACGACTTCAAGGGCAGATTCGT GTTCTCCCTGGACACCTCCGTGTCCACCGCCTACCTGCAGAT CTCCAGCCTGAAGGCCGAGGATACCGCCGTGTACTACTGCG |

TABLE 7-continued

Amino acid and nucleotide sequences of exemplary anti-LAG-3 antibody molecules

| | | |
|---|---|---|
| | | CCCGGAACCCCCCTTACTACTACGGCACCAACAACGCCGAG<br>GCCATGGACTATTGGGGCCAGGGCACCACCGTGACCGTGTC<br>CTCT |
| SEQ ID NO: 116 | Heavy chain | QVQLVQSGAEVKKPGASVKVSCKASGFTLTNYGMNWVRQAR<br>GQRLEWIGWINTDTGEPTYADDFKGRFVFSLDTSVSTAYLQISS<br>LKAEDTAVYYCARNPPYYYGTNNAEAMDYWGQGTTVTVSSA<br>STKGPSVFPLAPCSRSTSESTAALGCLVKDYFPEPVTVSWNSGA<br>LTSGVHTFPAVLQSSGLYSLSSVVTVPSSSLGTKTYTCNVDHKP<br>SNTKVDKRVESKYGPPCPPCPAPEFLGGPSVFLFPPKPKDTLMIS<br>RTPEVTCVVVDVSQEDPEVQFNWYVDGVEVHNAKTKPREEQF<br>NSTYRVVSVLTVLHQDWLNGKEYKCKVSNKGLPSSIEKTISKA<br>KGQPREPQVYTLPPSQEEMTKNQVSLTCLVKGFYPSDIAVEWE<br>SNGQPENNYKTTPPVLDSDGSFFLYSRLTVDKSRWQEGNVFSC<br>SVMHEALHNHYTQKSLSLSLG |
| SEQ ID NO: 123 | DNA heavy chain | CAAGTGCAGCTGGTGCAGTCGGGAGCCGAAGTGAAGAAGCC<br>TGGAGCCTCGGTGAAGGTGTCGTGCAAGGCATCCGGATTCA<br>CCCTCACCAATTACGGGATGAACTGGGTCAGACAGGCCCGG<br>GGTCAACGGCTGGAGTGGATCGGATGGATTAACACCGACAC<br>CGGGGAGCCTACCTACGCGGACGATTTCAAGGGACGGTTCG<br>TGTTCTCCCTCGACACCTCCGTGTCCACCGCCTACCTCCAAA<br>TCTCCTCACTGAAAGCGGAGGACACCGCCGTGTACTATTGC<br>GCGAGGAACCCGCCCTACTACTACGGAACCAACAACGCCGA<br>AGCCATGGACTACTGGGGCCAGGGCACCACTGTGACTGTGT<br>CCAGCGCGTCCACTAAGGGCCCGTCCGTGTTCCCCCTGGCAC<br>CTTGTAGCCGGAGCACTAGCGAATCCACCGCTGCCCTCGGCT<br>GCCTGGTCAAGGATTACTTCCCGGAGCCCGTGACCGTGTCCT<br>GGAACAGCGGAGCCCTGACCTCCGGAGTGCACACCTTCCCC<br>GCTGTGCTGCAGAGCTCCGGGCTGTACTCGCTGTCGTCGGTG<br>GTCACGGTGCCTTCATCTAGCCTGGGTACCAAGACCTACACT<br>TGCAACGTGGACCACAAGCCTTCCAACACTAAGGTGGACAA<br>GCGCGTCGAATCGAAGTACGGCCCACCGTGCCCGCCTTGTC<br>CCGCGCCGGAGTTCCTCGGCGGTCCCTCGGTCTTTCTGTTCC<br>CACCGAAAGCCCAAGGACACTTTGATGATTTCCCGCACCCTG<br>AAGTGACATGCGTGGTCGTGGACGTGTCACAGGAAGATCCG<br>GAGGTGCAGTTCAATTGGTACGTGGATGGCGTCGAGGTGCA<br>CAACGCCAAAACCAAGCCGAGGGAGGAGCAGTTCAACTCCA<br>CTTACCGCGTCGTGTCCGTGCTGACGGTGCTGCATCAGGACT<br>GGCTGAACGGGAAGGAGTACAAGTGCAAAGTGTCCAACAA<br>GGGACTTCCTAGCTCAATCGAAAAGACCATCTCGAAAGCCA<br>AGGGACAGCCCCGGGAACCCCAAGTGTATACCCTGCCACCG<br>AGCCAGGAAGAAATGACTAAGAACCAAGTCTCATTGACTTG<br>CCTTGTGAAGGGCTTCTACCCATCGGATATCGCCGTGGAATG<br>GGAGTCCAACGGCCAGCCGGAAAACAACTACAAGACCACCC<br>CTCCGGTGCTGGACTCAGACGGATCCTTCTTCCTCTACTCGC<br>GGCTGACCGTGGATAAGAGCAGATGGCAGGAGGGAAATGT<br>GTTCAGCTGTTCTGTGATGCATGAAGCCCTGCACAACCACTA<br>CACTCAGAAGTCCCTGTCCCTCTCCCTGGGA |
| SEQ ID NO: 124 | DNA heavy chain | CAGGTGCAGCTGGTGCAGTCTGGCGCCGAAGTGAAGAAACC<br>TGGCGCCTCCGTGAAGGTGTCCTGCAAGGCCTCTGGCTTCAC<br>CCTGACCAACTACGGCATGAACTGGGTGCGACAGGCCAGGG<br>GCCAGCGGCTGGAATGGATCGGCTGGATCAACACCGACACC<br>GGCGAGCCTACCTACGCCGACGACTTCAAGGGCAGATTCGT<br>GTTCTCCCTGGACACCTCCGTGTCCACCGCCTACCTGCAGAT<br>CTCCAGCCTGAAGGCCGAGGATACCGCCGTGTACTACTGCG<br>CCCGGAACCCCCCTTACTACTACGGCACCAACAACGCCGAG<br>GCCATGGACTATTGGGGCCAGGGCACCACCGTGACCGTGTC<br>CTCTGCTTCTACCAAGGGGCCCAGCGTGTTCCCCCTGGCCCC<br>CTGCTCCAGAAGCACCAGCGAGAGCACAGCCGCCCTGGGCT<br>GCCTGGTGAAGGACTACTTCCCCGAGCCCGTGACCGTGTCCT<br>GGAACAGCGGAGCCCTGACCAGCGGCGTGCACACCTTCCCC<br>GCCGTGCTGCAGAGCAGCGGCCTGTACAGCCTGAGCAGCGT<br>GGTGACCGTGCCCAGCAGCAGCCTGGGCACCAAGACCTACA<br>CCTGTAACGTGGACCACAAGCCCAGCAACACCAAGGTGGAC<br>AAGAGGGTGGAGAGCAAGTACGGCCCACCCTGCCCCCCCTG<br>CCCAGCCCCGAGTTCCTGGGCGGACCCAGCGTGTTCCTGTT<br>CCCCCCCAAGCCCAAGGACACCCTGATGATCAGCAGAACCC<br>CCGAGGTGACCTGTGTGGTGGTGGACGTGTCCCAGGAGGAC<br>CCCGAGGTCCAGTTCAACTGGTACGTGGACGGCGTGGAGGT<br>GCACAACGCCAAGACCAAGCCCAGAGAGGAGCAGTTTAAC<br>AGCACCTACCGGGTGGTGTCCGTGCTGACCGTGCTGCACCA<br>GGACTGGCTGAACGGCAAAGAGTACAAGTGTAAGGTCTCCA<br>ACAAGGGCCTGCCAAGCAGCATCGAAAAGACCATCAGCAA<br>GGCCAAGGGCCAGCCTAGAGAGCCCCAGGTCTACACCCTGC<br>CACCCAGCCAAGAGGAGATGACCAAGAACCAGGTGTCCCTG |

TABLE 7-continued

Amino acid and nucleotide sequences of exemplary anti-LAG-3 antibody molecules

```
                    ACCTGTCTGGTGAAGGGCTTCTACCCAAGCGACATCGCCGT
                    GGAGTGGGAGAGCAACGGCCAGCCCGAGAACAACTACAAG
                    ACCACCCCCCCAGTGCTGGACAGCGACGGCAGCTTCTTCCTG
                    TACAGCAGGCTGACCGTGGACAAGTCCAGATGGCAGGAGGG
                    CAACGTCTTTAGCTGCTCCGTGATGCACGAGGCCCTGCACAA
                    CCACTACACCCAGAAGAGCCTGAGCCTGTCCCTGGGC
```

BAP050-Clone I LC

| SEQ ID NO: 117 (Kabat) | LCDR1 | SSSQDISNYLN |
|---|---|---|
| SEQ ID NO: 118 (Kabat) | LCDR2 | YTSTLHL |
| SEQ ID NO: 119 (Kabat) | LCDR3 | QQYYNLPWT |
| SEQ ID NO: 120 (Chothia) | LCDR1 | SQDISNY |
| SEQ ID NO: 121 (Chothia) | LCDR2 | YTS |
| SEQ ID NO: 122 (Chothia) | LCDR3 | YYNLPW |
| SEQ ID NO: 125 | VL | DIQMTQSPSSLSASVGDRVTITCSSSQDISNYLNWYLQKPGQSP QLLIYYTSTLHLGVPSRFSGSGSGTEFTLTISSLQPDDFATYYCQ QYYNLPWTFGQGTKVEIK |
| SEQ ID NO: 126 | DNA VL | GATATTCAGATGACTCAGTCACCTAGTAGCCTGAGCGCTAGT GTGGGCGATAGAGTGACTATCACCTGTAGCTCTAGTCAGGA TATCTCTAACTACCTGAACTGGTATCTGCAGAAGCCCGGTCA ATCACCTCAGCTGCTGATCTACTACACTAGCACCCTGCACCT GGGCGTGCCCTCTAGGTTTAGCGGTAGCGGTAGTGGCACCG AGTTCACCCTGACTATCTCTAGCCTGCAGCCCGACGACTTCG CTACCTACTACTGTCAGCAGTACTATAACCTGCCCTGGACCT TCGGTCAAGGCACTAAGGTCGAGATTAAG |
| SEQ ID NO: 127 | DNA VL | GACATCCAGATGACCCAGTCCCCCTCCAGCCTGTCTGCTTCC GTGGGCGACAGAGTGACCATCACCTGTTCCTCCAGCCAGGA CATCTCCAACTACCTGAACTGGTATCTGCAGAAGCCCGGCC AGTCCCCTCAGCTGCTGATCTACTACACCTCCACCCTGCACC TGGGCGTGCCCTCCAGATTTTCCGGCTCTGGCTCTGGCACCG AGTTTACCCTGACCATCAGCTCCCTGCAGCCCGACGACTTCG CCACCTACTACTGCCAGCAGTACTACAACCTGCCCTGGACCT TCGGCCAGGGCACCAAGGTGGAAATCAAG |
| SEQ ID NO: 128 | Light chain | DIQMTQSPSSLSASVGDRVTITCSSSQDISNYLNWYLQKPGQSP QLLIYYTSTLHLGVPSRFSGSGSGTEFTLTISSLQPDDFATYYCQ QYYNLPWTFGQGTKVEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGEC |
| SEQ ID NO: 129 | DNA light chain | GATATTCAGATGACTCAGTCACCTAGTAGCCTGAGCGCTAGT GTGGGCGATAGAGTGACTATCACCTGTAGCTCTAGTCAGGA TATCTCTAACTACCTGAACTGGTATCTGCAGAAGCCCGGTCA ATCACCTCAGCTGCTGATCTACTACACTAGCACCCTGCACCT GGGCGTGCCCTCTAGGTTTAGCGGTAGCGGTAGTGGCACCG AGTTCACCCTGACTATCTCTAGCCTGCAGCCCGACGACTTCG CTACCTACTACTGTCAGCAGTACTATAACCTGCCCTGGACCT TCGGTCAAGGCACTAAGGTCGAGATTAAGCGTACGGTGGCC GCTCCCAGCGTGTTCATCTTCCCCCCCAGCGACGAGCAGCTG AAGAGCGGCACCGCCAGCGTGGTGTGCCTGCTGAACAACTT CTACCCCCGGGAGGCCAAGGTGCAGTGGAAGGTGGACAACG CCCTGCAGAGCGGCAACAGCCAGGAGAGCGTCACCGAGCA GGACAGCAAGGACTCCACCTACAGCCTGAGCAGCACCCTGA CCCTGAGCAAGGCCGACTACGAGAAGCATAAGGTGTACGCC TGCGAGGTGACCCACCAGGGCCTGTCCAGCCCCGTGACCAA GAGCTTCAACAGGGGCGAGTGC |
| SEQ ID NO: 130 | DNA light chain | GACATCCAGATGACCCAGTCCCCCTCCAGCCTGTCTGCTTCC GTGGGCGACAGAGTGACCATCACCTGTTCCTCCAGCCAGGA CATCTCCAACTACCTGAACTGGTATCTGCAGAAGCCCGGCC AGTCCCCTCAGCTGCTGATCTACTACACCTCCACCCTGCACC TGGGCGTGCCCTCCAGATTTTCCGGCTCTGGCTCTGGCACCG |

TABLE 7-continued

Amino acid and nucleotide sequences
of exemplary anti-LAG-3 antibody molecules

|  |  |  |
|---|---|---|
|  |  | AGTTTACCCTGACCATCAGCTCCCTGCAGCCCGACGACTTCG<br>CCACCTACTACTGCCAGCAGTACTACAACCTGCCCTGGACCT<br>TCGGCCAGGGCACCAAGGTGGAAATCAAGCGTACGGTGGCC<br>GCTCCCAGCGTGTTCATCTTCCCCCCAAGCGACGAGCAGCTG<br>AAGAGCGGCACCGCCAGCGTGGTGTGTCTGCTGAACAACTT<br>CTACCCCAGGGAGGCCAAGGTGCAGTGGAAGGTGGACAAC<br>GCCCTGCAGAGCGGCAACAGCCAGGAGAGCGTCACCGAGC<br>AGGACAGCAAGGACTCCACCTACAGCCTGAGCAGCACCCTG<br>ACCCTGAGCAAGGCCGACTACGAGAAGCACAAGGTGTACGC<br>CTGTGAGGTGACCCACCAGGGCCTGTCCAGCCCCGTGACCA<br>AGAGCTTCAACAGGGGCGAGTGC |
| BAP050-Clone J<br>HC |  |  |
| SEQ ID NO: 108<br>(Kabat) | HCDR1 | NYGMN |
| SEQ ID NO: 109<br>(Kabat) | HCDR2 | WINTDTGEPTYADDFKG |
| SEQ ID NO: 110<br>(Kabat) | HCDR3 | NPPYYYGTNNAEAMDY |
| SEQ ID NO: 111<br>(Chothia) | HCDR1 | GFTLTNY |
| SEQ ID NO: 112<br>(Chothia) | HCDR2 | NTDTGE |
| SEQ ID NO: 110<br>(Chothia) | HCDR3 | NPPYYYGTNNAEAMDY |
| SEQ ID NO: 131 | VH | QVQLVQSGAEVKKPGASVKVSCKASGFTLTNYGMNWVRQAP<br>GQGLEWMGWINTDTGEPTYADDFKGRFVFSLDTSVSTAYLQIS<br>SLKAEDTAVYYCARNPPYYYGTNNAEAMDYWGQGTTVTVSS |
| SEQ ID NO: 132 | DNA<br>VH | CAGGTGCAGCTGGTGCAGTCAGGCGCCGAAGTGAAGAAACC<br>CGGCGCTAGTGTGAAAGTCAGCTGTAAAGCTAGTGGCTTCA<br>CCCTGACTAACTACGGGATGAACTGGGTCCGCCAGGCCCCA<br>GGTCAAGGCCTCGAGTGGATGGGCTGGATTAACACCGACAC<br>CGGCGAGCCTACCTACGCCGACGACTTTAAGGGCAGATTCG<br>TGTTTAGCCTGGACACTAGTGTGTCTACCGCCTACCTGCAGA<br>TCTCTAGCCTGAAGGCCGAGGACACCGCCGTCTACTACTGC<br>GCTAGAAACCCCCCCTACTACTACGGCACTAACAACGCCGA<br>GGCTATGGACTACTGGGGTCAAGGCACTACCGTGACCGTGT<br>CTAGC |
| SEQ ID NO: 133 | DNA<br>VH | CAGGTGCAGCTGGTGCAGTCTGGCGCCGAAGTGAAGAAACC<br>TGGCGCCTCCGTGAAGGTGTCCTGCAAGGCCTCTGGCTTCAC<br>CCTGACCAACTACGGCATGAACTGGGTGCGACAGGCCCCTG<br>GACAGGGCCTGGAATGGATGGGCTGGATCAACACCGACACC<br>GGCGAGCCTACCTACGCCGACGACTTCAAGGGCAGATTCGT<br>GTTCTCCCTGGACACCTCCGTGTCCACCGCCTACCTGCAGAT<br>CTCCAGCCTGAAGGCCGAGGATACCGCCGTGTACTACTGCG<br>CCCGGAACCCCCCTTACTACTACGGCACCAACAACGCCGAG<br>GCCATGGACTATTGGGGCCAGGGCACCACCGTGACCGTGTC<br>CTCT |
| SEQ ID NO: 134 | Heavy<br>chain | QVQLVQSGAEVKKPGASVKVSCKASGFTLTNYGMNWVRQAP<br>GQGLEWMGWINTDTGEPTYADDFKGRFVFSLDTSVSTAYLQIS<br>SLKAEDTAVYYCARNPPYYYGTNNAEAMDYWGQGTTVTVSS<br>ASTKGPSVFPLAPCSRSTSESTAALGCLVKDYFPEPVTVSWNSG<br>ALTSGVHTFPAVLQSSGLYSLSSVVTVPSSSLGTKTYTCNVDHK<br>PSNTKVDKRVESKYGPPCPPCPAPEFLGGPSVFLFPPKPKDTLMI<br>SRTPEVTCVVVDVSQEDPEVQFNWYVDGVEVHNAKTKPREEQ<br>FNSTYRVVSVLTVLHQDWLNGKEYKCKVSNKGLPSSIEKTISK<br>AKGQPREPQVYTLPPSQEEMTKNQVSLTCLVKGFYPSDIAVEW<br>ESNGQPENNYKTTPPVLDSDGSFFLYSRLTVDKSRWQEGNVFS<br>CSVMHEALHNHYTQKSLSLSLG |
| SEQ ID NO: 135 | DNA<br>heavy<br>chain | CAGGTGCAGCTGGTGCAGTCAGGCGCCGAAGTGAAGAAACC<br>CGGCGCTAGTGTGAAAGTCAGCTGTAAAGCTAGTGGCTTCA<br>CCCTGACTAACTACGGGATGAACTGGGTCCGCCAGGCCCCA<br>GGTCAAGGCCTCGAGTGGATGGGCTGGATTAACACCGACAC<br>CGGCGAGCCTACCTACGCCGACGACTTTAAGGGCAGATTCG<br>TGTTTAGCCTGGACACTAGTGTGTCTACCGCCTACCTGCAGA |

TABLE 7-continued

Amino acid and nucleotide sequences
of exemplary anti-LAG-3 antibody molecules

| | | |
|---|---|---|
| | | TCTCTAGCCTGAAGGCCGAGGACACCGCCGTCTACTACTGC<br>GCTAGAAACCCCCCCTACTACTACGGCACTAACAACGCCGA<br>GGCTATGGACTACTGGGGTCAAGGCACTACCGTGACCGTGT<br>CTAGCGCTAGCACTAAGGGCCCGTCCGTGTTCCCCCTGGCAC<br>CTTGTAGCGGAGCACTAGCAATCCACCGCTGCCCTCGGCT<br>GCCTGGTCAAGGATTACTTCCCGGAGCCCGTGACCGTGTCCT<br>GGAACAGCGGAGCCCTGACCTCCGGAGTGCACACCTTCCCC<br>GCTGTGCTGCAGAGCTCCGGGCTGTACTCGCTGTCGTCGGTG<br>GTCACGGTGCCTTCATCTAGCCTGGGTACCAAGACCTACACT<br>TGCAACGTGGACCACAAGCCTTCCAACACTAAGGTGGACAA<br>GCGCGTCGAATCGAAGTACGGCCCACCGTGCCCGCCTTGTC<br>CCGCGCCGGAGTTCCTCGGCGGTCCCTCGGTCTTTCTGTTCC<br>CACCGAAGCCCAAGGACACTTTGATGATTTCCCGCACCCCTG<br>AAGTGACATGCGTGGTCGTGGACGTGTCACAGGAAGATCCG<br>GAGGTGCAGTTCAATTGGTACGTGGATGGCGTCGAGGTGCA<br>CAACGCCAAAACCAAGCCGAGGGAGGAGCAGTTCAACTCCA<br>CTTACCGCGTCGTGTCCGTGCTGACGGTGCTGCATCAGGACT<br>GGCTGAACGGGAAGGAGTACAAGTGCAAAGTGTCCAACAA<br>GGGACTTCCTAGCTCAATCGAAAAGACCATCTCGAAAGCCA<br>AGGGACAGCCCCGGGAACCCCAAGTGTATACCCTGCCACCG<br>AGCCAGGAAGAAATGACTAAGAACCAAGTCTCATTGACTTG<br>CCTTGTGAAGGGCTTCTACCCATCGGATATCGCCGTGGAATG<br>GGAGTCCAACGGCCAGCCGGAAAACAACTACAAGACCACCC<br>CTCCGGTGCTGGACTCAGACGGATCCTTCTTCCTCTACTCGC<br>GGCTGACCGTGGATAAGAGCAGATGGCAGGAGGGAAATGT<br>GTTCAGCTGTTCTGTGATGCATGAAGCCCTGCACAACCACTA<br>CACTCAGAAGTCCCTGTCCCTCTCCCTGGGA |
| SEQ ID NO: 136 | DNA<br>heavy<br>chain | CAGGTGCAGCTGGTGCAGTCTGGCGCCGAAGTGAAGAAACC<br>TGGCGCCTCCGTGAAGGTGTCCTGCAAGGCCTCTGGCTTCAC<br>CCTGACCAACTACGGCATGAACTGGGTGCGACAGGCCCCTG<br>GACAGGGCCTGGAATGGATGGGCTGGATCAACACCGACACC<br>GGCGAGCCTACCTACGCCGACGACTTCAAGGGCAGATTCGT<br>GTTCTCCCTGGACACCTCCGTGTCCACCGCCTACCTGCAGAT<br>CTCCAGCCTGAAGGCCGAGGATACCGCCGTGTACTACTGCG<br>CCCGGAACCCCCCTTACTACTACGGCACCAACAACGCCGAG<br>GCCATGGACTATTGGGGCCAGGGCACCACCGTGACCGTGTC<br>CTCTGCTTCTACCAAGGGGCCCAGCGTGTTCCCCCTGGCCCC<br>CTGCTCCAGAAGCACCAGCGAGAGCACAGCCGCCCTGGGCT<br>GCCTGGTGAAGGACTACTTCCCCGAGCCCGTGACCGTGTCCT<br>GGAACAGCGGAGCCCTGACCAGCGGCGTGCACACCTTCCCC<br>GCCGTGCTGCAGAGCAGCGGCCTGTACAGCCTGAGCAGCGT<br>GGTGACCGTGCCCAGCAGCAGCCTGGGCACCAAGACCTACA<br>CCTGTAACGTGGACCACAAGCCCAGCAACACCAAGGTGGAC<br>AAGAGGGTTGGAGAGCAAGTACGGCCCACCCTGCCCCCCCTG<br>CCCAGCCCCGAGTTCCTGGGCGGACCCAGCGTGTTCCTGTT<br>CCCCCCCAAGCCCAAGGACACCCTGATGATCAGCAGAACCC<br>CCGAGGTGACCTGTGTGGTGGTGGACGTGTCCCAGGAGGAC<br>CCCGAGGTCCAGTTCAACTGGTACGTGGACGGCGTGGAGGT<br>GCACAACGCCAAGACCAAGCCCAGAGAGGAGCAGTTTAAC<br>AGCACCTACCGGGTGGTGTCCGTGCTGACCGTGCTGCACCA<br>GGACTGGCTGAACGGCAAAGAGTACAAGTGTAAGGTCTCCA<br>ACAAGGGCCTGCCAAGCAGCATCGAAAAGACCATCAGCAA<br>GGCCAAGGGCCAGCCTAGAGAGCCCCAGGTCTACACCCTGC<br>CACCCAGCCAAGAGGAGATGACCAAGAACCAGGTGTCCCTG<br>ACCTGTCTGGTGAAGGGCTTCTACCCAAGCGACATCGCCGT<br>GGAGTGGGAGAGCAACGGCCAGCCCGAGAACAACTACAAG<br>ACCACCCCCCCAGTGCTGGACAGCGACGGCAGCTTCTTCCTG<br>TACAGCAGGCTGACCGTGGACAAGTCCAGATGGCAGGAGGG<br>CAACGTCTTTAGCTGCTCCGTGATGCACGAGGCCCTGCACAA<br>CCACTACACCCAGAAGAGCCTGAGCCTGTCCCTGGGC |

BAP050-Clone J LC

| SEQ ID NO: 117<br>(Kabat) | LCDR1 | SSSQDISNYLN |
|---|---|---|
| SEQ ID NO: 118<br>(Kabat) | LCDR2 | YTSTLHL |
| SEQ ID NO: 119<br>(Kabat) | LCDR3 | QQYYNLPWT |
| SEQ ID NO: 120<br>(Chothia) | LCDR1 | SQDISNY |

TABLE 7-continued

Amino acid and nucleotide sequences of exemplary anti-LAG-3 antibody molecules

| | | |
|---|---|---|
| SEQ ID NO: 121 (Chothia) | LCDR2 | YTS |
| SEQ ID NO: 122 (Chothia) | LCDR3 | YYNLPW |
| SEQ ID NO: 137 | VL | DIQMTQSPSSLSASVGDRVTITCSSSQDISNYLNWYQQKPGKAP KLLIYYTSTLHLGIPPRFSGSGYGTDFTLTINNIESEDAAYYFCQ QYYNLPWTFGQGTKVEIK |
| SEQ ID NO: 138 | DNA VL | GATATTCAGATGACTCAGTCACCTAGTAGCCTGAGCGCTAGT GTGGGCGATAGAGTGACTATCACCTGTAGCTCTAGTCAGGA TATCTCTAACTACCTGAACTGGTATCAGCAGAAGCCCGGTA AAGCCCCTAAGCTGCTGATCTACTACACTAGCACCCTGCACC TGGGAATCCCCCCTAGGTTTAGCGGTAGCGGCTACGGCACC GACTTCACCCTGACTATTAACAATATCGAGTCAGAGGACGC CGCCTACTACTTCTGTCAGCAGTACTATAACCTGCCCTGGAC CTTCGGTCAAGGCACTAAGGTCGAGATTAAG |
| SEQ ID NO: 139 | DNA VL | GACATCCAGATGACCCAGTCCCCCTCCAGCCTGTCTGCTTCC GTGGGCGACAGAGTGACCATCACCTGTTCCTCCAGCCAGGA CATCTCCAACTACCTGAACTGGTATCAGCAGAAGCCCGGCA AGGCCCCCAAGCTGCTGATCTACTACACCTCCACCCTGCACC TGGGCATCCCCCCTAGATTCTCCGGCTCTGGCTACGGCACCG ACTTCACCCTGACCATCAACAACATCGAGTCCGAGGACGCC GCCTACTACTTCTGCCAGCAGTACTACAACCTGCCCTGGACC TTCGGCCAGGGCACCAAGGTGGAAATCAAG |
| SEQ ID NO: 140 | Light chain | DIQMTQSPSSLSASVGDRVTITCSSSQDISNYLNWYQQKPGKAP KLLIYYTSTLHLGIPPRFSGSGYGTDFTLTINNIESEDAAYYFCQ QYYNLPWTFGQGTKVEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGEC |
| SEQ ID NO: 141 | DNA light chain | GATATTCAGATGACTCAGTCACCTAGTAGCCTGAGCGCTAGT GTGGGCGATAGAGTGACTATCACCTGTAGCTCTAGTCAGGA TATCTCTAACTACCTGAACTGGTATCAGCAGAAGCCCGGTA AAGCCCCTAAGCTGCTGATCTACTACACTAGCACCCTGCACC TGGGAATCCCCCCTAGGTTTAGCGGTAGCGGCTACGGCACC GACTTCACCCTGACTATTAACAATATCGAGTCAGAGGACGC CGCCTACTACTTCTGTCAGCAGTACTATAACCTGCCCTGGAC CTTCGGTCAAGGCACTAAGGTCGAGATTAAGCGTACGGTGG CCGCTCCCAGCGTGTTCATCTTCCCCCCCAGCGACGAGCAGC TGAAGAGCGGCACCGCCAGCGTGGTGTGCCTGCTGAACAAC TTCTACCCCGGGAGGCCAAGGTGCAGTGGAAGGTGGACAA CGCCCTGCAGAGCGGCAACAGCCAGGAGAGCGTCACCGAGC AGGACAGCAAGGACTCCACCTACAGCCTGAGCAGCACCCTG ACCCTGAGCAAGGCCGACTACGAGAAGCATAAGGTGTACGC CTGCGAGGTGACCCACCAGGGCCTGTCCAGCCCCGTGACCA AGAGCTTCAACAGGGGCGAGTGC |
| SEQ ID NO: 142 | DNA light chain | GACATCCAGATGACCCAGTCCCCCTCCAGCCTGTCTGCTTCC GTGGGCGACAGAGTGACCATCACCTGTTCCTCCAGCCAGGA CATCTCCAACTACCTGAACTGGTATCAGCAGAAGCCCGGCA AGGCCCCCAAGCTGCTGATCTACTACACCTCCACCCTGCACC TGGGCATCCCCCCTAGATTCTCCGGCTCTGGCTACGGCACCG ACTTCACCCTGACCATCAACAACATCGAGTCCGAGGACGCC GCCTACTACTTCTGCCAGCAGTACTACAACCTGCCCTGGACC TTCGGCCAGGGCACCAAGGTGGAAATCAAGCGTACGTGGC CGCTCCCAGCGTGTTCATCTTCCCCCCAAGCGACGAGCAGCT GAAGAGCGGCACCGCCAGCGTGGTGTGTCTGCTGAACAACT TCTACCCCAGGGAGGCCAAGGTGCAGTGGAAGGTGGACAAC GCCCTGCAGAGCGGCAACAGCCAGGAGAGCGTCACCGAGC AGGACAGCAAGGACTCCACCTACAGCCTGAGCAGCACCCTG ACCCTGAGCAAGGCCGACTACGAGAAGCACAAGGTGTACGC CTGTGAGGTGACCCACCAGGGCCTGTCCAGCCCCGTGACCA AGAGCTTCAACAGGGGCGAGTGC |

BAP050-Clone I HC

| | | |
|---|---|---|
| SEQ ID NO: 143 (Kabat) | HCDR1 | AATTACGGGATGAAC |
| SEQ ID NO: 144 (Kabat) | HCDR1 | AACTACGGCATGAAC |

TABLE 7-continued

Amino acid and nucleotide sequences of exemplary anti-LAG-3 antibody molecules

| | | |
|---|---|---|
| SEQ ID NO: 145 (Kabat) | HCDR2 | TGGATTAACACCGACACCGGGGAGCCTACCTACGCGGACGATTTCAAGGGA |
| SEQ ID NO: 146 (Kabat) | HCDR2 | TGGATCAACACCGACACCGGCGAGCCTACCTACGCCGACGACTTCAAGGGC |
| SEQ ID NO: 147 (Kabat) | HCDR3 | AACCCGCCCTACTACTACGGAACCAACAACGCCGAAGCCATGGACTAC |
| SEQ ID NO: 148 (Kabat) | HCDR3 | AACCCCCCTTACTACTACGGCACCAACAACGCCGAGGCCATGGACTAT |
| SEQ ID NO: 149 (Chothia) | HCDR1 | GGATTCACCCTCACCAATTAC |
| SEQ ID NO: 150 (Chothia) | HCDR1 | GGCTTCACCCTGACCAACTAC |
| SEQ ID NO: 151 (Chothia) | HCDR2 | AACACCGACACCGGGGAG |
| SEQ ID NO: 152 (Chothia) | HCDR2 | AACACCGACACCGGCGAG |
| SEQ ID NO: 147 (Chothia) | HCDR3 | AACCCGCCCTACTACTACGGAACCAACAACGCCGAAGCCATGGACTAC |
| SEQ ID NO: 148 (Chothia) | HCDR3 | AACCCCCCTTACTACTACGGCACCAACAACGCCGAGGCCATGGACTAT |
| BAP050-Clone I LC | | |
| SEQ ID NO: 153 (Kabat) | LCDR1 | AGCTCTAGTCAGGATATCTCTAACTACCTGAAC |
| SEQ ID NO: 154 (Kabat) | LCDR1 | TCCTCCAGCCAGGACATCTCCAACTACCTGAAC |
| SEQ ID NO: 155 (Kabat) | LCDR2 | TACACTAGCACCCTGCACCTG |
| SEQ ID NO: 156 (Kabat) | LCDR2 | TACACCTCCACCCTGCACCTG |
| SEQ ID NO: 157 (Kabat) | LCDR3 | CAGCAGTACTATAACCTGCCCTGGACC |
| SEQ ID NO: 158 (Kabat) | LCDR3 | CAGCAGTACTACAACCTGCCCTGGACC |
| SEQ ID NO: 159 (Chothia) | LCDR1 | AGTCAGGATATCTCTAACTAC |
| SEQ ID NO: 160 (Chothia) | LCDR1 | AGCCAGGACATCTCCAACTAC |
| SEQ ID NO: 161 (Chothia) | LCDR2 | TACACTAGC |
| SEQ ID NO: 162 (Chothia) | LCDR2 | TACACCTCC |
| SEQ ID NO: 163 (Chothia) | LCDR3 | TACTATAACCTGCCCTGG |
| SEQ ID NO: 164 (Chothia) | LCDR3 | TACTACAACCTGCCCTGG |
| BAP050-Clone J HC | | |
| SEQ ID NO: 165 (Kabat) | HCDR1 | AACTACGGGATGAAC |
| SEQ ID NO: 144 (Kabat) | HCDR1 | AACTACGGCATGAAC |

TABLE 7-continued

Amino acid and nucleotide sequences
of exemplary anti-LAG-3 antibody molecules

| | | |
|---|---|---|
| SEQ ID NO: 166 (Kabat) | HCDR2 | TGGATTAACACCGACACCGGCGAGCCTACCTACGCCGACGA CTTTAAGGGC |
| SEQ ID NO: 146 (Kabat) | HCDR2 | TGGATCAACACCGACACCGGCGAGCCTACCTACGCCGACGA CTTCAAGGGC |
| SEQ ID NO: 167 (Kabat) | HCDR3 | AACCCCCCCTACTACTACGGCACTAACAACGCCGAGGCTAT GGACTAC |
| SEQ ID NO: 148 (Kabat) | HCDR3 | AACCCCCCTTACTACTACGGCACCAACAACGCCGAGGCCAT GGACTAT |
| SEQ ID NO: 168 (Chothia) | HCDR1 | GGCTTCACCCTGACTAACTAC |
| SEQ ID NO: 150 (Chothia) | HCDR1 | GGCTTCACCCTGACCAACTAC |
| SEQ ID NO: 151 (Chothia) | HCDR2 | AACACCGACACCGGGGAG |
| SEQ ID NO: 152 (Chothia) | HCDR2 | AACACCGACACCGGCGAG |
| SEQ ID NO: 167 (Chothia) | HCDR3 | AACCCCCCCTACTACTACGGCACTAACAACGCCGAGGCTAT GGACTAC |
| SEQ ID NO: 148 (Chothia) | HCDR3 | AACCCCCCTTACTACTACGGCACCAACAACGCCGAGGCCAT GGACTAT |
| BAP050-Clone J LC | | |
| SEQ ID NO: 153 (Kabat) | LCDR1 | AGCTCTAGTCAGGATATCTCTAACTACCTGAAC |
| SEQ ID NO: 154 (Kabat) | LCDR1 | TCCTCCAGCCAGGACATCTCCAACTACCTGAAC |
| SEQ ID NO: 155 (Kabat) | LCDR2 | TACACTAGCACCCTGCACCTG |
| SEQ ID NO: 156 (Kabat) | LCDR2 | TACACCTCCACCCTGCACCTG |
| SEQ ID NO: 157 (Kabat) | LCDR3 | CAGCAGTACTATAACCTGCCCTGGACC |
| SEQ ID NO: 158 (Kabat) | LCDR3 | CAGCAGTACTACAACCTGCCCTGGACC |
| SEQ ID NO: 159 (Chothia) | LCDR1 | AGTCAGGATATCTCTAACTAC |
| SEQ ID NO: 160 (Chothia) | LCDR1 | AGCCAGGACATCTCCAACTAC |
| SEQ ID NO: 161 (Chothia) | LCDR2 | TACACTAGC |
| SEQ ID NO: 162 (Chothia) | LCDR2 | TACACCTCC |
| SEQ ID NO: 163 (Chothia) | LCDR3 | TACTATAACCTGCCCTGG |
| SEQ ID NO: 164 (Chothia) | LCDR3 | TACTACAACCTGCCCTGG |

Other Exemplary LAG-3 Inhibitors

In one embodiment, the LAG-3 inhibitor is an anti-LAG-3 antibody molecule. In one embodiment, the LAG-3 inhibitor is BMS-986016 (Bristol-Myers Squibb), also known as BMS986016. BMS-986016 and other anti-LAG-3 antibodies are disclosed in WO 2015/116539 and U.S. Pat. No. 9,505,839, incorporated by reference in their entirety. In one embodiment, the anti-LAG-3 antibody molecule comprises one or more of the CDR sequences (or collectively all of the CDR sequences), the heavy chain or light chain variable region sequence, or the heavy chain or light chain sequence of BMS-986016, e.g., as disclosed in Table 8.

In one embodiment, the anti-LAG-3 antibody molecule is TSR-033 (Tesaro). In one embodiment, the anti-LAG-3 antibody molecule comprises one or more of the CDR sequences (or collectively all of the CDR sequences), the heavy chain or light chain variable region sequence, or the heavy chain or light chain sequence of TSR-033.

In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059, incorporated In one embodiment, the anti-LAG-3 antibody is an antibody that competes for binding with, and/or binds to the same epitope on LAG-3 as, one of the anti-LAG-3 antibodies described herein.

In one embodiment, the anti-LAG-3 inhibitor is a soluble LAG-3 protein, e.g., IMP321 (Prima BioMed), e.g., as disclosed in WO 2009/044273, incorporated by reference in its entirety.

TABLE 8

Amino acid sequences of other exemplary anti-LAG-3 antibody molecules

BMS-986016

SEQ ID NO: 169 Heavy chain
QVQLQQWGAGLLKPSETLSLTCAVYGGSFSDYYWNWIRQPPGKG
LEWIGEINHRGSTNSNPSLKSRVTLSLDTSKNQFSLKLRSVTAADTA
VYYCAFGYSDYEYNWFDPWGQGTLVTVSSASTKGPSVFPLAPCSR
STSESTAALGCLVKDYFPEPVTVSWNSGALTSGVHTFPAVLQSSGL
YSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQF
NWYVDGVEVHNAKTKPREEQFNSTYRVVSVLTVLHQDWLNGKE
YKCKVSNKGLPSSIEKTISKAKGQPREPQVYTLPPSQEEMTKNQVS
LTCLVKGFYPSDIAVEWESNGQPENNYKTTPPVLDSDGSFFLYSRL
TVDKSRWQEGNVFSCSVMHEALHNHYTQKSLSLSLGK SEQ ID NO: 170 Light chain
EIVLTQSPATLSLSPGERATLSCRASQSISSYLAWYQQKPGQAPRLLI
YDASNRATGIPARFSGSGSGTDFTLTISSLEPEDFAVYYCQQRSNWP
LTFGQGTNLEIKRTVAAPSVFIFPPSDEQLKSGTASVVCLLNNFYPR
EAKVQWKVDNALQSGNSQESVTEQDSKDSTYSLSSTLTLSKADYE
KHKVYACEVTHQGLSSPVTKSFNRGEC

IMP731

SEQ ID NO: 171 Heavy chain
QVQLKESGPGLVAPSQSLSITCTVSGFSLTAYGVNWVRQPPGKGLE
WLGMIWDDGSTDYNSALKSRLSISKDNSKSQVFLKMNSLQTDDTA
RYYCAREGDVAFDYWGQGTTLTVSSASTKGPSVFPLAPSSKSTSG
GTAALGCLVKDYFPEPVTVSWNSGALTSGVHTFPAVLQSSGLYSLS
SVVTVPSSSLGTQTYICNVNHKPSNTKVDKKVEPKSCDKTHTCPPC
PAPELLGGPSVFLFPPKPKDTLMISRTPEVTCVVVDVSHEDPEVKFN
WYVDGVEVHNAKTKPREEQYNSTYRVVSVLTVLHQDWLNGKEY
KCKVSNKALPAPIEKTISKAKGQPREPQVYTLPPSRDELTKNQVSLT
CLVKGFYPSDIAVEWESNGQPENNYKTTPPVLDSDGSFFLYSKLTV
DKSRWQQGNVFSCSVMHEALHNHYTQKSLSLSPGK SEQ ID NO: 172 Light chain
DIVMTQSPSSLAVSVGQKVTMSCKSSQSLLNGSNQKNYLAWYQQ
KPGQSPKLLVYFASTRDSGVPDRFIGSGSGTDFTLTISSVQAEDLAD
YFCLQHFGTPPTFGGGTKLEIKRTVAAPSVFIFPPSDEQLKSGTASV
VCLLNNFYPREAKVQWKVDNALQSGNSQESVTEQDSKDSTYSLSS
TLTLSKADYEKHKVYACEVTHQGLSSPVTKSFNRGEC by reference in their entirety. In one embodiment, the anti-LAG-3 antibody molecule comprises one or more of the CDR sequences (or collectively all of the CDR sequences), the heavy chain or light chain variable region sequence, or the heavy chain or light chain sequence of IMP731, e.g., as disclosed in Table 8. In one embodiment, the anti-LAG-3 antibody molecule comprises one or more of the CDR sequences (or collectively all of the CDR sequences), the heavy chain or light chain variable region sequence, or the heavy chain or light chain sequence of GSK2831781.

In one embodiment, the anti-LAG-3 antibody molecule is IMP761 (Prima BioMed). In one embodiment, the anti-LAG-3 antibody molecule comprises one or more of the CDR sequences (or collectively all of the CDR sequences), the heavy chain or light chain variable region sequence, or the heavy chain or light chain sequence of IMP761.

Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entirety.

TIM-3 Inhibitors

In certain embodiments, the inhibitor of an immune checkpoint molecule is an inhibitor of TIM-3. In some embodiments, the compounds of Formula (I') or Formula (I), or a pharmaceutically acceptable salt, hydrate, solvate, prodrug, stereoisomer, or tautomer thereof, of the present disclosure are used in combination with a TIM-3 inhibitor to treat a disease, e.g., cancer. In some embodiments, the TIM-3 inhibitor is MGB453 (Novartis) or TSR-022 (Tesaro).

Exemplary TIM-3 Inhibitors

In one embodiment, the TIM-3 inhibitor is an anti-TIM-3 antibody molecule. In one embodiment, the TIM-3 inhibitor is an anti-TIM-3 antibody molecule as disclosed in US 2015/0218274, published on Aug. 6, 2015, entitled "Antibody Molecules to TIM-3 and Uses Thereof," incorporated by reference in its entirety.

In one embodiment, the anti-TIM-3 antibody molecule comprises at least one, two, three, four, five or six complementarity determining regions (CDRs) (or collectively all of the CDRs) from a heavy and light chain variable region comprising an amino acid sequence shown in Table 9 (e.g., from the heavy and light chain variable region sequences of ABTIM3-hum11 or ABTIM3-hum03 disclosed in Table 9), or encoded by a nucleotide sequence shown in Table 9. In some embodiments, the CDRs are according to the Kabat definition (e.g., as set out in Table 9). In some embodiments, the CDRs are according to the Chothia definition (e.g., as set out in Table 9). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 9, or encoded by a nucleotide sequence shown in Table 9.

In one embodiment, the anti-TIM-3 antibody molecule comprises a heavy chain variable region (VH) comprising a VHCDR1 amino acid sequence of SEQ ID NO: 174, a VHCDR2 amino acid sequence of SEQ ID NO: 175, and a VHCDR3 amino acid sequence of SEQ ID NO: 176; and a light chain variable region (VL) comprising a VLCDR1 amino acid sequence of SEQ ID NO: 183, a VLCDR2 amino acid sequence of SEQ ID NO: 184, and a VLCDR3 amino acid sequence of SEQ ID NO: 185, each disclosed in Table 9. In one embodiment, the anti-TIM-3 antibody molecule comprises a heavy chain variable region (VH) comprising a VHCDR1 amino acid sequence of SEQ ID NO: 174, a VHCDR2 amino acid sequence of SEQ ID NO: 193, and a VHCDR3 amino acid sequence of SEQ ID NO: 176; and a light chain variable region (VL) comprising a VLCDR1 amino acid sequence of SEQ ID NO: 183, a VLCDR2 amino acid sequence of SEQ ID NO: 184, and a VLCDR3 amino acid sequence of SEQ ID NO: 185, each disclosed in Table 9.

In one embodiment, the anti-TIM-3 antibody molecule comprises a VH comprising the amino acid sequence of SEQ ID NO: 179, or an amino acid sequence at least 85%, 90%, 95%, or 99% identical or higher to SEQ ID NO: 179. In one embodiment, the anti-TIM-3 antibody molecule comprises a VL comprising the amino acid sequence of SEQ ID NO: 189, or an amino acid sequence at least 85%, 90%, 95%, or 99% identical or higher to SEQ ID NO: 189. In one embodiment, the anti-TIM-3 antibody molecule comprises a VH comprising the amino acid sequence of SEQ ID NO: 195, or an amino acid sequence at least 85%, 90%, 95%, or 99% identical or higher to SEQ ID NO: 195. In one embodiment, the anti-TIM-3 antibody molecule comprises a VL comprising the amino acid sequence of SEQ ID NO: 199, or an amino acid sequence at least 85%, 90%, 95%, or 99% identical or higher to SEQ ID NO: 199. In one embodiment, the anti-TIM-3 antibody molecule comprises a VH comprising the amino acid sequence of SEQ ID NO: 179 and a VL comprising the amino acid sequence of SEQ ID NO: 189. In one embodiment, the anti-TIM-3 antibody molecule comprises a VH comprising the amino acid sequence of SEQ ID NO: 195 and a VL comprising the amino acid sequence of SEQ ID NO: 199.

In one embodiment, the antibody molecule comprises a VH encoded by the nucleotide sequence of SEQ ID NO: 180, or a nucleotide sequence at least 85%, 90%, 95%, or 99% identical or higher to SEQ ID NO: 180. In one embodiment, the antibody molecule comprises a VL encoded by the nucleotide sequence of SEQ ID NO: 190, or a nucleotide sequence at least 85%, 90%, 95%, or 99% identical or higher to SEQ ID NO: 190. In one embodiment, the antibody molecule comprises a VH encoded by the nucleotide sequence of SEQ ID NO: 196, or a nucleotide sequence at least 85%, 90%, 95%, or 99% identical or higher to SEQ ID NO: 196. In one embodiment, the antibody molecule comprises a VL encoded by the nucleotide sequence of SEQ ID NO: 200, or a nucleotide sequence at least 85%, 90%, 95%, or 99% identical or higher to SEQ ID NO: 200. In one embodiment, the antibody molecule comprises a VH encoded by the nucleotide sequence of SEQ ID NO: 180 and a VL encoded by the nucleotide sequence of SEQ ID NO: 190. In one embodiment, the antibody molecule comprises a VH encoded by the nucleotide sequence of SEQ ID NO: 196 and a VL encoded by the nucleotide sequence of SEQ ID NO: 200.

In one embodiment, the anti-TIM-3 antibody molecule comprises a heavy chain comprising the amino acid sequence of SEQ ID NO: 181, or an amino acid sequence at least 85%, 90%, 95%, or 99% identical or higher to SEQ ID NO: 181. In one embodiment, the anti-TIM-3 antibody molecule comprises a light chain comprising the amino acid sequence of SEQ ID NO: 191, or an amino acid sequence at least 85%, 90%, 95%, or 99% identical or higher to SEQ ID NO: 191. In one embodiment, the anti-TIM-3 antibody molecule comprises a heavy chain comprising the amino acid sequence of SEQ ID NO: 197, or an amino acid sequence at least 85%, 90%, 95%, or 99% identical or higher to SEQ ID NO: 197. In one embodiment, the anti-TIM-3 antibody molecule comprises a light chain comprising the amino acid sequence of SEQ ID NO: 201, or an amino acid sequence at least 85%, 90%, 95%, or 99% identical or higher to SEQ ID NO: 201. In one embodiment, the anti-TIM-3 antibody molecule comprises a heavy chain comprising the amino acid sequence of SEQ ID NO: 181 and a light chain comprising the amino acid sequence of SEQ ID NO: 191. In one embodiment, the anti-TIM-3 antibody molecule comprises a heavy chain comprising the amino acid sequence of SEQ ID NO: 197 and a light chain comprising the amino acid sequence of SEQ ID NO: 201.

In one embodiment, the antibody molecule comprises a heavy chain encoded by the nucleotide sequence of SEQ ID NO: 182, or a nucleotide sequence at least 85%, 90%, 95%, or 99% identical or higher to SEQ ID NO: 182. In one embodiment, the antibody molecule comprises a light chain encoded by the nucleotide sequence of SEQ ID NO: 192, or a nucleotide sequence at least 85%, 90%, 95%, or 99% identical or higher to SEQ ID NO: 192. In one embodiment, the antibody molecule comprises a heavy chain encoded by the nucleotide sequence of SEQ ID NO: 198, or a nucleotide sequence at least 85%, 90%, 95%, or 99% identical or higher to SEQ ID NO: 198. In one embodiment, the antibody molecule comprises a light chain encoded by the nucleotide sequence of SEQ ID NO: 202, or a nucleotide sequence at least 85%, 90%, 95%, or 99% identical or higher to SEQ ID NO: 202. In one embodiment, the antibody molecule comprises a heavy chain encoded by the nucleotide sequence of SEQ ID NO: 182 and a light chain encoded by the nucleotide sequence of SEQ ID NO: 192. In one embodiment, the antibody molecule comprises a heavy chain encoded by the nucleotide sequence of SEQ ID NO: 198 and a light chain encoded by the nucleotide sequence of SEQ ID NO: 202.

The antibody molecules described herein can be made by vectors, host cells, and methods described in US 2015/0218274, incorporated by reference in its entirety.

TABLE 9

Amino acid and nucleotide sequences of
exemplary anti-TIM-3 antibody molecules

ABTIM3-hum11

SEQ ID NO: 174 HCDR1 SYNMH
(Kabat)

SEQ ID NO: 175 HCDR2 DIYPGNGDTSYNQKFKG
(Kabat)

SEQ ID NO: 176 HCDR3 VGGAFPMDY
(Kabat)

SEQ ID NO: 177 HCDR1 GYTFTSY
(Chothia)

SEQ ID NO: 178 HCDR2 YPGNGD
(Chothia)

SEQ ID NO: 176 HCDR3 VGGAFPMDY
(Chothia)

SEQ ID NO: 179 VH QVQLVQSGAEVKKPGSSVKVSCKASGYTFTSYNMHWVRQAPGQ
GLEWMGDIYPGNGDTSYNQKFKGRVTITADKSTSTVYMELSSLR
SEDTAVYYCARVGGAFPMDYWGQGTTVTVSS

SEQ ID NO: 180 DNA CAGGTGCAGCTGGTGCAGTCAGGCGCCGAAGTGAAGAAACCC
VH GGCTCTAGCGTGAAAGTTTCTTGTAAAGCTAGTGGCTACACCT
TCACTAGCTATAATATGCACTGGGTTCGCCAGGCCCCAGGGCA
AGGCCTCGAGTGGATGGGCGATATCTACCCCGGGAACGGCGA
CACTAGTTATAATCAGAAGTTTAAGGGTAGAGTCACTATCACC
GCCGATAAGTCTACTAGCACCGTCTATATGGAACTGAGTTCCC
TGAGGTCTGAGGACACCGCCGTCTACTACTGCGCTAGAGTGG
GCGGAGCCTTCCCTATGGACTACTGGGGTCAAGGCACTACCGT
GACCGTGTCTAGC

SEQ ID NO: 181 Heavy QVQLVQSGAEVKKPGSSVKVSCKASGYTFTSYNMHWVRQAPGQ
chain GLEWMGDIYPGNGDTSYNQKFKGRVTITADKSTSTVYMELSSLR
SEDTAVYYCARVGGAFPMDYWGQGTTVTVSSASTKGPSVFPLA
PCSRSTSESTAALGCLVKDYFPEPVTVSWNSGALTSGVHTFPAVL
QSSGLYSLSSVVTVPSSSLGTKTYTCNVDHKPSNTKVDKRVESKY
GPPCPPCPAPEFLGGPSVFLFPPKPKDTLMISRTPEVTCVVVDVSQ
EDPEVQFNWYVDGVEVHNAKTKPREEQFNSTYRVVSVLTVLHQ
DWLNGKEYKCKVSNKGLPSSIEKTISKAKGQPREPQVYTLPPSQE
EMTKNQVSLTCLVKGFYPSDIAVEWESNGQPENNYKTTPPVLDS
DGSFFLYSRLTVDKSRWQEGNVFSCSVMHEALHNHYTQKSLSLS
LG SEQ ID NO: 182 DNA CAGGTGCAGCTGGTGCAGTCAGGCGCCGAAGTGAAGAAACCC
heavy GGCTCTAGCGTGAAAGTTTCTTGTAAAGCTAGTGGCTACACCT
chain TCACTAGCTATAATATGCACTGGGTTCGCCAGGCCCCAGGGCA
AGGCCTCGAGTGGATGGGCGATATCTACCCCGGGAACGGCGA
CACTAGTTATAATCAGAAGTTTAAGGGTAGAGTCACTATCACC
GCCGATAAGTCTACTAGCACCGTCTATATGGAACTGAGTTCCC
TGAGGTCTGAGGACACCGCCGTCTACTACTGCGCTAGAGTGG
GCGGAGCCTTCCCTATGGACTACTGGGGTCAAGGCACTACCGT
GACCGTGTCTAGCGCTAGCACTAAGGGCCCGTCCGTGTTCCCC
CTGGCACCTTGTAGCCGGAGCACTAGCGAATCCACCGCTGCCC
TCGGCTGCCTGGTCAAGGATTACTTCCCGGAGCCCGTGACCGT
GTCCTGGAACAGCGGAGCCCTGACCTCCGGAGTGCACACCTTC
CCCGCTGTGCTGCAGAGCTCCGGGCTGTACTCGCTGTCGTCGG
TGGTCACGGTGCCTTCATCTAGCCTGGGTACCAAGACCTACAC
TTGCAACGTGGACCACAAGCCTTCCAACACTAAGGTGGACAA
GCGCGTCGAATCGAAGTACGGCCCACCGTGCCCGCCTTGTCCC
GCGCCGGAGTTCCTCGGCGGTCCCTCGGTCTTTCTGTTCCCAC
CGAAGCCCAAGGACACTTTGATGATTTCCCGCACCCCTGAAGT
GACATGCGTGGTCGTGGACGTGTCACAGGAAGATCCGGAGGT
GCAGTTCAATTGGTACGTGGATGGCGTCGAGGTGCACAACGC
CAAAACCAAGCCGAGGGAGGAGCAGTTCAACTCCACTTACCG
CGTCGTGTCCGTGCTGACGGTGCTGCATCAGGACTGGCTGAAC
GGGAAGGAGTACAAGTGCAAAGTGTCCAACAAGGGACTTCCT
AGCTCAATCGAAAAGACCATCTCGAAAGCCAAGGGACAGCCC
CGGGAACCCCAAGTGTATACCCTGCCACCGAGCCAGGAAGAA
ATGACTAAGAACCAAGTCTCATTGACTTGCCTTGTGAAGGCT
TCTACCCATCGGATATCGCCGTGGAATGGGAGTCCAACGGCC
AGCCGGAAAACAACTACAAGACCACCCCTCCGGTGCTGGACT
CAGACTGGATCCTTCTTCCTCTACTCGCGGCTGACCGTGGATAA
GAGCAGATGGCAGGAGGGAAATGTGTTCAGCTGTTCTGTGAT
GCATGAAGCCCTGCACAACCACTACACTCAGAAGTCCCTGTCC TABLE 9-continued Amino acid and nucleotide sequences of exemplary anti-TIM-3 antibody molecules

|  |  |  |
|---|---|---|
|  |  | CTCTCCCTGGGA |
| SEQ ID NO: 183 (Kabat) | LCDR1 | RASESVEYYGTSLMQ |
| SEQ ID NO: 184 (Kabat) | LCDR2 | AASNVES |
| SEQ ID NO: 185 (Kabat) | LCDR3 | QQSRKDPST |
| SEQ ID NO: 186 (Chothia) | LCDR1 | SESVEYYGTSL |
| SEQ ID NO: 187 (Chothia) | LCDR2 | AAS |
| SEQ ID NO: 188 (Chothia) | LCDR3 | SRKDPS |
| SEQ ID NO: 189 | VL | AIQLTQSPSSLSASVGDRVTITCRASESVEYYGTSLMQWYQQKPG KAPKLLIYAASNVESGVPSRFSGSGSGTDFTLTISSLQPEDFATYF CQQSRKDPSTFGGGTKVEIK |
| SEQ ID NO: 190 | DNA VL | GCTATTCAGCTGACTCAGTCACCTAGTAGCCTGAGCGCTAGTG TGGGCGATAGAGTGACTATCACCTGTAGAGCTAGTGAATCAG TCGAGTACTACGGCACTAGCCTGATGCAGTGGTATCAGCAGA AGCCCGGGAAAGCCCCTAAGCTGCTGATCTACGCCGCCTCTAA CGTGGAATCAGGCGTGCCCTCTAGGTTTAGCGGTAGCGGTAGT GGCACCGACTTCACCCTGACTATCTCTAGCCTGCAGCCCGAGG ACTTCGCTACCTACTTCTGTCAGCAGTCTAGGAAGGACCCTAG CACCTTCGGCGGAGGCACTAAGGTCGAGATTAAG |
| SEQ ID NO: 191 | Light chain | AIQLTQSPSSLSASVGDRVTITCRASESVEYYGTSLMQWYQQKPG KAPKLLIYAASNVESGVPSRFSGSGSGTDFTLTISSLQPEDFATYF CQQSRKDPSTFGGGTKVEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC |
| SEQ ID NO: 192 | DNA light chain | GCTATTCAGCTGACTCAGTCACCTAGTAGCCTGAGCGCTAGTG TGGGCGATAGAGTGACTATCACCTGTAGAGCTAGTGAATCAG TCGAGTACTACGGCACTAGCCTGATGCAGTGGTATCAGCAGA AGCCCGGGAAAGCCCCTAAGCTGCTGATCTACGCCGCCTCTAA CGTGGAATCAGGCGTGCCCTCTAGGTTTAGCGGTAGCGGTAGT GGCACCGACTTCACCCTGACTATCTCTAGCCTGCAGCCCGAGG ACTTCGCTACCTACTTCTGTCAGCAGTCTAGGAAGGACCCTAG CACCTTCGGCGGAGGCACTAAGGTCGAGATTAAGCGTACGGT GGCCGCTCCCAGCGTGTTCATCTTCCCCCCCAGCGACGAGCAG CTGAAGAGCGGCACCGCCAGCGTGGTGTGCCTGCTGAACAAC TTCTACCCCCGGGAGGCCAAGGTGCAGTGGAAGGTGGACAAC GCCCTGCAGAGCGGCAACAGCCAGGAGAGCGTCACCGAGCAG GACAGCAAGGACTCCACCTACAGCCTGAGCAGCACCCTGACC CTGAGCAAGGCCGACTACGAGAAGCATAAGGTGTACGCCTGC GAGGTGACCCACCAGGGCCTGTCCAGCCCCGTGACCAAGAGC TTCAACAGGGGCGAGTGC |

ABTIM3-hum03

|  |  |  |
|---|---|---|
| SEQ ID NO: 174 (Kabat) | HCDR1 | SYNMH |
| SEQ ID NO: 193 (Kabat) | HCDR2 | DIYPGQGDTSYNQKFKG |
| SEQ ID NO: 176 (Kabat) | HCDR3 | VGGAFPMDY |
| SEQ ID NO: 177 (Chothia) | HCDR1 | GYTFTSY |
| SEQ ID NO: 194 (Chothia) | HCDR2 | YPGQGD |
| SEQ ID NO: 176 (Chothia) | HCDR3 | VGGAFPMDY |

TABLE 9-continued

Amino acid and nucleotide sequences of
exemplary anti-TIM-3 antibody molecules

SEQ ID NO: 195  VH
QVQLVQSGAEVKKPGASVKVSCKASGYTFTSYNMHWVRQAPG
QGLEWIGDIYPGQGDTSYNQKFKGRATMTADKSTSTVYMELSSL
RSEDTAVYYCARVGGAFPMDYWGQGTLVTVSS

SEQ ID NO: 196  DNA VH
CAGGTGCAGCTGGTGCAGTCAGGCGCCGAAGTGAAGAAACCC
GGCGCTAGTGTGAAAGTTAGCTGTAAAGCTAGTGGCTATACTT
TCACTTCTTATAATATGCACTGGGTCCGCCAGGCCCCAGGTCA
AGGCCTCGAGTGGATCGGCGATATCTACCCCGGTCAAGGCGA
CACTTCCTATAATCAGAAGTTTAAGGGTAGAGCTACTATGACC
GCCGATAAGTCTACTTCTACCGTCTATATGGAACTGAGTTCCC
TGAGGTCTGAGGACACCGCCGTCTACTACTGCGCTAGAGTGG
GCGGAGCCTTCCCAATGGACTACTGGGGTCAAGGCACCCTGG
TCACCGTGTCTAGC

SEQ ID NO: 197  Heavy chain
QVQLVQSGAEVKKPGASVKVSCKASGYTFTSYNMHWVRQAPG
QGLEWIGDIYPGQGDTSYNQKFKGRATMTADKSTSTVYMELSSL
RSEDTAVYYCARVGGAFPMDYWGQGTLVTVSSASTKGPSVFPL
APCSRSTSESTAALGCLVKDYFPEPVTVSWNSGALTSGVHTFPAV
LQSSGLYSLSSVVTVPSSSLGTKTYTCNVDHKPSNTKVDKRVESK
YGPPCPPCPAPEFLGGPSVFLFPPKPKDTLMISRTPEVTCVVVDVS
QEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLTCLVKGFYPSDIAVEWESNGQPENNYKTTPPVLD
SDGSFFLYSRLTVDKSRWQEGNVFSCSVMHEALHNHYTQKSLSL
SLG SEQ ID NO: 198  DNA heavy chain
CAGGTGCAGCTGGTGCAGTCAGGCGCCGAAGTGAAGAAACCC
GGCGCTAGTGTGAAAGTTAGCTGTAAAGCTAGTGGCTATACTT
TCACTTCTTATAATATGCACTGGGTCCGCCAGGCCCCAGGTCA
AGGCCTCGAGTGGATCGGCGATATCTACCCCGGTCAAGGCGA
CACTTCCTATAATCAGAAGTTTAAGGGTAGAGCTACTATGACC
GCCGATAAGTCTACTTCTACCGTCTATATGGAACTGAGTTCCC
TGAGGTCTGAGGACACCGCCGTCTACTACTGCGCTAGAGTGG
GCGGAGCCTTCCCAATGGACTACTGGGGTCAAGGCACCCTGG
TCACCGTGTCTAGCGCTAGCACTAAGGGCCCGTCCGTGTTCCC
CCTGGCACCTTGTAGCCGGAGCACTAGCGAATCCACCGCTGCC
CTCGGCTGCCTGGTCAAGGATTACTTCCCGGAGCCCGTGACCG
TGTCCTGGAACAGCGGAGCCCTGACCTCCGGAGTGCACACCTT
CCCCGCTGTGCTGCAGAGCTCCGGGCTGTACTCGCTGTCGTCG
GTGGTCACGGTGCCTTCATCTAGCCTGGGTACCAAGACCTACA
CTTGCAACGTGGACCACAAGCCTTCCAACACTAAGGTGGACA
AGCGCGTCGAATCGAAGTACGGCCCACCGTGCCCGCCTTGTCC
CGCGCCGGAGTTCCTCGGCGGTCCCTCGGTCTTTCTGTTCCCA
CCGAAGCCCAAGGACACTTTGATGATTTCCCGCACCCCTGAAG
TGACATGCGTGGTCGTGGACGTGTCACAGGAAGATCCGGAGG
TGCAGTTCAATTGGTACGTGGATGGCGTCGAGGTGCACAACG
CCAAAACCAAGCCGAGGGAGGAGCAGTTCAACTCCACTTACC
GCGTCGTGTCCGTGCTGACGGTGCTGCATCAGGACTGGCTGAA
CGGGAAGGAGTACAAGTGCAAAGTGTCCAACAAGGGACTTCC
TAGCTCAATCGAAAAGACCATCTCGAAAGCCAAGGGACAGCC
CCGGGAACCCCAAGTGTATACCCTGCCACCGAGCCAGGAAGA
AATGACTAAGAACCAAGTCTCATTGACTTGCCTTGTGAAGGGC
TTCTACCCATCGGATATCGCCGTGGAATGGGAGTCCAACGGCC
AGCCGGAAAACAACTACAAGACCACCCCTCCGGTGCTGGACT
CAGACGGATCCTTCTTCCTCTACTCGCGGCTGACCGTGGATAA
GAGCAGATGGCAGGAGGGAAATGTGTTCAGCTGTTCTGTGAT
GCATGAAGCCCTGCACAACCACTACACTCAGAAGTCCCTGTCC
CTCTCCCTGGGA SEQ ID NO: 183  LCDR1 (Kabat)
RASESVEYYGTSLMQ SEQ ID NO: 184  LCDR2 (Kabat)
AASNVES SEQ ID NO: 185  LCDR3 (Kabat)
QQSRKDPST SEQ ID NO: 186  LCDR1 (Chothia)
SESVEYYGTSL SEQ ID NO: 187  LCDR2 (Chothia)
AAS SEQ ID NO: 188  LCDR3 (Chothia)
SRKDPS TABLE 9-continued Amino acid and nucleotide sequences of
exemplary anti-TIM-3 antibody molecules SEQ ID NO: 199 VL
DIVLTQSPDSLAVSLGERATINCRASESVEYYGTSLMQWYQQKP
GQPPKLLIYAASNVESGVPDRFSGSGSGTDFTLTISSLQAEDVAVY
YCQQSRKDPSTFGGGTKVEIK SEQ ID NO: 200 DNA VL
GATATCGTCCTGACTCAGTCACCCGATAGCCTGGCCGTCAGCC
TGGGCGAGCGGGCTACTATTAACTGTAGAGCTAGTGAATCAG
TCGAGTACTACGGCACTAGCCTGATGCAGTGGTATCAGCAGA
AGCCCGGTCAACCCCCTAAGCTGCTGATCTACGCCGCCTCTAA
CGTGGAATCAGGCGTGCCCGATAGGTTTAGCGGTAGCGGTAG
TGGCACCGACTTCACCCTGACTATTAGTAGCCTGCAGGCCGAG
GACGTGGCCGTCTACTACTGTCAGCAGTCTAGGAAGGACCCTA
GCACCTTCGGCGGAGGCACTAAGGTCGAGATTAAG SEQ ID NO: 201 Light chain
DIVLTQSPDSLAVSLGERATINCRASESVEYYGTSLMQWYQQKP
GQPPKLLIYAASNVESGVPDRFSGSGSGTDFTLTISSLQAEDVAVY
YCQQSRKDPSTFGGGTKVEIKRTVAAPSVFIFPPSDEQLKSGTASV
VCLLNNFYPREAKVQWKVDNALQSGNSQESVTEQDSKDSTYSLS
STLTLSKADYEKHKVYACEVTHQGLSSPVTKSFNRGEC SEQ ID NO: 202 DNA light chain
GATATCGTCCTGACTCAGTCACCCGATAGCCTGGCCGTCAGCC
TGGGCGAGCGGGCTACTATTAACTGTAGAGCTAGTGAATCAG
TCGAGTACTACGGCACTAGCCTGATGCAGTGGTATCAGCAGA
AGCCCGGTCAACCCCCTAAGCTGCTGATCTACGCCGCCTCTAA
CGTGGAATCAGGCGTGCCCGATAGGTTTAGCGGTAGCGGTAG
TGGCACCGACTTCACCCTGACTATTAGTAGCCTGCAGGCCGAG
GACGTGGCCGTCTACTACTGTCAGCAGTCTAGGAAGGACCCTA
GCACCTTCGGCGGAGGCACTAAGGTCGAGATTAAGCGTACGG
TGGCCGCTCCCAGCGTGTTCATCTTCCCCCCCAGCGACGAGCA
GCTGAAGAGCGGCACCGCCAGCGTGGTGTGCCTGCTGAACAA
CTTCTACCCCCGGGAGGCCAAGGTGCAGTGGAAGGTGGACAA
CGCCCTGCAGAGCGGCAACAGCCAGGAGAGCGTCACCGAGCA
GGACAGCAAGGACTCCACCTACAGCCTGAGCAGCACCCTGAC
CCTGAGCAAGGCCGACTACGAGAAGCATAAGGTGTACGCCTG
CGAGGTGACCCACCAGGGCCTGTCCAGCCCCGTGACCAAGAG
CTTCAACAGGGGCGAGTGC

Other Exemplary TIM-3 Inhibitors

In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of TSR-022. In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121, e.g., as disclosed in Table 10. APE5137, APE5121, and other anti-TIM-3 antibodies are disclosed in WO 2016/161270, incorporated by reference in its entirety.

In one embodiment, the anti-TIM-3 antibody molecule is the antibody clone F38-2E2. In one embodiment, the anti-TIM-3 antibody molecule comprises one or more of the CDR sequences (or collectively all of the CDR sequences), the heavy chain or light chain variable region sequence, or the heavy chain or light chain sequence of F38-2E2.

Further known anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entirety.

In one embodiment, the anti-TIM-3 antibody is an antibody that competes for binding with, and/or binds to the same epitope on TIM-3 as, one of the anti-TIM-3 antibodies described herein.

TABLE 10

Amino acid sequences of other exemplary anti-TIM-3 antibody molecules

APE5137

SEQ ID NO: 203 VH
EVQLLESGGGLVQPGGSLRLSCAAASGFTFSSYDMSWVRQAPGKGLD
WVSTISGGGTYTYYQDSVKGRFTISRDNSKNTLYLQMNSLRAEDTAV
YYCASMDYWGQGTTVTVSSA

SEQ ID NO: 204 VL
DIQMTQSPSSLSASVGDRVTITCRASQSIRRYLNWYHQKPGKAPKLLI
YGASTLQSGVPSRFSGSGSGTDFTLTISSLQPEDFAVYYCQQSHSAPLT
FGGGTKVEIKR

TABLE 10-continued

Amino acid sequences of other exemplary anti-TIM-3 antibody molecules

APE5121

SEQ ID NO: 205 VH  EVQVLESGGGLVQPGGSLRLYCVASGFTFSGSYAMSWVRQAPGKGL
                   EWVSAISGSGGSTYYADSVKGRFTISRDNSKNTLYLQMNSLRAEDTA
                   VYYCAKKYYVGPADYWGQGTLVTVSSG

SEQ ID NO: 206 VL  DIVMTQSPDSLAVSLGERATINCKSSQSVLYSSNNKNYLAWYQHKPG
                   QPPKLLIYWASTRESGVPDRFSGSGSGTDFTLTISSLQAEDVAVYYCQ
                   QYYSSPLTFGGGTKIEVK

Cytokines

In yet another embodiment, the compounds of Formula (I') or Formula (I), or a pharmaceutically acceptable salt, hydrate, solvate, prodrug, stereoisomer, or tautomer thereof, of the present disclosure are used in combination with one or more cytokines, including but not limited to, interferon, IL-2, IL-15, IL-7, or IL21. In certain embodiments, compounds of Formula (I') or Formula (I), or a pharmaceutically acceptable salt, hydrate, solvate, prodrug, stereoisomer, or tautomer thereof, are administered in combination with an IL-15/IL-15Ra complex. In some embodiments, the IL-15/IL-15Ra complex is selected from NIZ985 (Novartis), ATL-803 (Altor) or CYP0150 (Cytune).

Exemplary IL-15/IL-15Ra Complexes

In one embodiment, the cytokine is IL-15 complexed with a soluble form of IL-15 receptor alpha (IL-15Ra). The IL-15/IL-15Ra complex may comprise IL-15 covalently or noncovalently bound to a soluble form of IL-15Ra. In a particular embodiment, the human IL-15 is noncovalently bonded to a soluble form of IL-15Ra. In a particular embodiment, the human IL-15 of the formulation comprises an amino acid sequence of SEQ ID NO: 207 in Table 11 or an amino acid sequence at least 85%, 90%, 95%, or 99% identical or higher to SEQ ID NO: 207, and the soluble form of human IL-15Ra comprises an amino acid sequence of SEQ ID NO: 208 in Table 11, or an amino acid sequence at least 85%, 90%, 95%, or 99% identical or higher to SEQ ID NO: 208, as described in WO 2014/066527, incorporated by reference in its entirety. The molecules described herein can be made by vectors, host cells, and methods described in WO 2007084342, incorporated by reference in its entirety.

TABLE 11

Amino acid and nucleotide sequences of exemplary IL-15/IL-15Ra complexes
NIZ985

SEQ ID NO: 207  Human       NWVNVISDLKKIEDLIQSMHIDATLYTESDVHPSCKVTAMKCFL
                IL-15       LELQVISLESGDASIHDTVENLIILANNSLSSNGNVTESGCKECEE
                            LEEKNIKEFLQSFVHIVQMFINTS SEQ ID NO: 208  Human       ITCPPPMSVEHADIWVKSYSLYSRERYICNSGFKRKAGTSSLTEC
                Soluble     VLNKATNVAHWTTPSLKCIRDPALVHQRPAPPSTVTTAGVTPQP
                IL-15Ra     ESLSPSGKEPAASSPSSNNTAATTAAIVPGSQLMPSKSPSTGTTEI
                            SSHESSHGTPSQTTAKNWELTASASHQPPGVYPQG Other Exemplar IL-15/IL-15Ra Complexes In one embodiment, the IL-15/IL-15Ra complex is ALT-803, an IL-15/IL-15Ra Fc fusion protein (IL-15N72D:IL-15RaSu/Fc soluble complex). ALT-803 is described in WO 2008/143794, incorporated by reference in its entirety. In one embodiment, the IL-15/IL-15Ra Fc fusion protein comprises the sequences as disclosed in Table 12.

In one embodiment, the IL-15/IL-15Ra complex comprises IL-15 fused to the sushi domain of IL-15Ra (CYP0150, Cytune). The sushi domain of IL-15Ra refers to a domain beginning at the first cysteine residue after the signal peptide of IL-15Ra, and ending at the fourth cysteine residue after said signal peptide. The complex of IL-15 fused to the sushi domain of IL-15Ra is described in WO 2007/04606 and WO 2012/175222, incorporated by reference in their entirety. In one embodiment, the IL-15/IL-15Ra sushi domain fusion comprises the sequences as disclosed in Table 12.

TABLE 12

Amino acid sequences of other exemplary IL-15/IL-15Ra complexes

ALT-803

| | | |
|---|---|---|
| SEQ ID NO: 209 | IL-15N72D | NWVNVISDLKKIEDLIQSMHIDATLYTESDVHPSCKVTAMKCF LLELQVISLESGDASIHDTVENLIILANDSLSSNGNVTESGCKEC EELEEKNIKEFLQSFVHIVQMFINTS |
| SEQ ID NO: 210 | IL-15RaSu/Fc | ITCPPPMSVEHADIWVKSYSLYSRERYICNSGFKRKAGTSSLTE CVLNKATNVAHWTTPSLKCIREPKSCDKTHTCPPCPAPELLGG PSVFLFPPKPKDTLMISRTPEVTCVVVDVSHEDPEVKFNWYVD GVEVHNAKTKPREEQYNSTYRVVSVLTVLHQDWLNGKEYKC KVSNKALPAPIEKTISKAKGQPREPQVYTLPPSRDELTKNQVSL TCLVKGFYPSDIAVEWESNGQPENNYKTTPPVLDSDGSFFLYS KLTVDKSRWQQGNVFSCSVMHEALHNHYTQKSLSLSPGK |

IL-15/IL-15Ra sushi domain fusion (CYP0150)

| | | |
|---|---|---|
| SEQ ID NO: 211 | Human IL-15 | NWVNVISDLKKIEDLIQSMHIDATLYTESDVHPSCKVTAMKCF LLELQVISLESGDASIHDTVENLIILANNSLSSNGNVTESGCKEC EELEXKNIKEFLQSFVHIVQMFINTS Where X is E or K |
| SEQ ID NO: 212 | Human IL-15Ra sushi and hinge domains | ITCPPPMSVEHADIWVKSYSLYSRERYICNSGFKRKAGTSSLTE CVLNKATNVAHWTTPSLKCIRDPALVHQRPAPP |

In yet another embodiment, the compounds of Formula (I') or Formula (I), or a pharmaceutically acceptable salt, hydrate, solvate, prodrug, stereoisomer, or tautomer thereof, of the present disclosure are used in combination with one or more agonists of toll like receptors (TLRs, e.g., TLR7, TLR8, TLR9) to treat a disease, e.g., cancer. In some embodiments, a compound of the present disclosure can be used in combination with a TLR7 agonist or a TLR7 agonist conjugate.

In some embodiments, the TLR7 agonist comprises a compound disclosed in International Application Publication No. WO2011/049677, which is hereby incorporated by reference in its entirety. In some embodiments, the TLR7 agonist comprises 3-(5-amino-2-(4-(2-(3,3-difluoro-3-phosphonopropoxy)ethoxy)-2-methylphenethyl)benzo[f][1,7]naphthyridin-8-yl)propanoic acid. In some embodiments, the TLR7 agonist comprises a compound of formula:

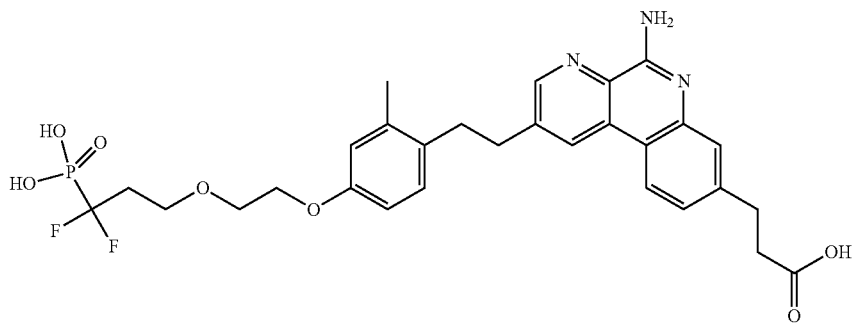

In another embodiment, the compounds of Formula (I') or Formula (I), or a pharmaceutically acceptable salt, hydrate, solvate, prodrug, stereoisomer, or tautomer thereof, of the present disclosure are used in combination with one or more angiogenesis inhibitors to treat cancer, e.g., Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-J][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aa,5(3,6aa)-octahydro-2-methylcyclopenta[c]pyrrol-5-yl]methoxy]-4-quinazolinamine (XL647, CAS 781613-23-8); 4-Methyl-3-

[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); or Aflibercept (Eylea®).

In another embodiment, the compounds of Formula (I') or Formula (I), or a pharmaceutically acceptable salt, hydrate, solvate, prodrug, stereoisomer, or tautomer thereof, of the present disclosure are used in combination with one or more heat shock protein inhibitors to treat cancer, e.g., Tanespimycin (17-allylamino-17-demethoxygeldanamycin, also known as KOS-953 and 17-AAG, available from SIGMA, and described in U.S. Pat. No. 4,261,989); Retaspimycin (IPI504), Ganetespib (STA-9090); [6-Chloro-9-(4-methoxy-3,5-dimethylpyridin-2-ylmethyl)-9H-purin-2-yl]amine (BIIB021 or —CNF2024, CAS 848695-25-0); trans-4-[[2-(Aminocarbonyl)-5-[4,5,6,7-tetrahydro-6,6-dimethyl-4-oxo-3-(trifluoromethyl)-1H-indazol-1-yl]phenyl]amino]cyclohexyl glycine ester (SNX5422 or PF04929113, CAS 908115-27-5); 5-[2,4-Dihydroxy-5-(1-methylethyl)phenyl]-N-ethyl-4-[4-(4-morpholinylmethyl)phenyl]-3-Isoxazolecarboxamide (AUY922, CAS 747412-49-3); or 17-Dimethylaminoethylamino-17-demethoxygeldanamycin (17-DMAG).

In yet another embodiment, the compounds of Formula (I') or Formula (I), or a pharmaceutically acceptable salt, hydrate, solvate, prodrug, stereoisomer, or tautomer thereof, of the present disclosure are used in combination with one or more HDAC inhibitors or other epigenetic modifiers. Exemplary HDAC inhibitors include, but are not limited to, Voninostat (Zolinza®); Romidepsin (Istodax®); Treichostatin A (TSA); Oxamflatin; Vorinostat (Zolinza®, Suberoylanilide hydroxamic acid); Pyroxamide (syberoyl-3-aminopyridineamide hydroxamic acid); Trapoxin A (RF-1023A); Trapoxin B (RF-10238); Cyclo[(αS,2S)-α-amino-η-oxo-2-oxiraneoctanoyl-O-methyl-D-tyrosyl-L-isoleucyl-L-prolyl] (Cyl-1); Cyclo[(αS,2S)-α-amino-η-oxo-2-oxiraneoctanoyl-O-methyl-D-tyrosyl-L-isoleucyl-(2S)-2-piperidinecarbonyl] (Cyl-2); Cyclic[L-alanyl-D-alanyl-(2S)-η-oxo-L-α-aminooxiraneoctanoyl-D-prolyl] (HC-toxin); Cyclo[(αS,2S)-α-amino-η-oxo-2-oxiraneoctanoyl-D-phenylalanyl-L-leucyl-(2S)-2-piperidinecarbonyl] (WF-3161); Chlamydocin ((S)-Cyclic(2-methylalanyl-L-phenylalanyl-D-prolyl-η-oxo-L-α-aminooxiraneoctanoyl); Apicidin (Cyclo(8-oxo-L-2-aminodecanoyl-1-methoxy-L-tryptophyl-L-isoleucyl-D-2-piperidinecarbonyl); Romidepsin (Istodax®, FR-901228); 4-Phenylbutyrate; Spiruchostatin A; Mylproin (Valproic acid); Entinostat (MS-275, N-(2-Aminophenyl)-4-[N-(pyridine-3-yl-methoxycarbonyl)-amino-methyl]-benzamide); Depudecin (4,5:8,9-dianhydro-1,2,6,7,11-pentadeoxy-D-threo-D-ido-Undeca-1,6-dienitol); 4-(Acetylamino)-N-(2-aminophenyl)-benzamide (also known as CI-994); N1-(2-Aminophenyl)-N8-phenyl-octanediamide (also known as BML-210); 4-(Dimethylamino)-N-(7-(hydroxyamino)-7-oxoheptyl)benzamide (also known as M344); (E)-3-(4-(((2-(1H-indol-3-yl)ethyl)(2-hydroxyethyl)amino)-methyl)phenyl)-N-hydroxyacrylamide; Panobinostat(Farydak®); Mocetinostat, and Belinostat (also known as PXD101, Beleodaq®, or (2E)-N-Hydroxy-3-[3-(phenylsulfamoyl)phenyl]prop-2-enamide), or chidamide (also known as CS055 or HBI-8000, (E)-N-(2-amino-5-fluorophenyl)-4-((3-(pyridin-3-yl)acrylamido)methyl)benzamide). Other epigenetic modifiers include but not limited to inhibitors of EZH2 (enhancer of zeste homolog 2), EED (embryonic ectoderm development), or LSD1 (lysine-specific histone demethylase 1A or KDM1A).

In yet another embodiment, the compounds of Formula (I') or Formula (I), or a pharmaceutically acceptable salt, hydrate, solvate, prodrug, stereoisomer, or tautomer thereof, of the present disclosure are used in combination with one or more inhibitors of indoleamine-pyrrole 2,3-dioxygenase (IDO), for example, Indoximod (also known as NLG-8189), α-Cyclohexyl-5H-imidazo[5,1-a]isoindole-5-ethanol (also known as NLG919), or (4E)-4-[(3-Chloro-4-fluoroanilino)-nitrosomethylidene]-1,2,5-oxadiazol-3-amine (also known as INCB024360), to treat cancer.

Chimeric Antigen Receptors

The present disclosure provides for the compounds of Formula (I') or Formula (I), or a pharmaceutically acceptable salt, hydrate, solvate, prodrug, stereoisomer, or tautomer thereof for use in combination with adoptive immunotherapy methods and reagents such as chimeric antigen receptor (CAR) immune effector cells, e.g., T cells, or chimeric TCR-transduced immune effector cells, e.g., T cells. This section describes CAR technology generally that is useful in combination with the compounds of Formula (I') or Formula (I), or a pharmaceutically acceptable salt, hydrate, solvate, prodrug, stereoisomer, or tautomer thereof, and describes CAR reagents, e.g., cells and compositions, and methods.

In general, aspects of the present disclosure pertain to or include an isolated nucleic acid molecule encoding a chimeric antigen receptor (CAR), wherein the CAR comprises an antigen binding domain (e.g., antibody or antibody fragment, TCR or TCR fragment) that binds to a tumor antigen as described herein, a transmembrane domain (e.g., a transmembrane domain described herein), and an intracellular signalling domain (e.g., an intracellular signalling domain described herein) (e.g., an intracellular signalling domain comprising a costimulatory domain (e.g., a costimulatory domain described herein) and/or a primary signalling domain (e.g., a primary signalling domain described herein). In other aspects, the present disclosure includes: host cells containing the above nucleic acids and isolated proteins encoded by such nucleic acid molecules. CAR nucleic acid constructs, encoded proteins, containing vectors, host cells, pharmaceutical compositions, and methods of administration and treatment related to the present disclosure are disclosed in detail in International Patent Application Publication No. WO2015142675, which is incorporated by reference in its entirety.

In one aspect, the disclosure pertains to an isolated nucleic acid molecule encoding a chimeric antigen receptor (CAR), wherein the CAR comprises an antigen binding domain (e.g., antibody or antibody fragment, TCR or TCR fragment) that binds to a tumor-supporting antigen (e.g., a tumor-supporting antigen as described herein), a transmembrane domain (e.g., a transmembrane domain described herein), and an intracellular signalling domain (e.g., an intracellular signalling domain described herein) (e.g., an intracellular signalling domain comprising a costimulatory domain (e.g., a costimulatory domain described herein) and/or a primary signalling domain (e.g., a primary signalling domain described herein). In some embodiments, the tumor-supporting antigen is an antigen present on a stromal cell or a myeloid-derived suppressor cell (MDSC). In other aspects, the disclosure features polypeptides encoded by such nucleic acids and host cells containing such nucleic acids and/or polypeptides.

Alternatively, aspects of the disclosure pertain to isolated nucleic acid encoding a chimeric T cell receptor (TCR) comprising a TCR alpha and/or TCR beta variable domain with specificity for a cancer antigen described herein. See for example, Dembic et al., Nature, 320, 232-238 (1986), Schumacher, Nat. Rev. Immunol., 2, 512-519 (2002), Kershaw et al., Nat. Rev. Immunol., 5, 928-940 (2005), Xue et al., *Clin. Exp. Immunol.*, 139, 167-172 (2005), Rossig et al., *Mol. Ther.*, 10, 5-18 (2004), and Murphy et al., Immunity, 22, 403-414 (2005); (Morgan et al. *J. Immunol.*, 171, 3287-3295 (2003), Hughes et al., *Hum. Gene Ther.*, 16, 1-16 (2005), Zhao et al., *J. Immunol.*, 174, 4415-4423 (2005), Roszkowski et al., *Cancer Res.*, 65, 1570-1576 (2005), and Engels et al., *Hum. Gene Ther.*, 16, 799-810 (2005); US2009/03046557, the contents of which are hereby incorporated by reference in their entirety. Such chimeric TCRs may recognize, for example, cancer antigens such as MART-1, gp-100, p53, and NY-ESO-1, MAGE A3/A6, MAGEA3, SSX2, HPV-16 E6 or HPV-16 E7. In other aspects, the disclosure features polypeptides encoded by such nucleic acids and host cells containing such nucleic acids and/or polypeptides.

Sequences of non-limiting examples of various components that can be part of a CAR are listed in Table 11a, where "aa" stands for amino acids, and "na" stands for nucleic acids that encode the corresponding peptide.

TABLE 11a

Sequences of various components of CAR (aa—amino acid sequence, na—nucleic acid sequence).

| SEQ ID NO: | description | Sequence |
|---|---|---|
| SEQ ID NO: 270 | EF-1 promoter (na) | CGTGAGGCTCCGGTGCCCGTCAGTGGGCAGAGCGCACATCGC CCACAGTCCCCGAGAAGTTGGGGGGAGGGGTCGGCAATTGAA CCGGTGCCTAGAGAAGGTGGCGCGGGGTAAACTGGGAAAGTG ATGTCGTGTACTGGCTCCGCCTTTTTCCCGAGGGTGGGGGAGA ACCGTATATAAGTGCAGTAGTCGCCGTGAACGTTCTTTTTCGC AACGGGTTTGCCGCCAGAACACAGGTAAGTGCCGTGTGTGGT TCCCGCGGGCCTGGCCTCTTTACGGGTTATGGCCCTTGCGTGC CTTGAATTACTTCCACCTGGCTGCAGTACGTGATTCTTGATCCC GAGCTTCGGGTTGGAAGTGGGTGGGAGAGTTCGAGGCCTTGC GCTTAAGGAGCCCCTTCGCCTCGTGCTTGAGTTGAGGCCTGGC CTGGGCGCTGGGGCCGCCGCGTGCGAATCTGGTGGCACCTTCG CGCCTGTCTCGCTGCTTTCGATAAGTCTCTAGCCATTTAAAATT TTTGATGACCTGCTGCGACGCTTTTTTTCTGGCAAGATAGTCTT GTAAATGCGGGCCAAGATCTGCACACTGGTATTTCGGTTTTTG GGGCCGCGGGCGGCGACGGGGCCCGTGCGTCCCAGCGCACAT GTTCGGCGAGGCGGGCCTGCGAGCGCGGCCACCGAGAATCG GACGGGGGTAGTCTCAAGCTGGCCGGCCTGCTCTGGTGCCTGG CCTCGCGCCGCCGTGTATCGCCCCGCCCTGGGCGGCAAGGCTG GCCCGGTCGGCACCAGTTGCGTGAGCGGAAAGATGGCCGCTT CCCGGCCCTGCTGCAGGGAGCTCAAAATGGAGGACGCGGCGC TCGGGAGAGCGGGCGGGTGAGTCACCCACACAAAGGAAAAG GGCCTTTCCGTCCTCAGCCGTCGCTTCATGTGACTCCACGGAG TACCGGGCGCCGTCCAGGCACCTCGATTAGTTCTCGAGCTTTT GGAGTACGTCGTCTTTAGGTTGGGGGGAGGGGTTTTATGCGAT GGAGTTTCCCCACACTGAGTGGGTGGAGACTGAAGTTAGGCC AGCTTGGCACTTGATGTAATTCTCCTTGGAATTTGCCCTTTTTG AGTTTGGATCTTGGTTCATTCTCAAGCCTCAGACAGTGGTTCA AAGTTTTTTTCTTCCATTTCAGGTGTCGTGA |
| SEQ ID NO: 268 | Leader (aa) | MALPVTALLLPLALLLHAARP |
| SEQ ID NO: 287 | Leader (na) | ATGGCCCTGCCTGTGACAGCCCTGCTGCTGCCTCTGGCTCTGC TGCTGCATGCCGCTAGACCC |
| SEQ ID NO: 288 | Leader (na) | ATGGCCCTCCCTGTCACCGCCCTGCTGCTTCCGCTGGCTCTTCT GCTCCACGCCGCTCGGCCC |
| SEQ ID NO: 250 | CD8 hinge (aa) | TTTPAPRPPTPAPTIASQPLSLRPEACRPAAGGAVHTRGLDFACD |
| SEQ ID NO: 254 | CD8 hinge (na) | ACCACGACGCCAGCGCCGCGACCACCAACACCGGCGCCCACC ATCGCGTCGCAGCCCCTGTCCCTGCGCCCAGAGGCGTGCCGGC CAGCGGCGGGGGGCGCAGTGCACACGAGGGGGCTGGACTTCG CCTGTGAT |
| SEQ ID NO: 253 | IgG4 hinge (aa) | ESKYGPPCPPCPAPEFLGGPSVFLFPPKPKDTLMISRTPEVTCVVV DVSQEDPEVQFNWYVDGVEVHNAKTKPREEQFNSTYRVVSVLT VLHQDWLNGKEYKCKVSNKGLPSSIEKTISKAKGQPREPQVYTL PPSQEEMTKNQVSLTCLVKGFYPSDIAVEWESNGQPENNYKTTPP VLDSDGSFFLYSRLTVDKSRWQEGNVFSCSVMHEALHNHYTQK SLSLSLGKM |
| SEQ ID NO: 255 | IgG4 hinge (na) | GAGAGCAAGTACGGCCCTCCCTGCCCCCCTTGCCCTGCCCCCG AGTTCCTGGGCGGACCCAGCGTGTTCCTGTTCCCCCCCAAGCC CAAGGACACCCTGATGATCAGCCGGACCCCCGAGGTGACCTG TGTGGTGGTGGACGTGTCCCAGGAGGACCCCGAGGTCCAGTT CAACTGGTACGTGGACGGCGTGGAGGTGCACAACGCCAAGAC CAAGCCCCGGGAGGAGCAGTTCAATAGCACCTACCGGGTGGT |

TABLE 11a-continued

Sequences of various components of CAR (aa—amino acid sequence, na—nucleic acid sequence).

| SEQ ID NO: | description | Sequence |
|---|---|---|
| | | GTCCGTGCTGACCGTGCTGCACCAGGACTGGCTGAACGGCAA GGAATACAAGTGTAAGGTGTCCAACAAGGGCCTGCCCAGCAG CATCGAGAAAACCATCAGCAAGGCCAAGGGCCAGCCTCGGGA GCCCCAGGTGTACACCCTGCCCCCTAGCCAAGAGGAGATGAC CAAGAACCAGGTGTCCCTGACCTGCCTGGTGAAGGGCTTCTAC CCCAGCGACATCGCCGTGGAGTGGGAGAGCAACGGCCAGCCC GAGAACAACTACAAGACCACCCCCCCTGTGCTGGACAGCGAC GGCAGCTTCTTCCTGTACAGCCGGCTGACCGTGGACAAGAGCC GGTGGCAGGAGGGCAACGTCTTTAGCTGCTCCGTGATGCACG AGGCCCTGCACAACCACTACACCCAGAAGAGCCTGAGCCTGT CCCTGGGCAAGATG |
| SEQ ID NO: 256 | IgD hinge (aa) | RWPESPKAQASSVPTAQPQAEGSLAKATTAPATTRNTGRGGEEK KKEKEKEEQEERETKTPECPSHTQPLGVYLLTPAVQDLWLRDKA TFTCFVVGSDLKDAHLTWEVAGKVPTGGVEEGLLERHSNGSQSQ HSRLTLPRSLWNAGTSVTCTLNHPSLPPQRLMALREPAAQAPVK LSLNLLASSDPPEAASWLLCEVSGFSPPNILLMWLEDQREVNTSG FAPARPPPQPGSTTFWAWSVLRVPAPPSPQPATYTCVVSHEDSRT LLNASRSLEVSYVTDH |
| SEQ ID NO: 257 | IgD hinge (na) | AGGTGGCCCGAAAGTCCCAAGGCCCAGGCATCTAGTGTTCCT ACTGCACAGCCCCAGGCAGAAGGCAGCCTAGCCAAAGCTACT ACTGCACCTGCCACTACGCGCAATACTGGCCGTGGCGGGGAG GAGAAGAAAAAGGAGAAAGAGAAAGAAGAACAGGAAGAGA GGGAGACCAAGACCCCTGAATGTCCATCCCATACCCAGCCGC TGGGCGTCTATCTCTTGACTCCCGCAGTACAGGACTTGTGGCT TAGAGATAAGGCCACCTTTACATGTTTCGTCGTGGGCTCTGAC CTGAAGGATGCCCATTTGACTTGGGAGGTTGCCGGAAAGGTA CCCACAGGGGGGGTTGAGGAAGGGTTGCTGGAGCGCCATTCC AATGGCTCTCAGAGCCAGCACTCAAGACTCACCCTTCCGAGAT CCCTGTGGAACGCCGGGACCTCTGTCACATGTACTCTAAATCA TCCTAGCCTGCCCCCACAGCGTCTGATGGCCCTTAGAGAGCCA GCCGCCCAGGCACCAGTTAAGCTTAGCCTGAATCTGCTCGCCA GTAGTGATCCCCCAGAGGCCGCCAGCTGGCTCTTATGCGAAGT GTCCGGCTTTAGCCCGCCCAACATCTTGCTCATGTGGCTGGAG GACCAGCGAGAAGTGAACACCAGCGGCTTCGCTCCAGCCCGG CCCCCACCCCAGCCGGGTTCTACCACATTCTGGGCCTGGAGTG TCTTAAGGGTCCAGCACCACCTAGCCCCCAGCCAGCCACATA CACCTGTGTTGTGTCCCATGAAGATAGCAGGACCCTGCTAAAT GCTTCTAGGAGTCTGGAGGTTTCCTACGTGACTGACCATT |
| SEQ ID NO: 258 | GS hinge/linker (aa) | GGGGSGGGGS |
| SEQ ID NO: 259 | GS hinge/linker (na) | GGTGGCGGAGGTTCTGGAGGTGGAGGTTCC |
| SEQ ID NO: 251 | CD8 transmembrane (aa) | IYIWAPLAGTCGVLLLSLVITLYC |
| SEQ ID NO: 252 | CD8 transmembrane (na) | ATCTACATCTGGGCGCCCTTGGCCGGGACTTGTGGGGTCCTTC TCCTGTCACTGGTTATCACCCTTTACTGC |
| SEQ ID NO: 289 | CD8 transmembrane (na) | ATCTACATTTGGGCCCCTCTGGCTGGTACTTGCGGGGTCCTGC TGCTTTCACTCGTGATCACTCTTTACTGT |
| SEQ ID NO: 264 | 4-1BB intracellular domain (aa) | KRGRKKLLYIFKQPFMRPVQTTQEEDGCSCRFPEEEEGGCEL |
| SEQ ID NO: 266 | 4-1BB intracellular domain (na) | AAACGGGGCAGAAAGAAACTCCTGTATATATTCAAACAACCA TTTATGAGACCAGTACAAACTACTCAAGAGGAAGATGGCTGT AGCTGCCGATTTCCAGAAGAAGAAGAAGGAGGATGTGAACTG |
| SEQ ID NO: 290 | 4-1BB intracellular domain (na) | AAGCGCGGTCGGAAGAAGCTGCTGTACATCTTTAAGCAACCC TTCATGAGGCCTGTGCAGACTACTCAAGAGGAGGACGGCTGT TCATGCCGGTTCCCAGAGGAGGAGGAAGGCGGCTGCGAACTG |

TABLE 11a-continued

Sequences of various components of CAR (aa—amino acid sequence, na—nucleic acid sequence).

| SEQ ID NO: | description | Sequence |
|---|---|---|
| SEQ ID NO: 265 | CD27 (aa) | QRRKYRSNKGESPVEPAEPCRYSCPREEEGSTIPIQEDYRKPEPACSP |
| SEQ ID NO: 267 | CD27 (na) | Caacgaaggaaatatagatcaaacaaaggagaaagtcctgtggagcctgcagagccttgtcgttaca<br>gctgccccagggaggagggggcagcaccatccccatccaggaggattaccgaaaaccggagcct<br>gcctgctccccc |
| SEQ ID NO: 260 | CD3-zeta (aa) | RVKFSRSADAPAYKQGQNQLYNELNLGRREEYDVLDKRRGRDP<br>EMGGKPRRKNPQEGLYNELQKDKMAEAYSEIGMKGERRRGKG<br>HDGLYQGLSTATKDTYDALHMQALPPR |
| SEQ ID NO: 262 | CD3-zeta (na) | AGAGTGAAGTTCAGCAGGAGCGCAGACGCCCCCGCGTACAAG<br>CAGGGCCAGAACCAGCTCTATAACGAGCTCAATCTAGGACGA<br>AGAGAGGAGTACGATGTTTTGGACAAGAGACGTGGCCGGGAC<br>CCTGAGATGGGGGGAAAGCCGAGAAGGAAGAACCCTCAGGA<br>AGGCCTGTACAATGAACTGCAGAAAGATAAGATGGCGGAGGC<br>CTACAGTGAGATTGGGATGAAAGGCGAGCGCCGGAGGGGCAA<br>GGGGCACGATGGCCTTTACCAGGGTCTCAGTACAGCCACCAA<br>GGACACCTACGACGCCCTTCACATGCAGGCCCTGCCCCCTCGC |
| SEQ ID NO: 291 | CD3-zeta (na) | CGCGTGAAATTCAGCCGCAGCGCAGATGCTCCAGCCTACAAG<br>CAGGGGCAGAACCAGCTCTACAACGAACTCAATCTTGGTCGG<br>AGAGAGGAGTACGACGTGCTGGACAAGCGGAGAGGACGGGA<br>CCCAGAAATGGGCGGGAAGCCGCGCAGAAAGAATCCCCAAG<br>AGGGCCTGTACAACGAGCTCCAAAAGGATAAGATGGCAGAAG<br>CCTATAGCGAGATTGGTATGAAAGGGGAACGCAGAAGAGGCA<br>AAGGCCACGACGGACTGTACCAGGGACTCAGCACCGCCACCA<br>AGGACACCTATGACGCTCTTCACATGCAGGCCCTGCCGCCTCGG |
| SEQ ID NO: 261 | CD3-zeta (aa) | RVKFSRSADAPAYQQGQNQLYNELNLGRREEYDVLDKRRGRDP<br>EMGGKPRRKNPQEGLYNELQKDKMAEAYSEIGMKGERRRGKG<br>HDGLYQGLSTATKDTYDALHMQALPPR |
| SEQ ID NO: 263 | CD3-zeta (na) | AGAGTGAAGTTCAGCAGGAGCGCAGACGCCCCCGCGTACCAG<br>CAGGGCCAGAACCAGCTCTATAACGAGCTCAATCTAGGACGA<br>AGAGAGGAGTACGATGTTTTGGACAAGAGACGTGGCCGGGAC<br>CCTGAGATGGGGGGAAAGCCGAGAAGGAAGAACCCTCAGGA<br>AGGCCTGTACAATGAACTGCAGAAAGATAAGATGGCGGAGGC<br>CTACAGTGAGATTGGGATGAAAGGCGAGCGCCGGAGGGGCAA<br>GGGGCACGATGGCCTTTACCAGGGTCTCAGTACAGCCACCAA<br>GGACACCTACGACGCCCTTCACATGCAGGCCCTGCCCCCTCGC |
| SEQ ID NO: 292 | Linker (aa) | GGGGS |
| SEQ ID NO: 293 | PD-1 extracellular domain (aa) | Pgwfldspdrpwnpptfspallvvtegdnatftcsfsntsesfvlnwyrmspsnqtdklaafpedrs<br>qpgqdcrfrvtqlpngrdfhmsvvrarrndsgtylcgaislapkaqikeslraelrvterraevptahp<br>spsprpagqfqtlv |
| SEQ ID NO: 294 | PD-1 extracellular domain (na) | Cccggatggtttctggactctccggatcgcccgtggaatcccccaaccttctcaccggcactcttggttg<br>tgactgagggcgataatgcgaccttcacgtgctcgttctccaacacctccgaatcattcgtgctgaactg<br>gtaccgcatgagcccgtcaaaccagaccgacaagctcgccgcgtttccggaagatcggtcgcaaccg<br>ggacaggattgtcggttccgcgtgactcaactgccgaatggcagagacttccacatgagcgtggtccg<br>cgctaggcgaaacgactccgggacctacctgtgcggagccatctcgctggcgcctaaggcccaaatc<br>aaagagagcttgagggccgaactgagagtgaccgagcgcagagctgaggtgccaactgcacatcca<br>tccccatcgcctcggcctgcggggcagtttcagaccctggtc |
| SEQ ID NO: 295 | PD-1 CAR (aa) with signal | Malpvtalllplallhaarppgwfldspdrpwnpptfspallvvtegdnatftcsfsntsesfvlnwy<br>rmspsnqtdklaafpedrsqpgqdcrfrvtqlpngrdfhmsvvrarrndsgtylcgaislapkaqik<br>eslraelrvterraevptahpspsprpagqfqtlvtttpaprpptpaptiasqplslrpeacrpaaggavh<br>trgldfacdiyiwaplagtcgvllllslvitlyckrgrkkllyifkqpfmrpvqttqeedgcscrfpeeee<br>ggcelrvkfsrsadapaykqgqnqlynelnlgrreeydvldkrrgrdpemggkprrknpqeglyn<br>elqkdkmaeayseigmkgerrrgkghdglyqglstatkdtydalhmqalppr |
| SEQ ID NO: 296 | PD-1 CAR (na) | Atggcctcccctgtcactgccctgcttctccccctcgcactcctgctccacgccgctagaccacccgga<br>tggtttctggactctccggatcgcccgtggaatcccccaaccttctcaccggcactcttggttgtgactga<br>gggcgataatgcgaccttcacgtgctcgttctccaacacctccgaatcattcgtgctgaactggtaccgc<br>atgagcccgtcaaaccagaccgacaagctcgccgcgtttccggaagatcggtcgcaaccgggacag<br>gattgtcggttccgcgtgactcaactgccgaatggcagagacttccacatgagcgtggtccgcgctagg<br>cgaaacgactccgggacctacctgtgcggagccatctcgctggcgcctaaggcccaaatcaaagaga<br>gcttgagggccgaactgagagtgaccgagcgcagagctgaggtgccaactgcacatccatccccatc<br>gcctcggcctgcggggcagtttcagaccctggtcacgaccactccggcgccgcgcccaccgactccg<br>gcccccaactatcgcgagccagcccctgtcgctgaggccggaagcatgccgccctgccgccggaggt TABLE 11a-continued Sequences of various components of CAR (aa—amino acid sequence, na—nucleic acid sequence).

| SEQ ID NO: | description | Sequence |
|---|---|---|
| | | gctgtgcatacccggggattggacttcgcatgcgacatctacatttgggctcctctcgccggaacttgtg gcgtgctccttctgtccctggtcatcaccctgtactgcaagcggggtcggaaaaagcttctgtacattttc aagcagcccttcatgagggccgtgcaaaccacccaggaggaggacggttgctcctgccggttccccg aagaggaagaaggaggttgcgagctgcgcgtgaagttctcccggagcgccgacgcccccgcctata agcagggccagaaccagctgtacaacgaactgaacctgggacggcgggaagagtacgatgtgctgg acaagcggcgcggccgggaccccgaaatgggcgggaagcctagaagaaagaaccctcaggaagg cctgtataacgagctgcagaaggacaagatggccgaggcctactccgaaattgggatgaagggagag cggcggaggggaaaggggcacgacggcctgtaccaaggactgtccaccgccaccaaggacacata cgatgccctgcacatgcaggcccttcccctcgc |
| SEQ ID NO: 297 | Linker (aa) | (Gly-Gly-Gly-Ser)n, where n = 1-10 |
| SEQ ID NO: 215 | Linker (aa) | (Gly4 Ser)4 |
| SEQ ID NO: 216 | Linker (aa) | (Gly4 Ser)3 |
| SEQ ID NO: 297 | Linker (aa) | (Gly3Ser) |
| SEQ ID NO: 298 | polyA (na) | [a]$_{50-5000}$ |
| SEQ ID NO: 299 | PD1 CAR (aa) | Pqwfldspdrpwnpptfspallvvteqdnatftcsfsntsesfvlnwvrmspsnqtdklaafpedrs qpgqdcrfrvtqlpngrdfhmsvvrarrndsqtylcqaislapkaqikeslraelryterraevptahp spsprpaqqfqtlvtttpaprpptpaptiasqplslrpeacrpaaggavhtrgldfacdiyiwaplagtc gvlllslvitlyckrgrkkllyifkqpfmrpvqttqeedgcscrfpeeeeggcelrvkfsrsadapayk qgqnqlynelnlgrreeydvldkrrgrdpemggkprrknpqeglynelqkdkmaeayseigmk gerrrgkghdglyqglstatkdtydalhmqalppr |
| SEQ ID NO: 300 | ICOS intracellular domain (aa) | TKKKYSSSVHDPNGEYMFMRAVNTAKKSRLTDVTL |
| SEQ ID NO: 301 | ICOS intracellular domain (na) | ACAAAAAAGAAGTATTCATCCAGTGTGCACGACCCTAACGGT GAATACATGTTCATGAGAGCAGTGAACACAGCCAAAAAATCC AGACTCACAGATGTGACCCTA |
| SEQ ID NO: 302 | ICOS TM domain (aa) | TTTPAPRPPTPAPTIASQPLSLRPEACRPAAGGAVHTRGLDFACDF WLPIGCAAFVVVCILGCILICWL |
| SEQ ID NO: 303 | ICOS TM domain (na) | ACCACGACGCCAGCGCCGCGACCACCAACACCGGCGCCCACC ATCGCGTCGCAGCCCCTGTCCCTGCGCCCAGAGGCGTGCCGGC CAGCGGCGGGGGCGCAGTGCACACGAGGGGGCTGGACTTCG CCTGTGATTTCTGGTTACCCATAGGATGTGCAGCCTTTGTTGTA GTCTGCATTTTGGGATGCATACTTATTTGTTGGCTT |
| SEQ ID NO: 304 | CD28 intracellular domain (aa) | RSKRSRLLHSDYMNMTPRRPGPTRKHYQPYAPPRDFAAYRS |
| SEQ ID NO: 305 | CD28 intracellular domain (na) | AGGAGTAAGAGGAGCAGGCTCCTGCACAGTGACTACATGAAC ATGACTCCCCGCCGCCCCGGGCCCACCCGCAAGCATTACCAGC CCTATGCCCCACCACGCGACTTCGCAGCCTATCGCTCC |

Targets

The present disclosure provides cells, e.g., immune effector cells (e.g., T cells, NK cells), that comprise or at any time comprised a gRNA molecule or CRISPR system as described herein, that are further engineered to contain one or more CARs that direct the immune effector cells to undesired cells (e.g., cancer cells). This is achieved through an antigen binding domain on the CAR that is specific for a cancer associated antigen. There are two classes of cancer associated antigens (tumor antigens) that can be targeted by the CARs of the instant disclosure: (1) cancer associated antigens that are expressed on the surface of cancer cells; and (2) cancer associated antigens that itself is intracellular, however, a fragment of such antigen (peptide) is presented on the surface of the cancer cells by MHC (major histocompatibility complex).

In some embodiments, the tumor antigen is chosen from one or more of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1) Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

A CAR described herein can comprise an antigen binding domain (e.g., antibody or antibody fragment, TCR or TCR fragment) that binds to a tumor-supporting antigen (e.g., a tumor-supporting antigen as described herein). In some embodiments, the tumor-supporting antigen is an antigen present on a stromal cell or a myeloid-derived suppressor cell (MDSC). Stromal cells can secrete growth factors to promote cell division in the microenvironment. MDSC cells can inhibit T cell proliferation and activation. Without wishing to be bound by theory, in some embodiments, the CAR-expressing cells destroy the tumor-supporting cells, thereby indirectly inhibiting tumor growth or survival.

In embodiments, the stromal cell antigen is chosen from one or more of: bone marrow stromal cell antigen 2 (BST2), fibroblast activation protein (FAP) and tenascin. In an embodiment, the FAP-specific antibody is, competes for binding with, or has the same CDRs as, sibrotuzumab. In embodiments, the MDSC antigen is chosen from one or more of: CD33, CD11b, C14, CD15, and CD66b. Accordingly, in some embodiments, the tumor-supporting antigen is chosen from one or more of: bone marrow stromal cell antigen 2 (BST2), fibroblast activation protein (FAP) or tenascin, CD33, CD1 b, C14, CD15, and CD66b.

Antigen Binding Domain Structures

In some embodiments, the antigen binding domain of the encoded CAR molecule comprises an antibody, an antibody fragment, an scFv, a Fv, a Fab, a (Fab')2, a single domain antibody (SDAB), a VH or VL domain, a camelid VHH domain or a bi-functional (e.g. bi-specific) hybrid antibody (e.g., Lanzavecchia et al., Eur. J. Immunol. 17, 105 (1987)).

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as (Gly$_4$Ser)n, where n is a positive integer equal to or greater than 1 (SEQ ID NO: 217). In one embodiment, the linker can be (Gly$_4$Ser)$_4$ (SEQ ID NO: 215) or (Gly$_4$Ser)$_3$ (SEQ ID NO: 216). Variation in the linker length may retain or enhance activity, giving rise to superior efficacy in activity studies.

In another aspect, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellular, however, a fragment of such antigen (peptide) is presented on the surface of the cancer cells by MHC.

In certain embodiments, the encoded antigen binding domain has a binding affinity KD of $10^{-4}$ M to $10^{-8}$ M.

In one embodiment, the encoded CAR molecule comprises an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In one embodiment, the antigen binding domain has a binding affinity that is at least five-fold, 10-fold, 20-fold, 30-fold, 50-fold, 100-fold or 1,000-fold less than a reference antibody, e.g., an antibody described herein. In one embodiment, the encoded antigen binding domain has a binding affinity at least 5-fold less than a reference antibody (e.g., an antibody from which the antigen binding domain is derived). In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan. In one aspect, the antigen binding domain of the CAR is a scFv antibody fragment that is humanized compared to the murine sequence of the scFv from which it is derived.

In one aspect, the antigen binding domain of a CAR of the disclosure (e.g., a scFv) is encoded by a nucleic acid molecule whose sequence has been codon optimized for expression in a mammalian cell. In one aspect, entire CAR construct of the disclosure is encoded by a nucleic acid molecule whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

Antigen Binding Domains (and the Targeted Antigens)

In one embodiment, an antigen binding domain against CD19 is an antigen binding portion, e.g., CDRs, of a CAR, antibody or antigen-binding fragment thereof described in, e.g., PCT publication WO2012/079000; PCT publication WO2014/153270; Kochenderfer, J. N. et al., J. Immunother. 32 (7), 689-702 (2009); Kochenderfer, J. N., et al., Blood, 116 (20), 4099-4102 (2010); PCT publication WO2014/031687; Bejcek, Cancer Research, 55, 2346-2351, 1995; or U.S. Pat. No. 7,446,190.

In one embodiment, an antigen binding domain against mesothelin is an antigen binding portion, e.g., CDRs, of an antibody, antigen-binding fragment or CAR described in, e.g., PCT publication WO2015/090230. In one embodiment, an antigen binding domain against mesothelin is an antigen binding portion, e.g., CDRs, of an antibody, antigen-binding fragment, or CAR described in, e.g., PCT publication WO1997/025068, WO1999/028471, WO2005/014652, WO2006/099141, WO2009/045957, WO2009/068204, WO2013/142034, WO2013/040557, or WO2013/063419. In one embodiment, an antigen binding domain against mesothelin is an antigen binding portion, e.g., CDRs, of an antibody, antigen-binding fragment, or CAR described in WO/2015/090230.

In one embodiment, an antigen binding domain against CD123 is an antigen binding portion, e.g., CDRs, of an antibody, antigen-binding fragment or CAR described in, e.g., PCT publication WO2014/130635. In one embodiment, an antigen binding domain against CD123 is an antigen binding portion, e.g., CDRs, of an antibody, antigen-binding fragment, or CAR described in, e.g., PCT publication WO2014/138805, WO2014/138819, WO2013/173820, WO2014/144622, WO2001/66139, WO2010/126066, WO2014/144622, or US2009/0252742. In one embodiment, an antigen binding domain against CD123 is an antigen binding portion, e.g., CDRs, of an antibody, antigen-binding fragment, or CAR described in WO/2016/028896.

In one embodiment, an antigen binding domain against EGFRvIII is an antigen binding portion, e.g., CDRs, of an antibody, antigen-binding fragment or CAR described in, e.g., WO/2014/130657.

In one embodiment, an antigen binding domain against CD22 is an antigen binding portion, e.g., CDRs, of an antibody described in, e.g., Haso et al., Blood, 121(7): 1165-1174 (2013); Wayne et al., Clin Cancer Res 16(6): 1894-1903 (2010); Kato et al., Leuk Res 37(1):83-88 (2013); Creative BioMart (creativebiomart.net): MOM-18047-S(P).

In one embodiment, an antigen binding domain against CS-1 is an antigen binding portion, e.g., CDRs, of Elotuzumab (BMS), see e.g., Tai et al., 2008, Blood 112(4): 1329-37; Tai et al., 2007, Blood. 110(5):1656-63.

In one embodiment, an antigen binding domain against CLL-1 is an antigen binding portion, e.g., CDRs, of an antibody available from R&D, ebiosciences, Abcam, for example, PE-CLL1-hu Cat #353604 (BioLegend); and PE-CLL1 (CLEC12A) Cat #562566 (BD). In one embodiment, an antigen binding domain against CLL-1 is an antigen binding portion, e.g., CDRs, of an antibody, antigen-binding fragment, or CAR described in WO/2016/014535.

In one embodiment, an antigen binding domain against CD33 is an antigen binding portion, e.g., CDRs, of an antibody described in, e.g., Bross et al., Clin Cancer Res 7(6):1490-1496 (2001) (Gemtuzumab Ozogamicin, hP67.6), Caron et al., Cancer Res 52(24):6761-6767 (1992) (Lintuzumab, HuM195), Lapusan et al., Invest New Drugs 30(3):1121-1131 (2012) (AVE9633), Aigner et al., Leukemia 27(5): 1107-1115 (2013) (AMG330, CD33 BiTE), Dutour et al., Adv hematol 2012:683065 (2012), and Pizzitola et al., Leukemia doi:10.1038/Lue.2014.62 (2014). In one embodiment, an antigen binding domain against CD33 is an antigen binding portion, e.g., CDRs, of an antibody, antigen-binding fragment, or CAR described in WO/2016/014576.

In one embodiment, an antigen binding domain against GD2 is an antigen binding portion, e.g., CDRs, of an antibody described in, e.g., Mujoo et al., Cancer Res. 47(4):1098-1104 (1987); Cheung et al., Cancer Res 45(6): 2642-2649 (1985), Cheung et al., J Clin Oncol 5(9):1430-1440 (1987), Cheung et al., J Clin Oncol 16(9):3053-3060 (1998), Handgretinger et al., Cancer Immunol Immunother 35(3):199-204 (1992). In some embodiments, an antigen binding domain against GD2 is an antigen binding portion of an antibody selected from mAb 14.18, 14G2a, ch14.18, hu14.18, 3F8, hu3F8, 3G6, 8B6, 60C3, 10B8, ME36.1, and 8H9, see e.g., WO2012033885, WO2013040371, WO2013192294, WO2013061273, WO2013123061, WO2013074916, and WO201385552. In some embodiments, an antigen binding domain against GD2 is an antigen binding portion of an antibody described in US Publication No.: 20100150910 or PCT Publication No.: WO 2011160119.

In one embodiment, an antigen binding domain against BCMA is an antigen binding portion, e.g., CDRs, of an antibody described in, e.g., WO2012163805, WO200112812, and WO2003062401. In one embodiment, an antigen binding domain against BCMA is an antigen binding portion, e.g., CDRs, of an antibody, antigen-binding fragment, or CAR described in WO/2016/014565.

In one embodiment, an antigen binding domain against Tn antigen is an antigen binding portion, e.g., CDRs, of an antibody described in, e.g., U.S. Pat. No. 8,440,798, Brooks et al., PNAS 107(22):10056-10061 (2010), and Stone et al., OncoImmunology 1(6):863-873(2012).

In one embodiment, an antigen binding domain against PSMA is an antigen binding portion, e.g., CDRs, of an antibody described in, e.g., Parker et al., Protein Expr Purif 89(2):136-145 (2013), US 20110268656 (J591 ScFv); Frigerio et al, European J Cancer 49(9):2223-2232 (2013) (scFvD2B); WO 2006125481 (mAbs 3/A12, 3/E7 and 3/F11) and single chain antibody fragments (scFv A5 and D7).

In one embodiment, an antigen binding domain against ROR1 is an antigen binding portion, e.g., CDRs, of an antibody described in, e.g., Hudecek et al., Clin Cancer Res 19(12):3153-3164 (2013); WO 2011159847; and US20130101607.

In one embodiment, an antigen binding domain against FLT3 is an antigen binding portion, e.g., CDRs, of an antibody described in, e.g., WO2011076922, U.S. Pat. No. 5,777,084, EP0754230, US20090297529, and several commercial catalog antibodies (R&D, ebiosciences, Abcam).

In one embodiment, an antigen binding domain against TAG72 is an antigen binding portion, e.g., CDRs, of an antibody described in, e.g., Hombach et al., Gastroenterology 113(4):1163-1170 (1997); and Abcam ab691.

In one embodiment, an antigen binding domain against FAP is an antigen binding portion, e.g., CDRs, of an antibody described in, e.g., Ostermann et al., Clinical Cancer Research 14:4584-4592 (2008) (FAPS), US Pat. Publication No. 2009/0304718; sibrotuzumab (see e.g., Hofheinz et al., Oncology Research and Treatment 26(1), 2003); and Tran et al., J Exp Med 210(6):1125-1135 (2013).

In one embodiment, an antigen binding domain against CD38 is an antigen binding portion, e.g., CDRs, of daratumumab (see, e.g., Groen et al., Blood 116(21):1261-1262 (2010); MOR202 (see, e.g., U.S. Pat. No. 8,263,746); or antibodies described in U.S. Pat. No. 8,362,211.

In one embodiment, an antigen binding domain against CD44v6 is an antigen binding portion, e.g., CDRs, of an antibody described in, e.g., Casucci et al., Blood 122(20): 3461-3472 (2013).

In one embodiment, an antigen binding domain against CEA is an antigen binding portion, e.g., CDRs, of an antibody described in, e.g., Chmielewski et al., Gastoenterology 143(4):1095-1107 (2012).

In one embodiment, an antigen binding domain against EPCAM is an antigen binding portion, e.g., CDRS, of an antibody selected from MT110, EpCAM-CD3 bispecific Ab (see, e.g., clinicaltrials.gov/ct2/show/NCT00635596); Edrecolomab; 3622W94; ING-1; and adecatumumab (MT201).

In one embodiment, an antigen binding domain against PRSS21 is an antigen binding portion, e.g., CDRs, of an antibody described in U.S. Pat. No. 8,080,650.

In one embodiment, an antigen binding domain against B7H3 is an antigen binding portion, e.g., CDRs, of an antibody MGA271 (Macrogenics).

In one embodiment, an antigen binding domain against KIT is an antigen binding portion, e.g., CDRs, of an antibody described in, e.g., U.S. Pat. No. 7,915,391, US20120288506, and several commercial catalog antibodies.

In one embodiment, an antigen binding domain against IL-13Ra2 is an antigen binding portion, e.g., CDRs, of an antibody described in, e.g., WO2008/146911, WO2004087758, several commercial catalog antibodies, and WO2004087758.

In one embodiment, an antigen binding domain against CD30 is an antigen binding portion, e.g., CDRs, of an antibody described in, e.g., U.S. Pat. No. 7,090,843 B1, and EP0805871.

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761; WO2005035577; and U.S. Pat. No. 6,437,098.

In one embodiment, an antigen binding domain against CD171 is an antigen binding portion, e.g., CDRs, of an antibody described in, e.g., Hong et al., J Immunother 37(2):93-104 (2014).

In one embodiment, an antigen binding domain against IL-11Ra is an antigen binding portion, e.g., CDRs, of an antibody available from Abcam (cat #ab55262) or Novus Biologicals (cat #EPR5446). In another embodiment, an antigen binding domain again IL-11Ra is a peptide, see, e.g., Huang et al., Cancer Res 72(1):271-281 (2012).

In one embodiment, an antigen binding domain against PSCA is an antigen binding portion, e.g., CDRs, of an antibody described in, e.g., Morgenroth et al., Prostate 67(10):1121-1131 (2007) (scFv 7F5); Nejatollahi et al., J of Oncology 2013(2013), article ID 839831 (scFv C5-II); and US Pat Publication No. 20090311181.

In one embodiment, an antigen binding domain against VEGFR2 is an antigen binding portion, e.g., CDRs, of an antibody described in, e.g., Chinnasamy et al., J Clin Invest 120(11):3953-3968 (2010).

In one embodiment, an antigen binding domain against LewisY is an antigen binding portion, e.g., CDRs, of an antibody described in, e.g., Kelly et al., Cancer Biother Radiopharm 23(4):411-423 (2008) (hu3S193 Ab (scFvs)); Dolezal et al., Protein Engineering 16(1):47-56 (2003) (NC10 scFv).

In one embodiment, an antigen binding domain against CD24 is an antigen binding portion, e.g., CDRs, of an antibody described in, e.g., Maliar et al., Gastroenterology 143(5):1375-1384 (2012).

In one embodiment, an antigen binding domain against PDGFR-beta is an antigen binding portion, e.g., CDRs, of an antibody Abcam ab32570.

In one embodiment, an antigen binding domain against SSEA-4 is an antigen binding portion, e.g., CDRs, of antibody MC813 (Cell Signalling), or other commercially available antibodies.

In one embodiment, an antigen binding domain against CD20 is an antigen binding portion, e.g., CDRs, of the antibody Rituximab, Ofatumumab, Ocrelizumab, Veltuzumab, or GA101.

In one embodiment, an antigen binding domain against Folate receptor alpha is an antigen binding portion, e.g., CDRs, of the antibody IMGN853, or an antibody described in US20120009181; U.S. Pat. No. 4,851,332, LK26: U.S. Pat. No. 5,952,484.

In one embodiment, an antigen binding domain against ERBB2 (Her2/neu) is an antigen binding portion, e.g., CDRs, of the antibody trastuzumab, or pertuzumab.

In one embodiment, an antigen binding domain against MUC1 is an antigen binding portion, e.g., CDRs, of the antibody SAR566658.

In one embodiment, the antigen binding domain against EGFR is antigen binding portion, e.g., CDRs, of the antibody cetuximab, panitumumab, zalutumumab, nimotuzumab, or matuzumab.

In one embodiment, an antigen binding domain against NCAM is an antigen binding portion, e.g., CDRs, of the antibody clone 2-2B: MAB5324 (EMD Millipore).

In one embodiment, an antigen binding domain against Ephrin B2 is an antigen binding portion, e.g., CDRs, of an antibody described in, e.g., Abengozar et al., Blood 119(19): 4565-4576 (2012).

In one embodiment, an antigen binding domain against IGF-I receptor is an antigen binding portion, e.g., CDRs, of an antibody described in, e.g., U.S. Pat. No. 8,344,112 B2; EP2322550 A1; WO 2006/138315, or PCT/US2006/022995.

In one embodiment, an antigen binding domain against CAIX is an antigen binding portion, e.g., CDRs, of the antibody clone 303123 (R&D Systems).

In one embodiment, an antigen binding domain against LMP2 is an antigen binding portion, e.g., CDRs, of an antibody described in, e.g., U.S. Pat. No. 7,410,640, or US20050129701.

In one embodiment, an antigen binding domain against gp100 is an antigen binding portion, e.g., CDRs, of the antibody HMB45, NKIbetaB, or an antibody described in WO2013165940, or US20130295007

In one embodiment, an antigen binding domain against tyrosinase is an antigen binding portion, e.g., CDRs, of an antibody described in, e.g., U.S. Pat. No. 5,843,674; or US19950504048.

In one embodiment, an antigen binding domain against EphA2 is an antigen binding portion, e.g., CDRs, of an antibody described in, e.g., Yu et al., Mol Ther 22(1):102-111 (2014).

In one embodiment, an antigen binding domain against GD3 is an antigen binding portion, e.g., CDRs, of an antibody described in, e.g., U.S. Pat. Nos. 7,253,263; 8,207, 308; US 20120276046; EP1013761 A3; 20120276046; WO2005035577; or U.S. Pat. No. 6,437,098.

In one embodiment, an antigen binding domain against fucosyl GM1 is an antigen binding portion, e.g., CDRs, of an antibody described in, e.g., US20100297138; or WO2007/067992.

In one embodiment, an antigen binding domain against sLe is an antigen binding portion, e.g., CDRs, of the antibody G193 (for lewis Y), see Scott A M et al, Cancer Res 60: 3254-61 (2000), also as described in Neeson et al, J Immunol May 2013 190 (Meeting Abstract Supplement) 177.10.

In one embodiment, an antigen binding domain against GM3 is an antigen binding portion, e.g., CDRs, of the antibody CA 2523449 (mAb 14F7).

In one embodiment, an antigen binding domain against HMWMAA is an antigen binding portion, e.g., CDRs, of an antibody described in, e.g., Kmiecik et al., Oncoimmunology 3(1):e27185 (2014) (PMID: 24575382) (mAb9.2.27); U.S. Pat. No. 6,528,481; WO2010033866; or US 20140004124.

In one embodiment, an antigen binding domain against o-acetyl-GD2 is an antigen binding portion, e.g., CDRs, of the antibody 8B6.

In one embodiment, an antigen binding domain against TEM 1/CD248 is an antigen binding portion, e.g., CDRs, of an antibody described in, e.g., Marty et al., Cancer Lett 235(2):298-308 (2006); Zhao et al., J Immunol Methods 363(2):221-232 (2011).

In one embodiment, an antigen binding domain against CLDN6 is an antigen binding portion, e.g., CDRs, of the antibody IMAB027 (Ganymed Pharmaceuticals), see e.g., clinicaltrial.gov/show/NCT02054351.

In one embodiment, an antigen binding domain against TSHR is an antigen binding portion, e.g., CDRs, of an antibody described in, e.g., U.S. Pat. Nos. 8,603,466; 8,501, 415; or U.S. Pat. No. 8,309,693.

In one embodiment, an antigen binding domain against GPRC5D is an antigen binding portion, e.g., CDRs, of the antibody FAB6300A (R&D Systems); or LS-A4180 (Lifespan Biosciences).

In one embodiment, an antigen binding domain against CD97 is an antigen binding portion, e.g., CDRs, of an antibody described in, e.g., U.S. Pat. No. 6,846,911; de Groot et al., J Immunol 183(6):4127-4134 (2009);

or an antibody from R&D:MAB3734.

In one embodiment, an antigen binding domain against ALK is an antigen binding portion, e.g., CDRs, of an antibody described in, e.g., Mino-Kenudson et al., Clin Cancer Res 16(5):1561-1571 (2010).

In one embodiment, an antigen binding domain against polysialic acid is an antigen binding portion, e.g., CDRs, of an antibody described in, e.g., Nagae et al., J Biol Chem 288(47):33784-33796 (2013).

In one embodiment, an antigen binding domain against PLAC 1 is an antigen binding portion, e.g., CDRs, of an antibody described in, e.g., Ghods et al., Biotechnol Appl Biochem 2013 doi: 10.1002/bab.1177.

In one embodiment, an antigen binding domain against GloboH is an antigen binding portion of the antibody VK9; or an antibody described in, e.g., Kudryashov V et al, Glycoconj J. 15(3):243-9 (1998), Lou et al., Proc Natl Acad Sci USA 111(7):2482-2487 (2014); MBr1: Bremer E-G et al. J Biol Chem 259:14773-14777 (1984).

In one embodiment, an antigen binding domain against NY-BR-1 is an antigen binding portion, e.g., CDRs of an antibody described in, e.g., Jager et al., Appl Immunohistochem Mol Morphol 15(1):77-83 (2007).

In one embodiment, an antigen binding domain against WT-1 is an antigen binding portion, e.g., CDRs, of an antibody described in, e.g., Dao et al., Sci Transl Med 5(176):176ra33 (2013); or WO2012/135854.

In one embodiment, an antigen binding domain against MAGE-A1 is an antigen binding portion, e.g., CDRs, of an antibody described in, e.g., Willemsen et al., J Immunol 174(12):7853-7858 (2005) (TCR-like scFv).

In one embodiment, an antigen binding domain against sperm protein 17 is an antigen binding portion, e.g., CDRs, of an antibody described in, e.g., Song et al., Target Oncol 2013 Aug. 14 (PMID: 23943313); Song et al., Med Oncol 29(4):2923-2931 (2012).

In one embodiment, an antigen binding domain against Tie 2 is an antigen binding portion, e.g., CDRs, of the antibody AB33 (Cell Signalling Technology).

In one embodiment, an antigen binding domain against MAD-CT-2 is an antigen binding portion, e.g., CDRs, of an antibody described in, e.g., PMID: 2450952; U.S. Pat. No. 7,635,753.

In one embodiment, an antigen binding domain against Fos-related antigen 1 is an antigen binding portion, e.g., CDRs, of the antibody 12F9 (Novus Biologicals).

In one embodiment, an antigen binding domain against MelanA/MART1 is an antigen binding portion, e.g., CDRs, of an antibody described in, EP2514766 A2; or U.S. Pat. No. 7,749,719.

In one embodiment, an antigen binding domain against sarcoma translocation breakpoints is an antigen binding portion, e.g., CDRs, of an antibody described in, e.g., Luo et al, EMBO Mol. Med. 4(6):453-461 (2012).

In one embodiment, an antigen binding domain against TRP-2 is an antigen binding portion, e.g., CDRs, of an antibody described in, e.g., Wang et al, J Exp Med. 184(6): 2207-16 (1996).

In one embodiment, an antigen binding domain against CYP1B1 is an antigen binding portion, e.g., CDRs, of an antibody described in, e.g., Maecker et al, Blood 102 (9): 3287-3294 (2003).

In one embodiment, an antigen binding domain against RAGE-1 is an antigen binding portion, e.g., CDRs, of the antibody MAB5328 (EMD Millipore).

In one embodiment, an antigen binding domain against human telomerase reverse transcriptase is an antigen binding portion, e.g., CDRs, of the antibody cat no: LS-B95-100 (Lifespan Biosciences) In one embodiment, an antigen binding domain against intestinal carboxyl esterase is an antigen binding portion, e.g., CDRs, of the antibody 4F12: cat no: LS-B6190-50 (Lifespan Biosciences).

In one embodiment, an antigen binding domain against mut hsp70-2 is an antigen binding portion, e.g., CDRs, of the antibody Lifespan Biosciences: monoclonal: cat no: LS-C133261-100 (Lifespan Biosciences).

In one embodiment, an antigen binding domain against CD79a is an antigen binding portion, e.g., CDRs, of the antibody Anti-CD79a antibody [HM47/A9] (ab3121), available from Abcam; antibody CD79A Antibody #3351 available from Cell Signalling Technology; or antibody HPA017748—Anti-CD79A antibody produced in rabbit, available from Sigma Aldrich.

In one embodiment, an antigen binding domain against CD79b is an antigen binding portion, e.g., CDRs, of the antibody polatuzumab vedotin, anti-CD79b described in Dornan et al., "Therapeutic potential of an anti-CD79b antibody-drug conjugate, anti-CD79b-vc-MMAE, for the treatment of non-Hodgkin lymphoma" Blood. 2009 Sep. 24; 114(13):2721-9. doi: 10.1182/blood-2009-02-205500. Epub 2009 Jul. 24, or the bispecific antibody Anti-CD79b/CD3 described in "4507 Pre-Clinical Characterization of T Cell-Dependent Bispecific Antibody Anti-CD79b/CD3 As a Potential Therapy for B Cell Malignancies" Abstracts of 56$^{th}$ ASH Annual Meeting and Exposition, San Francisco, Calif. Dec. 6-9, 2014.

In one embodiment, an antigen binding domain against CD72 is an antigen binding portion, e.g., CDRs, of the antibody J3-109 described in Myers, and Uckun, "An anti-CD72 immunotoxin against therapy-refractory B-lineage acute lymphoblastic leukemia." Leuk Lymphoma. 1995 June; 18(1-2):119-22, or anti-CD72 (10D6.8.1, mIgG1) described in Polson et al., "Antibody-Drug Conjugates for the Treatment of Non-Hodgkin's Lymphoma: Target and Linker-Drug Selection" Cancer Res Mar. 15, 2009 69; 2358.

In one embodiment, an antigen binding domain against LAIR1 is an antigen binding portion, e.g., CDRs, of the antibody ANT-301 LAIR1 antibody, available from ProSpec; or anti-human CD305 (LAIR1) Antibody, available from BioLegend.

In one embodiment, an antigen binding domain against FCAR is an antigen binding portion, e.g., CDRs, of the antibody CD89/FCAR Antibody (Catalog #10414-H08H), available from Sino Biological Inc.

In one embodiment, an antigen binding domain against LILRA2 is an antigen binding portion, e.g., CDRs, of the antibody LILRA2 monoclonal antibody (M17), clone 3C$_7$, available from Abnova, or Mouse Anti-LILRA2 antibody, Monoclonal (2D7), available from Lifespan Biosciences.

In one embodiment, an antigen binding domain against CD300LF is an antigen binding portion, e.g., CDRs, of the antibody Mouse Anti-CMRF35-like molecule 1 antibody, Monoclonal[UP-D2], available from BioLegend, or Rat Anti-CMRF35-like molecule 1 antibody, Monoclonal [234903], available from R&D Systems.

In one embodiment, an antigen binding domain against CLEC12A is an antigen binding portion, e.g., CDRs, of the antibody Bispecific T cell Engager (BiTE) scFv-antibody and ADC described in Noordhuis et al., "Targeting of CLEC12A In Acute Myeloid Leukemia by Antibody-Drug-Conjugates and Bispecific CLL-1xCD3 BiTE Antibody" 53$^{rd}$ ASH Annual Meeting and Exposition, Dec. 10-13, 2011, and MCLA-117 (Merus).

In one embodiment, an antigen binding domain against BST2 (also called CD317) is an antigen binding portion, e.g., CDRs, of the antibody Mouse Anti-CD317 antibody, Monoclonal[3H4], available from Antibodies-Online or Mouse Anti-CD317 antibody, Monoclonal[696739], available from R&D Systems.

In one embodiment, an antigen binding domain against EMR2 (also called CD312) is an antigen binding portion, e.g., CDRs, of the antibody Mouse Anti-CD312 antibody, Monoclonal[LS-B8033]available from Lifespan Biosciences, or Mouse Anti-CD312 antibody, Monoclonal [494025] available from R&D Systems.

In one embodiment, an antigen binding domain against LY75 is an antigen binding portion, e.g., CDRs, of the antibody Mouse Anti-Lymphocyte antigen 75 antibody, Monoclonal[HD30] available from EMD Millipore or Mouse Anti-Lymphocyte antigen 75 antibody, Monoclonal [A15797] available from Life Technologies.

In one embodiment, an antigen binding domain against GPC3 is an antigen binding portion, e.g., CDRs, of the antibody hGC33 described in Nakano K, Ishiguro T, Konishi H, et al. Generation of a humanized anti-glypican 3 antibody by CDR grafting and stability optimization. Anticancer Drugs. 2010 November; 21(10):907-916, or MDX-1414, HN3, or YP7, all three of which are described in Feng et al., "Glypican-3 antibodies: a new therapeutic target for liver cancer." FEBS Lett. 2014 Jan. 21; 588(2):377-82.

In one embodiment, an antigen binding domain against FCRL5 is an antigen binding portion, e.g., CDRs, of the anti-FcRL5 antibody described in Elkins et al., "FcRL5 as a target of antibody-drug conjugates for the treatment of multiple myeloma" Mol Cancer Ther. 2012 October; 11(10): 2222-32. In one embodiment, an antigen binding domain against FCRL5 is an antigen binding portion, e.g., CDRs, of the anti-FcRL5 antibody described in, for example, WO2001/038490, WO/2005/117986, WO2006/039238, WO2006/076691, WO2010/114940, WO2010/120561, or WO2014/210064.

In one embodiment, an antigen binding domain against IGLL1 is an antigen binding portion, e.g., CDRs, of the antibody Mouse Anti-Immunoglobulin lambda-like polypeptide 1 antibody, Monoclonal[AT1G4] available from Lifespan Biosciences, Mouse Anti-Immunoglobulin lambda-like polypeptide 1 antibody, Monoclonal[HSL11] available from BioLegend.

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed above.

In another aspect, the antigen binding domain comprises a humanized antibody or an antibody fragment. In some aspects, a non-human antibody is humanized, where specific sequences or regions of the antibody are modified to increase similarity to an antibody naturally produced in a human or fragment thereof. In one aspect, the antigen binding domain is humanized.

In an embodiment, the antigen-binding domain of a CAR, e.g., a CAR expressed by a cell of the disclosure, binds to CD19. CD19 is found on B cells throughout differentiation of the lineage from the pro/pre-B cell stage through the terminally differentiated plasma cell stage. In an embodiment, the antigen binding domain is a murine scFv domain that binds to human CD19, e.g., the antigen binding domain of CTL019 (e.g., SEQ ID NO: 218). In an embodiment, the antigen binding domain is a humanized antibody or antibody fragment, e.g., scFv domain, derived from the murine CTL019 scFv. In an embodiment, the antigen binding domain is a human antibody or antibody fragment that binds to human CD19. Exemplary scFv domains (and their sequences, e.g., CDRs, VL and VH sequences) that bind to CD19 are provided in Table 12a. The scFv domain sequences provided in Table 12a include a light chain variable region (VL) and a heavy chain variable region (VH). The VL and VH are attached by a linker comprising the sequence GGGGSGGGGSGGGGS (SEQ ID NO: 216), e.g., in the following orientation: VL-linker-VH.

TABLE 12a

Antigen Binding domains that bind CD19

| Antigen | Name | Amino Acid Sequence | SEQ ID NO: |
|---|---|---|---|
| CD19 | muCTL019 | DIQMTQTTSSLSASLGDRVTISCRASQDISKYLNWYQQKPDGTV KLLIYHTSRLHSGVPSRFSGSGSGTDYSLTISNLEQEDIATYFCQQ GNTLPYTFGGGTKLEITGGGGSGGGGSGGGGSEVKLQESGPGL VAPSQSLSVTCTVSGVSLPDYGVSWIRQPPRKGLEWLGVIWGSE TTYYNSALKSRLTIIKDNSKSQVFLKMNSLQTDDTAIYYCAKHY YYGGSYAMDYWGQGTSVTVSS | 218 |
| CD19 | huscFv1 | EIVMTQSPATLSLSPGERATLSCRASQDISKYLNWYQQKPGQAP RLLIYHTSRLHSGIPARFSGSGSGTDYTLTISSLQPEDFAVYFCQQ GNTLPYTFGQGTKLEIKGGGGSGGGGSGGGGSQVQLQESGPGL VKPSETLSLTCTVSGVSLPDYGVSWIRQPPGKGLEWIGVIWGSE TTYYSSSLKSRVTISKDNSKNQVSLKLSSVTAADTAVYYCAKH YYYGGSYAMDYWGQGTLVTVSS | 219 |
| CD19 | huscFv2 | EIVMTQSPATLSLSPGERATLSCRASQDISKYLNWYQQKPGQAP RLLIYHTSRLHSGIPARFSGSGSGTDYTLTISSLQPEDFAVYFCQQ GNTLPYTFGQGTKLEIKGGGGSGGGGSGGGGSQVQLQESGPGL VKPSETLSLTCTVSGVSLPDYGVSWIRQPPGKGLEWIGVIWGSE TTYYQSSLKSRVTISKDNSKNQVSLKLSSVTAADTAVYYCAKH YYYGGSYAMDYWGQGTLVTVSS | 220 |
| CD19 | huscFv3 | QVQLQESGPGLVKPSETLSLTCTVSGVSLPDYGVSWIRQPPGKG LEWIGVIWGSETTYYSSSLKSRVTISKDNSKNQVSLKLSSVTAA DTAVYYCAKHYYYGGSYAMDYWGQGTLVTVSSGGGGSGGGG SGGGGSEIVMTQSPATLSLSPGERATLSCRASQDISKYLNWYQQ KPGQAPRLLIYHTSRLHSGIPARFSGSGSGTDYTLTISSLQPEDFA VYFCQQGNTLPYTFGQGTKLEIK | 221 |
| CD19 | huscFv4 | QVQLQESGPGLVKPSETLSLTCTVSGVSLPDYGVSWIRQPPGKG LEWIGVIWGSETTYYQSSLKSRVTISKDNSKNQVSLKLSSVTAA DTAVYYCAKHYYYGGSYAMDYWGQGTLVTVSSGGGGSGGGG SGGGGSEIVMTQSPATLSLSPGERATLSCRASQDISKYLNWYQQ KPGQAPRLLIYHTSRLHSGIPARFSGSGSGTDYTLTISSLQPEDFA VYFCQQGNTLPYTFGQGTKLEIK | 222 |
| CD19 | huscFv5 | EIVMTQSPATLSLSPGERATLSCRASQDISKYLNWYQQKPGQAP RLLIYHTSRLHSGIPARFSGSGSGTDYTLTISSLQPEDFAVYFCQQ | 223 |

TABLE 12a-continued

Antigen Binding domains that bind CD19

| Antigen | Name | Amino Acid Sequence | SEQ ID NO: |
|---|---|---|---|
| | | GNTLPYTFGQGTKLEIKGGGGSGGGGSGGGGSGGGGSQVQLQE SGPGLVKPSETLSLTCTVSGVSLPDYGVSWIRQPPGKGLEWIGVI WGSETTYYSSSLKSRVTISKDNSKNQVSLKLSSVTAADTAVYYC AKHYYYGGSYAMDYWGQGTLVTVSS | |
| CD19 | huscFv6 | EIVMTQSPATLSLSPGERATLSCRASQDISKYLNWYQQKPGQAP RLLIYHTSRLHSGIPARFSGSGSGTDYTLTISSLQPEDFAVYFCQQ GNTLPYTFGQGTKLEIKGGGGSGGGGSGGGGSGGGGSQVQLQE SGPGLVKPSETLSLTCTVSGVSLPDYGVSWIRQPPGKGLEWIGVI WGSETTYYQSSLKSRVTISKDNSKNQVSLKLSSVTAADTAVYY CAKHYYYGGSYAMDYWGQGTLVTVSS | 224 |
| CD19 | huscFv7 | QVQLQESGPGLVKPSETLSLTCTVSGVSLPDYGVSWIRQPPGKG LEWIGVIWGSETTYYSSSLKSRVTISKDNSKNQVSLKLSSVTAA DTAVYYCAKHYYYGGSYAMDYWGQGTLVTVSSGGGGSGGGG SGGGGSGGGGSEIVMTQSPATLSLSPGERATLSCRASQDISKYL NWYQQKPGQAPRLLIYHTSRLHSGIPARFSGSGSGTDYTLTISSL QPEDFAVYFCQQGNTLPYTFGQGTKLEIK | 225 |
| CD19 | huscFv8 | QVQLQESGPGLVKPSETLSLTCTVSGVSLPDYGVSWIRQPPGKG LEWIGVIWGSETTYYQSSLKSRVTISKDNSKNQVSLKLSSVTAA DTAVYYCAKHYYYGGSYAMDYWGQGTLVTVSSGGGGSGGGG SGGGGSGGGGSEIVMTQSPATLSLSPGERATLSCRASQDISKYL NWYQQKPGQAPRLLIYHTSRLHSGIPARFSGSGSGTDYTLTISSL QPEDFAVYFCQQGNTLPYTFGQGTKLEIK | 226 |
| CD19 | huscFv9 | EIVMTQSPATLSLSPGERATLSCRASQDISKYLNWYQQKPGQAP RLLIYHTSRLHSGIPARFSGSGSGTDYTLTISSLQPEDFAVYFCQQ GNTLPYTFGQGTKLEIKGGGGSGGGGSGGGGSGGGGSQVQLQE SGPGLVKPSETLSLTCTVSGVSLPDYGVSWIRQPPGKGLEWIGVI WGSETTYYNSSLKSRVTISKDNSKNQVSLKLSSVTAADTAVYY CAKHYYYGGSYAMDYWGQGTLVTVSS | 227 |
| CD19 | HuscFv10 | QVQLQESGPGLVKPSETLSLTCTVSGVSLPDYGVSWIRQPPGKG LEWIGVIWGSETTYYNSSLKSRVTISKDNSKNQVSLKLSSVTAA DTAVYYCAKHYYYGGSYAMDYWGQGTLVTVSSGGGGSGGGG SGGGGSGGGGSEIVMTQSPATLSLSPGERATLSCRASQDISKYL NWYQQKPGQAPRLLIYHTSRLHSGIPARFSGSGSGTDYTLTISSL QPEDFAVYFCQQGNTLPYTFGQGTKLEIK | 228 |
| CD19 | HuscFv11 | EIVMTQSPATLSLSPGERATLSCRASQDISKYLNWYQQKPGQAP RLLIYHTSRLHSGIPARFSGSGSGTDYTLTISSLQPEDFAVYFCQQ GNTLPYTFGQGTKLEIKGGGGSGGGGSGGGGSQVQLQESGPGL VKPSETLSLTCTVSGVSLPDYGVSWIRQPPGKGLEWIGVIWGSE TTYYNSSLKSRVTISKDNSKNQVSLKLSSVTAADTAVYYCAKH YYYGGSYAMDYWGQGTLVTVSS | 229 |
| CD19 | HuscFv12 | QVQLQESGPGLVKPSETLSLTCTVSGVSLPDYGVSWIRQPPGKG LEWIGVIWGSETTYYNSSLKSRVTISKDNSKNQVSLKLSSVTAA DTAVYYCAKHYYYGGSYAMDYWGQGTLVTVSSGGGGSGGGG SGGGGSEIVMTQSPATLSLSPGERATLSCRASQDISKYLNWYQQ KPGQAPRLLIYHTSRLHSGIPARFSGSGSGTDYTLTISSLQPEDFA VYFCQQGNTLPYTFGQGTKLEIK | 230 |

The sequences of the CDR sequences of the scFv domains of the CD19 antigen binding domains provided in Table 12a are shown in Table 12b for the heavy chain variable domains and in Table 12c for the light chain variable domains. "ID" stands for the respective SEQ ID NO for each CDR.

TABLE 12b

Heavy Chain Variable Domain CDRs

| Description | FW | HCDR1 | ID | HCDR2 | ID | HCDR3 | ID |
|---|---|---|---|---|---|---|---|
| murine_CART19 | | GVSLPDYGVS | 306 | VIWGSETTYYNSALKS | 307 | HYYYGGSYAMDY | 231 |
| humanized_CART19 | a VH4 | GVSLPDYGVS | 306 | VIWGSETTYYSSSLKS | 308 | HYYYGGSYAMDY | 231 |

TABLE 12b-continued

| Heavy Chain Variable Domain CDRs | | | | | | | |
|---|---|---|---|---|---|---|---|
| Description | FW | HCDR1 | ID | HCDR2 | ID | HCDR3 | ID |
| humanized_CART19 b | VH4 | GVSLPDYGVS | 306 | VIWGSETTYYQSSLKS | 309 | HYYYGGSYAMDY | 231 |
| humanized_CART19 c | VH4 | GVSLPDYGVS | 306 | VIWGSETTYYNSSLKS | 310 | HYYYGGSYAMDY | 231 |

TABLE 12c

| Light Chain Variable Domain CDRs | | | | | | | |
|---|---|---|---|---|---|---|---|
| Description | FW | LCDR1 | ID | LCDR2 | ID | LCDR3 | ID |
| murine_CART19 | | RASQDISKYLN | 311 | HTSRLHS | 312 | QQGNTLPYT | 232 |
| humanized_CART19 a | VK3 | RASQDISKYLN | 311 | HTSRLHS | 312 | QQGNTLPYT | 232 |
| humanized_CART19 b | VK3 | RASQDISKYLN | 311 | HTSRLHS | 312 | QQGNTLPYT | 232 |
| humanized_CART19 c | VK3 | RASQDISKYLN | 311 | HTSRLHS | 312 | QQGNTLPYT | 232 |

In an embodiment, the antigen binding domain comprises an anti-CD19 antibody, or fragment thereof, e.g., a scFv. For example, the antigen binding domain comprises a variable heavy chain and a variable light chain listed in Table 12d. The linker sequence joining the variable heavy and variable light chains can be any of the linker sequences described herein, or alternatively, can be GSTSGSGKPGSGEGSTKG (SEQ ID NO: 233). The light chain variable region and heavy chain variable region of a scFv can be, e.g., in any of the following orientations: light chain variable region-linker-heavy chain variable region or heavy chain variable region-linker-light chain variable region.

TABLE 12d

| Additional Anti-CD19 antibody binding domains | | |
|---|---|---|
| Ab Name | VH Sequence | VL Sequence |
| SJ25-C1 | QVQLLESGAELVRPGSSVKISCKASGYA FSSYWMNWVKQRPGQGLEWIGQIYPGD GDTNYNGKFKGQATLTADKSSSTAYMQ LSGLTSEDSAVYSCARKTISSVVDFYFD YWGQGTTVT (SEQ ID NO: 234) | ELVLTQSPKFMSTSVGDRVSVTCKAS QNVGTNVAWYQQKPGQSPKPLIYSA TYRNSGVPDRFTGSGSGTDFTLTITNV QSKDLADYFYFCQYNRYPYTSGGGT KLEIKRRS (SEQ ID NO: 235) |
| ScFv Sequence | | |
| SJ25-C1 scFv | QVQLLESGAELVRPGSSVKISCKASGYAFSSYWMNWVKQRPGQGLEWIGQIYPGD GDTNYNGKFKGQATLTADKSSSTAYMQLSGLTSEDSAVYSCARKTISSVVDFYFD YWGQGTTVTGSTSGSGKPGSGEGSTKGELVLTQSPKFMSTSVGDRVSVTCKASQN VGTNVAWYQQKPGQSPKPLIYSATYRNSGVPDRFTGSGSGTDFTLTITNVQSKDLA DYFYFCQYNRYPYTSGGGTKLEIKRRS (SEQ ID NO: 236) | |

In one embodiment, the CD19 binding domain comprises one or more (e.g., all three) light chain complementary determining region 1 (LC CDR1), light chain complementary determining region 2 (LC CDR2), and light chain complementary determining region 3 (LC CDR3) of a CD19 binding domain described herein, e.g., provided in Table 12a or 15, and/or one or more (e.g., all three) heavy chain complementary determining region 1 (HC CDR1), heavy chain complementary determining region 2 (HC CDR2), and heavy chain complementary determining region 3 (HC CDR3) of a CD19 binding domain described herein, e.g., provided in Table 12a or 16. In one embodiment, the CD19 binding domain comprises one, two, or all of LC CDR1, LC CDR2, and LC CDR3 of any amino acid sequences as provided in Table 12c, incorporated herein by reference; and one, two or all of HC CDR1, HC CDR2, and HC CDR3 of any amino acid sequences as provided in Table 12b.

Any known CD19 CAR, e.g., the CD19 antigen binding domain of any known CD19 CAR, in the art can be used in accordance with the instant disclosure to construct a CAR. For example, LG-740; CD19 CAR described in the U.S. Pat. Nos. 8,399,645; 7,446,190; Xu et al., Leuk Lymphoma. 2013 54(2):255-260(2012); Cruz et al., Blood 122(17): 2965-2973 (2013); Brentjens et al., Blood, 118(18):4817-4828 (2011); Kochenderfer et al., Blood 116(20):4099-102 (2010); Kochenderfer et al., Blood 122 (25):4129-39(2013);

and 16th Annu Meet Am Soc Gen Cell Ther (ASGCT) (May 15-18, Salt Lake City) 2013, Abst 10. In one embodiment, an antigen binding domain against CD19 is an antigen binding portion, e.g., CDRs, of a CAR, antibody or antigen-binding fragment thereof described in, e.g., PCT publication WO2012/079000; PCT publication WO2014/153270; Kochenderfer, J. N. et al., J. Immunother. 32 (7), 689-702 (2009); Kochenderfer, J. N., et al., Blood, 116 (20), 4099-4102 (2010); PCT publication WO2014/031687; Bejcek, Cancer Research, 55, 2346-2351, 1995; or U.S. Pat. No. 7,446,190.

In an embodiment, the antigen-binding domain of CAR, e.g., a CAR expressed by a cell of the disclosure, binds to BCMA. BCMA is found preferentially expressed in mature B lymphocytes. In an embodiment, the antigen binding domain is a murine scFv domain that binds to human BCMA. In an embodiment, the antigen binding domain is a humanized antibody or antibody fragment, e.g., scFv domain that binds human BCMA. In an embodiment, the antigen binding domain is a human antibody or antibody fragment that binds to human BCMA. In embodiments, exemplary BCMA CAR constructs are generated using the VH and VL sequences from PCT Publication WO2012/0163805 (the contents of which are hereby incorporated by reference in its entirety). In embodiments, additional exemplary BCMA CAR constructs are generated using the VH and VL sequences from PCT Publication WO2016/014565 (the contents of which are hereby incorporated by reference in its entirety). In embodiments, additional exemplary BCMA CAR constructs are generated using the VH and VL sequences from PCT Publication WO2014/122144 (the contents of which are hereby incorporated by reference in its entirety). In embodiments, additional exemplary BCMA CAR constructs are generated using the CAR molecules, and/or the VH and VL sequences from PCT Publication WO2016/014789 (the contents of which are hereby incorporated by reference in its entirety). In embodiments, additional exemplary BCMA CAR constructs are generated using the CAR molecules, and/or the VH and VL sequences from PCT Publication WO2014/089335 (the contents of which are hereby incorporated by reference in its entirety). In embodiments, additional exemplary BCMA CAR constructs are generated using the CAR molecules, and/or the VH and VL sequences from PCT Publication WO2014/140248 (the contents of which are hereby incorporated by reference in its entirety).

Any known BCMA CAR, e.g., the BMCA antigen binding domain of any known BCMA CAR, in the art can be used in accordance with the instant disclosure. For example, those described herein.

Exemplary CAR Molecules

In one aspect, a CAR, e.g., a CAR expressed by the cell of the disclosure, comprises a CAR molecule comprising an antigen binding domain that binds to a B cell antigen, e.g., as described herein, such as CD19 or BCMA.

In one embodiment, the CAR comprises a CAR molecule comprising a CD19 antigen binding domain (e.g., a murine, human or humanized antibody or antibody fragment that specifically binds to CD19), a transmembrane domain, and an intracellular signalling domain (e.g., an intracellular signalling domain comprising a costimulatory domain and/or a primary signalling domain).

Exemplary CAR molecules described herein are provided in Table 12e. The CAR molecules in Table 12e comprise a CD19 antigen binding domain, e.g., an amino acid sequence of any CD19 antigen binding domain provided in Table 12a.

TABLE 12e

Exemplary CD19 CAR molecules

| Antigen | Name | Amino Acid Sequence | SEQ ID NO: |
|---|---|---|---|
| CD19 | CTL019 | MALPVTALLLPLALLLHAARPDIQMTQTTSSLSASLGDRVTISCR ASQDISKYLNWYQQKPDGTVKLLIYHTSRLHSGVPSRFSGSGSG TDYSLTISNLEQEDIATYFCQQGNTLPYTFGGGTKLEITGGGGSG GGGSGGGGSEVKLQESGPGLVAPSQSLSVTCTVSGVSLPDYGVS WIRQPPRKGLEWLGVIWGSETTYYNSALKSRLTIIKDNSKSQVFL KMNSLQTDDTAIYYCAKHYYYGGSYAMDYWGQGTSVTVSSTT TPAPRPPTPAPTIASQPLSLRPEACRPAAGGAVHTRGLDFACDIYI WAPLAGTCGVLLLSLVITLYCKRGRKKLLYIFKQPFMRPVQTTQ EEDGCSCRFPEEEEGGCELRVKFSRSADAPAYKQGQNQLYNELN LGRREEYDVLDKRRGRDPEMGGKPRRKNPQEGLYNELQKDKM AEAYSEIGMKGERRRGKGHDGLYQGLSTATKDTYDALHMQAL PPR | 237 |
| CD19 | CAR1 | MALPVTALLLPLALLLHAARPEIVMTQSPATLSLSPGERATLSCR ASQDISKYLNWYQQKPGQAPRLLIYHTSRLHSGIPARFSGSGSGT DYTLTISSLQPEDFAVYFCQQGNTLPYTFGQGTKLEIKGGGGSGG GGSGGGGSQVQLQESGPGLVKPSETLSLTCTVSGVSLPDYGVSW IRQPPGKGLEWIGVIWGSETTYYSSSLKSRVTISKDNSKNQVSLK LSSVTAADTAVYYCAKHYYYGGSYAMDYWGQGTLVTVSSTTT PAPRPPTPAPTIASQPLSLRPEACRPAAGGAVHTRGLDFACDIYIW APLAGTCGVLLLSLVITLYCKRGRKKLLYIFKQPFMRPVQTTQEE DGCSCRFPEEEEGGCELRVKFSRSADAPAYKQGQNQLYNELNLG RREEYDVLDKRRGRDPEMGGKPRRKNPQEGLYNELQKDKMAE AYSEIGMKGERRRGKGHDGLYQGLSTATKDTYDALHMQALPPR | 238 |
| CD19 | CAR 2 | MALPVTALLLPLALLLHAARPEIVMTQSPATLSLSPGERATLSCR ASQDISKYLNWYQQKPGQAPRLLIYHTSRLHSGIPARFSGSGSGT DYTLTISSLQPEDFAVYFCQQGNTLPYTFGQGTKLEIKGGGGSGG GGSGGGGSQVQLQESGPGLVKPSETLSLTCTVSGVSLPDYGVSW IRQPPGKGLEWIGVIWGSETTYYQSSLKSRVTISKDNSKNQVSLK LSSVTAADTAVYYCAKHYYYGGSYAMDYWGQGTLVTVSSTTT PAPRPPTPAPTIASQPLSLRPEACRPAAGGAVHTRGLDFACDIYIW | 239 |

TABLE 12e-continued

Exemplary CD19 CAR molecules

| Antigen | Name | Amino Acid Sequence | SEQ ID NO: |
|---|---|---|---|
| | | APLAGTCGVLLLSLVITLYCKRGRKKLLYIFKQPFMRPVQTTQEE DGCSCRFPEEEEGGCELRVKFSRSADAPAYKQGQNQLYNELNLG RREEYDVLDKRRGRDPEMGGKPRRKNPQEGLYNELQKDKMAE AYSEIGMKGERRRGKGHDGLYQGLSTATKDTYDALHMQALPPR | |
| CD19 | CAR 3 | MALPVTALLLPLALLLHAARPQVQLQESGPGLVKPSETLSLTCT VSGVSLPDYGVSWIRQPPGKGLEWIGVIWGSETTYYSSSLKSRVT ISKDNSKNQVSLKLSSVTAADTAVYYCAKHYYYGGSYAMDYW GQGTLVTVSSGGGGSGGGGSGGGGSEIVMTQSPATLSLSPGERA TLSCRASQDISKYLNWYQQKPGQAPRLLIYHTSRLHSGIPARFSG SGSGTDYTLTISSLQPEDFAVYFCQQGNTLPYTFGQGTKLEIKTT TPAPRPPTPAPTIASQPLSRPEACRPAAGGAVHTRGLDFACDIYI WAPLAGTCGVLLLSLVITLYCKRGRKKLLYIFKQPFMRPVQTTQ EEDGCSCRFPEEEEGGCELRVKFSRSADAPAYKQGQNQLYNELN LGRREEYDVLDKRRGRDPEMGGKPRRKNPQEGLYNELQKDKM AEAYSEIGMKGERRRGKGHDGLYQGLSTATKDTYDALHMQAL PPR | 240 |
| CD19 | CAR 4 | MALPVTALLLPLALLLHAARPQVQLQESGPGLVKPSETLSLTCT VSGVSLPDYGVSWIRQPPGKGLEWIGVIWGSETTYYQSSLKSRV TISKDNSKNQVSLKLSSVTAADTAVYYCAKHYYYGGSYAMDY WGQGTLVTVSSGGGGSGGGGSGGGGSEIVMTQSPATLSLSPGER ATLSCRASQDISKYLNWYQQKPGQAPRLLIYHTSRLHSGIPARFS GSGSGTDYTLTISSLQPEDFAVYFCQQGNTLPYTFGQGTKLEIKT TTPAPRPPTPAPTIASQPLSRPEACRPAAGGAVHTRGLDFACDIY IWAPLAGTCGVLLLSLVITLYCKRGRKKLLYIFKQPFMRPVQTTQ EEDGCSCRFPEEEEGGCELRVKFSRSADAPAYKQGQNQLYNELN LGRREEYDVLDKRRGRDPEMGGKPRRKNPQEGLYNELQKDKM AEAYSEIGMKGERRRGKGHDGLYQGLSTATKDTYDALHMQAL PPR | 241 |
| CD19 | CAR 5 | MALPVTALLLPLALLLHAARPEIVMTQSPATLSLSPGERATLSCR ASQDISKYLNWYQQKPGQAPRLLIYHTSRLHSGIPARFSGSGSGT DYTLTISSLQPEDFAVYFCQQGNTLPYTFGQGTKLEIKGGGGSGG GGSGGGGSQVQLQESGPGLVKPSETLSLTCTVSGVSLPD YGVSWIRQPPGKGLEWIGVIWGSETTYYSSSLKSRVTISKDNSKN QVSLKLSSVTAADTAVYYCAKHYYYGGSYAMDYWGQGTLVT VSSTTTPAPRPPTPAPTIASQPLSRPEACRPAAGGAVHTRGLDFA CDIYIWAPLAGTCGVLLLSLVITLYCKRGRKKLLYIFKQPFMRPV QTTQEEDGCSCRFPEEEEGGCELRVKFSRSADAPAYKQGQNQLY NELNLGRREEYDVLDKRRGRDPEMGGKPRRKNPQEGLYNELQK DKMAEAYSEIGMKGERRRGKGHDGLYQGLSTATKDTYDALHM QALPPR | 242 |
| CD19 | CAR 6 | MALPVTALLLPLALLLHAARPEIVMTQSPATLSLSPGERATLSCR ASQDISKYLNWYQQKPGQAPRLLIYHTSRLHSGIPARFSGSGSGT DYTLTISSLQPEDFAVYFCQQGNTLPYTFGQGTKLEIKGGGGSGG GGSGGGGSQVQLQESGPGLVKPSETLSLTCTVSGVSLPD YGVSWIRQPPGKGLEWIGVIWGSETTYYQSSLKSRVTISKDNSK NQVSLKLSSVTAADTAVYYCAKHYYYGGSYAMDYWGQGTLV TVSSTTTPAPRPPTPAPTIASQPLSRPEACRPAAGGAVHTRGLDF ACDIYIWAPLAGTCGVLLLSLVITLYCKRGRKKLLYIFKQPFMRP VQTTQEEDGCSCRFPEEEEGGCELRVKFSRSADAPAYKQGQNQL YNELNLGRREEYDVLDKRRGRDPEMGGKPRRKNPQEGLYNELQ KDKMAEAYSEIGMKGERRRGKGHDGLYQGLSTATKDTYDALH MQALPPR | 243 |
| CD19 | CAR 7 | MALPVTALLLPLALLLHAARPQVQLQESGPGLVKPSETLSLTCT VSGVSLPDYGVSWIRQPPGKGLEWIGVIWGSETTYYSSSLKSRVT ISKDNSKNQVSLKLSSVTAADTAVYYCAKHYYYGGSYAMDYW GQGTLVTVSSGGGGSGGGGSGGGGSGGGGSEIVMTQSPATLSLS PGERATLSCRASQDISKYLNWYQQKPGQAPRLLIYHTSRLHSGIP ARFSGSGSGTDYTLTISSLQPEDFAVYFCQQGNTLPYTFGQGTKL EIKTTTPAPRPPTPAPTIASQPLSRPEACRPAAGGAVHTRGLDFA CDIYIWAPLAGTCGVLLLSLVITLYCKRGRKKLLYIFKQPFMRPV QTTQEEDGCSCRFPEEEEGGCELRVKFSRSADAPAYKQGQNQLY NELNLGRREEYDVLDKRRGRDPEMGGKPRRKNPQEGLYNELQK DKMAEAYSEIGMKGERRRGKGHDGLYQGLSTATKDTYDALHM QALPPR | 244 |
| CD19 | CAR 8 | MALPVTALLLPLALLLHAARPQVQLQESGPGLVKPSETLSLTCT VSGVSLPDYGVSWIRQPPGKGLEWIGVIWGSETTYYQSSLKSRV TISKDNSKNQVSLKLSSVTAADTAVYYCAKHYYYGGSYAMDY WGQGTLVTVSSGGGGSGGGGSGGGGSGGGGSEIVMTQSPATLS | 245 |

TABLE 12e-continued

Exemplary CD19 CAR molecules

| Antigen | Name | Amino Acid Sequence | SEQ ID NO: |
|---|---|---|---|
| | | LSPGERATLSCRASQDISKYLNWYQQKPGQAPRLLIYHTSRLHSG IPARFSGSGSGTDYTLTISSLQPEDFAVYFCQQGNTLPYTFGQGT KLEIKTTTPAPRPPTPAPTIASQPLSRPEACRPAAGGAVHTRGLD FACDIYIWAPLAGTCGVLLLSLVITLYCKRGRKKLLYIFKQPFMR PVQTTQEEDGCSCRFPEEEEGGCELRVKFSRSADAPAYKQGQNQ LYNELNLGRREEYDVLDKRRGRDPEMGGKPRRKNPQEGLYNEL QKDKMAEAYSEIGMKGERRRGKGHDGLYQGLSTATKDTYDAL HMQALPPR | |
| CD19 | CAR 9 | MALPVTALLLPLALLLHAARPEIVMTQSPATLSLSPGERATLSCR ASQDISKYLNWYQQKPGQAPRLLIYHTSRLHSGIPARFSGSGSGT DYTLTISSLQPEDFAVYFCQQGNTLPYTFGQGTKLEIKGGGGSGG GGSGGGGSGGGGSQVQLQESGPGLVKPSETLSLTCTVSGVSLPD YGVSWIRQPPGKGLEWIGVIWGSETTYYNSSLKSRVTISKDNSK NQVSLKLSSVTAADTAVYYCAKHYYYGGSYAMDYWGQGTLV TVSSTTTPAPRPPTPAPTIASQPLSLRPEACRPAAGGAVHTRGLDF ACDIYIWAPLAGTCGVLLLSLVITLYCKRGRKKLLYIFKQPFMRP VQTTQEEDGCSCRFPEEEEGGCELRVKFSRSADAPAYKQGQNQL YNELNLGRREEYDVLDKRRGRDPEMGGKPRRKNPQEGLYNELQ KDKMAEAYSEIGMKGERRRGKGHDGLYQGLSTATKDTYDALH MQALPPR | 246 |
| CD19 | CAR 10 | MALPVTALLLPLALLLHAARPEIVMTQSPATLSLSPGERATLSCR ASQDISKYLNWYQQKPGQAPRLLIYHTSRLHSGIPARFSGSGSGT DYTLTISSLQPEDFAVYFCQQGNTLPYTFGQGTKLEIKGGGGSGG GGSGGGGSGGGGSQVQLQESGPGLVKPSETLSLTCTVSGVSLPD YGVSWIRQPPGKGLEWIGVIWGSETTYYNSSLKSRVTISKDNSK NQVSLKLSSVTAADTAVYYCAKHYYYGGSYAMDYWGQGTLV TVSSTTTPAPRPPTPAPTIASQPLSLRPEACRPAAGGAVHTRGLDF ACDIYIWAPLAGTCGVLLLSLVITLYCKRGRKKLLYIFKQPFMRP VQTTQEEDGCSCRFPEEEEGGCELRVKFSRSADAPAYKQGQNQL YNELNLGRREEYDVLDKRRGRDPEMGGKPRRKNPQEGLYNELQ KDKMAEAYSEIGMKGERRRGKGHDGLYQGLSTATKDTYDALH MQALPPR | 247 |
| CD19 | CAR 11 | MALPVTALLLPLALLLHAARPQVQLQESGPGLVKPSETLSLTCT VSGVSLPDYGVSWIRQPPGKGLEWIGVIWGSETTYYNSSLKSRV TISKDNSKNQVSLKLSSVTAADTAVYYCAKHYYYGGSYAMDY WGQGTLVTVSSGGGGSGGGGSGGGGSGGGGSEIVMTQSPATLS LSPGERATLSCRASQDISKYLNWYQQKPGQAPRLLIYHTSRLHSG IPARFSGSGSGTDYTLTISSLQPEDFAVYFCQQGNTLPYTFGQGT KLEIKTTTPAPRPPTPAPTIASQPLSRPEACRPAAGGAVHTRGLD FACDIYIWAPLAGTCGVLLLSLVITLYCKRGRKKLLYIFKQPFMR PVQTTQEEDGCSCRFPEEEEGGCELRVKFSRSADAPAYKQGQNQ LYNELNLGRREEYDVLDKRRGRDPEMGGKPRRKNPQEGLYNEL QKDKMAEAYSEIGMKGERRRGKGHDGLYQGLSTATKDTYDAL HMQALPPR | 248 |
| CD19 | CAR 12 | MALPVTALLLPLALLLHAARPEIVMTQSPATLSLSPGERATLSCR ASQDISKYLNWYQQKPGQAPRLLIYHTSRLHSGIPARFSGSGSGT DYTLTISSLQPEDFAVYFCQQGNTLPYTFGQGTKLEIKGGGGSGG GGSGGGGSQVQLQESGPGLVKPSETLSLTCTVSGVSLPDYGVSW IRQPPGKGLEWIGVIWGSETTYYNSSLKSRVTISKDNSKNQVSLK LSSVTAADTAVYYCAKHYYYGGSYAMDYWGQGTLVTVSSTTT PAPRPPTPAPTIASQPLSLRPEACRPAAGGAVHTRGLDFACDIYIW APLAGTCGVLLLSLVITLYCKRGRKKLLYIFKQPFMRPVQTTQEE DGCSCRFPEEEEGGCELRVKFSRSADAPAYKQGQNQLYNELNLG RREEYDVLDKRRGRDPEMGGKPRRKNPQEGLYNELQKDKMAE AYSEIGMKGERRRGKGHDGLYQGLSTATKDTYDALHMQALPPR | 249 |

In one aspect, a CAR, e.g., a CAR expressed by the cell of the disclosure, comprises a CAR molecule comprising an antigen binding domain that binds to BCMA, e.g., comprises a BCMA antigen binding domain (e.g., a murine, human or humanized antibody or antibody fragment that specifically binds to BCMA, e.g., human BCMA), a transmembrane domain, and an intracellular signalling domain (e.g., an intracellular signalling domain comprising a costimulatory domain and/or a primary signalling domain).

Exemplary CAR molecules of a CAR described herein are provided in Table 1 of WO2016/014565, which is incorporated by reference herein.

Transmembrane Domains

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR e.g., in one embodiment, the transmembrane domain may be from the same protein that the signalling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one aspect, the transmembrane domain is capable of signalling to the intracellular domain(s) whenever the CAR has bound to a target. A transmembrane domain of particular use in this disclosure may include at least the transmembrane region(s) of e.g., the alpha, beta or zeta chain of the T-cell receptor, CD28, CD27, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO: 250. In one aspect, the transmembrane domain comprises (e.g., consists of) a transmembrane domain of SEQ ID NO: 251.

In certain embodiments, the encoded transmembrane domain comprises an amino acid sequence of a CD8 transmembrane domain having at least one, two or three modifications but not more than 20, 10 or 5 modifications of the amino acid sequence of SEQ ID NO: 251, or a sequence with at least 95% identity to the amino acid sequence of SEQ ID NO: 251. In one embodiment, the encoded transmembrane domain comprises the sequence of SEQ ID NO: 251.

In other embodiments, the nucleic acid molecule encoding the CAR comprises a nucleotide sequence of a CD8 transmembrane domain, e.g., comprising the sequence of SEQ ID NO: 252 or SEQ ID NO: 289, or a sequence with at least 95% identity thereof.

In certain embodiments, the encoded antigen binding domain is connected to the transmembrane domain by a hinge region. In one embodiment, the encoded hinge region comprises the amino acid sequence of a CD8 hinge, e.g., SEQ ID NO: 250; or the amino acid sequence of an IgG4 hinge, e.g., SEQ ID NO: 253 or a sequence with at least 95% identity to SEQ ID NO: 250 or SEQ ID NO: 253. In other embodiments, the nucleic acid sequence encoding the hinge region comprises the sequence of SEQ ID NO: 254 or SEQ ID NO: 255, corresponding to a CD8 hinge or an IgG4 hinge, respectively, or a sequence with at least 95% identity to SEQ ID NO: 254 or 255.

In one aspect, the hinge or spacer comprises an IgG4 hinge. For example, in one embodiment, the hinge or spacer comprises a hinge of the amino acid sequence ESKYGPPCPPCPAPEFLGGPSVFLFPPKPKDTLMISRTPEVTCVVVDVSQEDPEVQFNWYVDGVE VHNAKTKPREEQFN-STYRVVSVLTVLHQDWLNGKEYKCKVSNKGLPSSIE KTISKAKGQPREPQ VYTLPPSQEEMTKNQVSLT-CLVKGFYPSDIAVEWESNGQPEN-NYKTTPPVLDSDGSFFLYSRLTV DKSRWQEGNVFSCSVMHEALHN-HYTQKSLSLSLGKM (SEQ ID NO: 253). In some embodiments, the hinge or spacer comprises a hinge encoded by the nucleotide sequence of GAGAGCAAGTACGGCCCTCCCTGCCCCCCTTGCCC TGCCCCCGAGTTCCTGGGCGGACCCAG CGTGTTCCTGTTCCCCCCCAAGCC-CAAGGACACCCTGAT-GATCAGCCGGACCCCCGAGGTGA CCTGTGTGGTGGTGGACGTGTCCCAG-GAGGACCCCGAGGTCCAGTT-CAACTGGTACGTGGAC GGCGTG-GAGGTGCACAACGCCAAGACCAAGCCCCGGGAGG AGCAGTTCAATAGCACCTACC GGGTGGTGTCCGTGCTGACCGTGCTGCACCAGGAC TGGCTGAACGGCAAGGAATACAAGTG TAAGGTGTCCAACAAGGGCCTGCCCAGCAG-CATCGAGAAAACCATCAGCAAGGCCAAGGGC CAGCCTCGGGAGCCCCAGGTGTACACCCTG CCCTAGCCAAGAGGAGATGACCAAGAACC AGGTGTCCCTGACCTGCCTGGTGAAGGGCTTC-TACCCCAGCGACATCGCCGTGGAGTGGGAG AGCAACGGCCAGCCCGAGAACAACTACAAGAC-CACCCCCCCTGTGCTGGACAGCGACGGCA GCTTCTTCCTGTA-CAGCCGGCTGACCGTGGACAAGAGCCGGTGGCAG-GAGGGCAACGTCTTT AGCTGCTCCGT-GATGCACGAGGCCCTGCACAACCACTACACCCAGA AGAGCCTGAGCCTGTC CCTGGGCAAGATG (SEQ ID NO: 255).

In one aspect, the hinge or spacer comprises an IgD hinge. For example, in one embodiment, the hinge or spacer comprises a hinge of the amino acid sequence of RWPESPKAQASSVPTAQPQAEGSLAKATTAPATTRN-TGRGGEEKKKEKEKEEQEERETKTPECP SHTQPLGVYLLTPAVQDLWLRDKATFTCFVVGSDLK-DAHLTWEVAGKVPTGGVEEGLLERHSN GSQSQHSRLTLPRSLWNAGTSVTCTLNHPSLPPQRL-MALREPAAQAPVKLSLNLLASSDPPEAAS WLLCE- VSGFSPPNILLMWLEDQREVNTSGFAPARPPPQPG-STTFWAWSVLRVPAPPSPQPATYTC VVSHEDSRTLLNASRSLEVSYVTDH (SEQ ID NO: 256). In some embodiments, the hinge or spacer comprises a hinge encoded by the nucleotide sequence of AGGTGGCCCGAAAGTCCCAAGGCCCAGG-CATCTAGTGTTCCTACTGCACAGCCCCAGGCAG AAGGCAGCCTAGCCAAAGCTACTACTGCACCTGC-CACTACGCGCAATACTGGCCGTGGCGG GGAG-GAGAAGAAAAAGGAGAAAGAGAAAGAAGAACAG-GAAGAGAGGGAGACCAAGACCC CTGAATGTCCATCCCATACCCAGCCGCTGGGCGTC-TATCTCTTGACTCCCGCAGTACAGGAC TTGTGGCT-TAGAGATAAGGCCACCTTTA-CATGTTTCGTCGTGGGCTCTGACCTGAAGGATGC CCATTTGACTTGGGAGGTTGCCGGAAAGGTACC-CACAGGGGGGGTTGAGGAAGGGTTGCTG GAGCGCCATTCCAATGGCTCTCAGAGCCAGCACT-CAAGACTCACCCTTCCGAGATCCCTGTG GAACGCCGGGACCTCTGTCACATGTACTCTAAAT-CATCCTAGCCTGCCCCCACAGCGTCTGA TGGCCCT-TAGAGAGCCAGCCGCCCAGGCACCAGTTAAGCT-TAGCCTGAATCTGCTCGCCAGT AGTGATCCCCCAGAGGCCGCCAGCTGGCTCT-TATGCGAAGTGTCCGGCTTTAGCCCGCCCAA CATCTTGCTCATGTGGCTG-GAGGACCAGCGAGAAGT-GAACACCAGCGGCTTCGCTCCAGCCC GGCCCC-CACCCCAGCCGGGTTCTACCACATTCTGGGCCTGG AGTGTCTTAAGGGTCCCAGCA CCACCTAGCCCCCAGCCAGCCACATA-CACCTGTGTTGTGTCCCATGAAGA-TAGCAGGACCCT GCTAAATGCTTCTAGGAGTCTG-GAGGTTTCCTACGTGACTGACCATT (SEQ ID NO: 257).

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO: 258). In some embodiments, the linker is encoded by the nucleotide sequence of GGTGGCGGAGGTTCTGGAGGTGGAGGTTCC (SEQ ID NO: 259).

In one aspect, the hinge or spacer comprises a KIR2DS2 hinge.

Signalling Domains

In embodiments of the disclosure having an intracellular signalling domain, such a domain can contain, e.g., one or more of a primary signalling domain and/or a costimulatory signalling domain. In some embodiments, the intracellular signalling domain comprises a sequence encoding a primary signalling domain. In some embodiments, the intracellular signalling domain comprises a costimulatory signalling domain. In some embodiments, the intracellular signalling domain comprises a primary signalling domain and a costimulatory signalling domain.

The intracellular signalling sequences within the cytoplasmic portion of the CAR of the disclosure may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signalling sequences. In one embodiment, a glycine-serine doublet can be used as a suitable linker. In one embodiment, a single amino acid, e.g., an alanine, a glycine, can be used as a suitable linker.

In one aspect, the intracellular signalling domain is designed to comprise two or more, e.g., 2, 3, 4, 5, or more, costimulatory signalling domains. In an embodiment, the two or more, e.g., 2, 3, 4, 5, or more, costimulatory signalling domains, are separated by a linker molecule, e.g., a linker molecule described herein. In one embodiment, the intracellular signalling domain comprises two costimulatory signalling domains. In some embodiments, the linker molecule is a glycine residue. In some embodiments, the linker is an alanine residue.

Primary Signalling Domains

A primary signalling domain regulates primary activation of the TCR complex either in a stimulatory way, or in an inhibitory way. Primary intracellular signalling domains that act in a stimulatory manner may contain signalling motifs, which are known as immunoreceptor tyrosine-based activation motifs or ITAMs.

Examples of ITAM containing primary intracellular signalling domains that are of particular use in the disclosure include those of CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In one embodiment, a CAR of the disclosure comprises an intracellular signalling domain, e.g., a primary signalling domain of CD3-zeta.

In one embodiment, the encoded primary signalling domain comprises a functional signalling domain of CD3 zeta. The encoded CD3 zeta primary signalling domain can comprise an amino acid sequence having at least one, two or three modifications but not more than 20, 10 or 5 modifications of the amino acid sequence of SEQ ID NO: 260 or SEQ ID NO: 261, or a sequence with at least 95% identity to the amino acid sequence of SEQ ID NO: 260 or SEQ ID NO: 261. In some embodiments, the encoded primary signalling domain comprises the sequence of SEQ ID NO: 260 or SEQ ID NO: 261. In other embodiments, the nucleic acid sequence encoding the primary signalling domain comprises the sequence of SEQ ID NO: 262, SEQ ID NO: 291, or SEQ ID NO: 263, or a sequence with at least 95% identity thereof.

Costimulatory Signalling Domains

In some embodiments, the encoded intracellular signalling domain comprises a costimulatory signalling domain. For example, the intracellular signalling domain can comprise a primary signalling domain and a costimulatory signalling domain. In some embodiments, the encoded costimulatory signalling domain comprises a functional signalling domain of a protein chosen from one or more of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

In certain embodiments, the encoded costimulatory signalling domain comprises an amino acid sequence having at least one, two or three modifications but not more than 20, 10 or 5 modifications of the amino acid sequence of SEQ ID NO: 264 or SEQ ID NO: 265, or a sequence with at least 95% identity to the amino acid sequence of SEQ ID NO: 264 or SEQ ID NO: 265. In one embodiment, the encoded costimulatory signalling domain comprises the sequence of SEQ ID NO: 264 or SEQ ID NO: 265. In other embodiments, the nucleic acid sequence encoding the costimulatory signalling domain comprises the sequence of SEQ ID NO: 266, SEQ ID NO: 290, or SEQ ID NO: 267, or a sequence with at least 95% identity thereof.

In other embodiments, the encoded intracellular domain comprises the sequence of SEQ ID NO: 264 or SEQ ID NO: 265 and the sequence of SEQ ID NO: 260 or SEQ ID NO: 261, wherein the sequences comprising the intracellular signalling domain are expressed in the same frame and as a single polypeptide chain.

In certain embodiments, the nucleic acid sequence encoding the intracellular signalling domain comprises the sequence of SEQ ID NO: 266, SEQ ID NO: 290, or SEQ ID NO: 267, or a sequence with at least 95% identity thereof, and the sequence of SEQ ID NO: 262, SEQ ID NO: 291, or SEQ ID NO: 263, or a sequence with at least 95% identity thereof.

In some embodiments, the nucleic acid molecule further encodes a leader sequence. In one embodiment, the leader sequence comprises the sequence of SEQ ID NO: 268.

In one aspect, the intracellular signalling domain is designed to comprise the signalling domain of CD3-zeta and the signalling domain of CD28. In one aspect, the intracellular signalling domain is designed to comprise the signalling domain of CD3-zeta and the signalling domain of 4-1BB. In one aspect, the signalling domain of 4-1BB is a signalling domain of SEQ ID NO: 264. In one aspect, the signalling domain of CD3-zeta is a signalling domain of SEQ ID NO: 260.

In one aspect, the intracellular signalling domain is designed to comprise the signalling domain of CD3-zeta and the signalling domain of CD27. In one aspect, the signalling domain of CD27 comprises the amino acid sequence of QRRKYRSNKGESPVEPAEPCRYSCPREEEGSTIP-IQEDYRKPEPACSP (SEQ ID NO: 265). In one aspect, the signalling domain of CD27 is encoded by the nucleic acid sequence of Caacgaaggaaatatagatcaaacaaaggagaaagtcctgtg-gagcctgcagagccttgtcgttacagctgccccagggaggaggagggcagcacc atccccatccaggaggattaccgaaaaccggagcctgcctgctccccc (SEQ ID NO: 267).

Vectors

In another aspect, the disclosure pertains to a vector comprising a nucleic acid sequence encoding a CAR described herein. In one embodiment, the vector is chosen from a DNA vector, an RNA vector, a plasmid, a lentivirus vector, adenoviral vector, or a retrovirus vector. In one embodiment, the vector is a lentivirus vector. These vectors or portions thereof may, among other things, be used to create template nucleic acids, as described herein for use with the CRISPR systems as described herein. Alternatively, the vectors may be used to deliver nucleic acid directly to the cell, e.g., the immune effector cell, e.g., the T cell, e.g., the allogeneic T cell, independent of the CRISPR system.

The present disclosure also provides vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the disclosure is an adenoviral vector (A5/35). In another embodiment, the expression of nucleic acids encoding CARs can be accomplished using of transposons such as sleeping beauty, crisper, CAS9, and zinc finger nucleases. See below June et al. 2009 *Nature Reviews Immunology* 9.10: 704-716, is incorporated herein by reference.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Disclosed herein are methods for producing an in vitro transcribed RNA CAR. The present disclosure also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO: 269). RNA so produced can efficiently transfect different kinds of cells. In one aspect, the template includes sequences for the CAR.

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, cells of the disclosure, e.g., T or NK cells, e.g., allogeneic T cells, e.g., described herein, (e.g., that express a CAR described herein) are generated by contacting the cells with (a) a composition comprising one or more gRNA molecules, e.g., as described herein, and one or more Cas molecules, e.g., a Cas9 molecule, e.g., as described herein, and (b) nucleic acid comprising sequence encoding a CAR, e.g., described herein (such as a template nucleic acid molecule as described herein). Without being bound by theory, said composition of (a), above, will induce a break at or near the genomic DNA targeted by the targeting domain of the gRNA molecule(s), and the nucleic acid of (b) will incorporate, e.g., partially or wholly, into the genome at or near said break, such that upon integration, the encoded CAR molecule is expressed. In embodiments, expression of the CAR will be controlled by promoters or other regulatory elements endogenous to the genome (e.g., the promoter controlling expression from the gene in which the nucleic acid of (b) was inserted). In other embodiments, the nucleic acid of (b) further comprises a promoter and/or other regulatory elements, e.g., as described herein, e.g., an EF1-alpha promoter, operably linked to the sequence encoding the CAR, such that upon integration, expression of the CAR is controlled by that promoter and/or other regulatory elements. Additional features of the disclosure relating to use of CRISPR/Cas9 systems, e.g., as described herein, to direct incorporation of nucleic acid sequence encoding a CAR, e.g., as described herein, are described elsewhere in this application, e.g., in the section relating to gene insertion and homologous recombination. In embodiments, the composition of a) above is a composition comprising RNPs comprising the one or more gRNA molecules. In embodiments, RNPs comprising gRNAs targeting unique target sequences are introduced into the cell simultaneously, e.g., as a mixture of RNPs comprising the one or more gRNAs. In embodiments, RNPs comprising gRNAs targeting unique target sequences are introduced into the cell sequentially.

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Promoters

In one embodiment, the vector further comprises a promoter. In some embodiments, the promoter is chosen from an EF-1 promoter, a CMV IE gene promoter, an EF-1α promoter, an ubiquitin C promoter, or a phosphoglycerate kinase (PGK) promoter. In one embodiment, the promoter is an EF-1 promoter. In one embodiment, the EF-1 promoter comprises the sequence of SEQ ID NO: 270.

Host Cells for CAR Expression

As noted above, in some aspects the disclosure pertains to a cell, e.g., an immune effector cell, (e.g., a population of cells, e.g., a population of immune effector cells) comprising a nucleic acid molecule, a CAR polypeptide molecule, or a vector as described herein.

In certain aspects of the present disclosure, immune effector cells, e.g., T cells, can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In one aspect, T cells are isolated from peripheral blood lymphocytes by lysing the red blood cells and depleting the monocytes, for example, by centrifugation through a PERCOLL™ gradient or by counterflow centrifugal elutriation.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6 \times 10^9$ CD25+ T cells. In other aspects, the population of immune effector cells to be depleted include about $1 \times 10^9$ to $1 \times 10^{10}$ CD25+ T cell, and any integer value in between. In one embodiment, the resulting population T regulatory depleted cells has $2 \times 10^9$ T regulatory cells, e.g., CD25+ cells, or less (e.g., $1\times10^9$, $5\times10^8$, $1\times10^8$, $5\times10^7$, $1\times10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD1 b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B7-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

Methods described herein can include a positive selection step. For example, T cells can isolated by incubation with anti-CD3/anti-CD28 (e.g., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours, e.g., 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 10 billion cells/ml, 9 billion/ml, 8 billion/ml, 7 billion/ml, 6 billion/ml, or 5 billion/ml is used. In one aspect, a concentration of 1 billion cells/ml is used. In yet one aspect, a concentration of cells from 75, 80, 85, 90, 95, or 100 million cells/ml is used. In further aspects, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5\times10^6$/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present disclosure.

Also contemplated in the context of the disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect, a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present disclosure, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

In some aspects, the cells of the disclosure (e.g., the immune effector cells of the disclosure, e.g., the CAR-expressing cells of the disclosure) are induced pluripotent stem cells ("iPSCs") or embryonic stem cells (ESCs), or are T cells generated from (e.g., differentiated from) said iPSC and/or ESC. iPSCs can be generated, for example, by methods known in the art, from peripheral blood T lymphocytes, e.g., peripheral blood T lymphocytes isolated from a healthy volunteer. As well, such cells may be differentiated into T cells by methods known in the art. See e.g., Themeli M. et al., *Nat. Biotechnol.*, 31, pp. 928-933 (2013); doi: 10.1038/nbt.2678; WO2014/165707, the contents of each of which are incorporated herein by reference in their entirety.

In another embodiment, the compounds of Formula (I') or Formula (I), or a pharmaceutically acceptable salt, hydrate, solvate, prodrug, stereoisomer, or tautomer thereof, of the present disclosure are used in combination with one or more of the therapeutic agents listed in Table 13 or listed in the patent and patent applications cited in Table 13, to treat cancer. Each publication listed in Table 13 is herein incorporated by reference in its entirety, including all structural formulae therein.

TABLE 13

| Second agent No. | Generic Name Tradename | Compound Structure | Patents/Patent Application Publications |
|---|---|---|---|
| A1 | Sotrastaurin | 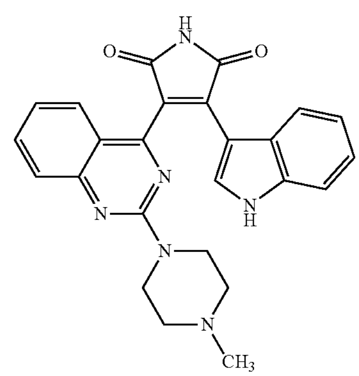 | EP 16822103<br>US 2007/142401<br>WO 2005/039549 |

TABLE 13-continued
| Second agent No. | Generic Name Tradename | Compound Structure | Patents/Patent Application Publications |
|---|---|---|---|
| A2 | Nilotinib HCl monohydrate TASIGNA ® | 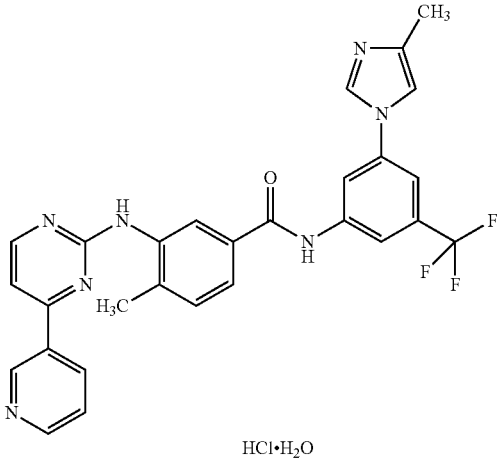<br>HCl·H₂O | WO 2004/005281<br>U.S. Pat. No. 7,169,791 |
| A3 | | 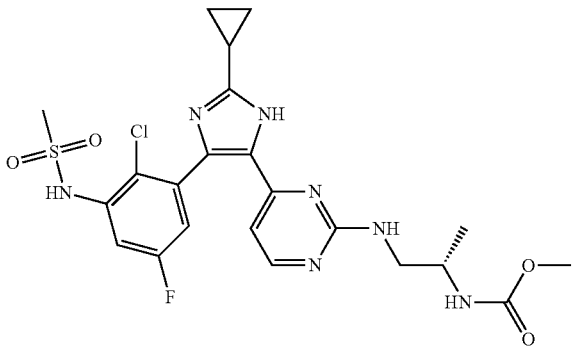 | WO2011/023773 |
| A4 | | 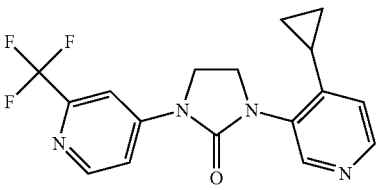 | WO2012/149413 |
| A6 | | 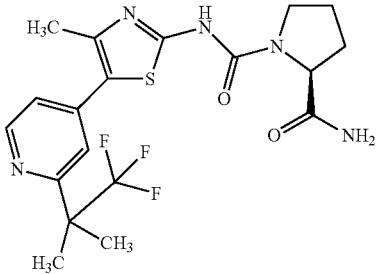 | WO 2010/029082 |

TABLE 13-continued

| Second agent No. | Generic Name Tradename | Compound Structure | Patents/Patent Application Publications |
|---|---|---|---|
| A7 | | 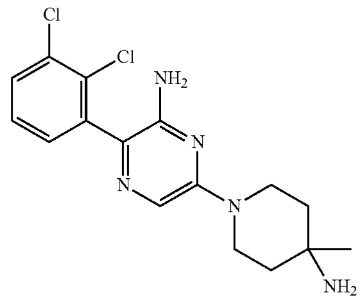 | WO2015/107493 |
| A8 | | | WO2015/107495 |
| A9 | | 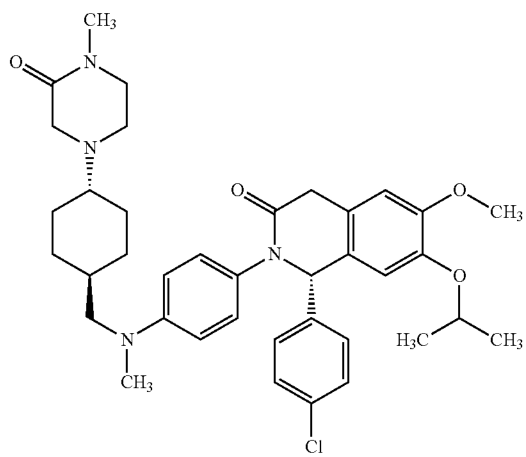 | WO 2011/076786 |
| A10 | Deferasirox EXJADE ® | 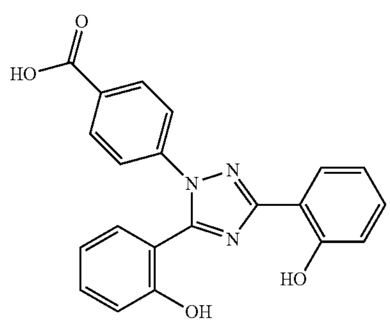 | WO 1997/049395 |
| A11 | Letrozole FEMARA ® | 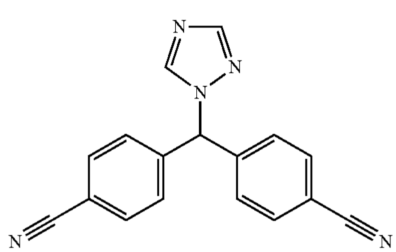 | U.S. Pat. No. 4,978,672 |

TABLE 13-continued
| Second agent No. | Generic Name Tradename | Compound Structure | Patents/Patent Application Publications |
|---|---|---|---|
| A12 | | 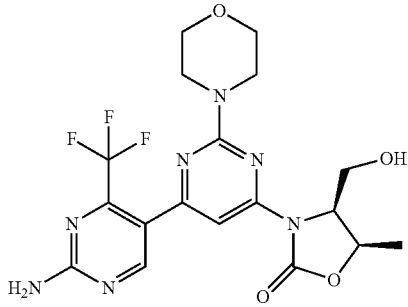 | WO 2013/124826 US 2013/0225574 |
| A13 | | 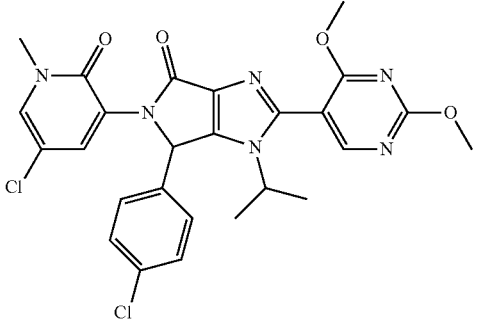 | WO 2013/111105 |
| A14 | | 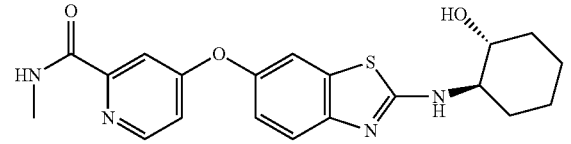 | WO2007/121484 |
| A15 | Imatinib mesylate GLEEVEC ® | <br>Mesylate | WO 1999/003854 |
| A16 | Capmatinib | 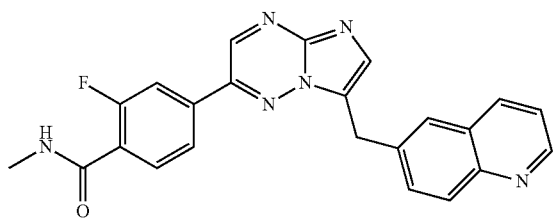<br>Dihydrochloric salt | EP 2099447 U.S. Pat. No. 7,767,675 U.S. Pat. No. 8,420,645 |
| A17 | Ruxolitinib Phosphate JAKAFI ® | 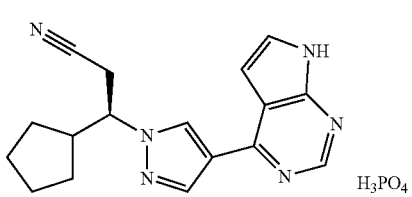 | WO 2007/070514; EP 2474545 U.S. Pat. No. 7,598,257; WO 2014/018632 |

TABLE 13-continued

| Second agent No. | Generic Name Tradename | Compound Structure | Patents/Patent Application Publications |
|---|---|---|---|
| A18 | Panobinostat | 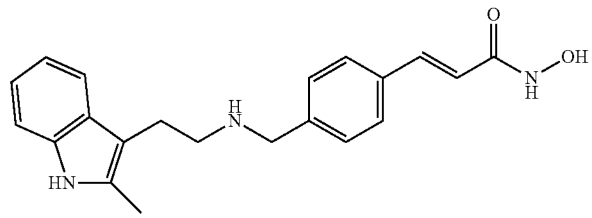 | WO 2014/072493<br>WO 2002/022577<br>EP 1870399 |
| A20 | | 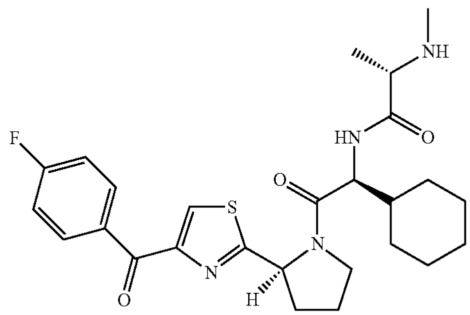 | WO 2008/016893<br>EP 2051990<br>U.S. Pat. No. 8,552,003 |
| A21 | | 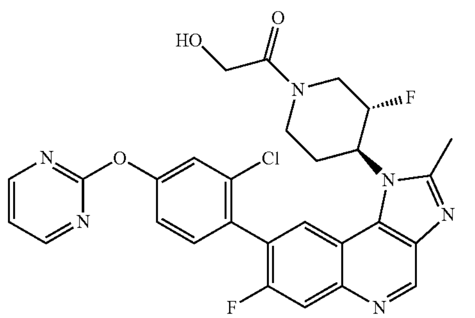 | WO2015/022662 |
| A22 | ceritinib<br>ZYKADIA ™ | 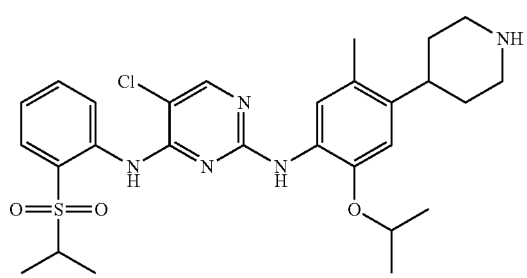 | WO 2008/073687<br>U.S. Pat. No. 8,039,479 |
| A23 | Ribociclib<br>KISQALI ® | 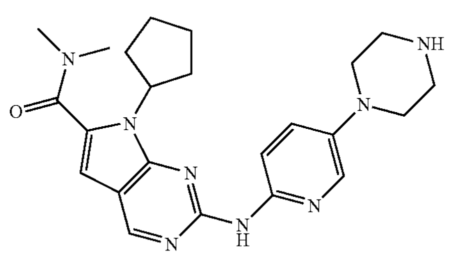 | U.S. Pat. No. 8,415,355<br>U.S. Pat. No. 8,685,980 |
| A24 | | 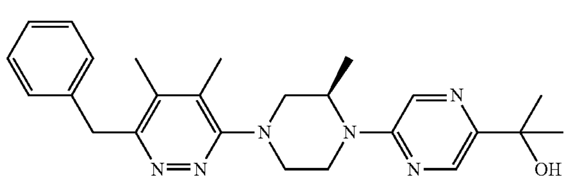 | WO 2010/007120 |

TABLE 13-continued

| Second agent No. | Generic Name Tradename | Compound Structure | Patents/Patent Application Publications |
|---|---|---|---|
| A26 | | (structure shown) | WO 2011/101409 |
| A27 | | Human monoclonal antibody to HER3 | WO 2012/022814<br>EP 2606070<br>U.S. Pat. No. 8,735,551 |
| A28 | | Antibody Drug Conjugate (ADC) | WO 2014/160160 |
| A29 | | Monoclonal antibody or Fab to M-CSF | WO 2004/045532 |
| A30 | Midostaurin | (structure shown) | WO 2003/037347<br>EP 1441737<br>US 2012/252785 |
| A31 | Everolimus<br>AFINITOR ® | (structure shown) | WO 1994/009010<br>WO 2014/085318 |

TABLE 13-continued

| Second agent No. | Generic Name Tradename | Compound Structure | Patents/Patent Application Publications |
|---|---|---|---|
| A32 | | 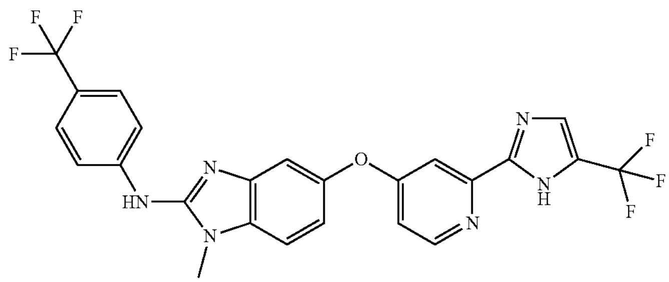 | WO 2007/030377<br>U.S. Pat. No. 7,482,367 |
| A34 | | 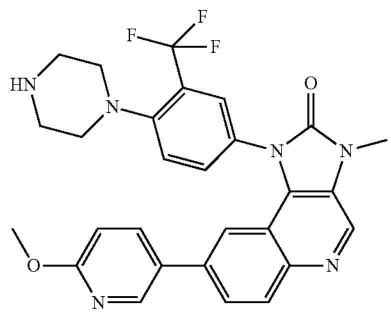 | WO 2006/122806 |
| A35 | | 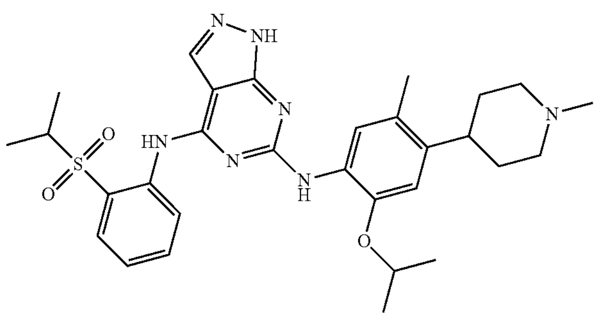 | WO 2008/073687<br>U.S. Pat. No. 8,372,858 |
| A36 | Valspodar<br>AMDRAY ™ | 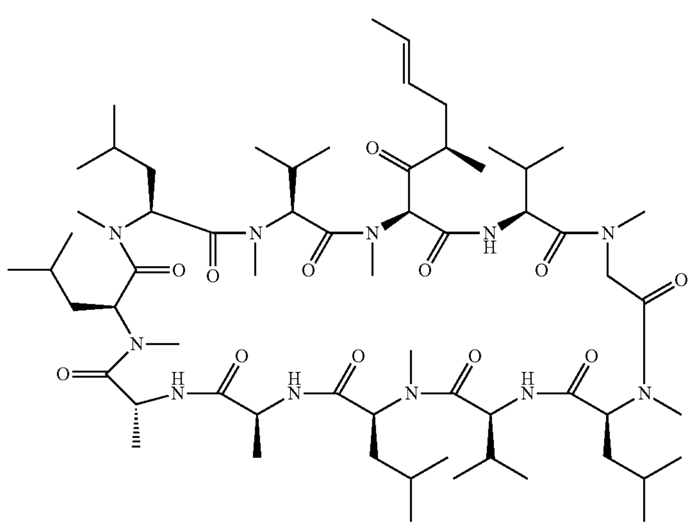 | EP 296122 |

TABLE 13-continued
| Second agent No. | Generic Name Tradename | Compound Structure | Patents/Patent Application Publications |
|---|---|---|---|
| A37 | Vatalanib succinate | 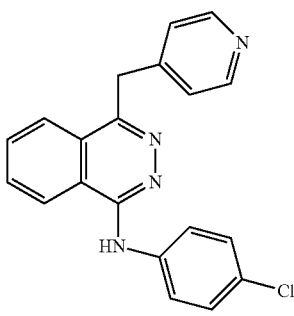<br>succinate | WO 98/35958 |
| A38 | | 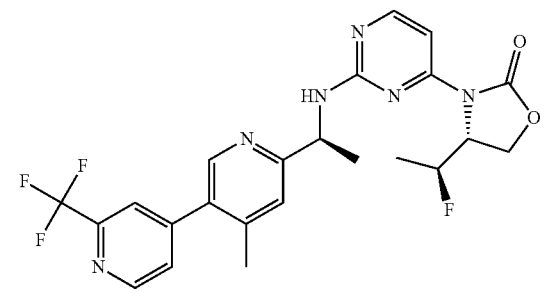 | WO2014/141104 |
| A39 | Asciminib | 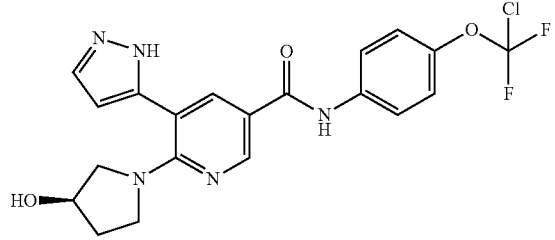 | WO2013/171639<br>WO2013/171640<br>WO2013/171641<br>WO2013/171642 |
| A42 | | 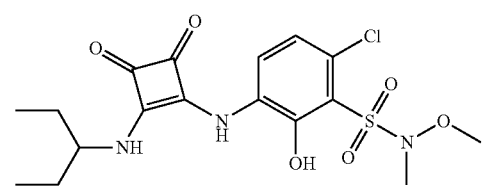<br>or a choline salt therof | WO2010/015613<br>WO2013030803<br>U.S. Pat. No. 7,989,497, |
| A43 | | | WO 2017/025918<br>WO2011/121418<br>U.S. Pat. No. 8,796,284 |
| A44 | | 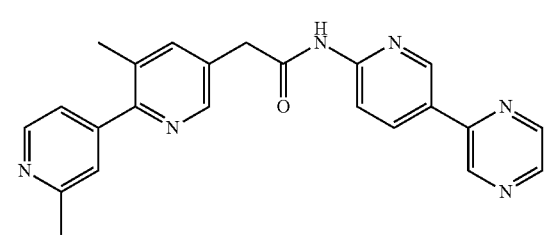 | WO2010/101849 |

TABLE 13-continued
| Second agent No. | Generic Name Tradename | Compound Structure | Patents/Patent Application Publications |
|---|---|---|---|
| A45 | | 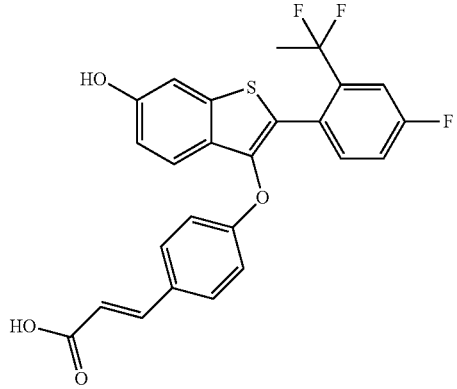 | WO2014/130310 |
| A46 | trametinib | 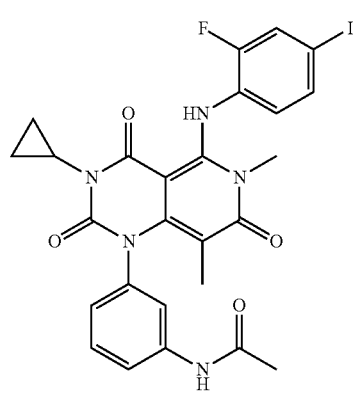 | WO2005/121142<br>U.S. Pat. No. 7,378,423 |
| A47 | dabrafenib | 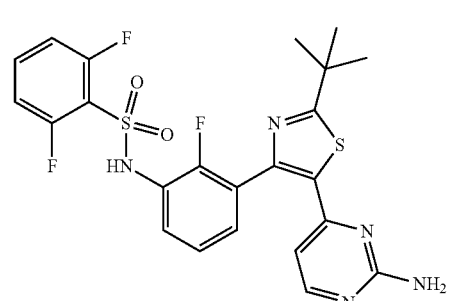 | WO 2009/137391<br>U.S. Pat. No. 7,994,185 |
| A49 | octreotide | 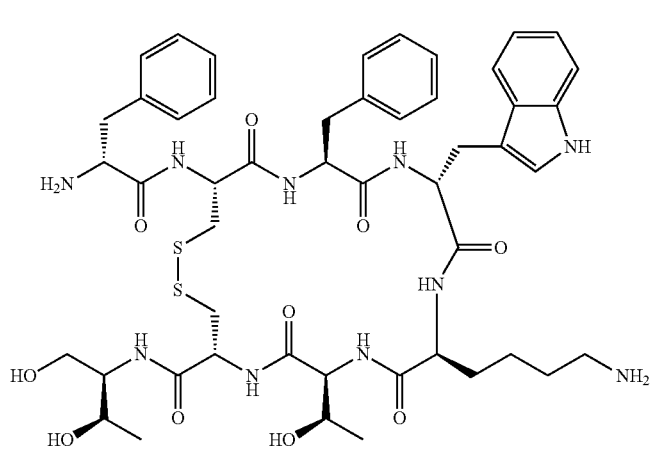 | U.S. Pat. No. 4,395,403<br>EP 0 029 579 |

TABLE 13-continued

| Second agent No. | Generic Name Tradename | Compound Structure | Patents/Patent Application Publications |
|---|---|---|---|
| A50 | | 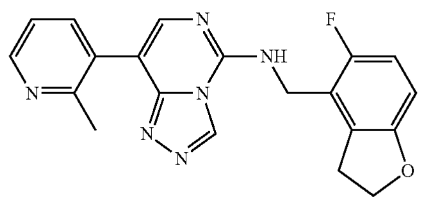 | WO2016/103155<br>U.S. Pat. No. 9,580,437<br>EP 3237418 |
| A51 | | 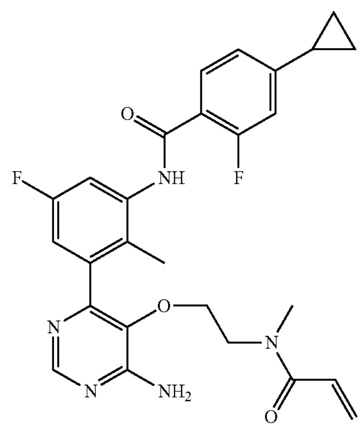 | U.S. Pat. No. 9,512,084<br>WO/2015/079417 |
| A52 | | 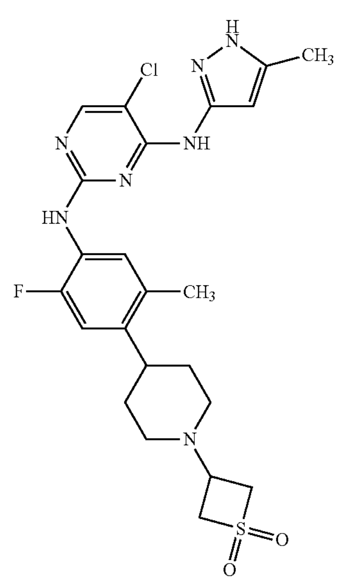 | WO 2010/002655<br>U.S. Pat. No. 8,519,129 |

TABLE 13-continued

| Second agent No. | Generic Name Tradename | Compound Structure | Patents/Patent Application Publications |
|---|---|---|---|
| A53 | | (structure) | WO 2010/002655<br>U.S. Pat. No. 8,519,129 |
| A54 | | (structure) | WO2010/002655 |

Estrogen Receptor Antagonists

In some embodiments, an estrogen receptor (ER) antagonist is used in combination with the compounds of Formula (I') or Formula (I), or a pharmaceutically acceptable salt, hydrate, solvate, prodrug, stereoisomer, or tautomer thereof, for treating a disease, e.g., cancer. In some embodiments, the estrogen receptor antagonist is a selective estrogen receptor degrader (SERD). SERDs are estrogen receptor antagonists which bind to the receptor and result in e.g., degradation or down-regulation of the receptor (Boer K. et al., (2017) Therapeutic Advances in Medical Oncology 9(7): 465-479). ER is a hormone-activated transcription factor important for e.g., the growth, development and physiology of the human reproductive system. ER is activated by, e.g., the hormone estrogen (17beta estradiol). ER expression and signalling is implicated in cancers (e.g., breast cancer), e.g., ER positive (ER+) breast cancer. In some embodiments, the SERD is chosen from LSZ 102, fulvestrant, brilanestrant, or elacestrant.

Exemplary Estrogen Receptor Antagonists

In some embodiments, the SERD comprises a compound disclosed in International Application Publication No. WO 2014/130310, which is hereby incorporated by reference in its entirety. In some embodiments, the SERD comprises LSZ102. LSZ102 has the chemical name: (E)-3-(4-((2-(2-(1,1-difluoroethyl)-4-fluorophenyl)-6-hydroxybenzo[b]thiophen-3-yl)oxy)phenyl)acrylic acid.

Other Exemplary Estrogen Receptor Antagonists

In some embodiments, the SERD comprises fulvestrant (CAS Registry Number: 129453-61-8), or a compound disclosed in International Application Publication No. WO 2001/051056, which is hereby incorporated by reference in its entirety. Fulvestrant is also known as ICI 182780, ZM 182780, FASLODEX®, or (7a,17(3)-7-{9-[(4,4,5,5,5-pentafluoropentyl)sulfinyl]nonyl}estra-1,3,5(10)-triene-3,17-diol. Fulvestrant is a high affinity estrogen receptor antagonist with an IC50 of 0.29 nM.

In some embodiments, the SERD comprises elacestrant (CAS Registry Number: 722533-56-4), or a compound disclosed in U.S. Pat. No. 7,612,114, which is incorporated by reference in its entirety. Elacestrant is also known as RAD1901, ER-306323 or (6R)-6-{2-[Ethyl({4-[2-(ethylamino)ethyl]phenyl}methyl)amino]-4-methoxyphenyl}-5,6,7,8-tetrahydronaphthalen-2-ol. Elacestrant is an orally bioavailable, non-steroidal combined selective estrogens receptor modulator (SERM) and a SERD. Elacestrant is also disclosed, e.g., in Garner F et al., (2015) Anticancer Drugs 26(9):948-56.

In some embodiments, the SERD is brilanestrant (CAS Registry Number: 1365888-06-7), or a compound disclosed in International Application Publication No. WO 2015/136017, which is incorporated by reference in its entirety. Brilanestrant is also known as GDC-0810, ARN810, RG-6046, RO-7056118 or (2E)-3-{4-[(1E)-2-(2-chloro-4-fluorophenyl)-1-(1H-indazol-5-yl)but-1-en-1-yl]phenyl}prop-2-enoic acid. Brilanestrant is a next-generation, orally bioavailable selective SERD with an IC50 of 0.7 nM. Brilanestrant is also disclosed, e.g., in Lai A. et al. (2015) Journal of Medicinal Chemistry 58 (12): 4888-4904.

In some embodiments, the SERD is chosen from RU 58668, GW7604, AZD9496, bazedoxifene, pipendoxifene, arzoxifene, OP-1074, or acolbifene, e.g., as disclosed in McDonell et al. (2015) Journal of Medicinal Chemistry 58(12) 4883-4887. Other exemplary estrogen receptor antagonists are disclosed, e.g., in WO 2011/156518, WO 2011/159769, WO 2012/037410, WO 2012/037411, and US 2012/0071535, all of which are hereby incorporated by reference in their entirety.

CDK4/6 Inhibitors

In some embodiments, an inhibitor of Cyclin-Dependent Kinases 4 or 6 (CDK4/6) is used in combination with the compounds of Formula (I') or Formula (I), or a pharmaceutically acceptable salt, hydrate, solvate, prodrug, stereoisomer, or tautomer thereof, for treating a disease, e.g., cancer. In some embodiments, the CDK4/6 inhibitor is chosen from ribociclib, abemaciclib (Eli Lilly), or palbociclib.

Exemplary CDK4/6 Inhibitors

In some embodiments, the CDK4/6 inhibitor comprises ribociclib (CAS Registry Number: 1211441-98-3), or a compound disclosed in U.S. Pat. Nos. 8,415,355 and 8,685,980, which are incorporated by reference in their entirety.

In some embodiments, the CDK4/6 inhibitor comprises a compound disclosed in International Application Publication No. WO 2010/020675 and U.S. Pat. Nos. 8,415,355 and 8,685,980, which are incorporated by reference in their entirety.

In some embodiments, the CDK4/6 inhibitor comprises ribociclib (CAS Registry Number: 1211441-98-3). Ribociclib is also known as LEE011, KISQALI®, or 7-cyclopentyl-N,N-dimethyl-2-((5-(piperazin-1-yl)pyridin-2-yl)amino)-7H-pyrrolo[2,3-d]pyrimidine-6-carboxamide.

Other Exemplary CDK46 Inhibitors

In some embodiments, the CDK4/6 inhibitor comprises abemaciclib (CAS Registry Number: 1231929-97-7). Abemaciclib is also known as LY835219 or N-[5-[(4-Ethyl-1-piperazinyl)methyl]-2-pyridinyl]-5-fluoro-4-[4-fluoro-2-methyl-1-(1-methylethyl)-1H-benzimidazol-6-yl]-2-pyrimidinamine. Abemaciclib is a CDK inhibitor selective for CDK4 and CDK6 and is disclosed, e.g., in Torres-Guzman R et al. (2017) Oncotarget 10.18632/oncotarget.17778.

In some embodiments, the CDK4/6 inhibitor comprises palbociclib (CAS Registry Number: 571190-30-2). Palbociclib is also known as PD-0332991, IBRANCE® or 6-Acetyl-8-cyclopentyl-5-methyl-2-{[5-(1-piperazinyl)-2-pyridinyl]amino}pyrido[2,3-d]pyrimidin-7(8H)-one. Palbociclib inhibits CDK4 with an IC50 of 11 nM, and inhibits CDK6 with an IC50 of 16 nM, and is disclosed, e.g., in Finn et al. (2009) Breast Cancer Research 11(5):R77.

CXCR2 Inhibitors

In some embodiments, an inhibitor of chemokine (C-X-C motif) receptor 2 (CXCR2) is used in combination with the compounds of Formula (I') or Formula (I), or a pharmaceutically acceptable salt, hydrate, solvate, prodrug, stereoisomer, or tautomer thereof, for treating a disease, e.g., cancer. In some embodiments, the CXCR2 inhibitor is chosen from 6-chloro-3-((3,4-dioxo-2-(pentan-3-ylamino)cyclobut-1-en-1-yl)amino)-2-hydroxy-N-methoxy-N-methylbenzenesulfonamide, danirixin, reparixin, or navarixin.

Exemplary CXCR2 Inhibitors

In some embodiments, the CXCR2 inhibitor comprises a compound disclosed in U.S. Pat. Nos. 7,989,497, 8,288,588, 8,329,754, 8,722,925, 9,115,087, U.S. Application Publication Nos. US 2010/0152205, US 2011/0251205 and US 2011/0251206, and International Application Publication Nos. WO 2008/061740, WO 2008/061741, WO 2008/062026, WO 2009/106539, WO2010/063802, WO 2012/062713, WO 2013/168108, WO 2010/015613 and WO 2013/030803. In some embodiments, the CXCR2 inhibitor comprises 6-chloro-3-((3,4-dioxo-2-(pentan-3-ylamino)cyclobut-1-en-1-yl)amino)-2-hydroxy-N-methoxy-N-methylbenzenesulfonamide or a choline salt thereof. In some embodiments, the CXCR2 inhibitor comprises 6-chloro-3-((3,4-dioxo-2-(pentan-3-ylamino)cyclobut-1-en-1-yl)amino)-2-hydroxy-N-methoxy-N-methylbenzenesulfonamide choline salt. In some embodiments, the CXCR2 inhibitor is 2-Hydroxy-N,N,N-trimethylethan-1-aminium 3-chloro-6-({3,4-dioxo-2-[(pentan-3-yl)amino]cyclobut-1-en-1-yl}amino)-2-(N-methoxy-N-methylsulfamoyl)phenolate (i.e., 6-chloro-3-((3,4-dioxo-2-(pentan-3-ylamino)cyclobut-1-en-1-yl)amino)-2-hydroxy-N-methoxy-N-methylbenzenesulfonamide choline salt) and has the following chemical structure:

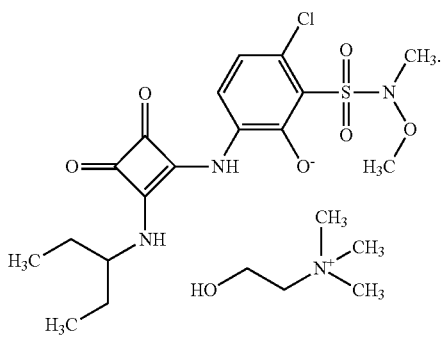

Other Exemplary CXCR2 Inhibitors

In some embodiments, the CXCR2 inhibitor comprises danirixin (CAS Registry Number: 954126-98-8). Danirixin is also known as GSK1325756 or 1-(4-chloro-2-hydroxy-3-piperidin-3-ylsulfonylphenyl)-3-(3-fluoro-2-methylphenyl)urea. Danirixin is disclosed, e.g., in Miller et al. *Eur J Drug*

*Metab Pharmacokinet* (2014) 39:173-181; and Miller et al. *BMC Pharmacology and Toxicology* (2015), 16:18.

In some embodiments, the CXCR2 inhibitor comprises reparixin (CAS Registry Number: 266359-83-5). Reparixin is also known as repertaxin or (2R)-2-[4-(2-methylpropyl)phenyl]-N-methylsulfonylpropanamide. Reparixin is a non-competitive allosteric inhibitor of CXCR1/2. Reparixin is disclosed, e.g., in Zarbock et al. *Br J Pharmacol.* 2008; 155(3):357-64.

In some embodiments, the CXCR2 inhibitor comprises navarixin. Navarixin is also known as MK-7123, SCH 527123, PS291822, or 2-hydroxy-N,N-dimethyl-3-[[2-[[(1R)-1-(5-methylfuran-2-yl)propyl]amino]-3,4-dioxocyclobuten-1-yl]amino]benzamide. Navarixin is disclosed, e.g., in Ning et al. *Mol Cancer Ther.* 2012; 11(6):1353-64.

Exemplary CSF-1 Binding Agents

In some embodiments, the CSF-1/1R binding agent comprises an inhibitor of macrophage colony-stimulating factor (M-CSF). M-CSF is also sometimes known as CSF-1. In certain embodiments, the CSF-1/1R binding agent is an antibody to CSF-1 (e.g., MCS110). In other embodiments, the CSF-1/1R binding agent is an inhibitor of CSF-1R (e.g., BLZ945).

In some embodiments, the CSF-1/1R binding agent comprises a monoclonal antibody or Fab to M-CSF (e.g., MCS110/H-RX1), or a binding agent to CSF-1 disclosed in International Application Publication Nos. WO 2004/045532 and WO 2005/068503, including H-RX1 or 5H4 (e.g., an antibody molecule or Fab fragment against M-CSF) and U.S. Pat. No. 9,079,956, which applications and patent are incorporated by reference in their entirety.

TABLE 13a

| Amino acid and nucleotide sequences of an exemplary anti-M-CSF antibody molecule (MCS110) | |
|---|---|
| (H-RX1) HC | QVQLQESGPGLVKPSQTLSLTCTVSDYSITSDYAWNWIRQFPGKGLEWMG YISYSGSTSYNPSLKSRITISRDTSKNQFSLQLNSVTAADTAVYYCASFDYA HAMDYWGQGTTVTVSSASTKGPSVFPLAPSSKSTSGGTAALGCLVKDYFP EPVTVSWNSGALTSGVHTFPAVLQSSGLYSLSSVVTVPSSSLGTQTYICNVN HKPSNTKVDKRVEPKSCDKTHTCPPCPAPELLGGPSVFLFPPKPKDTLMISR TPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR EEMTKNQVSLTCLVKGFYPSDIAVEWESNGQPENNYKTTPPVLDSDGSFFL YSKLTVDKSRWQQGNVFSCSVMHEALHNHYTQKSLSLSPGK (SEQ ID NO: 271) |
| (H-RX1) LC | DIVLTQSPAFLSVTPGEKVTFTCQASQSIGTSIHWYQQKTDQAPKLLIKYAS ESISGIPSRFSGSGSGTDFTLTISSVEAEDAADYYCQQINSWPTTFGGGTKLEI KRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC (SEQ ID NO: 272) |
| Heavy Chain CDR1 (Kabat) | SDYAWN (SEQ ID NO: 273) |
| Heavy Chain CDR2 (Kabat) | YISYSGSTSYNPSLKS (SEQ ID NO: 274) |
| Heavy Chain CDR3 (Kabat) | FDYAHAMDY (SEQ ID NO: 275) |
| Light Chain CDR1 (Kabat) | QASQSIGTSIH (SEQ ID NO: 276) |
| Light Chain CDR2 (Kabat) | YASESIS (SEQ ID NO: 277) |
| Light Chain CDR3 (Kabat) | QQINSWPTT (SEQ ID NO: 278) |

CSF-1/1R Binding Agents

In some embodiments, a CSF-1/1R binding agent is used in combination with the compounds of Formula (I') or Formula (I), or a pharmaceutically acceptable salt, hydrate, solvate, prodrug, stereoisomer, or tautomer thereof, for treating a disease, e.g., cancer. In some embodiments, the CSF-1/1R binding agent is chosen from an inhibitor of macrophage colony-stimulating factor (M-CSF), e.g., a monoclonal antibody or Fab to M-CSF (e.g., MCS110), a CSF-1R tyrosine kinase inhibitor (e.g., 4-((2-(((1R,2R)-2-hydroxycyclohexyl)amino)benzo[d]thiazol-6-yl)oxy)-N-methylpicolinamide or BLZ945), a receptor tyrosine kinase inhibitor (RTK) (e.g., pexidartinib), or an antibody targeting CSF-1R (e.g., emactuzumab or FPA008). In some embodiments, the CSF-1/1R inhibitor is BLZ945. In some embodiments, the CSF-1/1R binding agent is MCS110. In other embodiments, the CSF-1/1R binding agent is pexidartinib.

In another embodiment, the CSF-1/1R binding agent comprises a CSF-1R tyrosine kinase inhibitor, 4-((2-(((1R,2R)-2-hydroxycyclohexyl)amino)benzo[d]thiazol-6-yl)oxy)-N-methylpicolinamide (BLZ945), or a compound disclosed in International Application Publication No. WO 2007/121484, and U.S. Pat. Nos. 7,553,854, 8,173,689, and 8,710,048, which are incorporated by reference in their entirety.

Other Exemplary CSF-1/1R Binding Agents

In some embodiments, the CSF-1/1R binding agent comprises pexidartinib (CAS Registry Number 1029044-16-3). Pexidrtinib is also known as PLX3397 or 5-((5-chloro-1H-pyrrolo[2,3-b]pyridin-3-yl)methyl)-N-((6-(trifluoromethyl)pyridin-3-yl)methyl)pyridin-2-amine. Pexidartinib is a small-molecule receptor tyrosine kinase (RTK) inhibitor of KIT, CSF1R and FLT3. FLT3, CSF1R and FLT3 are overexpressed or mutated in many cancer cell types and play major roles in tumor cell proliferation and metastasis. PLX3397 can bind to and inhibit phosphorylation of stem cell factor receptor (KIT), colony-stimulating factor-1 receptor (CSF1R) and FMS-like tyrosine kinase 3 (FLT3), which may result in the inhibition of tumor cell proliferation and down-modulation of macrophages, osteoclasts and mast cells involved in the osteolytic metastatic disease.

In some embodiments, the CSF-1/1R binding agent is emactuzumab. Emactuzumab is also known as RG7155 or RO5509554. Emactuzumab is a humanized IgG1 mAb targeting CSF1R. In some embodiments, the CSF-1/1R binding agent is FPA008. FPA008 is a humanized mAb that inhibits CSF1R.

A2aR Antagonists

In some embodiments, an adenosine A2a receptor (A2aR) antagonist (e.g., an inhibitor of A2aR pathway, e.g., an adenosine inhibitor, e.g., an inhibitor of A2aR or CD-73) is used in combination with the compounds of Formula (I') or Formula (I), or a pharmaceutically acceptable salt, hydrate, solvate, prodrug, stereoisomer, or tautomer thereof, for treating a disease, e.g., cancer. In some embodiments, the A2aR antagonist is selected from PBF509 (NIR178) (Palobiofarma/Novartis), CPI444/V81444 (Corvus/Genentech), AZD4635/HTL-1071 (AstraZeneca/Heptares), Vipadenant (Redox/Juno), GBV-2034 (Globavir), AB928 (Arcus Biosciences), Theophylline, Istradefylline (Kyowa Hakko Kogyo), Tozadenant/SYN-115 (Acorda), KW-6356 (Kyowa Hakko Kogyo), ST-4206 (Leadiant Biosciences), and Preladenant/SCH 420814 (Merck/Schering).

Exemplary A2aR Antagonists

In some embodiments, the A2aR antagonist comprises PBF509 (NIR178) or a compound disclosed in U.S. Pat. No. 8,796,284 or in International Application Publication No. WO 2017/025918, herein incorporated by reference in their entirety. PBF509 (NIR178) is also known as NIR178.

Other Exemplary A2aR Antagonists

In certain embodiments, the A2aR antagonist comprises CPI444/V81444. CPI-444 and other A2aR antagonists are disclosed in International Application Publication No. WO 2009/156737, herein incorporated by reference in its entirety. In certain embodiments, the A2aR antagonist is (S)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine. In certain embodiments, the A2aR antagonist is (R)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine, or racemate thereof. In certain embodiments, the A2aR antagonist is 7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine.

In certain embodiments, the A2aR antagonist is AZD4635/HTL-1071. A2aR antagonists are disclosed in International Application Publication No. WO 2011/095625, herein incorporated by reference in its entirety. In certain embodiments, the A2aR antagonist is 6-(2-chloro-6-methylpyridin-4-yl)-5-(4-fluorophenyl)-1,2,4-triazin-3-amine.

In certain embodiments, the A2aR antagonist is ST-4206 (Leadiant Biosciences). In certain embodiments, the A2aR antagonist is an A2aR antagonist described in U.S. Pat. No. 9,133,197, herein incorporated by reference in its entirety.

In certain embodiments, the A2aR antagonist is an A2aR antagonist described in U.S. Pat. Nos. 8,114,845 and 9,029,393, U.S. Application Publication Nos. 2017/0015758 and 2016/0129108, herein incorporated by reference in their entirety.

In some embodiments, the A2aR antagonist is istradefylline (CAS Registry Number: 155270-99-8). Istradefylline is also known as KW-6002 or 8-[(E)-2-(3,4-dimethoxyphenyl)vinyl]-1,3-diethyl-7-methyl-3,7-dihydro-1H-purine-2,6-dione. Istradefylline is disclosed, e.g., in LeWitt et al. (2008) *Annals of Neurology* 63 (3): 295-302).

In some embodiments, the A2aR antagonist is tozadenant (Biotie). Tozadenant is also known as SYN115 or 4-hydroxy-N-(4-methoxy-7-morpholin-4-yl-1,3-benzothiazol-2-yl)-4-methylpiperidine-1-carboxamide. Tozadenant blocks the effect of endogenous adenosine at the A2a receptors, resulting in the potentiation of the effect of dopamine at the D2 receptor and inhibition of the effect of glutamate at the mGluR5 receptor. In some embodiments, the A2aR antagonist is preladenant (CAS Registry Number: 377727-87-2). Preladenant is also known as SCH 420814 or 2-(2-Furanyl)-7-[2-[4-[4-(2-methoxyethoxy)phenyl]-1-piperazinyl]ethyl]7H-pyrazolo[4,3-e][1,2,4]triazolo[1,5-c]pyrimidine-5-amine. Preladenant was developed as a drug that acted as a potent and selective antagonist at the adenosine A2A receptor.

In some embodiments, the A2aR antagonist is vipadenan. Vipadenan is also known as BIIB014, V2006, or 3-[(4-amino-3-methylphenyl)methyl]-7-(furan-2-yl)triazolo[4,5-d]pyrimidin-5-amine. Other exemplary A2aR antagonists include, e.g., ATL-444, MSX-3, SCH-58261, SCH-412,348, SCH-442,416, VER-6623, VER-6947, VER-7835, CGS-15943, and ZM-241,385.

In some embodiments, the A2aR antagonist is an A2aR pathway antagonist (e.g., a CD-73 inhibitor, e.g., an anti-CD73 antibody) is MEDI9447. MEDI9447 is a monoclonal antibody specific for CD73. Targeting the extracellular production of adenosine by CD73 may reduce the immunosuppressive effects of adenosine. MEDI9447 was reported to have a range of activities, e.g., inhibition of CD73 ectonucleotidase activity, relief from AMP-mediated lymphocyte suppression, and inhibition of syngeneic tumor growth. MEDI9447 can drive changes in both myeloid and lymphoid infiltrating leukocyte populations within the tumor microenvironment. These changes include, e.g., increases in CD8 effector cells and activated macrophages, as well as a reduction in the proportions of myeloid-derived suppressor cells (MDSC) and regulatory T lymphocytes.

IDO Inhibitors

In some embodiments, an inhibitor of indoleamine 2,3-dioxygenase (IDO) and/or tryptophan 2,3-dioxygenase (TDO) is used in combination with the compounds of Formula (I') or Formula (I), or a pharmaceutically acceptable salt, hydrate, solvate, prodrug, stereoisomer, or tautomer thereof, for treating a disease, e.g., cancer. In some embodiments, the IDO inhibitor is chosen from (4E)-4-[(3-chloro-4-fluoroanilino)-nitrosomethylidene]-1,2,5-oxadiazol-3-amine (also known as epacadostat or INCB24360), indoximod ( ), (1-methyl-D-tryptophan), α-cyclohexyl-5H-Imidazo[5,1-a]isoindole-5-ethanol (also known as NLG919), indoximod, and BMS-986205 (formerly F001287).

Exemplary IDO Inhibitors

In some embodiments, the IDO/TDO inhibitor is indoximod (New Link Genetics). Indoximod, the D isomer of 1-methyl-tryptophan, is an orally administered small-molecule indoleamine 2,3-dioxygenase (IDO) pathway inhibitor that disrupts the mechanisms by which tumors evade immune-mediated destruction.

In some embodiments, the IDO/TDO inhibitor is NLG919 (New Link Genetics). NLG919 is a potent IDO (indoleamine-(2,3)-dioxygenase) pathway inhibitor with Ki/EC50 of 7 nM/75 nM in cell-free assays.

In some embodiments, the IDO/TDO inhibitor is epacadostat (CAS Registry Number: 1204669-58-8). Epacadostat is also known as INCB24360 or INCB024360 (Incyte). Epacadostat is a potent and selective indoleamine 2,3-dioxygenase (IDO1) inhibitor with IC50 of 10 nM, highly selective over other related enzymes such as IDO2 or tryptophan 2,3-dioxygenase (TDO).

In some embodiments, the IDO/TDO inhibitor is F001287 (Flexus/BMS). F001287 is a small molecule inhibitor of indoleamine 2,3-dioxygenase 1 (IDO1).

STING Agonists

In some embodiments, a STING agonist is used in combination with the compounds of Formula (I') or Formula (I), or a pharmaceutically acceptable salt, hydrate, solvate, prodrug, stereoisomer, or tautomer thereof, for treating a disease, e.g., cancer. In some embodiments, the STING agonist is cyclic dinucleotide, e.g., a cyclic dinucleotide comprising purine or pyrimidine nucleobases (e.g., adenosine, guanine, uracil, thymine, or cytosine nucleobases). In some embodiments, the nucleobases of the cyclic dinucleotide comprise the same nucleobase or different nucleobases.

In some embodiments, the STING agonist comprises an adenosine or a guanosine nucleobase. In some embodiments, the STING agonist comprises one adenosine nucleobase and one guanosine nucleobase. In some embodiments, the STING agonist comprises two adenosine nucleobases or two guanosine nucleobases.

In some embodiments, the STING agonist comprises a modified cyclic dinucleotide, e.g., comprising a modified nucleobase, a modified ribose, or a modified phosphate linkage. In some embodiments, the modified cyclic dinucleotide comprises a modified phosphate linkage, e.g., a thiophosphate.

In some embodiments, the STING agonist comprises a cyclic dinucleotide (e.g., a modified cyclic dinucleotide) with 2',5' or 3',5' phosphate linkages. In some embodiments, the STING agonist comprises a cyclic dinucleotide (e.g., a modified cyclic dinucleotide) with Rp or Sp stereochemistry around the phosphate linkages.

In some embodiments, the STING agonist is MK-1454 (Merck). MK-1454 is a cyclic dinucleotide Stimulator of Interferon Genes (STING) agonist that activates the STING pathway. Exemplary STING agonist are disclosed, e.g., in PCT Publication No. WO 2017/027645.

Galectin Inhibitors

In some embodiments, a Galectin, e.g., Galectin-1 or Galectin-3, inhibitor is used in combination with the compounds of Formula (I') or Formula (I), or a pharmaceutically acceptable salt, hydrate, solvate, prodrug, stereoisomer, or tautomer thereof, for treating a disease, e.g., cancer. In some embodiments, the combination comprises a Galectin-1 inhibitor and a Galectin-3 inhibitor. In some embodiments, the combination comprises a bispecific inhibitor (e.g., a bispecific antibody molecule) targeting both Galectin-1 and Galectin-3. In some embodiments, the Galectin inhibitor is chosen from an anti-Galectin antibody molecule, GR-MD-02 (Galectin Therapeutics), Galectin-3C (Mandal Med), Anginex, or OTX-008 (OncoEthix, Merck). Galectins are a family of proteins that bind to beta galactosidase sugars.

The Galectin family of proteins comprises at least of Galectin-1, Galectin-2, Galectin-3, Galectin-4, Galectin-7, and Galectin-8. Galectins are also referred to as S-type lectins, and are soluble proteins with, e.g., intracellular and extracellular functions.

Galectin-1 and Galectin-3 are highly expressed in various tumor types. Galectin-1 and Galectin-3 can promote angiogenesis and/or reprogram myeloid cells toward a pro-tumor phenotype, e.g., enhance immunosuppression from myeloid cells. Soluble Galectin-3 can also bind to and/or inactivate infiltrating T cells.

Exemplary Galectin Inhibitors

In some embodiments, a Galectin inhibitor is an antibody molecule. In an embodiment, an antibody molecule is a monospecific antibody molecule and binds a single epitope. E.g., a monospecific antibody molecule having a plurality of immunoglobulin variable domain sequences, each of which binds the same epitope. In an embodiment, the Galectin inhibitor is an anti-Galectin, e.g., anti-Galectin-1 or anti-Galectin-3, antibody molecule. In some embodiments, the Galectin inhibitor is an anti-Galectin-1 antibody molecule. In some embodiments, the Galectin inhibitor is an anti-Galectin-3 antibody molecule.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap. In an embodiment, the first and second epitopes do not overlap. In an embodiment, the first and second epitopes are on different antigens, e.g., the different proteins (or different subunits of a multimeric protein). In an embodiment, a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule.

In an embodiment, the Galectin inhibitor is a multispecific antibody molecule. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap. In an embodiment, the first and second epitopes do not overlap. In an embodiment, the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody molecule comprises a half antibody having binding specificity for a first epitope and a half antibody having binding specificity for a second epitope. In an embodiment, a bispecific antibody molecule comprises a half antibody, or fragment thereof, having binding specificity for a first epitope and a half antibody, or fragment thereof, having binding specificity for a second epitope. In an embodiment, a bispecific antibody molecule comprises a scFv, or fragment thereof, have binding specificity for a first epitope and a scFv, or fragment thereof, have binding specificity for a second epitope. In an embodiment, the Galectin inhibitor is a bispecific antibody molecule. In an embodiment, the first epitope is located on Galectin-1, and the second epitope is located on Galectin-3.

Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also disclosed creating bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002/004587A1, US2002/076406A1, US2002/103345A1, US2003/207346A1, US2003/211078A1, US2004/219643A1, US2004/220388A1, US2004/242847A1, US2005/003403A1, US2005/004352A1, US2005/069552A1, US2005/079170A1, US2005/100543A1, US2005/136049A1, US2005/136051A1, US2005/163782A1, US2005/266425A1, US2006/083747A1, US2006/120960A1, US2006/204493A1, US2006/263367A1, US2007/004909A1, US2007/087381A1, US2007/128150A1, US2007/141049A1, US2007/154901A1, US2007/274985A1, US2008/050370A1, US2008/069820A1, US2008/152645A1, US2008/171855A1, US2008/241884A1, US2008/254512A1, US2008/260738A1, US2009/130106A1, US2009/148905A1, US2009/155275A1, US2009/162359A1, US2009/162360A1, US2009/175851A1, US2009/175867A1, US2009/232811A1, US2009/234105A1, US2009/263392A1, US2009/274649A1, EP346087A2, WO00/06605A2, WO02/072635A2, WO04/081051A1, WO06/020258A2, WO2007/044887A2, WO2007/095338A2, WO2007/137760A2, WO2008/119353A1, WO2009/021754A2, WO2009/068630A1, WO91/03493A1, WO93/23537A1, WO94/09131A1, WO94/12625A2, WO95/09917A1, WO96/37621A2, WO99/64460A1. The contents of the above-referenced applications are incorporated herein by reference in their entireties.

In other embodiments, the anti-Galectin, e.g., anti-Galectin-1 or anti-Galectin-3, antibody molecule (e.g., a monospecific, bispecific, or multispecific antibody molecule) is covalently linked, e.g., fused, to another partner e.g., a protein, e.g., as a fusion molecule for example a fusion protein. In one embodiment, a bispecific antibody molecule has a first binding specificity to a first target (e.g., to Galectin-1), a second binding specificity to a second target (e.g., Galectin-3).

This invention provides an isolated nucleic acid molecule encoding the above antibody molecule, vectors and host cells thereof. The nucleic acid molecule includes but is not limited to RNA, genomic DNA and cDNA.

In some embodiments, a Galectin inhibitor is a peptide, e.g., protein, which can bind to, and inhibit Galectin, e.g., Galectin-1 or Galectin-3, function. In some embodiments, the Galectin inhibitor is a peptide which can bind to, and inhibit Galectin-3 function. In some embodiments, the Galectin inhibitor is the peptide Galectin-3C. In some embodiments, the Galectin inhibitor is a Galectin-3 inhibitor disclosed in U.S. Pat. No. 6,770,622, which is hereby incorporated by reference in its entirety.

Galectin-3C is an N-terminal truncated protein of Galectin-3, and functions, e.g., as a competitive inhibitor of Galectin-3. Galectin-3C prevents binding of endogenous Galectin-3 to e.g., laminin on the surface of, e.g., cancer cells, and other beta-galactosidase glycoconjugates in the extracellular matrix (ECM). Galectin-3C and other exemplary Galectin inhibiting peptides are disclosed in U.S. Pat. No. 6,770,622.

In some embodiments, Galectin-3C comprises the amino acid sequence of SEQ ID NO: 279, or an amino acid substantially identical (e.g., 90, 95 or 99%) identical thereto.

```
                                          (SEQ ID NO: 279)
GAPAGPLIVPYNLPLPGGVVPRMLITILGTVKPNANRIALDFQRGND

VAFHFNPRFNENNRRVIVCNTKLDNNWGREERQSVFPFESGKPFKIQVL

VEPDHFKVAVNDAHLLQYNHRVKKLNEISKLGISGDIDITSASYTMI.
```

In some embodiments, the Galectin inhibitor is a peptide, which can bind to, and inhibit Galectin-1 function. In some embodiments, the Galectin inhibitor is the peptide Anginex: Anginex is an anti-angiongenic peptide that binds Galectin-1 (Salomonsson E, et al., (2011) Journal of Biological Chemistry, 286(16):13801-13804). Binding of Anginex to Galectin-1 can interfere with, e.g., the pro-angiongenic effects of Galectin-1.

In some embodiments, the Galectin, e.g., Galectin-1 or Galectin-3, inhibitor is a non-peptidic topomimetic molecule. In some embodiments, the non-peptidic topomimetic Galectin inhibitor is OTX-008 (OncoEthix). In some embodiments, the non-peptidic topomimetic is a non-peptidic topomimetic disclosed in U.S. Pat. No. 8,207,228, which is herein incorporated by reference in its entirety. OTX-008, also known as PTX-008 or Calixarene 0118, is a selective allosteric inhibitor of Galectin-1. OTX-008 has the chemical name: N-[2-(dimethylamino)ethyl]-2-{[26,27,28-tris({[2-(dimethylamino)ethyl]carbamoyl}methoxy) pentacyclo[19.3.1.1,7.1,15,]octacosa-1(25),3(28),4,6,9(27),1012,15,17,19(26),21,23-dodecaen-25-yl]oxy}acetamide.

In some embodiments, the Galectin, e.g., Galectin-1 or Galectin-3, inhibitor is a carbohydrate based compound. In some embodiments, the Galectin inhibitor is GR-MD-02 (Galectin Therapeutics).
In some embodiments, GR-MD-02 is a Galectin-3 inhibitor. GR-MD-02 is a galactose-pronged polysaccharide also referred to as, e.g., a galactoarabino-rhamnogalaturonate. GR-MD-02 and other galactose-pronged polymers, e.g., galactoarabino-rhamnogalaturonates, are disclosed in U.S. Pat. No. 8,236,780 and U.S. Publication 2014/0086932, the entire contents of which are herein incorporated by reference in their entirety.

MEK Inhibitors

In some embodiments, a MEK inhibitor is used in combination with the compounds of Formula (I') or Formula (I), or a pharmaceutically acceptable salt, hydrate, solvate, prodrug, stereoisomer, or tautomer thereof, for treating a disease, e.g., cancer. In some embodiments, the MEK inhibitor is chosen from Trametinib, selumetinib, AS703026, BIX 02189, BIX 02188, CI-1040, PD0325901, PD98059, U0126, XL-518, G-38963, or G02443714. In some embodiments, the MEK inhibitor is Trametinib.

Exemplary MEK Inhibitors

In some embodiments, the MEK inhibitor is trametinib. Trametinib is also known as JTP-74057, TMT212, N-(3-{3-cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide, or Mekinist (CAS Number 871700-17-3).

Other Exemplary MEK Inhibitors

In some embodiments the MEK inhibitor comprises selumetinib which has the chemical name: (5-[(4-bromo-2-chlorophenyl)amino]-4-fluoro-N-(2-hydroxyethoxy)-1-methyl-1H-benzimidazole-6-carboxamide. Selumetinib is also known as AZD6244 or ARRY 142886, e.g., as described in PCT Publication No. WO2003077914.

In some embodiments, the MEK inhibitor comprises AS703026, BIX 02189 or BIX 02188.

In some embodiments, the MEK inhibitor comprises 2-[(2-Chloro-4-iodophenyl)amino]-N-(cyclopropyl-methoxy)-3,4-difluoro-benzamide (also known as CI-1040 or PD184352), e.g., as described in PCT Publication No. WO2000035436).

In some embodiments, the MEK inhibitor comprises N-[(2R)-2,3-Dihydroxypropoxy]-3,4-difluoro-2-[(2-fluoro-4-iodophenyl)amino]-benzamide (also known as PD0325901), e.g., as described in PCT Publication No. WO2002006213).

In some embodiments, the MEK inhibitor comprises 2'-amino-3'-methoxyflavone (also known as PD98059) which is available from Biaffin GmbH & Co., KG, Germany.

In some embodiments, the MEK inhibitor comprises 2,3-bis[amino[(2-aminophenyl)thio]methylene]-butanedinitrile (also known as U0126), e.g., as described in U.S. Pat. No. 2,779,780).

In some embodiments, the MEK inhibitor comprises XL-518 (also known as GDC-0973) which has a CAS No. 1029872-29-4 and is available from ACC Corp.

In some embodiments, the MEK inhibitor comprises G-38963.

In some embodiments, the MEK inhibitor comprises G02443714 (also known as AS703206)

Additional examples of MEK inhibitors are disclosed in WO 2013/019906, WO 03/077914, WO 2005/121142, WO 2007/04415, WO 2008/024725 and WO 2009/085983, the contents of which are incorporated herein by reference. Further examples of MEK inhibitors include, but are not limited to, 2,3-Bis[amino[(2-aminophenyl)thio]methylene]-butanedinitrile (also known as U0126 and described in U.S. Pat. No. 2,779,780); (3S,4R,5Z,8S,9S,11E)-14-(Ethylamino)-8,9,16-trihydroxy-3,4-dimethyl-3,4,9, 19-tetrahydro-1H-2-benzoxacyclotetradecine-1,7(8H)-dione] (also known as E6201, described in PCT Publication No. WO2003076424); vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7 (3H,8H)-dione (TAK-733, CAS 1035555-63-5); pimasertib (AS-703026, CAS 1204531-26-9); 2-(2-Fluoro-4-iodophenylamino)-N-(2-hydroxyethoxy)-1,5-dimethyl-6-oxo-1,6-dihydropyridine-3-carboxamide (AZD 8330); and 3,4-Difluoro-2-[(2-fluoro-4-iodophenyl)amino]-N-(2-hydroxyethoxy)-5-[(3-oxo-[1,2]oxazinan-2-yl)methyl] benzamide (CH 4987655 or Ro 4987655).

c-MET Inhibitors

In some embodiments, a c-MET inhibitor is used in combination with the compounds of Formula (I') or Formula (I), or a pharmaceutically acceptable salt, hydrate, solvate, prodrug, stereoisomer, or tautomer thereof, for treating a disease, e.g., cancer. c-MET, a receptor tyrosine kinase overexpressed or mutated in many tumor cell types, plays key roles in tumor cell proliferation, survival, invasion, metastasis, and tumor angiogenesis. Inhibition of c-MET may induce cell death in tumor cells overexpressing c-MET protein or expressing constitutively activated c-MET protein.

In some embodiments, the c-MET inhibitor is chosen from capmatinib (1NC280), JNJ-3887605, AMG 337, LY2801653, MSC2156119J, crizotinib, tivantinib, or golvatinib.

Exemplary c-MET Inhibitors

In some embodiments, the c-MET inhibitor comprises capmatinib (1NC280), or a compound described in U.S. Pat. Nos. 7,767,675, and 8,461,330, which are incorporated by reference in their entirety.

Other Exemplary c-MET Inhibitors

In some embodiments, the c-MET inhibitor comprises JNJ-38877605. JNJ-38877605 is an orally available, small molecule inhibitor of c-Met. JNJ-38877605 selectively binds to c-MET, thereby inhibiting c-MET phosphorylation and disrupting c-Met signal transduction pathways.

In some embodiments, the c-Met inhibitor is AMG 208. AMG 208 is a selective small-molecule inhibitor of c-MET. AMG 208 inhibits the ligand-dependent and ligand-independent activation of c-MET, inhibiting its tyrosine kinase activity, which may result in cell growth inhibition in tumors that overexpress c-Met.

In some embodiments, the c-Met inhibitor comprises AMG 337. AMG 337 is an orally bioavailable inhibitor of c-Met. AMG 337 selectively binds to c-MET, thereby disrupting c-MET signal transduction pathways.

In some embodiments, the c-Met inhibitor comprises LY2801653. LY2801653 is an orally available, small molecule inhibitor of c-Met. LY2801653 selectively binds to c-MET, thereby inhibiting c-MET phosphorylation and disrupting c-Met signal transduction pathways.

In some embodiments, c-Met inhibitor comprises MSC2156119J. MSC2156119J is an orally bioavailable inhibitor of c-Met. MSC2156119J selectively binds to c-MET, which inhibits c-MET phosphorylation and disrupts c-Met-mediated signal transduction pathways.

In some embodiments, the c-MET inhibitor is capmatinib. Capmatinib is also known as INCB028060. Capmatinib is an orally bioavailable inhibitor of c-MET. Capmatinib selectively binds to c-Met, thereby inhibiting c-Met phosphorylation and disrupting c-Met signal transduction pathways.

In some embodiments, the c-MET inhibitor comprises crizotinib. Crizotinib is also known as PF-02341066. Crizotinib is an orally available aminopyridine-based inhibitor of the receptor tyrosine kinase anaplastic lymphoma kinase (ALK) and the c-Met/hepatocyte growth factor receptor (HGFR). Crizotinib, in an ATP-competitive manner, binds to and inhibits ALK kinase and ALK fusion proteins. In addition, crizotinib inhibits c-Met kinase, and disrupts the c-Met signalling pathway. Altogether, this agent inhibits tumor cell growth.

In some embodiments, the c-MET inhibitor comprises golvatinib. Golvatinib is an orally bioavailable dual kinase inhibitor of c-MET and VEGFR-2 with potential antineoplastic activity. Golvatinib binds to and inhibits the activities of both c-MET and VEGFR-2, which may inhibit tumor cell growth and survival of tumor cells that overexpress these receptor tyrosine kinases.

In some embodiments, the c-MET inhibitor is tivantinib. Tivantinib is also known as ARQ 197. Tivantinib is an orally bioavailable small molecule inhibitor of c-MET. Tivantinib binds to the c-MET protein and disrupts c-Met signal transduction pathways, which may induce cell death in tumor cells overexpressing c-MET protein or expressing constitutively activated c-Met protein.

TGF-β Inhibitors

In some embodiments, a transforming growth factor beta (also known as TGF-β TGFβ, TGFb, or TGF-beta, used interchangeably herein) inhibitor is used in combination with the compounds of Formula (I') or Formula (I), or a pharmaceutically acceptable salt, hydrate, solvate, prodrug, stereoisomer, or tautomer thereof, for treating a disease, e.g., cancer. In certain embodiments, a combination described herein comprises a transforming growth factor beta (also known as TGF-β TGFβ, TGFb, or TGF-beta, used interchangeably herein) inhibitor.

TGF-β belongs to a large family of structurally-related cytokines including, e.g., bone morphogenetic proteins (BMPs), growth and differentiation factors, activins and inhibins. In some embodiments, the TGF-3 inhibitors described herein can bind and/or inhibit one or more isoforms of TGF-β (e.g., one, two, or all of TGF-β1, TGF-β2, or TGF-β3).

Under normal conditions, TGF-β maintains homeostasis and limits the growth of epithelial, endothelial, neuronal and hematopoietic cell lineages, e.g., through the induction of anti-proliferative and apoptotic responses. Canonical and non-canonical signalling pathways are involved in cellular responses to TGF-β. Activation of the TGF-β/Smad canonical pathway can mediate the anti-proliferative effects of TGF-β. The non-canonical TGF-β pathway can activate additional intra-cellular pathways, e.g., mitogen-activated protein kinases (MAPK), phosphatidylinositol 3 kinase/Protein Kinase B, Rho-like GTPases (Tian et al. *Cell Signal.* 2011; 23(6):951-62; Blobe et al. *N Engl J Med.* 2000; 342(18):1350-8), thus modulating epithelial to mesenchymal transition (EMT) and/or cell motility.

Alterations of TGF-β signalling pathway are associated with human diseases, e.g., cancers, cardio-vascular diseases, fibrosis, reproductive disorders, and wound healing. Without wishing to be bound by theory, it is believed that in some embodiments, the role of TGF-β in cancer is dependent on the disease setting (e.g., tumor stage and genetic alteration) and/or cellular context. For example, in late stages of cancer, TGF-β can modulate a cancer-related process, e.g., by promoting tumor growth (e.g., inducing EMT), blocking anti-tumor immune responses, increasing tumor-associated fibrosis, or enhancing angiogenesis (Wakefield and Hill *Nat Rev Cancer.* 2013; 13(5):328-41). In certain embodiments, a combination comprising a TGF-β inhibitor described herein is used to treat a cancer in a late stage, a metastatic cancer, or an advanced cancer.

Preclinical evidence indicates that TGF-β plays an important role in immune regulation (Wojtowicz-Praga *Invest New Drugs.* 2003; 21(1):21-32; Yang et al. *Trends Immunol.* 2010; 31(6):220-7). TGF-β can down-regulate the host-immune response via several mechanisms, e.g., shift of the T-helper balance toward Th2 immune phenotype; inhibition of anti-tumoral Th1 type response and M1-type macrophages; suppression of cytotoxic CD8+T lymphocytes (CTL), NK lymphocytes and dendritic cell functions, generation of CD4+ CD25+T-regulatory cells; or promotion of M2-type macrophages with pro-tumoral activity mediated by secretion of immunosuppressive cytokines (e.g., IL10 or VEGF), pro-inflammatory cytokines (e.g., IL6, TNFα, or IL1) and generation of reactive oxygen species (ROS) with genotoxic activity (Yang et al. *Trends Immunol.* 2010; 31(6): 220-7; Truty and Urrutia Pancreatology. 2007; 7(5-6):423-35; Achyut et al *Gastroenterology.* 2011; 141(4):1167-78).

Exemplary TGF-β Inhibitors

In some embodiments, the TGF-β inhibitor comprises XOMA 089, or a compound disclosed in International Application Publication No. WO 2012/167143, which is incorporated by reference in its entirety.

XOMA 089 is also known as XPA.42.089. XOMA 089 is a fully human monoclonal antibody that specifically binds and neutralizes TGF-beta 1 and 2 ligands.

The heavy chain variable region of XOMA 089 has the amino acid sequence of: QVQLVQS- GAEVKKPGSSVKVSCK-
ASGGTFSSYAISWVRQAPGQGLEWMGGIIPIFGTAN-
YAQKF
QGRVTITADESTSTAYMELSSLRSEDTAVYYCAR-
GLWEVRALPSVYWGQGTLVTVSS (SEQ ID NO: 284) (disclosed as SEQ ID NO: 6 in WO 2012/167143). The light chain variable region of XOMA 089 has the amino acid sequence of: SYELTQPPSVSVAPGQTARITCGANDIG-SKSVHWYQQKAGQAPVLVVSEDIIRPSGIPERISG-SNSG NTATLTISRVEAGDEADYYCQVW-DRDSDQYVFGTGTKVTVLG (SEQ ID NO: 285) (disclosed as SEQ ID NO: 8 in WO 2012/167143).

XOMA 089 binds with high affinity to the human TGF-β isoforms. Generally, XOMA 089 binds with high affinity to TGF-β1 and TGF-β2, and to a lesser extent to TGF-β3. In Biacore assays, the $K_D$ of XOMA 089 on human TGF-β is 14.6 pM for TGF-β1, 67.3 pM for TGF-β2, and 948 pM for TGF-33. Given the high affinity binding to all three TGF-β isoforms, in certain embodiments, XOMA 089 is expected to bind to TGF-β1, 2 and 3 at a dose of XOMA 089 as described herein. XOMA 089 cross-reacts with rodent and cynomolgus monkey TGF-β and shows functional activity in vitro and in vivo, making rodent and cynomolgus monkey relevant species for toxicology studies.

Other Exemplary TGF-β Inhibitors

In some embodiments, the TGF-β inhibitor comprises fresolimumab (CAS Registry Number: 948564-73-6). Fresolimumab is also known as GC1008. Fresolimumab is a human monoclonal antibody that binds to and inhibits TGF-beta isoforms 1, 2 and 3.

The heavy chain of fresolimumab has the amino acid sequence of:

(SEQ ID NO: 280)
QVQLVQSGAEVKKPGSSVKVSCKASGYTFSSNVISWVRQAPGQGLEWMGG

VIPIVDIANYAQRFKGRVTITADESTSTTYMELSSLRSEDTAVYYCASTL

GLVLDAMDYWGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPSCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK.

The light chain of fresolimumab has the amino acid sequence of:

(SEQ ID NO: 281)
ETVLTQSPGTLSLSPGERATLSCRASQSLGSSYLAWYQQKPGQAPRLLIY

GASSRAPGIPDRFSGSGSGTDFTLTISRLEPEDFAVYYCQQYADSPITFG

QGTRLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC.

Fresolimumab is disclosed, e.g., in International Application Publication No. WO 2006/086469, and U.S. Pat. Nos. 8,383,780 and 8,591,901, which are incorporated by reference in their entirety.

IL-1β Inhibitors

The Interleukin-1 (IL-1) family of cytokines is a group of secreted pleotropic cytokines with a central role in inflammation and immune response. Increases in IL-1 are observed in multiple clinical settings including cancer (Apte et al. (2006) *Cancer Metastasis Rev.* p. 387-408; Dinarello (2010) *Eur. J. Immunol.* p. 599-606). The IL-1 family comprises, inter alia, IL-1 beta (IL-1b), and IL-1alpha (IL-1a). IL-1b is elevated in lung, breast and colorectal cancer (Voronov et al. (2014) *Front Physiol.* p. 114) and is associated with poor prognosis (Apte et al. (2000) *Adv. Exp. Med. Biol.* p. 277-88). Without wishing to be bound by theory, it is believed that in some embodiments, secreted IL-1b, derived from the tumor microenvironment and by malignant cells, promotes tumor cell proliferation, increases invasiveness and dampens anti-tumor immune response, in part by recruiting inhibitory neutrophils (Apte et al. (2006) *Cancer Metastasis Rev.* p. 387-408; Miller et al. (2007) *J. Immunol.* p. 6933-42). Experimental data indicate that inhibition of IL-1b results in a decrease in tumor burden and metastasis (Voronov et al. (2003) *Proc. Natl. Acad. Sci. U.S.A.* p. 2645-50).

In some embodiments, an interleukin-1 beta (IL-1(3) inhibitor is used in combination with the compounds of Formula (I') or Formula (I), or a pharmaceutically acceptable salt, hydrate, solvate, prodrug, stereoisomer, or tautomer thereof, for treating a disease, e.g., cancer. In some embodiments, the IL-13 inhibitor is chosen from canakinumab, gevokizumab, Anakinra, or Rilonacept. In some embodiments, the IL-1β inhibitor is canakinumab.

Exemplary IL-1 Inhibitors

In some embodiments, the IL-1(3 inhibitor is canakinumab. Canakinumab is also known as ACZ885 or ILARIS®. Canakinumab is a human monoclonal IgG1/K antibody that neutralizes the bioactivity of human IL-1β.

Canakinumab is disclosed, e.g., in WO 2002/16436, U.S. Pat. No. 7,446,175, and EP 1313769. The heavy chain variable region of canakinumab has the amino acid sequence of: MEFGLSWVFLVALLRGVQCQVQLVES-GGGVVQPGRSLRLS-
CAASGFTFSVYGMNWVRQAPGK GLEWVAII-WYDGDNQYYADSVKGRFTISRDNSKNTLYLQMNGL-RAEDTAVYYCARDLRTGPFD YWGQGTLVTVSS (SEQ ID NO: 282) (disclosed as SEQ ID NO: 1 in U.S. Pat. No. 7,446,175). The light chain variable region of canakinumab has the amino acid sequence of: MLPSQLIGFLLLWVPAS-RGEIVLTQSPDFQSVTPKEKVTIT-
CRASQSIGSSLHWYQQKPDQSPKLLI
KYASQSFSGVPSRFSGSGSGTDFTLTINSLEAE-
DAAAYYCHQSSSLPFTFGPGTKVDIK (SEQ ID NO: 283) (disclosed as SEQ ID NO: 2 in U.S. Pat. No. 7,446, 175).

Canakinumab has been used, e.g., for the treatment of Cryopyrin Associated Periodic Syndromes (CAPS), in adults and children, for the treatment of systemic juvenile idiopathic arthritis (SJIA), for the symptomatic treatment of acute gouty arthritis attacks in adults, and for other IL-1β driven inflammatory diseases. Without wishing to be bound by theory, it is believed that in some embodiments, IL-1β inhibitors, e.g., canakinumab, can increase anti-tumor immune response, e.g., by blocking one or more functions of IL-1b including, e.g., recruitment of immunosuppressive neutrophils to the tumor microenvironment, stimulation of tumor angiogenesis, and/or promotion of metastasis (Dinarello (2010) *Eur. J. Immunol.* p. 599-606).

In some embodiments, the combination described herein includes an IL-1(3 inhibitor, canakinumab, or a compound disclosed in WO 2002/16436, and an inhibitor of an immune checkpoint molecule, e.g., an inhibitor of PD-1 (e.g., an anti-PD-1 antibody molecule). IL-1 is a secreted pleotropic cytokine with a central role in inflammation and immune response. Increases in IL-1 are observed in multiple clinical settings including cancer (Apte et al. (2006) *Cancer Metastasis Rev.* p. 387-408; Dinarello (2010) *Eur. J. Immunol.* p. 599-606). IL-1b is elevated in lung, breast and colorectal cancer (Voronov et al. (2014) *Front Physiol.* p. 114) and is associated with poor prognosis (Apte et al. (2000) *Adv. Exp. Med. Biol.* p. 277-88). Without wishing to be bound by theory, it is believed that in some embodiments, secreted IL-1b, derived from the tumor microenvironment and by malignant cells, promotes tumor cell proliferation, increases invasiveness and dampens anti-tumor immune response, in part by recruiting inhibitory neutrophils (Apte et al. (2006) *Cancer Metastasis Rev.* p. 387-408; Miller et al. (2007) J. Immunol. p. 6933-42). Experimental data indicate that inhibition of IL-1b results in a decrease in tumor burden and metastasis (Voronov et al. (2003) *Proc. Natl. Acad. Sci. U.S.A.* p. 2645-50). Canakinumab can bind IL-1b and inhibit IL-1-mediated signalling. Accordingly, in certain embodiments, an IL-1β inhibitor, e.g., canakinumab, enhances, or is used to enhance, an immune-mediated anti-tumor effect of an inhibitor of PD-1 (e.g., an anti-PD-1 antibody molecule).

In some embodiments, the IL-1β inhibitor, canakinumab, or a compound disclosed in WO 2002/16436, and the inhibitor of an immune checkpoint molecule, e.g., an inhibitor of PD-1 (e.g., an anti-PD-1 antibody molecule), each is administered at a dose and/or on a time schedule, that in combination, achieves a desired anti-tumor activity.

MDM2 Inhibitors

In some embodiments, a mouse double minute 2 homolog (MDM2) inhibitor is used in combination with the compounds of Formula (I') or Formula (I), or a pharmaceutically acceptable salt, hydrate, solvate, prodrug, stereoisomer, or tautomer thereof, for treating a disease, e.g., cancer. The human homolog of MDM2 is also known as HDM2. In some embodiments, an MDM2 inhibitor described herein is also known as a HDM2 inhibitor. In some embodiments, the MDM2 inhibitor is chosen from HDM201 or CGM097.

In an embodiment the MDM2 inhibitor comprises (S)-1-(4-chlorophenyl)-7-isopropoxy-6-methoxy-2-(4-(methyl (((1r,4S)-4-(4-methyl-3-oxopiperazin-1-yl)cyclohexyl) methyl)amino)phenyl)-1,2-dihydroisoquinolin-3(4H)-one (also known as CGM097) or a compound disclosed in PCT Publication No. WO 2011/076786 to treat a disorder, e.g., a disorder described herein). In one embodiment, a therapeutic agent disclosed herein is used in combination with CGM097.

In an embodiment, an MDM2 inhibitor comprises an inhibitor of p53 and/or a p53/Mdm2 interaction. In an embodiment, the MDM2 inhibitor comprises (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (also known as HDM201), or a compound disclosed in PCT Publication No. WO2013/111105 to treat a disorder, e.g., a disorder described herein. In one embodiment, a therapeutic agent disclosed herein is used in combination with HDM201. In some embodiments, HDM201 is administered orally.

In one embodiment, the combination disclosed herein is suitable for the treatment of cancer in vivo. For example, the combination can be used to inhibit the growth of cancerous tumors. The combination can also be used in combination with one or more of: a standard of care treatment (e.g., for cancers or infectious disorders), a vaccine (e.g., a therapeutic cancer vaccine), a cell therapy, a radiation therapy, surgery, or any other therapeutic agent or modality, to treat a disorder herein. For example, to achieve antigen-specific enhancement of immunity, the combination can be administered together with an antigen of interest.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3rd edition, John Wiley & Sons). These groups are removed at a convenient stage of the compound synthesis using methods that are readily apparent to those skilled in the art.

Analytical Methods, Materials, and Instrumentation

Unless otherwise noted, reagents and solvents were used as received from commercial suppliers. Proton nuclear magnetic resonance (NMR) spectra were obtained on either Bruker Avance spectrometer or Varian Oxford 400 MHz spectrometer unless otherwise noted. Spectra are given in ppm (δ) and coupling constants, J, are reported in Hertz. Tetramethylsilane (($CH_3)_4$Si) was used as an internal standard. Chemical shifts are reported in ppm relative to dimethyl sulfoxide (δ 2.50), methanol (δ 3.31), chloroform (δ 7.26) or other solvent as indicated in NMR spectral data. A small amount of the dry sample (2-5 mg) is dissolved in an appropriate deuterated solvent (1 mL). The chemical names were generated using ChemBioDraw Ultra v14 from CambridgeSoft.

Mass spectra (ESI-MS) were collected using a Waters System (Acquity UPLC and a Micromass ZQ mass spectrometer) or Agilent-1260 Infinity (6120 Quadrupole); all masses reported are the m/z of the protonated parent ions unless recorded otherwise. The sample was dissolved in acquirable solvent such as MeCN, DMSO, or MeOH and was injected directly into the column using an automated sample handler. Abbreviations used in the following examples and elsewhere herein are:

AgOTf silver trifluoromethanesulfonate
AIBN azobisisobutyronitrile
aq aqueous
Boc tert-butyloxycarbonyl
Bu butyl
$Bu_4NI$ or TBAI tetrabutylammonium iodide
br broad
DAST diethylaminosulfur trifluoride
DBAD di-tert-butyl azodicarboxylate
DBU 1,8-Diazabicyclo[5.4.0]undec-7-ene
DCM dichloromethane or methylene chloride
d doublet
dd doublet of doublets
ddd doublet of doublet of doublets dddd doublet of doublet of doublets of doublets
DHP dihydropyran
DIAD diisopropyl azodicarboxylate
DMA N,N-dimethylacetamide
DMAP 4-Dimethylaminopyridine
DME 1,2-dimethoxyethane (glyme)
DMF N,N-dimethylformamide
DMP Dess-Martin periodinane
DMSO dimethylsulfoxide
dq doublet of quartets
dt doublet of triplets
dtd doublet of triplet of doublets
dtbbpy 4,4'-di-tert-butyl-2,2'-bipyridine
$EC_{50}$ half maximal effective concentration (qualified)
Et ethyl
$Et_2O$ diethyl ether
EtOAc ethyl acetate
EtOH ethanol
$Et_3SiH$ triethylsilane
g gram
h or hr hour
hept heptet
heptd heptet of doublets
HPLC high performance liquid chromatography
HRMS high resonance mass spectrometry
i-Pr isopropyl
i-$Pr_2$NEt or DIPEA N,N-diisopropylethylamine
IPA Iso-propanol
Ir[(dF($CF_3$)ppy)$_2$dtbbpy]$PF_6$ 4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate
LCMS liquid chromatography mass spectrometry
LDA lithium diisopropylamide
LED light-emitting diode
M molar
m multiplet
Me methyl
MeCN acetonitrile
MeOH methanol
mg milligram
MHz megahertz
min minutes
mL milliliter
mmol millimole
Ms methanesulfonyl
MsOH methanesulfonic acid
MS mass spectrometry
MTBE methyl tert-butyl ether
µW microwave
NaBH(OAc)$_3$ sodium triacetoxyborohydride
NaHCO$_3$ sodium carbonate
Na$_2$SO$_4$ sodium sulfate
NBS N-bromosuccinimide
NMP 1-methyl-2-pyrrolidinone
NMR Nuclear magnetic resonance
O/N overnight
Ph phenyl
PhMe toluene
Pyr pyridine
q quartet
qd quartet of doublets
quint quintet
quintd quintet of doublets
rt room temperature
Rt retention time RuPhos 2-dicyclohexylphosphino-2',6'-diisopropoxybiphenyl
s singlet
sat. saturated
SFC supercritical fluid chromatography
SPA scintillation proximity assay
SOCl$_2$ thionyl chloride
SEM 2-(trimethylsilyl)ethoxymethyl
t triplet
t-Bu or tBu tert-butyl
TBAB tetrabutylamonium bromide
TBAF tetrabutylamonium fluoride
TBS tert-butyldimethylsilyl
t-BuONa sodium tert-butoxidetd triplet of doublets
tdd triplet of doublet of doublets
TEA or Et$_3$N or NEt$_3$ triethyl amine
Tf trifluoromethanesulfonate or triflate
THF tetrahydrofuran
TFA or CF$_3$CO$_2$H trifluoroacetic acid
TFE 2,2,2-trifluoroethanol
Ti(i-OPr)$_4$ titanium(IV) isopropoxide
TLC thin layer chromatography
TMP 2,2,6,6-tetramethylpiperidine
TMS trimethylsilyl
Ts tosyl
ttd triplet of triplet of doublets
UPLC Ultra-Performance Liquid Chromatography Example 1: 3-(5-(((1S,2S)-2-aminocyclopentyl)oxy)-1-oxoisoindolin-2-yl)piperidine-2,6-dione HCl or CF$_3$CO$_2$H Salt (I-12)

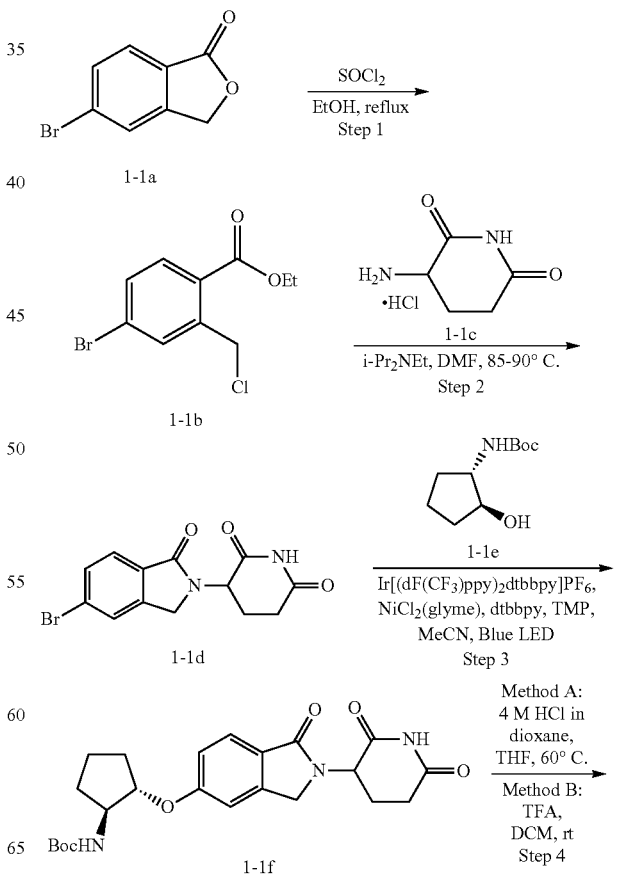

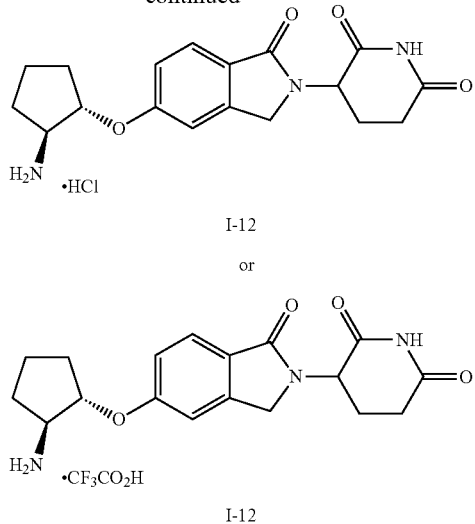

I-12 or

I-12

Step 1. Ethyl 4-bromo-2-(chloromethyl)benzoate (I-1b)

A stirred suspension of 5-bromophthalide (1-1a, 1200 g, 5.633 mol) in EtOH (12 L) was heated to 68-72° C. SOCl$_2$ (2.40 L, 33.0 mol) was then added dropwise over a period of 7 h. The reaction mixture was concentrated under reduced pressure to about 4 L, and then water (5 L) and MTBE (5 L) were added. The resulting mixture was stirred for 40 min. The phases were separated and the aqueous phase was extracted with MTBE (1×5 L). The combined organic layers were washed with 5% aq. NaHCO$_3$ (5 L), dried over Na$_2$SO$_4$, filtered, and concentrated to dryness to afford 1-1b (1450 g, 5.25 mol, 93% yield) as a pale brown solid. MS [M+Na]$^+$=298.9. $^1$H NMR (400 MHz, Chloroform-d) δ 7.85 (d, J=8.4 Hz, 1H), 7.72 (d, J=2.0 Hz, 1H), 7.52 (dd, J=8.3, 2.0 Hz, 1H), 5.00 (s, 2H), 4.38 (q, J=7.1 Hz, 2H), 1.40 (t, J=7.1 Hz, 3H).

Step 2. 3-(5-bromo-1-oxoisoindolin-2-yl)piperidine-2,6-dione (1-1d)

To a stirred suspension of 3-aminopiperidine-2,6-dione hydrochloride (1-1c, 596.3 g, 3.623 mol) and i-Pr$_2$NEt (2.50 L, 14.3 mol) in DMF (5.0 L) was added 1-1b (1000 g, 3.623 mmol) and the resulting reaction mixture was stirred at 85-90° C. for 24 h. The reaction mixture was then allowed to cool to room temperature, water (20 L) was added, and the resulting mixture was stirred for 12 h. The formed precipitate was filtered and washed with water (5 L) and MeOH (2 L). The crude solid was slurried in MeOH (5 L) for 1 h, filtered, and washed with MeOH (2 L). The resulting solid was then taken in EtOAc (10 L) and stirred for 1 h. The obtained suspension was then filtered, washed with EtOAc (5 L), and dried under reduced pressure at 45-50° C. to afford 1-1d (740 g, 2.29 mol, 63% yield) as an off-white solid. MS [M+H]$^+$=323.2. $^1$H NMR (400 MHz, DMSO-d$_6$) δ 10.99 (s, 1H), 7.91-7.88 (m, 1H), 7.72 (dd, J=8.1, 1.6 Hz, 1H), 7.67 (d, J=8.0 Hz, 1H), 5.11 (dd, J=13.3, 5.1 Hz, 1H), 4.47 (d, J=17.7 Hz, 1H), 4.34 (d, J=17.7 Hz, 1H), 2.98-2.83 (m, 1H), 2.65-2.55 (m, 1H), 2.45-2.29 (m, 1H), 2.01 (dtd, J=12.7, 5.3, 2.3 Hz, 1H).

Step 3. tert-butyl ((1S,2S)-2-((2-(2,6-dioxopiperidin-3-yl)-1-oxoisoindolin-5-yl)oxy)cyclopentyl)carbamate (1-1f)

To a stirred suspension of 3-(5-bromo-1-oxoisoindolin-2-yl)piperidine-2,6-dione (1-1d, 2.65 g, 8.20 mmol), tert-butyl ((1S,2S)-2-hydroxycyclopentyl)carbamate (1-1e, 1.50 g, 7.45 mmol), NiCl$_2$(glyme) (0.082 g, 0.37 mmol), dtbbpy (0.100 g, 0.373 mmol) and Ir[(dF(CF$_3$)ppy)$_2$dtbbpy]PF$_6$ (0.083 g, 0.075 mmol) in MeCN (25 mL) under a nitrogen atmosphere was added 2,2,6,6-tetramethylpiperidine (40-2, 1.90 mL, 11.2 mmol). The resulting mixture was then stirred vigorously for 70 h under irradiation of blue LED light at room temperature. The reaction mixture was then diluted with DCM (20 mL), filtered, and concentrated to dryness. The crude material was purified by silica gel chromatography eluting with 0% to 12% EtOH:EtOAc (v/v=1:3) in DCM to afford 1-1f (1.03 g, 2.11 mmol, 28% yield) as a white powder. MS [M-tBu+H]$^+$=388.1. $^1$H NMR (400 MHz, DCM-d$_2$) δ 8.02 (s, 1H), 7.68 (d, J=8.4 Hz, 1H), 7.15 (s, 1H), 7.05 (d, J=8.5 Hz, 1H), 5.11 (ddd, J=13.1, 5.1, 2.8 Hz, 1H), 4.68-4.61 (m, 1H), 4.57 (s, 1H), 4.40-4.25 (m, 2H), 4.04-3.97 (m, 1H), 2.95-2.71 (m, 2H), 2.41-2.24 (m, 1H), 2.21-1.98 (m, 3H), 1.89-1.70 (m, 3H), 1.53-1.44 (m, 1H), 1.41 (s, 9H).

Step 4. Method A. 3-(5-(((1S,2S)-2-aminocyclopentyl)oxy)-1-oxoisoindolin-2-yl)piperidine-2,6-dione hydrochloride (I-12)

To a stirred solution of tert-butyl ((1S,2S)-2-((2-(2,6-dioxopiperidin-3-yl)-1-oxoisoindolin-5-yl)oxy)cyclopentyl)carbamate (1-1f, 1.50 g, 2.99 mmol) in THF (5 mL) was added 4 M HCl in dioxane (2.0 mL, 8.0 mmol). Obtained reaction mixture was stirred for 2 h at 60° C. Formation of white precipitate was observed. The reaction mixture was diluted with Et$_2$O (15 mL) and filtered. The precipitate was washed with Et$_2$O (4×) and then dried under reduced pressure to afford the hydrochloride salt of I-12 (1.01 g, 2.66 mmol, 89% yield) as a white solid. MS [M+H]$^+$=344.1. $^1$H NMR (400 MHz, DMSO-d$_6$) δ 10.98 (s, 1H), 8.36 (s, 2H), 7.68-7.63 (m, 1H), 7.34-7.18 (m, 1H), 7.08 (dt, J=8.4, 2.3 Hz, 1H), 5.08 (dd, J=13.3, 5.1 Hz, 1H), 4.95-4.82 (m, 1H), 4.41 (dd, J=17.3, 3.5 Hz, 1H), 4.28 (dd, J=17.3, 2.8 Hz, 1H), 3.62 (s, 1H), 2.99-2.83 (m, 1H), 2.69-2.54 (m, 1H), 2.47-2.31 (m, 1H), 2.31-2.21 (m, 1H), 2.18-2.06 (m, 1H), 2.04-1.94 (m, 1H), 1.89-1.62 (m, 4H).

Step 5. Method B. 3-(5-(((1S,2S)-2-aminocyclopentyl)oxy)-1-oxoisoindolin-2-yl)piperidine-2,6-dione CF$_3$CO$_2$H Salt (I-12)

To a stirred solution of tert-butyl ((1S,2S)-2-((2-(2,6-dioxopiperidin-3-yl)-1-oxoisoindolin-5-yl)oxy)cyclopentyl)carbamate (1-1f, 573 mg, 1.29 mmol) in DCM (4.3 mL) was added CF$_3$CO$_2$H (1.1 mL, 13 mmol) and the resulting mixture was stirred at room temperature for 5 h. The solution was concentrated under reduced pressure and azeotroped with PhMe to afford the desired crude product (TFA salt of I-12) as a light yellow foam (assumed quantitative yield). The crude product carried onto the next step without further purification. MS [M+H]$^+$=344.4. $^1$H NMR (400 MHz, Methanol-d$_4$) δ 7.74 (dd, J=8.4, 1.3 Hz, 1H), 7.16 (d, J=0.7 Hz, 1H), 7.13-7.09 (m, 1H), 5.12 (ddd, J=13.4, 5.2, 2.7 Hz, 1H), 4.86-4.76 (m, 1H), 4.50-4.37 (m, 2H), 3.77 (td, J=8.1, 5.3 Hz, 1H), 2.90 (ddd, J=17.6, 13.5, 5.3 Hz, 1H), 2.78 (ddd, J=17.6, 4.7, 2.4 Hz, 1H), 2.55-2.40 (m, 1H), 2.42-2.23 (m, 2H), 2.16 (dtd, J=12.9, 5.3, 2.4 Hz, 1H), 1.99-1.87 (m, 2H), 1.87-1.74 (m, 1H), 1.79-1.65 (m, 1H).

Alternatively, Conversion of 1-1d to I-12 was Also Achieved Via the Following Synthetic Procedure:

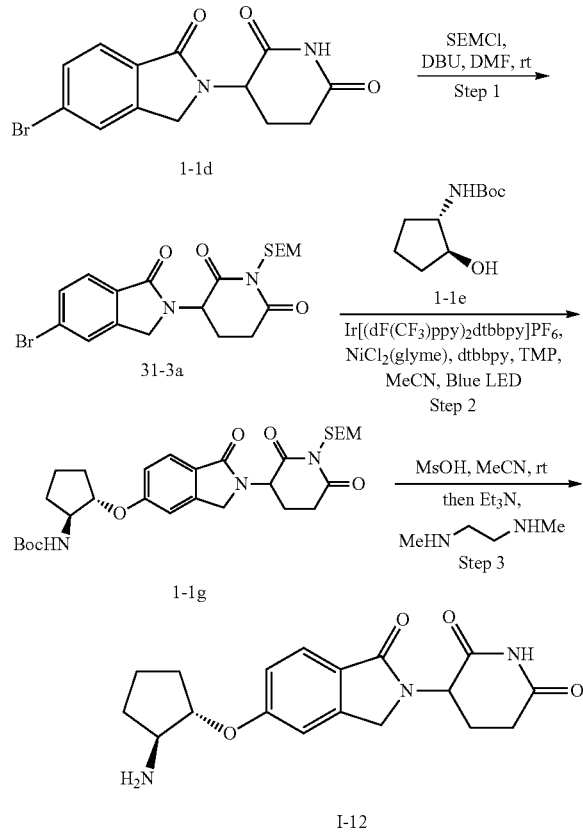

Step 1. 3-(5-bromo-1-oxoisoindolin-2-yl)-1-((2-(trimethylsilyl)ethoxy)methyl)piperidine-2,6-dione (31-3a)

To a stirred solution of 1-1d (10.0 g, 30.9 mmol) and DBU (6.9 mL, 46 mmol) in DMF (95 mL) was added SEMCl (6.6 mL, 37 mmol) at 0° C. and the resulting reaction mixture was allowed to warm to room temperature and then stirred for 5 h. An additional portion of DBU (3.5 mL, 23 mmol) and SEMCl (3.3 mL, 19 mmol) was added and stirring was continued for an additional 2 h. The reaction mixture was then quenched with sat. aq. NH$_4$Cl (250 mL) and extracted with EtOAc (×3). The combined organic phases were dried over Na$_2$SO$_4$, filtered, and concentrated to dryness. The crude material was dissolved in minimal amount of EtOAc (~50 mL) and Et$_2$O:heptane (v/v=1:2, 400 mL) was added. The resulting cloudy solution was left standing at −5° C. overnight. The formed precipitate was filtered, washed with heptane (×3), and dried under vacuum to afford 31-3a (11.53 g, 25.4 mmol, 82% yield) as an off-white solid. MS [M+H]$^+$=453.4. $^1$H NMR (400 MHz, Chloroform-d) δ 7.75 (d, J=8.6 Hz, 1H), 7.66-7.61 (m, 2H), 5.37-5.09 (m, 3H), 4.48 (d, J=16.2 Hz, 1H), 4.32 (d, J=16.2 Hz, 1H), 3.74-3.50 (m, 2H), 3.11-2.98 (m, 1H), 2.94-2.83 (m, 1H), 2.33 (qd, J=13.2, 4.7 Hz, 1H), 2.24-2.15 (m, 1H), 0.97-0.90 (m, 2H), 0.00 (s, 9H).

Step 2. tert-butyl ((1S,2S)-2-((2-(2,6-dioxo-1-((2-(trimethylsilyl)ethoxy)methyl)piperidin-3-yl)-1-oxoisoindolin-5-yl)oxy)cyclopentyl)carbamate (1-1g)

To a stirred solution of 31-3a (2.00 g, 4.41 mmol), 1-1e (0.888 g, 4.41 mmol), NiCl$_2$(glyme) (0.048 g, 0.22 mmol), dtbbpy (0.059 g, 0.22 mmol) and Ir[(dF(CF$_3$)ppy)$_2$dtbbpy]PF$_6$ (0.049 g, 0.044 mmol) in degassed MeCN (16 mL) under an atmosphere of nitrogen was added 2,2,6,6-tetramethylpiperidine (40-2, 0.75 mL, 4.4 mmol) and the resulting mixture was stirred vigorously for 24 h under irradiation of blue LED lights at room temperature. The reaction mixture was then filtered and concentrated to dryness. The crude material was purified by silica gel chromatography eluting with 0% to 100% EtOAc in heptane to afford 1-1g (2.19 g, 3.82 mmol, 87% yield) as a yellow solid. MS [M−H]$^-$=572.5. $^1$H NMR (400 MHz, DMSO-d$_6$) δ 7.63 (d, J=8.4 Hz, 1H), 7.22 (s, 1H), 7.11-7.05 (m, 1H), 5.29-5.16 (m, 1H), 5.12-5.02 (m, 2H), 4.69-4.64 (m, 1H), 4.50-4.36 (m, 1H), 4.24 (dd, J=17.0, 9.1 Hz, 1H), 3.95-3.85 (m, 1H), 3.64-3.47 (m, 2H), 3.13-3.01 (m, 1H), 2.87-2.74 (m, 1H), 2.49-2.31 (m, 1H), 2.12-1.97 (m, 3H), 1.86-1.60 (m, 3H), 1.59-1.47 (m, 1H), 1.40 (s, 9H), 0.90-0.83 (m, 2H), 0.00 (s, 9H).

Step 3. 3-(5-(((1S,2S)-2-aminocyclopentyl)oxy)-1-oxoisoindolin-2-yl)piperidine-2,6-dione (I-12)

To a solution of 1-1g (6.85 g, 9.55 mmol) in DCM (53 mL) under an atmosphere of nitrogen was added methanesulfonic acid (2.5 mL, 38 mmol) and the resulting mixture was stirred at rt overnight. The reaction mixture was cooled to 0° C. and triethylamine (10.7 mL, 76 mmol) and N1,N2-dimethylethane-1,2-diamine (1.23 mL, 11.5 mmol) were added and stirring was continued at rt for 4 h. Additional N1,N2-dimethylethane-1,2-diamine (0.51 mL, 4.8 mmol) was added and stirring was continued at rt for 30 minutes. The reaction mixture was quenched with a 50% saturated aqueous sodium hydrogen carbonate and extracted with DCM:isopropanol (v/v=4:1, ×4). The organic phases were combined, passed through a phase separator and concentrated to dryness. The material was suspended in minimal DCM and excess diethyl ether was added. The resulting suspension was sonicated for 1 hr, filtered, and rinsed with diethyl ether (×3). The solid was collected and dried in a high vacuum oven at 50° C. overnight to afford I-12 (3.02 g, 8.80 mmol, 92% yield) as a cream solid. MS [M+H]$^+$=344.1. $^1$H NMR (400 MHz, DMSO-d$_6$) δ 10.95 (s, 1H), 7.60 (d, J=8.4 Hz, 1H), 7.19-7.14 (m, 1H), 7.03 (dd, J=8.2, 2.2 Hz, 1H), 5.07 (dd, J=13.3, 5.1 Hz, 1H), 4.47-4.33 (m, 2H), 4.25 (d, J=17.1 Hz, 1H), 3.34-3.25 (m, 3H), 2.91 (ddd, J=17.5, 13.5, 5.3 Hz, 1H), 2.64-2.54 (m, 1H), 2.37 (qd, J=13.1, 4.1 Hz, 1H), 2.26-2.11 (m, 1H), 2.03-1.84 (m, 2H), 1.82-1.58 (m, 3H), 1.42-1.32 (m, 1H).

Example 2: 3-(5-(((1S,2S)-2-(diethylamino)cyclopentyl)oxy)-1-oxoisoindolin-2-yl)piperidine-2,6-dione (I-13)

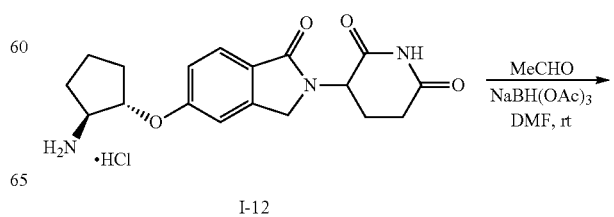

-continued

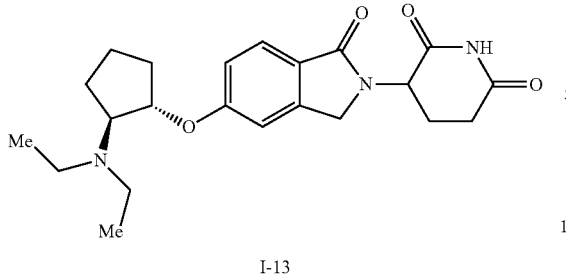

I-13

To a stirred solution of the HCl salt of I-12 (500 mg, 1.24 mmol) and NaBH(OAc)$_3$ (787 mg, 3.71 mmol) in DMF (10 mL) was added acetaldehyde (2-1, 0.21 mL, 3.7 mmol) in one portion and the resulting mixture was stirred for 2 h at room temperature. The reaction mixture was then concentrated to dryness and the crude material was purified by silica gel chromatography eluting with 0% to 10% Et$_3$N in EtOAc to afford I-13 (342 mg, 0.85 mmol, 69% yield) as a white powder. MS [M+H]$^+$=400.0. $^1$H NMR (400 MHz, DCM-d$_2$) δ 8.66 (s, 1H), 7.69-7.65 (m, 1H), 7.14-6.97 (m, 2H), 5.10 (ddd, J=13.3, 5.2, 3.5 Hz, 1H), 4.71-4.52 (m, 1H), 4.39-4.18 (m, 2H), 3.40-3.23 (m, 1H), 2.89-2.72 (m, 2H), 2.66-2.47 (m, 4H), 2.41-2.19 (m, 1H), 2.20-2.07 (m, 1H), 2.02-1.87 (m, 2H), 1.83-1.62 (m, 3H), 1.58-1.45 (m, 1H), 1.05-0.94 (m, 6H).

Example 3: 3-(1-oxo-5-(((1S,2S)-2-(piperidin-1-yl)cyclopentyl)oxy)isoindolin-2-yl)piperidine-2,6-dione (I-32)

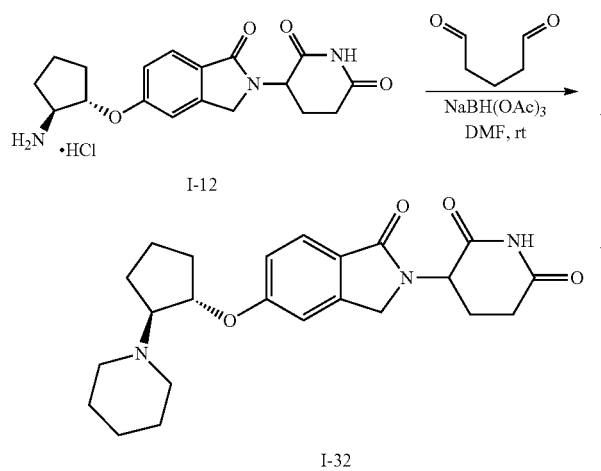

I-32

To a stirred solution of the HCl salt of I-12 (400 mg, 1.05 mmol) and NaBH(OAc)$_3$ (670 mg, 3.16 mmol) in DMF (10 mL) was added 25% glutaraldehyde in H$_2$O (0.42 mL, 1.1 mmol) and the resulting mixture was stirred for 40 min at room temperature. The reaction mixture was then concentrated to dryness and the crude material was purified by silica gel chromatography eluting with 0% to 10% Et$_3$N in EtOAc to afford I-32 (298 mg, 0.717 mmol, 68% yield) as a white powder. MS [M+H]$^+$=412.1. $^1$H NMR (400 MHz, DCM-d$_2$) δ 9.23 (br s, 1H), 7.84-7.52 (m, 1H), 7.08-6.81 (m, 2H), 5.18-4.94 (m, 1H), 4.81-4.60 (m, 1H), 4.32 (d, J=3.8 Hz, 1H), 4.14 (q, J=16.0 Hz, 1H), 3.10-2.71 (m, 3H), 2.57-2.25 (m, 4H), 2.20-2.05 (m, 2H), 2.04-1.88 (m, 2H), 1.79-1.62 (m, 3H), 1.60-1.46 (m, 5H), 1.45-1.34 (m, 2H).

Example 4: 3-(5-(((1S,2S)-2-(ethylamino)cyclopentyl)oxy)-1-oxoisoindolin-2-yl)piperidine-2,6-dione (I-29)

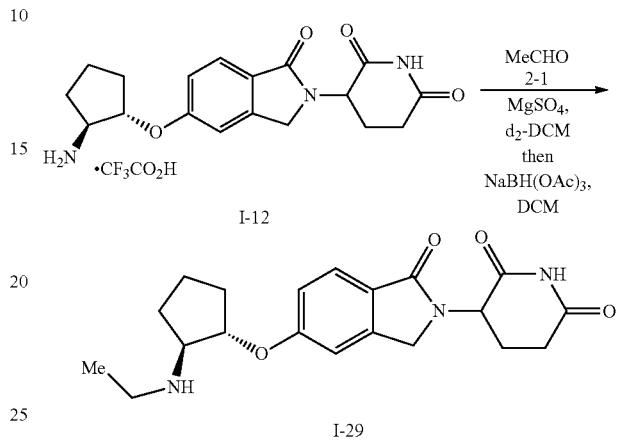

To a solution of the TFA salt of I-12 (19 mg, 0.055 mmol) in DCM-d$_2$ (0.5 mL) were added acetaldehyde (2-1, 0.02 mL, 0.3 mmol) and MgSO$_4$ (100 mg, 0.831 mmol) and the resulting mixture was stirred at room temperature for 5 h. The reaction mixture was then filtered and concentrated to dryness. The resulting material was taken up in DCM (0.5 mL) and NaBH(OAc)$_3$ (22 mg, 0.10 mmol) was added. After 30 min, the reaction was diluted with DCM and quenched with sat. aq. NaHCO$_3$. The phases were separated and the aqueous phase was extracted with EtOAc (5×5 mL). The combined organic layers were dried over Na$_2$SO$_4$, filtered, and concentrated to dryness. The crude material was purified by reverse phase HPLC (eluting with MeCN/H$_2$O with 10 mM NH$_4$OH) and collected into tubes containing formic acid (3 drops). The fractions containing the desired product were combined and lyophilized to afford I-29 (8 mg, 0.018 mmol, 33% yield) as a white powder. MS [M+H]$^+$=372.4. $^1$H NMR (400 MHz, DCM-d$_2$) δ 7.61 (d, J=8.3 Hz, 1H), 6.93 (d, J=2.1 Hz, 1H), 6.91 (dd, J=8.3, 2.1 Hz, 1H), 5.02 (dt, J=13.3, 5.5 Hz, 1H), 4.76-4.70 (m, 1H), 4.31-4.15 (m, 2H), 3.33 (td, J=7.4, 4.0 Hz, 1H), 2.83-2.66 (m, 5H), 2.31-2.17 (m, 1H), 2.14-2.01 (m, 3H), 1.79-1.63 (m, 3H), 1.63-1.52 (m, 1H), 1.11 (t, J=7.1 Hz, 3H).

Example 5: 3-(5-(((1S,2S)-2-(3-hydroxyazetidin-1-yl)cyclopentyl)oxy)-1-oxoisoindolin-2-yl)piperidine-2,6-dione HC(O)OH Salt (I-5)

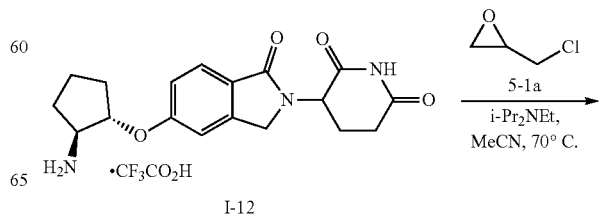

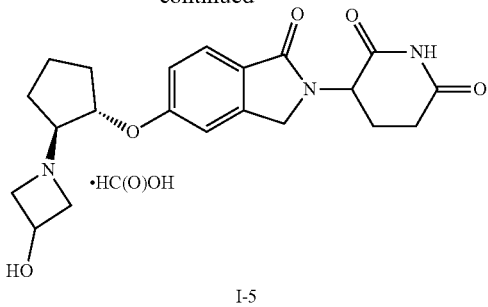

I-5

To a stirred solution of the TFA salt of I-12 (55 mg, 0.12 mmol) in MeCN (1 mL) was added i-Pr₂NEt (0.07 mL, 0.4 mmol) and epichlorohydrin (5-1a, 11 mg, 0.12 mmol) and the resulting reaction mixture was heated to 60° C. After 5 h the temperature was increased to 70° C. and the reaction mixture was stirred overnight. The mixture was then cooled to room temperature and another portion of epichlorohydrin (5-1a, 11 mg, 0.12 mmol) was added and the resulting mixture was heated to 70° C. for two days. The reaction mixture was cooled to room temperature and concentrated to dryness. The crude material was purified by reverse phase HPLC (eluting with MeCN/H₂O with 10 mM NH₄OH) and collected into tubes containing formic acid (3 drops). The fractions containing the desired product were combined and lyophilized to afford the formate salt of I-5 (11 mg, 0.023 mmol, 19.5% yield) as a white solid. MS [M+H]⁺=400.4. ¹H NMR (400 MHz, MeCN-d₃) δ 8.28 (s, 1H), 7.64 (d, J=8.4 Hz, 1H), 7.09-7.06 (m, 1H), 7.01 (dd, J=8.4, 2.3 Hz, 1H), 5.04 (ddd, J=13.4, 5.2, 2.0 Hz, 1H), 4.67 (dt, J=6.9, 4.0 Hz, 1H), 4.40-4.24 (m, 3H), 3.90 (dt, J=15.2, 7.6 Hz, 2H), 3.47-3.27 (m, 3H), 2.86-2.75 (m, 1H), 2.71 (ddd, J=17.6, 4.8, 2.6 Hz, 1H), 2.47-2.33 (m, 1H), 2.27-2.17 (m, 1H), 2.11 (dtd, J=13.0, 5.3, 2.6 Hz, 1H), 1.82-1.65 (m, 3H), 1.57-1.47 (m, 1H).

Example 6: 3-(5-(((1S,2S)-2-(1,4-dioxa-8-azaspiro[4.5]decan-8-yl)cyclopentyl)oxy)-1-oxoisoindolin-2-yl)piperidine-2,6-dione HC(O)OH Salt (I-17)

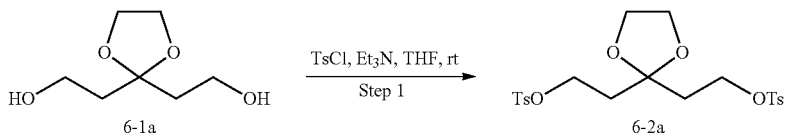

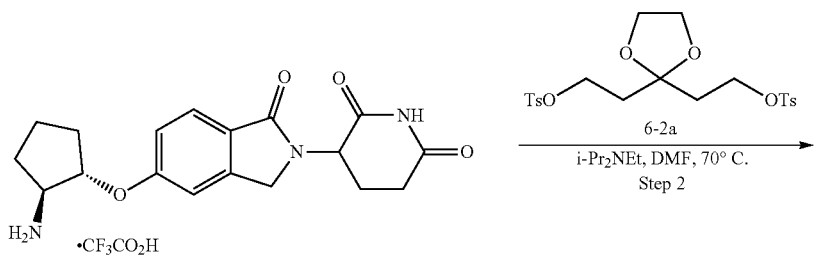

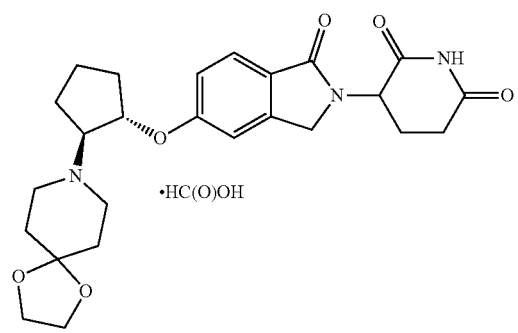

I-17

Step 1. (1,3-dioxolane-2,2-diyl)bis(ethane-2,1-diyl) bis(4-methylbenzenesulfonate) (6-2a)

To as stirred solution of 2,2'-(1,3-dioxolane-2,2-diyl)diethanol (6-1a, 300 mg, 1.85 mmol) and Et$_3$N (0.65 mL, 4.6 mmol) in THF (6 mL) at −10° C. was added a solution of TsCl (882 mg, 4.62 mmol) in THF (1 mL) and the resulting mixture was allowed to warm to room temperature and then stirred for 6 days. The reaction mixture was then filtered and concentrated to dryness. The crude material was purified by silica gel chromatography eluting with 0% to 60% EtOAc in heptane to give 6-2a (426 mg, 0.905 mmol, 49% yield) as a white cloudy oil that crystallized upon standing. MS [M+H]$^+$=471.3. $^1$H NMR (400 MHz, Chloroform-d) δ 7.77 (d, J=8.3 Hz, 4H), 7.39-7.32 (m, 4H), 4.07 (t, J=6.9 Hz, 4H), 3.84 (s, 4H), 2.45 (s, 6H), 1.95 (t, J=6.9 Hz, 4H).

Step 2. 3-(5-(((1S,2S)-2-(1,4-dioxa-8-azaspiro[4.5]decan-8-yl)cyclopentyl)oxy)-1-oxoisoindolin-2-yl)piperidine-2,6-dione HC(O)OH Salt (I-17)

To a stirred solution of the TFA salt of I-12 (25 mg, 0.055 mmol) and (1,3-dioxolane-2,2-diyl)bis(ethane-2,1-diyl) bis(4-methylbenzenesulfonate) (6-2a, 25 mg, 0.053 mmol) in DMF (1 mL) was added i-Pr$_2$NEt (0.05 mL, 0.3 mmol) and the resulting mixture was heated to 70° C. for two days. The reaction mixture was allowed to cool to room temperature and azeotroped with PhMe. The crude material was purified by reverse phase HPLC (eluting with MeCN/H$_2$O with 10 mM NH$_4$OH) and collected into tubes containing formic acid (3 drops). The fractions containing the desired product were combined and lyophilized to afford the formate salt of I-17 (4 mg, 0.007 mmol, 13.5% yield) as a white powder. MS [M+H]$^+$=470.5. $^1$H NMR (400 MHz, MeCN-d$_3$) δ 8.22 (d, J=1.0 Hz, 1H), 7.64 (d, J=8.4 Hz, 1H), 7.13-7.09 (m, 1H), 7.01 (dd, J=8.5, 2.3 Hz, 1H), 5.03 (ddd, J=13.4, 5.2, 2.2 Hz, 1H), 4.70 (ddd, J=7.6, 4.6, 2.7 Hz, 1H), 4.36 (dd, J=16.8, 5.5 Hz, 1H), 4.28 (dd, J=16.8, 2.1 Hz, 1H), 3.87 (s, 4H), 3.03-2.96 (m, 1H), 2.86-2.75 (m, 1H), 2.71 (ddd, J=17.7, 4.8, 2.5 Hz, 1H), 2.63-2.55 (m, 4H), 2.45-2.40 (m, 1H), 2.14-2.05 (m, 2H), 1.74-1.68 (m, 3H), 1.65 (t, J=5.7 Hz, 4H), 1.54 (dtd, J=12.0, 9.4, 7.1 Hz, 1H).

Example 7: 3-(5-(((1S,2S)-2-(8-oxa-3-azabicyclo[3.2.1]octan-3-yl)cyclopentyl)oxy)-1-oxoisoindolin-2-yl)piperidine-2,6-dione HC(O)OH Salt (I-18)

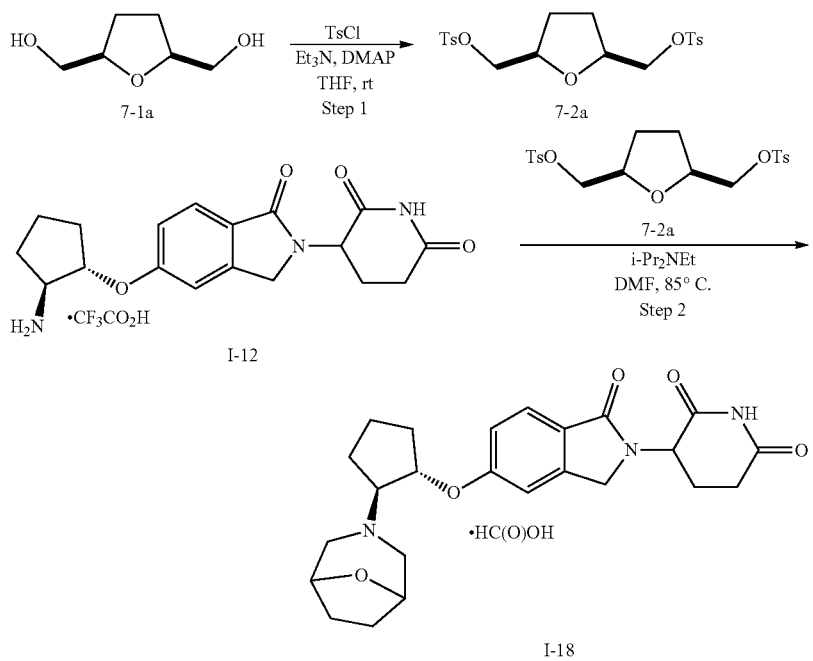

Step 1. (cis-tetrahydrofuran-2,5-diyl)bis(methylene) bis(4-methylbenzenesulfonate) (7-2a)

To a stirred solution of cis-2,5-bishydroxymethyl-tetrahydrofuran (7-1a, 263 mg, 1.99 mmol) and DMAP (24 mg, 0.20 mmol) in THF (7 mL) was added Et$_3$N (1.3 mL, 9.3 mmol) and the resulting mixture was cooled to 0° C. Tosyl chloride (835 mg, 4.38 mmol) was added and the resulting mixture was allowed to warm to room temperature and stirred overnight. The reaction mixture was then diluted with water (25 mL) and EtOAc (150 mL) was added. The organic layer was then washed with water (25 mL), sat. aq. NaHCO$_3$ (30 mL), and brine (30 mL), dried over MgSO$_4$, filtered, and concentrated to dryness. The crude material was purified by silica gel chromatography eluting with 0% to 60% EtOAc in heptane to afford the 7-2a as a white solid (488.6 mg, 1.098 mmol, 55% yield). MS [M+H$_2$O]$^+$=458.4. $^1$H NMR (400 MHz, DCM-d$_2$) δ 7.87-7.73 (m, 4H), 7.48-7.37 (m, 4H), 4.10 (dddd, J=11.1, 6.4, 4.3, 1.9 Hz, 2H), 4.02-3.85 (m, 4H), 2.49 (s, 6H), 2.07-1.91 (m, 2H), 1.76-1.61 (m, 2H).

Step 2. 3-(5-(((1S,2S)-2-(8-oxa-3-azabicyclo[3.2.1]octan-3-yl)cyclopentyl)oxy)-1-oxoisoindolin-2-yl)piperidine-2,6-dione HC(O)OH Salt (I-18)

To a stirred solution of the TFA salt of I-12 (54.9 mg, 0.120 mmol) and (cis-tetrahydrofuran-2,5-diyl)bis(methylene) bis(4-methylbenzenesulfonate) (7-2a, 68.3 mg, 0.155 mmol) in DMF (2 mL) was added i-Pr₂NEt (0.10 mL, 0.57 mmol) and the resulting mixture was stirred at room temperature for 2 days. The reaction mixture was then heated to 85° C. and stirred overnight. The resulting mixture was diluted with EtOAc (80 mL) and washed with sat. aq. NaHCO₃ (2×20 mL) and brine (20 mL). The organic layer was then dried over MgSO₄, filtered, and concentrated to dryness. The crude material was purified by reverse phase HPLC (eluting with MeCN/H₂O with 0.1% formic acid). The pure fractions were combined and lyophilized to afford the formate salt of I-18 as a white solid (2.3 mg, 4.5 μmol, 4% yield). MS [M+H]+=440.5. ¹H NMR (400 MHz, DMSO-d₆) δ 10.95 (s, 1H), 8.20 (s, 1H), 7.60 (d, J=8.4 Hz, 1H), 7.21 (t, J=2.7 Hz, 1H), 7.05 (dt, J=8.4, 1.9 Hz, 1H), 5.15-5.01 (m, 1H), 4.69 (d, J=6.9 Hz, 1H), 4.48-4.10 (m, 4H), 2.97-2.75 (m, 1H), 2.63-2.58 (m, 1H), 2.38 (dd, J=13.0, 4.3 Hz, 1H), 2.35-2.24 (m, 3H), 2.10-2.03 (m, 1H), 2.02-1.93 (m, 1H), 1.81 (d, J=7.4 Hz, 3H), 1.74-1.57 (m, 5H), 1.49 (d, J=12.2 Hz, 1H).

Example 8: 3-(5-(((1S,2S)-2-(ethyl(isopropyl)amino)cyclopentyl)oxy)-1-oxoisoindolin-2-yl)piperidine-2,6-dione HC(O)OH Salt (I-25)

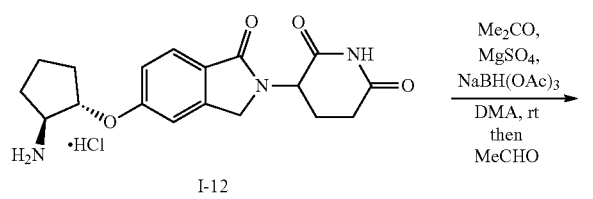

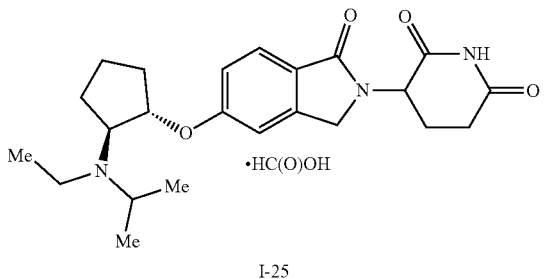

To a stirred suspension of the HCl salt of I-12 (50 mg, 0.13 mmol), acetone (0.03 mL, 0.4 mmol) and MgSO₄ (32 mg, 0.26 mmol) in DMA (1.0 mL) was added NaBH(OAc)₃ (84 mg, 0.40 mmol) and the resulting mixture was stirred overnight at room temperature. Acetaldehyde (2-1, 0.04 mL, 0.7 mmol) was then added and the resulting mixture was stirred for an additional 4 h. The reaction mixture was diluted with DMSO (0.5 mL) and filtered through a fritted syringe. The resulting solution was directly purified by reverse phase HPLC (eluting with MeCN/H₂O with 0.1% formic acid). The pure fractions were combined and lyophilized to afford the formate salt of I-25 (6.1 mg, 0.013 mmol, 10% yield) as a white solid. MS [M+H]+=414.2. ¹H NMR (400 MHz, MeCN-d₃) δ 8.79 (s, 1H), 8.23 (s, 1H), 7.54 (d, J=8.4 Hz, 1H), 7.04 (s, 1H), 6.95 (dd, J=8.4, 2.2 Hz, 1H), 4.95 (ddd, J=13.3, 5.2, 2.4 Hz, 1H), 4.91-4.84 (m, 1H), 4.27 (dd, J=16.7, 4.1 Hz, 1H), 4.19 (dd, J=16.7, 4.9 Hz, 1H), 3.56-3.44 (m, 1H), 3.29-3.17 (m, 1H), 2.85-2.57 (m, 4H), 2.31 (qd, J=13.2, 4.8 Hz, 1H), 2.09-1.97 (m, 2H), 1.96-1.88 (m, 1H), 1.74-1.55 (m, 4H), 1.14-0.96 (m, 9H).

Example 9: 3-(5-(((1S,2S)-2-(bis(cyclopropylmethyl)amino)cyclopentyl)oxy)-1-oxoisoindolin-2-yl)piperidine-2,6-dione (I-31)

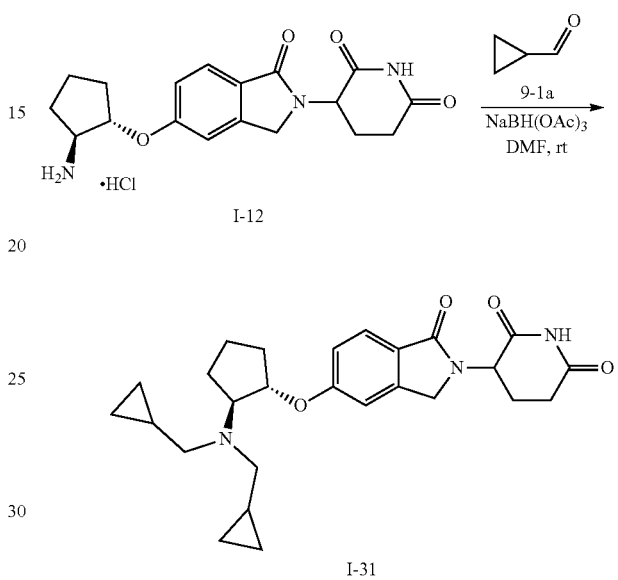

To a stirred solution of the HCl salt of I-12 (26 mg, 0.068 mmol) and NaBH(OAc)₃ (43.5 mg, 0.205 mmol) in DMF (1 mL) was added cyclopropanecarbaldehyde (9-1a, 0.02 mL, 0.2 mmol) and the resulting mixture was stirred overnight at room temperature. The reaction mixture was then concentrated to dryness and the crude material was purified by silica gel chromatography eluting with 0% to 10% Et₃N in EtOAc to afford I-31 (12.6 mg, 0.0272 mmol, 40% yield) as a white powder. MS [M+H]+=452.3. ¹H NMR (400 MHz, DCM-d₂) δ 8.24 (s, 1H), 7.68 (d, J=8.4 Hz, 1H), 7.17 (s, 1H), 7.10-7.00 (m, 1H), 5.22-5.02 (m, 1H), 4.62 (s, 1H), 4.41-4.21 (m, 2H), 3.70-3.46 (m, 1H), 2.89-2.72 (m, 2H), 2.66-2.23 (m, 5H), 2.20-2.10 (m, 1H), 1.92 (s, 2H), 1.84-1.63 (m, 3H), 1.54 (s, 1H), 0.97-0.82 (m, 2H), 0.45 (s, 4H), 0.23-0.01 (m, 4H).

Example 10: 3-(5-(((1S,2S)-2-(4,4-difluoropiperidin-1-yl)cyclopentyl)oxy)-1-oxoisoindolin-2-yl)piperidine-2,6-dione (I-8)

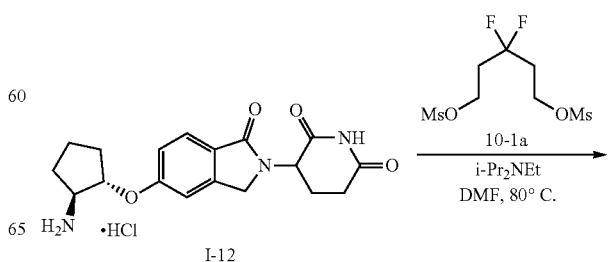

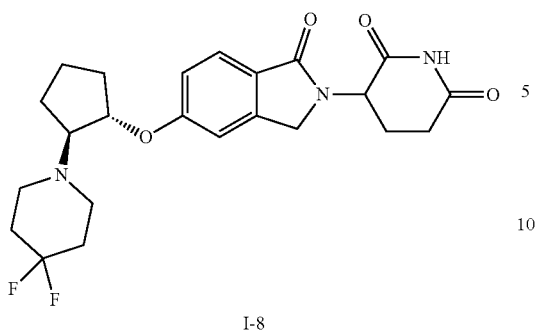

I-8

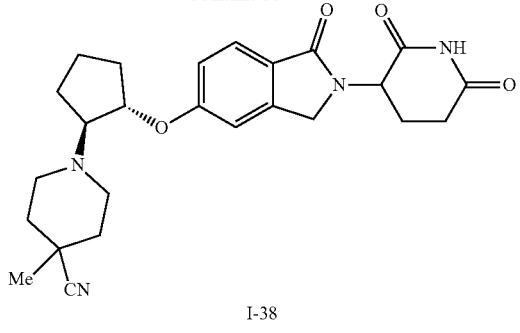

I-38

3,3-difluoropentane-1,5-diyl dimethanesulfonate 10-1a was prepared as described in U.S. Patent US2017/145026 A1.

To a stirred solution of the HCl salt of I-12 (26 mg, 0.068 mmol) and i-Pr$_2$NEt (0.05 mL, 0.3 mmol) in DMF (0.7 mL) was added 10-1a (30.4 mg, 0.103 mmol) and the resulting mixture was stirred at 80° C. for 72 h. The reaction mixture was then allowed to cool to room temperature and concentrated to dryness. The crude material was purified by silica gel chromatography eluting with 0% to 10% Et$_3$N in EtOAc to afford I-8 (2.4 mg, 5.3 µmol, 8% yield) as a white solid. MS [M+H]$^+$=448.1. $^1$H NMR (400 MHz, DCM-d$_2$) δ 8.03 (s, 1H), 7.68-7.57 (m, 1H), 6.99-6.84 (m, 2H), 5.04 (ddd, J=13.4, 5.3, 2.0 Hz, 1H), 4.60-4.50 (m, 1H), 4.31-4.17 (m, 2H), 3.03-2.89 (m, 1H), 2.84-2.68 (m, 2H), 2.63-2.47 (m, 4H), 2.34-2.18 (m, 1H), 2.15-2.07 (m, 1H), 2.03-1.79 (m, 5H), 1.75-1.62 (m, 3H), 1.53-1.41 (m, 2H).

Example 11: 1-((1S,2S)-2-((2-(2,6-dioxopiperidin-3-yl)-1-oxoisoindolin-5-yl)oxy)cyclopentyl)-4-methylpiperidine-4-carbonitrile (I-38)

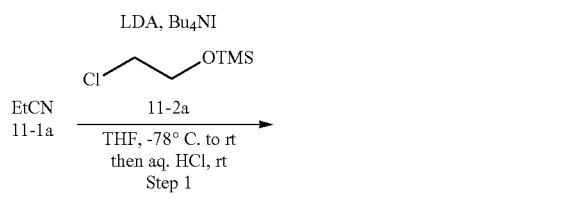

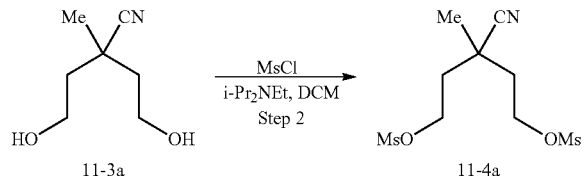

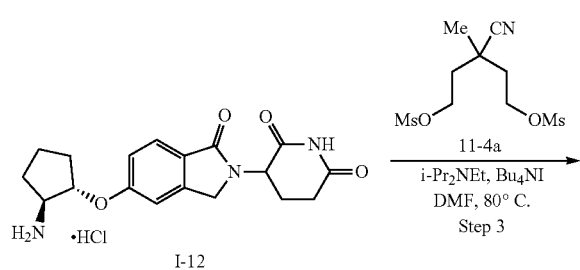

Step 1. 4-hydroxy-2-(2-hydroxyethyl)-2-methylbutanenitrile (11-3a)

To a stirred solution of propiononitrile (11-1a, 1.30 mL, 182 mmol) and Bu$_4$NI (0.67 g, 1.8 mmol) in THF (30 mL) under an atmosphere of nitrogen was added LDA (12.1 mL, 18.2 mmol, 1.5M in cyclohexane) dropwise at −78° C. and the resulting mixture was stirred for 30 min at −78° C., warmed to room temperature and then stirred for additional 30 min. The reaction mixture was cooled to −78° C. and (2-chloroethoxy)trimethylsilane (11-2a, 2.9 mL, 18 mmol) was added dropwise and the resulting mixture was then warmed to room temperature and stirred for 1 h. The reaction mixture was then cooled to −78° C. and another portion of LDA (12.1 mL, 18.2 mmol, 1.5 M in cyclohexane) was added dropwise. The resulting mixture was stirred for 30 min at −78° C., and then warmed to room temperature and stirred for additional 30 min. The reaction mixture was cooled to −78° C. and a second equivalent of (2-chloroethoxy)trimethylsilane (11-2a, 2.9 mL, 18 mmol) was added dropwise and the reaction mixture was allowed to warm room temperature and then stirred for 3 h. The reaction mixture was quenched with sat. aq. NH$_4$Cl and extracted with Et$_2$O (×3). The combined organic phases were concentrated to dryness. The crude product was dissolved in THF (10 mL) and 0.5 M HCl (5 mL) was added. The resulting mixture was stirred for 3 h at room temperature. The reaction mixture was then quenched with sat. aq. NaHCO$_3$ and extracted with EtOAc (×3). The combined organic phases were dried over Na$_2$SO$_4$, filtered, and concentrated to dryness. The crude product was purified by silica gel chromatography eluting with 0% to 100% EtOAc in heptane to afford 11-3a (250 mg, 1.75 mmol, 10% yield) as a colorless oil. $^1$H NMR (400 MHz, Chloroform-d) δ 3.95-3.84 (m, 4H), 2.23 (s, 2H), 2.05-1.95 (m, 2H), 1.93-1.84 (m, 2H), 1.43 (s, 3H).

Step 2. 3-cyano-3-methylpentane-1,5-diyl dimethanesulfonate (11-4a)

To a stirred solution of 11-3a (260 mg, 1.83 mmol) and i-Pr$_2$NEt (1.3 mL, 7.3 mmol) in DCM (3 mL) was added methanesulfonyl chloride (0.28 mL, 3.6 mmol) at 0° C. and the resulting mixture was stirred for 2 h at 0° C. and then at room temperature for 3 hours. The reaction mixture was then quenched with water (2 mL) and extracted with DCM (×2). The combined organic phases were dried over Na$_2$SO$_4$, filtered, and concentrated to dryness to afford crude 11-4a as a yellow oil. The crude product was carried onto the next step without further purification. $^1$H NMR (400 MHz, DCM-d$_2$) δ 4.36 (t, J=6.4 Hz, 4H), 3.01 (s, 6H), 2.12 (dt, J=14.7, 6.5 Hz, 2H), 1.99 (dt, J=14.7, 6.4 Hz, 2H), 1.41 (s, 3H).

Step 3. 1-((1S,2S)-2-((2-(2,6-dioxopiperidin-3-yl)-1-oxoisoindolin-5-yl)oxy)cyclopentyl)-4-methylpiperidine-4-carbonitrile (I-38)

To a stirred solution of HCl salt of I-12 (500 mg, 1.32 mmol), Bu$_4$NI (49 mg, 0.13 mmol) and i-Pr$_2$NEt (1.1 mL, 6.6 mmol) in DMF (3 mL) was added 11-4a (433 mg, 1.45 mmol) and the reaction mixture was stirred for 5 days at 80° C. The reaction mixture was concentrated to dryness. Crude product was purified by silica gel chromatography eluting with 0 to 100% EtOAc:EtOH (v/v=3:1) in DCM to afford I-38 (104.7 mg, 0.232 mmol, 18% yield) as a light beige solid. MS [M+H]$^+$=451.1. $^1$H NMR (400 MHz, DCM-d$_2$) 8.23 (s, 1H), 7.71-7.66 (m, 1H), 7.09-6.90 (m, 2H), 5.10 (ddd, J=13.3, 5.2, 3.1 Hz, 1H), 4.62 (s, 1H), 4.41-4.19 (m, 2H), 3.10-2.75 (m, 4H), 2.48-2.22 (m, 3H), 2.21-2.11 (m, 1H), 2.11-1.96 (m, 2H), 1.95-1.81 (m, 2H), 1.80-1.64 (m, 3H), 1.63-1.40 (m, 4H), 1.34 (s, 3H).

Example 12: 3-(5-(((1S,2S)-2-(benzylamino)cyclopentyl)oxy)-1-oxoisoindolin-2-yl)piperidine-2,6-dione (I-20)

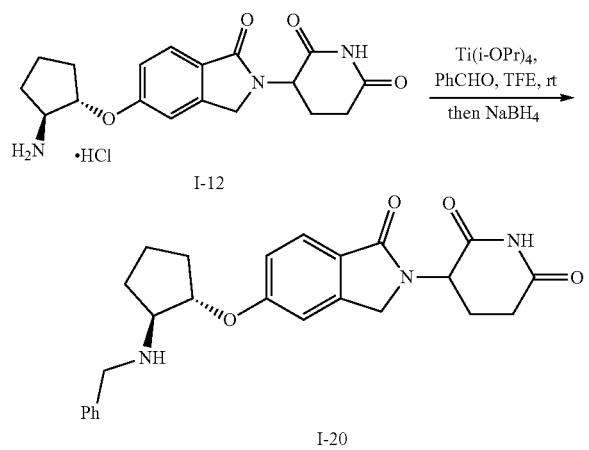

To a stirred solution of the HCl salt of I-12 (50 mg, 0.13 mmol) and benzaldehyde (0.02 mL, 0.2 mmol) in anhydrous 2,2,2-trifluoroethanol (1.2 mL) under an atmosphere of nitrogen was added Ti(i-OPr)$_4$ (0.04 mL, 0.1 mmol) and the resulting mixture was stirred at room temperature overnight. NaBH$_4$ (7.5 mg, 0.20 mmol) was then added in one portion and the resulting mixture was stirred for an additional 3 h at room temperature. The reaction mixture was quenched with aq. 1 M formic acid (0.2 mL) and filtered. The resulting solution was directly purified by reverse phase HPLC (eluting with MeCN/H$_2$O with 0.1% formic acid). The pure fractions were combined and lyophilized to afford I-20 (30.2 mg, 0.062 mmol, 47% yield) as a white powder. MS [M+H]$^+$=434.2. $^1$H NMR (400 MHz, DMSO-d$_6$) δ 10.97 (s, 1H), 7.58 (d, J=8.4 Hz, 1H), 7.38-7.26 (m, 4H), 7.23-7.16 (m, 1H), 7.13 (dd, J=6.6, 2.1 Hz, 1H), 7.00 (dt, J=8.4, 2.6 Hz, 1H), 5.07 (ddd, J=13.2, 5.1, 3.2 Hz, 1H), 4.71-4.55 (m, 1H), 4.43-4.16 (m, 2H), 3.80-3.67 (m, 2H), 3.14-3.04 (m, 1H), 2.91 (ddd, J=17.4, 13.6, 5.4 Hz, 1H), 2.64-2.54 (m, 1H), 2.45-2.31 (m, 1H), 2.20-2.08 (m, 1H), 2.03-1.94 (m, 1H), 1.93-1.83 (m, 1H), 1.81-1.59 (m, 3H), 1.57-1.45 (m, 1H).

Example 13: 3-(5-(((1S,2S)-2-aminocyclohexyl)oxy)-1-oxoisoindolin-2-yl)piperidine-2,6-dione hydrochloride (I-15)

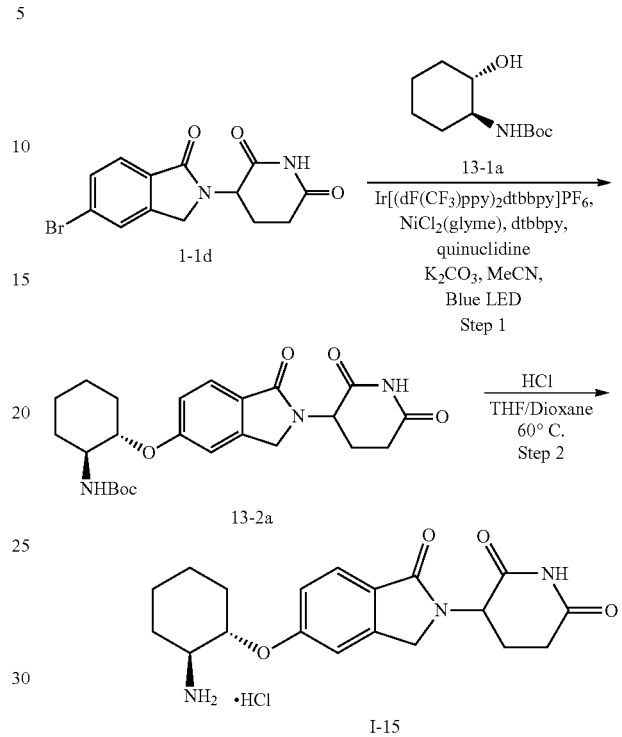

Step 1. tert-butyl ((1S,2S)-2-((2-(2,6-dioxopiperidin-3-yl)-1-oxoisoindolin-5-yl)oxy)cyclohexyl)carbamate (13-2a)

To 3-(5-bromo-1-oxoisoindolin-2-yl)piperidine-2,6-dione (I-1d, 1600 mg, 4.95 mmol), tert-butyl ((1S,2S)-2-hydroxycyclohexyl)carbamate (13-1a, 1066 mg, 4.95 mmol), NiCl$_2$(glyme) (54 mg, 0.25 mmol), dtbbpy (66 mg, 0.25 mmol), Ir[(dF(CF$_3$)ppy)$_2$dtbbpy]PF$_6$ (56 mg, 0.050 mmol), quinuclidine (55 mg, 0.50 mmol) and K$_2$CO$_3$ (684 mg, 4.95 mmol) under an atmosphere of nitrogen was added MeCN (30 mL) and the resulting mixture was then stirred vigorously for 70 h under irradiation of blue LED light at room temperature. The reaction mixture was then diluted with DCM (20 mL), filtered, and concentrated to dryness. The crude material was purified by silica gel chromatography eluting with 0% to 3% MeOH in DCM to afford 13-2a (282 mg, 0.616 mmol, 12% yield) as a white powder. MS [M-tBu+H]$^+$=402.3. $^1$H NMR (400 MHz, Chloroform-d) δ 7.97 (s, 1H), 7.82-7.70 (m, 1H), 7.13-6.92 (m, 2H), 5.19 (dd, J=13.2, 5.2 Hz, 1H), 4.56 (t, J=7.4 Hz, 1H), 4.42 (d, J=15.8 Hz, 1H), 4.27 (d, J=15.8 Hz, 1H), 4.23-4.16 (m, 1H), 3.78-3.66 (m, 1H), 2.95-2.74 (m, 2H), 2.33 (qd, J=13.0, 5.0 Hz, 1H), 2.25-2.16 (m, 2H), 2.14-2.04 (m, 2H), 1.85-1.74 (m, 1H), 1.46-1.33 (m, 3H), 1.41 (s, 9H).

Step 2. 3-(5-(((1S,2S)-2-aminocyclohexyl)oxy)-1-oxoisoindolin-2-yl)piperidine-2,6-dione hydrochloride (I-15)

To a stirred solution of tert-butyl ((1S,2S)-2-((2-(2,6-dioxopiperidin-3-yl)-1-oxoisoindolin-5-yl)oxy)cyclohexyl)carbamate (13-2a, 282 mg, 0.616 mmol) in THF (2 mL) was added 4 M HCl in dioxane (1.0 mL, 4.0 mmol) and the resulting mixture was stirred for 2 h at 60° C. Formation of white precipitate was observed. The reaction mixture was diluted with Et₂O (10 mL) and filtered. The precipitate was washed with Et₂O (×4) and then dried under reduced pressure to afford the hydrochloride salt of I-15 (242 mg, 0.614 mmol, 100% yield) as a white solid. MS [M+H]⁺=358.1. ¹H NMR (400 MHz, D₂O) δ 7.75 (d, J=8.5 Hz, 1H), 7.24 (s, 1H), 7.17 (dd, J=8.5, 2.1 Hz, 1H), 5.12 (dd, J=13.3, 5.2 Hz, 1H), 4.56 (dd, J=17.7, 1.8 Hz, 1H), 4.51-4.38 (m, 2H), 3.45 (ddd, J=12.1, 9.8, 4.3 Hz, 1H), 2.99-2.82 (m, 2H), 2.51 (qd, J=13.0, 5.4 Hz, 1H), 2.39-2.14 (m, 3H), 1.84 (t, J=10.1 Hz, 2H), 1.60 (qd, J=12.5, 4.0 Hz, 1H), 1.49-1.29 (m, 3H).

Alternatively, Conversion of 1-1d to I-15 was Also Achieved Via the Following Synthetic Procedure:

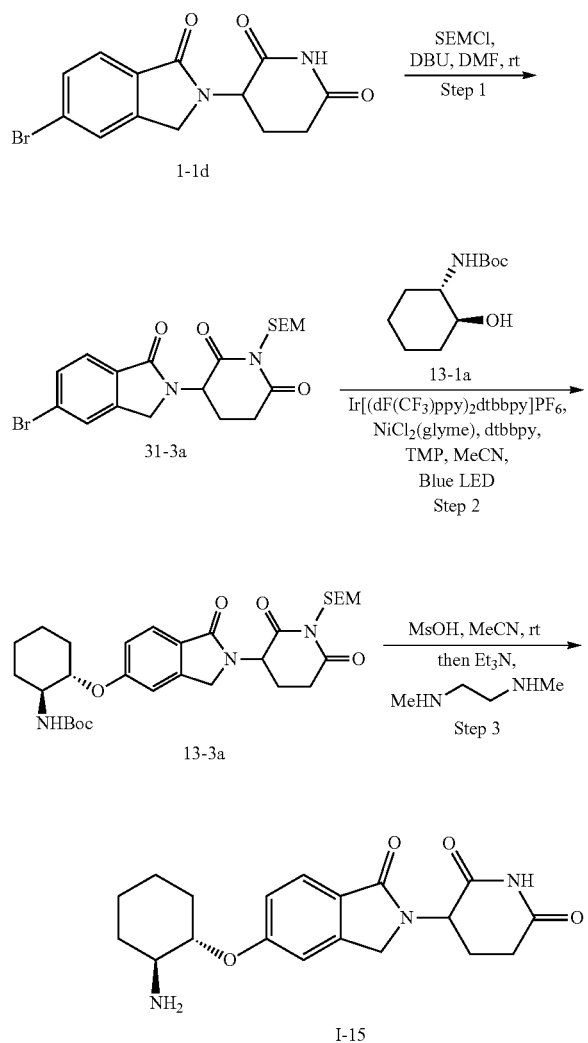

Step 1. 3-(5-bromo-1-oxoisoindolin-2-yl)-1-((2-(trimethylsilyl)ethoxy)methyl)piperidine-2,6-dione (31-3a)

To a stirred solution of 1-1d (10.0 g, 30.9 mmol) and DBU (6.9 mL, 46 mmol) in DMF (95 mL) was added SEMCl (6.6 mL, 37 mmol) at 0° C. and the resulting mixture was allowed to warm to room temperature and then stirred for 5 h. An additional portion of DBU (3.5 mL, 23 mmol) and SEMCl (3.3 mL, 19 mmol) was added and stirring was continued for additional 2 h. The reaction mixture was then quenched with sat. aq. NH₄Cl (250 mL) and extracted with EtOAc (×3). The combined organic phases were dried over Na₂SO₄, filtered, and concentrated to dryness. The crude material was dissolved in a minimal amount of EtOAc (~50 mL) and Et₂O:heptane (v/v=1:2, 400 mL) was added. The resulting cloudy solution was left standing at −5° C. overnight. The formed precipitate was filtered, washed with heptane (×3), and dried under vacuum to afford 31-3a (11.53 g, 25.4 mmol, 82% yield) as an off-white solid. MS [M+H]⁺=453.4. ¹H NMR (400 MHz, Chloroform-d) δ 7.75 (d, J=8.6 Hz, 1H), 7.66-7.61 (m, 2H), 5.37-5.09 (m, 3H), 4.48 (d, J=16.2 Hz, 1H), 4.32 (d, J=16.2 Hz, 1H), 3.74-3.50 (m, 2H), 3.11-2.98 (m, 1H), 2.94-2.83 (m, 1H), 2.33 (qd, J=13.2, 4.7 Hz, 1H), 2.24-2.15 (m, 1H), 0.97-0.90 (m, 2H), 0.00 (s, 9H).

Step 2. tert-butyl ((1S,2S)-2-((2-(2,6-dioxo-1-((2-(trimethylsilyl)ethoxy)methyl)piperidin-3-yl)-1-oxoisoindolin-5-yl)oxy)cyclohexyl)carbamate (13-3a)

To a stirred solution of 31-3a (5.00 g, 11.0 mmol), 13-1a (2.37 g, 11.0 mmol), NiCl₂(glyme) (0.121 g, 0.551 mmol), dtbbpy (0.148 g, 0.551 mmol) and Ir[(dF(CF₃)ppy)₂dtbbpy]PF₆ (0.124 g, 0.110 mmol) in degassed MeCN (24 mL) under an atmosphere of nitrogen was added 2,2,6,6-tetramethylpiperidine (40-2, 1.9 mL, 11 mmol) and the resulting mixture was stirred vigorously for 18 h under irradiation of blue LED lights at room temperature. The reaction mixture was then filtered and concentrated to dryness. The crude material was purified by silica gel chromatography eluting with 0% to 100% EtOAc in heptane to afford 13-3a (5.50 g, 9.36 mmol, 85% yield) as a yellow foam. MS [M−H]⁻=586.7.

Step 3. 3-(5-(((1S,2S)-2-aminocyclohexyl)oxy)-1-oxoisoindolin-2-yl)piperidine-2,6-dione (I-15)

To a solution of 13-3a (4.88 g, 8.30 mmol) in DCM (60 mL) under an atmosphere of nitrogen was added methanesulfonic acid (2.2 mL, 33 mmol) and the resulting mixture was stirred at rt overnight. The reaction mixture was cooled to 0° C. and triethylamine (9.3 mL, 66 mmol) and N1,N2-dimethylethane-1,2-diamine (1.1 mL, 10 mmol) were added. The reaction mixture was stirred at rt overnight, quenched with a 50% saturated aqueous sodium hydrogen carbonate, and extracted with DCM:isopropanol (v/v=5:1, ×4). The organic phases were combined, passed through a phase separator and concentrated to dryness. The crude material was suspended in minimal amount of MeCN, sonicated, and filtered. The resulting solid was rinsed with diethyl ether (×3) and dried under vacuum to afford I-12 (1.92 g, 5.37, 65% yield) as a pale yellow solid. MS [M+H]⁺=358.6. ¹H NMR (400 MHz, DMSO-d₆) δ 7.60 (d, J=8.4 Hz, 1H), 7.20 (s, 1H), 7.08 (dd, J=8.4, 2.2 Hz, 1H), 5.06 (dd, J=13.3, 5.1 Hz, 1H), 4.43-4.19 (m, 2H), 4.05-3.98 (m, 1H), 2.90 (ddd, J=17.3, 13.6, 5.5 Hz, 1H), 2.82-2.71 (m, 1H), 2.59 (ddd, J=17.3, 4.4, 2.3 Hz, 1H), 2.46-2.30 (m, 1H), 2.11-2.03 (m, 1H), 2.02-1.94 (m, 1H), 1.88-1.80 (m, 1H), 1.73-1.60 (m, 2H), 1.44-1.14 (m, 4H).

Example 14: 3-(5-(((1S,2S)-2-(benzylamino)cyclohexyl)oxy)-1-oxoisoindolin-2-yl)piperidine-2,6-dione (I-22) and 3-(5-(((1S,2S)-2-(dibenzylamino)cyclohexyl)oxy)-1-oxoisoindolin-2-yl)piperidine-2,6-dione (I-34)

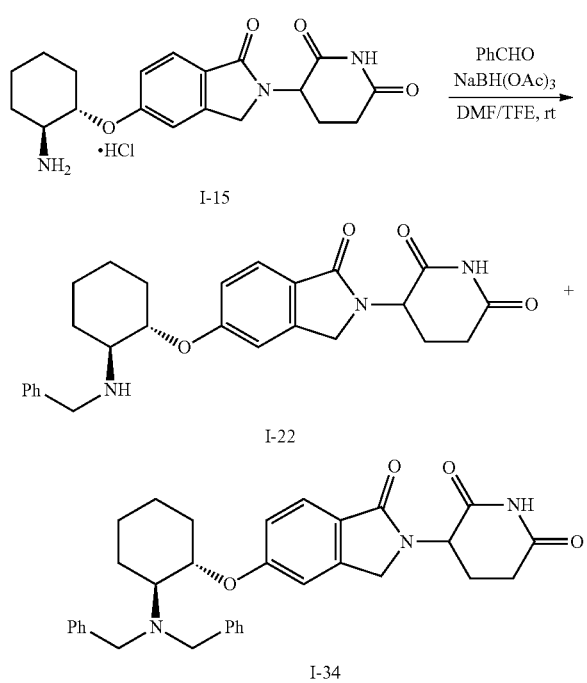

To a stirred solution of the HCl salt of I-15 (30.2 mg, 0.073 mmol) in DMF (2 mL) and trifluoroethanol (1 mL) was added benzaldehyde (7 µl, 0.07 mmol) and the resulting mixture was stirred overnight at room temperature. NaBH(OAc)$_3$ (46 mg, 0.22 mmol) was then added and the resulting mixture was stirred overnight. The reaction mixture was quenched by the addition of one drop of formic acid and then concentrated to dryness. The crude material was purified by silica gel chromatography eluting with 0% to 10% Et$_3$N in EtOAc to afford I-22 and I-34 in about 90% purity. Both compounds were repurified by reverse phase HPLC (eluting with MeCN/H$_2$O with 0.1% formic acid). Fractions containing the desired product were combined and lyophilized to afford I-22 (6.1 mg, 0.012 mmol, 17% yield) as a white solid and I-34 (7.1 mg, 0.012 mmol, 17% yield) as a white solid. MS of I-22 [M+H]+=448.2. $^1$H NMR of I-22 (400 MHz, MeCN-d$_3$) δ 7.61 (d, J=8.4 Hz, 1H), 7.33-7.26 (m, 4H), 7.25-7.19 (m, 1H), 7.12-7.08 (m, 1H), 7.03 (dd, J=8.4, 2.3 Hz, 1H), 5.03 (ddd, J=13.4, 5.2, 1.9 Hz, 1H), 4.42-4.16 (m, 3H), 3.88 (d, J=13.5 Hz, 1H), 3.77 (d, J=13.5 Hz, 1H), 2.88-2.64 (m, 3H), 2.42-2.32 (m, 2H), 2.18-2.02 (m, 3H), 1.79-1.64 (m, 2H), 1.46-1.21 (m, 4H). MS of I-34 [M+H]+=538.4. $^1$H NMR of I-34 (400 MHz, MeCN-d$_3$) δ 8.82 (s, 1H), 7.66 (d, J=8.2 Hz, 1H), 7.33-7.06 (m, 12H), 5.05 (dt, J=13.4, 5.0 Hz, 1H), 4.54 (tt, J=9.6, 4.4 Hz, 1H), 4.41-4.16 (m, 2H), 3.75 (d, J=13.7 Hz, 2H), 3.62 (dd, J=14.1, 4.4 Hz, 2H), 2.90-2.62 (m, 3H), 2.53-2.29 (m, 1H), 2.15-2.06 (m, 2H), 2.06-1.97 (m, 1H), 1.78-1.70 (m, 1H), 1.70-1.61 (m, 1H), 1.46 (qt, J=12.8, 3.3 Hz, 1H), 1.39-1.25 (m, 1H), 1.24-1.06 (m, 2H).

Alternative procedure for synthesis of 3-(5-(((1S,2S)-2-(benzylamino)cyclohexyl)oxy)-1-oxoisoindolin-2-yl)piperidine-2,6-dione (I-22)

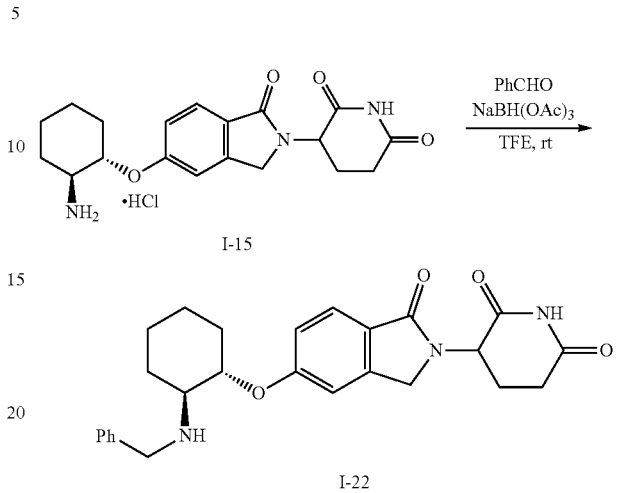

To a stirred solution of the HCl salt of I-15 (59 mg, 0.150 mmol) and benzaldehyde (0.08 mL, 0.8 mmol) in TFE (1 mL) was added NaBH(OAc)$_3$ (159 mg, 0.749 mmol) in one portion and the resulting mixture was stirred vigorously for 3 days at room temperature. The reaction mixture was concentrated to dryness. The crude material was purified by silica gel chromatography eluting with 0-100% EtOAc:EtOH (v/v=3:1, with 1% NEt$_3$) in DCM to afford I-22 (43 mg, 0.096 mmol, 64% yield) as a white solid.

Example 15: 3-(5-(((1S,2S)-2-(methylamino)cyclohexyl)oxy)-1-oxoisoindolin-2-yl)piperidine-2,6-dione (I-36)

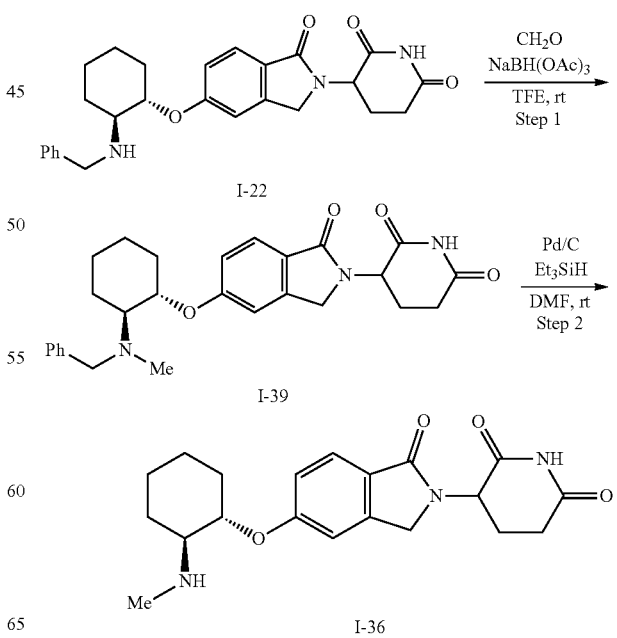

Step 1. 3-(5-(((1S,2S)-2-(benzyl(methyl)amino)cyclohexyl)oxy)-1-oxoisoindolin-2-yl)piperidine-2,6-dione (I-39)

To a stirred solution of I-22 (43 mg, 0.096 mmol) and NaBH(OAc)₃ (30.5 mg, 0.144 mmol) in TFE (1 mL) was added 37% formaldehyde in H₂O (0.014 mL, 0.19 mmol) and the resulting mixture was stirred at room temperature overnight. The reaction mixture was then diluted with DCM (5 mL), washed with sat. aq. NaHCO₃, dried over Na₂SO₄, filtered, and concentrated to dryness to afford I-39 (44 mg, 0.094 mmol, 98% yield) as a white powder. The product was carried onto the next step without further purification. MS [M+H]⁺=462.1.

Step 2. 3-(5-(((1S,2S)-2-(methylamino)cyclohexyl)oxy)-1-oxoisoindolin-2-yl)piperidine-2,6-dione (I-36)

To a stirred solution of I-39 (44 mg, 0.095 mmol) in DMF (1 mL) under an atmosphere of nitrogen was added Pd/C (10% wt, 10 mg, 9.5 μmol), followed by triethylsilane (0.05 mL, 0.3 mmol) and the resulting mixture was stirred at room temperature overnight. The reaction mixture was filtered through a pad of Celite® and concentrated to dryness. The crude material was purified by silica gel chromatography eluting with 0-100% EtOAc:EtOH (v/v=3:1, with 1% NEt₃) in DCM to afford I-36 (14.7 mg, 0.039 mmol, 41% yield) as a white powder. MS [M+H]⁺=372.1. ¹H NMR (400 MHz, DCM-d₂) δ 7.67 (dd, J=8.3, 1.6 Hz, 1H), 7.09-6.94 (m, 2H), 5.07 (dt, J=13.3, 5.1 Hz, 1H), 4.35-4.06 (m, 3H), 2.87-2.68 (m, 2H), 2.62 (dddd, J=10.8, 8.7, 4.2, 2.0 Hz, 1H), 2.38 (d, J=1.7 Hz, 3H), 2.32-2.18 (m, 1H), 2.16-2.01 (m, 3H), 1.80-1.65 (m, 2H), 1.42-1.10 (m, 5H).

Example 16: 3-(5-(((1S,2S)-2-(diethylamino)cyclohexyl)oxy)-1-oxoisoindolin-2-yl)piperidine-2,6-dione (I-14)

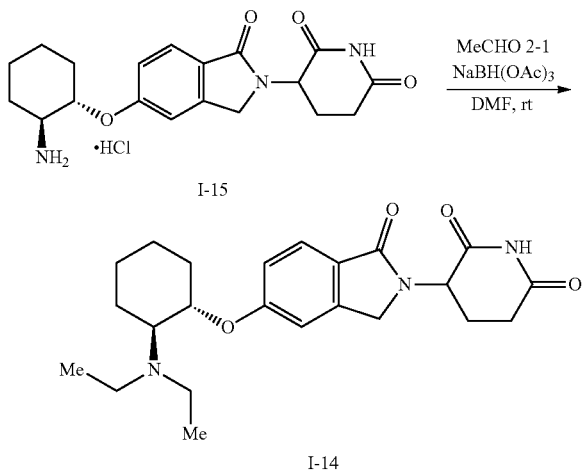

To a stirred solution of the HCl salt of I-15 (80 mg, 0.18 mmol) and NaBH(OAc)₃ (115 mg, 0.542 mmol) in DMF (2 mL) was added acetaldehyde (2-1, 0.03 mL, 0.5 mmol) and the resulting mixture was stirred for 2 hours at room temperature. The reaction mixture was then concentrated to dryness. The crude material was purified by silica gel chromatography eluting with 0% to 10% Et₃N in EtOAc to afford I-14 (30.1 mg, 0.073 mmol, 29% yield) as a white powder. MS [M+H]⁺=414.0. ¹H NMR (400 MHz, DCM-d₂) δ 8.78-8.37 (m, 1H), 7.73 (d, J=8.3 Hz, 1H), 7.16-6.93 (m, 2H), 5.18 (dd, J=13.3, 5.2 Hz, 1H), 4.46-4.24 (m, 3H), 2.94-2.77 (m, 3H), 2.70-2.51 (m, 4H), 2.43-2.29 (m, 1H), 2.28-2.16 (m, 2H), 1.94-1.71 (m, 3H), 1.48-1.23 (m, 4H), 0.97 (t, J=7.1 Hz, 6H).

Example 17: 3-(5-(((1S,2S)-2-(isobutylamino)cyclohexyl)oxy)-1-oxoisoindolin-2-yl)piperidine-2,6-dione HC(O)OH Salt (I-7)

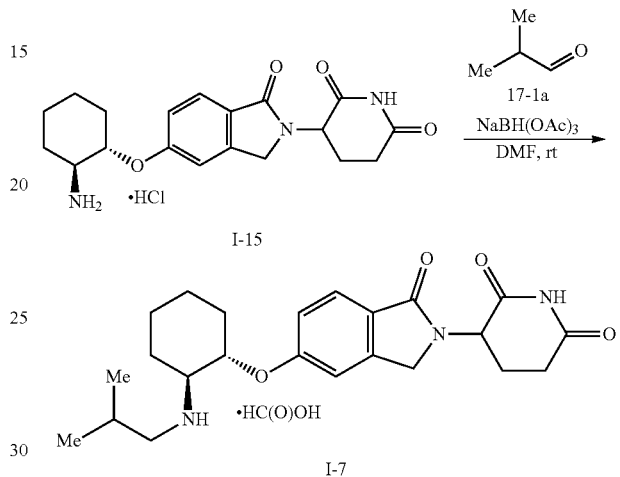

To a stirred solution of the HCl salt of I-15 (50 mg, 0.13 mmol) and NaBH(OAc)₃ (40.4 mg, 0.190 mmol) in DMF (1.5 mL) under an atmosphere of nitrogen was added isobutyraldehyde (17-1a, 0.014 mL, 0.15 mmol) in one portion and the resulting mixture was stirred for 40 min at room temperature. The reaction mixture was then concentrated to dryness. The crude material was purified by reverse phase HPLC (eluting with MeCN/H₂O with 5 mM NH₄OH) and collected into tubes containing formic acid (2 drops). The fractions containing desired product were combined and lyophilized to afford the formate salt of I-7 (17.3 mg, 0.037 mmol, 29% yield) as a white solid. MS [M+H]⁺=414.2. ¹H NMR (400 MHz, DCM-d₂) δ 8.32 (s, 1H), 7.97-7.39 (br s, 1H), 7.72-7.62 (m, 1H), 7.12-6.97 (m, 2H), 5.02 (dt, J=13.2, 5.6 Hz, 1H), 4.56 (dtd, J=13.9, 9.8, 4.1 Hz, 1H), 4.34-4.21 (m, 2H), 3.05-2.93 (m, 1H), 2.81-2.62 (m, 4H), 2.32-2.03 (m, 4H), 1.99-1.86 (m, 1H), 1.84-1.71 (m, 2H), 1.66-1.52 (m, 1H), 1.43-1.21 (m, 3H), 0.96-0.89 (m, 6H).

Example 18: 3-(5-(((3S,4S)-3-(benzylamino)tetrahydro-2H-pyran-4-yl)oxy)-1-oxoisoindolin-2-yl)piperidine-2,6-dione HC(O)OH Salt (I-21)

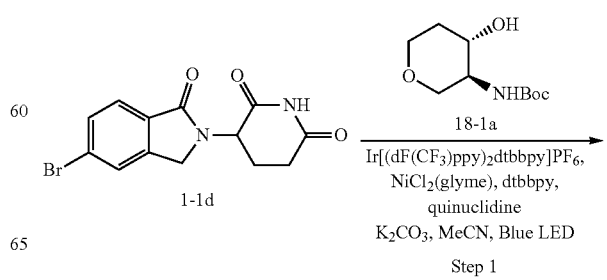

Step 1

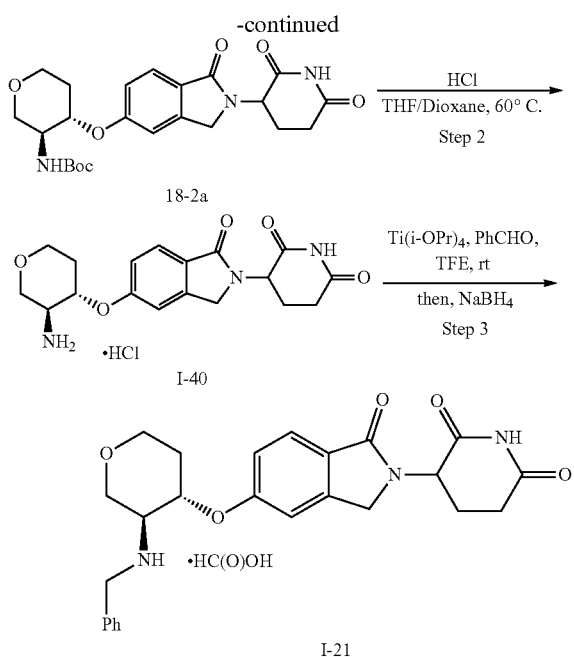

Step 1. tert-butyl ((3S,4S)-4-((2-(2,6-dioxopiperidin-3-yl)-1-oxoisoindolin-5-yl)oxy)tetrahydro-2H-pyran-3-yl)carbamate (18-2a)

To 3-(5-bromo-1-oxoisoindolin-2-yl)piperidine-2,6-dione (I-1d, 550 mg, 1.70 mmol), tert-butyl ((3S,4S)-4-hydroxytetrahydro-2H-pyran-3-yl)carbamate (18-1a, 499 mg, 2.30 mmol), NiCl$_2$(glyme) (19 mg, 0.085 mmol), dtbbpy (23 mg, 0.085 mmol), Ir[(dF(CF$_3$)ppy)$_2$dtbbpy]PF$_6$ (19 mg, 0.017 mmol), quinuclidine (18.9 mg, 0.170 mmol) and K$_2$CO$_3$ (235 mg, 1.70 mmol) under an atmosphere of nitrogen was added MeCN (15 mL) and the resulting mixture was degassed by bubbling nitrogen during sonication for 40 min. The reaction mixture was then stirred overnight under irradiation of blue LED light at room temperature for 120 h. The reaction mixture was diluted with DCM, filtered through a short pad of Celite®, and concentrated to dryness. The crude material was purified by silica gel chromatography eluting with 0% to 3% MeOH in DCM to afford 18-2a (143 mg, 0.305 mmol, 18% yield) as a white solid. MS [M-tBu+H]$^+$=404.2.

Step 2. 3-(5-(((3S,4S)-3-aminotetrahydro-2H-pyran-4-yl)oxy)-1-oxoisoindolin-2-yl)piperidine-2,6-dione Hydrochloride (I-40)

To a stirred solution of 18-2a (143 mg, 0.311 mmol) in THF (2 mL) was added 4 M HCl in dioxane (1.0 mL, 4.0 mmol) and the resulting mixture was stirred for 3 h at 60° C. Formation of a white precipitate was observed. The reaction mixture was diluted with Et$_2$O and filtered. The obtained precipitate was washed with Et$_2$O (4×) and dried under reduced pressure to afford the hydrochloride salt of I-40 (127 mg, 0.305 mmol, 96% yield) as a white solid. The product was carried onto the next step without further purification MS [M+H]$^+$=360.2.

Step 3. 3-(5-(((3S,4S)-3-(benzylamino)tetrahydro-2H-pyran-4-yl)oxy)-1-oxoisoindolin-2-yl)piperidine-2,6-dione HC(O)OH Salt (I-21)

To a stirred solution of I-40 (40 mg, 0.10 mmol) and benzaldehyde (0.015 mL, 0.15 mmol) in anhydrous TFE (1.2 mL) under atmosphere of nitrogen was added Ti(i-OPr)$_4$ (0.03 mL, 0.1 mmol) and the resulting mixture was stirred at room temperature overnight. NaBH$_4$ (6 mg, 0.2 mmol) was then added in one portion and the resulting mixture was stirred for 2 h at room temperature. The reaction mixture was quenched with H$_2$O (0.1 mL), stirred for 10 minutes, filtered, and concentrated to dryness. The crude material was purified by reverse phase HPLC (eluting with MeCN/H$_2$O with 0.1% formic acid). The fractions containing product were combined and lyophilized to afford the formate salt of I-21 (4.4 mg, 0.0087 mmol, 9% yield) as a white solid. MS [M+H]$^+$=450.4. $^1$H NMR (400 MHz, DMSO-d$_6$) δ 10.97 (s, 1H), 8.26 (s, 1H), 7.61 (d, J=8.4 Hz, 1H), 7.34-7.28 (m, 4H), 7.25-7.18 (m, 2H), 7.09 (dd, J=8.4, 2.2 Hz, 1H), 5.07 (dd, J=13.3, 5.0 Hz, 1H), 4.53-4.45 (m, 1H), 4.36 (dd, J=17.2, 12.2 Hz, 1H), 4.25 (dd, J=17.2, 8.5 Hz, 1H), 3.88 (dd, J=11.8, 4.5 Hz, 1H), 3.84-3.76 (m, 3H), 3.56-3.44 (m, 1H), 3.22 (dd, J=11.4, 8.1 Hz, 1H), 2.91 (ddd, J=17.2, 13.6, 5.4 Hz, 1H), 2.67 (td, J=7.8, 4.1 Hz, 1H), 2.63-2.55 (m, 1H), 2.45-2.32 (m, 1H), 2.19-2.09 (m, 1H), 2.03-1.94 (m, 1H), 1.52 (dtd, J=13.2, 9.2, 4.1 Hz, 1H).

Example 19: 3-(1-oxo-5-((((1S,2S)-2-(((1-(trifluoromethyl)cyclopropyl)methylamino)cyclohexyl)oxy)isoindolin-2-yl)piperidine-2,6-dione (I-11)

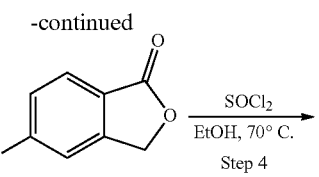

19-5a

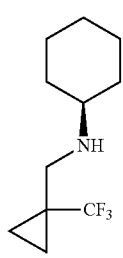

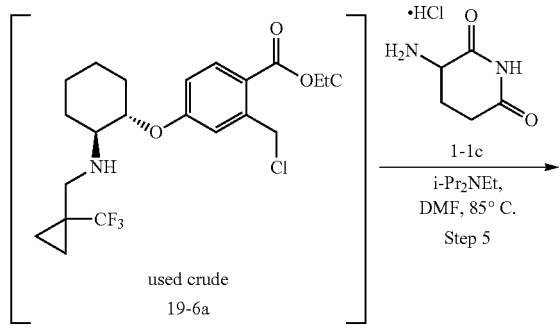

used crude
19-6a

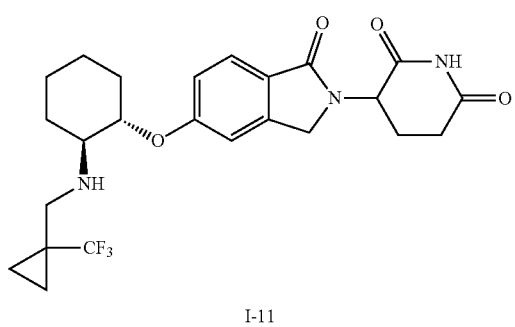

I-11

Step 1. tert-butyl ((1S,2S)-2-((1-oxo-1,3-dihydroisobenzofuran-5-yl)oxy)cyclohexyl)carbamate (19-2a)

To 5-bromoisobenzofuran-1(3H)-one (19-1a, 500 mg, 2.35 mmol), tert-butyl ((1S,2S)-2-hydroxycyclohexyl)carbamate (13-1a, 505 mg, 2.35 mmol), NiCl$_2$(glyme) (26 mg, 0.12 mmol), dtbbpy (32 mg, 0.12 mmol), Ir[(dF(CF$_3$)ppy)$_2$dtbbpy]PF$_6$ (26 mg, 0.023 mmol), quinuclidine (26 mg, 0.24 mmol) and K$_2$CO$_3$ (324 mg, 2.35 mmol) was added MeCN (30 mL) and the resulting mixture was stirred vigorously for 22 h under irradiation of blue LED light at room temperature. The reaction mixture was then concentrated to dryness and the crude material was purified by silica gel chromatography eluting with 0% to 100% EtOAc in heptane to afford 19-2a (732 mg, 1.93 mmol, 82% yield) as a white powder. MS [M-tBu+H]$^+$=292.1.

Step 2. 5-(((1S,2S)-2-aminocyclohexyl)oxy)isobenzofuran-1(3H)-one CF$_3$CO$_2$H Salt (19-3a)

To a stirred solution 19-2a (700 mg, 1.85 mmol) in DCM (0.6 mL) was added CF$_3$CO$_2$H (0.6 mL, 7.8 mmol) and the resulting mixture was stirred at room temperature overnight. The reaction mixture was then concentrated to dryness by azeotroping with heptane (3×) to afford the trifluoroacetate salt of 19-3a (710 mg, 1.83 mmol, 99% yield) as viscous yellow oil. The crude product was carried onto the next step without further purification. MS [M+H]$^+$=247.9.

Step 3. 5-(((1S,2S)-2-(((1-(trifluoromethyl)cyclopropyl)methyl)amino)cyclohexyl)oxy)isobenzofuran-1(3H)-one (19-5a)

To a stirred solution of 19-3a (300 mg, 0.830 mmol) and i-Pr$_2$NEt (0.43 mL, 2.5 mmol) in DMF (2.0 mL) was added 1-(bromomethyl)-1-(trifluoromethyl)cyclopropane (19-4a, 0.2 mL, 1 mmol) and the resulting mixture was stirred at 85° C. for 5 h. The reaction mixture was then concentrated to dryness and the crude material was purified by silica gel chromatography eluting with 0-100% EtOAc (with 1% NEt$_3$) in heptane to afford 19-5a (53 mg, 0.14 mmol, 17% yield) as a white powder. MS [M+H]$^+$=370.2. $^1$H NMR (400 MHz, DCM-d$_2$) δ 7.73 (d, J=8.5 Hz, 1H), 7.02 (dd, J=8.5, 2.2 Hz, 1H), 6.95 (s, 1H), 5.20 (s, 2H), 4.10 (ddd, J=10.0, 8.4, 4.2 Hz, 1H), 2.84 (q, J=13.1 Hz, 2H), 2.71 (ddd, J=10.6, 8.6, 4.1 Hz, 1H), 2.19-2.06 (m, 1H), 2.04-1.95 (m, 1H), 1.82-1.59 (m, 3H), 1.42-1.23 (m, 3H), 1.21-1.09 (m, 1H), 0.92-0.85 (m, 2H), 0.69-0.61 (m, 2H).

Step 4. Ethyl 2-(chloromethyl)-4-(((1S,2S)-2-(((1-(trifluoromethyl)cyclopropyl)methyl)amino)cyclohexyl)oxy)benzoate (19-6a)

To a stirred solution of 19-5a (53 mg, 0.14 mmol) in EtOH (0.5 mL) was added SOCl$_2$ (0.06 mL, 0.9 mmol) and the resulting mixture was stirred overnight at 70° C. An additional portion of SOCl$_2$ (0.02 mL, 0.3 mmol) was added and the reaction mixture was stirred for another 7 h at 70° C. The reaction mixture was then allowed to cool to room temperature and concentrated to dryness by azeotroping with heptane (2×) to afford crude 19-6a as a brown oil which was used in the next step without further purification. MS [M+H]$^+$=435.7.

Step 5. 3-(1-oxo-5-(((1S,2S)-2-(((1-(trifluoromethyl)cyclopropyl)methyl)amino)cyclohexyl)oxy) isoindolin-2-yl)piperidine-2,6-dione (I-11)

To a stirred solution of crude (19-6a) (~0.14 mmol) and i-Pr$_2$NEt (0.10 mL, 0.57 mmol) in DMF (0.5 mL) was added 3-aminopiperidine-2,6-dione hydrochloride (I-1c, 47 mg, 0.29 mmol) and the resulting mixture was stirred at 85° C. for 48 h. The reaction mixture was cooled to room temperature and concentrated to dryness. The crude material was purified by silica gel chromatography eluting with 0% to 10% Et$_3$N in EtOAc to afford I-11 (8.3 mg, 0.017 mmol, 12% yield over 2 steps) as a white solid. MS [M+H]$^+$=480.0. $^1$H NMR (400 MHz, DCM-d$_2$) δ 8.29 (s, 1H), 7.79-7.55 (m, 1H), 7.04-6.95 (m, 2H), 5.11 (ddd, J=13.3, 5.2, 2.9 Hz, 1H), 4.40-4.23 (m, 2H), 4.09 (td, J=9.2, 4.3 Hz, 1H), 2.91-2.77 (m, 4H), 2.77-2.65 (m, 1H), 2.32 (qd, J=12.8, 5.8 Hz, 1H), 2.22-2.07 (m, 2H), 2.05-1.94 (m, 1H), 1.81-1.63 (m, 3H), 1.44-1.13 (m, 4H), 0.94-0.86 (m, 2H), 0.70-0.64 (m, 2H).

Example 20: 3-(1-oxo-5-(((1S,2S)-2-(((R)-1-phenylethyl)amino)cyclohexyl)oxy)isoindolin-2-yl)piperidine-2,6-dione (I-23)

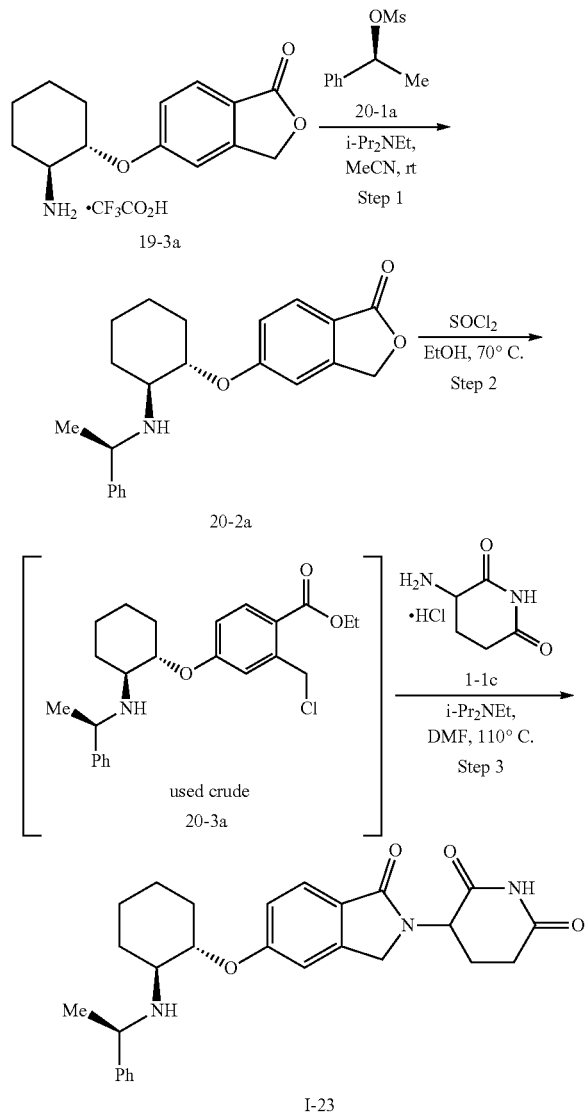

Step 1. 5-(((1S,2S)-2-(((R)-1-phenylethyl)amino)cyclohexyl)oxy)isobenzofuran-1(3H)-one (20-2a)

(S)-1-phenylethyl methanesulfonate 20-1a was prepared from (S)-1-phenylethanol as reported in U.S. Patent US2018/9796 A1, 2018 (also see Example 19, Steps 1 and 2).

To a stirred solution of 19-3a (170 mg, 0.471 mmol) and i-Pr$_2$NEt (0.41 mL, 2.35 mmol) in MeCN (1 mL) was added a solution of (S)-1-phenylethyl methanesulfonate 20-1a (451 mg, 2.25 mmol) in MeCN (1 mL) and the resulting mixture was stirred for 72 h at room temperature. The reaction mixture was then concentrated to dryness and the crude material was purified by silica gel chromatography eluting with 0% to 100% EtOAc (with 1% Et$_3$N) in heptane to afford 20-2a (60 mg, 0.17 mmol, 36% yield) as a white powder. MS [M+H]$^+$=352.0. $^1$H NMR (400 MHz, DCM-d$_2$) δ 7.72 (d, J=8.5 Hz, 1H), 7.38-7.22 (m, 5H), 6.98 (dd, J=8.5, 2.2 Hz, 1H), 6.83 (s, 1H), 5.17 (d, J=2.1 Hz, 2H), 4.13 (ddd, J=9.3, 7.8, 4.0 Hz, 1H), 3.91 (q, J=6.6 Hz, 1H), 2.54 (ddd, J=9.2, 7.8, 4.1 Hz, 1H), 2.11-2.00 (m, 2H), 1.86 (s, 1H), 1.75-1.59 (m, 2H), 1.41-1.12 (m, 4H) 1.27 (d, J=6.7 Hz, 3H).

Step 2. Ethyl 2-(chloromethyl)-4-(((1S,2S)-2-(((R)-1-phenylethyl)amino)cyclohexyl)oxy)benzoate (20-3a)

To a stirred solution of 20-2a (60 mg, 0.17 mmol) in EtOH (1.0 mL) was added SOCl$_2$ (0.074 mL, 1.0 mmol) and the resulting mixture was stirred at 70° C. overnight. The reaction mixture was then cooled to room temperature and concentrated to dryness by azeotroping with PhMe (×3) to afford crude 20-3a as a pale brown solid, which was carried onto the next step without further purification. MS [M+H]$^+$=416.1.

Step 3. 3-(1-oxo-5-(((1S,2S)-2-(((R)-1-phenylethyl)amino)cyclohexyl)oxy)isoindolin-2-yl)piperidine-2,6-dione (I-23)

To a stirred solution of crude 20-3a (~0.17 mmol) and i-Pr$_2$NEt (0.149 mL, 0.855 mmol) in DMF (1 mL) was added 3-aminopiperidine-2,6-dione hydrochloride (I-1c, 37.2 mg, 0.291 mmol) and the resulting mixture was stirred at 85° C. overnight and then at 110° C. for 4 h. The reaction mixture was allowed to cool to room temperature and concentrated to dryness. The crude material was purified by silica gel chromatography eluting with 0% to 10% Et$_3$N in EtOAc to afford I-23 (33.3 mg, 0.071 mmol, 42% yield over 2 steps) as an off-white powder. MS [M+H]$^+$=462.2. $^1$H NMR (400 MHz, DCM-d$_2$) δ 7.67 (d, J=8.4 Hz, 1H), 7.37-7.19 (m, 5H), 6.98-6.90 (m, 2H), 5.09 (ddd, J=13.4, 5.2, 2.6 Hz, 1H), 4.34-4.20 (m, 2H), 4.15-4.04 (m, 1H), 3.94-3.84 (m, 1H), 2.88-2.72 (m, 2H), 2.54-2.45 (m, 1H), 2.37-2.22 (m, 1H), 2.20-2.09 (m, 1H), 2.08-1.96 (m, 2H), 1.70-1.55 (m, 2H), 1.36-1.09 (m, 4H), 1.25 (d, J=6.7 Hz, 3H).

Example 21: 3-(5-(((1S,2S)-2-hydroxycyclohexyl)oxy)-1-oxoisoindolin-2-yl)piperidine-2,6-dione (I-27)

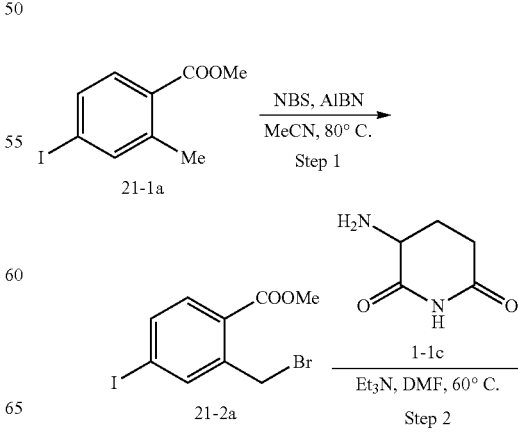

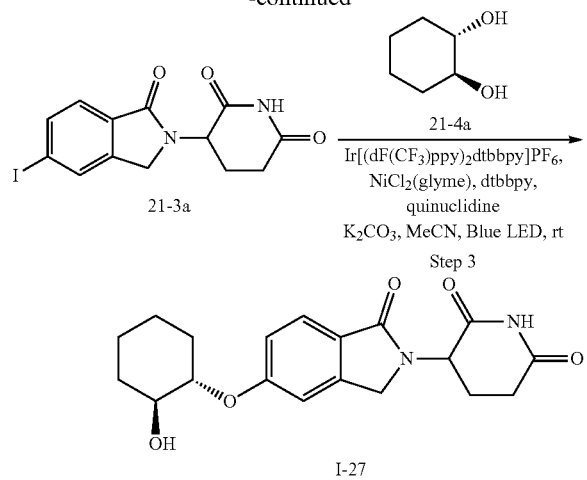

Step 1. Methyl 2-(bromomethyl)-4-iodobenzoate (21-2a)

Into a 3 L three-necked round-bottom flask, purged and maintained under an inert atmosphere of nitrogen, was placed methyl 4-iodo-2-methylbenzoate (21-1a, 170 g, 616 mmol), MeCN (1.0 L), AIBN (10.1 g, 61.5 mmol), and NBS (131.6 g, 739.2 mmol). The resulting solution was stirred overnight at 80° C. and then cooled to room temperature. The solids were filtered off and the resulting mixture was concentrated to dryness. The crude material was purified by silica gel chromatography eluting with 0% to 10% EtOAc/petroleum ether. The collected fractions were concentrated under vacuum to afford 21-2a (50.0 g, 141 mmol, 23% yield) as a white solid. $^1$H NMR (300 MHz, DMSO-$d_6$) δ 8.04-8.01 (m, 1H), 7.88-7.81 (m, 1H), 7.67-7.59 (m, 1H), 4.96 (s, 2H), 3.87 (s, 3H).

Step 2. 3-(5-iodo-1-oxoisoindolin-2-yl)piperidine-2,6-dione (21-3a)

1 L three-necked round-bottom flask was charged with 21-2a (50 g, 141 mmol), 3 aminopiperidine-2,6-dione CF$_3$CO$_2$H salt (I-1c, 34.18 g, 141.2 mmol), DMF (500 mL), and Et$_3$N (42.4 g, 419 mmol) and the resulting solution was stirred for 48 h at 60° C. The reaction mixture was cooled to room temperature and quenched by the addition of 500 mL of water/ice. The pH value of the solution was adjusted to pH=5 with 1 M aq. HCl. The solids were collected by filtration, washed with 3×500 mL of EtOAc and dried under vacuum to afford 21-3a (13 g, 35 mmol, 25% yield) as a grey solid. [M+H]$^+$=371.0. $^1$H NMR (300 MHz, DMSO-$d_6$) δ 11.00 (s, 1H), 8.06 (s, 1H), 7.90 (d, J=7.8 Hz, 1H), 7.52 (d, J=7.8 Hz, 1H), 5.14-5.08 (m, 1H), 4.47-4.28 (m, 2H), 2.97-2.85 (m, 1H), 2.73-2.01 (m, 2H), 1.98-1.20 (m, 1H).

Step 3. 3-(5-(((1S,2S)-2-hydroxycyclohexyl)oxy)-1-oxoisoindolin-2-yl)piperidine-2,6-dione (I-27)

To a stirred suspension of 3-(5-iodo-1-oxoisoindolin-2-yl)piperidine-2,6-dione (21-3a, 30 mg, 0.081 mmol), quinuclidine (1 mg, 8 μmol), Ir[(dF(CF$_3$)ppy)$_2$dtbbpy]PF$_6$ (1 mg, 0.8 μmol) and K$_2$CO$_3$ (11.2 mg, 0.09 mmol) in MeCN (1.5 mL) was added (1S,2S)-cyclohexane-1,2-diol (21-4a, 24 mg, 0.20 mmol), followed by an aliquot of Ni catalyst solution (0.025 M, 0.16 mL, 4 μmol), prepared by dissolving NiCl$_2$(glyme) (22 mg, 0.1 mmol) and dtbbpy (27 mg, 0.1 mmol) in MeCN (4 mL). The resulting mixture was degassed by bubbling nitrogen into the solution under sonication for 30 min and then stirred vigorously for 5 days under the irradiation of blue LED light at room temperature. The reaction mixture was diluted with MeCN (4 mL), filtered, and concentrated to dryness. The crude material was purified by reverse phase HPLC (eluting with MeCN/H$_2$O with 0.1% formic acid). The fractions containing product were combined and lyophilized to afford I-27 (3.2 mg, 0.0089 mmol, 11% yield) as a white solid. MS [M+H]$^+$=359.2. $^1$H NMR (400 MHz, DMSO-$d_6$) δ 10.95 (s, 1H), 7.59 (d, J=8.5 Hz, 1H), 7.31-7.14 (m, 1H), 7.06 (dd, J=8.4, 2.2 Hz, 1H), 5.06 (dd, J=13.3, 5.1 Hz, 1H), 4.95 (s, 1H), 4.37 (dd, J=17.1, 4.9 Hz, 1H), 4.24 (dd, J=17.1, 4.4 Hz, 1H), 4.20-4.06 (m, 1H), 3.62-3.50 (m, 1H), 2.90 (ddd, J=17.4, 13.6, 5.4 Hz, 1H), 2.65-2.52 (m, 1H), 2.37 (qd, J=13.2, 4.3 Hz, 1H), 2.10-1.91 (m, 2H), 1.91-1.82 (m, 1H), 1.71-1.57 (m, 2H), 1.42-1.18 (m, 4H).

Example 22: 3-(5-(((1R*, 2S*)-2-hydroxycyclohexyl)oxy)-1-oxoisoindolin-2-yl)piperidine-2,6-dione (I-37)

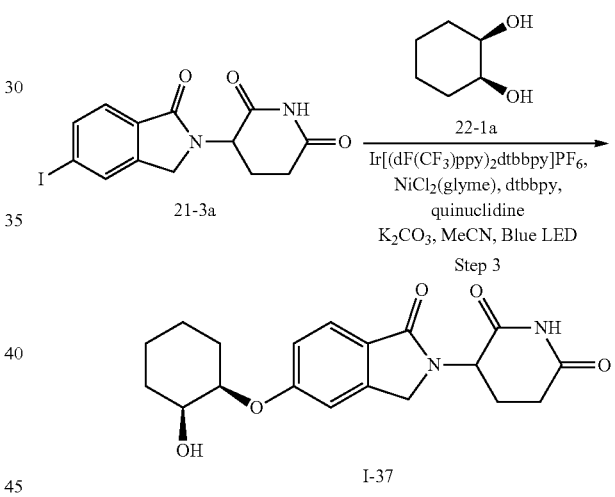

To a stirred suspension of 3-(5-iodo-1-oxoisoindolin-2-yl)piperidine-2,6-dione (21-3a, 30 mg, 0.081 mmol), Ir[(dF(CF$_3$)ppy)$_2$dtbbpy]PF$_6$ (1 mg, 0.8 μmol), quinuclidine (1 mg, 8 μmol), K$_2$CO$_3$ (1.2 mg, 0.09 mmol) in MeCN (1.5 mL) was added cis-cyclohexane-1,2-diol (22-1a, 24 mg, 0.20 mmol), followed by an aliquot of Ni catalyst solution (0.025 M, 0.16 mL, 4 μmol). prepared by dissolving NiCl$_2$(glyme) (22 mg, 0.1 mmol) and dtbbpy (27 mg, 0.1 mmol) in MeCN (4 mL). The resulting mixture was degassed by bubbling nitrogen through the mixture under sonication for 30 min and then stirred vigorously for 4 days under irradiation of blue LED light at room temperature. The reaction mixture was diluted with DCM (4 mL), filtered, and concentrated to dryness. The crude material was purified by reverse phase HPLC (eluting with MeCN/H$_2$O with 0.1% formic acid). The fractions containing the desired product were lyophilized to afford I-37 (2.1 mg, 0.0056 mmol, 7% yield) as a white solid. MS [M+H]$^+$=359.2. $^1$H NMR (400 MHz, Chloroform-d) δ 7.95 (s, 1H) 7.80 (d, J=8.4 Hz, 1H), 7.05 (d, J=8.4, 2.2 Hz, 1H), 7.00 (d, J=2.1 Hz, 1H), 5.20 (dd, J=13.1, 5.2 Hz, 1H), 4.50 (d, J=7.3 Hz, 1H), 4.44 (d, J=15.8

Hz, 1H), 4.29 (d, J=158 Hz, 1H), 3.96 (d, J=7.5 Hz, 1H), 2.98-2.75 (m, 2H), 2.34 (qd, J=13.1, 5.0 Hz, 1H), 2.27-2.17 (m, 1H), 2.07-1.85 (m, 2H), 1.79-1.68 (m, 2H), 1.68-1.62 (m, 2H), 1.46-1.32 (m, 3H).

Example 23: 3-(5-(((1R,2S)-2-(diethylamino)cyclohexyl)oxy)-1-oxoisoindolin-2-yl)piperidine-2,6-dione HC(O)OH Salt (I-35)

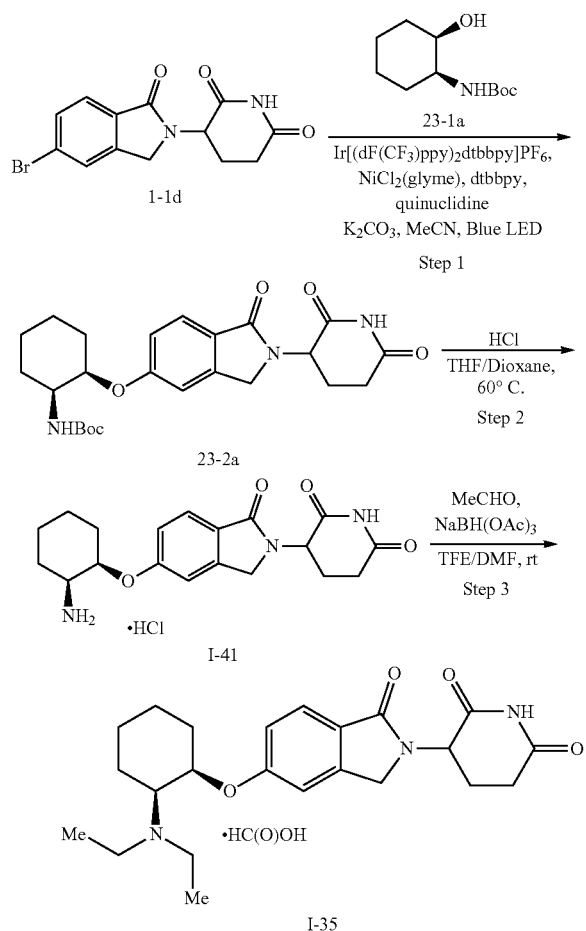

Step 1. tert-butyl (((1S,2R)-2-((2-(2,6-dioxopiperidin-3-yl)-1-oxoisoindolin-5-yl)oxy)cyclohexyl) carbamate (23-2a)

To 3-(5-bromo-1-oxoisoindolin-2-yl)piperidine-2,6-dione (I-1d, 800 mg, 2.48 mmol), NiCl$_2$(glyme) (27 mg, 0.12 mmol), dtbbpy (33 mg, 0.12 mmol), quinuclidine (28 mg, 0.25 mmol), tert-butyl ((1S,2R)-2-hydroxycyclohexyl)carbamate (23-1a, 533 mg, 2.48 mmol) and K$_2$CO$_3$ (342 mg, 2.48 mmol) under an atmosphere of nitrogen was added MeCN (15 mL). The resulting mixture was degassed by bubbling nitrogen through the mixture under sonication for 30 min and then stirred vigorously for 100 hours under irradiation of blue LED light at room temperature. The reaction mixture was diluted with DCM, filtered through a pad of Celite®, and concentrated to dryness. The crude material was purified by silica gel chromatography eluting with 0% to 3% MeOH in DCM to afford 23-2a (121 mg, 0.16 mmol, 6.5% yield) as a white solid with a purity of about 60%. The product was carried onto the next step without further purification. MS [M-tBu+H]$^+$=402.3.

Step 2. 3-(5-(((1R,2S)-2-aminocyclohexyl)oxy)-1-oxoisoindolin-2-yl)piperidine-2,6-dione hydrochloride (I-41)

To a stirred solution of 23-2a (121 mg, 0.161 mmol, ~60% pure) in THF (2 mL) was added 4 M HCl in dioxane (1.0 mL, 4.0 mmol) and the resulting mixture was stirred for 2 h a 60° C. Formation of white precipitate was observed. The reaction mixture was diluted with Et$_2$O and filtered. The white precipitate was washed with Et$_2$O (4×) and dried under vacuum to afford the hydrochloride salt of I-41 (64 mg, 0.16 mmol, 94% yield) as a white solid. The product was carried onto the next step without further purification. MS [M+H]$^+$=358.1.

Step 3. 3-(5-(((1R,2S)-2-(diethylamino)cyclohexyl)oxy)-1-oxoisoindolin-2-yl)piperidine-2,6-dione (I-35)

To a stirred solution of I-41 (50 mg, 0.13 mmol) and acetaldehyde (2-1, 0.03 mL, 0.5 mmol) in anhydrous TFE (2 mL) under and atmosphere of nitrogen was added NaBH(OAc)$_3$ (103 mg, 0.487 mmol) in one portion and the resulting mixture was stirred for 5 hours at room temperature. The reaction mixture was concentrated to dryness, redissolved in DMF (2 mL) and additional NaBH(OAc)$_3$ (103 mg, 0.487 mmol) and acetaldehyde (2-1, 0.03 mL, 0.5 mmol) were added. The resulting reaction mixture was stirred for 2.5 h and then quenched with 1 M aq. HCOOH (0.2 mL). The mixture was directly purified by reverse phase HPLC (eluting with MeCN/H$_2$O with 0.1% formic acid). The fractions containing product were combined and lyophilized to afford the formate salt of I-35 (10.9 mg, 0.023 mmol, 14% yield) as a white powder. MS [M+H]$^+$=414.3. $^1$H NMR (400 MHz, MeCN-d$_3$) δ 8.37 (s, 1H), 7.66 (d, J=8.4 Hz, 1H), 7.19-7.17 (m, 1H), 7.12 (dt, J=8.4, 2.2 Hz, 1H), 5.10-5.01 (m, 2H), 4.37 (dd, J=16.8, 2.9 Hz, 1H), 4.29 (dd, J=16.8, 3.8 Hz, 1H), 3.18 (d, J=12.5 Hz, 1H), 3.08-2.90 (m, 4H), 2.88-2.65 (m, 2H), 2.40 (qd, J=13.2, 4.9 Hz, 1H), 2.18-1.99 (m, 3H), 1.92-1.82 (m, 2H), 1.63-1.37 (m, 4H), 1.14 (t, J=7.2 Hz, 6H).

Example 24: 3-(5-(((1R,2R)-2-(diethylamino)cyclopentyl)oxy)-1-oxoisoindolin-2-yl)piperidine-2,6-dione HC(O)OH Salt (I-43)

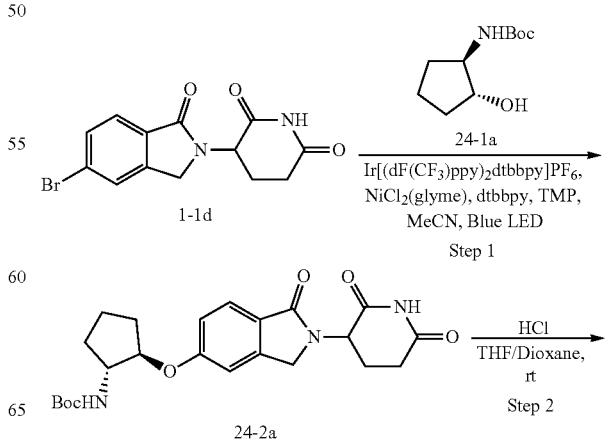

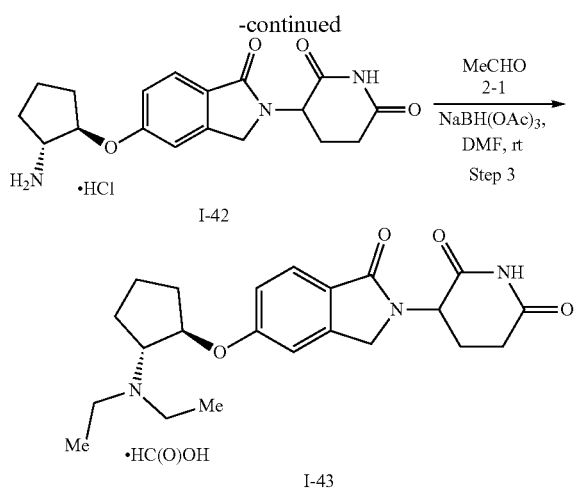

Step 1. tert-butyl ((1R,2R)-2-((2-(2,6-dioxopiperidin-3-yl)-1-oxoisoindolin-5-yl)oxy)cyclopentyl)carbamate (24-2a)

To a stirred suspension of 1-Id (263 mg, 0.813 mmol), tert-butyl ((1R,2R)-2-hydroxycyclopentyl)carbamate (24-1a, 149 mg, 0.740 mmol), NiCl$_2$(glyme) (9 mg, 0.04 mmol), dtbbpy (11 mg, 0.042 mmol), and Ir[(dF(CF$_3$)ppy)$_2$dtbbpy]PF$_6$ (10 mg, 9.1 µmol) in MeCN (2.5 mL) under an atmosphere of nitrogen was added 2,2,6,6-tetramethylpiperidine (40-2, 0.13 mL, 0.77 mmol) and the resulting mixture was stirred vigorously overnight under irradiation of blue LED light at room temperature. The reaction mixture was then diluted with EtOAc, filtered through Celite®, and concentrated to dryness. The crude material was purified by reverse phase HPLC (eluting with MeCN/H$_2$O with 0.1% formic acid). The fractions containing the desired product were combined and lyophilized to afford 24-2a as a white solid (30.8 mg, 0.067 mmol, 9% yield). MS [M+H]$^+$=444.5. $^1$H NMR (400 MHz, DMSO-d$_6$) δ 10.95 (s, 1H), 7.60 (d, J=8.4 Hz, 1H), 7.18 (s, 1H), 7.11-6.99 (m, 2H), 5.07 (ddd, J=13.4, 5.2, 1.9 Hz, 1H), 4.72-4.56 (m, 1H), 4.52-4.16 (m, 2H), 3.88 (s, 1H), 2.90 (ddd, J=18.3, 13.6, 5.4 Hz, 1H), 2.60 (dd, J=3.8, 1.8 Hz, 1H), 2.38 (dd, J=13.2, 4.5 Hz, 1H), 2.14-1.83 (m, 3H), 1.83-1.58 (m, 3H), 1.50 (dq, J=13.5, 7.1, 6.5 Hz, 1H), 1.38 (s, 9H).

Step 2. 3-(5-(((1R,2R)-2-aminocyclopentyl)oxy)-1-oxoisoindolin-2-yl)piperidine-2,6-dione hydrochloride (I-42)

To a stirred solution of 24-2a (30 mg, 0.068 mmol) in THF (1 mL) was added 4 M HCl in dioxane (0.1 mL, 0.4 mmol) and the resulting mixture was stirred at room temperature for 48 h. The reaction mixture was then filtered and the obtained white precipitate was washed with EtOAc multiple times. The solid was then collected to afford the hydrochloride salt of I-42 as a yellow solid (10 mg, 0.025 mmol, 37% yield). MS [M+H]$^+$=344.4. $^1$H NMR (400 MHz, DMSO-d$_6$) δ 10.97 (s, 1H), 8.31 (s, 3H), 7.66 (d, J=8.4 Hz, 1H), 7.22 (dd, J=4.6, 2.2 Hz, 1H), 7.08 (dt, J=8.4, 2.3 Hz, 1H), 5.14-5.02 (m, 1H), 4.85 (dt, J=7.3, 4.2 Hz, 1H), 4.47-4.23 (m, 2H), 3.68-3.62 (m, 1H), 2.91 (ddd, J=17.3, 13.6, 5.4 Hz, 1H), 2.66-2.56 (m, 1H), 2.44-2.34 (m, 1H), 2.31-2.22 (m, 1H), 2.17-2.06 (m, 1H), 2.06-1.92 (m, 1H), 1.90-1.62 (m, 4H).

Step 3. 3-(5-(((1R,2R)-2-(diethylamino)cyclopentyl)oxy)-1-oxoisoindolin-2-yl)piperidine-2,6-dione HC(O)OH Salt (I-43)

To a stirred solution of I-42 (10 mg, 0.026 mmol) and acetaldehyde (2-1, 4 µL, 0.08 mmol) in DMF (0.5 mL) was added sodium triacetoxyborohydride (17 mg, 0.079 mmol) in one portion and the resulting mixture was stirred at room temperature for 8 hours. The reaction mixture was then concentrated to dryness and the crude material was purified by reverse phase HPLC (eluting with MeCN/H$_2$O with 0.1% formic acid). The fractions containing the desired product were combined and lyophilized to afford the formate salt of I-43 as a white solid (7.8 mg, 0.017 mmol, 65% yield). MS [M+H]$^+$=400.5. $^1$H NMR (400 MHz, DMSO-d$_6$) δ 10.95 (s, 1H), 8.18 (s, 1H), 7.60 (d, J=8.4 Hz, 1H), 7.22 (t, J=1.9 Hz, 1H), 7.05 (dt, J=8.4, 2.0 Hz, 1H), 5.12-5.00 (m, 1H), 4.65 (s, 1H), 4.47-4.19 (m, 2H), 2.90 (ddd, J=18.3, 13.7, 5.4 Hz, 1H), 2.60 (d, J=2.9 Hz, 1H), 2.38 (dd, J=13.1, 4.5 Hz, 1H), 2.07-1.94 (m, 2H), 1.89 (d, J=6.3 Hz, 1H), 1.76-1.58 (m, 3H), 1.55-1.44 (m, 1H), 0.96 (t, J=7.1 Hz, 6H).

Example 25: 3-(5-(((1S,2R)-2-(diethylamino)cyclopentyl)oxy)-1-oxoisoindolin-2-yl)piperidine-2,6-dione HC(O)OH Salt (I-10)

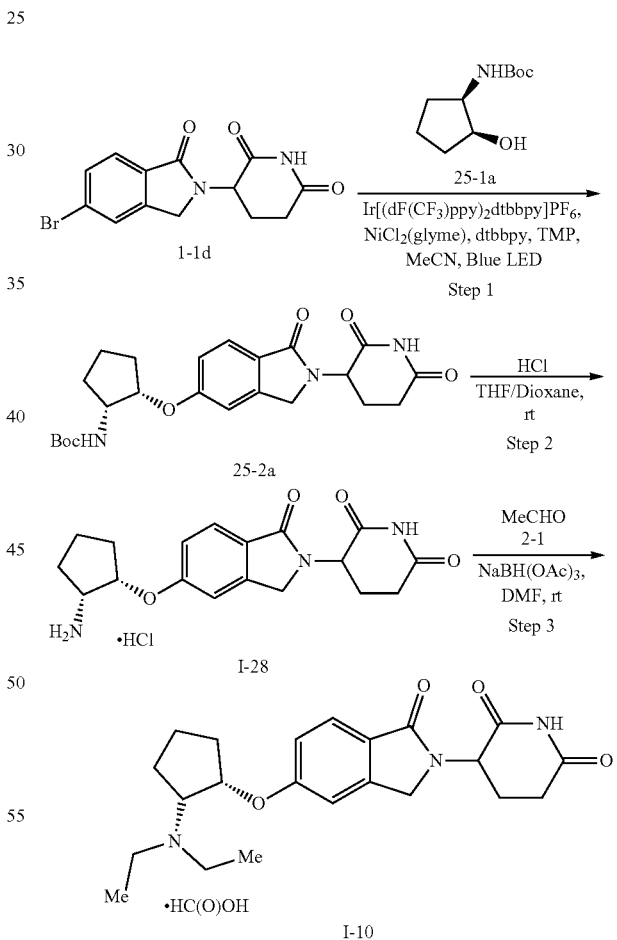

Step 1. tert-butyl ((1R,2S)-2-((2-(2,6-dioxopiperidin-3-yl)-1-oxoisoindolin-5-yl)oxy)cyclopentyl)carbamate (25-2a)

To a stirred suspension of 1-Id (280 mg, 0.868 mmol), tert-butyl ((1R,2S)-2-hydroxycyclopentyl)carbamate (25-

1a, 167 mg, 0.828 mmol), NiCl₂(glyme) (9.5 mg, 0.043 mmol), dtbbpy (11.5 mg, 0.043 mmol), and Ir[(dF(CF₃)ppy)₂dtbbpy]PF₆ (10 mg, 8.8 μmol) in MeCN (2.5 mL) under an atmosphere of nitrogen was added 2,2,6,6-tetramethylpiperidine (40-2, 0.15 mL, 0.89 mmol) and the resulting mixture was stirred overnight under the irradiation of blue LED light at room temperature. The reaction mixture was then diluted with EtOAc, filtered through Celite®, and concentrated to dryness. The crude material was purified by reverse phase HPLC (eluting with MeCN/H₂O with 0.1% formic acid). The fractions containing desired product were combined and lyophilized to afford 25-2a as a white solid (78.1 mg, 0.174 mmol, 21% yield). MS [M−H]⁻=442.4. ¹H NMR (400 MHz, DMSO-d₆) δ 10.95 (s, 1H), 7.58 (d, J=8.4 Hz, 1H), 7.12 (s, 1H), 7.02 (d, J=8.3 Hz, 1H), 6.81 (t, J=7.1 Hz, 1H), 5.06 (dd, J=13.3, 5.0 Hz, 1H), 4.75 (s, 1H), 4.45-4.17 (m, 2H), 3.92 (s, 1H), 2.90 (ddd, J=18.3, 13.6, 5.4 Hz, 1H), 2.60 (s, 1H), 2.38 (dd, J=13.2, 4.5 Hz, 1H), 2.07-1.91 (m, 2H), 1.91-1.80 (m, 1H), 1.80-1.62 (m, 3H), 1.62-1.45 (m, 1H), 1.30 (d, J=2.8 Hz, 9H).

Step 2. 3-(5-(((1S,2R)-2-aminocyclopentyl)oxy)-1-oxoisoindolin-2-yl)piperidine-2,6-dione hydrochloride (I-28)

To a stirred solution of 25-2a (78.1 mg, 0.176 mmol) in THF (1 mL) was added 4 M HCl in dioxane (0.15 mL, 0.60 mmol) and the resulting mixture was allowed to stir at room temperature for 36 h. The reaction mixture was filtered, washed with EtOAc multiple times, and dried under vacuum to afford hydrochloride salt of I-28 as a yellow solid. MS [M+H]⁺=344.4. ¹H NMR (400 MHz, DMSO-d₆) δ 10.97 (s, 1H), 8.10 (s, 3H), 7.68 (d, J=8.4 Hz, 1H), 7.23 (t, J=2.5 Hz, 1H), 7.13 (dt, J=8.5, 1.9 Hz, 1H), 5.08 (dd, J=13.3, 5.0 Hz, 1H), 4.88 (s, 1H), 4.50-4.22 (m, 2H), 3.69 (s, 1H), 2.91 (ddd, J=17.7, 13.4, 5.3 Hz, 1H), 2.65-2.57 (m, 1H), 2.38 (dd, J=13.2, 4.5 Hz, 1H), 2.16-1.92 (m, 3H), 1.88-1.73 (m, 3H), 1.73-1.59 (m, 1H).

Step 3. 3-(5-(((1S,2R)-2-(diethylamino)cyclopentyl)oxy)-1-oxoisoindolin-2-yl)piperidine-2,6-dione HC(O)OH Salt (I-10)

To a stirred solution of I-28 (50 mg, 0.13 mmol) and acetaldehyde (2-1, 0.02 mL, 0.4 mmol) in DMF (1 mL) was added sodium triacetoxyborohydride (85 mg, 0.40 mmol) in one portion and the resulting mixture was stirred at room temperature for 24 h. The reaction mixture was then concentrated to dryness and the crude material was purified by reverse phase HPLC (eluting with MeCN/H₂O with 0.1% formic acid). The fractions containing the desired product were combined and lyophilized to afford the formate salt of I-10 as a white solid (23.1 mg, 0.049 mmol, 37% yield). MS [M+H]⁺=400.5. ¹H NMR (400 MHz, DMSO-d₆) δ 10.95 (s, 1H), 8.16 (s, 1H), 7.61 (d, J=8.4 Hz, 1H), 7.16 (d, J=2.1 Hz, 1H), 7.05 (dd, J=8.4, 2.2 Hz, 1H), 5.07 (dd, J=13.3, 5.0 Hz, 1H), 4.88 (s, 1H), 4.50-4.16 (m, 2H), 3.09 (s, 1H), 2.96-2.80 (m, 1H), 2.75-2.62 (m, 5H), 2.64-2.53 (m, 1H), 2.39 (dd, J=13.2, 8.7 Hz, 1H), 2.03-1.67 (m, 5H), 1.67-1.57 (m, 1H), 0.95 (t, J=7.0 Hz, 6H).

Example 26: 3-(5-(((1S,2S)-2-(ethyl(2-fluoroethyl)amino)cyclopentyl)oxy)-1-oxoisoindolin-2-yl)piperidine-2,6-dione (I-24)

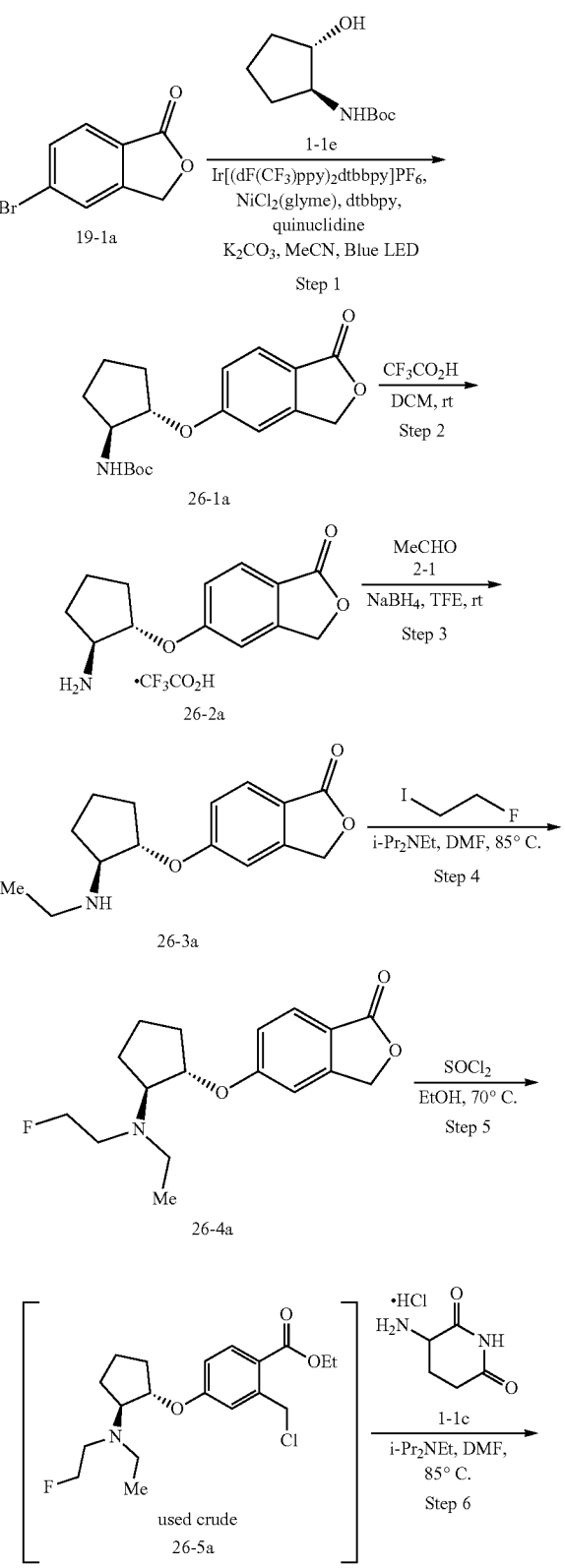

-continued

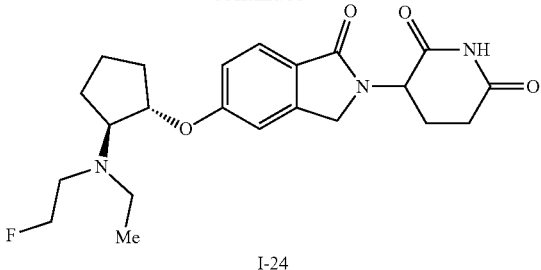

I-24

Step 1. tert-butyl ((1S,2S)-2-((1-oxo-1,3-dihydroisobenzofuran-5-yl)oxy)cyclopentyl)carbamate (26-1a)

To 5-bromoisobenzofuran-1(3H)-one (19-1a, 1.12 g, 5.26 mmol), tert-butyl ((1S,2S)-2-hydroxycyclopentyl)carbamate (1-1e, 1.06 g, 5.26 mmol), $NiCl_2$(glyme) (55 mg, 0.25 mmol), dtbbpy (67 mg, 0.25 mmol), $Ir[(dF(CF_3)ppy)_2dtbbpy]PF_6$ (56 mg, 0.050 mmol), quinuclidine (55 mg, 0.50 mmol) and $K_2CO_3$ (688 mg, 4.98 mmol) under an atmosphere of nitrogen was added MeCN (25 mL) and the resulting mixture was stirred vigorously for 30 hours under irradiation of blue LED light at room temperature. The reaction mixture was then diluted with DCM (20 mL), filtered through a pad of Celite R, and concentrated to dryness. The crude material was purified by silica gel chromatography eluting with 0% to 100% EtOAc in heptane to afford 26-1a (1.38 g, 3.89 mmol, 74% yield) as a white solid. MS $[M-tBu+H]^+$=278.1. $^1$H NMR (400 MHz, DCM-$d_2$) δ 7.75 (d, J=8.7 Hz, 1H), 7.24-7.03 (m, 2H), 5.23 (s, 2H), 4.69 (s, 1H), 4.60 (s, 1H), 4.09-3.99 (m, 1H), 2.22-2.02 (m, 2H), 1.91-1.75 (m, 3H), 1.59-1.48 (m, 1H), 1.43 (s, 9H).

Step 2. 5-(((1S,2S)-2-aminocyclopentyl)oxy)isobenzofuran-1 (3H)-one $CF_3CO_2H$ Salt (26-2a)

To a stirred solution of 26-1a (1.9 g, 5.70 mmol) in DCM (5 mL) was added TFA (2.18 mL, 28.5 mmol) and the resulting mixture was stirred at room temperature overnight. The reaction mixture was concentrated to dryness by azeotroping with PhMe (×2) to afford the trifluoroacetate salt of 26-2a (1.97 g, 5.45 mmol, 96% yield) as a white solid. The product was carried onto the next step without further purification. MS $[M+H]^+$=234.3.

Step 3. 5-(((1S,2S)-2-(ethylamino)cyclopentyl)oxy)isobenzofuran-1(3H)-one (26-3a)

To a stirred solution of 26-2a (155.6 mg, 0.448 mmol) and acetaldehyde (2-1, 0.03 mL, 0.5 mmol) in 2,2,2-trifluoroethanol (2 mL) under an atmosphere of nitrogen was added $NaBH(OAc)_3$ (199 mg, 0.939 mmol) in one portion and the resulting mixture was stirred at room temperature until complete consumption of the starting material was observed. The reaction mixture was diluted with water (20 mL) and basified with sat. aq. $NaHCO_3$. The aqueous solution was extracted with EtOAc (3×25 mL) and the combined organic phases were washed with brine (20 mL), dried over $MgSO_4$, filtered, and concentrated to dryness. The crude material was purified by silica gel chromatography eluting with 0% to 10% MeOH in DCM (with 0.1% $Et_3N$ modifier) to afford 26-3a (79.5 mg, 0.283 mmol, 63% yield) as a light yellow gum. MS $[M+H]^+$=262.3. $^1$H NMR (400 MHz, DCM-$d_2$) δ 7.79 (d, J=8.5 Hz, 1H), 7.07 (dd, J=8.5, 2.2 Hz, 1H), 7.01-6.99 (m, 1H), 5.26 (s, 2H), 4.57 (dt, J=6.4, 3.4 Hz, 1H), 3.31 (td, J=6.7, 3.7 Hz, 1H), 2.82-2.61 (m, 2H), 2.25-2.06 (m, 2H), 1.86-1.73 (m, 3H), 1.54-1.45 (m, 2H), 1.13 (t, J=7.1 Hz, 3H).

Step 4. 5-(((1S,2S)-2-(ethyl(2-fluoroethyl)amino)cyclopentyl)oxy)isobenzofuran-1 (3H)-one (26-4a)

To a stirred solution of 26-3a (79.5 mg, 0.304 mmol) and 1-fluoro-2-iodoethane (140 mg, 0.805 mmol) in DMF (1 mL) was added i-$Pr_2NEt$ (0.15 mL, 0.86 mmol) and the resulting mixture was stirred at 85° C. overnight. The reaction mixture was diluted with EtOAc (40 mL) and washed with 0.5 M aq. LiCl solution (10 mL), sat. aq. $NaHCO_3$ (10 mL), and brine (10 mL). The combined organic layers were dried over $MgSO_4$, filtered, and concentrated to dryness. The crude material was purified by silica gel chromatography eluting with 0% to 5% MeOH in DCM (with 0.1% $Et_3N$ modifier) to afford 26-4a as a colorless gum (39.8 mg, 0.128 mmol, 42% yield). MS $[M+H]^+$=308.3. $^1$H NMR (400 MHz, DCM-$d_2$) δ 7.79 (d, J=8.4 Hz, 1H), 7.22-7.05 (m, 2H), 5.26 (s, 2H), 4.75-4.30 (m, 2H), 3.41 (s, 1H), 2.93-2.74 (m, 2H), 2.73-2.56 (m, 2H), 2.02 (s, 2H), 1.85 (dd, J=25.5, 11.3 Hz, 3H), 1.55 (d, J=11.2 Hz, 2H), 1.08 (s, 3H).

Step 5. Ethyl 2-(chloromethyl)-4-(((1S,2S)-2-(ethyl(2-fluoroethyl)amino)cyclopentyl)oxy)benzoate (26-5a)

To a stirred solution of 26-4a (39.8 mg, 0.129 mmol) in EtOH (1 mL) was added $SOCl_2$ (0.05 mL, 0.7 mmol) and the resulting mixture was stirred at 70° C. overnight. The reaction mixture was diluted with water (10 mL), neutralized with sat. aq. $NaHCO_3$, and extracted with EtOAc (3×30 mL). The combined organic phases were then washed with 5% aq. $NaHCO_3$ solution (10 mL), brine (10 mL), dried over $MgSO_4$, filtered, and concentrated to dryness to afford the crude 26-5a as a brown-red gum (45.9 mg, 0.114 mmol, 88% yield). MS $[M+H]^+$=372.2. $^1$H NMR (400 MHz, DCM-$d_2$) δ 8.00 (d, J=8.8 Hz, 1H), 7.19 (d, J=2.6 Hz, 1H), 6.99 (dd, J=8.8, 2.6 Hz, 1H), 5.07 (s, 2H), 4.64 (d, J=4.9 Hz, 1H), 4.54 (t, J=5.5 Hz, 1H), 4.42 (t, J=5.5 Hz, 1H), 4.36 (q, J=7.1 Hz, 2H), 3.40 (td, J=8.4, 4.1 Hz, 1H), 2.84 (dt, J=24.5, 5.3 Hz, 2H), 2.68 (q, J=7.0 Hz, 2H), 2.10-1.95 (m, 2H), 1.88-1.73 (m, 2H), 1.57 (d, J=16.7 Hz, 2H), 1.41 (t, J=7.1 Hz, 3H), 1.08 (t, J=7.1 Hz, 3H).

Step 6. 3-(5-(((1S,2S)-2-(ethyl(2-fluoroethyl)amino)cyclopentyl)oxy)-1-oxoisoindolin-2-yl)piperidine-2,6-dione (I-24)

To a stirred solution of 3-aminopiperidine-2,6-dione hydrochloride (I-1c, 26 mg, 0.16 mmol) and i-$Pr_2NEt$ (0.07 mL, 0.38 mmol) in DMF (0.5 mL) was added a solution of 26-5a (45.9 mg, 0.123 mmol) in DMF (0.5 mL) and the resulting mixture was stirred at 85° C. until complete consumption of starting material was observed by LC-MS analysis. The reaction mixture was diluted with EtOAc (40 mL), washed with sat. aq. $NaHCO_3$ (3×10 mL), brine (10 mL), dried over $MgSO_4$, filtered, and concentrated to dryness. The crude material was purified by reverse phase HPLC (eluting with MeCN/$H_2O$ with 0.1% formic acid). The fractions containing the desired product were combined and lyophilized to afford I-24 as a white solid (6.5 mg, 0.015 mmol, 12% yield). MS $[M+H]^+$=418.4. $^1$H NMR (400 MHz, DMSO-d$_6$) δ 10.95 (s, 1H), 7.60 (d, J=8.4 Hz, 1H), 7.24 (d, J=2.1 Hz, 1H), 7.06 (dt, J=8.5, 2.0 Hz, 1H), 5.07 (dd, J=13.2, 5.1 Hz, 1H), 4.65 (s, 1H), 4.48 (t, J=5.3 Hz, 1H), 4.44-4.19 (m, 3H), 2.98-2.71 (m, 3H), 2.64-2.56 (m, 3H), 2.38 (dd, J=13.2, 4.5 Hz, 1H), 2.11-1.85 (m, 4H), 1.79-1.56 (m, 3H), 1.54-1.42 (m, 1H), 0.98 (t, J=7.1 Hz, 3H).

Example 27: 3-(5-(((1S,2S)-2-((2,2-difluoroethyl)(ethyl)amino)cyclopentyl)oxy)-1-oxoisoindolin-2-yl)piperidine-2,6-dione (I-1)

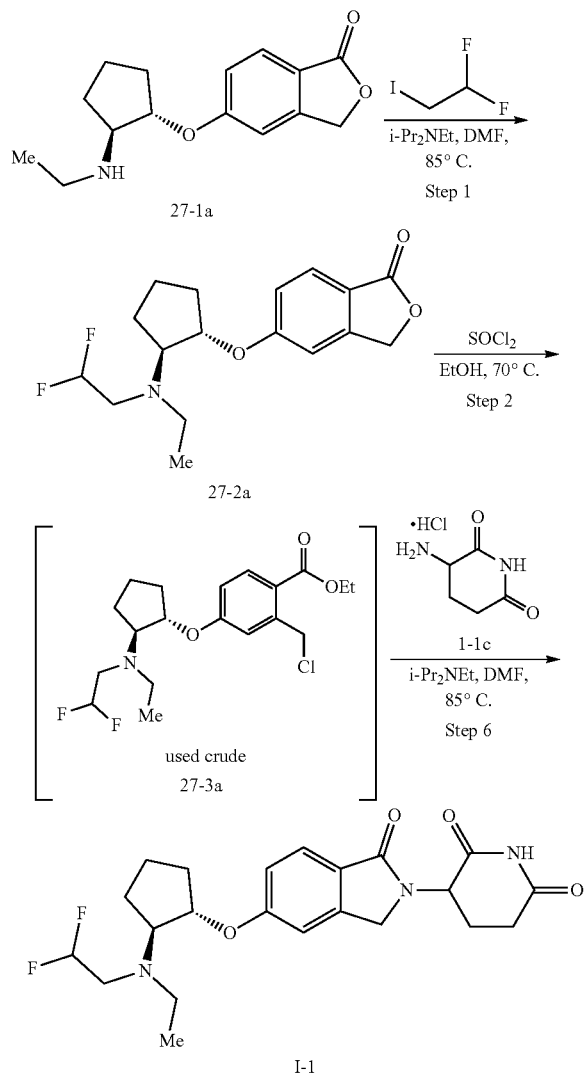

Step 1. 5-(((1S,2S)-2-((2,2-difluoroethyl)(ethyl)amino)cyclopentyl)oxy)isobenzofuran-1(3H)-one (27-2a)

To a stirred solution of 27-1a (47.1 mg, 0.180 mmol) and 1,1-difluoro-2-iodoethane (32 mg, 0.17 mmol) in DMF (1 mL) was added i-Pr$_2$NEt (0.07 mL, 0.4 mmol) and the resulting mixture was stirred at room temperature overnight. The reaction mixture was then heated to 85° C. and stirred until complete consumption of starting material was observed by LC-MS analysis. The solution was diluted with EtOAc (40 mL) and washed with 0.5 M aq. LiCl solution (10 mL), sat. aq. NaHCO$_3$ solution (10 mL), and brine (10 mL). The combined organic layers were dried over MgSO$_4$, filtered, and concentrated to dryness. The crude material was purified by silica gel chromatography eluting with 0% to 5% MeOH in DCM (0.1% Et$_3$N modifier) to afford the 27-2a as a colorless gum (28.2 mg, 0.077 mmol, 43% yield). MS [M+H]$^+$=326.3. $^1$H NMR (400 MHz, DCM-d$_2$) δ 7.79 (d, J=8.2 Hz, 1H), 7.13-7.06 (m, 2H), 5.79 (tt, J=56.4, 4.3 Hz, 1H), 5.26 (s, 2H), 4.72-4.56 (m, 1H), 3.42 (dt, J=13.5, 9.0 Hz, 1H), 2.97-2.82 (m, 3H), 2.78-2.64 (m, 1H), 2.23-1.97 (m, 2H), 1.92-1.74 (m, 3H), 1.55 (d, J=11.9 Hz, 2H), 1.09 (t, J=7.1 Hz, 2H).

Step 2. Ethyl 2-(chloromethyl)-4-(((1S,2S)-2-((2,2-difluoroethyl)(ethyl)amino)-cyclopentyl)oxy)benzoate (27-3a)

To a stirred solution of 27-2a (28.2 mg, 0.087 mmol) in EtOH (1 mL) was added SOCl$_2$ (0.04 mL, 0.55 mmol) and the resulting mixture was stirred at 70° C. overnight. The reaction mixture was then diluted with water (10 mL), neutralized with sat. aq. NaHCO$_3$, and extracted with EtOAc (3×30 mL). The combined organic phases were then washed with 5% aq. NaHCO$_3$ (10 mL), brine (10 mL), dried over MgSO$_4$, filtered, and concentrated to dryness to afford the crude 27-3a as a black gum which was carried onto the next step without further purification (29.7 mg, 0.061 mmol, 70% yield). MS [M+H]$^+$=390.4. $^1$H NMR (400 MHz, DCM-d$_2$) δ 8.00 (d, J=8.7 Hz, 1H), 7.16 (d, J=2.6 Hz, 1H), 6.97 (dd, J=8.8, 2.6 Hz, 1H), 5.80 (tt, J=56.4, 4.3 Hz, 1H), 5.08 (s, 2H), 4.63 (dt, J=7.6, 3.5 Hz, 1H), 4.36 (q, J=7.1 Hz, 2H), 3.42 (ddd, J=9.6, 7.5, 4.5 Hz, 1H), 2.98-2.84 (m, 2H), 2.81-2.64 (m, 2H), 2.04 (dddd, J=12.4, 10.8, 6.8, 2.5 Hz, 2H), 1.89-1.74 (m, 2H), 1.61-1.48 (m, 2H), 1.41 (t, J=7.1 Hz, 3H), 1.10 (t, J=7.1 Hz, 3H).

Step 3. 3-(5-(((1S,2S)-2-((2,2-difluoroethyl)(ethyl)amino)cyclopentyl)oxy)-1-oxoisoindolin-2-yl)piperidine-2,6-dione (I-1)

To a stirred solution of 3-aminopiperidine-2,6-dione hydrochloride (I-1c, 17 mg, 0.10 mmol) and i-Pr$_2$NEt (0.04 mL, 0.24 mmol) in DMF (0.5 mL) was added a solution of 27-3a (29.7 mg, 0.076 mmol) in DMF (0.5 mL) and the resulting mixture was stirred at 85° C. overnight. The reaction mixture was then cooled to room temperature, diluted with EtOAc (40 mL), washed with sat. aq. NaHCO$_3$ (3×10 mL), brine (10 mL), dried over MgSO$_4$, filtered, and concentrated to dryness. The crude material was purified by reverse phase HPLC (eluting with MeCN/H$_2$O with 0.1% formic acid). The fractions containing the desired product were combined and lyophilized. The product was repurified by silica gel chromatography eluting with 10% Et$_3$N in EtOAc to afford the I-1 as a white solid (1.7 mg, 3.79 µmol, 5% yield). MS [M+H]$^+$=436.4. $^1$H NMR (400 MHz, DMSO-d$_6$) δ 10.95 (s, 1H), 7.61 (d, J=8.4 Hz, 1H), 7.21 (d, J=2.1 Hz, 1H), 7.09-7.02 (m, 1H), 6.16-5.78 (m, 1H), 5.07 (dd, J=13.3, 5.1 Hz, 1H), 4.67 (s, 1H), 4.48-4.16 (m, 2H), 2.97-2.78 (m, 2H), 2.64-2.59 (m, 1H), 2.42-2.36 (m, 2H), 2.10-2.03 (m, 3H), 2.01-1.89 (m, 3H), 1.74-1.56 (m, 3H), 1.48 (d, J=10.6 Hz, 1H), 0.99 (t, J=7.0 Hz, 3H).

Example 28: 3-(5-(((1S,2S)-2-(3-azabicyclo[3.2.1] octan-3-yl)cyclopentyl)oxy)-1-oxoisoindolin-2-yl) piperidine-2,6-dione (I-16)

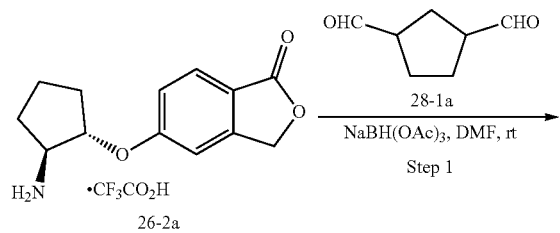

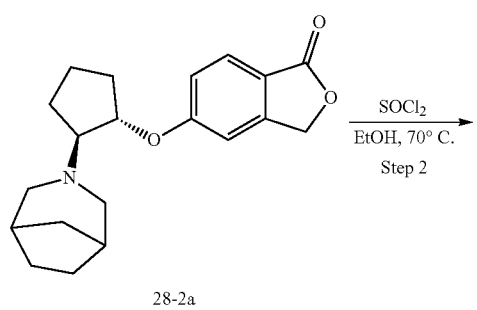

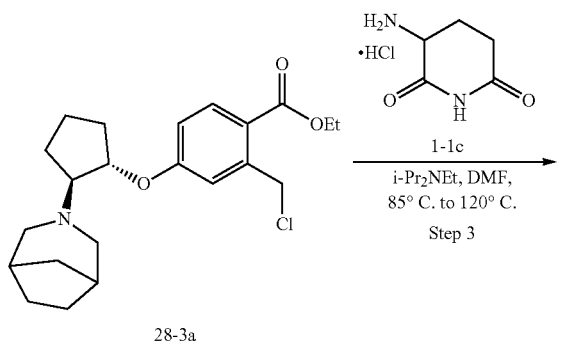

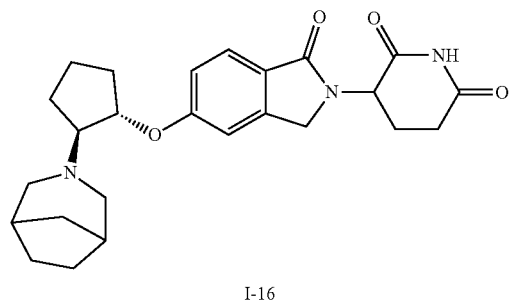

Step 1. 5-(((1S,2S)-2-(3-azabicyclo[3.2.1]octan-3-yl)cyclopentyl)oxy)isobenzofuran-1(3H)-one (28-2a)

Cyclopentane-1,3-dicarbaldehyde 28-1a was prepared as reported in *European Journal of Organic Chemistry*, 2007, 1, 53-61

To a stirred solution of 26-2a (186 mg, 0.537 mmol) and NaBH(OAc)$_3$ (243 mg, 1.15 mmol) in DMF (3 mL) under an atmosphere of nitrogen was added a solution of cyclopentane-1,3-dicarbaldehyde 28-1a (79 mg, 0.63 mmol) in DMF (2.5 mL) and the resulting mixture was stirred at room temperature overnight. The reaction mixture was diluted with water (20 mL), basified with sat. aq. NaHCO$_3$ and extracted with EtOAc (3×30 mL). The combined organic phases were washed with 0.5 M aq. LiCl, sat. aq. NaHCO$_3$, and brine, dried over MgSO$_4$, filtered, and concentrated to dryness. The crude material was purified by silica gel chromatography eluting with 0% to 20% MeOH in DCM (with 0.1% Et$_3$N modifier) to afford the 28-2a as a colorless gum (76.1 mg, 0.181 mmol, 34% yield). MS [M+H]$^+$=328.6.

Step 2. Ethyl 4-(((1S,2S)-2-(3-azabicyclo[3.2.1] octan-3-yl)cyclopentyl)oxy)-2-(chloromethyl)benzoate (28-3a)

To a stirred solution of 28-2a (76.1 mg, 0.232 mmol) in EtOH (2.5 mL) was added SOCl$_2$ (0.085 mL, 1.16 mmol) and the resulting mixture was stirred at 70° C. overnight. The reaction mixture was then diluted with water (10 mL), neutralized with sat. aq. NaHCO$_3$, and extracted with EtOAc (3×30 mL). The combined organic phases were washed with 5% NaHCO$_3$ solution (10 mL) and brine (10 mL), dried over MgSO$_4$, filtered, and concentrated to dryness. The crude material was purified by silica gel chromatography eluting with 0% to 15% MeOH in DCM (with 0.1% Et$_3$N modifier) to afford 28-3a as a yellow gum (56.2 mg, 0.122 mmol, 52% yield). MS [M+H]$^+$=392.4. $^1$H NMR (400 MHz, DCM-d$_2$) δ 8.00 (d, J=8.7 Hz, 1H), 7.09 (d, J=2.6 Hz, 1H), 7.02 (dd, J=8.7, 2.6 Hz, 1H), 5.08 (s, 2H), 4.72-4.63 (m, 1H), 4.36 (q, J=7.1 Hz, 2H), 2.93 (td, J=8.0, 3.7 Hz, 1H), 2.75-2.61 (m, 2H), 2.31-1.96 (m, 6H), 1.96-1.85 (m, 1H), 1.85-1.46 (m, 9H), 1.41 (t, J=7.1 Hz, 3H).

Step 3. 3-(5-(((1S,2S)-2-(3-azabicyclo[3.2.1]octan-3-yl)cyclopentyl)oxy)-1-oxoisoindolin-2-yl)piperidine-2,6-dione (I-16)

To a stirred solution of 3-aminopiperidine-2,6-dione hydrochloride (I-1c, 29 mg, 0.17 mmol) in DMF (0.7 mL) and i-Pr$_2$NEt (0.07 mL, 0.4 mmol) was added a solution of 28-3a (56.2 mg, 0.122 mmol) in DMF (0.7 mL) and the resulting mixture was stirred at 85° C. overnight. The reaction mixture was concentrated to dryness and the crude product was purified by silica gel chromatography eluting with EtOAc to afford a mixture of starting materials and product. The mixture was then dissolved in DMF (1 mL) and heated to 120° C. until complete consumption of starting materials was observed by LC-MS. The reaction mixture was concentrated to dryness and the crude material was purified by silica gel chromatography eluting with 0% to 100% EtOAc in heptane to afford I-16 as a white solid (7.3 mg, 0.016 mmol, 11% yield). MS [M+H]$^+$=438.5. $^1$H NMR (400 MHz, Chloroform-d) δ 7.88 (s, 1H), 7.80 (d, J=8.4 Hz, 1H), 7.13 (d, J=2.8 Hz, 1H), 7.09 (dt, J=8.4, 2.0 Hz, 1H), 5.23 (dd, J=13.2, 5.2 Hz, 1H), 4.62 (dd, J=7.1, 3.4 Hz, 1H), 4.54-4.25 (m, 2H), 3.01-2.77 (m, 4H), 2.62 (dd, J=18.5, 10.9 Hz, 2H), 2.37 (qd, J=13.1, 5.1 Hz, 1H), 2.30-2.14 (m, 4H), 2.11 (s, 1H), 2.07-1.93 (m, 1H), 1.93-1.58 (m, 8H), 1.52-1.44 (m, 1H), 1.37 (d, J=10.9 Hz, 1H).

Example 29: 3-(5-(((1S,2S)-2-morpholinocyclopentyl)oxy)-1-oxoisoindolin-2-yl)piperidine-2,6-dione (I-33)

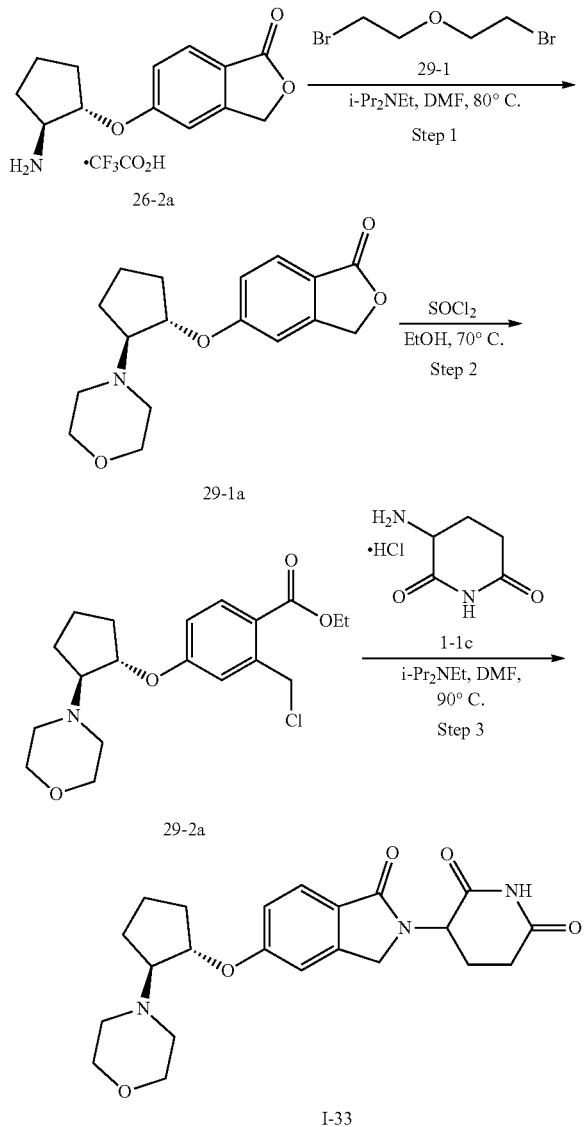

Step 1. 5-(((1S,2S)-2-morpholinocyclopentyl)oxy)isobenzofuran-1(3H)-one (29-1a)

To a stirred solution of 26-2a (145 mg, 0.42 mmol) and 1-bromo-2-(2-bromoethoxy)ethane (29-1, 111 mg, 0.479 mmol) in DMF (2 mL) was added i-Pr$_2$NEt (0.30 mL, 1.7 mmol) and the resulting mixture was stirred at 80° C. overnight. The reaction mixture was then diluted with EtOAc (80 mL) and washed with 0.5 M aq. LiCl solution (20 mL), sat. aq. NaHCO$_3$ (20 mL), and brine (20 mL). The organic layer was then dried over MgSO$_4$, filtered, and concentrated to dryness. The crude material was purified by silica gel chromatography eluting with 0% to 20% MeOH in DCM (with 0.1% Et$_3$N modifier) to afford the 29-1a as a brown solid (35.7 mg, 0.113 mmol, 27% yield). MS [M+H]$^+$ =304.3. $^1$H NMR (400 MHz, DCM-d$_2$) δ 7.80 (d, J=8.5 Hz, 1H), 7.06 (dd, J=8.5, 2.2 Hz, 1H), 6.97 (s, 1H), 5.26 (s, 2H), 4.70 (s, 1H), 3.68 (s, 4H), 3.03-2.88 (m, 1H), 2.63-2.39 (m, 4H), 2.22-2.00 (m, 2H), 1.81 (d, J=9.7 Hz, 2H), 1.55 (d, J=11.9 Hz, 2H).

Step 2. Ethyl 2-(chloromethyl)-4-(((1S,2S)-2-morpholinocyclopentyl)oxy)benzoate (29-2a)

To a stirred solution of 29-1a (35.7 mg, 0.113 mmol) in EtOH (1 mL) was added SOCl$_2$ (0.04 mL, 0.5 mmol) and the resulting mixture was stirred at 70° C. overnight. The reaction mixture was diluted with water (10 mL), neutralized with sat. aq. NaHCO$_3$, and extracted with EtOAc (3×30 mL). The combined organic phases were then washed with 5% aq. NaHCO$_3$ (10 mL) and brine (10 mL), dried over MgSO$_4$, filtered, and concentrated to dryness. The crude material was purified by silica gel chromatography eluting with 0% to 100% EtOAc in heptane to afford 29-2a as an amber gum (25.6 mg, 0.068 mmol, 58% yield). MS [M+H]$^+$ =368.3. $^1$H NMR (400 MHz, DCM-d$_2$) δ 8.00 (d, J=8.7 Hz, 1H), 7.10 (d, J=2.6 Hz, 1H), 6.91 (dd, J=8.7, 2.6 Hz, 1H), 5.08 (d, J=2.5 Hz, 2H), 4.69 (s, 1H), 4.36 (q, J=7.1 Hz, 2H), 3.68 (s, 4H), 2.93 (s, 1H), 2.54 (s, 3H), 2.18-1.96 (m, 2H), 1.87-1.71 (m, 3H), 1.64-1.49 (m, 2H), 1.41 (t, J=7.1 Hz, 3H).

Step 3. 3-(5-(((1S,2S)-2-morpholinocyclopentyl)oxy)-1-oxoisoindolin-2-yl)piperidine-2,6-dione (I-33)

To a stirred solution of 3-aminopiperidine-2,6-dione hydrochloride (1-1c, 14 mg, 0.086 mmol) and i-Pr$_2$NEt (0.030 mL, 0.17 mmol) in DMF (0.7 mL) was added a solution of 29-2a (25.6 mg, 0.068 mmol) in DMF (0.7 mL) and the resulting mixture was stirred at 90° C. overnight. The reaction mixture was diluted with EtOAc (40 mL), washed with sat. aq. NaHCO$_3$ (2×10 mL) and brine (10 mL), dried over MgSO$_4$, filtered, and concentrated to dryness. The crude material was purified by reverse phase HPLC (eluting with MeCN/H$_2$O with 0.1% formic acid). The fractions containing product were combined and lyophilized to afford I-33 as a white solid (3.5 mg, 8.3 μmol, 12% yield). MS [M+H]$^+$=414.4. $^1$H NMR (400 MHz, DMSO-d$_6$) δ 10.95 (s, 1H), 7.60 (d, J=8.4 Hz, 1H), 7.18 (d, J=2.2 Hz, 1H), 7.04 (dd, J=8.4, 1.9 Hz, 1H), 5.06 (dd, J=13.3, 5.1 Hz, 1H), 4.74 (d, J=2.9 Hz, 1H), 4.46-4.16 (m, 2H), 3.55 (t, J=4.6 Hz, 4H), 2.99-2.78 (m, 1H), 2.16-2.06 (m, 1H), 2.04-1.83 (m, 4H), 1.77-1.53 (m, 3H), 1.53-1.41 (m, 1H).

Example 30: Enantiomer 1-3-(5-((1S,2S)-2-(benzylamino)cyclobutoxy)-1-oxoisoindolin-2-yl)piperidine-2,6-dione HC(O)OH Salt (I-44) and Enantiomer 2-3-(5-((1R,2R)-2-(benzylamino)cyclobutoxy)-1-oxoisoindolin-2-yl)piperidine-2,6-dione (I-45)

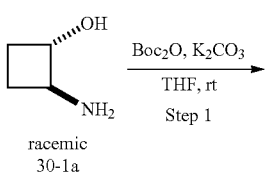

racemic
30-1a

-continued

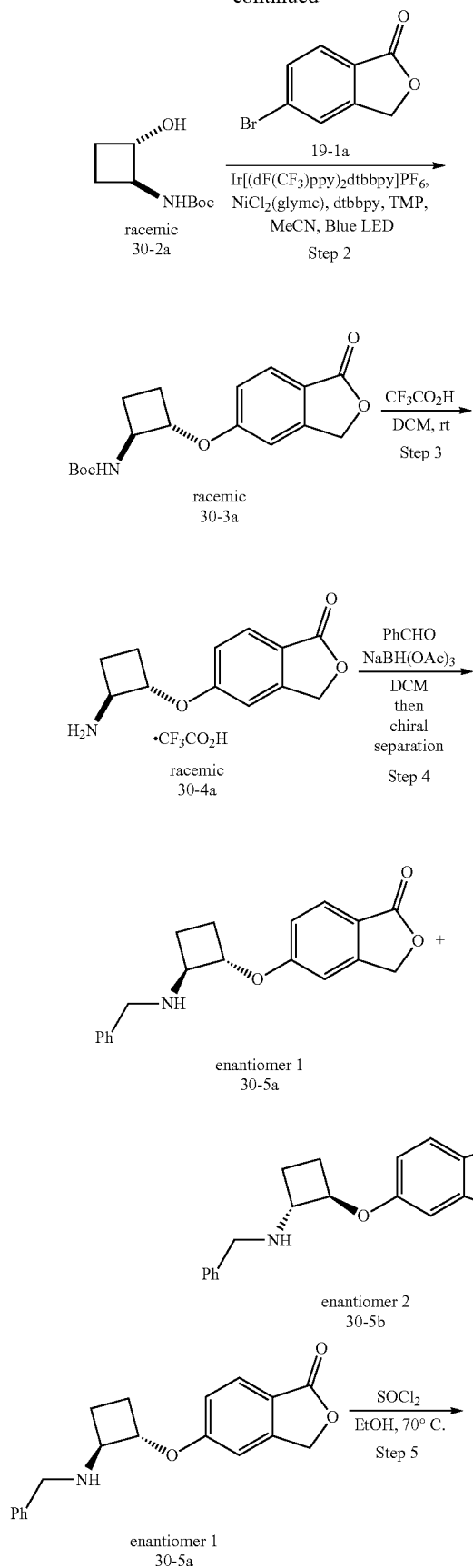

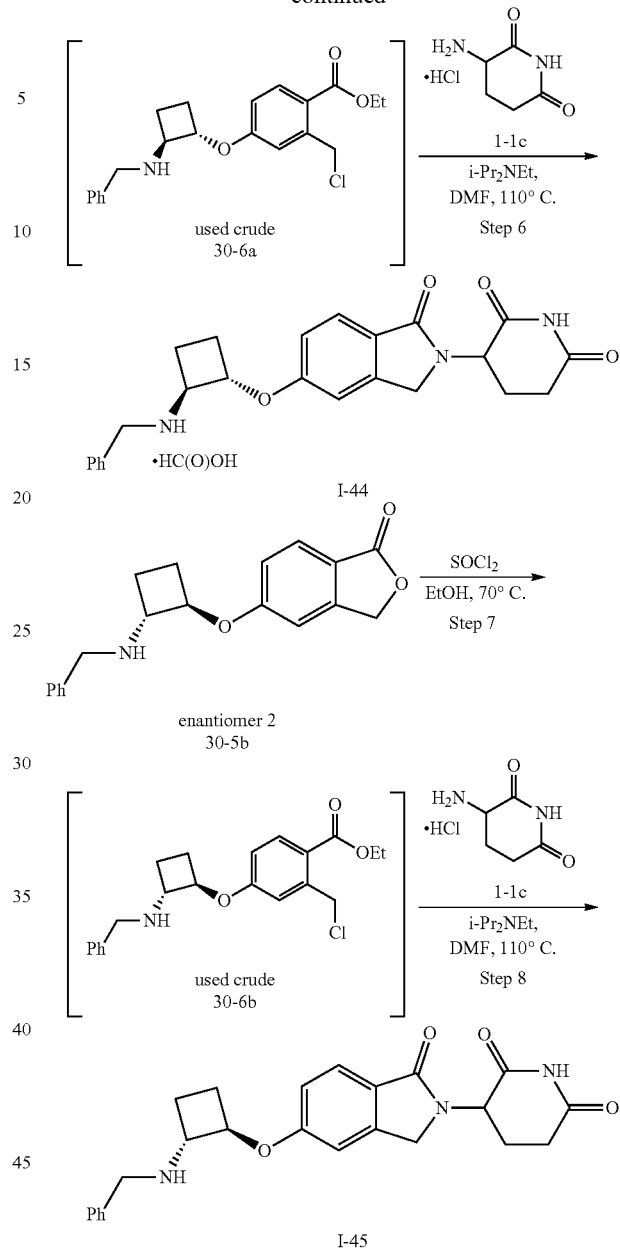

Step 1. Racemic trans-tert-butyl 2-hydroxycyclobutyl)carbamate (30-2a)

To a stirred suspension of racemic trans-2-aminocyclobutanol hydrochloride (30-1a, 500 mg, 4.05 mmol) and di-tert-butyl dicarbonate (971 mg, 4.45 mmol) in THF (15 mL) was added $K_2CO_3$ (615 mg, 4.45 mmol) and the resulting mixture was stirred vigorously at room temperature for 48 h. The reaction mixture was diluted with brine (5 mL) and extracted with EtOAc (×3). The combined organic phases were dried over $Na_2SO_4$, filtered, and concentrated. The crude material was purified by silica gel chromatography eluting with 0% to 100% EtOAc in heptane. The fractions containing the desired product were combined and concentrated to afford 30-2a (440 mg, 2.35 mmol, 58% yield) as a white solid. $^1$H NMR (400 MHz, DCM-$d_2$) δ 4.82 (s, 1H), 3.95-3.81 (m, 1H), 3.73-3.53 (m, 1H), 2.13-1.90 (m, 2H), 1.58-1.45 (m, 1H), 1.40 (s, 10H), 1.33-1.19 (m, 1H).

Step 2. Racemic tert-butyl (trans-2-((1-oxo-1,3-dihydroisobenzofuran-5-yl)oxy)cyclobutyl)carbamate (30-3a)

To 5-bromoisobenzofuran-1(3H)-one (19-1a, 300 mg, 1.41 mmol), racemic trans-tert-butyl-3-hydroxycyclopentyl)carbamate (30-2a, 440 mg, 2.35 mmol), $NiCl_2$(glyme) (15.5 mg, 0.070 mmol), dtbbpy (18.9 mg, 0.070 mmol), and $Ir[(dF(CF_3)ppy)_2dtbbpy]PF_6$ (15.8 mg, 0.014 mmol) under an atmosphere of nitrogen was added MeCN (4.7 mL) and 2,2,6,6-tetramethylpiperidine (40-2, 286 µl, 1.69 mmol) and the resulting mixture was stirred vigorously for 16 hours under irradiation of blue LED light at room temperature. The reaction mixture was filtered through a short pad of Celite® and concentrated to dryness. The crude material was purified by silica gel chromatography eluting with 0% to 100% EtOAc (with 1% $Et_3N$ modifier) in heptane to afford 30-3a (445 mg, 1.39 mmol, 99% yield) as a white solid. MS [M-tBu+H]$^+$=320.3.

Step 3. Racemic 5-(trans-2-aminocyclobutoxy) isobenzofuran-1(3H)-one $CF_3CO_2H$ Salt (30-4a)

To a stirred solution of 30-3a (660 mg, 2.67 mmol) in DCM (7 mL) was added TFA (1.59 mL, 20.7 mmol) and the resulting mixture was stirred at room temperature overnight. The reaction mixture was concentrated to dryness by azeotroping with PhMe (×3) to afford the trifluoroacetate salt of 30-4a (1.97 g, 5.45 mmol, 96% yield) as a brown oil. The crude product was carried onto the next step without further purification. MS [M+H]$^+$=220.4. $^1$H NMR (400 MHz, DMSO-$d_6$) δ 7.77 (d, J=8.4 Hz, 1H), 7.18 (d, J=2.3 Hz, 1H), 7.08 (dd, J=8.5, 2.3 Hz, 1H), 5.34 (s, 2H), 4.89-4.81 (m, 1H), 3.96-3.84 (m, 1H), 2.12-2.03 (m, 1H), 1.94-1.85 (m, 1H), 1.60-1.50 (m, 1H), 1.48-1.36 (m, 1H).

Step 4. 5-((1S,2S)-2-(benzylamino)cyclobutoxy)isobenzofuran-1(3H)-one (30-5a) and 5-((1R,2R)-2-(benzylamino)cyclobutoxy)isobenzofuran-1(3H)-one (30-5b)

To a solution of racemic 30-4a (85 mg, 0.388 mmol) in DCM (2 mL) was added benzaldehyde (0.039 mL, 0.39 mmol) and the reaction mixture was stirred at room temperature overnight. NaBH(OAc)$_3$ (82 mg, 0.39 mmol) was then added and the resulting mixture was stirred at rt for 1 h. The reaction mixture was then quenched with sat. aq. NaHCO$_3$ and the aqueous phase was extracted with DCM. The combined organic layers were dried over Na$_2$SO$_4$, filtered, and concentrated to dryness. The crude material was purified by silica gel column chromatography eluting with 0% to 10% MeOH in DCM to afford the desired racemic trans product (48 mg, 0.155 mmol, 40% yield) as a yellow oil. The enantiomers were separated using chiral SFC (Column: 2.1×25.0 cm Chiralpak AD-H; CO$_2$ co-solvent: MeOH/MeCN (v/v=1:3) with 0.25% isopropylamine; Isocratic method: 25% co-solvent at 80 g/min; System pressure: 125 bar; Column temperature: 25° C.; Sample diluent: MeOH) to afford enantiomer 1 (first peak, Rt=2.70 min, 16.9 mg, 0.055 mmol) and enantiomer 2 (second peak, Rt=3.39 min, 14.9 mg, 0.048 mmol). The absolute stereochemistry of the two enantiomers corresponding to the two product peaks is unknown and was assigned arbitrarily. MS [M+H]$^+$=310.3.

Step 5 and 6. Enantiomer 1-3-(5-((1S,2S)-2-(benzylamino)cyclobutoxy)-1-oxoisoindolin-2-yl)piperidine-2,6-dione HC(O)OH Salt (I-44)

To a stirred solution of enantiomer 1 (30-5a, 16.9 mg, 0.055 mmol) in EtOH (1 mL) was added SOCl$_2$ (0.04 mL, 0.55 mmol) and the resulting mixture was stirred at 70° C. overnight. The solution was allowed to cool to room temperature and then concentrated to dryness by azeotroping with PhMe (×3) to afford the crude 30-6a as a brown-red gum. MS [M+H]$^+$=374.4.

To a stirred solution of 3-aminopiperidine-2,6-dione hydrochloride (1-1c, 9.0 mg, 0.055 mmol) and i-Pr$_2$NEt (0.05 mL, 0.3 mmol) in DMF (0.5 mL) was added a solution of crude 30-6a (~0.055 mmol) in DMF (0.5 mL) and the resulting mixture was stirred at 85° C. overnight and then at 110° C. for 5 h. The reaction mixture was concentrated to dryness by azeotroping with PhMe and the resulting crude material was purified by reverse phase HPLC (eluting with MeCN/H$_2$O with 10 mM NH$_4$OH). The purified material was collected into tubes containing several drops of formic acid. The fractions containing product were combined and concentrated by lyophilizer to afford the formate salt of I-44 (enantiomer 1, 3 mg, 6.1 µmol, 11% yield) as a light brown powder. Absolute stereochemistry is unknown and was assigned arbitrarily. MS [M+H]$^+$=420.4. $^1$H NMR (400 MHz, DMSO-$d_6$) δ 10.96 (s, 1H), 8.38 (s, 1H), 7.61 (d, J=8.4 Hz, 1H), 7.34-7.27 (m, 4H), 7.24-7.17 (m, 2H), 7.06 (dd, J=8.4, 1.0 Hz, 1H), 6.59 (s, 1H), 5.07 (ddd, J=13.3, 5.1, 1.5 Hz, 1H), 4.50 (q, J=7.3 Hz, 1H), 4.38 (dd, J=17.2, 10.5 Hz, 1H), 4.25 (dd, J=17.2, 6.4 Hz, 1H), 3.76-3.66 (m, 2H), 2.91 (ddd, J=18.0, 13.6, 5.4 Hz, 1H), 2.63-2.59 (m, 1H), 2.04-1.94 (m, 2H), 1.50 (quint, J=9.9 Hz, 1H), 1.36 (quint, J=9.5 Hz, 1H).

Step 7 and 8. Enantiomer 2-3-(5-((1R,2R)-2-(benzylamino)cyclobutoxy)-1-oxoisoindolin-2-yl)piperidine-2,6-dione (I-45)

To a stirred solution of enantiomer 2 (30-5b, 14.9 mg, 0.048 mmol) in EtOH (1 mL) was added SOCl$_2$ (0.07 mL, 0.96 mmol) and the resulting reaction mixture was stirred at 70° C. overnight. The solution was allowed to cool to room temperature and concentrated to dryness by azeotroping with PhMe (×3) to afford the crude 30-6b as a brown-red gum. MS [M+H]$^+$=374.4.

To a stirred solution of 3-aminopiperidine-2,6-dione hydrochloride (I-1c, 7.9 mg, 0.048 mmol) and i-Pr$_2$NEt (0.04 mL, 0.2 mmol) in DMF (0.5 mL) was added a solution of crude 30-6b (~0.048 mmol) in DMF (0.5 mL) and the resulting mixture was stirred at 85° C. overnight and then at 110° C. for 5 h. The reaction was concentrated to dryness by azeotroping with PhMe and the resulting crude material was purified by reverse phase HPLC (eluting with MeCN/H$_2$O with 10 mM NH$_4$OH). The purified material was collected into tubes containing several drops of formic acid. Fractions containing product were combined and concentrated by lyophilizer to afford I-45 (enantiomer 2, 3 mg, 6 µmol, 13% yield) as a light brown powder. Absolute stereochemistry is unknown and was assigned arbitrarily. MS [M+H]$^+$=420.4. $^1$H NMR (400 MHz, MeCN-$d_3$) δ 7.52 (d, J=8.4 Hz, 1H), 7.28-7.21 (m, 2H), 7.19-7.13 (m, 2H), 7.12-7.05 (m, 2H), 6.98 (dd, J=8.4, 2.2 Hz, 1H), 5.03 (ddd, J=13.3, 5.2, 1.2 Hz, 1H), 4.43 (q, J=6.8 Hz, 1H), 4.36-4.23 (m, 2H), 3.75-3.64 (m, 2H), 3.31-3.22 (m, 1H), 2.64 (ddd, J=17.5, 4.5, 2.4 Hz, 1H), 2.47-2.33 (m, 1H), 2.30-2.19 (m, 1H), 2.09-1.99 (m, 2H), 1.49 (tdd, J=10.8, 9.4, 7.9 Hz, 1H), 1.37-1.27 (m, 1H).

Example 31: 3-(5-(((3aR*,6S*,6aS*)-1-methyloctahydrocyclopenta[b]pyrrol-6-yl)oxy)-1-oxoisoindolin-2-yl)piperidine-2,6-dione HC(O)OH Salt (I-3)

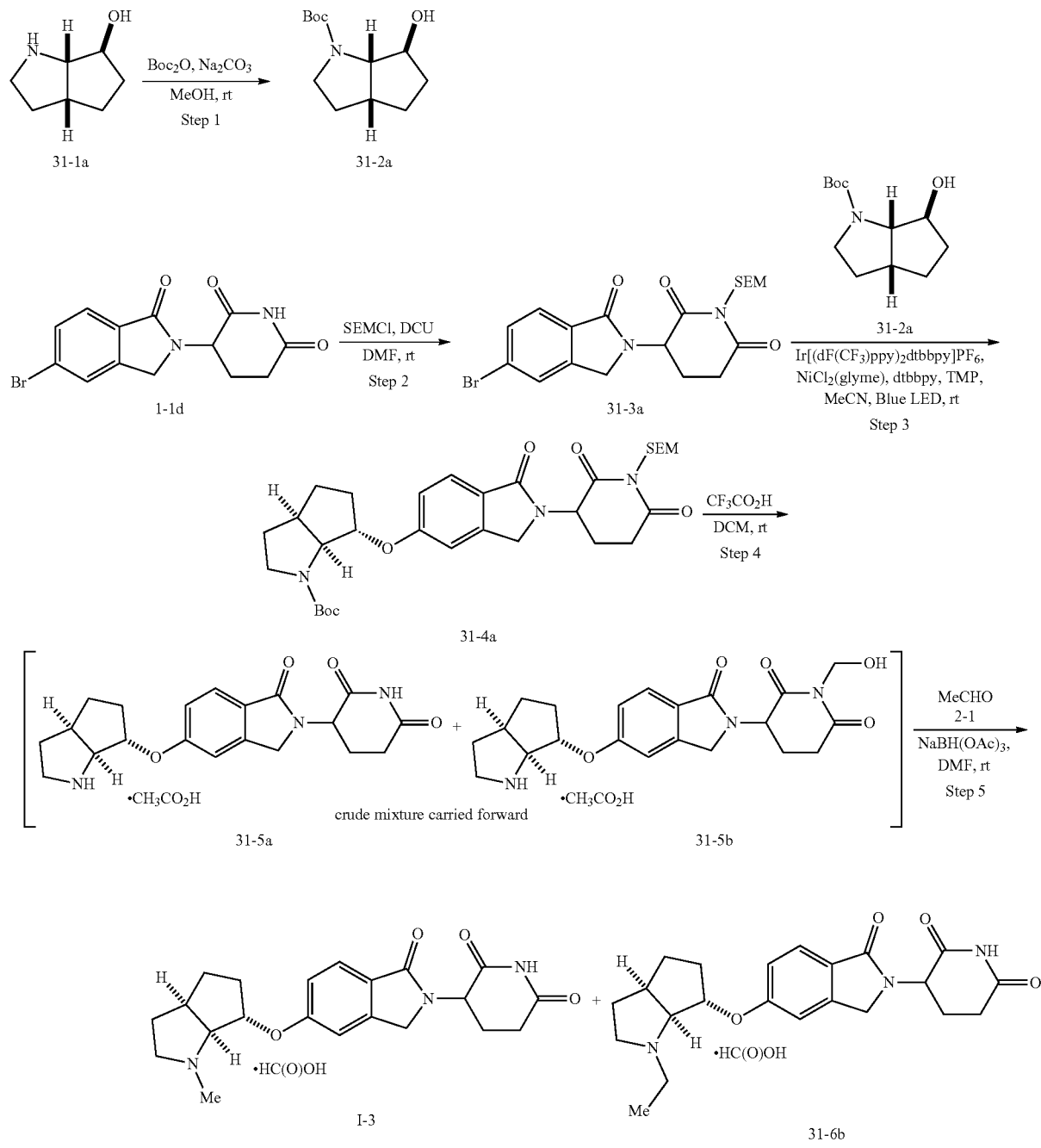

Step 1. Racemic tert-butyl (3aR*,6S*,6aS*)-6-hydroxyhexahydrocyclopenta[b]pyrrole-1(2H)-carboxylate (31-2a)

To a stirred solution of racemic (3aR*,6S*,6aS*)-octahydrocyclopenta[b]pyrrol-6-ol hydrochloride (31-1a, 1.00 g, 6.11 mmol) and di-tert-butyl dicarbonate (1.60 g, 7.33 mmol) in MeOH (10 mL) was added $Na_2CO_3$ (0.777 g, 7.33 mmol) and the resulting mixture was stirred vigorously at room temperature for 48 hours. The reaction mixture was then diluted with brine (25 mL) and extracted with DCM (×3). The combined organic phases were dried over $Na_2SO_4$, filtered, and concentrated to dryness to afford 31-2a (1.32 g, 5.81 mmol, 95% yield) as a viscous yellow oil. The product was carried onto the next step without further purification. $^1$H NMR (400 MHz, DCM-$d_2$) δ 3.95 (dt, J=9.0, 4.9 Hz, 1H), 3.74 (dd, J=9.1, 4.3 Hz, 1H), 3.42-3.28 (m, 2H), 2.87-2.73 (m, 1H), 1.98-1.87 (m, 3H), 1.64-1.48 (m, 3H), 1.44 (s, 9H), 1.37-1.27 (m, 1H).

Step 2. 3-(5-bromo-1-oxoisoindolin-2-yl)-1-((2-(trimethylsilyl)ethoxy)methyl)piperidine-2,6-dione (31-3a)

To a stirred solution of 1-1d (10.0 g, 30.9 mmol) and DBU (6.9 mL, 46 mmol) in DMF (95 mL) was added SEMCl (6.6 mL, 37 mmol) at 0° C. and the resulting reaction mixture was allowed to warm to room temperature and then stirred for 5 h. An additional portion of DBU (3.5 mL, 23 mmol) and SEMCl (3.3 mL, 19 mmol) was added and the reaction mixture was stirred for additional 2 h. The reaction mixture was then quenched with sat. aq. NH₄Cl (250 mL) and extracted with EtOAc (×3). The combined organic phases were dried over Na₂SO₄, filtered, and concentrated to dryness. The crude material was dissolved in minimal amount of EtOAc (~50 mL) and Et₂O:heptane (v/v=1:2, 400 mL) was added. The resulting cloudy solution was left standing at −5° C. overnight. The formed precipitate was filtered, washed with heptane (×3), and dried under vacuum to afford 31-3a (11.53 g, 25.4 mmol, 82% yield) as an off-white solid. MS [M+H]⁺=453.4. ¹H NMR (400 MHz, Chloroform-d) δ 7.75 (d, J=8.6 Hz, 1H), 7.66-7.61 (m, 2H), 5.37-5.09 (m, 3H), 4.48 (d, J=16.2 Hz, 1H), 4.32 (d, J=16.2 Hz, 1H), 3.74-3.50 (m, 2H), 3.11-2.98 (m, 1H), 2.94-2.83 (m, 1H), 2.33 (qd, J=13.2, 4.7 Hz, 1H), 2.24-2.15 (m, 1H), 0.97-0.90 (m, 2H), 0.00 (s, 9H).

Step 3. Racemic tert-butyl (3aR*,6S*,6aS*)-6-((2-(2,6-dioxo-1-((2-(trimethylsilyl)ethoxy)-methyl)piperidin-3-yl)-1-oxoisoindolin-5-yl)oxy)hexahydro-cyclopenta[b]pyrrole-1 (2H)-carboxylate (31-4a)

To a stirred solution of 31-3a (1396 mg, 3.08 mmol), 31-2a (700 mg, 3.08 mmol), NiCl₂(glyme) (34 mg, 0.15 mmol), dtbbpy (41 mg, 0.15 mmol) and Ir[(dF(CF₃)ppy)₂dtbbpy]PF₆ (34.5 mg, 0.031 mmol) in MeCN (5 mL) under an atmosphere of nitrogen was added 2,2,6,6-tetramethylpiperidine (40-2, 0.52 mL, 3.1 mmol) and the resulting mixture was stirred vigorously overnight under irradiation of blue LED light at room temperature. The reaction mixture was then diluted with DCM (20 mL), filtered, and concentrated to dryness. The crude material was purified by silica gel chromatography eluting with 0% to 100% EtOAc in heptane to afford 31-4a (840 mg, 1.40 mmol, 45.5% yield) as a yellow solid. MS [M−H]⁻=598.6. ¹H NMR (400 MHz, DCM-d₂) δ 7.67 (d, J=8.4 Hz, 1H), 7.47-6.91 (m, 2H), 5.23-5.06 (m, 3H), 5.00-4.76 (m, 1H), 4.37-4.22 (m, 2H), 4.14-4.09 (m, 1H), 3.65-3.49 (m, 3H), 3.17 (br s, 1H), 3.01-2.79 (m, 3H), 2.37-2.01 (m, 3H), 2.00-1.68 (m, 3H), 1.65-1.57 (m, 1H), 1.45-1.35 (m, 10H), 0.93-0.85 (m, 2H), −0.02 (s, 9H).

Step 4 and 5. Racemic 3-(5-(((3aR*,6S*,6aS*)-1-methyloctahydrocyclopenta[b]pyrrol-6-yl)oxy)-1-oxoisoindolin-2-yl)piperidine-2,6-dione HC(O)OH Salt (I-3)

To a stirred solution of 31-4a (210 mg, 0.350 mmol) in DCM (1 mL) was added TFA (1 mL, 13.07 mmol) and the resulting reaction mixture stirred for 2 h at room temperature. The reaction mixture was then concentrated to dryness by azeotroping with PhMe (×3) to afford a mixture of 31-5a and 31-5b based on a crude ¹H NMR analysis. The crude mixture was carried onto the next step without further purification.

To a crude mixture of 31-5a and 31-5b (~0.35 mmol) in DMF (1 mL) was added acetaldehyde (2-1, 0.06 mL, 1.1 mmol), followed by NaBH(OAc)₃ (148 mg, 0.700 mmol) and the resulting mixture was stirred for 6 h at room temperature. LC-MS analysis indicated formation of I-3 (MS [M+H]⁺=384.1, formed via reductive amination with formaldehyde that was released by 31-5b and 31-6b (MS [M+H]⁺=398.3) in a 2:1 ratio, respectively. The reaction mixture was then concentrated to dryness. The crude material was purified by reverse phase HPLC (eluting with MeCN/H₂O with 5 mM NH₄OH) and collected into tubes containing formic acid (2 drops). The fractions containing the desired product were combined and lyophilized to afford the formate salt of racemic I-3 (10.1 mg, 0.023 mmol, 7% yield). MS of I-3 [M+H]⁺=384.1. ¹H NMR (400 MHz, DCM-d₂) δ 8.26 (s, 1H), 7.80-7.62 (m, 1H), 7.08-6.92 (m, 2H), 5.11 (dd, J=13.3, 5.1 Hz, 1H), 4.63 (s, 1H), 4.38-4.23 (m, 2H), 3.00-2.70 (m, 5H), 2.53 (s, 1H), 2.42 (s, 3H), 2.38-2.12 (m, 3H), 2.04-1.93 (m, 3H), 1.89-1.81 (m, 1H), 1.53-1.35 (m, 2H).

Example 32: 3-(5-(((3R,4S)-4-(diethylamino)tetrahydrofuran-3-yl)oxy)-1-oxoisoindolin-2-yl)piperidine-2,6-dione HC(O)OH Salt (I-47)

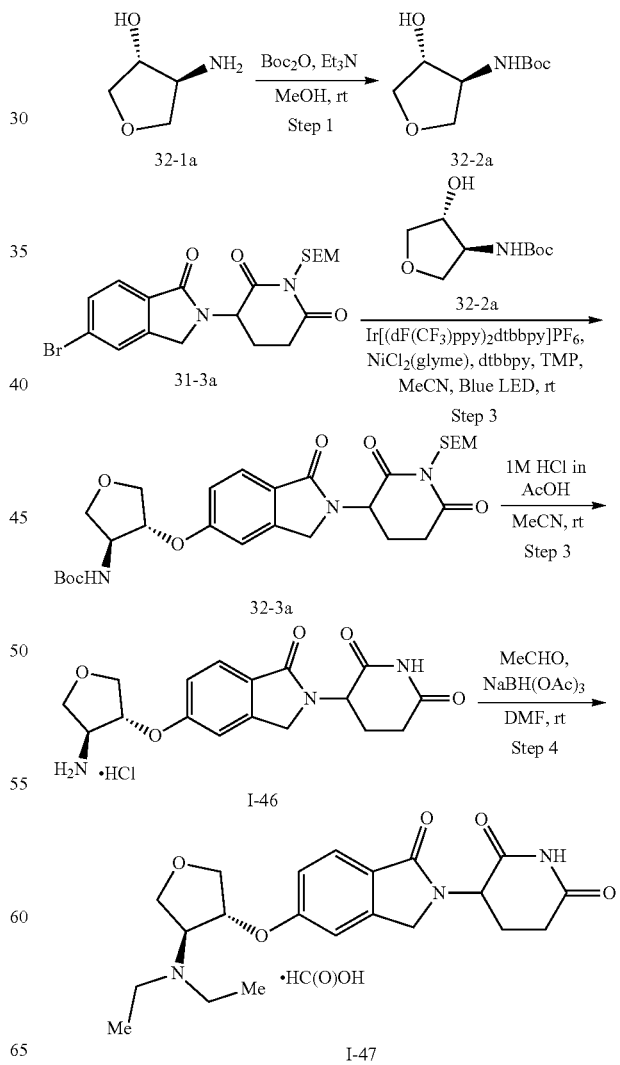

Step 1. tert-butyl ((3S,4R)-4-hydroxytetrahydrofuran-3-yl)carbamate (32-2a)

To a stirred solution of (3R,4S)-4-aminotetrahydrofuran-3-ol (32-1a, 482 mg, 4.67 mmol) and di-tert-butyl dicarbonate (1122 mg, 5.14 mmol) in MeOH (10 mL) was added Et$_3$N (1.6 mL, 11.48 mmol) and the resulting mixture was stirred at room temperature until complete consumption of starting material was observed. The reaction mixture was then concentrated to dryness. The crude material was treated with water (6 mL) and the resulting solid was then filtered off and washed with water to afford the desired product 32-2a (838.1 mg, 4.08 mmol, 87% yield) as a white solid. MS [M-tBu+H]$^+$=148.2. $^1$H NMR (400 MHz, Chloroform-d) δ 4.71 (s, 1H), 4.32 (dq, J=5.7, 2.9 Hz, 1H), 4.10 (ddd, J=16.0, 9.7, 5.6 Hz, 2H), 3.97 (dt, J=6.4, 3.2 Hz, 1H), 3.71 (dd, J=10.0, 3.3 Hz, 1H), 3.63 (dd, J=9.5, 3.4 Hz, 1H), 2.82 (s, 1H), 1.48 (s, 9H).

Step 2. tert-butyl ((3S,4R)-4-((2-(2,6-dioxo-1-((2-(trimethylsilyl)ethoxy)methyl)piperidin-3-yl)-1-oxoisoindolin-5-yl)oxy)tetrahydrofuran-3-yl)carbamate (32-3a)

To a stirred solution of (31-3a, 934.6 mg, 2.061 mmol), tert-butyl ((3S,4R)-4-hydroxytetrahydrofuran-3-yl)carbamate (32-2a, 395.4 mg, 1.946 mmol), NiCl$_2$(glyme) (25 mg, 0.11 mmol), dtbbpy (30 mg, 0.11 mmol), and Ir[(dF(CF$_3$)ppy)$_2$dtbbpy]PF$_6$ (20 mg, 0.018 mmol) in MeCN (5 mL) under an atmosphere of nitrogen was added 2,2,6,6-tetramethylpiperidine (40-2, 0.35 mL, 2.1 mmol) and the resulting mixture was stirred overnight under irradiation of blue LED light at room temperature. The reaction mixture was diluted with EtOAc and filtered through a pad of Celite®. The filtrate was then diluted with EtOAc (150 mL), washed with water (30 mL) and brine (20 mL), dried over MgSO$_4$, filtered, and concentrated to dryness. The crude material was purified by silica gel chromatography eluting with 0% to 100% EtOAc in heptane to afford 32-3a as a white solid (1.02 g, 1.59 mmol, 82% yield). MS [M+18]$^+$=593.6. $^1$H NMR (400 MHz, DMSO-d$_6$) δ 7.66 (d, J=8.4 Hz, 1H), 7.43 (d, J=6.3 Hz, 1H), 7.26 (s, 1H), 7.11 (dd, J=8.5, 2.2 Hz, 1H), 5.30-5.00 (m, 3H), 4.88 (d, J=4.2 Hz, 1H), 4.52-4.20 (m, 2H), 4.05 (qd, J=6.2, 5.2, 3.4 Hz, 4H), 3.84 (d, J=10.3 Hz, 1H), 3.64-3.50 (m, 3H), 3.08 (ddd, J=18.4, 13.6, 5.5 Hz, 1H), 2.82 (d, J=4.3 Hz, 1H), 2.46-2.36 (m, 1H), 2.10-2.02 (m, 1H), 1.43 (s, 9H), 1.20 (t, J=7.1 Hz, 1H), 0.94-0.75 (m, 2H). Note: TMS peak of SEM group is overlapping with reference Me$_4$Si.

Step 3. 3-(5-(((3R,4S)-4-aminotetrahydrofuran-3-yl)oxy)-1-oxoisoindolin-2-yl)piperidine-2,6-dione (I-46)

To a stirred solution of 32-3a (102 mg, 0.177 mmol) in MeCN (1 mL) was added 1 M HCl in acetic acid (0.9 mL, 0.9 mmol) and the resulting mixture was stirred at room temperature until complete consumption of starting materials was observed. The reaction mixture was then concentrated to dryness by azeotroping with DCM to afford the crude product I-46 as a white foam which was carried onto the next step without further purification. MS [M+H]$^+$=346.4. $^1$H NMR (400 MHz, DMSO-d$_6$) δ 11.96 (s, 1H), 8.38 (s, 3H), 7.70 (dd, J=8.4, 1.1 Hz, 1H), 7.27 (dd, J=7.4, 2.3 Hz, 1H), 7.17-7.09 (m, 1H), 5.30-4.94 (m, 2H), 4.54-4.20 (m, 2H), 4.08 (dd, J=10.2, 5.5 Hz, 1H), 3.93 (s, 1H), 3.87-3.76 (m, 2H), 3.05 (ddd, J=18.2, 13.5, 5.4 Hz, 1H), 2.88-2.71 (m, 1H), 2.43-2.34 (m, 1H), 2.07-2.00 (m, 1H).

Step 4. 3-(5-(((3R,4S)-4-(diethylamino)tetrahydrofuran-3-yl)oxy)-1-oxoisoindolin-2-yl)piperidine-2,6-dione HC(O)OH Salt (I-47)

To a solution of crude I-46 (65 mg, ~0.17 mmol) and acetaldehyde (2-1, 0.03 mL, 0.5 mmol) in DMF (1 mL) was added NaBH(OAc)$_3$ (108 mg, 0.511 mmol) in one portion and the resulting mixture was stirred at room temperature open to air for 4 hours. An additional portion of acetaldehyde (2-1, 0.03 mL, 0.5 mmol) and NaBH(OAc)$_3$ (69 mg, 0.32 mmol) were then added and the reaction mixture was stirred at room temperature until complete consumption of starting material was observed. The reaction mixture was then concentrated to dryness. The crude material was purified by reverse phase HPLC (eluting with MeCN/H$_2$O with 5 mM NH$_4$OH) and collected into tubes containing formic acid (2 drops). The fractions containing the desired product were combined and lyophilized to afford the formate salt of I-47 as a white solid (39.7 mg, 0.087 mmol, 51% yield). MS [M+H]$^+$=402.5. $^1$H NMR (400 MHz, DMSO-d$_6$) δ 10.95 (s, 1H), 8.23 (s, 1H), 7.63 (d, J=8.4 Hz, 1H), 7.25 (d, J=2.1 Hz, 1H), 7.09 (ddd, J=8.5, 2.3, 1.1 Hz, 1H), 5.07 (dd, J=13.3, 5.1 Hz, 1H), 4.90 (t, J=3.7 Hz, 1H), 4.48-4.19 (m, 2H), 4.08 (dd, J=10.5, 5.4 Hz, 1H), 3.99 (dd, J=9.2, 7.0 Hz, 1H), 3.72 (dt, J=10.4, 2.0 Hz, 1H), 3.60 (dd, J=9.2, 6.5 Hz, 1H), 3.47 (td, J=6.8, 2.5 Hz, 1H), 2.91 (ddd, J=17.3, 13.7, 5.5 Hz, 1H), 2.56 (t, J=7.0 Hz, 4H), 2.39 (dd, J=13.2, 4.5 Hz, 1H), 2.05-1.91 (m, 1H), 0.97 (t, J=7.0 Hz, 6H).

Example 33: 3-(5-(((1S,2S)-2-methoxycyclohexyl)oxy)-1-oxoisoindolin-2-yl)piperidine-2,6-dione (I-4)

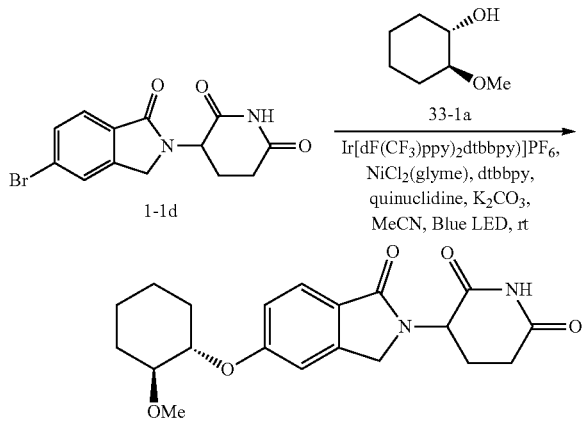

To a suspension of 1-1d (200 mg, 0.619 mmol) and (1S,2S)-2-methoxycyclohexan-1-ol (33-1a, 121 mg, 0.928 mmol) in MeCN (5 mL), whilst bubbling with nitrogen, was added Ir[dF(CF$_3$)ppy)$_2$dtbbpy]PF$_6$ (7 mg, 6 μmol), NiCl$_2$ (glyme) (7 mg, 0.03 mmol), dtbbpy (8 mg, 0.03 mmol), quinuclidine (7 mg, 0.06 mmol) and K$_2$CO$_3$ (128 mg, 0.928 mmol). The resulting suspension was sonicated and stirred vigorously under irradiation of blue LED light at room temperature for 16 h. The reaction mixture was diluted with excess EtOAc and the resulting solid was filtered and rinsed with EtOAc (×3). The filtrate was concentrated to dryness and the crude material was purified by silica gel chromatography eluting with 0% to 25% EtOH:EtOAc (v/v=1:3) in DCM, evaporating the appropriate fractions to dryness. Isolated material was purified by reverse phase HPLC (MeCN/H₂O with 0.1% formic acid). The fractions containing the desired product were combined and concentrated by lyophilizer to afford I-4 (7.0 mg, 0.018 mmol, 3% yield) as a white solid. MS [M+H]⁺=373.3. ¹H NMR (400 MHz, DMSO-d₆): δ 10.95 (s, 1H), 7.60 (d, J=8.4 Hz, 1H), 7.20 (s, 1H), 7.07 (d, J=8.9 Hz, 1H), 5.06 (dd, J=13.1, 5.0 Hz, 1H), 4.41-4.21 (m, 3H), shoulder on H₂O signal at 3.30 (3H), 2.96-2.84 (m, 1H), 2.64-2.56 (m, 3H), 2.43-2.34 (m, 1H), 2.07-1.94 (m, 2H), 1.69-1.57 (m, 2H), 1.45-1.22 (m, 4H)

Example 34: 3-(5-(((1S,2S)-2-methoxycyclopentyl)oxy)-1-oxoisoindolin-2-yl)piperidine-2,6-dione (I-26)

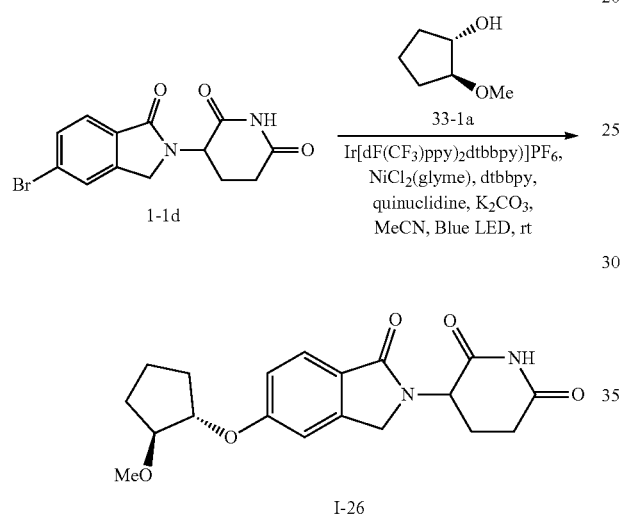

To a suspension of 1-1d (200 mg, 0.619 mmol) and (1S,2S)-2-methoxycyclopentan-1-ol (34-1a, 108 mg, 0.928 mmol) in MeCN (5 mL), whilst bubbling with nitrogen, was added Ir[dF(CF₃)ppy)₂dtbbpy)]PF₆ (7 mg, 6 µmol), NiCl₂ (glyme) (7 mg, 0.03 mmol), dtbbpy (8 mg, 0.03 mmol), quinuclidine (7 mg, 0.06 mmol) and K₂CO₃ (128 mg, 0.928 mmol). The resulting suspension was sonicated and stirred vigorously under irradiation of blue LED light at room temperature for 16 h. The reaction mixture was diluted with excess EtOAc and the resulting solid was filtered and rinsed with EtOAc (×3). The filtrate was concentrated to dryness and the crude material was purified by reverse phase HPLC (eluting with MeCN/H₂O with 0.1% formic acid). The fractions containing the desired product were combined and concentrated by lyophilizer to afford I-26 (38 mg, 0.10 mmol, 16% yield) as a white solid. MS [M+H]⁺=359.2. ¹H NMR (400 MHz, DMSO-d₆) δ 10.95 (s, 1H), 7.62 (d, J=8.4 Hz, 1H), 7.17 (d, J=2.1 Hz, 1H), 7.05 (dd, J=8.5, 2.1 Hz, 1H), 5.07 (dd, J=13.3, 5.2 Hz, 1H), 4.76-4.71 (m, 1H), 4.39 (dd, J=17.2, 4.5 Hz, 1H), 4.26 (dd, J=17.3, 3.3 Hz, 1H), 3.84-3.78 (m, 1H), 3.28 (s, 3H), 2.98-2.83 (m, 1H), 2.63-2.54 (m, 1H), 2.43-2.33 (m, 1H), 2.16-2.06 (m, 1H), 2.03-1.88 (m, 2H), 1.74-1.58 (m, 4H).

Example 35: 3-(1-oxo-5-(((1S,2S)-2-phenoxycyclohexyl)oxy)isoindolin-2-yl)piperidine-2,6-dione and 3-(1-oxo-5-(((1R,2R)-2-phenoxycyclohexyl)oxy)isoindolin-2-yl)piperidine-2,6-dione (I-19)

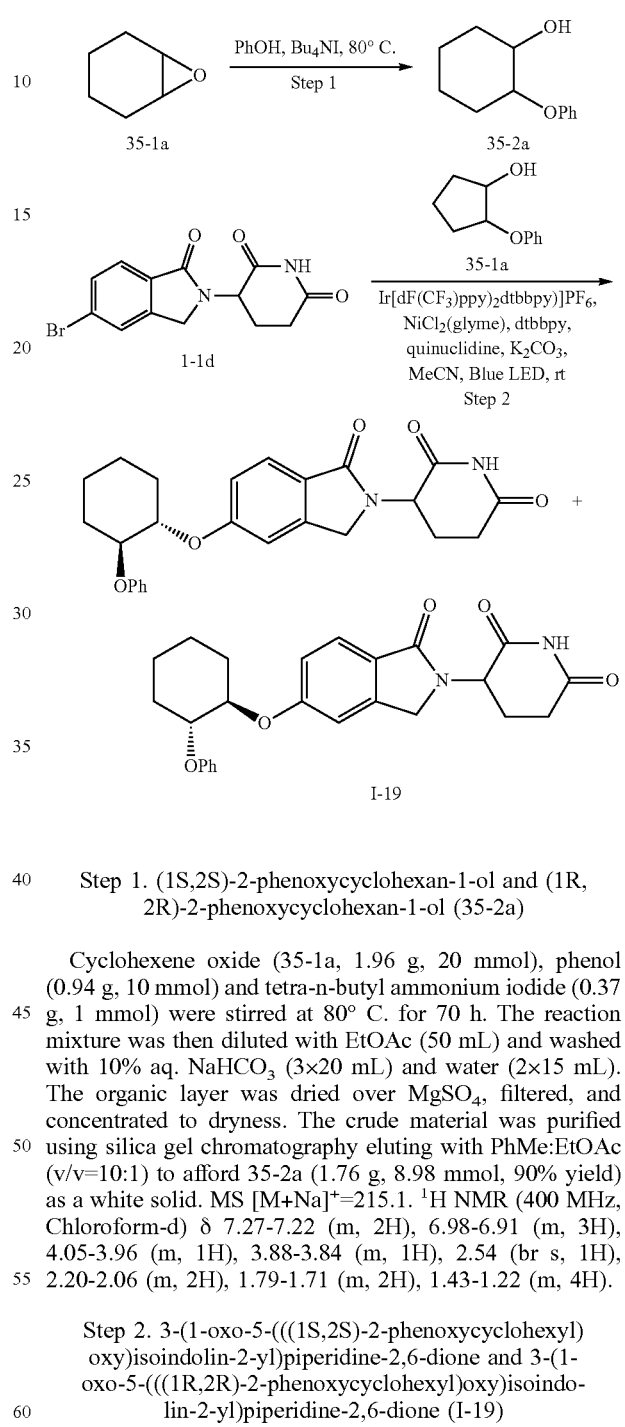

Step 1. (1S,2S)-2-phenoxycyclohexan-1-ol and (1R,2R)-2-phenoxycyclohexan-1-ol (35-2a)

Cyclohexene oxide (35-1a, 1.96 g, 20 mmol), phenol (0.94 g, 10 mmol) and tetra-n-butyl ammonium iodide (0.37 g, 1 mmol) were stirred at 80° C. for 70 h. The reaction mixture was then diluted with EtOAc (50 mL) and washed with 10% aq. NaHCO₃ (3×20 mL) and water (2×15 mL). The organic layer was dried over MgSO₄, filtered, and concentrated to dryness. The crude material was purified using silica gel chromatography eluting with PhMe:EtOAc (v/v=10:1) to afford 35-2a (1.76 g, 8.98 mmol, 90% yield) as a white solid. MS [M+Na]⁺=215.1. ¹H NMR (400 MHz, Chloroform-d) δ 7.27-7.22 (m, 2H), 6.98-6.91 (m, 3H), 4.05-3.96 (m, 1H), 3.88-3.84 (m, 1H), 2.54 (br s, 1H), 2.20-2.06 (m, 2H), 1.79-1.71 (m, 2H), 1.43-1.22 (m, 4H).

Step 2. 3-(1-oxo-5-(((1S,2S)-2-phenoxycyclohexyl)oxy)isoindolin-2-yl)piperidine-2,6-dione and 3-(1-oxo-5-(((1R,2R)-2-phenoxycyclohexyl)oxy)isoindolin-2-yl)piperidine-2,6-dione (I-19)

To a suspension of 1-1d (200 mg, 0.619 mmol) and 2-phenoxycyclohexan-1-ol (35-2a, mixture of trans isomers) (178 mg, 0.928 mmol) in MeCN (5 mL), whilst bubbling with nitrogen, was added Ir[dF(CF₃)ppy)₂dtbbpy)]PF₆ (7 mg, 6 µmol), NiCl₂(glyme) (7 mg, 0.03 mmol), dtbbpy (8 mg, 0.03 mmol), quinuclidine (7 mg, 0.06 mmol) and K₂CO₃ (128 mg, 0.928 mmol). The resulting suspension was sonicated and then stirred vigorously under irradiation of blue LED light at room temperature for 3 days. The reaction mixture was diluted with excess EtOAc and the resulting solid was filtered and rinsed with EtOAc (3×). The filtrate was concentrated to dryness and the crude material was purified by reverse phase HPLC (eluting with MeCN/H₂O with 0.1% formic acid). The fractions containing the desired product were combined and concentrated by lyophilizer to afford I-19 (6.0 mg, 0.013 mmol, 2% yield) as a white solid. MS [M+H]⁺=435.4. ¹H NMR (400 MHz, DMSO-d₆) δ 10.95 (s, 1H), 7.58 (d, J=8.5 Hz, 1H), 7.24 (t, J=7.4 Hz, 2H), 7.19 (s, 1H), 7.05-7.01 (m, 1H), 6.95-6.87 (m, 3H), 5.06 (dd, J=13.3, 5.1 Hz, 1H), 4.62-4.55 (m, 1H), 4.51-4.42 (m, 1H), 4.42-4.18 (m, 2H), 2.90 (m, 1H), 2.64-2.54 (m, 2H), 2.42-2.32 (m, 1H), 2.19-2.10 (m, 1H), 2.03-1.92 (m, 1H), 1.75-1.64 (m, 2H), 1.58-1.38 (m, 4H).

Example 36: 3-(5-(((1S,2S)-2-(benzyloxy)cyclopentyl)oxy)-1-oxoisoindolin-2-yl)piperidine-2,6-dione (I-9)

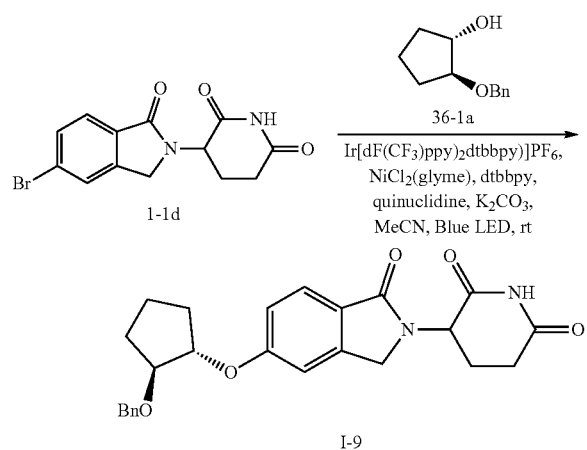

To a suspension of 1-1d (200 mg, 0.619 mmol) and (1S,2S)-2-(benzyloxy)cyclopentan-1-ol (36-1a, 268 mg, 1.39 mmol) in MeCN (5 mL), whilst bubbling with nitrogen, was added Ir[dF(CF₃)ppy]₂dtbbpy)]PF₆ (7 mg, 6 μmol), NiCl₂(glyme) (7 mg, 0.03 mmol), dtbbpy (8 mg, 0.03 mmol), quinuclidine (7 mg, 0.06 mmol) and K₂CO₃ (128 mg, 0.928 mmol). The resulting suspension was sonicated and then stirred vigorously under irradiation of blue LED light at room temperature for 3 days. The reaction mixture was diluted with excess EtOAc and the resulting solid was filtered and rinsed with EtOAc (×3). The filtrate was concentrated to dryness and the crude material was purified by silica gel chromatography eluting with 0% to 20% THF in DCM. The fractions containing the desired product were concentrated and further purified by reverse phase HPLC (eluting with MeCN/H₂O containing 0.1% formic acid). The fractions containing the desired product were combined and concentrated by lyophilizer to afford I-9 (21 mg, 0.046 mmol, 5% yield) as a white solid. MS [M+H]⁺=435.3. ¹H NMR (400 MHz, DMSO-d₆) δ 10.96 (s, 1H), 7.60 (d, J=8.4 Hz, 1H), 7.37-7.32 (m, 4H), 7.31-7.25 (m, 1H), 7.15 (s, 1H), 7.05-7.01 (m, 1H), 5.12-5.02 (m, 1H), 4.83-4.79 (m, 1H), 4.54 (qd, J=12.0, 1.6 Hz, 2H), 4.43-4.30 (m, 1H), 4.25 (dd, J=17.2, 8.7 Hz, 1H), 4.02-3.98 (m, 1H), 2.96-2.85 (m, 1H), 2.64-2.54 (m, 1H), 2.43-2.34 (m, 1H), 2.20-2.12 (m, 1H), 2.02-1.91 (m, 2H), 1.78-1.64 (m, 4H).

Example 37: 3-(5-(((1R,2R)-2-hydroxycyclopentyl)oxy)-1-oxoisoindolin-2-yl)piperidine-2,6-dione (I-6)

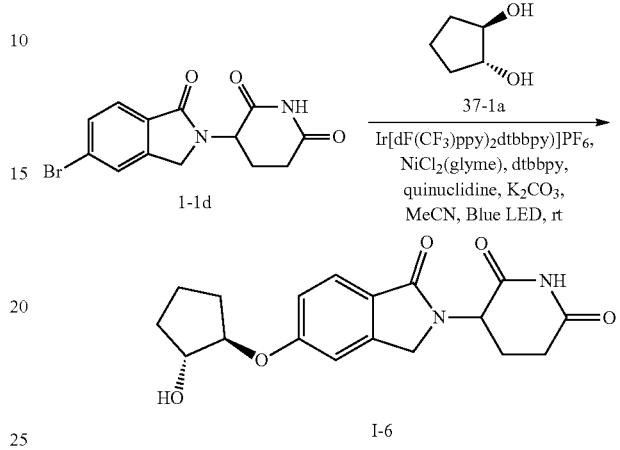

To a suspension of 1-1d (200 mg, 0.619 mmol) and ((1R,2R)-cyclopentane-1,2-diol (37-1a, 95 mg, 0.93 mmol) in MeCN (5 mL), whilst bubbling with nitrogen, was added Ir[dF(CF₃)ppy]₂dtbbpy)]PF₆ (7 mg, 6 μmol), NiCl₂(glyme) (7 mg, 0.03 mmol), dtbbpy (8 mg, 0.03 mmol), quinuclidine (7 mg, 0.06 mmol) and K₂CO₃ (128 mg, 0.928 mmol). The resulting suspension was sonicated and then stirred vigorously under irradiation of blue LED light at room temperature for 3 days. The reaction mixture was diluted with excess EtOAc and the resulting solid was filtered and rinsed with EtOAc (×3). The filtrate was concentrated to dryness and the crude material was purified by reverse phase HPLC (eluting with MeCN/H₂O with 0.1% formic acid). The fractions containing the desired product were combined and concentrated by lyophilizer to afford I-6 (17 mg, 0.047 mmol, 8% yield) as a white solid. MS [M+H]⁺=345.2. ¹H NMR (400 MHz, DMSO-d₆) δ 10.95 (s, 1H), 7.61 (d, J=8.4 Hz, 1H), 7.16 (d, J=1.7 Hz, 1H), 7.04 (dd, J=8.3, 2.01 Hz, 1H), 5.06 (dd, J=13.5, 5.1 Hz, 1H), 5.01 (t, J=4.0 Hz, 1H), 4.58-4.52 (m, 1H), 4.39 (dd, J=17.2, 5.1 Hz, 1H), 4.26 (dd, J=17.0, 3.9 Hz, 1H), 4.11-4.05 (m, 1H), 2.96-2.85 (m, 1H), 2.64-2.51 (m, 1H), 2.44-2.33 (m, 1H), 2.20-2.09 (m, 1H), 2.02-1.94 (m, 1H), 1.92-1.82 (m, 1H), 1.81-1.50 (m, 4H).

Example 38. 3-(5-(((1S,2R)-2-(benzylamino)cyclohexyl)oxy)-1-oxoisoindolin-2-yl)piperidine-2,6-dione (I-2)

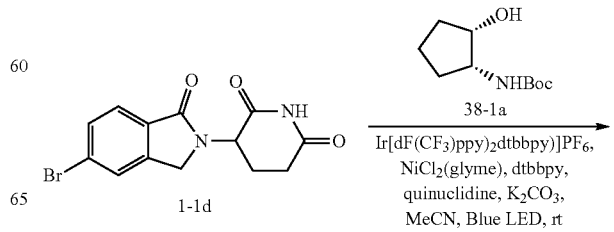

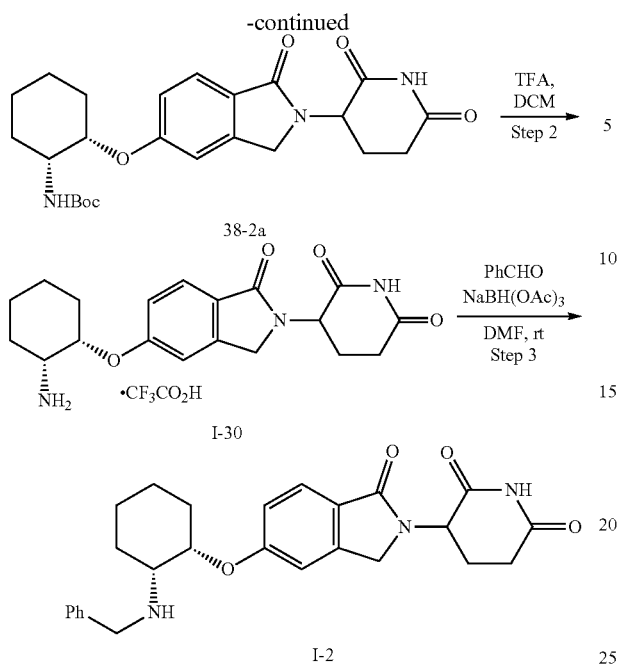

Step 1. tert-butyl ((1R,2S)-2-((2-(2,6-dioxopiperidin-3-yl)-1-oxoisoindolin-5-yl)oxy)cyclohexyl)carbamate (38-2a)

To a suspension of 1-Id (432 mg, 1.34 mmol)), tert-butyl ((1S,2S)-2-hydroxycyclohexyl) carbamate (38-1a, 1066 mg, 4.95 mmol), NiCl$_2$(glyme) (54 mg, 0.25 mmol), dtbbpy (66 mg, 0.2548 mmol), Ir[(dF(CF$_3$)ppy)$_2$dtbbpy]PF$_6$ (15 mg, 0.013 mmol) in MeCN (4.5 mL) under an atmosphere of nitrogen was added 2,2,6,6-tetramethylpiperidine (40-2, 226 μL, 1.34 mmol) and the resulting mixture was then stirred vigorously for 16 h under irradiation of blue LED light at room temperature. The reaction mixture was then diluted with EtOAc (20 mL), filtered, and concentrated to dryness. The crude material was purified by silica gel chromatography eluting with 0% to 100% EtOAc in heptanes to afford 38-2a (115 mg, 0.251 mmol, 19% yield) as a white powder. MS [M+H]$^+$=458.3.

Step 2. 3-(5-(((1S,2R)-2-aminocyclohexyl)oxy)-1-oxoisoindolin-2-yl)piperidine-2,6-dione CF$_3$CO$_2$H Salt (I-30)

To a stirred solution of 38-2a (115 mg, 0.251 mmol) in DCM (2.5 mL) was added TFA (194 μL, 2.51 mmol) and the resulting mixture was stirred for 48 h. The reaction mixture was concentrated to dryness and the crude material was purified by reverse phase HPLC (eluting with MeCN/H$_2$O with 0.1% formic acid) to afford the trifluoroacetate salt of I-30 (54 mg, 0.152 mmol, 60% yield). MS [M+H]$^+$=358.4. $^1$H NMR (400 MHz, DMSO-de) δ 10.97 (s, 1H), 7.68 (d, J=8.4 Hz, 1H), 7.27 (d, J=2.0 Hz, 1H), 7.17 (dt, J=8.4, 1.9 Hz, 1H), 5.08 (dd, J=13.3, 5.1 Hz, 1H), 4.76 (s, 1H), 4.41 (dd, J=17.4, 2.4 Hz, 1H), 4.28 (dd, J=17.3, 4.2 Hz, 1H), 3.42 (d, J=6.9 Hz, 1H), 2.91 (ddd, J=18.0, 13.6, 5.4 Hz, 1H), 2.06-1.93 (m, 2H), 1.75 (d, J=23.0 Hz, 3H), 1.64-1.49 (m, 1H), 1.40 (s, 3H).

Step 3. 3-(5-(((1S,2R)-2-(benzylamino)cyclohexyl)oxy)-1-oxoisoindolin-2-yl)piperidine-2,6-dione (I-2)

A solution of I-30 (54.2 mg, 0.152 mmol) and benzaldehyde (15 μL, 0.15 mmol) in DMF (0.7 mL) was stirred for 3 h. NaBH(OAc)$_3$ (31 mg, 0.15 mmol) was then added in one portion and the resulting reaction mixture was stirred vigorously for 16 h at room temperature. The reaction mixture was concentrated to dryness and the resulting crude material was purified by reverse phase HPLC (eluting with MeCN/H$_2$O with 0.1% formic acid). The fractions containing the desired product were combined and lyophilized to afford to afford I-2 (13.2 mg, 0.029 mmol, 20% yield) as a white solid. MS [M+H]$^+$=448.4. $^1$H NMR (400 MHz, DMSO-d$_6$) δ 10.96 (s, 1H), 7.61 (d, J=8.4 Hz, 1H), 7.28-7.14 (m, 4H), 7.10 (d, J=8.3 Hz, 1H), 6.51 (s, 1H), 5.07 (dd, J=13.2, 5.1 Hz, 1H), 4.73 (s, 1H), 4.37 (dd, J=17.1, 6.7 Hz, 1H), 4.25 (dd, J=17.5, 4.8 Hz, 1H), 3.72 (q, J=13.1 Hz, 2H), 2.97-2.85 (m, 1H), 2.76 (s, 1H), 1.99 (s, 2H), 1.91 (s, 1H), 1.66 (s, 3H), 1.49 (s, 2H), 1.42-1.21 (m, 1H).

Example 39: 3-(5-(((1S,2S)-2-(3-ethoxyazetidin-1-yl)cyclohexyl)oxy)-1-oxoisoindolin-2-yl)piperidine-2,6-dione (I-48)

Method A:

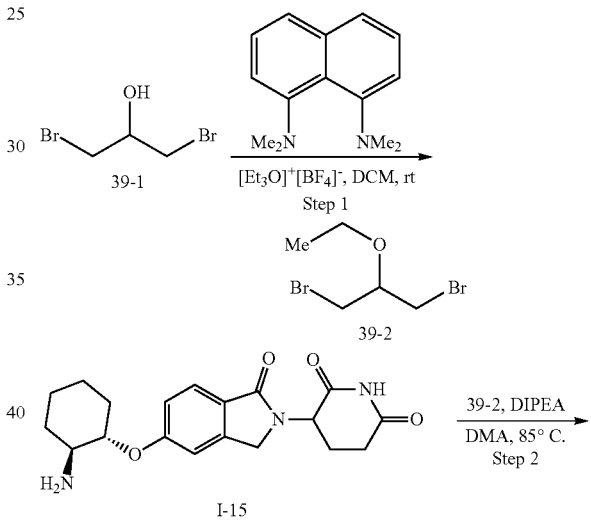

Method B:

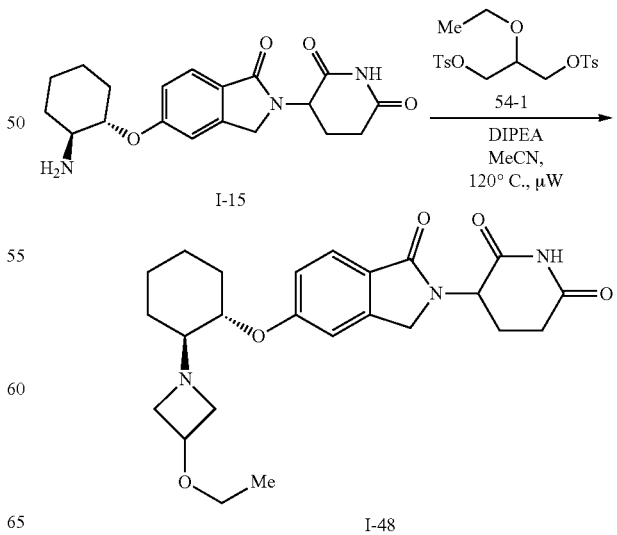

Method A: Step 1. 1,3-dibromo-2-ethoxypropane (39-2)

To a stirred solution of N1,N1,N8,N8-tetramethylnaphthalene-1,8-diamine (80.0 g, 372 mmol) and 1,3-dibromopropan-2-ol (39-1, 20.0 mL, 196 mmol) in DCM (150 mL) was added dropwise triethyloxonium tetrafluoroborate (63.3 g, 333 mmol), dissolved in DCM (50 mL) at 0° C. under positive pressure of nitrogen. After the addition was complete the reaction mixture was stirred at rt for 18 h. The mixture was filtered through a pad of silica gel eluting with DCM (5×350 mL). Each fraction was collected separately and the fractions containing product were combined and concentrated. The yellow oil was purified by filtration through a second silica gel pad eluting with 20% DCM in pentane to afford 39-2 (43.4 g, 159 mmol, 81% yield) was obtained as a colorless oil. $^1$H NMR (400 MHz, Methylene Chloride-$d_2$) δ 3.72-3.66 (m, 1H), 3.62 (q, J=7.0 Hz, 2H), 3.55 (d, J=5.2 Hz, 4H), 1.21 (t, J=7.0 Hz, 3H).

Step 2. 3-(5-(((1S,2S)-2-(3-ethoxyazetidin-1-yl)cyclohexyl)oxy)-1-oxoisoindolin-2-yl)piperidine-2,6-dione (I-48)

To a stirred suspension of 3-(5-(((1S,2S)-2-aminocyclohexyl)oxy)-1-oxoisoindolin-2-yl)piperidine-2,6-dione (I-15, 7.10 g, 17.9 mmol) and DIPEA (12.5 mL, 71.5 mmol) in DMA (100 mL) was added 39-2 (8.31 g, 30.4 mmol) and the resulting mixture was heated at 85° C. for 24 h under atmosphere of nitrogen. Additional 39-1 (4.0 g, 15 mmol) and DIPEA (6.0 mL, 34 mmol) were added and stirring was continued at 85° C. for an additional 24 h. Further 39-2 (0.80 g, 2.9 mmol) and DIPEA (1.2 mL, 6.9 mmol) were added and stirring was continued at 85° C. for an additional 24 h. The reaction mixture was allowed to cool rt and concentrated to dryness. The crude product was purified via silica gel chromatography eluting with 0-100% EtOAc:EtOH (v/v=3:1, with 0.1% NEt$_3$) in DCM (with 0.1% NEt$_3$) to afford I-48 (3.37 g, 7.63 mmol, 43% yield) as an off-white solid. MS [M+H]$^+$=442.5. $^1$H NMR (400 MHz, Methylene Chloride-$d_2$) δ 8.39-8.20 (m, 1H), 7.67 (dd, J=8.7, 1.7 Hz, 1H), 7.02-6.93 (m, 2H), 5.09 (ddd, J=13.3, 6.7, 5.2 Hz, 1H), 4.48-4.14 (m, 3H), 4.06-3.87 (m, 1H), 3.59 (s, 2H), 3.34 (q, J=7.0 Hz, 2H), 3.14 (s, 1H), 3.03-2.71 (m, 3H), 2.50-2.22 (m, 2H), 2.20-2.11 (m, 1H), 2.09-1.95 (m, 1H), 1.91-1.80 (m, 1H), 1.76-1.62 (m, 2H), 1.45-1.14 (m, 4H), 1.10 (t, J=7.0 Hz, 3H).

Method B:

Intermediate 54-1 was prepared according to literature procedure described in *Bioorganic and Medicinal Chemistry Letters*, 2003, 13, 1729-1732.

To a suspension of 3-(5-(((1S,2S)-2-aminocyclohexyl)oxy)-1-oxoisoindolin-2-yl)piperidine-2,6-dione (I-15, 100 mg, 0.28 mmol) in MeCN (3 mL), was added 2-ethoxypropane-1,3-diyl bis(4-methylbenzenesulfonate) (54-1, 180 mg, 0.42 mmol) and DIPEA (0.36 mL, 1.7 mmol) and the resulting mixture was stirred at 120° C. for 16 h under microwave irradiation. The reaction mixture was diluted with saturated aqueous sodium bicarbonate solution and extracted with DCM (3×30 mL). The combined organic phases were washed with brine, dried over anhydrous Na$_2$SO$_4$ and concentrated to dryness. The obtained crude material was purified by silica gel chromatography eluting with 6% MeOH in DCM to afford I-48 (20 mg, 0.045 mmol, 16%) as an off-white solid. The analytical data was identical to the one reported herein above for Example 39, Step 2.

Example 40: 3-(5-(((1S,2S)-2-aminocycloheptyl)oxy)-1-oxoisoindolin-2-yl)piperidine-2,6-dione (Int-40-5)

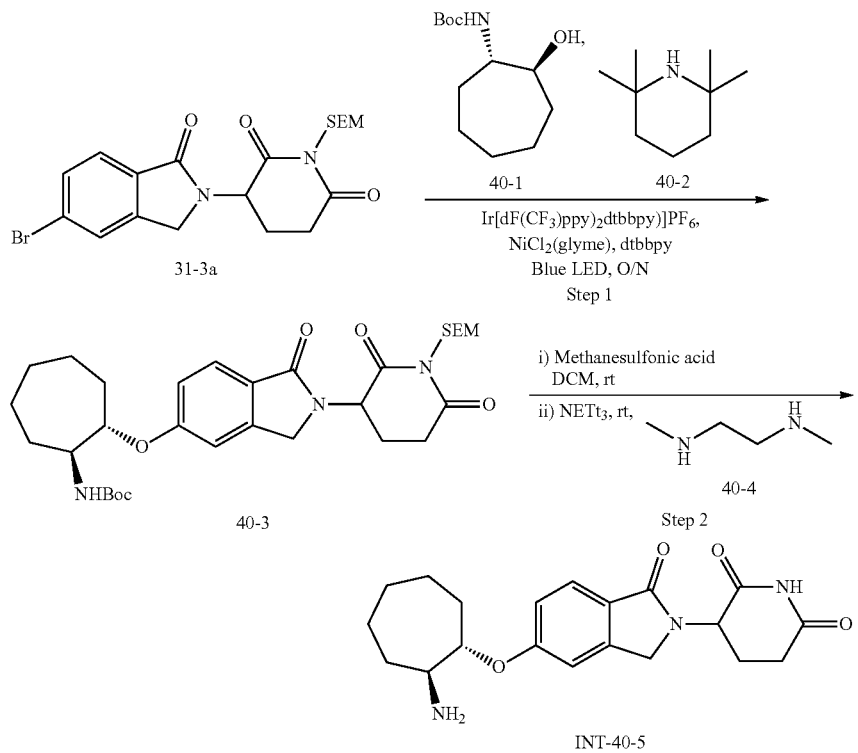

Step 1. Tert-butyl ((1S,2S)-2-((2-(2,6-dioxo-1-((2-(trimethylsilyl)ethoxy)methyl)piperidin-3-yl)-1-oxoisoindolin-5-yl)oxy)cycloheptyl)carbamate (40-3)

To a suspension of 3-(5-bromo-1-oxoisoindolin-2-yl)-1-((2-trimethylsilyl)ethoxy)methyl) piperidine-2,6-dione (31-3a) (5.00 g, 11.0 mmol) in MeCN (35 mL), whilst bubbling with nitrogen, was added tert-butyl ((1S,2S)-2-hydroxycycloheptyl)carbamate (40-1, 2.66 g, 11.6 mmol), 2,2,6,6-tetramethylpiperidine (40-2, 1.95 mL, 11.6 mmol), NiCl$_2$ (glyme) (0.121 g, 0.551 mmol), dtbbpy (0.148 g, 0.551 mmol) and Ir[(dF(CF$_3$)ppy)$_2$dtbbpy]PF$_6$ (0.124 g, 0.110 mmol). The suspension was sonicated and then stirred at rt under an atmosphere of nitrogen. The resulting solution was stirred under blue LED lights for 48 hours. A 50% saturated sodium hydrogen carbonate in water was then added and the resulting mixture was extracted with 20% i-PrOH in DCM (×3). The combined organic phases were passed through a phase separating column, concentrated under reduced pressure and then dried under high vacuum to afford crude 40-3, as a dark red solid, which was carried onto the next step without purification. MS [M−H]$^-$=600.5.

Step 2. 3-(5-(((1S,2S)-2-aminocycloheptyl)oxy)-1-oxoisoindolin-2-yl)piperidine-2,6-dione (INT-40-5)

To a solution of crude tert-butyl ((1S,2S)-2-((2-(2,6-dioxo-1-((2-(trimethylsilyl)ethoxy)methyl) piperidin-3-yl)-1-oxoisoindolin-5-yl)oxy)cycloheptyl)carbamate (40-3, 6.64 g, 11.0 mmol) in DCM (80 mL) under an atmosphere of nitrogen was added methanesulfonic acid (2.9 mL, 44 mmol) and the resulting mixture was stirred at rt overnight. Additional methanesulfonic acid (2.9 mL, 44 mmol) was added and the reaction mixture was stirred at rt for 4 hours and then cooled using an ice bath. Triethylamine (18.5 mL, 132 mmol) was added dropwise, under an atmosphere of nitrogen followed by N1,N2-dimethylethane-1,2-diamine (40-4, 1.4 mL, 13 mmol). The resulting mixture was stirred at rt overnight and then concentrated under reduced pressure. To the resulting residue was added to a 50% saturated sodium hydrogen carbonate in water solution (250 mL). The aqueous phase was extracted with 20% i-PrOH in DCM (×4). The combined organics were passed through a phase separating column and concentrated under reduced pressure. The crude material was treated with MeCN to provide a suspension, which was sonicated and filtered. The collected solid was washed with MeCN (×3) and then dried under vacuum to afford INT-40-5 (2.17 g, 5.84 mmol, 53% yield) as a cream-colored solid. MS [M+H]$^+$=372.3. Alternatively, the crude material was treated with excess diethyl ether to provide a suspension, which was sonicated and filtered. The collected solid was washed with diethyl ether (×3) and then was dried under vacuum to afford INT-40-5 (1.42 g, 3.82 mmol, 35% yield) as a pale yellow solid. MS [M+H]$^+$=372.3.

Example 41: 3-(5-(((1S,2S)-2-(ethylamino)cycloheptyl)oxy)-1-oxoisoindolin-2-yl)piperidine-2,6-dione (I-57)

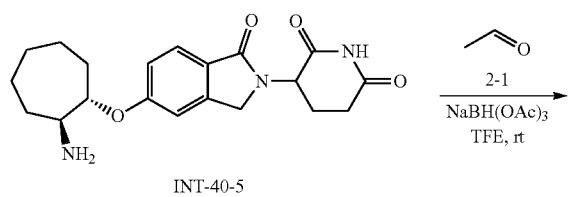

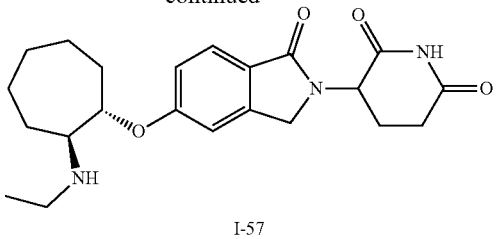

I-57

To a solution of 3-(5-(((1S,2S)-2-aminocycloheptyl)oxy)-1-oxoisoindolin-2-yl)piperidine-2,6-dione (INT-40-5, 92 mg, 0.25 mmol) in TFE (3 mL) was added acetaldehyde (2-1, 0.02 mL, 0.4 mmol). The resulting mixture was stirred at room temperature for 30 minutes and then sodium triacetoxyborohydride (157 mg, 0.743 mmol) was added. Stirring was continued at room temperature for 3 hours and then a saturated aqueous solution of sodium hydrogen carbonate (20 mL) was added. The reaction mixture was extracted with 20% i-PrOH in DCM (×3) and the combined organic phases were passed through a phase separating column and concentrated under reduced pressure. The crude product was purified via silica gel chromatography eluting with 0-100% EtOAc:EtOH (v/v=3:1, with 0.1% NEt$_3$) in DCM (with 0.1% NEt$_3$), to afford I-57 (64 mg, 0.15 mmol, 61% yield), as a pale yellow solid. MS [M+H]$^+$=400.5. $^1$H NMR (400 MHz, DMSO-d$_6$) δ 10.95 (s, 1H), 7.61 (d, J=8.4 Hz, 1H), 7.14 (s, 1H), 7.03 (dd, J=8.4, 2.2 Hz, 1H), 5.06 (dd, J=13.3, 5.1 Hz, 1H), 4.44-4.20 (m, 3H), 2.97-2.82 (m, 2H), 2.70-2.53 (m, 2H), 2.44-2.29 (m, 1H), 2.03-1.92 (m, 1H), 1.84-1.73 (m, 3H), 1.72-1.39 (m, 8H), 0.99 (t, J=7.1 Hz, 3H).

Example 42: 3-(5-(((1S,2S)-2-(benzylamino)cycloheptyl)oxy)-1-oxoisoindolin-2-yl)piperidine-2,6-dione (I-58)

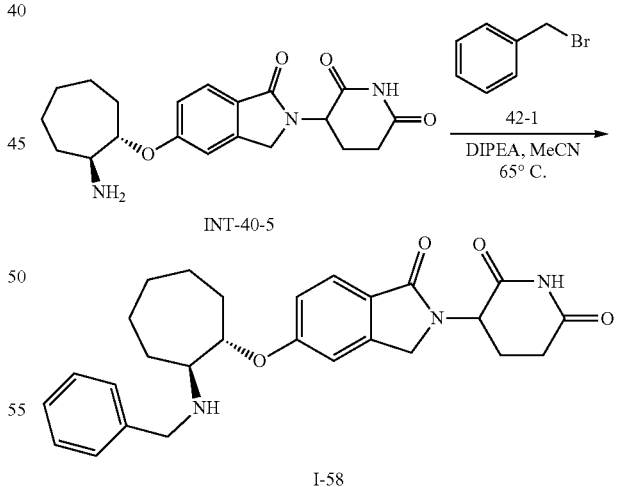

To a solution of 3-(5-(((1S,2S)-2-aminocycloheptyl)oxy)-1-oxoisoindolin-2-yl)piperidine-2,6-dione (INT-40-5, 46 mg, 0.12 mmol) in MeCN (2 mL) was added DIPEA (0.07 mL, 0.4 mmol) and benzyl bromide (42-1, 0.015 mL, 0.12 mmol). The resulting mixture was stirred at 65° C. overnight. Stirring was continued and then a saturated aqueous solution of sodium hydrogen carbonate (20 mL) was added. The reaction mixture was extracted with 20% i-PrOH in DCM (×3) and the combined organic phases were passed through a phase separating column and concentrated under reduced pressure. The crude product was purified via silica gel chromatography eluting with 0-100% EtOAc:EtOH (v/v=3:1, with 1% Et₃N) in DCM (with 1% Et₃N). The resulting material was dissolved in a minimal amount of DCM to which an excess of diethyl ether was added. The resulting suspension was sonicated, filtered, and rinsed with diethyl ether (×3). The obtained filtrate was collected and concentrated. The crude material was purified further via silica gel chromatography eluting with 0-20% i-PrOH (with 0.1% NEt₃) in DCM (with 0.1% NEt₃) to afford I-58 (11 mg, 0.02 mmol, 18% yield), as a white solid. MS [M+H]⁺=462.6. ¹H NMR (400 MHz, DMSO-d₆) δ (ppm); 10.95 (s, 1H), 7.60 (d, J=8.4 Hz, 1H), 7.33-7.24 (m, 4H), 7.23-1.17 (m, 1H), 7.11 (s, 1H), 7.00 (dd, J=8.4, 2.1 Hz, 1H), 5.07 (dd, J=13.3, 5.1 Hz, 1H), 4.48-4.20 (m, 3H), 3.85-3.63 (m, 2H), 2.96-2.82 (m, 2H), 2.59 (d, J=17.3 Hz, 1H), 2.38 (td, J=13.1, 4.5 Hz, 1H), 2.02-1.93 (m, 1H), 1.88-1.37 (m, 10H).

Example 43: 3-(5-(((1S,2S)-2-(diethylamino)cycloheptyl)oxy)-1-oxoisoindolin-2-yl)piperidine-2,6-dione (I-59)

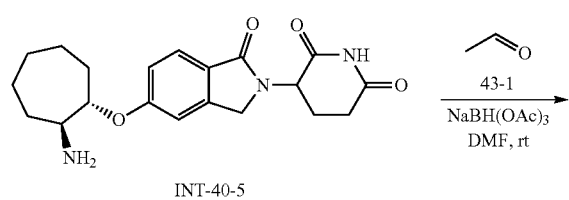

INT-40-5

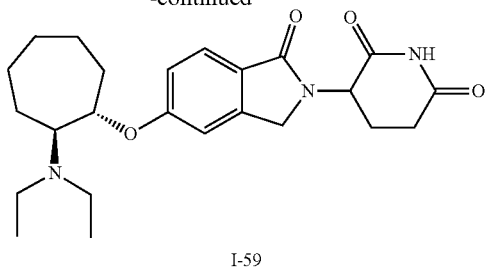

I-59

To a vial was added 3-(5-(((1S,2S)-2-aminocycloheptyl)oxy)-1-oxoisoindolin-2-yl)piperidine-2,6-dione (INT-40-5, 100 mg, 0.27 mmol), acetaldehyde (2-1, 76 μL, 1.4 mmol), and DMF (2.7 mL). The resulting mixture was stirred for 15 min under an N₂ atmosphere and sodium triacetoxyborohydride (285 mg, 1.35 mmol) was then added. The reaction mixture was stirred at rt for 4 h, added to a saturated aqueous bicarbonate solution, and extracted with EtOAc (×3). The organic phase was dried over MgSO₄, filtered, and concentrated to dryness. The crude product was purified via reverse phase HPLC (Column: X-bridge C18 OBD 5 um 30×50 mm; eluting with Water/MeCN with 0.1% Formic Acid; 75 ml/min, 1.5 mL injection; Gradient: 10-30% MeCN over 3.5 min) to afford the formate salt of I-59 (11 mg, 0.023 mmol, 36% yield), as a white solid. MS [M+H]⁺=428.3. ¹H NMR (400 MHz, DMSO-d₆) δ 10.96 (s, 1H), 7.59 (dd, J=8.4, 2.8 Hz, 1H), 7.15 (d, J=2.2 Hz, 1H), 7.02 (dt, J=8.4, 2.8 Hz, 1H), 5.11-5.01 (m, 1H), 4.63-4.58 (m, 1H), 4.43-4.19 (m, 2H), 2.97-2.85 (m, 2H), 2.64-2.52 (m, 2H), 2.43-2.31 (m, 3H), 2.02-1.79 (m, 3H), 1.76-1.64 (m, 3H), 1.61-1.23 (m, 6H), 0.91 (t, J=7.0 Hz, 6H).

Example 44: 3-(5-(((1S,2S)-2-(4-methoxy-4-methylpiperidin-1-yl)cycloheptyl)oxy)-1-oxoisoindolin-2-yl)piperidine-2,6-dione (I-60)

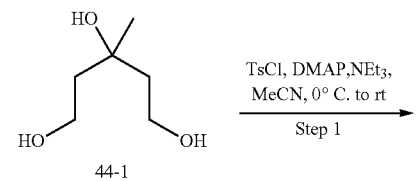

44-1

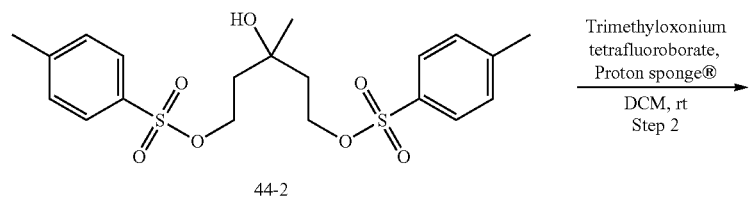

44-2

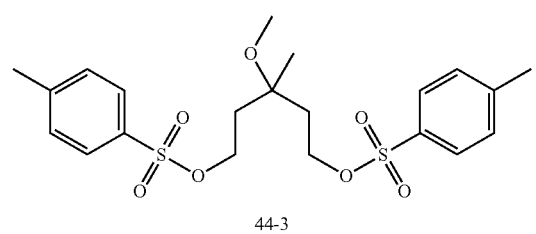

44-3

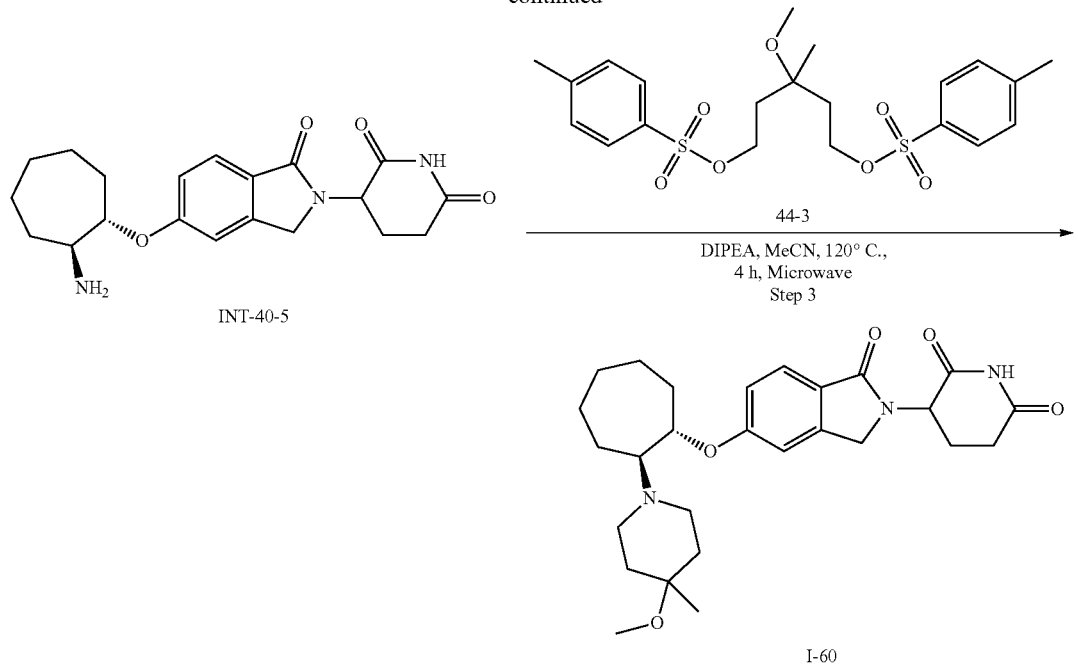

Step 1. 3-Hydroxy-3-methylpentane-1,5-diyl bis(4-methylbenzenesulfonate) (44-2)

DMAP (60 mg, 0.49 mmol) and TEA (2.4 mL, 17 mmol) were added to a solution of 3-methylpentane-1,3,5-triol (44-1, 580 mg, 4.32 mmol) in MeCN (20 mL) and the resulting solution was placed under an inert atmosphere and cooled to 0° C. A solution of TsCl (1813 mg, 9.51 mmol) in MeCN (5 mL) was then added and the reaction mixture was stirred at 0° C. for 1 h, warmed to rt, and stirred at rt for 4 h. The reaction mixture was filtered and concentrated to dryness. The crude material was purified via silica gel chromatography eluting with 0-60% EtOAc in heptane to afford 44-2 (1.40 g, 3.16 mmol, 73% yield) as a light brown oil. MS $[M+H_2O]^+$=460.3. $^1$H NMR (400 MHz, Chloroform-d) δ 7.80-7.75 (m, 4H), 7.38-7.32 (m, 4H), 4.16 (t, J=6.5 Hz, 4H), 2.46 (s, 6H), 1.88-1.75 (m, 4H), 1.17 (s, 3H).

Step 2. 3-Methoxy-3-methylpentane-1,5-diyl bis(4-methylbenzenesulfonate) (44-3)

Trimethyloxonium tetrafluoroborate (334 mg, 2.26 mmol) was added to a solution of 3-hydroxy-3-methylpentane-1,5-diyl bis(4-methylbenzenesulfonate) (44-2, 500 mg, 1.13 mmol) and Proton-sponge® (484 mg, 2.26 mmol) in DCM and the resulting mixture was stirred at rt overnight. The reaction mixture was then filtered and concentrated to dryness. The crude material was purified via silica gel chromatography eluting with 0-60% EtOAc in heptane to afford 44-3 (300 mg, 0.657 mmol, 58% yield) as a colorless oil. MS $[M+H_2O]^+$=474.5. $^1$H NMR (400 MHz, Chloroform-d) δ 7.80-7.75 (m, 4H), 7.37-7.32 (m, 4H), 4.11-4.00 (m, 4H), 3.02 (s, 3H), 2.45 (s, 6H), 1.87-1.75 (m, 4H), 1.08 (s, 3H).

Step 3. 3-(5-(((1S,2S)-2-(4-methoxy-4-methylpiperidin-1-yl)cycloheptyl)oxy)-1-oxoisoindolin-2-yl)piperidine-2,6-dione (I-60)

DIPEA (0.18 mL, 1.0 mmol) was added to a solution of 3-methoxy-3-methylpentane-1,5-diyl bis(4-methylbenzenesulfonate) (44-3, 184 mg, 0.404 mmol) and 3-(5-(((1S,2S)-2-aminocycloheptyl)oxy)-1-oxoisoindolin-2-yl)piperidine-2,6-dione (INT-40-5, 75 mg, 0.20 mmol) in MeCN (1.5 mL) and the resulting mixture was stirred at 120° C. under μW irradiation for 4 h. The reaction mixture was concentrated to dryness. The crude residue was taken up in DCM and washed with saturated NaHCO$_3$ (aq) and the phases were separated. The aqueous phase was extracted with DCM and the combined organic phases were dried over Na$_2$SO$_4$, filtered, and concentrated to dryness. The crude material was purified via silica gel chromatography eluting with 0-80% EtOAc:EtOH (v/v=3:1, with 0.1% NEt$_3$) in DCM (with 0.1% NEt$_3$) to afford I-60 (39 mg, 0.073 mmol, 36% yield) as an off-white solid. MS $[M+H]^+$=484.5. $^1$H NMR (400 MHz, DMSO-d$_6$) δ 10.95 (s, 1H), 7.59 (d, J=8.3 Hz, 1H), 7.21-7.15 (m, 1H), 7.04 (d, J=8.0 Hz, 1H), 5.06 (dd, J=13.2, 5.1 Hz, 1H), 4.67 (s, 1H), 4.37 (dd, J=17.1, 6.8 Hz, 1H), 4.25 (dd, J=17.1, 5.3 Hz, 1H), 3.00 (s, 3H), 2.97-2.84 (m, 1H), 2.80-2.71 (m, 1H), 2.62-2.55 (m, 2H), 2.48-2.31 (m, 4H), 2.02-1.87 (m, 2H), 1.84-1.60 (m, 4H), 1.60-1.39 (m, 5H), 1.39-1.20 (m, 4H), 0.98 (s, 3H).

Example 45: 3-(5-(((1S,2S)-2-(isobutylamino)cycloheptyl)oxy)-1-oxoisoindolin-2-yl)piperidine-2,6-dione (I-61)

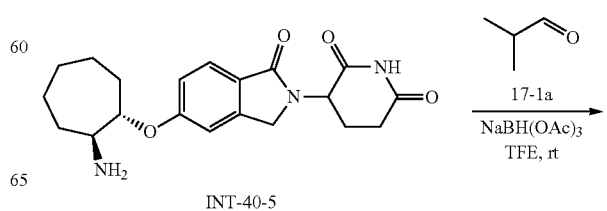

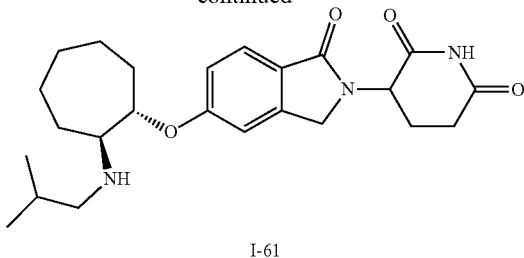

I-61

To a solution of 3-(5-(((1S,2S)-2-aminocycloheptyl)oxy)-1-oxoisoindolin-2-yl)piperidine-2,6-dione (INT-40-5, 100 mg, 0.269 mmol) in TFE (2 mL) was added isobutyraldehyde (17-1a, 0.03 mL, 0.3 mmol) and the resulting mixture was stirred at rt for 30 minutes. Sodium triacetoxyborohydride (171 mg, 0.808 mmol) was added. The reaction mixture was stirred at rt overnight and then a saturated aqueous solution of sodium hydrogen carbonate (20 mL) was added. The aqueous phase was extracted with 20% i-PrOH in DCM (×3). The combined organic phases were passed through a phase separating column and the organic solvent was concentrated to dryness. The crude material was purified via silica gel chromatography eluting with 0-100% EtOAc:EtOH (v/v=3:1, with 0.1% NEt$_3$) in DCM (with 0.1% NEt$_3$) to afford a yellow solid. The obtained solid was repurified via silica gel chromatography eluting with 0-100% EtOAc:EtOH (v/v=3:1, with 0.1% Et$_3$N) in DCM (with 0.1% NEt$_3$) to afford a yellow solid which was again repurified via silica gel chromatography eluting with 0-15% i-PrOH (with 1% Et$_3$N) in DCM (with 1% Et$_3$N) to afford I-61 (24 mg, 0.053 mmol, 20% yield) as a pale yellow solid. MS [M+H]$^+$=428.4. $^1$H NMR (400 MHz, DMSO-d$_6$) δ 10.95 (s, 1H), 7.61 (d, J=8.4 Hz, 1H), 7.14 (d, J=2.2 Hz, 1H), 7.06-6.99 (m, 1H), 5.06 (dd, J=13.2, 5.0 Hz, 1H), 4.44-4.19 (m, 3H), 2.90 (ddd, J=18.1, 13.6, 5.4 Hz, 1H), 2.83-2.77 (m, 1H), 2.64-2.55 (m, 1H), 2.44-2.27 (m, 3H), 2.02-1.94 (m, 1H), 1.87-1.38 (br multiplets, 11H), 0.83 (dd, J=6.6, 2.3 Hz, 6H).

Example 46: 3-(1-oxo-5-(((1S,2S)-2-(propylamino)cycloheptyl)oxy)isoindolin-2-yl)piperidine-2,6-dione (I-62)

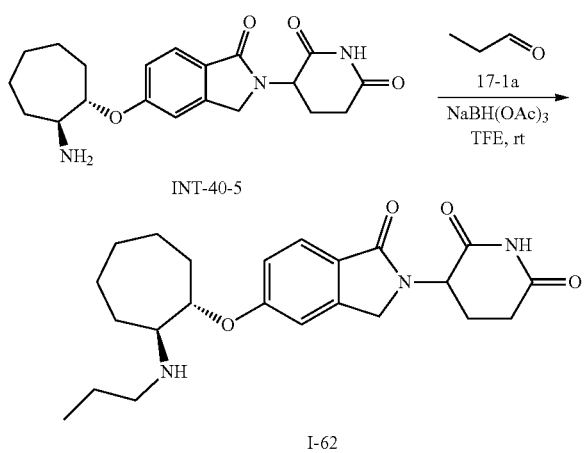

To a solution of 3-(5-(((1S,2S)-2-aminocycloheptyl)oxy)-1-oxoisoindolin-2-yl)piperidine-2,6-dione (INT 40-5, 100 mg, 0.269 mmol) in TFE (3 mL) was added propionaldehyde (46-1, 0.02 mL, 0.3 mmol). The resulting mixture was stirred at rt for 30 minutes and then sodium triacetoxyborohydride (171 mg, 0.808 mmol) was added. The reaction mixture was stirred at rt for 5 hours and then added to a saturated aqueous solution of sodium hydrogen carbonate (20 mL). The aqueous phase was extracted with 20% i-PrOH in DCM (×3). The combined organic phases were passed through a phase separating column and concentrated to dryness. The crude material was purified via silica gel chromatography eluting with 0-15% i-PrOH (with 0.1% NEt$_3$) in DCM (with 0.1% NEt$_3$) to afford I-62 (49 mg, 0.11 mmol, 42% yield) as a pale yellow solid. MS [M+H]$^+$=414.4. $^1$H NMR (400 MHz, DMSO-d$_6$) δ 10.95 (s, 1H), 7.61 (d, J=8.4 Hz, 1H), 7.14 (d, J=2.0 Hz, 1H), 7.06-6.99 (m, 1H), 5.06 (dd, J=13.2, 5.0 Hz, 1H), 4.44-4.20 (m, 3H), 2.89 (ddd, J=27.1, 14.0, 7.1 Hz, 1H), 2.88-2.80 (m, 1H), 2.65-2.52 (m, 2H), 2.48-2.28 (m, 2H), 2.04-1.92 (m, 1H), 1.86-1.43 (m, 10H), 1.42-1.31 (m, 2H), 0.83 (t, J=7.4 Hz, 3H).

Example 47: 3-(5-(((1S,2S)-2-(2-oxa-6-azaspiro[3.3]heptan-6-yl)cycloheptyl)oxy)-1-oxoisoindolin-2-yl)piperidine-2,6-dione HC(O)OH Salt (I-63)

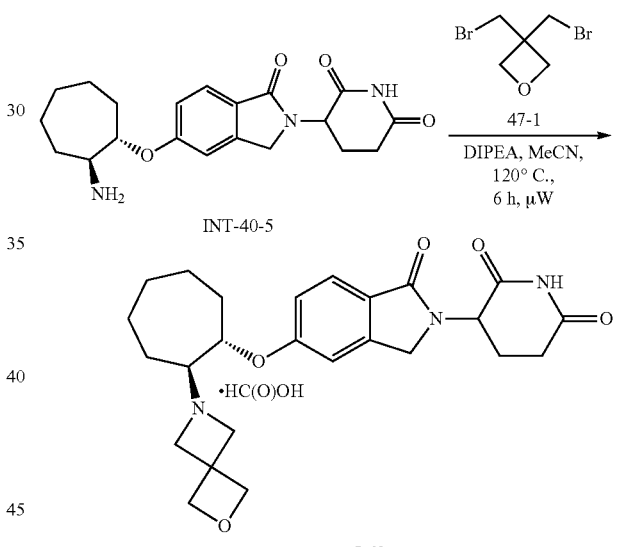

I-63

In a μW vial, 3-(5-(((1S,2S)-2-aminocycloheptyl)oxy)-1-oxoisoindolin-2-yl)piperidine-2,6-dione (INT-40-5, 101.8 mg, 0.274 mmol) and 3,3-bis(bromomethyl)oxetane (47-1, 85 mg, 0.35 mmol) were dissolved in MeCN (1 mL) and DIPEA (0.15 mL, 0.86 mmol). The resulting mixture was stirred in a μW reactor at 120° C. for 6 h, transferred to a reaction vial with MeCN, and then concentrated to dryness. The crude material was purified via silica gel chromatography eluting with 0-100% EtOAc:EtOH (v/v=3:1, with 0.1% NEt$_3$) in DCM (with 0.1% NEt$_3$) to afford a yellow solid. The obtained solid was then purified via reverse phase HPLC (Column: X-bridge C18 OBD 5 um 30×50 mm; Conditions: Water/MeCN with 0.1% Formic Acid; 75 mL/min; 1.5 mL injection; Gradient: 10-30% MeCN, 3.5 min gradient) to afford the formate salt of I-63 (38 mg, 0.075 mmol, 27% yield), as a white solid. MS [M+H]$^+$=454.4. $^1$H NMR (400 MHz, DMSO-d$_6$) δ 10.96 (s, 1H), 8.15 (s, 1H), 7.62 (d, J=8.4 Hz, 1H), 7.11 (s, 1H), 7.05-6.96 (m, 1H), 5.14-5.01 (m, 1H), 4.53 (s, 4H), 4.47-4.14 (m, 3H), 3.35 (d, J=7.24 Hz, 2H), 3.18 (d, J=7.1 Hz, 2H), 2.91 (ddd, J=17.7, 13.4, 5.2 Hz, 1H), 2.71-2.56 (m, 1H), 2.42-2.29 (m, 1H), 2.04-1.92 (m, 1H), 1.87-1.31 (m, 11H).

Example 48: 3-(5-(((1S,2S)-2-((((1r,4S)-4-methoxycyclohexyl)methyl)amino)cycloheptyl)oxy)-1-oxoisoindolin-2-yl)piperidine-2,6-dione (I-64)

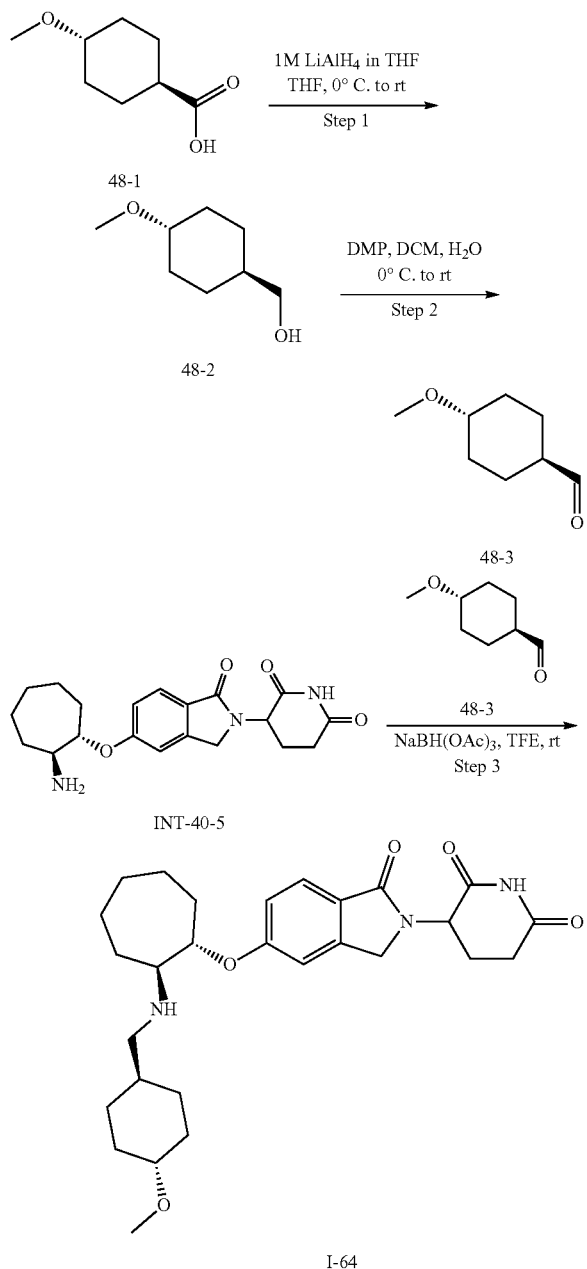

Step 1. ((1R,4R)-4-Methoxycyclohexyl)methanol (48-2)

To a solution of trans-4-methoxycyclohexane-1-carboxylic acid (48-1, 1.00 g, 6.32 mmol) in dry THF (10 mL), under an atmosphere of nitrogen and cooled using an ice bath, was added lithium aluminum hydride 1M in THF (9.5 mL, 9.5 mmol) dropwise. The resulting mixture was stirred using an ice bath for 2 h, then allowed to warm to room temperature and stirred for 16 h. A solution of saturated aqueous potassium sodium tartrate (Rochelle's Salt) (150 mL) was then added with stirring. The reaction mixture was extracted with DCM (×4) and the combined organic phases were passed through a phase separating column and concentrated to dryness to afford 48-2 (903 mg, 6.26 mmol, 99% yield) as a colorless oil. The product was carried onto the next step without purification. $^1$H NMR (400 MHz, DMSO-$d_6$) δ 4.36 (s, 1H), 3.21 (s, 3H), 3.19 (d, J=6.3 Hz, 2H), 3.02 (tt, J=10.7, 4.1 Hz, 1H), 2.07-1.91 (m, 2H), 1.80-1.66 (m, 2H), 1.36-1.21 (m, 1H), 1.11-0.96 (m, 2H), 0.87 (tdd, J=13.2, 11.6, 3.1 Hz, 2H).

Step 2. (1R,4R)-4-Methoxycyclohexane-1-carbaldehyde (48-3)

((1R,4R)-4-methoxycyclohexyl)methanol (48-2, 100 mg, 0.693 mmol) was dissolved in DCM (3 mL) and cooled using an ice bath. DMP (412 mg, 0.971 mmol) was then added followed by H$_2$O (0.02 mL, 0.9 mmol) and the resulting mixture was stirred at rt for 4 hours. A 1:1 mixture of a saturated aqueous solution of sodium thiosulphate (10 mL) and a saturated aqueous solution of sodium hydrogen carbonate (10 mL) was added and the mixture was extracted with DCM (×3). The combined organic phases were passed through a phase separating column and concentrated to dryness to afford a white solid. The crude material was suspended in excess diethyl ether, sonicated and filtered. The obtained solid was washed with diethyl ether (×2). The filtrate was then collected and concentrated to dryness to afford 48-3 (104 mg, 0.585 mmol, 84% yield) as a colorless oil. $^1$H NMR (400 MHz, DMSO-$d_6$) δ (ppm): 9.57 (d, J=1.2 Hz, 1H), 3.23 (s, 3H), 3.12-2.99 (m, 1H), 2.31-2.16 (m, 1H), 2.05-1.81 (m, 4H), 1.33-1.09 (m, 4H).

Step 3. 3-(5-(((1S,2S)-2-((((1R,4S)-4-methoxycyclohexyl)methyl)amino)cycloheptyl)oxy)-1-oxoisoindolin-2-yl)piperidine-2,6-dione (I-64)

To a solution of 3-(5-(((1S,2S)-2-aminocycloheptyl)oxy)-1-oxoisoindolin-2-yl)piperidine-2,6-dione (INT-40-5, 100 mg, 0.269 mmol) in TFE (2 mL) was added (1r,4r)-4-methoxycyclohexane-1-carbaldehyde (48-3, 42.1 mg, 0.296 mmol). The resulting mixture was stirred at rt for 30 minutes and then sodium triacetoxyborohydride (171 mg, 0.808 mmol) was added. The reaction mixture was stirred at rt overnight and then a saturated aqueous solution of sodium hydrogen carbonate (20 mL) was added. The mixture was extracted with 20% i-PrOH in DCM (×3) and the combined organic phases were passed through a phase separating column and concentrated to dryness. The crude material was purified via silica gel chromatography eluting with 0-15% i-PrOH (with 0.1% NEt$_3$) in DCM (with 0.1% NEt$_3$) to afford I-64 (50 mg, 0.095 mmol, 36% yield), as a pale yellow solid. MS [M+H]$^+$=498.4. $^1$H NMR (400 MHz, DMSO-$d_6$) δ (ppm): 10.95 (s, 1H), 7.61 (d, J=8.4 Hz, 1H), 7.13 (d, J=2.1 Hz, 1H), 7.02 (dt, J=8.4, 1.6 Hz, 1H), 5.11-5.02 (m, 1H), 4.43-4.21 (m, 3H), 3.20 (s, 3H), 3.05-2.84 (m, 2H), 2.83-2.74 (m, 1H), 2.64-2.54 (m, 1H), 2.45-2.27 (m, 3H), 2.02-1.90 (m, 3H), 1.85-1.58 (m, 7H), 1.58-1.38 (m, 5H), 1.33-1.21 (s, 1H), 1.02 (q, J=12.2 Hz, 2H), 0.93-0.76 (m, 2H).

Example 49: 3-(1-oxo-5-((((1S,2S)-2-(((tetrahydro-2H-pyran-4-yl)methyl)amino)cycloheptyl)oxy)isoindolin-2-yl)piperidine-2,6-dione (I-65)

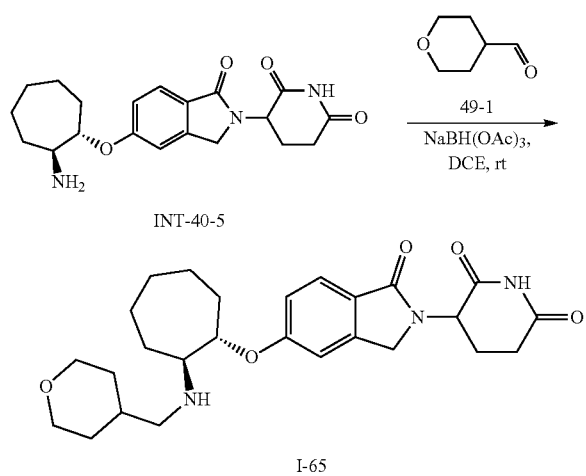

To a solution of 3-(5-(((1S,2S)-2-aminocycloheptyl)oxy)-1-oxoisoindolin-2-yl)piperidine-2,6-dione (INT-40-5, 100 mg, 0.269 mmol) in DCE (2 mL) was added tetrahydro-2H-pyran-4-carbaldehyde (49-1, 34 mg, 0.30 mmol). The resulting mixture was stirred at rt for 30 minutes, and then sodium triacetoxyborohydride (171 mg, 0.808 mmol) was added. The reaction mixture was stirred at rt overnight and then a saturated aqueous solution of sodium hydrogen carbonate (20 mL) was added. The aqueous mixture was extracted with 20% i-PrOH in DCM (×3) and the combined organics were passed through a phase separating column and concentrated to dryness. The crude material was purified by reverse phase HPLC (Column: X-bridge C18 OBD 5 um 30×50 mm; Conditions: Water/MeCN with 0.1% Formic Acid; 75 mL/min; 1.5 mL injection; Gradient: 10-30% MeCN, 3.5 min gradient). The fractions containing the desired product were combined and lyophilized to afford I-65 (43 mg, 0.075 mmol, 28% yield), as a white solid. MS [M+H]$^+$=470.4. $^1$H NMR (400 MHz, DMSO-d$_6$) δ (ppm): 10.95 (s, 1H), 7.61 (d, J=8.4 Hz, 1H), 7.17-7.09 (m, 1H), 7.02 (dt, J=8.4, 1.8 Hz, 1H), 5.06 (dd, J=13.4, 4.9 Hz, 1H), 4.42-4.19 (m, 3H), 3.79 (dd, J=11.5, 4.0 Hz, 2H), 3.27-3.17 (m, 2H), 2.96-2.79 (m, 2H), 2.65-2.55 (m, 1H), 2.47-2.31 (m, 3H), 2.03-1.92 (m, 1H), 1.85-1.38 (m, 13H), 1.16-0.99 (m, 2H).

Example 50: 3-(5-(((1S,2S)-2-(((3-methyloxetan-3-yl)methyl)amino)cycloheptyl)oxy)-1-oxoisoindolin-2-yl)piperidine-2,6-dione (I-66)

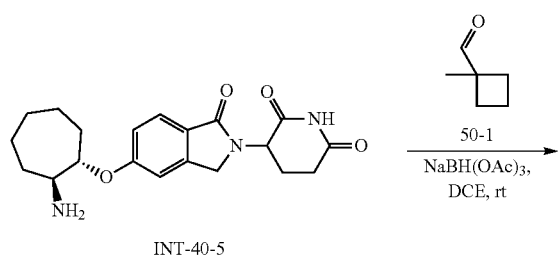

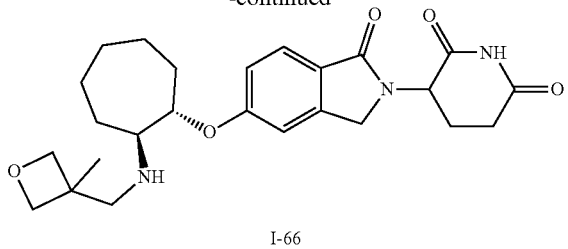

To a solution of 3-(5-(((1S,2S)-2-aminocycloheptyl)oxy)-1-oxoisoindolin-2-yl)piperidine-2,6-dione (INT-40-5, 100 mg, 0.269 mmol) in DCE (3 mL) was added 3-methyloxetane-3-carbaldehyde (50-1, 32 mg, 0.32 mmol). The resulting mixture was stirred at rt for 30 minutes and then sodium triacetoxyborohydride (171 mg, 0.808 mmol) was added. The reaction mixture was stirred at rt overnight and then a saturated aqueous solution of sodium hydrogen carbonate (20 mL) was added. The aqueous mixture was extracted with 20% i-PrOH in DCM (×3) and the combined organics were passed through a phase separating column and concentrated to dryness. The crude material was purified by reverse phase HPLC (Column: X-bridge C18 OBD 5 um 30×50 mm; Conditions: Water/MeCN with 0.1% Formic Acid; 75 mL/min; 1.5 mL injection; Gradient: 10-30% MeCN, 3.5 min gradient). The fractions containing the desired product were combined and lyophilized to afford I-66 (18 mg, 0.034 mmol, 13% yield) as a white solid. MS [M+H]$^+$=456.4. $^1$H NMR (400 MHz, DMSO-d$_6$) δ (ppm): 10.95 (s, 1H), 7.61 (d, J=8.4 Hz, 1H), 7.15 (s, 1H), 7.09-6.98 (m, 1H), 5.06 (dd, J=13.2, 5.0 Hz, 1H), 4.45-4.20 (m, 5H), 4.13 (dd, J=5.5, 2.9 Hz, 2H), 2.98-2.84 (m, 1H), 2.84-2.54 (m, 5H), 2.37 (dd, J=13.2, 4.5 Hz, 1H), 2.02-1.92 (m, 1H), 1.86-1.40 (m, 9H), 1.18 (s, 3H).

Example 51: 3-(5-(((1S,2S)-2-(((3-fluorobicyclo[0.1.1]pentan-1-yl)methyl)amino)cycloheptyl)oxy)-1-oxoisoindolin-2-yl)piperidine-2,6-dione (I-67)

Step 1. 3-fluorobicyclo[1.1.1]pentane-1-yl)methanol (51-2)

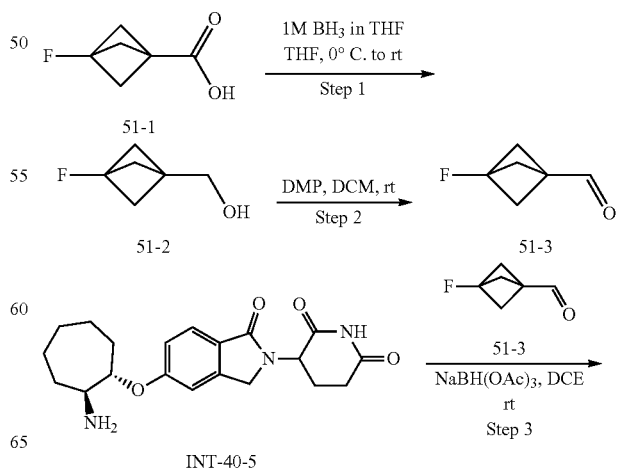

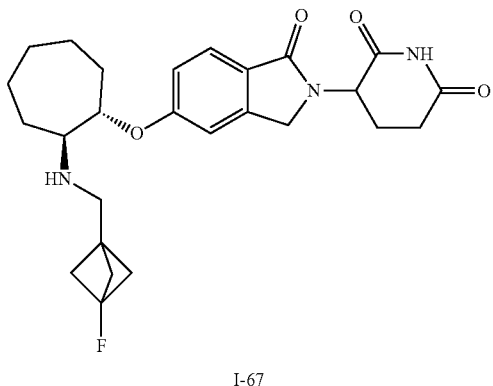

I-67

To a solution of 3-fluorobicyclo[1.1.1]pentane-1-carboxylic acid (51-1, 1000 mg, 7.69 mmol) in THF (3 mL) under a nitrogen atmosphere at 0° C. was added 1M BH₃ in THF (9.2 mL, 9.2 mmol) and the resulting mixture was stirred overnight at rt. The reaction mixture was then quenched with MeOH (2 mL) and concentrated to dryness to afford 51-2 (890 mg, 7.66 mmol, 100% yield) as a colorless oil which was carried onto the next step without purification. $^1$H NMR (400 MHz, DCM-d$_2$) δ 3.84 (s, 2H), 2.02 (d, J=2.7 Hz, 6H).

Step 2. 3-fluorobicyclo[1.1.1]pentane-1-carbaldehyde (51-3)

To a solution of (3-fluorobicyclo[1.1.1]pentan-1-yl)methanol (51-2, 890 mg, 7.66 mmol) in DCM (10 mL) was added DMP (4.87 g, 11.5 mmol) and the resulting mixture was stirred at rt for 6 h. The reaction mixture was diluted with Et₂O and filtered. The filtrate was concentrated to dryness to afford 51-3, which was carried onto the next step without purification (assumed quantitative yield). $^1$H NMR (400 MHz, DMSO-d$_6$) δ 9.29 (d, J=6.4 Hz, 1H), 1.91 (d, J=2.7 Hz, 6H).

Step 3. 3-(5-(((1S,2S)-2-(((3-fluorobicyclo[1.1.1]pentan-1-yl)methyl)amino)cycloheptyl)oxy)-1-oxoisoindolin-2-yl)piperidine-2,6-dione (51-4)

To a solution of 3-(5-(((1S,2S)-2-aminocycloheptyl)oxy)-1-oxoisoindolin-2-yl)piperidine-2,6-dione (INT-40-5, 102 mg, 0.275 mmol) in DCE (0.9 mL) was added pre-filtered 3-fluorobicyclo[1.1.1]pentane-1-carbaldehyde (51-3, 38 mg, 0.33 mmol). The resulting mixture was stirred at rt for 15 minutes and then sodium triacetoxyborohydride (87 mg, 0.41 mmol) was added. The reaction mixture was stirred at rt for 18 h and then quenched with saturated aqueous sodium bicarbonate and extracted with 20% i-PrOH in DCM (×3). The combined organic layers were passed through a phase separator and concentrated onto Celite®. The crude material was purified by silica gel chromatography eluting with 0-100% EtOAc:EtOH (v/v=3:1, with 1% NEt₃) in heptane to afford I-67 (52.4 mg, 0.107 mmol, 39% yield) as a white solid. MS [M+H]⁺=470.5. $^1$H NMR (400 MHz, DMSO-d$_6$) δ 10.96 (s, 1H), 7.62 (d, J=8.3 Hz, 1H), 7.15 (d, J=2.2 Hz, 1H), 7.03 (dd, J=8.4, 2.2 Hz, 1H), 5.07 (ddd, J=13.2, 5.2, 1.8 Hz, 1H), 4.50-4.18 (m, 3H), 2.99-2.72 (m, 4H), 2.64-2.55 (m, 1H), 2.44-2.35 (m, 1H), 2.04-1.93 (m, 1H), 1.89 (d, J=2.6 Hz, 6H), 1.82-1.39 (m, 10H).

Example 52: 3-(5-(((1S,2S)-2-(3-methoxyazetidin-1-yl)cycloheptyl)oxy)-1-oxoisoindolin-2-yl)piperidine-2,6-dione (I-68)

Step 1. 2-methoxypropane-1,3-diol (52-2)

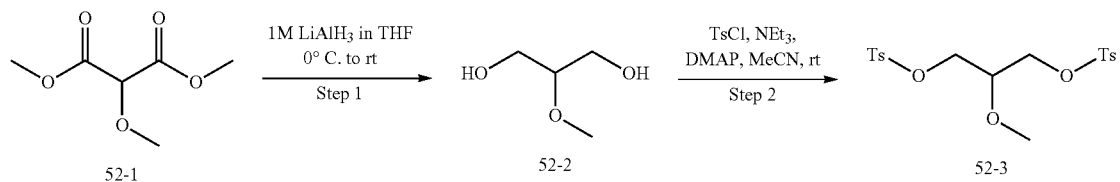

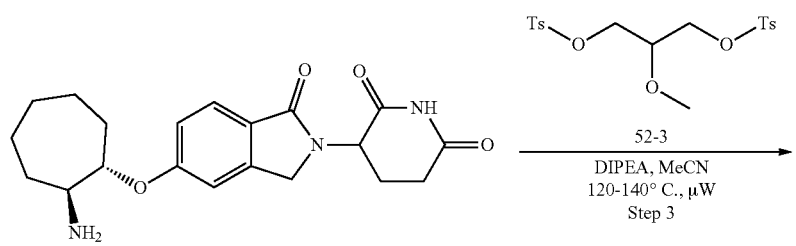

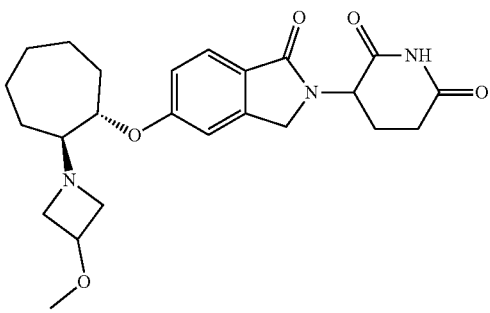

I-68

To a solution of dimethyl 2-methoxymalonate (52-1, 1.7 mL, 12 mmol) in dry THF (70 mL), under an atmosphere of nitrogen and cooled in an ice bath, was added lithium aluminum hydride 1M in THF (14.8 mL, 14.8 mmol) dropwise. The resulting mixture was stirred in an ice bath and then warmed to warm to rt and stirred at rt overnight. The reaction mixture was cooled using an ice bath and sodium sulfate decahydrate (4.77 g, 14.8 mmol) was added portion wise under a stream of nitrogen with vigorous stirring to provide a granular suspension. The suspension was filtered and the resulting solid was washed with THF (×3). The filtrate was concentrated to dryness to afford 52-2 (629 mg, 12.3 mmol, 48% yield) as a colorless oil. $^1$H NMR (400 MHz, DMSO-$d_6$) δ 4.47 (t, J=5.6 Hz, 2H), 3.50-3.33 (m, 4H), 3.31 (s, 3H), 3.12 (quint, J=5.1 Hz, 1H).

Step 2. 2-methoxypropane-1,3-diyl bis(4-methylbenzenesulfonate) (52-3)

DMAP (77 mg, 0.63 mmol) and TEA (1.05 mL, 7.54 mmol) were added to a solution of 2-methoxypropane-1,3-diol (52-2, 200 mg, 1.89 mmol) in MeCN (5 mL). TsCl (898 mg, 4.71 mmol) was added and the resulting mixture was stirred at rt overnight under an atmosphere of nitrogen. The reaction mixture was concentrated to dryness and the obtained residue treated with diethyl ether. The obtained suspension was filtered and the solid was washed with diethyl ether (×3). The filtrate was collected and concentrated to dryness to afford 52-3 (771 mg, 1.86 mmol, 99% yield) as a pale yellow oil. MS [M+H]$^+$=415.2. $^1$H NMR (400 MHz, Chloroform-d) δ 7.78-7.74 (m, 4H), 7.35 (dd, J=8.7, 0.7 Hz, 4H), 4.07-3.97 (m, 4H), 3.59 (quint, J=5.0 Hz, 1H), 3.28 (s, 3H), 2.46 (s, 6H).

Step 3. 3-(5-(((1S,2S)-2-(3-methoxyazetidin-1-yl)cycloheptyl)oxy)-1-oxoisoindolin-2-yl)piperidine-2,6-dione (I-68)

To a cloudy solution of 3-(5-(((1S,2S)-2-aminocycloheptyl)oxy)-1-oxoisoindolin-2-yl)piperidine-2,6-dione (INT-40-5, 100 mg, 0.269 mmol) in MeCN (2 mL) was added 2-methoxypropane-1,3-diyl bis(4-methylbenzenesulfonate) (52-3, 167 mg, 0.404 mmol) and DIPEA (0.28 mL, 1.6 mmol). The resulting mixture was stirred at 120° C. for 2 hours and then at 140° C. for 1 hour in the μW. A saturated aqueous solution of sodium hydrogen carbonate (20 mL) and water (20 mL) was then added and the resulting mixture was extracted with 20% i-PrOH in DCM (×3). The combined organics were passed through a phase separating column and concentrated to dryness. The crude material was purified via silica gel chromatography eluting with 0-15% i-PrOH (with 0.1% NEt$_3$) in DCM (with 0.1% NEt$_3$) to afford I-68 (40 mg, 0.09 mmol, 32% yield), as a pale yellow solid. MS [M+H]$^+$=442.3. $^1$H NMR (400 MHz, DMSO-$d_6$) δ (ppm): 10.95 (s, 1H), 7.62 (d, J=8.4 Hz, 1H), 7.12 (s, 1H), 7.00 (dd, J=8.5, 2.2 Hz, 1H), 5.13-4.99 (m, 1H), 4.44-4.20 (m, 3H), 3.84 (t, J=5.8 Hz, 1H), 3.53-3.46 (m, 1H), 3.39-3.33 (m, 1H), 3.10 (s, 3H), 2.96-2.85 (m, 2H), 2.80-2.73 (m, 1H), 2.64-2.52 (m, 2H), 2.46-2.28 (m, 1H), 2.04-1.93 (m, 1H), 1.88-1.34 (m, 10H).

Example 53: 3-(5-(((1S,2S)-2-(((3,3-difluorocyclobutyl)methyl)amino)cycloheptyl)oxy)-1-oxoisoindolin-2-yl)piperidine-2,6-dione (I-69)

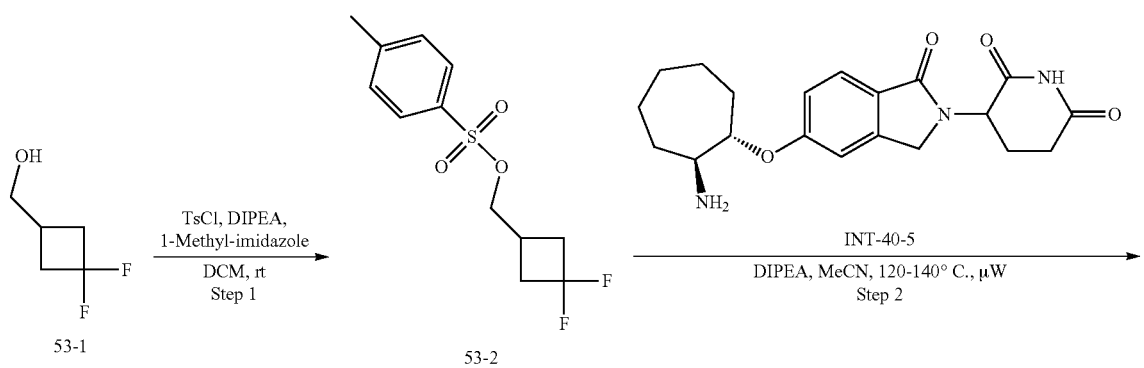

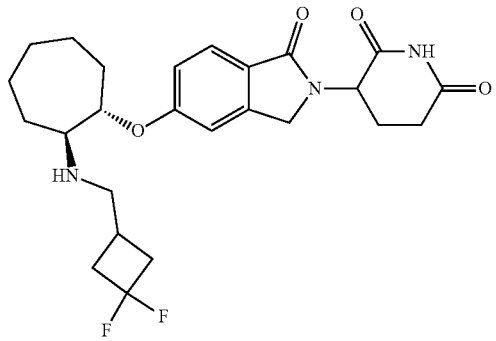

I-69

Step 1. (3,3-difluorocyclobutyl)methyl 4-methylbenzenesulfonate (53-2)

To a solution of (3,3-difluorocyclobutyl)methanol (53-1, 100 mg, 0.82 mmol) in DCM (3 mL) was added DIPEA (0.29 mL, 1.6 mmol), 1-methyl-1H-imidazole (0.13 mL, 1.6 mmol), followed by TsCl (234 mg, 1.23 mmol) dropwise, under a stream of nitrogen. The resulting mixture was stirred at rt overnight and then diluted with DCM (30 mL total). The organic phase was separated and washed with 1M HCl (aq) (×2), saturated aqueous solution of sodium hydrogen carbonate (×2) and brine (×1). The organic phase was passed through a phase separating column and concentrated to dryness to afford crude 53-2 (236 mg) as a white solid. The crude product was carried onto the next step without purification. MS [M+H$_2$O]$^+$=294.1. $^1$H NMR (400 MHz, DMSO-d$_6$) δ 7.83-7.77 (m, 2H), 7.53-7.47 (m, 2H), 4.09 (dt, J=6.6, 0.9 Hz, 2H), 2.67-2.53 (m, 2H), 2.48-2.38 (m, 1H), 2.43 (s, 3H), 2.37-2.21 (m, 2H).

Step 2. 3-(5-(((1S,2S)-2-(((3,3-difluorocyclobutyl)methyl)amino)cycloheptyl)oxy)-1-oxoisoindolin-2-yl)piperidine-2,6-dione (I-69)

To a suspension of 3-(5-(((1S,2S)-2-aminocycloheptyl)oxy)-1-oxoisoindolin-2-yl)piperidine-2,6-dione (INT-40-5, 112 mg, 0.302 mmol) in MeCN (2 mL), whilst bubbling with nitrogen, was added crude (3,3-difluorocyclobutyl)methyl 4-methylbenzenesulfonate (53-2, 92 mg, 0.33 mmol) and DIPEA (0.26 mL, 1.5 mmol). The resulting mixture was stirred at 120° C. for 2 hours and then at 140° C. for 9 hours in the μW. The reaction mixture was diluted with water (15 mL) and a saturated aqueous solution of sodium hydrogen carbonate (15 mL). The aqueous mixture was extracted with 20% i-PrOH in DCM (×3) and the combined organic phases were passed through a phase separating column and concentrated to dryness. The crude material was purified via silica gel chromatography eluting with 0-15% i-PrOH in DCM using 0.1% NEt$_3$ as a modifier, to afford I-69 (39 mg, 0.078 mmol, 26% yield) as a white solid. MS [M+H]$^+$=476.3. $^1$H NMR (400 MHz, DMSO-d$_6$) δ (ppm): 10.95 (s, 1H), 7.61 (d, J=8.4 Hz, 1H), 7.14 (d, J=2.2 Hz, 1H), 7.03 (dd, J=8.4, 2.2 Hz, 1H), 5.06 (dd, J=13.3, 5.1 Hz, 1H), 4.43-4.20 (m, 3H), 2.90 (ddd, J=18.1, 13.5, 5.3 Hz, 1H), 2.84-2.78 (m, 1H), 2.71-2.52 (m, 5H), 2.44-2.30 (m, 1H), 2.27-2.12 (m, 3H), 2.02-1.93 (m, 1H), 1.84-1.39 (m, 10H).

Example 54: 3-(5-(((1S,2S)-2-(3-ethoxyazetidin-1-yl)cycloheptyl)oxy)-1-oxoisoindolin-2-yl)piperidine-2,6-dione (I-55)

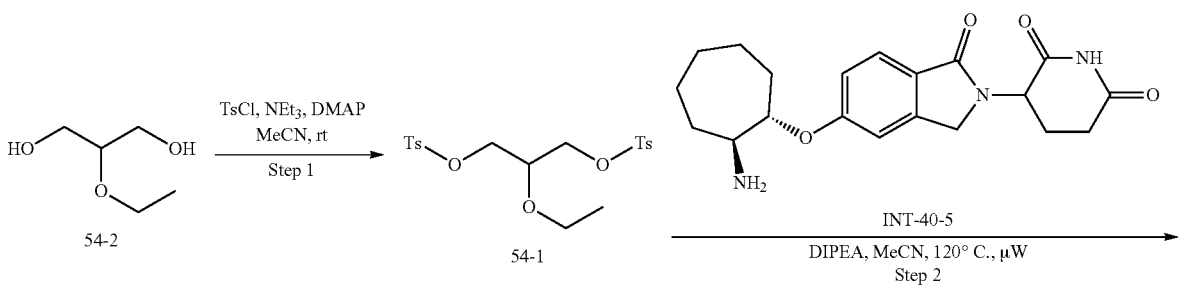

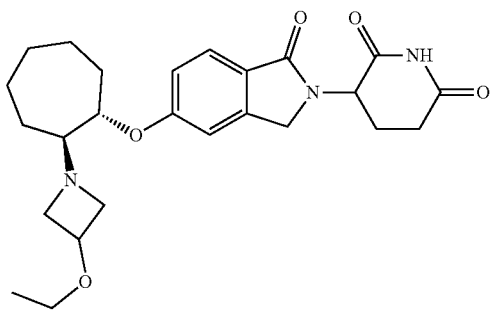

I-55

Step 1. 2-Ethoxypropane-1,3-diyl bis(4-methylbenzenesulfonate) (54-1)

TsCl (1368 mg, 7.18 mmol) was added to a solution of 2-ethoxypropane-1,3-diol (54-2, 392 mg, 3.26 mmol), DMAP (40 mg, 0.33 mmol), and TEA (1.8 mL, 13 mmol) in MeCN (10 mL). The resulting mixture was stirred at rt overnight and then filtered. The filtrate was collected and concentrated to dryness. The crude material was purified via silica gel chromatography eluting with 0-100% EtOAc in heptane to afford 54-1 (220 mg, 0.513 mmol, 16% yield) as a colorless oil. MS [M+H$_2$O]$^+$=446.2. $^1$H NMR (400 MHz, Chloroform-d) δ 7.78-7.72 (m, 4H), 7.38-7.32 (m, 4H), 4.05-3.96 (m, 4H), 3.68 (quint, J=5.1 Hz, 1H), 3.46 (q, J=7.0 Hz, 2H), 2.46 (s, 6H), 1.07 (t, J=7.0 Hz, 3H).

Step 3. 3-(5-(((1S,2S)-2-(3-ethoxyazetidin-1-yl)cycloheptyl)oxy)-1-oxoisoindolin-2-yl)piperidine-2,6-dione (I-55)

DIPEA (0.17 mL, 0.97 mmol) was added to a solution of 3-(5-(((1S,2S)-2-aminocycloheptyl)oxy)-1-oxoisoindolin-2-yl)piperidine-2,6-dione (INT-40-5, 60 mg, 0.16 mmol) and 2-ethoxypropane-1,3-diyl bis(4-methylbenzenesulfonate) (54-1, 220 mg, 0.51 mmol) in MeCN (2 mL). The resulting mixture was stirred at 120° C. under μW irradiation for 3 h and then concentrated to dryness. The crude residue was triturated with diethyl ether (3×). The crude product was purified via silica gel chromatography eluting 0-15% i-PrOH (with 0.1% NEt$_3$) in DCM (with 0.1% NEt$_3$). The obtained material was treated with 1:1 water/sat. aqueous Na$_2$CO$_3$ and extracted with DCM (×3). The combined organic phases were passed through a phase separating column and the solvent concentrated to dryness to afford I-55 (17 mg, 0.035 mmol, 22% yield) as an off-white solid. MS [M+H]$^+$=456.4. $^1$H NMR (400 MHz, DMSO-d$_6$) δ 10.96 (s, 1H), 7.61 (d, J=8.4 Hz, 1H), 7.12 (d, J=2.1 Hz, 1H), 7.00 (dd, J=8.7, 2.0 Hz, 1H), 5.07 (dd, J=13.2, 5.1 Hz, 1H), 4.39 (dd, J=17.1, 7.4 Hz, 2H), 4.25 (dd, J=17.2, 5.5 Hz, 1H), 3.91 (quint, J=5.9 Hz, 1H), 3.54-3.46 (m, 1H), 3.38-3.33 (m, 1H), 3.30-3.26 (m, 2H), 2.97-2.82 (m, 2H), 2.75 (t, J=6.4 Hz, 1H), 2.63-2.53 (m, 2H), 2.44-2.35 (m, 1H), 2.00-1.93 (m, 1H), 1.88-1.78 (m, 1H), 1.76-1.55 (m, 4H), 1.56-1.34 (m, 5H), 1.05 (t, J=7.0 Hz, 3H).

Example 55: 3-(1-oxo-5-(((1S,2S)-2-(propylamino)cyclohexyl)oxy)isoindolin-2-yl)piperidine-2,6-dione HC(O)OH Salt (I-71)

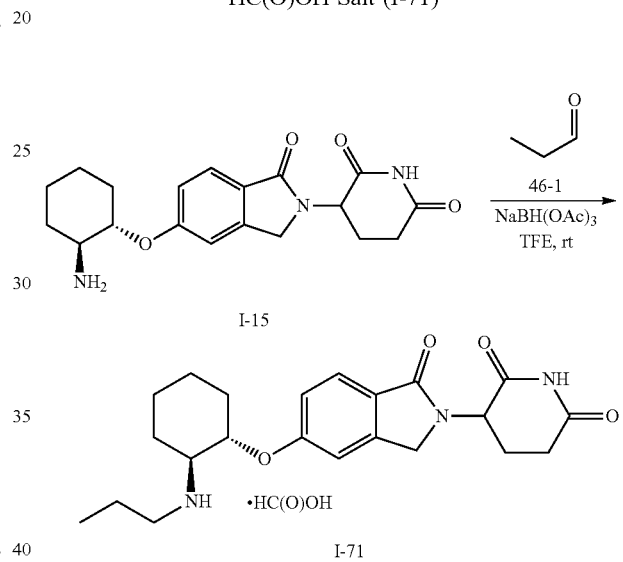

3-(5-(((1S,2S)-2-aminocyclohexyl)oxy)-1-oxoisoindolin-2-yl)piperidine-2,6-dione (I-15, 121.8 mg, 0.34 mmol) and propionaldehyde (46-1, 0.04 mL, 0.6 mmol) were dissolved in 2,2,2-trifluoroethanol (1 mL). Sodium triacetoxyborohydride (108 mg, 0.511 mmol) was added in one portion and the resulting mixture was stirred at room temperature for 1 h. The reaction mixture was then diluted with ethyl acetate (45 mL) and washed with saturated aqueous sodium bicarbonate solution (10 mL) and brine (10 mL). The organic phase was dried over magnesium sulfate, filtered, and concentrated to dryness. The crude material was purified by reverse phase HPLC (Column: Xbridge C18 OBD 5 um 30×50 mm; Conditions: Water/MeCN with 10 mM NH$_4$OH 75 mL/min; 1.5 mL injection; Gradient: 25-50% MeCN, 3.5 min gradient; collected fractions into tubes containing ~3 drops of formic acid) to afford the formate salt of I-71 (36 mg, 0.078 mmol, 23% yield), as a solid. MS [M+H]$^+$=400.5. $^1$H NMR (400 MHz, DMSO-d$_6$) δ 10.96 (s, 1H), 8.20 (s, 1H), 7.61 (d, J=8.4 Hz, 1H), 7.21 (s, 1H), 7.08 (ddd, J=8.5, 2.3, 1.0 Hz, 1H), 5.07 (dd, J=13.3, 5.1 Hz, 1H), 4.46-4.15 (m, 3H), 2.90 (ddd, J=17.2, 13.6, 5.4 Hz, 1H), 2.77-2.69 (m, 1H), 2.64-2.56 (m, 2H), 2.45-2.35 (m, 2H), 2.12-2.04 (m, 1H), 2.03-1.91 (m, 2H), 1.74-1.59 (m, 2H), 1.48-1.14 (m, 6H), 0.84 (t, J=7.4 Hz, 3H).

Example 56: 3-(5-(((1S,2S)-2-(dipropylamino)cyclohexyl)oxy)-1-oxoisoindolin-2-yl)piperidine-2,6-dione (I-72)

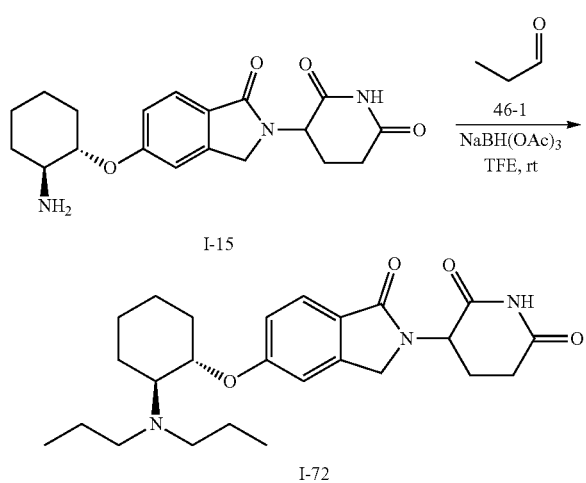

3-(5-(((1S,2S)-2-aminocyclohexyl)oxy)-1-oxoisoindolin-2-yl)piperidine-2,6-dione (I-15, 121.8 mg, 0.341 mmol) and propionaldehyde (46-1, 0.04 mL, 0.6 mmol) were dissolved in 2,2,2-trifluoroethanol (1 mL). Sodium triacetoxyborohydride (108 mg, 0.511 mmol) was added in one portion and the resulting mixture was stirred at room temperature for 1 h. The reaction mixture was diluted with ethyl acetate (45 mL) and washed with saturated aqueous sodium bicarbonate solution (10 mL) and brine (10 mL). The organic phase was dried over magnesium sulfate, filtered, and concentrated to dryness. The crude material was purified by reverse phase HPLC (Column: Xbridge C18 OBD 5 m 30×50 mm; Conditions: Water/MeCN with 10 mM NH$_4$OH 75 mL/min; 1.5 mL injection; Gradient: 25-50% MeCN, 3.5 min gradient; collected fractions collected fractions into tubes containing ~3 drops of formic acid) to afford crude material. Crude material was purified via silica gel chromatography eluting with 0-60% EtOAc:EtOH (v/v=3:1, with 1% Et$_3$N) in DCM (with 1% Et$_3$N) to afford I-72 (26 mg, 0.060 mmol, 18% yield) as a solid. MS [M+H]$^+$=442.6 m/z. $^1$H NMR (400 MHz, DMSO-d$_6$) δ 10.95 (s, 1H), 7.58 (d, J=8.4 Hz, 1H), 7.14 (s, 1H), 6.99 (dd, J=8.5, 2.3, 1.1 Hz, 1H), 5.06 (ddd, J=13.2, 5.1, 2.4 Hz, 1H), 4.44 (q, J=5.0 Hz, 1H), 4.41-4.19 (m, 2H), 2.90 (ddd, J=17.3, 13.7, 5.4 Hz, 1H), 2.69-2.55 (m, 2H), 2.48-2.36 (m, 5H), 2.14 (d, J=11.0 Hz, 1H), 2.05-1.91 (m, 1H), 1.83-1.57 (m, 3H), 1.44-1.20 (m, 8H), 0.76 (t, J=7.3 Hz, 6H).

Example 57: 3-(1-oxo-5-(((1S,2S)-2-((pyridin-4-ylmethyl)amino)cyclohexyl)oxy)isoindolin-2-yl)piperidine-2,6-dione HC(O)OH Salt (I-73)

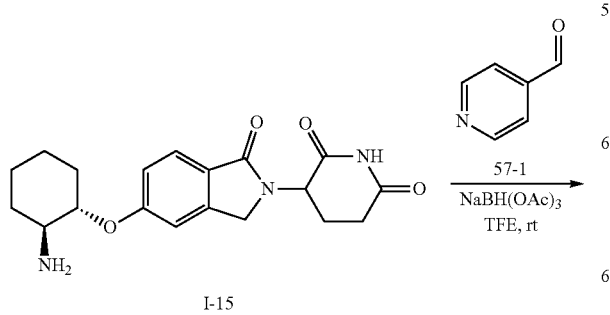

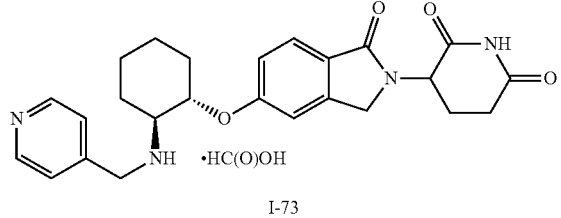

3-(5-(((1S,2S)-2-aminocyclohexyl)oxy)-1-oxoisoindolin-2-yl)piperidine-2,6-dione (I-15, 109.1 mg, 0.305 mmol) and isonicotinaldehyde (57-1, 0.03 mL, 0.3 mmol) were dissolved in 2,2,2-trifluoroethanol (1 mL), and sodium triacetoxyborohydride (83.2 mg, 0.393 mmol) was added in one portion. The resulting mixture was stirred at rt for 1 h. The reaction mixture was concentrated to dryness and the crude material was purified by silica gel chromatography eluting with 0-70% EtOAc:EtOH ((v/v=3:1, with 1% Et$_3$N) in DCM (with 1% Et$_3$N). The obtained material was purified by reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) to afford the formate salt of I-73 (21 mg, 0.042 mmol, 14% yield) as a white solid. MS [M+H]$^+$ =449.5. $^1$H NMR (400 MHz, DMSO-d$_6$) δ 10.96 (s, 1H), 8.50-8.43 (m, 2H), 8.14 (s, 1H), 7.60 (d, J=8.4 Hz, 1H), 7.39-7.29 (m, 2H), 7.23-7.16 (m, 1H), 7.07 (dd, J=8.4, 2.2 Hz, 1H), 5.07 (ddd, J=13.1, 5.0, 1.5 Hz, 1H), 4.47-4.19 (m, 3H), 3.91-3.75 (m, 2H), 2.91 (ddd, J=17.1, 13.5, 5.3 Hz, 1H), 2.67-2.55 (m, 2H), 2.44-2.34 (m, 1H), 2.07 (s, 1H), 2.03-1.89 (m, 2H), 1.64 (s, 2H), 1.45-1.13 (m, 4H).

Example 58: 3-(5-(((1S,2S)-2-(2-oxa-6-azaspiro[3.3]heptan-6-yl)cyclohexyl)oxy)-1-oxoisoindolin-2-yl)piperidine-2,6-dione (I-74)

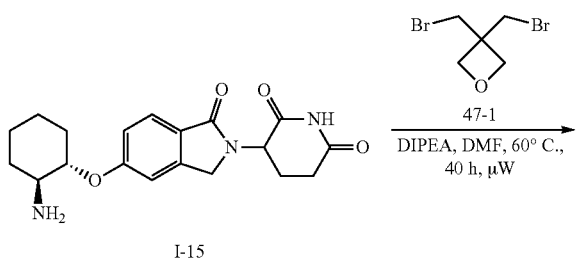

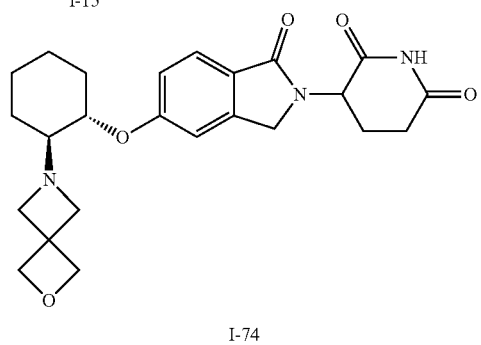

To 3-(5-(((1S,2S)-2-aminocyclohexyl)oxy)-1-oxoisoindolin-2-yl)piperidine-2,6-dione (I-15, 90.3 mg, 0.253 mmol) dissolved in DMF (2 mL) was added DIPEA (0.11 mL, 0.63 mmol) followed by a solution of 3,3-bis(bromomethyl)oxetane (47-1, 73.6 mg, 0.302 mmol) in DMF (1 mL). The resulting mixture was stirred at 60° C. for 40 h. The reaction mixture was concentrated to dryness and the crude product purified by silica gel chromatography eluting with 0-100% EtOAc:EtOH (v/v=3:1, with 1% Et$_3$N) in DCM (with 1% Et$_3$N) to afford I-74 (10 mg, 0.022 mmol, 9% yield), as a pale yellow solid. MS [M+H]$^+$=440.5. $^1$H NMR (400 MHz, DMSO-d$_6$) δ 10.96 (s, 1H), 7.62 (d, J=8.4 Hz, 1H), 7.16 (s, 1H), 7.08-6.97 (m, 1H), 5.07 (dd, J=13.0, 5.0 Hz, 1H), 4.54 (t, J=4.9 Hz, 4H), 4.45-4.32 (m, 1H), 4.25 (dd, J=25.4, 8.3 Hz, 2H), 3.37 (d, J=7.5 Hz, 2H), 3.25 (d, J=7.6 Hz, 2H), 2.91 (ddd, J=18.5, 13.6, 5.3 Hz, 1H), 2.59 (d, J=16.7 Hz, 1H), 2.43-2.34 (m, 1H), 2.25 (s, 1H), 1.99 (s, 2H), 1.82-1.70 (m, 1H), 1.61 (d, J=9.9 Hz, 2H), 1.39-1.26 (m, 2H), 1.19 (s, 1H), 1.07-0.99 (m, 1H).

Example 59: 3-(1-oxo-5-(((1S,2S)-2-((pyridin-3-ylmethyl)amino)cyclohexyl)oxy)isoindolin-2-yl)piperidine-2,6-dione (I-75)

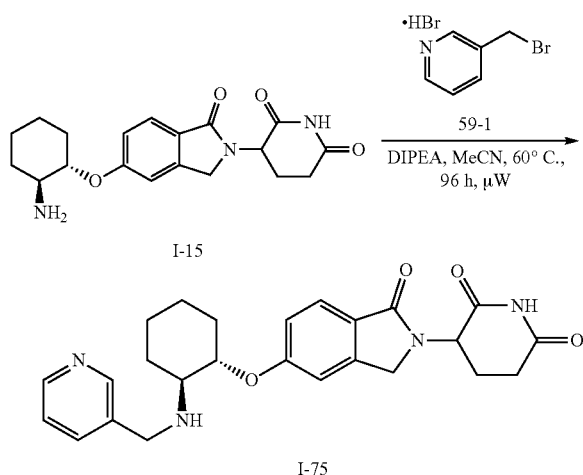

To 3-(5-(((1S,2S)-2-aminocyclohexyl)oxy)-1-oxoisoindolin-2-yl)piperidine-2,6-dione (I-15, 96.6 mg, 0.270 mmol) and 3-(bromomethyl)pyridine hydrobromide (59-1, 79.8 mg, 0.315 mmol) dissolved in MeCN (2 mL) was added DIPEA (0.15 mL, 0.87 mmol) and the resulting mixture was stirred at 60° C. for 4 days. The reaction mixture was concentrated to dryness and the crude material was purified by reverse phase HPLC (Column: Xbridge C18 OBD 5 um 30×50 mm; Conditions: Water/MeCN with 10 mM NH$_4$OH 75 mL/min; 1.5 mL injection; Gradient: 15-40% MeCN, 3.5 min gradient; collection tubes contain ~3 drops of formic acid). The obtained material was further purified via silica gel chromatography eluting with 5-100% EtOAc:EtOH (v/v=3:1, with 1% Et$_3$N) in DCM (with 1% Et$_3$N) to afford I-75 (17 mg, 0.039 mmol, 14% yield), as a white solid. MS [M+H]$^+$=449.5. $^1$H NMR (400 MHz, DMSO-d$_6$) δ 10.95 (s, 1H), 8.51 (s, 1H), 8.41 (d, J=4.7 Hz, 1H), 7.71 (d, J=7.8 Hz, 1H), 7.60 (d, J=8.4 Hz, 1H), 7.31 (dd, J=7.7, 4.7 Hz, 1H), 7.19 (s, 1H), 7.07 (dd, J=8.4, 2.2 Hz, 1H), 5.13-5.01 (m, 1H), 4.44-4.18 (m, 3H), 3.82 (q, J=14.2 Hz, 2H), 2.90 (ddd, J=17.1, 13.6, 5.4 Hz, 1H), 2.70-2.55 (m, 2H), 2.46-2.29 (m, 1H), 2.10-2.03 (m, 1H), 2.03-1.91 (m, 2H), 1.74-1.57 (m, 2H), 1.46-1.17 (m, 4H).

Example 60: 3-(5-(((1S,2S)-2-(((1-ethyl-1H-pyrazol-4-yl)methyl)amino)cyclohexyl)oxy)-1-oxoisoindolin-2-yl)piperidine-2,6-dione HC(O)OH Salt (I-76)

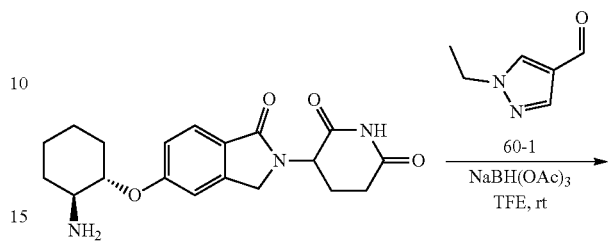

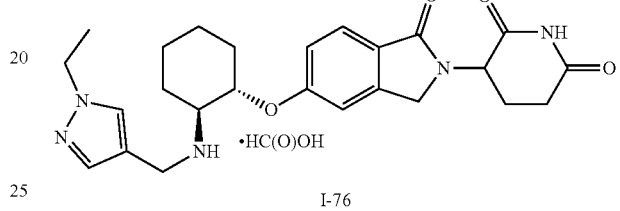

To 3-(5-(((1S,2S)-2-aminocyclohexyl)oxy)-1-oxoisoindolin-2-yl)piperidine-2,6-dione (I-15, 118.3 mg, 0.331 mmol) and 1-ethyl-1H-pyrazole-4-carbaldehyde (60-1, 46.1 mg, 0.371 mmol) in 2,2,2-trifluoroethanol (1.5 mL) was added sodium triacetoxyborohydride (98 mg, 0.46 mmol) in one portion. The resulting mixture was stirred at rt for 1 h and then diluted with ethyl acetate (80 mL) and washed with saturated aqueous sodium bicarbonate solution (10 mL) and brine (10 mL). The organic phase was then dried over magnesium sulfate, filtered, and concentrated. The crude material was purified by reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient) to afford the formate salt of I-76 (54 mg, 0.10 mmol, 32% yield) as a white solid. MS [M+H]$^+$=466.6. $^1$H NMR (400 MHz, DMSO-d$_6$) δ 10.95 (s, 1H), 8.15 (s, 2H), 7.68-7.53 (m, 2H), 7.34 (s, 1H), 7.20 (s, 1H), 7.08 (dd, J=8.5, 2.1 Hz, 1H), 5.07 (dd, J=13.2, 5.1 Hz, 1H), 4.47-4.19 (m, 3H), 4.06 (q, J=7.2 Hz, 2H), 3.80-3.62 (m, 2H), 2.90 (ddd, J=18.2, 13.7, 5.5 Hz, 1H), 2.80 (s, 1H), 2.59 (d, J=17.4 Hz, 1H), 2.41-2.33 (m, 1H), 2.08 (s, 1H), 2.06-1.93 (m, 2H), 1.67 (s, 2H), 1.46-1.17 (m, 7H).

Example 61: 3-(5-(((1S,2S)-2-(((1-isopropyl-1H-pyrazol-4-yl)methyl)amino)cyclohexyl)oxy)-1-oxoisoindolin-2-yl)piperidine-2,6-dione HC(O)OH Salt (I-77)

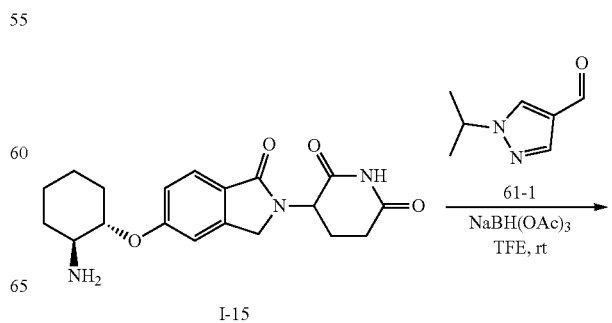

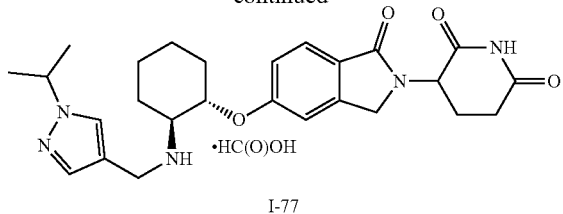

I-77

To 3-(5-(((1S,2S)-2-aminocyclohexyl)oxy)-1-oxoisoindolin-2-yl)piperidine-2,6-dione (I-15, 113.3 mg, 0.317 mmol) and 1-isopropyl-1H-pyrazole-4-carbaldehyde (61-1, 47.2 mg, 0.342 mmol) in 2,2,2-trifluoroethanol (1.5 mL) was added sodium triacetoxyborohydride (85.7 mg, 0.404 mmol) in one portion. The resulting mixture was stirred at rt for 2 h and then concentrated to dryness. The crude material was purified via silica gel chromatography eluting with 5-100% EtOAc:EtOH (v/v=3:1, with 1% Et$_3$N) in DCM (with 1% Et$_3$N) followed by purification via reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient) to afford the formate salt of I-77 (57 mg, 0.104 mmol, 33% yield), as a white solid. MS [M+H]$^+$=480.6. $^1$H NMR (400 MHz, DMSO-d$_6$) δ 10.95 (s, 1H), 8.16 (s, 2H), 7.66-7.54 (m, 2H), 7.32 (d, J=0.9 Hz, 1H), 7.20 (d, J=2.2 Hz, 1H), 7.08 (dd, J=8.4, 2.2 Hz, 1H), 5.07 (dd, J=13.3, 5.1 Hz, 1H), 4.50-4.17 (m, 4H), 3.79-3.60 (m, 2H), 2.90 (ddd, J=17.2, 13.6, 5.4 Hz, 1H), 2.78 (d, J=5.8 Hz, 1H), 2.63-2.57 (m, 1H), 2.42-2.33 (m, 1H), 2.10-2.06 (m, 1H), 2.05-1.94 (m, 2H), 1.67 (s, 2H), 1.43-1.15 (m, 10H).

Example 62: 3-(5-(((1S,2S)-2-(ethyl(methyl)amino)cyclohexyl)oxy)-1-oxoisoindolin-2-yl)piperidine-2,6-dione (I-78)

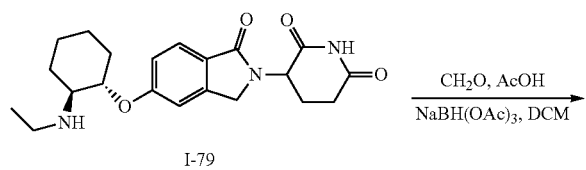

I-79

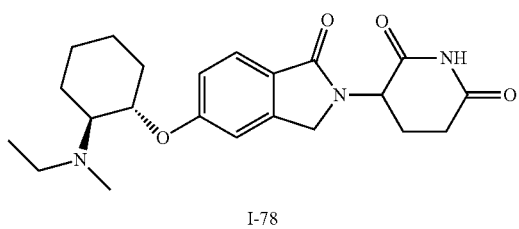

I-78

Paraformaldehyde (6.23 mg, 0.207 mmol) and sodium triacetoxyborohydride (44.5 mg, 0.210 mmol) were added sequentially to a solution of 3-(5-(((1S,2S)-2-(ethylamino)cyclohexyl)oxy)-1-oxoisoindolin-2-yl)piperidine-2,6-dione (I-79, 54 mg, 0.14 mmol) in DCM (1 mL) and the resulting mixture was stirred at rt. Acetic acid (2 μL, 0.03 mmol) was then added followed by an additional portion of sodium triacetoxyborohydride (44.5 mg, 0.210 mmol). The reaction mixture was stirred at rt for 16 h and then saturated NaHCO$_3$ (aq) (2 mL) was added. The mixture was extracted with DCM (×3) and the combined organic phases were concentrated to dryness. The crude material was purified via silica gel chromatography eluting with 0-20% i-PrOH in DCM using 0.1% TEA as a modifier, to afford I-78 (38 mg, 0.090 mmol, 64% yield), as a white solid. MS [M+H]$^+$=400.5. $^1$H NMR (400 MHz, DMSO-d$_6$) δ 10.95 (s, 1H), 7.60 (d, J=8.3 Hz, 1H), 7.17 (s, 1H), 7.03 (d, J=8.4 Hz, 1H), 5.06 (dd, J=13.4, 5.1 Hz, 1H), 4.55-4.44 (m, 1H), 4.38 (dd, J=17.0, 10.1 Hz, 1H), 4.25 (dd, J=17.0, 9.4 Hz, 1H), 2.97-2.85 (m, 1H), 2.74-2.64 (m, 1H), 2.63-2.52 (m, 3H), 2.44-2.34 (m, 1H), 2.19 (s, 3H), 2.15-2.06 (m, 1H), 2.03-1.93 (m, 1H), 1.79-1.58 (m, 3H), 1.43-1.20 (m, 4H), 0.91 (t, J=6.3 Hz, 3H).

Example 63: 3-(5-(((1S,2S)-2-(dimethylamino)cyclohexyl)oxy)-1-oxoisoindolin-2-yl)piperidine-2,6-dione (I-80)

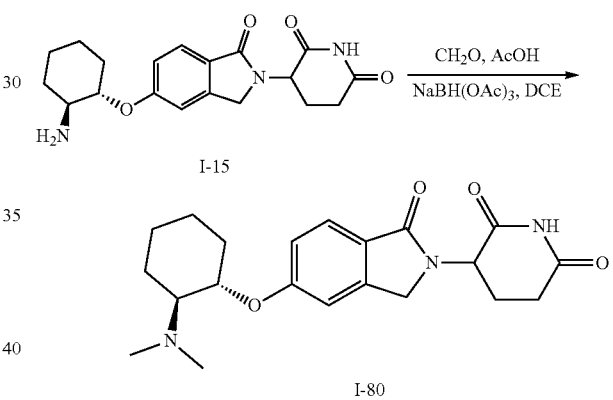

To a solution of 3-(5-(((1S,2S)-2-aminocyclohexyl)oxy)-1-oxoisoindolin-2-yl)piperidine-2,6-dione (I-15, 75 mg, 0.18 mmol) in DCE (1 mL) was added paraformaldehyde (14 mg, 0.47 mmol) followed by sodium triacetoxyborohydride (111 mg, 0.524 mmol) and acetic acid (2 μL, 0.04 mmol) was added and the resulting mixture was stirred at rt for 16 h. The reaction mixture was poured into sat. NaHCO$_3$ (aq) (2 mL) and extracted with DCM (×4). The combined organic layers were dried over Na$_2$SO$_4$, filtered, and concentrated to dryness. The crude material was purified via silica gel chromatography eluting with 0-20% i-PrOH in DCM using 0.1% Et$_3$N as a modifier. The obtained material was further purified via silica gel chromatography eluting with 0-10% EtOAc:EtOH (v/v=3:1, with 1% Et$_3$N) in DCM (with 1% Et$_3$N) to afford I-80 (32 mg, 0.079 mmol, 43% yield) as a yellow solid. MS [M+H]$^+$=386.5. $^1$H NMR (400 MHz, DMSO-d$_6$) 10.95 (s, 1H), 7.61 (d, J=8.4 Hz, 1H), 7.19 (s, 1H), 7.11-6.99 (m, 1H), 5.06 (dd, J=13.3, 5.1 Hz, 1H), 4.55-4.44 (m, 1H), 4.38 (dd, J=17.1, 8.8 Hz, 1H), 4.25 (dd, J=17.1, 8.2 Hz, 1H), 2.97-2.84 (m, 1H), 2.64-2.55 (m, 2H), 2.43-2.35 (m, 1H), 2.27 (s, 6H), 2.14-2.06 (m, 1H), 2.02-1.93 (m, 1H), 1.84-1.74 (m, 1H), 1.74-1.60 (m, 2H), 1.43-1.20 (m, 4H).

Example 64: 3-(5-(((1S,2S)-2-((oxetan-3-ylmethyl)amino)cyclohexyl)oxy)-1-oxoisoindolin-2-yl)piperidine-2,6-dione HC(O)OH Salt (I-81)

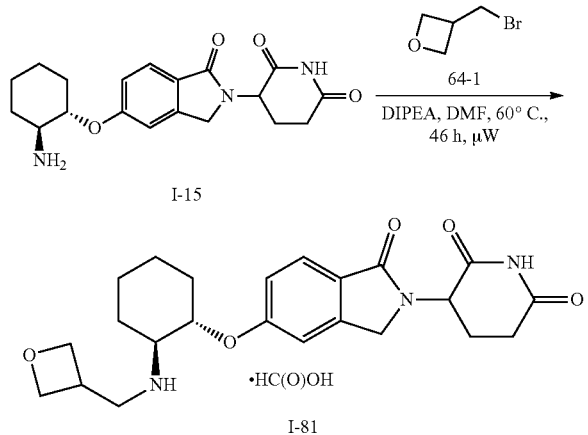

To 3-(5-(((1S,2S)-2-aminocyclohexyl)oxy)-1-oxoisoindolin-2-yl)piperidine-2,6-dione (I-15, 102.7 mg, 0.287 mmol) and 3-(bromomethyl)oxetane (64-1, 55 mg, 0.36 mmol) in DMF (1 mL) was added DIPEA (0.13 mL, 0.72 mmol) and the resulting mixture was stirred at 60° C. for 46 h. The reaction mixture was diluted with ethyl acetate (80 mL) and washed with saturated aqueous sodium bicarbonate solution (15 mL) and brine (15 mL). The organic phase was dried over magnesium sulfate, filtered, and concentrated to dryness. The crude material was purified via silica gel chromatography eluting with 5 to 100% EtOAc:EtOH (v/v=3:1, with 1% Et$_3$N) in DCM (with 1% Et$_3$N) and then further purified via reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) to afford the formate salt of I-81 (32 mg, 0.066 mmol, 23% yield) as a white solid. MS [M+H]$^+$=428.5. $^1$H NMR (400 MHz, DMSO-d$_6$) δ 10.95 (s, 1H), 8.14 (s, 1H), 7.61 (d, J=8.4 Hz, 1H), 7.20 (d, J=2.1 Hz, 1H), 7.08 (dd, J=8.4, 2.2 Hz, 1H), 5.07 (dd, J=13.3, 5.1 Hz, 1H), 4.57 (dd, J=7.4, 5.9 Hz, 2H), 4.38 (dd, J=17.2, 7.4 Hz, 1H), 4.31-4.14 (m, 4H), 3.04-2.82 (m, 4H), 2.77-2.66 (m, 1H), 2.59 (d, J=16.9 Hz, 1H), 2.38 (dd, J=13.2, 4.4 Hz, 1H), 2.10-2.03 (m, 1H), 2.03-1.92 (m, 2H), 1.71-1.62 (s, 2H), 1.40-1.17 (m, 4H).

Example 65: 3-(5-(((1S,2S)-2-((2-hydroxyethyl)amino)cyclohexyl)oxy)-1-oxoisoindolin-2-yl)piperidine-2,6-dione HC(O)OH Salt (I-82)

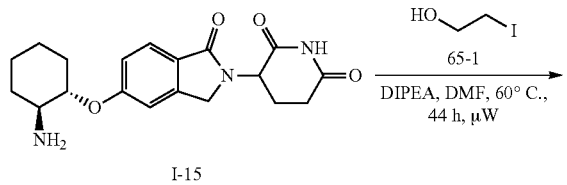

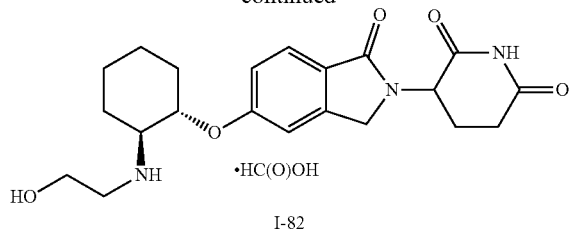

To 3-(5-(((1S,2S)-2-aminocyclohexyl)oxy)-1-oxoisoindolin-2-yl)piperidine-2,6-dione (I-15, 103 mg, 0.287 mmol) and 2-iodoethanol (65-1, 26 µL, 0.33 mmol) in DMF (1 mL) was added DIPEA (125 µL, 0.718 mmol) and the resulting mixture was stirred at 60° C. for 44 h. The reaction mixture was then diluted with ethyl acetate (80 mL) and washed with brine (2×15 mL). The organic phase was dried over magnesium sulfate, filtered, and concentrated to dryness. The crude material was purified via reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) and then further purified by reverse phase HPLC (Column: Xbridge C18 OBD 5 um 30×50 mm; Conditions: Water/MeCN with 10 mM NH$_4$OH 75 mL/min; 1.5 mL injection; Gradient: 10-30% MeCN, 3.5 min gradient: Collection tubes contain ~3 drops of formic acid) to afford the formate salt of I-82 (18 mg, 0.038 mmol, 13% yield) as a white solid. MS [M+H]$^+$=402.5. $^1$H NMR (400 MHz, DMSO-d$_6$) δ 10.96 (s, 1H), 8.17 (s, 2H), 7.61 (d, J=8.4 Hz, 1H), 7.21 (s, 1H), 7.07 (dd, J=8.4, 2.3 Hz, 1H), 5.07 (dd, J=13.3, 5.1 Hz, 1H), 4.38 (dd, J=17.2, 6.8 Hz, 1H), 4.26 (dd, J=17.2, 5.7 Hz, 2H), 3.47 (dt, J=10.5, 5.2 Hz, 2H), 2.90 (ddd, J=18.1, 13.6, 5.4 Hz, 1H), 2.76-2.67 (m, 2H), 2.65-2.57 (m, 1H), 2.38 (dd, J=13.2, 4.4 Hz, 1H), 2.07 (s, 1H), 2.03-1.92 (m, 2H), 1.66 (s, 2H), 1.26 (ddt, J=53.3, 21.2, 11.1 Hz, 4H).

Example 66: 3-(1-oxo-5-(((1S,2S)-2-(pyrrolidin-1-yl)cyclohexyl)oxy)isoindolin-2-yl)piperidine-2,6-dione HC(O)OH Salt (I-83)

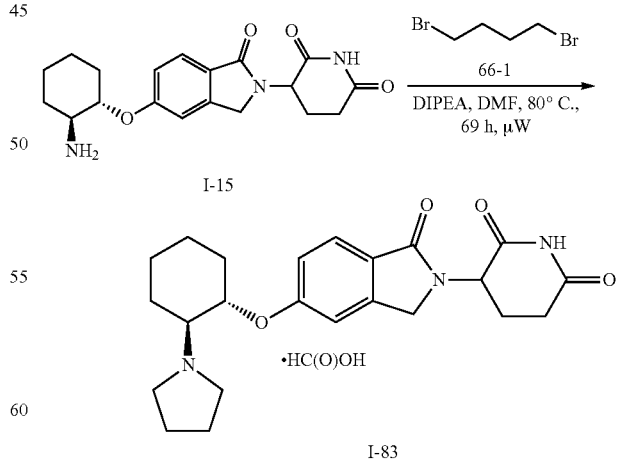

To 3-(5-(((1S,2S)-2-aminocyclohexyl)oxy)-1-oxoisoindolin-2-yl)piperidine-2,6-dione (I-15, 101 mg, 0.282 mmol) in DMF (2 mL) and DIPEA (0.12 mL, 0.69 mmol) was added a solution of 1,4-dibromobutane (66-1, 67.2 mg, 0.311 mmol) in DMF (1 mL) and the resulting mixture was stirred at 80° C. for 69 h. The reaction mixture was then diluted with ethyl acetate (80 mL) and washed with saturated sodium bicarbonate solution (10 mL) and brine (10 mL). The organic phase was then dried over magnesium sulfate, filtered, and concentrated to dryness. The crude material was purified via silica gel chromatography eluting with 0-80% EtOAc:EtOH (v/v=3:1, with 1% Et$_3$N) in DCM (with 1% Et$_3$N) and then further purified via reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) to afford the formate salt of I-83 (23 mg, 0.049 mmol, 18% yield) as a white solid. MS [M+H]$^+$=412.5. $^1$H NMR (400 MHz, DMSO-d$_6$) δ 10.95 (s, 1H), 8.15 (s, 1H), 7.61 (d, J=8.4 Hz, 1H), 7.20 (d, J=2.2 Hz, 1H), 7.07 (dd, J=8.3, 2.2 Hz, 1H), 5.06 (dd, J=13.3, 5.0 Hz, 1H), 4.60 (td, J=6.9, 3.4 Hz, 1H), 4.45-4.18 (m, 2H), 2.90 (ddd, J=18.5, 13.7, 5.4 Hz, 1H), 2.76-2.54 (m, 6H), 2.42-2.33 (m, 1H), 1.98 (td, J=7.2, 6.5, 2.7 Hz, 2H), 1.93-1.84 (m, 1H), 1.74-1.57 (m, 6H), 1.56-1.44 (m, 2H), 1.43-1.26 (m, 2H).

Example 67: 3-(5-(((1S,2S)-2-morpholinocyclohexyl)oxy)-1-oxoisoindolin-2-yl)piperidine-2,6-dione I-84)

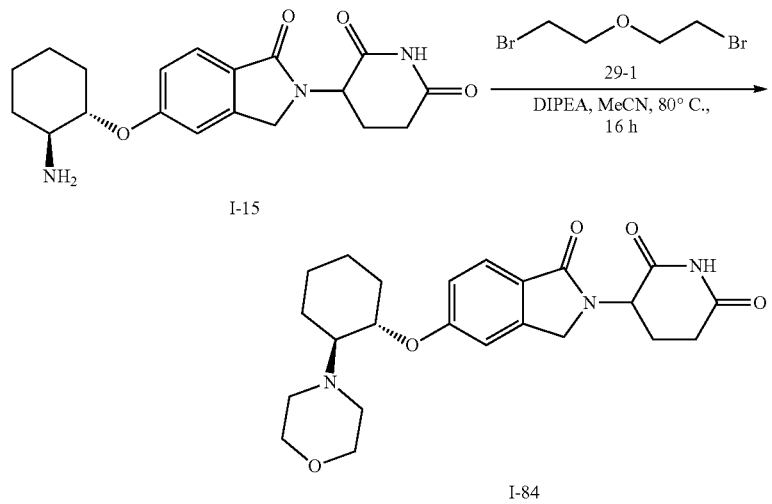

To a solution of 3-(5-(((1S,2S)-2-aminocyclohexyl)oxy)-1-oxoisoindolin-2-yl)piperidine-2,6-dione (I-15, 75 mg, 0.183 mmol) in MeCN (1 mL) was added DIPEA (0.16 mL, 0.91 mmol) followed by 1-bromo-2-(2-bromoethoxy)ethane (29-1, 127 mg, 0.548 mmol) and the resulting mixture was stirred at 80° C. for 16 h. The crude reaction mixture was filtered, diluted with several drops of water, and purified by directly injecting it onto reverse phase preparative HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient). The fractions containing the desired product were combined and lyophilized to afford I-84 (23 mg, 0.046 mmol, 25% yield) as a white solid. MS [M+H]$^+$=428.6. $^1$H NMR (400 MHz, DMSO-d$_6$) δ 10.95 (s, 1H), 7.61 (d, J=8.4 Hz, 1H), 7.20 (s, 1H), 7.06 (dd, J=8.5 Hz, 1H), 5.07 (dd, J=13.4, 4.9 Hz, 1H), 4.55-4.46 (m, 1H), 4.39 (dd, J=17.0, 10.8 Hz, 1H), 4.26 (dd, J=17.1, 11.2 Hz, 1H), 3.46-3.34 (m, 4H), 2.97-2.84 (m, 1H), 2.70-2.54 (m, 4H), 2.43-2.35 (m, 3H), 2.16-2.07 (m, 1H), 2.03-1.93 (m, 1H), 1.82-1.74 (m, 1H), 1.72-1.58 (m, 2H), 1.46-1.20 (m, 4H).

Example 68: 3-(1-oxo-5-(((1S,2S)-2-((pyridin-2-ylmethyl)amino)cyclohexyl)oxy)isoindolin-2-yl)piperidine-2,6-dione HC(O)OH Salt (I-85)

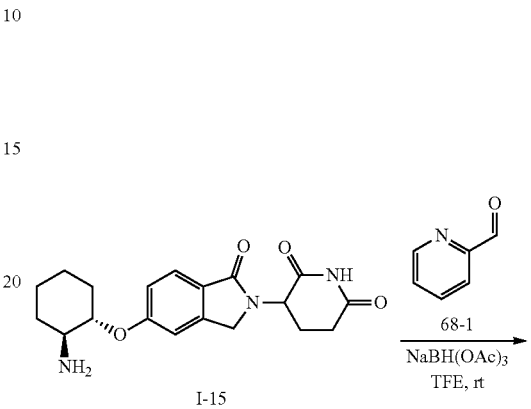

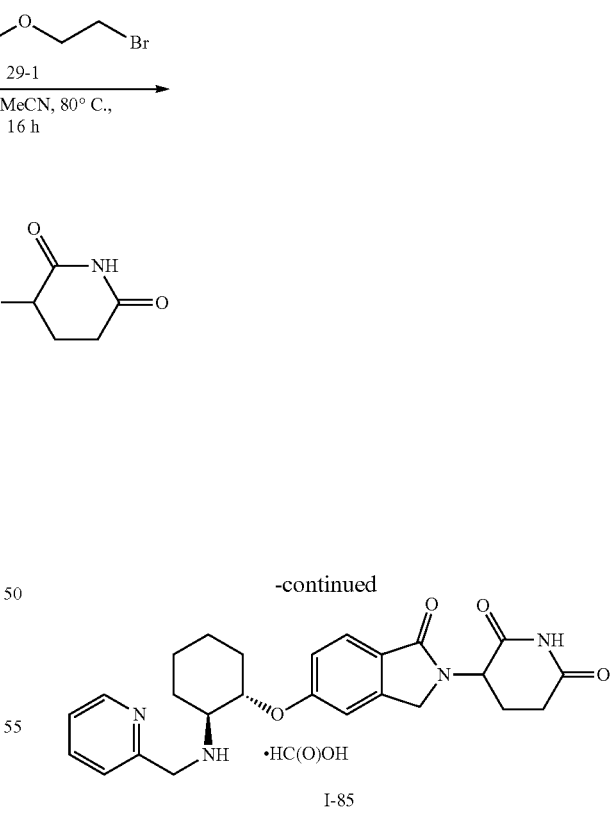

To 3-(5-(((1S,2S)-2-aminocyclohexyl)oxy)-1-oxoisoindolin-2-yl)piperidine-2,6-dione (I-15, 63.5 mg, 0.18 mmol) and picolinaldehyde (68-1, 20 mg, 0.18 mmol) in 2,2,2-trifluoroethanol (1 mL) was added sodium triacetoxyborohydride (53 mg, 0.25 mmol) in one portion and the resulting mixture was stirred at rt for 1 h. The reaction solution was diluted with ethyl acetate (80 mL) and washed with saturated sodium bicarbonate solution (10 mL) and brine (10 mL). The organic phase was then dried over magnesium sulfate, filtered, and concentrated to dryness. The crude material was purified via reverse phase preparative HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient) and then further purified via reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) to afford the formate salt of I-85 (35 mg, 0.070 mmol, 39% yield) as a solid. MS [M+H]$^+$=449.5. $^1$H NMR (400 MHz, DMSO-d$_6$) δ 10.96 (s, 1H), 8.48 (ddd, J=4.9, 1.8, 1.0 Hz, 1H), 8.14 (s, 1H), 7.72 (td, J=7.7, 1.8 Hz, 1H), 7.61 (d, J=8.4 Hz, 1H), 7.40 (d, J=7.8 Hz, 1H), 7.26-7.17 (m, 2H), 7.08 (dd, J=8.6, 2.2 Hz, 1H), 5.07 (dd, J=13.3, 5.1 Hz, 1H), 4.45-4.19 (m, 3H), 4.01-3.79 (m, 2H), 2.91 (ddd, J=18.1, 13.6, 5.5 Hz, 1H), 2.73 (s, 1H), 2.59 (d, J=17.1 Hz, 1H), 2.40 (td, J=13.1, 4.4 Hz, 1H), 2.11-2.07 (m, 1H), 2.04-1.96 (m, 2H), 1.75-1.57 (m, 2H), 1.42-1.20 (m, 4H).

Example 69: 3-(5-(((1S,2S)-2-((3-hydroxy-3-methylbutyl)amino)cyclohexyl)oxy)-1-oxoisoindolin-2-yl)piperidine-2,6-dione (I-86)

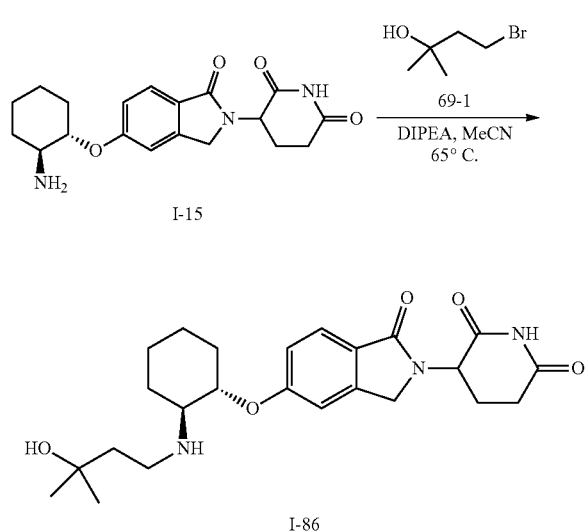

To a solution of 3-(5-(((1S,2S)-2-aminocyclohexyl)oxy)-1-oxoisoindolin-2-yl)piperidine-2,6-dione (I-15, 80 mg, 0.22 mmol) in MeCN (3 mL) was added 4-bromo-2-methylbutan-2-ol (69-1, 37.4 mg, 0.22 mmol) and DIPEA (0.12 mL, 0.67 mmol) and the resulting mixture was stirred at 65° C. for 16 h, at 100° C. for 30 minutes in the µW, at 120° C. for 30 minutes in the µW, and at 140° C. for 2 h and 30 minutes in the µW. The reaction mixture was then added to a saturated solution of sodium hydrogen carbonate (20 mL) and extracted with 20% i-PrOH in DCM (×3). The combined organic phases were passed through a phase separating column and then concentrated to dryness. The crude material was purified via reverse phase chromatography on C-18 column, eluting with 0-100% MeCN in water (with 0.1% Formic acid as a modifier). The fractions containing the desired product were combined and lyophilized to afford I-86 (16 mg, 0.031 mmol, 14% yield), as a white solid. MS [M+H]$^+$=444.6. $^1$H NMR (400 MHz, DMSO-d$_6$) δ (ppm) 10.95 (s, 1H), 7.62 (d, J=8.5 Hz, 1H), 7.21 (s, 1H), 7.08 (d, J=8.5 Hz, 1H), 5.07 (dd, J=13.3, 5.2 Hz, 1H), 4.44-4.20 (m, 3H), 2.96-2.69 (m, 4H), 2.66-2.53 (m, 1H), 2.39 (td, J=13.2, 4.4 Hz, 1H), 2.10 (d, J=10.9 Hz, 1H), 2.06-1.94 (m, 2H), 1.72-1.64 (m, 2H), 1.52 (t, J=7.1 Hz, 2H), 1.42-1.19 (m, 4H), 1.07 (s, 6H).

Example 70: 3-(5-(((1S,2S)-2-(((3-methyloxetan-3-yl)methyl)amino)cyclohexyl)oxy)-1-oxoisoindolin-2-yl)piperidine-2,6-dione HC(O)OH Salt (I-87)

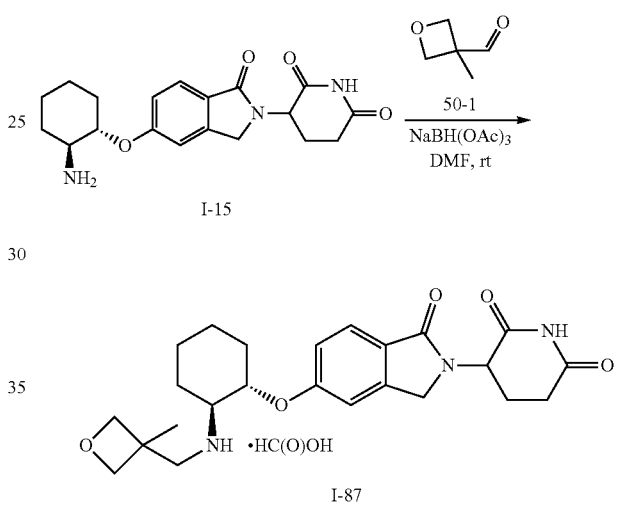

To a solution of 3-(5-(((1S,2S)-2-aminocyclohexyl)oxy)-1-oxoisoindolin-2-yl)piperidine-2,6-dione (I-15, 100 mg, 0.280 mmol) in DMF (1 mL) was added 3-methyloxetane-3-carbaldehyde (50-1, 34 mg, 0.34 mmol) and the resulting mixture was stirred at rt for 10 mins. Sodium triacetoxyborohydride (71 mg, 0.34 mmol) was then added and the reaction mixture was stirred at rt for 1 h, diluted with DCM, and Celite was added. The resulting suspension concentrated to dryness. The crude material was purified by silica gel chromatography eluting with 0-100% EtOAc in heptane followed by 0 to 100% EtOAc/EtOH (v/v=3:1, with 1% NEt$_3$) in DCM and further purified by reverse phase HPLC (Column: Xbridge C18 OBD 5 m 30×50 mm; Conditions: Water/MeCN with 10 mM NH$_4$OH 75 mL/min; 1.5 mL injection; Gradient: 15-40% MeCN, 3.5 min gradient; collection tubes contained ~3 drops of formic acid) to afford the formate salt of I-87 (40 mg, 0.080 mmol, 29% yield) as a white solid. MS [M+H]$^+$=442.3. $^1$H NMR (400 MHz, DMSO-d$_6$) δ 8.24 (s, 2H), 7.60 (d, J=8.4 Hz, 1H), 7.20 (s, 1H), 7.07 (dd, J=8.4, 2.1 Hz, 1H), 5.06 (dd, J=13.3, 5.1 Hz, 1H), 4.37 (dd, J=17.1, 8.6 Hz, 1H), 4.30-4.17 (m, 4H), 4.11 (dd, J=5.4, 2.7 Hz, 2H), 2.96-2.85 (m, 1H), 2.80-2.68 (m, 2H), 2.68-2.53 (m, 2H), 2.35 (dd, J=15.9, 11.3 Hz, 1H), 2.11-2.04 (m, 1H), 2.02-1.92 (m, 2H), 1.71-1.62 (m, 2H), 1.41-1.19 (m, 4H), 1.15 (s, 3H).

Example 71: 3-(5-(((1S,2S)-2-(4-methoxy-4-methylpiperidin-1-yl)cyclohexyl)oxy)-1-oxoisoindolin-2-yl)piperidine-2,6-dione (I-88)

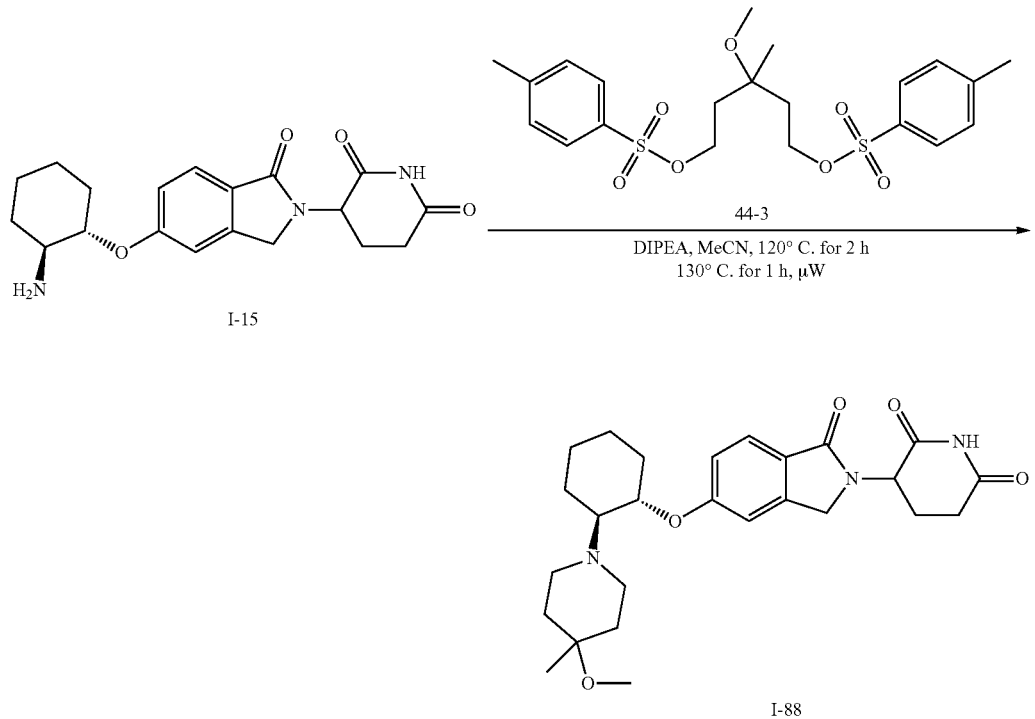

To a solution of 3-(5-(((1S,2S)-2-aminocyclohexyl)oxy)-1-oxoisoindolin-2-yl)piperidine-2,6-dione (I-15, 29.7 mg, 0.083 mmol) in MeCN (1 mL) was added DIPEA (0.09 mL, 0.5 mmol) followed by 3-methoxy-3-methylpentane-1,5-diyl bis(4-methylbenzenesulfonate) (44-3, 38 mg, 0.083 mmol) and the resulting mixture was stirred at 120° C. under μW irradiation for 2 h, then at 130° C. for 1 h in the μW. The reaction mixture was concentrated to dryness and the crude material was dissolved in DCM and washed with saturated NaHCO$_3$ (aq). The phases were separated and the aqueous phase was extracted with DCM. The combined organic phases were dried over Na$_2$SO$_4$, filtered, and concentrated to dryness. The crude material was purified via silica gel chromatography eluting with 0-100% EtOAc:EtOH (v/v=3:1, with 0.1% NEt$_3$) in DCM (with 0.1% NEt$_3$) to afford I-88 (15 mg, 0.029 mmol, 35% yield) as a white solid. MS [M+H]$^+$=470.6. $^1$H NMR (400 MHz, DMSO-d$_6$) δ 10.95 (s, 1H), 7.59 (d, J=8.4 Hz, 1H), 7.18 (s, 1H), 7.04 (d, J=8.4 Hz, 1H), 5.07 (dd, J=13.3, 5.2 Hz, 1H), 4.52-4.42 (m, 1H), 4.37 (dd, J=17.2, 3.7 Hz, 1H), 4.25 (dd, J=17.1, 3.8 Hz, 1H), 3.33-3.31 (m, 2H, shoulder on H$_2$O signal), 2.97-2.93 (m, 3H), 2.93-2.85 (m, 1H), 2.63-2.55 (m, 3H), 2.45-2.35 (m, 2H), 2.15-2.08 (m, 1H), 2.03-1.94 (m, 1H), 1.79-1.58 (m, 3H), 1.53-1.42 (m, 2H), 1.40-1.04 (m, 6H), 0.92 (s, 3H)

Example 72: 3-(5-(((1S,2S)-2-(3-methoxyazetidin-1-yl)cyclohexyl)oxy)-1-oxoisoindolin-2-yl)piperidine-2,6-dione (I-89)

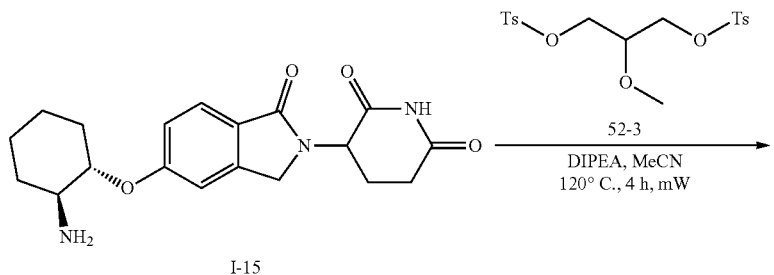

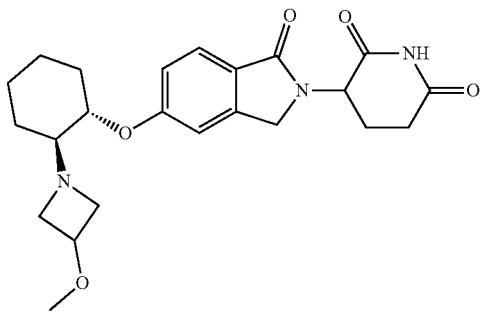

I-89

To a solution of 3-(5-(((1S,2S)-2-aminocyclohexyl)oxy)-1-oxoisoindolin-2-yl)piperidine-2,6-dione (I-15, 50 mg, 0.14 mmol) in MeCN (1.5 mL) was added DIPEA (0.15 mL, 0.84 mmol), followed by 2-methoxypropane-1,3-diyl bis(4-methylbenzenesulfonate) (52-3, 174 mg, 0.42 mmol) and the resulting mixture was stirred at 120° C. under μW irradiation for 4 h. The reaction mixture was concentrated to dryness, the obtained residue dissolved in DCM and washed with saturated NaHCO₃(aq). The phases were separated and the aqueous phase was extracted with DCM. The combined organic layers were dried over Na₂SO₄, filtered and concentrated. The crude material was purified via silica gel chromatography eluting with 0-100% EtOAc:EtOH (v/v=3:1, with 0.1% NEt₃) in DCM (with 0.1% NEt₃) to afford I-89 (32 mg, 0.067 mmol, 48% yield) as a white solid. MS [M+H]⁺=428.4. ¹H NMR (400 MHz, DMSO-d₆) δ 10.95 (s, 1H), 7.61 (d, J=8.4 Hz, 1H), 7.16 (d, J=2.0 Hz, 1H), 7.02 (dd, J=8.4, 2.2 Hz, 1H), 5.06 (dd, J=13.3, 5.1 Hz, 1H), 4.43-4.33 (m, 1H), 4.30-4.19 (m, 2H), 3.90-3.76 (m, 1H), 3.50-3.40 (m, 2H), 3.11 (s, 3H), 3.02-2.79 (m, 3H), 2.63-2.55 (m, 1H), 2.43-2.27 (m, 2H), 1.98 (d, J=10.3 Hz, 2H), 1.83-1.73 (m, 1H), 1.69-1.58 (m, 2H), 1.35 (t, J=8.8 Hz, 2H), 1.31-1.21 (m, 1H), 1.13-1.03 (m, 1H).

Example 73: 3-(5-(((1S,2S)-2-(((6-methylpyridin-2-yl)methyl)amino)cyclohexyl)oxy)-1-oxoisoindolin-2-yl)piperidine-2,6-dione HC(O)OH Salt (I-90)

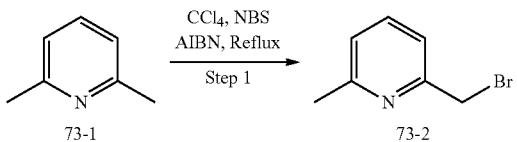

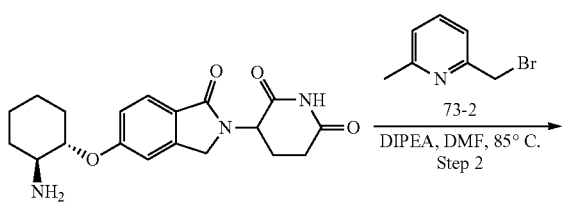

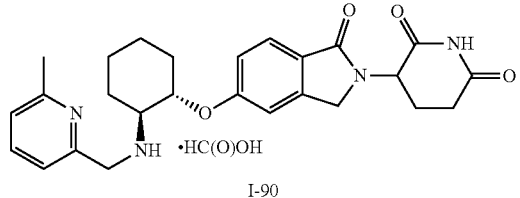

I-90

Step 1. 2-(bromomethyl)-6-methylpyridine (73-2)

To 2,6-lutidine (73-1, 23 mL, 0.20 mol) in carbon tetrachloride (250 mL) was added NBS (35.6 g, 0.20 mol) and AIBN (0.5 g) to give a yellow suspension. The resulting suspension was stirred at reflux for 8 h to give a solution and then cooled to rt. The resultant suspension was filtered and the obtained solid was rinsed with carbon tetrachloride. The filtrate was collected and concentrated to dryness to afford 73-2 (33.7 g, 0.18 mol, 91% yield) as a violet colored oil which was carried onto the next step without purification. MS [M+H]⁺=185.6.

Step 2. 3-(5-(((1S,2S)-2-(((6-methylpyridin-2-yl)methyl)amino)cyclohexyl)oxy)-1-oxoisoindolin-2-yl)piperidine-2,6-dione HC(O)OH Salt (I-90)

To 3-(5-(((1S,2S)-2-aminocyclohexyl)oxy)-1-oxoisoindolin-2-yl)piperidine-2,6-dione (I-15, 88.7 mg, 0.25 mmol) and 2-(bromomethyl)-6-methylpyridine (73-2, 50 mg, 0.269 mmol) in DMF (1 mL) was added DIPEA (0.12 mL, 0.69 mmol). The reaction mixture was stirred at 85° C. for 3 days. The reaction mixture was concentrated to dryness. The crude material was purified by silica gel chromatography eluting with 0-100% EtOAc:EtOH (v/v=3:1, with 0.1% NEt₃) in DCM (with 0.1% NEt₃). The obtained material was further purified via reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient) to afford the formate salt of I-90 (4.0 mg, 7.47 μmol, 3% yield) as a yellow solid. MS [M+H]⁺=463.5. ¹H NMR (400 MHz, DMSO-d₆) δ 10.95 (s, 1H), 8.17 (s, 2H), 7.65-7.55 (m, 2H), 7.23-7.16 (m, 2H), 7.11-7.04 (m, 2H), 5.06 (dd, J=13.3, 5.1 Hz, 1H), 4.47-4.18 (m, 3H), 3.90-3.74 (m, 2H), 2.90 (ddd, J=17.8, 13.5, 5.4 Hz, 1H), 2.72-2.64 (m, 1H), 2.59 (d, J=17.1 Hz, 1H), 2.45-2.34 (m, 4H), 2.11-2.04 (m, 1H), 2.03-1.91 (m, 2H), 1.72-1.61 (m, 2H), 1.45-1.15 (m, 4H).

Example 74: 3-(5-(((1S,2S)-2-(((5-methoxypyridin-2-yl)methyl)amino)cyclohexyl)oxy)-1-oxoisoindolin-2-yl)piperidine-2,6-dione (I-91)

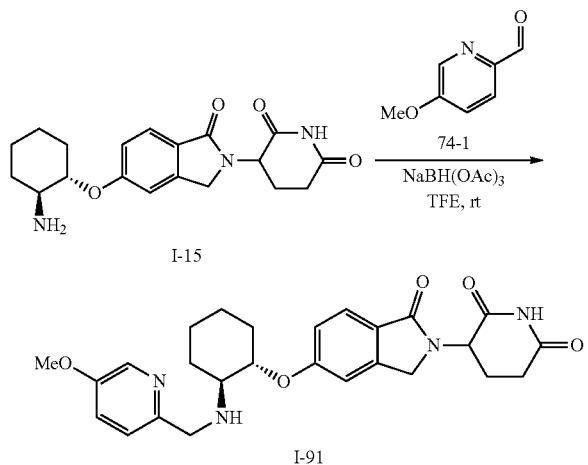

To 3-(5-(((1S,2S)-2-aminocyclohexyl)oxy)-1-oxoisoindolin-2-yl)piperidine-2,6-dione (I-15, 106 mg, 0.30 mmol) and 2-formyl-5-methoxypyridine (74-1, 43 mg, 0.32 mmol) in 2,2,2-trifluoroethanol (1.5 mL) was added sodium triacetoxyborohydride (88 mg, 0.42 mmol) in one portion and the resulting mixture was stirred at room temperature for 90 min and then concentrated to dryness. The crude material was purified via reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient) and then further purified by silica gel chromatography eluting with 0-100% EtOAc:EtOH (v/v=3:1, with 0.1% NEt$_3$) in DCM (with 0.1% NEt$_3$) to afford I-91 (54.5 mg, 0.112 mmol, 38% yield) as a white solid. MS [M+H]$^+$=479.5. $^1$H NMR (400 MHz, DMSO-d$_6$) δ 10.96 (s, 1H), 8.19 (t, J=1.8 Hz, 1H), 7.61 (d, J=8.4 Hz, 1H), 7.33 (d, J=1.8 Hz, 2H), 7.19 (s, 1H), 7.07 (dt, J=8.4, 2.0 Hz, 1H), 5.07 (dd, J=13.3, 5.1 Hz, 1H), 4.48-4.16 (m, 3H), 3.92-3.83 (m, 1H), 3.83-3.75 (m, 4H), 2.91 (ddd, J=17.2, 13.6, 5.4 Hz, 1H), 2.79-2.65 (m, 1H), 2.59 (d, J=17.4 Hz, 1H), 2.45-2.28 (m, 1H), 2.11-1.95 (m, 3H), 1.74-1.59 (m, 2H), 1.45-1.21 (m, 4H).

Example 75: 3-(5-(((1S,2S)-2-(((6-methoxypyridin-3-yl)methyl)amino)cyclohexyl)oxy)-1-oxoisoindolin-2-yl)piperidine-2,6-dione HC(O)OH Salt (I-92)

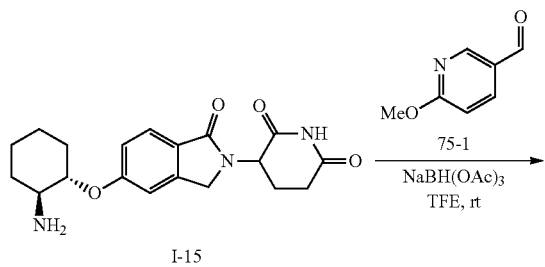

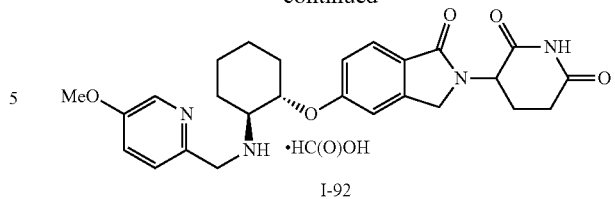

To 3-(5-(((1S,2S)-2-aminocyclohexyl)oxy)-1-oxoisoindolin-2-yl)piperidine-2,6-dione (I-15, 75 mg, 0.210 mmol) and 6-methoxy-3-pyridinecarboxaldehyde (75-1, 30.5 mg, 0.222 mmol) in 2,2,2-trifluoroethanol (1 mL) was added sodium triacetoxyborohydride (58 mg, 0.27 mmol) in one portion and the resulting mixture was stirred at rt for 2 h and then concentrated to dryness. The crude material was purified via reverse phase HPLC (Column: X-bridge C18 OBD 5 m 30×50 mm; Conditions: Water/MeCN with 0.1% Formic Acid 75 mL/min; 1.5 mL injection; Gradient: 10-30% MeCN, 3.5 min gradient) to afford a formate salt of I-92 (34 mg, 0.063 mmol, 30% yield) as a white solid. MS [M+H]$^+$=479.5. $^1$H NMR (400 MHz, DMSO-d$_6$) δ 10.96 (s, 1H), 8.14 (s, 1H), 8.10-8.04 (m, 1H), 7.68-7.58 (m, 2H), 7.18 (s, 1H), 7.06 (dd, J=8.4, 2.2 Hz, 1H), 6.76 (dd, J=8.4, 0.7 Hz, 1H), 5.07 (dd, J=13.1, 5.1 Hz, 1H), 4.49-4.17 (m, 3H), 3.83-3.69 (m, 2H), 3.81 (s, 3H), 2.91 (ddd, J=18.2, 13.7, 5.5 Hz, 1H), 2.64-2.55 (m, 1H), 2.46-2.28 (m, 2H), 2.09-2.03 (m, 1H), 1.98 (t, J=5.1 Hz, 2H), 1.65 (d, J=9.9 Hz, 2H), 1.29 (dt, J=37.1, 9.2 Hz, 4H).

Example 76: 3-(5-(((1S,2S)-2-((2-hydroxy-2-methylpropyl)amino)cyclohexyl)oxy)-1-oxoisoindolin-2-yl)piperidine-2,6-dione HC(O)OH Salt (I-93)

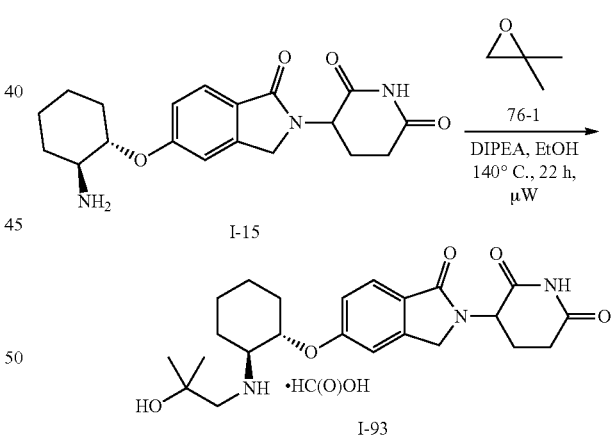

2,2-dimethyloxirane (76-1, 0.015 mL, 0.17 mmol) and DIPEA (0.04 mL, 0.2 mmol) were added to a solution of 3-(5-(((1S,2S)-2-aminocyclohexyl)oxy)-1-oxoisoindolin-2-yl)piperidine-2,6-dione (I-15, 50 mg, 0.14 mmol) in EtOH (1.5 mL) and the resulting solution was stirred at 140° C. under μW irradiation for 1 h. Additional 2,2-dimethyloxirane (50 μL) was added and stirring was continued in the μW at 140° C. for 21 h. The reaction mixture was filtered and concentrated. The crude material was purified via reverse phase HPLC (Column: Xbridge C18 OBD 5 um 30×50 mm; Conditions: Water/MeCN with 10 mM NH$_4$OH 75 mL/min; 1.5 mL injection; Gradient: 15-40% MeCN, 3.5 min gradient; collection tubes contained several drops of formic acid)

to afford the formate salt of I-93 (12 mg, 0.023 mmol, 17% yield) as a white solid. MS [M+H]$^+$=430.5. $^1$H NMR (400 MHz, DMSO-d$_6$) δ 10.94 (br s, 1H), 8.22 (s, 1H), 7.61 (d, J=8.4 Hz, 1H), 7.21 (s, 1H), 7.06 (dd, J=8.4, 2.2 Hz, 1H), 5.06 (dd, J=13.3, 5.0 Hz, 1H), 4.38 (dd, J=17.2, 8.7 Hz, 1H), 4.30-4.19 (m, 3H), 2.96-2.84 (m, 1H), 2.66-2.54 (m, 1H), 2.47-2.35 (m, 3H), 2.12-2.03 (m, 1H), 2.03-1.91 (m, 2H), 1.73-1.60 (m, 2H), 1.42-1.12 (m, 4H), 1.03 (d, J=5.4 Hz, 6H).

Example 77: (1S,3r)-3-(((((1S,2S)-2-((2-(2,6-dioxopiperidin-3-yl)-1-oxoisoindolin-5-yl)oxy)cyclohexyl)amino)methyl)-1-methylcyclobutane-1-carbonitrile and (1R,3s)-3-(((((1S,2S)-2-((2-(2,6-dioxopiperidin-3-yl)-1-oxoisoindolin-5-yl)oxy)cyclohexyl)amino)methyl)-1-methylcyclobutane-1-carbonitrile (I-94 & I-95)

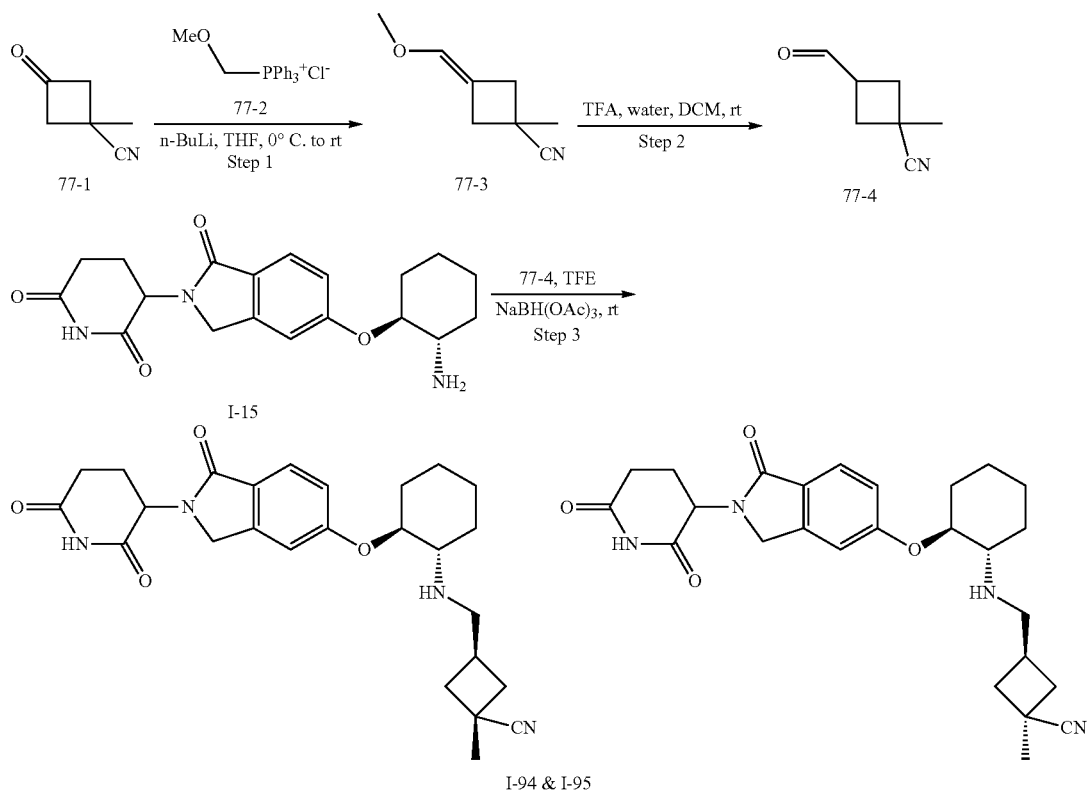

Step 1. 3-(Methoxymethylene)-1-methylcyclobutane-1-carbonitrile (77-3)

To a stirred suspension of (methoxymethyl)triphenylphosphonium chloride (77-2, 1828 mg, 5.33 mmol) in THF (30 mL) at 0° C. under an atmosphere of nitrogen was added n-BuLi (2.3 mL, 6.1 mmol, 2.7 M solution in heptane) and the resulting deep-red solution was stirred at 0° C. for 40 minutes. A solution of 1-methyl-3-oxocyclobutane-1-carbonitrile (77-1, 582 mg, 5.33 mmol) in THF (4 mL) was then added and the reaction mixture was stirred overnight, allowing the reaction to slowly warm to rt. The mixture was concentrated to dryness and the crude material purified via silica gel chromatography eluting with 0-100% EtOAc in diethyl ether to afford 77-3 (459 mg, 3.35 mmol, 63% yield) as a pale orange brown colored oil. $^1$H NMR (400 MHz, DMSO-d$_6$) δ 6.10-5.94 (m, 1H), 3.51 (s, 3H), 3.19-2.97 (m, 2H), 2.81-2.57 (m, 2H), 1.47 (s, 3H).

Step 2. 3-Formyl-1-methylcyclobutane-1-carbonitrile (77-4)

To 3-(methoxymethylene)-1-methylcyclobutane-1-carbonitrile (77-3, 118 mg, 0.860 mmol) in DCM (2 mL) at rt was added trifluoroacetic acid (0.70 mL, 9.1 mmol) and water (100 μL, 5.6 mmol) and the resulting mixture was stirred at rt for 40 min and then saturated sodium bicarbonate. The aqueous mixture was extracted with DCM, the phases separated and the organic phase passed through a phase separating column. The organic solvent was evaporated to dryness to afford 77-4 as an oil, which was carried onto the next step without purification. $^1$H NMR (400 MHz, DMSO-d$_6$) δ 9.66 (dd, J=10.5, 1.3 Hz, 1H), 3.45-3.30 (m, 1H), 2.75-2.56 (m, 2H), 2.39-2.11 (m, 2H), 1.53 (s, 3H).

Step 3. 3-(((((1S,2S)-2-((2-(2,6-dioxopiperidin-3-yl)-1-oxoisoindolin-5-yl)oxy)cyclohexyl)amino)methyl)-1-methylcyclobutane-1-carbonitrile (I-94)

To 3-(5-(((1S,2S)-2-aminocyclohexyl)oxy)-1-oxoisoindolin-2-yl)piperidine-2,6-dione (I-15, 300 mg, 0.336 mmol) in TFE (1 mL) was added a solution of 3-formyl-1-methylcyclobutane-1-carbonitrile (77-4, 108 mg, 0.873 mmol) in TFE (1 mL). The resulting mixture was stirred at rt for 5 minutes and then sodium triacetoxyborohydride (213 mg, 1.00 mmol) was added. The reaction mixture was stirred at rt for 3 days and then concentrated to dryness. The crude material purified via silica gel chromatography eluting with 0-100% EtOAc:EtOH (v/v=3:1, with 0.1% Et$_3$N as a modifier) in DCM to afford a mixture of I-94 and I-95 (40 mg, 0.082 mmol) as 66:34 mixture of diastereoisomers. MS [M+H]$^+$=465.2.

The diastereomeric mixture of I-94 and I-95 (30 mg) was separated using chiral SFC (Column: Chiralpak IH 21×250 mm; Flow rate: 80 g per minute; Cosolvent: 30% IPA with 10 mM NH$_3$) to isolate the two diastereomers. Peak 1: diastereomer 1 (I-94, 13 mg, 0.026 mmol, 8% yield). Chiral SFC Rt=2.39 mins. MS [M+H]$^+$=465.5. $^1$H NMR (400 MHz, DCM-d$_2$) δ 7.71 (d, J=8.9 Hz, 1H), 7.11-6.89 (m, 2H), 5.11 (dd, J=13.4, 5.1 Hz, 1H), 4.40-4.23 (m, 2H), 4.21-4.05 (m, 1H), 2.85-2.77 (m, 2H), 2.74-2.47 (m, 4H), 2.32 (qd, J=12.8, 6.0 Hz, 1H), 2.25-2.17 (m, 2H), 2.17-2.04 (m, 4H), 1.79-1.71 (m, 2H), 1.49 (s, 2H), 1.40 (s, 1H), 1.38-1.22 (m, 5H), 1.20 (s, 1H). Peak 2: diastereomer 2 (I-95, 14 mg, 0.028 mmol, 8% yield). Chiral SFC Rt=2.70 mins. MS [M+H]$^+$=465.3. $^1$H NMR (400 MHz, DCM-d$_2$) δ 7.70 (d, J=8.3 Hz, 1H), 7.17-6.92 (m, 2H), 5.11 (dd, J=13.5, 5.2 Hz, 1H), 4.34-4.24 (m, 2H), 4.24-4.16 (m, 1H), 2.88-2.65 (m, 5H), 2.62-2.52 (m, 1H), 2.41-2.03 (m, 7H), 1.80-1.71 (m, 2H), 1.49 (s, 2H), 1.40 (s, 1H), 1.37-1.24 (m, 5H), 1.21 (s, 1H). The relative stereochemistry of the cyclobutane substituents was not determined and was arbitrarily assigned.

Example 78: 3-(5-(((1S,2S)-2-(4-hydroxypiperidin-1-yl)cyclopentyl)oxy)-1-oxoisoindolin-2-yl)piperidine-2,6-dione HC(O)OH Salt (I-96)

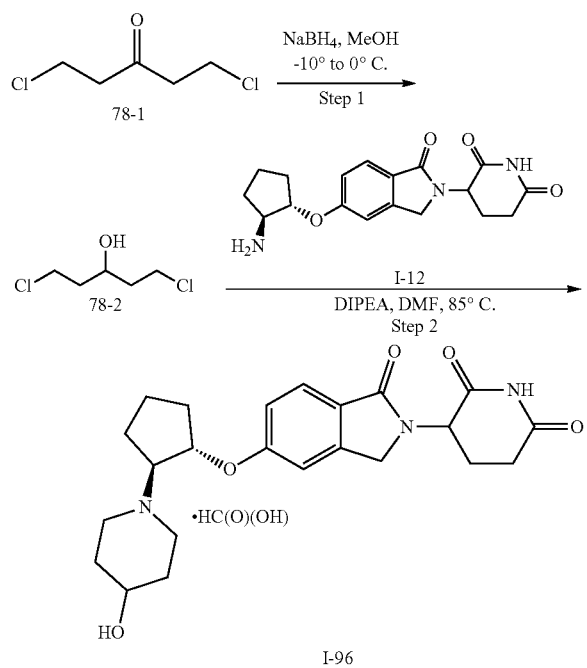

Step 1. 1,5-dichloropentan-3-ol (78-2)

To a solution of 1,5-dichloropentan-3-one (78-1, 260 mg, 1.68 mmol) in MeOH (2 mL) and cooled to −10° C. was added sodium borohydride (64 mg, 1.7 mmol) and the resulting mixture was stirred in an ice bath for 4 h. The reaction mixture was then poured into ice water and extracted with DCM (×3). The combined organic phases were washed with brine, passed through a phase separator, and concentrated to dryness to afford 78-2 (267 mg, 1.55 mmol, 92% yield) as a pale yellow oil. The product was carried onto the next step without purification. $^1$H NMR (400 MHz, Chloroform-d) δ 4.14 (quint, J=6.2 Hz, 1H), 3.77-3.63 (m, 4H), 1.97-1.87 (m, 4H).

Step 2. 3-(5-(((1S,2S)-2-(4-hydroxypiperidin-1-yl)cyclopentyl)oxy)-1-oxoisoindolin-2-yl)piperidine-2,6-dione HC(O)OH Salt (I-96)

To 3-(5-(((1S,2S)-2-aminocyclopentyl)oxy)-1-oxoisoindolin-2-yl)piperidine-2,6-dione (I-12, 52 mg, 0.11 mmol) dissolved in DMF (1 mL) was added DIPEA (0.10 mL, 0.57 mmol), followed by a solution of 1,5-dichloropentan-3-ol (78-2, 19 mg, 0.11 mmol) in DMF (1 mL) and the resulting mixture was stirred at 85° C. overnight. The reaction mixture was cooled to rt and additional 1,5-dichloropentan-3-ol (78-2, 19 mg, 0.11 mmol) was added and stirring was continued at 85° C. overnight. The reaction mixture was cooled to rt, azeotroped with toluene (×2), and concentrated. The crude material was purified by reverse phase HPLC (Method Column: Xbridge C18 OBD 5 um 30×50 mm; Conditions: Water/MeCN with 10 mM NH$_4$OH 75 mL/min; 1.5 mL injection; Gradient: 15-40% MeCN, 3.5 min gradient; fractions collected into tubes containing several drops of formic acid) to afford the formate salt of I-96 (9 mg, 0.018 mmol) as a pale brown solid. MS [M+H]$^+$=428.5. $^1$H NMR (400 MHz, DMSO-d$_6$) δ 10.95 (s, 1H), 8.15 (s, 1H), 7.60 (d, J=8.4 Hz, 1H), 7.18 (d, J=2.1 Hz, 1H), 7.07-6.98 (m, 1H), 5.07 (dd, J=13.0, 4.9 Hz, 1H), 4.73-4.67 (m, 1H), 4.53-4.47 (m, 1H), 4.38 (dd, J=17.2, 9.8 Hz, 1H), 4.25 (dd, J=17.2, 8.3 Hz, 1H), 3.46-3.38 (m, 1H), 2.96-2.81 (m, 2H), 2.81-2.69 (m, 2H), 2.64-2.56 (m, 1H), 2.40-2.34 (m, 1H), 2.17-2.10 (m, 2H), 2.04-1.84 (m, 3H), 1.75-1.56 (m, 5H), 1.53-1.42 (m, 1H), 1.41-1.29 (m, 2H).

Example 79: 3-(1-oxo-5-(((1S,2S)-2-(piperidin-1-yl)cyclohexyl)oxy)isoindolin-2-yl)piperidine-2,6-dione (I-97)

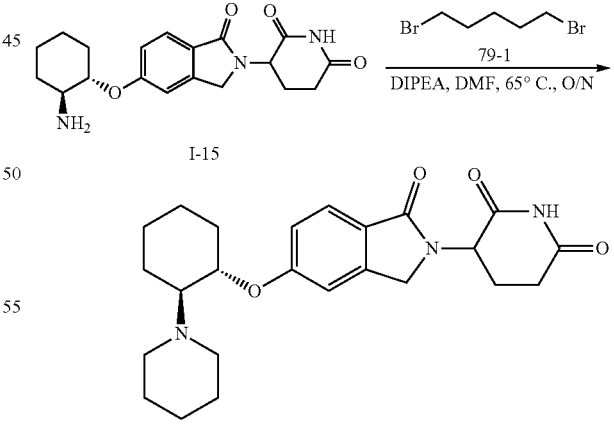

To a solution of 3-(5-(((1S,2S)-2-aminocyclohexyl)oxy)-1-oxoisoindolin-2-yl)piperidine-2,6-dione (I-15, 80 mg, 0.22 mmol) in DMF (3 mL) was added DIPEA (0.098 mL, 0.56 mmol) and 1,5-dibromopentane (79-1, 0.03 mL, 0.2 mmol) and the resulting mixture was stirred at 65° C. overnight. The reaction mixture was then cooled to rt and a saturated aqueous solution of sodium hydrogen carbonate (20 mL) was added. The aqueous mixture was extracted with 20% i-PrOH in DCM (×3). The combined organic phases were washed with water and brine, passed through a phase separating column, and concentrated to dryness. The crude material was purified via silica gel chromatography eluting with 0-100% 3:1 EtOAc:EtOH (v/v=3:1, with 0.1% NEt$_3$) in DCM (with 0.1% NEt$_3$) to afford I-97 (25 mg, 0.056 mmol, 25% yield) as a white solid. MS [M+H]$^+$=426.4. $^1$H NMR (400 MHz, DMSO-d$_6$) δ 10.95 (s, 1H), 7.60 (d, J=8.4 Hz, 1H), 7.18 (s, 1H), 7.04 (d, J=8.3 Hz, 1H), 5.06 (dd, J=13.3, 5.1 Hz, 1H), 4.47 (br s, 1H), 4.42-4.18 (m, 2H), 2.90 (ddd, J=17.8, 13.2, 5.3 Hz, 1H), 2.69-2.44 (m, 6H), 2.39 (td, J=13.2, 4.5 Hz, 1H), 2.11 (s, 1H), 2.03-1.91 (m, 1H), 1.81-1.56 (m, 3H), 1.47-1.12 (m, 10H).

Example 80: 3-(1-oxo-5-((((1S,2S)-2-(((tetrahydro-2H-pyran-4-yl)methyl)amino)cyclohexyl)oxy)isoindolin-2-yl)piperidine-2,6-dione (I-98)

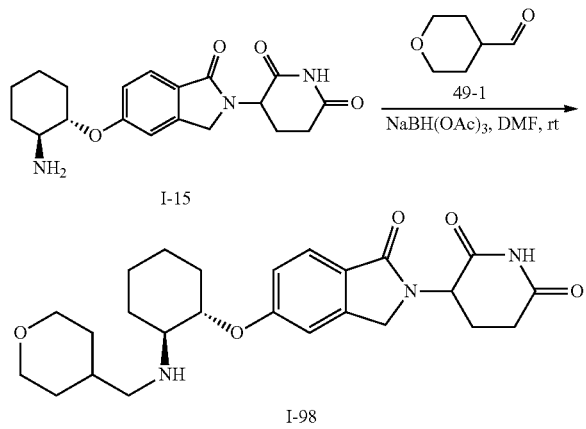

To a solution of 3-(5-(((1S,2S)-2-aminocyclohexyl)oxy)-1-oxoisoindolin-2-yl)piperidine-2,6-dione (I-15, 0.15 g, 0.17 mmol) in DMF (1 mL), was added tetrahydro-2H-pyran-4-carbaldehyde (49-1, 0.021 mL, 0.21 mmol) and the resulting mixture was stirred at rt for 15 minutes. Sodium triacetoxyborohydride (55 mg, 0.26 mmol) was added and stirring was continued at rt for 16 h. Additional tetrahydro-2H-pyran-4-carbaldehyde (49-1, 0.01 mL, 0.1 mmol) was added and the resulting mixture was stirred at rt for 15 minutes. Additional sodium triacetoxyborohydride (36 mg, 0.17 mmol) was added with stirring at rt for 1.5 h. The reaction mixture was diluted with dichloromethane and concentrated onto Celite®. The obtained material was purified by silica gel chromatography eluting with 0-100% EtOAc:EtOH (v/v=3:1, with 1% NEt$_3$) in heptane to afford I-98 (72.8 mg, 0.160 mmol, 93% yield) as a white solid. LCMS [M+H]$^+$=456.3. $^1$H NMR (400 MHz, DMSO-d$_6$) δ 10.96 (s, 1H), 7.61 (d, J=8.4 Hz, 1H), 7.20 (t, J=2.5 Hz, 1H), 7.06 (dt, J=8.5, 2.0 Hz, 1H), 5.07 (dd, J=13.3, 5.1 Hz, 1H), 4.38 (dd, J=17.2, 8.2 Hz, 1H), 4.32-4.15 (m, 2H), 3.86-3.68 (m, 2H), 3.29-3.18 (m, 2H), 2.91 (ddd, J=17.5, 13.6, 5.4 Hz, 1H), 2.69-2.55 (m, 2H), 2.48-2.31 (m, 3H), 2.12-2.02 (m, 1H), 2.02-1.92 (m, 2H), 1.69-1.48 (m, 5H), 1.38-0.99 (m, 6H).

Example 81: 3-(5-(((1S,2S)-2-((((1R,3S)-3-methoxycyclobutyl)methyl)amino)cyclohexyl)oxy)-1-oxoisoindolin-2-yl)piperidine-2,6-dione and 3-(5-(((1S,2S)-2-((((1R,3R)-3-methoxycyclobutyl)methyl)amino)cyclohexyl)oxy)-1-oxoisoindolin-2-yl)piperidine-2,6-dione (I-99 & I-100)

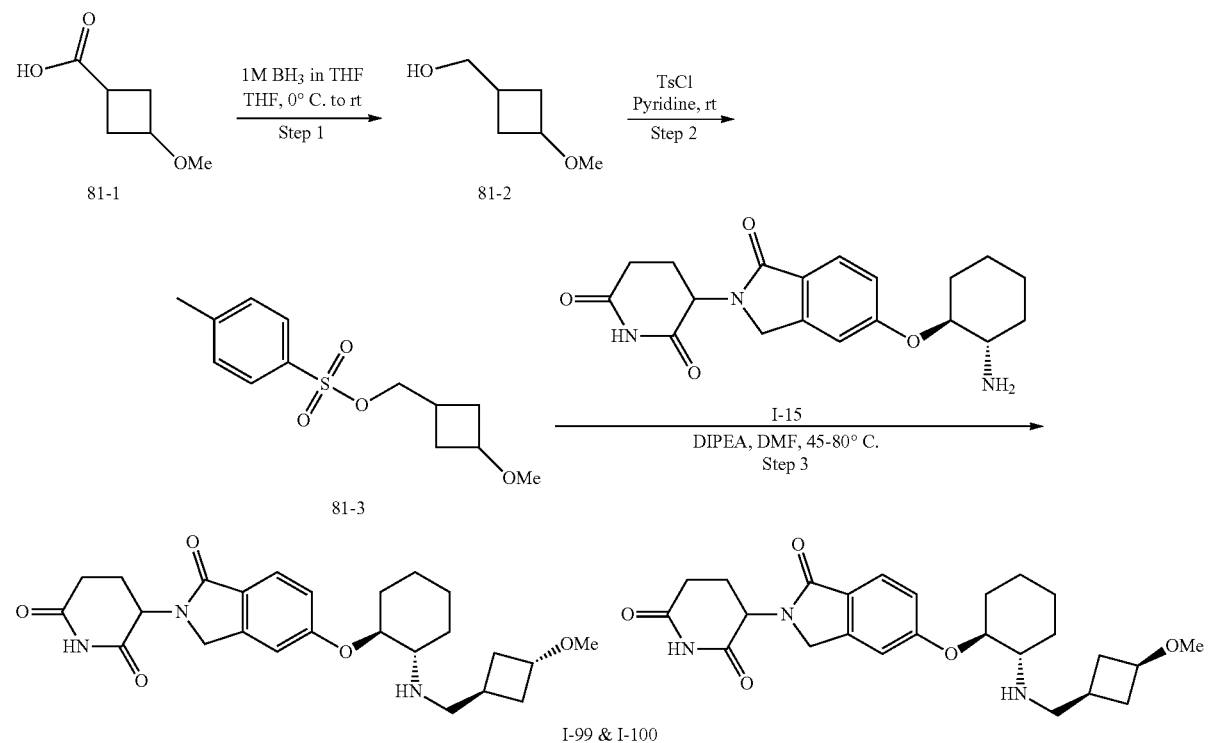

Step 1. (3-Methoxycyclobutyl)methanol (81-2)

To a solution of 3-methoxycyclobutane-1-carboxylic acid (81-1, 444 mg, 3.41 mmol) in THF (10 mL) at 0° C. was added BH₃ in THF (10.2 mL, 10.2 mmol, 1M) and the resulting mixture was allowed to warm slowly to rt and then stirred at rt for 18 h. MeOH was slowly added, followed by the addition of aqueous saturated bicarbonate solution. The aqueous mixture was extracted with DCM and the organic phase was passed through a phase collector and concentrated to dryness to afford 81-2. The crude material was taken through to the next step without purification.

Step 2. (3-Methoxycyclobutyl)methyl 4-methylbenzenesulfonate (81-3)

To a solution of (3-methoxycyclobutyl)methanol (81-2, 411 mg, 3.54 mmol) in pyridine (8 mL) was added TsCl (1012 mg, 5.31 mmol). The resulting mixture was stirred at rt for 2 h and then diluted with DCM and washed with a saturated aqueous bicarbonate solution. The organic phase was passed through a phase separating column and concentrated to dryness. The crude material was purified via silica gel chromatography eluting with 0-100% EtOAc in heptanes to afford 81-3 (300 mg, 1.11 mmol, 31% yield), as a 2:1 mixture of diastereomers. $^1$H NMR (400 MHz, DMSO-$d_6$, major diastereoisomer) δ 7.81-7.76 (m, 2H), 7.51-7.47 (m, 2H), 3.97 (d, J=6.1 Hz, 2H), 3.71-3.57 (m, 1H), 3.06 (s, 3H), 2.50 (quint, J=1.8 Hz, 1H), 2.43 (s, 3H), 2.22-2.15 (m, 2H), 1.48 (m, 2H). $^1$H NMR (400 MHz, DMSO-$d_6$, minor diastereoisomer) δ 7.81-7.76 (m, 2H), 7.51-7.47 (m, 2H), 4.06-4.00 (m, 2H), 3.87-3.79 (m, 1H), 3.06 (s, 3H), 2.43 (s, 3H), 2.13-2.04 (m, 2H), 1.93-1.89 (m, 3H).

Step 3. 3-(5-(((1S,2S)-2-(((((1R,3S)-3-methoxycyclobutyl)methyl)amino)cyclohexyl)oxy)-1-oxoisoindolin-2-yl)piperidine-2,6-dione and 3-(5-(((1S,2S)-2-(((((1R,3R)-3-methoxycyclobutyl)methyl)amino)cyclohexyl)oxy)-1-oxoisoindolin-2-yl)piperidine-2,6-dione (I-99) & (I-100)

To a vial containing 3-(5-(((1S,2S)-2-aminocyclohexyl)oxy)-1-oxoisoindolin-2-yl)piperidine-2,6-dione (I-15, 322 mg, 0.369 mmol), was added a solution of (3-methoxycyclobutyl)methyl 4-methylbenzenesulfonate (81-3, 300 mg, 1.11 mmol) in DMF (3 mL), followed by the addition of DIPEA (0.32 mL, 1.85 mmol). The reaction mixture was stirred at 45° C. for 16 h, then at 80° C. for 16 h. The reaction mixture was diluted with acetone, absorbed onto Celite® and concentrated to dryness. The crude material was purified via silica gel chromatography eluting with 0-100% EtOAc in heptanes and then 0-100% EtOAc/EtOH (v/v=3:1) in DCM. The obtained material was purified further via reverse phase HPLC (10-30% MeCN, 3.5 min gradient X-bridge C18 OBD 30×50 mm 5 um column MeCN/H₂O w/0.1% Formic Acid 75 ml/min 1.5 mL injection) to afford the formate salt of a mixture of diastereomers I-99 and I-100 (87 mg, 0.17 mmol, 3% yield) as an oil. MS [M+H]⁺=456.5

The mixture of I-99 and I-100 (81 mg) was separated using chiral SFC (Column: Chiralpak AD 21×250 mm; Flow rate: 80 g per minute; Cosolvent: 25% EtOH with 10 mM NH₃) to afford I-99 and I-100 as Peak 1 and Peak 2. Peak 1 (I-99): The material from SFC Peak 1 was repurified via reverse phase HPLC (Method: eluting with 5-20% MeCN over 3.5 min; Conditions: MeCN/H₂O+0.1% Formic Acid at 75 mL/min; 1.5 mL injection; Column: XBridge C18 OBD 30×50 mm) and further purified via reverse phase HPLC (Column: Xbridge C18 OBD 5 um 30×50 mm; Conditions: Water/MeCN with 10 mM NH₄OH 75 mL/min; 1.5 mL injection; Gradient: 15-40% MeCN, 3.5 min gradient; collection tubes contained several drops of formic acid) to afford the formate salt of Peak 1 (I-99, 9 mg, 0.028 mmol). Chiral SFC Rt=1.67 mins. MS [M+H]⁺=456.5. $^1$H NMR (400 MHz, Methylene Chloride-$d_2$) δ 7.70 (d, J=9.1 Hz, 1H), 7.06-6.95 (m, 2H), 5.12 (dd, J=13.3, 5.2 Hz, 1H), 4.43-4.25 (m, 2H), 4.21-4.09 (m, 1H), 3.87 (quint, J=6.6 Hz, 1H), 3.14 (s, 3H), 2.88-2.79 (m, 2H), 2.76-2.68 (m, 2H), 2.68-2.59 (m, 1H), 2.38-2.24 (m, 2H), 2.23-2.03 (m, 5H), 2.01-1.87 (m, 5H), 1.77-1.70 (m, 2H), 1.37-1.33 (m, 2H). The relative stereochemistry of the cyclobutane substituents was not determined and was assigned arbitrarily.

Peak 2 (I-100): The material from SFC Peak 2 was purified via reverse phase HPLC (Method: eluting with 5-20% MeCN over 3.5 min. Conditions: MeCN/H₂O+0.1% Formic Acid at 75 mL/min; 1.5 mL injection; Column: XBridge C18 OBD 30×50 mm) to afford the formate salt of Peak 2 (I-100, 14 mg, 0.027 mmol). Chiral SFC Rt=2.52 mins. MS [M+H]⁺=456.6. $^1$H NMR (400 MHz, Methylene Chloride-$d_2$) δ 7.70 (d, J=9.0 Hz, 1H), 7.08-6.98 (m, 2H), 5.23-5.01 (m, 1H), 4.36-4.24 (m, 2H), 4.15 (s, 1H), 3.76-3.62 (m, 1H), 3.15 (s, 3H), 2.86-2.69 (m, 3H), 2.64-2.60 (m, 1H), 2.36-2.26 (m, 2H), 2.22-2.10 (m, 3H), 2.09-2.02 (m, 1H), 2.00-1.85 (m, 2H), 1.79-1.68 (m, 2H), 1.54-1.43 (m, 1H), 1.38-1.31 (m, 2H), 1.31-1.22 (m, 3H). The relative stereochemistry of the cyclobutane substituents was not determined and was assigned arbitrarily.

Example 83: 3-(5-(((1S,2S)-2-((((1r,4S)-4-methoxycyclohexyl)methyl)amino)cyclohexyl)oxy)-1-oxoisoindolin-2-yl)piperidine-2,6-dione (I-101)

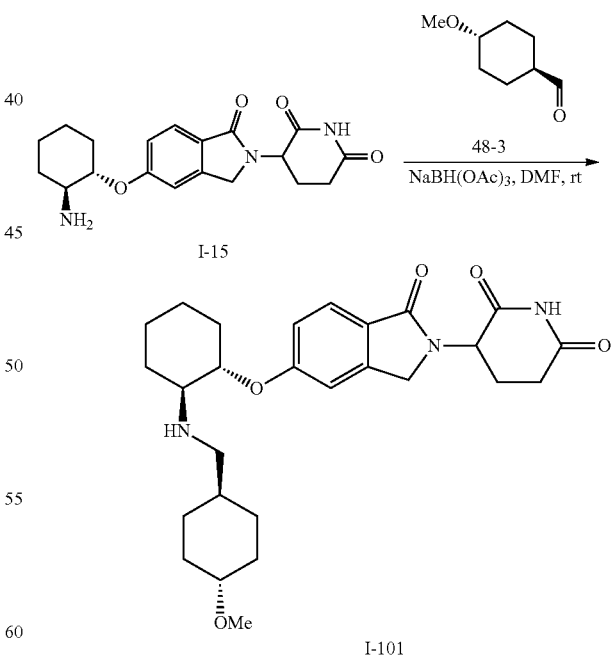

To a solution of 3-(5-(((1S,2S)-2-aminocyclohexyl)oxy)-1-oxoisoindolin-2-yl)piperidine-2,6-dione (I-15, 0.16 g, 0.18 mmol) in DMF (1.1 mL) was added (1r,4r)-4-methoxycyclohexane-1-carbaldehyde (48-3, 37 mg, 0.26 mmol) and the resulting mixture was stirred at rt for 15 minutes. Sodium triacetoxyborohydride (58 mg, 0.28 mmol) was added and stirring was continued at rt for 1 h. Additional (1r,4r)-4-methoxycyclohexane-1-carbaldehyde (48-3, 7.3 mg, 0.051) was added and the resulting mixture was stirred at rt for 15 minutes. Additional sodium triacetoxyborohydride (25 mg, 0.12 mmol) was added and stirring was continued at rt for 16 h. The reaction mixture was quenched with sat. aqueous sodium bicarbonate and extracted with 20% isopropanol in DCM (×3). The organic phases were combined, passed through a phase separator, and concentrated onto Celite®. The crude material was purified by silica gel chromatography eluting with 0-100% EtOAc:EtOH (v/v=3:1, with 1% Et$_3$N as a modifier) in heptane and then purified further by reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient). The fractions containing the desired product were combined and lyophilized to afford I-101 (57 mg, 0.10 mmol, 55% yield) as a white solid. MS [M+H]$^+$=484.5. $^1$H NMR (400 MHz, DMSO-d$_6$) δ 10.96 (s, 1H), 7.61 (d, J=8.3 Hz, 1H), 7.19 (d, J=2.3 Hz, 1H), 7.06 (dt, J=8.4, 1.9 Hz, 1H), 5.07 (dd, J=13.3, 5.0 Hz, 1H), 4.38 (dd, J=17.3, 7.9 Hz, 1H), 4.31-4.14 (m, 2H), 3.19 (s, 3H), 3.05-2.84 (m, 2H), 2.70-2.55 (m, 2H), 2.46-2.29 (m, 3H), 2.13-1.88 (m, 5H), 1.82-1.59 (m, 4H), 1.40-1.10 (m, 5H), 1.07-0.95 (m, 2H), 0.91-0.75 (m, 2H).

Example 84: 3-(5-(((1S,2S)-2-(((4-methyltetrahydro-2H-pyran-4-yl)methyl)amino)cyclohexyl)oxy)-1-oxoisoindolin-2-yl)piperidine-2,6-dione (I-102)

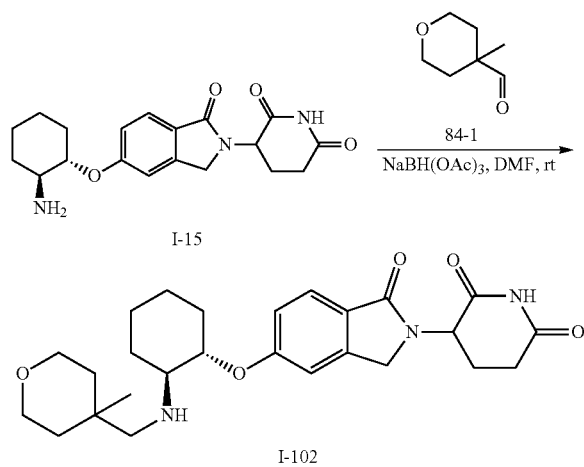

To a solution of 3-(5-(((1S,2S)-2-aminocyclohexyl)oxy)-1-oxoisoindolin-2-yl)piperidine-2,6-dione (I-15, 0.16 g, 0.45 mmol) in DMF (0.92 mL) was added 4-methyltetrahydro-2H-pyran-4-carbaldehyde (84-1, 28 mg, 0.22 mmol) and the resulting mixture was stirred at rt for 15 minutes. Sodium triacetoxyborohydride (58 mg, 0.28 mmol) was added and stirring was continued at rt for 1 h. Additional 4-methyltetrahydro-2H-pyran-4-carbaldehyde (4.7 mg, 0.037 mmol) was added and the reaction mixture stirred at rt for 15 minutes. Additional sodium triacetoxyborohydride (19 mg, 0.092 mmol) was added and stirring was continued at rt for 16 h. The reaction mixture was then diluted with MeCN and concentrated onto Celite®. The crude material was purified by silica gel chromatography eluting with 0-100% EtOAc:EtOH (v/v=3:1, with 1% Et$_3$N as a modifier) in heptane to afford I-102 (99 mg, 0.21 mmol, 47% yield) as a white solid. MS [M+H]$^+$=470.5. $^1$H NMR (400 MHz, DMSO-d$_6$) δ 10.96 (s, 1H), 7.61 (d, J=8.4 Hz, 1H), 7.21 (d, J=2.0 Hz, 1H), 7.07 (dt, J=8.7, 1.7 Hz, 1H), 5.07 (dd, J=13.2, 5.0 Hz, 1H), 4.38 (dd, J=17.2, 9.0 Hz, 1H), 4.31-4.16 (m, 2H), 3.53 (dt, J=11.9, 4.7 Hz, 2H), 3.44 (ddd, J=11.8, 9.0, 3.2 Hz, 2H), 2.90 (ddd, J=17.2, 13.6, 5.5 Hz, 1H), 2.65-2.54 (m, 2H), 2.48-2.29 (m, 3H), 2.15-2.02 (m, 1H), 2.02-1.93 (m, 2H), 1.72-1.60 (m, 2H), 1.48-1.08 (m, 8H), 0.87 (s, 3H).

Example 85: 3-(1-oxo-5-(((1S,2S)-2-((pyrimidin-5-ylmethyl)amino)cyclohexyl)oxy)isoindolin-2-yl)piperidine-2,6-dione (I-103)

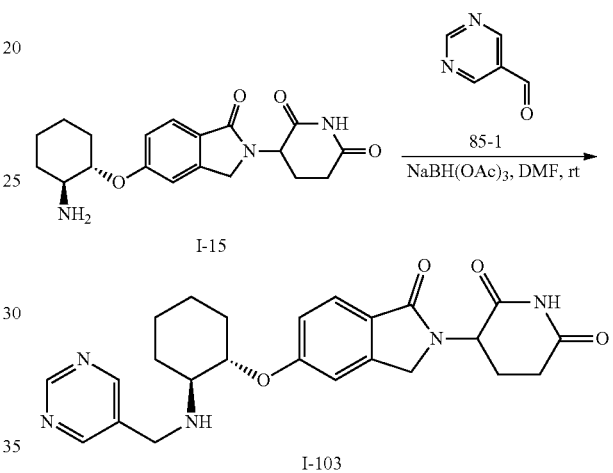

To a solution of 3-(5-(((1S,2S)-2-aminocyclohexyl)oxy)-1-oxoisoindolin-2-yl)piperidine-2,6-dione (I-15, 0.16 g, 0.184 mmol) in DMF (2 mL) was added pyrimidine-5-carbaldehyde (85-1, 0.02 mL, 0.26 mmol) and the resulting mixture was stirred at rt for 15 minutes. Sodium triacetoxyborohydride (58 mg, 0.28 mmol) was added and stirring was continued at rt for 24 h. Additional pyrimidine-5-carbaldehyde (85-1, 12 mg, 0.11 mmol) was added and the reaction mixture was stirred at rt for 15 min. Additional sodium triacetoxyborohydride (25 mg, 0.12 mmol) was added stirring was continued at rt for 1 h. Additional pyrimidine-5-carbaldehyde (85-1, 12 mg, 0.11 mmol) was added and the reaction mixture was stirred at rt for 15 minutes. Sodium triacetoxyborohydride (25 mg, 0.12 mmol) was the again added and stirring was continued at rt for 1 h. The reaction mixture was then quenched with saturated aqueous sodium bicarbonate and extracted with 20% i-PrOH in DCM (×3). The combined organic phases were passed through a phase separating column and concentrated onto Celite®. The crude material was purified by silica gel chromatography eluting with 0-100% EtOAc:EtOH (v/v=3:1, with 1% Et$_3$N as a modifier) in heptane to afford I-103 (67 mg, 0.14 mmol, 79% yield) as a white solid. MS [M+H]$^+$=450.3. $^1$H NMR (400 MHz, DMSO-d$_6$) δ 10.96 (s, 1H), 9.04 (s, 1H), 8.74 (s, 2H), 7.61 (d, J=8.3 Hz, 1H), 7.20 (s, 1H), 7.08 (d, J=8.5 Hz, 1H), 5.07 (dd, J=13.3, 5.1 Hz, 1H), 4.43-4.18 (m, 3H), 3.92-3.76 (m, 1H), 3.14-3.03 (m, 1H), 2.91 (ddd, J=17.9, 13.5, 5.3 Hz, 1H), 2.64-2.55 (m, 1H), 2.44-2.31 (m, 2H), 2.29 (s, 1H), 2.13-1.93 (m, 3H), 1.73-1.59 (m, 2H), 1.42-1.13 (m, 4H).

Example 86: 3-(1-oxo-5-(((1S,2S)-2-((2-(tetrahydro-2H-pyran-4-yl)ethyl)amino)cyclohexyl)oxy)isoindolin-2-yl)piperidine-2,6-dione (I-104)

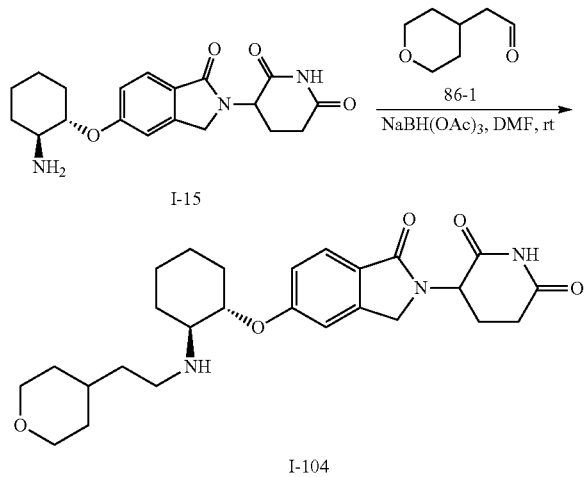

To a solution of 3-(5-(((1S,2S)-2-aminocyclohexyl)oxy)-1-oxoisoindolin-2-yl)piperidine-2,6-dione (I-15, 0.16 g, 0.18 mmol) in DMF (2 ml) was added tetrahydropyranyl-4-acetaldehyde (86-1, 0.034 mL, 0.26 mmol) and the resulting mixture was stirred at rt for 15 minutes. Sodium triacetoxyborohydride (58 mg, 0.275 mmol) was added and stirring was continued at rt for 1 h. Additional tetrahydropyranyl-4-acetaldehyde (86-1, 8 µL, 0.06 mmol) was added and the reaction mixture was stirred at rt for 15 minutes. Additional sodium triacetoxyborohydride (25 mg, 0.12 mmol) was added and stirring was continued at rt for 1 h. The reaction mixture was quenched with saturated aqueous sodium bicarbonate and extracted with 20% i-PrOH in DCM (×3). The combined organic phases were passed through a phase separating column and concentrated onto Celite®. The crude material was purified by silica gel chromatography eluting with 0-100% EtOAc:EtOH (v/v=3:1, with 1% Et$_3$N as a modifier) in heptane to afford I-104 (87 mg, 0.18 mmol, 99%) as a white solid. MS [M+H]$^+$=470.5. $^1$H NMR (400 MHz, DMSO-d$_6$) δ 10.96 (s, 1H), 7.61 (d, J=8.4 Hz, 1H), 7.21 (d, J=2.7 Hz, 1H), 7.07 (d, J=8.4 Hz, 1H), 5.07 (dd, J=13.3, 5.1 Hz, 1H), 4.38 (dd, J=17.2, 7.1 Hz, 1H), 4.25 (dd, J=17.0, 6.1 Hz, 2H), 3.77 (dd, J=11.3, 4.2 Hz, 2H), 3.23-3.12 (m, 2H), 2.98-2.82 (m, 1H), 2.74-2.55 (m, 4H), 2.38 (qd, J=13.2, 3.9 Hz, 1H), 2.11-2.03 (m, 1H), 2.02-1.92 (m, 2H), 1.72-1.59 (m, 2H), 1.54-1.44 (m, 3H), 1.40-0.98 (m, 8H).

Example 87: 3-(5-(((1S,2S)-2-(2-oxa-7-azaspiro[3.5]nonan-7-yl)cyclohexyl)oxy)-1-oxoisoindolin-2-yl)piperidine-2,6-dione HC(O)OH Salt (I-105)

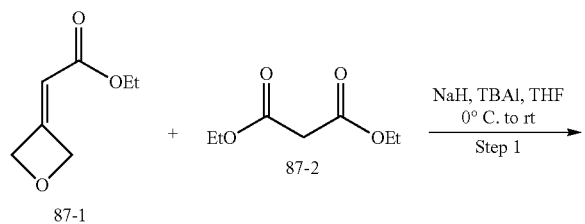

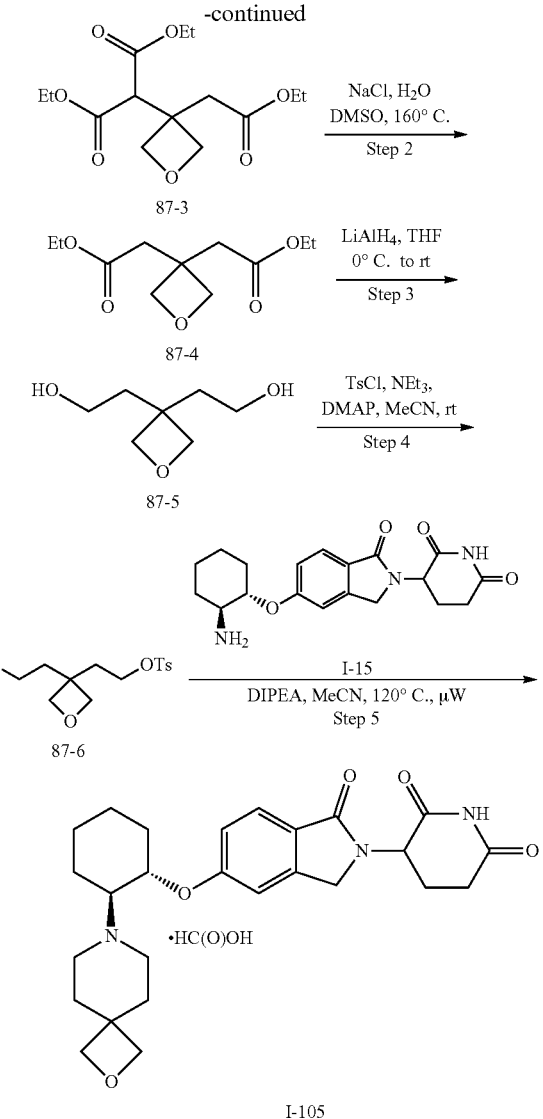

Step 1. Diethyl 2-(3-(2-ethoxy-2-oxoethyl)oxetan-3-yl)malonate (87-3)

A suspension of 60% sodium hydride in mineral oil (4.21 g, 105 mmol) in THF (70 mL), under an atmosphere of nitrogen, was cooled to 0° C. and diethyl malonate (87-2, 18.5 mL, 122 mmol) was added dropwise. The resulting mixture was allowed to warm to rt and stirred at rt for 20 minutes. TBAI (5.17 g, 14.0 mmol) was then added, followed by a solution of ethyl 2-(oxetan-3-ylidene)acetate (87-1, 4.96 g, 34.9 mmol) in THF (8.5 mL) dropwise. The reaction mixture was stirred at rt overnight, cooled to 0° C., quenched with acetic acid (7.5 mL), allowed to warm to room temperature, and stirred at rt for 30 min. The solution was diluted with diethyl ether (250 mL) and the organic phase washed with brine (50 mL), dried over magnesium sulfate, filtered, and concentrated. The crude material was purified via silica gel chromatography eluting with 0-40% EtOAc in heptane to afford 87-3 (7.98 g, 25.1 mmol, 72% yield) as a colorless oil. MS [M+H]$^+$=303.3. $^1$H NMR (400 MHz, DCM-d$_2$) δ 4.71 (d, J=6.8 Hz, 2H), 4.52 (d, J≤6.8 Hz, 2H), 4.20 (q, J=7.1 Hz, 4H), 4.11 (q, J=7.1 Hz, 2H), 3.93 (s, 1H), 2.94 (s, 2H), 1.30-1.24 (m, 9H).

Step 2. Diethyl 2,2'-(oxetane-3,3-diyl)diacetate (87-4)

To a solution of diethyl 2-(3-(2-ethoxy-2-oxoethyl) oxetan-3-yl)malonate (87-3, 7.98 g, 26.4 mmol) in DMSO (100 mL) and water (1.5 mL, 83 mmol) was added sodium chloride (3.09 g, 52.8 mmol). The resulting mixture was stirred at 160° C. for 2 h, and cooled to rt and stirred at rt overnight. The reaction mixture was diluted with diethyl ether (300 mL) and washed with brine (2×80 mL). The organic phase was then dried over magnesium sulfate, filtered, and concentrated to dryness. The crude product was diluted with DMSO (50 mL) and water (1.5 mL, 83 mmol) and sodium chloride (3.09 g, 52.8 mmol) was added. The solution was then stirred at 160° C. for 2 days. The solution was diluted with diethyl ether (300 mL) and washed with brine (80 mL). The organic layer was then dried over magnesium sulfate, filtered, and concentrated. The crude material was purified via silica gel chromatography eluting with 0-50% EtOAc in heptane to afford 87-4 (4.28 g, 18.6 mmol, 70% yield), as a colorless oil. MS [M+H]$^+$=231.3. $^1$H NMR (400 MHz, DCM-d$_2$) δ 4.54-4.48 (m, 2H), 4.28-4.16 (m, 2H), 4.16-4.06 (m, 4H), 2.87 (s, 4H), 1.33-1.21 (m, 6H).

Step 3. 2,2'-(oxetane-3,3-diyl)bis(ethan-1-ol) (87-5)

To LiAlH$_4$ (2.15 g, 56.6 mmol) dissolved in THF (75 mL) under an atmosphere of nitrogen and cooled to 0° C., was added a solution of diethyl 2,2'-(oxetane-3,3-diyl)diacetate (87-4, 4.28 g, 18.6 mmol) in THF (10 mL). The resulting mixture was allowed to slowly warmed to rt and stirred at rt for 1 h. The reaction mixture was cooled to 0° C. and water (4.2 mL) and 1M NaOH (aq) (8.4 mL) were added. The solution was filtered through Celite®, and the Celite® pad was rinsed with EtOAc. The solution was concentrated, diluted with ethyl acetate (150 mL), and washed with brine (40 mL). The organic phase was dried over magnesium sulfate, filtered, and concentrated to dryness to afford 87-5 (434 mg, 2.97 mmol, 16% yield) a yellow solid, which was carried onto the next step without purification.

Step 4. Oxetane-3,3-diylbis(ethane-2,1-diyl) bis(4-methylbenzenesulfonate) (87-6)

To 2,2'-(oxetane-3,3-diyl)bis(ethan-1-ol) (87-5, 434 mg, 2.97 mmol) and tosyl chloride (1.43 g, 7.52 mmol) dissolved in MeCN (15 mL) was added TEA (1.5 mL, 12 mmol) and DMAP (36 mg, 0.30 mmol) and the resulting mixture was stirred at rt overnight. The solution was then diluted with EtOAc (250 mL) and washed with water (50 mL) and brine (40 mL). The organic phase was dried over magnesium sulfate, filtered, and concentrated. The crude material was purified via silica gel chromatography eluting with 0-100% EtOAc in heptane to afford 87-6 (170 mg, 026 mmol, 9% yield). MS [M+H]$^+$=455.4. $^1$H NMR (400 MHz, DCM-d$_2$) δ 7.83-7.71 (m, 4H), 7.46-7.35 (m, 4H), 4.39-4.33 (m, 2H), 4.29 (s, 2H), 4.05 (t, J=6.4 Hz, 4H), 2.46 (s, 6H), 2.04-1.96 (m, 4H).

Step 5. 3-(5-(((1S,2S)-2-(2-oxa-7-azaspiro[3.5] nonan-7-yl)cyclohexyl)oxy)-1-oxoisoindolin-2-yl) piperidine-2,6-dione HC(O)OH Salt (I-105)

3-(5-(((1S,2S)-2-aminocyclohexyl)oxy)-1-oxoisoindolin-2-yl)piperidine-2,6-dione (I-15, 101.8 mg, 0.29 mmol) and oxetane-3,3-diylbis(ethane-2,1-diyl) bis(4-methylbenzenesulfonate) (87-6, 169.7 mg, 0.37 mmol) were dissolved in MeCN (2 mL) and DIPEA (0.15 mL, 0.86 mmol) and the resulting mixture was stirred at 120° C. in a μW reactor for 4 h. The reaction mixture was concentrated to dryness and the crude material was purified by silica gel chromatography eluting with 0-100% EtOAc:EtOH (v/v=3:1, with 0.1% Et$_3$N) in DCM (with 0.1% Et$_3$N) and then purified further via reverse phase preparative HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient) to afford the formate salt of I-105 (18 mg, 0.035 mmol, 12% yield) as a white solid. MS [M+H]$^+$=468.4. $^1$H NMR (400 MHz, DMSO-d$_6$) δ 10.95 (s, 1H), 8.14 (s, 1H), 7.59 (dd, J=8.4, 1.0 Hz, 1H), 7.17 (s, 1H), 7.02 (dt, J=8.4, 2.9 Hz, 1H), 5.06 (dd, J=13.2, 5.1 Hz, 1H), 4.50-4.19 (m, 3H), 4.19-4.04 (m, 4H), 2.90 (ddd, J=18.0, 13.5, 5.3 Hz, 1H), 2.63-2.53 (m, 3H), 2.46-2.34 (m, 3H), 2.16-2.08 (m, 1H), 2.05-1.91 (m, 1H), 1.78-1.45 (m, 7H), 1.42-1.12 (m, 5H).

Example 88: 3-(5-(((1S,2S)-2-(((4-methoxytetrahydro-2H-pyran-4-yl)methyl)amino)cyclohexyl) oxy)-1-oxoisoindolin-2-yl)piperidine-2,6-dione (I-106)

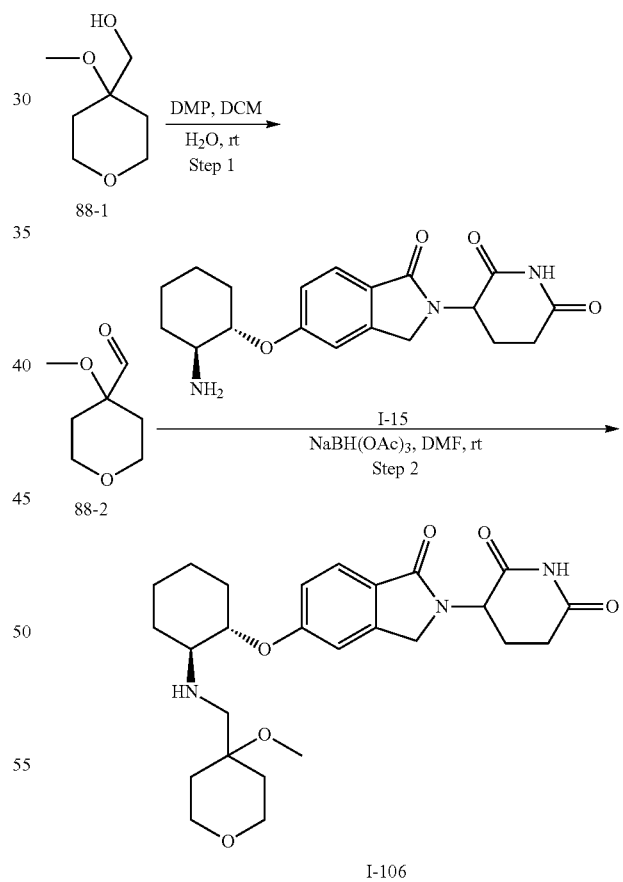

Step 1.
4-Methoxytetrahydro-2H-pyran-4-carbaldehyde (88-2)

To (4-methoxyoxan-4-yl)methanol (88-1, 0.200 g, 1.37 mmol) dissolved in DCM (6.8 mL) and cooled to 0° C. was added DMP (812 mg, 1.92 mmol) followed by 2 drops of water. The resulting mixture was stirred at 0° C. for 1 h and then at rt for 1 h. The reaction mixture was quenched with 1:1:2 saturated aqueous sodium bicarbonate:saturated aqueous sodium thiosulfate:diethyl ether and stirred until the cloudy mixture turned clear. The organic phase was separated and the aqueous phase was extracted with diethyl ether (×2). The combined organic phases were passed through a phase separator and concentrated to afford 88-2 as a colorless oil, which was taken onto the next reaction without purification.

Step 2. 3-(5-(((1S,2S)-2-(((4-methoxytetrahydro-2H-pyran-4-yl)methyl)amino)cyclohexyl)oxy)-1-oxoisoindolin-2-yl)piperidine-2,6-dione (I-106)

To a solution of 3-(5-(((1S,2S)-2-aminocyclohexyl)oxy)-1-oxoisoindolin-2-yl)piperidine-2,6-dione (I-15, 0.10 g, 0.12 mmol) in DMF (1.5 mL) was added 4-methoxytetrahydro-2H-pyran-4-carbaldehyde (88-2, 31 mg, 0.16 mmol) and the resulting mixture was stirred at rt for 15 minutes. Sodium triacetoxyborohydride (36 mg, 0.17 mmol) was added and stirring was continued at rt for 18 h. The reaction mixture was concentrated down, magnesium sulfate (14 mg, 0.12 mmol) was added, and stirring was continued at 45° C. for 16 h. Additional 4-methoxytetrahydro-2H-pyran-4-carbaldehyde (88-2, 22 mg, 0.12 mmol) was added and the reaction mixture stirred at r.t. for 15 minutes. Sodium triacetoxyborohydride (29 mg, 0.14 mmol) was added and stirring was continued at rt for 1 h. Additional 4-methoxytetrahydro-2H-pyran-4-carbaldehyde (88-2, 22 mg, 0.12 mmol) was added and stirring was continued at rt for 15 mins. Sodium triacetoxyborohydride (29 mg, 0.14 mmol) was then again added. The reaction mixture was stirred at rt for 1 h and then quenched with saturated aqueous sodium bicarbonate and extracted with 20% i-PrOH in DCM (×3). The combined organic phases were passed through a phase separator and concentrated onto Celite®. The crude material was purified by silica gel chromatography eluting with 0-100% EtOAc:EtOH (v/v=3:1, with 1% Et₃N) in heptane to afford I-106 (57 mg, 0.11 mmol, 97% yield) as a white solid. MS [M+H]⁺=486.3. ¹H NMR (400 MHz, DMSO-d₆) δ 10.96 (s, 1H), 7.61 (d, J=8.3 Hz, 1H), 7.21 (s, 1H), 7.07 (dd, J=8.6, 2.2 Hz, 1H), 5.07 (dd, J=13.2, 5.0 Hz, 1H), 4.38 (dd, J=17.2, 11.5 Hz, 1H), 4.32-4.15 (m, 2H), 3.55-3.42 (m, 4H), 3.04 (s, 3H), 2.91 (ddd, J=17.1, 13.5, 5.3 Hz, 1H), 2.69-2.53 (m, 4H), 2.43-2.31 (m, 1H), 2.15-2.04 (m, 1H), 2.01-1.93 (m, 2H), 1.75-1.11 (m, 10H).

Example 89: 3-(5-(((1S,2S)-2-(((2,2-dimethyltetrahydro-2H-pyran-4-yl)methyl)amino)cyclohexyl)oxy)-1-oxoisoindolin-2-yl)piperidine-2,6-dione (I-107)

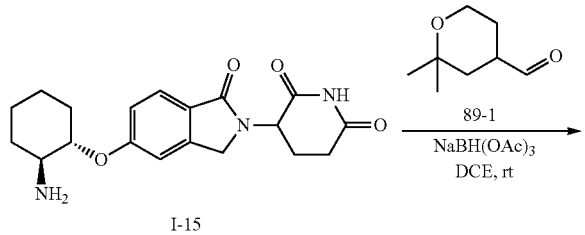

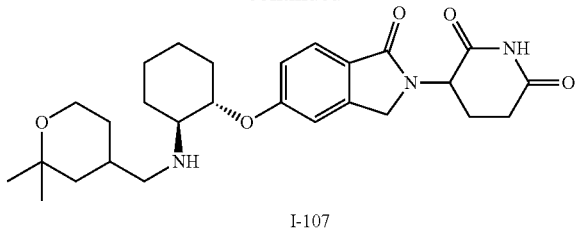

To a solution of 3-(5-(((1S,2S)-2-aminocyclohexyl)oxy)-1-oxoisoindolin-2-yl)piperidine-2,6-dione (I-15, 100 mg, 0.280 mmol) in DCE (2 mL) was added 2,2-dimethyltetrahydro-2H-pyran-4-carbaldehyde (89-1, 42 mg, 0.29 mmol) and the resulting mixture was stirred at rt for 30 minutes. Sodium triacetoxyborohydride (178 mg, 0.839 mmol) was added and stirring was continued at rt for 2 days. The reaction mixture was then added to a saturated aqueous solution of sodium hydrogen carbonate (20 mL). The aqueous phase was extracted with 20% i-PrOH/DCM (×3) and the combined organic phases were passed through a phase separating column and concentrated. The crude material was purified via silica gel chromatography eluting with 0-15% i-PrOH (with 0.1% Et₃N) in DCM (with 0.1% NEt₃) to afford I-107 (42 mg, 0.083 mmol, 30% yield) as a yellow solid. MS [M+H]⁺=484.4. ¹H NMR (400 MHz, DMSO-d₆) δ (ppm) 10.95 (s, 1H), 7.65-7.55 (m, 1H), 7.20 (d, J=2.3 Hz, 1H), 7.06 (dd, J=8.4, 2.1 Hz, 1H), 5.06 (dd, J=13.3, 5.1 Hz, 1H), 4.43-4.18 (m, 3H), 3.58-3.51 (m, 1H), 3.51-3.42 (m, 1H), 2.90 (ddd, J=17.2, 13.6, 5.4 Hz, 1H), 2.68-2.54 (m, 2H), 2.47-2.31 (m, 3H), 2.10-2.01 (m, 1H), 2.01-1.90 (m, 2H), 1.75-1.60 (m, 3H), 1.59-1.11 (m, 6H), 1.11-1.01 (m, 6H), 1.01-0.78 (m, 2H).

Example 90: 3-(5-(((1S,2S)-2-(3-(benzyloxy)azetidin-1-yl)cyclohexyl)oxy)-1-oxoisoindolin-2-yl)piperidine-2,6-dione (I-54)

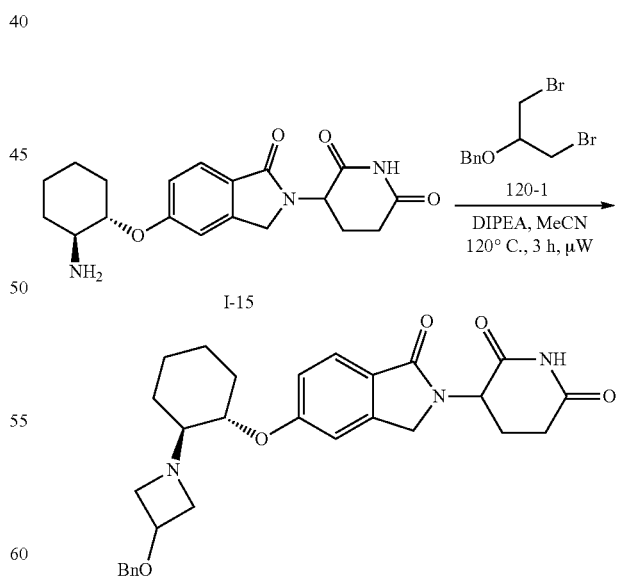

A solution of 3-(5-(((1S,2S)-2-aminocyclohexyl)oxy)-1-oxoisoindolin-2-yl)piperidine-2,6-dione (I-15, 50 mg, 0.14 mmol), (((1,3-dibromopropan-2-yl)oxy)methyl)benzene (120-1, 129 mg, 0.42 mmol), and DIPEA (0.12 mL, 0.70 mmol) in MeCN (1 mL) was stirred at 120° C. under μW irradiation for 3 h. The reaction mixture was then concentrated to dryness, treated with DCM, and washed with saturated NaHCO$_3$ (aq). The phases were separated and the aqueous phase was extracted with DCM (×3). The combined organic phases were concentrated. The crude material was purified via silica gel chromatography eluting with 0-100% EtOAc:EtOH (v/v=3:1, with 0.1% Et$_3$N) in DCM (with 0.1% Et$_3$N) and then further purified via reverse phase HPLC (Column: X-bridge C18 OBD 5 um 30×50 mm; Conditions: Water/MeCN with 0.1% Formic Acid 75 mL/min; 1.5 mL injection; Gradient: 15-40% MeCN, 3.5 min gradient. The fractions containing the desired product were combined and lyophilized to afford I-54 (7 mg, 0.012 mmol, 9% yield) as a white solid. MS [M+H]$^+$=504.5. $^1$H NMR (400 MHz, DCM-d$_2$) δ 8.21 (br s, 1H), 7.61 (d, J=8.4 Hz, 1H), 7.28-7.16 (m, 5H), 6.93 (s, 1H), 6.91-6.85 (m, 1H), 5.10-4.94 (m, 1H), 4.31 (s, 2H), 4.29-4.16 (m, 3H), 4.12-4.02 (m, 1H), 3.61 (s, 2H), 3.31-2.93 (m, 2H), 2.84-2.65 (m, 2H), 2.58-2.34 (m, 1H), 2.33-2.17 (m, 1H), 2.12-2.04 (m, 1H), 1.97 (s, 1H), 1.81 (s, 1H), 1.64 (s, 2H), 1.36-1.05 (m, 4H).

Example 91: 3-(1-oxo-5-(((1S,2S)-2-(3-(pyridazin-3-yloxy)azetidin-1-yl)cyclohexyl)oxy)isoindolin-2-yl)piperidine-2,6-dione HC(O)OH Salt (I-204)

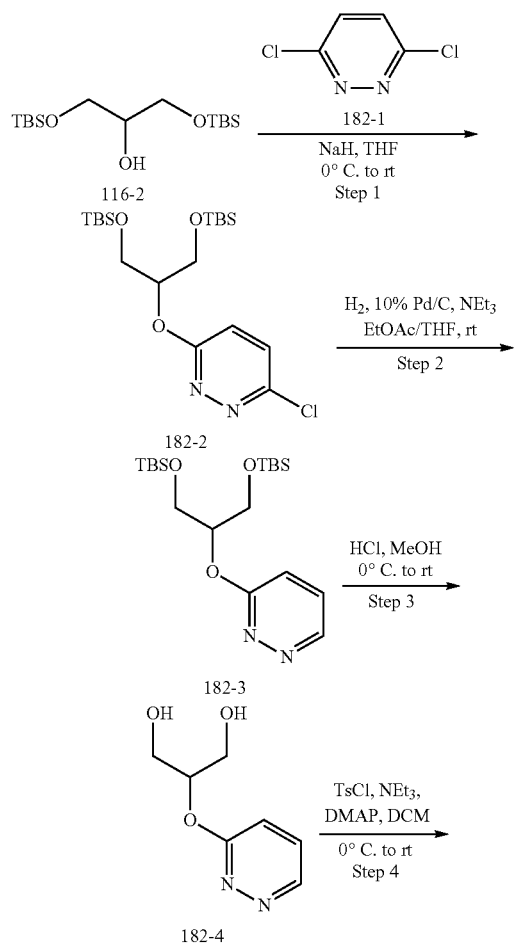

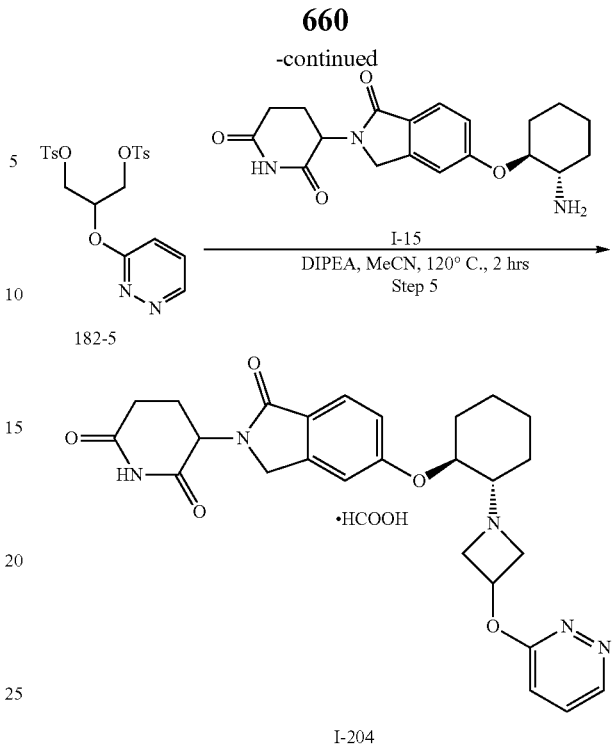

Step 1. 3-chloro-6-((2,2,3,3,9,9,10,10-octamethyl-4,8-dioxa-3,9-disilaundecan-6-yl)oxy)pyridazine (182-2)

To a solution of 2,2,3,3,9,9,10,10-octamethyl-4,8-dioxa-3,9-disilaundecan-6-ol (116-2, 2.00 g, 6.25 mmol) in THF (50 mL) was added NaH (0.370 g, 9.37 mmol) portion wise at 0° C. and the resulting mixture was stirred at rt for 1 h. The reaction mixture was cooled to 0° C., 3,6-dichloropyridazine (182-1, 0.920 g, 6.25 mmol) was added and was then refluxed for 16 h. The reaction mixture was quenched with cold water and extracted with EtOAc (3×50 mL). The combined organic phases were washed with water, brine, dried over Na$_2$SO$_4$, filtered, and concentrated to dryness. The obtained crude material was purified by silica gel chromatography eluting with 10% EtOAc in hexanes to afford 182-2 (2.20 g, 5.08 mmol, 81% yield) as colorless liquid. $^1$H NMR (400 MHz, CDCl$_3$): δ 7.35 (d, J=9.2 z, 1H), 6.95-6.94 (m, 1H), 3.94-3.91 (m, 4H), 3.65-3.64 (m, 1H), 0.86 (s, 18H), 0.02 (s, 12H).

Step 2. 3-((2,2,3,3,9,9,10,10-octamethyl-4,8-dioxa-3,9-disilaundecan-6-yl)oxy)pyridazine (182-3)

To a flask containing a deoxygenated solution of 182-2 (2.20 g, 5.03 mmol) in EtOAc-THF (1:1) (40 mL) under inert atmosphere was added Et$_3$N (2.2 mL, 15 mmol) and 10% Pd—C (0.55 g, 25% wt/wt) and the flask was purged with hydrogen and then stirred under a hydrogen atmosphere using a balloon at rt for 2 h. The reaction mixture was filtered through Celite®, the pad was washed with EtOAc, and the filtrate was concentrated to dryness to afford crude 182-3 (2.0 g), as pale yellow liquid. The crude material was carried on to the next step without purification. MS [M+H]$^+$=399.3.

Step 3. 2-(pyridazin-3-yloxy)propane-1,3-diol (182-5)

To a stirred solution of 182-3 (2.00 g, 5.02 mmol) in MeOH (30 mL) was added concentrated HCl (4.0 mL) drop wise at 0° C. and the resulting mixture was stirred at room temperature for 4 h. The reaction mixture was concentrated to dryness. The obtained crude material was diluted with cooled water, basified with NaHCO₃ and concentrated to dryness. The residue obtained was stirred with 10% MeOH in DCM, filtered and the filtrate was concentrated to dryness to afford crude 182-4 (0.60 g), as pale brown liquid. The crude material was carried on to the next step without purification. ¹H NMR (300 MHz, CDCl₃): δ 8.38 (d, J=4.2 Hz, 1H), 7.73-7.39 (m, 1H), 7.06 (d, J=4.2 Hz, 1H), 4.68-4.63 (m, 2H), 4.16-4.13 (m, 1H), 3.81-3.68 (m, 2H).

Step 4. 2-(pyridazin-3-yloxy)propane-1,3-diyl bis(4-methylbenzenesulfonate) (182-5)

To a solution of 182-4 (0.60 g, 3.50 mmol) in DCM (30 mL) was added Et₃N (2.02 mL, 14.10 mmol), DMAP (0.017 g, 0.14 mmol) and TsCl (1.40 g, 7.70 mmol) at 0° C. and the resulting mixture was stirred at rt for 3 h. The reaction mixture was quenched with cooled water and extracted with DCM (3×30 mL). The combined organic extracts were washed with water, brine, dried over anhydrous Na₂SO₄, filtered, and concentrated to dryness. The obtained crude material was purified by silica gel chromatography eluting with 50% EtOAc in hexanes to afford 182-5 (0.80 g, 1.67 mmol, 50% yield) as colorless liquid. MS [M+H]⁺=479.1.

Step 5. 3-(1-oxo-5-(((1S,2S)-2-(3-(pyridazin-3-yloxy)azetidin-1-yl)cyclohexyl)oxy)isoindolin-2-yl)piperidine-2,6-dione HC(O)OH Salt (I-204)

To a solution of I-15 (200 mg, 0.56 mmol) in MeCN (5 mL) was added 182-5 (168 mg, 0.66 mmol) and DIPEA (0.72 mL, 3.36 mmol) and the resulting mixture was stirred at 120° C. for 2 h. The reaction mixture was then diluted with sat. sodium bicarbonate solution and extracted with DCM (3×30 mL). The combined organic phases were washed with brine, dried over Na₂SO₄, filtered, and concentrated under reduced pressure. The obtained crude material was purified by reverse phase HPLC (Column: LUNA C18 (250 mm×21.2 mm), 5.0 g, Mobile phase A: 0.01% HCOOH (aq), Mobile phase B: MeCN, Method: 0-75% MeCN over 6 minutes. Flow rate: 20 ml/min) to afford the formate salt of I-204 (12 mg, 0.02 mmol, 5% yield), as a white solid. MS [M+H]⁺=492.4. ¹H NMR (400 MHz, DMSO-d₆): δ 10.97 (s, 1H), 8.01-7.99 (m, 1H), 7.90-7.89 (m, 1H), 7.57 (d, J=8.4 Hz, 2H), 7.17 (s, 1H), 7.05 (d, J=8.4 Hz, 1H), 6.93-6.90 (m, 1H), 6.35-6.34 (m, 1H), 5.31-5.26 (m, 1H), 5.08-5.04 (m, 1H), 4.30-4.23 (m, 4H), 3.85-3.75 (m, 1H), 2.91-2.89 (m, 2H), 2.66-2.60 (m, 1H), 2.36-2.32 (m, 1H), 2.07-1.96 (m, 3H), 1.90-1.85 (m, 1H), 1.70-1.65 (m, 2H), 1.37-1.31 (m, 4H).

Example 92: 3-(5-(((1S,2S)-2-((7-oxaspiro[3.5]nonan-2-yl)amino)cyclohexyl)oxy)-1-oxoisoindolin-2-yl)piperidine-2,6-dione (I-110)

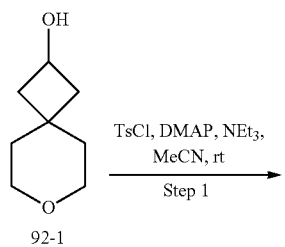

Step 1. 7-oxaspiro[3.5]nonan-2-yl 4-methylbenzenesulfonate (92-2)

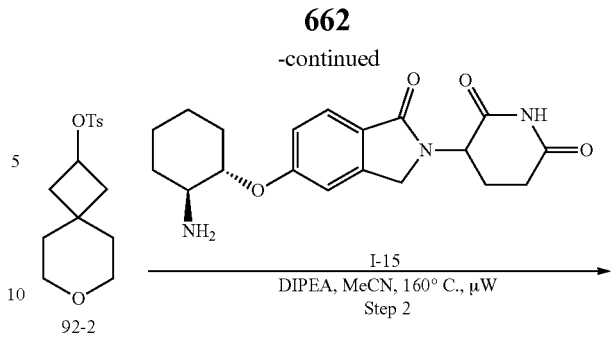

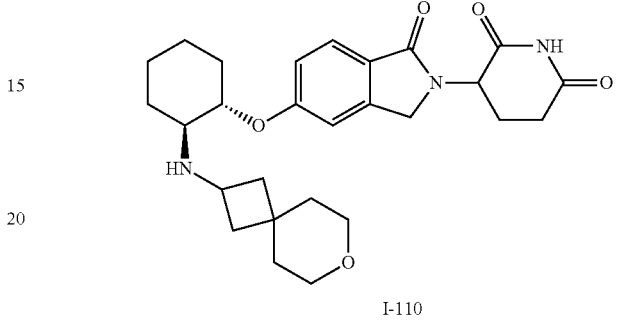

TsCl (174 mg, 0.914 mmol) was added to a solution of 7-oxaspiro[3.5]nonan-2-ol (92-1, 100 mg, 0.703 mmol), DMAP (9 mg, 0.07 mmol) and TEA (0.20 mL, 1.4 mmol) in MeCN (3 mL). The resulting mixture was stirred at rt for 16 h and then concentrated to dryness. The crude material was treated with diethyl ether and the obtained solid was rinsed with diethyl ether several times. The filtrate was collected and concentrated to dryness to afford crude 92-2 (240 mg) as a gold colored oil. ¹H NMR (400 MHz, Chloroform-d) δ 7.80-7.75 (m, 2H), 7.36-7.32 (m, 2H), 4.88-4.77 (m, 1H), 3.59-3.50 (m, 4H), 2.46 (s, 3H), 2.31-2.21 (m, 2H), 1.98-1.89 (m, 2H), 1.58-1.55 (m, 2H), 1.53-1.49 (m, 2H).

Step 2. 3-(5-(((1S,2S)-2-((7-oxaspiro[3.5]nonan-2-yl)amino)cyclohexyl)oxy)-1-oxoisoindolin-2-yl)piperidine-2,6-dione (I-110)

To a solution of 3-(5-(((1S,2S)-2-aminocyclohexyl)oxy)-1-oxoisoindolin-2-yl)piperidine-2,6-dione (I-15, 100 mg, 0.280 mmol) and crude 7-oxaspiro[3.5]nonan-2-yl 4-methylbenzenesulfonate (92-2, 134 mg, 0.420 mmol) in MeCN (1 mL) was added DIPEA (0.15 mL, 0.84 mmol) and the resulting mixture was stirred at 160° C. under μW irradiation for 18 h. The reaction mixture was concentrated, taken up in DCM (10 mL), and extracted with 1M HCl (aq) (3×10 mL). The combined aqueous phases were washed with DCM (3×10 mL). The phases were separated and the aqueous phase was cooled and basified to a pH of 9-10 using solid NaHCO₃. The basic layer was extracted with DCM (4×20 mL) and the combined organic phases were dried over Na₂SO₄, filtered, and concentrated. The crude material was purified by reverse phase HPLC (Column: Xbridge C18 OBD 5 um 30×50 mm; Conditions: Water/MeCN with 10 mM NH₄OH 75 mL/min; 1.5 mL injection; Gradient: 25-50% MeCN, 3.5 min gradient; collection tubes contained several drops of formic acid) and then treated with DCM and washed with saturated aqueous NaHCO₃. The phases were separated and the organic phase was concentrated to dryness to afford I-110 (6 mg, 0.01 mmol, 4% yield), as a white solid. MS [M+H]$^+$=482.4. $^1$H NMR (400 MHz, DCM-d$_2$) δ 7.62 (dd, J=8.1, 0.9 Hz, 1H), 6.96-6.91 (m, 2H), 5.07-4.98 (m, 1H), 4.32-4.17 (m, 2H), 4.04-3.96 (m, 1H), 3.52-3.35 (m, 4H), 3.28 (quint, J=7.7 Hz, 1H), 2.78-2.57 (m, 3H), 2.32-2.16 (m, 1H), 2.16-1.99 (m, 4H), 1.97-1.88 (m, 1H), 1.68-1.57 (m, 2H), 1.50-0.99 (m, 11H)

Example 93: 1-(((((1S,2S)-2-((2-(2,6-dioxopiperidin-3-yl)-1-oxoisoindolin-5-yl)oxy)cyclohexyl)amino)methyl)cyclobutane-1-carbonitrile (I-111)

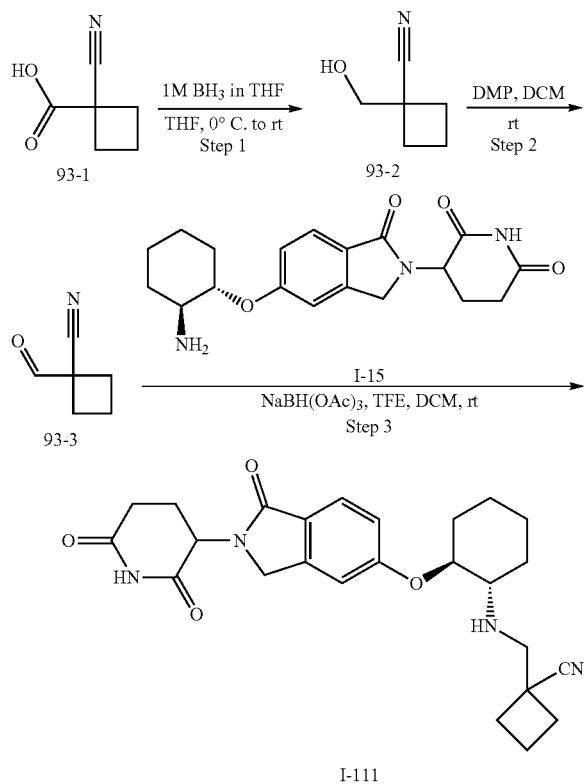

Step 1.
1-(Hydroxymethyl)cyclobutane-1-carbonitrile (93-2)

To a solution of 1-cyanocyclobutane-1-carboxylic acid (93-1, 450 mg, 3.6 mmol) in THF (18 mL) at 0° C. was added 1M BH$_3$ in THF (11 mL, 11 mmol). The resulting mixture was allowed to warm slowly to rt and then stirred at rt for 18 h. MeOH was then slowly, followed by aqueous saturated aqueous bicarbonate solution until neutralized. The aqueous solution was extracted with DCM, the phases were separated, and the organic phase was passed through a phase separating column and concentrated to afford 93-2 (540 mg, 3.55 mmol, 99% yield) as a crude oil which was taken onto the next step without purification. $^1$H NMR (400 MHz, DMSO-d$_6$) δ 4.31 (t, J=5.2 Hz, 1H), 3.35-3.29 (m, 2H), 1.54-1.47 (m, 2H), 1.45-1.24 (m, 4H).

Step 2. 1-Formylcyclobutane-1-carbonitrile (93-3)

To a solution of 1-(hydroxymethyl)cyclobutane-1-carbonitrile (93-2, 360 mg, 2.34 mmol) in DCM (6 mL) was added DMP (1.50 g, 3.55 mmol) and the resulting mixture was stirred at rt for 4 h. Additional DMP (280 mg, 0.66 mmol) was added and stirring was continued at rt for 16 h. The reaction mixture was diluted with 20% sodium thiosulfate (aq) and extracted with EtOAc (×2). The combined organic phases were dried over Na$_2$SO$_4$, filtered, and concentrated to afford 93-3 (272 mg, 2.34 mmol, quantitative yield) as a crude orange yellow oil that was used in the next step without purification.

Step 3. 1-(((((1S,2S)-2-((2-(2,6-dioxopiperidin-3-yl)-1-oxoisoindolin-5-yl)oxy)cyclohexyl)amino)methyl)cyclobutane-1-carbonitrile (I-111)

To a solution of 3-(5-(((1S,2S)-2-aminocyclohexyl)oxy)-1-oxoisoindolin-2-yl)piperidine-2,6-dione (I-15, 200 mg, 0.560 mmol) in TFE (3 mL) was added 1-formylcyclobutane-11-carbonitrile (93-3, 183 mg, 1.68 mmol, in DCM (3 mL) followed by sodium triacetoxyborohydride (356 mg, 1.68 mmol). The resulting mixture stirred at rt for 3 days. Additional sodium triacetoxyborohydride (225 mg, 1.06 mmol) was added and stirring was continued at 40° C. and then at rt. The reaction mixture was filtered over Celite® eluting with DCM and the filtrate was concentrated to dryness. The crude material was purified via C-18 reverse phase chromatography eluting with 10-100% MeCN/water with 0.1% formic acid and the further purified using reverse phase HPLC (Column: Xbridge C18 OBD 5 um 30×50 mm; Conditions: Water/MeCN with 10 mM NH$_4$OH 75 mL/min; 1.5 mL injection; Gradient: 25-50% MeCN, 3.5 min gradient; collection tubes contained several drops of formic acid). The fraction containing the desired product were combined and lyophilized to afford I-111 (0.7 mg, 1 μmol, 0.2% yield). MS [M+H]$^+$=451.2. $^1$H NMR (400 MHz, DCM-d$_2$) δ 7.95 (s, 1H), 7.71 (d, J=8.5 Hz, 1H), 7.04 (d, J=5.7 Hz, 2H), 5.13 (dt, J=13.5, 4.3 Hz, 1H), 4.48-4.23 (m, 2H), 4.17-4.10 (m, 1H), 2.95 (s, 2H), 2.89-2.73 (m, 3H), 2.47-2.31 (m, 2H), 2.24-1.91 (m, 7H), 1.77 (m, 4H), 1.44-1.22 (m, 4H).

Example 94: 3-(5-(((1S,2S)-2-(3-(2-chlorophenoxy)azetidin-1-yl)cyclohexyl)oxy)-1-oxoisoindolin-2-yl)piperidine-2,6-dione (I-112)

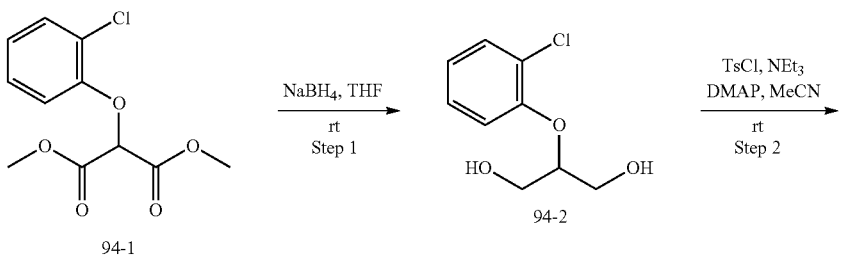

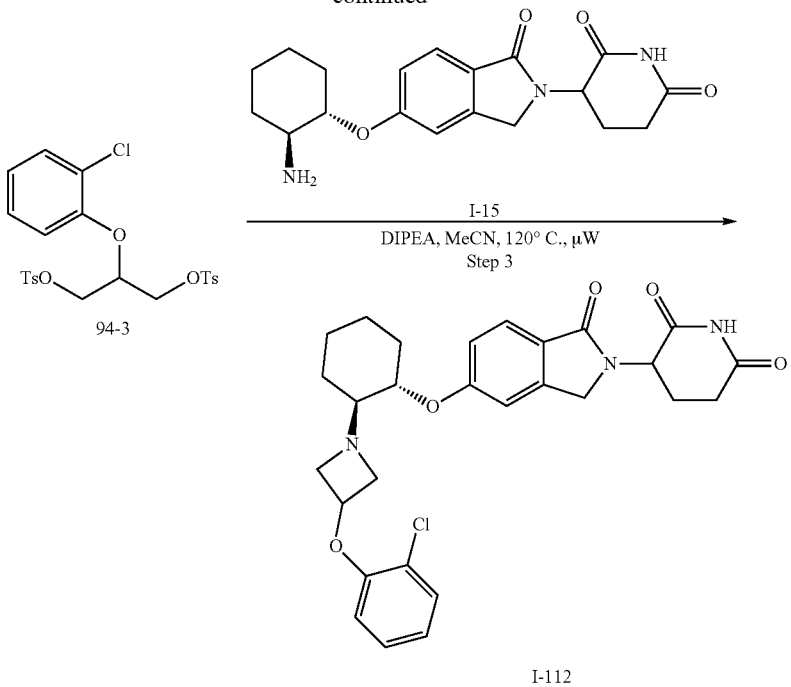

Step 1. 2-(2-chlorophenoxy)propane-1,3-diol (94-2)

Sodium borohydride (189 mg, 5.00 mmol) was added to a solution of dimethyl 2-(2-chlorophenoxy)malonate (94-1, 259 mg, 1.0 mmol) in THF (4 mL) and MeOH (1.0 mL). The resulting mixture was stirred at rt for 90 minutes and then quenched with water. The phases were separated and the aqueous phase was extracted with EtOAc (×3). The combined organic layers were washed with brine, dried over Na$_2$SO$_4$, filtered, and concentrated to dryness to afford 94-2 (105 mg, 0.518 mmol, 52% yield) as a colorless oil. $^1$H NMR (400 MHz, Chloroform-d) δ 7.20-7.15 (m, 2H), 6.89-6.81 (m, 2H), 4.31 (quint, J=4.8 Hz, 1H), 3.89-3.76 (m, 4H).

Step 2. 2-(2-chlorophenoxy)propane-1,3-diyl bis(4-methylbenzenesulfonate) (94-3)

TsCl (350 mg, 1.84 mmol) was added to a solution of 2-(2-chlorophenoxy)propane-1,3-diol (94-2, 105 mg, 0.52 mmol), DMAP (6 mg, 0.05 mmol), and TEA (0.3 mL, 2 mmol) in MeCN (2 mL). The resulting mixture was stirred at rt for 4 h, and then filtered and concentrated. The crude material was purified via silica gel chromatography eluting with 0-60% EtOAc in heptane to afford 94-3 (160 mg, 0.313 mmol, 60% yield) as a yellow solid. MS [M+H$_2$O]$^+$=528.2. $^1$H NMR (400 MHz, Chloroform-d) δ 7.75-7.70 (m, 4H), 7.34-7.29 (m, 4H), 7.17-7.13 (m, 2H), 6.68-6.63 (m, 2H), 4.52 (quint, J=5.0 Hz, 1H), 4.22-4.12 (m, 4H), 2.45 (s, 6H).

Step 3. 3-(5-(((1S,2S)-2-(3-(2-chlorophenoxy)azetidin-1-yl)cyclohexyl)oxy)-1-oxoisoindolin-2-yl)piperidine-2,6-dione (I-112)

DIPEA (0.10 mL, 0.57 mmol) was added to a solution of 3-(5-(((1S,2S)-2-aminocyclohexyl)oxy)-1-oxoisoindolin-2-yl)piperidine-2,6-dione (I-15, 50 mg, 0.14 mmol) and 2-(2-chlorophenoxy)propane-1,3-diyl bis(4-methylbenzenesulfonate) (94-3, 71.5 mg, 0.14 mmol) in MeCN (0.75 mL). The resulting mixture was stirred at 120° C. under μW irradiation for 4 h and then was concentrated. The crude material was purified via silica gel chromatography eluting with 0-50% EtOAc:EtOH (v/v=3:1, with 0.1% Et$_3$N) in DCM (with 0.1% Et$_3$N) to afford I-112 (30 mg, 0.054 mmol, 39% yield) as a white solid. MS [M+H]$^+$=524.3. $^1$H NMR (400 MHz, DMSO-d$_6$) δ 10.95 (s, 1H), 7.61 (d, J=8.4 Hz, 1H), 7.32-7.26 (m, 2H), 7.17 (s, 1H), 7.03 (d, J=8.2 Hz, 1H), 6.88-6.80 (m, 2H), 5.06 (dd, J=13.2, 5.1 Hz, 1H), 4.70 (quint, J=5.6 Hz, 1H), 4.38 (dd, J=17.2, 7.0 Hz, 1H), 4.32-4.21 (m, 2H), 3.76-3.64 (m, 2H), 3.22-3.14 (m, 1H), 3.09-3.01 (m, 1H), 2.95-2.85 (m, 1H), 2.64-2.55 (m, 1H), 2.44-2.34 (m, 2H), 2.04-1.94 (m, 2H), 1.89-1.79 (m, 1H), 1.71-1.61 (m, 2H), 1.42-1.32 (m, 2H), 1.31-1.05 (m, 2H).

Example 95: 3-(5-(((1S,2S)-2-(3-(2-methoxyphenoxy)azetidin-1-yl)cyclohexyl)oxy)-1-oxoisoindolin-2-yl)piperidine-2,6-dione (I-113)

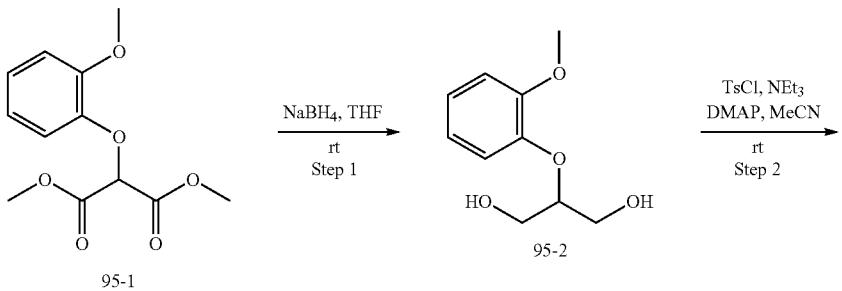

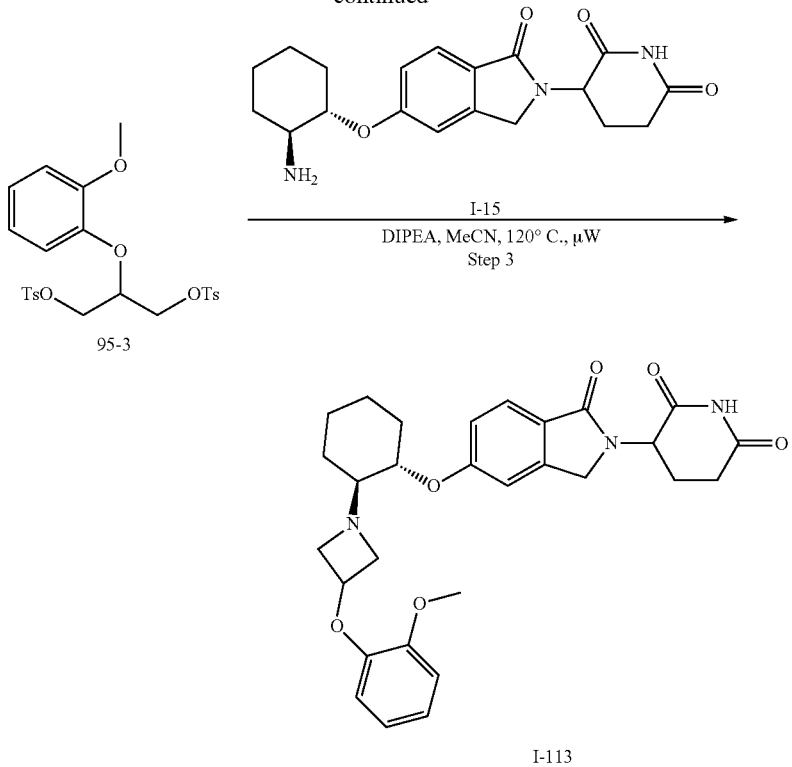

Step 1. 2-(2-methoxyphenoxy)propane-1,3-diol (95-2)

Sodium borohydride (189 mg, 5.00 mmol) was added to a solution of dimethyl 2-(2-methoxyphenoxy)malonate (95-1, 254 mg, 1 mmol) in THF (4 mL) and MeOH (1 mL). The resulting mixture was stirred at rt for 90 minutes and then quenched with water. The layers separated and the aqueous phase was extracted with EtOAc (×3). The combined organic layers were washed with brine, dried over $Na_2SO_4$, filtered, and concentrated to afford 95-2 (103 mg, 0.520 mmol, 52% yield), which was taken onto the next step without purification.

Step 2. 2-(2-methoxyphenoxy)propane-1,3-diyl bis(4-methylbenzenesulfonate) (95-3)

TsCl (248 mg, 1.30 mmol) was added to a solution of 2-(2-methoxyphenoxy)propane-1,3-diol (95-2, 103 mg, 0.520 mmol), DMAP (6 mg, 0.05 mmol), and TEA (0.3 mL, 2 mmol) in MeCN (2 mL). The resulting mixture was stirred at rt for 4 h and then concentrated. The crude material was purified via silica gel chromatography eluting with 0-60% EtOAc in heptane to afford 95-3 (100 mg, 0.20 mmol, 38% yield) as a light brown oil. MS $[M+H]^+=507.2$. $^1$H NMR (400 MHz, Chloroform-d) δ 7.78-7.72 (m, 4H), 7.35-7.30 (m, 4H), 7.01 (ddd, J=8.2, 6.6, 2.5 Hz, 1H), 6.85 (dd, J=8.1, 1.3 Hz, 1H), 6.81-6.74 (m, 2H), 4.44 (quint, J=5.0 Hz, 1H), 4.26-4.15 (m, 4H), 3.76 (s, 3H), 2.45 (s, 6H)

Step 3. 3-(5-(((1S,2S)-2-(3-(2-methoxyphenoxy)azetidin-1-yl)cyclohexyl)oxy)-1-oxoisoindolin-2-yl)piperidine-2,6-dione (I-113)

DIPEA (0.05 mL, 0.3 mmol) was added to a solution of 3-(5-(((1S,2S)-2-aminocyclohexyl)oxy)-1-oxoisoindolin-2-yl)piperidine-2,6-dione (I-15, 35.3 mg, 0.1 mmol) and 2-(2-methoxyphenoxy)propane-1,3-diyl bis(4-methylbenzenesulfonate) (95-3, 50 mg, 0.1 mmol) in MeCN (0.75 mL). The resulting mixture was stirred at 120° C. under μW irradiation for 8 h and then concentrated. The crude material was purified via silica gel chromatography eluting with 0-65% EtOAc:EtOH (v/v=3:1, with 0.1% $Et_3N$) in DCM (with 0.1% $Et_3N$) to afford I-113 (20 mg, 0.037 mmol, 37% yield) as a white solid. MS $[M+H]^+=520.4$. $^1$H NMR (400 MHz, DMSO-$d_6$) δ 10.95 (s, 1H), 7.61 (d, J=8.4 Hz, 1H), 7.18 (d, J=2.2 Hz, 1H), 7.04 (dd, J=8.5, 2.2 Hz, 1H), 6.95 (dd, J=8.0, 1.6 Hz, 1H), 6.88 (td, J=7.7, 1.6 Hz, 1H), 6.81 (td, J=7.7, 1.7 Hz, 1H), 6.70 (dd, J=7.9, 1.6 Hz, 1H), 5.06 (dd, J=13.3, 5.1 Hz, 1H), 4.69-4.59 (m, 1H), 4.38 (dd, J=17.2, 6.4 Hz, 1H), 4.26 (dd, J=17.1, 5.2 Hz, 2H), 3.76-3.64 (m, 2H), 3.74 (s, 3H), 3.25-3.17 (m, 1H), 3.05 (t, J=6.4 Hz, 1H), 2.97-2.84 (m, 1H), 2.64-2.55 (m, 1H), 2.45-2.33 (m, 2H), 2.05-1.93 (m, 2H), 1.90-1.78 (m, 1H), 1.70-1.59 (m, 2H), 1.42-1.05 (m, 4H).

Example 96: 3-(1-oxo-5-(((1S,2S)-2-((pyrazolo[1,5-a]pyrimidin-6-ylmethyl)amino)cyclohexyl)oxy)isoindolin-2-yl)piperidine-2,6-dione (I-114)

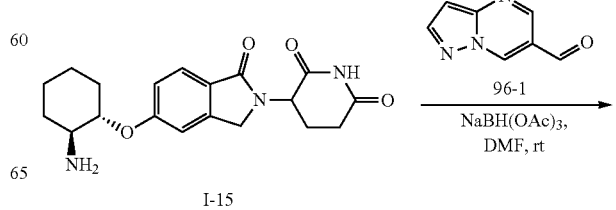

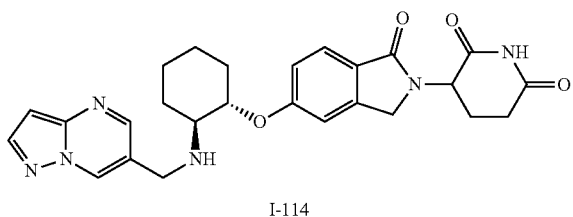

I-114

To a solution of 3-(5-(((1S,2S)-2-aminocyclohexyl)oxy)-1-oxoisoindolin-2-yl)piperidine-2,6-dione (I-15, 0.10 g, 0.28 mmol) in DMF (0.93 mL), was added pyrazolo[1,5-a]pyrimidine-6-carbaldehyde (96-1, 49 mg, 0.34 mmol) and the resulting mixture was stirred at rt for 15 minutes. Sodium triacetoxyborohydride (89 mg, 0.42 mmol) was added and stirring was continued at rt for 16 h. The reaction mixture was concentrated and then diluted with DCM (1 mL) and MeCN (2 mL). Additional pyrazolo[1,5-a]pyrimidine-6-carbaldehyde (96-1, 20 mg, 0.14 mmol) was added and the reaction mixture was sonicated for 30 minutes at rt. Sodium triacetoxyborohydride (50 mg, 0.24 mmol) was added and the resulting mixture was sonicated for another 30 minutes at rt. The reaction mixture was concentrated onto Celite® and the crude material was purified by silica gel chromatography eluting with 0-100% EtOAc:EtOH (v/v=3:1, with 0.1% Et$_3$N) in heptane and then further purified by reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) to afford the formate salt of I-114 (9 mg, 0.02 mmol, 6% yield) as a white solid. MS [M+H]$^+$=489.4 $^1$H NMR (400 MHz, DMSO-d$_6$) δ 10.96 (s, 1H), 9.00-8.95 (m, 1H), 8.53 (t, J=2.2 Hz, 1H), 8.14 (d, J=2.1 Hz, 1H), 7.58 (dd, J=8.4, 2.0 Hz, 1H), 7.17 (dd, J=4.3, 2.1 Hz, 1H), 7.07 (ddd, J=8.4, 3.6, 2.2 Hz, 1H), 6.66 (d, J=2.4 Hz, 1H), 5.06 (dd, J=13.3, 5.1 Hz, 1H), 4.39-4.15 (m, 3H), 3.89 (q, J=14.3 Hz, 2H), 2.91 (ddd, J=17.1, 13.5, 5.4 Hz, 1H), 2.71-2.55 (m, 2H), 2.44-2.35 (m, 1H), 2.13-1.92 (m, 3H), 1.65 (d, J=10.1 Hz, 2H), 1.42-1.23 (m, 4H).

Example 97: 3-(5-(((1S,2S)-2-((4,4-difluorocyclohexyl)amino)cyclohexyl)oxy)-1-oxoisoindolin-2-yl)piperidine-2,6-dione (I-115)

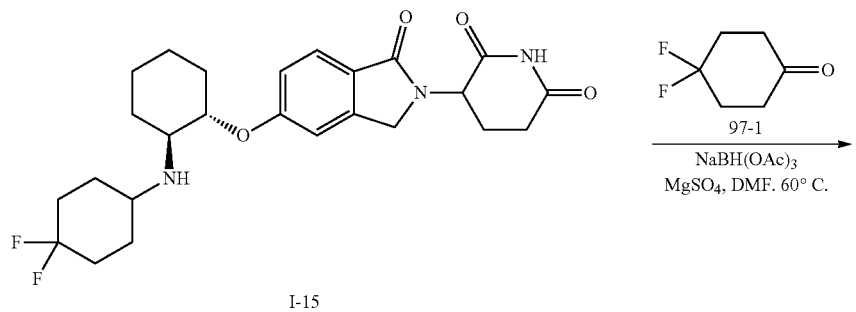

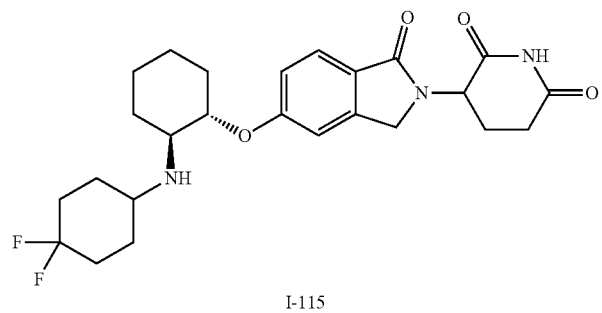

I-115

To 3-(5-(((1S,2S)-2-aminocyclohexyl)oxy)-1-oxoisoindolin-2-yl)piperidine-2,6-dione (I-15, 50 mg, 0.14 mmol), 4,4-difluorocyclohexan-1-one (97-1, 375 mg, 2.8 mmol), and MgSO$_4$ (51 mg, 0.42 mmol) in DMF (0.5 mL) was added with NaBH(OAc)$_3$ (59 mg, 0.28 mmol) in one portion. The resulting mixture was stirred at 60° C. for 16 h and then diluted with DCM (2 mL), filtered, and concentrated. The crude material was purified via silica gel chromatography eluting with 0-100% EtOAc:EtOH (v/v=3:1, with 1% Et$_3$N) in DCM to afford I-115 (36 mg, 0.08 mmol, 55% yield) as a white solid. MS [M+H]$^+$=476.3. $^1$H NMR (400 MHz, DCM-d$_2$) δ 7.69 (d, J=8.4 Hz, 1H), 7.10-6.86 (m, 2H), 5.10 (ddd, J=13.3, 5.2, 2.4 Hz, 1H), 4.43-4.21 (m, 2H), 4.13-3.96 (m, 1H), 2.93-2.70 (m, 4H), 2.31 (qd, J=12.9, 5.9 Hz, 1H), 2.21-2.09 (m, 2H), 2.07-1.89 (m, 5H), 1.88-1.64 (m, 6H), 1.42-1.24 (m, 5H).

Example 98: 3-(5-(((1S,2S)-2-((2,4-difluorobenzyl)amino)cyclohexyl)oxy)-1-oxoisoindolin-2-yl)piperidine-2,6-dione (I-116)

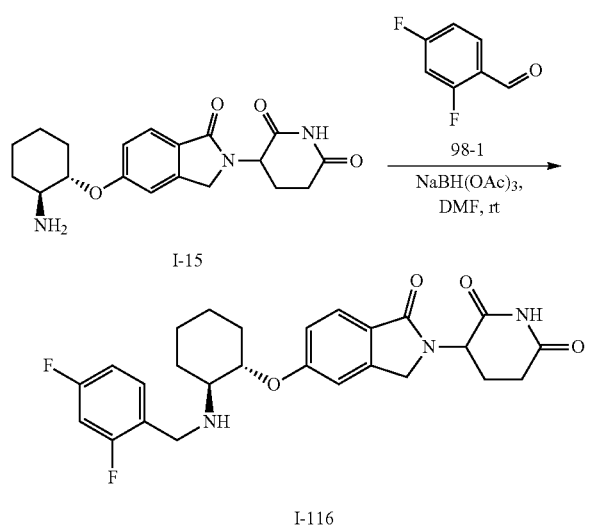

To a solution of 3-(5-(((1S,2S)-2-aminocyclohexyl)oxy)-1-oxoisoindolin-2-yl)piperidine-2,6-dione (I-15, 100 mg, 0.28 mmol) in DMF (2 mL) under an atmosphere of nitrogen was added 2,4-difluorobenzaldehyde (98-1, 0.03 mL, 0.31 mmol) and the resulting mixture was stirred at rt for 30 minutes. Sodium triacetoxyborohydride (178 mg, 0.839 mmol) was then added and stirring was continued at rt for 16 h. The reaction mixture was added to a saturated aqueous solution of sodium hydrogen carbonate (30 mL). The resulting suspension was sonicated and filtered and the solid was rinsed with water (×3). The filtrate was extracted with 20% i-PrOH in DCM (×3). The combined organic phases were passed through a phase separating column and concentrated. The isolated solid and product from extraction were combined and purified via silica gel chromatography eluting with 0-15% i-PrOH (with 0.1% NEt$_3$) in DCM (with 0.1% NEt$_3$) to afford I-116 (22 mg, 0.04 mmol, 15% yield) as a white solid. MS [M+H]$^+$ 484.2. $^1$H NMR (400 MHz, DMSO-d$_6$) δ (ppm): 10.95 (s, 1H), 7.60 (d, J=8.4 Hz, 1H), 7.48 (td, J=8.7, 6.8 Hz, 1H), 7.20-7.10 (m, 2H), 7.08-6.98 (m, 2H), 5.06 (dd, J=13.3, 5.1 Hz, 1H), 4.42-4.19 (m, 3H), 3.87-3.73 (m, 2H), 2.90 (ddd, J=18.0, 13.6, 5.4 Hz, 1H), 2.68-2.55 (m, 2H), 2.39 (td, J=13.0, 4.3 Hz, 1H), 2.10-2.02 (m, 1H), 2.02-1.93 (m, 2H), 1.70-1.61 (m, 2H), 1.41-1.16 (m, 4H).

Example 99: 3-(5-(((1S,2S)-2-(3-isopropoxyazetidin-1-yl)cyclohexyl)oxy)-1-oxoisoindolin-2-yl)piperidine-2,6-dione (I-53)

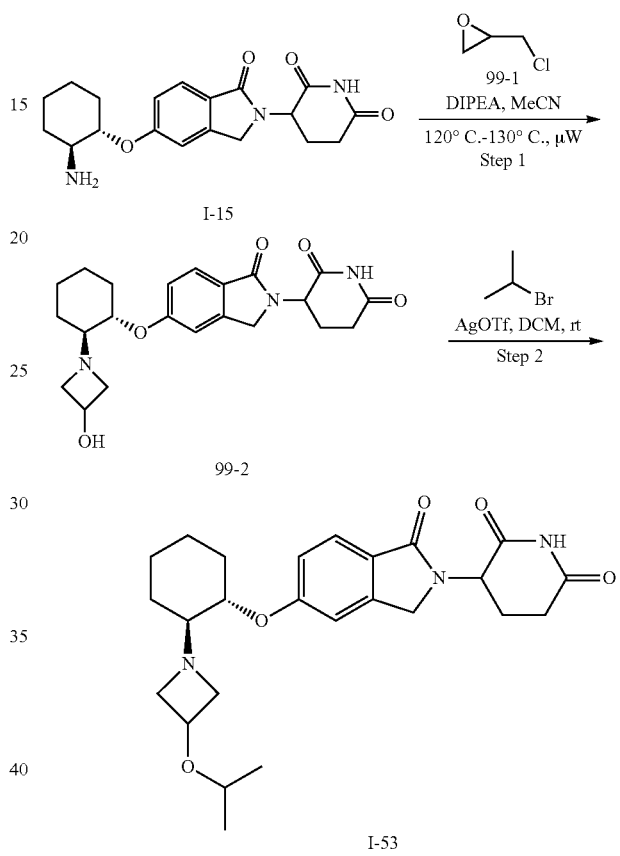

Step 1. 3-(5-(((1S,2S)-2-(3-hydroxyazetidin-1-yl)cyclohexyl)oxy)-1-oxoisoindolin-2-yl)piperidine-2,6-dione (99-2)

Epichlorohydrin (99-1, 0.12 mL, 1.5 mmol) and DIPEA (0.12 mL, 0.70 mmol) were added to a solution of 3-(5-(((1S,2S)-2-aminocyclohexyl)oxy)-1-oxoisoindolin-2-yl)piperidine-2,6-dione (I-15, 50 mg, 0.14 mmol) in MeCN (4 mL) and the resulting mixture was stirred at 120° C. under μW irradiation for 1 h, then stirred at 130° C. under μW irradiation for 1 h. The reaction mixture was concentrated, taken up in DCM, and extracted with 1M HCl (aq) (×3). The combined aqueous phases were washed with DCM. The phases were separated and the aqueous phase was cooled and basified to a pH of 9-10 with solid NaHCO$_3$. The basic aqueous phase was extracted with DCM (×4) and the combined organic phases were dried over Na$_2$SO$_4$, filtered, and concentrated to afford crude 99-2 (80 mg) as a pale yellow solid. MS [M+H]$^+$=414.3, which was taken onto the next step without purification.

Step 2. 3-(5-(((1S,2S)-2-(3-isopropoxyazetidin-1-yl)cyclohexyl)oxy)-1-oxoisoindolin-2-yl)piperidine-2,6-dione (I-53)

2-Bromopropane (165-1, 0.16 mL, 1.7 mmol) was added to a solution of 3-(5-(((1S,2S)-2-(3-hydroxyazetidin-1-yl)cyclohexyl)oxy)-1-oxoisoindolin-2-yl)piperidine-2,6-dione (99-2, 70 mg, 0.17 mmol) and AgOTf (217 mg, 0.85 mmol) in DCM (0.5 mL) and the resulting mixture was stirred at rt for 16 h. The reaction mixture was diluted with DCM and filtered. The filtrate was washed with saturated NaHCO$_3$ (aq) and the phases were separated. The aqueous phase was extracted with DCM and the combined organic layers were dried over Na$_2$SO$_4$, filtered, and concentrated to dryness. The crude material was purified via silica gel chromatography eluting with 0-100% EtOAc:EtOH (v/v=3:1, with 0.1% NEt$_3$) in DCM (with 0.1% NEt$_3$) to afford I-53 (9 mg, 0.02 mmol, 11% yield) as a pale yellow solid. MS [M+H]$^+$ =456.4. $^1$H NMR (400 MHz, DMSO-d$_6$) δ 10.96 (s, 1H), 7.61 (d, J=8.4 Hz, 1H), 7.15 (s, 1H), 7.02 (dd, J=8.4, 2.2 Hz, 1H), 5.07 (dd, J=13.3, 5.1 Hz, 1H), 4.38 (dd, J=17.2, 5.8 Hz, 1H), 4.28-4.18 (m, 2H), 4.01-3.91 (m, 1H), 3.54-3.42 (m, 3H), 2.98-2.84 (m, 2H), 2.77 (t, J=6.4 Hz, 1H), 2.63-2.55 (m, 1H), 2.42-2.35 (m, 1H), 2.31-2.24 (m, 1H), 2.02-1.91 (m, 2H), 1.78 (d, J=12.3 Hz, 1H), 1.68-1.55 (m, 2H), 1.40-1.19 (m 4H), 1.02 (d, J=6.1 Hz, 6H).

Example 100: 3-(5-(((1S,2S)-2-(((1R,2R)-2-methoxycyclopentyl)amino)cyclohexyl)oxy)-1-oxoisoindolin-2-yl)piperidine-2,6-dione and 3-(5-(((1S,2S)-2-(((1S,2S)-2-methoxycyclopentyl)amino)cyclohexyl)oxy)-1-oxoisoindolin-2-yl)piperidine-2,6-dione (I-118 & I-119)

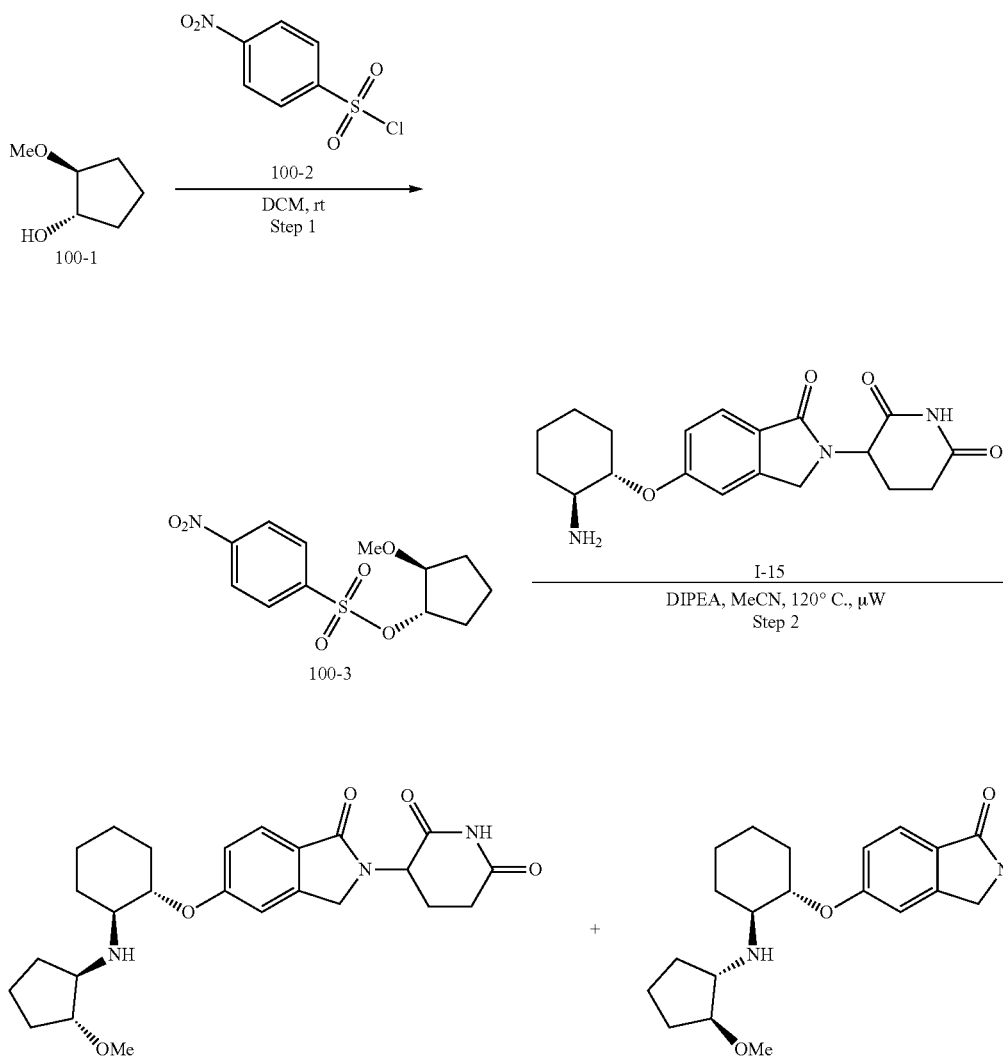

I-118 & I-119

Step 1. (1S,2S)-2-methoxycyclopentyl 4-nitrobenzenesulfonate (100-3)

To (1S,2S)-2-methoxycyclopentan-1-ol (100-1, 110 mg, 0.95 mmol) and 1-methyl-1H-imidazole (0.38 mL, 4.7 mmol) in DCM (10 mL) was added 4-nitrobenzenesulfonyl chloride (100-2, 210 mg, 0.95 mmol). The resulting mixture was stirred overnight at rt and then quenched with saturated aqueous $NaHCO_3$ and extracted with DCM (×3). The combined organic phases were dried over $Na_2SO_4$, filtered, and concentrated to afford 100-3 (128 mg, 0.43 mmol, 45% yield). The crude product was taken onto the next step without purification.

Step 2. 3-(5-(((1S,2S)-2-(((1R,2R)-2-methoxycyclopentyl)amino)cyclohexyl)oxy)-1-oxoisoindolin-2-yl)piperidine-2,6-dione or 3-(5-(((1S,2S)-2-(((1S,2S)-2-methoxycyclopentyl)amino)cyclohexyl)oxy)-1-oxoisoindolin-2-yl)piperidine-2,6-dione (I-118 & I-119)

To 3-(5-(((1S,2S)-2-aminocyclohexyl)oxy)-1-oxoisoindolin-2-yl)piperidine-2,6-dione (I-15, 50 mg, 0.14 mmol) in DIPEA (0.15 mL, 0.84 mmol) and MeCN (0.5 mL) was added (1S,2S)-2-methoxycyclopentyl 4-nitrobenzenesulfonate (100-3, 105 mg, 0.35 mmol) and the resulting mixture was stirred at 120° C. for 4 h. The reaction mixture was concentrated and the crude material was purified by reverse phase HPLC (Column: Xbridge C18 OBD 5 um 30×50 mm; Conditions: Water/MeCN with 5 mM $NH_4OH$ 75 mL/min; 1.5 mL injection; Gradient: 15-40% MeCN, 3.5 min gradient; collected fractions contained ~3 drops of formic acid). The fractions containing the desired product were combined and lyophilized to afford one diastereomer (I-118, 4.5 mg, 8.6 µmol, 6% yield) as a white solid. MS [M+H]$^+$=456.3. $^1$H NMR (400 MHz, MeCN-d$_3$) δ 7.62 (d, J=8.4 Hz, 1H), 7.17-7.10 (m, 1H), 7.03 (dd, J=8.4, 2.2 Hz, 1H), 5.03 (ddd, J=13.4, 5.2, 2.5 Hz, 1H), 4.34 (d, J=16.7 Hz, 1H), 4.26 (dd, J=16.7, 3.8 Hz, 1H), 4.12 (s, 1H), 3.51-3.33 (m, 1H), 3.22 (d, J=2.2 Hz, 3H), 3.14-3.05 (m, 1H), 2.89-2.66 (m, 3H), 2.39 (qd, J=13.2, 4.9 Hz, 1H), 2.12-2.04 (m, 4H), 1.91-1.84 (m, 1H), 1.80-1.67 (m, 3H), 1.64-1.46 (m, 3H), 1.42-1.35 (m, 2H), 1.32-1.26 (m, 2H). The relative stereochemistry of the substituents on the cyclopentane ring was not determined and was assigned arbitrarily.

A second impure product was isolated which was further purified by reverse phase HPLC (Column: Xbridge C18 OBD 5 um 30×50 mm; Conditions: Water/MeCN with 5 mM $NH_4OH$ 75 mL/min; 1.5 mL injection; Gradient: 25-50% MeCN, 3.5 min gradient; collected fractions contained ~3 drops of formic acid) to afford the formate salt of the second diastereomer (I-119, 4.4 mg, 8.8 µmol, 6% yield) as a white solid. MS [M+H]$^+$=456.3. $^1$H NMR (400 MHz, MeCN-d$_3$+ drop of D$_2$O) δ 8.29 (s, 1H), 7.60 (dd, J=8.4, 2.9 Hz, 1H), 7.07 (d, J=2.2 Hz, 1H), 7.03-6.94 (m, 1H), 4.96 (ddd, J=13.4, 5.2, 1.4 Hz, 1H), 4.35-4.17 (m, 3H), 3.71-3.54 (m, 1H), 3.27 (s, 2H), 3.25-3.17 (m, 1H), 3.10 (d, J=0.9 Hz, 1H), 2.91-2.81 (m, 1H), 2.80-2.72 (m, 1H), 2.67-2.59 (m, 1H), 2.32 (qd, J=13.2, 4.9 Hz, 1H), 2.17-2.00 (m, 3H), 1.82-1.44 (m, 7H), 1.42-1.16 (m, 5H). The relative stereochemistry of the substituents on the cyclopentane ring was not determined and was assigned arbitrarily.

Example 101: 3-((((1S,2S)-2-((2-(2,6-dioxopiperidin-3-yl)-1-oxoisoindolin-5-yl)oxy)cyclohexyl)amino)methyl)bicyclo[1.1.1]pentane-1-carbonitrile (I-120)

Step 1. 3-formylbicyclo[1.1.1]pentane-1-carbonitrile (101-2)

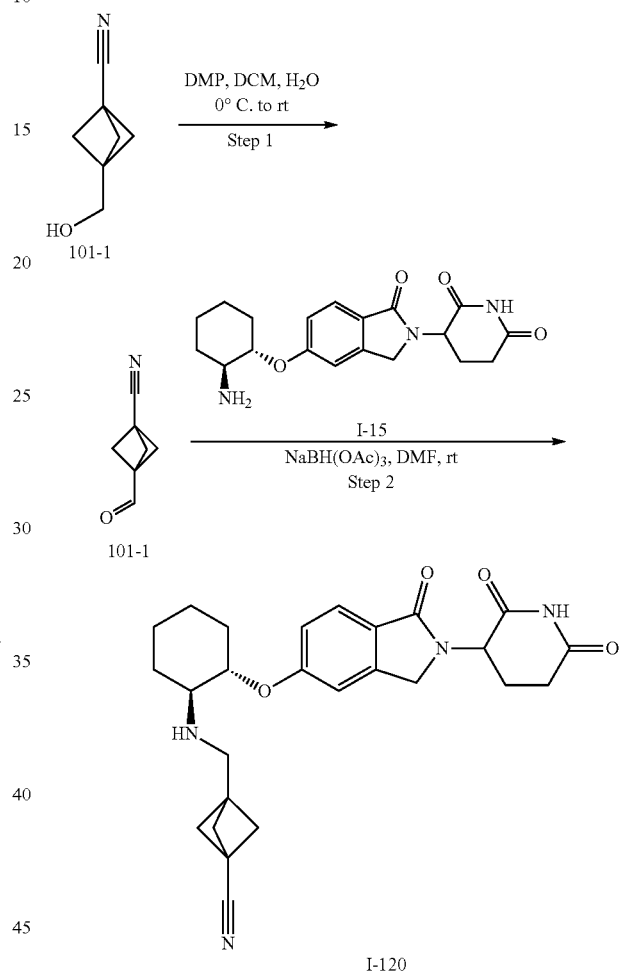

3-(hydroxymethyl)bicyclo[1.1.1]pentane-1-carbonitrile (101-1, 124 mg, 1.01 mmol) was dissolved in DCM (5.0 mL) and cooled to 0° C. DMP (540 mg, 1.27 mmol) was added followed by 2 drops of water. The resulting mixture was stirred at rt for 2 h, quenched with saturated aqueous sodium bicarbonate:saturated aqueous sodium thiosulfate:diethyl ether (v/v/v=1:1:2) and then stirred until the cloudy mixture turned clear. The organic phase was separated and the aqueous phase was extracted with diethyl ether (×2). The combined organic phases were passed through a phase separator and concentrated. The crude material was dissolved in DCM (5.0 mL) and cooled to 0° C. DMP (780 mg, 1.84 mmol) was added followed by 3 drops of water. The resulting mixture was stirred at rt for 18 h, quenched with saturated aqueous sodium bicarbonate:saturated aqueous sodium thiosulfate:diethyl ether (v/v/v=1:1:2), and then stirred until the cloudy mixture turned clear. The organic phase was separated and the aqueous phase was extracted with diethyl ether (×2). The combined organic phases were passed through a phase separator and concentrated to afford crude 101-2 as a cream-colored oil. The crude material was taken onto the next step without purification.

Step 2. 3-((((1S,2S)-2-((2-(2,6-dioxopiperidin-3-yl)-1-oxoisoindolin-5-yl)oxy)cyclohexyl)amino)methyl)bicyclo[1.1.1]pentane-1-carbonitrile (I-120)

To a solution of 3-(5-(((1S,2S)-2-aminocyclohexyl)oxy)-1-oxoisoindolin-2-yl)piperidine-2,6-dione (I-15, 0.15 g, 0.42 mmol) in DMF (1 mL) was added 3-formylbicyclo[1.1.1]pentane-1-carbonitrile (101-2, 61 mg, 0.50 mmol) and the resulting mixture was stirred at rt for 15 minutes. Sodium triacetoxyborohydride (133 mg, 0.630 mmol) was added and stirring was continued at rt for 1.5 h. The reaction mixture was then quenched with saturated aqueous sodium bicarbonate and extracted with 20% i-PrOH in DCM (×3). The combined organic phases were passed through a phase separator and concentrated onto Celite®. The crude product was purified by silica gel chromatography eluting with 0-100% EtOAc:EtOH (v/v=3:1, with 1% Et$_3$N) in heptane to afford I-120 (67.7 mg, 0.14 mmol, 34% yield) as a cream-colored solid. MS [M+H]$^+$=463.2. $^1$H NMR (400 MHz, DMSO-d$_6$) δ 10.96 (s, 1H), 7.61 (d, J=8.4 Hz, 1H), 7.20 (d, J=2.2 Hz, 1H), 7.07 (dd, J=8.2, 2.3 Hz, 1H), 5.07 (dd, J=13.3, 5.1 Hz, 1H), 4.38 (dd, J=17.1, 8.5 Hz, 1H), 4.32-4.14 (m, 2H), 2.91 (ddd, J=17.1, 13.6, 5.3 Hz, 1H), 2.70-2.55 (m, 4H), 2.40 (td, J=13.1, 4.5 Hz, 1H), 2.11-2.02 (br s, 6H), 2.02-1.94 (m, 1H), 1.94-1.85 (m, 1H), 1.70-1.59 (m, 2H), 1.39-1.08 (m, 5H).

Example 102: 3-(5-(((1S,2S)-2-(3-(3-fluorophenoxy)azetidin-1-yl)cyclohexyl)oxy)-1-oxoisoindolin-2-yl)piperidine-2,6-dione (I-121)

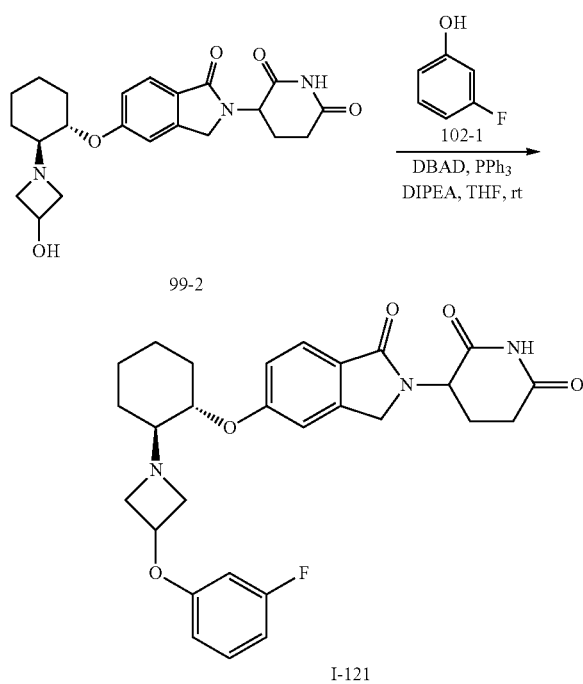

To a solution of di-tert-butyl (E)-diazene-1,2-dicarboxylate (16.7 mg, 0.073 mmol) in THF (0.25 mL) was added to a solution of 3-(5-(((1S,2S)-2-(3-hydroxyazetidin-1-yl)cyclohexyl)oxy)-1-oxoisoindolin-2-yl)piperidine-2,6-dione (99-2, 20 mg, 0.048 mmol), triphenylphosphine (19 mg, 0.073 mmol), DIPEA (0.013 mL, 0.073 mmol) and 3-fluorophenol (102-1, 4 µL, 0.05 mmol) in THF (0.25 mL). The resulting mixture was stirred at rt for 16 h and then diluted with DCM and washed with 50% saturated Na$_2$CO$_3$ (aq). The phases were separated and the aqueous phase was extracted with DCM. The combined organic layers were dried and concentrated. The crude material was purified via reverse phase HPLC (Column: XBridge C18 OBD 30×50 mm; 15-40% MeCN in H$_2$O+0.1% Formic Acid over 3.5 min at 75 mL/min). The fractions containing the desired product were combined and lyophilized to afford I-121 (8 mg, 0.01 mmol, 27% yield) as a white solid. MS [M+H]$^+$=508.3. $^1$H NMR (400 MHz, DMSO-d$_6$) δ 10.96 (s, 1H), 7.61 (d, J=8.4 Hz, 1H), 7.28 (q, J=8.2 Hz, 1H), 7.21-7.13 (m, 2H), 7.04 (dd, J=8.4, 2.2 Hz, 1H), 6.79-6.72 (m, 1H), 6.71-6.63 (m, 2H), 6.62-6.53 (m, 2H), 5.07 (dd, J=13.3, 5.1 Hz, 1H), 4.78-4.71 (m, 1H), 4.38 (dd, J=17.2, 6.8 Hz, 1H), 4.25 (dd, J=17.2, 5.5 Hz, 2H), 3.79-3.65 (m, 1H), 3.22-3.12 (m, 1H), 3.05 (t, J=6.5 Hz, 1H), 2.95-2.85 (m, 1H), 2.63-2.53 (m, 1H), 2.04-1.92 (m, 2H), 1.88-1.77 (m, 1H), 1.69-1.54 (m, 2H), 1.45-1.22 (m, 4H).

Example 103: 3-(5-(((1S,2S)-2-(((3,3-difluorocyclobutyl)methyl)amino)cyclohexyl)oxy)-1-oxoisoindolin-2-yl)piperidine-2,6-dione (I-122)

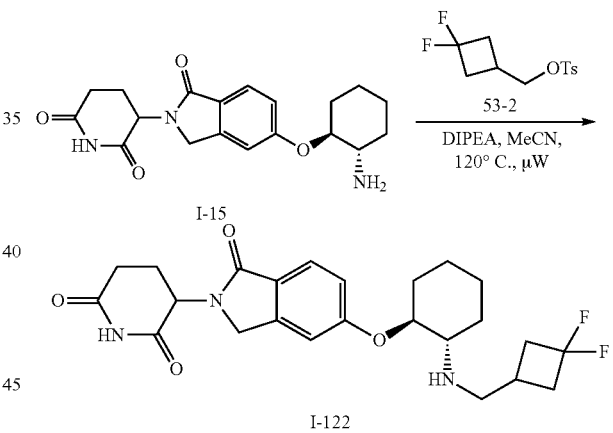

To a solution of 3-(5-(((1S,2S)-2-aminocyclohexyl)oxy)-1-oxoisoindolin-2-yl)piperidine-2,6-dione (I-15, 200 mg, 0.56 mmol) in MeCN (10 mL) was added (3,3-difluorocyclobutyl)methyl 4-methylbenzenesulfonate (53-2, 262 mg, 0.95 mmol) and DIPEA (0.49 mL, 2.8 mmol) and the resulting mixture was stirred at 120° C. for 16 h under µW irradiation. The reaction mixture was then diluted with saturated aqueous sodium bicarbonate solution and extracted with EtOAc (3×30 mL). The combined organic phases were washed with brine, dried over Na$_2$SO$_4$, filtered, and concentrated. The crude material was purified via silica gel chromatography eluting with 5% MeOH in DCM to afford I-122 (80 mg, 0.17 mmol, 31% yield) as an off-white solid. MS [M+H]$^+$=462.5. $^1$H NMR (400 MHz, DMSO-d$_6$): δ 10.97 (s, 1H), 7.62 (d, J=8.4 Hz, 1H), 7.197 (s, 1H), 7.06 (d, J=8.4 Hz, 1H), 5.08 (dd, J=13.2, 4.8 Hz, 1H), 4.40-4.23 (m, 4H), 2.95-2.86 (m, 1H), 2.66-2.61 (m, 3H), 2.56-2.33 (m, 2H), 2.19-2.16 (m, 3H), 2.08-1.92 (m, 3H), 1.75-1.64 (m, 3H), 1.35-1.14 (m, 5H).

Example 104: 3-(5-(((1S,2S)-2-(((4-methoxycyclohexyl)methyl)amino)cyclohexyl)oxy)-1-oxoisoindolin-2-yl)piperidine-2,6-dione (I-123)

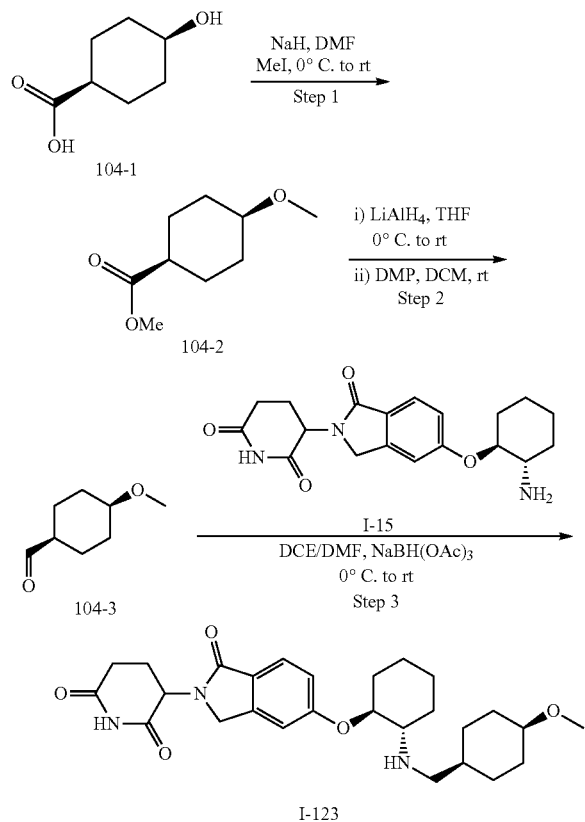

Step 1. cis-Methyl 4-methoxycyclohexane-1-carboxylate (104-2)

To a solution of cis-4-hydroxycyclohexane-1-carboxylic acid (104-1, 2.00 g, 13.9 mmol) in DMF (20 mL) was added NaH (1.38 g, 34.7 mmol) in small portions at 0° C. and the resulting mixture was stirred for 30 min. Methyl iodide (2.6 mL, 42 mmol) was added and stirring was continued at rt for 4 h. Upon complete consumption of the starting material, the reaction mixture was quenched with ice-cold water and extracted with EtOAc (2×100 mL). The combined organic phases were washed with brine, dried over $Na_2SO_4$, filtered, and concentrated to dryness. The obtained crude material was purified by silica gel chromatography eluting with 20% EtOAc in heptanes to afford compound 104-2 (1.20 g, 6.97 mmol, 52% yield) as an oil. $^1H$ NMR (600 MHz, $CDCl_3$): δ 3.65 (s, 3H), 3.36-3.32 (m, 1H), 3.28 (s, 3H), 2.36-2.32 (m, 1H), 1.88-1.79 (m, 4H), 1.65-1.61 (m, 2H), 1.58-1.47 (m, 2H).

Step 2. cis-4-Methoxycyclohexane-1-carbaldehyde (104-3)

To a solution of cis-methyl 4-methoxycyclohexane-1-carboxylate (104-2, 1.2 g, 6.97 mmol) in THF (15 mL) was added $LiAlH_4$ (387 mg, 10.46 mmol) dropwise at 0° C. and the resulting mixture was warmed to rt and stirred for 4 h. Upon complete consumption of the starting material, the reaction mixture was quenched with ice-cold water and extracted with EtOAc (3×50 mL). The organic phase was washed with brine, dried over $Na_2SO_4$, filtered, and concentrated to dryness. This material was taken in DCM (10 mL), DMP (1.30 g, 6.25 mmol) was added and the resulting mixture was stirred at rt for 4 h. Upon complete consumption of the starting material, the reaction mixture was diluted with DCM (10 mL), filtered through a small pad of Celite® and washed with DCM (10 mL). The combined filtrate was dried over $Na_2SO_4$, filtered, and concentrated under reduced pressure. The crude material was purified by silica gel chromatography eluting with 10% EtOAc in hexanes to afford 104-3 (450 mg, 3.17 mmol, 76% yield) as colorless liquid. $^1H$ NMR (300 MHz, $CDCl_3$): δ 9.61 (s, 1H), 3.37-3.35 (m, 1H), 3.30 (s, 3H), 2.29-2.21 (m, 1H), 1.82-1.57 (m, 8H).

Step 3. 3-(5-(((1S,2S)-2-(((4-methoxycyclohexyl)methyl)amino)cyclohexyl)oxy)-1-oxoisoindolin-2-yl)piperidine-2,6-dione (I-123)

To a solution of 3-(5-(((1S,2S)-2-aminocyclohexyl)oxy)-1-oxoisoindolin-2-yl)piperidine-2,6-dione (I-15, 0.20 g, 0.56 mmol) and cis-4-methoxycyclohexane-1-carbaldehyde (104-3, 0.12 g, 0.84 mmol) in DCE-DMF (9:1) (10 mL) was added $NaBH(OAc)_3$ (0.18 g, 0.84 mmol) at 0° C. and the resulting mixture was stirred at rt for 16 h. The reaction mixture was then quenched with saturated aqueous sodium bicarbonate solution and extracted with EtOAc (3×30 mL). The combined organic phases were washed with brine, dried over $Na_2SO_4$, filtered, and concentrated under reduced pressure. The obtained crude material was purified via silica gel chromatography eluting with 5% MeOH in DCM to afford I-123 (50 mg, 0.10 mmol, 18% yield). MS $[M+H]^+=484.5$. $^1H$ NMR (400 MHz, DMSO-$d_6$): δ 10.97 (s, 1H), 7.62 (d, J=8.4 Hz, 1H), 7.197 (s, 1H), 7.06 (d, J=8.4 Hz, 1H), 5.08 (dd, J=13.2, 4.8 Hz, 1H), 4.41-4.22 (m, 4H), 3.16 (s, 3H), 2.95-2.86 (m, 2H), 2.61-2.33 (m, 5H), 2.08-1.98 (m, 3H), 1.72-1.64 (m, 4H), 1.45-1.29 (m, 7H), 1.27-1.14 (m, 4H).

Example 105: 3-(5-(((1S,2S)-2-(3-(cyclopropylmethoxy)azetidin-1-yl)cyclohexyl)oxy)-1-oxoisoindolin-2-yl)piperidine-2,6-dione (I-51)

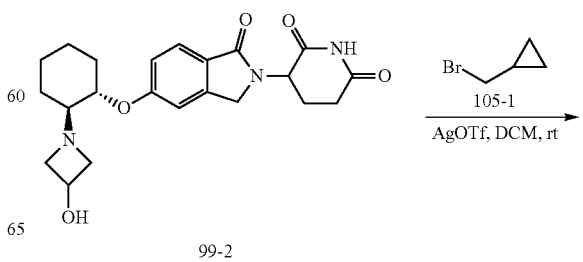

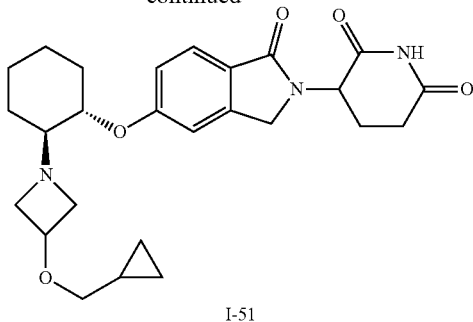

I-51

(Bromomethyl)cyclopropane (105-1, 123 µL, 1.27 mmol) was added to a solution of 3-(5-(((1S,2S)-2-(3-hydroxyazetidin-1-yl)cyclohexyl)oxy)-1-oxoisoindolin-2-yl)piperidine-2,6-dione (99-2, 70 mg, 0.10 mmol) and AgOTf (163 mg, 0.63 mmol) (mixed with Celite® 1:1) in DCM (1 mL) and the resulting mixture was stirred at rt for 3 h. The reaction mixture was then diluted with DCM, filtered, and concentrated to dryness. The crude material was taken up in 1M HCl (aq) and washed with EtOAc (×3). The acidic layer was basified using NaHCO$_3$ and extracted with DCM. The combined organic phases were dried over Na$_2$SO$_4$, filtered, and concentrated to dryness. The crude material was purified via silica gel chromatography eluting 0-100% EtOAc:EtOH (v/v=3:1, with 0.1% Et$_3$N) in DCM (with 0.1% Et$_3$N) to afford I-51 (13 mg, 0.026 mmol, 26% yield) as a pale yellow solid. MS [M+H]$^+$=468.3. $^1$H NMR (400 MHz, DMSO-d$_6$) δ 10.96 (s, 1H), 7.61 (d, J=8.4 Hz, 1H), 7.16 (s, 1H), 7.02 (d, J=8.4 Hz, 1H), 5.07 (dd, J=13.3, 5.1 Hz, 1H), 4.38 (dd, J=17.2, 5.5 Hz, 1H), 4.25 (dd, J=17.3, 5.0 Hz, 2H), 3.98-3.84 (m, 1H), 3.51-3.38 (s, 2H), 3.11 (d, J=6.8 Hz, 1H), 3.04-2.77 (m, 2H), 2.59 (d, J=16.6 Hz, 1H), 2.43-2.34 (m, 2H), 2.12-2.02 (m, 1H), 2.02-1.89 (m, 2H), 1.86-1.70 (m, 2H), 1.67-1.50 (m, 2H), 1.48-1.00 (m, 6H), 0.49-0.38 (m, 1H), 0.15-0.08 (m, 1H).

Example 106: 3-(1-oxo-5-(((1S,2S)-2-(3-(2,2,2-trifluoroethoxy)azetidin-1-yl)cyclohexyl)oxy)isoindolin-2-yl)piperidine-2,6-dione (I-49)

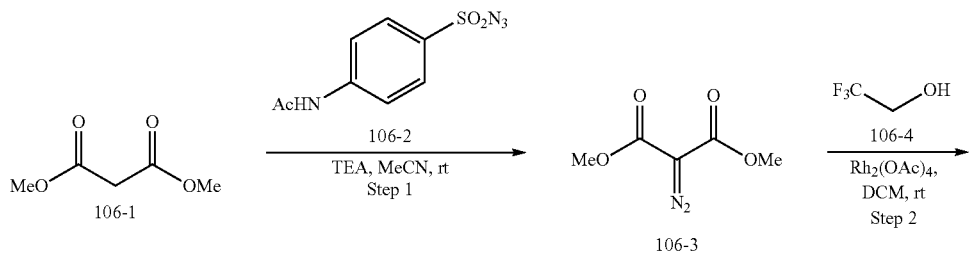

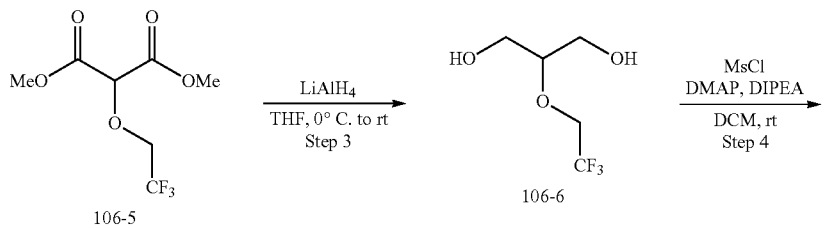

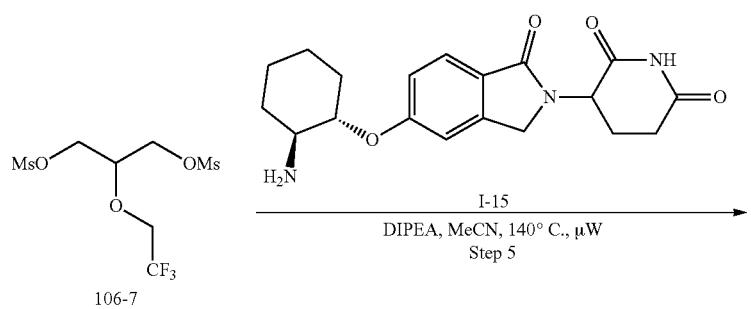

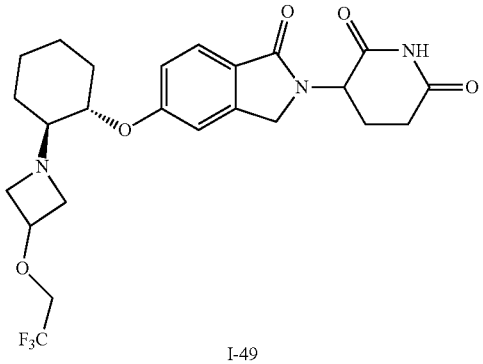

I-49

Step 1. Dimethyl 2-diazomalonate (106-3)

To a solution of 4-acetamidobenzenesulfonyl azide (106-2, 6.47 g, 26.1 mmol), TEA (5.8 mL, 42 mmol) and MeCN (80 mL) was added dimethyl malonate (106-1, 2.0 mL, 17 mmol) dropwise at 0° C. and the resulting mixture was stirred vigorously overnight. The reaction mixture was then diluted with $Et_2O$ (200 mL) and filtered. The filtrate was concentrated, the crude material was dissolved in minimal amount of DCM, and excess heptane was added until precipitation of a white solid occurred. The solids were filtered off and the filtrate was concentrated. This sequence was repeated three more times to afford 106-3 (1.92 g, 12.1 mmol, 70% yield) as a pale yellow oil. $^1$H NMR (400 MHz, Chloroform-d) δ 3.86 (s, 6H).

Step 2. Dimethyl 2-(2,2,2-trifluoroethoxy)malonate (106-5)

To a solution of dimethyl 2-diazomalonate (106-3, 500 mg, 3.16 mmol), TFE (106-4, 1.04 mL, 15.8 mmol) and DCM (4 mL) under an atmosphere of nitrogen was added rhodium (II) acetate (12.5 mg, 0.032 mmol) in a single portion and the resulting mixture was stirred at rt overnight. The reaction mixture was concentrated to dryness and the crude material purified via silica gel chromatography eluting with 100% DCM to afford 106-5 (640 mg, 2.80 mmol, 88% yield) as a yellow oil. $^1$H NMR (400 MHz, Chloroform-d) δ 4.73 (s, 1H), 4.11 (q, J=8.5 Hz, 2H), 3.84 (s, 6H).

Step 3. 2-(2,2,2-trifluoroethoxy)propane-1,3-diol (106-6)

To a solution of dimethyl 2-(2,2,2-trifluoroethoxy)malonate (106-5, 640 mg, 2.8 mmol) in THF (10 mL) under an atmosphere of nitrogen was added 2M $LiAlH_4$ in THF (2.8 mL, 5.7 mmol) dropwise at 0° C. The resulting mixture was stirred at 30 min at 0° C. and then at rt overnight. The reaction mixture was cooled to 0° C., diluted with THF (20 mL), and $Na_2SO_4 \cdot 10H_2O$ (900 mg) was added slowly portion wise. After stirring for 10 min, $Na_2SO_4$ (approx. 300 mg) was added stirring was continued vigorously for 10 min and then the rest of $Na_2SO_4 \cdot 10H_2O$ (444 mg) was added portion wise. Additional $Na_2SO_4$ (approx. 300 mg) was added and stirring was continued for 3 hours at rt. The reaction mixture was filtered through a pad of Celite® (washed with minimal amount of EtOAc). The filtrate was concentrated to dryness to afford 106-6 (273 mg, 1.57 mmol, 56% yield) as a colorless oil, which was carried onto the next step without purification. $^1$H NMR (400 MHz, DCM-$d_2$) δ 4.04 (q, J=8.8 Hz, 2H), 3.77-3.66 (m, 4H), 3.65-3.58 (m, 1H).

Step 4. 2-(2,2,2-trifluoroethoxy)propane-1,3-diyl dimethanesulfonate (106-7)

To a solution of 2-(2,2,2-trifluoroethoxy)propane-1,3-diol (106-6, 273 mg, 1.57 mmol), DIPEA (0.68 mL, 3.9 mmol), DMAP (19 mg, 0.16 mmol) in DCM (5 mL) was added MsCl (0.27 mL, 3.5 mmol) dropwise at 0° C. and the resulting mixture was stirred at rt for 4 h. The reaction mixture was then quenched with saturated aqueous $NaHCO_3$ at 0° C. and extracted with DCM (×2). The combined organic phases were dried over $Na_2SO_4$, filtered, and concentrated to afford 106-7. The crude material was taken onto the next step without purification.

Step 5. 3-(1-oxo-5-(((1S,2S)-2-(3-(2,2,2-trifluoroethoxy)azetidin-1-yl)cyclohexyl)oxy)isoindolin-2-yl)piperidine-2,6-dione (I-49)

To a solution of 3-(5-(((1S,2S)-2-aminocyclohexyl)oxy)-1-oxoisoindolin-2-yl)piperidine-2,6-dione (I-15, 380 mg, 1.06 mmol) and DIPEA (1.1 mL, 6.3 mmol) in MeCN (1 mL) was added a solution of 2-(2,2,2-trifluoroethoxy)propane-1,3-diyl dimethanesulfonate (106-7, 527 mg, 1.60 mmol) in MeCN (1 mL). The resulting mixture was stirred at 140° C. for 14 h in the μW and then concentrated. The crude material was purified via silica gel chromatography eluting with 0 to 100% EtOAc:EtOH (v/v=3:1, with 1% $Et_3N$) in DCM to afford I-49 (41.6 mg, 0.081 mmol, 8% yield) as a white powder. MS $[M+H]^+$=496.2. $^1$H NMR (400 MHz, DCM-$d_2$) δ 8.75 (s, 1H), 7.70 (dd, J=8.7, 4.4 Hz, 1H), 7.03-6.86 (m, 2H), 5.11 (ddd, J=13.5, 8.5, 5.2 Hz, 1H), 4.39-4.18 (m, 3H), 4.13 (quint, J=5.9 Hz, 1H), 3.75 (q, J=8.8 Hz, 2H), 3.62 (dq, J=14.7, 6.6 Hz, 2H), 3.24 (q, J=7.2 Hz, 1H), 3.04 (t, J=6.7 Hz, 1H), 2.91-2.74 (m, 2H), 2.49-2.38 (m, 1H), 2.37-2.25 (m, 1H), 2.22-2.13 (m, 1H), 2.09-2.01 (m, 1H), 1.92-1.83 (m, 1H), 1.79-1.66 (m, 2H), 1.45-1.10 (m, 4H).

Example 107: 3-(5-(((1S,2S)-2-(3-(2,2-difluoroeth-oxy)azetidin-1-yl)cyclohexyl)oxy)-1-oxoisoindolin-2-yl)piperidine-2,6-dione (I-50)

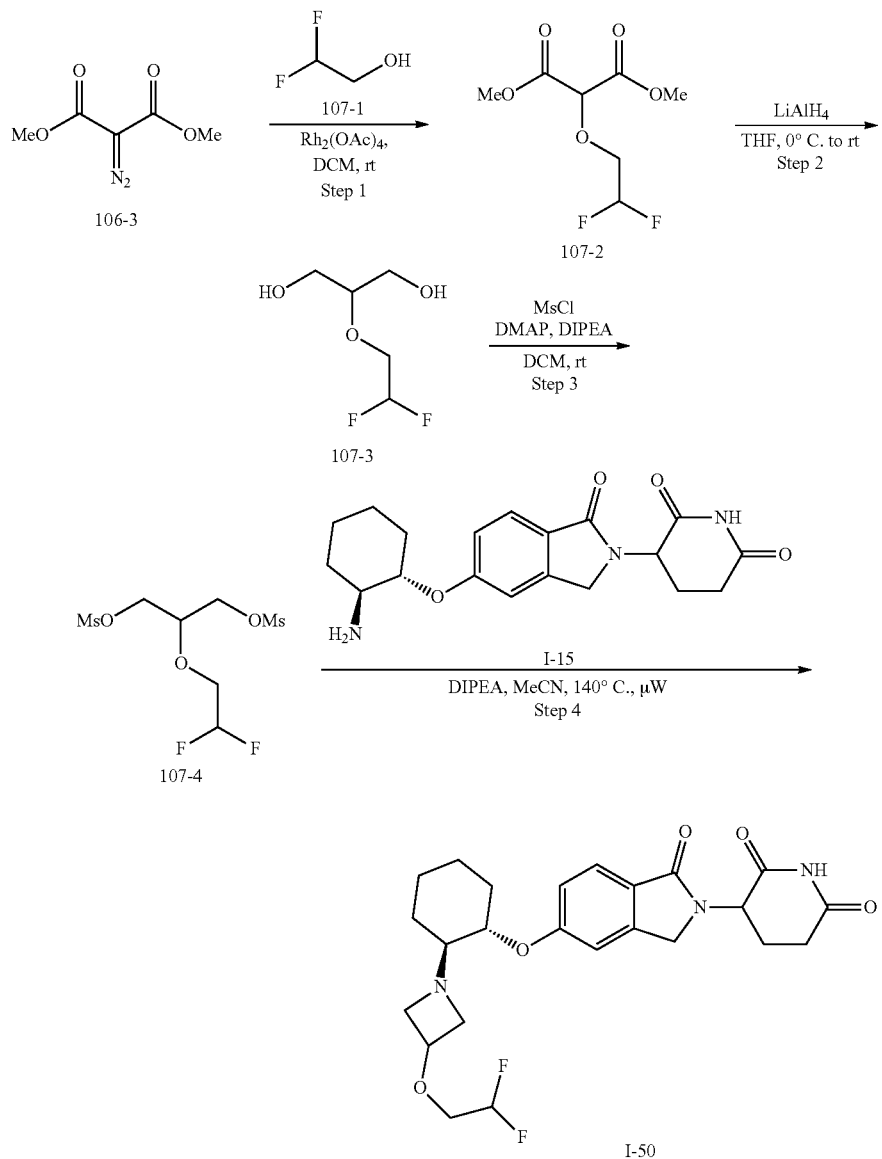

Step 1. Dimethyl 2-(2,2-difluoroethoxy)malonate (107-2)

To dimethyl 2-diazomalonate (106-3, 500 mg, 3.16 mmol), 2,2-difluoroethan-1-ol (107-1, 1297 mg, 15.8 mmol) and DCM (4 mL) under nitrogen atmosphere was added rhodium (II) acetate (12.5 mg, 0.032 mmol) in a single portion. The reaction mixture was stirred at rt overnight. The reaction mixture was concentrated to dryness. The crude material was purified via silica gel chromatography eluting with 100% DCM to afford 107-2 (470 mg, 2.22 mmol, 70% yield) as a yellow oil. $^1$H NMR (400 MHz, Chloroform-d) δ 6.00 (tt, J=55.2, 4.2 Hz, 1H), 4.76 (t, J=6.4 Hz, 1H), 3.96-3.87 (m, 2H), 3.85 (s, 6H).

Step 2. 2-(2,2-difluoroethoxy)propane-1,3-diol (107-3)

To dimethyl 2-(2,2-difluoroethoxy)malonate (107-2, 470 mg, 2.22 mmol) in THF (5 mL) under nitrogen atmosphere was added 2M LiAlH$_4$ in THF (2.2 mL, 4.4 mmol) dropwise at 0° C. The reaction mixture was stirred for 30 min at 0° C. and at rt overnight. The reaction mixture was cooled to 0° C., diluted with THF (20 mL) and Na$_2$SO$_4$.10H$_2$O (1071 mg) was added slowly portionwise. The reaction mixture was stirred vigorously for 1 hour. Celite R was added to the reaction mixture until the solids were free flowing and the reaction mixture was stirred for 40 min at rt. Suspension was filtered, washing with THF (minimal) and concentrated to dryness to afford 107-3 (147 mg, 0.942 mmol, 43% yield) as a colorless oil. ¹H NMR (400 MHz, DCM-d₂) δ 6.17-5.78 (m, 1H), 3.97-3.82 (m, 2H), 3.81-3.57 (m, 5H).

Step 3. 2-(2,2-difluoroethoxy)propane-1,3-diyl dimethanesulfonate (107-4)

To 2-(2,2-difluoroethoxy)propane-1,3-diol (107-3, 147 mg, 0.942 mmol), DIPEA (0.41 mL, 2.4 mmol), and DMAP (11.5 mg, 0.094 mmol) in DCM (5 mL) was added MsCl (0.16 mL, 2.07 mmol) dropwise at 0° C. The resulting mixture was stirred at rt for 4 h. The reaction mixture was then quenched with saturated aqueous NaHCO₃ at 0° C. and then extracted with DCM (×2). The combined organic phases were dried over Na₂SO₄, filtered, and concentrated to dryness to afford 107-4, which was taken onto the next step without purification.

Step 4. 3-(5-(((1S,2S)-2-(3-(2,2-difluoroethoxy)azetidin-1-yl)cyclohexyl)oxy)-1-oxoisoindolin-2-yl)piperidine-2,6-dione (I-50)

To 3-(5-(((1S,2S)-2-aminocyclohexyl)oxy)-1-oxoisoindolin-2-yl)piperidine-2,6-dione (I-15, 220 mg, 0.62 mmol), DIPEA (0.64 mL, 3.7 mmol) and MeCN (1 mL) was added a solution of 2-(2,2-difluoroethoxy)propane-1,3-diyl dimethanesulfonate (107-4, 288 mg, 0.92 mmol) in MeCN (1 mL). The resulting mixture was stirred for 14 hours at 140° C. in the μW. The reaction mixture was then concentrated and the crude material was purified via silica gel chromatography eluting with 0 to 100% EtOAc:EtOH (v/v=3:1, with 1% Et₃N) in DCM to afford I-50 (20 mg, 0.04 mmol, 7% yield) as a white solid. MS [M+H]⁺=478.5. ¹H NMR (400 MHz, DCM-d₂) δ 8.31 (s, 1H), 7.86-7.46 (m, 1H), 7.08-6.81 (m, 2H), 5.81 (tt, J=55.3, 3.9 Hz, 1H), 5.22-5.01 (m, 1H), 4.39-4.14 (m, 3H), 4.06 (quint, J=5.8 Hz, 1H), 3.68-3.45 (m, 4H), 3.33-3.09 (m, 1H), 3.06-2.93 (m, 1H), 2.89-2.72 (m, 2H), 2.46-2.35 (m, 1H), 2.35-2.24 (m, 1H), 2.21-2.11 (m, 1H), 2.07-1.99 (m, 1H), 1.92-1.81 (m, 1H), 1.76-1.65 (m, 2H), 1.45-1.22 (m, 3H), 1.19-1.07 (m, 1H).

Example 108: 3-(5-(((1S,2S)-2-(3-(3,3-difluorocyclobutoxy)azetidin-1-yl)cyclohexyl)oxy)-1-oxoisoindolin-2-yl)piperidine-2,6-dione (I-56)

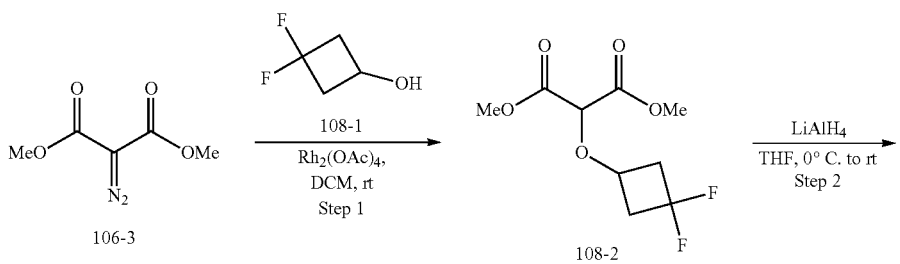

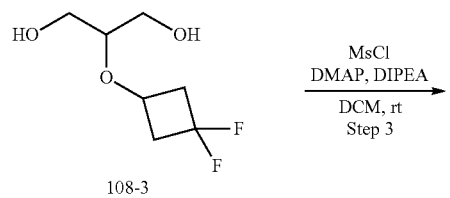

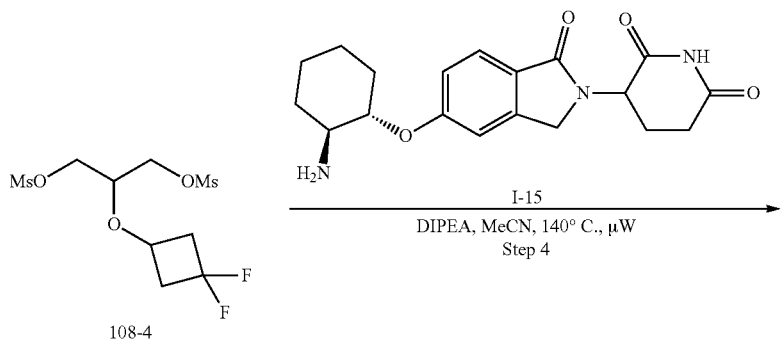

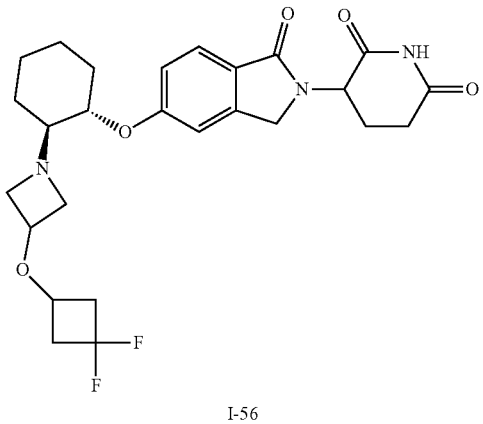

I-56

Step 1. Dimethyl 2-(3,3-difluorocyclobutoxy)malonate (108-2)

To dimethyl 2-diazomalonate (106-3, 500 mg, 3.16 mmol), 3,3-difluorocyclobutan-1-ol (108-1, 513 mg, 4.74 mmol), and DCM (4 mL) under an atmosphere of nitrogen was added rhodium (II) acetate (12.5 mg, 0.032 mmol) in a single portion. The reaction mixture was stirred at rt overnight and then concentrated to dryness. The crude material was purified via silica gel chromatography eluting with 100% DCM to afford 108-2 (649 mg, 2.72 mmol, 86% yield) as a yellow oil. $^1$H NMR (400 MHz, Chloroform-d) δ 4.47 (s, 1H), 4.19-4.12 (m, 1H), 3.82 (s, 6H), 2.95-2.84 (m, 2H), 2.77-2.66 (m, 2H).

Step 2. 2-(3,3-difluorocyclobutoxy)propane-1,3-diol (108-3)

To dimethyl 2-(3,3-difluorocyclobutoxy)malonate (108-2, 744 mg, 3.10 mmol) in THF (6 mL) under an atmosphere of nitrogen was added 2M LiAlH$_4$ in THF (3.1 mL, 6.3 mmol) dropwise at 0° C. The resulting mixture was stirred for 30 min at 0° C. and then at rt overnight. The reaction mixture was cooled to 0° C., diluted with THF (20 mL), and Na$_2$SO$_4$.10H$_2$O (1071 mg) was added slowly portionwise. The resulting mixture was stirred vigorously for 1 hour and Celite® was added until the solids were free flowing. The reaction mixture was stirred for 40 min at rt. The suspension was filtered, washed with THF (minimal), and the filtrate was concentrated to dryness to afford 108-3 (499 mg, 2.74 mmol, 88% yield) as a colorless oil. $^1$H NMR (400 MHz, DCM-d$_2$) δ 4.35-4.12 (m, 1H), 3.86-3.75 (m, 1H), 3.71-3.59 (m, 4H), 3.48-3.39 (m, 1H), 2.91-2.81 (m, 2H), 2.60-2.46 (m, 2H), 2.26-2.11 (m, 1H).

Step 3. 2-(3,3-difluorocyclobutoxy)propane-1,3-diyl dimethanesulfonate (108-4)

To 2-(3,3-difluorocyclobutoxy)propane-1,3-diol (108-3, 483 mg, 2.65 mmol), DIPEA (1.2 mL, 6.6 mmol), and DMAP (32 mg, 0.27 mmol) in DCM (5 mL) was added MsCl (0.45 mL, 5.8 mmol) dropwise at 0° C. The resulting mixture was stirred at rt for 4 h and then quenched with saturated aqueous NaHCO$_3$ at 0° C. and extracted with DCM (x2). The combined organic phases were dried over Na$_2$SO$_4$, filtered, and concentrated to dryness to afford 108-4, which was taken onto the next step without purification.

Step 4. 3-(5-(((1S,2S)-2-(3-(3,3-difluorocyclobutoxy)azetidin-1-yl)cyclohexyl)oxy)-1-oxoisoindolin-2-yl)piperidine-2,6-dione (I-56)

To 3-(5-(((1S,2S)-2-aminocyclohexyl)oxy)-1-oxoisoindolin-2-yl)piperidine-2,6-dione (I-15, 450 mg, 1.26 mmol), DIPEA (1.3 mL, 7.5 mmol), and MeCN (2.5 mL) was added a solution of 2-(3,3-difluorocyclobutoxy)propane-1,3-diyl dimethanesulfonate (108-4, 852 mg, 2.52 mmol) in MeCN (1 mL). The resulting mixture was stirred for 14 hours at 140° C. in the μW and then concentrated. The crude material was purified via silica gel chromatography eluting with 0 to 100% EtOAc:EtOH (v/v=3:1, with 1% Et$_3$N) in DCM to afford I-56 (30 mg, 0.058 mmol, 5% yield) as a white solid. MS [M+H]$^+$=504.4. $^1$H NMR (400 MHz, DCM-d$_2$) δ 8.79 (s, 1H), 7.71 (s, 1H), 7.18-6.69 (m, 2H), 5.11 (ddd, J=13.5, 8.6, 5.1 Hz, 1H), 4.39-4.16 (m, 3H), 4.05-3.93 (m, 1H), 3.92-3.81 (m, 1H), 3.61 (s, 2H), 3.29-3.13 (m, 1H), 3.07-2.91 (m, 1H), 2.91-2.72 (m, 4H), 2.57-2.39 (m, 3H), 2.39-2.24 (m, 1H), 2.21-2.13 (m, 1H), 2.10-2.00 (m, 1H), 1.92-1.83 (m, 1H), 1.77-1.68 (m, 2H), 1.48-1.12 (m, 4H).

Example 109: 4-(((((1S,2S)-2-((2-(2,6-dioxopiperidin-3-yl)-1-oxoisoindolin-5-yl)oxy)cyclohexyl)amino)methyl)benzonitrile HC(O)OH Salt (I-129) and 4-(((((1S,2S)-2-((2-(2,6-dioxopiperidin-3-yl)-1-oxoisoindolin-5-yl)oxy)cyclohexyl)(methyl)amino)methyl)benzonitrile HC(O)OH Salt (I-130)

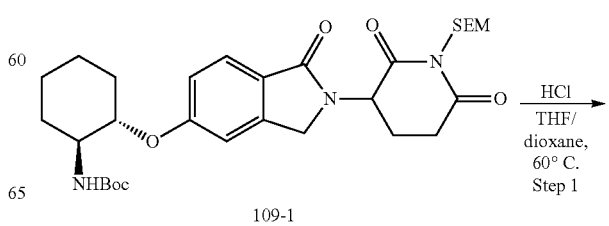

109-1

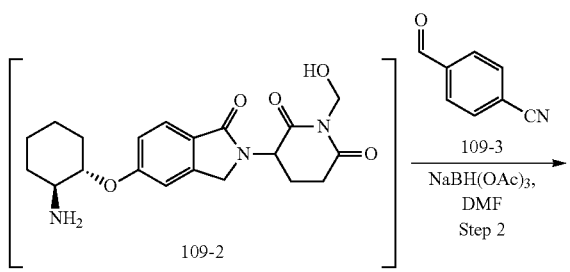

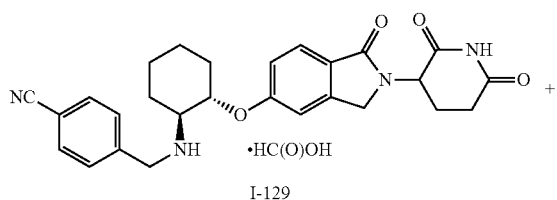

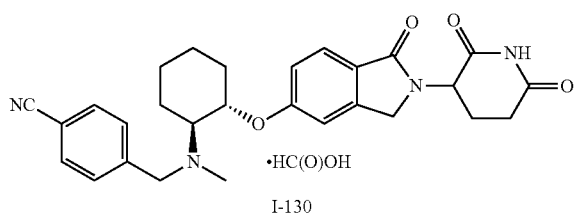

Step 1. 3-(5-(((1S,2S)-2-aminocyclohexyl)oxy)-1-oxoisoindolin-2-yl)-1-(hydroxymethyl)piperidine-2,6-dione (109-2)

To a stirred solution of tert-butyl ((1S,2S)-2-((2-(2,6-dioxo-1-((2-(trimethylsilyl)ethoxy)methyl)piperidin-3-yl)-1-oxoisoindolin-5-yl)oxy)cyclohexyl)carbamate (109-1, 860 mg, 1.46 mmol) in THF (4 mL) was added 4M hydrogen chloride in dioxane (8.0 mL, 32 mmol) and the resulting mixture stirred for 8 hours at 60° C. The reaction mixture was filtered and the obtained solid was washed with Et$_2$O (×3) and vacuum dried overnight to afford crude hydrochloride salt of 109-2 (525 mg, 1.08 mmol, 74% yield) as a white solid. The product was used in the next step without further purification. MS [M+2H]$^+$=389.3.

Step 2. 4-(((((1S,2S)-2-((2-(2,6-dioxopiperidin-3-yl)-1-oxoisoindolin-5-yl)oxy)cyclohexyl)amino)methyl) benzonitrile HC(O)OH Salt (I-129) and 4-(((((1S,2S)-2-((2-(2,6-dioxopiperidin-3-yl)-1-oxoisoindolin-5-yl)oxy)cyclohexyl)(methyl)amino)methyl) benzonitrile HC(O)OH Salt (I-130)

To a stirred solution of crude 109-2 (180 mg, 0.425 mmol), NaBH(OAc)$_3$ (135 mg, 0.637 mmol), and DMF (1 mL) under an atmosphere of nitrogen was added 4-formylbenzonitrile (109-3, 58.5 mg, 0.446 mmol) in one portion and the resulting mixture was stirred 2 h at room temperature and then concentrated. The crude material was purified by reverse phase HPLC (Column: Xbridge C18 OBD 5 um 30×50 mm; Conditions: Water/MeCN with 5 mM NH$_4$OH 75 mL/min; 1.5 mL injection; Gradient: 25-50% MeCN, 3.5 min gradient; collected fractions contained ~2 drops of formic acid) to afford the formate salt of I-129 (31 mg, 0.060 mmol, 14% yield) as a white solid and the formate salt of I-130 (25 mg, 0.048 mmol, 11% yield) as a white solid. Data for I-129: MS [M+H]$^+$=473.1. $^1$H NMR (400 MHz, MeCN-d$_3$) δ 8.88 (br s, 1H), 8.10 (s, 1H), 7.71-7.58 (m, 3H), 7.50-7.41 (m, 2H), 7.13-7.07 (m, 1H), 7.03 (dd, J=8.4, 2.3 Hz, 1H), 5.04 (ddd, J=13.4, 5.2, 2.1 Hz, 1H), 4.37-4.18 (m, 3H), 3.94 (d, J=14.8 Hz, 1H), 3.87 (d, J=14.7 Hz, 1H), 2.88-2.67 (m, 3H), 2.18-1.98 (m, 3H), 1.77-1.66 (m, 2H), 1.48-1.16 (m, 4H). Data for I-130: MS [M+H]$^+$=487.1. $^1$H NMR (400 MHz, DCM-d$_2$) δ 8.28 (s, 1H), 7.73 (d, J=8.4 Hz, 1H), 7.53 (dd, J=8.3, 2.5 Hz, 2H), 7.39 (t, J=8.3 Hz, 2H), 7.08-6.92 (m, 2H), 5.19-5.05 (m, 1H), 4.42-4.23 (m, 3H), 3.86 (d, J=14.6 Hz, 1H), 3.77 (dd, J=14.6, 3.8 Hz, 1H), 2.97-2.72 (m, 3H), 2.41-2.25 (m, 1H), 2.22 (d, J=2.3 Hz, 3H), 2.25-2.14 (m, 2H), 2.02-1.91 (m, 1H), 1.83-1.67 (m, 2H), 1.53-1.20 (m, 4H).

Example 110: 3-(5-(((1S,2S)-2-(3-isopropoxyazetidin-1-yl)cyclopentyl)oxy)-1-oxoisoindolin-2-yl)piperidine-2,6-dione (I-205)

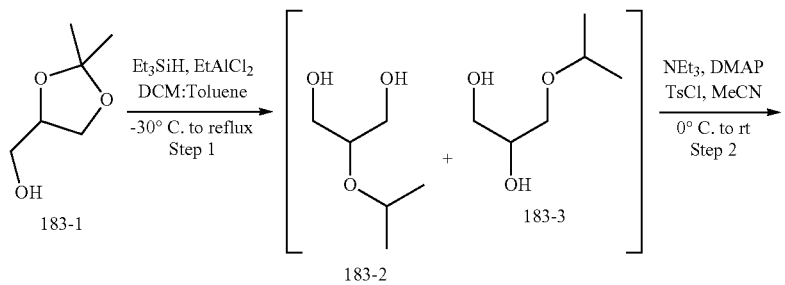

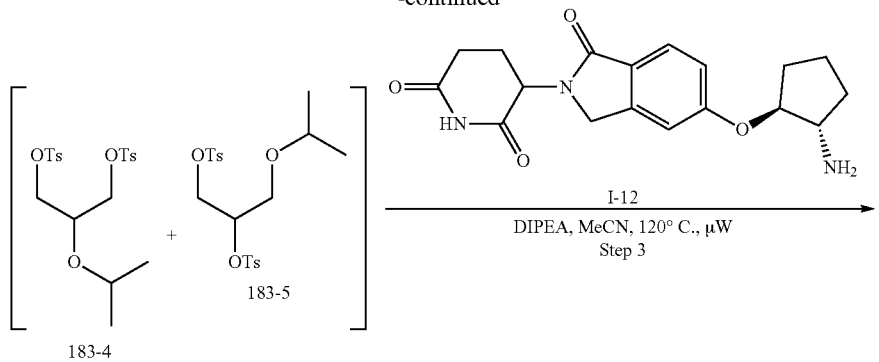

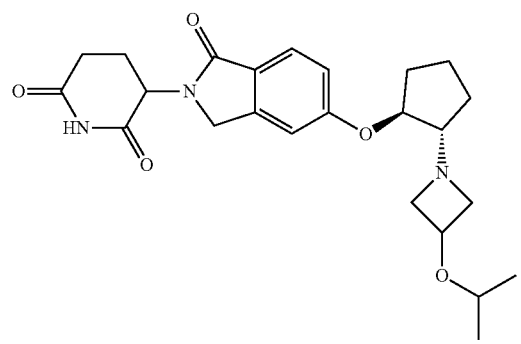

I-205

Step 1. 2-isopropoxypropane-1,3-diol & 3-isopropoxypropane-1,2-diol (183-2 and 183-3)

To a solution of (2,2-dimethyl-1,3-dioxolan-4-yl)methanol (183-1, 3.00 g, 22.7 mmol) in DCM (100 mL) was added triethyl silane (4.39 g, 27.2 mmol) and ethyl aluminum dichloride (25% in toluene (25.4 mL, 49.9 mmol) at −30° C. and the resulting mixture was stirred at rt for 2 h. The reaction mixture was quenched with aq. NaHCO$_3$ solution and extracted with DCM (3×100 mL). The combined organic phases were dried over anhydrous Na$_2$SO$_4$, filtered, and concentrated to dryness to afford a mixture of crude 183-2 and 183-3 (1.3 g, crude) as colorless liquid. The crude material was taken onto the next step without purification.

Step 2. 2-isopropoxypropane-1,3-diyl bis(4-methylbenzenesulfonate) & 3-isopropoxypropane-1,2-diyl bis(4-methylbenzenesulfonate) (183-4 and 183-5)

To a solution of a mixture of 183-2 and 183-3 (1.3 g, 9.6 mmol) in CH$_3$CN (30 mL) was added Et$_3$N (5.3 mL, 38 mmol), DMAP (0.04 g, 0.3 mmol) and TsCl (4.00 g, 21.1 mmol) at 0° C. and resulting mixture was stirred at room temperature for 16 h. The reaction mixture was then filtered and the filtrate was concentrated to dryness. The obtained crude material was purified by silica gel chromatography eluting with 10% EtOAc in hexanes to afford a mixture of 183-4 and 183-5 (3.1 g, 7.0 mmol, 73% yield) as a pale brown liquid. MS [M+H+18]$^+$=460.1.

Step 3. 3-(5-(((1S,2S)-2-(3-isopropoxyazetidin-1-yl)cyclopentyl)oxy)-1-oxoisoindolin-2-yl)piperidine-2,6-dione (I-205)

To a solution of I-12 (400 mg, 1.2 mmol) in MeCN (10 mL) was added a mixture of 183-4 and 183-5 (670 mg, 1.5 mmol) and DIPEA (0.62 mL, 3.5 mmol) and resulting mixture was stirred at 120° C. for 16 h under microwave irradiation. The reaction mixture was then diluted with sat. sodium bicarbonate solution and extracted with DCM (3×30 mL). The combined organic phases were washed with brine, dried over anhydrous Na$_2$SO$_4$, filtered, and concentrated to dryness. The obtained crude material was purified via preparative TLC in 3% MeOH in DCM as eluent to afford compound I-205 (20 mg, 0.05 mmol, 4% yield) as an off-white solid. MS [M+H]$^+$=442.4. $^1$H NMR (400 MHz, DMSO-d$_6$): δ 10.97 (s, 1H), 7.61 (d, J=8.4 Hz, 1H), 7.15 (s, 1H), 7.03 (d, J=8.4 Hz, 1H), 5.08 (dd, J=13.2, 4.8 Hz, 1H), 4.80-4.69 (m, 1H), 4.40-4.22 (m, 2H), 3.61-3.49 (m, 1H), 3.15-2.85 (m, 2H), 2.60-2.31 (m, 3H), 2.25-1.98 (m, 3H), 1.95-1.66 (m, 5H), 1.50-1.49 (m, 2H), 1.07-1.01 (m, 7H).

Example 111: 3-(5-(((1S,2S)-2-(ethylamino)cyclohexyl)oxy)-1-oxoisoindolin-2-yl)piperidine-2,6-dione (I-79) HC(O)OH Salt

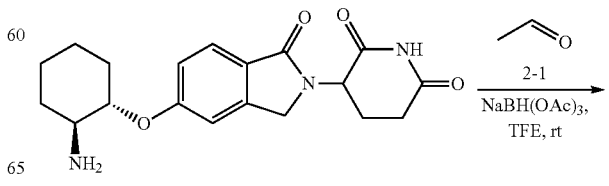

I-15

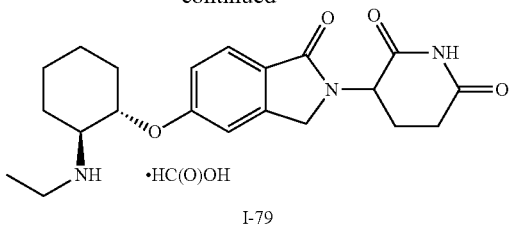

I-79

To 3-(5-(((1S,2S)-2-aminocyclohexyl)oxy)-1-oxoisoindolin-2-yl)piperidine-2,6-dione (I-15, 103 mg, 0.25 mmol), acetaldehyde (2-1, 0.021 mL, 0.37 mmol) and trifluoroethanol (1 mL) under an atmosphere of nitrogen was added NaBH(OAc)$_3$ (78 mg, 0.37 mmol) in one portion. The resulting mixture was stirred at rt for 1 h and then diluted with DCM and concentrated onto Celite®. The crude material was purified via silica gel chromatography eluting with 0-100% EtOAc:EtOH (v/v=3:1, with 0.1% Et$_3$N) in DCM and then further purified by reverse phase HPLC (Column: Xbridge C18 OBD 5 um 30×50 mm; Conditions: Water/MeCN with 5 mM NH$_4$OH 75 mL/min; 1.5 mL injection; Gradient: 25-50% MeCN, 3.5 min gradient; collected fractions contained ~3 drops of formic acid). The fractions containing the desired product were combined and lyophilized to afford the formate salt of I-79 (30 mg, 0.067 mmol, 30% yield). MS [M+H]$^+$=386.1. $^1$H NMR (400 MHz, DMSO-d$_6$) δ 8.29 (s, 2H), 7.61 (d, J=8.3 Hz, 1H), 7.21 (d, J=1.9 Hz, 1H), 7.08 (dd, J=8.4, 2.2 Hz, 1H), 5.07 (dd, J=13.3, 5.1 Hz, 1H), 4.43-4.33 (m, 1H), 4.30-4.19 (m, 2H), 2.97-2.84 (m, 1H), 2.70 (ddd, J=18.2, 7.7, 3.3 Hz, 2H), 2.63-2.55 (m, 2H), 2.42-2.26 (m, 1H), 2.08-2.04 (m, 1H), 2.02-1.90 (m, 2H), 1.71-1.61 (m, 2H), 1.41-1.15 (m, 4H), 1.00 (t, J=7.1 Hz, 3H).

Example 112: 3-(5-(((1S,2S)-2-(isopropylamino)cyclohexyl)oxy)-1-oxoisoindolin-2-yl)piperidine-2,6-dione (I-131)

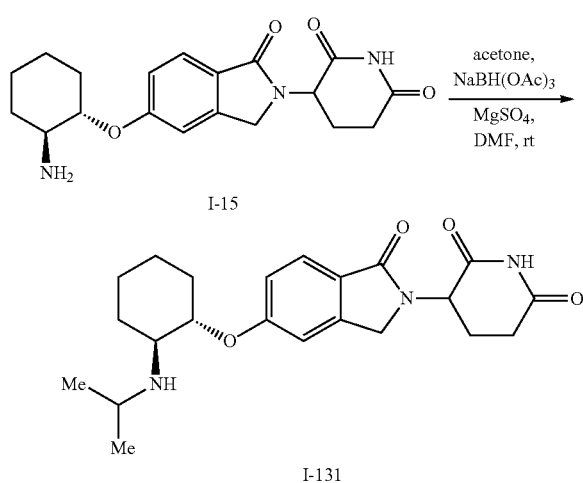

To 3-(5-(((1S,2S)-2-aminocyclohexyl)oxy)-1-oxoisoindolin-2-yl)piperidine-2,6-dione (I-15, 90 mg, 0.25 mmol), acetone (0.09 mL, 1 mmol), and MgSO$_4$ (61 mg, 0.50 mmol) in DMF (1.0 mL) was added NaBH(OAc)$_3$ (107 mg, 0.50 mmol) in one portion and the resulting mixture was stirred overnight at room temperature. The reaction mixture was then filtered and concentrated to dryness. The crude material was purified via silica gel chromatography eluting with 0 to 100% EtOH:EtOAc (v/v=3:1, with 1% Et$_3$N) in DCM to afford I-131 (95 mg, 0.24 mmol, 94% yield) as a white solid. MS [M+H]$^+$=400.1. $^1$H NMR (400 MHz, DCM-d$_2$) δ 7.67 (d, J=8.3 Hz, 1H), 7.07-6.87 (m, 2H), 5.30 (br s, 1H), 5.04 (dd, J=13.3, 5.2 Hz, 1H), 4.29-4.21 (m, 1H), 4.15 (tt, J=9.3, 4.6 Hz, 1H), 2.98 (heptd, J=6.3, 1.8 Hz, 1H), 2.87-2.80 (m, 1H), 2.78-2.67 (m, 2H), 2.30-2.14 (m, 1H), 2.13-1.99 (m, 3H), 1.91 (s, 1H), 1.76-1.62 (m, 2H), 1.41-1.16 (m, 4H), 1.11-0.99 (m, 6H).

Example 113: 3-((((1S,2S)-2-((2-(2,6-dioxopiperidin-3-yl)-1-oxoisoindolin-5-yl)oxy)cyclohexyl)amino)methyl)benzonitrile (I-132)

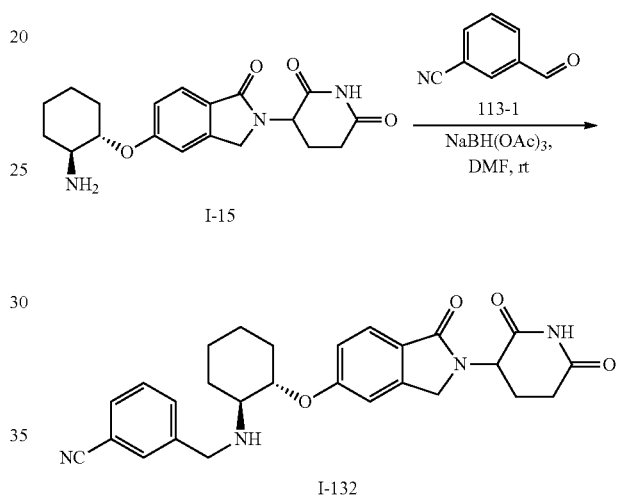

To a solution of 3-(5-(((1S,2S)-2-aminocyclohexyl)oxy)-1-oxoisoindolin-2-yl)piperidine-2,6-dione (I-15, 30 mg, 0.074 mmol) in DMF (0.5 mL) was added 3-formylbenzonitrile (113-1, 10 mg, 0.076) and sodium triacetoxyborohydride (32 mg, 0.15 mmol) and the resulting mixture was stirred at rt for 2 h. Additional 3-formylbenzonitrile (113-1, 5 mg) was added and stirring was continued at rt for 4 h. Additional sodium triacetoxyborohydride (40 mg) was added and the reaction mixture was stirred at rt for 16 h. Further sodium triacetoxyborohydride (30 mg) was added and stirring was continued at 60° C. for 2 h. The crude reaction mixture was diluted with DMSO (1 mL) and purified by reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient). The fractions containing the desired product were combined and lyophilized to afford I-132 (9.0 mg, 0.017 mmol, 23% yield). MS [M+H]$^+$=473.3. $^1$H NMR (400 MHz, MeCN-d$_3$) δ 8.83 (s, 1H), 7.68 (d, J=1.7 Hz, 1H), 7.65-7.53 (m, 3H), 7.44 (t, J=7.7 Hz, 1H), 7.11-7.08 (m, 1H), 7.06-7.01 (m, 1H), 5.04 (ddd, J=13.4, 5.2, 2.7 Hz, 1H), 4.40-4.27 (m, 2H), 4.26-4.15 (m, 1H), 3.90 (d, J=14.5 Hz, 1H), 3.83 (d, J=14.5 Hz, 1H), 2.88-2.64 (m, 3H), 2.40 (qd, J=13.2, 4.9 Hz, 1H), 2.07-2.01 (m, 1H), 1.81-1.65 (m, 2H), 1.47-1.17 (m, 4H).

Example 114: 3-(5-((((1S,2S)-2-(((3-fluorobicyclo [1.1.1]pentan-1-yl)methyl)amino)cyclohexyl)oxy)-1-oxoisoindolin-2-yl)piperidine-2,6-dione (I-133)

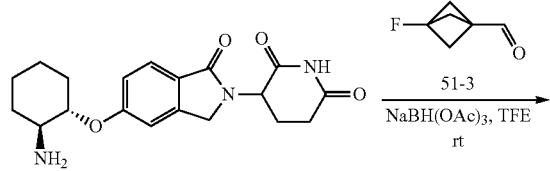

To 3-(5-(((1S,2S)-2-aminocyclohexyl)oxy)-1-oxoisoindolin-2-yl)piperidine-2,6-dione (I-15, 80 mg, 0.22 mmol) and 3-fluorobicyclo[1.1.1]pentane-1-carbaldehyde (51-3, 38.3 mg, 0.34 mmol) in TFE (1.0 mL) was added NaBH(OAc)$_3$ (316 mg, 0.45 mmol) in one portion. The resulting mixture was stirred at room temperature for 16 h, then filtered, and concentrated. The crude material was purified via silica gel chromatography eluting with 0 to 100% EtOH:EtOAc (v/v=1:3, with 1% NEt$_3$) in DCM to afford I-133 (72 mg, 0.16 mmol, 70% yield) as a white solid. MS [M+H]$^+$=456.2. $^1$H NMR (400 MHz, DCM-d$_2$) δ 7.68 (d, J=8.2 Hz, 1H), 7.02-6.96 (m, 2H), 5.07 (dd, J=13.3, 5.2 Hz, 1H), 4.37-4.20 (m, 2H), 4.18-4.06 (m, 1H), 2.97 (d, J=12.6 Hz, 1H), 2.83 (d, J=12.7 Hz, 1H), 2.79-2.59 (m, 3H), 2.36-2.17 (m, 1H), 2.17-2.06 (m, 2H), 2.05-1.96 (m, 1H), 1.89 (d, J=2.7, Hz, 6H), 1.75-1.65 (m, 2H), 1.36-1.13 (m, 4H).

Example 115: 3-(5-((2-(3,3-difluoropyrrolidin-1-yl) cyclohexyl)oxy)-1-oxoisoindolin-2-yl)piperidine-2,6-dione (I-134)

Step 1. 5-((2-oxocyclohexyl)oxy)isobenzofuran-1 (3H)-one (115-3)

5-hydroxyisobenzofuran-1(3H)-one (115-2, 415 mg, 2.76 mmol), 2-bromocyclohexanone (115-1, 508 mg, 2.87 mmol), and potassium carbonate (807 mg, 5.84 mmol) were treated with DMF (10 mL) and the resulting mixture was stirred at rt for 2 days. The reaction mixture was then diluted with ethyl acetate (150 mL) and washed with 0.5 M LiCl (aq) (2×20 mL), saturated aqueous sodium bicarbonate solution (30 mL) and brine (25 mL). The organic phase was collected, dried over magnesium sulfate, filtered, and concentrated to dryness. The crude material was purified via silica gel chromatography eluting with 0-100% EtOAc in hexane to afford 115-3 (471 mg, 1.72 mmol, 62% yield) as a beige solid. MS [M+H]$^+$=247.2. $^1$H NMR (400 MHz, DCM-d) δ 7.84 (d, J=8.5 Hz, 1H), 7.06 (d, J=8.5 Hz, 1H), 6.90 (s, 1H), 5.29 (d, J=3.5 Hz, 2H), 4.87 (dd, J=10.7, 5.7 Hz, 1H), 2.64 (d, J=13.3 Hz, 1H), 2.52 (t, J=13.7 Hz, 2H), 2.26-2.00 (m, 3H), 1.87 (q, J=12.5 Hz, 2H).

Step 2. 5-(((1R,2R)-2-(3,3-difluoropyrrolidin-1-yl) cyclohexyl)oxy)isobenzofuran-1(3H)-one or 5-(((1S,2S)-2-(3,3-difluoropyrrolidin-1-yl)cyclohexyl)oxy)isobenzofuran-1 (3H)-one (115-5)

5-((2-oxocyclohexyl)oxy)isobenzofuran-1(3H)-one (115-3, 151 mg, 0.613 mmol), 3,3-difluoropyrrolidine hydrochloride (115-4, 101 mg, 0.704 mmol), and sodium triacetoxyborohydride (194 mg, 0.915 mmol) were dissolved in DMF (2 mL) under an atmosphere of nitrogen and the resulting mixture stirred at rt overnight. The reaction mixture was then diluted with ethyl acetate (80 mL) and water (20 mL). The mixture was basified with saturated aqueous sodium bicarbonate solution. The organic layer was washed with 0.5 M lithium chloride solution (20 mL) and brine (20 mL), dried over magnesium sulfate, filtered, and concentrated to dryness. The crude material was purified via silica gel chromatography eluting with 0-100% EtOAc (with 0.1% NEt$_3$) in heptane (with 0.1% NEt$_3$) to afford a mixture of trans products (58 mg, 0.17 mmol, 28% yield) as a colorless oil. The isolated trans products were separated by chiral SFC (Method 2.1×25.0 cm Chiralpak AD-H, CO$_2$ Co-solvent: MeOH/i-PrOH (1:1); Isocratic method: 10% Co-solvent at 80 g/min; 100 bar, 25° C.). Peak 1 was isolated to afford a single enantiomer 115-5 (20 mg, 0.059 mmol, 10% yield). MS [M+H]$^+$=338.5. $^1$H NMR (400 MHz, DCM-d$_2$) δ 7.81 (d, J=8.4 Hz, 1H), 7.08 (d, J=8.5 Hz, 1H), 6.99 (s, 1H), 5.26 (s, 2H), 4.52-4.31 (m, 1H), 3.10 (dq, J=37.3, 12.1 Hz, 2H), 2.99-2.82 (m, 2H), 2.79-2.62 (m, 1H), 2.30-2.09 (m, 3H), 2.09-1.94 (m, 1H), 1.86-1.71 (m, 2H), 1.51-1.30 (m, 4H). Chiral SFC Peak 1: Rt=1.91 min. Absolute stereochemistry not determined.

Step 3. Single Enantiomer of Ethyl 2-(chloromethyl)-4-((~2-(3,3-difluoropyrrolidin-1-yl)cyclohexyl)oxy)benzoate (115-6)

To single enantiomer of 5-((~2-(3,3-difluoropyrrolidin-1-yl)cyclohexyl)oxy)isobenzofuran-1(3H)-one (115-5, Peak 1, 20 mg, 0.060 mmol) dissolved in EtOH (1 mL) was added thionyl chloride (30 μL, 0.41 mmol) and the resulting mixture was stirred at 70° C. for 16 h. Additional thionyl chloride (50 μL, 0.69 mmol) was added and stirring was continued at 70° C. for 16 h. The reaction mixture was diluted with water (10 mL) and neutralized with saturated aqueous sodium bicarbonate solution. The aqueous mixture was extracted with ethyl acetate (3×15 mL) and the combined organic phases were washed with brine (10 mL), dried over magnesium sulfate, filtered and concentrated to afford 115-6 (20 mg, 43 μmol, 71% yield) as an amber colored gum. MS [M+H]$^+$=402.5.

Step 4. Single Enantiomer of 3-(5-((~2-(3,3-difluoropyrrolidin-1-yl)cyclohexyl)oxy)-1-oxoisoindolin-2-yl)piperidine-2,6-dione (I-134)

A mixture of single enantiomer of ethyl 2-(chloromethyl)-4-((~2-(3,3-difluoropyrrolidin-1-yl)cyclohexyl)oxy)benzoate (115-6, 20.4 mg, 0.051 mmol) in DMF (0.5 mL) and DIPEA (40 μL, 0.23 mmol) was purged with nitrogen three times. 3-Aminopiperidine-2,6-dione hydrochloride (I-1c, 14 mg, 0.083 mmol) was then added in one portion and the reaction mixture was purged with nitrogen again and was stirred at 80° C. for 2 hours and then at 110° C. for 27 h. The reaction mixture was then diluted with ethyl acetate (40 mL) and washed with saturated aqueous sodium bicarbonate solution (2×10 mL) and brine (10 mL). The organic phase was dried over magnesium sulfate, filtered, and concentrated to dryness. The crude material was purified by reverse phase HPLC (Column: Xbridge C18 OBD 5 um 30×50 mm; Conditions: Water/MeCN with 10 mM NH$_4$OH 75 mL/min; 1.5 mL injection; Gradient: 25-50% MeCN, 3.5 min gradient; collected fractions contained ~3 drops of formic acid). The fractions containing the desired product were combined and lyophilized to afford I-134 (6.0 mg, 0.014 mmol, 27% yield) as a white solid. MS [M+H]$^+$=448.5. $^1$H NMR (400 MHz, DMSO-d$_6$) δ 10.95 (s, 1H), 7.62 (d, J=8.4 Hz, 1H), 7.21 (d, J=2.1 Hz, 1H), 7.07 (dd, J=8.4, 2.2 Hz, 1H), 5.07 (dd, J=13.3, 5.1 Hz, 1H), 4.58-4.50 (m, 1H), 4.44-4.20 (m, 2H), 3.20-3.06 (m, 1H), 3.06-2.88 (m, 2H), 2.88-2.80 (m, 2H), 2.66-2.55 (m, 2H), 2.38 (dd, J=13.2, 4.5 Hz, 1H), 2.24-2.08 (m, 2H), 2.05-1.93 (m, 2H), 1.93-1.82 (m, 1H), 1.63 (s, 2H), 1.52-1.18 (m, 4H).

Example 116: 3-(1-oxo-5-(((1S,2S)-2-(3-(pyridin-3-yloxy)azetidin-1-yl)cyclohexyl)oxy)isoindolin-2-yl)piperidine-2,6-dione (I-135)

Step 1: 2,2,3,3,9,9,10,10-octamethyl-4,8-dioxa-3,9-disilaundecan-6-ol (116-2)

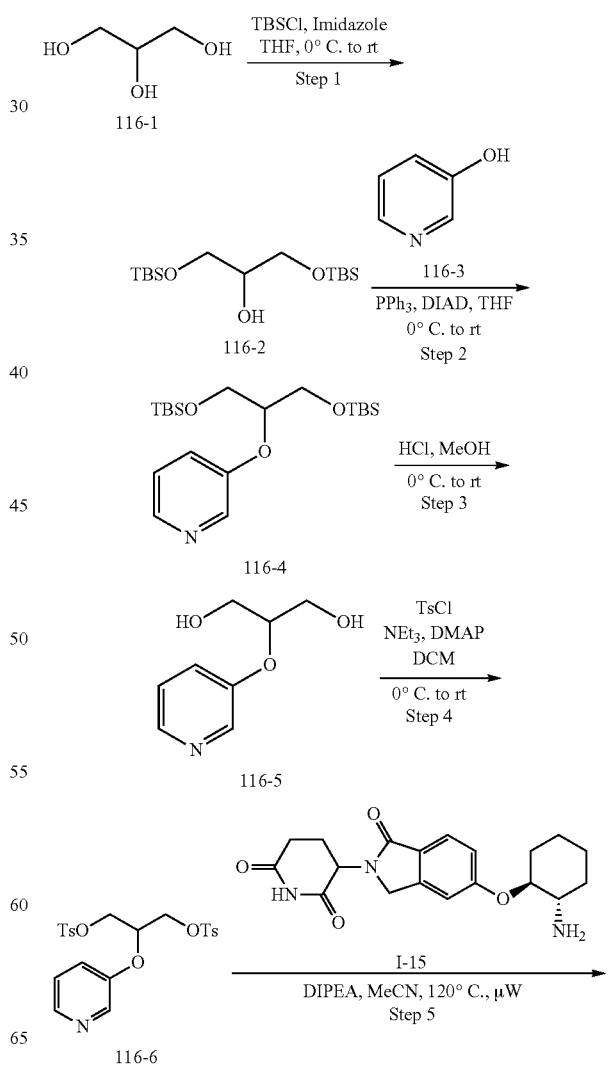

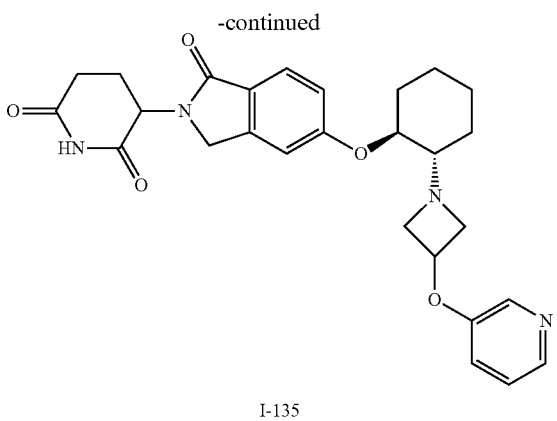

I-135

To a solution of propane-1,2,3-triol (116-1, 5.00 g, 54.3 mmol) in THF (120 mL), Imidazole (8.13 g, 119 mmol) and TBS chloride (16.4 g, 109 mmol) were added at 0° C. and stirred at room temperature for 16 h. The reaction mixture was diluted with cold water, extracted with EtOAc (3×100 mL). The combined organic extracts were washed with water, brine, dried over anhydrous $Na_2SO_4$ and concentrated to dryness. The obtained crude material was purified by silica gel chromatography eluting with 15% EtOAc in Hexane to afford 116-2 (14.0 g, 43.7 mmol, 80%) as a colorless oil. $^1$H NMR (400 MHz, DMSO-$d_6$): δ 4.59-4.61 (m, 1H), 3.52-3.32 (m, 5H), 0.86 (s, 18H), 0.03 (s, 12H).

Step 2: 3-((2,2,3,3,9,9,10,10-octamethyl-4,8-dioxa-3,9-disilaundecan-6-yl)oxy)pyridine (116-4)

To a stirred solution of 2,2,3,3,9,9,10,10-octamethyl-4,8-dioxa-3,9-disilaundecan-6-ol (116-2, 4.05 g, 12.6 mmol), pyridin-3-ol (116-3, 1.00 g, 10.5 mmol) and $PPh_3$ (3.30 g, 12.6 mmol) in THF (50 mL), at 0° C. was added DIAD (2.55 g, 12.6 mmol) drop wise and the resulting mixture was stirred at room temperature for 16 h. The reaction mixture was quenched with cold water and extracted with EtOAc (3×50 mL). The combined organic phases were washed with water, brine, dried over anhydrous $Na_2SO_4$, filtered, and concentrated to dryness. The obtained crude material was purified by silica gel chromatography eluting with 20-40% EtOAc in Hexane to afford 116-4 (1.60 g, 4.02 mmol, 38%) as a colorless oil. $^1$H NMR (300 MHz, $CDCl_3$): δ 8.35-8.31 (m, 1H), 8.21-8.18 (m, 1H), 7.30-7.15 (m, 2H), 4.39-4.35 (m, 1H), 3.87-3.76 (m, 4H), 0.88 (s, 18H), 0.02 (s, 12H).

Step 3: 2-(pyridin-3-yloxy)propane-1,3-diol (116-5)

To a stirred solution of 3-((2,2,3,3,9,9,10,10-octamethyl-4,8-dioxa-3,9-disilaundecan-6-yl)oxy)pyridine (116-4, 1.60 g, 4.02 mmol) in MeOH (30 mL) at 0° C. was added concentrated HCl (3.20 mL) drop wise and the resulting mixture was stirred at room temperature for 4 h. The reaction mixture was concentrated to dryness. The obtained crude material was diluted with cold water, basified with $NaHCO_3$, and the aqueous mixture was concentrated to dryness. The residue obtained was stirred with 10% MeOH in DCM, filtered, and the filtrate was concentrated to dryness to afford 116-5 (0.800 g, crude) as pale brown oil. The product was carried on to the next step without purification. [M+H]$^+$=170.20.

Step 4: 2-(pyridin-3-yloxy)propane-1,3-diyl bis(4-methylbenzenesulfonate) (116-6)

To a solution of 2-(pyridin-3-yloxy)propane-1,3-diol (116-5, 0.80 g, 4.73 mmol) in DCM (40 mL), $Et_3N$ (1.91 g, 18.9 mmol) at 0° C. was added DMAP (0.190 g, 1.56 mmol) and tosyl chloride (2.25 g, 11.8 mmol) and the resulting mixture was stirred at room temperature for 3 h. The reaction mixture was quenched with cold water and extracted with DCM (3×30 mL). The combined organic phases were washed water, brine, dried over anhydrous $Na_2SO_4$, filtered, and concentrated to dryness. The obtained crude material was purified by silica gel chromatography eluting with 50% EtOAc in hexane to afford 116-6 (1.30 g, 2.72 mmol, 58%) as colorless oil. MS [M+H]$^+$=478.10.

Step 5. 3-(1-oxo-5-(((1S,2S)-2-(3-(pyridin-3-yloxy)azetidin-1-yl)cyclohexyl)oxy)isoindolin-2-yl)piperidine-2,6-dione (I-135)

To a solution of 3-(5-(((1S,2S)-2-aminocyclohexyl)oxy)-1-oxoisoindolin-2-yl)piperidine-2,6-dione (I-15, 200 mg, 0.56 mmol) in acetonitrile (10 mL) was added 2-(pyridin-3-yloxy)propane-1,3-diyl bis(4-methylbenzenesulfonate) (116-6, 401 mg, 0.84 mmol) and DIPEA (0.43 g, 3.36 mmol) and the resulting mixture was stirred at 120° C. for 16 hr under microwave irradiation. The reaction mixture was diluted with saturated aqueous sodium bicarbonate solution and extracted with DCM (3×30 mL). The combined organic phases were washed with brine, dried over anhydrous $Na_2SO_4$, filtered, and concentrated to dryness. The obtained crude material was purified by reverse phase HPLC (Column: LUNA C18 (250 mm×21.2 mm), 5.0 g, Mobile phase-A: 0.01% HCOOH (aq), Mobile phase-B: acetonitrile; Method: 0/10, 2/10, 8/50. Flow rate: 20 mL/min). The fractions containing the desired product were combined and lyophilized to afford I-135 (25 mg, 0.05 mmol, 9%) as white solid. MS [M+H]$^+$=491.20. $^1$H NMR (400 MHz, DMSO-$d_6$): δ 10.96 (s, 1H), 8.18-8.13 (m, 2H), 7.62 (d, J=8.4 Hz, 1H), 7.31-7.23 (m, 2H), 7.17 (s, 1H), 7.05 (d, J=8.4 Hz, 1H), 5.09 (dd, J=13.2, 4.8 Hz, 1H), 4.81-4.78 (m, 1H), 4.41-4.22 (m, 3H), 3.78-3.73 (m, 2H), 3.24-3.21 (m, 2H), 3.09-3.08 (m, 1H), 2.94-2.87 (m, 1H), 2.85-2.32 (m, 4H), 2.07-1.98 (m, 2H), 1.98-1.81 (m, 1H), 1.66-1.64 (m, 2H), 1.36-1.23 (m, 2H).

Example 117: 3-(5-(((1S,2S)-2-(ethyl((3-fluorobicyclo[1.1.1]pentan-1-yl)methyl)amino)cyclopentyl)oxy)-1-oxoisoindolin-2-yl)piperidine-2,6-dione (I-136)

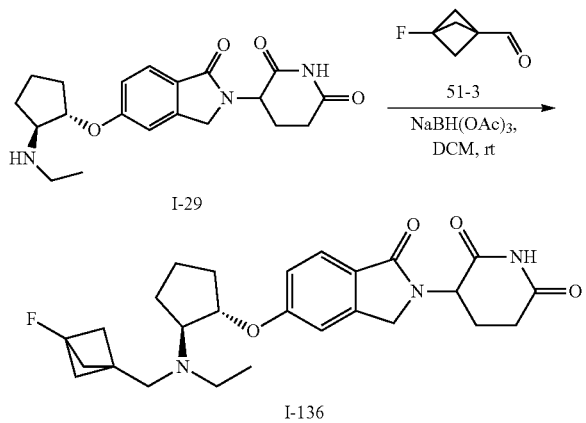

I-29

I-136

To a solution of 3-(5-(((1S,2S)-2-(ethylamino)cyclopentyl)oxy)-1-oxoisoindolin-2-yl)piperidine-2,6-dione (I-29, 12 mg, 0.032 mmol) in DCM (0.5 mL) was added 3-fluorobicyclo[1.1.1]pentane-1-carbaldehyde (51-3, 7.4 mg, 0.065 mmol). Sodium triacetoxyborohydride (21 mg, 0.097 mmol) was added and the resulting mixture was stirred at rt for 1 h. The reaction mixture was then concentrated to dryness and the crude material was purified by reverse phase HPLC (Method Column: Xbridge C18 OBD 5 um 30×50 mm; Conditions: Water/MeCN with 10 mM NH$_4$OH 75 mL/min; 1.5 mL injection; Gradient: 35-60% MeCN, 3.5 min gradient; collected fractions contained several drops of formic acid). The fractions containing the desired product were combined and lyophilized to afford I-136 (6.0 mg, 11 μmol, 34% yield) as a white solid. MS [M+H]$^+$=470.2. $^1$H NMR (400 MHz, DCM-d$_2$) δ 8.01 (s, 1H), 7.62 (d, J=8.4 Hz, 1H), 7.01 (t, J=2.4 Hz, 1H), 6.97 (dd, J=8.4, 2.2 Hz, 1H), 5.04 (ddd, J=13.3, 5.1, 2.2 Hz, 1H), 4.60-4.48 (s, 1H), 4.32-4.17 (m, 2H), 3.35-3.23 (m, 1H), 2.84-2.67 (m, 4H), 2.61-2.50 (m, 2H), 2.34-2.19 (m, 1H), 2.15-2.04 (m, 1H), 1.97-1.83 (m, 8H), 1.75-1.59 (m, 3H), 1.55-1.41 (m, 1H), 0.94 (t, J=7.1 Hz, 3H).

Example 118: 3-(1-oxo-5-(((1S,2S)-2-(4-oxopiperidin-1-yl)cyclopentyl)oxy)isoindolin-2-yl)piperidine-2,6-dione (I-137)

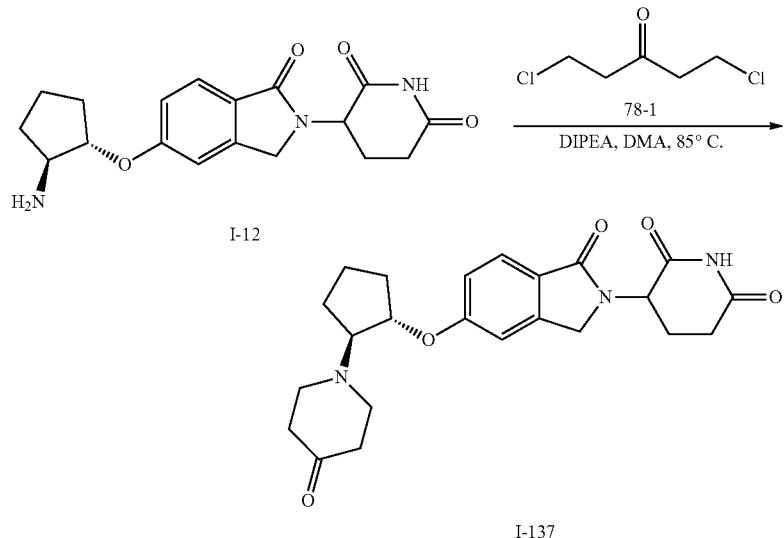

3-(5-(((1S,2S)-2-aminocyclopentyl)oxy)-1-oxoisoindolin-2-yl)piperidine-2,6-dione (I-12, 99 mg, 0.14 mmol) was dissolved in DMA (1 mL) and DIPEA (0.07 mL, 0.4 mmol) was added, followed by a solution of 1,5-dichloropentan-3-one (78-1, 21 mg, 0.14 mmol) in DMA (1 mL). The resulting solution was stirred at 85° C. for 2 h and then at rt overnight. Additional 1,5-dichloropentan-3-one (78-1, 21 mg, 0.14 mmol) in DMA (200 uL) was added and stirring was continues at 85° C. for 2 h. The reaction mixture was then cooled to rt, DIPEA (0.07 mL, 0.4 mmol) was added and the mixture was heated to 85° C. for 5 h. The reaction mixture was poured into saturated aqueous NaHCO$_3$ and extracted with DCM: i-PrOH (4:1). The combined organic phases were washed with brine, dried over Na$_2$SO$_4$, filtered, and concentrated. The crude material was purified via silica gel chromatography eluting with 0-10% i-PrOH in DCM to afford I-137 (11 mg, 0.024 mmol, 18% yield) as an off-white solid. MS [M+H]$^+$=426.5. $^1$H NMR (400 MHz, DMSO-d$_6$) δ 10.95 (s, 1H), 7.61 (d, J=8.4 Hz, 1H), 7.23-7.18 (m, 1H), 7.08-7.03 (m, 1H), 5.07 (dd, J=13.3, 5.1 Hz, 1H), 4.83-4.76 (m, 1H), 4.43-4.33 (m, 1H), 4.33-4.22 (m, 1H), 3.16-3.07 (m, 1H), 2.97-2.85 (m, 1H), 2.78 (t, J=6.1 Hz, 4H), 2.63-2.55 (m, 1H), 2.44-2.29 (m, 5H), 2.18-2.04 (m, 1H), 2.03-1.92 (m, 2H), 1.77-1.61 (m, 3H), 1.61-1.49 (m, 1H).

Example 119: 3-(5-(((1S,2S)-2-(4-hydroxy-4-methylpiperidin-1-yl)cyclopentyl)oxy)-1-oxoisoindolin-2-yl)piperidine-2,6-dione HC(O)OH Salt (I-138)

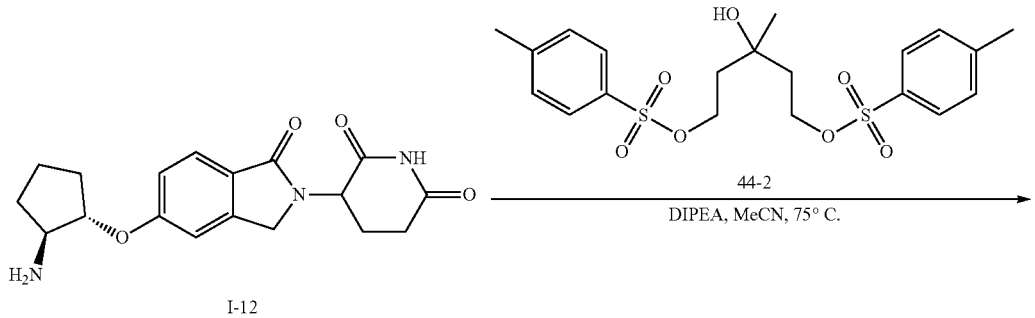

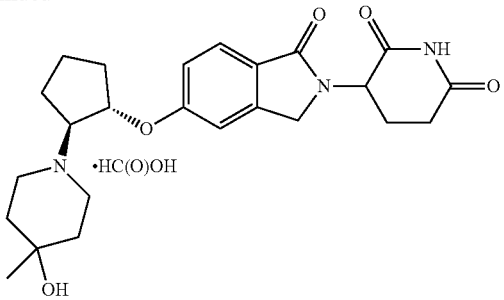

I-138

3-(5-(((1S,2S)-2-aminocyclopentyl)oxy)-1-oxoisoindolin-2-yl)piperidine-2,6-dione (I-12, 70.0 mg, 0.153 mmol) was dissolved in MeCN (1 mL) and DIPEA (0.16 mL, 0.92 mmol) was added, followed by a solution of 3-hydroxy-3-methylpentane-1,5-diyl bis(4-methylbenzenesulfonate) (44-2, 203 mg, 0.459 mmol) in MeCN (1 mL) and the resulting solution was stirred at 75° C. overnight. The reaction mixture was then concentrated and the crude material was purified by reverse phase HPLC (Method Column: Xbridge C18 OBD 5 um 30×50 mm; Conditions: Water/MeCN with 10 mM NH$_4$OH 75 mL/min; 1.5 mL injection; Gradient: 15-40% MeCN, 3.5 min gradient; collected fractions contained ~3 drops of formic acid) to afford the formate salt of I-138 (11.0 mg, 22.0 µmol, 14% yield) as a white solid. MS [M+H]$^+$=442.6. $^1$H NMR (400 MHz, DMSO-d$_6$) δ 10.96 (s, 1H), 8.17 (s, 1H), 7.60 (d, J=8.4 Hz, 1H), 7.18 (d, J=2.1 Hz, 1H), 7.03 (dd, J=8.4, 1.6 Hz, 1H), 5.10-5.02 (m, 1H), 4.73-4.66 (m, 1H), 4.38 (dd, J=17.1, 9.3 Hz, 1H), 4.25 (dd, J=17.2, 7.9 Hz, 1H), 4.06 (s, 1H), 2.97-2.84 (m, 2H), 2.64-2.55 (m, 1H), 2.48-2.34 (m, 5H), 2.11-1.87 (m, 3H), 1.72-1.55 (m, 3H), 1.54-1.37 (m, 5H), 1.07 (s, 3H).

Example 120: 3-(5-(((1S,2S)-2-(3-hydroxypyrrolidin-1-yl)cyclopentyl)oxy)-1-oxoisoindolin-2-yl)piperidine-2,6-dione HC(O)OH Salt (I-139)

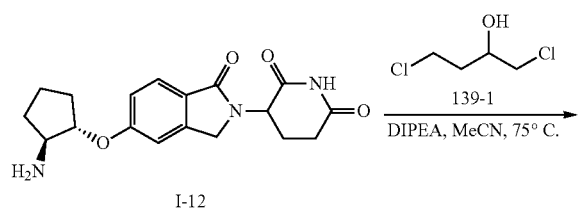

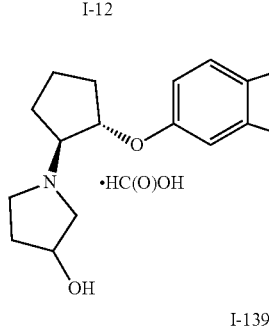

I-139

To 3-(5-(((1S,2S)-2-aminocyclopentyl)oxy)-1-oxoisoindolin-2-yl)piperidine-2,6-dione (I-12, 56.0 mg, 0.163 mmol) dissolved in MeCN (1 mL) was added DIPEA (0.17 mL, 0.98 mmol) followed by a solution of 1,4-dichlorobutan-2-ol (139-1, 70.0 mg, 0.489 mmol) in MeCN (1 mL) and the resulting mixture was stirred at 75° C. overnight. The reaction mixture was then cooled to rt and additional DIPEA (0.17 mL, 0.98 mmol) and 1,4-dichlorobutan-2-ol (139-1, 70.0 mg, 0.489 mmol) were added. The reaction mixture was stirred at 75° C. overnight and then concentrated. The crude material was purified by reverse phase HPLC (Method Column: Xbridge C18 OBD 5 um 30×50 mm; Conditions: Water/MeCN with 10 mM NH$_4$OH 75 mL/min; 1.5 mL injection; Gradient: 10-30% MeCN, 3.5 min gradient; collected fractions contained ~3 drops of formic acid) to afford the formate salt of I-139 (13 mg, 25 µmol, 16% yield) as a white solid. MS [M+H]$^+$=414.5. $^1$H NMR (400 MHz, DMSO-d$_6$) δ 10.95 (s, 1H), 8.20 (s, 1H), 7.61 (d, J=8.4 Hz, 1H), 7.17-7.13 (m, 1H), 7.02 (dd, J=8.2, 2.2 Hz, 1H), 5.10-5.02 (m, 1H), 4.73-4.59 (m, 2H), 4.39 (dd, J=17.2, 8.1 Hz, 1H), 4.25 (dd, J=17.1, 6.7 Hz, 1H), 4.18-4.10 (m, 1H), 2.96-2.85 (m, 1H), 2.80-2.71 (m, 2H), 2.65-2.54 (m, 2H), 2.46-2.35 (m, 3H), 2.19-2.08 (m, 1H), 2.02-1.85 (m, 3H), 1.73-1.45 (m, 5H).

Example 120: 3-(5-(((1S,2S)-2-(3-(benzyloxy)azetidin-1-yl)cyclopentyl)oxy)-1-oxoisoindolin-2-yl)piperidine-2,6-dione (I-52)

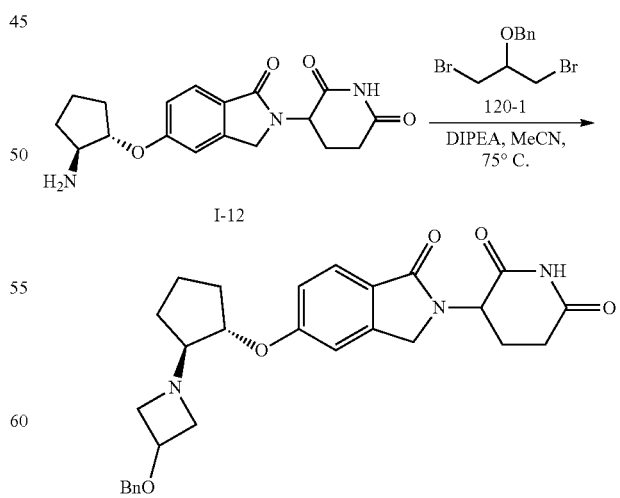

To 3-(5-(((1S,2S)-2-aminocyclopentyl)oxy)-1-oxoisoindolin-2-yl)piperidine-2,6-dione (I-12, 65.0 mg, 0.142 mmol)

dissolved in MeCN (1 mL) was added DIPEA (0.10 mL, 0.57 mmol), followed by a solution of (((1,3-dibromopropan-2-yl)oxy)methyl)benzene (120-1, 109 mg, 0.354 mmol) in MeCN (1 mL). The resulting solution was stirred at 75° C. Upon complete consumption of starting materials, the reaction mixture was cooled to rt, azeotroped with toluene (2×), and concentrated to dryness. The crude material was purified by reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient). The fractions containing the desired product were combined and lyophilized to afford I-52 (4.70 mg, 8.60 μmol, 6% yield) as a glassy solid. MS [M+H]$^+$=490.6. $^1$H NMR (400 MHz, Chloroform-d) δ 8.11-8.03 (m, 1H), 7.81-7.75 (m, 1H), 7.40-7.32 (m, 3H), 7.32-7.27 (m, 2H), 6.98-6.92 (m, 2H), 5.25-5.14 (m, 1H), 5.06-4.99 (m, 1H), 4.55-4.40 (m, 5H), 4.40-4.26 (m, 2H), 3.83 (s, 1H), 3.73-3.59 (m, 2H), 2.97-2.77 (m, 2H), 2.43-2.27 (m, 2H), 2.26-2.18 (m, 1H), 2.18-2.08 (m, 1H), 1.99-1.87 (m, 1H), 1.87-1.68 (m, 3H).

Example 121: 3-(5-(((1S,2S)-2-(3-hydroxy-3-methylazetidin-1-yl)cyclopentyl)oxy)-1-oxoisoindolin-2-yl)piperidine-2,6-dione HCl Salt (I-141)

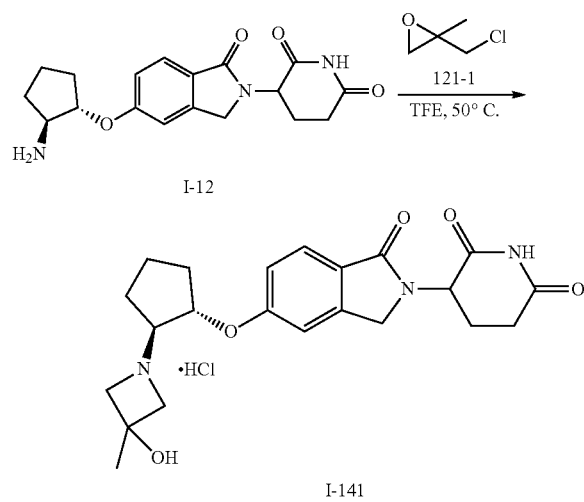

2-(chloromethyl)-2-methyloxirane (121-1, 20.0 mg, 0.188 mmol) was added to a solution of 3-(5-(((1S,2S)-2-aminocyclopentyl)oxy)-1-oxoisoindolin-2-yl)piperidine-2,6-dione (I-12, 56.0 mg, 0.163 mmol) in TFE (0.75 mL). The resulting mixture was stirred at rt over 3 days, then heated to 50° C., and stirred at 50° C. for 6 h. The reaction mixture was then heated to 70° C. overnight with stirring, cooled to rt and concentrated to dryness. The crude material was triturated with acetone (×3) and the resultant solid dried under vacuum to afford the HCl salt of I-141 (28.0 mg, 57.0 μmol, 35% yield) as an orange solid. MS [M+H]$^+$=414.5. $^1$H NMR (400 MHz, DMSO-d$_6$) δ 10.96 (s, 1H), 7.67 (d, J=8.4 Hz, 1H), 7.20 (s, 1H), 7.09 (d, J=8.3 Hz, 1H), 5.14-5.01 (m, 1H), 4.94-4.75 (m, 1H), 4.47-4.36 (m, 1H), 4.34-4.18 (m, 1H), 4.17-3.81 (m, 4H), 2.98-2.83 (m, 1H), 2.64-2.55 (m, 1H), 2.45-2.35 (m, 2H), 2.21-2.10 (m, 1H), 2.03-1.94 (m, 1H), 1.87-1.53 (m, 5H), 1.51-1.30 (m, 3H).

Example 122: 3-(5-(((1S,2S)-2-(isobutylamino)cyclopentyl)oxy)-1-oxoisoindolin-2-yl)piperidine-2,6-dione (I-142)

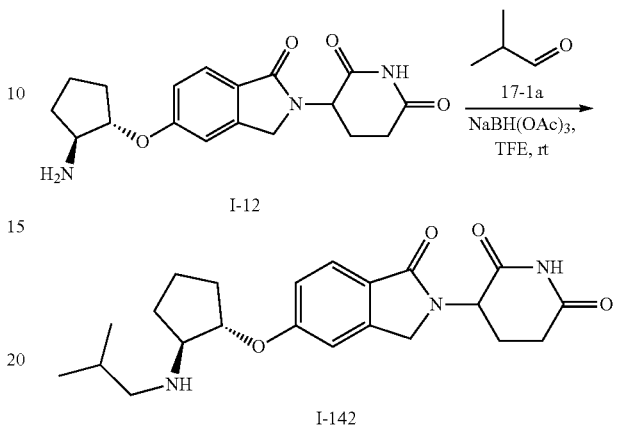

To 3-(5-(((1S,2S)-2-aminocyclopentyl)oxy)-1-oxoisoindolin-2-yl)piperidine-2,6-dione (I-12, 80.0 mg, 0.175 mmol) dissolved in TFE (1.5 mL) was added isobutyraldehyde (17-1a, 16 μL, 0.18 mmol) followed by sodium triacetoxyborohydride (74 mg, 0.35 mmol) and the resulting mixture was stirred at rt overnight. Additional isobutyraldehyde (17-1a, 16 μL, 0.18 mmol), TFE (1 mL), and sodium triacetoxyborohydride (74 mg, 0.35 mmol) were added until complete consumption of I-12 was observed. The reaction mixture was then poured into saturated NaHCO$_3$ (aq) (2 mL) and extracted with DCM (3×20 mL). The combined organic phases were concentrated to dryness. The crude material was purified via silica gel chromatography eluting with 0-10% i-PrOH (with 0.1% NEt$_3$) in DCM (with 0.1% NEt$_3$) to afford I-142 (45.0 mg, 0.107 mmol, 61% yield) as a white solid. MS [M+H]$^+$=400.5. $^1$H NMR (400 MHz, DMSO-d$_6$) δ 10.95 (s, 1H), 7.61 (d, J=8.3 Hz, 1H), 7.21-7.16 (m, 1H), 7.04 (d, J=8.5 Hz, 1H), 5.07 (dd, J=13.1, 4.7 Hz, 1H), 4.58 (s, 1H), 4.38 (dd, J=17.1, 9.5 Hz, 1H), 4.26 (dd, J=17.1, 8.3 Hz, 1H), 3.10 (s, 1H), 2.97-2.84 (m, 1H), 2.63-2.53 (m, 1H), 2.44-2.34 (m, 2H), 2.18-2.05 (m, 1H), 2.02-1.87 (m, 2H), 1.79-1.54 (m, 5H), 1.53-1.38 (m, 1H), 0.87 (d, J=6.5 Hz, 6H).

Example 123: 3-(5-(((1S,2S)-2-(ethyl(methyl)amino)cyclopentyl)oxy)-1-oxoisoindolin-2-yl)piperidine-2,6-dione (I-143)

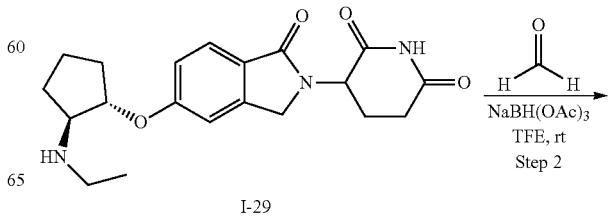

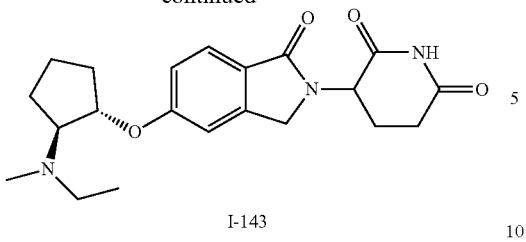

I-143

To a solution of 3-(5-(((1S,2S)-2-(ethylamino)cyclopentyl)oxy)-1-oxoisoindolin-2-yl)piperidine-2,6-dione (I-29, 30.0 mg, 81.0 μmol) in DCE (1 mL) was added paraformaldehyde (13.0 mg, 0.433 mmol) followed by sodium triacetoxyborohydride (20.0 mg, 94.0 μmol) and acetic acid (1 μL, 17.0 μmol) and the resulting mixture was stirred at rt overnight. The reaction mixture was then poured into saturated NaHCO$_3$(aq) (2 mL) and extracted with i-PrOH:DCM (1:9) (×4). The combined organic phases were dried over Na$_2$SO$_4$, filtered, and concentrated to dryness. The crude material was purified via silica gel chromatography eluting with 0-20% i-PrOH (with 0.1% NEt$_3$) in DCM (with 0.1% NEt$_3$) to afford I-143 (16.0 mg, 39.0 μmol, 49% yield) as a white solid. MS [M+H]$^+$=386.5. $^1$H NMR (400 MHz, DMSO-d$_6$) δ 10.95 (s, 1H), 7.61 (d, J=8.4 Hz, 1H), 7.19 (s, 1H), 7.05 (d, J=8.5 Hz, 1H), 5.07 (dd, J=13.2, 5.1 Hz, 1H), 4.69 (s, 1H), 4.39 (dd, J=17.1, 10.3 Hz, 1H), 4.26 (dd, J=17.1, 8.5 Hz, 1H), 3.12-2.97 (m, 1H), 2.97-2.84 (m, 1H), 2.64-2.55 (m, 2H), 2.45-2.34 (m, 2H), 2.16 (s, 3H), 2.10-2.02 (m, 1H), 2.02-1.93 (m, 1H), 1.93-1.81 (m, 1H), 1.74-1.57 (m, 3H), 1.50 (s, 1H), 0.97 (s, 3H).

Example 124: 3-(1-oxo-5-(((1S,2S)-2-((3aR,6aS)-tetrahydro-1H-furo[3,4-c]pyrrol-5(3H)-yl)cyclopentyl)oxy)isoindolin-2-yl)piperidine-2,6-dione (I-144)

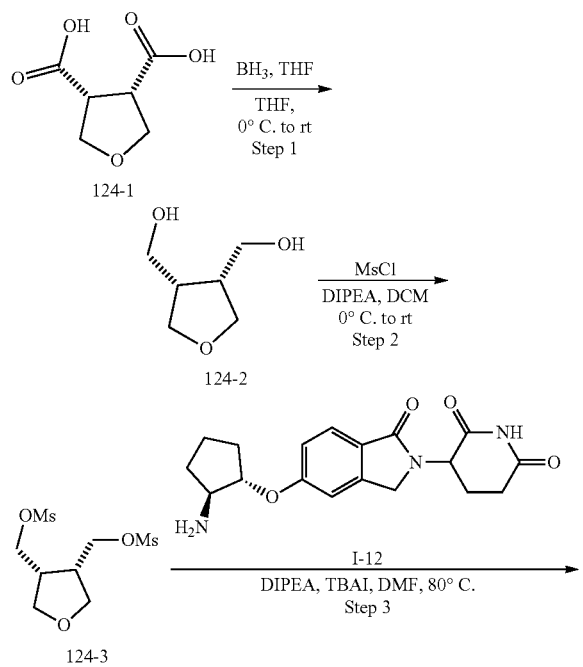

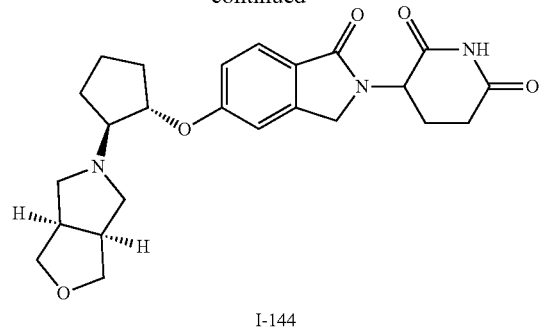

I-144

Step 1. ((3R,4S)-tetrahydrofuran-3,4-diyl)dimethanol (124-2)

To cis-tetrahydrofuran-3,4-dicarboxylic acid (124-1, 690 mg, 4.31 mmol) in THF (8 mL) at 0° C. and under an atmosphere of nitrogen atmosphere was added BH$_3$ (17.2 mL, 17.2 mmol) (1M in THF) and the resulting mixture was stirred at rt overnight. The reaction mixture was then quenched with MeOH (2 mL) at 0° C. and concentrated to dryness to afford 124-2 as a colorless oil. The crude product was taken on to the next step without purification. $^1$H NMR (400 MHz, Chloroform-d) δ 4.28-4.12 (m, 2H), 4.00-3.87 (m, 2H), 3.82-3.65 (m, 2H), 3.59-3.44 (m, 2H), 1.64-1.48 (m, 2H), 1.48-1.32 (m, 2H).

Step 2. ((3R,4S)-tetrahydrofuran-3,4-diyl)bis(methylene) dimethanesulfonate (124-3)

To the crude ((3R,4S)-tetrahydrofuran-3,4-diyl)dimethanol (124-2, 569 mg, 4.31 mmol) in DIPEA (3.15 mL, 18.1 mmol) and DCM (10 mL) was added methanesulfonyl chloride (0.733 mL, 9.47 mmol) at 0° C. The resulting mixture was stirred at rt for 3 h, then diluted with H$_2$O and extracted with DCM (×3). The combined organic phases were concentrated to dryness to afford 124-3 (1.21 g, 4.19 mmol, 97% yield) as a brown oil. $^1$H NMR (400 MHz, Chloroform-d) δ 4.41-4.34 (m, 2H), 4.32-4.25 (m, 2H), 4.04-3.96 (m, 2H), 3.79-3.71 (m, 2H), 3.08 (s, 6H), 2.92-2.80 (m, 2H).

Step 3. 3-(1-oxo-5-(((1S,2S)-2-((3aR,6aS)-tetrahydro-1H-furo[3,4-c]pyrrol-5(3H)-yl)cyclopentyl)oxy)isoindolin-2-yl)piperidine-2,6-dione (I-144)

To a solution of 3-(5-(((1S,2S)-2-aminocyclopentyl)oxy)-1-oxoisoindolin-2-yl)piperidine-2,6-dione (I-12, 500 mg, 1.46 mmol), DIPEA (1.3 mL, 7.3 mmol) and TBAI (27 mg, 0.073 mmol) in DMF (5 mL) was added ((3R,4S)-tetrahydrofuran-3,4-diyl)bis(methylene) dimethanesulfonate (124-3, 1.05 g, 3.64 mmol) and the resulting mixture was stirred at 80° C. for 55 h. The reaction mixture was then concentrated and the obtained crude material was purified via silica gel chromatography eluting with 0 to 100% EtOAc:EtOH (v/v=3:1, with 0.1% NEt$_3$) in DCM (with 0.1% NEt$_3$) to afford I-144 (30.4 mg, 68.0 μmol, 5% yield) as a light beige solid. MS [M+H]$^+$=440.3. $^1$H NMR (400 MHz, DCM-d$_2$) δ 7.66 (dd, J=8.6, 4.2 Hz, 1H), 7.00-6.88 (m, 2H), 5.19-4.96 (m, 1H), 4.74-4.57 (m, 1H), 4.38-4.14 (m, 2H), 3.77-3.60 (m, 2H), 3.55-3.41 (m, 2H), 2.89-2.60 (m, 7H), 2.49-2.31

(m, 2H), 2.30-2.18 (m, 1H), 2.16-2.03 (m, 2H), 2.02-1.85 (m, 1H), 1.81-1.65 (m, 3H), 1.62-1.50 (m, 1H).

Example 125: 3-(1-oxo-5-(((1S,2S)-2-((pyridin-2-ylmethyl)amino)cyclopentyl)oxy)isoindolin-2-yl)piperidine-2,6-dione HC(O)OH Salt (I-145)

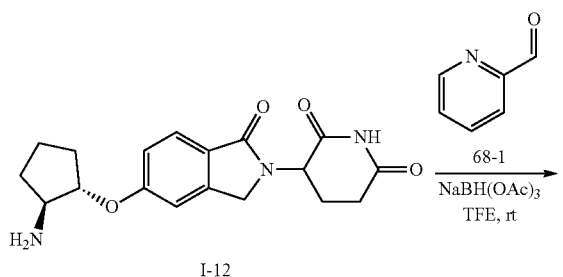

To 3-(5-(((1S,2S)-2-aminocyclopentyl)oxy)-1-oxoisoindolin-2-yl)piperidine-2,6-dione (I-12, 71.6 mg, 0.184 mmol) and picolinaldehyde (68-1, 22.9 mg, 0.214 mmol) in 2,2,2-trifluoroethanol (1 mL) was added sodium triacetoxyborohydride (55.3 mg, 0.261 mmol) in one portion and the resulting mixture was stirred at rt for 1 h. Additional picolinaldehyde (68-1, 20 mg, 0.19 mmol) and sodium triacetoxyborohydride (39 mg, 0.18 mmol) were added until complete disappearance of I-12 was observed. The reaction mixture was diluted with EtOAc (80 mL) and washed with saturated sodium bicarbonate solution (10 mL) and brine (10 mL). The organic phase was then dried over magnesium sulfate, filtered, and concentrated to dryness. The crude reaction mixture was purified by reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) to afford the formate salt of I-145 (49.8 mg, 0.103 mmol, 56% yield) as a white solid. MS [M+H]+=435.5. 1H NMR (400 MHz, DMSO-d6) δ 10.96 (s, 1H), 8.53-8.45 (m, 1H), 8.14 (s, 1H), 7.74 (tt, J=7.6, 2.0 Hz, 1H), 7.63-7.57 (m, 1H), 7.47-7.40 (m, 1H), 7.27-7.20 (m, 1H), 7.14 (dd, J=4.1, 2.2 Hz, 1H), 7.06-6.92 (m, 1H), 5.07 (ddd, J=13.3, 5.1, 2.4 Hz, 1H), 4.72-4.64 (m, 1H), 4.45-4.19 (m, 2H), 3.97-3.82 (m, 2H), 3.21-3.15 (m, 2H), 2.91 (ddd, J=18.2, 13.7, 5.4 Hz, 1H), 2.63-2.55 (m, 1H), 2.44-2.34 (m, 1H), 2.21-2.11 (m, 1H), 2.04-1.87 (m, 2H), 1.83-1.60 (m, 3H), 1.59-1.47 (m, 1H).

Example 126: 3-(1-oxo-5-(((1S,2S)-2-(pyrrolidin-1-yl)cyclopentyl)oxy)isoindolin-2-yl)piperidine-2,6-dione (I-146)

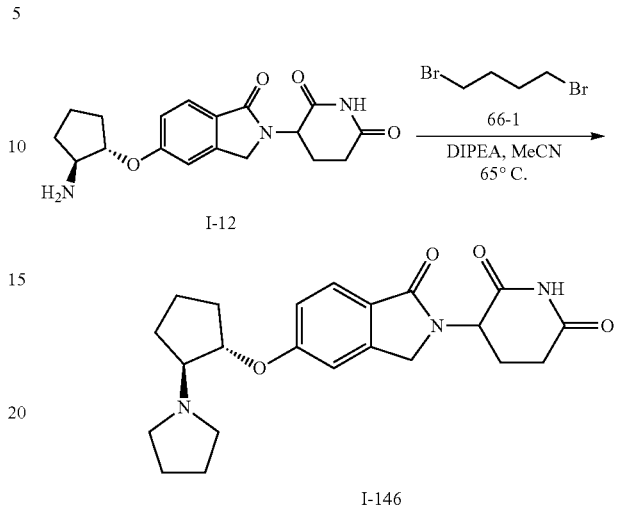

To a solution of 3-(5-(((1S,2S)-2-aminocyclopentyl)oxy)-1-oxoisoindolin-2-yl)piperidine-2,6-dione (I-12, 100 mg, 0.291 mmol) in MeCN (3 mL) was added 1,4-dibromobutane (66-1, 0.035 mL, 0.29 mmol) and DIPEA (0.11 mL, 0.64 mmol) and the resulting mixture was stirred at 65° C. overnight. The reaction mixture was cooled to rt and then added to a saturated aqueous solution of sodium hydrogen carbonate (20 mL). The aqueous mixture was extracted with 20% i-PrOH in DCM (×3). The combined organic phases were passed through a phase separating column and the organic solvent concentrated to dryness. The crude material was purified via silica gel chromatography eluting with 0-100% EtOAc:EtOH (v/v=3:1, with 0.1% NEt3) in DCM (with 0.1% NEt3) to afford I-146 (47 mg, 12 μmol, 39% yield) as a pale yellow solid. MS [M+H]+=398.5. 1H NMR (400 MHz, DMSO-d6) δ (ppm): 10.95 (s, 1H), 7.61 (d, J=8.4 Hz, 1H), 7.15 (s, 1H), 7.03 (d, J=8.4 Hz, 1H), 5.06 (dd, J=12.8, 5.2 Hz, 1H), 4.79-4.68 (m, 1H), 4.44-4.20 (m, 2H), 2.90 (ddd, J=18.0, 13.7, 5.4 Hz, 1H), 2.83-2.70 (s, 1H), 2.65-2.50 (m, 4H, obscured by DMSO-signal), 2.39 (td, J=13.2, 4.4 Hz, 2H), 2.21-2.10 (s, 1H), 2.02-1.88 (d, J=14.4 Hz, 2H), 1.75-1.51 (m, 8H).

Example 127: 3-(5-(((1S,2S)-2-(2-oxa-6-azaspiro[3.3]heptan-6-yl)cyclopentyl)oxy)-1-oxoisoindolin-2-yl)piperidine-2,6-dione (I-147)

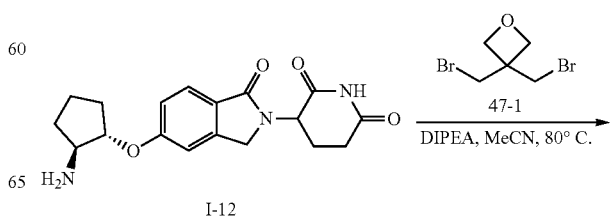

713

-continued

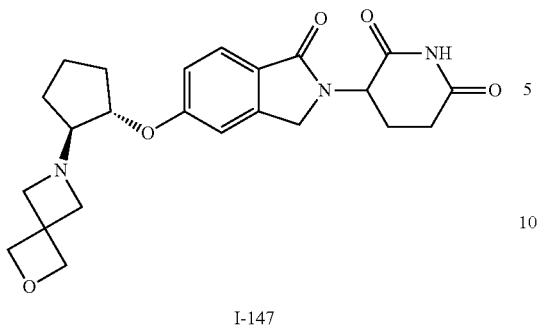

I-147

To a solution of 3-(5-(((1S,2S)-2-aminocyclopentyl)oxy)-1-oxoisoindolin-2-yl)piperidine-2,6-dione (I-12, 30 mg, 0.087 mmol) in MeCN (2 mL) was added DIPEA (0.076 mL, 0.44 mmol) followed by 3,3-bis(bromomethyl)oxetane (47-1, 64 mg, 0.26 mmol) and the resulting mixture was stirred at 80° C. for 2 days. The reaction mixture was then cooled to rt and additional 3,3-bis(bromomethyl)oxetane (47-1, 64 mg, 0.26 mmol) and DIPEA (0.076 mL, 0.44 mmol) were added. The reaction mixture was stirred at 80° C. for 3 days and then concentrated to dryness, taken up in DCM, and poured into saturated aqueous NaHCO$_3$. The phases were separated and the aqueous phase was extracted with DCM (×3). The combined organic phases were dried over Na$_2$SO$_4$, filtered, and concentrated to dryness. The crude material was purified via silica gel chromatography eluting with 0-15% i-PrOH (with 0.1% NEt$_3$) in DCM (with 0.1% NEt$_3$). The obtained product was taken up in DCM and washed with saturated NaHCO$_3$ (aq). The phases were separated and the aqueous phase was extracted with DCM (×2). The combined organic phases were concentrated to dryness to afford I-147 (13 mg, 0.027 mmol, 32% yield) a light brown solid. MS [M+H]$^+$=426.5. $^1$H NMR (400 MHz, DMSO-d$_6$) δ 10.96 (s, 1H), 7.61 (d, J=8.4 Hz, 1H), 7.13 (d, J=2.2 Hz, 1H), 7.01 (dt, J=8.6, 1.9 Hz, 1H), 5.07 (dd, J=13.3, 5.1 Hz, 1H), 4.60-4.54 (m, 4H), 4.50 (dd, J=6.1, 2.2 Hz, 1H), 4.39 (dd, J=17.2, 2.9 Hz, 1H), 4.26 (d, J=17.1 Hz, 1H), 3.30-3.26 (m, 4H, shoulder on H$_2$O signal), 2.96-2.84 (m, 1H), 2.78-2.72 (m, 1H), 2.62-2.55 (m, 1H), 2.45-2.35 (m, 1H), 2.12-2.02 (m, 1H), 2.03-1.90 (m, 1H), 1.79-1.52 (m, 4H), 1.40-1.30 (m, 1H).

Example 128: 3-(5-(((1S,2S)-2-(bis((3-methyl-oxetan-3-yl)methyl)amino)cyclopentyl)oxy)-1-oxoisoindolin-2-yl)piperidine-2,6-dione (I-148)

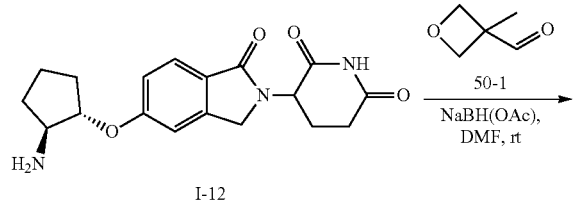

714

-continued

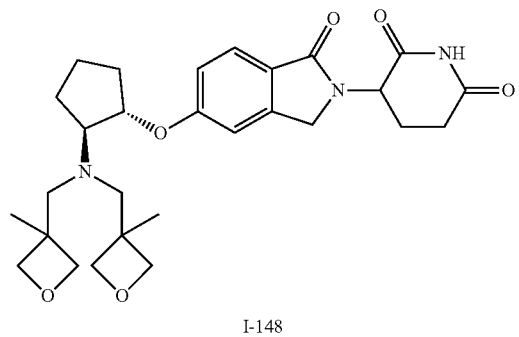

I-148

To a suspension of 3-(5-(((1S,2S)-2-aminocyclopentyl)oxy)-1-oxoisoindolin-2-yl)piperidine-2,6-dione (I-12, 146 mg, 0.130 mmol) in DMF (1 mL) was added 3-methyloxetane-3-carbaldehyde (50-1, 40 mg, 0.39 mmol), followed by sodium triacetoxyborohydride (83 mg, 0.39 mmol). The reaction mixture was stirred at rt for 1 h. Additional 3-methyloxetane-3-carbaldehyde (50-1, 50 mg, 0.49 mmol) and sodium triacetoxyhydroborate (60 mg, 0.28 mmol) were added and stirring was continued at rt for 16 h. Additional 3-methyloxetane-3-carbaldehyde (50-1, 50 mg, 0.490 mmol) and sodium triacetoxyhydroborate (60 mg, 0.28 mmol) were added and stirring was continued at rt for 8 h. The reaction mixture was then was concentrated onto Celite®, azeotroping with heptanes (×2). The crude material was purified via silica gel chromatography eluting with 0-100% EtOAc in heptane to afford I-148 (98.0 mg, 0.186 mmol, 91% yield) as a colorless oil. MS [M+H]$^+$=512.2. $^1$H NMR (400 MHz, DMSO-d$_6$) δ 10.96 (s, 1H), 7.61 (d, J=8.4 Hz, 1H), 7.15 (s, 1H), 7.02 (dd, J=8.3, 2.2 Hz, 1H), 5.06 (dd, J=14.0, 4.4 Hz, 1H), 4.68 (s, 1H), 4.46-4.19 (m, 6H), 4.12 (d, J=5.6 Hz, 4H), 2.88 (t, J=6.2 Hz, 1H), 2.72 (d, J=3.4 Hz, 1H), 2.59 (d, J=13.2 Hz, 4H), 2.45-2.27 (m, 2H), 2.10-1.92 (m, 2H), 1.81 (d, J=8.9 Hz, 1H), 1.73-1.39 (m, 4H), 1.27 (s, 6H).

Example 129: 3-(5-(((1S,2S)-2-(4-methylpiperidin-1-yl)cyclopentyl)oxy)-1-oxoisoindolin-2-yl)piperidine-2,6-dione (I-149)

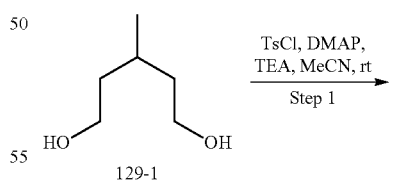

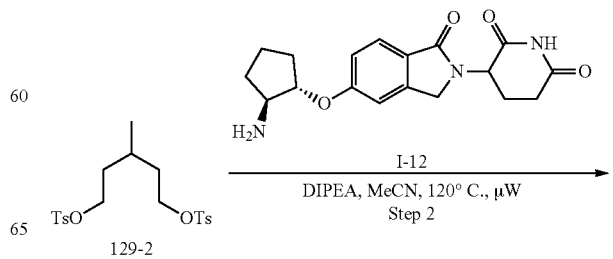

-continued

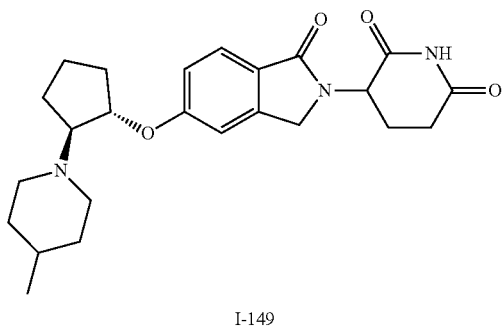

I-149

Step 1. 3-methylpentane-1,5-diyl bis(4-methylbenzenesulfonate) (129-2)

To a solution of 3-methylpentane-1,5-diol (129-1, 650 mg, 5.50 mmol) in MeCN (15 mL) was added DMAP (100 mg, 0.819 mmol) and TEA (3.1 mL, 22 mmol), followed by TsCl (3.00 g, 15.7 mmol) and the resulting mixture was stirred at rt for 3 h. The reaction mixture was then filtered and concentrated to dryness. The crude material was purified via silica gel chromatography eluting with 0-50% EtOAc in heptane to afford 129-2 (2.27 g, 5.32 mmol, 97% yield) as a light yellow oil. MS [M+H$_2$O]$^+$=444.5. $^1$H NMR (400 MHz, Chloroform-d) δ 7.80-7.76 (m, 4H), 7.35 (dd, J=8.7, 0.7 Hz, 4H), 4.05-3.97 (m, 4H), 2.46 (s, 6H), 1.70-1.58 (m, 3H), 1.49-1.36 (m, 2H), 0.78 (d, J=6.5 Hz, 3H).

Step 2. 3-(5-(((1S,2S)-2-(4-methylpiperidin-1-yl)cyclopentyl)oxy)-1-oxoisoindolin-2-yl)piperidine-2,6-dione (I-149)

To a solution of 3-(5-(((1S,2S)-2-aminocyclopentyl)oxy)-1-oxoisoindolin-2-yl)piperidine-2,6-dione (I-12, 75.0 mg, 0.218 mmol) in MeCN (2 mL) was added DIPEA (0.23 mL, 1.3 mmol), followed by 3-methylpentane-1,5-diyl bis(4-methylbenzenesulfonate) (129-2, 466 mg, 1.09 mmol) and the resulting solution was stirred at 120° C. under μW irradiation for 1 h. The reaction mixture was then concentrated to dryness. The crude material was purified via silica gel chromatography eluting with 0-10% i-PrOH (with 0.1% NEt$_3$) in DCM (with 0.1% NEt$_3$). The obtained material was taken up in DCM and washed with saturated NaHCO$_3$ (aq). The phases were separated and the aqueous phase was extracted with DCM. The combined organic phases were concentrated to dryness to afford I-149 (36.0 mg, 0.080 mmol, 37% yield) as an off-white solid. MS [M+H]$^+$=426.4. $^1$H NMR (400 MHz, DMSO-d$_6$) δ 10.95 (s, 1H), 7.60 (d, J=8.4 Hz, 1H), 7.18 (d, J=2.2 Hz, 1H), 7.03 (d, J=8.3 Hz, 1H), 5.06 (dd, J=13.2, 5.0 Hz, 1H), 4.73-4.66 (m, 1H), 4.45-4.18 (m, 2H), 2.97-2.76 (m, 3H), 2.63-2.55 (m, 1H), 2.44-2.35 (m, 1H), 2.10-1.83 (m, 5H), 1.75-1.42 (m, 5H), 1.37-1.19 (m, 2H), 1.17-1.01 (m, 2H), 0.99-0.92 (m, 1H), 0.86 (d, J=6.5 Hz, 3H).

Example 130: 3-(1-oxo-5-(((1S,2S)-2-((pyridin-3-ylmethyl)amino)cyclopentyl)oxy)isoindolin-2-yl)piperidine-2,6-dione HC(O)OH Salt (I-150)

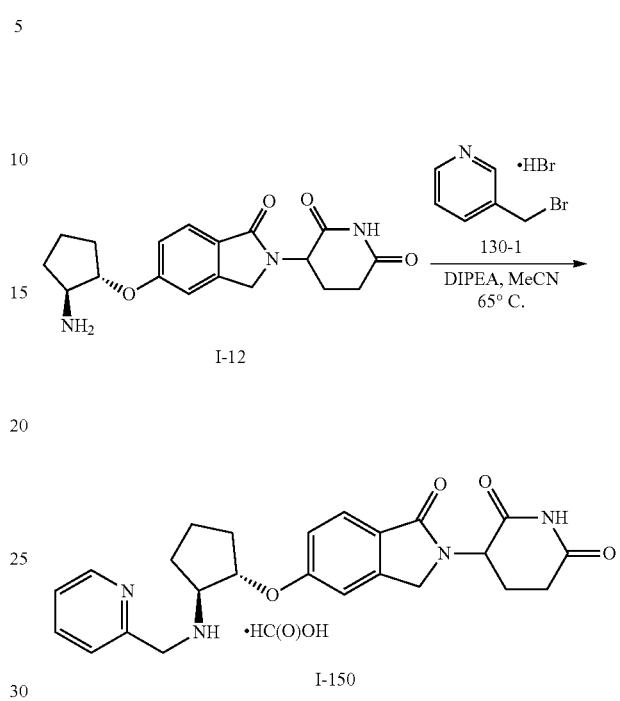

To a solution of 3-(5-(((1S,2S)-2-aminocyclopentyl)oxy)-1-oxoisoindolin-2-yl)piperidine-2,6-dione (I-12, 100 mg, 0.291 mmol) in MeCN (3 mL) was added 3-(bromomethyl)pyridine HBr (130-1, 73.7 mg, 0.291 mmol) and DIPEA (0.11 mL, 0.64 mmol) and the resulting mixture was stirred at 65° C. for 3 hours. The reaction mixture was cooled to rt and then added to a saturated aqueous solution of sodium hydrogen carbonate (20 mL). The aqueous mixture was extracted with 20% i-PrOH in DCM (×3). The combined organic phases were passed through a phase separating column and the organic solvent concentrated to dryness. The crude material was purified via silica gel chromatography eluting with 0-100% EtOAc:EtOH (v/v=3:1, with 0.1% NEt$_3$) in DCM (with 0.1% NEt$_3$). The obtained material was treated with 1:1 MeCN/diethyl ether. The resulting suspension was sonicated and filtered and the obtained solid was washed with diethyl ether. The filtrate was collected and concentrated to dryness. The material was purified by reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) to afford the formate salt of I-150 (8.0 mg, 0.016 mmol, 5% yield). MS [M+H]$^+$=435.6. $^1$H NMR (400 MHz, DMSO-d$_6$) δ 10.96 (s, 1H), 8.55 (s, 1H), 8.43 (d, J=4.8 Hz, 1H), 8.12 (s, 1H), 7.76 (d, J=7.9 Hz, 1H), 7.59 (d, J=8.4 Hz, 1H), 7.33 (dd, J=7.8, 4.8 Hz, 1H), 7.14 (s, 1H), 7.04-6.96 (m, 1H), 5.11-5.02 (m, 1H), 4.69-4.64 (m, 1H), 4.42-4.21 (m, 2H), 3.87-3.75 (m, 2H), 3.18-3.12 (m, 2H), 2.91 (ddd, J=17.7, 13.6, 5.4 Hz, 1H), 2.60 (d, J=17.7 Hz, 1H), 2.45-2.32 (m, 1H), 2.20-2.09 (m, 1H), 2.02-1.88 (m, 2H), 1.80-1.60 (multiplets, 3H), 1.58-1.48 (m, 1H).

Example 131: 3-(1-oxo-5-((((1S,2S)-2-((pyridin-4-ylmethyl)amino)cyclopentyl)oxy)isoindolin-2-yl)piperidine-2,6-dione (I-151)

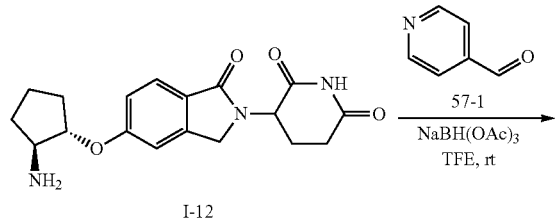

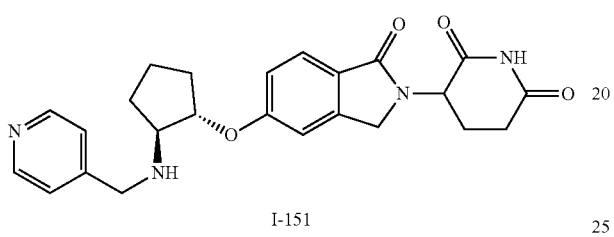

To a solution of 3-(5-((((1S,2S)-2-aminocyclopentyl)oxy)-1-oxoisoindolin-2-yl)piperidine-2,6-dione (I-12, 100 mg, 0.291 mmol) in TFE (3 mL) was added isonicotinaldehyde (57-1, 31 mg, 0.29 mmol) and the resulting mixture was stirred at rt for 15 minutes. Sodium triacetoxyborohydride (93 mg, 0.44 mmol) was added and stirring was continued at rt for 3 hours. The reaction mixture was then added to a saturated aqueous solution of sodium hydrogen carbonate (20 mL). The aqueous mixture was extracted with 20% i-PrOH in DCM (×3). The combined organic phases were passed through a phase separating column and the organic solvent evaporated concentrated to dryness. The crude material was purified via silica gel chromatography eluting with 0-100% EtOAc:EtOH (v/v=3:1, with 0.1% NEt$_3$) in DCM (with 0.1% NEt$_3$) and then further purified by reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) to afford crude material. The obtained material was then again purified via silica gel chromatography eluting with 0-20% i-PrOH (with 0.1% NEt$_3$) in DCM (with 0.1% NEt$_3$) to afford I-151 (10.0 mg, 0.022 mmol, 8% yield) as a white solid. MS [M+H]$^+$=435.5. $^1$H NMR (400 MHz, DMSO-d$_6$) δ (ppm); 10.96 (s, 1H), 8.56-8.43 (m, 2H), 7.60 (d, J=8.4 Hz, 1H), 7.45-7.33 (m, 2H), 7.15 (d, J=8.0 Hz, 1H), 7.05-6.98 (m, 1H), 5.12-5.02 (m, 1H), 4.72-4.57 (br m, 1H), 4.43-4.20 (m, 2H), 3.78 (br s, 2H), 3.14-3.04 (m, 1H), 2.99-2.82 (m, 1H), 2.60 (d, J=17.6 Hz, 2H), 2.39 (br d, J=12.3 Hz, 1H), 2.23-2.10 (br m, 1H), 2.04-1.86 (m, 2H), 1.84-1.45 (br m, 4H).

Example 132: 3-(5-((((1S,2S)-2-(4-methoxy-4-methylpiperidin-1-yl)cyclopentyl)oxy)-1-oxoisoindolin-2-yl)piperidine-2,6-dione (I-152)

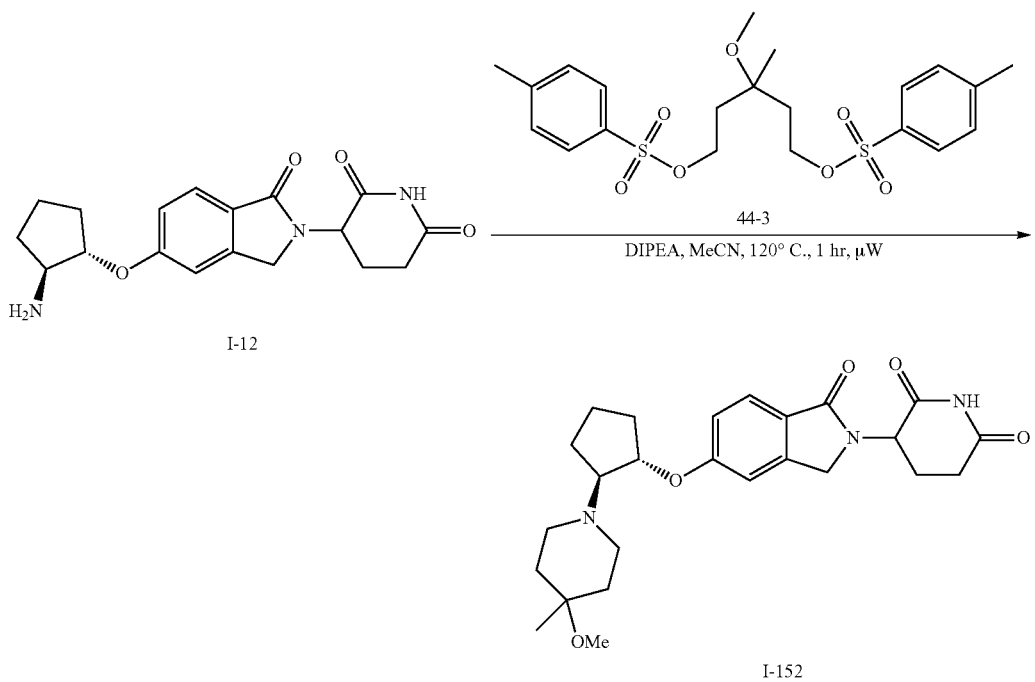

To a solution of 3-(5-((((1S,2S)-2-aminocyclopentyl)oxy)-1-oxoisoindolin-2-yl)piperidine-2,6-dione (I-12, 50.0 mg, 0.146 mmol) in MeCN (1.5 mL) was added DIPEA (0.13 mL, 0.73 mmol), followed by 3-methoxy-3-methylpentane-1,5-diyl bis(4-methylbenzenesulfonate) (44-3, 165 mg, 0.361 mmol) and the resulting solution was stirred at 120° C. under µW irradiation for 1 h. The reaction mixture was then concentrated to dryness and the crude residue was taken up in DCM and washed with saturated NaHCO$_3$ (aq) and the phases were separated. The aqueous layer was extracted with DCM and the combined organic phases were dried over Na$_2$SO$_4$, filtered, and concentrated to dryness. The crude material was purified via silica gel chromatography eluting with 0-10% i-PrOH (with 0.1% NEt$_3$) in DCM (with 0.1% NEt$_3$) to afford I-152 (22.0 mg, 0.046 mmol, 32% yield) as an off-white solid. MS [M+H]$^+$=456.6. $^1$H NMR (400 MHz, DMSO-d$_6$) δ 10.95 (s, 1H), 7.61 (d, J=8.4 Hz, 1H), 7.18 (d, J=2.2 Hz, 1H), 7.03 (d, J=8.4 Hz, 1H), 5.07 (dd, J=13.4, 5.0 Hz, 1H), 4.69 (s, 1H), 4.47-4.17 (m, 2H), 3.06 (s, 3H), 2.97-2.82 (m, 2H), 2.59 (d, J=16.9 Hz, 1H), 2.45-2.28 (m, 5H), 2.11-1.85 (m, 3H), 1.72-1.55 (m, 5H), 1.43 (s, 3H), 1.06 (s, 3H).

Example 133: 3-(5-(((1S,2S)-2-(4,4-dimethylpiperidin-1-yl)cyclopentyl)oxy)-1-oxoisoindolin-2-yl)piperidine-2,6-dione (I-153)

Step 1. 3,3-dimethylpentane-1,5-diol (133-2)

to 0° C. and quenched with water (8 mL). K$_2$CO$_3$ was added and the aqueous mixture was extracted with Et$_2$O (×3). The combined organic phases were concentrated to dryness to afford crude 133-2 (516 mg) as a light yellow oil. The product was taken onto the next step without purification. $^1$H NMR (400 MHz, Chloroform-d) δ 3.75 (t, J=7.0 Hz, 4H), 1.58 (t, J=7.0 Hz, 4H), 0.95 (s, 6H).

Step 2. 3,3-dimethylpentane-1,5-diyl bis(4-methylbenzenesulfonate) (133-3)

To a solution of 3,3-dimethylpentane-1,5-diol (133-2, 516 mg, 3.90 mmol) in MeCN (20 mL) was added DMAP (238 mg, 1.95 mmol) and TEA (2.2 mL, 16 mmol), followed by TsCl (1.86 g, 9.76 mmol) and the resulting mixture was stirred at rt overnight. The reaction mixture was then filtered and concentrated to dryness. The crude material was purified via silica gel chromatography eluting 0-50% EtOAc in

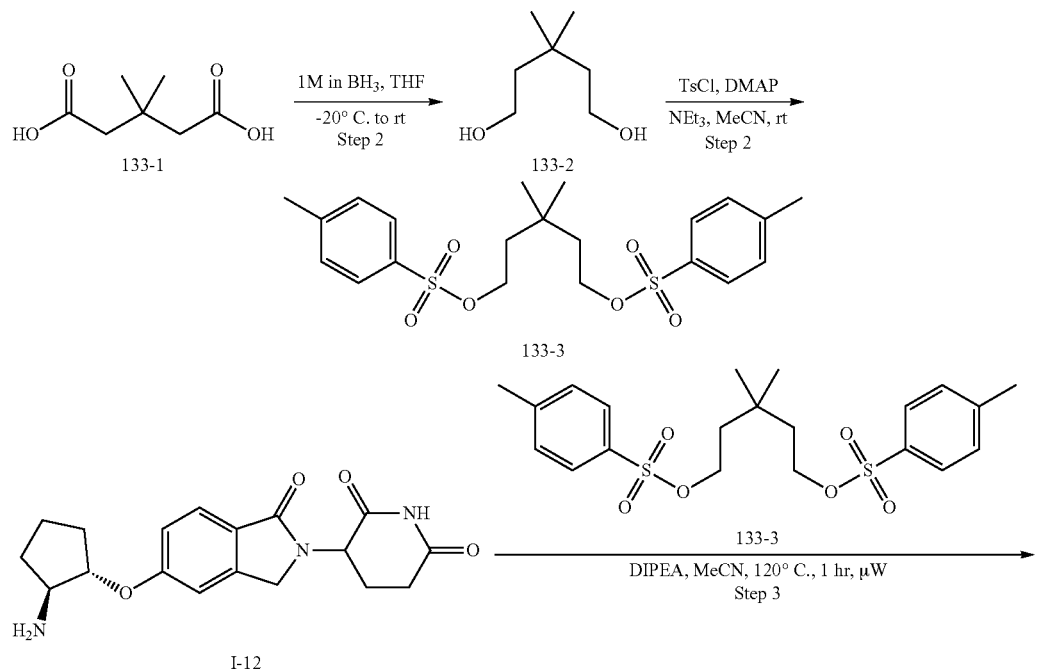

To a solution of 3,3-dimethylpentanedioic acid (133-1, 600 mg, 3.75 mmol) in THF (15 mL) cooled to −20° C. was slowly added BH$_3$ (1M in THF) (9.4 mL, 9.4 mmol) and the resulting mixture was stirred at −20° C., then warmed to rt and stirred at rt overnight. The reaction mixture was cooled heptane to afford 133-3 (860 mg, 1.95 mmol, 50% yield) as a pale yellow solid. MS [M+H]$^+$=441.5. $^1$H NMR (400 MHz, Chloroform-d) δ 7.80-7.75 (m, 4H), 7.38-7.33 (m, 4H), 4.03 (t, J=7.1 Hz, 4H), 2.46 (s, 6H), 1.56 (t, J=7.1 Hz, 4H), 0.85 (s, 6H).

Step 3. 3-(5-(((1S,2S)-2-(4,4-dimethylpiperidin-1-yl)cyclopentyl)oxy)-1-oxoisoindolin-2-yl)piperidine-2,6-dione (I-153)

To a solution of 3-(5-(((1S,2S)-2-aminocyclopentyl)oxy)-1-oxoisoindolin-2-yl)piperidine-2,6-dione (I-12, 50.0 mg, 0.146 mmol) in MeCN (2 mL) was added DIPEA (0.13 mL, 0.73 mmol), followed by 3,3-dimethylpentane-1,5-diyl bis(4-methylbenzenesulfonate) (133-3, 96.0 mg, 0.218 mmol) and the resulting solution was stirred at 120° C. under μW irradiation for 3 h. The reaction mixture was then concentrated to dryness. The crude material was taken up in DCM and washed with saturated aqueous NaHCO$_3$. The phases were separated and the aqueous phase was extracted with DCM and the combined organic phases were dried over Na$_2$SO$_4$, filtered, and concentrated. The crude product was purified via silica gel chromatography eluting with 0-10% i-PrOH (with 0.1% NEt$_3$) in DCM (with 0.1% NEt$_3$) to afford I-153 (26 mg, 0.056 mmol, 39% yield) as an off-white solid. MS [M+H]$^+$=440.6. $^1$H NMR (400 MHz, DMSO-d$_6$) δ 10.95 (s, 1H), 7.60 (d, J=8.4 Hz, 1H), 7.18 (d, J=2.1 Hz, 1H), 7.03 (d, J=8.2 Hz, 1H), 5.06 (dd, J=13.2, 5.1 Hz, 1H), 4.70 (s, 1H), 4.39 (dd, J=17.1, 9.9 Hz, 1H), 4.26 (dd, J=17.1, 8.1 Hz, 1H), 2.96-2.81 (m, 2H), 2.65-2.55 (m, 1H), 2.47-2.30 (m, 5H), 2.12-1.86 (m, 3H), 1.72-1.55 (m, 3H), 1.56-1.41 (m, 1H), 1.37-1.23 (m, 4H), 0.88 (s, 6H).

Example 134: 3-(5-(((1S,2S)-2-(4-methoxypiperidin-1-yl)cyclopentyl)oxy)-1-oxoisoindolin-2-yl)piperidine-2,6-dione (I-154)

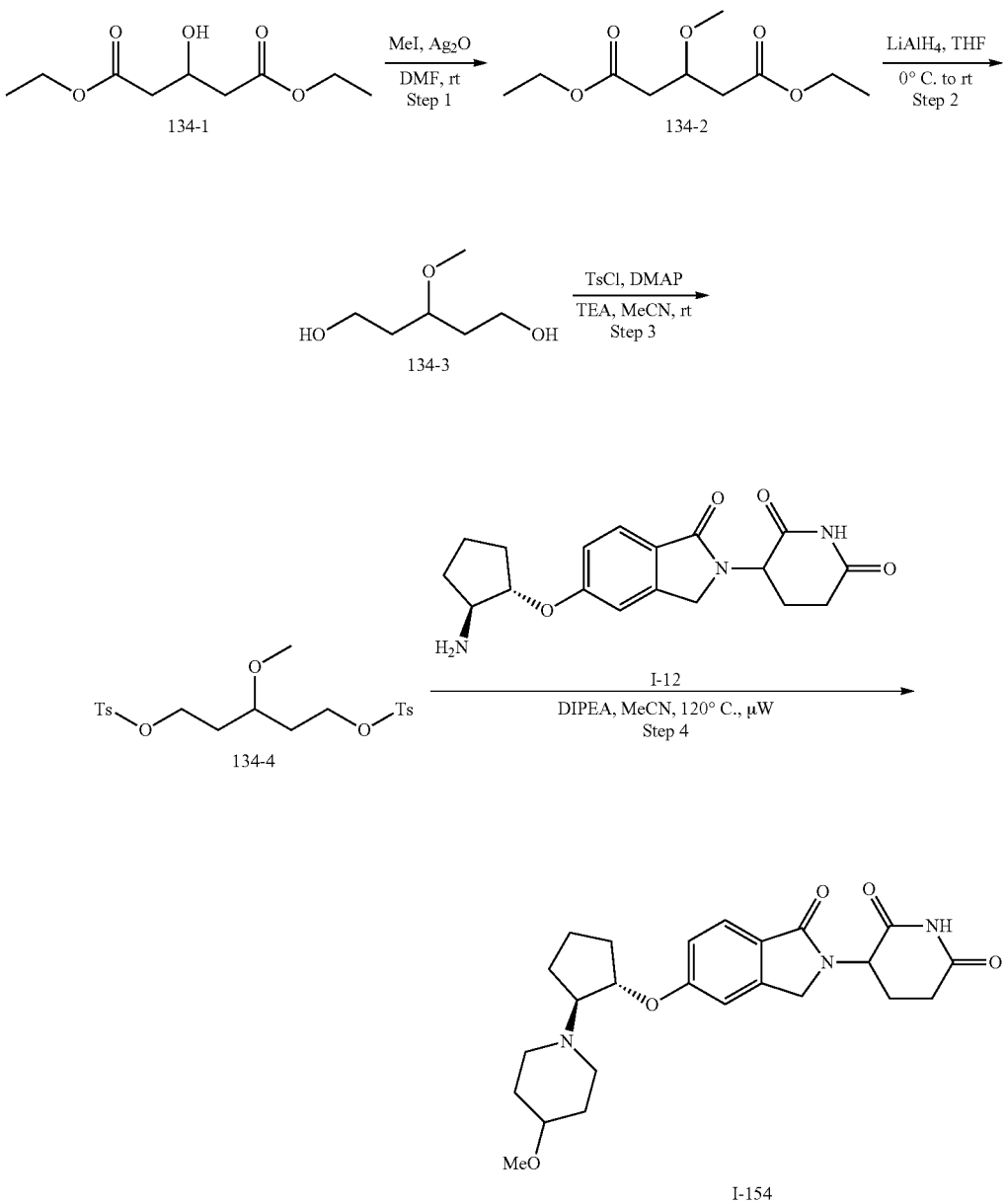

Step 1. Diethyl 3-methoxypentanedioate (134-2)

To a mixture of diethyl 3-hydroxygluturate (134-1, 0.455 mL, 2.45 mmol) and silver oxide (1.42 g, 6.12 mmol) in DMF (5 mL), was added methyl iodide (0.77 mL, 12 mmol) dropwise during which the reaction temperature was maintained at 25-30° C. with a water bath. The resulting mixture was then stirred at rt over 3 days. The reaction mixture was filtered and the formed precipitate was washed with diethyl ether. The filtrate was washed with 5% $NaHSO_3$ (aq) and brine and the organic phase was dried over $Na_2SO_4$, filtered, and concentrated to dryness to afford 134-2 (440 mg, 2.02 mmol, 82% yield) as a colorless oil. $^1$H NMR (400 MHz, Chloroform-d) δ 4.25-4.13 (m, 4H), 4.13-4.05 (m, 1H), 3.41 (s, 3H), 2.71-2.51 (m, 4H), 1.36-1.21 (m, 6H).

Step 2. 3-methoxypentane-1,5-diol (134-3)

To a solution of diethyl 3-methoxypentanedioate (134-2, 250 mg, 1.15 mmol) in THF (20 mL) cooled to 0° C. was slowly added 1M lithium aluminum hydride in THF (3.44 mL, 3.44 mmol) and the resulting mixture was stirred at 0° C. and then warmed to rt and stirred at rt for 3 h. The reaction mixture was cooled to 0° C., quenched with saturated $Na_2SO_4$ (aq), and filtered. The obtained precipitate was washed with diethyl ether. The filtrate was washed with 5% $NaHSO_3$ (aq) and brine, dried over $Na_2SO_4$, filtered, and concentrated to dryness to afford 134-3 which was taken on to the next step without purification.

Step 3. 3-methoxypentane-1,5-diyl bis(4-methylbenzenesulfonate) (134-4)

To a solution of 3-methoxypentane-1,5-diol (134-3, 92.0 mg, 0.686 mmol) in MeCN (5 mL) was added DMAP (42 mg, 0.34 mmol) and TEA (0.38 mL, 2.7 mmol), followed by TsCl (327 mg, 1.71 mmol) and the resulting mixture was stirred at rt overnight. The reaction mixture was then filtered and concentrated to dryness. The obtained residue was treated with diethyl ether and filtered. The filtrate was concentrated to dryness and the crude material was purified via silica gel chromatography eluting with 0-60% EtOAc in heptane to afford 134-4 (40.0 mg, 0.090 mmol, 13% yield) a light yellow oil. MS $[M+H_2O]^+$=460.5. $^1$H NMR (400 MHz, Chloroform-d) δ 7.81-7.76 (m, 4H), 7.38-7.32 (m, 4H), 4.13-4.01 (m, 4H), 3.42-3.32 (m, 1H), 3.15 (s, 3H), 2.45 (s, 6H), 1.84-1.68 (m, 4H).

Step 4. 3-(5-(((1S,2S)-2-(4-methoxypiperidin-1-yl)cyclopentyl)oxy)-1-oxoisoindolin-2-yl)piperidine-2,6-dione (I-154)

To a solution of 3-(5-(((1S,2S)-2-aminocyclopentyl)oxy)-1-oxoisoindolin-2-yl)piperidine-2,6-dione (I-12, 31 mg, 0.090 mmol) in MeCN (1 mL) was added DIPEA (0.047 mL, 0.27 mmol), followed by 3-methoxypentane-1,5-diyl bis(4-methylbenzenesulfonate) (134-4, 40 mg, 0.090 mmol) and the resulting solution was stirred at 120° C. under μW irradiation for 4 h. The reaction mixture was concentrated to dryness and the crude residue was taken up in DCM and washed with saturated $NaHCO_3$(aq). The phases were separated and the aqueous phase was extracted with DCM. The combined organic phases were dried over $Na_2SO_4$, filtered, and concentrated to dryness. The crude material was purified via silica gel chromatography eluting with 0-10% i-PrOH (with 0.1% $NEt_3$) in DCM (with 0.1% $NEt_3$) to afford I-154 (11 mg, 0.022 mmol, 25% yield) as an off-white solid. MS $[M+H]^+$=442.6. $^1$H NMR (400 MHz, DMSO-$d_6$) δ 10.95 (s, 1H), 7.60 (d, J=8.4 Hz, 1H), 7.18 (d, J=1.7 Hz, 1H), 7.03 (d, J=8.6 Hz, 1H), 5.07 (dd, J=13.2, 5.0 Hz, 1H), 4.73-4.66 (m, 1H), 4.45-4.18 (m, 2H), 3.20 (s, 3H), 3.17-3.09 (m, 1H), 2.97-2.81 (m, 2H), 2.79-2.66 (m, 1H), 2.59 (d, J=17.0 Hz, 1H), 2.44-2.34 (m, 1H), 2.22-1.86 (m, 5H), 1.86-1.74 (m, 2H), 1.72-1.54 (m, 4H), 1.53-1.31 (m, 3H).

Example 135: 3-(5-(((1S,2S)-2-(ethyl(oxetan-3-ylmethyl)amino)cyclopentyl)oxy)-1-oxoisoindolin-2-yl)piperidine-2,6-dione (I-155)

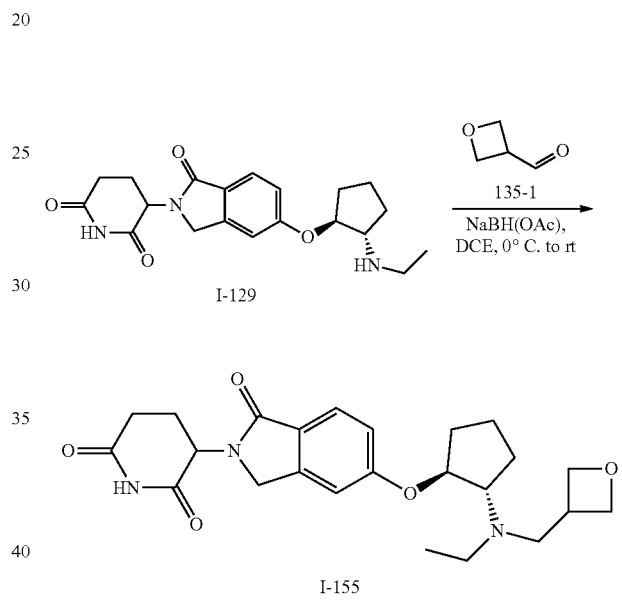

To a solution of 3-(5-(((1S,2S)-2-(ethylamino)cyclopentyl)oxy)-1-oxoisoindolin-2-yl)piperidine-2,6-dione (I-29, 0.18 g, 0.49 mmol) and oxetane-3-carbaldehyde (135-1, 60 mg, 0.73 mmol) in DCE (10 mL) at 0° C. was added NaBH(OAc)$_3$ (0.15 g, 0.73 mmol) and the resulting mixture was stirred at rt for 16 h. The reaction mixture was quenched with saturated aqueous sodium bicarbonate solution and extracted with EtOAc (2×30 mL). The combined organic phases were washed with brine, dried over $Na_2SO_4$, filtered, and concentrated under reduced pressure. The obtained crude material was purified via silica gel chromatography eluting with 5% MeOH in DCM to afford compound I-155 (70 mg, 0.16 mmol, 33% yield) as an off-white solid. MS $[M+H]^+$=442.2. $^1$H NMR (400 MHz, DMSO-$d_6$): δ 10.97 (s, 1H), 7.61 (d, J=8.8 Hz, 1H), 7.22 (s, 1H), 7.06 (d, J=8.8 Hz, 1H), 5.10-5.05 (m, 1H), 4.66-4.62 (m, 1H), 4.57-4.53 (m, 2H), 4.37-4.25 (m, 2H), 4.21-4.18 (m, 2H), 3.22-3.12 (m, 2H), 2.92-2.89 (m, 1H), 2.75-2.72 (m, 2H), 2.60-2.55 (m, 1H), 2.46-2.32 (m, 3H), 2.05-1.95 (m, 2H), 1.90-1.88 (m, 1H), 1.66-1.62 (m, 3H), 1.52-1.49 (m, 1H), 0.96-0.93 (m, 3H).

Example 136: 3-(5-(((1S,2S)-2-(isoindolin-2-yl)cyclopentyl)oxy)-1-oxoisoindolin-2-yl)piperidine-2,6-dione (I-156)

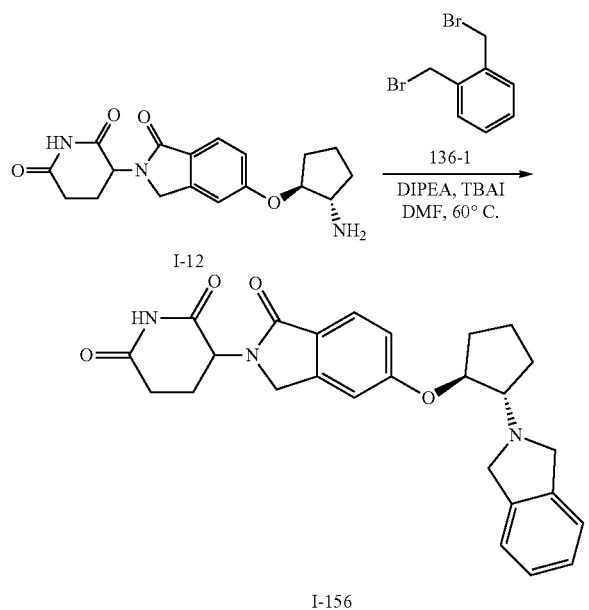

To a stirred solution of 3-(5-(((1S,2S)-2-aminocyclopentyl)oxy)-1-oxoisoindolin-2-yl)piperidine-2,6-dione (I-12, 200 mg, 0.580 mmol) and DIPEA (0.300 mL, 1.74 mmol) in DMF (10 mL) was added 1,2-bis(bromomethyl)benzene (136-1, 230 mg, 0.860 mmol), followed by TBAI (20 mg, 0.060 mmol) and the resulting mixture was stirred at 60° C. for 16 h. The reaction mixture was then cooled to rt, diluted with EtOAc. The organic phase was washed with saturated aqueous NaHCO$_3$ and brine, dried over Na$_2$SO$_4$, filtered, and concentrated under reduced pressure. The obtained crude material was purified via silica gel chromatography eluting with 10% MeOH in DCM and then further purified by reverse phase HPLC (Column: ZOBRAX ECLIPS XDB C18 (150×21.5 µm), Mobile phase A: 0.01% TFA (aq), Mobile phase B: MeCN, Time (min)/% B: 0/25, 2/35, 9/65, Flow rate: 18 ml/min) to afford I-156 (15 mg, 0.03 mmol, 6% yield) as a white solid. MS [M+H]$^+$=446.2. $^1$H NMR (400 MHz, DMSO-d$_6$): δ 10.98 (s, 1H), 7.63 (d, J=8.8 Hz, 1H), 7.23-7.15 (m, 5H), 7.08 (d, J=8.8 Hz, 1H), 5.10-5.06 (m, 1H), 4.86-4.84 (m, 1H), 4.42 (d, J=17.2, 1H), 4.28 (d, J=17.2, 1H), 3.96-3.87 (m, 3H) 3.20-3.16 (m, 1H), 2.95-2.86 (m, 1H), 2.67-2.61 (m, 1H), 2.40-2.32 (m, 2H), 2.21-2.10 (m, 1H), 2.08-1.96 (m, 2H), 1.75-1.65 (m, 4H).

Example 137: 3-(5-(((1S,2S)-2-(3-methoxyazetidin-1-yl)cyclopentyl)oxy)-1-oxoisoindolin-2-yl)piperidine-2,6-dione (I-157)

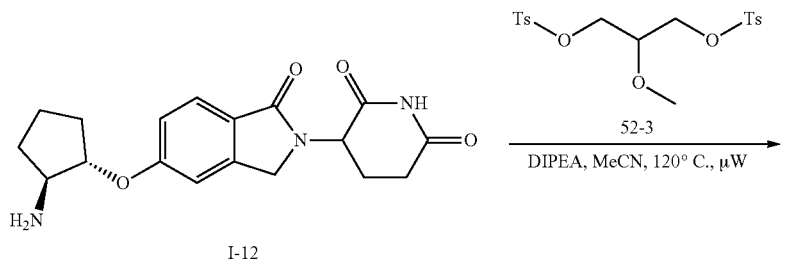

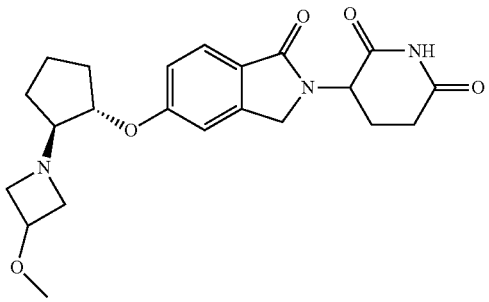

To a solution of 3-(5-(((1S,2S)-2-aminocyclopentyl)oxy)-1-oxoisoindolin-2-yl)piperidine-2,6-dione (I-12, 50.0 mg, 0.146 mmol) in MeCN (1.5 mL) was added DIPEA (0.15 mL, 0.87 mmol), followed by 2-methoxypropane-1,3-diyl bis(4-methylbenzenesulfonate) (52-3, 177 mg, 0.427 mmol) and the resulting solution was stirred at 120° C. under μW irradiation for 4 h. The reaction mixture was concentrated to dryness and the crude residue was taken up in DCM and washed with saturated NaHCO$_3$ (aq). The phases were separated and the aqueous phase was extracted with DCM. The combined organic phases were dried over Na$_2$SO$_4$, filtered, and concentrated to dryness. The crude material was purified via silica gel chromatography eluting with 0-100% EtOAc:EtOH (v/v=3:1, with 0.1% NEt$_3$) in DCM (with 0.1% NEt$_3$) to afford I-157 (13.0 mg, 0.028 mmol, 19% yield) as clear glassy solid. MS [M+H]$^+$=414.4. $^1$H NMR (400 MHz, DMSO-d$_6$) δ 10.95 (s, 1H), 7.61 (d, J=8.4 Hz, 1H), 7.14 (d, J=2.1 Hz, 1H), 7.02 (dd, J=8.3, 2.2 Hz, 1H), 5.75 (s, 1H), 5.07 (dd, J=13.3, 5.1 Hz, 1H), 4.56-4.50 (m, 1H), 4.39 (dd, J=17.2, 3.8 Hz, 1H), 4.26 (dd, J=17.1, 3.6 Hz, 1H), 3.97-3.87 (m, 1H), 3.54-3.44 (m, 2H), 3.13 (s, 3H), 2.89-2.78 (m, 3H), 2.63-2.55 (m, 1H), 2.43-2.35 (m, 1H), 2.15-2.04 (m, 1H), 2.03-1.94 (m, 1H), 1.82-1.72 (m, 1H), 1.72-1.55 (m, 3H), 1.44-1.35 (m, 1H).

Example 138: 3-(5-(((1S,2S)-2-(4-ethoxy-4-methylpiperidin-1-yl)cyclopentyl)oxy)-1-oxoisoindolin-2-yl)piperidine-2,6-dione (I-158)

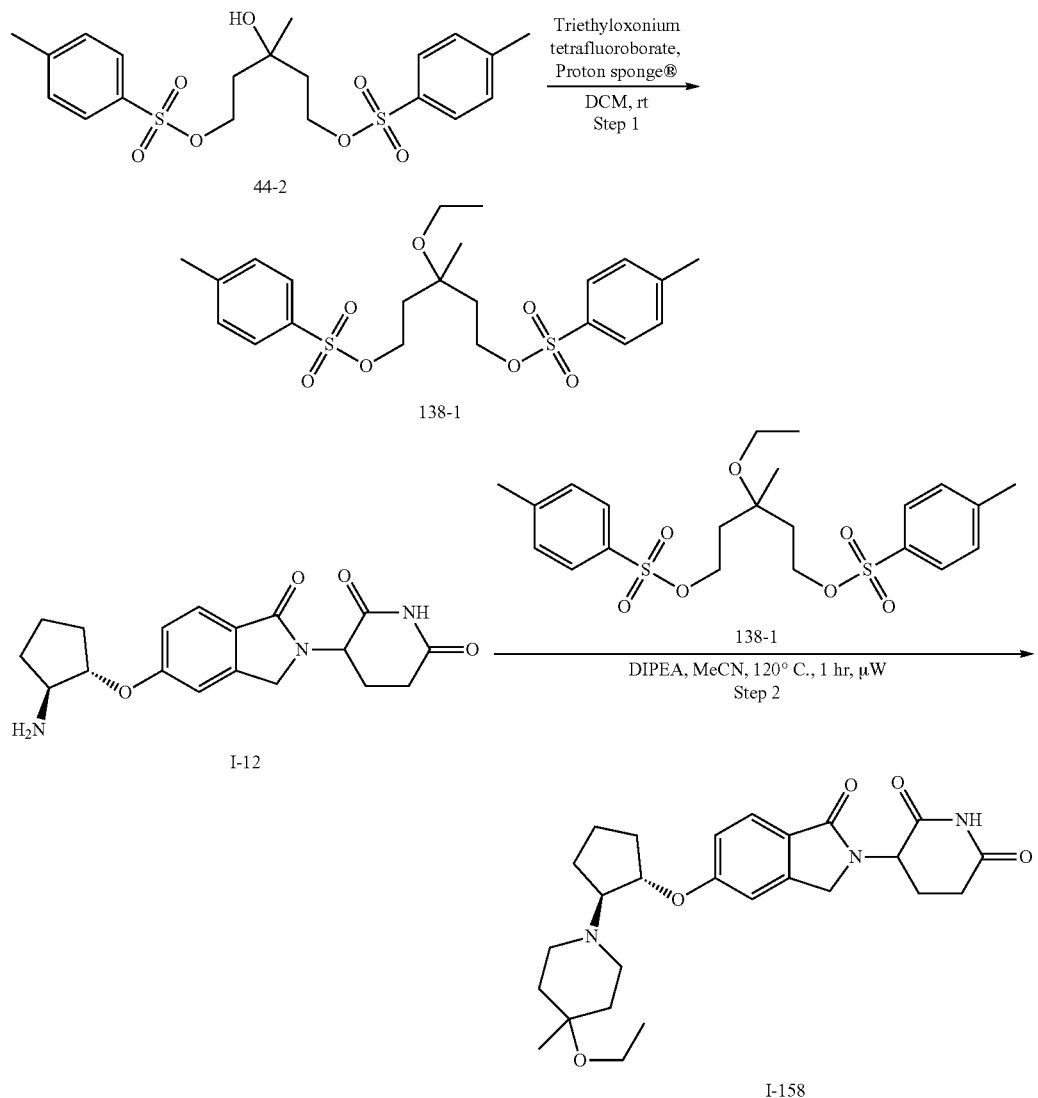

Step 1. 3-ethoxy-3-methylpentane-1,5-diyl bis(4-methylbenzenesulfonate) (138-1)

To a solution of 3-hydroxy-3-methylpentane-1,5-diyl bis(4-methylbenzenesulfonate) (44-2, 250 mg, 0.565 mmol) and Proton-sponge® (242 mg, 1.13 mmol) in DCM was added triethyloxonium tetrafluoroborate (1M in DCM) (1.1 mL, 1.1 mmol) and the resulting mixture was stirred at rt overnight. Additional triethyloxonium tetrafluoroborate (1M in DCM) (1.1 mL, 1.1 mmol) was added and stirring was continued at rt overnight. The reaction mixture was then filtered and concentrated to dryness. The crude material was purified via silica gel chromatography eluting with 0-60%

EtOAc in heptane to afford 138-1 (61.0 mg, 0.130 mmol, 23% yield) as a colorless oil. MS [M+H$_2$O]$^+$=488.4. $^1$H NMR (400 MHz, Chloroform-d) δ 7.80-7.75 (m, 4H), 7.37-7.33 (m, 4H), 4.11-4.01 (m, 4H), 3.18 (q, J=7.0 Hz, 2H), 2.45 (s, 6H), 1.88-1.72 (m, 4H), 1.08 (s, 3H), 1.00 (t, J=6.9 Hz, 3H).

Step 2. 3-(5-(((1S,2S)-2-(4-ethoxy-4-methylpiperidin-1-yl)cyclopentyl)oxy)-1-oxoisoindolin-2-yl)piperidine-2,6-dione (I-158)

To a solution of 3-ethoxy-3-methylpentane-1,5-diyl bis(4-methylbenzenesulfonate) (138-1, 61 mg, 0.13 mmol) and 3-(5-(((1S,2S)-2-aminocyclopentyl)oxy)-1-oxoisoindolin-2-yl)piperidine-2,6-dione (I-12, 40 mg, 0.12 mmol) in MeCN (1 mL) was added DIPEA (0.10 mL, 0.58 mmol) and the resulting solution was stirred at 120° C. under μW irradiation for 12 h. The reaction mixture was then concentrated to dryness and the crude residue was taken up in DCM and washed with saturated NaHCO$_3$ (aq). The phases were separated and the aqueous phase was extracted with DCM. The combined organic phases were dried over Na$_2$SO$_4$, filtered, and concentrated to dryness. The crude material was purified via silica gel chromatography eluting with 0-100% EtOAc:EtOH (v/v=3:1, with 0.1% NEt$_3$) in DCM (with 0.1% NEt$_3$) to afford I-158 (10 mg, 0.019 mmol, 16% yield) as clear glassy solid. MS [M+H]$^+$=470.5. $^1$H NMR (400 MHz, DMSO-d$_6$) δ 10.95 (s, 1H), 7.60 (d, J=8.4 Hz, 1H), 7.20-7.14 (m, 1H), 7.03 (d, J=8.3 Hz, 1H), 5.06 (dd, J=13.3, 5.1 Hz, 1H), 4.73-4.65 (m, 1H), 4.43-4.19 (m, 2H), 3.30-3.24 (m, 3H, shoulder on H$_2$O signal), 2.98-2.81 (m, 2H), 2.64-2.54 (m, 1H), 2.47-2.34 (m, 4H), 2.11-1.88 (m, 3H), 1.73-1.55 (m, 5H), 1.54-1.35 (m, 3H), 1.10-1.00 (m, 6H).

Example 139: 3-(5-(((1S,2S)-2-((((1r,4S)-4-methoxycyclohexyl)methyl)amino)cyclopentyl)oxy)-1-oxoisoindolin-2-yl)piperidine-2,6-dione (I-159)

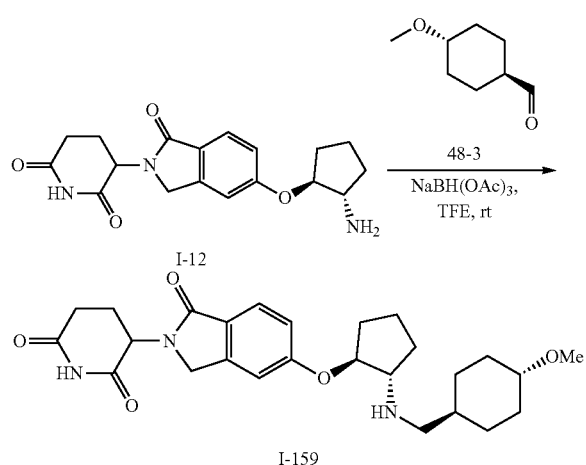

To a solution of 3-(5-(((1S,2S)-2-aminocyclopentyl)oxy)-1-oxoisoindolin-2-yl)piperidine-2,6-dione (I-12, 0.20 g, 0.53 mmol) and (1r,4r)-4-methoxycyclohexane-1-carbaldehyde (48-3, 0.15 g, 1.1 mmol) in TFE (10 mL) was added NaBH(OAc)$_3$ (0.17 g, 0.78 mmol) at 0° C. and the resulting mixture was stirred at rt for 16 h. The reaction mixture was quenched with water and extracted with DCM (3×50 mL). The combined organic phases were washed with brine, dried over Na$_2$SO$_4$, filtered, and concentrated under reduced pressure. The obtained crude material was purified via silica gel chromatography eluting with 5% MeOH in DCM to afford I-159 (22 mg, 0.050 mmol, 10% yield) as a pale green solid. [M+H]$^+$=470.3. $^1$H NMR (400 MHz, DMSO-d$_6$): δ 10.97 (s, 1H), 7.60 (d, J=8.8 Hz, 1H), 7.17 (s, 1H), 7.04 (d, J=8.8 Hz, 1H), 5.12-5.05 (m, 1H), 4.58-4.52 (m, 1H), 4.38-4.25 (m, 2H), 3.20 (s, 3H), 3.19-2.87 (m, 3H), 2.62-2.51 (m, 2H), 2.38-2.32 (m, 2H), 2.13-2.09 (m, 1H), 1.98-1.95 (m, 4H), 1.79-1.62 (m, 5H), 1.42-1.28 (m, 3H), 1.05-0.72 (m, 4H).

Example 140: (1S,4r)-4-((((1S,2S)-2-((2-(2,6-dioxopiperidin-3-yl)-1-oxoisoindolin-5-yl)oxy)cyclopentyl)amino)methyl)cyclohexane-1-carbonitrile (I-160)

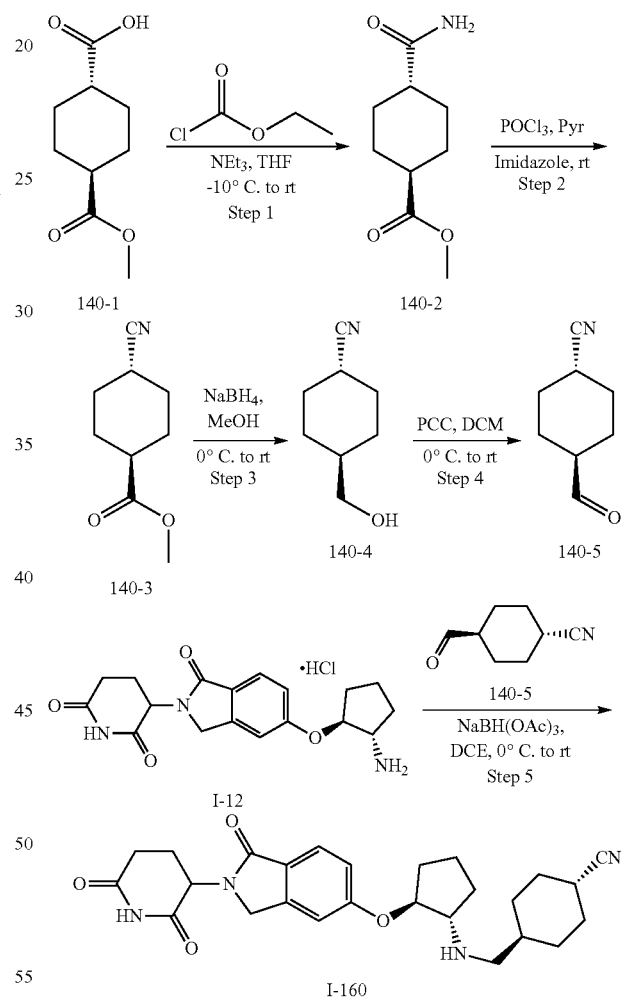

Step 1. Methyl 4-carbamoylcyclohexane-1-carboxylate (140-2)

To a cooled solution of (1r,4r)-4-(methoxycarbonyl)cyclohexane-1-carboxylic acid (140-1, 5.00 g, 15.2 mmol) in tetrahydrofuran (100 mL) at −10° C. was sequentially added TEA (7.2 mL, 38 mmol) and ethyl chloroformate (2.25 mL, 22.9 mmol) under an atmosphere of nitrogen and the resulting mixture was stirred at room temperature for 3 h. The reaction mixture was then cooled to −10° C., ammonium hydroxide (25.0 mL, 91.2 mmol) was added and the mixture warmed to room temperature and stirred overnight. The reaction mixture was diluted with water and extracted with EtOAc (3×50 mL). The combined organic phases were washed with brine (50 mL), dried over $Na_2SO_4$, filtered, and concentrated to afford 140-2 (4.80 g, 25.9 mmol, 96% yield) as a white solid. $^1H$ NMR (400 MHz, DMSO-$d_6$): δ 7.18 (br s, 1H), 6.68 (br s, 1H), 3.58 (s, 3H), 2.28-2.20 (m, 1H), 2.18-1.98 (m, 1H), 1.92-1.86 (m, 2H), 1.78-1.74 (m, 2H), 1.35-1.30 (m, 4H).

Step 2. Methyl 4-cyanocyclohexane-1-carboxylate (140-3)

To a solution of the methyl 4-carbamoylcyclohexane-1-carboxylate (140-2, 2.80 g, 11.4 mmol) in pyridine (28.0 mL) was added imidazole (0.790 g, 11.4 mmol) and phosphorous oxychloride (2.80 mL) in one portion at 0° C. under an atmosphere of nitrogen and the resulting mixture was stirred at room temperature for 4 h. The reaction mixture was then quenched with water and extracted with EtOAc (3×50 mL). The combined organic phases were washed with 2 M hydrochloric acid (aq), dried over $Na_2SO_4$, filtered, and concentrated. The obtained crude material was purified via silica gel chromatography eluting with 30% EtOAc in hexanes to afford 140-3 (1.60 g, 9.58 mmol, 64% yield) as a white solid. $^1H$ NMR (300 MHz, $CDCl_3$): δ 3.67 (s, 3H), 2.48-2.33 (m, 2H), 2.16-2.02 (m, 4H), 1.69-1.48 (m, 4H).

Step 3. 4-(hydroxymethyl)cyclohexane-1-carbonitrile (140-4)

To a solution of methyl 4-cyanocyclohexane-1-carboxylate (140-3, 1.00 g, 5.90 mmol) in MeOH (10 mL) at 0° C. was added $NaBH_4$ (0.540 g, 14.8 mmol) in small portions at 0° C. and the resulting mixture was allowed to warm to rt and stirred at rt for 6 h. The reaction mixture was then quenched with ice-cold water and extracted with EtOAc (3×50 mL). The combined organic phases were washed with brine (50 mL), dried over $Na_2SO_4$, filtered, and concentrated. The obtained crude material was purified via silica gel chromatography eluting with 30% EtOAc in hexanes to afford 140-4 (0.520 g, 3.74 mmol, 63% yield) as an off-white solid. $^1H$ NMR (400 MHz, $CDCl_3$): δ 3.49-3.47 (m, 2H), 2.41-2.34 (m, 1H), 2.18-2.11 (m, 2H), 1.91-1.86 (m, 2H), 1.63-1.49 (m, 3H), 1.39-1.36 (m, 1H), 1.05-0.95 (m, 2H).

Step 4. 4-formylcyclohexane-1-carbonitrile (140-5)

To a solution of 4-(hydroxymethyl)cyclohexane-1-carbonitrile (140-4, 0.400 g, 2.87 mmol) in DCM (20 mL) at 0° C. was added PCC (1.23 g, 5.74 mmol) and the resulting mixture was stirred at rt for 6 h. The reaction mixture was then filtered through Celite® and washed with DCM. The filtrate was concentrated to dryness and the crude material was purified via silica gel chromatography eluting with 40% EtOAc in hexanes to afford 140-5 (0.150 g, 1.09 mmol, 38%) as pale yellow oil. $^1H$ NMR (400 MHz, $CDCl_3$): δ 9.64 (s, 1H), 2.51-2.33 (m, 2H), 2.11-2.06 (m, 4H), 1.69-1.64 (m, 2H), 1.50-1.45 (m, 2H).

Step 5. (1S,4r)-4-(((((1S,2S)-2-((2-(2,6-dioxopiperidin-3-yl)-1-oxoisoindolin-5-yl)oxy)cyclopentyl) amino)methyl)cyclohexane-1-carbonitrile (I-160)

To a solution of 3-(5-(((1S,2S)-2-aminocyclopentyl)oxy)-1-oxoisoindolin-2-yl)piperidine-2,6-dione hydrochloride (I-12, 0.250 g, 0.658 mmol) and (1r,4r)-4-formylcyclohexane-1-carbonitrile (140-5, 0.135 g, 0.987 mmol) in DCE (10 mL) at 0° C. was added $NaBH(OAc)_3$ (0.418 g, 1.97 mmol) and the resulting mixture was stirred at rt for 16 h. The reaction mixture was then quenched with saturated aqueous sodium bicarbonate solution and extracted with DCM (3×30 mL). The combined organic phases were washed with brine, dried over $Na_2SO_4$, filtered, and concentrated under reduced pressure. The obtained crude material was purified by reverse phase HPLC (Column: KINETEX EVO C18, (21.2 mm×150 mm), Mobile phase: A:0.01% ammonia, B: acetonitrile, Flow rate: 18 ml/min, Time (min)/% B 0/20, 2/30, 8/50) to afford I-160 (0.020 g, 0.172 mmol, 26% yield) as a white solid. MS [M+H]$^+$=465.15. $^1H$ NMR (400 MHz, DMSO-$d_6$): δ 10.97 (s, 1H), 7.60 (d, J=8.8 Hz, 1H), 7.16 (s, 1H), 7.03 (d, J=8.8 Hz, 1H), 5.10-5.05 (m, 1H), 4.54-4.52 (m, 1H), 4.36-4.25 (m, 2H), 3.06-3.02 (m, 1H), 2.90-2.88 (m, 1H), 2.66-2.55 (m, 2H), 2.38-2.33 (m, 4H), 2.07-1.85 (m, 4H), 1.78-1.61 (m, 6H), 1.44-1.37 (m, 4H), 0.91-0.88 (m, 2H).

Example 141: 3-(5-(((1S,2S)-2-(((4-methoxycyclohexyl)methyl)amino)cyclopentyl)oxy)-1-oxoisoindolin-2-yl)piperidine-2,6-dione TFA Salt (I-161)

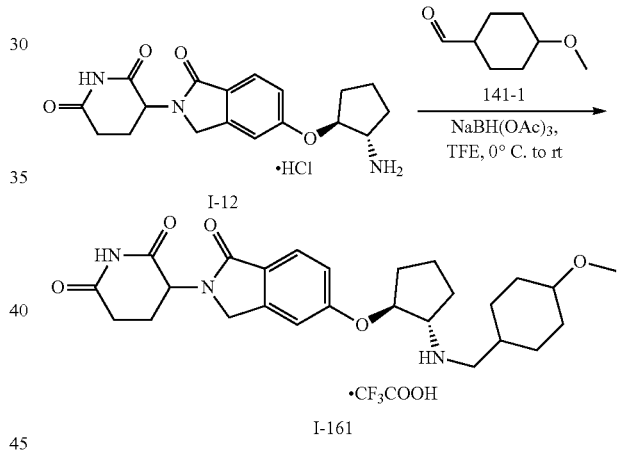

To a solution of 3-(5-(((1S,2S)-2-aminocyclopentyl)oxy)-1-oxoisoindolin-2-yl)piperidine-2,6-dione hydrochloride (I-12, 0.200 g, 0.526 mmol) and 4-methoxycyclohexane-1-carbaldehyde (141-1, 0.112 g, 0.782 mmol) in TFE (10 mL) at 0° C. was added $NaBH(OAc)_3$ (0.167 g, 0.782 mmol) and the resulting mixture was stirred at rt for 2 h. The reaction mixture was then concentrated to dryness and the obtained residue was diluted with saturated aqueous sodium bicarbonate solution and extracted with EtOAc (3×30 mL). The combined organic phases were washed with brine, dried over $Na_2SO_4$, filtered, and concentrated to dryness. The obtained crude material was purified by reverse phase HPLC (Column: KINETEX EVO C18 (150 mm×21.0 mm), 5.0g, Mobile phase: 0.05% TFA in water (A): MeCN (B); Flow: 20 mL/min; Time (min)/% B: 0/10, 2/20, 10/50) to afford the TFA salt of I-161 (0.013 mg, 0.027 mmol, 5% yield) as pale green solid. MS [M+H]$^+$=470.3. $^1H$ NMR (400 MHz, DMSO-$d_6$): δ 10.99 (s, 1H), 8.79 (br s, 2H), 7.68 (d, J=8.4 Hz, 1H), 7.17 (s, 1H), 7.07 (d, J=8.8 Hz, 1H), 5.08 (dd, J=13.2, 4.8 Hz, 1H), 4.96-4.94 (m, 1H), 4.40-4.24 (m, 2H), 3.71-6.62 (m, 4H), 3.21 (s, 3H), 3.08-3.04 (m, 1H), 2.95-

2.86 (m, 3H), 2.55-2.35 (m, 2H), 2.22-2.15 (m, 2H), 2.02-1.95 (m, 3H), 1.80-1.62 (m, 5H), 1.07-0.96 (m, 4H).

z

A 2-5 mL μW vial was charged with 3-(5-(((1S,2S)-2-aminocyclopentyl)oxy)-1-oxoisoindolin-2-yl)piperidine-2,6-dione (I-12, 100 mg, 0.291 mmol), DIPEA (0.25 mL, 1.5 mmol), oxetane-3,3-diylbis(ethane-2,1-diyl) bis(4-methylbenzenesulfonate) (87-6, 139 mg, 0.306 mmol) and MeCN (1 mL). The resulting mixture was stirred for 4 hours at 120° C. in the μW and then concentrated to dryness. The crude material was purified by reverse phase HPLC (Column: Xbridge C18 OBD 5 um 30×50 mm; Conditions: Water/MeCN with 5 mM NH₄OH 75 mL/min; 1.5 mL injection; Gradient: 15-40% MeCN, 3.5 min gradient; collected fractions contained ~1 drop of formic acid) and then further purified by reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) to afford the formate salt of I-162 (2.0 mg, 4.7 μmol, 1% yield) as a white solid. MS [M+H]⁺ =454.5. ¹H NMR (400 MHz, Deuterium Oxide) δ 8.45 (s, 1H), 7.77 (d, J=8.5 Hz, 1H), 7.22-7.09 (m, 2H), 5.14 (ddd, J=13.3, 5.3, 2.1 Hz, 1H), 5.05-4.95 (m, 1H), 4.64-4.44 (m, 6H), 3.87-3.71 (m, 1H), 3.43-3.06 (m, 3H), 3.00-2.84 (m, 2H), 2.53 (qd, J=12.9, 5.4 Hz, 1H), 2.40-2.22 (m, 4H), 2.21-2.03 (m, 3H), 1.92-1.72 (m, 5H).

Example 143: 3-(((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile HC(O)OH Salt (I-163) and (1R,3S)-3-((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile and (1S,3R)-3-(((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile (I-164 and I-165)

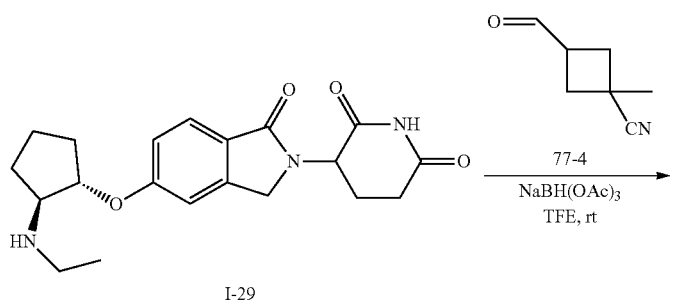

I-29

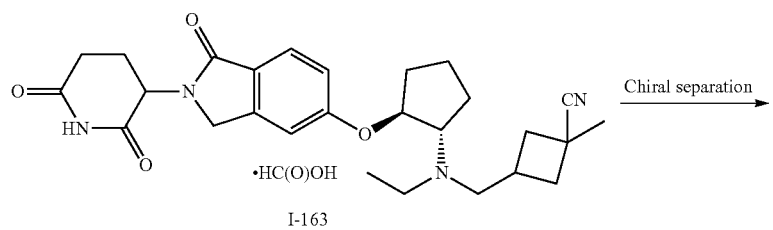

I-163

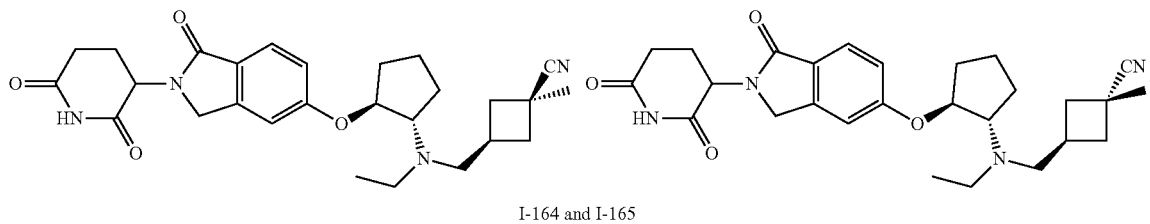

I-164 and I-165

To a solution of 3-(5-(((1S,2S)-2-(ethylamino)cyclopentyl)oxy)-1-oxoisoindolin-2-yl)piperidine-2,6-dione (I-29, 91 mg, 0.25 mmol) in TFE (1 mL) was added 3-formyl-1-methylcyclobutane-1-carbonitrile (77-4, 91 mg, 0.74 mmol), followed by sodium triacetoxyborohydride (156 mg, 0.735 mmol) and the resulting mixture was stirred at rt overnight. Additional 3-formyl-1-methylcyclobutane-1-carbonitrile (77-4, 120 mg) and sodium triacetoxyborohydride (170 mg, 0.80 mmol) was added until complete disappearance of I-29 was observed. The reaction mixture was then concentrated to dryness and the crude material was purified by reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient) to afford the formate salt of I-163 (38 mg, 0.078 mmol, 32% yield) as a white solid, as a mixture of diastereoisomers. MS [M+H]$^+$=479.5. (3-((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile HC(O)OH salt (I-163, 34 mg) was purified using chiral SFC (Column: Chiralpak IH 21×250 mm; Flow rate: 80 g per minute; Cosolvent: 30% i-PrOH with 10 mM NH$_3$) followed by purification via reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient) to afford two diastereomeric products I-164 and I-165.

Peak 1: Isolated diastereomer I-164 (7 mg, 0.014 mmol, 21% yield) as a white solid. Chiral SFC: Rt=2.25 mins. MS [M+H]$^+$=479.2. $^1$H NMR (400 MHz, Methylene Chloride-d) δ 8.02 (s, 1H), 7.72 (d, J=8.5 Hz, 1H), 7.11-6.93 (m, 2H), 5.25-5.05 (m, 1H), 4.49-4.27 (m, 2H), 3.66-3.32 (m, 1H), 3.22-2.73 (m, 5H), 2.72-2.40 (m, 2H), 2.41-1.93 (m, 7H), 1.96-1.63 (m, 5H), 1.62-1.33 (m, 3H), 1.28-0.94 (m, 3H). Peak 2: Isolated diastereomer I-165 (3 mg, 6 μmol, 9% yield) as a white solid. Chiral SFC Rt=2.65 mins. MS [M+H]$^+$=479.5. $^1$H NMR (400 MHz, Methylene Chloride-d) δ 8.06 (s, 1H), 7.72 (d, J=8.4 Hz, 1H), 7.16-6.93 (m, 2H), 5.12 (dd, J=13.2, 5.2 Hz, 1H), 4.50-4.26 (m, 2H), 3.65-3.35 (m, 1H), 3.32-2.68 (m, 6H), 2.73-2.45 (m, 2H), 2.41-2.02 (m, 6H), 1.96-1.64 (m, 5H), 1.54-1.36 (m, 3H), 1.28-0.97 (m, 3H). Relative stereochemistry of the substituents on the cyclobutane ring was not determined and assigned arbitrarily.

Example 144: 3-(1-oxo-5-(((1S,2S)-2-(3-(2,2,2-trifluoroethoxy)azetidin-1-yl)cyclopentyl)oxy)isoindolin-2-yl)piperidine-2,6-dione (I-206)

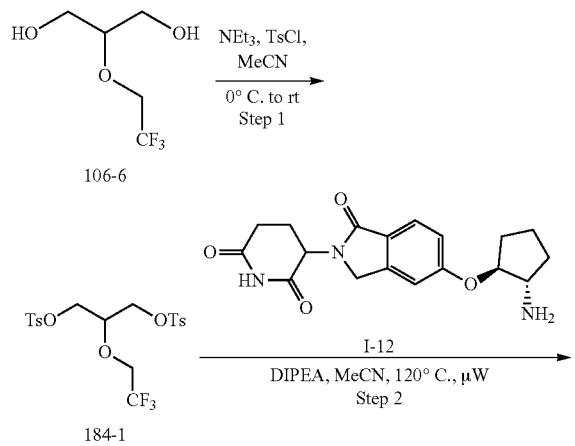

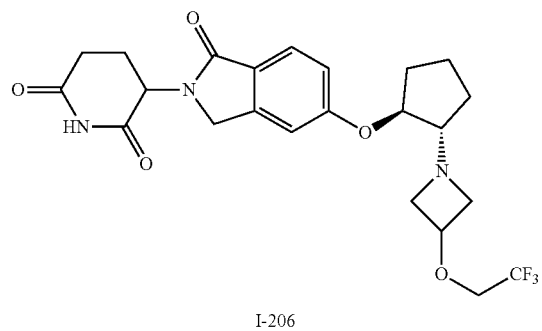

I-206

Step 1. 2-(2,2,2-trifluoroethoxy)propane-1,3-diyl bis(4-methylbenzenesulfonate) (184-1)

To a solution of 106-6 (0.7 g, 4.0 mmol) in DCM (30 mL) was added Et$_3$N (2.2 mL, 16.1 mmol), DMAP (0.017 g, 0.1 mmol) and TsCl (1.68 g, 8.8 mmol) at 0° C. and resulting mixture was stirred at room temperature for 16 h. The reaction mixture was quenched with cold water and extracted with DCM (3×30 mL). The combined organic phases were washed water, brine, dried over anhydrous Na$_2$SO$_4$, filtered, and concentrated to dryness. The obtained crude material was purified by silica gel chromatography eluting with 10% EtOAc in hexanes to afford 184-1 (0.83 g, 1.7 mmol, 43%) as pale yellow liquid. MS [M+H+18]$^+$=500.1. $^1$H NMR (300 MHz, Chloroform-d) δ 7.68 (d, J=8.1 Hz, 4H), 7.37 (d, J=8.1 Hz, 4H), 4.05 (d, J=5.1 Hz, 4H), 3.87-3.84 (m, 3H), 2.46 (s, 6H).

Step 2. 3-(1-oxo-5-(((1S,2S)-2-(3-(2,2,2-trifluoroethoxy)azetidin-1-yl)cyclopentyl)oxy)isoindolin-2-yl)piperidine-2,6-dione (I-206)

To a solution of I-12 (300 mg, 0.56 mmol) in acetonitrile (10 mL) was added 184-1 (631 mg, 1.31 mmol) and DIPEA (0.77 mL, 4.4 mmol) and resulting mixture was stirred at 120° C. for 9 h under microwave irradiation. Upon complete consumption of starting material, the reaction mixture was diluted with sat. sodium bicarbonate solution and extracted with DCM (3×30 mL). The combined organic phases were washed with brine, dried over Na$_2$SO$_4$, filtered, and concentrated under reduced pressure. The obtained crude material was purified by silica gel chromatography eluting with 10% MeOH in DCM to afford compound I-206 (33 mg, 0.06 mmol, 8% yield) as an off-white solid. MS [M+H]$^+$=482.4. $^1$H NMR (400 MHz, DMSO-d$_6$): δ 10.97 (s, 1H), 7.62 (d, J=8.4 Hz, 1H), 7.14 (s, 1H), 7.03 (d, J=8.4 Hz, 1H), 5.08-5.04 (m, 1H), 4.58-4.54 (m, 1H), 4.36-4.35 (m, 1H), 4.27-4.20 (m, 2H), 4.05-3.98 (m, 2H), 3.52-3.49 (m, 2H), 2.95-2.87 (m, 4H), 2.66-2.60 (m, 1H), 2.49-2.48 (m, 1H), 2.55-2.45 (m, 2H), 1.80-1.63 (m, 4H), 1.37-1.31 (m, 1H).

Example 145: 3-(5-(((1S,2S)-2-(4-fluoropiperidin-1-yl)cyclopentyl)oxy)-1-oxoisoindolin-2-yl)piperidine-2,6-dione (I-166)

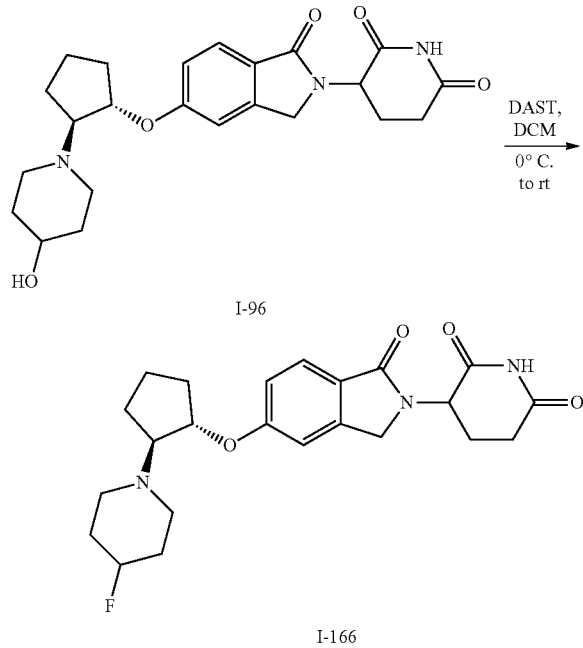

To a solution of 3-(5-(((1S,2S)-2-(4-hydroxypiperidin-1-yl)cyclopentyl)oxy)-1-oxoisoindolin-2-yl)piperidine-2,6-dione (I-96, 20 mg, 0.047 mmol) in DCM (2 mL) and cooled to 0° C. was added a solution of DAST (17 mg, 0.11 mmol) in DCM (0.2 mL) and the resulting mixture was stirred at 0° C. for 1 h, and then warmed to rt. Upon complete consumption of starting material, the reaction mixture was quenched with saturated NaHCO$_3$(aq). The phases were separated and the aqueous phase was extracted with DCM. The combined organic phases were dried over Na$_2$SO$_4$, filtered, and concentrated to dryness. The crude material was purified via silica gel chromatography eluting with 0-100% EtOAc:EtOH (v/v=3:1, with 0.1% NEt$_3$) in DCM (with 0.1% NEt$_3$) and then further purified by reverse phase HPLC (Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient). The fractions containing the desired product were combined and lyophilized to afford I-166 (2.0 mg, 4.7 μmol, 10% yield) as a white solid. MS [M+H]$^+$=430.4. $^1$H NMR (400 MHz, DMSO-d$_6$) δ 10.95 (s, 1H), 7.60 (d, J=8.4 Hz, 1H), 7.19 (d, J=2.2 Hz, 1H), 7.06-7.01 (m, 1H), 5.06 (dd, J=13.1, 5.0 Hz, 1H), 4.76-4.67 (m, 2H), 4.39 (dd, J=17.1, 9.8 Hz, 1H), 4.26 (dd, J=17.1, 8.5 Hz, 1H), 2.96-2.84 (m, 2H), 2.65-2.55 (m, 3H), 2.43-2.34 (m, 3H), 2.12-2.01 (m, 1H), 2.01-1.74 (m, 4H), 1.76-1.55 (m, 5H), 1.55-1.41 (m, 1H).

Example 146: 3-(5-(((1S,2S)-2-(1,5-oxazocan-5-yl)cyclopentyl)oxy)-1-oxoisoindolin-2-yl)piperidine-2,6-dione HC(O)OH Salt (I-167)

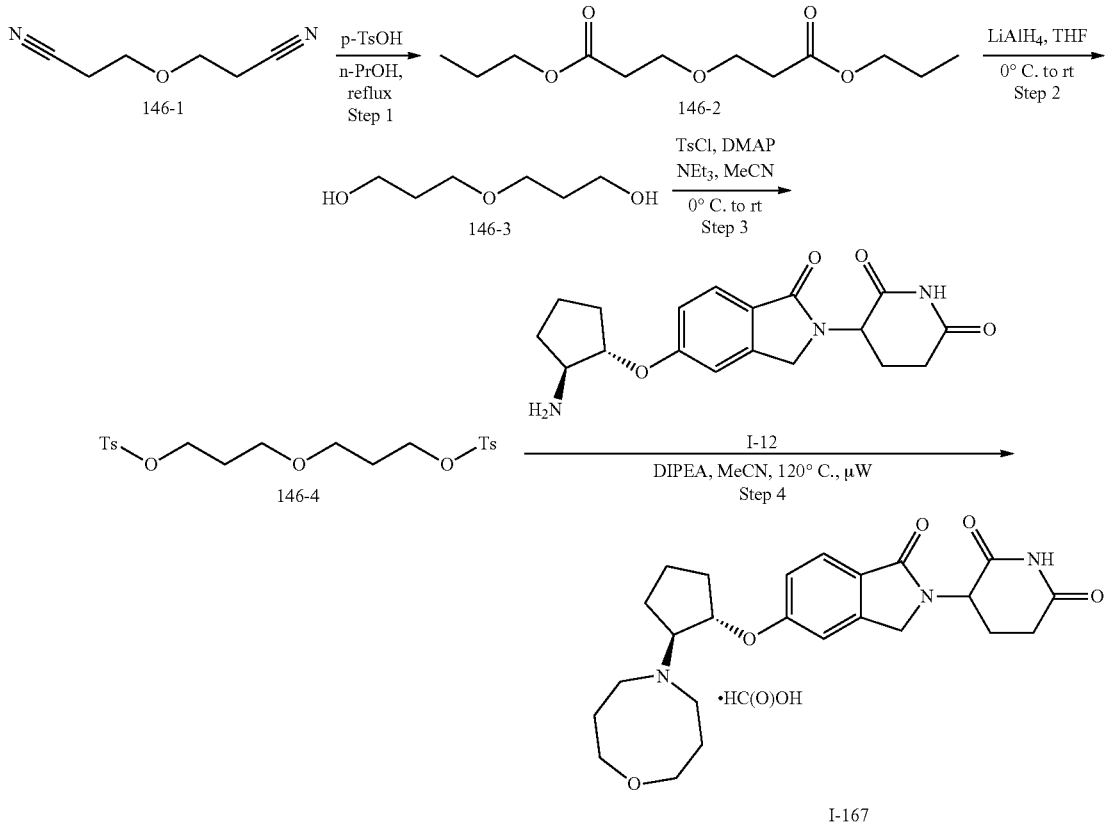

Step 1. Dipropyl 3,3'-oxydipropanoate (146-2)

A suspension of p-toluenesulfonic acid (61.3 g, 322 mmol) in n-propanol (100 mL) was added 2-cyanoethyl ether (146-1, 10.0 g, 9.62 mmol) and the resulting mixture was stirred at reflux overnight. The reaction mixture was then cooled to rt, concentrated to roughly 50 mL, and treated with water and heptanes. The phases were separated and the organic phase was washed with aqueous $NaHCO_3$ and brine. The organic phase was dried over $Na_2SO_4$, filtered, and concentrated to dryness. The crude material was purified via silica gel chromatography eluting with 0-100% EtOAc in heptanes to afford 146-2 (11.6 g, 47.1 mmol, 59% yield). $^1$H NMR (400 MHz, Chloroform-d) δ 4.07 (t, J=6.7 Hz, 4H), 3.75 (t, J=6.5 Hz, 4H), 2.59 (t, J=6.5 Hz, 4H), 1.66 (quint, J=7.0 Hz, 4H), 0.96 (t, J=7.4 Hz, 6H).

Step 2. 3,3'-oxybis(propan-1-ol) (146-3)

To a solution of dipropyl 3,3'-oxydipropanoate (146-2, 500 mg, 2.03 mmol) in THF (10 mL) at 0° C. was added lithium aluminum hydride (1M in THF) (3.05 mL, 3.05 mmol) and the resulting mixture was stirred at 0° C. and then at rt. Upon complete consumption of starting material, the reaction mixture was cooled to 0° C., slowly quenched with 10% $H_2SO_4$ (aq) (0.5 mL), and stirred at rt overnight. The organic phase was isolated and then dried over $Na_2SO_4$, filtered, and concentrated to dryness to afford 146-3 (269 mg, 2.00 mmol, 99% yield) as a colorless oil. $^1$H NMR (400 MHz, Chloroform-d) δ 3.74-3.59 (m, 4H), 3.58-3.49 (m, 4H), 1.84-1.66 (m, 4H).

Step 3. Oxybis(propane-3,1-diyl) bis(4-methylbenzenesulfonate) (146-4)

To a solution of 3,3'-oxybis(propan-1-ol) (146-3, 269 mg, 2.01 mmol), DMAP (8.08 mg, 0.066 mmol), and TEA (1.1 mL, 8.0 mmol) in MeCN (8 mL) and cooled to 0° C. was added TsCl (841 mg, 4.41 mmol) and the resulting mixture was stirred for 4 h. The reaction mixture was filtered and concentrated to dryness. The crude material was triturated with diethyl ether and the filtrate was collected and concentrated to dryness. The obtained product was purified via silica gel chromatography eluting with 0-80% EtOAc in heptane to afford 146-4 (670 mg, 1.51 mmol, 76% yield) as an off-white solid. MS [M+H]$^+$=443.2. $^1$H NMR (400 MHz, Chloroform-d) δ 7.84-7.73 (m, 4H), 7.40-7.32 (m, 4H), 4.07 (t, J=6.2 Hz, 4H), 3.35 (t, J=6.0 Hz, 4H), 2.45 (s, 6H), 1.82 (quint, J=6.1 Hz, 4H).

Step 4. 3-(5-(((1S,2S)-2-(1,5-oxazocan-5-yl)cyclopentyl)oxy)-1-oxoisoindolin-2-yl)piperidine-2,6-dione HC(O)OH Salt (I-167)

To a solution of oxybis(propane-3,1-diyl) bis(4-methylbenzenesulfonate) (146-4, 193 mg, 0.437 mmol) and 3-(5-(((1S,2S)-2-aminocyclopentyl)oxy)-1-oxoisoindolin-2-yl)piperidine-2,6-dione (I-12, 100 mg, 0.291 mmol) in MeCN (2.5 mL) was added DIPEA (0.25 mL, 1.5 mmol) and the resulting solution was stirred at 120° C. under µW irradiation for 3 h. The reaction mixture was then concentrated to dryness and the obtained residue taken up in DCM and washed with saturated $NaHCO_3$ (aq). The organic phases were separated and the aqueous phase was extracted with DCM. The combined organic phases were dried over $Na_2SO_4$, filtered, and concentrated to dryness. The crude material was purified via silica gel chromatography eluting with 0-60% EtOAc:EtOH (v/v=3:1, with 0.1% NEt$_3$) in DCM (with 0.1% NEt$_3$) and the obtained product was taken up in DCM and washed with sat. $NaHCO_3$ (aq) and the phases were separated via phase separator. The aqueous layer was extracted with DCM and the combined organic phases were concentrated to dryness. The crude material was dissolved in a minimal amount of EtOAc, cooled to 0° C. and diethyl ether was slowly added. The solvent was decanted and the solid material was dried under vacuum. The solid was purified further by reverse phase HPLC (Column: Xbridge C18 OBD 5 um 30×50 mm; Conditions: Water/MeCN with 10 mM NH$_4$OH 75 mL/min; 1.5 mL injection; Gradient: 25-50% MeCN, 3.5 min gradient; collected fractions contain ~3 drops of formic acid) to afford the formate salt of I-167 (6.0 mg, 0.012 mmol, 4% yield) as a white solid. MS [M+H]$^+$=442.4. $^1$H NMR (400 MHz, DMSO-d$_6$) δ 10.94 (br s, 1H), 8.24 (s, 1H), 7.60 (d, J=8.4 Hz, 1H), 7.29-7.18 (m, 1H), 7.08-7.00 (m, 1H), 5.06 (dd, J=13.3, 5.1 Hz, 1H), 4.71-4.63 (m, 1H), 4.43-4.19 (m, 2H), 3.63 (t, J=5.3 Hz, 4H), 2.96-2.84 (m, 1H), 2.68 (t, J=6.0 Hz, 4H), 2.64-2.55 (m, 1H), 2.43-2.35 (m, 2H), 2.16-2.03 (m, 1H), 2.03-1.85 (m, 2H), 1.75-1.55 (m, 7H), 1.55-1.44 (m, 1H).

Example 147: 3-(5-(((1S,2S)-2-(3,3-dimethylpiperidin-1-yl)cyclopentyl)oxy)-1-oxoisoindolin-2-yl)piperidine-2,6-dione and 3-(5-(((1R,2R)-2-(3,3-dimethylpiperidin-1-yl)cyclopentyl)oxy)-1-oxoisoindolin-2-yl)piperidine-2,6-dione (I-168 and I-169)

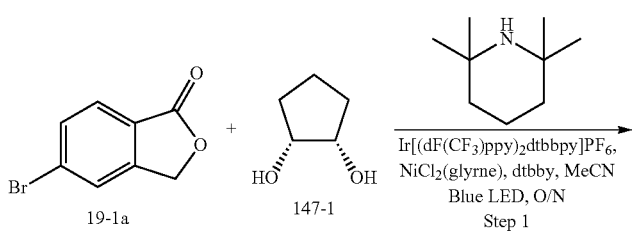

-continued
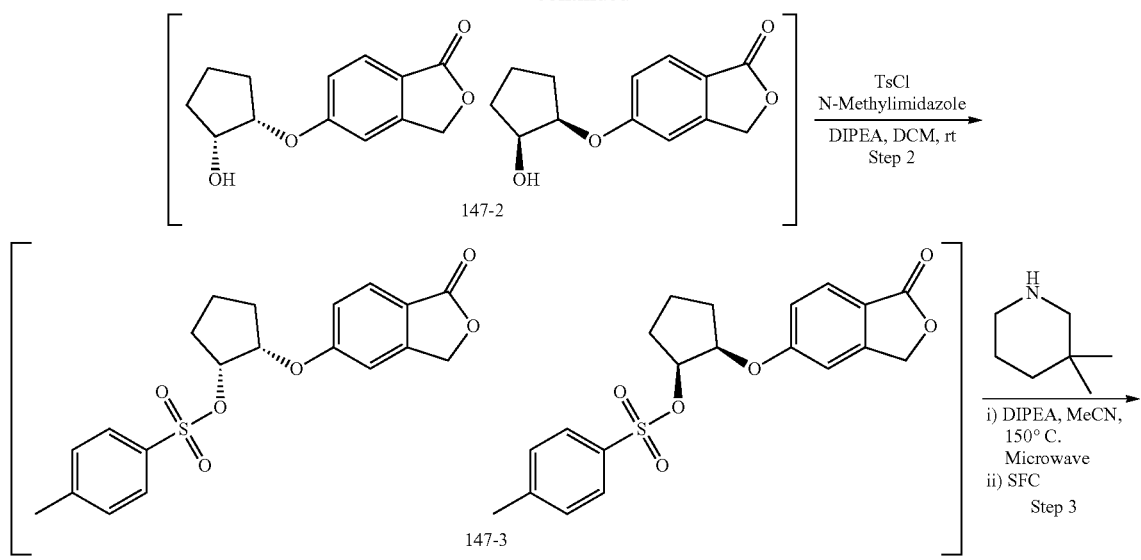
147-2
147-3
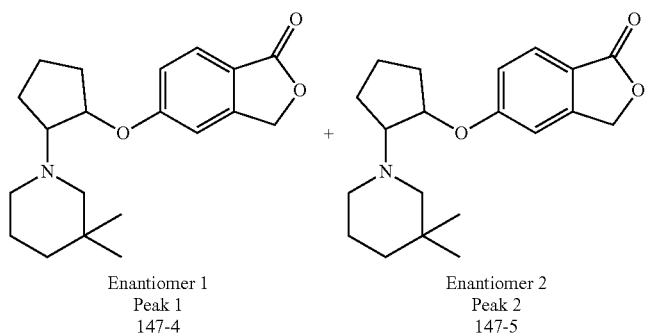
Enantiomer 1
Peak 1
147-4
Enantiomer 2
Peak 2
147-5
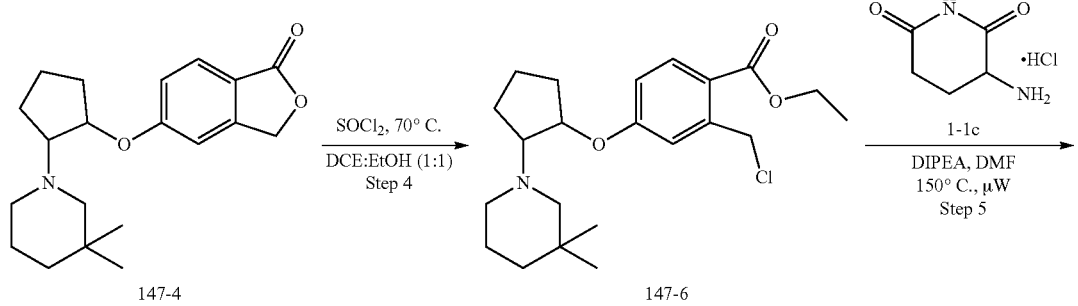
147-4
147-6
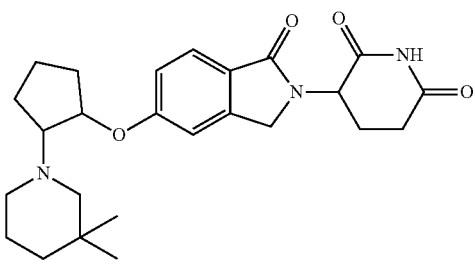
I-168

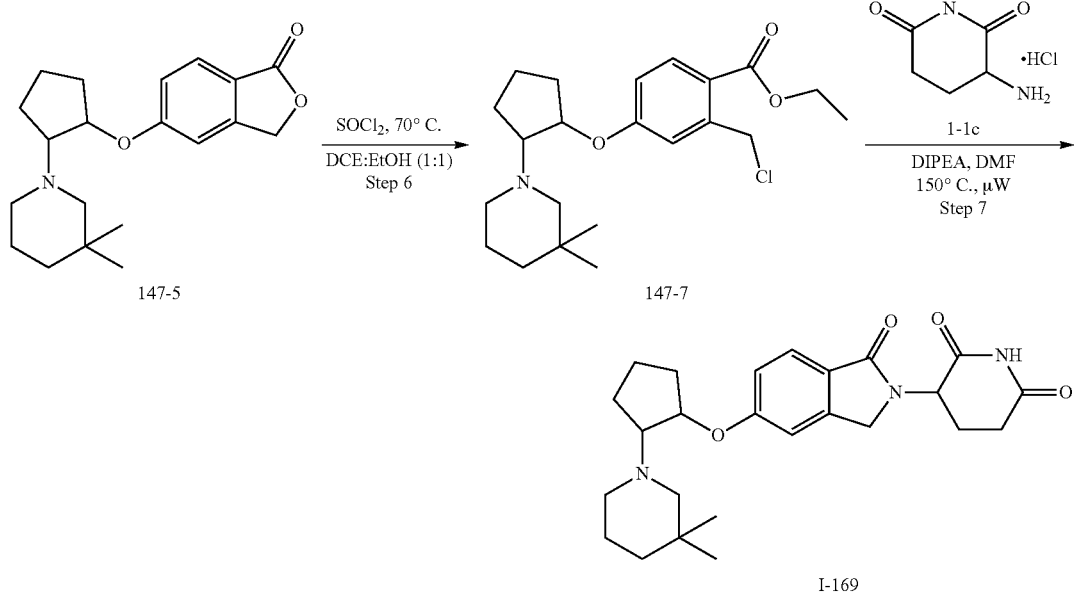

Step 1. A mixture of 5-(((1S,2R)-2-hydroxycyclopentyl)oxy)isobenzofuran-1(3H)-one and 5-(((1R,2S)-2-hydroxycyclopentyl)oxy)isobenzofuran-1(3H)-one (147-2)

To a mixture of 5-bromoisobenzofuran-1(3H)-one (19-1a, 1.00 g, 4.69 mmol), dtbbpy (63 mg, 0.24 mmol), NiCl$_2$ (glyme) (52 mg, 0.24 mmol) and Ir[(dF(CF$_3$)ppy)$_2$dtbbpy] PF$_6$ (53 mg, 47 μmol) in a flask was added MeCN (15.7 mL) and the flask was evacuated and backfilled with nitrogen three times. Cis-1,2-pentanediol (147-1, 0.47 mL, 5.6 mmol) and 2,2,6,6-tetramethylpiperidine (0.83 mL, 4.9 mmol) were added and the flask was again evacuated and backfilled with nitrogen twice. The resulting mixture was stirred under blue LED light for 16 h, filtered, and concentrated onto Celite®. The crude material was purified by silica gel chromatography eluting with 0-100% EtOAc in heptanes to afford 147-2 (787 mg, 3.36 mmol, 72% yield, mixture of isomers) as a yellow solid. MS [M+H]$^+$=235.2. $^1$H NMR (400 MHz, Chloroform-d$_6$) δ 7.84 (d, J=8.5 Hz, 1H), 7.09 (dd, J=8.5, 2.2 Hz, 1H), 6.98 (d, J=2.1 Hz, 1H), 5.26 (s, 2H), 4.66 (dt, J=6.3, 4.6 Hz, 1H), 4.32 (td, J=5.7, 4.3 Hz, 1H), 2.16-2.06 (m, 1H), 2.04-1.79 (m, 4H), 1.74-1.61 (m, 1H).

Step 2. A mixture of (1S,2R)-2-((1-oxo-1,3-dihydroisobenzofuran-5-yl)oxy)cyclopentyl 4-methylbenzenesulfonate and (1R,2S)-2-((1-oxo-1,3-dihydroisobenzofuran-5-yl)oxy)cyclopentyl 4-methylbenzenesulfonate (147-3)

To a mixture of 5-(((1S,2R)-2-hydroxycyclopentyl)oxy)isobenzofuran-1(3H)-one and 5-(((1R,2S)-2-hydroxycyclopentyl)oxy)isobenzofuran-1(3H)-one (147-2, 0.100 g, 0.427 mmol) in DCM (3 mL) was added TsCl (179 mg, 0.939 mmol) and DIPEA (0.30 mL, 1.7 mmol) and the resulting mixture was stirred for 2 h at rt. 1-methylimidazole (34 μL, 0.43 mmol) was then added and the reaction mixture was stirred at rt for 2.5 h. The reaction mixture was quenched with saturated aqueous sodium bicarbonate and extracted with dichloromethane (×3). The organic phases were combined, passed through a phase separator, and concentrated onto Celite®. The crude material was purified by silica gel chromatography eluting with 0-100% EtOAc in heptanes to afford 147-3 (787 mg, 3.36 mmol, 92% yield) as an orange solid. MS [M+H]$^+$=389.3. $^1$H NMR (400 MHz, Chloroform-d) δ 7.74-7.61 (m, 3H), 7.15 (d, J=8.1 Hz, 2H), 6.85 (dd, J=8.5, 2.2 Hz, 1H), 6.76 (d, J=2.1 Hz, 1H), 5.23-5.10 (m, 2H), 4.91 (td, J=6.1, 4.2 Hz, 1H), 4.63 (dt, J=5.9, 4.5 Hz, 1H), 2.33 (s, 3H), 2.15-1.87 (m, 5H), 1.70-1.58 (m, 1H).

Step 3. 5-(((1S,2S)-2-(3,3-dimethylpiperidin-1-yl)cyclopentyl)oxy)isobenzofuran-1(3H)-one and 5-(((1R,2R)-2-(3,3-dimethylpiperidin-1-yl)cyclopentyl)oxy)isobenzofuran-1(3H)-one (147-4 and 147-5)

To a μW vial with MeCN (0.3 mL) was added a mixture of (1S,2R)-2-((1-oxo-1,3-dihydroisobenzofuran-5-yl)oxy)cyclopentyl 4-methylbenzenesulfonate and (1R,2S)-2-((1-oxo-1,3-dihydroisobenzofuran-5-yl)oxy)cyclopentyl 4-methylbenzenesulfonate (147-3, 0.100 g, 0.257 mmol) and 3,3-dimethylpiperidine (0.04 mL, 0.3 mmol) and the vial was evacuated and backfilled with nitrogen three times. The resulting mixture was stirred at 150° C. for 3 h under μW irradiation, then quenched with water and extracted with dichloromethane (×3). The organic phases were combined, passed through a phase separator and concentrated onto Celite®. The crude material was purified by silica gel chromatography eluting with 0-100% EtOAc in heptanes to afford 147-4 (53.0 mg, 0.161 mmol, 63% yield) as a yellow oil and a mixture of isomer products. MS [M+H]$^+$=330.3. The mixture of isomers were separated via chiral SFC [Column 2.1×25.0 cm Chiralpak AD-H; CO$_2$ Co-solvent MeOH and 5% Water with 0.25% Isopropylamine; Isocratic Method 20% Co-solvent at 80 g/min at 100 bar at 25° C.] to afford two enantiomers of trans isomer products: Peak 1: Enantiomer 1 of 2-((1-oxo-1,3-dihydroisobenzofuran-5-yl)oxy)cyclopentyl 4-methylbenzenesulfonate (147-4, 15.0 mg, 0.045 mmol, 18% yield) as a yellow oil. Chiral SFC Rt 2.61 min. Peak 2: Enantiomer 2 of 2-((1-oxo-1,3-dihydroisobenzofuran-5-yl)oxy)cyclopentyl 4-methylbenzenesulfonate (147-5, 18.0 mg, 0.054 mmol, 21% yield) as a yellow oil. Chiral SFC Rt 3.00 min. Absolute stereochemistry not determined.

Step 4. Single Enantiomer of Ethyl 2-(chloromethyl)-4-((~2-(3,3-dimethylpiperidin-1-yl)cyclopentyl)oxy)benzoate (147-6)

To a solution of a single enantiomer of 2-((1-oxo-1,3-dihydroisobenzofuran-5-yl)oxy)cyclopentyl 4-methylbenzenesulfonate (Peak 1, 147-4, 15 mg, 0.045 mmol) in dichloroethane (1 mL) and EtOH (1 mL) stirred at 70° C. was added thionyl chloride (0.04 mL, 0.5 mmol) dropwise and the resulting mixture was stirred at 70° C. overnight. The reaction mixture was cooled to rt, diluted with water and quenched with saturated aqueous sodium bicarbonate. The resulting mixture was extracted with EtOAc (×3) and the combined organic phases were passed through a phase separator and concentrated to dryness to afford 147-6 as a crude brown oil. The product was carried onto the next step without purification. MS [M+H]$^+$=394.2.

Step 5. Single Enantiomer of 3-(5-((~2-(3,3-dimethylpiperidin-1-yl)cyclopentyl)oxy)-1-oxoisoindolin-2-yl)piperidine-2,6-dione (I-168)

To a flask containing 3-aminopiperidine-2,6-dione hydrochloride (I-1c, 15 mg, 0.090 mmol) in DMF (0.75 mL) was added DIPEA (0.04 mL, 0.2 mmol) and the flask was evacuated and backfilled with nitrogen three times. The resulting mixture was stirred at rt for 15 minutes, 147-6 (18 mg, 0.045 mmol) dissolved in DMF (1.1 mL) was added and the flask was evacuated and backfilled with nitrogen three times. The resulting mixture was stirred at 85° C. overnight and then stirred at 150° C. for 6 h under µW irradiation. The reaction mixture was concentrated to dryness and the crude material was purified by silica gel chromatography eluting with 0-100% EtOAc:EtOH (v/v=3:1, with 1% NEt$_3$) in heptane and then was further purified by reverse phase HPLC (Method Column: Xbridge C18 OBD 5 um 30×50 mm; Conditions: Water/MeCN with 5 mM NH$_4$OH 75 mL/min; 1.5 mL injection; Gradient: 45-70% MeCN, 3.5 min gradient; collected fractions contain ~3 drops of formic acid). The fractions containing the desired product were combined and lyophilized to afford I-168 (enantiomer 1, 2.1 mg, 4.2 µmol, 9% yield) as a white solid. MS [M+H]$^+$=440.3. $^1$H NMR (400 MHz, MeCN-d$_3$) δ 8.83 (s, 1H), 7.65 (d, J=8.4 Hz, 1H), 7.22 (d, J=2.2 Hz, 1H), 7.08 (dd, J=8.4, 2.2 Hz, 1H), 5.07 (dd, J=13.4, 5.2 Hz, 1H), 4.78 (ddd, J=7.1, 4.2, 2.0 Hz, 1H), 4.34 (qd, J=16.7, 4.4 Hz, 2H), 3.01 (td, J=8.1, 7.6, 4.0 Hz, 1H), 2.84 (ddd, J=17.7, 13.3, 5.3 Hz, 2H), 2.74 (ddd, J=17.7, 4.8, 2.5 Hz, 1H), 2.56-2.36 (m, 3H), 2.30-2.19 (m, 2H), 2.17-2.00 (m, 2H), 1.82-1.57 (m, 6H), 1.31-1.24 (m, 2H), 0.96 (d, J=8.1 Hz, 6H).

Step 6. Single Enantiomer of Ethyl 2-(chloromethyl)-4-((-2-(3,3-dimethylpiperidin-1-yl)cyclopentyl)oxy)benzoate (147-7)

To a solution of a single enantiomer of 2-((1-oxo-1,3-dihydroisobenzofuran-5-yl)oxy)cyclopentyl 4-methylbenzenesulfonate (Peak 2, 147-5, 18 mg, 0.054 mmol) in dichloroethane (1 mL) and EtOH (1 mL) stirred at 70° C. was added thionyl chloride (0.05 mL, 0.7 mmol) dropwise and the resulting mixture was stirred at 70° C. overnight. The reaction mixture was cooled to rt, diluted with water, and quenched with saturated aqueous sodium bicarbonate. The resulting mixture was extracted with EtOAc (×3) and the combined organic phases were passed through a phase separator and concentrated to dryness to afford 147-7 as a crude brown oil. The product was carried onto the next step without purification. MS [M+H]$^+$=394.4.

Step 7. Single Enantiomer of 3-(5-((-2-(3,3-dimethylpiperidin-1-yl)cyclopentyl)oxy)-1-oxoisoindolin-2-yl)piperidine-2,6-dione (I-169)

To a flask containing 3-aminopiperidine-2,6-dione hydrochloride (I-1c, 18 mg, 0.11 mmol) in DMF (0.75 mL) was added DIPEA (0.05 mL, 0.3 mmol) and the flask was evacuated and backfilled with nitrogen three times. The resulting mixture was stirred at rt for 15 minutes, then 147-7 (18 mg, 0.054 mmol) dissolved in DMF (1.1 mL) was added and the flask was evacuated and backfilled with nitrogen three times. The resulting mixture was stirred at 85° C. overnight then stirred at 150° C. for 6 h under µW irradiation. The reaction mixture was concentrated to dryness and the crude material purified by silica gel chromatography eluting with 0-100% EtOAc:EtOH (v/v=3:1, with 1% NEt$_3$) in heptane and then was further purified by reverse phase HPLC (Method Column: Xbridge C18 OBD 5 um 30×50 mm; Conditions: Water/MeCN with 5 mM NH$_4$OH 75 mL/min; 1.5 mL injection; Gradient: 45-70% MeCN, 3.5 min gradient; collected fractions contain ~3 drops of formic acid). The fractions containing the desired product were combined and lyophilized to afford I-169 (enantiomer 2, 1.5 mg, 2.9 µmol, 5% yield) as a white solid. MS [M+H]$^+$=440.5. $^1$H NMR (400 MHz, MeCN-d$_3$) δ 8.82 (s, 1H), 7.65 (d, J=8.4 Hz, 1H), 7.23 (d, J=2.2 Hz, 1H), 7.08 (dd, J=8.4, 2.2 Hz, 1H), 5.07 (dd, J=13.4, 5.2 Hz, 1H), 4.79-4.69 (m, 1H), 4.34 (qd, J=16.7, 4.5 Hz, 2H), 3.01-2.93 (m, 1H), 2.84 (ddd, J=17.7, 13.3, 5.4 Hz, 1H), 2.74 (ddd, J=17.7, 4.8, 2.5 Hz, 1H), 2.49-2.36 (m, 3H), 2.24-2.10 (m, 3H), 2.09-2.00 (m, 1H), 1.94-1.88 (m, 1H), 1.82-1.57 (m, 6H), 1.29-1.19 (m, 2H), 0.95 (d, J=8.7 Hz, 6H).

Example 148: 3-(5-(((1S,2S)-2-(ethyl(((1r,4S)-4-methoxycyclohexyl)methyl)amino)cyclopentyl)oxy)-1-oxoisoindolin-2-yl)piperidine-2,6-dione (I-170)

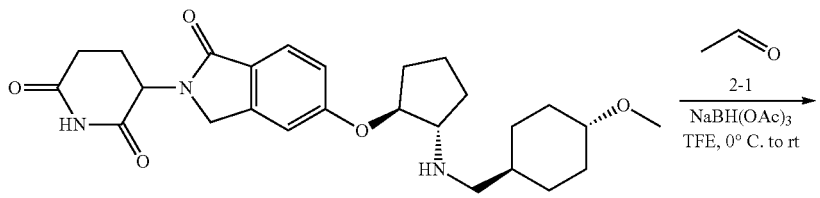

I-159

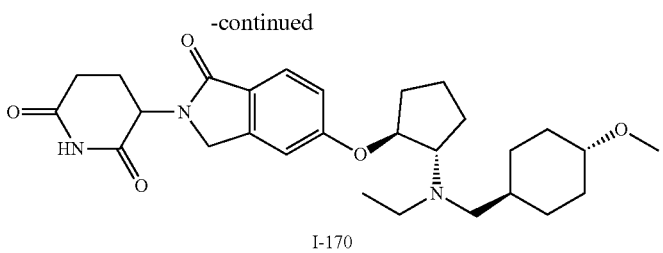

I-170

To a solution of 3-(5-((((1S,2S)-2-(((((1r,4S)-4-methoxycyclohexyl)methyl)amino)cyclopentyl) oxy)-1-oxoisoindolin-2-yl)piperidine-2,6-dione (I-159, 0.10 g, 0.21 mmol) and acetaldehyde (2-1, 0.020 g, 0.43 mmol) in TFE (3 mL) was added NaBH(OAc)$_3$ (0.067 g, 0.32 mmol) at 0° C. and the resulting mixture was stirred at rt for 4 h. The reaction mixture was quenched with water and extracted with DCM (3×30 mL). The combined organic phases were washed with brine, dried over Na$_2$SO$_4$, filtered, and concentrated to dryness. The crude material was purified via silica gel chromatography eluting with 5% MeOH in DCM to afford I-170 (0.023 mg, 0.046 mmol, 23% yield) as an off-white solid. MS [M+H]$^+$=498.4. $^1$H NMR (400 MHz, DMSO-d$_6$): δ 10.97 (s, 1H), 7.60 (d, J=8.8 Hz, 1H), 7.24 (s, 1H), 7.07 (dd, J=8.8, 2.0 Hz, 1H), 5.08-5.06 (m, 1H), 4.62-4.59 (m, 1H), 4.40-.21 (m, 2H), 3.35-3.33 (m, 1H), 3.02 (s, 3H), 2.99 (m, 3H), 2.67-2.35 (m, 4H), 2.19-2.13 (m, 2H), 2.02-1.95 (m, 3H), 1.85-1.82 (m, 2H), 1.75-1.25 (m, 7H), 1.05-0.92 (m, 4H), 0.85-0.65 (m, 2H).

Example 149: 3-(5-(((1S,2S)-2-((((1R,4S)-4-methoxycyclohexyl)methyl)(methyl)amino)cyclopentyl)oxy)-1-oxoisoindolin-2-yl)piperidine-2,6-dione (I-171)

To a solution of compound 3-(5-(((1S,2S)-2-((((1R,4S)-4-methoxycyclohexyl)methyl)amino)cyclopentyl)oxy)-1-oxoisoindolin-2-yl)piperidine-2,6-dione (I-159, 0.10 g, 0.21 mmol) and formaldehyde (37% in water) (0.04 mL, 0.4 mmol) in TFE (4 mL) was added NaBH(OAc)$_3$ (0.067 g, 0.32 mmol) at 0° C. and the resulting mixture was stirred at rt for 16 h. The reaction mixture was concentrated to dryness and the residue was diluted with saturated aqueous sodium bicarbonate solution and extracted with EtOAc (3×30 mL). The combined organic phases were washed with brine, dried over Na$_2$SO$_4$, filtered, and concentrated under reduced pressure. The obtained crude material was purified by silica gel chromatography eluting with 4% MeOH in DCM to afford I-171 (0.040 mg, 0.082 mmol, 39% yield) as an off-white solid. MS [M+H]$^+$=484.3. $^1$H NMR (400 MHz, DMSO-d$_6$): δ 10.98 (s, 1H), 7.61 (d, J=8.4 Hz, 1H), 7.21 (s, 1H), 7.07 (d, J=8.0 Hz, 1H), 5.09-5.04 (m, 1H), 4.68-4.65 (m, 1H), 4.41-4.23 (m, 2H), 3.19 (s, 3H), 3.0-2.67 (m, 3H), 2.67-2.33 (m, 2H), 2.15-2.08 (m, 5H), 2.07-1.96 (m, 4H), 1.83-1.36 (m, 6H), 1.51-1.48 (m, 2H), 1.25-1.22 (m, 2H), 0.83-0.80 (m, 2H).

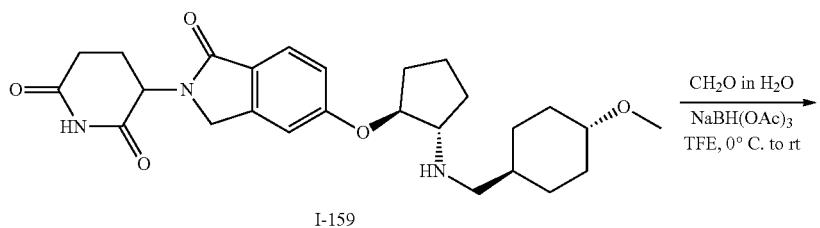

I-159

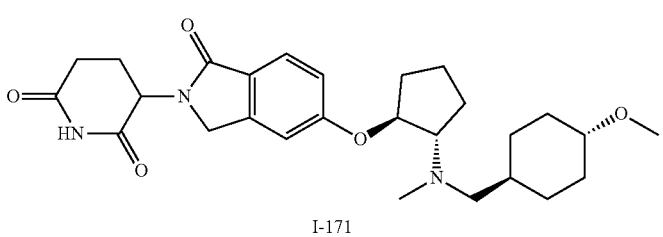

I-171

Example 150: Mixture of 3-(5-(((1S,2S)-2-(diethyl-amino)-4,4-dimethylcyclopentyl)oxy)-1-oxoisoindo-lin-2-yl)piperidine-2,6-dione and 3-(5-(((1R,2R)-2-(diethylamino)-4,4-dimethylcyclopentyl)oxy)-1-oxoisoindolin-2-yl)piperidine-2,6-dione HC(O)OH Salt (I-172)
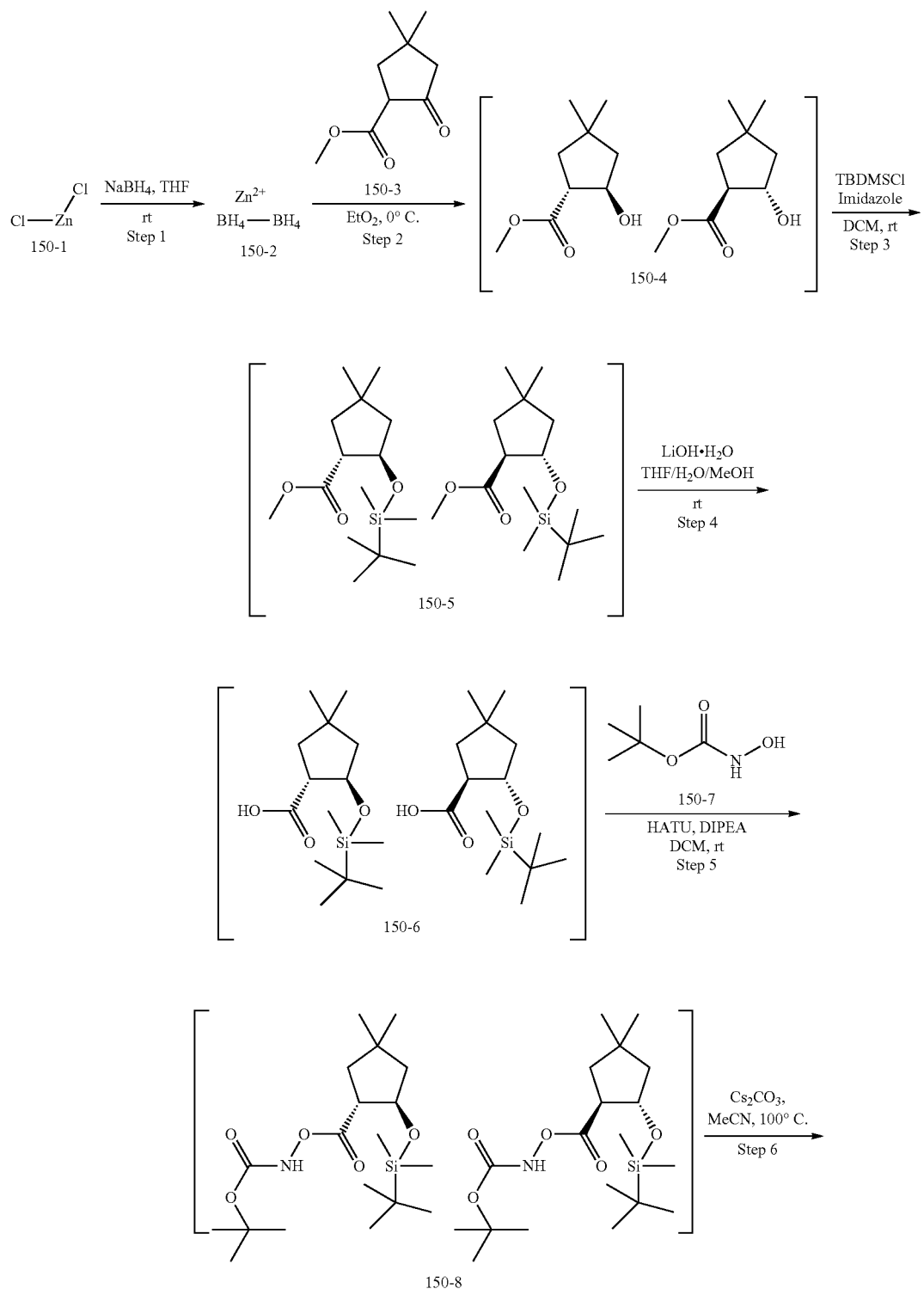

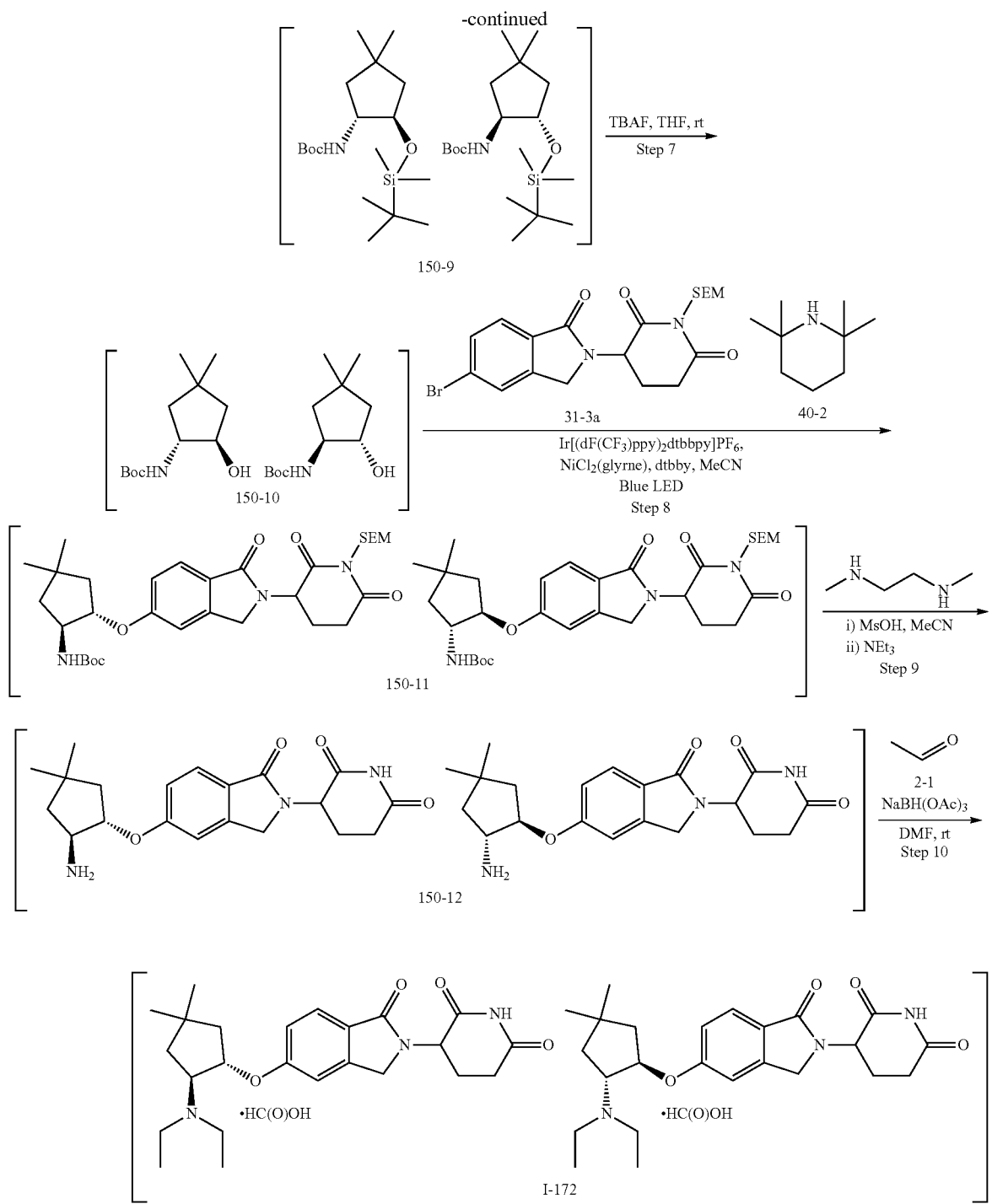

Step 1. Zinc(II) Tetrahydroborate (150-2)

To a 100 mL round bottomed flask with a stir bar was added zinc chloride (150-1, 3.04 g, 22.3 mmol) and sodium borohydride (1.95 g, 51.4 mmol) and the flask was purged with nitrogen gas. THF (50 mL) was then added and the resulting mixture was stirred at rt for 3 days. The reaction mixture was filtered to afford 150-2 as a colorless solution (~0.4 M) that was directly used in the next step without purification.

Step 2. A mixture of Methyl (1R,2R)-2-hydroxy-4,4-dimethylcyclopentane-1-carboxylate and methyl (1S,2S)-2-hydroxy-4,4-dimethylcyclopentane-1-carboxylate (150-4)

To methyl 4,4-dimethyl-2-oxocyclopentane-1-carboxylate (150-3, 420 mg, 2.47 mmol) dissolved in Et$_2$O (8 mL) and cooled to 0° C. was added zinc(II) tetrahydroborate (150-2, 7.5 mL, 3.0 mmol, 0.4M in THF) and the resulting solution was stirred at 0° C. for 1 hour. The reaction mixture was quenched with saturated aqueous ammonium acetate solution (10 mL) dropwise and then stirred for 15 minutes. The aqueous phase was extracted with dichloromethane, and the combined organic phases were passed through a phase separator and concentrated to dryness. The crude material purified via silica gel chromatography eluting with 0-40% EtOAc in heptane to afford 150-4 (284 mg, 1.65 mmol, 67% yield) as a mixture of trans isomers. MS [M+H]$^+$=173.3. $^1$H NMR (400 MHz, Chloroform-d) δ 4.45 (qd, J=7.9, 0.5 Hz, 1H), 3.72 (s, 3H), 2.83 (ddd, J=10.5, 8.9, 7.9 Hz, 1H), 1.97-1.79 (m, 2H), 1.73-1.63 (m, 1H), 1.55-1.44 (m, 1H), 1.11 (s, 3H), 1.04 (s, 3H).

Step 3. A mixture of Methyl (1R,2R)-2-((tert-butyldimethylsilyl)oxy)-4,4-dimethylcyclopentane-1-carboxylate and methyl (1S,2S)-2-((tert-butyldimethylsilyl)oxy)-4,4-dimethylcyclopentane-1-carboxylate (150-5)

To a mixture of methyl (1R,2R)-2-hydroxy-4,4-dimethylcyclopentane-1-carboxylate and methyl (1S,2S)-2-hydroxy-4,4-dimethylcyclopentane-1-carboxylate (150-4, 284 mg, 1.65 mmol) and imidazole (289 mg, 4.25 mmol) dissolved in DCM (6 mL) was added TBDMSCl (295 mg, 1.96 mmol) and the resulting mixture was stirred at rt overnight. The reaction mixture was diluted with EtOAc (80 mL) and washed with water (20 mL), saturated aqueous sodium bicarbonate solution (20 mL) and brine (15 mL). The organic phase was then dried over magnesium sulfate, filtered, and concentrated to afford 150-5 (522 mg, 1.73 mmol) which was carried onto the next step without purification. MS [M+H]$^+$=287.3. $^1$H NMR (400 MHz, DCM-d$_2$) δ 4.52-4.38 (m, 1H), 3.64 (s, 3H), 2.81 (ddd, J=10.0, 8.7, 6.9 Hz, 1H), 1.89-1.72 (m, 2H), 1.59 (dd, J=12.9, 10.1 Hz, 1H), 1.45 (ddd, J=12.9, 6.7, 1.0 Hz, 1H), 1.08 (s, 3H), 1.03 (s, 3H), 0.86 (s, 9H), 0.02 (d, J=3.5 Hz, 6H).

Step 4. A mixture of (1R,2R)-2-((tert-butyldimethylsilyl)oxy)-4,4-dimethylcyclopentane-1-carboxylic Acid and (1S,2S)-2-((tert-butyldimethylsilyl)oxy)-4,4-dimethylcyclopentane-1-carboxylic Acid (150-6)

A mixture of methyl (1R,2R)-2-((tert-butyldimethylsilyl)oxy)-4,4-dimethylcyclopentane-1-carboxylate and methyl (1S,2S)-2-((tert-butyldimethylsilyl)oxy)-4,4-dimethylcyclopentane-1-carboxylate (150-5, 522 mg, 1.82 mmol) and lithium hydroxide monohydrate (777 mg, 18.5 mmol) were dissolved in THF (3 mL), MeOH (3 mL), and Water (1 mL) and stirred at rt overnight. The reaction solution was diluted with water (60 mL) and acidified with 1 N HCl (aq) solution to a ~pH 5. The aqueous mixture was extracted with EtOAc (3×100 mL) and the combined organic phases were dried over magnesium sulfate, filtered, and concentrated to afford 150-6 (465 mg, 1.62 mmol, 89% yield) as a colorless oil, which was carried onto the next step without purification. MS [M+H]$^+$=273.4. $^1$H NMR (400 MHz, DMSO-d$_6$) δ 12.05 (s, 1H), 4.43 (q, J=6.7 Hz, 1H), 2.66 (ddd, J=9.7, 8.9, 6.5 Hz, 1H), 1.83-1.69 (m, 2H), 1.49 (dd, J=12.8, 9.7 Hz, 1H), 1.37 (ddd, J=12.7, 6.5, 1.0 Hz, 1H), 1.05 (s, 3H), 0.99 (s, 3H), 0.84 (s, 9H), 0.01 (d, J=2.0 Hz, 6H).

Step 5. A mixture of tert-butyl (((1R,2R)-2-((tert-butyldimethylsilyl)oxy)-4,4-dimethylcyclopentane-1-carbonyl)oxy)carbamate and tert-butyl (((1S,2S)-2-((tert-butyldimethylsilyl)oxy)-4,4-dimethylcyclopentane-1-carbonyl)oxy)carbamate (150-8)

To a mixture of (1R,2R)-2-((tert-butyldimethylsilyl)oxy)-4,4-dimethylcyclopentane-1-carboxylic acid and (1S,2S)-2-((tert-butyldimethylsilyl)oxy)-4,4-dimethylcyclopentane-1-carboxylic acid (150-6, 465 mg, 1.71 mmol), N-Boc-hydroxylamine (150-7, 258 mg, 1.94 mmol), and HATU (692 mg, 1.82 mmol) dissolved in DCM (8 mL) was added DIPEA (0.75 mL, 4.3 mmol) was added and the resulting mixture was stirred at rt overnight. The reaction mixture was diluted with EtOAc (150 mL) and washed with water (30 mL), saturated aqueous sodium bicarbonate (30 mL), and brine (20 mL). The organic phase was then dried over magnesium sulfate, filtered, and concentrated to dryness. The crude material was purified via silica gel chromatography eluting with 0-20% EtOAc in heptane to afford 150-8 (347 mg, 0.851 mmol, 50% yield) as a colorless oil. MS [M+H]$^+$=386.5. $^1$H NMR (400 MHz, DCM-d$_2$) δ 7.84 (s, 1H), 4.55 (dt, J=7.3, 6.4 Hz, 1H), 2.97 (ddd, J=9.8, 9.0, 6.6 Hz, 1H), 1.91 (ddd, J=13.0, 9.0, 1.1 Hz, 1H), 1.82 (dd, J=12.9, 7.3 Hz, 1H), 1.66 (dd, J=13.0, 9.8 Hz, 1H), 1.54-1.49 (m, 1H), 1.47 (s, 9H), 1.11 (s, 3H), 1.04 (s, 3H), 0.86 (s, 9H), 0.03 (d, J=2.1 Hz, 6H).

Step 6. A mixture of tert-butyl ((1R,2R)-2-((tert-butyldimethylsilyl)oxy)-4,4-dimethylcyclopentyl) carbamate and tert-butyl ((1S,2S)-2-((tert-butyldimethylsilyl)oxy)-4,4-dimethylcyclopentyl)carbamate (150-9)

A mixture of tert-butyl (((1R,2R)-2-((tert-butyldimethylsilyl)oxy)-4,4-dimethylcyclopentane-1-carbonyl)oxy)carbamate and tert-butyl (((1S,2S)-2-((tert-butyldimethylsilyl)oxy)-4,4-dimethylcyclopentane-1-carbonyl)oxy)carbamate (150-8, 347 mg, 0.896 mmol) and cesium carbonate (336 mg, 1.03 mmol) in MeCN (7 mL) was stirred at 100° C. for 5 hours. The reaction mixture was then diluted with EtOAc and filtered through Celite®. The filtrate was concentrated to dryness and the crude material purified via silica gel chromatography eluting with 0-20% EtOAc in heptane to afford 150-9 (108 mg, 0.315 mmol, 35% yield) as a white solid. MS [M+H]$^+$=344.4. $^1$H NMR (400 MHz, DCM-d$_2$) δ 4.45 (s, 1H), 3.85-3.68 (m, 1H), 1.89 (dd, J=13.1, 7.8 Hz, 1H), 1.75 (dd, J=13.1, 7.2 Hz, 1H), 1.41 (s, 9H), 1.28-1.21 (m, 2H), 1.08 (s, 3H), 1.02 (s, 3H), 0.88 (s, 9H), 0.05 (d, J=4.9 Hz, 6H).

Step 7. A mixture of tert-butyl ((1R,2R)-2-hydroxy-4,4-dimethylcyclopentyl)carbamate and tert-butyl ((1S,2S)-2-hydroxy-4,4-dimethylcyclopentyl)carbamate (150-10)

To a mixture of tert-butyl ((1R,2R)-2-((tert-butyldimethylsilyl)oxy)-4,4-dimethylcyclopentyl)carbamate and tert-butyl ((1S,2S)-2-((tert-butyldimethylsilyl)oxy)-4,4-dimethylcyclopentyl)carbamate (150-9, 30.9 mg, 0.128 mmol) in THF (2 mL) was added TBAF (1M in THF) (0.350 mL, 0.350 mmol) and the resulting mixture was stirred at room temperature overnight. The reaction solution was concentrated to dryness and the crude material purified via silica gel chromatography eluting with 0-50% EtOAc in heptane to afford 150-10 (30.9 mg, 0.128 mmol, 52% yield). MS [M+H-t-Bu]$^+$=174. $^1$H NMR (400 MHz, Chloroform-d) δ 4.67 (s, 1H), 3.84-3.72 (m, 1H), 1.91 (ddd, J=11.6, 8.1, 3.5 Hz, 2H), 1.53 (dd, J=13.4, 7.4 Hz, 2H), 1.45 (s, 9H), 1.11 (s, 3H), 1.05 (s, 3H).

Step 8. A mixture of tert-butyl ((1S,2S)-2-((2-(2,6-dioxo-1-((2-(trimethylsilyl)ethoxy)methyl) piperidin-3-yl)-1-oxoisoindolin-5-yl)oxy)-4,4-dimethylcyclopentyl)carbamate and tert-butyl ((1R,2R)-2-((2-(2,6-dioxo-1-((2-(trimethylsilyl)ethoxy)methyl) piperidin-3-yl)-1-oxoisoindolin-5-yl)oxy)-4,4-dimethylcyclopentyl)carbamate (150-11)

To a mixture of tert-butyl ((1R,2R)-2-hydroxy-4,4-dimethylcyclopentyl)carbamate and tert-butyl ((1S,2S)-2-hydroxy-4,4-dimethylcyclopentyl)carbamate (150-10, 30.0 mg, 0.131 mmol), 3-(5-bromo-1-oxoisoindolin-2-yl)-1-((2-(trimethylsilyl)ethoxy)methyl)piperidine-2,6-dione (31-3a, 62.0 mg, 0.137 mmol), NiCl$_2$(glyme) (1.4 mg, 6.5 μmol), dtbbpy (1.8 mg, 6.5 μmol), and Ir[(dF(CF$_3$)ppy)$_2$dtbbpy]PF$_6$ (1.5 mg, 1.3 μmol) purged with nitrogen was added MeCN (1 mL) and 2,2,6,6-tetramethylpiperidine (40-2, 0.024 mL, 0.14 mmol) and the resulting mixture was stirred under blue LED lights at rt for 18 hours. The reaction mixture was diluted with EtOAc and filtered through Celite®, rinsing with EtOAc. The filtrate was concentrated to dryness and purified via silica gel chromatography eluting with 0-100% EtOAc in heptane to afford 150-11 (29.1 mg, 0.034 mmol, 26% yield) as a yellow solid. MS [M+H$_2$O]$^+$=619.5. $^1$H NMR (400 MHz, DCM-d$_2$) δ 7.71 (dd, J=8.6, 4.2 Hz, 1H), 7.02 (d, J=6.8 Hz, 2H), 5.25-5.05 (m, 2H), 4.66 (s, 1H), 4.38-4.30 (m, 2H), 3.69-3.50 (m, 2H), 3.06-2.77 (m, 2H), 2.31 (dd, J=13.7, 4.7 Hz, 1H), 2.21-2.13 (m, 1H), 2.11-2.01 (m, 2H), 1.66 (dd, J=13.9, 4.2 Hz, 1H), 1.48-1.44 (m, 3H), 1.41 (s, 9H), 1.13 (d, J=7.9 Hz, 6H), 0.95-0.89 (m, 2H), 0.00 (s, 9H).

Step 9. A mixture of 3-(5-(((1S,2S)-2-amino-4,4-dimethylcyclopentyl)oxy)-1-oxoisoindolin-2-yl)piperidine-2,6-dione and 3-(5-(((1R,2R)-2-amino-4,4-dimethylcyclopentyl)oxy)-1-oxoisoindolin-2-yl)piperidine-2,6-dione (150-12)

To a mixture of tert-butyl ((1S,2S)-2-((2-(2,6-dioxo-1-((2-(trimethylsilyl)ethoxy)methyl) piperidin-3-yl)-1-oxoisoindolin-5-yl)oxy)-4,4-dimethylcyclopentyl)carbamate and tert-butyl ((1R,2R)-2-((2-(2,6-dioxo-1-((2-(trimethylsilyl)ethoxy)methyl)piperidin-3-yl)-1-oxoisoindolin-5-yl)oxy)-4,4-dimethylcyclopentyl)carbamate (150-11, 29 mg, 0.048 mmol) in MeCN (1 mL) was added methanesulfonic acid (0.013 mL, 0.20 mmol) and the resulting mixture was stirred at rt overnight. The reaction mixture was cooled to 0° C. and whilst under a stream of nitrogen, TEA (0.067 mL, 0.48 mmol) was added. The solution was warmed to room temperature and then stirred for 30 minutes. N1,N2-dimethylethane-1,2-diamine (6 μL, 0.05 mmol) was then added and the resulting mixture was stirred at rt overnight. The reaction mixture was concentrated to approximately half volume and a 1:1 mixture of saturated aqueous sodium bicarbonate and water (30 mL) was added. The aqueous mixture was extracted with DCM/isopropanol 4:1 mixture (3×30 mL) and the combined organic phases were dried over magnesium sulfate, filtered, and concentrated to dryness to afford 150-12 as a yellow solid, which was carried onto the next step without purification. MS [M+H]$^+$=372.4.

Step 10. A mixture of 3-(5-(((1S,2S)-2-(diethylamino)-4,4-dimethylcyclopentyl)oxy)-1-oxoisoindolin-2-yl)piperidine-2,6-dione and 3-(5-(((1R,2R)-2-(diethylamino)-4,4-dimethylcyclopentyl)oxy)-1-oxoisoindolin-2-yl)piperidine-2,6-dione HC(O)OH Salt (I-172)

To a mixture of 3-(5-(((1S,2S)-2-amino-4,4-dimethylcyclopentyl)oxy)-1-oxoisoindolin-2-yl)piperidine-2,6-dione and 3-(5-(((1R,2R)-2-amino-4,4-dimethylcyclopentyl)oxy)-1-oxoisoindolin-2-yl)piperidine-2,6-dione (150-12, 18 mg, 0.048 mmol) and acetaldehyde (2-1, 8 μL, 0.15 mmol) dissolved in DMF (0.5 mL) was added sodium triacetoxyborohydride (56 mg, 0.26 mmol) in one portion and the resulting mixture was stirred at rt overnight. The reaction mixture was then diluted with EtOAc (45 mL) and washed with saturated aqueous sodium bicarbonate solution (10 mL) and brine (10 mL). The organic phase was dried over magnesium sulfate, filtered, and concentrated to dryness. The crude material was purified via silica gel chromatography eluting with 0 to 80% EtOAc:EtOH (v/v=3:1, with 0.1% NEt$_3$) in DCM (with 0.1% NEt$_3$) and then further purified by reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient) to afford the formate salt of I-172 (6.0 mg, 0.012 mmol, 25% yield) as a white solid. MS [M+H]$^+$=428.4. $^1$H NMR (400 MHz, DMSO-d$_6$) δ 10.95 (s, 1H), 8.18 (s, 1H), 7.60 (d, J=8.4 Hz, 1H), 7.16 (s, 1H), 7.02 (d, J=8.4 Hz, 1H), 5.06 (dd, J=13.3, 5.1 Hz, 1H), 4.76-4.63 (m, 1H), 4.45-4.18 (m, 2H), 3.48 (dt, J=11.8, 6.3 Hz, 2H), 2.97-2.83 (m, 1H), 2.63-2.51 (m, 3H), 2.44-2.31 (m, 2H), 1.98 (dd, J=14.3, 7.5 Hz, 2H), 1.72 (dd, J=12.3, 7.2 Hz, 1H), 1.55-1.35 (m, 2H), 1.06 (d, J=4.6 Hz, 6H), 0.94 (t, J=7.0 Hz, 6H).

Example 151: 3-(5-(((1S,2S)-2-(((4,4-difluorocyclohexyl)methyl)amino)cyclopentyl)oxy)-1-oxoisoindolin-2-yl)piperidine-2,6-dione (I-173)

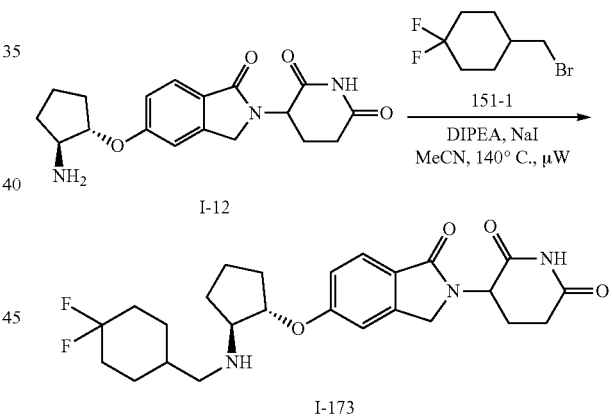

To a solution of 3-(5-(((1S,2S)-2-aminocyclopentyl)oxy)-1-oxoisoindolin-2-yl)piperidine-2,6-dione (I-12, 100 mg, 0.291 mmol) in MeCN (1.5 mL) was added 4-(bromomethyl)-1,1-difluorocyclohexane (151-1, 68 mg, 0.32 mmol) and DIPEA (153 μL, 0.874 mmol) and the resulting mixture was stirred at 140° C. for 45 minutes in the μW. NaI (48 mg, 0.32 mmol) was added and stirring was continued at 140° C. for 2 h and 45 minutes in the μW. The reaction mixture was then added to a saturated solution of aqueous sodium hydrogen carbonate (20 mL) and extracted with 20% i-PrOH in DCM (×2). The combined organic phases were passed through a phase separating column and concentrated to dryness. The crude material was purified via silica gel chromatography eluting with 0-15% i-PrOH (with 0.1% NEt$_3$) in DCM (with 0.1% NEt$_3$) to afford I-173 (20 mg, 0.040 mmol, 14% yield) as a cream-colored solid. MS [M+H]$^+$=476.4. $^1$H NMR (400 MHz, DMSO-d$_6$) δ (ppm):

10.95 (s, 1H), 7.61 (d, J=8.4 Hz, 1H), 7.17 (s, 1H), 7.04 (d, J=8.4 Hz, 1H), 5.11-4.97 (m, 1H), 4.65-4.52 (m, 1H), 4.44-4.19 (m, 2H), 3.18-3.03 (m, 1H), 2.90 (ddd, J=18.3, 13.6, 5.4 Hz, 1H), 2.59 (d, J=17.6 Hz, 1H), 2.47-2.28 (m, 2H), 2.17-2.05 (m, 1H), 2.04-1.87 (d, J=13.0 Hz, 4H), 1.86-1.58 (m, 8H), 1.56-1.38 (m, 2H), 1.21-1.07 (m, 2H).

Example 152: 3-(5-((((1S,2S)-2-(((1H-indol-5-yl)methyl)amino)cyclopentyl)oxy)-1-oxoisoindolin-2-yl)piperidine-2,6-dione (I-174)

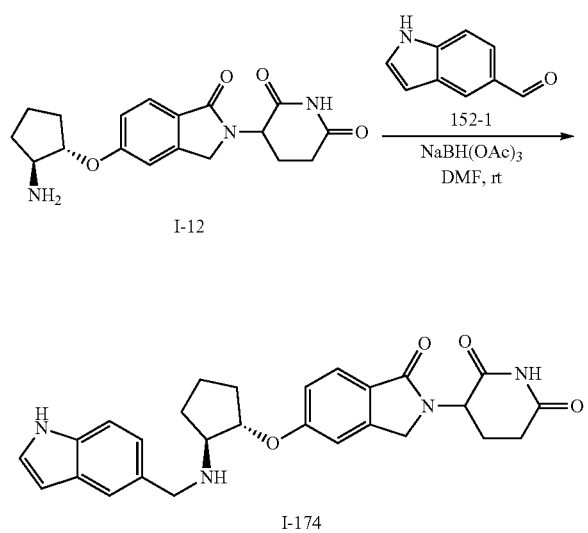

To a solution of 3-(5-(((1S,2S)-2-aminocyclopentyl)oxy)-1-oxoisoindolin-2-yl)piperidine-2,6-dione (I-12, 100 mg, 0.291 mmol) in DMF (2 mL) under an atmosphere of nitrogen, was added 1H-indole-5-carbaldehyde (152-1, 46.5 mg, 0.320 mmol) and the resulting mixture was stirred at rt for 30 minutes. Sodium triacetoxyborohydride (185 mg, 0.874 mmol) was added and stirring was continued at rt overnight. The reaction mixture was then added to a saturated aqueous solution of sodium hydrogen carbonate (30 mL) and extracted with 20% i-PrOH in DCM (×3). The combined organic phases were passed through a phase separating column and concentrated to dryness. The crude material was purified via silica gel chromatography eluting with 0-20% i-PrOH (with 0.1% NEt₃) in DCM (with 0.1% NEt₃) and then further purified via silica gel chromatography eluting with 0-15% i-PrOH (with 0.1% NEt₃) in DCM (with 0.1% NEt₃) to afford I-174 (12 mg, 0.023 mmol, 8% yield) as a cream-colored solid. MS [M+H]⁺=473.4. ¹H NMR (400 MHz, DMSO-d₆) δ (ppm): 10.95 (s, 2H), 7.56 (dd, J=8.4, 1.9 Hz, 1H), 7.48 (s, 1H), 7.31 (d, J=11.9 Hz, 1H), 7.28 (s, 1H), 7.11-7.05 (m, 2H), 6.99 (dd, J=8.4, 2.4 Hz, 1H), 6.37-6.33 (m, 1H), 5.06 (dd, J=13.3, 5.1 Hz, 1H), 4.69-4.62 (m, 1H), 4.36-4.09 (m, 2H), 3.95-3.68 (m, 2H), 3.20-3.12 (m, 1H), 2.91 (ddd, J=18.1, 13.7, 5.4 Hz, 1H), 2.60 (d, J=17.1 Hz, 1H), 2.39 (td, J=13.1, 4.5 Hz, 1H), 2.21-2.09 (m, 1H), 2.04-1.84 (m, 2H), 1.84-1.60 (m, 3H), 1.53 (d, J=9.3 Hz, 1H).

Example 153: 3-(5-(((1S,2S)-2-(4-(tert-butoxy)piperidin-1-yl)cyclopentyl)oxy)-1-oxoisoindolin-2-yl)piperidine-2,6-dione (I-175)

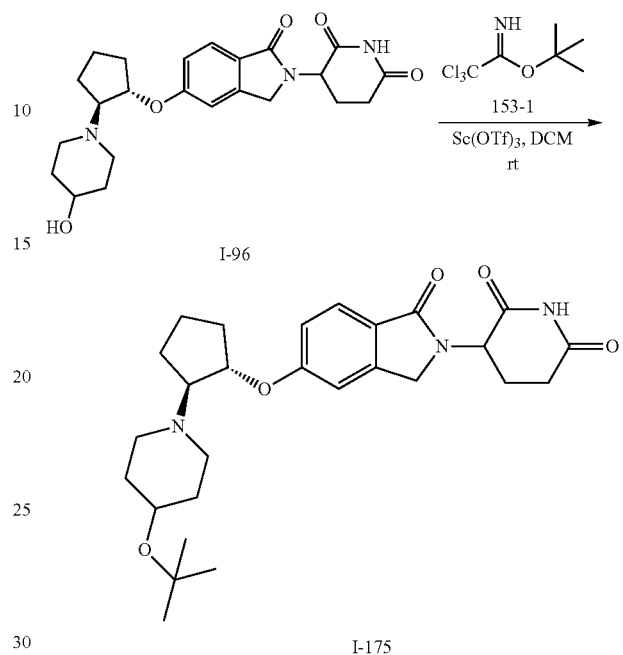

Tert-butyl 2,2,2-trichloroacetimidate (153-1, 5.0 μL, 0.028 mmol) was added to a suspension of 3-(5-(((1S,2S)-2-(4-hydroxypiperidin-1-yl)cyclopentyl)oxy)-1-oxoisoindolin-2-yl)piperidine-2,6-dione (I-96, 10 mg, 0.023 mmol) and scandium triflate (1.2 mg, 2.3 μmol) in dry DCM (0.25 mL) and the resulting mixture was stirred at rt for 24 h. Further scandium triflate (1.2 mg, 2.3 μmol) and tert-butyl 2,2,2-trichloroacetimidate (5 μL, 0.03 mmol) were added and stirring was continued at rt for several days. The reaction mixture was then filtered through Celite® and concentrated to dryness. The crude material was purified by reverse phase HPLC (Column: X-bridge C18 OBD 5 um 30×50 mm; Conditions: Water/MeCN with 0.1% Formic Acid 75 mL/min; 1.5 mL injection; Gradient: 15-40% MeCN, 3.5 min gradient). The fractions containing the desired product were combined and lyophilized to afford I-175 (3.0 mg, 5.3 μmol, 23% yield) as a white solid. MS [M+H]⁺=484.4. ¹H NMR (400 MHz, Methylene Chloride-d₂) δ 8.07 (s, 1H), 7.71 (d, J=8.3 Hz, 1H), 7.08-6.95 (m, 2H), 5.18-5.07 (m, 1H), 4.91 (s, 1H), 4.43-4.22 (m, 2H), 3.55 (s, 1H), 3.25-2.74 (m, 6H), 2.60-2.24 (m, 3H), 2.24-2.01 (m, 3H), 1.94-1.66 (m, 6H), 1.56 (s, 2H), 1.16 (s, 9H).

Example 154: Single Enantiomer of 3-(5-((2-(2-oxa-8-azaspiro[4.5]decan-8-yl)cyclopentyl)oxy)-1-oxoisoindolin-2-yl)piperidine-2,6-dione (I-176)

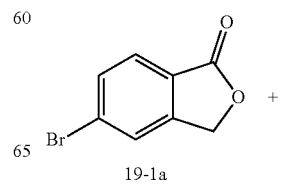

759
-continued

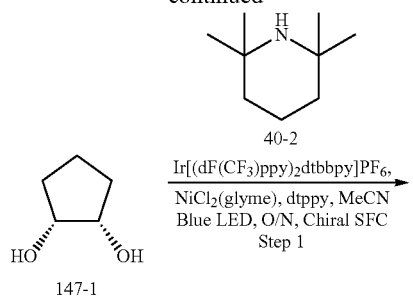

40-2

Ir[(dF(CF3)ppy)2dtbbpy]PF6,
NiCl2(glyme), dtppy, MeCN
Blue LED, O/N, Chiral SFC
Step 1

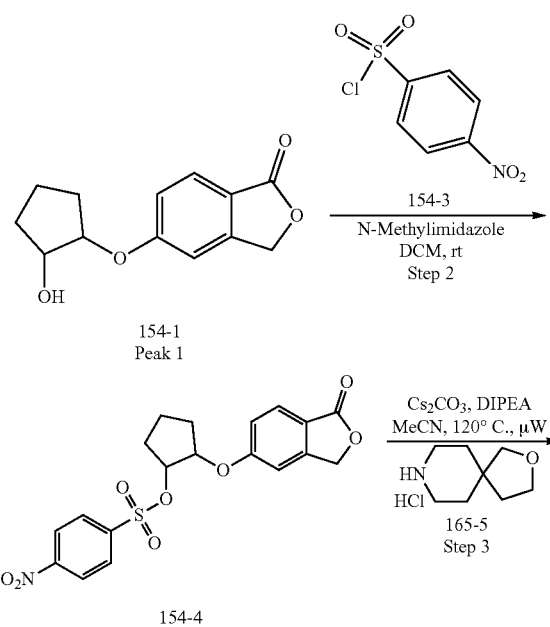

154-1
Peak 1

154-3
N-Methylimidazole
DCM, rt
Step 2

Cs2CO3, DIPEA
MeCN, 120° C., μW 165-5
Step 3

154-4

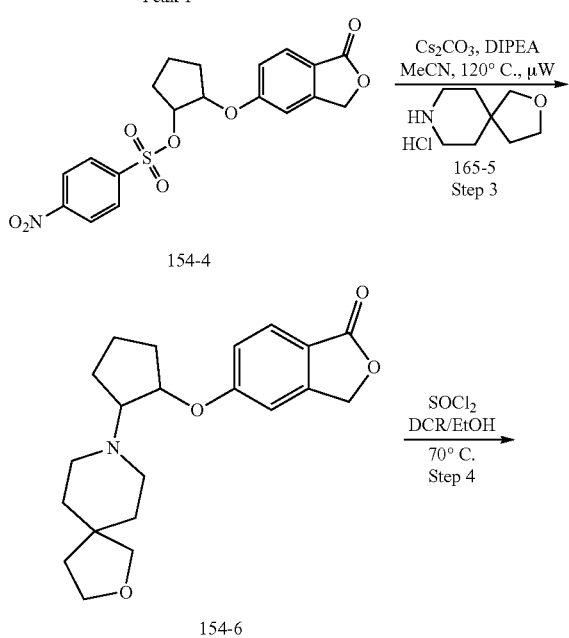

154-6

SOCl2
DCR/EtOH
70° C.
Step 4

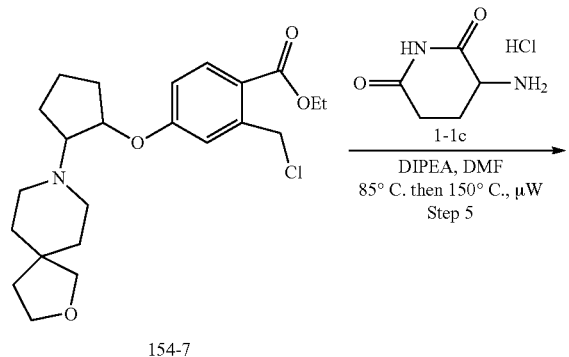

154-7

1-1c

DIPEA, DMF
85° C. then 150° C., μW
Step 5

760
-continued

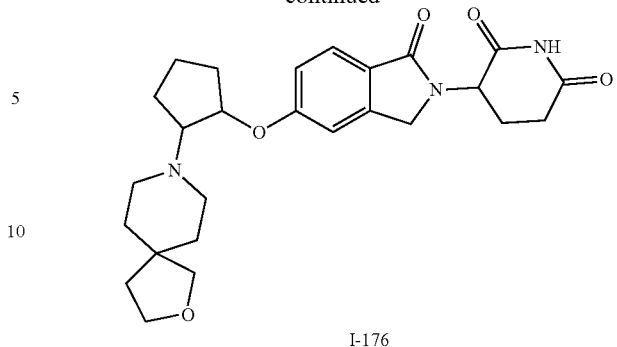

I-176

Step 1. Single Enantiomer of 5-((2-hydroxycyclopentyl)oxy)isobenzofuran-1(3H)-one (154-1)

5-bromoisobenzofuran-1(3H)-one (19-1a, 2.50 g, 11.7 mmol), dtbbpy (157 mg, 0.587 mmol), NiCl2(glyme) (129 mg, 0.587 mmol), and Ir[(dF(CF3)ppy)2dtbbpy]PF6 (131 mg, 0.117 mmol) and MeCN (35 mL) were placed in a flask and the flask was then evacuated and backfilled with nitrogen three times. Cis-1,2-pentanediol (147-1, 1.17 mL, 14.1 mmol) and 2,2,6,6-tetramethylpiperidine (40-2, 2.1 mL, 12 mmol) were added and the flask was again evacuated and backfilled with nitrogen twice more. The resulting mixture was stirred under blue LED lights at rt for 18 h. The reaction mixture was filtered, concentrated onto Celite® and purified by silica gel chromatography eluting with 0-100% EtOAc in heptane to afford the desired product (1.96 g, 8.37 mmol, 71% yield) as a yellow solid as a mixture of cis isomers. MS [M+H]$^+$=235.3. The mixture of isomers was separated via chiral SFC [Column: 2.1×25.0 cm Chiralpak AD-H; CO2 Co-solvent: 20% MeOH: Flow rate 80 g/min at 125 bar at 25° C.] to afford two cis isomers: Peak 1: 154-1 (1.01 g, 4.32 mmol, 37% yield) as a pale yellow oil. Chiral SFC Rt=1.71 min. Peak 2: 154-2 (1.03 g, 4.38 mmol, 37% yield) as a pale yellow oil. Chiral SFC Rt=1.87 min. Absolute stereochemistry not determined.

Step 2. Single Enantiomer of 2-((1-oxo-1,3-dihydroisobenzofuran-5-yl)oxy)cyclopentyl 4-nitrobenzenesulfonate (154-4)

To a solution of 154-1 (Peak 1, 0.500 g, 2.13 mmol) in DCM (14.2 mL) was added 4-nitrobenzenesulfonyl chloride (154-3, 1.42 g, 6.40 mmol) and 1-methylimidazole (0.34 mL, 4.27 mmol) and the resulting mixture was stirred at rt for 20 h. Additional 4-nitrobenzenesulfonyl chloride (378 mg, 1.71 mmol) and 1-methylimidazole (0.17 mL, 2.1 mmol) were added and stirring was continued at rt for 2 h. The reaction mixture was then quenched with saturated aqueous sodium bicarbonate and extracted with dichloromethane (×3). The combined organic phases were passed through a phase separator and concentrated onto Celite®. The Celite® residue was purified by silica gel chromatography eluting with 0-100% EtOAc in heptane and was further purified by silica gel chromatography eluting with 0-100% EtOAc in heptane to afford 154-4 (738 mg, 1.76 mmol, 82% yield) as a white solid. MS [M+H]$^+$=420.2.

Step 3. Single Enantiomer of 5-((2-(2-oxa-8-azaspiro[4.5]decan-8-yl)cyclopentyl)oxy)isobenzofuran-1(3H)-one (154-6)

A suspension of 2-oxa-8-azaspiro[4.5]decane hydrochloride (154-5, 83.0 mg, 0.465 mmol) and Cs2CO3 (0.186 g, 0.572 mmol) in MeCN (1.4 mL) was stirred at rt for 20 minutes. The suspension was then then added to 154-4 (0.150 g, 0.358 mmol) followed by the addition of DIPEA (0.094 mL, 0.54 mmol). The resulting mixture was purged with nitrogen with sonication for 20 minutes and then stirred at 120° C. for 3 h under µW radiation. The reaction mixture was quenched with water and extracted with dichloromethane. The combined organic phases were passed through a phase separator and concentrated onto Celite®. The crude material was purified by silica gel chromatography eluting with 0-100% EtOAc in heptane and then with 0-20% MeOH in DCM to afford 154-6 (81.5 mg, 0.228 mmol, 64% yield) as a cream-colored solid. MS [M+H]$^+$=358.2. $^1$H NMR (400 MHz, Chloroform-d) δ 7.79 (d, J=8.5 Hz, 1H), 7.00 (dd, J=8.5, 2.1 Hz, 1H), 6.95-6.85 (m, 1H), 5.24 (s, 2H), 4.91-4.74 (m, 1H), 3.83 (t, J=7.1 Hz, 2H), 3.53 (s, 2H), 3.03-2.92 (m, 1H), 2.67-2.48 (m, 4H), 2.15-2.05 (m, 2H), 1.83-1.59 (m, 10H).

Step 4. Single Enantiomer of Ethyl 4-((2-(2-oxa-8-azaspiro[4.5]decan-8-yl)cyclopentyl)oxy)-2-(chloromethyl)benzoate (154-7)

To a stirred suspension of 154-6 (81.5 mg, 0.228 mmol) in dichloroethane (1.1 mL) and EtOH (1.1 mL) at 70° C. was added thionyl chloride (0.20 mL, 2.7 mmol) dropwise and the resulting mixture was stirred at 70° C. overnight. The reaction mixture was then cooled to rt, diluted with water, and quenched with saturated aqueous sodium bicarbonate. The aqueous layer was extracted with EtOAc (×3) and the combined organic phases were passed through a phase separator and concentrated to dryness to afford 154-7 as a crude brown oil. The crude product was carried on to the next step without purification. MS [M+H]$^+$=422.4.

Step 5. Single Enantiomer of 3-(5-((2-(2-oxa-8-azaspiro[4.5]decan-8-yl)cyclopentyl)oxy)-1-oxoisoindolin-2-yl)piperidine-2,6-dione (I-176)

To a flask containing 3-aminopiperidine-2,6-dione hydrochloride (I-1c, 75.0 mg, 0.456 mmol) in DMF (0.9 mL) was added DIPEA (0.2 mL, 1 mmol) and the flask was evacuated and backfilled with nitrogen three times. The resulting mixture was stirred at rt for 15 minutes, 154-7 (96 mg, 0.23 mmol) dissolved in DMF (1.37 mL) was added and the flask was again evacuated and backfilled with nitrogen three times. The reaction mixture was stirred at 85° C. overnight and then at 150° C. for 5 h under µW irradiation. The reaction mixture was concentrated to dryness and purified by silica gel chromatography eluting with 0-100% EtOAc:EtOH (v/v=3:1, with 1% NEt$_3$) in heptane to afford I-176 (61.7 mg, 0.128 mmol, 56% yield) as a cream-colored solid. MS [M+H]$^+$=468.2. $^1$H NMR (400 MHz, DMSO-d$_6$) δ 10.96 (s, 1H), 7.60 (d, J=8.4 Hz, 1H), 7.18 (d, J=2.2 Hz, 1H), 7.03 (dt, J=8.7, 1.9 Hz, 1H), 5.07 (dd, J=13.4, 5.1 Hz, 1H), 4.77-4.63 (m, 1H), 4.38 (dd, J=17.2, 9.6 Hz, 1H), 4.25 (dd, J=17.2, 7.9 Hz, 1H), 3.69 (t, J=7.1 Hz, 2H), 3.44 (dd, J=11.6, 5.1 Hz, 1H), 3.39 (s, 2H), 2.97-2.80 (m, 2H), 2.63-2.53 (m, 2H), 2.46-2.34 (m, 4H), 2.06-1.90 (m, 3H), 1.70-1.57 (m, 5H), 1.51-1.45 (m, 4H). Absolute stereochemistry not determined.

Example 155: 3-(5-(((1S,2S)-2-(3-(2-chlorophenoxy)azetidin-1-yl)cyclopentyl)oxy)-1-oxoisoindolin-2-yl)piperidine-2,6-dione (I-177)

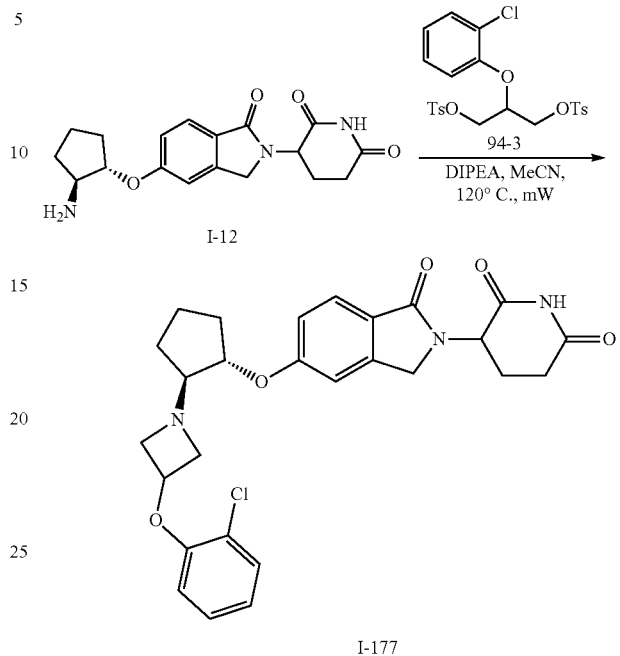

To a solution of 3-(5-(((1S,2S)-2-aminocyclopentyl)oxy)-1-oxoisoindolin-2-yl)piperidine-2,6-dione (I-12, 50.0 mg, 0.146 mmol) and 2-(2-chlorophenoxy)propane-1,3-diyl bis (4-methylbenzenesulfonate) (94-3, 74.4 mg, 0.146 mmol) in MeCN (0.75 mL) was added DIPEA (0.10 mL, 0.57 mmol) and the resulting mixture was stirred at 120° C. under µW irradiation for 8 h and then concentrated. The crude product was purified via silica gel chromatography eluting with 0-50% EtOAc:EtOH (v/v=3:1, with 0.1% NEt$_3$) in DCM (with 0.1% NEt$_3$) to afford I-177 (34.0 mg, 0.063 mmol, 44% yield) as a white solid. MS [M+H]$^+$=510.4. $^1$H NMR (400 MHz, DMSO-d$_6$) δ 10.95 (s, 1H), 7.61 (d, J=8.4 Hz, 1H), 7.34-7.26 (m, 2H), 7.14 (d, J=2.2 Hz, 1H), 7.03 (dd, J=8.3, 2.2 Hz, 1H), 6.89-6.82 (m, 2H), 5.06 (dd, J=13.3, 5.1 Hz, 1H), 4.77 (quint, J=5.5 Hz, 1H), 4.61-4.54 (m, 1H), 4.38 (dd, J=17.2, 5.7 Hz, 1H), 4.25 (dd, J=17.2, 4.9 Hz, 1H), 3.73 (q, J=7.9, 7.4 Hz, 2H), 3.13-3.01 (m, 2H), 2.98-2.82 (m, 2H), 2.65-2.54 (m, 1H), 2.43-2.35 (m, 1H), 2.20-2.07 (m, 1H), 2.05-1.90 (m, 1H), 1.85-1.75 (m, 1H), 1.75-1.55 (m, 3H), 1.50-1.36 (m, 1H).

Example 156: 3-(5-(((1S,2S)-2-(3-(2-methoxyphenoxy)azetidin-1-yl)cyclopentyl)oxy)-1-oxoisoindolin-2-yl)piperidine-2,6-dione (I-178)

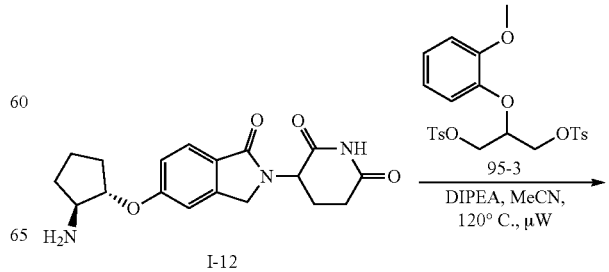

-continued

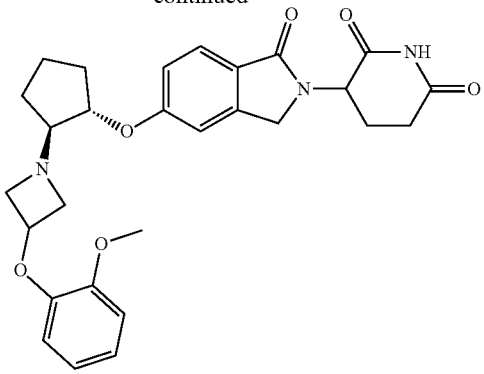

I-178

To a solution of 3-(5-(((1S,2S)-2-aminocyclopentyl)oxy)-1-oxoisoindolin-2-yl)piperidine-2,6-dione (I-12, 33 mg, 0.099 mmol) and 2-(2-methoxyphenoxy)propane-1,3-diyl bis(4-methylbenzenesulfonate) (95-3, 50 mg, 0.099 mmol) in MeCN (0.75 mL) was added DIPEA (0.052 mL, 0.30 mmol) and resulting mixture was stirred at 120° C. under μW irradiation for 8 h. The reaction mixture was concentrated to dryness and purified via silica gel chromatography eluting with 0-100% EtOAc:EtOH (v/v=3:1, with 0.1% NEt$_3$) in DCM (with 0.1% NEt$_3$) to afford I-178 (16 mg, 0.028 mmol, 29% yield) as a pale yellow solid. MS [M+H]$^+$=506.4. $^1$H NMR (400 MHz, DMSO-d$_6$) δ 10.95 (s, 1H), 7.62 (d, J=8.4 Hz, 1H), 7.15 (s, 1H), 7.04 (d, J=8.4 Hz, 1H), 6.97 (d, J=8.0 Hz, 1H), 6.91 (d, J=8.1 Hz, 1H), 6.86-6.79 (m, 1H), 6.73 (d, J=7.8 Hz, 1H), 5.10-5.01 (m, 1H), 4.75-4.66 (m, 1H), 4.62-4.54 (m, 1H), 4.39 (dd, J=17.2, 5.4 Hz, 1H), 4.26 (dd, J=17.3, 5.3 Hz, 1H), 3.74 (m, 5H), 3.15-3.00 (m, 2H), 2.90 (ddd, J=18.4, 13.4, 5.4 Hz, 2H), 2.63-2.54 (m, 1H), 2.46-2.33 (m, 1H), 2.21-2.07 (m, 1H), 2.04-1.92 (m, 1H), 1.84-1.54 (m, 4H), 1.49-1.38 (m, 1H).

Example 157: Single Enantiomer of 3-(5-((2-(6-azaspiro[3.5]nonan-6-yl)cyclopentyl)oxy)-1-oxoisoindolin-2-yl)piperidine-2,6-dione (I-179)

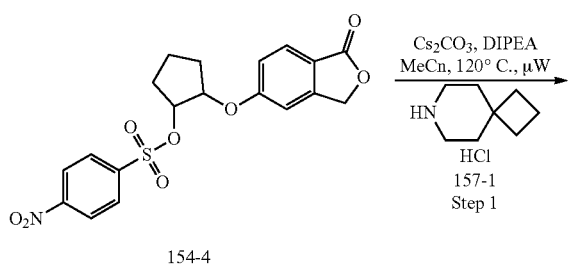

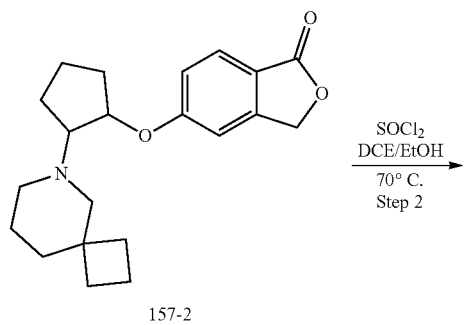

-continued

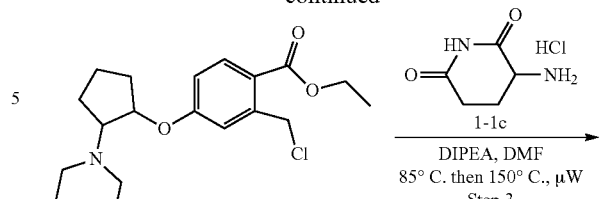

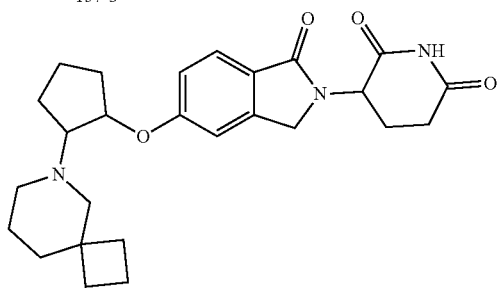

I-179

Step 1. Single Enantiomer of 5-((2-(6-azaspiro[3.5]nonan-6-yl)cyclopentyl)oxy)isobenzofuran-1(3H)-one (157-2)

To a suspension of 154-4 (Example 154, Step 2, 0.150 g, 0.358 mmol) in MeCN (1.2 mL) was added sequentially 6-azaspiro[3.5]nonane (157-1, 54.0 mg, 0.429 mmol), and DIPEA (0.094 mL, 0.54 mmol) and the resulting mixture was purged with nitrogen with sonication for 20 minutes and then stirred at 120° C. for 3 h under μW radiation. The reaction mixture was quenched with water and extracted with dichloromethane. The combined organic phases were passed through a phase separator and concentrated onto Celite®. The crude material was purified by silica gel chromatography eluting with 0-100% EtOAc in heptane to afford 157-2 (83.0 mg, 0.243 mmol, 68% yield) as a pale brown solid. MS [M+H]$^+$=341.9. $^1$H NMR (400 MHz, Chloroform-d) δ 7.84-7.76 (m, 1H), 7.13-7.04 (m, 2H), 5.24 (s, 2H), 4.84-4.60 (m, 1H), 3.04-2.91 (m, 1H), 2.55-2.21 (m, 4H), 2.06-1.93 (m, 2H), 1.91-1.59 (m, 10H), 1.56-1.43 (m, 4H).

Step 2. Single Enantiomer of Ethyl 4-((2-(6-azaspiro[3.5]nonan-6-yl)cyclopentyl)oxy)-2-(chloromethyl)benzoate (157-3)

A suspension of 157-2 (83.0 mg, 0.243 mmol) in dichloroethane (1.2 mL) and Ethanol (1.2 mL) was stirred at 70° C. and thionyl chloride (0.21 mL, 2.9 mmol) was then added dropwise. The resulting mixture was stirred at 70° C. overnight and then cooled to rt, diluted with water, and quenched with saturated aqueous sodium bicarbonate. The reaction mixture was extracted with EtOAc (×3). The combined organic phases were passed through a phase separator and concentrated to dryness to afford 157-3 as a crude brown oil. The crude product was taken on to the next step without purification. MS [M+H]$^+$=406.3.

Step 3. Single Enantiomer of cis isomer of 3-(5-((2-(6-azaspiro[3.5]nonan-6-yl)cyclopentyl)oxy)-1-oxoisoindolin-2-yl)piperidine-2,6-dione (I-179)

To a flask containing a solution of 3-aminopiperidine-2,6-dione hydrochloride (I-1c, 80.0 mg, 0.486 mmol) in DMF (1 mL) was added DIPEA (0.2 mL, 1 mmol) and the flask was evacuated and backfilled with nitrogen three times. The resulting mixture was stirred at rt for 15 minutes and then 157-3 (99.0 mg, 0.243 mmol) dissolved in DMF (1.5 mL) was added and the flask was again evacuated and backfilled with nitrogen three times. The reaction mixture was stirred at 85° C. overnight and then stirred at 150° C. for 4 h under μW irradiation. The reaction mixture was concentrated to dryness and the crude material purified by silica gel chromatography eluting with 0-100% EtOAc:EtOH (v/v=3:1, with 0.1% NEt$_3$) in heptane (with 0.1% NEt$_3$) to afford crude material. The material was further purified by silica gel chromatography eluting with 0-100% EtOAc:EtOH (v/v=3:1, with 1% NEt$_3$) in heptane to afford I-179 (21.8 mg, 0.045 mmol, 19% yield) as a white solid. MS [M+H]$^+$=452.5. $^1$H NMR (400 MHz, DMSO-d$_6$) δ 10.96 (s, 1H), 7.60 (d, J=8.5 Hz, 1H), 7.26 (d, J=2.2 Hz, 1H), 7.07 (dt, J=8.5, 2.6 Hz, 1H), 5.07 (ddd, J=13.4, 5.2, 1.9 Hz, 1H), 4.77-4.64 (m, 1H), 4.38 (dd, J=17.1, 9.1 Hz, 1H), 4.25 (dd, J=17.2, 6.7 Hz, 1H), 2.96-2.84 (m, 2H), 2.63-2.55 (m, 1H), 2.43-2.23 (m, 5H), 2.07-1.92 (m, 2H), 1.92-1.74 (m, 3H), 1.72-1.57 (m, 7H), 1.56-1.46 (m, 1H), 1.45-1.35 (m, 4H). Absolute stereochemistry not determined Example 158: 3-(5-(((1S,2S)-2-(ethyl(((1s,3R)-3-methoxycyclobutyl)methyl)amino)cyclopentyl)oxy)-1-oxoisoindolin-2-yl)piperidine-2,6-dione (I-180)

Step 1. ((1S,3S)-3-methoxycyclobutyl)methanol (158-2)

To a solution of cis-3-methoxycyclobutane-1-carboxylic acid (158-1, 1.0 g, 7.7 mmol) in THF (20 mL) at 0° C. was added 1M BH$_3$ in THF (17 mL, 17 mmol). The resulting mixture was allowed to warm slowly to rt and then stirred at rt for 18 h. The reaction mixture was slowly quenched by adding MeOH dropwise and then stirred for 20 min. The mixture was then concentrated to dryness. The crude material was dissolved in MeOH (50 mL), stirred at rt for 3 h and then concentrated to dryness to afford crude 158-2 (910 mg, 7.8 mmol). The crude product was taken on to the next step without purification. $^1$H NMR (400 MHz, DMSO-d$_6$) δ 4.45 (t, J=5.4 Hz, 1H), 3.76-3.56 (m, 1H), 3.35-3.29 (m, 2H), 3.08 (s, 3H), 2.22-2.06 (m, 2H), 1.97-1.77 (m, 1H), 1.51 (tdd, J=9.2, 7.7, 2.7 Hz, 2H).

Step 2. ((1S,3S)-3-methoxycyclobutyl)methyl 4-methylbenzenesulfonate (158-3)

To a solution of ((1S,3S)-3-methoxycyclobutyl)methanol (158-2, 910 mg, 7.83 mmol) in pyridine (12 mL) was added tosyl chloride (2.20 g, 11.8 mmol) and the resulting mixture was stirred at rt overnight. The reaction mixture was diluted with EtOAc and washed with water. The phases were separated and the aqueous phase was extracted with EtOAc (×1). The combined organics were dried over Na$_2$SO$_4$,

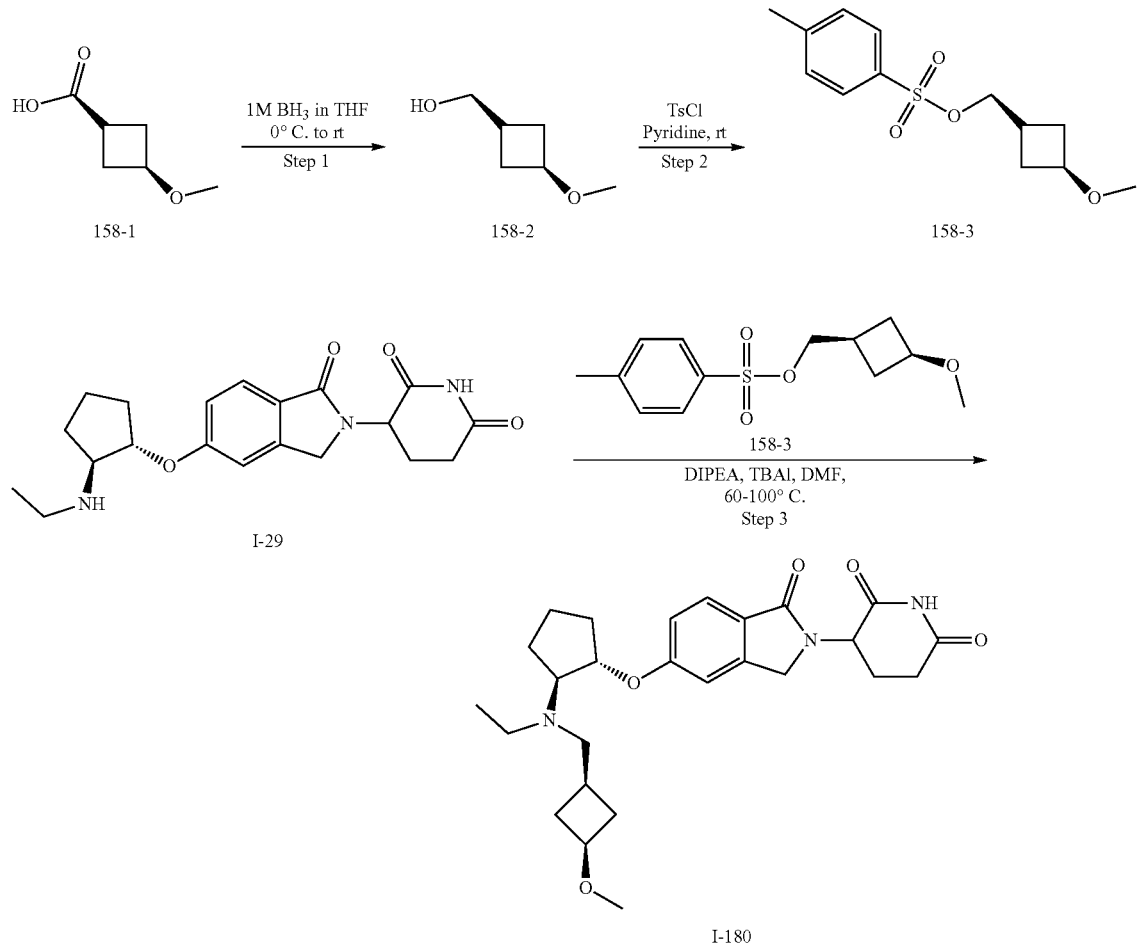

filtered, and concentrated to dryness. The crude material was purified via silica gel chromatography eluting with 0-100% EtOAc/heptanes to afford 158-3 (1.40 g, 5.18 mmol, 66% yield) as a colorless oil. MS [M+H]$^+$=271.2. $^1$H NMR (400 MHz, DMSO-d$_6$) δ 7.77 (d, J=8.4 Hz, 2H), 7.57-7.43 (m, 2H), 3.97 (d, J=6.1 Hz, 2H), 3.73-3.52 (m, 1H), 3.05 (s, 3H), 2.42 (s, 3H), 2.28-1.94 (m, 3H), 1.56-1.37 (m, 2H).

Step 3. 3-(5-(((1S,2S)-2-(ethyl(((1S,3R)-3-methoxycyclobutyl)methyl)amino)cyclopentyl)oxy)-1-oxoisoindolin-2-yl)piperidine-2,6-dione (I-180)

To 3-(5-(((1S,2S)-2-(ethylamino)cyclopentyl)oxy)-1-oxoisoindolin-2-yl)piperidine-2,6-dione (I-29, 91 mg, 0.25 mmol) and ((1S,3S)-3-methoxycyclobutyl)methyl 4-methylbenzenesulfonate (158-3, 199 mg, 0.735 mmol) dissolved in DMF (0.6 mL) was added DIPEA (0.2 mL, 1 mmol) and the resulting mixture was stirred at rt for 18 h and then stirred at 60° C. for 16 h. TBAI (catalytic amount) and further ((1S,3S)-3-methoxycyclobutyl)methyl 4-methylbenzenesulfonate (158-3, ~150-200 mg) were added and stirring was continued at 100° C. for 3 days. Further ((1s,3s)-3-methoxycyclobutyl)methyl 4-methylbenzenesulfonate (158-3, ~200 mg) and TBAI was added and stirring was continued at 100° C. for 3 h. Further DIPEA (200 μL) was added and stirring was continued at 100° C. for 4 h. The reaction mixture was cooled to rt, diluted with acetone, and concentrated to dryness onto Celite®. The crude material was purified via silica gel chromatography eluting with 0-100% EtOAc:EtOH (v/v=3:1) in DCM and the further purified via reverse phase chromatography on C-18 column eluting with 10-60% MeCN in water with 0.1% formic acid as a modifier. The obtained material was purified further via reverse phase HPLC (Column: Xbridge C18 OBD 5 um 30×50 mm; Conditions: Water/MeCN with 5 mM NH$_4$OH 75 mL/min; 1.5 mL injection; Gradient: 5-95% MeCN, 3.5 min gradient) to afford I-180 (22 mg, 0.045 mmol, 18% yield) as a white solid. MS [M+H]$^+$=470.3. $^1$H NMR (400 MHz, DMSO-d$_6$) δ 8.31 (s, 1H), 7.60 (d, J=8.3 Hz, 1H), 7.28 (d, J=1.9 Hz, 1H), 7.08 (dt, J=8.4, 2.4 Hz, 1H), 5.08 (ddd, J=13.6, 5.1, 2.1 Hz, 1H), 4.67-4.56 (m, 1H), 4.46-4.16 (m, 2H), 3.65 (t, J=7.2 Hz, 1H), 3.24 (tt, J=8.8, 4.0 Hz, 2H), 3.07 (s, 3H), 3.01-2.81 (m, 1H), 2.72-2.56 (m, 1H), 2.45-2.19 (m, 5H), 2.07-1.78 (m, 5H), 1.73-1.57 (m, 3H), 1.54-1.34 (m, 3H), 0.95 (t, J=7.0 Hz, 3H).

Example 159: Single Enantiomer of trans-3-(5-((2-(diethylamino)-4,4-dimethylcyclopentyl)oxy)-1-oxoisoindolin-2-yl)piperidine-2,6-dione (I-181)

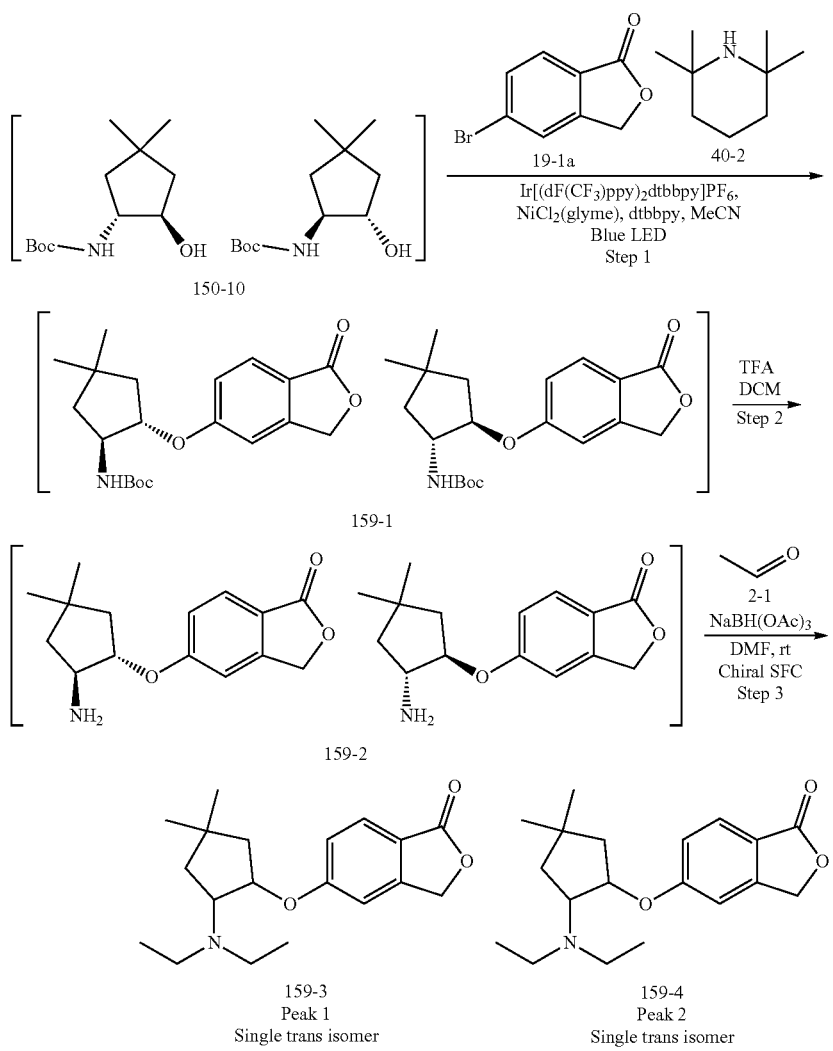

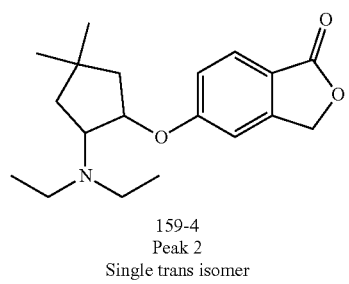 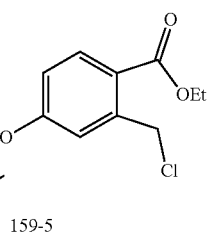 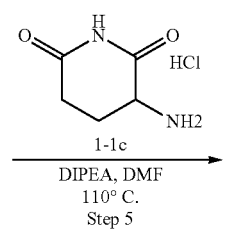

159-4
Peak 2
Single trans isomer 159-5

1-1c

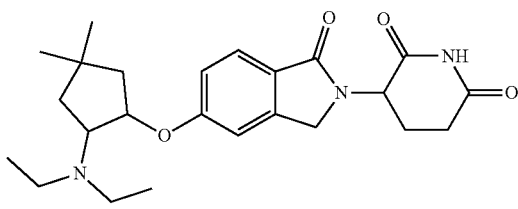

I-181

Step 1. A mixture of tert-butyl ((1S,2S)-4,4-dimethyl-2-((1-oxo-1,3-dihydroisobenzofuran-5-yl)oxy) cyclopentyl)carbamate and tert-butyl ((1S,2S)-4,4-dimethyl-2-((1-oxo-1,3-dihydroisobenzofuran-5-yl)oxy)cyclopentyl)carbamate (159-1)

To 5-bromoisobenzofuran-1(3H)-one (19-1a, 43.2 mg, 0.203 mmol), a mixture of tert-butyl ((1R,2R)-2-hydroxy-4,4-dimethylcyclopentyl)carbamate and tert-butyl ((1S,2S)-2-hydroxy-4,4-dimethylcyclopentyl)carbamate (150-10, 42 mg, 0.18 mmol), NiCl$_2$(glyme) (2 mg, 9 µmol), dtbbpy (2 mg, 9 µmol), and Ir[(dF(CF$_3$)ppy)$_2$dtbbpy]PF$_6$ (2 mg, 2 µmol) under an atmosphere of nitrogen was added MeCN (1 mL) and 2,2,6,6-tetramethylpiperidine (40-2, 34 µL, 0.20 mmol) and the resulting mixture was stirred under blue LED lights at rt for 2 h. The reaction mixture was diluted with EtOAc and filtered through Celite®. The filtrate was collected and concentrated to dryness. The crude material was purified via silica gel chromatography eluting with 0-70% EtOAc in heptane to afford 159-1 (47.1 mg, 0.117 mmol, 64% yield) as a white solid. MS [M+H]$^+$=362.4. $^1$H NMR (400 MHz, DCM-d$_2$) δ 7.79 (d, J=8.5 Hz, 1H), 7.09 (d, J=8.6 Hz, 1H), 7.02 (s, 1H), 5.25 (s, 2H), 4.78-4.67 (m, 1H), 4.32-4.20 (m, 1H), 2.09 (dd, J=13.9, 7.2 Hz, 2H), 1.70 (dd, J=14.0, 4.1 Hz, 1H), 1.53-1.48 (m, 1H), 1.44 (s, 9H), 1.18 (s, 3H), 1.17 (s, 3H).

Step 2. A mixture of 5-(((1S,2S)-2-amino-4,4-dimethylcyclopentyl)oxy)isobenzofuran-1(3H)-one and 5-(((1S,2S)-2-amino-4,4-dimethylcyclopentyl)oxy)isobenzofuran-1(3H)-one (159-2)

To a mixture of tert-butyl ((1S,2S)-4,4-dimethyl-2-((1-oxo-1,3-dihydroisobenzofuran-5-yl)oxy)cyclopentyl)carbamate and tert-butyl ((1S,2S)-4,4-dimethyl-2-((1-oxo-1,3-dihydroisobenzofuran-5-yl)oxy)cyclopentyl)carbamate (159-1, 47.1 mg, 0.130 mmol) in DCM (1 mL) was added TFA (0.100 mL, 1.30 mmol) and the resulting mixture was stirred at rt overnight. The reaction mixture was concentrated to dryness and azeotroped with MeOH and DCM to afford 159-2 (77.8 mg, 0.176 mmol) as a crude solid. The product was taken on to the next step without purification. MS [M+H]$^+$=262.3.

Step 3. 5-(((1S,2S)-2-(diethylamino)-4,4-dimethylcyclopentyl)oxy)isobenzofuran-1(3H)-one and 5-(((1R,2R)-2-(diethylamino)-4,4-dimethylcyclopentyl)oxy)isobenzofuran-1(3H)-one (159-3 and 159-4)

To a mixture of 5-(((1S,2S)-2-amino-4,4-dimethylcyclopentyl)oxy)isobenzofuran-1(3H)-one and 5-(((1S,2S)-2-amino-4,4-dimethylcyclopentyl)oxy)isobenzofuran-1(3H)-one (159-2, 49 mg, 0.13 mmol) and acetaldehyde (2-1, 0.022 mL, 0.39 mmol) dissolved in DMF (1 mL) was added sodium triacetoxyborohydride (0.14 g, 0.65 mmol) in one portion and the resulting mixture was stirred at rt overnight. The reaction mixture was diluted with EtOAc (45 mL) and washed with saturated aqueous sodium bicarbonate solution (10 mL) and brine (10 mL). The organic phase was dried over magnesium sulfate, filtered, and concentrated to dryness. The crude material was purified via silica gel chromatography eluting with 5-100% EtOAc (with 0.1% NEt$_3$) in heptane (with 0.1% NEt$_3$) to afford a mixture two trans isomers. The trans isomers were separated via chiral SFC (Method: Column Chiralpak IE (5 uM) 21×250 mm Mobile Phase: 40% MeOH w/10 mM NH$_3$/CO$_2$ 80g/min 125 bar 6.2 min; Injection 5.6 mg (11.2 mg/mL in MeOH) to afford two products: Peak 1: 159-3 (14.2 mg, 0.041 mmol) as a solid. Chiral SFC Rt 1.02 min. MS [M+H]$^+$=318.3. $^1$H NMR (400 MHz, DCM-d$_2$) δ 7.82 (d, J=8.4 Hz, 1H), 7.12-7.03 (m, 1H), 6.99 (s, 1H), 5.66 (s, 1H), 5.28 (s, 2H), 3.87 (s, 1H), 3.40-3.23 (m, 2H), 3.05 (dt, J=13.5, 6.7 Hz, 2H), 2.44-2.27 (m, 2H), 1.98 (t, J=9.9 Hz, 1H), 1.72 (d, J=14.4 Hz, 1H), 1.37 (dd, J=8.3, 6.1 Hz, 6H), 1.22 (s, 3H), 1.16 (s, 3H). Peak 2: 159-4 (8.2 mg, 0.025 mmol) as a solid. Chiral SFC Rt 1.22 min. MS [M+H]$^+$=318.3. $^1$H NMR (400 MHz, DCM-d$_2$) δ 7.82 (d, J=8.5 Hz, 1H), 7.07 (dd, J=8.4, 2.2 Hz, 1H), 6.99 (s, 1H), 5.74-5.61 (m, 1H), 5.29 (d, J=1.7 Hz, 2H), 3.87 (s, 1H), 3.32 (dt, J=12.8, 6.6 Hz, 2H), 3.04 (dq, J=13.5, 6.6 Hz, 2H), 2.46-2.25 (m, 2H), 2.03-1.91 (m, 1H), 1.78-1.69 (m, 1H), 1.41-1.34 (m, 6H), 1.22 (s, 3H), 1.16 (s, 3H). Absolute stereochemistry not determined.

Step 4. Single Enantiomer of trans-Ethyl 2-(chloromethyl)-4-((2-(diethylamino)-4,4-dimethylcyclopentyl)oxy)benzoate (159-5)

To 159-4 (Peak 2, 8.2 mg, 0.026 mmol) dissolved in Ethanol (1 mL) was added thionyl chloride (0.010 mL, 0.14 mmol) and the resulting mixture was stirred at 70° C. overnight. Additional thionyl chloride (0.010 mL, 0.14 mmol) was added and stirring was continued at 70° C. overnight. The reaction mixture was concentrated to dryness to afford 159-5. The crude material was taken on to the next step without purification. MS [M+H]⁺=382.3.

Step 5. Single Enantiomer of trans-3-(5-((2-(diethylamino)-4,4-dimethylcyclopentyl)oxy)-1-oxoisoindolin-2-yl)piperidine-2,6-dione (I-181)

To a solution of 159-5 (9.9 mg, 0.026 mmol) in DMF (0.5 mL) and DIPEA (0.030 mL, 0.17 mmol) under an atmosphere of nitrogen was added 3-aminopiperidine-2,6-dione hydrochloride (I-1c, 6.4 mg, 0.039 mmol). The resulting mixture was sparged with nitrogen and stirred at 110° C. overnight. The reaction mixture was then diluted with EtOAc (40 mL) and washed with saturated aqueous sodium bicarbonate solution (2×10 mL) and brine (10 mL). The organic phase was dried over magnesium sulfate, filtered, and concentrated to dryness. The crude material was purified via reverse phase HPLC (Column: X-bridge C18 OBD 5 um 30×50 mm; Conditions: Water/MeCN with 0.1% Formic Acid, 75 mL/min; 1.5 mL injection; Gradient: 10-30% MeCN, 3.5 min gradient) then further purified via silica gel chromatography eluting with 0-100% EtOAc:EtOH (v/v=3:1, with 1% NEt₃) in DCM (with 1% NEt₃) to afford I-181 (2.3 mg, 4.6 μmol) as a white solid. MS [M+H]⁺=428.3. ¹H NMR (400 MHz, DMSO-d₆) δ 10.96 (s, 1H), 7.60 (d, J=8.4 Hz, 1H), 7.23-7.15 (m, 1H), 7.03 (dd, J=8.4, 2.0 Hz, 1H), 5.07 (dd, J=13.3, 5.1 Hz, 1H), 4.74-4.63 (m, 1H), 4.46-4.16 (m, 2H), 3.56-3.42 (m, 1H), 1H obscured by asymmetric DMSO signal, 2.91 (ddd, J=18.2, 13.5, 5.4 Hz, 1H), 1.98 (dd, J=13.8, 8.4 Hz, 2H), 1.72 (dd, J=12.4, 7.3 Hz, 1H), 1.58-1.38 (m, 2H), 1.06 (d, J=4.6 Hz, 6H), 0.95 (t, J=7.0 Hz, 6H). Absolute stereochemistry not determined Example 160: 3-(5-(((1S,2S)-2-(ethyl(((1r,3S)-3-methoxycyclobutyl)methyl)amino)cyclopentyl)oxy)-1-oxoisoindolin-2-yl)piperidine-2,6-dione (I-182)

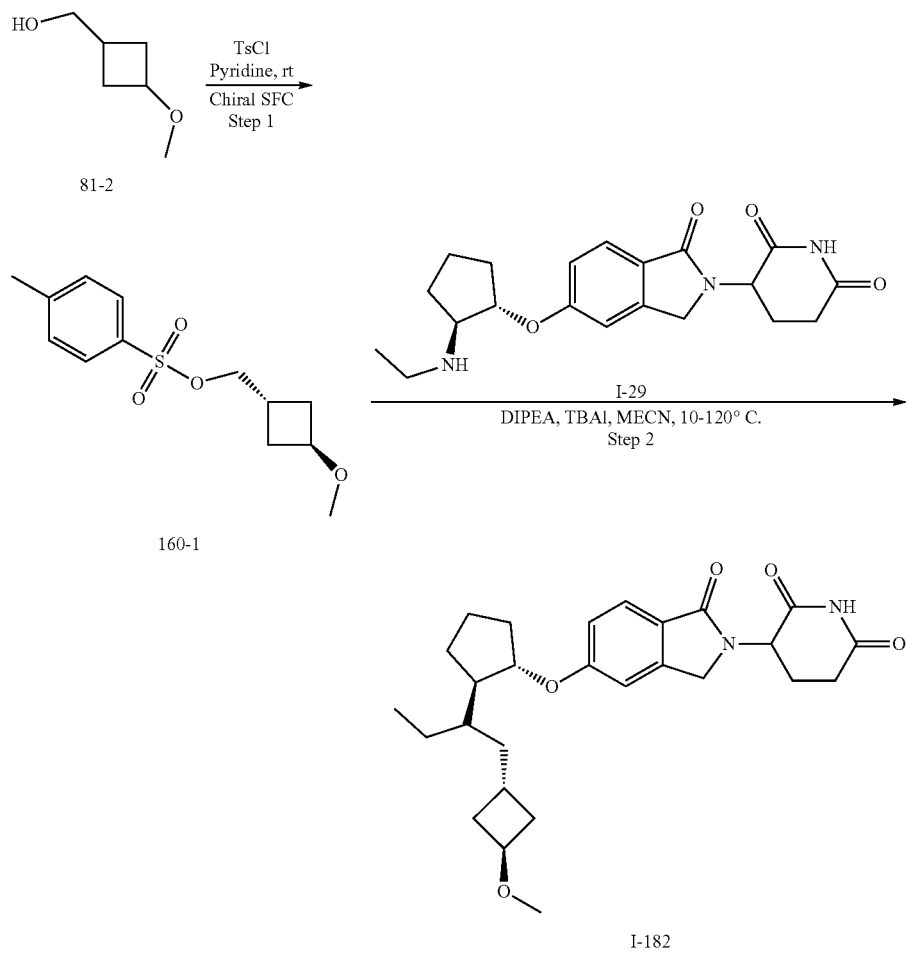

Step 1. ((1r,3r)-3-methoxycyclobutyl)methyl 4-methylbenzenesulfonate (160-1)

To a solution of (3-methoxycyclobutyl)methanol (81-2, 1.40 g, 7.83 mmol) in pyridine (13 mL) was added TsCl (2.20 g, 12.0 mmol) and the resulting mixture was stirred at rt overnight. Upon complete consumption of starting material, the reaction mixture was added to aqueous bicarbonate solution and extracted with DCM (×2). The organic phase was passed through a phase separator and concentrated to dryness. The crude material was purified via silica gel chromatography eluting with 0-100% EtOAc in heptanes to afford 160-1 (730 mg, 2.70 mmol, mixture of cis and trans isomers) as a colorless oil. The two isomers were separated via chiral SFC (Method: Column: ChiralPak IG 21×250 mm, Flow Rate: 80 g per minute cosolvent: 10% t-PrOH) to give 160-1 (300 mg, 1.11 mmol, 14% yield) Peak 1 as the trans isomer as determined with the aid of COSY, ROESY, HSQC and NOE NMR experiments. $^1$H NMR (400 MHz, DMSO-d$_6$) δ 7.90-7.69 (m, 2H), 7.55-7.33 (m, 2H), 4.03 (d, J=7.1 Hz, 2H), 3.89-3.74 (m, 1H), 3.06 (s, 3H), 2.43 (s, 4H), 1.96-1.85 (m, 4H).

Step 2. 3-(5-(((1S,2S)-2-(ethyl(((1r,3S)-3-methoxy-cyclobutyl)methyl)amino)cyclopentyl)oxy)-1-oxoisoindolin-2-yl)piperidine-2,6-dione (I-182)

To a solution of ((1r,3r)-3-methoxycyclobutyl)methyl 4-methylbenzenesulfonate (160-1, 90 mg, 0.33 mmol) and 3-(5-(((1S,2S)-2-(ethylamino)cyclopentyl)oxy)-1-oxoisoindolin-2-yl)piperidine-2,6-dione (I-29, 82 mg, 0.22 mmol) in MeCN (1.5 mL) was added DIPEA (0.11 mL, 0.66 mmol) and the resulting mixture was stirred at 100° C. under μW irradiation for 1 h. A catalytic amount of TBAI was added and the resulting mixture was stirred at 120° C. under μW irradiation for 8 h. Additional ((1r,3r)-3-methoxycyclobutyl) methyl 4-methylbenzenesulfonate (160-1, 90 mg, 0.33 mmol) in MeCN (0.15 mL) and additional TBAI (catalytic amount) was added and stirring was continued at 120° C. under μW irradiation for 4 h. The crude reaction mixture was purified by reverse phase HPLC (Column: Xbridge C18 OBD 5 um 30×50 mm; Conditions: Water/MeCN with 5 mM NH$_4$OH 75 mL/min; 1.5 mL injection; Gradient: 5-95% MeCN, 3.5 min gradient: Collection tubes contained several drops of formic acid) and then further purified by reverse phase HPLC (Column: X-bridge C18 OBD 5 um 30×50 mm; Conditions: Water/MeCN with 0.1% TFA 75 mL/min; 1.5 mL injection; Gradient: 5-95% MeCN, 3.5 min gradient) to afford TFA salt. The isolated product was dissolved in DCM and filtered through a SP—HCO$_3$ column eluting with DCM to afford I-182 (12 mg, 0.02 mmol, 11% yield) as a white solid. MS [M+H]$^+$=470.5. $^1$H NMR (400 MHz, Methylene Chloride-d$_2$) δ 8.06 (s, 1H), 7.70 (d, J=8.4 Hz, 1H), 7.14 (s, 1H), 7.07 (d, J=8.3 Hz, 1H), 5.13 (ddd, J=13.3, 5.2, 3.4 Hz, 1H), 4.57 (s, 1H), 4.41-4.23 (m, 2H), 3.85 (quint, J=6.4 Hz, 1H), 3.33 (s, 1H), 3.15 (s, 3H), 2.95-2.74 (m, 2H), 2.61-2.41 (m, 4H), 2.41-2.27 (m, 2H), 2.24-2.15 (m, 1H), 2.03-1.89 (m, 5H), 1.85-1.68 (m, 3H), 1.67-1.44 (m, 2H), 1.04-0.98 (m, 2H).

Example 161: Single Enantiomer of 3-(5-((2-(8-oxa-2-azaspiro[4.5]decan-2-yl)cyclopentyl)oxy)-1-oxoisoindolin-2-yl)piperidine-2,6-dione (I-183)

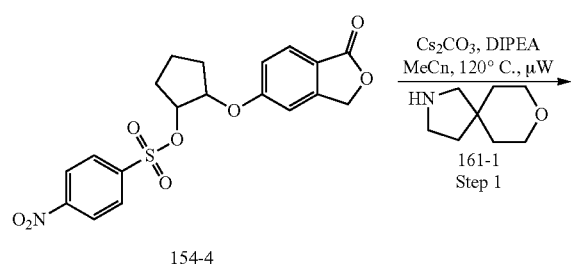

Step 1. Single Enantiomer of 5-((2-(8-oxa-2-azaspiro[4.5]decan-2-yl)cyclopentyl)oxy)isobenzofuran-1(3H)-one (161-2)

8-oxa-2-azaspiro[4.5]decane hemioxalate (161-1, 200 mg, 0.537 mmol) in methanol (1 mL) was loaded onto a 1 g (0.78 mmol) SCX column. The column was flushed with methanol (×2) and eluted with 2N NH$_3$ in MeOH (×3). The eluant was concentrated to dryness and used in the reaction. To 154-1 (Peak 1, Example 154, 100 mg, 0.238 mmol) in MeCN (0.8 mL) was added 8-oxa-2-azaspiro[4.5]decane (161-1, 40 mg, 0.29 mmol) and DIPEA (60 μL, 0.36 mmol) and the resulting mixture was purged with nitrogen while sonicating for 20 minutes and then stirred at 120° C. for 3 h under μW radiation. The reaction mixture was added to water and extracted with dichloromethane. The combined organic phases were passed through a phase separator and concentrated onto Celite®. The crude material was purified by silica gel chromatography eluting with 0-100% EtOAc in heptane then 0-20% MeOH in DCM to afford 161-2 (66.3 mg, 0.185 mmol, 78% yield) as a light yellow oil. MS [M+H]$^+$=358.2. $^1$H NMR (400 MHz, Chloroform-d) δ 7.81 (d, J=8.5 Hz, 1H), 7.01 (dd, J=8.5, 2.1 Hz, 1H), 6.90 (d, J=2.0 Hz, 1H), 5.25 (s, 2H), 4.88-4.55 (m, 1H), 3.63 (dt, J=8.8, 3.6 Hz, 4H), 2.95-2.35 (m, 5H), 2.24-1.96 (m, 2H), 1.86-1.42 (m, 10H).

Step 2. Single Enantiomer of Ethyl 4-((2-(8-oxa-2-azaspiro[4.5]decan-2-yl)cyclopentyl)oxy)-2-(chloromethyl)benzoate (161-3)

To a suspension of 161-2 (66.3 mg, 0.185 mmol) in DCE (0.9 mL) and Ethanol (0.9 mL) stirred at 70° C. was added thionyl chloride (160 μL, 2.23 mmol) dropwise and the resulting mixture was stirred at 70° C. overnight. The reaction mixture was then cooled to rt, diluted with water, and quenched with saturated aqueous sodium bicarbonate. The mixture was extracted with EtOAc (×3) and the combined organic phases were passed through a phase separator and concentrated to afford 161-3 as a brown oil. The crude product was taken on to the next step without purification. MS [M+H]$^+$=422.3

Step 3. Single Enantiomer of 3-(5-((2-(8-oxa-2-azaspiro[4.5]decan-2-yl)cyclopentyl)oxy)-1-oxoisoindolin-2-yl)piperidine-2,6-dione (I-183)

To flask containing a solution of 3-aminopiperidine-2,6-dione hydrochloride (I-1c, 60.9 mg, 0.370 mmol) in DMF (740 μL) was added DIPEA (162 μL, 0.925 mmol) and the flask was evacuated and backfilled with nitrogen three times. The resulting mixture was stirred at rt. for 15 minutes, then 161-3 (78.0 mg, 0.185 mmol) in DMF (1.1 mL) was added and the flask was again evacuated and backfilled with nitrogen three times. The reaction mixture was stirred at 85° C. overnight then stirred at 150° C. for 6 h under μW irradiation. The reaction mixture was then concentrated to dryness and the crude material purified by silica gel chromatography eluting with 0-100% EtOAc:EtOH (v/v=3:1, with 1% NEt$_3$) in heptane. The obtained material was then dissolved in 4:1 DCM:isopropanol and washed with saturated aqueous sodium bicarbonate. The aqueous layer was extracted twice more with 4:1 DCM:isopropanol. The combined organic phases were concentrated to dryness to afford I-183 (30.7 mg, 0.064 mmol, 35% yield) as a pale purple solid. MS [M+H]$^+$=468.5. $^1$H NMR (400 MHz, MeCN-d$_3$) δ 8.94 (s, 1H), 7.53 (dd, J=8.4, 1.6 Hz, 1H), 6.97 (d, J=2.2 Hz, 1H), 6.90 (dd, J=8.4, 2.2 Hz, 1H), 4.94 (ddd, J=13.4, 5.1, 2.1 Hz, 1H), 4.61-4.52 (m, 1H), 4.31-4.10 (m, 2H), 3.44 (q, J=5.3 Hz, 4H), 2.78-2.61 (m, 3H), 2.61-2.46 (m, 2H), 2.41 (dd, J=9.3, 1.0 Hz, 1H), 2.37-2.21 (m, 2H), 2.10-1.97 (m, 3H), 1.68-1.55 (m, 3H), 1.54-1.33 (m, 7H).

Example 162: 3-(1-oxo-5-(((1S,2S)-2-thiomorpholinocyclopentyl)oxy)isoindolin-2-yl)piperidine-2,6-dione (I-184)

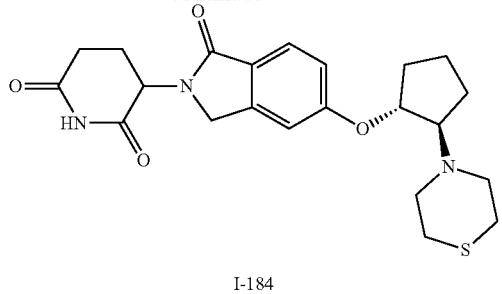

I-184

Step 1. Bis(2-bromoethyl)sulfane (162-2)

To a stirred solution of 2,2'-thiobis(ethan-1-ol) (162-1, 2.50 g, 20.5 mmol) in THF (50 mL) was added PBr$_3$ (1.35 mL, 14.3 mmol) at 15° C. and the resulting mixture was stirred at rt for 16 h. The reaction mixture was filtered and the filtrate concentrated to dryness. The obtained crude material was purified via silica gel chromatography eluting with 7% EtOAc in hexanes to afford 162-2 (1.41 g, 5.69 mmol, 28% yield) as a colorless liquid. $^1$H NMR (300 MHz, CDCl$_3$): δ 3.48 (t, J=7.2 Hz, 4H), 2.98 (t, J=7.8 Hz, 4H).

Step 2. 3-(1-oxo-5-(((1S,2S)-2-thiomorpholinocyclopentyl)oxy)isoindolin-2-yl)piperidine-2,6-dione (I-184)

To a solution of 3-(5-(((1S,2S)-2-aminocyclopentyl)oxy)-1-oxoisoindolin-2-yl)piperidine-2,6-dione (I-12, 200 mg, 0.582 mmol) in MeCN (10 mL), was added bis(2-bromoethyl)sulfane (162-2, 433 mg, 1.75 mmol) and DIPEA (0.62 mL, 3.5 mmol) and the resulting mixture stirred at 120° C. for 16 h under μW irradiation. The reaction mixture was diluted with saturated aqueous sodium bicarbonate solution and extracted with EtOAc (3×30 mL). The combined organic phases were washed with brine, dried over Na$_2$SO$_4$, filtered, and concentrated to dryness. The obtained crude material was purified via silica gel chromatography eluting with 5% MeOH in DCM to afford I-184 (95.0 mg, 0.221 mmol, 38% yield) as brown solid. MS [M+H]$^+$=430.1. $^1$H NMR (400 MHz, DMSO-d$_6$): δ 10.97 (s, 1H), 7.60 (d, J=8.4 Hz, 1H), 7.19 (s, 1H), 7.07 (dd, J=8.8, 2.0 Hz, 1H), 5.09 (dd, J=13.2, 4.8 Hz, 1H), 4.40-4.23 (m, 3H), 2.95-2.86 (m, 1H), 2.64-2.42 (m, 5H), 2.19-2.07 (m, 4H), 2.06-1.98 (m, 2H), 1.75-1.64 (m, 3H), 1.35-1.143 (m, 4H).

Example 163: 3-(5-(((1S,2S)-2-(1,4-oxazepan-4-yl)cyclopentyl)oxy)-1-oxoisoindolin-2-yl)piperidine-2,6-dione (I-185)

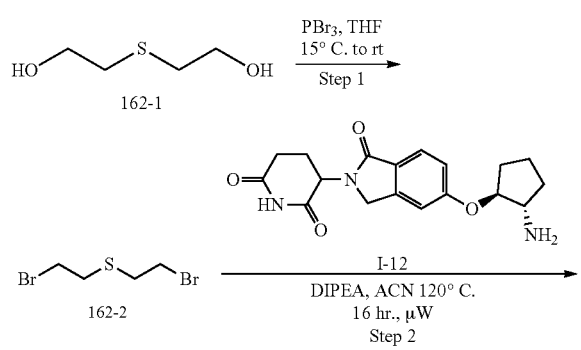

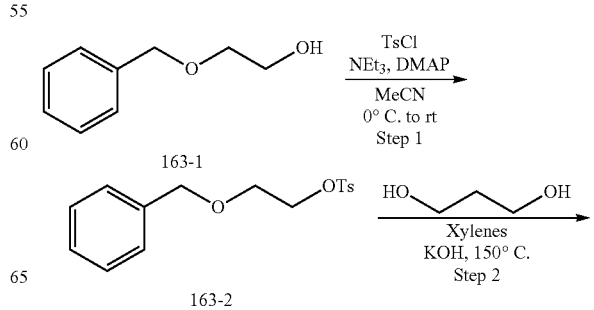

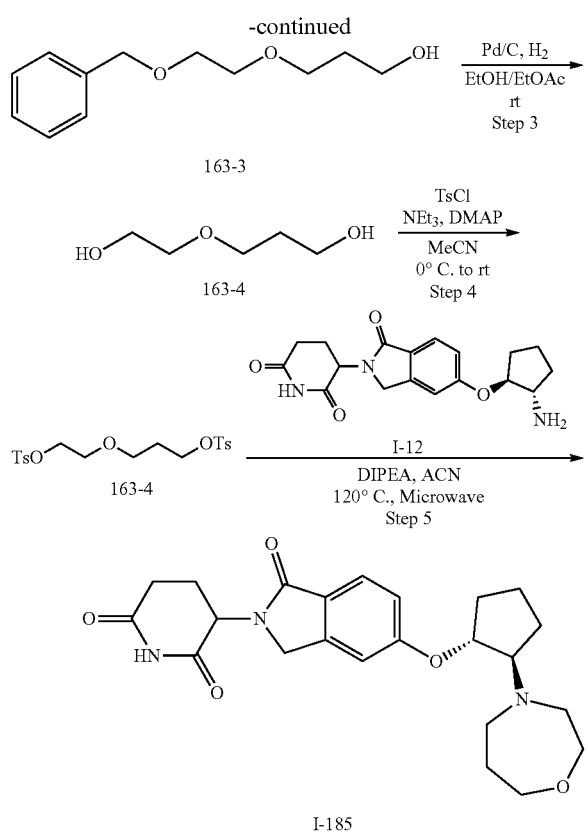

Step 1. 2-(benzyloxy)ethyl 4-methylbenzenesulfonate (163-2)

To a solution of 2-(benzyloxy)ethan-1-ol (163-1, 2.00 g, 13.1 mmol) in MeCN (10 mL) at 0° C. was added TEA (3.6 mL, 19 mmol), DMAP (48 mg, 0.39 mmol) and 4-methylbenzenesulfonyl chloride (3.75 g, 19.7 mmol) sequentially and the resulting mixture was stirred at rt for 3 h. The reaction mixture was filtered and the filtrate was concentrated to dryness. The obtained crude material was purified via silica gel chromatography eluting with 15% EtOAc in hexanes to afford 163-2 (3.41 g, 11.1 mmol, 85% yield) as a white solid. MS [M+H]$^+$=307.3.

Step 2. 3-(2-(benzyloxy)ethoxy)propan-1-ol (163-3)

To a solution of 2-(benzyloxy)ethyl 4-methylbenzenesulfonate (163-2, 2.20 g, 7.18 mmol) in xylenes (40 mL) was added propane-1,3-diol (1.64 g, 21.5 mmol) and KOH (1.20 g, 21.5 mmol) and the resulting mixture was stirred at 150° C. for 16 h. The reaction mixture was diluted with DCM and washed with brine, dried over Na$_2$SO$_4$, filtered, and concentrated to dryness. The obtained crude material was purified via silica gel chromatography eluting with 4% MeOH in DCM to afford 163-3 (1.20 g, 5.70 mmol, 79% yield) as a colorless oil. MS [M+H]$^+$=211.3.

Step 3. 3-(2-hydroxyethoxy)propan-1-ol (163-4)

To a solution of 3-(2-(benzyloxy)ethoxy)propan-1-ol (163-3, 1.20 g, 5.71 mmol) in EtOH-EtOAc (4:1, 12 mL) under an inert atmosphere was added 10% Pd/C (240 mg). The resulting mixture was stirred under an atmosphere of hydrogen at rt for 16 h. The reaction mixture was filtered and the filtrate was concentrated to dryness to afford 163-4 (0.60 g, 4.50 mmol, 88% yield) which was carried on to the next step without purification. $^1$H NMR (400 MHz, DMSO-d$_6$): δ 4.56 (t, J=5.2 Hz, 1H), 4.38 (t, J=5.2 Hz, 1H), 3.49-3.34 (m, 8H), 1.6-1.61 (m, 2H).

Step 4. 3-(2-(tosyloxy)ethoxy)propyl 4-methylbenzenesulfonate (163-5)

To a solution of 3-(2-hydroxyethoxy)propan-1-ol (163-4, 100 mg, 0.830 mmol) in MeCN (10 mL) at 0° C. was added TEA (0.46 mL, 3.3 mmol), DMAP (3 mg, 0.02 mmol) and 4-methylbenzenesulfonyl chloride (354 mg, 1.83 mmol) sequentially and the resulting mixture was stirred at rt for 16 h. The reaction mixture was filtered and the filtrate was concentrated to dryness. The crude material was purified via silica gel chromatography eluting with 30% EtOAc in hexanes to afford 163-5 (230 mg, 0.540 mmol, 65% yield) as an off-white solid. MS [M+H$_2$O]$^+$=445.9. $^1$H NMR (300 MHz, CDCl$_3$): δ 7.78 (d, J=11.2 Hz, 4H), 7.33 (d, J=11.2 Hz, 4H), 4.06 (m, 4H), 3.49 (m, 4H), 2.45 (s, 6H), 1.82 (m, 2H).

Step 5. 3-(5-(((1S,2S)-2-(1,4-oxazepan-4-yl)cyclopentyl)oxy)-1-oxoisoindolin-2-yl)piperidine-2,6-dione (I-185)

To a solution of 3-(5-(((1S,2S)-2-aminocyclopentyl)oxy)-1-oxoisoindolin-2-yl)piperidine-2,6-dione (I-12, 150 mg, 0.440 mmol) in MeCN (5 mL), was added 3-(2-(tosyloxy)ethoxy)propyl 4-methylbenzenesulfonate (163-5, 224 mg, 0.530 mmol) and DIPEA (0.46 mL, 2.6 mmol) and the resulting mixture was stirred at 120° C. for 16 h under μW irradiation. After complete consumption of the starting material, the reaction mixture was diluted with saturated sodium bicarbonate solution and extracted with EtOAc (3×30 mL). The combined organic phases were washed with brine, dried over Na$_2$SO$_4$, filtered, and concentrated under reduced pressure. The obtained crude material was purified via silica gel chromatography eluting with 5% MeOH in DCM to afford I-185 (70.0 mg, 0.160 mmol, 38% yield) as a brown solid. MS [M+H]$^+$=428.2. $^1$H NMR (400 MHz, DMSO-d$_6$): δ 10.97 (s, 1H), 7.60 (d, J=8.8 Hz, 1H), 7.25 (s, 1H), 7.05 (dd, J=8.8, 2.0 Hz, 1H), 5.10-5.02 (m, 1H), 4.69-4.65 (m, 1H), 4.38-4.26 (m, 2H), 3.68-3.58 (m, 4H), 3.23-3.19 (m, 1H), 2.92-2.90 (m, 1H), 2.69-2.65 (m, 4H), 2.49-2.35 (m, 2H), 2.05-1.92 (m, 4H), 1.78-1.45 (m, 5H).

Example 164: 3-(5-(((1S,2S)-2-(4-(cyclopropylmethoxy)piperidin-1-yl)cyclopentyl)oxy)-1-oxoisoindolin-2-yl)piperidine-2,6-dione (I-186)

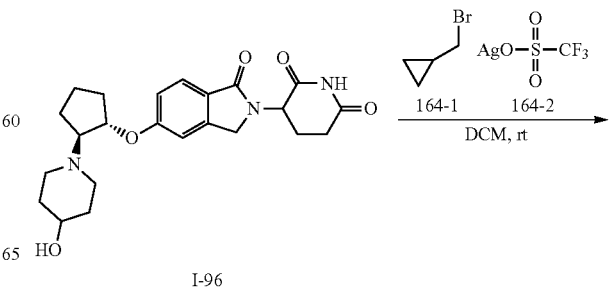

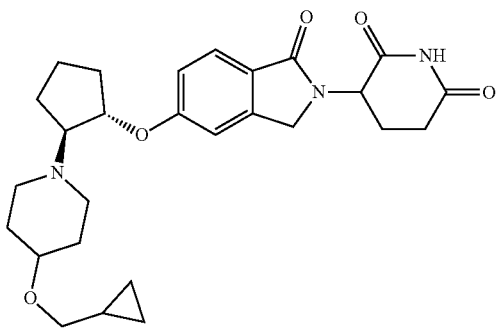

I-186

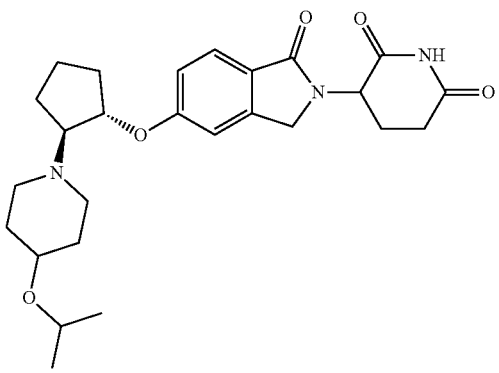

I-187

To a solution of 3-(5-(((1S,2S)-2-(4-hydroxypiperidin-1-yl)cyclopentyl)oxy)-1-oxoisoindolin-2-yl)piperidine-2,6-dione (I-96, 50.0 mg, 0.117 mmol) and AgOTf (164-2, 150 mg, 0.585 mmol) in DCM (0.5 mL) was added (bromomethyl)cyclopropane (164-1, 0.11 mL, 1.2 mmol) and the resulting mixture was stirred at rt overnight. The reaction mixture was filtered and washed with 50% saturated aqueous Na$_2$CO$_3$. The phases were separated and the aqueous layer was extracted with DCM. The combined organic phases were dried over Na$_2$SO$_4$, filtered, and concentrated to dryness. The crude material was purified by silica gel chromatography eluting with 0-100% EtOAc:EtOH (v/v=3:1, with 0.1% NEt$_3$) in DCM (with 0.1% NEt$_3$) to afford I-186 (9.0 mg, 0.017 mmol, 14% yield) as an off-white solid. MS [M+H]$^+$=482.4. $^1$H NMR (400 MHz, DMSO-d$_6$) δ 10.96 (s, 1H), 7.74-7.56 (m, 1H), 7.18 (s, 1H), 7.13-6.98 (m, 1H), 5.07 (dd, J=13.2, 5.3 Hz, 1H), 4.74-4.65 (m, 1H), 4.38 (dd, J=17.2, 9.7 Hz, 1H), 4.25 (dd, J=17.1, 8.4 Hz, 1H), 3.96 (quint, J=7.2 Hz, 1H), 3.27-3.19 (m, 1H), 2.96-2.80 (m, 2H), 2.80-2.68 (m, 2H), 2.62-2.54 (m, 1H), 2.46-2.35 (m, 1H), 2.27-2.03 (m, 6H), 2.03-1.85 (m, 2H), 1.86-1.52 (m, 8H), 1.52-1.28 (m, 3H).

Example 165: 3-(5-(((1S,2S)-2-(4-isopropoxypiperidin-1-yl)cyclopentyl)oxy)-1-oxoisoindolin-2-yl)piperidine-2,6-dione (I-187)

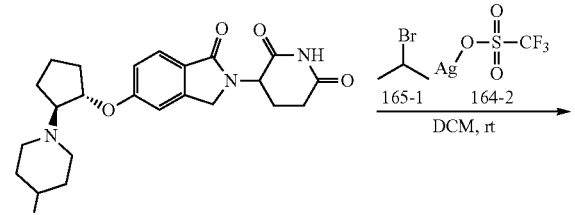

To a solution of 3-(5-(((1S,2S)-2-(4-hydroxypiperidin-1-yl)cyclopentyl)oxy)-1-oxoisoindolin-2-yl)piperidine-2,6-dione (I-96, 50.0 mg, 0.117 mmol) and AgOTf (164-2, 150 mg, 0.585 mmol) in DCM (0.5 mL) was added 2-Bromopropane (165-1, 0.110 mL, 1.17 mmol) and the resulting mixture was stirred at rt overnight. The reaction mixture was filtered and washed with 50% saturated aqueous Na$_2$CO$_3$. The phases were separated and the aqueous layer was extracted with DCM. The combined organic phases were dried over Na$_2$SO$_4$, filtered, and concentrated to dryness. The crude material was purified by silica gel chromatography eluting with 0-100% EtOAc:EtOH (v/v=3:1, with 0.1% NEt$_3$) in DCM (with 0.1% NEt$_3$) to afford I-187 (14.0 mg, 0.027 mmol, 23% yield) as a pale brown solid. MS [M+H]$^+$=470.4. $^1$H NMR (400 MHz, DMSO-d$_6$) δ 10.96 (s, 1H), 7.60 (d, J=8.3 Hz, 1H), 7.20-7.15 (m, 1H), 7.03 (d, J=8.6 Hz, 1H), 5.07 (dd, J=13.3, 5.1 Hz, 1H), 4.73-4.65 (m, 1H), 4.39 (dd, J=17.1, 9.9 Hz, 1H), 4.25 (dd, J=17.1, 8.5 Hz, 1H), 3.70-3.61 (m, 1H), 2.96-2.81 (m, 2H), 2.80-2.67 (m, 2H), 2.64-2.54 (m, 1H), 2.44-2.35 (m, 1H), 2.21-2.02 (m, 3H), 2.02-1.84 (m, 2H), 1.80-1.69 (m, 2H), 1.69-1.55 (m, 3H), 1.54-1.40 (m, 1H), 1.41-1.28 (m, 2H), 1.20-1.13 (m, 1H), 1.04 (d, J=5.9 Hz, 6H).

Example 166: 3-(5-(((1S,2S)-2-((3aR,4R,7S,7aS)-octahydro-2H-4,7-epoxyisoindol-2-yl)cyclopentyl)oxy)-1-oxoisoindolin-2-yl)piperidine-2,6-dione (I-188)

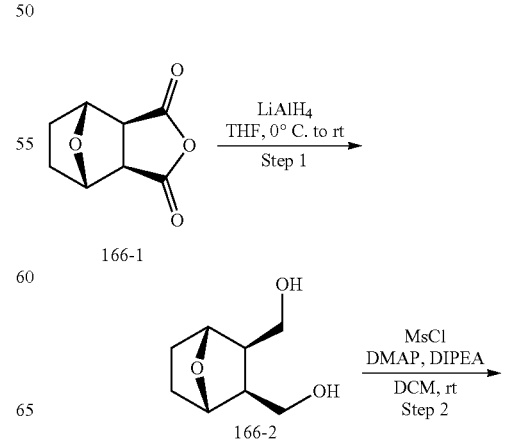

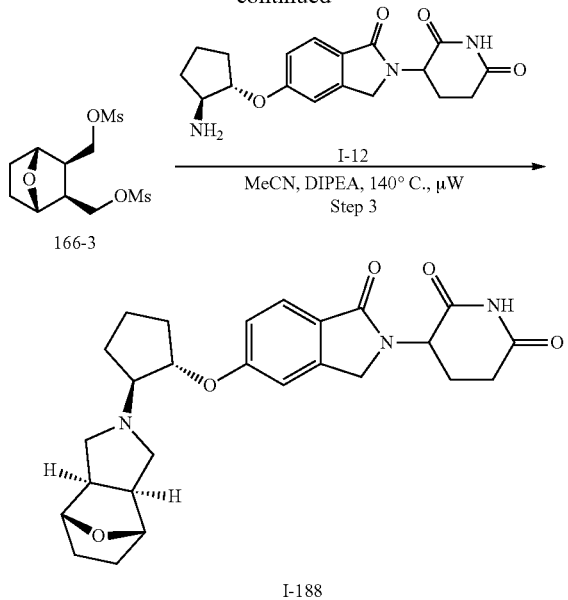

Step 3. 3-(5-(((1S,2S)-2-((3aR,4R,7S,7aS)-octa-hydro-2H-4,7-epoxyisoindol-2-yl)cyclopentyl)oxy)-1-oxoisoindolin-2-yl)piperidine-2,6-dione (I-188)

To 3-(5-(((1S,2S)-2-aminocyclopentyl)oxy)-1-oxoisoindolin-2-yl)piperidine-2,6-dione (I-12, 100 mg, 0.291 mmol) in DIPEA (0.30 mL, 1.7 mmol) and MeCN (1 mL) was added ((1R,2R,3S,4S)-7-oxabicyclo[2.2.1]heptane-2,3-diyl)bis(methylene) dimethanesulfonate (166-3, 110 mg, 0.349 mmol) and the resulting mixture was stirred for at 140° C. for 12 h under μW irradiation. The reaction mixture was concentrated to dryness and the crude product purified via silica gel chromatography eluting with 0-100% EtOAc:EtOH (v/v=3:1, with 0.1% NEt$_3$) in DCM to afford I-188 (9.30 mg, 0.019 mmol, 7% yield) as white powder. MS [M+H]$^+$=466.2. $^1$H NMR (400 MHz, DCM-d$_2$) δ 9.51 (br s, 1H), 7.67 (t, J=9.2 Hz, 1H), 7.05-6.76 (m, 2H), 5.07 (dd, J=13.1, 5.5 Hz, 1H), 4.77-4.53 (m, 1H), 4.47-4.23 (m, 1H), 4.23-4.01 (m, 3H), 3.27-3.00 (m, 2H), 2.93-2.70 (m, 3H), 2.33-1.91 (m, 8H), 1.77-1.51 (m, 6H), 1.40-1.25 (m, 2H).

Example 167: 3-(5-(((1S,2S)-2-(4-ethoxypiperidin-1-yl)cyclopentyl)oxy)-1-oxoisoindolin-2-yl)piperidine-2,6-dione (I-189)

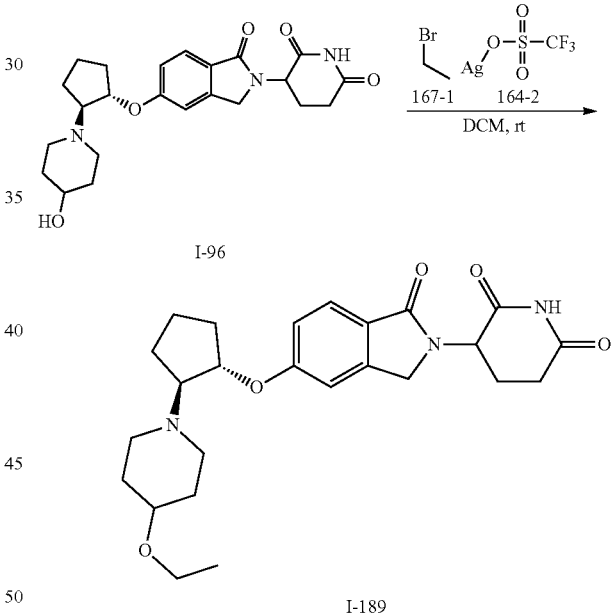

Step 1. ((1R,2R,3S,4S)-7-oxabicyclo[2.2.1]heptane-2,3-diyl)dimethanol (166-2)

To a solution of Norcantharidin (166-1, 1.00 g, 5.95 mmol) in THF (20 mL) under an atmosphere of nitrogen was added LiAlH$_4$ (8.9 mL, 18 mmol) dropwise at 0° C. and the resulting mixture was stirred for 30 min at 0° C. and then at rt overnight. The reaction mixture was cooled to 0° C., diluted with THF (20 mL) and Na$_2$SO$_4$.10H$_2$O (1.50 g) was added slowly portionwise. After stirring for 10 min, Na$_2$SO$_4$ (approx. 500 mg) was added. The reaction mixture was stirred vigorously for 10 min and then the rest of Na$_2$SO$_4$.10H$_2$O (2.30 g) was added portionwise. Additional Na$_2$SO$_4$ (approx. 500 mg) was added and the reaction mixture was stirred for 1 hour at rt, filtered through a pad of Celite® washing with minimal amount of EtOAc. The filtrate was concentrated to dryness to afford 166-2 (623 mg, 3.94 mmol, 66% yield) as colorless oil, which was carried on to the next step without purification. $^1$H NMR (400 MHz, Chloroform-d) δ 4.32 (t, J=2.7 Hz, 2H), 3.85-3.77 (m, 2H), 3.77-3.65 (m, 2H), 2.28-2.13 (m, 2H), 1.77-1.67 (m, 2H), 1.57-1.50 (m, 2H).

Step 2. ((1R,2R,3S,4S)-7-oxabicyclo[2.2.1]heptane-2,3-diyl)bis(methylene) dimethanesulfonate (166-3)

To ((1R,2R,3S,4S)-7-oxabicyclo[2.2.1]heptane-2,3-diyl)dimethanol (166-2, 83.0 mg, 0.525 mmol), DMAP (6 mg, 0.05 mmol), DIPEA (0.46 mL, 2.6 mmol) in DCM (2 mL) was added MsCl (0.10 mL, 1.3 mmol) in one portion at 0° C. and the resulting mixture was stirred at rt overnight. The reaction mixture was poured into cold saturated aqueous NaHCO$_3$ and extracted with DCM (×2). The combined organic phases were dried over Na$_2$SO$_4$, filtered, and concentrated to dryness to afford 166-3 (153 mg, 0.487 mmol, 93% yield) as a brown oil, which was carried on to the next step without purification. $^1$H NMR (400 MHz, Chloroform-d) δ 4.48 (dd, J=3.4, 2.2 Hz, 2H), 4.24-4.11 (m, 4H), 3.05 (s, 6H), 2.44-2.35 (m, 2H), 1.84-1.77 (m, 2H), 1.59-1.55 (m, 2H).

To a solution of 3-(5-(((1S,2S)-2-(4-hydroxypiperidin-1-yl)cyclopentyl)oxy)-1-oxoisoindolin-2-yl)piperidine-2,6-dione (I-96, 75.0 mg, 0.175 mmol) and AgOTf (164-2, 225 mg, 0.877 mmol) in DCM (0.5 mL) was added bromoethane (167-1, 0.13 mL, 1.8 mmol) and the resulting mixture was stirred at rt for 3 h. The reaction mixture was filtered and washed with 50% saturated Na$_2$CO$_3$ (aq). The phases were separated and the aqueous phase was extracted with DCM. The combined organic phases were dried over Na$_2$SO$_4$, filtered, and concentrated to dryness. The crude material was purified via silica gel chromatography eluting with 0-100% EtOAc:EtOH (v/v=3:1, with 0.1% NEt$_3$) in DCM (with 0.1% NEt$_3$) and then further purified via reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient). The fractions containing the desired product were combined and lyophilized to afford I-189 (5.0 mg, 9.5 μmol, 5% yield) as a white solid. MS [M+H]$^+$=456.3. $^1$H NMR (400 MHz, DCM-d$_2$) δ 8.04 (br s, 1H), 7.62 (d, J=8.3 Hz, 1H), 6.97-6.84 (m, 2H), 5.12-4.97 (m, 1H), 4.83 (br s, 1H), 4.34-4.11 (m, 2H), 3.37 (q, J=7.0 Hz, 2H), 3.29 (br s, 1H), 3.00 (br s, 1H), 2.94-2.63 (m, 4H), 2.43 (br s, 1H), 2.36-2.20 (m, 1H), 2.19-1.78 (m, 5H), 1.78-1.45 (m, 6H), 1.06 (t, J=7.0 Hz, 3H).

Example 168: 3-(5-(((1S,2S)-2-(7,8-dihydro-1,6-naphthyridin-6(5H)-yl)cyclopentyl)oxy)-1-oxoisoindolin-2-yl)piperidine-2,6-dione (I-190)

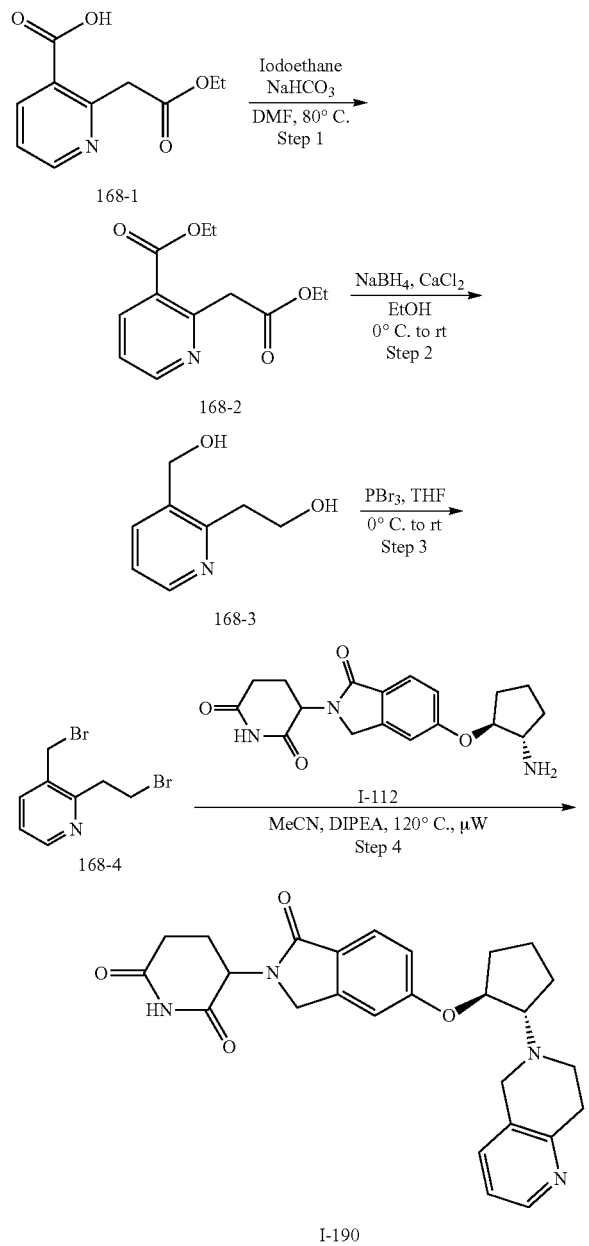

Step 1. Ethyl 2-(2-ethoxy-2-oxoethyl)nicotinate (168-2)

To a solution of 2-(2-ethoxy-2-oxoethyl)nicotinic acid (3.50 g, 16.7 mmol) in DMF (50 mL) was added NaHCO$_3$ (1.61 g, 19.2 mmol) and iodoethane (2.0 mL, 25 mmol) and the resulting mixture was stirred at 80° C. for 4 h. The reaction mixture was diluted with water and extracted with EtOAc (2×100 mL). The combined organic phases were washed with brine, dried over Na$_2$SO$_4$, filtered, and concentrated to dryness. The obtained crude material was purified via silica gel chromatography eluting with 15% EtOAc in hexanes to afford 168-2 (3.30 g, 13.9 mmol, 83% yield) as a pale yellow oil. MS [M+H]$^+$=237.9.

Step 2. 2-(3-(hydroxymethyl)pyridin-2-yl)ethan-1-ol (168-3)

To a solution of ethyl 2-(2-ethoxy-2-oxoethyl)nicotinate (168-2, 4.00 g, 16.9 mmol) in EtOH (50 mL) at 0° C. was added NaBH$_4$ (3.18 g, 84.3 mmol) and CaCl$_2$ (1.68 g, 15.2 mmol) and the resulting mixture was stirred at rt for 16 h. The reaction mixture was cooled to 0° C. quenched with 50% aqueous EtOH (10 mL) and concentrated to dryness. The obtained residue was diluted with EtOH, refluxed for 2 h, the solids were filtered off, and the filtrate was concentrated to dryness. The crude material was purified via silica gel chromatography eluting with 5% MeOH in DCM to afford 168-3 (2.00 g, 13.1 mmol, 77% yield) as a yellow oil. MS [M+H]$^+$=154.3.

Step 3. 2-(2-bromoethyl)-3-(bromomethyl)pyridine (168-4)

To a stirred solution of 2-(3-(hydroxymethyl)pyridin-2-yl)ethan-1-ol (168-3, 2.00 g, 13.1 mmol) in THF (50 mL) at 0° C. was added PBr$_3$ (3.7 mL, 39 mmol) and the resulting mixture was stirred at rt for 16 h. The reaction mixture was quenched with saturated aqueous sodium bicarbonate solution and extracted with EtOAc (2×75 mL). The combined organic phases were washed with brine, dried over Na$_2$SO$_4$, filtered, and concentrated to dryness. The obtained crude material was purified via silica gel chromatography eluting with 1% MeOH in DCM to afford 168-4 (0.780 g, 0.484 mmol, 21%) as a brown solid. $^1$H NMR (600 MHz, CDCl$_3$): 8.49 (d, J=4.8 Hz, 1H), 7.62 (d, J=7.8 Hz, 1H), 7.181-7.148 (m, 1H), 4.61-4.46 (m, 4H), 3.42-3.35 (m, 2H).

Step 4. 3-(5-(((1S,2S)-2-(7,8-dihydro-1,6-naphthyridin-6(5H)-yl)cyclopentyl)oxy)-1-oxoisoindolin-2-yl)piperidine-2,6-dione (I-190)

To a solution of 3-(5-(((1S,2S)-2-aminocyclopentyl)oxy)-1-oxoisoindolin-2-yl)piperidine-2,6-dione (I-12, 200 mg, 0.580 mmol) in MeCN (10 mL) was added 2-(2-bromoethyl)-3-(bromomethyl)pyridine (168-4, 243 mg, 0.873 mmol) and DIPEA (0.62 mL, 3.5 mmol) and the resulting mixture was stirred at 120° C. for 16 h under μW irradiation. The reaction mixture was diluted with saturated aqueous sodium bicarbonate solution and extracted with EtOAc (3×30 mL). The combined organic phases were washed with brine, dried over Na$_2$SO$_4$, filtered, and concentrated to dryness. The obtained crude material was purified by silica gel chromatography eluting with 5% MeOH in DCM to afford I-190 (45.0 mg, 970 μmol, 17% yield) as a pale yellow solid. MS [M+H]$^+$=461.5. $^1$H NMR (400 MHz, DMSO-d$_6$): δ 10.97 (s, 1H), 8.319-8.31 (m, 1H), 7.63 (d, J=8.4 Hz, 1H), 7.45 (d, J=7.2 Hz, 1H), 7.21 (s, 1H), 7.14-7.06 (m, 2H), 5.09-5.05 (m, 1H), 4.90-4.86 (m, 1H), 4.42 (d, J=17.2 Hz, 1H), 4.29 (d, J=17.2 Hz, 1H), 38 (d, J=14.8 Hz, 1H), 3.67 (d, J=15.6 Hz, 1H), 3.14-2.95 (m, 1H), 2.95-2.81 (m, 5H), 2.67-2.33 (m, 2H), 2.12-1.96 (m, 3H), 1.73-159 (m, 4H).

Example 169: 3-(5-(((1S,2S)-2-((((1s,4R)-4-methoxycyclohexyl)methyl)amino)cyclopentyl)oxy)-1-oxoisoindolin-2-yl)piperidine-2,6-dione (I-191)

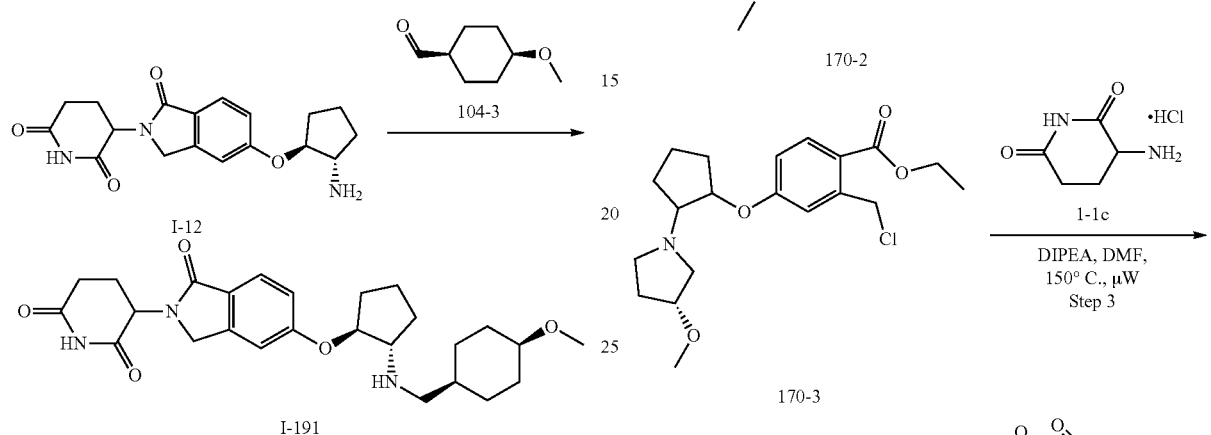

To a solution of 3-(5-(((1S,2S)-2-aminocyclopentyl)oxy)-1-oxoisoindolin-2-yl)piperidine-2,6-dione (I-12, 0.20 g, 0.52 mmol) and (1s,4s)-4-methoxycyclohexane-1-carbaldehyde (104-3, 0.11 g, 0.79 mmol) in TFE (10 mL) at 0° C. was added NaBH(OAc)$_3$ (0.17 g, 0.79 mmol) and the resulting mixture was stirred at rt for 16 h. After complete consumption of starting material, the reaction mixture was quenched with water and extracted with DCM (3×30 mL). The combined organic phases were washed with brine, dried over Na$_2$SO$_4$, filtered, and concentrated to dryness. The obtained crude material was purified silica gel chromatography eluting with 4% MeOH in DCM to afford I-191 (52 mg, 0.11 mmol, 21% yield) as off white solid. MS [M+H]$^+$=470.3. $^1$H NMR (400 MHz, DMSO-d$_6$): δ 10.97 (s, 1H), 7.61 (d, J=8.4 Hz 1H), 7.18 (s, 1H), 7.04 (d, J=9.2 Hz, 1H), 5.09-5.06 (m, 1H), 4.55 (bs, 1H), 4.4 (dd, J=17.2 Hz, 1H), 4.28 (dd, J=17.2 Hz, 1H), 3.17 (s, 3H), 3.087 (bs, 1H), 2.90-2.86 (m, 1H), 2.56-2.38 (m, 2H), 2.38-2.33 (m, 3H), 2.10-2.09 (m, 1H), 1.99-1.88 (m, 3H), 1.75-1.615 (m, 5H), 1.48-1.32 (m, 5H), 1.23-176 (m, 3H).

Example 170: Single Enantiomer of 3-(5-((2-((R)-3-methoxypyrrolidin-1-yl)cyclopentyl)oxy)-1-oxoisoindolin-2-yl)piperidine-2,6-dione (I-192)

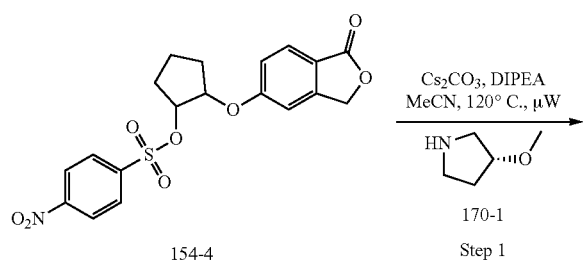

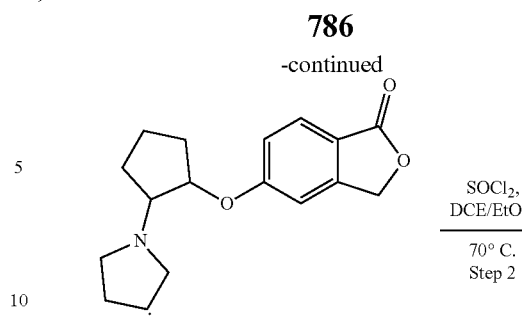

Step 1. Single Enantiomer of 5-((2-((R)-3-methoxypyrrolidin-1-yl)cyclopentyl)oxy)isobenzofuran-1(3H)-one (170-2)

(R)-3-methoxypyrrolidine hydrochloride (170-1, 31 mg, 0.23 mmol) and Cs$_2$CO$_3$ (99 mg, 0.31 mmol) were suspended in MeCN (1.4 mL) and the resulting mixture stirred at rt. for 20 minutes. The reaction mixture was added to a flask containing 154-4 (Example 154, 80 mg, 0.19 mmol) and DIPEA (50 µL, 0.29 mmol) and then purged with nitrogen while sonicating for 20 minutes. The resulting mixture was stirred at 120° C. for 3 h under µW radiation. Additional Cs$_2$CO$_3$ (99 mg, 0.31 mmol) and (R)-3-methoxypyrrolidine hydrochloride (31 mg, 0.23 mmol) were added and stirring was continued at 120° C. for 3 h under µW radiation. The reaction mixture was quenched with water and extracted with dichloromethane. The organic phases were combined, passed through a phase separator, and concentrated onto Celite®. The crude material was purified by silica gel chromatography eluting with 0-100% EtOAc in heptane then 0-20% MeOH in DCM to afford 170-2 (12.3 mg, 0.0390 mmol, 20% yield) as a brown oil. MS [M+H]$^+$=318.2.

Step 2. Single Enantiomer of Ethyl 2-(chloromethyl)-4-((2-((R)-3-methoxypyrrolidin-1-yl)cyclopentyl)oxy)benzoate (170-3)

To a stirred suspension of 170-2 (12.3 mg, 0.0390 mmol)) in DCE (0.19 mL) and ethanol (0.190 mL) at 70° C. was added thionyl chloride (0.034 mL, 0.47 mmol) dropwise and the resulting mixture was stirred at 70° C. overnight. The reaction mixture was then cooled to rt, diluted with water, quenched with saturated aqueous sodium bicarbonate and extracted with EtOAc (×3). The combined organic phases were passed through a phase separator and concentrated to afford 170-3 as a brown oil. The crude material was used directly in the next reaction. MS [M+H]$^+$=382.2

Step 3. Single Enantiomer of 3-(5-((2-((R)-3-methoxypyrrolidin-1-yl)cyclopentyl)oxy)-1-oxoisoindolin-2-yl)piperidine-2,6-dione (I-192)

To a flask containing a solution of 3-aminopiperidine-2,6-dione hydrochloride (I-1c, 13 mg, 0.078 mmol) in DMF (0.16 mL) was added DIPEA (34 μL, 0.20 mmol) and the flask was evacuated and backfilled with nitrogen three times. The resulting mixture was stirred at rt. for 15 minutes, 170-3 (15 mg, 0.039 mmol) in DMF (0.23 mL) was added and the flask was again evacuated and backfilled with nitrogen three times. The reaction mixture was stirred at 85° C. overnight, stirred at 150° C. for 6 h under μW irradiation and concentrated to dryness. The crude material was purified by silica gel chromatography eluting with 0-100% EtOAc:EtOH (v/v=3:1, with 1% NEt$_3$) in heptane and then further purified by reverse phase HPLC (Column: Xbridge C18 OBD 5 um 30×50 mm; Conditions: Water/MeCN with 5 mM NH$_4$OH 75 mL/min; 1.5 mL injection; Gradient: 15-40% MeCN, 3.5 min gradient: Collection tubes contained ~3 drops of formic acid). The fractions containing the desired product were combined and lyophilized to afford I-192 (2.0 mg, 3.9 μmol, 10% yield) as a white solid. MS [M+H]$^+$ 428.2. $^1$H NMR (400 MHz, MeCN-d$_3$) δ 8.74 (s, 1H), 7.54 (d, J=8.4 Hz, 1H), 6.98 (d, J=2.2 Hz, 1H), 6.92 (dd, J=8.5, 2.2 Hz, 1H), 4.95 (ddd, J=13.3, 5.2, 1.5 Hz, 1H), 4.67 (dt, J=6.8, 3.7 Hz, 1H), 4.30-4.14 (m, 2H), 3.78 (ddt, J=8.8, 6.1, 3.1 Hz, 1H), 3.11 (s, 3H), 2.86-2.78 (m, 2H), 2.73-2.58 (m, 5H), 2.57-2.50 (m, 1H), 2.31 (qd, J=13.1, 4.7 Hz, 1H), 2.15-1.98 (m, 2H), 1.94-1.88 (m, 1H), 1.67-1.49 (m, 5H). Absolute stereochemistry not determined.

Example 171: Single Enantiomer of 3-(5-((2-((S)-3-methoxypyrrolidin-1-yl)cyclopentyl)oxy)-1-oxoisoindolin-2-yl)piperidine-2,6-dione (I-193)

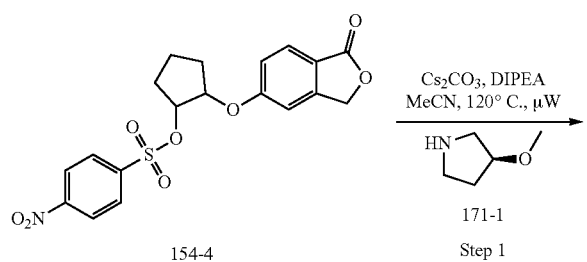

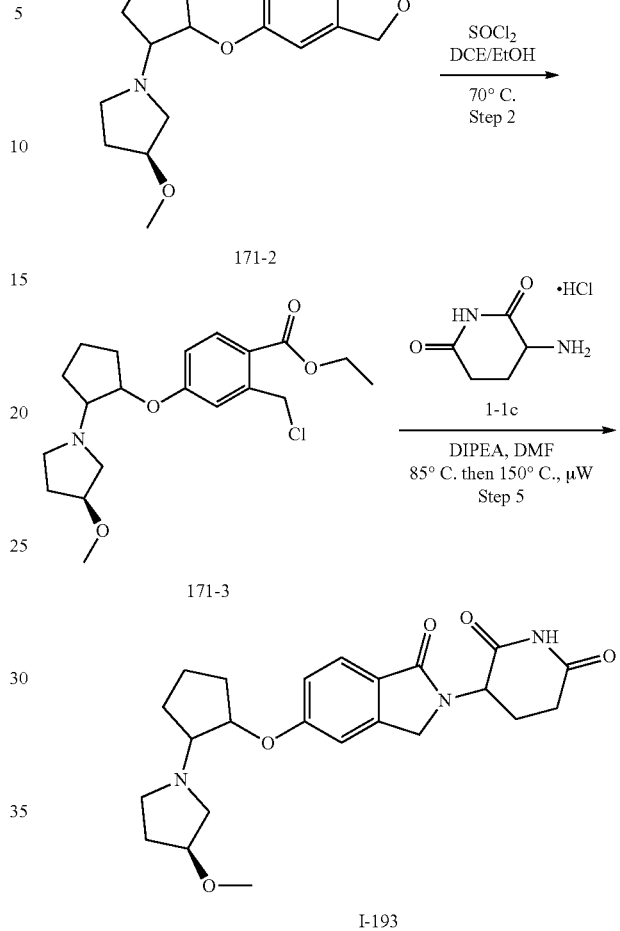

Step 1. Single Enantiomer of 5-((2-((S)-3-methoxypyrrolidin-1-yl)cyclopentyl)oxy)isobenzofuran-1(3H)-one (171-2)

(S)-3-methoxypyrrolidine hydrochloride (171-1, 20 mg, 0.15 mmol) and Cs$_2$CO$_3$ (65 mg, 0.20 mmol) were suspended in MeCN (1.4 mL) and the resulting mixture stirred at rt for 20 minutes and then added to a flask containing 154-4 (Example 154, 52 mg, 0.12 mmol) and DIPEA (0.032 mL, 0.19 mmol). The flask was purged with nitrogen while sonicating for 20 minutes. The reaction mixture was stirred at 120° C. for 3 h under μW radiation and then quenched with water and extracted with dichloromethane. The organic phases were combined, passed through a phase separator and concentrated onto Celite®. The crude material was purified by silica gel chromatography eluting with 0-100% EtOAc in heptane then 0-20% MeOH in DCM to afford 171-2 (18 mg, 0.055 mmol, 20% yield) as pale yellow oil. MS [M+H]$^+$=318.0. $^1$H NMR (400 MHz, Chloroform-d) δ 7.82 (d, J=8.5 Hz, 1H), 7.01 (dd, J=8.5, 2.1 Hz, 1H), 6.93-6.85 (m, 1H), 5.26 (s, 2H), 4.92-4.55 (m, 1H), 4.02-3.66 (m, 1H), 3.29 (s, 3H), 3.08-2.85 (m, 3H), 2.82-2.53 (m, 2H), 2.27-2.17 (m, 1H), 2.13-2.03 (m, 2H), 1.95-1.72 (m, 5H).

Step 2. Single Enantiomer of Ethyl 2-(chloromethyl)-4-((2-((S)-3-methoxypyrrolidin-1-yl)cyclopentyl)oxy)benzoate (171-3)

To a stirred suspension of 171-2 (17 mg, 0.055 mmol) in DCE (0.28 mL) and ethanol (0.28 mL) at 70° C. was added thionyl chloride (0.048 mL, 0.66 mmol) dropwise and the resulting mixture was stirred at 70° C. overnight. The reaction mixture was cooled to rt, diluted with water, and quenched with saturated aqueous sodium bicarbonate. The aqueous mixture was extracted with EtOAc (×3). The combined organic phases were passed through a phase separator and concentrated to afford 171-3 as a brown oil, which was used directly in next reaction without purification. MS [M+H]$^+$=382.3

Step 3. Single Enantiomer of 3-(5-((2-((S)-3-methoxypyrrolidin-1-yl)cyclopentyl)oxy)-1-oxoisoindolin-2-yl)piperidine-2,6-dione (I-193)

To a flask containing a solution of 3-aminopiperidine-2,6-dione hydrochloride (I-1c, 18.1 mg, 0.11 mmol) in DMF (0.22 mL) was added DIPEA (48 µL, 0.28 mmol) and flask was evacuated and backfilled with nitrogen three times. The resulting mixture was stirred at rt. for 15 minutes, 171-3 (21 mg, 0.055 mmol) in DMF (0.33 mL) was added and the flask was again evacuated and backfilled with nitrogen three times. The reaction mixture was stirred at 85° C. overnight, stirred at 150° C. for 6 h under µW irradiation and then concentrated to dryness. The crude material was purified by silica gel chromatography eluting with 0-100% EtOAc:EtOH (v/v=3:1, with 1% NEt$_3$) in heptane and then further purified by reverse phase HPLC (Column: Xbridge C18 OBD 5 um 30×50 mm; Conditions: Water/MeCN with 5 mM NH$_4$OH 75 mL/min; 1.5 mL injection; Gradient: 15-40% MeCN, 3.5 min gradient; Collection tubes contain ~3 drops of formic acid). The fractions containing the desired product were combined and lyophilized to afford I-193 (5.5 mg, 11 µmol, 20% yield) as a white solid. MS [M+H]$^+$=428.3. $^1$H NMR (400 MHz, MeCN-d$_3$) δ 8.80 (s, 1H), 7.55 (d, J=8.4 Hz, 1H), 6.98 (d, J=2.2 Hz, 1H), 6.92 (dd, J=8.3, 2.1 Hz, 1H), 4.95 (ddd, J=13.6, 5.3, 2.3 Hz, 1H), 4.78-4.70 (m, 1H), 4.30-4.14 (m, 2H), 3.82 (tt, J=6.0, 2.9 Hz, 1H), 3.10 (s, 3H), 3.00-2.87 (m, 2H), 2.85-2.75 (m, 1H), 2.74-2.58 (m, 4H), 2.30 (qdd, J=13.4, 4.8, 2.8 Hz, 1H), 2.15-1.88 (m, 4H), 1.73-1.51 (m, 5H). Absolute stereochemistry not determined.

Example 172: 3-(5-(((1S,2S)-2-(((3,3-difluorocyclobutyl)methyl)amino)cyclopentyl)oxy)-1-oxoisoindolin-2-yl)piperidine-2,6-dione (I-194)

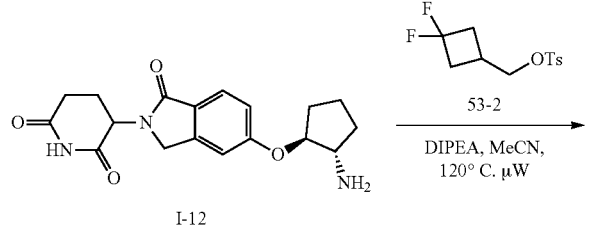

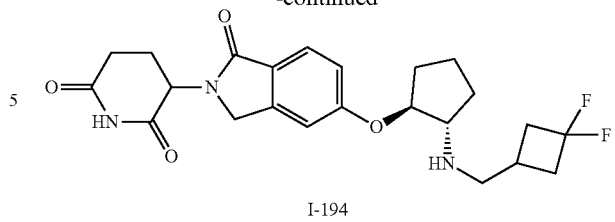

To a solution of 3-(5-(((1S,2S)-2-aminocyclopentyl)oxy)-1-oxoisoindolin-2-yl)piperidine-2,6-dione (I-12, 200 mg, 0.58 mmol) in MeCN (10 mL), (3,3-difluorocyclobutyl)methyl 4-methylbenzenesulfonate (53-2, 240 mg, 0.87 mmol) and DIPEA (0.32 mL, 1.7 mmol) were added and stirred at 120° C. for 16 h under µW irradiation. The reaction was diluted with saturated aqueous sodium bicarbonate solution and extracted with EtOAc (3×30 mL). The combined organic phases were washed with brine, dried over Na$_2$SO$_4$, filtered, and concentrated to dryness. The obtained crude material was purified via silica gel chromatography eluting with 6% MeOH in DCM to afford I-194 (50 mg, 0.11 mmol, 19% yield) as a pale brown solid. MS [M+H]$^+$=448.25. $^1$H NMR (400 MHz, DMSO-d$_6$): δ 10.98 (s, 1H), 7.62 (d, J=8.8 Hz, 1H), 7.17 (s, 1H), 7.04 (d, J=8.8 Hz, 1H), 5.07 (dd, J=13.2, 4.8 Hz, 1H), 4.58-4.54 (m, 1H), 4.41-4.22 (m, 2H), 3.13-3.11 (m, 1H), 2.95-2.87 (m, 2H), 2.67-2.51 (m, 5H), 2.42-2.12 (m, 6H), 1.99-1.85 (m, 2H), 1.72-1.55 (m, 2H), 1.48-1.39 (m, 1H).

Example 173: 3-(5-(((1S,2S)-2-(4-(difluoromethoxy)piperidin-1-yl)cyclopentyl)oxy)-1-oxoisoindolin-2-yl)piperidine-2,6-dione HC(O)OH Salt (I-195)

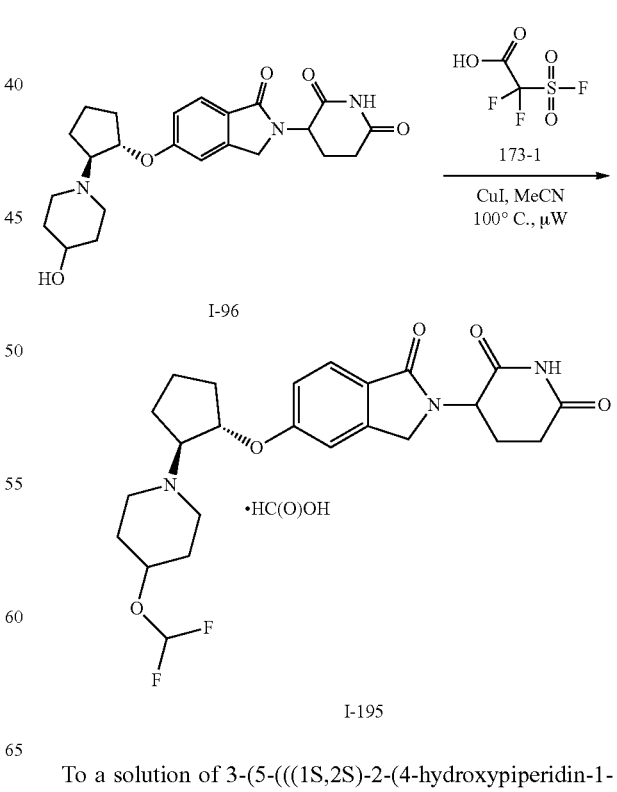

To a solution of 3-(5-(((1S,2S)-2-(4-hydroxypiperidin-1-yl)cyclopentyl)oxy)-1-oxoisoindolin-2-yl)piperidine-2,6-dione (I-96, 100 mg, 0.234 mmol) in MeCN (4 mL), whilst bubbling with nitrogen, was added 2,2-difluoro-2-(fluorosulfonyl)acetic acid (173-1, 208 mg, 1.17 mmol) and CuI (9 mg, 0.5 µmol) and the resulting mixture was stirred at 100° C. for 1 hour in the µW. The reaction mixture was added to water (20 mL) and saturated aqueous sodium hydrogen carbonate (20 mL). The aqueous mixture was extracted with 20% i-PrOH in DCM (×3) and the combined organic phases were passed through a phase separating column and concentrated to dryness. The crude material was purified via silica gel chromatography eluting with 0-15% i-PrOH (with 0.1% NEt$_3$) in DCM (with 0.1% NEt$_3$) and then further purified via reverse phase HPLC (Column: X-bridge C18 OBD 5 um 30×50 mm; Conditions: Water/MeCN with 0.1% Formic Acid 75 mL/min; 1.5 mL injection; Gradient: 10-30% MeCN, 3.5 min gradient) to afford the formate salt of I-195 (7.0 mg, 0.013 mmol, 5% yield) as a white solid. MS [M+H]$^+$=478.3. $^1$H NMR (400 MHz, DMSO-d$_6$) δ 10.95 (s, 1H), 7.60 (d, J=8.4 Hz, 1H), 7.18 (s, 1H), 7.03 (d, J=8.6 Hz, 1H), 6.69 (t, J=77.9 Hz, 1H), 5.06 (dd, J=13.2, 5.1 Hz, 1H), 4.74-4.67 (m, 1H), 4.45-4.19 (m, 2H), 4.15-4.02 (m, 1H), 2.98-2.82 (m, 2H), 2.80-2.65 (m, 2H), 2.59 (d, J=16.9 Hz, 1H), 2.40 (td, J=13.1, 4.5 Hz, 1H), 2.30-2.19 (m, 2H), 2.14-1.77 (m, 5H), 1.73-1.40 (m, 6H).

Example 174: 3-(5-(((1S,2S)-2-(1,3-dihydro-2H-pyrrolo[3,4-c]pyridin-2-yl)cyclopentyl)oxy)-1-oxoisoindolin-2-yl)piperidine-2,6-dione (I-196)

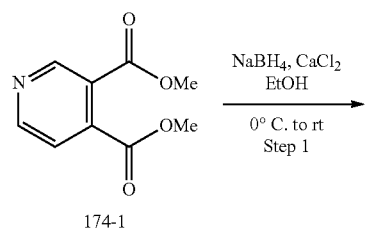

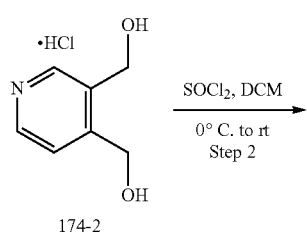

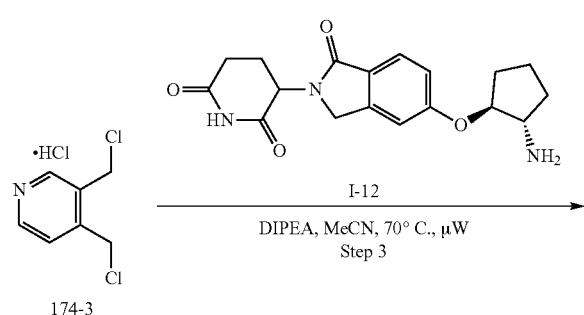

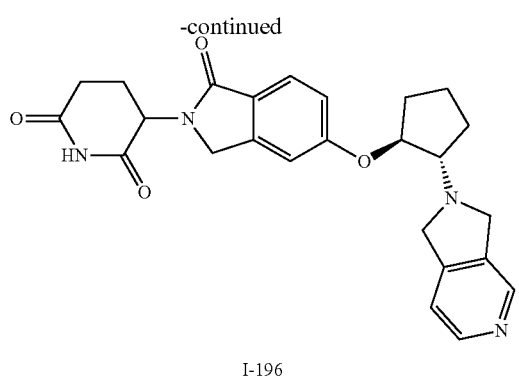

I-196

Step 1. Pyridine-3,4-diyldimethanol hydrochloride (174-2)

To a solution of dimethyl pyridine-3,4-dicarboxylate (174-1, 1.50 g, 7.68 mmol) in EtOH (45 mL) at 0° C. was added NaBH$_4$ (1.45 g, 38.4 mmol) and CaCl$_2$ (0.760 g, 6.92 mmol) and the resulting mixture was stirred at rt for 16 h. The reaction mixture was cooled to 0° C., quenched with 50% aqueous EtOH (10 mL), and concentrated to dryness. The obtained residue was diluted with EtOH, refluxed for 2 h, the solids were filtered off, and the filtrate was concentrated under reduced pressure. The obtained crude material was treated with 1,4-dioxane-HCl, stirred for 1 h and concentrated to dryness. The residue was triturated with diethyl ether and dried under high vacuum to afford the HCl salt of 174-2 (1.30 g, 7.40 mmol, 96% yield) as white solid. MS [M+H]$^+$=140.2.

Step 2. 3,4-Bis(chloromethyl)pyridine hydrochloride (174-3)

To a stirred solution of pyridine-3,4-diyldimethanol hydrochloride (174-2, 800 mg, 4.55 mmol) in DCM (15 mL) at 0° C. was added SOCl$_2$ (15 mL) and the resulting mixture was stirred at rt for 16 h. The reaction mixture was concentrated to dryness. The obtained crude material was treated with 1,4-dioxane-HCl, stirred for 1 h and concentrated to dryness. The crude material was triturated with diethyl ether and dried under high vacuum to afford the HCl salt of 174-3 (800 mg, 3.76 mmol, 83% yield) as a white solid. MS [M+H]$^+$=176.2.

Step 3. 3-(5-(((1S,2S)-2-(1,3-dihydro-2H-pyrrol[3,4-c]pyridin-2-yl)cyclopentyl)oxy)-1-oxoisoindolin-2-yl)piperidine-2,6-dione (I-196)

To a solution of 3-(5-(((1S,2S)-2-aminocyclopentyl)oxy)-1-oxoisoindolin-2-yl)piperidine-2,6-dione (I-12, 150 mg, 0.440 mmol) in MeCN (10 mL) was added 3,4-bis(chloromethyl)pyridine hydrochloride (174-3, 139 mg, 0.650 mmol) and DIPEA (0.39 mL, 2.2 mmol) and the resulting mixture was stirred at 70° C. for 16 h under µW irradiation. The reaction mixture was cooled to rt and filtered. The filtrate was treated with 1,4-dioxane-HCl and stirred for 1 h. The resulting solution was lyophilized, the obtained crude material was purified by reverse phase HPLC (Column: KINETEX (150 mm×21.2 mm), Mobile phase A: 0.01% HCOOH (aq), Mobile phase B: MeCN, Time (min)/% B: 0/5, 2/10, 10/628.4 Flow rate: 20 ml/min, Diluent: Mobile phase). The fractions containing the desired product were combined and lyophilized to afford I-196 (15.0 mg, 33.0 µmol, 7% yield). MS [M+H]$^+$=447.4. $^1$H NMR (400 MHz, DMSO-d$_6$): δ 10.97 (s, 1H), 8.46 (s, 1H), 8.39-8.38 (m, 1H) 7.62 (d, J=8.4 Hz, 1H), 7.36-7.30 (m, 1H), 7.21 (s, 1H), 7.09 (d, J=8.4 Hz, 1H), 5.09-5.04 (m, 1H), 4.90-4.85 (m, 1H), 4.43-4.22 (m, 3H), 3.99-3.96 (m, 3H), 3.29-3.24 (m, 1H), 2.95-2.86 (m, 2H), 2.66-2.32 (m, 1H), 2.30-2.22 (m, 2H), 2.0-1.96 (m, 2H), 1.74-1.65 (m, 3H).

Example 175: 3-(5-(((1S,2S)-1-amino-2,3-dihydro-1H-inden-2-yl)oxy)-1-oxoisoindolin-2-yl)piperidine-2,6-dione HC(O)OH Salt (I-197)

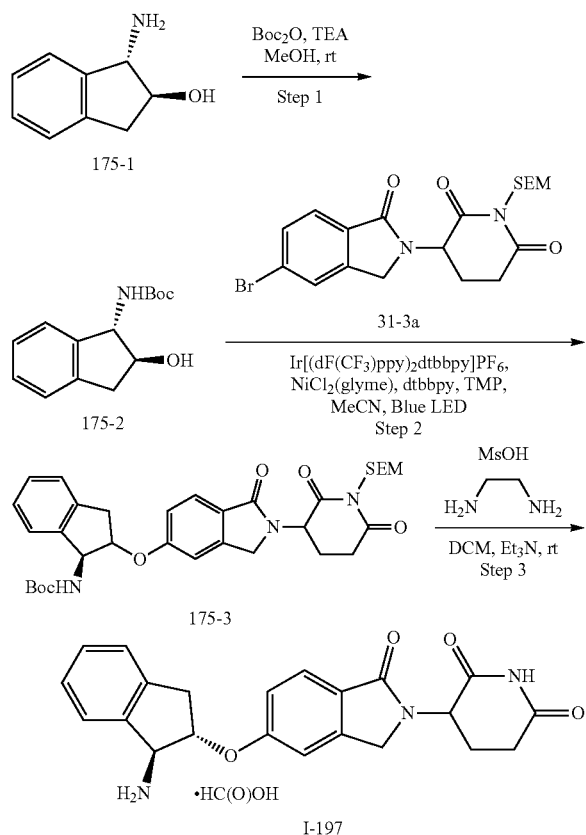

Step 1. tert-butyl ((1S,2S)-2-hydroxy-2,3-dihydro-1H-inden-1-yl)carbamate (175-2)

A mixture of (3aR,6S,6aS)-octahydrocyclopenta[b]pyrrol-6-ol (175-1, 2.00 g, 13.4 mmol), di-tert-butyl dicarbonate (3.51 g, 16.1 mmol), TEA (2.8 mL, 20 mmol) and MeOH (10 mL) was stirred vigorously at rt for 48 hours. The reaction mixture was diluted with brine (25 mL) and extracted with DCM (×3). The combined organic phases were dried over Na$_2$SO$_4$, filtered, and concentrated to afford 175-2 (3.28 g, 13.2 mmol, 98% yield) as a yellow oil. The product was used in the next step without purification. $^1$H NMR (400 MHz, DCM-d$_2$) δ 7.37-7.09 (m, 4H), 5.09 (s, 1H), 4.84 (t, J=6.2 Hz, 1H), 4.34 (td, J=7.8, 6.3 Hz, 1H), 3.97 (s, 1H), 3.23 (dd, J=15.7, 7.6 Hz, 1H), 2.82 (dd, J=15.7, 8.1 Hz, 1H), 1.46 (s, 9H).

Step 2. tert-butyl ((1S)-2-((2-(2,6-dioxo-1-((2-(trimethylsilyl)ethoxy)methyl)piperidin-3-yl)-1-oxoisoindolin-5-yl)oxy)-2,3-dihydro-1H-inden-1-yl)carbamate (175-3)

To a mixture of 3-(5-bromo-1-oxoisoindolin-2-yl)-1-((2-(trimethylsilyl)ethoxy)methyl)piperidine-2,6-dione (31-3a, 2.0 g, 4.4 mmol), Ir[(dF(CF$_3$)ppy)$_2$dtbbpy]PF$_6$ (0.049 g, 0.044 mmol), NiCl$_2$(glyme) (0.048 g, 0.22 mmol), TMP (1.1 mL, 6.6 mmol) and tert-butyl ((1S,2S)-2-hydroxy-2,3-dihydro-1H-inden-1-yl)carbamate (175-2, 1.21 g, 4.9 mmol) under an atmosphere of nitrogen was MeCN (20 mL) and the resulting mixture was stirred under irradiation of Blue LED lights for 20 h. The reaction mixture was filtered through a pad of Celite and concentrated to dryness. The crude material was purified via silica gel chromatography eluting with 0 to 40% EtOAc:EtOH (v/v=3:1) in DCM to afford 175-3 (2.51 g, 4.04 mmol, 92% yield) as a pale yellow solid. MS [M−H]$^-$=620.2.

Step 3. 3-(5-(((1S,2S)-1-amino-2,3-dihydro-1H-inden-2-yl)oxy)-1-oxoisoindolin-2-yl)piperidine-2,6-dione HC(O)OH Salt (I-197)

To tert-butyl ((1S,2S)-2-((2-(2,6-dioxo-1-((2-(trimethylsilyl)ethoxy)methyl)piperidin-3-yl)-1-oxoisoindolin-5-yl)oxy)-2,3-dihydro-1H-inden-1-yl)carbamate (175-3, 1.92 g, 3.09 mmol) in DCM (7 mL) was added methanesulfonic acid (0.80 mL, 12 mmol) and the resulting mixture was stirred at rt for 20 h. TEA (4.3 mL, 31 mmol) was added dropwise at 0° C. and the reaction mixture was allowed to reach rt. N1,N2-dimethylethane-1,2-diamine (0.37 mL, 3.4 mmol) was added and stirring was continued at rt overnight. The reaction mixture was diluted with 50% saturated aqueous NaHCO$_3$ in water and extracted with DCM:i-PrOH (v/v=4:1) (×2). The combined organic phases were concentrated to dryness to afford crude I-197 (1.18 g, 3.09 mmol). A small amount of crude material was purified by reverse phase HPLC (Method Column: X-bridge C18 OBD 5 um 30×50 mm; Conditions: Water/MeCN with 0.1% Formic Acid 75 mL/min; 1.5 mL injection; Gradient: 5-20% MeCN, 3.5 min gradient) to afford the formate salt of I-197 (5.0 mg, 0.01 mmol, 0.4% yield) as a white solid. MS [M+H]$^+$=392.1. $^1$H NMR (400 MHz, DMSO-d$_6$) δ 10.97 (s, 1H), 8.30 (s, 1H), 7.63 (d, J=8.4 Hz, 1H), 7.47-7.31 (m, 1H), 7.31-7.17 (m, 4H), 7.12 (dd, J=8.4, 2.2 Hz, 1H), 5.08 (dd, J=13.3, 5.1 Hz, 1H), 4.84 (q, J=4.8 Hz, 1H), 4.52-4.21 (m, 3H), 3.61-3.54 (m, 2H), 3.10-2.75 (m, 2H), 2.66-2.55 (m, 1H), 2.46-2.26 (m, 1H), 2.06-1.93 (m, 1H).

Example 176: 3-(5-(((1S,2S)-1-(ethylamino)-2,3-dihydro-1H-inden-2-yl)oxy)-1-oxoisoindolin-2-yl)piperidine-2,6-dione HC(O)OH Salt (I-198)

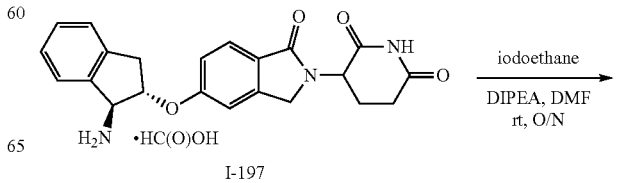

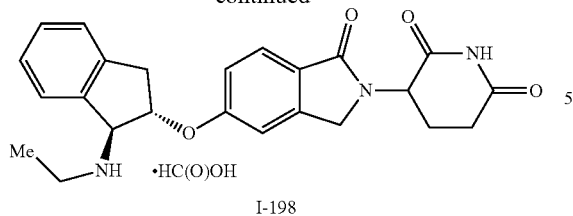

I-198

To 3-(5-(((1S,2S)-1-amino-2,3-dihydro-1H-inden-2-yl)oxy)-1-oxoisoindolin-2-yl)piperidine-2,6-dione HC(O)OH salt (I-197, 60 mg, 0.14 mmol) in DIPEA (0.2 mL, 0.6 mmol) and DMF (1 mL) was added iodoethane (0.016 mL, 0.20 mmol) in one portion and the resulting mixture was stirred at rt overnight. The reaction mixture was concentrated to dryness and the crude material was purified by reverse phase HPLC (Column: Xbridge C18 OBD 5 um 30×50 mm; Conditions: Water/MeCN with 5 mM NH$_4$OH 75 mL/min; 1.5 mL injection; Gradient: 15-40% MeCN, 3.5 min gradient; collected fractions contain a drop of formic acid) to afford the formate salt of I-198 (19 mg, 0.041 mmol, 29% yield) as a white powder. MS [M+H]$^+$=420.5. $^1$H NMR (400 MHz, Deuterium Oxide) δ 8.45 (s, 1H), 7.77 (d, J=8.5 Hz, 1H), 7.49 (d, J=7.1 Hz, 1H), 7.43-7.32 (m, 3H), 7.22 (s, 1H), 7.15 (d, J=8.6 Hz, 1H), 5.24-5.18 (m, 1H), 5.13 (dd, J=13.3, 4.9 Hz, 1H), 4.64-4.42 (m, 3H), 3.65 (dd, J=17.3, 5.8 Hz, 1H), 3.07 (d, J=17.2 Hz, 1H), 2.98-2.77 (m, 4H), 2.60-2.42 (m, 1H), 2.36-2.20 (m, 1H), 1.15 (t, J=7.1 Hz, 3H).

Example 177: 3-(5-(((1S,2S)-1-(diethylamino)-2,3-dihydro-1H-inden-2-yl)oxy)-1-oxoisoindolin-2-yl)piperidine-2,6-dione (I-199)

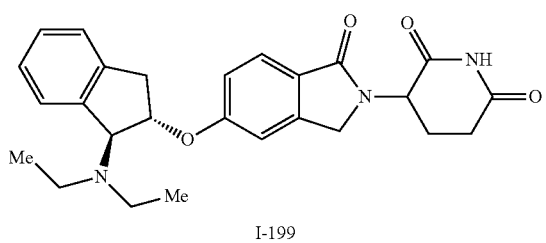

I-199

To 3-(5-(((1S,2S)-1-amino-2,3-dihydro-1H-inden-2-yl)oxy)-1-oxoisoindolin-2-yl)piperidine-2,6-dione HC(O)OH salt (I-197, 120 mg, 0.267 mmol), acetaldehyde (2-1, 0.06 mL, 1 mmol) in TFE (2 mL) was added NaBH(OAc)$_3$ (226 mg, 1.07 mmol) in one portion and the resulting mixture was stirred at rt overnight. The reaction mixture was concentrated to dryness and the crude material purified via silica gel chromatography eluting with 0 to 100% EtOAc:EtOH (v/v=3:1, with 0.1% NEt$_3$) in DCM (with 0.1% NEt$_3$) to afford I-199 (18.9 mg, 0.0410 mmol, 15% yield) as a white powder. MS [M+H]$^+$=448.1. $^1$H NMR (400 MHz, DCM-d$_2$) δ 8.47 (s, 1H), 7.96-7.57 (m, 1H), 7.40-7.27 (m, 1H), 7.26-7.14 (m, 3H), 7.13-7.00 (m, 2H), 5.21-4.97 (m, 2H), 4.72 (d, J=4.0 Hz, 1H), 4.51-4.21 (m, 2H), 3.50 (dd, J=16.9, 7.3 Hz, 1H), 2.94 (dd, J=16.9, 4.4 Hz, 1H), 2.87-2.78 (m, 2H), 2.66-2.44 (m, 4H), 2.42-2.24 (m, 1H), 2.22-2.13 (m, 1H), 1.07 (t, J=7.1 Hz, 6H).

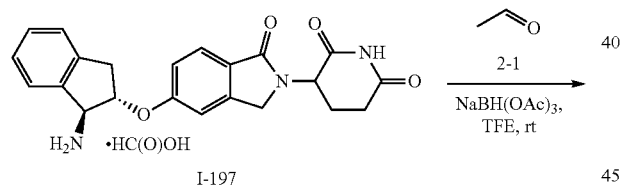

I-197

Example 178: 3-(5-(((1S,2S)-1-(ethyl(methyl)amino)-2,3-dihydro-1H-inden-2-yl)oxy)-1-oxoisoindolin-2-yl)piperidine-2,6-dione (I-200) and 3-(5-(((1S,2S)-1-(dimethylamino)-2,3-dihydro-1H-inden-2-yl)oxy)-1-oxoisoindolin-2-yl)piperidine-2,6-dione HC(O)OH Salt (I-201)

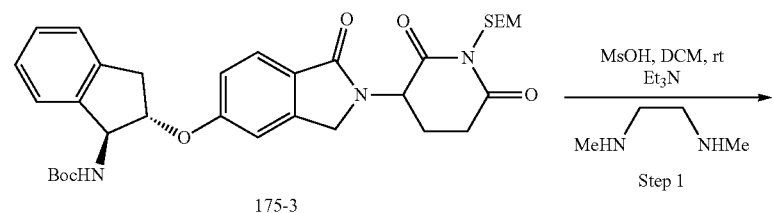

175-3

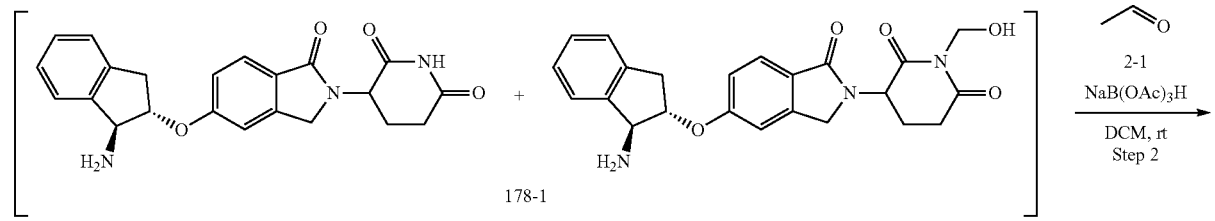

178-1

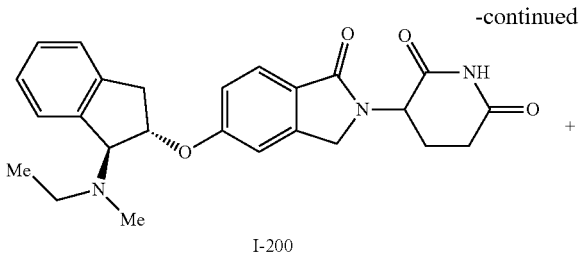

I-200

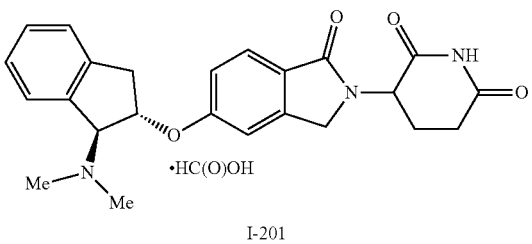

I-201

Step 1. Mixture of 3-(5-(((1S,2S)-1-amino-2,3-dihydro-1H-inden-2-yl)oxy)-1-oxoisoindolin-2-yl)piperidine-2,6-dione and 3-(5-(((1S,2S)-1-amino-2,3-dihydro-1H-inden-2-yl)oxy)-1-oxoisoindolin-2-yl)-1-(hydroxymethyl)piperidine-2,6-dione (178-1)

To tert-butyl ((1S,2S)-2-((2-(2,6-dioxo-1-((2-(trimethylsilyl)ethoxy)methyl)piperidin-3-yl)-1-oxoisoindolin-5-yl)oxy)-2,3-dihydro-1H-inden-1-yl)carbamate (175-3, 1.92 g, 3.09 mmol) in DCM (7 mL) was added methanesulfonic acid (0.80 mL, 12 mmol) and the resulting mixture was stirred at rt for 20 hr. TEA (4.3 mL, 31 mmol) was added dropwise at 0° C. and the reaction mixture was allowed to reach rt. N1,N2-dimethylethane-1,2-diamine (0.37 mL, 3.4 mmol) was added and stirring was continued at rt overnight. The reaction mixture was diluted with 50% saturated aqueous $NaHCO_3$ in water and extracted with DCM:i-PrOH (v/v=4:1) (×2). The combined organic phases were concentrated to dryness to afford 178-1 (1.18 g, 3.09 mmol), which was carried on to the next step without purification.

Step 2. 3-(5-(((1S,2S)-1-(ethyl(methyl)amino)-2,3-dihydro-1H-inden-2-yl)oxy)-1-oxoisoindolin-2-yl)piperidine-2,6-dione (I-200) and 3-(5-(((1S,2S)-1-(dimethylamino)-2,3-dihydro-1H-inden-2-yl)oxy)-1-oxoisoindolin-2-yl)piperidine-2,6-dione HC(O)OH Salt (I-201)

To a mixture of 3-(5-(((1S,2S)-1-amino-2,3-dihydro-1H-inden-2-yl)oxy)-1-oxoisoindolin-2-yl)piperidine-2,6-dione and 3-(5-(((1S,2S)-1-amino-2,3-dihydro-1H-inden-2-yl)oxy)-1-oxoisoindolin-2-yl)-1-(hydroxymethyl)piperidine-2,6-dione (178-1, 100 mg, 0.222 mmol) and $NaBH(OAc)_3$ (141 mg, 0.667 mmol) in DCM (2 mL) under an atmosphere of nitrogen was added acetaldehyde (2-1, 0.037 mL, 0.67 mmol) in one portion and the resulting mixture was stirred for at rt for 2 days and then concentrated to dryness. The crude material was purified by reverse phase HPLC (Column: Xbridge C18 OBD 5 um 30×50 mm; Conditions: Water/MeCN with 5 mM $NH_4OH$ 75 mL/min; 1.5 mL injection; Gradient: 15-40% MeCN, 3.5 min gradient; collected fractions contain a drop of formic acid) to afford the formic acid salt I-201 (13.0 mg, 0.028 mmol, 12% yield) was obtained as a white powder.

The fractions that contained impure I-200 were combined, lyophilized and then further via silica gel chromatography eluting with 0-100% EtOAc:EtOH (v/v=3:1, with 0.1% $NEt_3$) in DCM (with 0.1% $NEt_3$) to afford I-200 (8.9 mg, 0.021 mmol, 9% yield) as a white powder. Data for I-200: MS $[M+H]^+$=434.2. $^1H$ NMR (400 MHz, DCM-$d_2$) δ 8.21 (s, 1H), 7.73 (d, J=8.2 Hz, 1H), 7.37-7.30 (m, 1H), 7.28-7.17 (m, 3H), 7.11-7.04 (m, 2H), 5.19-5.05 (m, 2H), 4.57 (d, J=3.5 Hz, 1H), 4.42-4.26 (m, 2H), 3.49 (dd, J=17.0, 7.0 Hz, 1H), 2.96 (dd, J=17.0, 3.9 Hz, 1H), 2.90-2.73 (m, 2H), 2.56 (q, J=7.1 Hz, 2H), 2.41-2.27 (m, 1H), 2.20 (s, 3H), 2.19-2.13 (m, 1H), 1.10 (t, J=7.1 Hz, 3H). Data for I-201: MS $[M+H]^+$=420.2. $^1H$ NMR (400 MHz, DCM-$d_2$) δ 8.20 (s, 1H), 8.11 (s, 1H), 7.74 (d, J=8.4 Hz, 1H), 7.47 (d, J=7.2 Hz, 1H), 7.37-7.22 (m, 3H), 7.14-7.09 (m, 1H), 7.05 (dd, J=8.4, 2.2 Hz, 1H), 5.27-5.19 (m, 1H), 5.13 (dd, J=13.3, 5.1 Hz, 1H), 4.61 (d, J=3.0 Hz, 1H), 4.43-4.28 (m, 2H), 3.54 (dd, J=17.1, 6.7 Hz, 1H), 3.02 (dd, J=17.1, 3.3 Hz, 1H), 2.90-2.74 (m, 2H), 2.40 (s, 6H), 2.38-2.25 (m, 1H), 2.24-2.14 (m, 1H).

Example 179: 3-(5-(((1R,2S,3S)-2-(diethylamino)-3-methylcyclopentyl)oxy)-1-oxoisoindolin-2-yl)piperidine-2,6-dione HC(O)OH Salt (I-207) and 3-(5-(((1R,2R,3S)-2-(diethylamino)-3-methylcyclopentyl)oxy)-1-oxoisoindolin-2-yl)piperidine-2,6-dione (I-208)

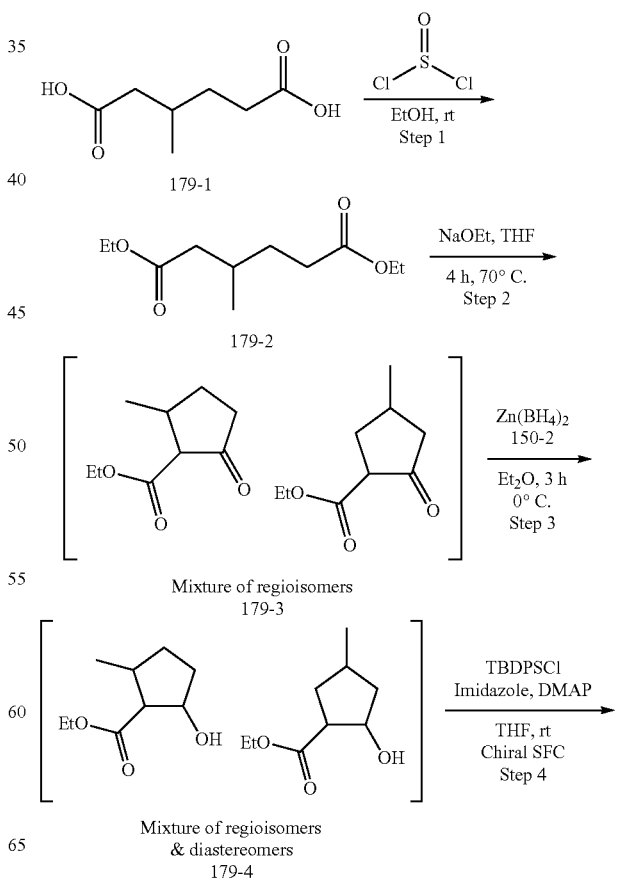

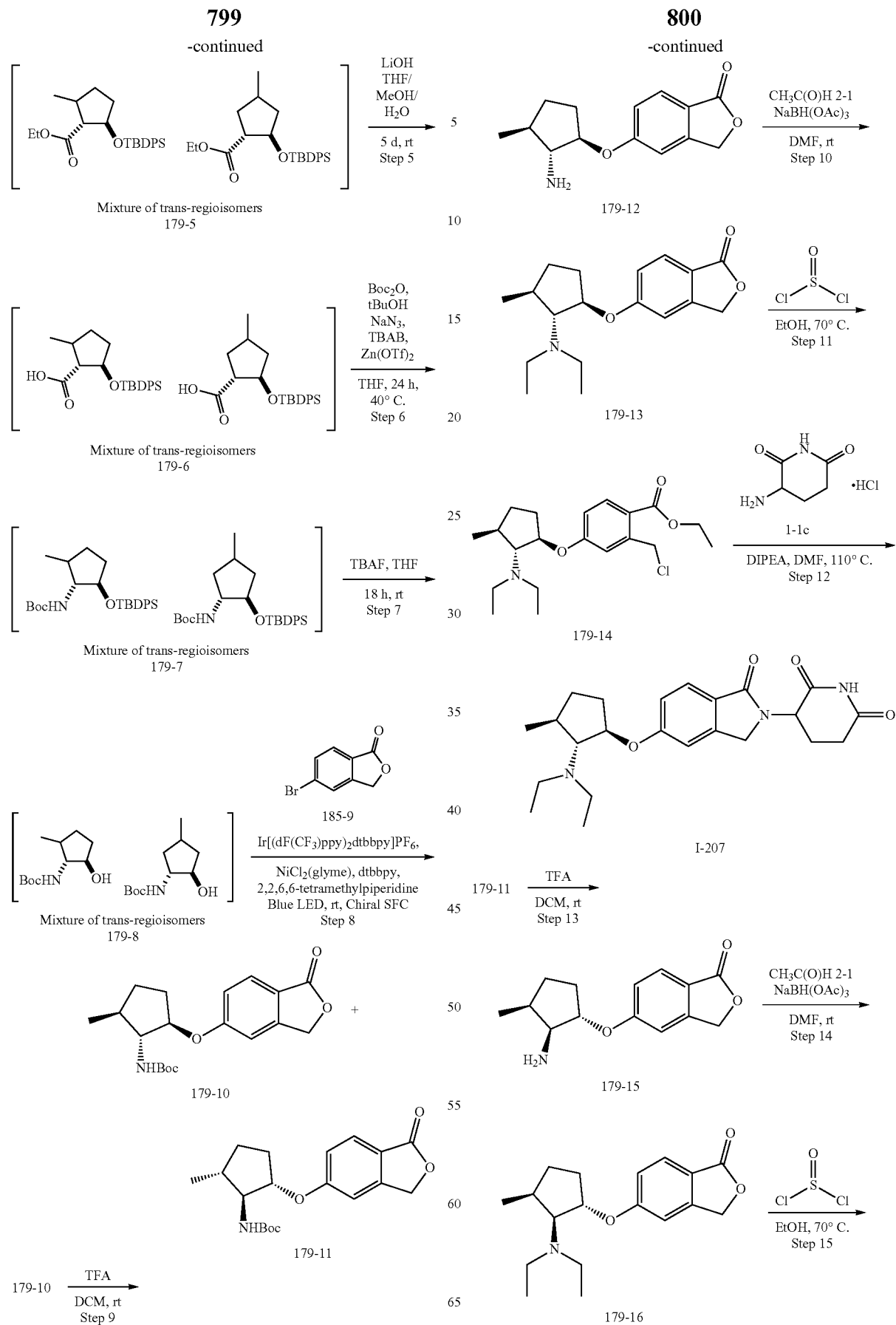

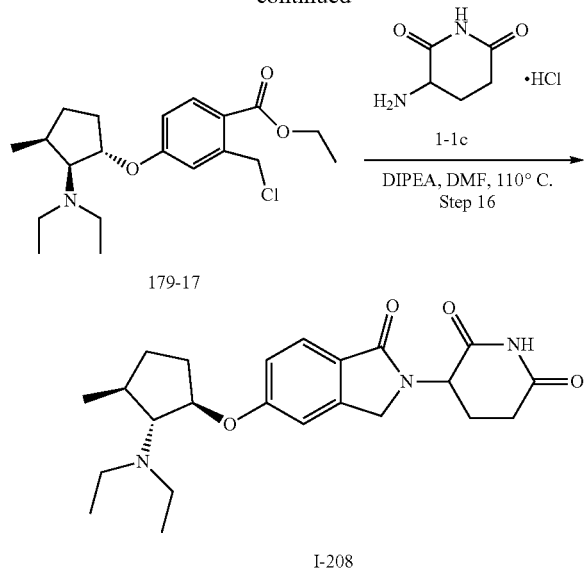

Step 1. Diethyl 3-methylhexanedioate (179-2)

To a solution of 3-methyladipic acid (179-1, 2.00 g, 12.6 mmol) in ethanol (20 mL) was added thionyl chloride (2.0 mL, 27 mmol) dropwise and the resulting mixture was stirred for 1 hour at room temperature. The reaction solution was diluted with a 1:1 solution of sat. sodium bicarbonate solution (50 mL) and extracted with dichloromethane (3×50 mL). The combined organic phases were then dried over magnesium sulfate, filtered, and concentrated to afford crude 186-2 (2.71 g, 12.5 mmol). The crude product was carried onto the next step without purification. MS [M+H]$^+$=217.2. $^1$H NMR (400 MHz, Chloroform-d) δ 4.22-4.09 (m, 4H), 2.45-2.26 (m, 3H), 2.23-2.09 (m, 1H), 1.81-1.65 (m, 1H), 1.62-1.47 (m, 1H), 1.36 (t, J=7.1 Hz, 1H), 1.33-1.19 (m, 6H), 0.98 (d, J=6.7 Hz, 3H).

Step 2. Ethyl 2-methyl-5-oxocyclopentane-1-carboxylate (179-3)

To a solution of diethyl 3-methylhexanedioate (179-2, 2.71 g, 12.5 mmol) in THF (60 mL) was added sodium ethoxide (5.70 mL, 15.3 mmol) and the resulting mixture was stirred at 70° C. overnight. The reaction solution was quenched with water (40 mL) and then extracted with dichloromethane (3×40 mL), The combined organic phases were dried over magnesium sulfate, filtered, and concentrated to dryness. The crude material was purified by silica gel chromatography eluting with 0-40% EtOAc in heptanes to afford 179-3 (1.42 g, 8.31 mmol, 66% yield mixture of regioisomers) as a liquid. MS [M+H]$^+$=171.1.

Step 3. Ethyl trans-2-hydroxy-5-methylcyclopentane-1-carboxylate (179-4)

To a solution of ethyl 2-methyl-5-oxocyclopentane-1-carboxylate (179-3, 1.42 g, 8.31 mmol) in Et$_2$O (28 mL) was added zinc(II) tetrahydroborate (150-2, 24 mL, 9.60 mmol, 0.4M in THF) and the resulting mixture was stirred at 0° C. for 1 hour. The reaction mixture was then quenched dropwise with sat. ammonium acetate solution (100 mL) and extracted with dichloromethane (3×80 mL). The combined organic phases were then dried over magnesium sulfate, filtered, and concentrated to dryness. The crude product was purified by silica gel chromatography eluting with 0-20% EtOAc in heptane to afford 179-4 (496 mg, 2.88 mmol, 35% yield, mixture of regioisomers and diastereomers) as a colorless liquid. MS [M+H]$^+$=173.2.

Step 4. Ethyl trans-2-((tert-butyldiphenylsilyl)oxy)-5-methylcyclopentane-1-carboxylate (179-5)

To a solution of ethyl trans-2-hydroxy-5-methylcyclopentane-1-carboxylate (179-4, 496.4 mg, 2.88 mmol), imidazole (498 mg, 7.32 mmol), and DMAP (31.7 mg, 0.259 mmol) in THF (10 mL) was added TBDPSCl (0.90 mL, 3.5 mmol) and the resulting mixture was stirred at rt overnight. The reaction mixture was diluted with ethyl acetate (160 mL) and washed with water (30 mL), saturated aqueous sodium bicarbonate solution (30 mL), and brine (20 mL). The organic phase was then dried over magnesium sulfate, filtered, and concentrated to dryness. The crude product was purified by silica gel chromatography eluting with 0-10% EtOAc in heptane to afford 179-5, as a clear, viscous liquid. This sample was then further purified using chiral SFC (Column: 2.1×25.0 cm Chiralpak OD-H; CO$_2$ co-solvent: heptane/2-propanol (v/v=9:1) with 10 mM NH$_3$; Isocratic method: 15% co-solvent at 80 g/min; System pressure: 150 bar) to afford 179-5 (513 mg, 1.19 mmol, 41% yield, mixture of trans-regioisomers) as a colorless oil. Chiral SFC Peak 1: Rt 0.83 mins; MS [M+18]$^+$=428.4.

Step 5. trans-2-((tert-butyldiphenylsilyl)oxy)-5-methylcyclopentane-1-carboxylic Acid (179-6)

Ethyl trans-2-((tert-butyldiphenylsilyl)oxy)-5-methylcyclopentane-1-carboxylate (179-5, 513 mg, 1.25 mmol) and lithium hydroxide monohydrate (519.9 mg, 12.39 mmol) were dissolved in THF (3 mL), MeOH (3 mL), and Water (1 mL) in a reaction vial with stir bar and the resulting solution was stirred at rt for 5 days. The reaction mixture was diluted with water (30 mL) and acidified with 1 N HCl solution to ~pH 5. The solution was then extracted with ethyl acetate (3×50 mL). The combined organic phases were then dried over magnesium sulfate, filtered, and concentrated to dryness to afford crude 179-6 (591 mg, 1.54 mmol, mixture of trans-regioisomers) as a yellow oil that was used in the next step without purification. MS [M]$^-$=381.3.

Step 6. tert-butyl (trans-2-((tert-butyldiphenylsilyl)oxy)-5-methylcyclopentyl)carbamate (179-7)

To a reaction vial containing trans-2-((tert-butyldiphenylsilyl)oxy)-5-methylcyclopentane-1-carboxylic acid (179-6, 478 mg, 1.25 mmol), TBAB (60 mg, 0.19 mmol), and zinc trifluoromethanesulfonate (23 mg, 0.062 mmol, 0.4M in THF) was added sodium azide (298 mg, 4.58 mmol) and THF (4 mL) and the reaction vial was placed under an atmosphere of nitrogen. Boc-anhydride (320 mg, 1.47 mmol) and tert-butanol (0.072 mL, 0.75 mmol) were then added and the resulting mixture was stirred at 40° C. for 24 hours. The reaction mixture was quenched with 10% sodium nitrite solution (25 mL) and ethyl acetate (10 mL) and stirring was continued at rt for 30 minutes. The solution was diluted with ethyl acetate (120 mL) and washed with saturated aq. sodium bicarbonate solution (2×20 mL) and brine (20 mL). The organic phase was dried over magnesium sulfate, filtered, and concentrated to dryness. The crude product was purified by silica gel chromatography eluting with 0-20% EtOAc in heptane to afford 179-7 (274 mg, 0.603 mmol, 48% yield) as a clear liquid, as a mixture of trans-regioisomers. MS [M+H]$^+$=454.4.

Step 7. tert-butyl
(trans-2-hydroxy-5-methylcyclopentyl)carbamate
(179-8)

To a reaction vial with stir bar containing a solution of tert-butyl (trans-2-((tert-butyldiphenylsilyl)oxy)-5-methylcyclopentyl)carbamate (179-7, 162 mg, 0.358 mmol) in THF (2 mL) was added 1M TBAF in THF (0.45 mL, 0.45 mmol) and the resulting mixture was stirred at rt overnight. The reaction solution was concentrated to dryness. The crude material was purified by silica gel chromatography eluting with 0-50% EtOAc in heptane to afford 179-8 (92.1 mg, 0.342 mmol, 96% yield) as a white solid, as a mixture of trans-regioisomers. MS [M+H]$^+$=216.3.

Step 8. tert-butyl ((1R,2S,5R)-2-methyl-5-((1-oxo-1,
3-dihydroisobenzofuran-5-yl)oxy)cyclopentyl)carbamate (179-10) and tert-butyl ((1S,2R,5S)-2-
methyl-5-((1-oxo-1,3-dihydroisobenzofuran-5-yl)
oxy)cyclopentyl)carbamate (179-11)

To a reaction vial with stir bar was added 5-bromoisobenzofuran-1(3H)-one (179-9, 89.8 mg, 0.422 mmol), tert-butyl (trans-2-hydroxy-5-methylcyclopentyl)carbamate (179-8, 92.1 mg, 0.428 mmol), NiCl$_2$(glyme) (4.5 mg, 0.020 mmol), dtbbpy (10 mg, 0.038 mmol), and Ir[(dF(CF$_3$)ppy)$_2$dtbbpy] PF$_6$ (4.6 mg, 4.1 µmol) and the reaction vial was then purged with nitrogen gas. MeCN (2 mL) and 2,2,6,6-tetramethylpiperidine (0.08 mL, 0.5 mmol) were added and the resulting mixture was stirred under blue LED lights at rt over 3 d. The crude solution was diluted with ethyl acetate and filtered through Celite®. The precipitate was washed with ethyl acetate and the filtrate concentrated to dryness. The crude material was purified by silica gel chromatography eluting with 0-55% EtOAc in heptane to provide the racemic trans products. The mixture was separated by chiral SFC (Column: 2.1×25.0 cm Chiralpak IH; CO$_2$ co-solvent: IPA; Isocratic method: 35% co-solvent at 80 g/min; System pressure: 150 bar) to afford: Enantiomer 1 (179-10) (Chiral SFC Rt=2.07 mins, 24.0 mg, 0.068 mmol, 16% yield) as a white solid, MS [M-tBu+H]$^+$=292.3 $^1$H NMR (400 MHz, Methylene Chloride-d) δ 7.75 (d, J=8.5 Hz, 1H), 7.04 (dd, J=8.5, 2.1 Hz, 1H), 7.00-6.90 (m, 1H), 5.21 (s, 2H), 4.71-4.50 (m, 2H), 3.61 (td, J=8.5, 5.0 Hz, 1H), 2.19-2.04 (m, 1H), 1.97-1.75 (m, 3H), 1.53-1.46 (m, 1H), 1.41 (s, 9H), 1.11 (d, J=6.5 Hz, 3H): Enantiomer 2 (179-11) (Chiral SFC Rt=2.30 mins, 25.0 mg, 0.071 mmol, 17% yield) as a white solid, MS [M-tBu+H]$^+$=292.3. $^1$H NMR (400 MHz, Methylene Chloride-d) δ 7.75 (d, J=8.5 Hz, 1H), 7.04 (dd, J=8.5, 2.1 Hz, 1H), 6.96 (s, 1H), 5.21 (s, 2H), 4.74-4.49 (m, 2H), 3.61 (td, J=8.5, 4.9 Hz, 1H), 2.21-2.03 (m, 1H), 1.98-1.73 (m, 3H), 1.52-1.47 (m, 1H), 1.41 (s, 9H), 1.11 (d, J=6.5 Hz, 3H). The absolute stereochemistry of the two enantiomers corresponding to the two product peaks is unknown and was assigned arbitrarily.

Step 9. 5-(((1R,2R,3S)-2-amino-3-methylcyclopentyl)oxy)isobenzofuran-1(3H)-one (179-12)

To a reaction vial with stir bar containing a solution of tert-butyl ((1R,2S,5R)-2-methyl-5-((1-oxo-1,3-dihydroisobenzofuran-5-yl)oxy)cyclopentyl)carbamate (179-10, Peak 1, 24 mg, 0.069 mmol) in DCM (1 mL) was added TFA (0.05 mL, 0.65 mmol) and the resulting solution was stirred at rt for 14 h. The solution was then concentrated to dryness. The obtained product was then azeotroped with methanol and dichloromethane to afford the crude 179-12 as a clear gum which was carried on to the next step without purification MS [M+H]$^+$=248.3.

Step 10. 5-(((1R,2R,3S)-2-(diethylamino)-3-methylcyclopentyl)oxy)isobenzofuran-1(3H)-one (179-13)

To a reaction vial with stir bar containing a solution of 5-(((1R,2R,3S)-2-amino-3-methylcyclopentyl)oxy)isobenzofuran-1(3H)-one (179-12, 25 mg, 0.069 mmol) and acetaldehyde (0.02 mL, 0.356 mmol) in DMF (0.5 mL) was added sodium triacetoxyborohydride (78 mg, 0.368 mmol) in one portion and the resulting mixture was stirred at rt for 23 h. The reaction mixture was diluted dichloromethane and 50% sat. aqueous sodium bicarbonate solution (10 mL) and passed through a phase separator. The aqueous solution was extracted with dichloromethane. The combined organic phases were then concentrated to dryness to afford crude 179-13 as an amber liquid. MS [M+H]$^+$=304.3. The product was carried through to the next step without purification.

Step 11. Ethyl 2-(chloromethyl)-4-(((1R,2R,3S)-2-
(diethylamino)-3-methylcyclopentyl)oxy)benzoate
(179-14)

To a solution of 5-(((1R,2R,3S)-2-(diethylamino)-3-methylcyclopentyl)oxy)isobenzofuran-1 (3H)-one (179-13, 21 mg, 0.069 mmol) in ethanol (1 mL) was added thionyl chloride (0.03 mL, 0.4 mmol) and the resulting mixture was stirred at 70° C. for 17 h. The reaction mixture was concentrated and azeotroped with dichloromethane to afford crude 179-14 as a light brown solid. The product was carried through to the next step without purification. MS [M+H]$^+$=368.3.

Step 12. 3-(5-(((1R,2R,3S)-2-(diethylamino)-3-
methylcyclopentyl)oxy)-1-oxoisoindolin-2-yl)piperidine-2,6-dione HC(O)OH Salt (I-207)

To a solution of ethyl 2-(chloromethyl)-4-(((1R,2R,3S)-2-(diethylamino)-3-methylcyclopentyl)oxy)benzoate (179-14, 25.5 mg, 0.069 mmol) in DMF (0.5 mL) and DIPEA (0.07 mL, 0.4 mmol) sparged with nitrogen was added 3-aminopiperidine-2,6-dione hydrochloride (I-1c, 18.8 mg, 0.114 mmol) in one portion and the resulting mixture was sparged with nitrogen again. The reaction mixture was stirred at 110° C. for 20 h and then diluted with ethyl acetate (40 mL). The aqueous mixture was washed with sat. aqueous sodium bicarbonate solution (2×10 mL) and brine (10 mL), dried over magnesium sulfate, filtered and concentrated to dryness. The crude product was purified by silica gel chromatography eluting with 0-100% EtOH:EtOAc (v/v=1:3) in DCM with 0.1% triethylamine modifier and then further purified by reverse phase HPLC (Column: X-bridge C18 OBD 5 m 30×50 mm; Conditions: Water/MeCN with 0.1% Formic Acid 75 mL/min; 1.5 mL injection; Gradient: 5-20% MeCN, 3.5 min gradient) to afford the formate salt of I-207 (0.5 mg, 1 µmol, 2% yield). MS [M+H]$^+$=414.4. $^1$H NMR (400 MHz, Acetonitrile-d$_3$) δ 8.79 (s, 1H), 8.10 (s, 1H), 7.63 (d, J=8.4 Hz, 1H), 7.13-7.06 (m, 1H), 7.01 (dd, J=8.4, 2.2 Hz, 1H), 5.11-4.94 (m, 1H), 4.85-4.73 (m, 1H), 4.43-4.22 (m, 2H), 3.02 (dd, J=9.3, 5.0 Hz, 1H), 2.89-2.58 (m, 7H), 1.75-1.66 (m, 1H), 1.37 (dtd, J=12.4, 10.2, 7.7 Hz, 1H), 1.12 (d, J=6.5 Hz, 3H), 1.06 (t, J=7.1 Hz, 6H).

Step 13. 5-(((1S,2R,5S)-2-amino-3-methylcyclopentyl)oxy)isobenzofuran-1(3H)-one (179-15)

To a reaction vial with stir bar containing a solution of tert-butyl ((1S,2R,5S)-2-methyl-5-((1-oxo-1,3-dihydroisobenzofuran-5-yl)oxy)cyclopentyl)carbamate (179-11, Peak 2, 25 mg, 0.072 mmol) in DCM (1 mL) was added TFA (0.05 mL, 0.65 mmol) and the resulting solution was stirred at rt for 14 h. The reaction mixture was concentrated to dryness and then azeotroped with methanol and dichloromethane to afford the crude 179-15 as a clear gum. The product was carried through to the next step without purification. MS [M+H]⁺=248.3.

Step 14. 5-(((1S,2s,3S)-2-(diethylamino)-3-methylcyclopentyl)oxy)isobenzofuran-1(3H)-one (179-16)

To a reaction vial with stir bar containing a solution of 5-(((1S,2R,5S)-2-amino-3-methylcyclopentyl)oxy)isobenzofuran-1(3H)-one (179-15, 26 mg, 0.072 mmol) and acetaldehyde (0.02 mL, 0.4 mmol) in DMF (0.5 mL) was added sodium triacetoxyborohydride (82 mg, 0.39 mmol) in one portion and the resulting mixture was stirred at room temperature for 23 h. The reaction solution was diluted dichloromethane and 50% sat. aqueous sodium bicarbonate solution (10 mL) and passed through a phase separator. The aqueous solution was extracted with dichloromethane and then concentrated to dryness to afford crude 179-16 (25 mg, 0.065 mmol, 90% yield) as an amber liquid. The product was carried through to the next step without purification. MS [M+H]⁺=304.4.

Step 15. Ethyl 2-(chloromethyl)-4-(((1S,2S,3S)-2-(diethylamino)-3-methylcyclopentyl)oxy)benzoate (179-17)

To a solution of 5-(((1S,2S,3S)-2-(diethylamino)-3-methylcyclopentyl)oxy)isobenzofuran-1(3H)-one (179-16, 22 mg, 0.073 mmol) in EtOH (1 mL) was added thionyl chloride (0.03 mL, 0.4 mmol) and the resulting mixture was stirred at 70° C. for 17 h. The reaction solution was concentrated and azeotroped with dichloromethane to afford crude 179-17 as a dark brown gum. The crude material was taken through to the next reaction step without purification. MS [M+H]⁺=368.3.

Step 16. 3-(5-(((1S,2S,3S)-2-(diethylamino)-3-methylcyclopentyl)oxy)-1-oxoisoindolin-2-yl)piperidine-2,6-dione (I-208)

To a solution of ethyl 2-(chloromethyl)-4-(((1S,2S,3S)-2-(diethylamino)-3-methylcyclopentyl)oxy)benzoate (179-17, 26.7 mg, 0.073 mmol) in DMF (0.5 mL) and DIPEA (0.07 mL, 0.4 mmol) and sparged with nitrogen was added 3-aminopiperidine-2,6-dione hydrochloride (I-1c, 19.5 mg, 0.118 mmol) in one portion and the resulting mixture was again sparged with nitrogen. The reaction mixture was stirred at 110° C. for 20 h and then diluted with ethyl acetate (40 mL). The mixture was washed with sat. aqueous sodium bicarbonate solution (2×10 mL) and brine (10 mL), dried over magnesium sulfate, filtered, and concentrated to dryness. The crude product was purified by silica gel chromatography eluting with 0-100% EtOH:EtOAc (v/v=1:3) in DCM with 0.1% triethylamine modifier and then further purified by reverse phase HPLC (Column: X-bridge C18 OBD 5 m 30×50 mm; Conditions: Water/MeCN with 0.1% Formic Acid 75 mL/min; 1.5 mL injection; Gradient: 5-20% MeCN, 3.5 min gradient). The fractions containing the desired product were combined and lyophilized to afford I-208 (1.1 mg, 2.27 μmol, 3% yield): MS [M+H]⁺=414.4. ¹H NMR (400 MHz, DMSO-d₆) δ 10.96 (s, 1H), 7.60 (d, J=8.5 Hz, 1H), 7.20-7.14 (m, 1H), 7.07-6.98 (m, 1H), 5.12-5.01 (m, 1H), 4.76-4.66 (m, 1H), 4.44-4.22 (m, 2H), 2.96-2.82 (m, 2H), 2.06-1.92 (m, 2H), 1.89-1.71 (m, 3H), 1.66-1.53 (m, 1H), 1.38-1.25 (m, 2H), 1.05 (d, J=6.3 Hz, 3H), 0.99 (t, J=7.0 Hz, 6H).

Example 180: 3-(5-(((1S,2S)-2-(3-ethoxyazetidin-1-yl)cyclopentyl)oxy)-1-oxoisoindolin-2-yl)piperidine-2,6-dione (I-202)

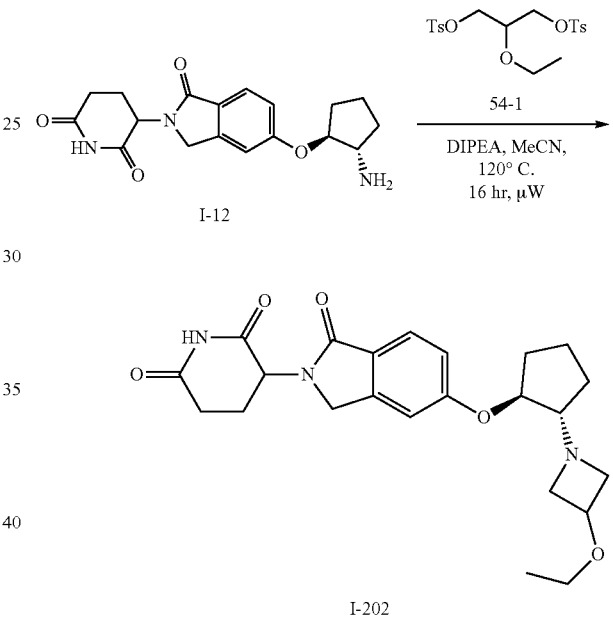

To a solution of 3-(5-(((1S,2S)-2-aminocyclopentyl)oxy)-1-oxoisoindolin-2-yl)piperidine-2,6-dione (I-12, 200 mg, 0.580 mmol) in acetonitrile (5 mL) was added 2-ethoxypropane-1,3-diyl bis(4-methylbenzenesulfonate) (54-1, 374 mg, 0.870 mmol) and DIPEA (0.36 mL, 1.7 mmol) and the resulting mixture was stirred at 120° C. for 16 h under microwave irradiation. The reaction mixture was diluted with saturated aqueous sodium bicarbonate solution and extracted with DCM (3×30 mL). The combined organic extracts were washed with brine, dried over Na₂SO₄ and concentrated to dryness. The obtained crude material was purified by silica gel chromatography eluting with 6% MeOH in DCM to afford I-202 (25.0 mg, 0.0580 mmol, 10% yield) as a white solid. MS [M+H]⁺=428.25. ¹H NMR (400 MHz, DMSO-d₆): δ 10.97 (s, 1H), 7.60 (d, J=8.4 Hz, 1H), 7.13 (s, 1H), 7.02 (d, J=8.4 Hz, 1H), 5.09 (dd, J=13.2, 4.8 Hz, 1H), 4.52 (bs, 1H), 4.40-4.23 (m, 2H), 4.00-3.97 (m, 1H), 3.52-3.56 (m, 2H), 2.87-2.810 (m, 5H), 2.60-2.32 (m, 2H), 2.10-1.96 (m, 3H), 1.75-1.63 (m, 4H), 1.39-1.38 (m, 1H), 1.07 (t, 6.8 Hz, 3H).

Example 181: 3-(1-oxo-5-(((1S,2S)-2-(3-(pyridin-3-yloxy)azetidin-1-yl)cyclopentyl)oxy)isoindolin-2-yl)piperidine-2,6-dione (I-203)

Example 182: 3-(5-(((1S,2S)-2-aminocyclopentyl)oxy)-4-fluoro-1-oxoisoindolin-2-yl)piperidine-2,6-dione (I-213) and 3-(5-(((1S,2S)-2-(diethylamino)cyclopentyl)oxy)-4-fluoro-1-oxoisoindolin-2-yl)piperidine-2,6-dione (I-214)

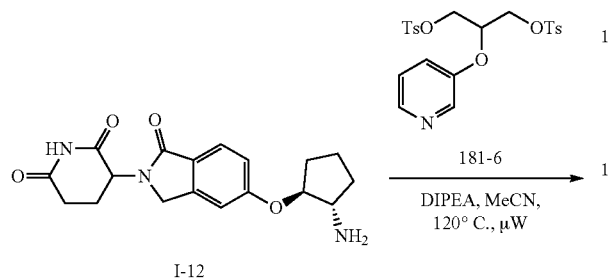

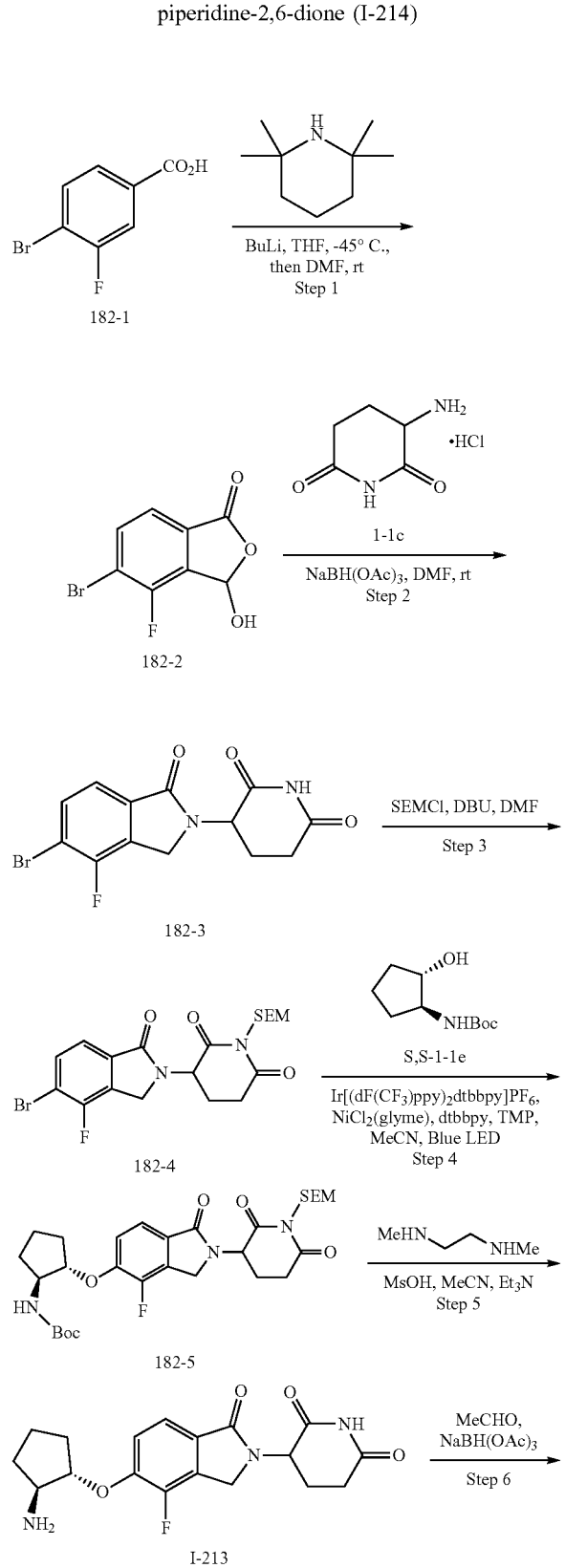

To a solution of 3-(5-(((1S,2S)-2-aminocyclopentyl)oxy)-1-oxoisoindolin-2-yl)piperidine-2,6-dione (I-12, 200 mg, 0.580 mmol) in acetonitrile (10 mL) was added 2-(pyridin-3-yloxy)propane-1,3-diyl bis(4-methylbenzenesulfonate) (181-6, 330 mg, 0.690 mmol) and DIPEA (0.45 g, 3.5 mmol) and the resulting mixture was stirred at 120° C. for 16 h under microwave irradiation. The reaction mixture was diluted with saturated aqueous sodium bicarbonate solution and extracted with DCM (3×30 mL). The combined organic phases were washed with brine, dried over anhydrous $Na_2SO_4$ and concentrated to dryness. The obtained crude material was purified by reverse phase HPLC (Column: ZORBAXECLIPSEXDB C18 (150 mm×19 mm), 5.0 g, Mobile phase-A: 0.01% HCOOH (aq), Mobile phase-B: acetonitrile, Time (min)/% B: 0/5, 2/20, 10/40. Flow rate: 20 ml/min). The fractions containing the desired product were combined and lyophilized to afford I-203 (25.0 mg, 50.0 μmol, 9% yield) as white solid. MS [M+H]$^+$=477.3. $^1$H NMR (400 MHz, DMSO-$d_6$): δ 10.96 (s, 1H), 8.20-8.17 (m, 2H), 7.62 (d, J=8.4 Hz, 1H), 7.33-7.25 (m, 2H), 7.15 (s, 1H), 7.04 (d, J=8.4 Hz, 1H), 5.09 (dd, J=13.2, 4.8 Hz, 1H), 4.81-4.78 (m, 1H), 4.58-4.22 (m, 3H), 3.77-3.73 (m, 2H), 3.12-2.67 (m, 4H), 2.60-2.32 (m, 4H), 2.14-2.12 (m, 1H), 1.98-1.95 (m, 1H), 1.80-1.65 (m, 4H), 1.44-1.41 (m, 1H).

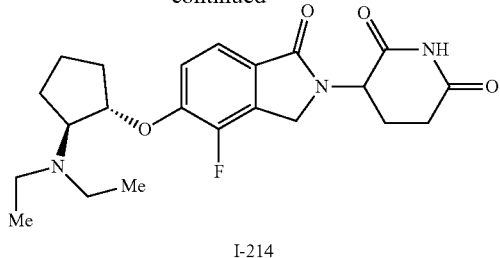

I-214

Step 1. 5-bromo-4-fluoro-3-hydroxyisobenzofuran-1(3H)-one (182-2)

To a stirred solution of TMP (9.7 mL, 57 mmol) in THF (40 mL) under an atmosphere of nitrogen was added BuLi (2.7 M in heptane, 20.3 mL, 54.7 mmol) dropwise at 0° C. and the resulting mixture was stirred for 30 min at 0° C. The reaction mixture was then cooled to about −45° C. (using dry ice/MeCN bath) and 4-bromo-3-fluorobenzoic acid (182-1, 4.99 g, 22.8 mmol), dissolved in THF (15 mL), was added dropwise and stirring was continued at −45° C. for 5 h. DMF (2.7 mL, 34 mmol) was then added dropwise and the reaction mixture was allowed to warm to rt and stirred overnight. The reaction mixture was quenched with aq. 3M HCl (40 mL) at 0° C. and extracted with DCM (×3). The combined organic phases were dried over $Na_2SO_4$, filtered, and concentrated to dryness. The crude product was purified via silica gel chromatography eluting with 0 to 100% EtOAc in heptane to afford 182-2 (2.91 g, 11.4 mmol, 50% yield) as a pale brown solid. MS $[M+H]^+=247.0$. $^1$H NMR (400 MHz, Acetonitrile-$d_3$) δ 7.90 (dd, J=8.0, 5.8 Hz, 1H), 7.56 (d, J=8.0 Hz, 1H), 6.72 (s, 1H), 5.92 (br s, 1H).

Step 2. 3-(5-bromo-4-fluoro-1-oxoisoindolin-2-yl)piperidine-2,6-dione (182-3)

To a stirred solution of 182-2 (2.90 g, 11.7 mmol) in DMF (20 mL) was added 3-aminopiperidine-2,6-dione HCl salt (I-1c, 2.90 g, 17.6 mmol) and NaBH(OAc)₃ (6.22 g, 29.3 mmol) and the resulting mixture was stirred for 2 days at rt. The reaction mixture was diluted with H₂O (50 mL) and cooled to 0° C. with water/ice bath which resulted in the formation of precipitate. The resulting mixture was filtered and the dark blue solid was washed with Et₂O (×3). The obtained solid was dried in a vacuum oven to afford 182-3 (1.89 g, 5.31 mmol, 45% yield) as a grey solid. MS $[M+H]^+=341.1$. $^1$H NMR (400 MHz, DMSO-$d_6$) δ 11.02 (s, 1H), 7.88 (dd, J=8.0, 6.0 Hz, 1H), 7.55 (d, J=8.0 Hz, 1H), 5.12 (dd, J=13.3, 5.1 Hz, 1H), 4.62 (d, J=17.6 Hz, 1H), 4.45 (d, J=17.6 Hz, 1H), 2.99-2.85 (m, 1H), 2.66-2.55 (m, 1H), 2.47-2.36 (m, 1H), 2.05-1.96 (m, 1H).

Step 3. 3-(5-bromo-4-fluoro-1-oxoisoindolin-2-yl)-1-((2-(trimethylsilyl)ethoxy)methyl)piperidine-2,6-dione (182-4)

To a stirred suspension of 182-3 (500 mg, 1.47 mmol) and DBU (0.44 mL, 2.9 mmol) in DMF (4 mL) was added SEMCl (0.39 mL, 2.2 mmol) in one portion at 0° C. and the resulting mixture was stirred at room temperature overnight. The reaction mixture was quenched with sat. aq. NH₄Cl, extracted with EtOAc (×3). The combined organic phases were dried over sodium sulfate, filtered and concentrated to dryness. The crude product was purified by silica gel chromatography eluting with 0 to 100% EtOAc in heptane to afford 182-4 (232 mg, 0.463 mmol, 32% yield) as an off-white solid. MS $[M−H]^−=469.1$. $^1$H NMR (400 MHz, Chloroform-d) δ 7.70 (dd, J=8.0, 5.8 Hz, 1H), 7.56 (d, J=8.1 Hz, 1H), 5.31-5.15 (m, 3H), 4.55 (d, J=16.4 Hz, 1H), 4.40 (d, J=16.4 Hz, 1H), 3.66-3.58 (m, 2H), 3.04 (ddd, J=17.9, 4.7, 2.5 Hz, 1H), 2.96-2.84 (m, 1H), 2.35 (qd, J=13.3, 4.7 Hz, 1H), 2.26-2.16 (m, 1H), 0.97-0.90 (m, 2H), 0.00 (s, 9H).

Step 4. tert-butyl ((1S,2S)-2-((2-(2,6-dioxo-1-((2-(trimethylsilyl)ethoxy)methyl)piperidin-3-yl)-4-fluoro-1-oxoisoindolin-5-yl)oxy)cyclopentyl)carbamate (182-5)

To a mixture of 182-4 (232 mg, 0.492 mmol), tert-butyl ((1S,2S)-2-hydroxycyclopentyl)carbamate (1-1e, 149 mg, 0.738 mmol), NiCl₂(glyme) (5.4 mg, 0.025 mmol), dtbbpy (6.6 mg, 0.025 mmol) and Ir[(dF(CF₃)ppy)₂dtbbpy]PF₆ (5.5 mg, 4.9 μmol) in MeCN (4 mL) under nitrogen atmosphere was added 2,2,6,6-tetramethylpiperidine (TMP, 0.13 mL, 0.74 mmol). The resulting mixture was then stirred vigorously for 49 hours under irradiation of Blue LED lights at room temperature. The reaction mixture was filtered and concentrated to dryness. The crude product was purified by silica gel chromatography eluting with 0 to 10% EtOH in DCM to afford 182-5 (207 mg, 0.175 mmol, purity ~50%, 36% yield) as pale yellow solid. MS $[M−H]^−=590.1$. The compound was carried forward to the next step without further purification.

Step 5. 3-(5-(((1S,2S)-2-aminocyclopentyl)oxy)-4-fluoro-1-oxoisoindolin-2-yl)piperidine-2,6-dione (I-213)

To a solution 182-5 (207 mg, 0.175 mmol, ~50% purity) in MeCN (1 mL) was added methanesulfonic acid (0.11 mL, 1.7 mmol) and the resulting mixture was stirred overnight at rt. Et₃N (0.37 mL, 2.6 mmol) was then added dropwise at 0° C. and the reaction mixture was allowed to warm to rt. N,N-dimethylethylenediamine (0.03 mL, 0.3 mmol) was added and stirring was continued overnight at rt. The reaction mixture was diluted with sat. aq. NaHCO₃ and extracted with DCM:EtOH (v/v=4:1) (×3). The combined organic phases were concentrated to dryness. The crude product was purified by silica gel chromatography eluting with 0 to 100% EtOAc:EtOH (v/v=3:1, with 1% Et₃N) in DCM to afford I-213 (37 mg, 0.10 mmol, 58% yield) as white solid. MS $[M+H]^+=362.2$. $^1$H NMR (400 MHz, Acetonitrile-$d_3$) δ 7.50 (d, J=8.3 Hz, 1H), 7.27 (t, J=7.8 Hz, 1H), 5.03 (dd, J=13.4, 5.2 Hz, 1H), 4.53-4.27 (m, 3H), 3.38 (tt, J=5.8, 2.8 Hz, 1H), 2.88-2.66 (m, 2H), 2.41 (qd, J=13.2, 4.9 Hz, 1H), 2.23-2.15 (m, 1H), 2.13-2.07 (m, 1H, shoulder on residual H₂O peak), 2.04-1.97 (m, 3H), 1.82-1.68 (m, 3H), 1.46-1.34 (m, 1H).

Step 6. 3-(5-(((1S,2S)-2-(diethylamino)cyclopentyl)oxy)-4-fluoro-1-oxoisoindolin-2-yl)piperidine-2,6-dione (I-214)

To a stirred solution of I-213 (35 mg, 0.097 mmol) and NaBH(OAc)₃ (62 mg, 0.29 mmol) in DMF (1 mL) was added acetaldehyde (0.02 mL, 0.3 mmol) and the resulting mixture was stirred at rt for 35 min. The reaction mixture was concentrated to dryness. The crude product was purified by silica gel chromatography eluting with 0 to 100% EtOAc:EtOH (v/v=3:1, with 1% Et₃N) in DCM to afford I-214 (29 mg, 0.068 mmol, 70% yield) as white solid. MS $[M+H]^+=418.3$. $^1$H NMR (400 MHz, Methylene Chloride-d$_2$) δ 8.81 (s, 1H), 7.53 (d, J=8.3 Hz, 1H), 7.28 (ddd, J=8.5, 7.3, 2.3 Hz, 1H), 5.10 (dd, J=13.4, 5.2 Hz, 1H), 4.66 (dt, J=7.0, 3.1 Hz, 1H), 4.45-4.30 (m, 2H), 3.41-3.26 (m, 1H), 2.88-2.73 (m, 2H), 2.64-2.48 (m, 4H), 2.38-2.25 (m, 1H), 2.21-2.10 (m, 1H), 2.01-1.89 (m, 2H), 1.84-1.76 (m, 1H), 1.76-1.68 (m, 2H), 1.59-1.47 (m, 1H), 0.99 (t, J=7.1 Hz, 6H).

Example 183: 3-(5-(((1S,2S)-2-aminocyclopentyl)oxy)-6-fluoro-1-oxoisoindolin-2-yl)piperidine-2,6-dione (I-215) and 3-(5-(((1S,2S)-2-(diethylamino)cyclopentyl)oxy)-6-fluoro-1-oxoisoindolin-2-yl)piperidine-2,6-dione (I-216)

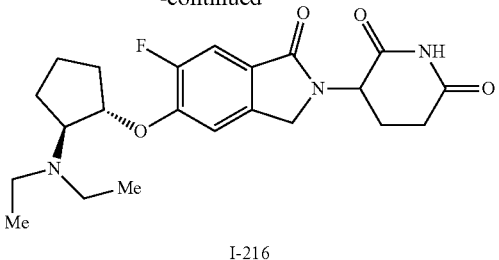

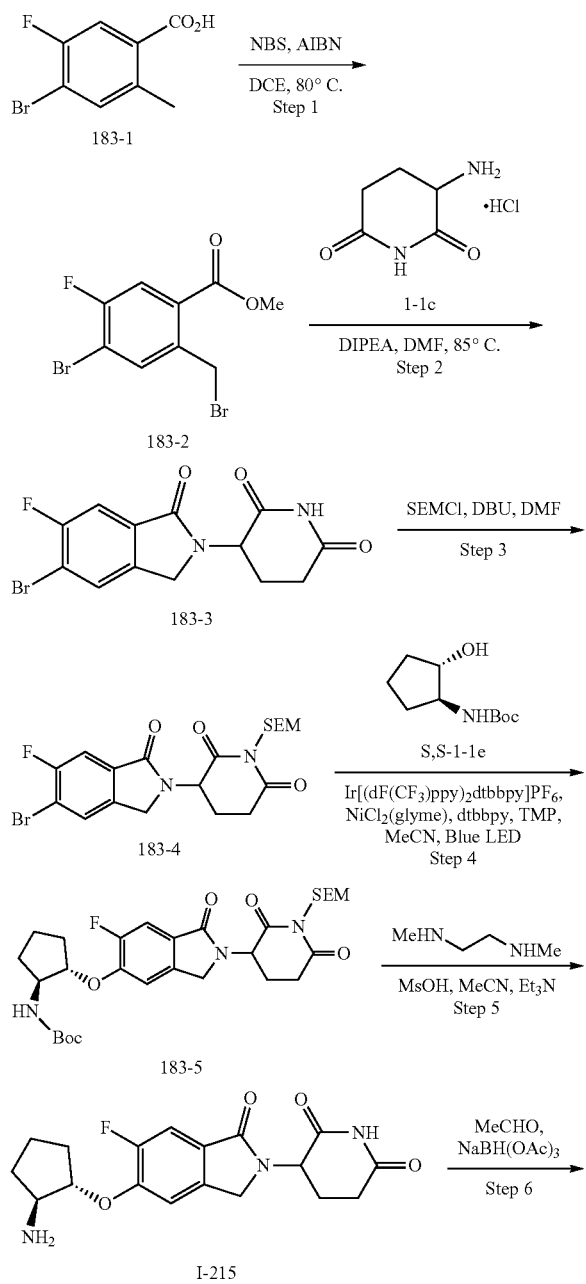

Step 1. Methyl 4-bromo-2-(bromomethyl)-5-fluorobenzoate (183-2)

To a stirred solution of 4-bromo-5-fluoro-2-methylbenzoate (183-1, 2700 mg, 10.93 mmol) in DCE (25 mL) under an atmosphere of nitrogen was added NBS (2140 mg, 12.02 mmol) followed by AIBN (90 mg, 0.55 mmol), and the resulting mixture was stirred vigorously at 85° C. for 8 h. The reaction mixture was quenched with sat. aq. Na$_2$S$_2$O$_3$ and then extracted with DCM (×3). The combined organic phases were concentrated to dryness. The crude product was purified via silica gel chromatography eluting with 0 to 50% EtOAc in heptane to afford 183-2 (3.37 g, 9.30 mmol, 85% yield) as a colorless oil. $^1$H NMR (400 MHz, Chloroform-d) δ 7.73 (d, J=9.0 Hz, 1H), 7.69 (d, J=6.5 Hz, 1H), 4.89 (s, 2H), 3.95 (s, 3H).

Step 2. 3-(5-bromo-6-fluoro-1-oxoisoindolin-2-yl)piperidine-2,6-dione (183-3)

To a solution of 183-2 (3.37 g, 9.30 mmol) in DMF (20 mL) was added 3-aminopiperidine-2,6-dione HCl salt (I-1c, 2.30 g, 14.0 mmol), followed by DIPEA (8.1 mL, 47 mmol), and the resulting mixture was stirred at 85° C. for 2 days. Excess DIPEA was removed by concentrating the mixture to a constant volume at 100 mbar and at a temperature of 40° C. The reaction mixture was then poured into conical flask containing H$_2$O (80 mL). The precipitate that formed was filtered and washed with H$_2$O (×2) and Et$_2$O (×2). The obtained solid was dried in the vacuum oven for 5 hours to afford 183-3 (2.22 g, 6.51 mmol, 70% yield) as a dark grey solid. MS [M+H]$^+$=341.1. $^1$H NMR (400 MHz, DMSO-d$_6$) δ 11.01 (s, 1H), 8.05 (d, J=6.0 Hz, 1H), 7.71 (d, J=7.7 Hz, 1H), 5.12 (dd, J=13.3, 5.1 Hz, 1H), 4.46 (d, J=17.5 Hz, 1H), 4.33 (d, J=17.5 Hz, 1H), 2.97-2.83 (m, 1H), 2.65-2.56 (m, 1H), 2.39 (qd, J=13.2, 4.5 Hz, 1H), 2.09-1.94 (m, 1H).

Step 3. 3-(5-bromo-6-fluoro-1-oxoisoindolin-2-yl)-1-((2-(trimethylsilyl)ethoxy)methyl)piperidine-2,6-dione (183-4)

To a stirred solution of 183-3 (800 mg, 2.35 mmol) and DBU (0.70 mL, 4.7 mmol) in DMF (5 mL). was added SEMCl (0.62 mL, 3.5 mmol) at 0° C. and the resulting mixture was stirred at room temperature overnight. Additional DBU (0.70 mL, 4.7 mmol) and SEMCl (0.62 mL, 3.5 mmol) were added at 0° C. and stirring was continued for 2 hours at rt. The reaction mixture was quenched with sat. aq. NH$_4$Cl and extracted with EtOAc (×3). The combined organic phases were concentrated to dryness. The crude product was purified by silica gel chromatography eluting with 0 to 30% acetone in heptane to afford 183-4 (683 mg, 1.45 mmol, 62% yield) as a white solid. MS [M+H]$^+$=471.2. $^1$H NMR (400 MHz, Methylene Chloride-d) δ 7.73 (d, J=5.7

Hz, 1H), 7.57 (d, J=7.3 Hz, 1H), 5.23-5.09 (m, 3H), 4.36 (q, J=16.2 Hz, 2H), 3.62-3.57 (m, 2H), 2.99 (ddd, J=17.9, 4.8, 2.6 Hz, 1H), 2.87 (ddd, J=18.0, 13.3, 5.5 Hz, 1H), 2.32 (qd, J=13.2, 4.8 Hz, 1H), 2.25-2.14 (m, 1H), 0.94-0.87 (m, 2H), 0.00 (s, 9H).

Step 4. tert-butyl ((1S,2S)-2-((2-(2,6-dioxo-1-((2-(trimethylsilyl)ethoxy)methyl)piperidin-3-yl)-6-fluoro-1-oxoisoindolin-5-yl)oxy)cyclopentyl)carbamate (183-5)

To a mixture of 183-4 (683 mg, 1.45 mmol), tert-butyl ((1S,2S)-2-hydroxycyclopentyl)carbamate (1-1e, 350 mg, 1.74 mmol), NiCl$_2$(glyme) (16 mg, 0.072 mmol), dtbbpy (19 mg, 0.072 mmol) and Ir[(dF(CF$_3$)ppy)$_2$dtbbpy]PF$_6$ (16 mg, 0.014 mmol) in MeCN (8 mL) under an atmosphere of nitrogen was added 2,2,6,6-tetramethylpiperidine (0.37 mL, 2.2 mmol) and the resulting mixture was stirred vigorously for 48 hours under irradiation of Blue LED lights at room temperature. The reaction mixture was then filtered and concentrated to dryness. The crude product was purified by silica gel chromatography eluting with 0 to 100% EtOAc in heptane to afford 183-5 (420 mg, 0.639 mmol, 44% yield) as a yellow solid. MS [M+Na]$^+$=614.2. $^1$H NMR (400 MHz, Methylene Chloride-d$_2$) δ 7.62-7.49 (m, 1H), 7.47 (d, J=9.7 Hz, 1H), 5.22-5.04 (m, 3H), 4.78-4.67 (m, 1H), 4.57 (s, 1H), 4.40-4.25 (m, 2H), 4.12-3.99 (m, 1H), 3.63-3.56 (m, 2H), 3.02-2.79 (m, 2H), 2.40-2.24 (m, 1H), 2.22-2.13 (m, 2H), 2.12-2.02 (m, 1H), 1.96-1.85 (m, 2H), 1.84-1.71 (m, 1H), 1.60-1.49 (m, 1H), 1.42 (s, 9H), 0.94-0.87 (m, 2H), 0.00 (s, 9H).

Step 5. 3-(5-(((1S,2S)-2-aminocyclopentyl)oxy)-6-fluoro-1-oxoisoindolin-2-yl)piperidine-2,6-dione (I-215)

To a stirred solution of 183-5 (420 mg, 0.639 mmol) in MeCN (2 mL) was added methanesulfonic acid (0.5 mL, 7 mmol) and the resulting mixture stirred overnight at rt. Et$_3$N (1.5 mL, 11 mmol) was added dropwise at 0° C. and the reaction mixture was allowed to reach rt. N1,N2-dimethylethane-1,2-diamine (0.15 mL, 1.4 mmol) was then added and stirring was continued overnight at rt. The reaction mixture was diluted with sat. aq. NaHCO$_3$ and extracted with DCM:EtOH (v/v=4:1) (×4). The combined organic phases were concentrated to dryness. The crude product was purified by silica gel chromatography eluting with 0 to 100% EtOAc:EtOH (v/v=3:1, with 1% Et$_3$N) in DCM to afford I-215 (183 mg, 0.496 mmol, 78% yield) as white solid. MS [M+H]$^+$=362.1. $^1$H NMR (400 MHz, DMSO-d$_6$) δ 10.99 (s, 1H), 7.57 (d, J=9.8 Hz, 1H), 7.51 (t, J=6.0 Hz, 1H), 5.09 (dt, J=13.1, 4.6 Hz, 1H), 4.94-4.85 (m, 1H), 4.41 (dd, J=17.3, 7.2 Hz, 1H), 4.29 (dd, J=17.3, 8.0 Hz, 1H), 3.79-3.58 (m, 1H), 2.98-2.84 (m, 1H), 2.75-2.54 (m, 1H), 2.45-2.32 (m, 1H), 2.30-2.20 (m, 1H), 2.20-2.07 (m, 1H), 2.04-1.94 (m, 1H), 1.87-1.61 (m, 4H).

Step 6. 3-(5-(((1S,2S)-2-(diethylamino)cyclopentyl)oxy)-6-fluoro-1-oxoisoindolin-2-yl)piperidine-2,6-dione (I-216)

To a stirred solution of I-215 (150 mg, 0.415 mmol) and NaBH(OAc)$_3$ (264 mg, 1.25 mmol) in DMF (2 mL) was added acetaldehyde (0.07 mL, 1 mmol) and the resulting mixture was stirred at rt overnight. The reaction mixture was concentrated to dryness. The crude product was purified by silica gel chromatography eluting with EtOAc:EtOH (v/v=3: 1, with 1% Et$_3$N) in DCM to afford I-216 (87.5 mg, 0.206 mmol, 50% yield) as white solid. MS [M+H]$^+$=418.2. $^1$H NMR (400 MHz, Methylene Chloride-d$_2$) δ 8.45 (br s, 1H), 7.51 (dd, J=9.8, 3.1 Hz, 1H), 7.37 (t, J=7.3 Hz, 1H), 5.16 (ddd, J=13.3, 5.3, 3.5 Hz, 1H), 4.74 (s, 1H), 4.48-4.17 (m, 2H), 3.51-3.34 (m, 1H), 2.96-2.80 (m, 2H), 2.73-2.56 (m, 4H), 2.45-2.28 (m, 1H), 2.27-2.17 (m, 1H), 2.10-1.96 (m, 2H), 1.93-1.74 (m, 3H), 1.64 (s, 1H), 1.07 (t, J=7.1 Hz, 6H).

Biological Assays and Data

The activity of a compound according to the present disclosure can be assessed by the following in vitro methods.

Example 184: Prolabel Quantification of IKZF1, IKZF2, or GSPT1 Protein Levels in 293GT Cells The Prolabel system from DiscoverX was used to develop high-throughput and quantitative assays to measure changes in IKZF1, IKZF2 and GSPT1 protein levels in response to compounds. The prolabel tag is derived from the alpha fragment of beta galactosidase and has the following protein sequence: mssnslavvlqrrdwenpgvtqlnrlaahppfaswrnseeart-drpsqqlrslnge. The complementary fragment of beta-galactosidase (from DiscoverX), is added to the prolabel tag to form an active beta galactosidase enzyme whose activity can be precisely measured. In this way, the levels of a fusion protein with the prolabel tag can be quantified in cell lysates.

Lentiviral vectors, based on the Invitrogen pLenti6.2/V5 DEST backbone, were constructed that placed the prolabel tag upstream of IKZF1, IKZF2 or GSPT1 and expressed the fusion protein from a CMV promoter.

To ensure moderate and consistent expression of the prolabel fusion proteins across all cells in the population, stable cell lines were constructed from cells expressing a single copy of the construct. Lentivirus packaged with the constructs was made using the Virapower kit from Invitrogen. Strongly adherent 293GT cell, GripTite 293 MSR cells from Thermo Fisher Scientific (Catalog number: R79507), were infected with the virus at low multiplicity of infection and selected by 5 µg/mL blasticidin for 2 weeks.

The levels of prolabel tagged fusion proteins in compound treated cell lines were measured as follows:

Day 1, Cells were diluted to 1.0×10$^6$ cells/ml in normal growth medium. 17.5 µL of cells were plated in each well of a solid white 384 well plate. Plates were incubated overnight in a 37° C. tissue culture incubator.

Day 2, Serial dilutions of compounds were made in 384 well plates from 10 mM stocks. 15 µL of DMSO was added to each well of a 384 well plate. In the first column 15 µL of stock compound was added. The solution was mixed and 15 µL was transferred to the next column. This was repeated until 20 two-fold dilutions were prepared. 2.5 µL of diluted compounds were transferred into 60 µL of cell culture medium in another 384 well plate, and mixed well. 2.5 µL of this mixture was added to the plated cells. The final DMSO concentration was 0.5% and the highest concentration of compound was 50 µM. Plates were incubated overnight (e.g., about 14 h, 18 h, or 24 h) in a 37° C. tissue culture incubator.

Day 3, Plates were removed from the incubator and allowed to equilibrate at rt for 30 minutes. Prolabel substrate (DiscoverX PathHunter Prolabel Detection Kit, User manual: 93-0180) was added as described by the manufacturers protocols. Plates were incubated at rt for three hours and luminescence was read using an Envision reader (Perkin Elmer) Data was analyzed and visualized using the Spotfire software package.

Table 14 shows Helios (IKZF2), Ikaros (IKZF1) and G1 to S phase transition 1 protein (GSPT1) degradation activity of compounds of the disclosure in Pro-label assays in 293GT cells, (% degradation is at 10 μM).

| Cmpd No. | IKZF2 EC$_{50}$ (mM) | IKZF2% protein reduction at 10 μM, 24 h | IKZF1 EC$_{50}$ (mM) | GSPT1 EC$_{50}$ (mM) |
|---|---|---|---|---|
| I-1 | — | 10% | >30 | >30 |
| I-2 | — | 10% | >30 | >30 |
| I-3 | 0.256 | 40% | >30 | — |
| I-4 | 4.2 | 25% | >30 | — |
| I-5 | 0.170 | 60% | >30 | — |
| I-6 | — | 5% | >30 | — |
| I-7 | 0.037 | 85% | >30 | — |
| I-8 | 0.176 | 50% | >30 | >30 |
| I-9 | >30 | 0% | >30 | — |
| I-10 | >30 | 0% | >30 | — |
| I-11 | 0.129 | 75% | >30 | >30 |
| I-12 | 0.139 | 65% | >30 | >30 |
| I-13 | 0.016 | 85% | >30 | >30 |
| I-14 | 0.282 | 60% | >30 | >30 |
| I-15 | 0.565 | 50% | >30 | >50 |
| I-16 | 0.032 | 85% | >30 | >30 |
| I-17 | 0.018 | 80% | >30 | — |
| I-18 | 0.266 | 50% | >30 | — |
| I-19 | — | 10% | >30 | — |
| I-20 | 0.025 | 75% | >30 | >30 |
| I-21 | 0.237 | 30% | >30 | >30 |
| I-22 | 0.016 | 80% | >50 | >30 |
| I-23 | 0.067 | 80% | >30 | >30 |
| I-24 | 0.064 | 80% | >30 | >30 |
| I-25 | 0.025 | 80% | >30 | >30 |
| I-26 | >30 | 0% | >30 | — |
| I-27 | 0.548 | 50% | >30 | — |
| I-28 | >30 | 0% | >30 | >30 |
| I-29 | 0.028 | 80% | >30 | — |
| I-30 | >30 | 0% | >30 | >30 |
| I-31 | 0.006 | 90% | 3.2 | >30 |
| I-32 | 0.011 | 85% | >30 | >30 |
| I-33 | 0.163 | 55% | >30 | >30 |
| I-34 | >30 | 0% | >50 | — |
| I-35 | — | 10% | >30 | >30 |
| I-36 | 0.037 | 80% | >30 | — |
| I-37 | >30 | 0% | >50 | >50 |
| I-49 | 0.007 | 86% | >30 | >30 |
| I-50 | 0.007 | 85% | >30 | — |
| I-51 | 0.006 | 90% | >30 | >30 |
| I-52 | 0.005 | 89% | >30 | — |
| I-53 | 0.003 | 88% | >30 | — |
| I-48 | 0.003 | 89% | >30 | >30 |
| I-54 | 0.001 | 91% | >30 | — |
| I-55 | 0.004 | 91% | >30 | >30 |
| I-56 | 0.002 | 91% | >30 | >30 |
| I-38 | 0.015 | 86% | >30 | >50 |
| I-39 | 0.11 | 57% | >30 | — |
| I-43 | >30 | 0% | >30 | — |
| I-44 | 0.465 | 42% | >30 | — |
| I-46 | >30 | 0% | >30 | — |
| I-47 | >30 | 11% | >30 | — |
| I-136 | 0.131 | 58% | >30 | — |
| I-96 | 0.099 | 81% | >30 | — |
| I-137 | 0.030 | 80% | >30 | — |
| I-138 | 0.049 | 83% | >30 | — |
| I-139 | 0.048 | 83% | >30 | — |
| I-141 | 0.157 | 77% | >30 | — |
| I-142 | 0.034 | 83% | >30 | — |
| I-143 | 0.022 | 81% | >30 | — |
| I-144 | 0.015 | 88% | >30 | — |
| I-145 | 0.161 | 52% | >30 | — |
| I-146 | 0.014 | 83% | >30 | — |
| I-147 | 0.159 | 44% | >30 | — |
| I-148 | 9.938 | 33% | >30 | — |
| I-149 | 0.012 | 77% | >30 | — |
| I-150 | 0.243 | 51% | >30 | — |
| I-151 | 0.443 | 53% | >30 | — |
| I-152 | 0.052 | 82% | >30 | — |
| I-153 | 0.014 | 85% | >30 | — |
| I-154 | 0.034 | 83% | >30 | — |
| I-155 | 0.485 | 65% | 0.10 | — |
| I-156 | 0.133 | 70% | >30 | — |
| I-157 | 0.071 | 61% | >30 | — |
| I-158 | 0.027 | 82% | >30 | — |
| I-159 | 0.040 | 75% | >30 | >30 |
| I-160 | 0.077 | 75% | >30 | — |
| I-161 | 0.032 | 80% | >30 | — |
| I-162 | 0.082 | 64% | >30 | — |
| I-163 | 0.039 | 78% | >30 | — |
| I-164 | 0.23 | 71% | >30 | — |
| I-165 | 0.071 | 72% | >30 | — |
| I-166 | 0.007 | 81% | >30 | — |
| I-167 | 0.062 | 75% | >30 | — |
| I-168 | 0.009 | 83% | >30 | — |
| I-169 | >30 | 2% | >30 | — |
| I-170 | 0.194 | 67% | >30 | — |
| I-171 | 0.021 | 74% | >30 | — |
| I-172 | 0.124 | 58% | >30 | — |
| I-173 | 0.037 | 84% | >30 | >30 |
| I-174 | 0.085 | 86% | >30 | — |
| I-175 | — | — | >30 | — |
| I-176 | 0.027 | 89% | >30 | — |
| I-177 | 0.002 | 92% | >30 | — |
| I-178 | 0.006 | 92% | >30 | — |
| I-179 | 0.007 | 85% | >30 | — |
| I-180 | 0.017 | 81% | >30 | — |
| I-182 | 0.017 | 76% | >30 | — |
| I-183 | 0.010 | 84% | >30 | — |
| I-184 | 0.053 | 38% | >30 | — |
| I-185 | 0.096 | 66% | — | — |
| I-187 | 0.012 | 79% | >30 | — |
| I-186 | 0.007 | 86% | >30 | — |
| I-188 | 0.003 | 70% | >30 | — |
| I-189 | 0.104 | 70% | >30 | — |
| I-190 | 1.089 | 39% | >30 | — |
| I-191 | 0.065 | 83% | >30 | >30 |
| I-192 | 0.035 | 77% | >30 | — |
| I-193 | 0.039 | 79% | >30 | — |
| I-194 | 0.015 | 83% | >30 | >30 |
| I-195 | 0.005 | 85% | >30 | >30 |
| I-196 | 0.084 | 68% | >30 | — |
| I-197 | 0.084 | 68% | >30 | — |
| I-198 | 0.076 | 67% | >30 | — |
| I-199 | 0.130 | 71% | >30 | — |
| I-200 | 0.057 | 71% | >30 | — |
| I-201 | 0.260 | 46% | >30 | — |
| I-71 | 0.018 | 88% | >30 | — |
| I-72 | 0.361 | 57% | >30 | — |
| I-73 | 0.136 | 66% | >30 | — |
| I-74 | 0.037 | 58% | >30 | — |
| I-75 | 0.065 | 79% | >30 | — |
| I-76 | 0.137 | 79% | >30 | — |
| I-77 | 0.141 | 86% | >30 | — |
| I-78 | 0.880 | 50% | >30 | — |
| I-80 | 0.263 | 65% | >30 | — |
| I-81 | 0.046 | 85% | >30 | — |
| I-82 | 2.64 | 58% | >30 | — |
| I-83 | 0.029 | 86% | >30 | — |
| I-84 | 0.118 | 35% | >30 | — |
| I-85 | 0.087 | 69% | >30 | — |
| I-86 | 0.177 | 76% | >30 | — |
| I-87 | 0.082 | 79% | >30 | — |
| I-88 | 5.528 | 57% | >30 | — |
| I-89 | 0.038 | 82% | >30 | >30 |
| I-90 | 0.246 | 57% | >30 | — |
| I-91 | 0.129 | 58% | >30 | — |
| I-92 | 0.124 | 60% | >30 | — |
| I-93 | 0.345 | 60% | >30 | — |
| I-95 | 0.036 | 84% | >30 | — |
| I-94 | 0.074 | 84% | >30 | — |
| I-97 | 0.592 | 36% | >30 | — |

| Cmpd No. | IKZF2 EC$_{50}$ (mM) | IKZF2% protein reduction at 10 μM, 24 h | IKZF1 EC$_{50}$ (mM) | GSPT1 EC$_{50}$ (mM) |
|---|---|---|---|---|
| I-98 | 0.055 | 80% | >30 | — |
| I-101 | 0.067 | 73% | >30 | — |
| I-102 | 0.067 | 73% | >30 | — |
| I-103 | 0.060 | 54% | — | — |
| I-104 | 0.028 | 87% | >30 | — |
| I-105 | 0.234 | 52% | >30 | — |
| I-106 | 0.411 | 51% | >30 | — |
| I-107 | 0.016 | 89% | >30 | — |
| I-110 | 0.022 | 89% | >30 | — |
| I-111 | 0.364 | 59% | >30 | — |
| I-112 | 0.0002 | 95% | >30 | — |
| I-113 | 0.0008 | 93% | >30 | >30 |
| I-114 | 0.458 | 54% | >30 | — |
| I-115 | 0.008 | 90% | >30 | — |
| I-116 | 0.041 | 65% | >30 | — |
| I-119 | 0.091 | 59% | — | — |
| I-118 | 0.045 | 67% | — | — |
| I-120 | 0.212 | 66% | >30 | >30 |
| I-121 | 0.0003 | 94% | >30 | — |
| I-122 | 0.027 | 84% | >30 | >30 |
| I-123 | 0.196 | 82% | >30 | — |
| I-129 | 0.082 | 70% | >30 | — |
| I-130 | 0.050 | 50% | >30 | — |
| I-79 | 0.027 | 85% | >30 | — |
| I-131 | 0.012 | 91% | >30 | — |
| I-132 | 0.134 | 80% | >30 | — |
| I-133 | 0.045 | 81% | >30 | — |
| I-134 | 0.207 | 56% | >30 | — |
| I-135 | 0.003 | 92% | — | >30 |
| I-57 | 0.047 | 80% | >30 | — |
| I-58 | 0.064 | 75% | >30 | — |
| I-59 | 1.31 | 39% | >30 | — |
| I-60 | 0.157 | 61% | >30 | — |
| I-61 | 0.028 | 84% | >30 | >30 |
| I-62 | 0.057 | 88 | >30 | — |
| I-63 | 0.011 | 85% | >30 | >30 |
| I-64 | 0.036 | 84% | >30 | — |
| I-65 | 0.157 | 76% | >30 | — |
| I-66 | 0.096 | 81% | >30 | — |
| I-67 | 0.066 | 74% | >30 | — |
| I-68 | 0.004 | 90% | >30 | >30 |
| I-69 | 0.014 | 84% | >30 | >30 |
| I-99 | 0.11 | 86% | >30 | — |
| I-100 | 0.044 | 86% | >30 | — |
| I-213 | >30 | 20% | >30 | — |
| I-214 | 0.33 | 40% | >30 | — |
| I-215 | >30 | 30% | >30 | — |
| I-216 | 0.12 | 60% | >30 | — |

Example 185: Quantification of In Vitro Suppressive Potency of Primary Human Regulatory T Cells Expanded in the Presence of Compounds Materials and Methods
Treg Cell Sorting:

Human buffy coats are obtained from BioreclamationIVT, in the USA. CD4+ T cells are isolated from said buffy coats using the RosetteSep Human CD4+ T cell enrichment Cocktail (Stemcell technologies, USA) and gradient centrifugation over Ficoll Paque Plus (GE HealthCare LifeSciences, USA) as per manufacturer's recommendations. Cells are resuspended in RPMI medium supplemented with 1% penicillin-Streptomycin solution, 10% Fetal Bovine Serum, HEPES (10 mM), MEM NEAA (100 nM), sodium pyruvate (1 mM) (all supplements from Thermo Fisher Scientific, USA), thereafter referred to as complete RPMI (cRPMI), and rested overnight at 37° C., 5% CO$_2$ in the presence of 2U/mL rhIL-2 (Proleukin, Novartis). Cells are collected and resuspended in autoMACS Running Buffer supplemented with BSA (Miltenyi Biotec, USA) and labelled using CD4-FITC antibody (clone RPA-T4), CD25-APC antibody (clone M-A251) (Biolegend) and CD25 Microbeads (Miltenyi Biotec, USA). CD25-enriched cells are then isolated using the autoMACS Pro Separator. A highly purified population of Treg cells are then obtained by further sorting CD4+ CD25Hi cells using a Sony SH800 cell sorter. The resulting Treg cell population is routinely above 90% pure according to FOXP3 expression.

Treg Cell Expansion:

Purified Treg cells are plated in cRPMI in 96-well, round-bottom plates at a density of 25000-50000 cells per well and activated in the presence of 500 U/mL rhIL2, and Treg expander Dynabeads (Thermo Fisher Scientific, USA) according to manufacturer's recommendations, in the presence or absence of 100 μM rapamycin (Thermo Fisher Scientific, USA). The compounds of the present disclosure are then added at a final concentration of 10 M and DMSO is added as a vehicle control. Cells are incubated at 37° C., 5% CO$_2$ for a total of 12-14 days. The compound and rhIL2 are replenished every 48h during the entirety of the culture.

Phenotypic Analysis of Expanded Treg Cells:

Cell are collected and counted and the fold expansion is calculated as (number of cells recovered)/(number of cells plated). A fraction of the cells is fixed and permeabilized using the eBioscience Foxp3 staining Buffer kit (eBioscience, Thermo Fisher Scientific, USA) and stained with Helios-PECyanine7 antibody (Clone 22F6). To determine IL2-expression, expanded Treg cells are further incubated in the presence of the eBioscience Cell Stimulation Cocktail with Protein inhibitors (Thermo Fisher Scientific) for 4 hours, followed by fixation and staining with IL2-BV711 antibody (clone MQ1-17H12) (Biolegend, USA). Cells are acquired on an LSRFortessa (Becton Dickinson, USA) and analysis is performed using the FlowJo software (TreeStar, USA).

Functional Analysis of Expanded Treg Cells:

Primary human PBMCs are obtained from freshly prepared buffy coats (BioReclamationIVT) using gradient centrifugation over Ficoll Paque Plus as per manufacturer's recommendations. Cells are then labelled with CFSE (5(6)-Carboxyfluorescein diacetate N-succinimidyl ester, Sigma-Aldrich, USA) and plated in triplicates cRPMI in round bottom 96-well plates, alone or with expanded Treg cells at a 1:2 PBMC:Treg ratio. The compounds of the present disclosure are then added at a final concentration of 10 M and DMSO is added as a vehicle control. Cells are activated using soluble anti-CD3 antibody (clone OKT3) (eBioscience, ThermoFisher Scientific, USA) at a final concentration of 100 ng/ml. Cells are incubated at 37° C., 5% CO$_2$ for a total of 4-5 days. At the end of the culture, cells are stained using the Live/dead Blue viability stain (Thermo Fisher Scientific, USA) as per manufacturer's instructions, followed by staining with CD4-BUV737 (Clone SK3) (BDBiosciences, USA) and CD8-BV711 (clone RPA-T8) (Biolegend, USA). Cells are acquired on an LSRFortessa (Becton Dickinson, USA) and analysis is performed using the FlowJo software (TreeStar, USA). Proliferation is assessed in each population as the proportion of cells having diluted CFSE. Suppression is assessed for each condition in comparison to the responders plated alone.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound of Formula (I')

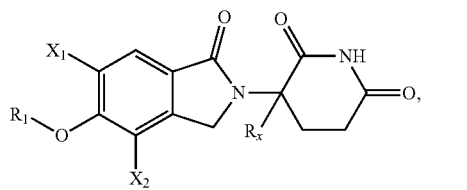

wherein:
X₁ and X₂ are each independently H, $(C_1-C_4)$alkyl, $(C_1-C_6)$alkoxy, $(C_1-C_4)$haloalkyl, $(C_1-C_6)$haloalkoxy, $(C_3-C_7)$cycloalkyl, halogen, —CN, —OH, or —NH₂,
$R_x$ is H or D;
$R_1$ is

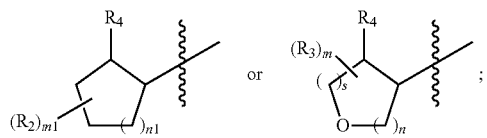

each $R_2$ is independently at each occurrence $(C_1-C_6)$alkyl, $(C_1-C_6)$alkoxy, $(C_1-C_6)$haloalkyl, $(C_1-C_6)$haloalkoxy, halogen, —CN, —OH, or —NH₂; or
two $R_2$ together with the carbon atoms to which they are attached form a $(C_3-C_7)$cycloalkyl or a 4- to 7-membered heterocycloalkyl ring consisting of 1-3 heteroatoms selected from O, N, and S; or two $R_2$ together when on adjacent carbon atoms form a phenyl or a 5- or 6-membered heteroaryl ring consisting of 1-3 heteroatoms selected from O, N, and S; or $R_2$ and $R_6$ together with the carbon and nitrogen atoms to which they are attached form a 4- to 6-membered heterocycloalkyl ring optionally consisting of 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH₂;

each $R_3$ is $(C_1-C_6)$alkyl, $(C_1-C_6)$alkoxy, $(C_1-C_6)$haloalkyl, $(C_1-C_6)$haloalkoxy, halogen, —OH, or —NH₂;

$R_4$ is —OR₅ or —NR₆R₆';

$R_5$ is H, $(C_1-C_6)$alkyl, $(C_1-C_6)$haloalkyl, $(C_3-C_7)$cycloalkyl, 5- or 6-membered heterocycloalkyl consisting of 1-3 heteroatoms selected from O, N, and S, $(C_6-C_{10})$aryl, or 5- or 6-membered heteroaryl consisting of 1-3 heteroatoms selected from O, N, and S, wherein the alkyl is optionally substituted with one to three substituents independently selected from $(C_6-C_{10})$aryl and 5- or 6-membered heteroaryl consisting of 1-3 heteroatoms selected from O, N, and S;

$R_6$ and $R_6'$ are each independently H, $(C_1-C_6)$alkyl, $(C_1-C_6)$haloalkyl, $(C_2-C_6)$hydroxyalkyl, $(C_3-C_7)$cycloalkyl, 5- or 6-membered heterocycloalkyl consisting of 1-3 heteroatoms selected from O, N, and S, $(C_6-C_{10})$aryl, or 5- or 6-membered heteroaryl consisting of 1-3 heteroatoms selected from O, N, and S, wherein the alkyl is optionally substituted with one to three $R_7$ and wherein the cycloalkyl, heterocycloalkyl, aryl, and heteroaryl are optionally substituted with one to four $R_{12}$; or $R_6$ and $R_{6'}$ together with the nitrogen atom to which they are attached form a 4- to 8-membered heterocycloalkyl ring optionally consisting of 1-2 additional heteroatoms selected from O, N, and S, and optionally substituted with one to four $R_8$; or $R_2$ and $R_6$ together with the carbon and nitrogen atoms to which they are attached form a 4- to 6-membered heterocycloalkyl ring optionally consisting of 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_7$ is $(C_3-C_7)$cycloalkyl, 4- to 7-membered heterocycloalkyl ring consisting of 1-3 heteroatoms selected from O, N, and S, $(C_6-C_{10})$aryl, or 5- or 6-membered heteroaryl consisting of 1-3 heteroatoms selected from O, N, and S, wherein the cycloalkyl, heterocycloalkyl, aryl, and heteroaryl are optionally substituted with one to four $R_9$;

each $R_8$ is independently at each occurrence halogen, $(C_1-C_6)$alkyl, $(C_1-C_6)$alkoxy, $(C_1-C_6)$haloalkyl, $(C_1-C_6)$haloalkoxy, —CN, —OH, —NR$_{13}$R$_{14}$, —NH$_2$, —O(C$_3$-C$_7$)cycloalkyl, —O-4- to 7-membered heterocycloalkyl ring consisting of 1-3 heteroatoms selected from O, N, and S, —O(C$_6$-C$_{10}$)aryl, or —O-5- or 6-membered heteroaryl consisting of 1-3 heteroatoms selected from O, N, and S, wherein the alkoxy is optionally substituted with one to three $R_{10}$ and the cycloalkyl, heterocycloalkyl, aryl, and heteroaryl are optionally substituted with one to three $R_{11}$; or two $R_8$ together with the atoms to which they are attached form a $(C_4-C_7)$cycloalkyl or a 4- to 7-membered heterocycloalkyl ring consisting of 1-2 heteroatoms selected from O, N, and S optionally substituted with two $R_{15}$; or two $R_8$ when on adjacent atoms together with the atoms to which they are attached form a $(C_6-C_{10})$aryl, or 5- or 6-membered heteroaryl consisting of 1-3 heteroatoms selected from O, N, and S; or two $R_8$ together with the same atom to which they are attached form a =(O);

each $R_9$ is independently at each occurrence $(C_1-C_6)$alkyl, $(C_1-C_6)$haloalkyl, $(C_1-C_6)$alkoxy, $(C_1-C_6)$haloalkoxy, halogen, $(C_3-C_6)$cycloalkyl, —OH, —CN, —NH$_2$, or —NR$_{13}$R$_{14}$; or two $R_9$ together with the atoms to which they are attached form a $(C_4-C_7)$cycloalkyl or a 5- to 7-membered heterocycloalkyl ring consisting of 1-2 heteroatoms selected from O, N, and S optionally substituted with one or more substituents each independently selected from $(C_1-C_6)$alkyl, $(C_1-C_6)$haloalkyl, halogen, —OH, —CN, and —NH$_2$; or two $R_9$ when on adjacent atoms together with the atoms to which they are attached form a $(C_6-C_{10})$aryl, or 5- or 6-membered heteroaryl consisting of 1-3 heteroatoms selected from O, N, and S;

each $R_{10}$ is independently at each occurrence selected from $(C_3-C_7)$cycloalkyl, 4- to 7-membered heterocycloalkyl ring consisting of 1-3 heteroatoms selected from O, N, and S, $(C_6-C_{10})$aryl, and 5- or 6-membered heteroaryl consisting of 1-3 heteroatoms selected from O, N, and S;

each $R_{11}$ is independently at each occurrence selected from $(C_1-C_6)$alkyl, $(C_1-C_6)$haloalkyl, $(C_1-C_6)$alkoxy, $(C_1-C_6)$haloalkoxy, halogen, —OH, —CN, and —NH$_2$;

each $R_{12}$ is independently at each occurrence $(C_1-C_6)$alkyl, $(C_1-C_6)$haloalkyl, $(C_1-C_6)$alkoxy, $(C_1-C_6)$haloalkoxy, halogen, —OH, —CN, or —NH$_2$;

two $R_{12}$ together with the atoms to which they are attached form a $(C_4-C_7)$cycloalkyl or a 4- to 7-membered heterocycloalkyl ring consisting of 1-2 heteroatoms selected from O, N, and S;

$R_{13}$ and $R_{14}$ are each independently selected from $(C_1-C_6)$alkyl, $(C_1-C_6)$haloalkyl, $(C_3-C_7)$cycloalkyl, 4- to 7-membered heterocycloalkyl ring consisting of 1-3 heteroatoms selected from O, N, and S, $(C_6-C_{10})$aryl, and 5- or 6-membered heteroaryl consisting of 1-3 heteroatoms selected from O, N, and S;

two $R_{15}$ together with the atoms to which they are attached form a $(C_4-C_7)$cycloalkyl or a 4- to 7-membered heterocycloalkyl ring consisting of 1-2 heteroatoms selected from O, N, and S;

m and m1 are each independently 0, 1 or 2;

n1 is 0, 1, 2, or 3; and each s and n is independently 1, 2, or 3, wherein s+n is ≤4;

or a pharmaceutically acceptable salt, stereoisomer, or tautomer thereof.

2. The compound according to claim 1, having a Formula (I),

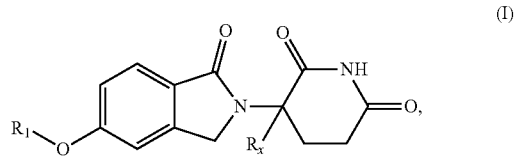

wherein:

$R_x$ is H or D;

$R_1$ is

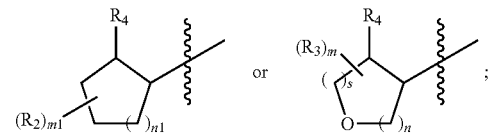

each $R_2$ is independently at each occurrence $(C_1-C_6)$alkyl, $(C_1-C_6)$alkoxy, $(C_1-C_6)$haloalkyl, $(C_1-C_6)$haloalkoxy, halogen, —CN, —OH, or —NH$_2$; or two $R_2$ together with the carbon atoms to which they are attached form a $(C_3-C_7)$cycloalkyl or a 4- to 7-membered heterocycloalkyl ring consisting of 1-3 heteroatoms selected from O, N, and S; or two $R_2$ together when on adjacent carbon atoms form a phenyl or a 5- or 6-membered heteroaryl ring consisting of 1-3 heteroatoms selected from O, N, and S; or $R_2$ and $R_6$ together with the carbon and nitrogen atoms to which they are attached form a 5- or 6-membered heterocycloalkyl ring optionally consisting of 1-2 additional heteroatoms selected from O, N, and S, and optionally substituted with one to four substituents each independently selected from $(C_1-C_6)$alkyl, $(C_1-C_6)$haloalkyl, halogen, —OH, —CN, and —NH$_2$;

each $R_3$ is $(C_1-C_6)$alkyl, $(C_1-C_6)$alkoxy, $(C_1-C_6)$haloalkyl, $(C_1-C_6)$haloalkoxy, halogen, —OH, or —NH$_2$;

$R_4$ is —OR$_5$ or —NR$_6$R$_{6'}$;

R$_5$ is H, (C$_1$-C$_6$)alkyl, (C$_1$-C$_6$)haloalkyl, (C$_3$-C$_7$)cycloalkyl, 5- or 6-membered heterocycloalkyl consisting of 1-3 heteroatoms selected from O, N, and S, (C$_6$-C$_{10}$)aryl, or 5- or 6-membered heteroaryl consisting of 1-3 heteroatoms selected from O, N, and S, wherein the alkyl is optionally substituted with one to three substituents independently selected from (C$_6$-C$_{10}$)aryl and 5- or 6-membered heteroaryl consisting of 1-3 heteroatoms selected from O, N, and S;

R$_6$ and R$_{6'}$ are each independently H, (C$_1$-C$_6$)alkyl, (C$_1$-C$_6$)haloalkyl, (C$_3$-C$_7$)cycloalkyl, 5- or 6-membered heterocycloalkyl consisting of 1-3 heteroatoms selected from O, N, and S, (C$_6$-C$_{10}$)aryl, or 5- or 6-membered heteroaryl consisting of 1-3 heteroatoms selected from O, N, and S, wherein the alkyl is optionally substituted with one to three R$_7$; or R$_6$ and R$_{6'}$ together with the nitrogen atom to which they are attached form a 4- to 7-membered heterocycloalkyl ring optionally consisting of 1-2 additional heteroatoms selected from O, N, and S, and optionally substituted with one to four R$_8$; or R$_2$ and R$_6$ together with the carbon and nitrogen atoms to which they are attached form a 5- or 6-membered heterocycloalkyl ring optionally consisting of 1-2 additional heteroatoms selected from O, N, and S, and optionally substituted with one to four substituents each independently selected from (C$_1$-C$_6$)alkyl, (C$_1$-C$_6$)haloalkyl, halogen, —OH, —CN, and —NH$_2$;

each R$_7$ is (C$_3$-C$_7$)cycloalkyl, 4- to 7-membered heterocycloalkyl ring consisting of 1-3 heteroatoms selected from O, N, and S, (C$_6$-C$_{10}$)aryl, or 5- or 6-membered heteroaryl consisting of 1-3 heteroatoms selected from O, N, and S, wherein the cycloalkyl, heterocycloalkyl, aryl, and heteroaryl are optionally substituted with one to four R$_9$;

each R$_3$ is independently at each occurrence halogen, (C$_1$-C$_6$)alkyl, (C$_1$-C$_6$)alkoxy, (C$_1$-C$_6$)haloalkyl, (C$_1$-C$_6$)haloalkoxy, —CN, —OH, or —NH$_2$, wherein the alkoxy is optionally substituted with one to three substituents independently selected from (C$_3$-C$_7$)cycloalkyl, 4- to 7-membered heterocycloalkyl ring consisting of 1-3 heteroatoms selected from O, N, and S, (C$_6$-C$_{10}$)aryl, and 5- or 6-membered heteroaryl consisting of 1-3 heteroatoms selected from O, N, and S; or two R$_8$ together with the atoms to which they are attached form a (C$_5$-C$_7$)cycloalkyl or a 4- to 7-membered heterocycloalkyl ring consisting of 1-2 heteroatoms selected from O, N, and S;

each R$_9$ is independently at each occurrence (C$_1$-C$_6$)alkyl, (C$_1$-C$_6$)haloalkyl, halogen, —OH, —CN, or —NH$_2$; or two R$_9$ together with the atoms to which they are attached form a (C$_5$-C$_7$)cycloalkyl or a 5- to 7-membered heterocycloalkyl ring consisting of 1-2 heteroatoms selected from O, N, and S optionally substituted with one or more substituents each independently selected from (C$_1$-C$_6$)alkyl, (C$_1$-C$_6$)haloalkyl, halogen, —OH, —CN, and —NH$_2$;

m and m1 are each independently 0, 1, or 2;

n1 is 0, 1, 2, or 3; and each s and n is independently 1, 2, or 3, wherein s+n is ≤4;

or a pharmaceutically acceptable salt, stereoisomer, or tautomer thereof.

3. The compound according to claim 1, wherein R$_1$ is

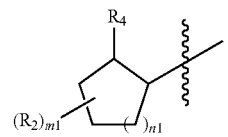

4. The compound according to claim 1, wherein n1 is 0, 1, or 2.

5. The compound according to claim 1, wherein m1 is 0.

6. The compound according to claim 1, wherein m1 is 2.

7. The compound according to claim 1, wherein R$_1$ is

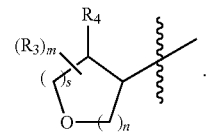

8. The compound according to claim 7, wherein n is 2 and s is 1 or 2.

9. The compound according to claim 8, wherein m is 0 or 1.

10. The compound according to claim 1, having a Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (In), Formula (Io), or Formula (Ip):

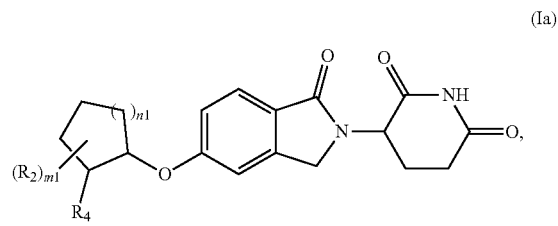

(Ia)

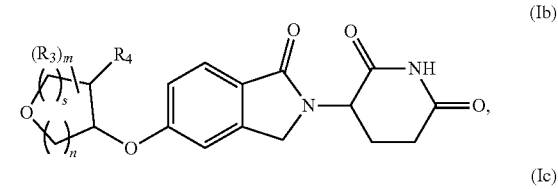

(Ib)

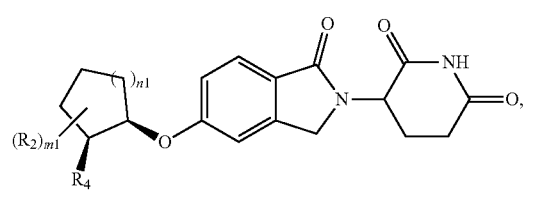

(Ic)

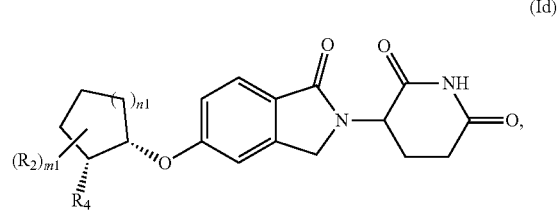

(Id)

or a pharmaceutically acceptable salt, stereoisomer, or tautomer thereof.

11. The compound according to claim 10, wherein $R_4$ is —$OR_5$.

12. The compound according to claim 10, wherein $R_4$ is —$NR_6R_{6'}$.

13. The compound according to claim 1, having a Formula (Iq), Formula (Ir), Formula (Is), or Formula (It):

-continued

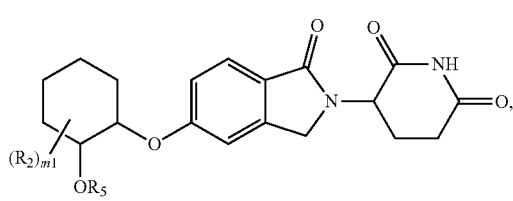

(It)

or a pharmaceutically acceptable salt, stereoisomer, or tautomer thereof.

14. The compound according to claim 1 selected from:
3-(5-(((1S,2S)-2-((2,2-difluoroethyl)(ethyl)amino)cyclopentyl)oxy)-1-oxoisoindolin-2-yl)piperidine-2,6-dione;
3-(5-(((1S,2R)-2-((2,2-difluoroethyl)(ethyl)amino)cyclopentyl)oxy)-1-oxoisoindolin-2-yl)piperidine-2,6-dione;
3-(5-(((1R,2S)-2-((2,2-difluoroethyl)(ethyl)amino)cyclopentyl)oxy)-1-oxoisoindolin-2-yl)piperidine-2,6-dione;
3-(5-(((1R,2R)-2-((2,2-difluoroethyl)(ethyl)amino)cyclopentyl)oxy)-1-oxoisoindolin-2-yl)piperidine-2,6-dione;
3-(5-((2-((2,2-difluoroethyl)(ethyl)amino)cyclopentyl)oxy)-1-oxoisoindolin-2-yl)piperidine-2,6-dione;
3-(5-(((1S,2R)-2-(benzylamino)cyclohexyl)oxy)-1-oxoisoindolin-2-yl)piperidine-2,6-dione;
3-(5-(((1S,2S)-2-(benzylamino)cyclohexyl)oxy)-1-oxoisoindolin-2-yl)piperidine-2,6-dione;
3-(5-(((1R,2S)-2-(benzylamino)cyclohexyl)oxy)-1-oxoisoindolin-2-yl)piperidine-2,6-dione;
3-(5-(((1R,2R)-2-(benzylamino)cyclohexyl)oxy)-1-oxoisoindolin-2-yl)piperidine-2,6-dione;
3-(5-((2-(benzylamino)cyclohexyl)oxy)-1-oxoisoindolin-2-yl)piperidine-2,6-dione;
3-(5-((1-methyloctahydrocyclopenta[b]pyrrol-6-yl)oxy)-1-oxoisoindolin-2-yl)piperidine-2,6-dione;
3-(5-(((1S,2S)-2-methoxycyclohexyl)oxy)-1-oxoisoindolin-2-yl)piperidine-2,6-dione;
3-(5-(((1S,2R)-2-methoxycyclohexyl)oxy)-1-oxoisoindolin-2-yl)piperidine-2,6-dione;
3-(5-(((1R,2S)-2-methoxycyclohexyl)oxy)-1-oxoisoindolin-2-yl)piperidine-2,6-dione;
3-(5-(((1R,2R)-2-methoxycyclohexyl)oxy)-1-oxoisoindolin-2-yl)piperidine-2,6-dione;
3-(5-((2-methoxycyclohexyl)oxy)-1-oxoisoindolin-2-yl)piperidine-2,6-dione;
3-(5-(((1S,2S)-2-(3-hydroxyazetidin-1-yl)cyclopentyl)oxy)-1-oxoisoindolin-2-yl)piperidine-2,6-dione;
3-(5-(((1S,2R)-2-(3-hydroxyazetidin-1-yl)cyclopentyl)oxy)-1-oxoisoindolin-2-yl)piperidine-2,6-dione;
3-(5-(((1R,2S)-2-(3-hydroxyazetidin-1-yl)cyclopentyl)oxy)-1-oxoisoindolin-2-yl)piperidine-2,6-dione;
3-(5-(((1R,2R)-2-(3-hydroxyazetidin-1-yl)cyclopentyl)oxy)-1-oxoisoindolin-2-yl)piperidine-2,6-dione;
3-(5-((2-(3-hydroxyazetidin-1-yl)cyclopentyl)oxy)-1-oxoisoindolin-2-yl)piperidine-2,6-dione;
3-(5-(((1R,2R)-2-hydroxycyclopentyl)oxy)-1-oxoisoindolin-2-yl)piperidine-2,6-dione;
3-(5-(((1R,2S)-2-hydroxycyclopentyl)oxy)-1-oxoisoindolin-2-yl)piperidine-2,6-dione;
3-(5-(((1S,2R)-2-hydroxycyclopentyl)oxy)-1-oxoisoindolin-2-yl)piperidine-2,6-dione;
3-(5-(((1S,2S)-2-hydroxycyclopentyl)oxy)-1-oxoisoindolin-2-yl)piperidine-2,6-dione;
3-(5-((2-hydroxycyclopentyl)oxy)-1-oxoisoindolin-2-yl)piperidine-2,6-dione;
3-(5-(((1S,2S)-2-(isobutylamino)cyclohexyl)oxy)-1-oxoisoindolin-2-yl)piperidine-2,6-dione;
3-(5-(((1S,2R)-2-(isobutylamino)cyclohexyl)oxy)-1-oxoisoindolin-2-yl)piperidine-2,6-dione;
3-(5-(((1R,2S)-2-(isobutylamino)cyclohexyl)oxy)-1-oxoisoindolin-2-yl)piperidine-2,6-dione;
3-(5-(((1R,2R)-2-(isobutylamino)cyclohexyl)oxy)-1-oxoisoindolin-2-yl)piperidine-2,6-dione;
3-(5-((2-(isobutylamino)cyclohexyl)oxy)-1-oxoisoindolin-2-yl)piperidine-2,6-dione;
3-(5-(((1S,2S)-2-(4,4-difluoropiperidin-1-yl)cyclopentyl)oxy)-1-oxoisoindolin-2-yl)piperidine-2,6-dione;
3-(5-(((1S,2R)-2-(4,4-difluoropiperidin-1-yl)cyclopentyl)oxy)-1-oxoisoindolin-2-yl)piperidine-2,6-dione;
3-(5-(((1R,2R)-2-(4,4-difluoropiperidin-1-yl)cyclopentyl)oxy)-1-oxoisoindolin-2-yl)piperidine-2,6-dione;
3-(5-(((1R,2S)-2-(4,4-difluoropiperidin-1-yl)cyclopentyl)oxy)-1-oxoisoindolin-2-yl)piperidine-2,6-dione;
3-(5-((2-(4,4-difluoropiperidin-1-yl)cyclopentyl)oxy)-1-oxoisoindolin-2-yl)piperidine-2,6-dione;
3-(5-(((1S,2S)-2-(benzyloxy)cyclopentyl)oxy)-1-oxoisoindolin-2-yl)piperidine-2,6-dione;
3-(5-(((1S,2R)-2-(benzyloxy)cyclopentyl)oxy)-1-oxoisoindolin-2-yl)piperidine-2,6-dione;
3-(5-(((1R,2R)-2-(benzyloxy)cyclopentyl)oxy)-1-oxoisoindolin-2-yl)piperidine-2,6-dione;
3-(5-(((1R,2S)-2-(benzyloxy)cyclopentyl)oxy)-1-oxoisoindolin-2-yl)piperidine-2,6-dione;
3-(5-((2-(benzyloxy)cyclopentyl)oxy)-1-oxoisoindolin-2-yl)piperidine-2,6-dione;
3-(5-(((1S,2R)-2-(diethylamino)cyclopentyl)oxy)-1-oxoisoindolin-2-yl)piperidine-2,6-dione;
3-(5-(((1S,2S)-2-(diethylamino)cyclopentyl)oxy)-1-oxoisoindolin-2-yl)piperidine-2,6-dione;
3-(5-(((1R,2S)-2-(diethylamino)cyclopentyl)oxy)-1-oxoisoindolin-2-yl)piperidine-2,6-dione;
3-(5-(((1R,2R)-2-(diethylamino)cyclopentyl)oxy)-1-oxoisoindolin-2-yl)piperidine-2,6-dione;
3-(5-((2-(diethylamino)cyclopentyl)oxy)-1-oxoisoindolin-2-yl)piperidine-2,6-dione;
3-(1-oxo-5-(((1S,2S)-2-(((1-(trifluoromethyl)cyclopropyl)methyl)amino)cyclohexyl)oxy)isoindolin-2-yl)piperidine-2,6-dione;
3-(1-oxo-5-(((1R,2S)-2-(((1-(trifluoromethyl)cyclopropyl)methyl)amino)cyclohexyl)oxy)isoindolin-2-yl)piperidine-2,6-dione;
3-(1-oxo-5-(((1R,2R)-2-(((1-(trifluoromethyl)cyclopropyl)methyl)amino)cyclohexyl)oxy)isoindolin-2-yl)piperidine-2,6-dione;
3-(1-oxo-5-(((1S,2R)-2-(((1-(trifluoromethyl)cyclopropyl)methyl)amino)cyclohexyl)oxy)isoindolin-2-yl)piperidine-2,6-dione;
3-(1-oxo-5-((2-(((1-(trifluoromethyl)cyclopropyl)methyl)amino)cyclohexyl)oxy)isoindolin-2-yl)piperidine-2,6-dione;
3-(5-(((1S,2S)-2-aminocyclopentyl)oxy)-1-oxoisoindolin-2-yl)piperidine-2,6-dione;
3-(5-(((1S,2R)-2-aminocyclopentyl)oxy)-1-oxoisoindolin-2-yl)piperidine-2,6-dione;
3-(5-(((1R,2R)-2-aminocyclopentyl)oxy)-1-oxoisoindolin-2-yl)piperidine-2,6-dione;
3-(5-(((1R,2S)-2-aminocyclopentyl)oxy)-1-oxoisoindolin-2-yl)piperidine-2,6-dione;

3-(5-((2-aminocyclopentyl)oxy)-1-oxoisoindolin-2-yl)piperidine-2,6-dione;
3-(5-(((1S,2S)-2-(diethylamino)cyclohexyl)oxy)-1-oxoisoindolin-2-yl)piperidine-2,6-dione;
3-(5-(((1S,2R)-2-(diethylamino)cyclohexyl)oxy)-1-oxoisoindolin-2-yl)piperidine-2,6-dione;
3-(5-(((1R,2R)-2-(diethylamino)cyclohexyl)oxy)-1-oxoisoindolin-2-yl)piperidine-2,6-dione;
3-(5-(((1R,2S)-2-(diethylamino)cyclohexyl)oxy)-1-oxoisoindolin-2-yl)piperidine-2,6-dione;
3-(5-((2-(diethylamino)cyclohexyl)oxy)-1-oxoisoindolin-2-yl)piperidine-2,6-dione;
3-(5-(((1S,2S)-2-aminocyclohexyl)oxy)-1-oxoisoindolin-2-yl)piperidine-2,6-dione;
3-(5-(((1S,2R)-2-aminocyclohexyl)oxy)-1-oxoisoindolin-2-yl)piperidine-2,6-dione;
3-(5-(((1R,2R)-2-aminocyclohexyl)oxy)-1-oxoisoindolin-2-yl)piperidine-2,6-dione;
3-(5-(((1R,2S)-2-aminocyclohexyl)oxy)-1-oxoisoindolin-2-yl)piperidine-2,6-dione;
3-(5-((2-aminocyclohexyl)oxy)-1-oxoisoindolin-2-yl)piperidine-2,6-dione;
3-(5-(((1S,2S)-2-(3-azabicyclo[3.2.1]octan-3-yl)cyclopentyl)oxy)-1-oxoisoindolin-2-yl)piperidine-2,6-dione;
3-(5-(((1S,2R)-2-(3-azabicyclo[3.2.1]octan-3-yl)cyclopentyl)oxy)-1-oxoisoindolin-2-yl)piperidine-2,6-dione;
3-(5-(((1R,2R)-2-(3-azabicyclo[3.2.1]octan-3-yl)cyclopentyl)oxy)-1-oxoisoindolin-2-yl)piperidine-2,6-dione;
3-(5-(((1R,2S)-2-(3-azabicyclo[3.2.1]octan-3-yl)cyclopentyl)oxy)-1-oxoisoindolin-2-yl)piperidine-2,6-dione;
3-(5-((2-(3-azabicyclo[3.2.1]octan-3-yl)cyclopentyl)oxy)-1-oxoisoindolin-2-yl)piperidine-2,6-dione;
3-(5-(((1S,2S)-2-(1,4-dioxa-8-azaspiro[4.5]decan-8-yl)cyclopentyl)oxy)-1-oxoisoindolin-2-yl)piperidine-2,6-dione;
3-(5-(((1S,2R)-2-(1,4-dioxa-8-azaspiro[4.5]decan-8-yl)cyclopentyl)oxy)-1-oxoisoindolin-2-yl)piperidine-2,6-dione;
3-(5-(((1R,2R)-2-(1,4-dioxa-8-azaspiro[4.5]decan-8-yl)cyclopentyl)oxy)-1-oxoisoindolin-2-yl)piperidine-2,6-dione;
3-(5-(((1R,2S)-2-(1,4-dioxa-8-azaspiro[4.5]decan-8-yl)cyclopentyl)oxy)-1-oxoisoindolin-2-yl)piperidine-2,6-dione;
3-(5-((2-(1,4-dioxa-8-azaspiro[4.5]decan-8-yl)cyclopentyl)oxy)-1-oxoisoindolin-2-yl)piperidine-2,6-dione;
3-(5-(((1S,2S)-2-(8-oxa-3-azabicyclo[3.2.1]octan-3-yl)cyclopentyl)oxy)-1-oxoisoindolin-2-yl)piperidine-2,6-dione;
3-(5-(((1S,2R)-2-(8-oxa-3-azabicyclo[3.2.1]octan-3-yl)cyclopentyl)oxy)-1-oxoisoindolin-2-yl)piperidine-2,6-dione;
3-(5-(((1R,2R)-2-(8-oxa-3-azabicyclo[3.2.1]octan-3-yl)cyclopentyl)oxy)-1-oxoisoindolin-2-yl)piperidine-2,6-dione;
3-(5-(((1R,2S)-2-(8-oxa-3-azabicyclo[3.2.1]octan-3-yl)cyclopentyl)oxy)-1-oxoisoindolin-2-yl)piperidine-2,6-dione;
3-(5-((2-(8-oxa-3-azabicyclo[3.2.1]octan-3-yl)cyclopentyl)oxy)-1-oxoisoindolin-2-yl)piperidine-2,6-dione;
3-(1-oxo-5-(((1S,2S)-2-phenoxycyclohexyl)oxy)isoindolin-2-yl)piperidine-2,6-dione;
3-(1-oxo-5-(((1S,2R)-2-phenoxycyclohexyl)oxy)isoindolin-2-yl)piperidine-2,6-dione;
3-(1-oxo-5-(((1R,2R)-2-phenoxycyclohexyl)oxy)isoindolin-2-yl)piperidine-2,6-dione;
3-(1-oxo-5-(((1R,2S)-2-phenoxycyclohexyl)oxy)isoindolin-2-yl)piperidine-2,6-dione;
3-(1-oxo-5-((2-phenoxycyclohexyl)oxy)isoindolin-2-yl)piperidine-2,6-dione;
3-(5-(((1S,2S)-2-(benzylamino)cyclopentyl)oxy)-1-oxoisoindolin-2-yl)piperidine-2,6-dione;
3-(5-(((1S,2R)-2-(benzylamino)cyclopentyl)oxy)-1-oxoisoindolin-2-yl)piperidine-2,6-dione;
3-(5-(((1R,2R)-2-(benzylamino)cyclopentyl)oxy)-1-oxoisoindolin-2-yl)piperidine-2,6-dione;
3-(5-(((1R,2S)-2-(benzylamino)cyclopentyl)oxy)-1-oxoisoindolin-2-yl)piperidine-2,6-dione;
3-(5-((2-(benzylamino)cyclopentyl)oxy)-1-oxoisoindolin-2-yl)piperidine-2,6-dione;
3-(5-(((3S,4S)-3-(benzylamino)tetrahydro-2H-pyran-4-yl)oxy)-1-oxoisoindolin-2-yl)piperidine-2,6-dione;
3-(5-(((3R,4S)-3-(benzylamino)tetrahydro-2H-pyran-4-yl)oxy)-1-oxoisoindolin-2-yl)piperidine-2,6-dione;
3-(5-(((3R,4R)-3-(benzylamino)tetrahydro-2H-pyran-4-yl)oxy)-1-oxoisoindolin-2-yl)piperidine-2,6-dione;
3-(5-(((3S,4R)-3-(benzylamino)tetrahydro-2H-pyran-4-yl)oxy)-1-oxoisoindolin-2-yl)piperidine-2,6-dione;
3-(5-((3-(benzylamino)tetrahydro-2H-pyran-4-yl)oxy)-1-oxoisoindolin-2-yl)piperidine-2,6-dione;
3-(5-(((1S,2S)-2-(benzylamino)cyclohexyl)oxy)-1-oxoisoindolin-2-yl)piperidine-2,6-dione;
3-(5-(((1S,2R)-2-(benzylamino)cyclohexyl)oxy)-1-oxoisoindolin-2-yl)piperidine-2,6-dione;
3-(5-(((1R,2R)-2-(benzylamino)cyclohexyl)oxy)-1-oxoisoindolin-2-yl)piperidine-2,6-dione;
3-(5-(((1R,2S)-2-(benzylamino)cyclohexyl)oxy)-1-oxoisoindolin-2-yl)piperidine-2,6-dione;
3-(5-((2-(benzylamino)cyclohexyl)oxy)-1-oxoisoindolin-2-yl)piperidine-2,6-dione;
3-(1-oxo-5-(((1S,2S)-2-(((R)-1-phenylethyl)amino)cyclohexyl)oxy)isoindolin-2-yl)piperidine-2,6-dione;
3-(1-oxo-5-(((1S,2R)-2-(((R)-1-phenylethyl)amino)cyclohexyl)oxy)isoindolin-2-yl)piperidine-2,6-dione;
3-(1-oxo-5-(((1R,2R)-2-(((R)-1-phenylethyl)amino)cyclohexyl)oxy)isoindolin-2-yl)piperidine-2,6-dione;
3-(1-oxo-5-(((1R,2S)-2-(((R)-1-phenylethyl)amino)cyclohexyl)oxy)isoindolin-2-yl)piperidine-2,6-dione;
3-(1-oxo-5-((2-(((R)-1-phenylethyl)amino)cyclohexyl)oxy)isoindolin-2-yl)piperidine-2,6-dione;
3-(5-(((1S,2S)-2-(ethyl(2-fluoroethyl)amino)cyclopentyl)oxy)-1-oxoisoindolin-2-yl)piperidine-2,6-dione;
3-(5-(((1S,2R)-2-(ethyl(2-fluoroethyl)amino)cyclopentyl)oxy)-1-oxoisoindolin-2-yl)piperidine-2,6-dione;
3-(5-(((1R,2R)-2-(ethyl(2-fluoroethyl)amino)cyclopentyl)oxy)-1-oxoisoindolin-2-yl)piperidine-2,6-dione;
3-(5-(((1R,2S)-2-(ethyl(2-fluoroethyl)amino)cyclopentyl)oxy)-1-oxoisoindolin-2-yl)piperidine-2,6-dione;
3-(5-((2-(ethyl(2-fluoroethyl)amino)cyclopentyl)oxy)-1-oxoisoindolin-2-yl)piperidine-2,6-dione;
3-(5-(((1S,2S)-2-(ethyl(isopropyl)amino)cyclopentyl)oxy)-1-oxoisoindolin-2-yl)piperidine-2,6-dione;
3-(5-(((1S,2R)-2-(ethyl(isopropyl)amino)cyclopentyl)oxy)-1-oxoisoindolin-2-yl)piperidine-2,6-dione;
3-(5-(((1R,2R)-2-(ethyl(isopropyl)amino)cyclopentyl)oxy)-1-oxoisoindolin-2-yl)piperidine-2,6-dione;
3-(5-(((1R,2S)-2-(ethyl(isopropyl)amino)cyclopentyl)oxy)-1-oxoisoindolin-2-yl)piperidine-2,6-dione;

3-(5-((2-(ethyl(isopropyl)amino)cyclopentyl)oxy)-1-oxoisoindolin-2-yl)piperidine-2,6-dione;
3-(5-(((1S,2S)-2-methoxycyclopentyl)oxy)-1-oxoisoindolin-2-yl)piperidine-2,6-dione;
3-(5-(((1S,2R)-2-methoxycyclopentyl)oxy)-1-oxoisoindolin-2-yl)piperidine-2,6-dione;
3-(5-(((1R,2R)-2-methoxycyclopentyl)oxy)-1-oxoisoindolin-2-yl)piperidine-2,6-dione;
3-(5-(((1R,2S)-2-methoxycyclopentyl)oxy)-1-oxoisoindolin-2-yl)piperidine-2,6-dione;
3-(5-((2-methoxycyclopentyl)oxy)-1-oxoisoindolin-2-yl)piperidine-2,6-dione;
3-(5-(((1S,2S)-2-hydroxycyclohexyl)oxy)-1-oxoisoindolin-2-yl)piperidine-2,6-dione;
3-(5-(((1S,2R)-2-hydroxycyclohexyl)oxy)-1-oxoisoindolin-2-yl)piperidine-2,6-dione;
3-(5-(((1R,2R)-2-hydroxycyclohexyl)oxy)-1-oxoisoindolin-2-yl)piperidine-2,6-dione;
3-(5-(((1R,2S)-2-hydroxycyclohexyl)oxy)-1-oxoisoindolin-2-yl)piperidine-2,6-dione;
3-(5-((2-hydroxycyclohexyl)oxy)-1-oxoisoindolin-2-yl)piperidine-2,6-dione;
3-(5-(((1S,2S)-2-(ethylamino)cyclopentyl)oxy)-1-oxoisoindolin-2-yl)piperidine-2,6-dione;
3-(5-(((1S,2R)-2-(ethylamino)cyclopentyl)oxy)-1-oxoisoindolin-2-yl)piperidine-2,6-dione;
3-(5-(((1R,2R)-2-(ethylamino)cyclopentyl)oxy)-1-oxoisoindolin-2-yl)piperidine-2,6-dione;
3-(5-(((1R,2S)-2-(ethylamino)cyclopentyl)oxy)-1-oxoisoindolin-2-yl)piperidine-2,6-dione;
3-(5-((2-(ethylamino)cyclopentyl)oxy)-1-oxoisoindolin-2-yl)piperidine-2,6-dione;
3-(5-(((1S,2S)-2-(bis(cyclopropylmethyl)amino)cyclopentyl)oxy)-1-oxoisoindolin-2-yl)piperidine-2,6-dione;
3-(5-(((1R,2S)-2-(bis(cyclopropylmethyl)amino)cyclopentyl)oxy)-1-oxoisoindolin-2-yl)piperidine-2,6-dione;
3-(5-(((1R,2R)-2-(bis(cyclopropylmethyl)amino)cyclopentyl)oxy)-1-oxoisoindolin-2-yl)piperidine-2,6-dione;
3-(5-(((1S,2R)-2-(bis(cyclopropylmethyl)amino)cyclopentyl)oxy)-1-oxoisoindolin-2-yl)piperidine-2,6-dione;
3-(5-((2-(bis(cyclopropylmethyl)amino)cyclopentyl)oxy)-1-oxoisoindolin-2-yl)piperidine-2,6-dione;
3-(1-oxo-5-(((1S,2S)-2-(piperidin-1-yl)cyclopentyl)oxy)isoindolin-2-yl)piperidine-2,6-dione;
3-(1-oxo-5-(((1S,2R)-2-(piperidin-1-yl)cyclopentyl)oxy)isoindolin-2-yl)piperidine-2,6-dione;
3-(1-oxo-5-(((1R,2R)-2-(piperidin-1-yl)cyclopentyl)oxy)isoindolin-2-yl)piperidine-2,6-dione;
3-(1-oxo-5-(((1R,2S)-2-(piperidin-1-yl)cyclopentyl)oxy)isoindolin-2-yl)piperidine-2,6-dione;
3-(1-oxo-5-((2-(piperidin-1-yl)cyclopentyl)oxy)isoindolin-2-yl)piperidine-2,6-dione;
3-(5-(((1S,2S)-2-morpholinocyclopentyl)oxy)-1-oxoisoindolin-2-yl)piperidine-2,6-dione;
3-(5-(((1S,2R)-2-morpholinocyclopentyl)oxy)-1-oxoisoindolin-2-yl)piperidine-2,6-dione;
3-(5-(((1R,2R)-2-morpholinocyclopentyl)oxy)-1-oxoisoindolin-2-yl)piperidine-2,6-dione;
3-(5-(((1R,2S)-2-morpholinocyclopentyl)oxy)-1-oxoisoindolin-2-yl)piperidine-2,6-dione;
3-(5-((2-morpholinocyclopentyl)oxy)-1-oxoisoindolin-2-yl)piperidine-2,6-dione;
3-(5-(((1S,2S)-2-(dibenzylamino)cyclohexyl)oxy)-1-oxoisoindolin-2-yl)piperidine-2,6-dione;
3-(5-(((1S,2R)-2-(dibenzylamino)cyclohexyl)oxy)-1-oxoisoindolin-2-yl)piperidine-2,6-dione;
3-(5-(((1R,2R)-2-(dibenzylamino)cyclohexyl)oxy)-1-oxoisoindolin-2-yl)piperidine-2,6-dione;
3-(5-(((1R,2S)-2-(dibenzylamino)cyclohexyl)oxy)-1-oxoisoindolin-2-yl)piperidine-2,6-dione;
3-(5-((2-(dibenzylamino)cyclohexyl)oxy)-1-oxoisoindolin-2-yl)piperidine-2,6-dione;
cis-3-(5-((2-(diethylamino)cyclohexyl)oxy)-1-oxoisoindolin-2-yl)piperidine-2,6-dione;
trans-3-(5-((2-(diethylamino)cyclohexyl)oxy)-1-oxoisoindolin-2-yl)piperidine-2,6-dione;
3-(5-(((1S,2S)-2-(methylamino)cyclohexyl)oxy)-1-oxoisoindolin-2-yl)piperidine-2,6-dione;
3-(5-(((1S,2R)-2-(methylamino)cyclohexyl)oxy)-1-oxoisoindolin-2-yl)piperidine-2,6-dione;
3-(5-(((1R,2R)-2-(methylamino)cyclohexyl)oxy)-1-oxoisoindolin-2-yl)piperidine-2,6-dione;
3-(5-(((1R,2S)-2-(methylamino)cyclohexyl)oxy)-1-oxoisoindolin-2-yl)piperidine-2,6-dione;
3-(5-((2-(methylamino)cyclohexyl)oxy)-1-oxoisoindolin-2-yl)piperidine-2,6-dione;
1-((1S,2S)-2-((2-(2,6-dioxopiperidin-3-yl)-1-oxoisoindolin-5-yl)oxy)cyclopentyl)-4-methylpiperidine-4-carbonitrile;
1-((1R,2S)-2-((2-(2,6-dioxopiperidin-3-yl)-1-oxoisoindolin-5-yl)oxy)cyclopentyl)-4-methylpiperidine-4-carbonitrile;
1-((1R,2R)-2-((2-(2,6-dioxopiperidin-3-yl)-1-oxoisoindolin-5-yl)oxy)cyclopentyl)-4-methylpiperidine-4-carbonitrile;
1-((1S,2R)-2-((2-(2,6-dioxopiperidin-3-yl)-1-oxoisoindolin-5-yl)oxy)cyclopentyl)-4-methylpiperidine-4-carbonitrile;
1-(2-((2-(2,6-dioxopiperidin-3-yl)-1-oxoisoindolin-5-yl)oxy)cyclopentyl)-4-methylpiperidine-4-carbonitrile;
3-(5-(((1S,2S)-2-(benzyl(methyl)amino)cyclohexyl)oxy)-1-oxoisoindolin-2-yl)piperidine-2,6-dione;
3-(5-(((1S,2R)-2-(benzyl(methyl)amino)cyclohexyl)oxy)-1-oxoisoindolin-2-yl)piperidine-2,6-dione;
3-(5-(((1R,2R)-2-(benzyl(methyl)amino)cyclohexyl)oxy)-1-oxoisoindolin-2-yl)piperidine-2,6-dione;
3-(5-(((1R,2S)-2-(benzyl(methyl)amino)cyclohexyl)oxy)-1-oxoisoindolin-2-yl)piperidine-2,6-dione;
3-(5-((2-(benzyl(methyl)amino)cyclohexyl)oxy)-1-oxoisoindolin-2-yl)piperidine-2,6-dione;
3-(5-(((3S,4S)-3-aminotetrahydro-2H-pyran-4-yl)oxy)-1-oxoisoindolin-2-yl)piperidine-2,6-dione;
3-(5-(((3R,4S)-3-aminotetrahydro-2H-pyran-4-yl)oxy)-1-oxoisoindolin-2-yl)piperidine-2,6-dione;
3-(5-(((3R,4R)-3-aminotetrahydro-2H-pyran-4-yl)oxy)-1-oxoisoindolin-2-yl)piperidine-2,6-dione;
3-(5-(((3S,4R)-3-aminotetrahydro-2H-pyran-4-yl)oxy)-1-oxoisoindolin-2-yl)piperidine-2,6-dione;
3-(5-((3-aminotetrahydro-2H-pyran-4-yl)oxy)-1-oxoisoindolin-2-yl)piperidine-2,6-dione;
3-(5-((1S,2S)-2-(benzylamino)cyclobutoxy)-1-oxoisoindolin-2-yl)piperidine-2,6-dione;
3-(5-((1R,2R)-2-(benzylamino)cyclobutoxy)-1-oxoisoindolin-2-yl)piperidine-2,6-dione;
3-(5-((1S,2R)-2-(benzylamino)cyclobutoxy)-1-oxoisoindolin-2-yl)piperidine-2,6-dione;
3-(5-((1R,2S)-2-(benzylamino)cyclobutoxy)-1-oxoisoindolin-2-yl)piperidine-2,6-dione;

3-(5-(2-(benzylamino)cyclobutoxy)-1-oxoisoindolin-2-yl)piperidine-2,6-dione;
3-(5-(((3R,4S)-4-aminotetrahydrofuran-3-yl)oxy)-1-oxoisoindolin-2-yl)piperidine-2,6-dione;
3-(5-(((3R,4R)-4-aminotetrahydrofuran-3-yl)oxy)-1-oxoisoindolin-2-yl)piperidine-2,6-dione;
3-(5-(((3S,4R)-4-aminotetrahydrofuran-3-yl)oxy)-1-oxoisoindolin-2-yl)piperidine-2,6-dione;
3-(5-(((3S,4S)-4-aminotetrahydrofuran-3-yl)oxy)-1-oxoisoindolin-2-yl)piperidine-2,6-dione;
3-(5-((4-aminotetrahydrofuran-3-yl)oxy)-1-oxoisoindolin-2-yl)piperidine-2,6-dione;
3-(5-(((3R,4S)-4-(diethylamino)tetrahydrofuran-3-yl)oxy)-1-oxoisoindolin-2-yl)piperidine-2,6-dione;
3-(5-(((3R,4R)-4-(diethylamino)tetrahydrofuran-3-yl)oxy)-1-oxoisoindolin-2-yl)piperidine-2,6-dione;
3-(5-(((3S,4R)-4-(diethylamino)tetrahydrofuran-3-yl)oxy)-1-oxoisoindolin-2-yl)piperidine-2,6-dione;
3-(5-(((3S,4S)-4-(diethylamino)tetrahydrofuran-3-yl)oxy)-1-oxoisoindolin-2-yl)piperidine-2,6-dione;
3-(5-((4-(diethylamino)tetrahydrofuran-3-yl)oxy)-1-oxoisoindolin-2-yl)piperidine-2,6-dione;
3-(5-(((1S,2S)-2-(ethylamino)cyclohexyl)oxy)-1-oxoisoindolin-2-yl)piperidine-2,6-dione;
3-(5-(((1S,2R)-2-(ethylamino)cyclohexyl)oxy)-1-oxoisoindolin-2-yl)piperidine-2,6-dione;
3-(5-(((1R,2R)-2-(ethylamino)cyclohexyl)oxy)-1-oxoisoindolin-2-yl)piperidine-2,6-dione;
3-(5-(((1R,2S)-2-(ethylamino)cyclohexyl)oxy)-1-oxoisoindolin-2-yl)piperidine-2,6-dione;
3-(5-((2-(ethylamino)cyclohexyl)oxy)-1-oxoisoindolin-2-yl)piperidine-2,6-dione;
4-((((1S,2S)-2-((2-(2,6-dioxopiperidin-3-yl)-1-oxoisoindolin-5-yl)oxy)cyclohexyl)amino)methyl)benzonitrile;
4-((((1R,2S)-2-((2-(2,6-dioxopiperidin-3-yl)-1-oxoisoindolin-5-yl)oxy)cyclohexyl)amino)methyl)benzonitrile;
4-((((1R,2R)-2-((2-(2,6-dioxopiperidin-3-yl)-1-oxoisoindolin-5-yl)oxy)cyclohexyl)amino)methyl)benzonitrile;
4-((((1S,2R)-2-((2-(2,6-dioxopiperidin-3-yl)-1-oxoisoindolin-5-yl)oxy)cyclohexyl)amino)methyl)benzonitrile;
4-(((2-((2-(2,6-dioxopiperidin-3-yl)-1-oxoisoindolin-5-yl)oxy)cyclohexyl)amino)methyl)benzonitrile;
3-(5-((1S,2S)-2-(diethylamino)cyclobutoxy)-1-oxoisoindolin-2-yl)piperidine-2,6-dione;
3-(5-((1R,2S)-2-(diethylamino)cyclobutoxy)-1-oxoisoindolin-2-yl)piperidine-2,6-dione;
3-(5-((1R,2R)-2-(diethylamino)cyclobutoxy)-1-oxoisoindolin-2-yl)piperidine-2,6-dione;
3-(5-((1S,2R)-2-(diethylamino)cyclobutoxy)-1-oxoisoindolin-2-yl)piperidine-2,6-dione;
3-(5-(2-(diethylamino)cyclobutoxy)-1-oxoisoindolin-2-yl)piperidine-2,6-dione;
3-(5-(((1S,2S)-2-(ethyl((3-fluorobicyclo[1.1.1]pentan-1-yl)methyl)amino)cyclopentyl)oxy)-1-oxoisoindolin-2-yl)piperidine-2,6-dione;
3-(5-(((1S,2R)-2-(ethyl((3-fluorobicyclo[1.1.1]pentan-1-yl)methyl)amino)cyclopentyl)oxy)-1-oxoisoindolin-2-yl)piperidine-2,6-dione;
3-(5-(((1R,2R)-2-(ethyl((3-fluorobicyclo[1.1.1]pentan-1-yl)methyl)amino)cyclopentyl)oxy)-1-oxoisoindolin-2-yl)piperidine-2,6-dione;
3-(5-(((1R,2S)-2-(ethyl((3-fluorobicyclo[1.1.1]pentan-1-yl)methyl)amino)cyclopentyl)oxy)-1-oxoisoindolin-2-yl)piperidine-2,6-dione;
3-(5-((2-(ethyl((3-fluorobicyclo[1.1.1]pentan-1-yl)methyl)amino)cyclopentyl)oxy)-1-oxoisoindolin-2-yl)piperidine-2,6-dione;
3-((((1S,2S)-2-((2-(2,6-dioxopiperidin-3-yl)-1-oxoisoindolin-5-yl)oxy)cyclohexyl)amino)methyl)benzonitrile;
3-((((1R,2S)-2-((2-(2,6-dioxopiperidin-3-yl)-1-oxoisoindolin-5-yl)oxy)cyclohexyl)amino)methyl)benzonitrile;
3-((((1R,2R)-2-((2-(2,6-dioxopiperidin-3-yl)-1-oxoisoindolin-5-yl)oxy)cyclohexyl)amino)methyl)benzonitrile;
3-((((1S,2R)-2-((2-(2,6-dioxopiperidin-3-yl)-1-oxoisoindolin-5-yl)oxy)cyclohexyl)amino)methyl)benzonitrile;
3-(((2-((2-(2,6-dioxopiperidin-3-yl)-1-oxoisoindolin-5-yl)oxy)cyclohexyl)amino)methyl)benzonitrile;
3-(5-(((1S,2S)-2-(isopropylamino)cyclohexyl)oxy)-1-oxoisoindolin-2-yl)piperidine-2,6-dione;
3-(5-(((1S,2R)-2-(isopropylamino)cyclohexyl)oxy)-1-oxoisoindolin-2-yl)piperidine-2,6-dione;
3-(5-(((1R,2S)-2-(isopropylamino)cyclohexyl)oxy)-1-oxoisoindolin-2-yl)piperidine-2,6-dione;
3-(5-(((1R,2R)-2-(isopropylamino)cyclohexyl)oxy)-1-oxoisoindolin-2-yl)piperidine-2,6-dione;
3-(5-((2-(isopropylamino)cyclohexyl)oxy)-1-oxoisoindolin-2-yl)piperidine-2,6-dione;
2-((((1S,2S)-2-((2-(2,6-dioxopiperidin-3-yl)-1-oxoisoindolin-5-yl)oxy)cyclohexyl)amino)methyl)benzonitrile;
2-((((1R,2S)-2-((2-(2,6-dioxopiperidin-3-yl)-1-oxoisoindolin-5-yl)oxy)cyclohexyl)amino)methyl)benzonitrile;
2-((((1R,2R)-2-((2-(2,6-dioxopiperidin-3-yl)-1-oxoisoindolin-5-yl)oxy)cyclohexyl)amino)methyl)benzonitrile;
2-((((1S,2R)-2-((2-(2,6-dioxopiperidin-3-yl)-1-oxoisoindolin-5-yl)oxy)cyclohexyl)amino)methyl)benzonitrile;
2-(((2-((2-(2,6-dioxopiperidin-3-yl)-1-oxoisoindolin-5-yl)oxy)cyclohexyl)amino)methyl)benzonitrile;
3-(5-(((1S,2S)-2-(((3-fluorobicyclo[1.1.1]pentan-1-yl)methyl)amino)cyclohexyl)oxy)-1-oxoisoindolin-2-yl)piperidine-2,6-dione;
3-(5-(((1R,2S)-2-(((3-fluorobicyclo[1.1.1]pentan-1-yl)methyl)amino)cyclohexyl)oxy)-1-oxoisoindolin-2-yl)piperidine-2,6-dione;
3-(5-(((1R,2R)-2-(((3-fluorobicyclo[1.1.1]pentan-1-yl)methyl)amino)cyclohexyl)oxy)-1-oxoisoindolin-2-yl)piperidine-2,6-dione;
3-(5-(((1S,2R)-2-(((3-fluorobicyclo[1.1.1]pentan-1-yl)methyl)amino)cyclohexyl)oxy)-1-oxoisoindolin-2-yl)piperidine-2,6-dione;
3-(5-((2-(((3-fluorobicyclo[1.1.1]pentan-1-yl)methyl)amino)cyclohexyl)oxy)-1-oxoisoindolin-2-yl)piperidine-2,6-dione;
3-(5-(((1S,2S)-2-(4-hydroxy-4-methylpiperidin-1-yl)cyclopentyl)oxy)-1-oxoisoindolin-2-yl)piperidine-2,6-dione;
3-(5-(((1S,2R)-2-(4-hydroxy-4-methylpiperidin-1-yl)cyclopentyl)oxy)-1-oxoisoindolin-2-yl)piperidine-2,6-dione;
3-(5-(((1R,2R)-2-(4-hydroxy-4-methylpiperidin-1-yl)cyclopentyl)oxy)-1-oxoisoindolin-2-yl)piperidine-2,6-dione;
3-(5-(((1R,2S)-2-(4-hydroxy-4-methylpiperidin-1-yl)cyclopentyl)oxy)-1-oxoisoindolin-2-yl)piperidine-2,6-dione;
3-(5-((2-(4-hydroxy-4-methylpiperidin-1-yl)cyclopentyl)oxy)-1-oxoisoindolin-2-yl)piperidine-2,6-dione;
3-(5-(((1S,2S)-2-(4-hydroxy-4-(trifluoromethyl)piperidin-1-yl)cyclopentyl)oxy)-1-oxoisoindolin-2-yl)piperidine-2,6-dione;
3-(5-(((1S,2R)-2-(4-hydroxy-4-(trifluoromethyl)piperidin-1-yl)cyclopentyl)oxy)-1-oxoisoindolin-2-yl)piperidine-2,6-dione;

3-(5-((((1R,2R)-2-(4-hydroxy-4-(trifluoromethyl)piperidin-1-yl)cyclopentyl)oxy)-1-oxoisoindolin-2-yl)piperidine-2,6-dione;

3-(5-((((1R,2S)-2-(4-hydroxy-4-(trifluoromethyl)piperidin-1-yl)cyclopentyl)oxy)-1-oxoisoindolin-2-yl)piperidine-2,6-dione;

3-(5-((2-(4-hydroxy-4-(trifluoromethyl)piperidin-1-yl)cyclopentyl)oxy)-1-oxoisoindolin-2-yl)piperidine-2,6-dione;

1-(((1S,2S)-2-((2-(2,6-dioxopiperidin-3-yl)-1-oxoisoindolin-5-yl)oxy)cyclopentyl)-4-(trifluoromethyl)piperidine-4-carbonitrile;

1-(((1R,2S)-2-((2-(2,6-dioxopiperidin-3-yl)-1-oxoisoindolin-5-yl)oxy)cyclopentyl)-4-(trifluoromethyl)piperidine-4-carbonitrile;

1-(((1R,2R)-2-((2-(2,6-dioxopiperidin-3-yl)-1-oxoisoindolin-5-yl)oxy)cyclopentyl)-4-(trifluoromethyl)piperidine-4-carbonitrile;

1-(((1S,2R)-2-((2-(2,6-dioxopiperidin-3-yl)-1-oxoisoindolin-5-yl)oxy)cyclopentyl)-4-(trifluoromethyl)piperidine-4-carbonitrile;

1-(2-((2-(2,6-dioxopiperidin-3-yl)-1-oxoisoindolin-5-yl)oxy)cyclopentyl)-4-(trifluoromethyl)piperidine-4-carbonitrile;

3-(5-((((1S,2S)-2-(2-oxa-7-azaspiro[3.5]nonan-7-yl)cyclopentyl)oxy)-1-oxoisoindolin-2-yl)piperidine-2,6-dione;

3-(5-((((1S,2R)-2-(2-oxa-7-azaspiro[3.5]nonan-7-yl)cyclopentyl)oxy)-1-oxoisoindolin-2-yl)piperidine-2,6-dione;

3-(5-((((1R,2R)-2-(2-oxa-7-azaspiro[3.5]nonan-7-yl)cyclopentyl)oxy)-1-oxoisoindolin-2-yl)piperidine-2,6-dione;

3-(5-((((1R,2S)-2-(2-oxa-7-azaspiro[3.5]nonan-7-yl)cyclopentyl)oxy)-1-oxoisoindolin-2-yl)piperidine-2,6-dione;

3-(5-((2-(2-oxa-7-azaspiro[3.5]nonan-7-yl)cyclopentyl)oxy)-1-oxoisoindolin-2-yl)piperidine-2,6-dione;

3-(1-oxo-5-(((1S,2S)-2-(3-(2,2,2-trifluoroethoxy)azetidin-1-yl)cyclohexyl)oxy)isoindolin-2-yl)piperidine-2,6-dione;

3-(1-oxo-5-(((1R,2S)-2-(3-(2,2,2-trifluoroethoxy)azetidin-1-yl)cyclohexyl)oxy)isoindolin-2-yl)piperidine-2,6-dione;

3-(1-oxo-5-(((1S,2R)-2-(3-(2,2,2-trifluoroethoxy)azetidin-1-yl)cyclohexyl)oxy)isoindolin-2-yl)piperidine-2,6-dione;

3-(1-oxo-5-(((1R,2R)-2-(3-(2,2,2-trifluoroethoxy)azetidin-1-yl)cyclohexyl)oxy)isoindolin-2-yl)piperidine-2,6-dione;

3-(1-oxo-5-((2-(3-(2,2,2-trifluoroethoxy)azetidin-1-yl)cyclohexyl)oxy)isoindolin-2-yl)piperidine-2,6-dione;

3-(5-((((1S,2S)-2-(3-(2,2-difluoroethoxy)azetidin-1-yl)cyclohexyl)oxy)-1-oxoisoindolin-2-yl)piperidine-2,6-dione;

3-(5-((((1R,2S)-2-(3-(2,2-difluoroethoxy)azetidin-1-yl)cyclohexyl)oxy)-1-oxoisoindolin-2-yl)piperidine-2,6-dione;

3-(5-((((1S,2R)-2-(3-(2,2-difluoroethoxy)azetidin-1-yl)cyclohexyl)oxy)-1-oxoisoindolin-2-yl)piperidine-2,6-dione;

3-(5-((((1R,2R)-2-(3-(2,2-difluoroethoxy)azetidin-1-yl)cyclohexyl)oxy)-1-oxoisoindolin-2-yl)piperidine-2,6-dione;

3-(5-((2-(3-(2,2-difluoroethoxy)azetidin-1-yl)cyclohexyl)oxy)-1-oxoisoindolin-2-yl)piperidine-2,6-dione;

3-(5-((((1S,2S)-2-(3-(cyclopropylmethoxy)azetidin-1-yl)cyclohexyl)oxy)-1-oxoisoindolin-2-yl)piperidine-2,6-dione;

3-(5-((((1R,2S)-2-(3-(cyclopropylmethoxy)azetidin-1-yl)cyclohexyl)oxy)-1-oxoisoindolin-2-yl)piperidine-2,6-dione;

3-(5-((((1S,2R)-2-(3-(cyclopropylmethoxy)azetidin-1-yl)cyclohexyl)oxy)-1-oxoisoindolin-2-yl)piperidine-2,6-dione;

3-(5-((((1R,2R)-2-(3-(cyclopropylmethoxy)azetidin-1-yl)cyclohexyl)oxy)-1-oxoisoindolin-2-yl)piperidine-2,6-dione;

3-(5-((2-(3-(cyclopropylmethoxy)azetidin-1-yl)cyclohexyl)oxy)-1-oxoisoindolin-2-yl)piperidine-2,6-dione;

3-(5-((((1S,2S)-2-(3-(benzyloxy)azetidin-1-yl)cyclopentyl)oxy)-1-oxoisoindolin-2-yl)piperidine-2,6-dione;

3-(5-((((1R,2S)-2-(3-(benzyloxy)azetidin-1-yl)cyclopentyl)oxy)-1-oxoisoindolin-2-yl)piperidine-2,6-dione;

3-(5-((((1S,2R)-2-(3-(benzyloxy)azetidin-1-yl)cyclopentyl)oxy)-1-oxoisoindolin-2-yl)piperidine-2,6-dione;

3-(5-((((1R,2R)-2-(3-(benzyloxy)azetidin-1-yl)cyclopentyl)oxy)-1-oxoisoindolin-2-yl)piperidine-2,6-dione;

3-(5-((2-(3-(benzyloxy)azetidin-1-yl)cyclopentyl)oxy)-1-oxoisoindolin-2-yl)piperidine-2,6-dione;

3-(5-((((1S,2S)-2-(3-isopropoxyazetidin-1-yl)cyclohexyl)oxy)-1-oxoisoindolin-2-yl)piperidine-2,6-dione;

3-(5-((((1R,2S)-2-(3-isopropoxyazetidin-1-yl)cyclohexyl)oxy)-1-oxoisoindolin-2-yl)piperidine-2,6-dione;

3-(5-((((1S,2R)-2-(3-isopropoxyazetidin-1-yl)cyclohexyl)oxy)-1-oxoisoindolin-2-yl)piperidine-2,6-dione;

3-(5-((((1R,2R)-2-(3-isopropoxyazetidin-1-yl)cyclohexyl)oxy)-1-oxoisoindolin-2-yl)piperidine-2,6-dione;

3-(5-((2-(3-isopropoxyazetidin-1-yl)cyclohexyl)oxy)-1-oxoisoindolin-2-yl)piperidine-2,6-dione;

3-(5-((((1R,2R)-2-(3-ethoxyazetidin-1-yl)cyclohexyl)oxy)-1-oxoisoindolin-2-yl)piperidine-2,6-dione;

3-(5-((((1R,2S)-2-(3-ethoxyazetidin-1-yl)cyclohexyl)oxy)-1-oxoisoindolin-2-yl)piperidine-2,6-dione;

3-(5-((((1S,2R)-2-(3-ethoxyazetidin-1-yl)cyclohexyl)oxy)-1-oxoisoindolin-2-yl)piperidine-2,6-dione;

3-(5-((((1S,2S)-2-(3-ethoxyazetidin-1-yl)cyclohexyl)oxy)-1-oxoisoindolin-2-yl)piperidine-2,6-dione;

3-(5-((2-(3-ethoxyazetidin-1-yl)cyclohexyl)oxy)-1-oxoisoindolin-2-yl)piperidine-2,6-dione;

3-(5-((((1S,2S)-2-(3-(benzyloxy)azetidin-1-yl)cyclohexyl)oxy)-1-oxoisoindolin-2-yl)piperidine-2,6-dione;

3-(5-((((1R,2S)-2-(3-(benzyloxy)azetidin-1-yl)cyclohexyl)oxy)-1-oxoisoindolin-2-yl)piperidine-2,6-dione;

3-(5-((((1S,2R)-2-(3-(benzyloxy)azetidin-1-yl)cyclohexyl)oxy)-1-oxoisoindolin-2-yl)piperidine-2,6-dione;

3-(5-((((1R,2R)-2-(3-(benzyloxy)azetidin-1-yl)cyclohexyl)oxy)-1-oxoisoindolin-2-yl)piperidine-2,6-dione;

3-(5-((2-(3-(benzyloxy)azetidin-1-yl)cyclohexyl)oxy)-1-oxoisoindolin-2-yl)piperidine-2,6-dione;

3-(5-((((1S,2S)-2-(3-ethoxyazetidin-1-yl)cycloheptyl)oxy)-1-oxoisoindolin-2-yl)piperidine-2,6-dione;

3-(5-((((1R,2S)-2-(3-ethoxyazetidin-1-yl)cycloheptyl)oxy)-1-oxoisoindolin-2-yl)piperidine-2,6-dione;

3-(5-((((1S,2R)-2-(3-ethoxyazetidin-1-yl)cycloheptyl)oxy)-1-oxoisoindolin-2-yl)piperidine-2,6-dione;

3-(5-((((1R,2R)-2-(3-ethoxyazetidin-1-yl)cycloheptyl)oxy)-1-oxoisoindolin-2-yl)piperidine-2,6-dione;

3-(5-((2-(3-ethoxyazetidin-1-yl)cycloheptyl)oxy)-1-oxoisoindolin-2-yl)piperidine-2,6-dione;

3-(5-((((1S,2S)-2-(3-(3,3-difluorocyclobutoxy)azetidin-1-yl)cyclohexyl)oxy)-1-oxoisoindolin-2-yl)piperidine-2,6-dione;

3-(5-(((1R,2S)-2-(3-(3,3-difluorocyclobutoxy)azetidin-1-yl)cyclohexyl)oxy)-1-oxoisoindolin-2-yl)piperidine-2,6-dione;
3-(5-(((1S,2R)-2-(3-(3,3-difluorocyclobutoxy)azetidin-1-yl)cyclohexyl)oxy)-1-oxoisoindolin-2-yl)piperidine-2,6-dione;
3-(5-(((1R,2R)-2-(3-(3,3-difluorocyclobutoxy)azetidin-1-yl)cyclohexyl)oxy)-1-oxoisoindolin-2-yl)piperidine-2,6-dione;
3-(5-((2-(3-(3,3-difluorocyclobutoxy)azetidin-1-yl)cyclohexyl)oxy)-1-oxoisoindolin-2-yl)piperidine-2,6-dione;
3-(5-(((1S,2S)-2-(4-hydroxypiperidin-1-yl)cyclopentyl)oxy)-1-oxoisoindolin-2-yl)piperidine-2,6-dione;
3-(5-(((1S,2R)-2-(4-hydroxypiperidin-1-yl)cyclopentyl)oxy)-1-oxoisoindolin-2-yl)piperidine-2,6-dione;
3-(5-(((1R,2R)-2-(4-hydroxypiperidin-1-yl)cyclopentyl)oxy)-1-oxoisoindolin-2-yl)piperidine-2,6-dione;
3-(5-(((1R,2S)-2-(4-hydroxypiperidin-1-yl)cyclopentyl)oxy)-1-oxoisoindolin-2-yl)piperidine-2,6-dione;
3-(5-((2-(4-hydroxypiperidin-1-yl)cyclopentyl)oxy)-1-oxoisoindolin-2-yl)piperidine-2,6-dione;
3-(1-oxo-5-(((1S,2S)-2-(4-oxopiperidin-1-yl)cyclopentyl)oxy)isoindolin-2-yl)piperidine-2,6-dione;
3-(5-(((1S,2S)-2-(3-hydroxypyrrolidin-1-yl)cyclopentyl)oxy)-1-oxoisoindolin-2-yl)piperidine-2,6-dione;
3-(5-(((1S,2R)-2-(3-hydroxypyrrolidin-1-yl)cyclopentyl)oxy)-1-oxoisoindolin-2-yl)piperidine-2,6-dione;
3-(5-(((1R,2R)-2-(3-hydroxypyrrolidin-1-yl)cyclopentyl)oxy)-1-oxoisoindolin-2-yl)piperidine-2,6-dione;
3-(5-(((1R,2S)-2-(3-hydroxypyrrolidin-1-yl)cyclopentyl)oxy)-1-oxoisoindolin-2-yl)piperidine-2,6-dione;
3-(5-((2-(3-hydroxypyrrolidin-1-yl)cyclopentyl)oxy)-1-oxoisoindolin-2-yl)piperidine-2,6-dione;
3-(5-(((1S,2S)-2-(3-hydroxy-3-methylazetidin-1-yl)cyclopentyl)oxy)-1-oxoisoindolin-2-yl)piperidine-2,6-dione;
3-(5-(((1S,2R)-2-(3-hydroxy-3-methylazetidin-1-yl)cyclopentyl)oxy)-1-oxoisoindolin-2-yl)piperidine-2,6-dione;
3-(5-(((1R,2R)-2-(3-hydroxy-3-methylazetidin-1-yl)cyclopentyl)oxy)-1-oxoisoindolin-2-yl)piperidine-2,6-dione;
3-(5-(((1R,2S)-2-(3-hydroxy-3-methylazetidin-1-yl)cyclopentyl)oxy)-1-oxoisoindolin-2-yl)piperidine-2,6-dione;
3-(5-((2-(3-hydroxy-3-methylazetidin-1-yl)cyclopentyl)oxy)-1-oxoisoindolin-2-yl)piperidine-2,6-dione;
3-(5-(((1S,2S)-2-(isobutylamino)cyclopentyl)oxy)-1-oxoisoindolin-2-yl)piperidine-2,6-dione;
3-(5-(((1S,2R)-2-(isobutylamino)cyclopentyl)oxy)-1-oxoisoindolin-2-yl)piperidine-2,6-dione;
3-(5-(((1R,2R)-2-(isobutylamino)cyclopentyl)oxy)-1-oxoisoindolin-2-yl)piperidine-2,6-dione;
3-(5-(((1R,2S)-2-(isobutylamino)cyclopentyl)oxy)-1-oxoisoindolin-2-yl)piperidine-2,6-dione;
3-(5-((2-(isobutylamino)cyclopentyl)oxy)-1-oxoisoindolin-2-yl)piperidine-2,6-dione;
3-(5-(((1S,2S)-2-(ethyl(methyl)amino)cyclopentyl)oxy)-1-oxoisoindolin-2-yl)piperidine-2,6-dione;
3-(5-(((1S,2R)-2-(ethyl(methyl)amino)cyclopentyl)oxy)-1-oxoisoindolin-2-yl)piperidine-2,6-dione;
3-(5-(((1R,2R)-2-(ethyl(methyl)amino)cyclopentyl)oxy)-1-oxoisoindolin-2-yl)piperidine-2,6-dione;
3-(5-(((1R,2S)-2-(ethyl(methyl)amino)cyclopentyl)oxy)-1-oxoisoindolin-2-yl)piperidine-2,6-dione;
3-(5-((2-(ethyl(methyl)amino)cyclopentyl)oxy)-1-oxoisoindolin-2-yl)piperidine-2,6-dione;
3-(1-oxo-5-(((1S,2S)-2-((3aR,6aS)-tetrahydro-1H-furo[3,4-c]pyrrol-5(3H)-yl)cyclopentyl)oxy)isoindolin-2-yl)piperidine-2,6-dione;
3-(1-oxo-5-(((1S,2R)-2-((3aR,6aS)-tetrahydro-1H-furo[3,4-c]pyrrol-5(3H)-yl)cyclopentyl)oxy)isoindolin-2-yl)piperidine-2,6-dione;
3-(1-oxo-5-(((1R,2R)-2-((3aR,6aS)-tetrahydro-1H-furo[3,4-c]pyrrol-5(3H)-yl)cyclopentyl)oxy)isoindolin-2-yl)piperidine-2,6-dione;
3-(1-oxo-5-(((1R,2S)-2-((3aR,6aS)-tetrahydro-1H-furo[3,4-c]pyrrol-5(3H)-yl)cyclopentyl)oxy)isoindolin-2-yl)piperidine-2,6-dione;
3-(1-oxo-5-((2-((3aR,6aS)-tetrahydro-1H-furo[3,4-c]pyrrol-5(3H)-yl)cyclopentyl)oxy)isoindolin-2-yl)piperidine-2,6-dione;
3-(1-oxo-5-((2-(tetrahydro-1H-furo[3,4-c]pyrrol-5(3H)-yl)cyclopentyl)oxy)isoindolin-2-yl)piperidine-2,6-dione;
3-(1-oxo-5-(((1S,2S)-2-((pyridin-2-ylmethyl)amino)cyclopentyl)oxy)isoindolin-2-yl)piperidine-2,6-dione;
3-(1-oxo-5-(((1S,2R)-2-((pyridin-2-ylmethyl)amino)cyclopentyl)oxy)isoindolin-2-yl)piperidine-2,6-dione;
3-(1-oxo-5-(((1R,2R)-2-((pyridin-2-ylmethyl)amino)cyclopentyl)oxy)isoindolin-2-yl)piperidine-2,6-dione
3-(1-oxo-5-(((1R,2S)-2-((pyridin-2-ylmethyl)amino)cyclopentyl)oxy)isoindolin-2-yl)piperidine-2,6-dione;
3-(1-oxo-5-((2-((pyridin-2-ylmethyl)amino)cyclopentyl)oxy)isoindolin-2-yl)piperidine-2,6-dione;
3-(1-oxo-5-(((1S,2S)-2-(pyrrolidin-1-yl)cyclopentyl)oxy)isoindolin-2-yl)piperidine-2,6-dione;
3-(1-oxo-5-(((1S,2R)-2-(pyrrolidin-1-yl)cyclopentyl)oxy)isoindolin-2-yl)piperidine-2,6-dione;
3-(1-oxo-5-(((1R,2R)-2-(pyrrolidin-1-yl)cyclopentyl)oxy)isoindolin-2-yl)piperidine-2,6-dione;
3-(1-oxo-5-(((1R,2S)-2-(pyrrolidin-1-yl)cyclopentyl)oxy)isoindolin-2-yl)piperidine-2,6-dione;
3-(1-oxo-5-((2-(pyrrolidin-1-yl)cyclopentyl)oxy)isoindolin-2-yl)piperidine-2,6-dione;
3-(5-(((1S,2S)-2-(2-oxa-6-azaspiro[3.3]heptan-6-yl)cyclopentyl)oxy)-1-oxoisoindolin-2-yl)piperidine-2,6-dione;
3-(5-(((1S,2R)-2-(2-oxa-6-azaspiro[3.3]heptan-6-yl)cyclopentyl)oxy)-1-oxoisoindolin-2-yl)piperidine-2,6-dione;
3-(5-(((1R,2R)-2-(2-oxa-6-azaspiro[3.3]heptan-6-yl)cyclopentyl)oxy)-1-oxoisoindolin-2-yl)piperidine-2,6-dione;
3-(5-(((1R,2S)-2-(2-oxa-6-azaspiro[3.3]heptan-6-yl)cyclopentyl)oxy)-1-oxoisoindolin-2-yl)piperidine-2,6-dione;
3-(5-((2-(2-oxa-6-azaspiro[3.3]heptan-6-yl)cyclopentyl)oxy)-1-oxoisoindolin-2-yl)piperidine-2,6-dione;
3-(5-(((1S,2S)-2-(bis((3-methyloxetan-3-yl)methyl)amino)cyclopentyl)oxy)-1-oxoisoindolin-2-yl)piperidine-2,6-dione;
3-(5-(((1S,2R)-2-(bis((3-methyloxetan-3-yl)methyl)amino)cyclopentyl)oxy)-1-oxoisoindolin-2-yl)piperidine-2,6-dione;
3-(5-(((1R,2R)-2-(bis((3-methyloxetan-3-yl)methyl)amino)cyclopentyl)oxy)-1-oxoisoindolin-2-yl)piperidine-2,6-dione;
3-(5-(((1R,2S)-2-(bis((3-methyloxetan-3-yl)methyl)amino)cyclopentyl)oxy)-1-oxoisoindolin-2-yl)piperidine-2,6-dione;

3-(5-((2-(bis((3-methyloxetan-3-yl)methyl)amino)cyclopentyl)oxy)-1-oxoisoindolin-2-yl)piperidine-2,6-dione;
3-(5-((((1S,2S)-2-(4-methylpiperidin-1-yl)cyclopentyl)oxy)-1-oxoisoindolin-2-yl)piperidine-2,6-dione;
3-(5-((((1S,2R)-2-(4-methylpiperidin-1-yl)cyclopentyl)oxy)-1-oxoisoindolin-2-yl)piperidine-2,6-dione;
3-(5-((((1R,2R)-2-(4-methylpiperidin-1-yl)cyclopentyl)oxy)-1-oxoisoindolin-2-yl)piperidine-2,6-dione;
3-(5-((((1R,2S)-2-(4-methylpiperidin-1-yl)cyclopentyl)oxy)-1-oxoisoindolin-2-yl)piperidine-2,6-dione;
3-(5-((2-(4-methylpiperidin-1-yl)cyclopentyl)oxy)-1-oxoisoindolin-2-yl)piperidine-2,6-dione;
3-(1-oxo-5-((((1S,2S)-2-((pyridin-3-ylmethyl)amino)cyclopentyl)oxy)isoindolin-2-yl)piperidine-2,6-dione;
3-(1-oxo-5-((((1S,2R)-2-((pyridin-3-ylmethyl)amino)cyclopentyl)oxy)isoindolin-2-yl)piperidine-2,6-dione;
3-(1-oxo-5-((((1R,2R)-2-((pyridin-3-ylmethyl)amino)cyclopentyl)oxy)isoindolin-2-yl)piperidine-2,6-dione;
3-(1-oxo-5-((((1R,2S)-2-((pyridin-3-ylmethyl)amino)cyclopentyl)oxy)isoindolin-2-yl)piperidine-2,6-dione;
3-(1-oxo-5-((2-((pyridin-3-ylmethyl)amino)cyclopentyl)oxy)isoindolin-2-yl)piperidine-2,6-dione;
3-(1-oxo-5-((((1S,2S)-2-((pyridin-4-ylmethyl)amino)cyclopentyl)oxy)isoindolin-2-yl)piperidine-2,6-dione;
3-(1-oxo-5-((((1S,2R)-2-((pyridin-4-ylmethyl)amino)cyclopentyl)oxy)isoindolin-2-yl)piperidine-2,6-dione;
3-(1-oxo-5-((((1R,2R)-2-((pyridin-4-ylmethyl)amino)cyclopentyl)oxy)isoindolin-2-yl)piperidine-2,6-dione;
3-(1-oxo-5-((((1R,2S)-2-((pyridin-4-ylmethyl)amino)cyclopentyl)oxy)isoindolin-2-yl)piperidine-2,6-dione;
3-(1-oxo-5-((2-((pyridin-4-ylmethyl)amino)cyclopentyl)oxy)isoindolin-2-yl)piperidine-2,6-dione;
3-(5-((((1S,2S)-2-(4-methoxy-4-methylpiperidin-1-yl)cyclopentyl)oxy)-1-oxoisoindolin-2-yl)piperidine-2,6-dione;
3-(5-((((1S,2R)-2-(4-methoxy-4-methylpiperidin-1-yl)cyclopentyl)oxy)-1-oxoisoindolin-2-yl)piperidine-2,6-dione;
3-(5-((((1R,2R)-2-(4-methoxy-4-methylpiperidin-1-yl)cyclopentyl)oxy)-1-oxoisoindolin-2-yl)piperidine-2,6-dione;
3-(5-((((1R,2S)-2-(4-methoxy-4-methylpiperidin-1-yl)cyclopentyl)oxy)-1-oxoisoindolin-2-yl)piperidine-2,6-dione;
3-(5-((2-(4-methoxy-4-methylpiperidin-1-yl)cyclopentyl)oxy)-1-oxoisoindolin-2-yl)piperidine-2,6-dione;
3-(5-((((1S,2S)-2-(4,4-dimethylpiperidin-1-yl)cyclopentyl)oxy)-1-oxoisoindolin-2-yl)piperidine-2,6-dione;
3-(5-((((1S,2R)-2-(4,4-dimethylpiperidin-1-yl)cyclopentyl)oxy)-1-oxoisoindolin-2-yl)piperidine-2,6-dione;
3-(5-((((1R,2R)-2-(4,4-dimethylpiperidin-1-yl)cyclopentyl)oxy)-1-oxoisoindolin-2-yl)piperidine-2,6-dione;
3-(5-((((1R,2S)-2-(4,4-dimethylpiperidin-1-yl)cyclopentyl)oxy)-1-oxoisoindolin-2-yl)piperidine-2,6-dione;
3-(5-((2-(4,4-dimethylpiperidin-1-yl)cyclopentyl)oxy)-1-oxoisoindolin-2-yl)piperidine-2,6-dione;
3-(5-((((1S,2S)-2-(4-methoxypiperidin-1-yl)cyclopentyl)oxy)-1-oxoisoindolin-2-yl)piperidine-2,6-dione;
3-(5-((((1S,2R)-2-(4-methoxypiperidin-1-yl)cyclopentyl)oxy)-1-oxoisoindolin-2-yl)piperidine-2,6-dione;
3-(5-((((1R,2R)-2-(4-methoxypiperidin-1-yl)cyclopentyl)oxy)-1-oxoisoindolin-2-yl)piperidine-2,6-dione;
3-(5-((((1R,2S)-2-(4-methoxypiperidin-1-yl)cyclopentyl)oxy)-1-oxoisoindolin-2-yl)piperidine-2,6-dione;
3-(5-((2-(4-methoxypiperidin-1-yl)cyclopentyl)oxy)-1-oxoisoindolin-2-yl)piperidine-2,6-dione;
3-(5-((((1S,2S)-2-(ethyl(oxetan-3-ylmethyl)amino)cyclopentyl)oxy)-1-oxoisoindolin-2-yl)piperidine-2,6-dione;
3-(5-((((1S,2R)-2-(ethyl(oxetan-3-ylmethyl)amino)cyclopentyl)oxy)-1-oxoisoindolin-2-yl)piperidine-2,6-dione;
3-(5-((((1R,2R)-2-(ethyl(oxetan-3-ylmethyl)amino)cyclopentyl)oxy)-1-oxoisoindolin-2-yl)piperidine-2,6-dione;
3-(5-((((1R,2S)-2-(ethyl(oxetan-3-ylmethyl)amino)cyclopentyl)oxy)-1-oxoisoindolin-2-yl)piperidine-2,6-dione;
3-(5-((2-(ethyl(oxetan-3-ylmethyl)amino)cyclopentyl)oxy)-1-oxoisoindolin-2-yl)piperidine-2,6-dione;
3-(5-((((1S,2S)-2-(isoindolin-2-yl)cyclopentyl)oxy)-1-oxoisoindolin-2-yl)piperidine-2,6-dione;
3-(5-((((1S,2R)-2-(isoindolin-2-yl)cyclopentyl)oxy)-1-oxoisoindolin-2-yl)piperidine-2,6-dione;
3-(5-((((1R,2R)-2-(isoindolin-2-yl)cyclopentyl)oxy)-1-oxoisoindolin-2-yl)piperidine-2,6-dione;
3-(5-((((1R,2S)-2-(isoindolin-2-yl)cyclopentyl)oxy)-1-oxoisoindolin-2-yl)piperidine-2,6-dione;
3-(5-((2-(isoindolin-2-yl)cyclopentyl)oxy)-1-oxoisoindolin-2-yl)piperidine-2,6-dione;
3-(5-((((1S,2S)-2-(3-methoxyazetidin-1-yl)cyclopentyl)oxy)-1-oxoisoindolin-2-yl)piperidine-2,6-dione;
3-(5-((((1S,2R)-2-(3-methoxyazetidin-1-yl)cyclopentyl)oxy)-1-oxoisoindolin-2-yl)piperidine-2,6-dione;
3-(5-((((1R,2R)-2-(3-methoxyazetidin-1-yl)cyclopentyl)oxy)-1-oxoisoindolin-2-yl)piperidine-2,6-dione;
3-(5-((((1R,2S)-2-(3-methoxyazetidin-1-yl)cyclopentyl)oxy)-1-oxoisoindolin-2-yl)piperidine-2,6-dione;
3-(5-((2-(3-methoxyazetidin-1-yl)cyclopentyl)oxy)-1-oxoisoindolin-2-yl)piperidine-2,6-dione;
3-(5-((((1S,2S)-2-(4-ethoxy-4-methylpiperidin-1-yl)cyclopentyl)oxy)-1-oxoisoindolin-2-yl)piperidine-2,6-dione;
3-(5-((((1S,2R)-2-(4-ethoxy-4-methylpiperidin-1-yl)cyclopentyl)oxy)-1-oxoisoindolin-2-yl)piperidine-2,6-dione;
3-(5-((((1R,2R)-2-(4-ethoxy-4-methylpiperidin-1-yl)cyclopentyl)oxy)-1-oxoisoindolin-2-yl)piperidine-2,6-dione;
3-(5-((((1R,2S)-2-(4-ethoxy-4-methylpiperidin-1-yl)cyclopentyl)oxy)-1-oxoisoindolin-2-yl)piperidine-2,6-dione;
3-(5-((2-(4-ethoxy-4-methylpiperidin-1-yl)cyclopentyl)oxy)-1-oxoisoindolin-2-yl)piperidine-2,6-dione;
3-(5-((((1S,2S)-2-(((((1R,4S)-4-methoxycyclohexyl)methyl)amino)cyclopentyl)oxy)-1-oxoisoindolin-2-yl)piperidine-2,6-dione;
3-(5-((((1S,2R)-2-(((((1R,4R)-4-methoxycyclohexyl)methyl)amino)cyclopentyl)oxy)-1-oxoisoindolin-2-yl)piperidine-2,6-dione;
3-(5-((((1R,2R)-2-(((((1R,4R)-4-methoxycyclohexyl)methyl)amino)cyclopentyl)oxy)-1-oxoisoindolin-2-yl)piperidine-2,6-dione;
3-(5-((((1R,2S)-2-(((((1R,4S)-4-methoxycyclohexyl)methyl)amino)cyclopentyl)oxy)-1-oxoisoindolin-2-yl)piperidine-2,6-dione;
3-(5-((2-(((((1R,4R)-4-methoxycyclohexyl)methyl)amino)cyclopentyl)oxy)-1-oxoisoindolin-2-yl)piperidine-2,6-dione;
3-(5-((2-(((4-methoxycyclohexyl)methyl)amino)cyclopentyl)oxy)-1-oxoisoindolin-2-yl)piperidine-2,6-dione;

(1S,4R)-4-(((((1S,2S)-2-((2-(2,6-dioxopiperidin-3-yl)-1-oxoisoindolin-5-yl)oxy)cyclopentyl)amino)methyl)cyclohexane-1-carbonitrile;
(1R,4r)-4-(((((1R,2S)-2-((2-(2,6-dioxopiperidin-3-yl)-1-oxoisoindolin-5-yl)oxy)cyclopentyl)amino)methyl)cyclohexane-1-carbonitrile;
(1R,4r)-4-(((((1R,2R)-2-((2-(2,6-dioxopiperidin-3-yl)-1-oxoisoindolin-5-yl)oxy)cyclopentyl)amino)methyl)cyclohexane-1-carbonitrile;
(1S,4r)-4-(((((1S,2R)-2-((2-(2,6-dioxopiperidin-3-yl)-1-oxoisoindolin-5-yl)oxy)cyclopentyl)amino)methyl)cyclohexane-1-carbonitrile;
(1r,4r)-4-(((2-((2-(2,6-dioxopiperidin-3-yl)-1-oxoisoindolin-5-yl)oxy)cyclopentyl)amino)methyl)cyclohexane-1-carbonitrile;
4-(((2-((2-(2,6-dioxopiperidin-3-yl)-1-oxoisoindolin-5-yl)oxy)cyclopentyl)amino)methyl)cyclohexane-1-carbonitrile;
3-(5-(((1S,2S)-2-(((4-methoxycyclohexyl)methyl)amino)cyclopentyl)oxy)-1-oxoisoindolin-2-yl)piperidine-2,6-dione;
3-(5-(((1S,2R)-2-(((4-methoxycyclohexyl)methyl)amino)cyclopentyl)oxy)-1-oxoisoindolin-2-yl)piperidine-2,6-dione;
3-(5-(((1R,2R)-2-(((4-methoxycyclohexyl)methyl)amino)cyclopentyl)oxy)-1-oxoisoindolin-2-yl)piperidine-2,6-dione;
3-(5-(((1R,2S)-2-(((4-methoxycyclohexyl)methyl)amino)cyclopentyl)oxy)-1-oxoisoindolin-2-yl)piperidine-2,6-dione;
3-(5-((2-(((4-methoxycyclohexyl)methyl)amino)cyclopentyl)oxy)-1-oxoisoindolin-2-yl)piperidine-2,6-dione;
3-(5-(((1S,2S)-2-(2-oxa-7-azaspiro[3.5]nonan-7-yl)cyclopentyl)oxy)-1-oxoisoindolin-2-yl)piperidine-2,6-dione;
3-(5-(((1S,2R)-2-(2-oxa-7-azaspiro[3.5]nonan-7-yl)cyclopentyl)oxy)-1-oxoisoindolin-2-yl)piperidine-2,6-dione;
3-(5-(((1R,2R)-2-(2-oxa-7-azaspiro[3.5]nonan-7-yl)cyclopentyl)oxy)-1-oxoisoindolin-2-yl)piperidine-2,6-dione;
3-(5-(((1R,2S)-2-(2-oxa-7-azaspiro[3.5]nonan-7-yl)cyclopentyl)oxy)-1-oxoisoindolin-2-yl)piperidine-2,6-dione;
3-(5-((2-(2-oxa-7-azaspiro[3.5]nonan-7-yl)cyclopentyl)oxy)-1-oxoisoindolin-2-yl)piperidine-2,6-dione;
3-(((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile;
(1S,3R)-3-(((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile;
(1R,3S)-3-(((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile;
trans-3-(((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile;
cis-3-(((((1S,2S)-2-((2-(2,6-dioxopiperidin-3-yl)-1-oxoisoindolin-5-yl)oxy)cyclopentyl)(ethyl)amino)methyl)-1-methylcyclobutane-1-carbonitrile;
3-(5-(((1S,2S)-2-(4-fluoropiperidin-1-yl)cyclopentyl)oxy)-1-oxoisoindolin-2-yl)piperidine-2,6-dione;
3-(5-(((1S,2R)-2-(4-fluoropiperidin-1-yl)cyclopentyl)oxy)-1-oxoisoindolin-2-yl)piperidine-2,6-dione;
3-(5-(((1R,2R)-2-(4-fluoropiperidin-1-yl)cyclopentyl)oxy)-1-oxoisoindolin-2-yl)piperidine-2,6-dione;
3-(5-(((1R,2S)-2-(4-fluoropiperidin-1-yl)cyclopentyl)oxy)-1-oxoisoindolin-2-yl)piperidine-2,6-dione;
3-(5-((2-(4-fluoropiperidin-1-yl)cyclopentyl)oxy)-1-oxoisoindolin-2-yl)piperidine-2,6-dione;
3-(5-(((1S,2S)-2-(1,5-oxazocan-5-yl)cyclopentyl)oxy)-1-oxoisoindolin-2-yl)piperidine-2,6-dione;
3-(5-(((1S,2R)-2-(1,5-oxazocan-5-yl)cyclopentyl)oxy)-1-oxoisoindolin-2-yl)piperidine-2,6-dione;
3-(5-(((1R,2R)-2-(1,5-oxazocan-5-yl)cyclopentyl)oxy)-1-oxoisoindolin-2-yl)piperidine-2,6-dione;
3-(5-(((1R,2S)-2-(1,5-oxazocan-5-yl)cyclopentyl)oxy)-1-oxoisoindolin-2-yl)piperidine-2,6-dione;
3-(5-((2-(1,5-oxazocan-5-yl)cyclopentyl)oxy)-1-oxoisoindolin-2-yl)piperidine-2,6-dione;
3-(5-((2-(3,3-dimethylpiperidin-1-yl)cyclopentyl)oxy)-1-oxoisoindolin-2-yl)piperidine-2,6-dione;
3-(5-(((1R,2S)-2-(3,3-dimethylpiperidin-1-yl)cyclopentyl)oxy)-1-oxoisoindolin-2-yl)piperidine-2,6-dione;
3-(5-(((1R,2R)-2-(3,3-dimethylpiperidin-1-yl)cyclopentyl)oxy)-1-oxoisoindolin-2-yl)piperidine-2,6-dione;
3-(5-(((1S,2R)-2-(3,3-dimethylpiperidin-1-yl)cyclopentyl)oxy)-1-oxoisoindolin-2-yl)piperidine-2,6-dione;
3-(5-(((1S,2S)-2-(3,3-dimethylpiperidin-1-yl)cyclopentyl)oxy)-1-oxoisoindolin-2-yl)piperidine-2,6-dione;
3-(5-(((1S,2S)-2-(ethyl(((1R,4S)-4-methoxycyclohexyl)methyl)amino)cyclopentyl)oxy)-1-oxoisoindolin-2-yl)piperidine-2,6-dione;
3-(5-(((1S,2S)-2-(((((1R,4S)-4-methoxycyclohexyl)methyl)(methyl)amino)cyclopentyl)oxy)-1-oxoisoindolin-2-yl)piperidine-2,6-dione;
trans-3-(5-((2-(diethylamino)-4,4-dimethylcyclopentyl)oxy)-1-oxoisoindolin-2-yl)piperidine-2,6-dione;
cis-3-(5-((2-(diethylamino)-4,4-dimethylcyclopentyl)oxy)-1-oxoisoindolin-2-yl)piperidine-2,6-dione;
3-(5-((2-(diethylamino)-4,4-dimethylcyclopentyl)oxy)-1-oxoisoindolin-2-yl)piperidine-2,6-dione;
3-(5-(((1R,2S)-2-(diethylamino)-4,4-dimethylcyclopentyl)oxy)-1-oxoisoindolin-2-yl)piperidine-2,6-dione;
3-(5-(((1R,2R)-2-(diethylamino)-4,4-dimethylcyclopentyl)oxy)-1-oxoisoindolin-2-yl)piperidine-2,6-dione;
3-(5-(((1S,2R)-2-(diethylamino)-4,4-dimethylcyclopentyl)oxy)-1-oxoisoindolin-2-yl)piperidine-2,6-dione;
3-(5-(((1S,2S)-2-(diethylamino)-4,4-dimethylcyclopentyl)oxy)-1-oxoisoindolin-2-yl)piperidine-2,6-dione;
3-(5-(((1S,2S)-2-(((4,4-difluorocyclohexyl)methyl)amino)cyclopentyl)oxy)-1-oxoisoindolin-2-yl)piperidine-2,6-dione;
3-(5-(((1S,2R)-2-(((4,4-difluorocyclohexyl)methyl)amino)cyclopentyl)oxy)-1-oxoisoindolin-2-yl)piperidine-2,6-dione;
3-(5-(((1R,2R)-2-(((4,4-difluorocyclohexyl)methyl)amino)cyclopentyl)oxy)-1-oxoisoindolin-2-yl)piperidine-2,6-dione;
3-(5-(((1R,2S)-2-(((4,4-difluorocyclohexyl)methyl)amino)cyclopentyl)oxy)-1-oxoisoindolin-2-yl)piperidine-2,6-dione;
3-(5-((2-(((4,4-difluorocyclohexyl)methyl)amino)cyclopentyl)oxy)-1-oxoisoindolin-2-yl)piperidine-2,6-dione;
3-(5-(((1S,2S)-2-(((1H-indol-5-yl)methyl)amino)cyclopentyl)oxy)-1-oxoisoindolin-2-yl)piperidine-2,6-dione;
3-(5-(((1S,2R)-2-(((1H-indol-5-yl)methyl)amino)cyclopentyl)oxy)-1-oxoisoindolin-2-yl)piperidine-2,6-dione;

3-(5-(((1R,2R)-2-(((1H-indol-5-yl)methyl)amino)cyclopentyl)oxy)-1-oxoisoindolin-2-yl)piperidine-2,6-dione;
3-(5-(((1R,2S)-2-(((1H-indol-5-yl)methyl)amino)cyclopentyl)oxy)-1-oxoisoindolin-2-yl)piperidine-2,6-dione;
3-(5-((2-(((1H-indol-5-yl)methyl)amino)cyclopentyl)oxy)-1-oxoisoindolin-2-yl)piperidine-2,6-dione;
3-(5-(((1S,2S)-2-(4-(tert-butoxy)piperidin-1-yl)cyclopentyl)oxy)-1-oxoisoindolin-2-yl)piperidine-2,6-dione;
3-(5-(((1S,2R)-2-(4-(tert-butoxy)piperidin-1-yl)cyclopentyl)oxy)-1-oxoisoindolin-2-yl)piperidine-2,6-dione;
3-(5-(((1R,2R)-2-(4-(tert-butoxy)piperidin-1-yl)cyclopentyl)oxy)-1-oxoisoindolin-2-yl)piperidine-2,6-dione;
3-(5-(((1R,2S)-2-(4-(tert-butoxy)piperidin-1-yl)cyclopentyl)oxy)-1-oxoisoindolin-2-yl)piperidine-2,6-dione;
3-(5-((2-(4-(tert-butoxy)piperidin-1-yl)cyclopentyl)oxy)-1-oxoisoindolin-2-yl)piperidine-2,6-dione;
3-(5-((2-(2-oxa-8-azaspiro[4.5]decan-8-yl)cyclopentyl)oxy)-1-oxoisoindolin-2-yl)piperidine-2,6-dione;
3-(5-(((1R,2S)-2-(2-oxa-8-azaspiro[4.5]decan-8-yl)cyclopentyl)oxy)-1-oxoisoindolin-2-yl)piperidine-2,6-dione;
3-(5-(((1R,2R)-2-(2-oxa-8-azaspiro[4.5]decan-8-yl)cyclopentyl)oxy)-1-oxoisoindolin-2-yl)piperidine-2,6-dione;
3-(5-(((1S,2R)-2-(2-oxa-8-azaspiro[4.5]decan-8-yl)cyclopentyl)oxy)-1-oxoisoindolin-2-yl)piperidine-2,6-dione;
3-(5-(((1S,2S)-2-(2-oxa-8-azaspiro[4.5]decan-8-yl)cyclopentyl)oxy)-1-oxoisoindolin-2-yl)piperidine-2,6-dione;
3-(5-(((1S,2S)-2-(3-(2-chlorophenoxy)azetidin-1-yl)cyclopentyl)oxy)-1-oxoisoindolin-2-yl)piperidine-2,6-dione;
3-(5-(((1S,2R)-2-(3-(2-chlorophenoxy)azetidin-1-yl)cyclopentyl)oxy)-1-oxoisoindolin-2-yl)piperidine-2,6-dione;
3-(5-(((1R,2R)-2-(3-(2-chlorophenoxy)azetidin-1-yl)cyclopentyl)oxy)-1-oxoisoindolin-2-yl)piperidine-2,6-dione;
3-(5-(((1R,2S)-2-(3-(2-chlorophenoxy)azetidin-1-yl)cyclopentyl)oxy)-1-oxoisoindolin-2-yl)piperidine-2,6-dione;
3-(5-((2-(3-(2-chlorophenoxy)azetidin-1-yl)cyclopentyl)oxy)-1-oxoisoindolin-2-yl)piperidine-2,6-dione;
3-(5-(((1S,2S)-2-(3-(2-methoxyphenoxy)azetidin-1-yl)cyclopentyl)oxy)-1-oxoisoindolin-2-yl)piperidine-2,6-dione;
3-(5-(((1S,2R)-2-(3-(2-methoxyphenoxy)azetidin-1-yl)cyclopentyl)oxy)-1-oxoisoindolin-2-yl)piperidine-2,6-dione;
3-(5-(((1R,2R)-2-(3-(2-methoxyphenoxy)azetidin-1-yl)cyclopentyl)oxy)-1-oxoisoindolin-2-yl)piperidine-2,6-dione;
3-(5-(((1R,2S)-2-(3-(2-methoxyphenoxy)azetidin-1-yl)cyclopentyl)oxy)-1-oxoisoindolin-2-yl)piperidine-2,6-dione;
3-(5-((2-(3-(2-methoxyphenoxy)azetidin-1-yl)cyclopentyl)oxy)-1-oxoisoindolin-2-yl)piperidine-2,6-dione;
3-(5-((2-(6-azaspiro[3.5]nonan-6-yl)cyclopentyl)oxy)-1-oxoisoindolin-2-yl)piperidine-2,6-dione;
3-(5-(((1S,2R)-2-(6-azaspiro[3.5]nonan-6-yl)cyclopentyl)oxy)-1-oxoisoindolin-2-yl)piperidine-2,6-dione;
3-(5-(((1R,2R)-2-(6-azaspiro[3.5]nonan-6-yl)cyclopentyl)oxy)-1-oxoisoindolin-2-yl)piperidine-2,6-dione;
3-(5-(((1R,2S)-2-(6-azaspiro[3.5]nonan-6-yl)cyclopentyl)oxy)-1-oxoisoindolin-2-yl)piperidine-2,6-dione;
3-(5-(((1S,2S)-2-(6-azaspiro[3.5]nonan-6-yl)cyclopentyl)oxy)-1-oxoisoindolin-2-yl)piperidine-2,6-dione;
3-(5-(((1S,2S)-2-(ethyl(((1S,3R)-3-methoxycyclobutyl)methyl)amino)cyclopentyl)oxy)-1-oxoisoindolin-2-yl)piperidine-2,6-dione;
3-(5-(((1S,2R)-2-(ethyl(((1s,3S)-3-methoxycyclobutyl)methyl)amino)cyclopentyl)oxy)-1-oxoisoindolin-2-yl)piperidine-2,6-dione;
3-(5-(((1R,2R)-2-(ethyl(((1s,3S)-3-methoxycyclobutyl)methyl)amino)cyclopentyl)oxy)-1-oxoisoindolin-2-yl)piperidine-2,6-dione;
3-(5-(((1R,2S)-2-(ethyl(((1s,3R)-3-methoxycyclobutyl)methyl)amino)cyclopentyl)oxy)-1-oxoisoindolin-2-yl)piperidine-2,6-dione;
3-(5-((2-(ethyl(((1s,3s)-3-methoxycyclobutyl)methyl)amino)cyclopentyl)oxy)-1-oxoisoindolin-2-yl)piperidine-2,6-dione;
3-(5-(((1S,2S)-2-(diethylamino)-4,4-dimethylcyclopentyl)oxy)-1-oxoisoindolin-2-yl)piperidine-2,6-dione;
3-(5-(((1S,2R)-2-(diethylamino)-4,4-dimethylcyclopentyl)oxy)-1-oxoisoindolin-2-yl)piperidine-2,6-dione;
3-(5-(((1R,2R)-2-(diethylamino)-4,4-dimethylcyclopentyl)oxy)-1-oxoisoindolin-2-yl)piperidine-2,6-dione;
3-(5-(((1R,2S)-2-(diethylamino)-4,4-dimethylcyclopentyl)oxy)-1-oxoisoindolin-2-yl)piperidine-2,6-dione;
3-(5-((2-(diethylamino)-4,4-dimethylcyclopentyl)oxy)-1-oxoisoindolin-2-yl)piperidine-2,6-dione;
3-(5-(((1S,2S)-2-(ethyl(((1R,3S)-3-methoxycyclobutyl)methyl)amino)cyclopentyl)oxy)-1-oxoisoindolin-2-yl)piperidine-2,6-dione;
3-(5-(((1S,2R)-2-(ethyl(((1r,3R)-3-methoxycyclobutyl)methyl)amino)cyclopentyl)oxy)-1-oxoisoindolin-2-yl)piperidine-2,6-dione;
3-(5-(((1R,2R)-2-(ethyl(((1r,3R)-3-methoxycyclobutyl)methyl)amino)cyclopentyl)oxy)-1-oxoisoindolin-2-yl)piperidine-2,6-dione;
3-(5-(((1R,2S)-2-(ethyl(((1r,3S)-3-methoxycyclobutyl)methyl)amino)cyclopentyl)oxy)-1-oxoisoindolin-2-yl)piperidine-2,6-dione;
3-(5-((2-(ethyl(((1r,3r)-3-methoxycyclobutyl)methyl)amino)cyclopentyl)oxy)-1-oxoisoindolin-2-yl)piperidine-2,6-dione;
3-(5-((2-(8-oxa-2-azaspiro[4.5]decan-2-yl)cyclopentyl)oxy)-1-oxoisoindolin-2-yl)piperidine-2,6-dione;
3-(5-(((1R,2S)-2-(8-oxa-2-azaspiro[4.5]decan-2-yl)cyclopentyl)oxy)-1-oxoisoindolin-2-yl)piperidine-2,6-dione;
3-(5-(((1R,2R)-2-(8-oxa-2-azaspiro[4.5]decan-2-yl)cyclopentyl)oxy)-1-oxoisoindolin-2-yl)piperidine-2,6-dione;
3-(5-(((1S,2R)-2-(8-oxa-2-azaspiro[4.5]decan-2-yl)cyclopentyl)oxy)-1-oxoisoindolin-2-yl)piperidine-2,6-dione;
3-(5-(((1S,2S)-2-(8-oxa-2-azaspiro[4.5]decan-2-yl)cyclopentyl)oxy)-1-oxoisoindolin-2-yl)piperidine-2,6-dione;
3-(1-oxo-5-(((1S,2S)-2-thiomorpholinocyclopentyl)oxy)isoindolin-2-yl)piperidine-2,6-dione;
3-(1-oxo-5-(((1S,2R)-2-thiomorpholinocyclopentyl)oxy)isoindolin-2-yl)piperidine-2,6-dione;
3-(1-oxo-5-(((1R,2R)-2-thiomorpholinocyclopentyl)oxy)isoindolin-2-yl)piperidine-2,6-dione;

3-(1-oxo-5-(((1R,2S)-2-thiomorpholinocyclopentyl)oxy)
isoindolin-2-yl)piperidine-2,6-dione;
3-(1-oxo-5-((2-thiomorpholinocyclopentyl)oxy)isoindo-
lin-2-yl)piperidine-2,6-dione;
3-(5-(((1S,2S)-2-(1,4-oxazepan-4-yl)cyclopentyl)oxy)-1-
oxoisoindolin-2-yl)piperidine-2,6-dione;
3-(5-(((1S,2R)-2-(1,4-oxazepan-4-yl)cyclopentyl)oxy)-1-
oxoisoindolin-2-yl)piperidine-2,6-dione;
3-(5-(((1R,2R)-2-(1,4-oxazepan-4-yl)cyclopentyl)oxy)-
1-oxoisoindolin-2-yl)piperidine-2,6-dione;
3-(5-(((1R,2S)-2-(1,4-oxazepan-4-yl)cyclopentyl)oxy)-1-
oxoisoindolin-2-yl)piperidine-2,6-dione;
3-(5-((2-(1,4-oxazepan-4-yl)cyclopentyl)oxy)-1-oxoi-
soindolin-2-yl)piperidine-2,6-dione;
3-(5-(((1S,2S)-2-(4-isopropoxypiperidin-1-yl)cyclopen-
tyl)oxy)-1-oxoisoindolin-2-yl)piperidine-2,6-dione;
3-(5-(((1S,2R)-2-(4-isopropoxypiperidin-1-yl)cyclopen-
tyl)oxy)-1-oxoisoindolin-2-yl)piperidine-2,6-dione;
3-(5-(((1R,2R)-2-(4-isopropoxypiperidin-1-yl)cyclopen-
tyl)oxy)-1-oxoisoindolin-2-yl)piperidine-2,6-dione;
3-(5-(((1R,2S)-2-(4-isopropoxypiperidin-1-yl)cyclopen-
tyl)oxy)-1-oxoisoindolin-2-yl)piperidine-2,6-dione;
3-(5-((2-(4-isopropoxypiperidin-1-yl)cyclopentyl)oxy)-
1-oxoisoindolin-2-yl)piperidine-2,6-dione;
3-(5-(((1S,2S)-2-(4-(cyclopropylmethoxy)piperidin-1-yl)
cyclopentyl)oxy)-1-oxoisoindolin-2-yl)piperidine-2,6-
dione;
3-(5-(((1S,2R)-2-(4-(cyclopropylmethoxy)piperidin-1-yl)
cyclopentyl)oxy)-1-oxoisoindolin-2-yl)piperidine-2,6-
dione;
3-(5-(((1R,2R)-2-(4-(cyclopropylmethoxy)piperidin-1-
yl)cyclopentyl)oxy)-1-oxoisoindolin-2-yl)piperidine-
2,6-dione;
3-(5-(((1R,2S)-2-(4-(cyclopropylmethoxy)piperidin-1-yl)
cyclopentyl)oxy)-1-oxoisoindolin-2-yl)piperidine-2,6-
dione;
3-(5-((2-(4-(cyclopropylmethoxy)piperidin-1-yl)cyclo-
pentyl)oxy)-1-oxoisoindolin-2-yl)piperidine-2,6-di-
one;
3-(5-(((1S,2S)-2-((3aR,4R,7S,7aS)-octahydro-2H-4,7-
epoxyisoindol-2-yl)cyclopentyl)oxy)-1-oxoisoindolin-
2-yl)piperidine-2,6-dione;
3-(5-(((1S,2R)-2-((3aR,4R,7S,7aS)-octahydro-2H-4,7-
epoxyisoindol-2-yl)cyclopentyl)oxy)-1-oxoisoindolin-
2-yl)piperidine-2,6-dione;
3-(5-(((1R,2R)-2-((3aR,4R,7S,7aS)-octahydro-2H-4,7-
epoxyisoindol-2-yl)cyclopentyl)oxy)-1-oxoisoindolin-
2-yl)piperidine-2,6-dione;
3-(5-(((1R,2S)-2-((3aR,4R,7S,7aS)-octahydro-2H-4,7-
epoxyisoindol-2-yl)cyclopentyl)oxy)-1-oxoisoindolin-
2-yl)piperidine-2,6-dione;
3-(5-((2-((3aR,4R,7S,7aS)-octahydro-2H-4,7-epoxyi-
soindol-2-yl)cyclopentyl)oxy)-1-oxoisoindolin-2-yl)
piperidine-2,6-dione;
3-(5-(((1S,2S)-2-(4-ethoxypiperidin-1-yl)cyclopentyl)
oxy)-1-oxoisoindolin-2-yl)piperidine-2,6-dione;
3-(5-(((1S,2R)-2-(4-ethoxypiperidin-1-yl)cyclopentyl)
oxy)-1-oxoisoindolin-2-yl)piperidine-2,6-dione;
3-(5-(((1R,2R)-2-(4-ethoxypiperidin-1-yl)cyclopentyl)
oxy)-1-oxoisoindolin-2-yl)piperidine-2,6-dione;
3-(5-(((1R,2S)-2-(4-ethoxypiperidin-1-yl)cyclopentyl)
oxy)-1-oxoisoindolin-2-yl)piperidine-2,6-dione;
3-(5-((2-(4-ethoxypiperidin-1-yl)cyclopentyl)oxy)-1-
oxoisoindolin-2-yl)piperidine-2,6-dione;
3-(5-(((1S,2S)-2-(7,8-dihydro-1,6-naphthyridin-6(5H)-
yl)cyclopentyl)oxy)-1-oxoisoindolin-2-yl)piperidine-
2,6-dione;
3-(5-(((1S,2R)-2-(7,8-dihydro-1,6-naphthyridin-6(5H)-
yl)cyclopentyl)oxy)-1-oxoisoindolin-2-yl)piperidine-
2,6-dione;
3-(5-(((1R,2R)-2-(7,8-dihydro-1,6-naphthyridin-6(5H)-
yl)cyclopentyl)oxy)-1-oxoisoindolin-2-yl)piperidine-
2,6-dione;
3-(5-(((1R,2S)-2-(7,8-dihydro-1,6-naphthyridin-6(5H)-
yl)cyclopentyl)oxy)-1-oxoisoindolin-2-yl)piperidine-
2,6-dione;
3-(5-((2-(7,8-dihydro-1,6-naphthyridin-6(5H)-yl)cyclo-
pentyl)oxy)-1-oxoisoindolin-2-yl)piperidine-2,6-di-
one;
3-(5-(((1S,2S)-2-((((1S,4R)-4-methoxycyclohexyl)
methyl)amino)cyclopentyl)oxy)-1-oxoisoindolin-2-yl)
piperidine-2,6-dione;
3-(5-(((1S,2R)-2-((((1s,4S)-4-methoxycyclohexyl)
methyl)amino)cyclopentyl)oxy)-1-oxoisoindolin-2-yl)
piperidine-2,6-dione;
3-(5-(((1R,2R)-2-((((1s,4S)-4-methoxycyclohexyl)
methyl)amino)cyclopentyl)oxy)-1-oxoisoindolin-2-yl)
piperidine-2,6-dione;
3-(5-(((1R,2S)-2-((((1s,4R)-4-methoxycyclohexyl)
methyl)amino)cyclopentyl)oxy)-1-oxoisoindolin-2-yl)
piperidine-2,6-dione;
3-(5-((2-((((1s,4s)-4-methoxycyclohexyl)methyl)amino)
cyclopentyl)oxy)-1-oxoisoindolin-2-yl)piperidine-2,6-
dione;
3-(5-(((1S,2S)-2-((R)-3-methoxypyrrolidin-1-yl)cyclo-
pentyl)oxy)-1-oxoisoindolin-2-yl)piperidine-2,6-di-
one;
3-(5-(((1S,2R)-2-((R)-3-methoxypyrrolidin-1-yl)cyclo-
pentyl)oxy)-1-oxoisoindolin-2-yl)piperidine-2,6-di-
one;
3-(5-(((1R,2R)-2-((R)-3-methoxypyrrolidin-1-yl)cyclo-
pentyl)oxy)-1-oxoisoindolin-2-yl)piperidine-2,6-di-
one;
3-(5-(((1R,2S)-2-((R)-3-methoxypyrrolidin-1-yl)cyclo-
pentyl)oxy)-1-oxoisoindolin-2-yl)piperidine-2,6-di-
one;
3-(5-((2-((R)-3-methoxypyrrolidin-1-yl)cyclopentyl)
oxy)-1-oxoisoindolin-2-yl)piperidine-2,6-dione;
3-(5-(((1S,2S)-2-((S)-3-methoxypyrrolidin-1-yl)cyclo-
pentyl)oxy)-1-oxoisoindolin-2-yl)piperidine-2,6-di-
one;
3-(5-(((1S,2R)-2-((S)-3-methoxypyrrolidin-1-yl)cyclo-
pentyl)oxy)-1-oxoisoindolin-2-yl)piperidine-2,6-di-
one;
3-(5-(((1R,2R)-2-((S)-3-methoxypyrrolidin-1-yl)cyclo-
pentyl)oxy)-1-oxoisoindolin-2-yl)piperidine-2,6-di-
one;
3-(5-(((1R,2S)-2-((S)-3-methoxypyrrolidin-1-yl)cyclo-
pentyl)oxy)-1-oxoisoindolin-2-yl)piperidine-2,6-di-
one;
3-(5-((2-((S)-3-methoxypyrrolidin-1-yl)cyclopentyl)
oxy)-1-oxoisoindolin-2-yl)piperidine-2,6-dione;
3-(5-(((1S,2S)-2-(((3,3-difluorocyclobutyl)methyl)
amino)cyclopentyl)oxy)-1-oxoisoindolin-2-yl)piperi-
dine-2,6-dione;
3-(5-(((1S,2R)-2-(((3,3-difluorocyclobutyl)methyl)
amino)cyclopentyl)oxy)-1-oxoisoindolin-2-yl)piperi-
dine-2,6-dione;
3-(5-(((1R,2R)-2-(((3,3-difluorocyclobutyl)methyl)
amino)cyclopentyl)oxy)-1-oxoisoindolin-2-yl)piperi-
dine-2,6-dione;
3-(5-(((1R,2S)-2-(((3,3-difluorocyclobutyl)methyl)
amino)cyclopentyl)oxy)-1-oxoisoindolin-2-yl)piperi-
dine-2,6-dione;

3-(5-((2-(((3,3-difluorocyclobutyl)methyl)amino)cyclopentyl)oxy)-1-oxoisoindolin-2-yl)piperidine-2,6-dione;
3-(5-(((1S,2S)-2-(4-(difluoromethoxy)piperidin-1-yl)cyclopentyl)oxy)-1-oxoisoindolin-2-yl)piperidine-2,6-dione;
3-(5-(((1S,2R)-2-(4-(difluoromethoxy)piperidin-1-yl)cyclopentyl)oxy)-1-oxoisoindolin-2-yl)piperidine-2,6-dione;
3-(5-(((1R,2R)-2-(4-(difluoromethoxy)piperidin-1-yl)cyclopentyl)oxy)-1-oxoisoindolin-2-yl)piperidine-2,6-dione;
3-(5-(((1R,2S)-2-(4-(difluoromethoxy)piperidin-1-yl)cyclopentyl)oxy)-1-oxoisoindolin-2-yl)piperidine-2,6-dione;
3-(5-((2-(4-(difluoromethoxy)piperidin-1-yl)cyclopentyl)oxy)-1-oxoisoindolin-2-yl)piperidine-2,6-dione;
3-(5-(((1S,2S)-2-(1,3-dihydro-2H-pyrrolo[3,4-c]pyridin-2-yl)cyclopentyl)oxy)-1-oxoisoindolin-2-yl)piperidine-2,6-dione;
3-(5-(((1S,2R)-2-(1,3-dihydro-2H-pyrrolo[3,4-c]pyridin-2-yl)cyclopentyl)oxy)-1-oxoisoindolin-2-yl)piperidine-2,6-dione;
3-(5-(((1R,2R)-2-(1,3-dihydro-2H-pyrrolo[3,4-c]pyridin-2-yl)cyclopentyl)oxy)-1-oxoisoindolin-2-yl)piperidine-2,6-dione;
3-(5-(((1R,2S)-2-(1,3-dihydro-2H-pyrrolo[3,4-c]pyridin-2-yl)cyclopentyl)oxy)-1-oxoisoindolin-2-yl)piperidine-2,6-dione;
3-(5-((2-(1,3-dihydro-2H-pyrrolo[3,4-c]pyridin-2-yl)cyclopentyl)oxy)-1-oxoisoindolin-2-yl)piperidine-2,6-dione;
3-(1-oxo-5-(((1S,2S)-2-(propylamino)cyclohexyl)oxy)isoindolin-2-yl)piperidine-2,6-dione;
3-(1-oxo-5-(((1S,2R)-2-(propylamino)cyclohexyl)oxy)isoindolin-2-yl)piperidine-2,6-dione;
3-(1-oxo-5-(((1R,2R)-2-(propylamino)cyclohexyl)oxy)isoindolin-2-yl)piperidine-2,6-dione;
3-(1-oxo-5-(((1R,2S)-2-(propylamino)cyclohexyl)oxy)isoindolin-2-yl)piperidine-2,6-dione;
3-(1-oxo-5-((2-(propylamino)cyclohexyl)oxy)isoindolin-2-yl)piperidine-2,6-dione;
3-(5-(((1S,2S)-2-(dipropylamino)cyclohexyl)oxy)-1-oxoisoindolin-2-yl)piperidine-2,6-dione;
3-(5-(((1S,2R)-2-(dipropylamino)cyclohexyl)oxy)-1-oxoisoindolin-2-yl)piperidine-2,6-dione;
3-(5-(((1R,2R)-2-(dipropylamino)cyclohexyl)oxy)-1-oxoisoindolin-2-yl)piperidine-2,6-dione;
3-(5-(((1R,2S)-2-(dipropylamino)cyclohexyl)oxy)-1-oxoisoindolin-2-yl)piperidine-2,6-dione;
3-(5-((2-(dipropylamino)cyclohexyl)oxy)-1-oxoisoindolin-2-yl)piperidine-2,6-dione;
3-(1-oxo-5-(((1S,2S)-2-((pyridin-4-ylmethyl)amino)cyclohexyl)oxy)isoindolin-2-yl)piperidine-2,6-dione;
3-(1-oxo-5-(((1S,2R)-2-((pyridin-4-ylmethyl)amino)cyclohexyl)oxy)isoindolin-2-yl)piperidine-2,6-dione;
3-(1-oxo-5-(((1R,2R)-2-((pyridin-4-ylmethyl)amino)cyclohexyl)oxy)isoindolin-2-yl)piperidine-2,6-dione;
3-(1-oxo-5-(((1R,2S)-2-((pyridin-4-ylmethyl)amino)cyclohexyl)oxy)isoindolin-2-yl)piperidine-2,6-dione;
3-(1-oxo-5-((2-((pyridin-4-ylmethyl)amino)cyclohexyl)oxy)isoindolin-2-yl)piperidine-2,6-dione;
3-(5-(((1S,2S)-2-(2-oxa-6-azaspiro[3.3]heptan-6-yl)cyclohexyl)oxy)-1-oxoisoindolin-2-yl)piperidine-2,6-dione;
3-(5-(((1S,2R)-2-(2-oxa-6-azaspiro[3.3]heptan-6-yl)cyclohexyl)oxy)-1-oxoisoindolin-2-yl)piperidine-2,6-dione;
3-(5-(((1R,2R)-2-(2-oxa-6-azaspiro[3.3]heptan-6-yl)cyclohexyl)oxy)-1-oxoisoindolin-2-yl)piperidine-2,6-dione;
3-(5-(((1R,2S)-2-(2-oxa-6-azaspiro[3.3]heptan-6-yl)cyclohexyl)oxy)-1-oxoisoindolin-2-yl)piperidine-2,6-dione;
3-(5-((2-(2-oxa-6-azaspiro[3.3]heptan-6-yl)cyclohexyl)oxy)-1-oxoisoindolin-2-yl)piperidine-2,6-dione;
3-(1-oxo-5-(((1S,2S)-2-((pyridin-3-ylmethyl)amino)cyclohexyl)oxy)isoindolin-2-yl)piperidine-2,6-dione;
3-(1-oxo-5-(((1S,2R)-2-((pyridin-3-ylmethyl)amino)cyclohexyl)oxy)isoindolin-2-yl)piperidine-2,6-dione;
3-(1-oxo-5-(((1R,2R)-2-((pyridin-3-ylmethyl)amino)cyclohexyl)oxy)isoindolin-2-yl)piperidine-2,6-dione;
3-(1-oxo-5-(((1R,2S)-2-((pyridin-3-ylmethyl)amino)cyclohexyl)oxy)isoindolin-2-yl)piperidine-2,6-dione;
3-(1-oxo-5-((2-((pyridin-3-ylmethyl)amino)cyclohexyl)oxy)isoindolin-2-yl)piperidine-2,6-dione;
3-(5-(((1S,2S)-2-(((1-ethyl-1H-pyrazol-4-yl)methyl)amino)cyclohexyl)oxy)-1-oxoisoindolin-2-yl)piperidine-2,6-dione;
3-(5-(((1S,2R)-2-(((1-ethyl-1H-pyrazol-4-yl)methyl)amino)cyclohexyl)oxy)-1-oxoisoindolin-2-yl)piperidine-2,6-dione;
3-(5-(((1R,2R)-2-(((1-ethyl-1H-pyrazol-4-yl)methyl)amino)cyclohexyl)oxy)-1-oxoisoindolin-2-yl)piperidine-2,6-dione;
3-(5-(((1R,2S)-2-(((1-ethyl-1H-pyrazol-4-yl)methyl)amino)cyclohexyl)oxy)-1-oxoisoindolin-2-yl)piperidine-2,6-dione;
3-(5-((2-(((1-ethyl-1H-pyrazol-4-yl)methyl)amino)cyclohexyl)oxy)-1-oxoisoindolin-2-yl)piperidine-2,6-dione;
3-(5-(((1S,2S)-2-(((1-isopropyl-1H-pyrazol-4-yl)methyl)amino)cyclohexyl)oxy)-1-oxoisoindolin-2-yl)piperidine-2,6-dione;
3-(5-(((1S,2R)-2-(((1-isopropyl-1H-pyrazol-4-yl)methyl)amino)cyclohexyl)oxy)-1-oxoisoindolin-2-yl)piperidine-2,6-dione;
3-(5-(((1R,2R)-2-(((1-isopropyl-1H-pyrazol-4-yl)methyl)amino)cyclohexyl)oxy)-1-oxoisoindolin-2-yl)piperidine-2,6-dione;
3-(5-(((1R,2S)-2-(((1-isopropyl-1H-pyrazol-4-yl)methyl)amino)cyclohexyl)oxy)-1-oxoisoindolin-2-yl)piperidine-2,6-dione;
3-(5-((2-(((1-isopropyl-1H-pyrazol-4-yl)methyl)amino)cyclohexyl)oxy)-1-oxoisoindolin-2-yl)piperidine-2,6-dione;
3-(5-(((1S,2S)-2-(ethyl(methyl)amino)cyclohexyl)oxy)-1-oxoisoindolin-2-yl)piperidine-2,6-dione;
3-(5-(((1S,2R)-2-(ethyl(methyl)amino)cyclohexyl)oxy)-1-oxoisoindolin-2-yl)piperidine-2,6-dione;
3-(5-(((1R,2R)-2-(ethyl(methyl)amino)cyclohexyl)oxy)-1-oxoisoindolin-2-yl)piperidine-2,6-dione;
3-(5-(((1R,2S)-2-(ethyl(methyl)amino)cyclohexyl)oxy)-1-oxoisoindolin-2-yl)piperidine-2,6-dione;
3-(5-((2-(ethyl(methyl)amino)cyclohexyl)oxy)-1-oxoisoindolin-2-yl)piperidine-2,6-dione;
3-(5-(((1S,2S)-2-(dimethylamino)cyclohexyl)oxy)-1-oxoisoindolin-2-yl)piperidine-2,6-dione;
3-(5-(((1S,2R)-2-(dimethylamino)cyclohexyl)oxy)-1-oxoisoindolin-2-yl)piperidine-2,6-dione;
3-(5-(((1R,2R)-2-(dimethylamino)cyclohexyl)oxy)-1-oxoisoindolin-2-yl)piperidine-2,6-dione;

3-(5-((((1R,2S)-2-(dimethylamino)cyclohexyl)oxy)-1-oxoisoindolin-2-yl)piperidine-2,6-dione;
3-(5-((2-(dimethylamino)cyclohexyl)oxy)-1-oxoisoindolin-2-yl)piperidine-2,6-dione;
3-(5-((((1S,2S)-2-((oxetan-3-ylmethyl)amino)cyclohexyl)oxy)-1-oxoisoindolin-2-yl)piperidine-2,6-dione;
3-(5-((((1S,2R)-2-((oxetan-3-ylmethyl)amino)cyclohexyl)oxy)-1-oxoisoindolin-2-yl)piperidine-2,6-dione;
3-(5-((((1R,2R)-2-((oxetan-3-ylmethyl)amino)cyclohexyl)oxy)-1-oxoisoindolin-2-yl)piperidine-2,6-dione;
3-(5-((((1R,2S)-2-((oxetan-3-ylmethyl)amino)cyclohexyl)oxy)-1-oxoisoindolin-2-yl)piperidine-2,6-dione;
3-(5-((2-((oxetan-3-ylmethyl)amino)cyclohexyl)oxy)-1-oxoisoindolin-2-yl)piperidine-2,6-dione;
3-(5-((((1S,2S)-2-((2-hydroxyethyl)amino)cyclohexyl)oxy)-1-oxoisoindolin-2-yl)piperidine-2,6-dione;
3-(5-((((1S,2R)-2-((2-hydroxyethyl)amino)cyclohexyl)oxy)-1-oxoisoindolin-2-yl)piperidine-2,6-dione;
3-(5-((((1R,2R)-2-((2-hydroxyethyl)amino)cyclohexyl)oxy)-1-oxoisoindolin-2-yl)piperidine-2,6-dione;
3-(5-((((1R,2S)-2-((2-hydroxyethyl)amino)cyclohexyl)oxy)-1-oxoisoindolin-2-yl)piperidine-2,6-dione;
3-(5-((2-((2-hydroxyethyl)amino)cyclohexyl)oxy)-1-oxoisoindolin-2-yl)piperidine-2,6-dione;
3-(1-oxo-5-((((1S,2S)-2-(pyrrolidin-1-yl)cyclohexyl)oxy)isoindolin-2-yl)piperidine-2,6-dione;
3-(1-oxo-5-((((1S,2R)-2-(pyrrolidin-1-yl)cyclohexyl)oxy)isoindolin-2-yl)piperidine-2,6-dione;
3-(1-oxo-5-((((1R,2R)-2-(pyrrolidin-1-yl)cyclohexyl)oxy)isoindolin-2-yl)piperidine-2,6-dione;
3-(1-oxo-5-((((1R,2S)-2-(pyrrolidin-1-yl)cyclohexyl)oxy)isoindolin-2-yl)piperidine-2,6-dione;
3-(1-oxo-5-((2-(pyrrolidin-1-yl)cyclohexyl)oxy)isoindolin-2-yl)piperidine-2,6-dione;
3-(5-((((1S,2S)-2-morpholinocyclohexyl)oxy)-1-oxoisoindolin-2-yl)piperidine-2,6-dione;
3-(5-((((1S,2R)-2-morpholinocyclohexyl)oxy)-1-oxoisoindolin-2-yl)piperidine-2,6-dione;
3-(5-((((1R,2R)-2-morpholinocyclohexyl)oxy)-1-oxoisoindolin-2-yl)piperidine-2,6-dione;
3-(5-((((1R,2S)-2-morpholinocyclohexyl)oxy)-1-oxoisoindolin-2-yl)piperidine-2,6-dione;
3-(5-((2-morpholinocyclohexyl)oxy)-1-oxoisoindolin-2-yl)piperidine-2,6-dione;
3-(1-oxo-5-((((1S,2S)-2-((pyridin-2-ylmethyl)amino)cyclohexyl)oxy)isoindolin-2-yl)piperidine-2,6-dione;
3-(1-oxo-5-((((1S,2R)-2-((pyridin-2-ylmethyl)amino)cyclohexyl)oxy)isoindolin-2-yl)piperidine-2,6-dione;
3-(1-oxo-5-((((1R,2R)-2-((pyridin-2-ylmethyl)amino)cyclohexyl)oxy)isoindolin-2-yl)piperidine-2,6-dione;
3-(1-oxo-5-((((1R,2S)-2-((pyridin-2-ylmethyl)amino)cyclohexyl)oxy)isoindolin-2-yl)piperidine-2,6-dione;
3-(1-oxo-5-((2-((pyridin-2-ylmethyl)amino)cyclohexyl)oxy)isoindolin-2-yl)piperidine-2,6-dione;
3-(5-((((1S,2S)-2-((3-hydroxy-3-methylbutyl)amino)cyclohexyl)oxy)-1-oxoisoindolin-2-yl)piperidine-2,6-dione;
3-(5-((((1S,2R)-2-((3-hydroxy-3-methylbutyl)amino)cyclohexyl)oxy)-1-oxoisoindolin-2-yl)piperidine-2,6-dione;
3-(5-((((1R,2R)-2-((3-hydroxy-3-methylbutyl)amino)cyclohexyl)oxy)-1-oxoisoindolin-2-yl)piperidine-2,6-dione;
3-(5-((((1R,2S)-2-((3-hydroxy-3-methylbutyl)amino)cyclohexyl)oxy)-1-oxoisoindolin-2-yl)piperidine-2,6-dione;
3-(5-((2-((3-hydroxy-3-methylbutyl)amino)cyclohexyl)oxy)-1-oxoisoindolin-2-yl)piperidine-2,6-dione;
3-(5-((((1S,2S)-2-(((3-methyloxetan-3-yl)methyl)amino)cyclohexyl)oxy)-1-oxoisoindolin-2-yl)piperidine-2,6-dione;
3-(5-((((1S,2R)-2-(((3-methyloxetan-3-yl)methyl)amino)cyclohexyl)oxy)-1-oxoisoindolin-2-yl)piperidine-2,6-dione;
3-(5-((((1R,2R)-2-(((3-methyloxetan-3-yl)methyl)amino)cyclohexyl)oxy)-1-oxoisoindolin-2-yl)piperidine-2,6-dione;
3-(5-((((1R,2S)-2-(((3-methyloxetan-3-yl)methyl)amino)cyclohexyl)oxy)-1-oxoisoindolin-2-yl)piperidine-2,6-dione;
3-(5-((2-(((3-methyloxetan-3-yl)methyl)amino)cyclohexyl)oxy)-1-oxoisoindolin-2-yl)piperidine-2,6-dione;
3-(5-((((1S,2S)-2-(4-methoxy-4-methylpiperidin-1-yl)cyclohexyl)oxy)-1-oxoisoindolin-2-yl)piperidine-2,6-dione;
3-(5-((((1S,2R)-2-(4-methoxy-4-methylpiperidin-1-yl)cyclohexyl)oxy)-1-oxoisoindolin-2-yl)piperidine-2,6-dione;
3-(5-((((1R,2R)-2-(4-methoxy-4-methylpiperidin-1-yl)cyclohexyl)oxy)-1-oxoisoindolin-2-yl)piperidine-2,6-dione;
3-(5-((((1R,2S)-2-(4-methoxy-4-methylpiperidin-1-yl)cyclohexyl)oxy)-1-oxoisoindolin-2-yl)piperidine-2,6-dione;
3-(5-((2-(4-methoxy-4-methylpiperidin-1-yl)cyclohexyl)oxy)-1-oxoisoindolin-2-yl)piperidine-2,6-dione;
3-(5-((((1S,2S)-2-(3-methoxyazetidin-1-yl)cyclohexyl)oxy)-1-oxoisoindolin-2-yl)piperidine-2,6-dione;
3-(5-((((1S,2R)-2-(3-methoxyazetidin-1-yl)cyclohexyl)oxy)-1-oxoisoindolin-2-yl)piperidine-2,6-dione;
3-(5-((((1R,2R)-2-(3-methoxyazetidin-1-yl)cyclohexyl)oxy)-1-oxoisoindolin-2-yl)piperidine-2,6-dione;
3-(5-((((1R,2S)-2-(3-methoxyazetidin-1-yl)cyclohexyl)oxy)-1-oxoisoindolin-2-yl)piperidine-2,6-dione;
3-(5-((2-(3-methoxyazetidin-1-yl)cyclohexyl)oxy)-1-oxoisoindolin-2-yl)piperidine-2,6-dione;
3-(5-((((1S,2S)-2-(((6-methylpyridin-2-yl)methyl)amino)cyclohexyl)oxy)-1-oxoisoindolin-2-yl)piperidine-2,6-dione;
3-(5-((((1S,2R)-2-(((6-methylpyridin-2-yl)methyl)amino)cyclohexyl)oxy)-1-oxoisoindolin-2-yl)piperidine-2,6-dione;
3-(5-((((1R,2R)-2-(((6-methylpyridin-2-yl)methyl)amino)cyclohexyl)oxy)-1-oxoisoindolin-2-yl)piperidine-2,6-dione;
3-(5-((((1R,2S)-2-(((6-methylpyridin-2-yl)methyl)amino)cyclohexyl)oxy)-1-oxoisoindolin-2-yl)piperidine-2,6-dione;
3-(5-((2-(((6-methylpyridin-2-yl)methyl)amino)cyclohexyl)oxy)-1-oxoisoindolin-2-yl)piperidine-2,6-dione;
3-(5-((((1S,2S)-2-(((5-methoxypyridin-2-yl)methyl)amino)cyclohexyl)oxy)-1-oxoisoindolin-2-yl)piperidine-2,6-dione;
3-(5-((((1S,2R)-2-(((5-methoxypyridin-2-yl)methyl)amino)cyclohexyl)oxy)-1-oxoisoindolin-2-yl)piperidine-2,6-dione;
3-(5-((((1R,2R)-2-(((5-methoxypyridin-2-yl)methyl)amino)cyclohexyl)oxy)-1-oxoisoindolin-2-yl)piperidine-2,6-dione;
3-(5-((((1R,2S)-2-(((5-methoxypyridin-2-yl)methyl)amino)cyclohexyl)oxy)-1-oxoisoindolin-2-yl)piperidine-2,6-dione;

3-(5-((2-(((5-methoxypyridin-2-yl)methyl)amino)cyclohexyl)oxy)-1-oxoisoindolin-2-yl)piperidine-2,6-dione;
3-(5-(((1S,2S)-2-(((6-methoxypyridin-3-yl)methyl)amino)cyclohexyl)oxy)-1-oxoisoindolin-2-yl)piperidine-2,6-dione;
3-(5-(((1S,2R)-2-(((6-methoxypyridin-3-yl)methyl)amino)cyclohexyl)oxy)-1-oxoisoindolin-2-yl)piperidine-2,6-dione;
3-(5-(((1R,2R)-2-(((6-methoxypyridin-3-yl)methyl)amino)cyclohexyl)oxy)-1-oxoisoindolin-2-yl)piperidine-2,6-dione;
3-(5-(((1R,2S)-2-(((6-methoxypyridin-3-yl)methyl)amino)cyclohexyl)oxy)-1-oxoisoindolin-2-yl)piperidine-2,6-dione;
3-(5-((2-(((6-methoxypyridin-3-yl)methyl)amino)cyclohexyl)oxy)-1-oxoisoindolin-2-yl)piperidine-2,6-dione;
3-(5-(((1S,2S)-2-((2-hydroxy-2-methylpropyl)amino)cyclohexyl)oxy)-1-oxoisoindolin-2-yl)piperidine-2,6-dione;
3-(5-(((1S,2R)-2-((2-hydroxy-2-methylpropyl)amino)cyclohexyl)oxy)-1-oxoisoindolin-2-yl)piperidine-2,6-dione;
3-(5-(((1R,2R)-2-((2-hydroxy-2-methylpropyl)amino)cyclohexyl)oxy)-1-oxoisoindolin-2-yl)piperidine-2,6-dione;
3-(5-(((1R,2S)-2-((2-hydroxy-2-methylpropyl)amino)cyclohexyl)oxy)-1-oxoisoindolin-2-yl)piperidine-2,6-dione;
3-(5-((2-((2-hydroxy-2-methylpropyl)amino)cyclohexyl)oxy)-1-oxoisoindolin-2-yl)piperidine-2,6-dione;
3-((((1S,2S)-2-((2-(2,6-dioxopiperidin-3-yl)-1-oxoisoindolin-5-yl)oxy)cyclohexyl)amino)methyl)-1-methylcyclobutane-1-carbonitrile;
3-((((1R,2S)-2-((2-(2,6-dioxopiperidin-3-yl)-1-oxoisoindolin-5-yl)oxy)cyclohexyl)amino)methyl)-1-methylcyclobutane-1-carbonitrile;
3-((((1R,2R)-2-((2-(2,6-dioxopiperidin-3-yl)-1-oxoisoindolin-5-yl)oxy)cyclohexyl)amino)methyl)-1-methylcyclobutane-1-carbonitrile;
3-((((1S,2R)-2-((2-(2,6-dioxopiperidin-3-yl)-1-oxoisoindolin-5-yl)oxy)cyclohexyl)amino)methyl)-1-methylcyclobutane-1-carbonitrile;
3-(((2-((2-(2,6-dioxopiperidin-3-yl)-1-oxoisoindolin-5-yl)oxy)cyclohexyl)amino)methyl)-1-methylcyclobutane-1-carbonitrile;
(1S,3R)-3-((((1S,2S)-2-((2-(2,6-dioxopiperidin-3-yl)-1-oxoisoindolin-5-yl)oxy)cyclohexyl)amino)methyl)-1-methylcyclobutane-1-carbonitrile;
(1R,3R)-3-((((1R,2S)-2-((2-(2,6-dioxopiperidin-3-yl)-1-oxoisoindolin-5-yl)oxy)cyclohexyl)amino)methyl)-1-methylcyclobutane-1-carbonitrile;
(1R,3R)-3-((((1R,2R)-2-((2-(2,6-dioxopiperidin-3-yl)-1-oxoisoindolin-5-yl)oxy)cyclohexyl)amino)methyl)-1-methylcyclobutane-1-carbonitrile;
(1S,3r)-3-((((1S,2R)-2-((2-(2,6-dioxopiperidin-3-yl)-1-oxoisoindolin-5-yl)oxy)cyclohexyl)amino)methyl)-1-methylcyclobutane-1-carbonitrile;
(1r,3r)-3-(((2-((2-(2,6-dioxopiperidin-3-yl)-1-oxoisoindolin-5-yl)oxy)cyclohexyl)amino)methyl)-1-methylcyclobutane-1-carbonitrile;
(1R,3S)-3-((((1S,2S)-2-((2-(2,6-dioxopiperidin-3-yl)-1-oxoisoindolin-5-yl)oxy)cyclohexyl)amino)methyl)-1-methylcyclobutane-1-carbonitrile;
(1S,3s)-3-((((1R,2S)-2-((2-(2,6-dioxopiperidin-3-yl)-1-oxoisoindolin-5-yl)oxy)cyclohexyl)amino)methyl)-1-methylcyclobutane-1-carbonitrile;
(1S,3s)-3-((((1R,2R)-2-((2-(2,6-dioxopiperidin-3-yl)-1-oxoisoindolin-5-yl)oxy)cyclohexyl)amino)methyl)-1-methylcyclobutane-1-carbonitrile;
(1R,3s)-3-((((1S,2R)-2-((2-(2,6-dioxopiperidin-3-yl)-1-oxoisoindolin-5-yl)oxy)cyclohexyl)amino)methyl)-1-methylcyclobutane-1-carbonitrile;
(1s,3s)-3-(((2-((2-(2,6-dioxopiperidin-3-yl)-1-oxoisoindolin-5-yl)oxy)cyclohexyl)amino)methyl)-1-methylcyclobutane-1-carbonitrile;
3-(1-oxo-5-(((1S,2S)-2-(piperidin-1-yl)cyclohexyl)oxy)isoindolin-2-yl)piperidine-2,6-dione;
3-(1-oxo-5-(((1S,2R)-2-(piperidin-1-yl)cyclohexyl)oxy)isoindolin-2-yl)piperidine-2,6-dione;
3-(1-oxo-5-(((1R,2R)-2-(piperidin-1-yl)cyclohexyl)oxy)isoindolin-2-yl)piperidine-2,6-dione;
3-(1-oxo-5-(((1R,2S)-2-(piperidin-1-yl)cyclohexyl)oxy)isoindolin-2-yl)piperidine-2,6-dione;
3-(1-oxo-5-((2-(piperidin-1-yl)cyclohexyl)oxy)isoindolin-2-yl)piperidine-2,6-dione;
3-(1-oxo-5-(((1S,2S)-2-(((tetrahydro-2H-pyran-4-yl)methyl)amino)cyclohexyl)oxy)isoindolin-2-yl)piperidine-2,6-dione;
3-(1-oxo-5-(((1S,2R)-2-(((tetrahydro-2H-pyran-4-yl)methyl)amino)cyclohexyl)oxy)isoindolin-2-yl)piperidine-2,6-dione;
3-(1-oxo-5-(((1R,2R)-2-(((tetrahydro-2H-pyran-4-yl)methyl)amino)cyclohexyl)oxy)isoindolin-2-yl)piperidine-2,6-dione;
3-(1-oxo-5-(((1R,2S)-2-(((tetrahydro-2H-pyran-4-yl)methyl)amino)cyclohexyl)oxy)isoindolin-2-yl)piperidine-2,6-dione;
3-(1-oxo-5-((2-(((tetrahydro-2H-pyran-4-yl)methyl)amino)cyclohexyl)oxy)isoindolin-2-yl)piperidine-2,6-dione;
3-(5-(((1S,2S)-2-(((3-methoxycyclobutyl)methyl)amino)cyclohexyl)oxy)-1-oxoisoindolin-2-yl)piperidine-2,6-dione;
3-(5-(((1S,2R)-2-(((3-methoxycyclobutyl)methyl)amino)cyclohexyl)oxy)-1-oxoisoindolin-2-yl)piperidine-2,6-dione;
3-(5-(((1R,2R)-2-(((3-methoxycyclobutyl)methyl)amino)cyclohexyl)oxy)-1-oxoisoindolin-2-yl)piperidine-2,6-dione;
3-(5-(((1R,2S)-2-(((3-methoxycyclobutyl)methyl)amino)cyclohexyl)oxy)-1-oxoisoindolin-2-yl)piperidine-2,6-dione;
3-(5-((2-(((3-methoxycyclobutyl)methyl)amino)cyclohexyl)oxy)-1-oxoisoindolin-2-yl)piperidine-2,6-dione;
3-(5-(((1S,2S)-2-((((1S,3R)-3-methoxycyclobutyl)methyl)amino)cyclohexyl)oxy)-1-oxoisoindolin-2-yl)piperidine-2,6-dione;
3-(5-(((1S,2R)-2-((((1s,3S)-3-methoxycyclobutyl)methyl)amino)cyclohexyl)oxy)-1-oxoisoindolin-2-yl)piperidine-2,6-dione;
3-(5-(((1R,2R)-2-((((1s,3S)-3-methoxycyclobutyl)methyl)amino)cyclohexyl)oxy)-1-oxoisoindolin-2-yl)piperidine-2,6-dione;
3-(5-(((1R,2S)-2-((((1s,3R)-3-methoxycyclobutyl)methyl)amino)cyclohexyl)oxy)-1-oxoisoindolin-2-yl)piperidine-2,6-dione;
3-(5-((2-((((1s,3s)-3-methoxycyclobutyl)methyl)amino)cyclohexyl)oxy)-1-oxoisoindolin-2-yl)piperidine-2,6-dione;
3-(5-(((1S,2S)-2-(((cis-3-methoxycyclobutyl)methyl)amino)cyclohexyl)oxy)-1-oxoisoindolin-2-yl)piperidine-2,6-dione;

3-(5-(((1S,2R)-2-(((cis-3-methoxycyclobutyl)methyl)amino)cyclohexyl)oxy)-1-oxoisoindolin-2-yl)piperidine-2,6-dione;
3-(5-(((1R,2R)-2-(((cis-3-methoxycyclobutyl)methyl)amino)cyclohexyl)oxy)-1-oxoisoindolin-2-yl)piperidine-2,6-dione;
3-(5-(((1R,2S)-2-(((cis-3-methoxycyclobutyl)methyl)amino)cyclohexyl)oxy)-1-oxoisoindolin-2-yl)piperidine-2,6-dione;
3-(5-((2-(((cis-3-methoxycyclobutyl)methyl)amino)cyclohexyl)oxy)-1-oxoisoindolin-2-yl)piperidine-2,6-dione;
3-(5-(((1S,2S)-2-((((1R,3S)-3-methoxycyclobutyl)methyl)amino)cyclohexyl)oxy)-1-oxoisoindolin-2-yl)piperidine-2,6-dione;
3-(5-(((1S,2R)-2-((((1s,3S)-3-methoxycyclobutyl)methyl)amino)cyclohexyl)oxy)-1-oxoisoindolin-2-yl)piperidine-2,6-dione;
3-(5-(((1R,2R)-2-((((1s,3S)-3-methoxycyclobutyl)methyl)amino)cyclohexyl)oxy)-1-oxoisoindolin-2-yl)piperidine-2,6-dione;
3-(5-(((1R,2S)-2-((((1s,3R)-3-methoxycyclobutyl)methyl)amino)cyclohexyl)oxy)-1-oxoisoindolin-2-yl)piperidine-2,6-dione;
3-(5-((2-((((1s,3s)-3-methoxycyclobutyl)methyl)amino)cyclohexyl)oxy)-1-oxoisoindolin-2-yl)piperidine-2,6-dione;
3-(5-(((1S,2S)-2-(((trans-3-methoxycyclobutyl)methyl)amino)cyclohexyl)oxy)-1-oxoisoindolin-2-yl)piperidine-2,6-dione;
3-(5-(((1S,2R)-2-(((trans-3-methoxycyclobutyl)methyl)amino)cyclohexyl)oxy)-1-oxoisoindolin-2-yl)piperidine-2,6-dione;
3-(5-(((1R,2R)-2-(((trans-3-methoxycyclobutyl)methyl)amino)cyclohexyl)oxy)-1-oxoisoindolin-2-yl)piperidine-2,6-dione;
3-(5-(((1R,2S)-2-(((trans-3-methoxycyclobutyl)methyl)amino)cyclohexyl)oxy)-1-oxoisoindolin-2-yl)piperidine-2,6-dione;
3-(5-((2-(((trans-3-methoxycyclobutyl)methyl)amino)cyclohexyl)oxy)-1-oxoisoindolin-2-yl)piperidine-2,6-dione;
3-(5-(((1S,2S)-2-((((1r,4S)-4-methoxycyclohexyl)methyl)amino)cyclohexyl)oxy)-1-oxoisoindolin-2-yl)piperidine-2,6-dione;
3-(5-(((1S,2R)-2-((((1r,4R)-4-methoxycyclohexyl)methyl)amino)cyclohexyl)oxy)-1-oxoisoindolin-2-yl)piperidine-2,6-dione;
3-(5-(((1R,2R)-2-((((1r,4R)-4-methoxycyclohexyl)methyl)amino)cyclohexyl)oxy)-1-oxoisoindolin-2-yl)piperidine-2,6-dione;
3-(5-(((1R,2S)-2-((((1r,4S)-4-methoxycyclohexyl)methyl)amino)cyclohexyl)oxy)-1-oxoisoindolin-2-yl)piperidine-2,6-dione;
3-(5-((2-((((1r,4r)-4-methoxycyclohexyl)methyl)amino)cyclohexyl)oxy)-1-oxoisoindolin-2-yl)piperidine-2,6-dione;
3-(5-(((1S,2S)-2-(((4-methyltetrahydro-2H-pyran-4-yl)methyl)amino)cyclohexyl)oxy)-1-oxoisoindolin-2-yl)piperidine-2,6-dione;
3-(5-(((1S,2R)-2-(((4-methyltetrahydro-2H-pyran-4-yl)methyl)amino)cyclohexyl)oxy)-1-oxoisoindolin-2-yl)piperidine-2,6-dione;
3-(5-(((1R,2R)-2-(((4-methyltetrahydro-2H-pyran-4-yl)methyl)amino)cyclohexyl)oxy)-1-oxoisoindolin-2-yl)piperidine-2,6-dione;
3-(5-(((1R,2S)-2-(((4-methyltetrahydro-2H-pyran-4-yl)methyl)amino)cyclohexyl)oxy)-1-oxoisoindolin-2-yl)piperidine-2,6-dione;
3-(5-((2-(((4-methyltetrahydro-2H-pyran-4-yl)methyl)amino)cyclohexyl)oxy)-1-oxoisoindolin-2-yl)piperidine-2,6-dione;
3-(1-oxo-5-(((1S,2S)-2-((pyrimidin-5-ylmethyl)amino)cyclohexyl)oxy)isoindolin-2-yl)piperidine-2,6-dione;
3-(1-oxo-5-(((1S,2R)-2-((pyrimidin-5-ylmethyl)amino)cyclohexyl)oxy)isoindolin-2-yl)piperidine-2,6-dione;
3-(1-oxo-5-(((1R,2R)-2-((pyrimidin-5-ylmethyl)amino)cyclohexyl)oxy)isoindolin-2-yl)piperidine-2,6-dione;
3-(1-oxo-5-(((1R,2S)-2-((pyrimidin-5-ylmethyl)amino)cyclohexyl)oxy)isoindolin-2-yl)piperidine-2,6-dione;
3-(1-oxo-5-((2-((pyrimidin-5-ylmethyl)amino)cyclohexyl)oxy)isoindolin-2-yl)piperidine-2,6-dione;
3-(1-oxo-5-(((1S,2S)-2-((2-(tetrahydro-2H-pyran-4-yl)ethyl)amino)cyclohexyl)oxy)isoindolin-2-yl)piperidine-2,6-dione;
3-(1-oxo-5-(((1S,2R)-2-((2-(tetrahydro-2H-pyran-4-yl)ethyl)amino)cyclohexyl)oxy)isoindolin-2-yl)piperidine-2,6-dione;
3-(1-oxo-5-(((1R,2R)-2-((2-(tetrahydro-2H-pyran-4-yl)ethyl)amino)cyclohexyl)oxy)isoindolin-2-yl)piperidine-2,6-dione;
3-(1-oxo-5-(((1R,2S)-2-((2-(tetrahydro-2H-pyran-4-yl)ethyl)amino)cyclohexyl)oxy)isoindolin-2-yl)piperidine-2,6-dione;
3-(1-oxo-5-((2-((2-(tetrahydro-2H-pyran-4-yl)ethyl)amino)cyclohexyl)oxy)isoindolin-2-yl)piperidine-2,6-dione;
3-(5-(((1S,2S)-2-(2-oxa-7-azaspiro[3.5]nonan-7-yl)cyclohexyl)oxy)-1-oxoisoindolin-2-yl)piperidine-2,6-dione;
3-(5-(((1S,2R)-2-(2-oxa-7-azaspiro[3.5]nonan-7-yl)cyclohexyl)oxy)-1-oxoisoindolin-2-yl)piperidine-2,6-dione;
3-(5-(((1R,2R)-2-(2-oxa-7-azaspiro[3.5]nonan-7-yl)cyclohexyl)oxy)-1-oxoisoindolin-2-yl)piperidine-2,6-dione;
3-(5-(((1R,2S)-2-(2-oxa-7-azaspiro[3.5]nonan-7-yl)cyclohexyl)oxy)-1-oxoisoindolin-2-yl)piperidine-2,6-dione;
3-(5-((2-(2-oxa-7-azaspiro[3.5]nonan-7-yl)cyclohexyl)oxy)-1-oxoisoindolin-2-yl)piperidine-2,6-dione;
3-(5-(((1S,2S)-2-(((4-methoxytetrahydro-2H-pyran-4-yl)methyl)amino)cyclohexyl)oxy)-1-oxoisoindolin-2-yl)piperidine-2,6-dione;
3-(5-(((1S,2R)-2-(((4-methoxytetrahydro-2H-pyran-4-yl)methyl)amino)cyclohexyl)oxy)-1-oxoisoindolin-2-yl)piperidine-2,6-dione;
3-(5-(((1R,2R)-2-(((4-methoxytetrahydro-2H-pyran-4-yl)methyl)amino)cyclohexyl)oxy)-1-oxoisoindolin-2-yl)piperidine-2,6-dione;
3-(5-(((1R,2S)-2-(((4-methoxytetrahydro-2H-pyran-4-yl)methyl)amino)cyclohexyl)oxy)-1-oxoisoindolin-2-yl)piperidine-2,6-dione;
3-(5-((2-(((4-methoxytetrahydro-2H-pyran-4-yl)methyl)amino)cyclohexyl)oxy)-1-oxoisoindolin-2-yl)piperidine-2,6-dione;
3-(5-(((1S,2S)-2-(((2,2-dimethyltetrahydro-2H-pyran-4-yl)methyl)amino)cyclohexyl)oxy)-1-oxoisoindolin-2-yl)piperidine-2,6-dione;
3-(5-(((1S,2R)-2-(((2,2-dimethyltetrahydro-2H-pyran-4-yl)methyl)amino)cyclohexyl)oxy)-1-oxoisoindolin-2-yl)piperidine-2,6-dione;

3-(5-(((1R,2R)-2-(((2,2-dimethyltetrahydro-2H-pyran-4-yl)methyl)amino)cyclohexyl)oxy)-1-oxoisoindolin-2-yl)piperidine-2,6-dione;
3-(5-(((1R,2S)-2-(((2,2-dimethyltetrahydro-2H-pyran-4-yl)methyl)amino)cyclohexyl)oxy)-1-oxoisoindolin-2-yl)piperidine-2,6-dione;
3-(5-((2-(((2,2-dimethyltetrahydro-2H-pyran-4-yl)methyl)amino)cyclohexyl)oxy)-1-oxoisoindolin-2-yl)piperidine-2,6-dione;
3-(5-(((1S,2S)-2-((7-oxaspiro[3.5]nonan-2-yl)amino)cyclohexyl)oxy)-1-oxoisoindolin-2-yl)piperidine-2,6-dione;
3-(5-(((1S,2R)-2-((7-oxaspiro[3.5]nonan-2-yl)amino)cyclohexyl)oxy)-1-oxoisoindolin-2-yl)piperidine-2,6-dione;
3-(5-(((1R,2R)-2-((7-oxaspiro[3.5]nonan-2-yl)amino)cyclohexyl)oxy)-1-oxoisoindolin-2-yl)piperidine-2,6-dione;
3-(5-(((1R,2S)-2-((7-oxaspiro[3.5]nonan-2-yl)amino)cyclohexyl)oxy)-1-oxoisoindolin-2-yl)piperidine-2,6-dione;
3-(5-((2-((7-oxaspiro[3.5]nonan-2-yl)amino)cyclohexyl)oxy)-1-oxoisoindolin-2-yl)piperidine-2,6-dione;
1-(((((1S,2S)-2-((2-(2,6-dioxopiperidin-3-yl)-1-oxoisoindolin-5-yl)oxy)cyclohexyl)amino)methyl)cyclobutane-1-carbonitrile;
1-(((((1R,2S)-2-((2-(2,6-dioxopiperidin-3-yl)-1-oxoisoindolin-5-yl)oxy)cyclohexyl)amino)methyl)cyclobutane-1-carbonitrile;
1-(((((1R,2R)-2-((2-(2,6-dioxopiperidin-3-yl)-1-oxoisoindolin-5-yl)oxy)cyclohexyl)amino)methyl)cyclobutane-1-carbonitrile;
1-(((((1S,2R)-2-((2-(2,6-dioxopiperidin-3-yl)-1-oxoisoindolin-5-yl)oxy)cyclohexyl)amino)methyl)cyclobutane-1-carbonitrile;
1-(((2-((2-(2,6-dioxopiperidin-3-yl)-1-oxoisoindolin-5-yl)oxy)cyclohexyl)amino)methyl)cyclobutane-1-carbonitrile;
3-(5-(((1S,2S)-2-(3-(2-chlorophenoxy)azetidin-1-yl)cyclohexyl)oxy)-1-oxoisoindolin-2-yl)piperidine-2,6-dione;
3-(5-(((1S,2R)-2-(3-(2-chlorophenoxy)azetidin-1-yl)cyclohexyl)oxy)-1-oxoisoindolin-2-yl)piperidine-2,6-dione;
3-(5-(((1R,2R)-2-(3-(2-chlorophenoxy)azetidin-1-yl)cyclohexyl)oxy)-1-oxoisoindolin-2-yl)piperidine-2,6-dione;
3-(5-(((1R,2S)-2-(3-(2-chlorophenoxy)azetidin-1-yl)cyclohexyl)oxy)-1-oxoisoindolin-2-yl)piperidine-2,6-dione;
3-(5-((2-(3-(2-chlorophenoxy)azetidin-1-yl)cyclohexyl)oxy)-1-oxoisoindolin-2-yl)piperidine-2,6-dione;
3-(5-(((1S,2S)-2-(3-(2-methoxyphenoxy)azetidin-1-yl)cyclohexyl)oxy)-1-oxoisoindolin-2-yl)piperidine-2,6-dione;
3-(5-(((1S,2R)-2-(3-(2-methoxyphenoxy)azetidin-1-yl)cyclohexyl)oxy)-1-oxoisoindolin-2-yl)piperidine-2,6-dione;
3-(5-(((1R,2R)-2-(3-(2-methoxyphenoxy)azetidin-1-yl)cyclohexyl)oxy)-1-oxoisoindolin-2-yl)piperidine-2,6-dione;
3-(5-(((1R,2S)-2-(3-(2-methoxyphenoxy)azetidin-1-yl)cyclohexyl)oxy)-1-oxoisoindolin-2-yl)piperidine-2,6-dione;
3-(5-((2-(3-(2-methoxyphenoxy)azetidin-1-yl)cyclohexyl)oxy)-1-oxoisoindolin-2-yl)piperidine-2,6-dione;
3-(1-oxo-5-(((1S,2S)-2-((pyrazolo[1,5-a]pyrimidin-6-ylmethyl)amino)cyclohexyl)oxy)isoindolin-2-yl)piperidine-2,6-dione;
3-(1-oxo-5-(((1S,2R)-2-((pyrazolo[1,5-a]pyrimidin-6-ylmethyl)amino)cyclohexyl)oxy)isoindolin-2-yl)piperidine-2,6-dione;
3-(1-oxo-5-(((1R,2R)-2-((pyrazolo[1,5-a]pyrimidin-6-ylmethyl)amino)cyclohexyl)oxy)isoindolin-2-yl)piperidine-2,6-dione;
3-(1-oxo-5-(((1R,2S)-2-((pyrazolo[1,5-a]pyrimidin-6-ylmethyl)amino)cyclohexyl)oxy)isoindolin-2-yl)piperidine-2,6-dione;
3-(1-oxo-5-((2-((pyrazolo[1,5-a]pyrimidin-6-ylmethyl)amino)cyclohexyl)oxy)isoindolin-2-yl)piperidine-2,6-dione;
3-(5-(((1S,2S)-2-((4,4-difluorocyclohexyl)amino)cyclohexyl)oxy)-1-oxoisoindolin-2-yl)piperidine-2,6-dione;
3-(5-(((1S,2R)-2-((4,4-difluorocyclohexyl)amino)cyclohexyl)oxy)-1-oxoisoindolin-2-yl)piperidine-2,6-dione;
3-(5-(((1R,2R)-2-((4,4-difluorocyclohexyl)amino)cyclohexyl)oxy)-1-oxoisoindolin-2-yl)piperidine-2,6-dione;
3-(5-(((1R,2S)-2-((4,4-difluorocyclohexyl)amino)cyclohexyl)oxy)-1-oxoisoindolin-2-yl)piperidine-2,6-dione;
3-(5-((2-((4,4-difluorocyclohexyl)amino)cyclohexyl)oxy)-1-oxoisoindolin-2-yl)piperidine-2,6-dione;
3-(5-(((1S,2S)-2-((2,4-difluorobenzyl)amino)cyclohexyl)oxy)-1-oxoisoindolin-2-yl)piperidine-2,6-dione;
3-(5-(((1S,2R)-2-((2,4-difluorobenzyl)amino)cyclohexyl)oxy)-1-oxoisoindolin-2-yl)piperidine-2,6-dione;
3-(5-(((1R,2R)-2-((2,4-difluorobenzyl)amino)cyclohexyl)oxy)-1-oxoisoindolin-2-yl)piperidine-2,6-dione;
3-(5-(((1R,2S)-2-((2,4-difluorobenzyl)amino)cyclohexyl)oxy)-1-oxoisoindolin-2-yl)piperidine-2,6-dione;
3-(5-((2-((2,4-difluorobenzyl)amino)cyclohexyl)oxy)-1-oxoisoindolin-2-yl)piperidine-2,6-dione;
3-(5-(((1S,2S)-2-((2-methoxycyclopentyl)amino)cyclohexyl)oxy)-1-oxoisoindolin-2-yl)piperidine-2,6-dione;
3-(5-(((1S,2R)-2-((2-methoxycyclopentyl)amino)cyclohexyl)oxy)-1-oxoisoindolin-2-yl)piperidine-2,6-dione;
3-(5-(((1R,2R)-2-((2-methoxycyclopentyl)amino)cyclohexyl)oxy)-1-oxoisoindolin-2-yl)piperidine-2,6-dione;
3-(5-(((1R,2S)-2-((2-methoxycyclopentyl)amino)cyclohexyl)oxy)-1-oxoisoindolin-2-yl)piperidine-2,6-dione;
3-(5-((2-((2-methoxycyclopentyl)amino)cyclohexyl)oxy)-1-oxoisoindolin-2-yl)piperidine-2,6-dione;
3-(5-(((1S,2S)-2-(((1R,2R)-2-methoxycyclopentyl)amino)cyclohexyl)oxy)-1-oxoisoindolin-2-yl)piperidine-2,6-dione;
3-(5-(((1S,2R)-2-(((1R,2R)-2-methoxycyclopentyl)amino)cyclohexyl)oxy)-1-oxoisoindolin-2-yl)piperidine-2,6-dione;
3-(5-(((1R,2R)-2-(((1R,2R)-2-methoxycyclopentyl)amino)cyclohexyl)oxy)-1-oxoisoindolin-2-yl)piperidine-2,6-dione;
3-(5-(((1R,2S)-2-(((1R,2R)-2-methoxycyclopentyl)amino)cyclohexyl)oxy)-1-oxoisoindolin-2-yl)piperidine-2,6-dione;
3-(5-((2-(((1R,2R)-2-methoxycyclopentyl)amino)cyclohexyl)oxy)-1-oxoisoindolin-2-yl)piperidine-2,6-dione;
3-(5-(((1S,2S)-2-(((1S,2S)-2-methoxycyclopentyl)amino)cyclohexyl)oxy)-1-oxoisoindolin-2-yl)piperidine-2,6-dione;
3-(5-(((1S,2R)-2-(((1S,2S)-2-methoxycyclopentyl)amino)cyclohexyl)oxy)-1-oxoisoindolin-2-yl)piperidine-2,6-dione;

3-(5-(((1R,2R)-2-(((1S,2S)-2-methoxycyclopentyl)amino)cyclohexyl)oxy)-1-oxoisoindolin-2-yl)piperidine-2,6-dione;
3-(5-(((1R,2S)-2-(((1S,2S)-2-methoxycyclopentyl)amino)cyclohexyl)oxy)-1-oxoisoindolin-2-yl)piperidine-2,6-dione;
3-(5-((2-(((1S,2S)-2-methoxycyclopentyl)amino)cyclohexyl)oxy)-1-oxoisoindolin-2-yl)piperidine-2,6-dione;
3-((((1S,2S)-2-((2-(2,6-dioxopiperidin-3-yl)-1-oxoisoindolin-5-yl)oxy)cyclohexyl)amino)methyl)bicyclo[1.1.1]pentane-1-carbonitrile;
3-((((1R,2S)-2-((2-(2,6-dioxopiperidin-3-yl)-1-oxoisoindolin-5-yl)oxy)cyclohexyl)amino)methyl)bicyclo[1.1.1]pentane-1-carbonitrile;
3-((((1R,2R)-2-((2-(2,6-dioxopiperidin-3-yl)-1-oxoisoindolin-5-yl)oxy)cyclohexyl)amino)methyl)bicyclo[1.1.1]pentane-1-carbonitrile;
3-((((1S,2R)-2-((2-(2,6-dioxopiperidin-3-yl)-1-oxoisoindolin-5-yl)oxy)cyclohexyl)amino)methyl)bicyclo[1.1.1]pentane-1-carbonitrile;
3-(((2-((2-(2,6-dioxopiperidin-3-yl)-1-oxoisoindolin-5-yl)oxy)cyclohexyl)amino)methyl)bicyclo[1.1.1]pentane-1-carbonitrile;
3-(5-(((1S,2S)-2-(3-(3-fluorophenoxy)azetidin-1-yl)cyclohexyl)oxy)-1-oxoisoindolin-2-yl)piperidine-2,6-dione;
3-(5-(((1S,2R)-2-(3-(3-fluorophenoxy)azetidin-1-yl)cyclohexyl)oxy)-1-oxoisoindolin-2-yl)piperidine-2,6-dione;
3-(5-(((1R,2R)-2-(3-(3-fluorophenoxy)azetidin-1-yl)cyclohexyl)oxy)-1-oxoisoindolin-2-yl)piperidine-2,6-dione;
3-(5-(((1R,2S)-2-(3-(3-fluorophenoxy)azetidin-1-yl)cyclohexyl)oxy)-1-oxoisoindolin-2-yl)piperidine-2,6-dione;
3-(5-((2-(3-(3-fluorophenoxy)azetidin-1-yl)cyclohexyl)oxy)-1-oxoisoindolin-2-yl)piperidine-2,6-dione;
3-(5-(((1S,2S)-2-(((3,3-difluorocyclobutyl)methyl)amino)cyclohexyl)oxy)-1-oxoisoindolin-2-yl)piperidine-2,6-dione;
3-(5-(((1S,2R)-2-(((3,3-difluorocyclobutyl)methyl)amino)cyclohexyl)oxy)-1-oxoisoindolin-2-yl)piperidine-2,6-dione;
3-(5-(((1R,2R)-2-(((3,3-difluorocyclobutyl)methyl)amino)cyclohexyl)oxy)-1-oxoisoindolin-2-yl)piperidine-2,6-dione;
3-(5-(((1R,2S)-2-(((3,3-difluorocyclobutyl)methyl)amino)cyclohexyl)oxy)-1-oxoisoindolin-2-yl)piperidine-2,6-dione;
3-(5-((2-(((3,3-difluorocyclobutyl)methyl)amino)cyclohexyl)oxy)-1-oxoisoindolin-2-yl)piperidine-2,6-dione;
3-(5-(((1S,2S)-2-((((1S,4R)-4-methoxycyclohexyl)methyl)amino)cyclohexyl)oxy)-1-oxoisoindolin-2-yl)piperidine-2,6-dione;
3-(5-(((1S,2R)-2-((((1s,4S)-4-methoxycyclohexyl)methyl)amino)cyclohexyl)oxy)-1-oxoisoindolin-2-yl)piperidine-2,6-dione;
3-(5-(((1R,2R)-2-((((1s,4S)-4-methoxycyclohexyl)methyl)amino)cyclohexyl)oxy)-1-oxoisoindolin-2-yl)piperidine-2,6-dione;
3-(5-(((1R,2S)-2-((((1s,4R)-4-methoxycyclohexyl)methyl)amino)cyclohexyl)oxy)-1-oxoisoindolin-2-yl)piperidine-2,6-dione;
3-(5-((2-((((1s,4s)-4-methoxycyclohexyl)methyl)amino)cyclohexyl)oxy)-1-oxoisoindolin-2-yl)piperidine-2,6-dione;
3-(5-(((1S,2S)-2-(((4-methoxycyclohexyl)methyl)amino)cyclohexyl)oxy)-1-oxoisoindolin-2-yl)piperidine-2,6-dione;
3-(5-(((1S,2S)-2-(((cis-4-methoxycyclohexyl)methyl)amino)cyclohexyl)oxy)-1-oxoisoindolin-2-yl)piperidine-2,6-dione;
3-(5-(((1S,2S)-2-(((trans-4-methoxycyclohexyl)methyl)amino)cyclohexyl)oxy)-1-oxoisoindolin-2-yl)piperidine-2,6-dione;
3-(5-(((1S,2S)-2-(bis(((1R,4S)-4-methoxycyclohexyl)methyl)amino)cyclohexyl)oxy)-1-oxoisoindolin-2-yl)piperidine-2,6-dione;
3-(5-(((1S,2R)-2-(bis(((1r,4R)-4-methoxycyclohexyl)methyl)amino)cyclohexyl)oxy)-1-oxoisoindolin-2-yl)piperidine-2,6-dione;
3-(5-(((1R,2R)-2-(bis(((1r,4R)-4-methoxycyclohexyl)methyl)amino)cyclohexyl)oxy)-1-oxoisoindolin-2-yl)piperidine-2,6-dione;
3-(5-(((1R,2S)-2-(bis(((1r,4S)-4-methoxycyclohexyl)methyl)amino)cyclohexyl)oxy)-1-oxoisoindolin-2-yl)piperidine-2,6-dione;
3-(5-((2-(bis(((1r,4R)-4-methoxycyclohexyl)methyl)amino)cyclohexyl)oxy)-1-oxoisoindolin-2-yl)piperidine-2,6-dione;
4-((((1S,2S)-2-((2-(2,6-dioxopiperidin-3-yl)-1-oxoisoindolin-5-yl)oxy)cyclohexyl)amino)methyl)benzonitrile;
4-((((1R,2S)-2-((2-(2,6-dioxopiperidin-3-yl)-1-oxoisoindolin-5-yl)oxy)cyclohexyl)amino)methyl)benzonitrile;
4-((((1R,2R)-2-((2-(2,6-dioxopiperidin-3-yl)-1-oxoisoindolin-5-yl)oxy)cyclohexyl)amino)methyl)benzonitrile;
4-((((1S,2R)-2-((2-(2,6-dioxopiperidin-3-yl)-1-oxoisoindolin-5-yl)oxy)cyclohexyl)amino)methyl)benzonitrile;
4-(((2-((2-(2,6-dioxopiperidin-3-yl)-1-oxoisoindolin-5-yl)oxy)cyclohexyl)amino)methyl)benzonitrile;
4-((((1S,2S)-2-((2-(2,6-dioxopiperidin-3-yl)-1-oxoisoindolin-5-yl)oxy)cyclohexyl)(methyl)amino)methyl)benzonitrile;
4-((((1R,2S)-2-((2-(2,6-dioxopiperidin-3-yl)-1-oxoisoindolin-5-yl)oxy)cyclohexyl)(methyl)amino)methyl)benzonitrile;
4-((((1R,2R)-2-((2-(2,6-dioxopiperidin-3-yl)-1-oxoisoindolin-5-yl)oxy)cyclohexyl)(methyl)amino)methyl)benzonitrile;
4-((((1S,2R)-2-((2-(2,6-dioxopiperidin-3-yl)-1-oxoisoindolin-5-yl)oxy)cyclohexyl)(methyl)amino)methyl)benzonitrile;
4-(((2-((2-(2,6-dioxopiperidin-3-yl)-1-oxoisoindolin-5-yl)oxy)cyclohexyl)(methyl)amino)methyl)benzonitrile;
3-(5-(((1S,2S)-2-(((3-fluorobicyclo[1.1.1]pentan-1-yl)methyl)amino)cyclohexyl)oxy)-1-oxoisoindolin-2-yl)piperidine-2,6-dione;
3-(5-(((1S,2R)-2-(((3-fluorobicyclo[1.1.1]pentan-1-yl)methyl)amino)cyclohexyl)oxy)-1-oxoisoindolin-2-yl)piperidine-2,6-dione;
3-(5-(((1R,2R)-2-(((3-fluorobicyclo[1.1.1]pentan-1-yl)methyl)amino)cyclohexyl)oxy)-1-oxoisoindolin-2-yl)piperidine-2,6-dione;
3-(5-(((1R,2S)-2-(((3-fluorobicyclo[1.1.1]pentan-1-yl)methyl)amino)cyclohexyl)oxy)-1-oxoisoindolin-2-yl)piperidine-2,6-dione;
3-(5-((2-(((3-fluorobicyclo[1.1.1]pentan-1-yl)methyl)amino)cyclohexyl)oxy)-1-oxoisoindolin-2-yl)piperidine-2,6-dione;
3-(5-((2-(3,3-difluoropyrrolidin-1-yl)cyclohexyl)oxy)-1-oxoisoindolin-2-yl)piperidine-2,6-dione;

3-(5-((((1S,2S)-2-(3,3-difluoropyrrolidin-1-yl)cyclohexyl)oxy)-1-oxoisoindolin-2-yl)piperidine-2,6-dione;
3-(5-((((1S,2R)-2-(3,3-difluoropyrrolidin-1-yl)cyclohexyl)oxy)-1-oxoisoindolin-2-yl)piperidine-2,6-dione;
3-(5-((((1R,2R)-2-(3,3-difluoropyrrolidin-1-yl)cyclohexyl)oxy)-1-oxoisoindolin-2-yl)piperidine-2,6-dione;
3-(5-((((1R,2S)-2-(3,3-difluoropyrrolidin-1-yl)cyclohexyl)oxy)-1-oxoisoindolin-2-yl)piperidine-2,6-dione;
3-(5-((((1S,2S)-2-(ethylamino)cycloheptyl)oxy)-1-oxoisoindolin-2-yl)piperidine-2,6-dione;
3-(5-((((1S,2R)-2-(ethylamino)cycloheptyl)oxy)-1-oxoisoindolin-2-yl)piperidine-2,6-dione;
3-(5-((((1R,2R)-2-(ethylamino)cycloheptyl)oxy)-1-oxoisoindolin-2-yl)piperidine-2,6-dione;
3-(5-((((1R,2S)-2-(ethylamino)cycloheptyl)oxy)-1-oxoisoindolin-2-yl)piperidine-2,6-dione;
3-(5-((2-(ethylamino)cycloheptyl)oxy)-1-oxoisoindolin-2-yl)piperidine-2,6-dione;
3-(5-((((1S,2S)-2-(benzylamino)cycloheptyl)oxy)-1-oxoisoindolin-2-yl)piperidine-2,6-dione;
3-(5-((((1S,2R)-2-(benzylamino)cycloheptyl)oxy)-1-oxoisoindolin-2-yl)piperidine-2,6-dione;
3-(5-((((1R,2R)-2-(benzylamino)cycloheptyl)oxy)-1-oxoisoindolin-2-yl)piperidine-2,6-dione;
3-(5-((((1R,2S)-2-(benzylamino)cycloheptyl)oxy)-1-oxoisoindolin-2-yl)piperidine-2,6-dione;
3-(5-((2-(benzylamino)cycloheptyl)oxy)-1-oxoisoindolin-2-yl)piperidine-2,6-dione;
3-(5-((((1S,2S)-2-(diethylamino)cycloheptyl)oxy)-1-oxoisoindolin-2-yl)piperidine-2,6-dione;
3-(5-((((1S,2R)-2-(diethylamino)cycloheptyl)oxy)-1-oxoisoindolin-2-yl)piperidine-2,6-dione;
3-(5-((((1R,2R)-2-(diethylamino)cycloheptyl)oxy)-1-oxoisoindolin-2-yl)piperidine-2,6-dione;
3-(5-((((1R,2S)-2-(diethylamino)cycloheptyl)oxy)-1-oxoisoindolin-2-yl)piperidine-2,6-dione;
3-(5-((2-(diethylamino)cycloheptyl)oxy)-1-oxoisoindolin-2-yl)piperidine-2,6-dione;
3-(5-((((1S,2S)-2-(4-methoxy-4-methylpiperidin-1-yl)cycloheptyl)oxy)-1-oxoisoindolin-2-yl)piperidine-2,6-dione;
3-(5-((((1S,2R)-2-(4-methoxy-4-methylpiperidin-1-yl)cycloheptyl)oxy)-1-oxoisoindolin-2-yl)piperidine-2,6-dione;
3-(5-((((1R,2R)-2-(4-methoxy-4-methylpiperidin-1-yl)cycloheptyl)oxy)-1-oxoisoindolin-2-yl)piperidine-2,6-dione;
3-(5-((((1R,2S)-2-(4-methoxy-4-methylpiperidin-1-yl)cycloheptyl)oxy)-1-oxoisoindolin-2-yl)piperidine-2,6-dione;
3-(5-((2-(4-methoxy-4-methylpiperidin-1-yl)cycloheptyl)oxy)-1-oxoisoindolin-2-yl)piperidine-2,6-dione;
3-(5-((((1S,2S)-2-(isobutylamino)cycloheptyl)oxy)-1-oxoisoindolin-2-yl)piperidine-2,6-dione;
3-(5-((((1S,2R)-2-(isobutylamino)cycloheptyl)oxy)-1-oxoisoindolin-2-yl)piperidine-2,6-dione;
3-(5-((((1R,2R)-2-(isobutylamino)cycloheptyl)oxy)-1-oxoisoindolin-2-yl)piperidine-2,6-dione;
3-(5-((((1R,2S)-2-(isobutylamino)cycloheptyl)oxy)-1-oxoisoindolin-2-yl)piperidine-2,6-dione;
3-(5-((2-(isobutylamino)cycloheptyl)oxy)-1-oxoisoindolin-2-yl)piperidine-2,6-dione;
3-(1-oxo-5-((((1S,2S)-2-(propylamino)cycloheptyl)oxy)isoindolin-2-yl)piperidine-2,6-dione;
3-(1-oxo-5-((((1S,2R)-2-(propylamino)cycloheptyl)oxy)isoindolin-2-yl)piperidine-2,6-dione;
3-(1-oxo-5-((((1R,2R)-2-(propylamino)cycloheptyl)oxy)isoindolin-2-yl)piperidine-2,6-dione;
3-(1-oxo-5-((((1R,2S)-2-(propylamino)cycloheptyl)oxy)isoindolin-2-yl)piperidine-2,6-dione;
3-(1-oxo-5-((2-(propylamino)cycloheptyl)oxy)isoindolin-2-yl)piperidine-2,6-dione;
3-(5-((((1S,2S)-2-(2-oxa-6-azaspiro[3.3]heptan-6-yl)cycloheptyl)oxy)-1-oxoisoindolin-2-yl)piperidine-2,6-dione;
3-(5-((((1S,2R)-2-(2-oxa-6-azaspiro[3.3]heptan-6-yl)cycloheptyl)oxy)-1-oxoisoindolin-2-yl)piperidine-2,6-dione;
3-(5-((((1R,2R)-2-(2-oxa-6-azaspiro[3.3]heptan-6-yl)cycloheptyl)oxy)-1-oxoisoindolin-2-yl)piperidine-2,6-dione;
3-(5-((((1R,2S)-2-(2-oxa-6-azaspiro[3.3]heptan-6-yl)cycloheptyl)oxy)-1-oxoisoindolin-2-yl)piperidine-2,6-dione;
3-(5-((2-(2-oxa-6-azaspiro[3.3]heptan-6-yl)cycloheptyl)oxy)-1-oxoisoindolin-2-yl)piperidine-2,6-dione;
3-(5-((((1S,2S)-2-(((((1R,4S)-4-methoxycyclohexyl)methyl)amino)cycloheptyl)oxy)-1-oxoisoindolin-2-yl)piperidine-2,6-dione;
3-(5-((((1S,2R)-2-(((((1r,4R)-4-methoxycyclohexyl)methyl)amino)cycloheptyl)oxy)-1-oxoisoindolin-2-yl)piperidine-2,6-dione;
3-(5-((((1R,2R)-2-(((((1r,4R)-4-methoxycyclohexyl)methyl)amino)cycloheptyl)oxy)-1-oxoisoindolin-2-yl)piperidine-2,6-dione;
3-(5-((((1R,2S)-2-(((((1r,4S)-4-methoxycyclohexyl)methyl)amino)cycloheptyl)oxy)-1-oxoisoindolin-2-yl)piperidine-2,6-dione;
3-(5-((2-(((((1r,4r)-4-methoxycyclohexyl)methyl)amino)cycloheptyl)oxy)-1-oxoisoindolin-2-yl)piperidine-2,6-dione;
3-(1-oxo-5-((((1S,2S)-2-(((tetrahydro-2H-pyran-4-yl)methyl)amino)cycloheptyl)oxy) isoindolin-2-yl)piperidine-2,6-dione;
3-(1-oxo-5-((((1S,2R)-2-(((tetrahydro-2H-pyran-4-yl)methyl)amino)cycloheptyl)oxy)isoindolin-2-yl)piperidine-2,6-dione;
3-(1-oxo-5-((((1R,2R)-2-(((tetrahydro-2H-pyran-4-yl)methyl)amino)cycloheptyl)oxy)isoindolin-2-yl)piperidine-2,6-dione;
3-(1-oxo-5-((((1R,2S)-2-(((tetrahydro-2H-pyran-4-yl)methyl)amino)cycloheptyl)oxy)isoindolin-2-yl)piperidine-2,6-dione;
3-(1-oxo-5-((2-(((tetrahydro-2H-pyran-4-yl)methyl)amino)cycloheptyl)oxy)isoindolin-2-yl)piperidine-2,6-dione;
3-(5-((((1S,2S)-2-(((3-methyloxetan-3-yl)methyl)amino)cycloheptyl)oxy)-1-oxoisoindolin-2-yl)piperidine-2,6-dione;
3-(5-((((1S,2R)-2-(((3-methyloxetan-3-yl)methyl)amino)cycloheptyl)oxy)-1-oxoisoindolin-2-yl)piperidine-2,6-dione;
3-(5-((((1R,2R)-2-(((3-methyloxetan-3-yl)methyl)amino)cycloheptyl)oxy)-1-oxoisoindolin-2-yl)piperidine-2,6-dione;
3-(5-((((1R,2S)-2-(((3-methyloxetan-3-yl)methyl)amino)cycloheptyl)oxy)-1-oxoisoindolin-2-yl)piperidine-2,6-dione;
3-(5-((2-(((3-methyloxetan-3-yl)methyl)amino)cycloheptyl)oxy)-1-oxoisoindolin-2-yl)piperidine-2,6-dione;
3-(5-((((1S,2S)-2-(((3-fluorobicyclo[1.1.1]pentan-1-yl)methyl)amino)cycloheptyl)oxy)-1-oxoisoindolin-2-yl)piperidine-2,6-dione;

3-(5-(((1S,2R)-2-(((3-fluorobicyclo[1.1.1]pentan-1-yl)methyl)amino)cycloheptyl)oxy)-1-oxoisoindolin-2-yl)piperidine-2,6-dione;
3-(5-(((1R,2R)-2-(((3-fluorobicyclo[1.1.1]pentan-1-yl)methyl)amino)cycloheptyl)oxy)-1-oxoisoindolin-2-yl)piperidine-2,6-dione;
3-(5-(((1R,2S)-2-(((3-fluorobicyclo[1.1.1]pentan-1-yl)methyl)amino)cycloheptyl)oxy)-1-oxoisoindolin-2-yl)piperidine-2,6-dione;
3-(5-((2-(((3-fluorobicyclo[1.1.1]pentan-1-yl)methyl)amino)cycloheptyl)oxy)-1-oxoisoindolin-2-yl)piperidine-2,6-dione;
3-(5-(((1S,2S)-2-(3-methoxyazetidin-1-yl)cycloheptyl)oxy)-1-oxoisoindolin-2-yl)piperidine-2,6-dione;
3-(5-(((1S,2R)-2-(3-methoxyazetidin-1-yl)cycloheptyl)oxy)-1-oxoisoindolin-2-yl)piperidine-2,6-dione;
3-(5-(((1R,2R)-2-(3-methoxyazetidin-1-yl)cycloheptyl)oxy)-1-oxoisoindolin-2-yl)piperidine-2,6-dione;
3-(5-(((1R,2S)-2-(3-methoxyazetidin-1-yl)cycloheptyl)oxy)-1-oxoisoindolin-2-yl)piperidine-2,6-dione;
3-(5-((2-(3-methoxyazetidin-1-yl)cycloheptyl)oxy)-1-oxoisoindolin-2-yl)piperidine-2,6-dione;
3-(5-(((1S,2S)-2-(((3,3-difluorocyclobutyl)methyl)amino)cycloheptyl)oxy)-1-oxoisoindolin-2-yl)piperidine-2,6-dione;
3-(5-(((1S,2R)-2-(((3,3-difluorocyclobutyl)methyl)amino)cycloheptyl)oxy)-1-oxoisoindolin-2-yl)piperidine-2,6-dione;
3-(5-(((1R,2R)-2-(((3,3-difluorocyclobutyl)methyl)amino)cycloheptyl)oxy)-1-oxoisoindolin-2-yl)piperidine-2,6-dione;
3-(5-(((1R,2S)-2-(((3,3-difluorocyclobutyl)methyl)amino)cycloheptyl)oxy)-1-oxoisoindolin-2-yl)piperidine-2,6-dione;
3-(5-((2-(((3,3-difluorocyclobutyl)methyl)amino)cycloheptyl)oxy)-1-oxoisoindolin-2-yl)piperidine-2,6-dione;
3-(5-((2-(diethylamino)-3-methylcyclopentyl)oxy)-1-oxoisoindolin-2-yl)piperidine-2,6-dione;
3-(5-(((1S,2S)-2-(diethylamino)-3-methylcyclopentyl)oxy)-1-oxoisoindolin-2-yl)piperidine-2,6-dione;
3-(5-(((1S,2R)-2-(diethylamino)-3-methylcyclopentyl)oxy)-1-oxoisoindolin-2-yl)piperidine-2,6-dione;
3-(5-(((1R,2R)-2-(diethylamino)-3-methylcyclopentyl)oxy)-1-oxoisoindolin-2-yl)piperidine-2,6-dione;
3-(5-(((1R,2S)-2-(diethylamino)-3-methylcyclopentyl)oxy)-1-oxoisoindolin-2-yl)piperidine-2,6-dione;
3-(1-oxo-5-(((1S,2S)-2-(3-(pyridazin-3-yloxy)azetidin-1-yl)cyclohexyl)oxy)isoindolin-2-yl)piperidine-2,6-dione;
3-(1-oxo-5-(((1S,2R)-2-(3-(pyridazin-3-yloxy)azetidin-1-yl)cyclohexyl)oxy)isoindolin-2-yl)piperidine-2,6-dione;
3-(1-oxo-5-(((1R,2R)-2-(3-(pyridazin-3-yloxy)azetidin-1-yl)cyclohexyl)oxy)isoindolin-2-yl)piperidine-2,6-dione;
3-(1-oxo-5-(((1R,2S)-2-(3-(pyridazin-3-yloxy)azetidin-1-yl)cyclohexyl)oxy)isoindolin-2-yl)piperidine-2,6-dione;
3-(1-oxo-5-((2-(3-(pyridazin-3-yloxy)azetidin-1-yl)cyclohexyl)oxy)isoindolin-2-yl)piperidine-2,6-dione;
3-(5-(((1S,2S)-2-(3-isopropoxyazetidin-1-yl)cyclopentyl)oxy)-1-oxoisoindolin-2-yl)piperidine-2,6-dione;
3-(5-(((1S,2R)-2-(3-isopropoxyazetidin-1-yl)cyclopentyl)oxy)-1-oxoisoindolin-2-yl)piperidine-2,6-dione;
3-(5-(((1R,2R)-2-(3-isopropoxyazetidin-1-yl)cyclopentyl)oxy)-1-oxoisoindolin-2-yl)piperidine-2,6-dione;
3-(5-(((1R,2S)-2-(3-isopropoxyazetidin-1-yl)cyclopentyl)oxy)-1-oxoisoindolin-2-yl)piperidine-2,6-dione;
3-(5-((2-(3-isopropoxyazetidin-1-yl)cyclopentyl)oxy)-1-oxoisoindolin-2-yl)piperidine-2,6-dione;
3-(1-oxo-5-(((1S,2S)-2-(3-(2,2,2-trifluoroethoxy)azetidin-1-yl)cyclopentyl)oxy)isoindolin-2-yl)piperidine-2,6-dione;
3-(1-oxo-5-(((1S,2R)-2-(3-(2,2,2-trifluoroethoxy)azetidin-1-yl)cyclopentyl)oxy)isoindolin-2-yl)piperidine-2,6-dione;
3-(1-oxo-5-(((1R,2R)-2-(3-(2,2,2-trifluoroethoxy)azetidin-1-yl)cyclopentyl)oxy)isoindolin-2-yl)piperidine-2,6-dione;
3-(1-oxo-5-(((1R,2S)-2-(3-(2,2,2-trifluoroethoxy)azetidin-1-yl)cyclopentyl)oxy)isoindolin-2-yl)piperidine-2,6-dione;
3-(1-oxo-5-((2-(3-(2,2,2-trifluoroethoxy)azetidin-1-yl)cyclopentyl)oxy)isoindolin-2-yl)piperidine-2,6-dione;
3-(5-(((1S,2S)-2-(3,3-dimethylpiperidin-1-yl)cyclopentyl)oxy)-1-oxoisoindolin-2-yl)piperidine-2,6-dione;
3-(5-(((1S,2R)-2-(3,3-dimethylpiperidin-1-yl)cyclopentyl)oxy)-1-oxoisoindolin-2-yl)piperidine-2,6-dione;
3-(5-(((1R,2S)-2-(3,3-dimethylpiperidin-1-yl)cyclopentyl)oxy)-1-oxoisoindolin-2-yl)piperidine-2,6-dione;
3-(5-(((1R,2R)-2-(3,3-dimethylpiperidin-1-yl)cyclopentyl)oxy)-1-oxoisoindolin-2-yl)piperidine-2,6-dione;
3-(5-((2-(3,3-dimethylpiperidin-1-yl)cyclopentyl)oxy)-1-oxoisoindolin-2-yl)piperidine-2,6-dione;
3-(5-(((1S,2S)-2-(3-isopropoxyazetidin-1-yl)cyclopentyl)oxy)-1-oxoisoindolin-2-yl)piperidine-2,6-dione;
3-(5-(((1S,2R)-2-(3-isopropoxyazetidin-1-yl)cyclopentyl)oxy)-1-oxoisoindolin-2-yl)piperidine-2,6-dione;
3-(5-(((1R,2R)-2-(3-isopropoxyazetidin-1-yl)cyclopentyl)oxy)-1-oxoisoindolin-2-yl)piperidine-2,6-dione;
3-(5-(((1R,2S)-2-(3-isopropoxyazetidin-1-yl)cyclopentyl)oxy)-1-oxoisoindolin-2-yl)piperidine-2,6-dione;
3-(5-((2-(3-isopropoxyazetidin-1-yl)cyclopentyl)oxy)-1-oxoisoindolin-2-yl)piperidine-2,6-dione;
3-(5-(((1S,2S,3S,4R)-3-(3-ethoxyazetidin-1-yl)bicyclo[2.2.1]heptan-2-yl)oxy)-1-oxoisoindolin-2-yl)piperidine-2,6-dione;
3-(5-(((1S,2S,3R,4R)-3-(3-ethoxyazetidin-1-yl)bicyclo[2.2.1]heptan-2-yl)oxy)-1-oxoisoindolin-2-yl)piperidine-2,6-dione;
3-(5-(((1S,2R,3R,4R)-3-(3-ethoxyazetidin-1-yl)bicyclo[2.2.1]heptan-2-yl)oxy)-1-oxoisoindolin-2-yl)piperidine-2,6-dione;
3-(5-(((1S,2R,3S,4R)-3-(3-ethoxyazetidin-1-yl)bicyclo[2.2.1]heptan-2-yl)oxy)-1-oxoisoindolin-2-yl)piperidine-2,6-dione;
3-(5-(((1S,4R)-3-(3-ethoxyazetidin-1-yl)bicyclo[2.2.1]heptan-2-yl)oxy)-1-oxoisoindolin-2-yl)piperidine-2,6-dione;
3-(5-(((1R,2S,3S,4S)-3-(3-ethoxyazetidin-1-yl)bicyclo[2.2.1]heptan-2-yl)oxy)-1-oxoisoindolin-2-yl)piperidine-2,6-dione;
3-(5-(((1R,2S,3R,4S)-3-(3-ethoxyazetidin-1-yl)bicyclo[2.2.1]heptan-2-yl)oxy)-1-oxoisoindolin-2-yl)piperidine-2,6-dione;
3-(5-(((1R,2R,3R,4S)-3-(3-ethoxyazetidin-1-yl)bicyclo[2.2.1]heptan-2-yl)oxy)-1-oxoisoindolin-2-yl)piperidine-2,6-dione;
3-(5-(((1R,2R,3S,4S)-3-(3-ethoxyazetidin-1-yl)bicyclo[2.2.1]heptan-2-yl)oxy)-1-oxoisoindolin-2-yl)piperidine-2,6-dione;

3-(5-(((1R,4S)-3-(3-ethoxyazetidin-1-yl)bicyclo[2.2.1]heptan-2-yl)oxy)-1-oxoisoindolin-2-yl)piperidine-2,6-dione;

3-(1-oxo-5-(((1S,2S)-2-(3-(pyrazin-2-yloxy)azetidin-1-yl)cyclohexyl)oxy)isoindolin-2-yl)piperidine-2,6-dione;

3-(1-oxo-5-(((1S,2R)-2-(3-(pyrazin-2-yloxy)azetidin-1-yl)cyclohexyl)oxy)isoindolin-2-yl)piperidine-2,6-dione;

3-(1-oxo-5-(((1R,2R)-2-(3-(pyrazin-2-yloxy)azetidin-1-yl)cyclohexyl)oxy)isoindolin-2-yl)piperidine-2,6-dione;

3-(1-oxo-5-(((1R,2S)-2-(3-(pyrazin-2-yloxy)azetidin-1-yl)cyclohexyl)oxy)isoindolin-2-yl)piperidine-2,6-dione;

3-(1-oxo-5-((2-(3-(pyrazin-2-yloxy)azetidin-1-yl)cyclohexyl)oxy)isoindolin-2-yl)piperidine-2,6-dione;

3-(5-(((1S,2S)-2-aminocyclopentyl)oxy)-4-fluoro-1-oxoisoindolin-2-yl)piperidine-2,6-dione;

3-(5-(((1S,2R)-2-aminocyclopentyl)oxy)-4-fluoro-1-oxoisoindolin-2-yl)piperidine-2,6-dione;

3-(5-(((1R,2R)-2-aminocyclopentyl)oxy)-4-fluoro-1-oxoisoindolin-2-yl)piperidine-2,6-dione;

3-(5-(((1R,2S)-2-aminocyclopentyl)oxy)-4-fluoro-1-oxoisoindolin-2-yl)piperidine-2,6-dione;

3-(5-((2-aminocyclopentyl)oxy)-4-fluoro-1-oxoisoindolin-2-yl)piperidine-2,6-dione;

3-(5-(((1S,2S)-2-(diethylamino)cyclopentyl)oxy)-4-fluoro-1-oxoisoindolin-2-yl)piperidine-2,6-dione;

3-(5-(((1S,2R)-2-(diethylamino)cyclopentyl)oxy)-4-fluoro-1-oxoisoindolin-2-yl)piperidine-2,6-dione;

3-(5-(((1R,2R)-2-(diethylamino)cyclopentyl)oxy)-4-fluoro-1-oxoisoindolin-2-yl)piperidine-2,6-dione;

3-(5-(((1R,2S)-2-(diethylamino)cyclopentyl)oxy)-4-fluoro-1-oxoisoindolin-2-yl)piperidine-2,6-dione;

3-(5-((2-(diethylamino)cyclopentyl)oxy)-4-fluoro-1-oxoisoindolin-2-yl)piperidine-2,6-dione;

3-(5-(((1S,2S)-2-aminocyclopentyl)oxy)-6-fluoro-1-oxoisoindolin-2-yl)piperidine-2,6-dione;

3-(5-(((1S,2R)-2-aminocyclopentyl)oxy)-6-fluoro-1-oxoisoindolin-2-yl)piperidine-2,6-dione;

3-(5-(((1R,2R)-2-aminocyclopentyl)oxy)-6-fluoro-1-oxoisoindolin-2-yl)piperidine-2,6-dione;

3-(5-(((1R,2S)-2-aminocyclopentyl)oxy)-6-fluoro-1-oxoisoindolin-2-yl)piperidine-2,6-dione;

3-(5-((2-aminocyclopentyl)oxy)-6-fluoro-1-oxoisoindolin-2-yl)piperidine-2,6-dione;

3-(5-(((1S,2S)-2-(diethylamino)cyclopentyl)oxy)-6-fluoro-1-oxoisoindolin-2-yl)piperidine-2,6-dione;

3-(5-(((1S,2R)-2-(diethylamino)cyclopentyl)oxy)-6-fluoro-1-oxoisoindolin-2-yl)piperidine-2,6-dione;

3-(5-(((1R,2R)-2-(diethylamino)cyclopentyl)oxy)-6-fluoro-1-oxoisoindolin-2-yl)piperidine-2,6-dione;

3-(5-(((1R,2S)-2-(diethylamino)cyclopentyl)oxy)-6-fluoro-1-oxoisoindolin-2-yl)piperidine-2,6-dione; and 3-(5-((2-(diethylamino)cyclopentyl)oxy)-6-fluoro-1-oxoisoindolin-2-yl)piperidine-2,6-dione;

or a pharmaceutically acceptable salt, stereoisomer, or tautomer thereof.

15. A pharmaceutical composition comprising a therapeutically effective amount of a compound according to claim 1, or a pharmaceutically acceptable salt thereof, and a pharmaceutically acceptable carrier or excipient.

16. The pharmaceutical composition of claim 15 further comprising at least one additional pharmaceutical agent.

* * * * *

SEQUENCE LISTING

<160> NUMBER OF SEQ ID NOS: 314

<210> SEQ ID NO 1
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Val
        35                  40                  45

Gly Val Ile Trp Gly Gly Gly Thr Tyr Tyr Ala Ser Ser Leu Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Ala Tyr Gly His Asp Gly Gly Phe Ala Met Asp Tyr Trp Gly
            100                 105                 110

Gln Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ser Asn
            20                  25                  30

Val Ala Trp Tyr Gln Gln Arg Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gly Gln Ser Tyr Ser Tyr Pro Phe
                85                  90                  95

Thr Phe Gly Gln Gly Thr Lys Leu Glu Ile Lys
            100                 105

<210> SEQ ID NO 3
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 3

| Glu | Val | Gln | Leu | Val | Glu | Ser | Gly | Gly | Gly | Leu | Val | Gln | Ser | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Ser | Leu | Ser | Ser | Tyr |
|---|---|---|---|---|---|---|---|---|---|---|---|---|---|---|---|
| | | | 20 | | | | | 25 | | | | | 30 | | |

| Gly | Val | Asp | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Val | Ile | Trp | Gly | Gly | Gly | Thr | Tyr | Tyr | Ala | Ser | Ser | Leu | Met |
|---|---|---|---|---|---|---|---|---|---|---|---|---|---|---|
| 50 | | | | | 55 | | | | | 60 | | | | |

| Gly | Arg | Phe | Thr | Ile | Ser | Arg | Asp | Asn | Ser | Lys | Asn | Thr | Leu | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Arg | Ala | Glu | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Arg | His | Ala | Tyr | Gly | His | Asp | Gly | Phe | Ala | Met | Asp | Tyr | Trp | Gly |
|---|---|---|---|---|---|---|---|---|---|---|---|---|---|---|
| | | | | 100 | | | | | 105 | | | | 110 | |

| Gln | Gly | Thr | Leu | Val | Thr | Val | Ser | Ser | Ala | Ser | Thr | Lys | Gly | Pro | Ser |
|---|---|---|---|---|---|---|---|---|---|---|---|---|---|---|---|
| | | | 115 | | | | | 120 | | | | | 125 | | |

| Val | Phe | Pro | Leu | Ala | Pro | Ser | Ser | Lys | Ser | Thr | Ser | Gly | Gly | Thr | Ala |
|---|---|---|---|---|---|---|---|---|---|---|---|---|---|---|---|
| | 130 | | | | | 135 | | | | | 140 | | | | |

| Ala | Leu | Gly | Cys | Leu | Val | Lys | Asp | Tyr | Phe | Pro | Glu | Pro | Val | Thr | Val |
|---|---|---|---|---|---|---|---|---|---|---|---|---|---|---|---|
| 145 | | | | | 150 | | | | | 155 | | | | | 160 |

| Ser | Trp | Asn | Ser | Gly | Ala | Leu | Thr | Ser | Gly | Val | His | Thr | Phe | Pro | Ala |
|---|---|---|---|---|---|---|---|---|---|---|---|---|---|---|---|
| | | | | 165 | | | | | 170 | | | | | 175 | |

| Val | Leu | Gln | Ser | Ser | Gly | Leu | Tyr | Ser | Leu | Ser | Ser | Val | Val | Thr | Val |
|---|---|---|---|---|---|---|---|---|---|---|---|---|---|---|---|
| | | | | 180 | | | | | 185 | | | | | 190 | |

| Pro | Ser | Ser | Ser | Leu | Gly | Thr | Gln | Thr | Tyr | Ile | Cys | Asn | Val | Asn | His |
|---|---|---|---|---|---|---|---|---|---|---|---|---|---|---|---|
| | | | 195 | | | | | 200 | | | | | 205 | | |

| Lys | Pro | Ser | Asn | Thr | Lys | Val | Asp | Lys | Arg | Val | Glu | Pro | Lys | Ser | Cys |
|---|---|---|---|---|---|---|---|---|---|---|---|---|---|---|---|
| | 210 | | | | | 215 | | | | | 220 | | | | |

| Asp | Lys | Thr | His | Thr | Cys | Pro | Pro | Cys | Pro | Ala | Pro | Glu | Leu | Leu | Gly |
|---|---|---|---|---|---|---|---|---|---|---|---|---|---|---|---|
| 225 | | | | | 230 | | | | | 235 | | | | | 240 |

| Gly | Pro | Ser | Val | Phe | Leu | Phe | Pro | Pro | Lys | Pro | Lys | Asp | Thr | Leu | Met |
|---|---|---|---|---|---|---|---|---|---|---|---|---|---|---|---|
| | | | | 245 | | | | | 250 | | | | | 255 | |

| Ile | Ser | Arg | Thr | Pro | Glu | Val | Thr | Cys | Val | Val | Val | Asp | Val | Ser | His |
|---|---|---|---|---|---|---|---|---|---|---|---|---|---|---|---|
| | | | 260 | | | | | 265 | | | | | 270 | | |

| Glu | Asp | Pro | Glu | Val | Lys | Phe | Asn | Trp | Tyr | Val | Asp | Gly | Val | Glu | Val |
|---|---|---|---|---|---|---|---|---|---|---|---|---|---|---|---|
| | | 275 | | | | | 280 | | | | | 285 | | | |

| His | Asn | Ala | Lys | Thr | Lys | Pro | Arg | Glu | Glu | Gln | Tyr | Asn | Ser | Thr | Tyr |
|---|---|---|---|---|---|---|---|---|---|---|---|---|---|---|---|
| | 290 | | | | | 295 | | | | | 300 | | | | |

| Arg | Val | Val | Ser | Val | Leu | Thr | Val | Leu | His | Gln | Asp | Trp | Leu | Asn | Gly |
|---|---|---|---|---|---|---|---|---|---|---|---|---|---|---|---|
| 305 | | | | | 310 | | | | | 315 | | | | | 320 |

| Lys | Glu | Tyr | Lys | Cys | Lys | Val | Ser | Asn | Lys | Ala | Leu | Pro | Ala | Pro | Ile |
|---|---|---|---|---|---|---|---|---|---|---|---|---|---|---|---|
| | | | | 325 | | | | | 330 | | | | | 335 | |

| Glu | Lys | Thr | Ile | Ser | Lys | Ala | Lys | Gly | Gln | Pro | Arg | Glu | Pro | Gln | Val |
|---|---|---|---|---|---|---|---|---|---|---|---|---|---|---|---|
| | | | 340 | | | | | 345 | | | | | 350 | | |

| Tyr | Thr | Leu | Pro | Pro | Ser | Arg | Glu | Glu | Met | Thr | Lys | Asn | Gln | Val | Ser |
|---|---|---|---|---|---|---|---|---|---|---|---|---|---|---|---|
| | | 355 | | | | | 360 | | | | | 365 | | | |

| Leu | Thr | Cys | Leu | Val | Lys | Gly | Phe | Tyr | Pro | Ser | Asp | Ile | Ala | Val | Glu |
|---|---|---|---|---|---|---|---|---|---|---|---|---|---|---|---|
| | 370 | | | | | 375 | | | | | 380 | | | | |

| Trp | Glu | Ser | Asn | Gly | Gln | Pro | Glu | Asn | Asn | Tyr | Lys | Thr | Thr | Pro | Pro |
|---|---|---|---|---|---|---|---|---|---|---|---|---|---|---|---|
| 385 | | | | | 390 | | | | | 395 | | | | | 400 |

```
Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 4
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ser Asn
            20                  25                  30

Val Ala Trp Tyr Gln Gln Arg Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gly Gln Ser Tyr Ser Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
gaggtgcagc tggtggaatc tggcggcgga ctggtgcagt ccggcggctc tctgagactg    60
```

```
tcttgcgctg cctccggctt ctccctgtcc tcttacggcg tggactgggt gcgacaggcc    120
cctggcaagg gcctggaatg ggtgggagtg atctggggcg gaggcggcac ctactacgcc    180
tcttccctga tgggccggtt caccatctcc cgggacaact ccaagaacac cctgtacctg    240
cagatgaact ccctgcgggc cgaggacacc gccgtgtact actgcgccag acacgcctac    300
ggccacgacg gcggcttcgc catggattat tggggccagg gcaccctggt gacagtgtcc    360
tcc                                                                  363
```

<210> SEQ ID NO 6
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6

```
gagatcgtga tgacccagtc ccccgccacc ctgtctgtgt ctcccggcga gagagccacc     60
ctgagctgca gagcctccga gtccgtgtcc tccaacgtgg cctggtatca gcagagacct    120
ggtcaggccc ctcggctgct gatctacggc gcctctaacc gggccaccgg catccctgcc    180
agattctccg gctccggcag cggcaccgac ttcaccctga ccatctcccg gctggaaccc    240
gaggacttcg ccgtgtacta ctgcgggcag tcctactcat acccttcac cttcggccag    300 ggcaccaagc tggaaatcaa g                                              321
```

<210> SEQ ID NO 7
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

```
gaggtgcagc tggtggaatc tggcggcgga ctggtgcagt ccggcggctc tctgagactg     60
tcttgcgctg cctccggctt ctccctgtcc tcttacggcg tggactgggt gcgacaggcc    120
cctggcaagg gcctggaatg ggtgggagtg atctggggcg gaggcggcac ctactacgcc    180
tcttccctga tgggccggtt caccatctcc cgggacaact ccaagaacac cctgtacctg    240
cagatgaact ccctgcgggc cgaggacacc gccgtgtact actgcgccag acacgcctac    300
ggccacgacg gcggcttcgc catggattat tggggccagg gcaccctggt gacagtgtcc    360
tccgctagca ccaagggccc aagtgtgttt cccctggccc cagcagcaa gtctacttcc    420 ggcggaactg ctgccctggg ttgcctggtg aaggactact ccccgagcc cgtgacagtg    480 tcctggaact ctggggctct gacttccggc gtgcacacct cccgccgt gctgcagagc    540 agcggcctgt acagcctgag cagcgtggtg acagtgccct ccagctctct gggaacccag    600
acctatatct gcaacgtgaa ccacaagccc agcaacacca aggtggacaa gagagtggag    660
cccaagagct gcgacaagac ccacacctgc cccccctgcc cagctccaga actgctggga    720
gggccttccg tgttcctgtt ccccccaag cccaaggaca cctgatgat cagcaggacc    780 cccgaggtga cctgcgtggt ggtggacgtg tcccacgagg acccagaggt gaagttcaac    840
tggtacgtgg acggcgtgga ggtgcacaac gccaagacca gcccagaga ggagcagtac    900
```

```
aacagcacct acagggtggt gtccgtgctg accgtgctgc accaggactg gctgaacggc    960
aaagaataca agtgcaaagt ctccaacaag gccctgccag ccccaatcga aaagacaatc   1020
agcaaggcca agggccagcc acgggagccc caggtgtaca ccctgccccc cagccgggag   1080
gagatgacca agaaccaggt gtccctgacc tgtctggtga agggcttcta ccccagcgat   1140
atcgccgtgg agtgggagag caacggccag cccgagaaca actacaagac cacccccca    1200 gtgctggaca cgacggcag cttcttcctg tacagcaagc tgaccgtgga caagtccagg    1260
tggcagcagg gcaacgtgtt cagctgcagc gtgatgcacg aggccctgca caaccactac   1320
acccagaagt ccctgagcct gagccccggc aag                                1353
```

<210> SEQ ID NO 8
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

```
gagatcgtga tgacccagtc ccccgccacc ctgtctgtgt ctcccggcga gagagccacc     60
ctgagctgca gagcctccga gtccgtgtcc tccaacgtgg cctggtatca gcagagacct    120
ggtcaggccc ctcggctgct gatctacggc gcctctaacc gggccaccgg catccctgcc    180
agattctccg gctccggcag cggcaccgac ttcaccctga ccatctcccg gctggaaccc    240
gaggacttcg ccgtgtacta ctgcggccag tcctactcat accccttcac cttcggccag    300
ggcaccaagc tggaaatcaa gcgtacggtg gccgctccca gcgtgttcat cttccccccc    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag cacccctgacc    540 ctgagcaagg ccgactacga aagcataag gtgtacgcct gcgaggtgac ccaccagggc    600
ctgtccagcc ccgtgaccaa gagcttcaac aggggcgagt gc                      642
```

<210> SEQ ID NO 9
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 9

Ser Tyr Gly Val Asp
1               5

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 10

Gly Phe Ser Leu Ser Ser Tyr
1               5

```
<210> SEQ ID NO 11
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Val Ile Trp Gly Gly Gly Gly Thr Tyr Tyr Ala Ser Ser Leu Met Gly
1               5                   10                  15

<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Trp Gly Gly Gly Gly
1               5

<210> SEQ ID NO 13
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

His Ala Tyr Gly His Asp Gly Gly Phe Ala Met Asp Tyr
1               5                   10

<210> SEQ ID NO 14
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Arg Ala Ser Glu Ser Val Ser Ser Asn Val Ala
1               5                   10

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Glu Ser Val Ser Ser Asn
1               5

<210> SEQ ID NO 16
<211> LENGTH: 7
```

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Ala Ser Asn Arg Ala Thr
1               5

<210> SEQ ID NO 17
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Ala Ser
1

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Gln Ser Tyr Ser Tyr Pro Phe Thr
1               5

<210> SEQ ID NO 19
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Tyr Ser Tyr Pro Phe
1               5

<210> SEQ ID NO 20
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Ser Met Val Arg Gly Asp Tyr Tyr Gly Met Asp
                100                 105                 110

Val Trp Gly Gln Gly Thr Thr Val Thr Val Ser Ser
            115                 120

<210> SEQ ID NO 21
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
             35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Tyr
                 85                  90                  95

Thr Phe Gly Gln Gly Thr Lys Leu Glu Ile Lys
            100                 105

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Thr Tyr Trp Met His
 1               5

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asn Ile Tyr Pro Gly Thr Gly Gly Ser Asn Phe Asp Glu Lys Phe Lys
 1               5                  10                  15

Asn
```

```
<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Trp Thr Thr Gly Thr Gly Ala Tyr
1               5

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Tyr Thr Phe Thr Thr Tyr
1               5

<210> SEQ ID NO 26
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Tyr Pro Gly Thr Gly Gly
1               5

<210> SEQ ID NO 27
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
```

<210> SEQ ID NO 28
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

```
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctaccccg gcaccggcgg ctctaacttc     180
gacgagaagt ttaagaatag agtgactatc accgccgata gtctactagc caccgcctat     240
atggaactgt ctagcctgag atcagaggac accgccgtct actactgcac taggtggact     300
accggcacag gcgcctactg gggtcaaggc actaccgtga ccgtgtctag c              351
```

<210> SEQ ID NO 29
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220
```

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 30
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

```
gaggtgcagc tggtgcagtc aggcgccgaa gtgaagaagc ccggcgagtc actgagaatt    60
agctgtaaag gttcaggcta caccttcact acctactgga tgcactgggt ccgccaggct   120
accggtcaag gcctcgagtg gatgggtaat atctaccccg caccggcgg ctctaacttc   180
gacgagaagt ttaagaatag agtgactatc accgccgata gtctactag caccgcctat   240
atggaactgt ctagcctgag atcagaggac accgccgtct actactgcac taggtggact   300
accggcacag cgcctactg gggtcaaggc actaccgtga ccgtgtctag cgctagcact   360
aagggcccgt ccgtgttccc cctggcacct tgtagccgga gcactagcga atccaccgct   420
gccctcggct gcctggtcaa ggattacttc ccggagcccg tgaccgtgtc ctggaacagc   480
ggagccctga cctccggagt gcacaccttc cccgctgtgc tgcagagctc cgggctgtac   540
tcgctgtcgt cggtggtcac ggtgccttca tctagcctgg gtaccaagac ctacacttgc   600
aacgtggacc acaagccttc caacactaag gtggacaagc gcgtcgaatc gaagtacggc   660
ccaccgtgcc cgccttgtcc cgcgccggag ttcctcggcg gtccctcggt ctttctgttc   720
```

-continued

```
ccaccgaagc ccaaggacac tttgatgatt tcccgcaccc ctgaagtgac atgcgtggtc    780
gtggacgtgt cacaggaaga tccggaggtg cagttcaatt ggtacgtgga tggcgtcgag    840
gtgcacaacg ccaaaaccaa gccgagggag gagcagttca actccactta ccgcgtcgtg    900
tccgtgctga cggtgctgca tcaggactgg ctgaacggga aggagtacaa gtgcaaagtg    960
tccaacaagg gacttcctag ctcaatcgaa aagaccatct cgaaagccaa gggacagccc   1020
cgggaacccc aagtgtatac cctgccaccg agccaggaag aaatgactaa gaaccaagtc   1080
tcattgactt gccttgtgaa gggcttctac ccatcggata tcgccgtgga atgggagtcc   1140
aacggccagc cggaaaacaa ctacaagacc acccctccgg tgctggactc agacggatcc   1200
ttcttcctct actcgcggct gaccgtggat aagagcagat ggcaggaggg aaatgtgttc   1260
agctgttctg tgatgcatga agccctgcac aaccactaca ctcagaagtc cctgtccctc   1320
tccctggga                                                           1329
```

<210> SEQ ID NO 31
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 31

Lys Ser Ser Gln Ser Leu Leu Asp Ser Gly Asn Gln Lys Asn Phe Leu
1               5                   10                  15

Thr

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

Trp Ala Ser Thr Arg Glu Ser
1               5

<210> SEQ ID NO 33
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

Tyr Gly Arg Lys Lys Arg Arg Gln Arg Arg Leu Tyr Arg Ser Pro
1               5                   10                  15

Ala Met Pro Glu Asn Leu
            20

<210> SEQ ID NO 34
<211> LENGTH: 13
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 34

Ser Gln Ser Leu Leu Asp Ser Gly Asn Gln Lys Asn Phe
1               5                   10

<210> SEQ ID NO 35
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Trp Ala Ser
1

<210> SEQ ID NO 36
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Asp Tyr Ser Tyr Pro Tyr
1               5

<210> SEQ ID NO 37
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 38
<211> LENGTH: 339
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic polynucleotide"

<400> SEQUENCE: 38

```
gagatcgtcc tgactcagtc acccgctacc ctgagcctga gccctggcga gcgggctaca    60
ctgagctgta aatctagtca gtcactgctg gatagcggta atcagaagaa cttcctgacc   120
tggtatcagc agaagcccgg taaagcccct aagctgctga tctactgggc ctctactaga   180
gaatcaggcg tgccctctag gtttagcggt agcggtagtg gcaccgactt caccttcact   240
atctctagcc tgcagcccga ggatatcgct acctactact gtcagaacga ctatagctac   300
ccctacacct tcggtcaagg cactaaggtc gagattaag                          339
```

<210> SEQ ID NO 39
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 40
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40

```
gagatcgtcc tgactcagtc acccgctacc ctgagcctga gccctggcga gcgggctaca      60
ctgagctgta aatctagtca gtcactgctg gatagcggta atcagaagaa cttcctgacc     120
tggtatcagc agaagcccgg taaagcccct aagctgctga tctactgggc ctctactaga     180
gaatcaggcg tgccctctag gtttagcggt agcggtagtg gcaccgactt caccttcact     240
atctctagcc tgcagcccga ggatatcgct acctactact gtcagaacga ctatagctac     300
ccctacacct tcggtcaagg cactaaggtc gagattaagc gtacggtggc cgctcccagc     360
gtgttcatct ccccccccag cgacgagcag ctgaagagcg gcaccgccag cgtggtgtgc     420
ctgctgaaca acttctaccc ccgggaggcc aaggtgcagt ggaaggtgga caacgccctg     480
cagagcggca acagccagga gagcgtcacc gagcaggaca gcaaggactc cacctacagc     540
ctgagcagca ccctgaccct gagcaaggcc gactacgaga gcataaggt gtacgcctgc     600
gaggtgaccc accagggcct gtccagcccc gtgaccaaga gcttcaacag gggcgagtgc     660
```

<210> SEQ ID NO 41
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

```
Glu Ile Val Leu Thr Gln Ser Pro Ala Thr Leu Ser Leu Ser Pro Gly
1               5                   10                  15
Glu Arg Ala Thr Leu Ser Cys Lys Ser Ser Gln Ser Leu Leu Asp Ser
            20                  25                  30
Gly Asn Gln Lys Asn Phe Leu Thr Trp Tyr Gln Gln Lys Pro Gly Gln
        35                  40                  45
Ala Pro Arg Leu Leu Ile Tyr Trp Ala Ser Thr Arg Glu Ser Gly Val
    50                  55                  60
Pro Ser Arg Phe Ser Gly Ser Gly Ser Gly Thr Asp Phe Thr Phe Thr
65                  70                  75                  80
Ile Ser Ser Leu Glu Ala Glu Asp Ala Ala Thr Tyr Tyr Cys Gln Asn
                85                  90                  95
Asp Tyr Ser Tyr Pro Tyr Thr Phe Gly Gln Gly Thr Lys Val Glu Ile
                100                 105                 110
Lys
```

<210> SEQ ID NO 42
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42

```
gagatcgtcc tgactcagtc acccgctacc ctgagcctga gccctggcga gcgggctaca      60
ctgagctgta aatctagtca gtcactgctg gatagcggta atcagaagaa cttcctgacc     120
tggtatcagc agaagcccgg tcaagcccct agactgctga tctactgggc ctctactaga     180
```

| gaatcaggcg tgccctctag gtttagcggt agcggtagtg gcaccgactt caccttcact | 240 |
|---|---|
| atctctagcc tggaagccga ggacgccgct acctactact gtcagaacga ctatagctac | 300 |
| ccctacacct tcggtcaagg cactaaggtc gagattaag | 339 |

<210> SEQ ID NO 43
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 44
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 44

| gagatcgtcc tgactcagtc acccgctacc ctgagcctga gccctggcga gcgggctaca | 60 |
|---|---|
| ctgagctgta aatctagtca gtcactgctg gatagcggta atcagaagaa cttcctgacc | 120 |
| tggtatcagc agaagcccgg tcaagcccct agactgctga tctactgggc ctctactaga | 180 |

-continued

```
gaatcaggcg tgccctctag gtttagcggt agcggtagtg gcaccgactt caccttcact    240
atctctagcc tggaagccga ggacgccgct acctactact gtcagaacga ctatagctac    300
ccctacacct tcggtcaagg cactaaggtc gagattaagc gtacggtggc cgctcccagc    360
gtgttcatct tccccccag cgacgagcag ctgaagagcg gcaccgccag cgtggtgtgc    420
ctgctgaaca acttctaccc ccgggaggcc aaggtgcagt ggaaggtgga caacgccctg    480
cagagcggca acagccagga gagcgtcacc gagcaggaca gcaaggactc cacctacagc    540
ctgagcagca ccctgaccct gagcaaggcc gactacgaga agcataaggt gtacgcctgc    600
gaggtgaccc caggggcct gtccagcccc gtgaccaaga gcttcaacag gggcgagtgc    660
```

<210> SEQ ID NO 45
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 45

```
acctactgga tgcac                                                      15
```

<210> SEQ ID NO 46
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 46

```
aatatctacc ccggcaccgg cggctctaac ttcgacgaga agtttaagaa t              51
```

<210> SEQ ID NO 47
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 47

```
tggactaccg gcacaggcgc ctac                                            24
```

<210> SEQ ID NO 48
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 48

```
ggctacacct tcactaccta c                                               21
```

<210> SEQ ID NO 49
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
taccccggca ccggcggc                                                    18

<210> SEQ ID NO 50
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
aaatctagtc agtcactgct ggatagcggt aatcagaaga acttcctgac c                51

<210> SEQ ID NO 51
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
tgggcctcta ctagagaatc a                                                21

<210> SEQ ID NO 52
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
cagaacgact atagctaccc ctacacc                                          27

<210> SEQ ID NO 53
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
agtcagtcac tgctggatag cggtaatcag aagaacttc                             39

<210> SEQ ID NO 54
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54 tgggcctct                                                              9

<210> SEQ ID NO 55

```
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
gactatagct acccctac                                                        18

<210> SEQ ID NO 56
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56
```

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln

-continued

```
                290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
            435                 440

<210> SEQ ID NO 57
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 58
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

```
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 59
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 60
<211> LENGTH: 447
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

```
Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380
```

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 61
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
            85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 62
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

```
Ser Tyr Trp Met Tyr
1               5
```

<210> SEQ ID NO 63
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

```
Arg Ile Asp Pro Asn Ser Gly Ser Thr Lys Tyr Asn Glu Lys Phe Lys
1               5                   10                  15

Asn
```

<210> SEQ ID NO 64
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

```
Asp Tyr Arg Lys Gly Leu Tyr Ala Met Asp Tyr
1               5                   10
```

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

```
Gly Tyr Thr Phe Thr Ser Tyr
1               5
```

<210> SEQ ID NO 66
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

```
Asp Pro Asn Ser Gly Ser
1               5
```

<210> SEQ ID NO 67
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

```
Glu Val Gln Leu Val Gln Ser Gly Ala Glu Val Lys Lys Pro Gly Ala
1               5                   10                  15
```

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
            115                 120

<210> SEQ ID NO 68
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68
gaagtgcagc tggtgcagtc aggcgccgaa gtgaagaaac ccggcgctac cgtgaagatt        60
agctgtaaag tctcaggcta caccttcact agctactgga tgtactgggt ccgacaggct       120
agagggcaaa gactggagtg gatcggtaga atcgacccta atagcggctc tactaagtat       180
aacgagaagt ttaagaatag gttcactatt agtagggata ctctaagaa cacccctgtac       240 ctgcagatga atagcctgag agccgaggac accgccgtct actactgcgc tagagactat       300
agaaagggcc tgtacgctat ggactactgg ggtcaaggca ctaccgtgac cgtgtcttca       360

<210> SEQ ID NO 69
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

```
Gly Thr Thr Val Thr Val Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
            435                 440                 445

<210> SEQ ID NO 70
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Lys Ala Ser Gln Asp Val Gly Thr Ala Val Ala
1               5                   10
```

```
<210> SEQ ID NO 71
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Trp Ala Ser Thr Arg His Thr
1               5

<210> SEQ ID NO 72
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Gln Gln Tyr Asn Ser Tyr Pro Leu Thr
1               5

<210> SEQ ID NO 73
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Ser Gln Asp Val Gly Thr Ala
1               5

<210> SEQ ID NO 74
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Trp Ala Ser
1

<210> SEQ ID NO 75
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Tyr Asn Ser Tyr Pro Leu
1               5

<210> SEQ ID NO 76
<211> LENGTH: 1338
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 76
gaagtgcagc tggtgcagtc aggcgccgaa gtgaagaaac ccggcgctac cgtgaagatt      60
agctgtaaag tctcaggcta caccttcact agctactgga tgtactgggt ccgacaggct     120
agagggcaaa gactggagtg gatcggtaga atcgacccta atagcggctc tactaagtat     180
aacgagaagt ttaagaatag gttcactatt agtagggata actctaagaa caccctgtac     240
ctgcagatga atagcctgag agccgaggac accgccgtct actactgcgc tagagactat     300
agaaagggcc tgtacgctat ggactactgg ggtcaaggca ctaccgtgac cgtgtcttca     360
gctagcacta agggcccgtc cgtgttcccc tggcacctt gtagccggag cactagcgaa      420
tccaccgctg ccctcggctg cctggtcaag gattacttcc cggagcccgt gaccgtgtcc     480
tggaacagcg gagccctgac ctccggagtg cacaccttcc ccgctgtgct gcagagctcc     540
gggctgtact cgctgtcgtc ggtggtcacg gtgccttcat ctagcctggg taccaagacc     600
tacacttgca acgtggacca caagccttcc aacactaagg tggacaagcg cgtcgaatcg     660
aagtacggcc accgtgccc gccttgtccc cgcgccggagt tcctcggcgg tccctcggtc     720
tttctgttcc caccgaagcc caaggacact ttgatgattt cccgcacccc tgaagtgaca     780
tgcgtggtcg tggacgtgtc acaggaagat ccggaggtgc agttcaattg gtacgtggat     840
ggcgtcgagg tgcacaacgc caaaaccaag ccgagggagg agcagttcaa ctccacttac     900
cgcgtcgtgt ccgtgctgac ggtgctgcat caggactggc tgaacgggaa ggagtacaag     960
tgcaaagtgt ccaacaaggg acttcctagc tcaatcgaaa agaccatctc gaaagccaag    1020
ggacagcccc gggaacccca agtgtatacc ctgccaccga gccaggaaga aatgactaag    1080
aaccaagtct cattgacttg ccttgtgaag ggcttctacc catcggatat cgccgtggaa    1140
tgggagtcca acggccagcc ggaaaacaac tacaagacca cccctccggt gctggactca    1200
gacggatcct tcttcctcta ctcgcggctg accgtggata agagcagatg gcaggaggga    1260
aatgtgttca gctgttctgt gatgcatgaa gccctgcaca ccactacac tcagaagtcc    1320 ctgtccctct ccctggga                                                 1338

<210> SEQ ID NO 77
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80
```

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 78
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
gctattcagc tgactcagtc acctagtagc ctgagcgcta gtgtgggcga tagagtgact      60
atcacctgta aagcctctca ggacgtgggc accgccgtgg cctggtatct gcagaagcct    120
ggtcaatcac ctcagctgct gatctactgg gcctctacta gacacaccgg cgtgccctct    180
aggtttagcg gtagcggtag tggcaccgac ttcaccttca ctatctcttc actggaagcc    240
gaggacgccg ctacctacta ctgtcagcag tataatagct accccctgac cttcggtcaa    300
ggcactaagg tcgagattaa g                                              321

<210> SEQ ID NO 79
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 80
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80
gctattcagc tgactcagtc acctagtagc ctgagcgcta gtgtgggcga tagagtgact       60
atcacctgta aagcctctca ggacgtgggc accgccgtgg cctggtatct gcagaagcct      120
ggtcaatcac ctcagctgct gatctactgg gcctctacta cacaccggg cgtgccctct       180 aggtttagcg gtagcggtag tggcaccgac ttcaccttca ctatctcttc actggaagcc      240
gaggacgccg ctacctacta ctgtcagcag tataatagct accccctgac cttcggtcaa      300
ggcactaagg tcgagattaa gcgtacggtg gccgctccca gcgtgttcat cttcccccc       360 agcgacgagc agctgaagag cggcaccgcc agcgtggtgt gcctgctgaa caacttctac      420
ccccgggagg ccaaggtgca gtggaaggtg gacaacgccc tgcagagcgg caacagccag      480
gagagcgtca ccgagcagga cagcaaggac tccacctaca gcctgagcag cacc ctgacc     540 ctgagcaagg ccgactacga gaagcataag gtgtacgcct gcgaggtgac ccaccagggc      600
ctgtccagcc ccgtgaccaa gagcttcaac aggggcgagt gc                         642

<210> SEQ ID NO 81
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 82
<211> LENGTH: 360

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82
gaagtgcagc tggtgcagtc aggcgccgaa gtgaagaaac ccggcgctac cgtgaagatt    60
agctgtaaag tctcaggcta caccttcact agctactgga tgtactgggt ccgacaggct   120
accggtcaag gcctggagtg gatgggtaga atcgacccta atagcggctc tactaagtat   180
aacgagaagt ttaagaatag agtgactatc accgccgata gtctactagc accgcctat   240 atggaactgt ctagcctgag atcagaggac accgccgtct actactgcgc tagagactat   300
agaaagggcc tgtacgctat ggactactgg ggtcaaggca ctaccgtgac cgtgtcttca   360

<210> SEQ ID NO 83
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83
```

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr

```
                245                 250                 255
Pro Glu Val Thr Cys Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
            325                 330                 335
Ser Lys Ala Lys Gly Gln Pro Arg Glu Pro Gln Val Tyr Thr Leu Pro
        340                 345                 350
Pro Ser Gln Glu Glu Met Thr Lys Asn Gln Val Ser Leu Thr Cys Leu
    355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
            405                 410                 415
Trp Gln Glu Gly Asn Val Phe Ser Cys Ser Val Met His Glu Ala Leu
        420                 425                 430
His Asn His Tyr Thr Gln Lys Ser Leu Ser Leu Ser Leu Gly
    435                 440                 445
```

<210> SEQ ID NO 84
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 84

```
gaagtgcagc tggtgcagtc aggcgccgaa gtgaagaaac ccggcgctac cgtgaagatt    60
agctgtaaag tctcaggcta caccttcact agctactgga tgtactgggt ccgacaggct   120
accggtcaag gcctggagtg gatgggtaga atcgacccta atagcggctc tactaagtat   180
aacgagaagt ttaagaatag agtgactatc accgccgata gtctactagc accgccctat   240
atggaactgt ctagcctgag atcagaggac accgccgtct actactgcgc tagagactat   300
agaaagggcc tgtacgctat ggactactgg ggtcaaggca ctaccgtgac cgtgtcttca   360
gctagcacta agggcccgtc cgtgttcccc ctggcaccct gtagccggag cactagcgaa   420
tccaccgctg ccctcggctg cctggtcaag gattacttcc cggagcccgt gaccgtgtcc   480
tggaacagcg gagccctgac ctccggagtg cacaccttcc ccgctgtgct gcagagctcc   540
gggctgtact cgctgtcgtc ggtggtcacg gtgccttcat ctagcctggg taccaagacc   600
tacacttgca acgtggacca caagccttcc aacactaagg tggacaagcg cgtcgaatcg   660
aagtacggcc caccgtgccc gccttgtccc gcgccggagt tcctcggcgg tccctcggtc   720
tttctgttcc caccgaagcc caaggacact ttgatgattt cccgcacccc tgaagtgaca   780
tgcgtggtcg tggacgtgtc acaggaagat ccggaggtgc agttcaattg gtacgtggat   840
ggcgtcgagg tgcacaacgc caaaaccaag ccgagggagg agcagttcaa ctccacttac   900
```

```
cgcgtcgtgt ccgtgctgac ggtgctgcat caggactggc tgaacgggaa ggagtacaag    960
tgcaaagtgt ccaacaaggg acttcctagc tcaatcgaaa agaccatctc gaaagccaag   1020
ggacagcccc gggaacccca agtgtatacc ctgccaccga gccaggaaga aatgactaag   1080
aaccaagtct cattgacttg ccttgtgaag ggcttctacc catcggatat cgccgtggaa   1140
tgggagtcca acggccagcc ggaaaacaac tacaagacca cccctccggt gctggactca   1200
gacggatcct tcttcctcta ctcgcggctg accgtggata gagcagatg gcaggaggga    1260 aatgtgttca gctgttctgt gatgcatgaa gccctgcaca accactacac tcagaagtcc   1320
ctgtccctct ccctggga                                                 1338
```

<210> SEQ ID NO 85
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 85

```
Asp Val Val Met Thr Gln Ser Pro Leu Ser Leu Pro Val Thr Leu Gly
1               5                   10                  15
Gln Pro Ala Ser Ile Ser Cys Lys Ala Ser Gln Asp Val Gly Thr Ala
            20                  25                  30
Val Ala Trp Tyr Gln Gln Lys Pro Gly Gln Ala Pro Arg Leu Leu Ile
        35                  40                  45
Tyr Trp Ala Ser Thr Arg His Thr Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Asn Ser Tyr Pro Leu
                85                  90                  95
Thr Phe Gly Gln Gly Thr Lys Val Glu Ile Lys
            100                 105
```

<210> SEQ ID NO 86
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86

```
gacgtcgtga tgactcagtc acccctgagc ctgcccgtga ccctggggca gcccgcctct     60
attagctgta aagcctctca ggacgtgggc accgccgtgg cctggtatca gcagaagcca    120
gggcaagccc ctagactgct gatctactgg gcctctacta gacacaccgg cgtgccctct    180
aggtttagcg gtagcggtag tggcaccgag ttcaccctga ctatctcttc actgcagccc    240
gacgacttcg ctacctacta ctgtcagcag tataatagct accccctgac cttcggtcaa    300
ggcactaagg tcgagattaa g                                              321
```

<210> SEQ ID NO 87
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 87

```
Asp Val Val Met Thr Gln Ser Pro Leu Ser Leu Pro Val Thr Leu Gly
1               5                   10                  15
Gln Pro Ala Ser Ile Ser Cys Lys Ala Ser Gln Asp Val Gly Thr Ala
            20                  25                  30
Val Ala Trp Tyr Gln Gln Lys Pro Gly Gln Ala Pro Arg Leu Leu Ile
        35                  40                  45
Tyr Trp Ala Ser Thr Arg His Thr Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Asn Ser Tyr Pro Leu
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 88
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88

```
gacgtcgtga tgactcagtc acccctgagc ctgcccgtga ccctggggca gcccgcctct    60
attagctgta aagcctctca ggacgtgggc accgccgtgg cctggtatca gcagaagcca   120
gggcaagccc ctagactgct gatctactgg gcctctacta gacacaccgg cgtgccctct   180
aggtttagcg gtagcggtag tggcaccgag ttcacccctga ctatctcttc actgcagccc   240
gacgacttcg ctacctacta ctgtcagcag tataatagct accccctgac cttcggtcaa   300
ggcactaagg tcgagattaa gcgtacggtg gccgctccca gcgtgttcat cttccccccc   360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
```

```
ctgagcaagg ccgactacga gaagcataag gtgtacgcct gcgaggtgac ccaccagggc      600
ctgtccagcc ccgtgaccaa gagcttcaac aggggcgagt gc                         642
```

<210> SEQ ID NO 89
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89

```
agctactgga tgtac                                                        15
```

<210> SEQ ID NO 90
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90

```
agaatcgacc ctaatagcgg ctctactaag tataacgaga agtttaagaa t                51
```

<210> SEQ ID NO 91
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91

```
gactatagaa agggcctgta cgctatggac tac                                    33
```

<210> SEQ ID NO 92
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92

```
ggctacacct tcactagcta c                                                 21
```

<210> SEQ ID NO 93
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93

```
gaccctaata gcggctct                                                     18
```

<210> SEQ ID NO 94
<211> LENGTH: 33
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 94
aaagcctctc aggacgtggg caccgccgtg gcc                              33

<210> SEQ ID NO 95
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
tgggcctcta ctagacacac c                                           21

<210> SEQ ID NO 96
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
cagcagtata atagctaccc cctgacc                                     27

<210> SEQ ID NO 97
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
tctcaggacg tgggcaccgc c                                           21

<210> SEQ ID NO 98
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98 tgggcctct                                                          9

<210> SEQ ID NO 99
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
tataatagct accccctg                                               18
```

```
<210> SEQ ID NO 100
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
```

```
                355                 360                 365
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
                435                 440                 445

<210> SEQ ID NO 101
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 102
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 102

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 103
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 104
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Glu Val Gln Leu Val Glu Ser Gly Gly Gly Leu Val Gln Pro Gly Gly
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |
| Ser | Leu | Arg | Leu | Ser | Cys | Ala | Ala | Ser | Gly | Phe | Thr | Phe | Ser | Arg | Tyr |
|   |   |   | 20 |   |   |   |   | 25 |   |   |   |   | 30 |
| Trp | Met | Ser | Trp | Val | Arg | Gln | Ala | Pro | Gly | Lys | Gly | Leu | Glu | Trp | Val |
|   |   |   | 35 |   |   |   |   | 40 |   |   |   |   | 45 |
| Ala | Asn | Ile | Lys | Gln | Asp | Gly | Ser | Glu | Lys | Tyr | Tyr | Val | Asp | Ser | Val |
|   | 50 |   |   |   |   | 55 |   |   |   |   | 60 |
| Lys | Gly | Arg | Phe | Thr | Ile | Ser | Arg | Asp | Asn | Ala | Lys | Asn | Ser | Leu | Tyr |
| 65 |   |   |   |   | 70 |   |   |   |   | 75 |   |   |   |   | 80 |
| Leu | Gln | Met | Asn | Ser | Leu | Arg | Ala | Glu | Asp | Thr | Ala | Val | Tyr | Tyr | Cys |
|   |   |   |   | 85 |   |   |   |   | 90 |   |   |   |   | 95 |
| Ala | Arg | Glu | Gly | Gly | Trp | Phe | Gly | Glu | Leu | Ala | Phe | Asp | Tyr | Trp | Gly |
|   |   |   | 100 |   |   |   |   | 105 |   |   |   |   | 110 |
| Gln | Gly | Thr | Leu | Val | Thr | Val | Ser | Ser | Ala | Ser | Thr | Lys | Gly | Pro | Ser |
|   |   |   | 115 |   |   |   |   | 120 |   |   |   |   | 125 |
| Val | Phe | Pro | Leu | Ala | Pro | Ser | Ser | Lys | Ser | Thr | Ser | Gly | Gly | Thr | Ala |
|   | 130 |   |   |   |   | 135 |   |   |   |   | 140 |
| Ala | Leu | Gly | Cys | Leu | Val | Lys | Asp | Tyr | Phe | Pro | Glu | Pro | Val | Thr | Val |
| 145 |   |   |   |   | 150 |   |   |   |   | 155 |   |   |   |   | 160 |
| Ser | Trp | Asn | Ser | Gly | Ala | Leu | Thr | Ser | Gly | Val | His | Thr | Phe | Pro | Ala |
|   |   |   |   | 165 |   |   |   |   | 170 |   |   |   |   | 175 |
| Val | Leu | Gln | Ser | Ser | Gly | Leu | Tyr | Ser | Leu | Ser | Ser | Val | Val | Thr | Val |
|   |   |   | 180 |   |   |   |   | 185 |   |   |   |   | 190 |
| Pro | Ser | Ser | Ser | Leu | Gly | Thr | Gln | Thr | Tyr | Ile | Cys | Asn | Val | Asn | His |
|   |   |   | 195 |   |   |   |   | 200 |   |   |   |   | 205 |
| Lys | Pro | Ser | Asn | Thr | Lys | Val | Asp | Lys | Arg | Val | Glu | Pro | Lys | Ser | Cys |
|   | 210 |   |   |   |   | 215 |   |   |   |   | 220 |
| Asp | Lys | Thr | His | Thr | Cys | Pro | Pro | Cys | Pro | Ala | Pro | Glu | Phe | Glu | Gly |
| 225 |   |   |   |   | 230 |   |   |   |   | 235 |   |   |   |   | 240 |
| Gly | Pro | Ser | Val | Phe | Leu | Phe | Pro | Pro | Lys | Pro | Lys | Asp | Thr | Leu | Met |
|   |   |   |   | 245 |   |   |   |   | 250 |   |   |   |   | 255 |
| Ile | Ser | Arg | Thr | Pro | Glu | Val | Thr | Cys | Val | Val | Val | Asp | Val | Ser | His |
|   |   |   | 260 |   |   |   |   | 265 |   |   |   |   | 270 |
| Glu | Asp | Pro | Glu | Val | Lys | Phe | Asn | Trp | Tyr | Val | Asp | Gly | Val | Glu | Val |
|   |   |   | 275 |   |   |   |   | 280 |   |   |   |   | 285 |
| His | Asn | Ala | Lys | Thr | Lys | Pro | Arg | Glu | Glu | Gln | Tyr | Asn | Ser | Thr | Tyr |
|   | 290 |   |   |   |   | 295 |   |   |   |   | 300 |
| Arg | Val | Val | Ser | Val | Leu | Thr | Val | Leu | His | Gln | Asp | Trp | Leu | Asn | Gly |
| 305 |   |   |   |   | 310 |   |   |   |   | 315 |   |   |   |   | 320 |
| Lys | Glu | Tyr | Lys | Cys | Lys | Val | Ser | Asn | Lys | Ala | Leu | Pro | Ala | Ser | Ile |
|   |   |   |   | 325 |   |   |   |   | 330 |   |   |   |   | 335 |
| Glu | Lys | Thr | Ile | Ser | Lys | Ala | Lys | Gly | Gln | Pro | Arg | Glu | Pro | Gln | Val |
|   |   |   | 340 |   |   |   |   | 345 |   |   |   |   | 350 |
| Tyr | Thr | Leu | Pro | Pro | Ser | Arg | Glu | Glu | Met | Thr | Lys | Asn | Gln | Val | Ser |
|   |   |   | 355 |   |   |   |   | 360 |   |   |   |   | 365 |
| Leu | Thr | Cys | Leu | Val | Lys | Gly | Phe | Tyr | Pro | Ser | Asp | Ile | Ala | Val | Glu |
|   | 370 |   |   |   |   | 375 |   |   |   |   | 380 |
| Trp | Glu | Ser | Asn | Gly | Gln | Pro | Glu | Asn | Asn | Tyr | Lys | Thr | Thr | Pro | Pro |
| 385 |   |   |   |   | 390 |   |   |   |   | 395 |   |   |   |   | 400 |
| Val | Leu | Asp | Ser | Asp | Gly | Ser | Phe | Phe | Leu | Tyr | Ser | Lys | Leu | Thr | Val |
|   |   |   | 405 |   |   |   |   | 410 |   |   |   |   | 415 |
| Asp | Lys | Ser | Arg | Trp | Gln | Gln | Gly | Asn | Val | Phe | Ser | Cys | Ser | Val | Met |
|   |   |   | 420 |   |   |   |   | 425 |   |   |   |   | 430 |

```
His Glu Ala Leu His Asn His Tyr Thr Gln Lys Ser Leu Ser Leu Ser
        435                 440                 445

Pro Gly Lys
    450

<210> SEQ ID NO 105
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 106
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30
```

-continued

```
Ala Ile Ser Trp Val Arg Gln Ala Pro Gly Gln Gly Leu Glu Trp Met
            35                  40                  45

Gly Gly Ile Ile Pro Ile Phe Gly Lys Ala His Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
            115                 120

<210> SEQ ID NO 107
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 108
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Asn Tyr Gly Met Asn
1               5

<210> SEQ ID NO 109
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Trp Ile Asn Thr Asp Thr Gly Glu Pro Thr Tyr Ala Asp Asp Phe Lys
```

-continued

```
1               5                   10                  15
Gly

<210> SEQ ID NO 110
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Asn Pro Pro Tyr Tyr Tyr Gly Thr Asn Asn Ala Glu Ala Met Asp Tyr
1               5                   10                  15

<210> SEQ ID NO 111
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Gly Phe Thr Leu Thr Asn Tyr
1               5

<210> SEQ ID NO 112
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Asn Thr Asp Thr Gly Glu
1               5

<210> SEQ ID NO 113
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
                20                  25                  30

Gly Met Asn Trp Val Arg Gln Ala Arg Gly Gln Arg Leu Glu Trp Ile
            35                  40                  45

Gly Trp Ile Asn Thr Asp Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95
```

```
Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125
```

<210> SEQ ID NO 114
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 114

```
caagtgcagc tggtgcagtc gggagccgaa gtgaagaagc ctggagcctc ggtgaaggtg    60
tcgtgcaagg catccggatt caccctcacc aattacggga tgaactgggt cagacaggcc   120
cggggtcaac ggctggagtg gatcggatgg attaacaccg acaccgggga gcctacctac   180
gcggacgatt tcaagggacg gttcgtgttc tccctcgaca cctccgtgtc caccgcctac   240
ctccaaatct cctcactgaa agcggaggac accgccgtgt actattgcgc gaggaacccg   300
ccctactact acggaaccaa caacgccgaa gccatggact actggggcca gggcaccact   360
gtgactgtgt ccagc                                                    375
```

<210> SEQ ID NO 115
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115

```
caggtgcagc tggtgcagtc tggcgccgaa gtgaagaaac tggcgcctc cgtgaaggtg    60
tcctgcaagg cctctggctt caccctgacc aactacggca tgaactgggt gcgacaggcc   120
aggggccagc ggctggaatg gatcggctgg atcaacaccg acaccggcga gcctacctac   180
gccgacgact tcaagggcag attcgtgttc tccctggaca cctccgtgtc caccgcctac   240
ctgcagatct ccagcctgaa ggccgaggat accgccgtgt actactgcgc ccggaacccc   300
ccttactact acggcaccaa caacgccgag gccatggact attggggcca gggcaccacc   360
gtgaccgtgt cctct                                                    375
```

<210> SEQ ID NO 116
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 116

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45
```

```
Gly Trp Ile Asn Thr Asp Thr Gly Glu Pro Thr Tyr Ala Asp Asp Phe
     50              55                      60

Lys Gly Arg Phe Val Phe Ser Leu Asp Thr Ser Val Ser Thr Ala Tyr
 65              70                  75                      80

Leu Gln Ile Ser Ser Leu Lys Ala Glu Asp Thr Ala Val Tyr Tyr Cys
                 85              90                      95

Ala Arg Asn Pro Pro Tyr Tyr Gly Thr Asn Asn Ala Glu Ala Met
             100             105             110

Asp Tyr Trp Gly Gln Gly Thr Thr Val Thr Val Ser Ser Ala Ser Thr
             115             120             125

Lys Gly Pro Ser Val Phe Pro Leu Ala Pro Cys Ser Arg Ser Thr Ser
 130             135             140

Glu Ser Thr Ala Ala Leu Gly Cys Leu Val Lys Asp Tyr Phe Pro Glu
 145             150             155             160

Pro Val Thr Val Ser Trp Asn Ser Gly Ala Leu Thr Ser Gly Val His
                 165             170             175

Thr Phe Pro Ala Val Leu Gln Ser Ser Gly Leu Tyr Ser Leu Ser Ser
             180             185             190

Val Val Thr Val Pro Ser Ser Ser Leu Gly Thr Lys Thr Tyr Thr Cys
             195             200             205

Asn Val Asp His Lys Pro Ser Asn Thr Lys Val Asp Lys Arg Val Glu
 210             215             220

Ser Lys Tyr Gly Pro Pro Cys Pro Pro Cys Pro Ala Pro Glu Phe Leu
 225             230             235             240

Gly Gly Pro Ser Val Phe Leu Phe Pro Pro Lys Pro Lys Asp Thr Leu
             245             250             255

Met Ile Ser Arg Thr Pro Glu Val Thr Cys Val Val Val Asp Val Ser
             260             265             270

Gln Glu Asp Pro Glu Val Gln Phe Asn Trp Tyr Val Asp Gly Val Glu
             275             280             285

Val His Asn Ala Lys Thr Lys Pro Arg Glu Glu Gln Phe Asn Ser Thr
 290             295             300

Tyr Arg Val Val Ser Val Leu Thr Val Leu His Gln Asp Trp Leu Asn
 305             310             315             320

Gly Lys Glu Tyr Lys Cys Lys Val Ser Asn Lys Gly Leu Pro Ser Ser
             325             330             335

Ile Glu Lys Thr Ile Ser Lys Ala Lys Gly Gln Pro Arg Glu Pro Gln
             340             345             350

Val Tyr Thr Leu Pro Pro Ser Gln Glu Glu Met Thr Lys Asn Gln Val
             355             360             365

Ser Leu Thr Cys Leu Val Lys Gly Phe Tyr Pro Ser Asp Ile Ala Val
 370             375             380

Glu Trp Glu Ser Asn Gly Gln Pro Glu Asn Asn Tyr Lys Thr Thr Pro
 385             390             395             400

Pro Val Leu Asp Ser Asp Gly Ser Phe Phe Leu Tyr Ser Arg Leu Thr
             405             410             415

Val Asp Lys Ser Arg Trp Gln Glu Gly Asn Val Phe Ser Cys Ser Val
             420             425             430

Met His Glu Ala Leu His Asn His Tyr Thr Gln Lys Ser Leu Ser Leu
             435             440             445

Ser Leu Gly
 450
```

```
<210> SEQ ID NO 117
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Ser Ser Ser Gln Asp Ile Ser Asn Tyr Leu Asn
1               5                   10

<210> SEQ ID NO 118
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Tyr Thr Ser Thr Leu His Leu
1               5

<210> SEQ ID NO 119
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Gln Gln Tyr Tyr Asn Leu Pro Trp Thr
1               5

<210> SEQ ID NO 120
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Ser Gln Asp Ile Ser Asn Tyr
1               5

<210> SEQ ID NO 121
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Tyr Thr Ser
1

<210> SEQ ID NO 122
<211> LENGTH: 6
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic peptide"

<400> SEQUENCE: 122

Tyr Tyr Asn Leu Pro Trp
1               5

<210> SEQ ID NO 123
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 123

```
caagtgcagc tggtgcagtc gggagccgaa gtgaagaagc ctggagcctc ggtgaaggtg      60
tcgtgcaagg catccggatt caccctcacc aattacggga tgaactgggt cagacaggcc     120
cggggtcaac ggctggagtg gatcggatgg attaacaccg acaccgggga gcctacctac     180
gcggacgatt tcaagggacg gttcgtgttc tccctcgaca cctccgtgtc caccgcctac     240
ctccaaatct cctcactgaa agcggaggac accgccgtgt actattgcgc gaggaacccg     300
ccctactact acggaaccaa caacgccgaa gccatggact actggggcca gggcaccact     360
gtgactgtgt ccagcgcgtc cactaagggc ccgtccgtgt tcccctggc accttgtagc      420 cggagcacta gcgaatccac cgctgccctc ggctgcctgg tcaaggatta cttcccggag     480
cccgtgaccg tgtcctggaa cagcggagcc ctgacctccg gagtgcacac cttccccgct     540
gtgctgcaga gctccgggct gtactcgctg tcgtcggtgg tcacggtgcc ttcatctagc     600
ctgggtacca agacctacac ttgcaacgtg gaccacaagc cttccaacac taaggtggac     660
aagcgcgtcg aatcgaagta cggcccaccg tgcccgcctt gtcccgcgcc ggagttcctc     720
ggcggtccct cggtctttct gttcccaccg aagcccaagg acactttgat gatttcccgc     780 accccctgaag tgacatgcgt ggtcgtggac gtgtcacagg aagatccgga ggtgcagttc     840
aattggtacg tggatggcgt cgaggtgcac aacgccaaaa ccaagccgag ggaggagcag     900
ttcaactcca cttaccgcgt cgtgtccgtg ctgacggtgc tgcatcagga ctggctgaac     960
gggaaggagt acaagtgcaa agtgtccaac aagggacttc ctagctcaat cgaaaagacc    1020
atctcgaaag ccaagggaca gccccgggaa cccaagtgt ataccctgcc accgagccag    1080
gaagaaatga ctaagaacca agtctcattg acttgccttg tgaagggctt ctacccatcg    1140
gatatcgccg tggaatggga gtccaacggc cagccggaaa acaactacaa gaccacccct    1200
ccggtgctgg actcagacgg atccttcttc ctctactcgc ggctgaccgt ggataagagc    1260
agatggcagg agggaaatgt gttcagctgt tctgtgatgc atgaagccct gcacaaccac    1320
tacactcaga agtccctgtc cctctccctg gga                                 1353
```

<210> SEQ ID NO 124
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 124

```
caggtgcagc tggtgcagtc tggcgccgaa gtgaagaaac ctggcgcctc cgtgaaggtg      60
tcctgcaagg cctctggctt caccctgacc aactacggca tgaactgggt gcgacaggcc     120
aggggccagc ggctggaatg gatcggctgg atcaacaccg acaccggcga gcctacctac     180
gccgacgact tcaagggcag attcgtgttc tccctggaca cctccgtgtc caccgcctac     240
ctgcagatct ccagcctgaa ggccgaggat accgccgtgt actactgcgc ccggaacccc     300
ccttactact acggcaccaa caacgccgag gccatggact attggggcca gggcaccacc     360
gtgaccgtgt cctctgcttc taccaagggg ccagcgtgt tccccctggc ccctgctcc      420
agaagcacca gcgagagcac agccgccctg ggctgcctgg tgaaggacta cttccccgag     480
cccgtgaccg tgtcctggaa cagcggagcc ctgaccagcg gcgtgcacac cttccccgcc     540
gtgctgcaga gcagcggcct gtacagcctg agcagcgtgg tgaccgtgcc cagcagcagc     600
ctgggcacca agacctacac ctgtaacgtg gaccacaagc ccagcaacac caaggtggac     660
aagagggtgg agagcaagta cggcccaccc tgccccccct gcccagcccc cgagttcctg     720
ggcggaccca gcgtgttcct gttccccccc aagcccaagg acaccctgat gatcagcaga     780
acccccgagg tgacctgtgt ggtggtggac gtgtcccagg aggaccccga ggtccagttc     840
aactggtacg tggacggcgt ggaggtgcac aacgccaaga ccaagcccag agaggagcag     900
tttaacagca cctaccgggt ggtgtccgtg ctgaccgtgc tgcaccagga ctggctgaac     960
ggcaaagagt acaagtgtaa ggtctccaac aagggcctgc caagcagcat cgaaaagacc    1020
atcagcaagg ccaagggcca gcctagagag ccccaggtct acaccctgcc acccagccaa    1080
gaggagatga ccaagaacca ggtgtccctg acctgtctgg tgaagggctt ctacccaagc    1140
gacatcgccg tggagtggga gagcaacggc cagcccgaga caactacaa gaccacccc     1200
ccagtgctgg acagcgacgg cagcttcttc ctgtacagca ggctgaccgt ggacaagtcc    1260
agatggcagg agggcaacgt ctttagctgc tccgtgatgc acgaggccct gcacaaccac    1320
tacacccaga gagcctgag cctgtccctg ggc                                   1353
```

<210> SEQ ID NO 125
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 125

```
Asp Ile Gln Met Thr Gln Ser Pro Ser Ser Leu Ser Ala Ser Val Gly
1               5                   10                  15
Asp Arg Val Thr Ile Thr Cys Ser Ser Ser Gln Asp Ile Ser Asn Tyr
            20                  25                  30
Leu Asn Trp Tyr Leu Gln Lys Pro Gly Gln Ser Pro Gln Leu Leu Ile
        35                  40                  45
Tyr Tyr Thr Ser Thr Leu His Leu Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Tyr Asn Leu Pro Trp
                85                  90                  95
Thr Phe Gly Gln Gly Thr Lys Val Glu Ile Lys
            100                 105
```

<210> SEQ ID NO 126
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 126

```
gatattcaga tgactcagtc acctagtagc ctgagcgcta gtgtgggcga tagagtgact      60
atcacctgta gctctagtca ggatatctct aactacctga actggtatct gcagaagccc     120
ggtcaatcac ctcagctgct gatctactac actagcaccc tgcacctggg cgtgccctct     180
aggtttagcg gtagcggtag tggcaccgag ttcaccctga ctatctctag cctgcagccc     240
gacgacttcg ctacctacta ctgtcagcag tactataacc tgccctggac cttcggtcaa     300
ggcactaagg tcgagattaa g                                                321
```

<210> SEQ ID NO 127
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 127

```
gacatccaga tgacccagtc cccctccagc ctgtctgctt ccgtgggcga cagagtgacc      60
atcacctgtt cctccagcca ggacatctcc aactacctga actggtatct gcagaagccc     120
ggccagtccc ctcagctgct gatctactac acctccaccc tgcacctggg cgtgccctcc     180
agattttccg gctctggctc tggcaccgag tttaccctga ccatcagctc cctgcagccc     240
gacgacttcg ccacctacta ctgccagcag tactacaacc tgccctggac cttcggccag     300
ggcaccaagg tggaaatcaa g                                                321
```

<210> SEQ ID NO 128
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 128

```
Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
                20                  25                  30

Leu Asn Trp Tyr Leu Gln Lys Pro Gly Gln Ser Pro Gln Leu Leu Ile
            35                  40                  45

Tyr Tyr Thr Ser Thr Leu His Leu Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asn Leu Pro Trp
                85                  90                  95
```

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 129
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 129
gatattcaga tgactcagtc acctagtagc ctgagcgcta gtgtgggcga tagagtgact      60
atcacctgta gctctagtca ggatatctct aactacctga actggtatct gcagaagccc     120
ggtcaatcac ctcagctgct gatctactac actagcaccc tgcacctggg cgtgccctct     180
aggtttagcg gtagcggtag tggcaccgag ttcaccctga ctatctctag cctgcagccc     240
gacgacttcg ctacctacta ctgtcagcag tactataacc tgccctggac cttcggtcaa     300
ggcactaagg tcgagattaa gcgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag cacccctgacc     540 ctgagcaagg ccgactacga gaagcataag gtgtacgcct gcgaggtgac ccaccagggc     600
ctgtccagcc ccgtgaccaa gagcttcaac aggggcgagt gc                         642

<210> SEQ ID NO 130
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 130
gacatccaga tgacccagtc ccctccagc ctgtctgctt ccgtgggcga cagagtgacc      60
atcacctgtt cctccagcca ggacatctcc aactacctga actggtatct gcagaagccc    120
ggccagtccc ctcagctgct gatctactac acctccaccc tgcacctggg cgtgccctcc    180
agattttccg gctctggctc tggcaccgag tttaccctga ccatcagctc cctgcagccc    240
gacgacttcg ccacctacta ctgccagcag tactacaacc tgccctggac cttcggccag    300

```
ggcaccaagg tggaaatcaa gcgtacggtg gccgctccca gcgtgttcat cttcccccca    360
agcgacgagc agctgaagag cggcaccgcc agcgtggtgt gtctgctgaa caacttctac    420
cccagggagg ccaaggtgca gtggaaggtg acaacgccc tgcagagcgg caacagccag    480
gagagcgtca ccgagcagga cagcaaggac tccacctaca gcctgagcag caccctgacc    540
ctgagcaagg ccgactacga gaagcacaag gtgtacgcct gtgaggtgac ccaccagggc    600
ctgtccagcc ccgtgaccaa gagcttcaac aggggcgagt gc                       642
```

<210> SEQ ID NO 131
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125
```

<210> SEQ ID NO 132
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 132

```
caggtgcagc tggtgcagtc aggcgccgaa gtgaagaaac ccggcgctag tgtgaaagtc    60
agctgtaaag ctagtggctt caccctgact aactacggga tgaactgggt ccgccaggcc   120
ccaggtcaag gcctcgagtg gatgggctgg attaacaccg acaccggcga gcctacctac   180
gccgacgact ttaagggcag attcgtgttt agcctggaca ctagtgtgtc taccgcctac   240
ctgcagatct ctagcctgaa ggccgaggac accgccgtct actactgcgc tagaaacccc   300
ccctactact acggcactaa caacgccgag gctatggact actggggtca aggcactacc   360
gtgaccgtgt ctagc                                                     375
```

<210> SEQ ID NO 133
<211> LENGTH: 375
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 133

```
caggtgcagc tggtgcagtc tggcgccgaa gtgaagaaac tggcgcctc cgtgaaggtg      60 tcctgcaagg cctctggctt caccctgacc aactacggca tgaactgggt gcgacaggcc    120
cctggacagg gcctggaatg gatgggctgg atcaacaccg acaccggcga gcctacctac    180
gccgacgact tcaagggcag attcgtgttc tccctggaca cctccgtgtc caccgcctac    240
ctgcagatct ccagcctgaa ggccgaggat accgccgtgt actactgcgc ccggaacccc    300
ccttactact acggcaccaa caacgccgag gccatggact attggggcca gggcaccacc    360
gtgaccgtgt cctct                                                     375
```

<210> SEQ ID NO 134
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240
```

```
Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

Gln Glu Asp Pro Glu Val Gln Phe Asn Trp Tyr Val Asp Gly Val Glu
    275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450

<210> SEQ ID NO 135
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135
caggtgcagc tggtgcagtc aggcgccgaa gtgaagaaac cggcgctag tgtgaaagtc     60 agctgtaaag ctagtggctt caccctgact aactacggga tgaactgggt ccgccaggcc    120
ccaggtcaag gcctcgagtg gatgggctgg attaacaccg acaccggcga gcctacctac    180
gccgacgact ttaagggcag attcgtgttt agcctggaca ctagtgtgtc taccgcctac    240
ctgcagatct ctagcctgaa ggccgaggac accgccgtct actactgcgc tagaaacccc    300
ccctactact acggcactaa caacgccgag gctatggact actggggtca aggcactacc    360
gtgaccgtgt ctagcgctag cactaagggc ccgtccgtgt tccccctggc accttgtagc    420
cggagcacta gcgaatccac cgctgccctc ggctgcctgg tcaaggatta cttcccggag    480
cccgtgaccg tgtcctggaa cagcggagcc ctgacctccg gagtgcacac cttcccgct    540 gtgctgcaga gctccgggct gtactcgctg tcgtcggtgg tcacggtgcc ttcatctagc    600
ctgggtacca agacctacac ttgcaacgtg gaccacaagc cttccaacac taaggtggac    660
aagcgcgtcg aatcgaagta cggccccacc tgccgcgctt gtcccgcgcc ggagttcctc    720
ggcggtccct cggtctttct gttcccaccg aagcccaagg acactttgat gatttcccgc    780
```

```
accccctgaag tgacatgcgt ggtcgtggac gtgtcacagg aagatccgga ggtgcagttc    840
aattggtacg tggatggcgt cgaggtgcac aacgccaaaa ccaagccgag ggaggagcag    900
ttcaactcca cttaccgcgt cgtgtccgtg ctgaccgtgc tgcatcagga ctggctgaac    960
gggaaggagt acaagtgcaa agtgtccaac aagggacttc ctagctcaat cgaaaagacc   1020
atctcgaaag ccaagggaca gccccgggaa ccccaagtgt ataccctgcc accgagccag   1080
gaagaaatga ctaagaacca agtctcattg acttgccttg tgaagggctt ctacccatcg   1140
gatatcgccg tggaatggga gtccaacggc cagccggaaa acaactacaa gaccacccct   1200
ccggtgctgg actcagacgg atccttcttc ctctactcgc ggctgaccgt ggataagagc   1260
agatggcagg agggaaatgt gttcagctgt tctgtgatgc atgaagccct gcacaaccac   1320
tacactcaga agtccctgtc cctctccctg gga                                1353
```

<210> SEQ ID NO 136
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 136

```
caggtgcagc tggtgcagtc tggcgccgaa gtgaagaaac ctggcgcctc cgtgaaggtg     60
tcctgcaagg cctctggctt caccctgacc aactacggca tgaactgggt gcgacaggcc    120
cctggacagg gcctggaatg gatgggctgg atcaacaccg acaccggcga gcctacctac    180
gccgacgact tcaagggcag attcgtgttc tccctggaca cctccgtgtc caccgcctac    240
ctgcagatct ccagcctgaa ggccgaggat accgccgtgt actactgcgc ccggaacccc    300
ccttactact acggcaccaa caacgccgag gccatggact attggggcca gggcaccacc    360
gtgaccgtgt cctctgcttc taccaagggg ccagcgtgt tccccctggc ccctgctcc    420 agaagcacca gcgagagcac agccgccctg ggctgcctgg tgaaggacta cttcccgag    480 cccgtgaccg tgtcctggaa cagcggagcc ctgaccagcg gcgtgcacac cttccccgcc    540
gtgctgcaga gcagcggcct gtacagcctg agcagcgtgg tgaccgtgcc cagcagcagc    600
ctgggcacca agacctacac ctgtaacgtg gaccacaagc ccagcaacac caaggtggac    660
aagagggtgg agagcaagta cggcccaccc tgccccccct gcccagcccc cgagttcctg    720
ggcggaccca gcgtgttcct gttccccccc aagcccaagg acaccctgat gatcagcaga    780
acccccgagg tgacctgtgt ggtggtggac gtgtcccagg aggaccccga ggtccagttc    840
aactggtacg tggacggcgt ggaggtgcac aacgccaaga ccaagccag agaggagcag    900 tttaacagca cctaccgggt ggtgtccgtg ctgaccgtgc tgcaccagga ctggctgaac    960
ggcaaagagt acaagtgtaa ggtctccaac aagggcctgc caagcagcat cgaaaagacc   1020
atcagcaagg ccaagggcca gcctagagag ccccaggtct acaccctgcc acccagccaa   1080
gaggagatga ccaagaacca ggtgtccctg acctgtctgg tgaagggctt ctacccaagc   1140
gacatcgccg tggagtggga gagcaacggc cagcccgaga acaactacaa gaccaccccc   1200
ccagtgctgg acagcgacgg cagcttcttc ctgtacagca ggctgaccgt ggacaagtcc   1260
agatggcagg agggcaacgt ctttagctgc tccgtgatgc acgaggccct gcacaaccac   1320
tacacccaga agagcctgag cctgtccctg ggc                                1353
```

<210> SEQ ID NO 137
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 137

```
Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 138
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 138

```
gatattcaga tgactcagtc acctagtagc ctgagcgcta gtgtgggcga tagagtgact    60
atcacctgta gctctagtca ggatatctct aactacctga actggtatca gcagaagccc   120
ggtaaagccc ctaagctgct gatctactac actagcaccc tgcacctggg aatccccct    180
aggtttagcg gtagcggcta cggcaccgac ttcaccctga ctattaacaa tatcgagtca   240
gaggacgccg cctactactt ctgtcagcag tactataacc tgccctggac cttcggtcaa   300
ggcactaagg tcgagattaa g                                              321
```

<210> SEQ ID NO 139
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 139

```
gacatccaga tgacccagtc ccctccagc ctgtctgctt ccgtgggcga cagagtgacc    60
atcacctgtt cctccagcca ggacatctcc aactacctga actggtatca gcagaagccc   120
ggcaaggccc ccaagctgct gatctactac acctccaccc tgcacctggg catccccct    180
agattctccg gctctggcta cggcaccgac ttcaccctga ccatcaacaa catcgagtcc   240
gaggacgccg cctactactt ctgccagcag tactacaacc tgccctggac cttcggccag   300
```
ggcaccaagg tggaaatcaa g         321

<210> SEQ ID NO 140
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 141
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 141
gatattcaga tgactcagtc acctagtagc ctgagcgcta gtgtgggcga tagagtgact      60
atcacctgta gctctagtca ggatatctct aactacctga ctggtatca gcagaagccc      120 ggtaaagccc ctaagctgct gatctactac actagcaccc tgcacctggg aatccccccct    180 aggtttagcg gtagcggcta cggcaccgac ttcaccctga ctattaacaa tatcgagtca     240
gaggacgccg cctactactt ctgtcagcag tactataacc tgccctggac cttcggtcaa    300
ggcactaagg tcgagattaa gcgtacggtg gccgctccca gcgtgttcat cttccccccc    360

```
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga aagcataag gtgtacgcct gcgaggtgac ccaccagggc     600
ctgtccagcc ccgtgaccaa gagcttcaac aggggcgagt gc                       642
```

```
<210> SEQ ID NO 142
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 142
```

```
gacatccaga tgacccagtc cccctccagc ctgtctgctt ccgtgggcga cagagtgacc    60
atcacctgtt cctccagcca ggacatctcc aactacctga actggtatca gcagaagccc   120
ggcaaggccc ccaagctgct gatctactac acctccaccc tgcacctggg catccccccct  180 agattctccg gctctggcta cggcaccgac ttcaccctga ccatcaacaa catcgagtcc   240
gaggacgccg cctactactt ctgccagcag tactacaacc tgccctggac cttcggccag   300
ggcaccaagg tggaaatcaa gctacggtg ccgctccca gcgtgttcat cttcccccca     360
agcgacgagc agctgaagag cggcaccgcc agcgtggtgt gtctgctgaa caacttctac   420
cccagggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga aagcacaag gtgtacgcct gtgaggtgac ccaccagggc    600
ctgtccagcc ccgtgaccaa gagcttcaac aggggcgagt gc                      642
```

```
<210> SEQ ID NO 143
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
aattacggga tgaac                                                     15
```

```
<210> SEQ ID NO 144
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
aactacggca tgaac                                                     15
```

```
<210> SEQ ID NO 145
<211> LENGTH: 51
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 145
tggattaaca ccgacaccgg ggagcctacc tacgcggacg atttcaaggg a         51

<210> SEQ ID NO 146
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
tggatcaaca ccgacaccgg cgagcctacc tacgccgacg acttcaaggg c         51

<210> SEQ ID NO 147
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
aacccgccct actactacgg aaccaacaac gccgaagcca tggactac              48

<210> SEQ ID NO 148
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148 aaccccccett actactacgg caccaacaac gccgaggcca tggactat              48

<210> SEQ ID NO 149
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
ggattcaccc tcaccaatta c                                           21

<210> SEQ ID NO 150
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
ggcttcaccc tgaccaacta c                                           21
```

```
<210> SEQ ID NO 151
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
aacaccgaca ccgggag                                                    18

<210> SEQ ID NO 152
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
aacaccgaca ccggcgag                                                   18

<210> SEQ ID NO 153
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
agctctagtc aggatatctc taactacctg aac                                  33

<210> SEQ ID NO 154
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
tcctccagcc aggacatctc caactacctg aac                                  33

<210> SEQ ID NO 155
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
tacactagca ccctgcacct g                                               21

<210> SEQ ID NO 156
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 156
tacacctcca ccctgcacct g                                              21

<210> SEQ ID NO 157
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
cagcagtact ataacctgcc ctggacc                                         27

<210> SEQ ID NO 158
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
cagcagtact acaacctgcc ctggacc                                         27

<210> SEQ ID NO 159
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
agtcaggata tctctaacta c                                               21

<210> SEQ ID NO 160
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
agccaggaca tctccaacta c                                               21

<210> SEQ ID NO 161
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161 tacactagc                                                              9

<210> SEQ ID NO 162
<211> LENGTH: 9
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 162 tacacctcc                                                               9

<210> SEQ ID NO 163
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
tactataacc tgccctgg                                                    18

<210> SEQ ID NO 164
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
tactacaacc tgccctgg                                                    18

<210> SEQ ID NO 165
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
aactacggga tgaac                                                       15

<210> SEQ ID NO 166
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
tggattaaca ccgacaccgg cgagcctacc tacgccgacg actttaaggg c                51

<210> SEQ ID NO 167
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
aaccccccct actactacgg cactaacaac gccgaggcta tggactac                   48
```

<210> SEQ ID NO 168
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 168
ggcttcaccc tgactaacta c                                      21

<210> SEQ ID NO 169
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 169

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285
```

```
Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 170
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 170

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 171
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asn Trp Val Arg Gln Pro Pro Gly Lys Gly Leu Glu Trp Leu
        35                  40                  45

Gly Met Ile Trp Asp Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Glu Gly Asp Val Ala Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

```
              325                 330                 335
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 172
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Asp Ile Val Met Thr Gln Ser Pro Ser Ser Leu Ala Val Ser Val Gly
1               5                   10                  15

Gln Lys Val Thr Met Ser Cys Lys Ser Ser Gln Ser Leu Leu Asn Gly
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Asp Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Leu Gln
                85                  90                  95

His Phe Gly Thr Pro Pro Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 173
```

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Gly Phe Thr Leu Thr Asn Tyr Gly Met Asn
1               5                   10

<210> SEQ ID NO 174
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Ser Tyr Asn Met His
1               5

<210> SEQ ID NO 175
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Asp Ile Tyr Pro Gly Asn Gly Asp Thr Ser Tyr Asn Gln Lys Phe Lys
1               5                   10                  15

Gly

<210> SEQ ID NO 176
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Val Gly Gly Ala Phe Pro Met Asp Tyr
1               5

<210> SEQ ID NO 177
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Gly Tyr Thr Phe Thr Ser Tyr
1               5

<210> SEQ ID NO 178
<211> LENGTH: 6
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Tyr Pro Gly Asn Gly Asp
1               5

<210> SEQ ID NO 179
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser
        115

<210> SEQ ID NO 180
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 180
caggtgcagc tggtgcagtc aggcgccgaa gtgaagaaac ccggctctag cgtgaaagtt      60
tcttgtaaag ctagtggcta caccttcact agctataata tgcactgggt tcgccaggcc     120
ccagggcaag gcctcgagtg gatgggcgat atctaccccg ggaacggcga cactagttat     180
aatcagaagt ttaagggtag agtcactatc accgccgata gtctactagc accgtctat     240 atggaactga gttccctgag gtctgaggac accgccgtct actactgcgc tagagtgggc     300
ggagccttcc ctatggacta ctggggtcaa ggcactaccg tgaccgtgtc tagc            354

<210> SEQ ID NO 181
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 181

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

```
Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440
```

<210> SEQ ID NO 182
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 182

```
caggtgcagc tggtgcagtc aggcgccgaa gtgaagaaac ccggctctag cgtgaaagtt      60
tcttgtaaag ctagtggcta caccttcact agctataata tgcactgggt tcgccaggcc     120
ccagggcaag gcctcgagtg gatgggcgat atctaccccg gaacggcga cactagttat     180
aatcagaagt ttaagggtag agtcactatc accgccgata gtctactag caccgtctat     240
atggaactga gttccctgag gtctgaggac accgccgtct actactgcgc tagagtgggc     300
ggagccttcc ctatggacta ctggggtcaa ggcactaccg tgaccgtgtc tagcgctagc     360
actaagggcc cgtccgtgtt cccctggca ccttgtagcc ggagcactag cgaatccacc     420
gctgccctcg gctgcctggt caaggattac ttcccggagc ccgtgaccgt gtcctggaac     480
agcggagccc tgacctccgg agtgcacacc ttccccgctg tgctgcagag ctccgggctg     540
tactcgctgt cgtcggtggt cacggtgcct tcatctagcc tgggtaccaa gacctacact     600
tgcaacgtgg accacaagcc ttccaacact aaggtggaca agcgcgtcga atcgaagtac     660
ggcccaccgt gccccgcctt gcccgcgccg gagttcctcg gcggtccctc ggtctttctg     720
ttcccaccga agcccaagga cactttgatg atttcccgca ccctgaagt gacatgcgtg     780
gtcgtggacg tgtcacagga agatccggag gtgcagttca attggtacgt ggatggcgtc     840
gaggtgcaca acgccaaaac caagccgagg gaggagcagt tcaactccac ttaccgcgtc     900
gtgtccgtgc tgacggtgct gcatcaggac tggctgaacg gaaggagta caagtgcaaa     960
gtgtccaaca agggacttcc tagctcaatc gaaaagacca tctcgaaagc caagggacag    1020
ccccgggaac cccaagtgta taccctgcca ccgagccagg aagaaatgac taagaaccaa    1080
gtctcattga cttgccttgt gaagggcttc tacccatcgg atatcgccgt ggaatgggag    1140
tccaacggcc agccggaaaa caactacaag accacccctc cggtgctgga ctcagacgga    1200
tccttcttcc tctactcgcg gctgaccgtg gataagagca gatggcagga gggaaatgtg    1260
ttcagctgtt ctgtgatgca tgaagccctg cacaaccact acactcagaa gtccctgtcc    1320
ctctcccctgg ga                                                       1332
```

<210> SEQ ID NO 183
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Arg Ala Ser Glu Ser Val Glu Tyr Tyr Gly Thr Ser Leu Met Gln
1               5                   10                  15

<210> SEQ ID NO 184
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Ala Ala Ser Asn Val Glu Ser
1               5

<210> SEQ ID NO 185
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Gln Gln Ser Arg Lys Asp Pro Ser Thr
1               5

<210> SEQ ID NO 186
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Ser Glu Ser Val Glu Tyr Tyr Gly Thr Ser Leu
1               5                   10

<210> SEQ ID NO 187
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Ala Ala Ser
1

<210> SEQ ID NO 188
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Ser Arg Lys Asp Pro Ser
1               5

```
<210> SEQ ID NO 189
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 189
```

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr Tyr
            20                  25                  30

Gly Thr Ser Leu Met Gln Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys Gln Gln Ser Arg
                85                  90                  95

Lys Asp Pro Ser Thr Phe Gly Gly Gly Thr Lys Val Glu Ile Lys
            100                 105                 110

```
<210> SEQ ID NO 190
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 190
```
gctattcagc tgactcagtc acctagtagc ctgagcgcta gtgtgggcga tagagtgact      60
atcacctgta gagctagtga atcagtcgag tactacggca ctagcctgat gcagtggtat     120
cagcagaagc ccgggaaagc ccctaagctg ctgatctacg ccgcctctaa cgtggaatca     180
ggcgtgccct ctaggtttag cggtagcggt agtggcaccg acttcaccct gactatctct     240
agcctgcagc ccgaggactt cgctacctac ttctgtcagc agtctaggaa ggaccctagc     300
accttcggcg gaggcactaa ggtcgagatt aag                                  333

```
<210> SEQ ID NO 191
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 191
```

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr Tyr
            20                  25                  30

Gly Thr Ser Leu Met Gln Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

```
Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Phe Cys Gln Gln Ser Arg
                 85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 192
<211> LENGTH: 654
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 192
gctattcagc tgactcagtc acctagtagc ctgagcgcta gtgtgggcga tagagtgact    60
atcacctgta gagctagtga atcagtcgag tactacggca ctagcctgat gcagtggtat   120
cagcagaagc ccgggaaagc ccctaagctg ctgatctacg ccgcctctaa cgtggaatca   180
ggcgtgccct ctaggtttag cggtagcggt agtggcaccg acttcaccct gactatctct   240
agcctgcagc ccgaggactt cgctacctac ttctgtcagc agtctaggaa ggaccctagc   300
accttcggcg gaggcactaa ggtcgagatt aagcgtacgg tggccgctcc cagcgtgttc   360
atcttccccc ccagcgacga gcagctgaag agcggcaccg ccagcgtggt gtgcctgctg   420
aacaacttct accccggga ggccaaggtg cagtggaagg tggacaacgc cctgcagagc   480
ggcaacagcc aggagagcgt caccgagcag gacagcaagg actccaccta cagcctgagc   540
agcaccctga ccctgagcaa ggccgactac gagaagcata aggtgtacgc ctgcgaggtg   600
acccaccagg gcctgtccag ccccgtgacc aagagcttca caggggcga gtgc           654
```

```
<210> SEQ ID NO 193
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Asp Ile Tyr Pro Gly Gln Gly Asp Thr Ser Tyr Asn Gln Lys Phe Lys
  1               5                  10                  15
```

Gly

<210> SEQ ID NO 194
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Tyr Pro Gly Gln Gly Asp
1               5

<210> SEQ ID NO 195
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser
        115

<210> SEQ ID NO 196
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 196
caggtgcagc tggtgcagtc aggcgccgaa gtgaagaaac cggcgctagt gtgaaagtt       60 agctgtaaag ctagtggcta ctttcact tcttataata tgcactgggt ccgccaggcc      120
ccaggtcaag gcctcgagtg gatcggcgat atctacccccg gtcaaggcga cacttcctat    180
aatcagaagt ttaagggtag agctactatg accgccgata gtctacttc taccgtctat    240 atggaactga gttccctgag gtctgaggac accgccgtct actactgcgc tagagtgggc   300
ggagccttcc caatggacta ctggggtcaa ggcaccctgg tcaccgtgtc tagc         354

```
<210> SEQ ID NO 197
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Ile
            35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

```
Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440
```

<210> SEQ ID NO 198
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 198

```
caggtgcagc tggtgcagtc aggcgccgaa gtgaagaaac ccggcgctag tgtgaaagtt      60
agctgtaaag ctagtggcta tactttcact tcttataata tgcactgggt ccgccaggcc     120
ccaggtcaag gcctcgagtg gatcggcgat atctaccccg gtcaaggcga cacttcctat     180
aatcagaagt ttaagggtag agctactatg accgccgata agtctacttc taccgtctat     240
atggaactga gttccctgag gtctgaggac accgccgtct actactgcgc tagagtgggc     300
ggagccttcc caatggacta ctggggtcaa ggcaccctgg tcaccgtgtc tagcgctagc     360
actaagggcc cgtccgtgtt cccccctggca ccttgtagcc ggagcactag cgaatccacc     420
gctgccctcg gctgcctggt caaggattac ttccccgagc ccgtgaccgt gtcctggaac     480
agcggagccc tgacctccgg agtgcacacc ttccccgctg tgctgcagag ctccgggctg     540
tactcgctgt cgtcggtggt cacggtgcct tcatctagcc tgggtaccaa gacctacact     600
tgcaacgtgg accacaagcc ttccaacact aaggtggaca gcgcgtcga atcgaagtac     660
ggcccaccgt gcccgccttg tccgcgccg gagttcctcg gcggtccctc ggtctttctg     720
ttcccaccga agcccaagga cactttgatg atttcccgca cccctgaagt gacatgcgtg     780
gtcgtggacg tgtcacagga agatccggag gtgcagttca attggtacgt ggatggcgtc     840
gaggtgcaca cgccaaaac caagccgagg gaggagcagt tcaactccac ttaccgcgtc     900
gtgtccgtgc tgacggtgct gcatcaggac tggctgaacg gaaggagta caagtgcaaa     960
gtgtccaaca agggacttcc tagctcaatc gaaaagacca tctcgaaagc caagggacag    1020
ccccgggaac ccaagtgta ccctgcca ccgagccagg aagaaatgac taagaaccaa    1080
gtctcattga cttgccttgt gaagggcttc taccatcgg atatcgccgt ggaatgggag    1140
tccaacggcc agccggaaaa caactacaag accaccctc cggtgctgga ctcagacgga    1200
tccttcttcc tctactcgcg gctgaccgtg gataagagca gatggcagga gggaaatgtg    1260
ttcagctgtt ctgtgatgca tgaagccctg cacaaccact acactcagaa gtccctgtcc    1320
ctctccctgg ga                                                       1332
```

<210> SEQ ID NO 199
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys
            100                 105                 110

<210> SEQ ID NO 200
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 200
gatatcgtcc tgactcagtc acccgatagc ctggccgtca gcctgggcga gcgggctact      60
attaactgta gagctagtga atcagtcgag tactacggca ctagcctgat gcagtggtat     120
cagcagaagc ccggtcaacc ccctaagctg ctgatctacg ccgcctctaa cgtggaatca     180
ggcgtgcccg ataggtttag cggtagcggt agtggcaccg acttcaccct gactattagt     240
agcctgcagg ccgaggacgt ggccgtctac tactgtcagc agtctaggaa ggaccctagc     300
accttcggcg gaggcactaa ggtcgagatt aag                                  333

<210> SEQ ID NO 201
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 201

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

-continued

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 202
<211> LENGTH: 654
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 202
gatatcgtcc tgactcagtc acccgatagc ctggccgtca gcctgggcga gcgggctact    60
attaactgta gagctagtga atcagtcgag tactacggca ctagcctgat gcagtggtat   120
cagcagaagc ccggtcaacc ccctaagctg ctgatctacg ccgcctctaa cgtggaatca   180
ggcgtgcccg ataggtttag cggtagcggt agtggcaccg acttcaccct gactattagt   240
agcctgcagg ccgaggacgt ggccgtctac tactgtcagc agtctaggaa ggaccctagc   300
accttcggcg gaggcactaa ggtcgagatt aagcgtacgg tggccgctcc cagcgtgttc   360
atcttccccc ccagcgacga gcagctgaag agcggcaccg ccagcgtggt gtgcctgctg   420
aacaacttct accccgggga ggccaaggtg cagtggaagg tggacaacgc cctgcagagc   480
ggcaacagcc aggagagcgt caccgagcag gacagcaagg actccaccta cagcctgagc   540
agcaccctga ccctgagcaa ggccgactac gagaagcata aggtgtacgc ctgcgaggtg   600
acccaccagg gcctgtccag ccccgtgacc aagagcttca caggggcga gtgc          654

<210> SEQ ID NO 203
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ala Ser Gly Phe Thr Phe Ser Ser
            20                  25                  30

Tyr Asp Met Ser Trp Val Arg Gln Ala Pro Gly Lys Gly Leu Asp Trp
            35                  40                  45

Val Ser Thr Ile Ser Gly Gly Gly Thr Tyr Tyr Tyr Gln Asp Ser
 50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Ser Met Asp Tyr Trp Gly Gln Gly Thr Thr Val Thr Val Ser
            100                 105                 110

Ser Ala

<210> SEQ ID NO 204
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 204

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Arg Arg Tyr
             20                  25                  30

Leu Asn Trp Tyr His Gln Lys Pro Gly Lys Ala Pro Lys Leu Leu Ile
         35                  40                  45

Tyr Gly Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Ser His Ser Ala Pro Leu
                 85                  90                  95

Thr Phe Gly Gly Gly Thr Lys Val Glu Ile Lys Arg
            100                 105

<210> SEQ ID NO 205
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205

Glu Val Gln Val Leu Glu Ser Gly Gly Gly Leu Val Gln Pro Gly Gly
 1               5                  10                  15

Ser Leu Arg Leu Tyr Cys Val Ala Ser Gly Phe Thr Phe Ser Gly Ser
             20                  25                  30

Tyr Ala Met Ser Trp Val Arg Gln Ala Pro Gly Lys Gly Leu Glu Trp
         35                  40                  45

Val Ser Ala Ile Ser Gly Ser Gly Gly Ser Thr Tyr Tyr Ala Asp Ser
 50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Lys Lys Tyr Tyr Val Gly Pro Ala Asp Tyr Trp Gly Gln Gly
            100                 105                 110

Thr Leu Val Thr Val Ser Ser Gly
            115                 120

<210> SEQ ID NO 206
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 206

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln His Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Leu Thr Phe Gly Gly Gly Thr Lys Ile Glu Val
            100                 105                 110

Lys

<210> SEQ ID NO 207
<211> LENGTH: 114
<212> TYPE: PRT
<213> ORGANISM: Homo sapiens

<400> SEQUENCE: 207

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 208
<211> LENGTH: 170
<212> TYPE: PRT
<213> ORGANISM: Homo sapiens -continued

<400> SEQUENCE: 208

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly
                165                 170

<210> SEQ ID NO 209
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 210
<211> LENGTH: 297
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 210

```
Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg Glu Pro Lys Ser Cys Asp Lys Thr His Thr Cys Pro Pro Cys Pro
65                  70                  75                  80
Ala Pro Glu Leu Leu Gly Gly Pro Ser Val Phe Leu Phe Pro Pro Lys
                85                  90                  95
Pro Lys Asp Thr Leu Met Ile Ser Arg Thr Pro Glu Val Thr Cys Val
            100                 105                 110
Val Val Asp Val Ser His Glu Asp Pro Glu Val Lys Phe Asn Trp Tyr
        115                 120                 125
Val Asp Gly Val Glu Val His Asn Ala Lys Thr Lys Pro Arg Glu Glu
    130                 135                 140
Gln Tyr Asn Ser Thr Tyr Arg Val Val Ser Val Leu Thr Val Leu His
145                 150                 155                 160
Gln Asp Trp Leu Asn Gly Lys Glu Tyr Lys Cys Lys Val Ser Asn Lys
                165                 170                 175
Ala Leu Pro Ala Pro Ile Glu Lys Thr Ile Ser Lys Ala Lys Gly Gln
            180                 185                 190
Pro Arg Glu Pro Gln Val Tyr Thr Leu Pro Pro Ser Arg Asp Glu Leu
        195                 200                 205
Thr Lys Asn Gln Val Ser Leu Thr Cys Leu Val Lys Gly Phe Tyr Pro
    210                 215                 220
Ser Asp Ile Ala Val Glu Trp Glu Ser Asn Gly Gln Pro Glu Asn Asn
225                 230                 235                 240
Tyr Lys Thr Thr Pro Pro Val Leu Asp Ser Asp Gly Ser Phe Phe Leu
                245                 250                 255
Tyr Ser Lys Leu Thr Val Asp Lys Ser Arg Trp Gln Gln Gly Asn Val
            260                 265                 270
Phe Ser Cys Ser Val Met His Glu Ala Leu His Asn His Tyr Thr Gln
        275                 280                 285
Lys Ser Leu Ser Leu Ser Pro Gly Lys
    290                 295
```

<210> SEQ ID NO 211
<211> LENGTH: 114
<212> TYPE: PRT
<213> ORGANISM: Homo sapiens
<220> FEATURE:
<221> NAME/KEY: VARIANT
<222> LOCATION: (93)..(93)
<223> OTHER INFORMATION: /replace="Lys"
<220> FEATURE:
<221> NAME/KEY: SITE
<222> LOCATION: (1)..(114)
<223> OTHER INFORMATION: /note="Variant residues given in the sequence
      have no preference with respect to those in the annotations
      for variant positions"

<400> SEQUENCE: 211

Asn Trp Val Asn Val Ile Ser Asp Leu Lys Lys Ile Glu Asp Leu Ile

```
            1               5                  10                 15
      Gln Ser Met His Ile Asp Ala Thr Leu Tyr Thr Glu Ser Asp Val His
                     20                  25                  30
      Pro Ser Cys Lys Val Thr Ala Met Lys Cys Phe Leu Leu Glu Leu Gln
                 35                  40                  45
      Val Ile Ser Leu Glu Ser Gly Asp Ala Ser Ile His Asp Thr Val Glu
             50                  55                  60
      Asn Leu Ile Ile Leu Ala Asn Asn Ser Leu Ser Ser Asn Gly Asn Val
      65                  70                  75                  80
      Thr Glu Ser Gly Cys Lys Glu Cys Glu Glu Leu Glu Glu Lys Asn Ile
                         85                  90                  95
      Lys Glu Phe Leu Gln Ser Phe Val His Ile Val Gln Met Phe Ile Asn
                     100                 105                 110
      Thr Ser

<210> SEQ ID NO 212
<211> LENGTH: 77
<212> TYPE: PRT
<213> ORGANISM: Homo sapiens

<400> SEQUENCE: 212

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Ala Leu Val His Gln Arg Pro Ala Pro Pro
65                  70                  75

<210> SEQ ID NO 213
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Gly Tyr Thr Phe Thr Thr Tyr Trp Met His
1               5                   10

<210> SEQ ID NO 214
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Gly Tyr Thr Phe Thr Ser Tyr Trp Met Tyr
1               5                   10

<210> SEQ ID NO 215
<211> LENGTH: 20
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Gly Gly Gly Gly Ser Gly Gly Gly Ser Gly Gly Gly Ser Gly
1               5                   10                  15

Gly Gly Gly Ser
            20

<210> SEQ ID NO 216
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Gly Gly Gly Gly Ser Gly Gly Gly Ser Gly Gly Gly Gly Ser
1               5                   10                  15

<210> SEQ ID NO 217
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Gly Gly Gly Gly Ser
1               5

<210> SEQ ID NO 218
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 218

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125
```

Ser Gly Pro Gly Leu Val Ala Pro Ser Gln Ser Leu Ser Val Thr Cys
            130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
                180                 185                 190

Lys Asp Asn Ser Lys Ser Gln Val Phe Leu Lys Met Asn Ser Leu Gln
                195                 200                 205

Thr Asp Asp Thr Ala Ile Tyr Tyr Cys Ala Lys His Tyr Tyr Tyr Gly
                210                 215                 220

Gly Ser Tyr Ala Met Asp Tyr Trp Gly Gln Gly Thr Ser Val Thr Val
225                 230                 235                 240

Ser Ser

<210> SEQ ID NO 219
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
                20                  25                  30

Leu Asn Trp Tyr Gln Gln Lys Pro Gly Gln Ala Pro Arg Leu Leu Ile
            35                  40                  45

Tyr His Thr Ser Arg Leu His Ser Gly Ile Pro Ala Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Ser Gln Val Gln Leu Gln Glu
            115                 120                 125

Ser Gly Pro Gly Leu Val Lys Pro Ser Glu Thr Leu Ser Leu Thr Cys
            130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Ser Ser Ser Leu Lys Ser Arg Val Thr Ile Ser
                180                 185                 190

Lys Asp Asn Ser Lys Asn Gln Val Ser Leu Lys Leu Ser Ser Val Thr
                195                 200                 205

Ala Ala Asp Thr Ala Val Tyr Tyr Cys Ala Lys His Tyr Tyr Tyr Gly
                210                 215                 220

Gly Ser Tyr Ala Met Asp Tyr Trp Gly Gln Gly Thr Leu Val Thr Val

Ser Ser

<210> SEQ ID NO 220
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 220

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 221
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 221

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr

```
                     20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Tyr Ser Ser Leu Lys
        50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser Gly Gly Gly Ser Gly Gly
            115                 120                 125

Gly Ser Gly Gly Gly Gly Ser Glu Ile Val Met Thr Gln Ser Pro Ala
        130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
                180                 185                 190

Ile Pro Ala Arg Phe Ser Gly Ser Gly Ser Gly Thr Asp Tyr Thr Leu
            195                 200                 205

Thr Ile Ser Ser Leu Gln Pro Glu Asp Phe Ala Val Tyr Phe Cys Gln
        210                 215                 220

Gln Gly Asn Thr Leu Pro Tyr Thr Phe Gly Gln Gly Thr Lys Leu Glu
225                 230                 235                 240

Ile Lys

<210> SEQ ID NO 222
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 222

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser Gly Gly Gly Ser Gly Gly
            115                 120                 125
```

```
Gly Ser Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Thr Asp Tyr Thr Leu
        195                 200                 205

Thr Ile Ser Ser Leu Gln Pro Glu Asp Phe Ala Val Tyr Phe Cys Gln
210                 215                 220

Gln Gly Asn Thr Leu Pro Tyr Thr Phe Gly Gln Gly Thr Lys Leu Glu
225                 230                 235                 240

Ile Lys

<210> SEQ ID NO 223
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 223

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240
```

Thr Leu Val Thr Val Ser Ser
            245

<210> SEQ ID NO 224
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 224

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245

<210> SEQ ID NO 225
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 225

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Ser Ser Ser Leu Lys
 50                  55                  60

Ser Arg Val Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Glu Ile Val Met
        130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
            195                 200                 205

Thr Asp Tyr Thr Leu Thr Ile Ser Ser Leu Gln Pro Glu Asp Phe Ala
        210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 226
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 226

Gln Val Gln Leu Gln Glu Ser Gly Pro Gly Leu Val Lys Pro Ser Glu
 1               5                  10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Gln Ser Ser Leu Lys
 50                  55                  60

Ser Arg Val Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly

-continued

```
            115                 120                 125
Gly Ser Gly Gly Gly Ser Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245

<210> SEQ ID NO 227
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 227

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Asn Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220
```

His Tyr Tyr Tyr Gly Gly Ser Tyr Ala Met Asp Tyr Trp Gln Gly
225                 230                 235                 240

Thr Leu Val Thr Val Ser Ser
            245

<210> SEQ ID NO 228
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 228

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 229
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 229

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
            35                  40                  45

Tyr His Thr Ser Arg Leu His Ser Gly Ile Pro Ala Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Ser Gln Val Gln Leu Gln Glu
            115                 120                 125

Ser Gly Pro Gly Leu Val Lys Pro Ser Glu Thr Leu Ser Leu Thr Cys
        130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Asn Ser Ser Leu Lys Ser Arg Val Thr Ile Ser
                180                 185                 190

Lys Asp Asn Ser Lys Asn Gln Val Ser Leu Lys Leu Ser Ser Val Thr
            195                 200                 205

Ala Ala Asp Thr Ala Val Tyr Tyr Cys Ala Lys His Tyr Tyr Tyr Gly
        210                 215                 220

Gly Ser Tyr Ala Met Asp Tyr Trp Gly Gln Gly Thr Leu Val Thr Val
225                 230                 235                 240

Ser Ser

<210> SEQ ID NO 230
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 230

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Tyr Asn Ser Ser Leu Lys
50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110
```

```
Gly Thr Leu Val Thr Val Ser Ser Gly Gly Gly Gly Ser Gly Gly Gly
        115                 120                 125
Gly Ser Gly Gly Gly Ser Glu Ile Val Met Thr Gln Ser Pro Ala
        130                 135                 140
Thr Leu Ser Leu Ser Pro Gly Glu Arg Ala Thr Leu Ser Cys Arg Ala
145                 150                 155                 160
Ser Gln Asp Ile Ser Lys Tyr Leu Asn Trp Tyr Gln Gln Lys Pro Gly
                165                 170                 175
Gln Ala Pro Arg Leu Leu Ile Tyr His Thr Ser Arg Leu His Ser Gly
            180                 185                 190
Ile Pro Ala Arg Phe Ser Gly Ser Gly Ser Gly Thr Asp Tyr Thr Leu
        195                 200                 205
Thr Ile Ser Ser Leu Gln Pro Glu Asp Phe Ala Val Tyr Phe Cys Gln
210                 215                 220
Gln Gly Asn Thr Leu Pro Tyr Thr Phe Gly Gln Gly Thr Lys Leu Glu
225                 230                 235                 240
Ile Lys

<210> SEQ ID NO 231
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

His Tyr Tyr Tyr Gly Gly Ser Tyr Ala Met Asp Tyr
1               5                   10

<210> SEQ ID NO 232
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Gln Gln Gly Asn Thr Leu Pro Tyr Thr
1               5

<210> SEQ ID NO 233
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Gly Ser Thr Ser Gly Ser Gly Lys Pro Gly Ser Gly Glu Gly Ser Thr
1               5                   10                  15
Lys Gly

<210> SEQ ID NO 234
<211> LENGTH: 119
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 234

Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Ser Cys
                85                  90                  95

Ala Arg Lys Thr Ile Ser Ser Val Val Asp Phe Tyr Phe Asp Tyr Trp
                100                 105                 110

Gly Gln Gly Thr Thr Val Thr
            115

<210> SEQ ID NO 235
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 235

Glu Leu Val Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Pro Leu Ile
            35                  40                  45

Tyr Ser Ala Thr Tyr Arg Asn Ser Gly Val Pro Asp Arg Phe Thr Gly
        50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Tyr Phe Cys Gln Tyr Asn Arg Tyr Pro
                85                  90                  95

Tyr Thr Ser Gly Gly Gly Thr Lys Leu Glu Ile Lys Arg Arg Ser
                100                 105                 110

<210> SEQ ID NO 236
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 236

Gln Val Gln Leu Leu Glu Ser Gly Ala Glu Leu Val Arg Pro Gly Ser
1               5                   10                  15
```

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Thr Ala Tyr
65                  70                  75                  80

Met Gln Leu Ser Gly Leu Thr Ser Glu Asp Ser Ala Val Tyr Ser Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Gly Ser Thr Ser Gly Ser Lys Pro
            115                 120                 125

Gly Ser Gly Glu Gly Ser Thr Lys Gly Glu Leu Val Leu Thr Gln Ser
        130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
            195                 200                 205

Thr Leu Thr Ile Thr Asn Val Gln Ser Lys Asp Leu Ala Asp Tyr Phe
        210                 215                 220

Tyr Phe Cys Gln Tyr Asn Arg Tyr Pro Tyr Thr Ser Gly Gly Gly Thr
225                 230                 235                 240

Lys Leu Glu Ile Lys Arg Arg Ser
            245

<210> SEQ ID NO 237
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 237

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr 115                 120                 125
    Gly Gly Gly Gly Ser Gly Gly Gly Ser Gly Gly Gly Ser Glu
                130                 135                 140

Val Lys Leu Gln Glu Ser Gly Pro Gly Leu Val Ala Pro Ser Gln Ser
    145                 150                 155                 160

Leu Ser Val Thr Cys Thr Val Ser Gly Val Ser Leu Pro Asp Tyr Gly
                    165                 170                 175

Val Ser Trp Ile Arg Gln Pro Pro Arg Lys Gly Leu Glu Trp Leu Gly
                180                 185                 190

Val Ile Trp Gly Ser Glu Thr Thr Tyr Tyr Asn Ser Ala Leu Lys Ser
                195                 200                 205

Arg Leu Thr Ile Ile Lys Asp Asn Ser Lys Ser Gln Val Phe Leu Lys
                210                 215                 220

Met Asn Ser Leu Gln Thr Asp Asp Thr Ala Ile Tyr Tyr Cys Ala Lys
    225                 230                 235                 240

His Tyr Tyr Tyr Gly Gly Ser Tyr Ala Met Asp Tyr Trp Gly Gln Gly
                    245                 250                 255

Thr Ser Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
    305                 310                 315                 320

Val Leu Leu Leu Ser Leu Val Ile Thr Leu Tyr Cys Lys Arg Gly Arg
                    325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
    385                 390                 395                 400

Gly Arg Arg Glu Glu Tyr Asp Val Leu Asp Lys Arg Arg Gly Arg Asp
                    405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
                450                 455                 460

Gln Gly Leu Ser Thr Ala Thr Lys Asp Thr Tyr Asp Ala Leu His Met
    465                 470                 475                 480

Gln Ala Leu Pro Pro Arg
                485

<210> SEQ ID NO 238
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 238

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
        50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Ser Leu Lys Ser
        195                 200                 205

Arg Val Thr Ile Ser Lys Asp Asn Ser Lys Asn Gln Val Ser Leu Lys
210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
370                 375                 380

Pro Ala Tyr Lys Gln Gly Gln Asn Gln Leu Tyr Asn Glu Leu Asn Leu
385                 390                 395                 400

```
Gly Arg Arg Glu Glu Tyr Asp Val Leu Asp Lys Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 239
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 239

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
```

```
                   260                 265                 270
Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
        370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 240
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 240

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125
```

Asp Tyr Trp Gly Gln Gly Thr Leu Val Thr Val Ser Ser Gly Gly Gly
130                 135                 140

Gly Ser Gly Gly Gly Ser Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
                180                 185                 190

Gln Gln Lys Pro Gly Gln Ala Pro Arg Leu Leu Ile Tyr His Thr Ser
                195                 200                 205

Arg Leu His Ser Gly Ile Pro Ala Arg Phe Ser Gly Ser Gly Ser Gly
210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 241
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 241

```
Met Ala Leu Pro Val Thr Ala Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
        195                 200                 205

Arg Leu His Ser Gly Ile Pro Ala Arg Phe Ser Gly Ser Gly Ser Gly
    210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
```

```
                        405                 410                 415
Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 242
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 242

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Ser
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270
```

```
Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 243
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 243

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
                100                 105                 110

Asn Thr Leu Pro Tyr Thr Phe Gly Gln Gly Thr Lys Leu Glu Ile Lys
                115                 120                 125
```

```
Gly Gly Gly Ser Gly Gly Gly Ser Gly Gly Gly Ser Gly
    130             135             140
Gly Gly Gly Ser Gln Val Gln Leu Gln Glu Ser Gly Pro Gly Leu Val
145             150                 155                 160
Lys Pro Ser Glu Thr Leu Ser Leu Thr Cys Thr Val Ser Gly Val Ser
                165                 170                 175
Leu Pro Asp Tyr Gly Val Ser Trp Ile Arg Gln Pro Pro Gly Lys Gly
            180                 185                 190
Leu Glu Trp Ile Gly Val Ile Trp Gly Ser Glu Thr Thr Tyr Tyr Gln
        195                 200                 205
Ser Ser Leu Lys Ser Arg Val Thr Ile Ser Lys Asp Asn Ser Lys Asn
210                 215                 220
Gln Val Ser Leu Lys Leu Ser Ser Val Thr Ala Ala Asp Thr Ala Val
225                 230                 235                 240
Tyr Tyr Cys Ala Lys His Tyr Tyr Gly Gly Ser Tyr Ala Met Asp
                245                 250                 255
Tyr Trp Gly Gln Gly Thr Leu Val Thr Val Ser Ser Thr Thr Thr Pro
            260                 265                 270
Ala Pro Arg Pro Pro Thr Pro Ala Pro Thr Ile Ala Ser Gln Pro Leu
        275                 280                 285
Ser Leu Arg Pro Glu Ala Cys Arg Pro Ala Ala Gly Gly Ala Val His
290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
                325                 330                 335
Cys Lys Arg Gly Arg Lys Lys Leu Leu Tyr Ile Phe Lys Gln Pro Phe
            340                 345                 350
Met Arg Pro Val Gln Thr Thr Gln Glu Glu Asp Gly Cys Ser Cys Arg
        355                 360                 365
Phe Pro Glu Glu Glu Glu Gly Gly Cys Glu Leu Arg Val Lys Phe Ser
370                 375                 380
Arg Ser Ala Asp Ala Pro Ala Tyr Lys Gln Gly Gln Asn Gln Leu Tyr
385                 390                 395                 400
Asn Glu Leu Asn Leu Gly Arg Arg Glu Glu Tyr Asp Val Leu Asp Lys
                405                 410                 415
Arg Arg Gly Arg Asp Pro Glu Met Gly Gly Lys Pro Arg Arg Lys Asn
            420                 425                 430
Pro Gln Glu Gly Leu Tyr Asn Glu Leu Gln Lys Asp Lys Met Ala Glu
        435                 440                 445
Ala Tyr Ser Glu Ile Gly Met Lys Gly Glu Arg Arg Arg Gly Lys Gly
450                 455                 460
His Asp Gly Leu Tyr Gln Gly Leu Ser Thr Ala Thr Lys Asp Thr Tyr
465                 470                 475                 480
Asp Ala Leu His Met Gln Ala Leu Pro Pro Arg
                485                 490
```

<210> SEQ ID NO 244
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 244

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415
```

-continued

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 245
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 245

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

```
Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
            290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 246
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 246

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
```

```
                130             135             140
Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Asn
        195                 200                 205

Ser Ser Leu Lys Ser Arg Val Thr Ile Ser Lys Asp Asn Ser Lys Asn
210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 247
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 247
```

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Lys Pro Gly Gln Ala
    50                  55                  60

Pro Arg Leu Leu Ile Tyr His Thr Ser Arg Leu His Ser Gly Ile Pro
65              70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
        130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Asn
        195                 200                 205

Ser Ser Leu Lys Ser Arg Val Thr Ile Ser Lys Asp Asn Ser Lys Asn
210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415
```

-continued

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 248
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 248

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Asn Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu

```
            275                 280                 285
Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Cys Glu Leu Arg Val Lys Phe Ser
370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 249
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 249

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140
```

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 250
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 250

-continued

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 251
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 252
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252

```
atctacatct gggcgccctt ggccgggact tgtggggtcc ttctcctgtc actggttatc    60 acccttact gc                                                         72
```

<210> SEQ ID NO 253
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 253

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125
```

```
Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225             230

<210> SEQ ID NO 254
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 254
accacgacgc cagcgccgcg accaccaaca ccggcgccca ccatcgcgtc gcagcccctg      60
tccctgcgcc cagaggcgtg ccggccagcg gcgggggggcg cagtgcacac gaggggggctg    120 gacttcgcct gtgat                                                      135

<210> SEQ ID NO 255
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 255
gagagcaagt acggccctcc ctgcccccct tgccctgccc ccgagttcct gggcggaccc      60
agcgtgttcc tgttcccccc caagcccaag gacacccctga tgatcagccg gacccccgag    120
gtgacctgtg tggtggtgga cgtgtcccag gaggaccccg aggtccagtt caactggtac    180
gtggacggcg tggaggtgca caacgccaag accaagcccc gggaggagca gttcaatagc    240
acctaccggg tggtgtccgt gctgaccgtg ctgcaccagg actggctgaa cggcaaggaa    300
tacaagtgta aggtgtccaa caagggcctg cccagcagca tcgagaaaac catcagcaag    360
gccaagggcc agcctcggga gccccaggtg tacaccctgc cccctagcca agaggagatg    420
accaagaacc aggtgtccct gacctgcctg gtgaagggct ctacccccag cgacatcgcc    480
gtggagtggg agagcaacgg ccagcccgag aacaactaca agaccacccc ccctgtgctg    540
gacagcgacg gcagcttctt cctgtacagc cggctgaccg tggacaagag ccggtggcag    600
gagggcaacg tctttagctg ctccgtgatg cacgaggccc tgcacaacca ctacacccag    660
aagagcctga gcctgtccct gggcaagatg                                     690

<210> SEQ ID NO 256
<211> LENGTH: 282
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 256

```
Arg Trp Pro Glu Ser Pro Lys Ala Gln Ala Ser Ser Val Pro Thr Ala
1               5                   10                  15
Gln Pro Gln Ala Glu Gly Ser Leu Ala Lys Ala Thr Thr Ala Pro Ala
            20                  25                  30
Thr Thr Arg Asn Thr Gly Arg Gly Gly Glu Glu Lys Lys Lys Glu Lys
        35                  40                  45
Glu Lys Glu Glu Gln Glu Glu Arg Glu Thr Lys Thr Pro Glu Cys Pro
    50                  55                  60
Ser His Thr Gln Pro Leu Gly Val Tyr Leu Leu Thr Pro Ala Val Gln
65                  70                  75                  80
Asp Leu Trp Leu Arg Asp Lys Ala Thr Phe Thr Cys Phe Val Val Gly
                85                  90                  95
Ser Asp Leu Lys Asp Ala His Leu Thr Trp Glu Val Ala Gly Lys Val
            100                 105                 110
Pro Thr Gly Gly Val Glu Glu Gly Leu Leu Glu Arg His Ser Asn Gly
        115                 120                 125
Ser Gln Ser Gln His Ser Arg Leu Thr Leu Pro Arg Ser Leu Trp Asn
    130                 135                 140
Ala Gly Thr Ser Val Thr Cys Thr Leu Asn His Pro Ser Leu Pro Pro
145                 150                 155                 160
Gln Arg Leu Met Ala Leu Arg Glu Pro Ala Ala Gln Ala Pro Val Lys
                165                 170                 175
Leu Ser Leu Asn Leu Leu Ala Ser Ser Asp Pro Pro Glu Ala Ala Ser
            180                 185                 190
Trp Leu Leu Cys Glu Val Ser Gly Phe Ser Pro Pro Asn Ile Leu Leu
        195                 200                 205
Met Trp Leu Glu Asp Gln Arg Glu Val Asn Thr Ser Gly Phe Ala Pro
    210                 215                 220
Ala Arg Pro Pro Pro Gln Pro Gly Ser Thr Thr Phe Trp Ala Trp Ser
225                 230                 235                 240
Val Leu Arg Val Pro Ala Pro Pro Ser Pro Gln Pro Ala Thr Tyr Thr
                245                 250                 255
Cys Val Val Ser His Glu Asp Ser Arg Thr Leu Leu Asn Ala Ser Arg
            260                 265                 270
Ser Leu Glu Val Ser Tyr Val Thr Asp His
        275                 280
```

<210> SEQ ID NO 257
<211> LENGTH: 847
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 257

```
aggtggcccg aaagtcccaa ggcccaggca tctagtgttc ctactgcaca gccccaggca    60
gaaggcagcc tagccaaagc tactactgca cctgccacta cgcgcaatac tggccgtggc   120
ggggaggaga agaaaaagga gaagagaaa gaagaacagg aagagaggga gaccaagacc   180
```

```
cctgaatgtc catcccatac ccagccgctg ggcgtctatc tcttgactcc cgcagtacag    240
gacttgtggc ttagagataa ggccacctttt acatgtttcg tcgtgggctc tgacctgaag    300
gatgcccatt tgacttggga ggttgccgga aaggtaccca cagggggggt tgaggaaggg    360
ttgctggagc gccattccaa tggctctcag agccagcact caagactcac ccttccgaga    420
tccctgtgga acgccgggac ctctgtcaca tgtactctaa atcatcctag cctgccccca    480
cagcgtctga tggcccttag agagccagcc gcccaggcac cagttaagct tagcctgaat    540
ctgctcgcca gtagtgatcc cccagaggcc gccagctggc tcttatgcga agtgtccggc    600
tttagcccgc caacatcttt gctcatgtgg ctggaggacc agcgagaagt gaacaccagc    660
ggcttcgctc cagcccggcc cccaccccag ccgggttcta ccacattctg ggcctggagt    720
gtcttaaggg tcccagcacc acctagcccc cagccagcca catacacctg tgttgtgtcc    780
catgaagata gcaggaccct gctaaatgct tctaggagtc tggaggtttc ctacgtgact    840
gaccatt                                                              847
```

<210> SEQ ID NO 258
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 258

Gly Gly Gly Gly Ser Gly Gly Gly Gly Ser
1               5                   10

<210> SEQ ID NO 259
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 259
ggtggcggag gttctggagg tggaggttcc                                      30

<210> SEQ ID NO 260
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 260

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg

```
                    65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110

<210> SEQ ID NO 261
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 261

Arg Val Lys Phe Ser Arg Ser Ala Asp Ala Pro Ala Tyr Gln Gln Gly
  1               5                  10                  15
Gln Asn Gln Leu Tyr Asn Glu Leu Asn Leu Gly Arg Arg Glu Glu Tyr
                 20                  25                  30
Asp Val Leu Asp Lys Arg Arg Gly Arg Asp Pro Glu Met Gly Gly Lys
             35                  40                  45
Pro Arg Arg Lys Asn Pro Gln Glu Gly Leu Tyr Asn Glu Leu Gln Lys
         50                  55                  60
Asp Lys Met Ala Glu Ala Tyr Ser Glu Ile Gly Met Lys Gly Glu Arg
 65                  70                  75                  80
Arg Arg Gly Lys Gly His Asp Gly Leu Tyr Gln Gly Leu Ser Thr Ala
                 85                  90                  95
Thr Lys Asp Thr Tyr Asp Ala Leu His Met Gln Ala Leu Pro Pro Arg
            100                 105                 110

<210> SEQ ID NO 262
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 262
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc      240
cggaggggca aggggcacga tggcctttac cagggtctca gtacagccac caaggacacc     300
tacgacgccc ttcacatgca ggccctgccc cctcgc                              336

<210> SEQ ID NO 263
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 263
agagtgaagt tcagcaggag cgcagacgcc cccgcgtacc agcagggcca gaaccagctc      60
```

```
tataacgagc tcaatctagg acgaagagag gagtacgatg ttttggacaa gagacgtggc    120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgc                              336
```

<210> SEQ ID NO 264
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 264

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 265
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 265

```
Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45
```

<210> SEQ ID NO 266
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 266

```
aaacggggca gaaagaaact cctgtatata ttcaaacaac catttatgag accagtacaa    60
actactcaag aggaagatgg ctgtagctgc cgatttccag aagaagaaga aggaggatgt    120
gaactg                                                              126
```

<210> SEQ ID NO 267
<211> LENGTH: 144
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 267

```
caacgaagga aatatagatc aaacaaagga gaaagtcctg tggagcctgc agagccttgt      60
cgttacagct gccccaggga ggaggagggc agcaccatcc ccatccagga ggattaccga     120
aaaccggagc ctgcctgctc cccc                                            144
```

<210> SEQ ID NO 268
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 268

```
Met Ala Leu Pro Val Thr Ala Leu Leu Leu Pro Leu Ala Leu Leu Leu
 1               5                  10                  15

His Ala Ala Arg Pro
            20
```

<210> SEQ ID NO 269
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(2000)
<223> OTHER INFORMATION: /note="This sequence may encompass 50-2000 nucleotides

<400> SEQUENCE: 269

```
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
```

| | |
|---|---|
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaaaaa aaaaaaaaaa aaaaaaaaaa aaaaaaaaaa | 1200 |
| aaaaaaaaaa aaaaaaaaaa aaaaaaaaaa aaaaaaaaaa aaaaaaaaaa aaaaaaaaaa | 1260 |
| aaaaaaaaaa aaaaaaaaaa aaaaaaaaaa aaaaaaaaaa aaaaaaaaaa aaaaaaaaaa | 1320 |
| aaaaaaaaaa aaaaaaaaaa aaaaaaaaaa aaaaaaaaaa aaaaaaaaaa aaaaaaaaaa | 1380 |
| aaaaaaaaaa aaaaaaaaaa aaaaaaaaaa aaaaaaaaaa aaaaaaaaaa aaaaaaaaaa | 1440 |
| aaaaaaaaaa aaaaaaaaaa aaaaaaaaaa aaaaaaaaaa aaaaaaaaaa aaaaaaaaaa | 1500 |
| aaaaaaaaaa aaaaaaaaaa aaaaaaaaaa aaaaaaaaaa aaaaaaaaaa aaaaaaaaaa | 1560 |
| aaaaaaaaaa aaaaaaaaaa aaaaaaaaaa aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaaa aaaaaaaaaa aaaaaaaaaa aaaaaaaaaa aaaaaaaaaa aaaaaaaaaa | 1740 |
| aaaaaaaaaa aaaaaaaaaa aaaaaaaaaa aaaaaaaaaa aaaaaaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaaaaaaa aaaaaaaaaa aaaaaaaaaa aaaaaaaaaa | 1920 |
| aaaaaaaaaa aaaaaaaaaa aaaaaaaaaa aaaaaaaaaa aaaaaaaaaa aaaaaaaaaa | 1980 |
| aaaaaaaaaa aaaaaaaaaa | 2000 |

<210> SEQ ID NO 270
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 270

| | |
|---|---|
| cgtgaggctc cggtgcccgt cagtgggcag agcgcacatc gcccacagtc cccgagaagt | 60 |
| tgggggagg ggtcggcaat tgaaccggtg cctagagaag gtggcgcggg gtaaactggg | 120 |
| aaagtgatgt cgtgtactgg ctccgccttt ttcccgaggg tggggagaa ccgtatataa | 180 |
| gtgcagtagt cgccgtgaac gttcttttc gcaacgggtt tgccgccaga acacaggtaa | 240 |
| gtgccgtgtg tggttcccgc gggcctggcc tctttacggg ttatgccct tgcgtgcctt | 300 |
| gaattacttc cacctggctg cagtacgtga ttcttgatcc cgagcttcgg gttggaagtg | 360 |
| ggtgggagag ttcgaggcct tgcgcttaag gagccccttc gcctcgtgct tgagttgagg | 420 |
| cctggcctgg gcgctgggc cgccgcgtgc gaatctggtg gcaccttcgc gcctgtctcg | 480 |
| ctgctttcga taagtctcta gccatttaaa attttttgatg acctgctgcg acgctttttt | 540 |
| tctggcaaga tagtcttgta aatgcgggcc aagatctgca cactggtatt tcggttttg | 600 |
| gggccgcggg cggcgacggg gcccgtgcgt cccagcgcac atgttcggcg aggcggggcc | 660 |
| tgcgagcgcg gccaccgaga atcggacggg ggtagtctca agctggccgg cctgctctgg | 720 |
| tgcctggcct cgcgccgccg tgtatcgccc cgccctgggc ggcaaggctg gcccggtcgg | 780 |
| caccagttgc gtgagcggaa agatggccgc ttccgggccc tgctgcaggg agctcaaaat | 840 |
| ggaggacgcg gcgctcggga gagcgggcgg gtgagtcacc cacacaaagg aaaagggcct | 900 |
| ttccgtcctc agccgtcgct tcatgtgact ccacggagta ccgggcgccg tccaggcacc | 960 |
| tcgattagtt ctcgagcttt tggagtacgt cgtctttagg ttgggggag gggttttatg | 1020 |

```
cgatggagtt tccccacact gagtgggtgg agactgaagt taggccagct tggcacttga    1080
tgtaattctc cttggaattt gccctttttg agtttggatc ttggttcatt ctcaagcctc    1140
agacagtggt tcaaagtttt tttcttccat ttcaggtgtc gtga                     1184
```

<210> SEQ ID NO 271
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 271

```
Gln Val Gln Leu Gln Glu Ser Gly Pro Gly Leu Val Lys Pro Ser Gln
1               5                   10                  15

Thr Leu Ser Leu Thr Cys Thr Val Ser Asp Tyr Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Gln Leu Asn Ser Val Thr Ala Ala Asp Thr Ala Val Tyr Tyr Cys
                85                  90                  95

Ala Ser Phe Asp Tyr Ala His Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
```

```
                     325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 272
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 272

Asp Ile Val Leu Thr Gln Ser Pro Ala Phe Leu Ser Val Thr Pro Gly
1               5                   10                  15

Glu Lys Val Thr Phe Thr Cys Gln Ala Ser Gln Ser Ile Gly Thr Ser
            20                  25                  30

Ile His Trp Tyr Gln Gln Lys Asp Gln Ala Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Val Glu Ala
65                  70                  75                  80

Glu Asp Ala Ala Asp Tyr Tyr Cys Gln Gln Ile Asn Ser Trp Pro Thr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 273
```

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Ser Asp Tyr Ala Trp Asn
1               5

<210> SEQ ID NO 274
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 274

Tyr Ile Ser Tyr Ser Gly Ser Thr Ser Tyr Asn Pro Ser Leu Lys Ser
1               5                   10                  15

<210> SEQ ID NO 275
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Phe Asp Tyr Ala His Ala Met Asp Tyr
1               5

<210> SEQ ID NO 276
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Gln Ala Ser Gln Ser Ile Gly Thr Ser Ile His
1               5                   10

<210> SEQ ID NO 277
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

Tyr Ala Ser Glu Ser Ile Ser
1               5

<210> SEQ ID NO 278
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 278

Gln Gln Ile Asn Ser Trp Pro Thr Thr
1               5

<210> SEQ ID NO 279
<211> LENGTH: 143
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 279

Gly Ala Pro Ala Gly Pro Leu Ile Val Pro Tyr Asn Leu Pro Leu Pro
1               5                   10                  15

Gly Gly Val Val Pro Arg Met Leu Ile Thr Ile Leu Gly Thr Val Lys
            20                  25                  30

Pro Asn Ala Asn Arg Ile Ala Leu Asp Phe Gln Arg Gly Asn Asp Val
        35                  40                  45

Ala Phe His Phe Asn Pro Arg Phe Asn Glu Asn Asn Arg Arg Val Ile
    50                  55                  60

Val Cys Asn Thr Lys Leu Asp Asn Asn Trp Gly Arg Glu Glu Arg Gln
65                  70                  75                  80

Ser Val Phe Pro Phe Glu Ser Gly Lys Pro Phe Lys Ile Gln Val Leu
                85                  90                  95

Val Glu Pro Asp His Phe Lys Val Ala Val Asn Asp Ala His Leu Leu
            100                 105                 110

Gln Tyr Asn His Arg Val Lys Lys Leu Asn Glu Ile Ser Lys Leu Gly
        115                 120                 125

Ile Ser Gly Asp Ile Asp Ile Thr Ser Ala Ser Tyr Thr Met Ile
    130                 135                 140

<210> SEQ ID NO 280
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 280

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
```

-continued

```
                100                 105                 110
Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 281
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 281

Glu Thr Val Leu Thr Gln Ser Pro Gly Thr Leu Ser Leu Ser Pro Gly
1               5                   10                  15
```

-continued

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 282
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 282

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser
    130                 135

<210> SEQ ID NO 283
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 283

Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Phe Thr Phe Gly Pro Gly Thr Lys Val Asp Ile Lys
        115                 120                 125

<210> SEQ ID NO 284
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 284

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Trp Glu Val Arg Ala Leu Pro Ser Val Tyr Trp Gly
            100                 105                 110

Gln Gly Thr Leu Val Thr Val Ser Ser
        115                 120

<210> SEQ ID NO 285
<211> LENGTH: 109
<212> TYPE: PRT
<213> ORGANISM: Artificial Sequence
<220> FEATURE:
<221> NAME/KEY: source -continued
<223> OTHER INFORMATION: /note="Description of Artificial Sequence:
    Synthetic polypeptide"

<400> SEQUENCE: 285

Ser Tyr Glu Leu Thr Gln Pro Pro Ser Val Ser Val Ala Pro Gly Gln
1               5                   10                  15

Thr Ala Arg Ile Thr Cys Gly Ala Asn Asp Ile Gly Ser Lys Ser Val
            20                  25                  30

His Trp Tyr Gln Gln Lys Ala Gly Gln Ala Pro Val Leu Val Val Ser
        35                  40                  45

Glu Asp Ile Ile Arg Pro Ser Gly Ile Pro Glu Arg Ile Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Ser Asp Gln
                85                  90                  95

Tyr Val Phe Gly Thr Gly Thr Lys Val Thr Val Leu Gly
            100                 105

<210> SEQ ID NO 286
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 286

Gln Asn Asp Tyr Ser Tyr Pro Tyr Thr
1               5

<210> SEQ ID NO 287
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 287
atggccctgc ctgtgacagc cctgctgctg cctctggctc tgctgctgca tgccgctaga      60
ccc                                                                  63

<210> SEQ ID NO 288
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 288
atggccctcc ctgtcaccgc cctgctgctt ccgctggctc ttctgctcca cgccgctcgg      60
ccc                                                                  63

<210> SEQ ID NO 289
<211> LENGTH: 72
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 289
atctacattt gggcccctct ggctggtact tgcggggtcc tgctgctttc actcgtgatc    60
actctttact gt                                                        72

<210> SEQ ID NO 290
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 290
aagcgcggtc ggaagaagct gctgtacatc tttaagcaac ccttcatgag gcctgtgcag    60
actactcaag aggaggacgg ctgttcatgc cggttcccag aggaggagga aggcggctgc   120
gaactg                                                              126

<210> SEQ ID NO 291
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 291
cgcgtgaaat tcagccgcag cgcagatgct ccagcctaca agcaggggca gaaccagctc    60
tacaacgaac tcaatcttgg tcggagagag gagtacgacg tgctggacaa gcggagagga   120
cgggacccag aaatgggcgg gaagccgcgc agaaagaatc cccaagaggg cctgtacaac   180
gagctccaaa aggataagat ggcagaagcc tatagcgaga ttggtatgaa aggggaacgc   240
agaagaggca aggccacga cggactgtac cagggactca gcaccgccac caaggacacc    300
tatgacgctc ttcacatgca ggccctgccg cctcgg                             336

<210> SEQ ID NO 292
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Gly Gly Gly Gly Ser
1               5

<210> SEQ ID NO 293
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 293
```

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 294
<211> LENGTH: 450
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 294
cccggatggt ttctggactc tccggatcgc ccgtggaatc ccccaacctt ctcaccggca      60
ctcttggttg tgactgaggg cgataatgcg accttcacgt gctcgttctc aacacctcc     120
gaatcattcg tgctgaactg gtaccgcatg agcccgtcaa accagaccga caagctcgcc    180
gcgtttccgg aagatcggtc gcaaccggga caggattgtc ggttccgcgt gactcaactg    240
ccgaatggca gagacttcca catgagcgtg gtccgcgcta ggcgaaacga ctccgggacc    300
tacctgtgcg gagccatctc gctggcgcct aaggcccaaa tcaaagagag cttgagggcc    360
gaactgagag tgaccgagcg cagagctgag gtgccaactg cacatccatc cccatcgcct    420
cggcctgcgg ggcagtttca gaccctggtc                                     450

<210> SEQ ID NO 295
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 295

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45
```

```
Asp Asn Ala Thr Phe Thr Cys Ser Phe Ser Asn Thr Ser Glu Ser Phe
 50                  55                  60
Val Leu Asn Trp Tyr Arg Met Ser Pro Ser Asn Gln Thr Asp Lys Leu
 65                  70                  75                  80
Ala Ala Phe Pro Glu Asp Arg Ser Gln Pro Gly Gln Asp Cys Arg Phe
                 85                  90                  95
Arg Val Thr Gln Leu Pro Asn Gly Arg Asp Phe His Met Ser Val Val
            100                 105                 110
Arg Ala Arg Arg Asn Asp Ser Gly Thr Tyr Leu Cys Gly Ala Ile Ser
            115                 120                 125
Leu Ala Pro Lys Ala Gln Ile Lys Glu Ser Leu Arg Ala Glu Leu Arg
130                 135                 140
Val Thr Glu Arg Arg Ala Glu Val Pro Thr Ala His Pro Ser Pro Ser
145                 150                 155                 160
Pro Arg Pro Ala Gly Gln Phe Gln Thr Leu Val Thr Thr Thr Pro Ala
                165                 170                 175
Pro Arg Pro Pro Thr Pro Ala Pro Thr Ile Ala Ser Gln Pro Leu Ser
            180                 185                 190
Leu Arg Pro Glu Ala Cys Arg Pro Ala Ala Gly Gly Ala Val His Thr
            195                 200                 205
Arg Gly Leu Asp Phe Ala Cys Asp Ile Tyr Ile Trp Ala Pro Leu Ala
210                 215                 220
Gly Thr Cys Gly Val Leu Leu Leu Ser Leu Val Ile Thr Leu Tyr Cys
225                 230                 235                 240
Lys Arg Gly Arg Lys Lys Leu Leu Tyr Ile Phe Lys Gln Pro Phe Met
                245                 250                 255
Arg Pro Val Gln Thr Thr Gln Glu Glu Asp Gly Cys Ser Cys Arg Phe
            260                 265                 270
Pro Glu Glu Glu Glu Gly Gly Cys Glu Leu Arg Val Lys Phe Ser Arg
            275                 280                 285
Ser Ala Asp Ala Pro Ala Tyr Lys Gln Gly Gln Asn Gln Leu Tyr Asn
290                 295                 300
Glu Leu Asn Leu Gly Arg Arg Glu Glu Tyr Asp Val Leu Asp Lys Arg
305                 310                 315                 320
Arg Gly Arg Asp Pro Glu Met Gly Gly Lys Pro Arg Arg Lys Asn Pro
                325                 330                 335
Gln Glu Gly Leu Tyr Asn Glu Leu Gln Lys Asp Lys Met Ala Glu Ala
            340                 345                 350
Tyr Ser Glu Ile Gly Met Lys Gly Glu Arg Arg Arg Gly Lys Gly His
            355                 360                 365
Asp Gly Leu Tyr Gln Gly Leu Ser Thr Ala Thr Lys Asp Thr Tyr Asp
370                 375                 380
Ala Leu His Met Gln Ala Leu Pro Pro Arg
385                 390

<210> SEQ ID NO 296
<211> LENGTH: 1182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 296
atggccctcc ctgtcactgc cctgcttctc ccccctcgcac tcctgctcca cgccgctaga     60
```

-continued

```
ccacccggat ggtttctgga ctctccggat cgcccgtgga atcccccaac cttctcaccg      120
gcactcttgg ttgtgactga gggcgataat gcgaccttca cgtgctcgtt ctccaacacc      180
tccgaatcat tcgtgctgaa ctggtaccgc atgagcccgt caaaccagac cgacaagctc      240
gccgcgtttc cggaagatcg gtcgcaaccg ggacaggatt gtcggttccg cgtgactcaa      300
ctgccgaatg cagagactt ccacatgagc gtggtccgcg ctaggcgaaa cgactccggg       360
acctacctgt gcggagccat ctcgctggcg cctaaggccc aaatcaaaga gagcttgagg      420
gccgaactga gagtgaccga gcgcagagct gaggtgccaa ctgcacatcc atccccatcg     480
cctcggcctg cggggcagtt tcagaccctg gtcacgacca ctccggcgcc gcgcccaccg     540
actccggccc caactatcgc gagccagccc ctgtcgctga ggccggaagc atgccgccct     600
gccgccggag gtgctgtgca tacccgggga ttggacttcg catgcgacat ctacatttgg     660
gctcctctcg ccggaacttg tggcgtgctc cttctgtccc tggtcatcac cctgtactgc     720
aagcggggtc ggaaaaagct tctgtacatt ttcaagcagc ccttcatgag gcccgtgcaa     780
accacccagg aggaggacgg ttgctcctgc cggttccccg aagaggaaga aggaggttgc     840
gagctgcgcg tgaagttctc ccggagcgcc gacgcccccg cctataagca gggccagaac    900
cagctgtaca acgaactgaa cctgggacgg cgggaagagt acgatgtgct ggacaagcgg    960
cgcggccggg accccgaaat gggcgggaag cctagaagaa agaaccctca ggaaggcctg   1020
tataacgagc tgcagaagga caagatggcc gaggcctact ccgaaattgg gatgaaggga   1080
gagcggcgga ggggaaaggg gcacgacggc ctgtaccaag gactgtccac cgccaccaag   1140
gacacatacg atgccctgca catgcaggcc cttccccctc gc                      1182
```

<210> SEQ ID NO 297
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Gly Gly Gly Ser
1

<210> SEQ ID NO 298
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 50-5000
      nucleotides

<400> SEQUENCE: 298

```
aaaaaaaaaa aaaaaaaaaa aaaaaaaaaa aaaaaaaaaa aaaaaaaaaa aaaaaaaaaa       60
aaaaaaaaaa aaaaaaaaaa aaaaaaaaaa aaaaaaaaaa aaaaaaaaaa aaaaaaaaaa      120
aaaaaaaaaa aaaaaaaaaa aaaaaaaaaa aaaaaaaaaa aaaaaaaaaa aaaaaaaaaa      180
aaaaaaaaaa aaaaaaaaaa aaaaaaaaaa aaaaaaaaaa aaaaaaaaaa aaaaaaaaaa      240
```

-continued

| | |
|---|---|
| aaaaaaaaaa aaaaaaaaaa aaaaaaaaaa aaaaaaaaaa aaaaaaaaaa aaaaaaaaaa | 300 |
| aaaaaaaaaa aaaaaaaaaa aaaaaaaaaa aaaaaaaaaa aaaaaaaaaa aaaaaaaaaa | 360 |
| aaaaaaaaaa aaaaaaaaaa aaaaaaaaaa aaaaaaaaaa aaaaaaaaaa aaaaaaaaaa | 420 |
| aaaaaaaaaa aaaaaaaaaa aaaaaaaaaa aaaaaaaaaa aaaaaaaaaa aaaaaaaaaa | 480 |
| aaaaaaaaaa aaaaaaaaaa aaaaaaaaaa aaaaaaaaaa aaaaaaaaaa aaaaaaaaaa | 540 |
| aaaaaaaaaa aaaaaaaaaa aaaaaaaaaa aaaaaaaaaa aaaaaaaaaa aaaaaaaaaa | 600 |
| aaaaaaaaaa aaaaaaaaaa aaaaaaaaaa aaaaaaaaaa aaaaaaaaaa aaaaaaaaaa | 660 |
| aaaaaaaaaa aaaaaaaaaa aaaaaaaaaa aaaaaaaaaa aaaaaaaaaa aaaaaaaaaa | 720 |
| aaaaaaaaaa aaaaaaaaaa aaaaaaaaaa aaaaaaaaaa aaaaaaaaaa aaaaaaaaaa | 780 |
| aaaaaaaaaa aaaaaaaaaa aaaaaaaaaa aaaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaaaa | 1020 |
| aaaaaaaaaa aaaaaaaaaa aaaaaaaaaa aaaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaaaaa aaaaaaaaaa aaaaaaaaaa aaaaaaaaaa | 1200 |
| aaaaaaaaaa aaaaaaaaaa aaaaaaaaaa aaaaaaaaaa aaaaaaaaaa aaaaaaaaaa | 1260 |
| aaaaaaaaaa aaaaaaaaaa aaaaaaaaaa aaaaaaaaaa aaaaaaaaaa aaaaaaaaaa | 1320 |
| aaaaaaaaaa aaaaaaaaaa aaaaaaaaaa aaaaaaaaaa aaaaaaaaaa aaaaaaaaaa | 1380 |
| aaaaaaaaaa aaaaaaaaaa aaaaaaaaaa aaaaaaaaaa aaaaaaaaaa aaaaaaaaaa | 1440 |
| aaaaaaaaaa aaaaaaaaaa aaaaaaaaaa aaaaaaaaaa aaaaaaaaaa aaaaaaaaaa | 1500 |
| aaaaaaaaaa aaaaaaaaaa aaaaaaaaaa aaaaaaaaaa aaaaaaaaaa aaaaaaaaaa | 1560 |
| aaaaaaaaaa aaaaaaaaaa aaaaaaaaaa aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaaa aaaaaaaaaa aaaaaaaaaa aaaaaaaaaa aaaaaaaaaa aaaaaaaaaa | 1740 |
| aaaaaaaaaa aaaaaaaaaa aaaaaaaaaa aaaaaaaaaa aaaaaaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaaaaaaa aaaaaaaaaa aaaaaaaaaa aaaaaaaaaa | 1920 |
| aaaaaaaaaa aaaaaaaaaa aaaaaaaaaa aaaaaaaaaa aaaaaaaaaa aaaaaaaaaa | 1980 |
| aaaaaaaaaa aaaaaaaaaa aaaaaaaaaa aaaaaaaaaa aaaaaaaaaa aaaaaaaaaa | 2040 |
| aaaaaaaaaa aaaaaaaaaa aaaaaaaaaa aaaaaaaaaa aaaaaaaaaa aaaaaaaaaa | 2100 |
| aaaaaaaaaa aaaaaaaaaa aaaaaaaaaa aaaaaaaaaa aaaaaaaaaa aaaaaaaaaa | 2160 |
| aaaaaaaaaa aaaaaaaaaa aaaaaaaaaa aaaaaaaaaa aaaaaaaaaa aaaaaaaaaa | 2220 |
| aaaaaaaaaa aaaaaaaaaa aaaaaaaaaa aaaaaaaaaa aaaaaaaaaa aaaaaaaaaa | 2280 |
| aaaaaaaaaa aaaaaaaaaa aaaaaaaaaa aaaaaaaaaa aaaaaaaaaa aaaaaaaaaa | 2340 |
| aaaaaaaaaa aaaaaaaaaa aaaaaaaaaa aaaaaaaaaa aaaaaaaaaa aaaaaaaaaa | 2400 |
| aaaaaaaaaa aaaaaaaaaa aaaaaaaaaa aaaaaaaaaa aaaaaaaaaa aaaaaaaaaa | 2460 |
| aaaaaaaaaa aaaaaaaaaa aaaaaaaaaa aaaaaaaaaa aaaaaaaaaa aaaaaaaaaa | 2520 |
| aaaaaaaaaa aaaaaaaaaa aaaaaaaaaa aaaaaaaaaa aaaaaaaaaa aaaaaaaaaa | 2580 |
| aaaaaaaaaa aaaaaaaaaa aaaaaaaaaa aaaaaaaaaa aaaaaaaaaa aaaaaaaaaa | 2640 |

```
aaaaaaaaaa aaaaaaaaaa aaaaaaaaaa aaaaaaaaaa aaaaaaaaaa aaaaaaaaaa    2700
aaaaaaaaaa aaaaaaaaaa aaaaaaaaaa aaaaaaaaaa aaaaaaaaaa aaaaaaaaaa    2760
aaaaaaaaaa aaaaaaaaaa aaaaaaaaaa aaaaaaaaaa aaaaaaaaaa aaaaaaaaaa    2820
aaaaaaaaaa aaaaaaaaaa aaaaaaaaaa aaaaaaaaaa aaaaaaaaaa aaaaaaaaaa    2880
aaaaaaaaaa aaaaaaaaaa aaaaaaaaaa aaaaaaaaaa aaaaaaaaaa aaaaaaaaaa    2940
aaaaaaaaaa aaaaaaaaaa aaaaaaaaaa aaaaaaaaaa aaaaaaaaaa aaaaaaaaaa    3000
aaaaaaaaaa aaaaaaaaaa aaaaaaaaaa aaaaaaaaaa aaaaaaaaaa aaaaaaaaaa    3060
aaaaaaaaaa aaaaaaaaaa aaaaaaaaaa aaaaaaaaaa aaaaaaaaaa aaaaaaaaaa    3120
aaaaaaaaaa aaaaaaaaaa aaaaaaaaaa aaaaaaaaaa aaaaaaaaaa aaaaaaaaaa    3180
aaaaaaaaaa aaaaaaaaaa aaaaaaaaaa aaaaaaaaaa aaaaaaaaaa aaaaaaaaaa    3240
aaaaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aaaaaaaaaa aaaaaaaaaa aaaaaaaaaa    3360
aaaaaaaaaa aaaaaaaaaa aaaaaaaaaa aaaaaaaaaa aaaaaaaaaa aaaaaaaaaa    3420
aaaaaaaaaa aaaaaaaaaa aaaaaaaaaa aaaaaaaaaa aaaaaaaaaa aaaaaaaaaa    3480
aaaaaaaaaa aaaaaaaaaa aaaaaaaaaa aaaaaaaaaa aaaaaaaaaa aaaaaaaaaa    3540
aaaaaaaaaa aaaaaaaaaa aaaaaaaaaa aaaaaaaaaa aaaaaaaaaa aaaaaaaaaa    3600
aaaaaaaaaa aaaaaaaaaa aaaaaaaaaa aaaaaaaaaa aaaaaaaaaa aaaaaaaaaa    3660
aaaaaaaaaa aaaaaaaaaa aaaaaaaaaa aaaaaaaaaa aaaaaaaaaa aaaaaaaaaa    3720
aaaaaaaaaa aaaaaaaaaa aaaaaaaaaa aaaaaaaaaa aaaaaaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
```
aaaaaaaaaa aaaaaaaaa                                             5000

<210> SEQ ID NO 299
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 299

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

```
Gly Leu Ser Thr Ala Thr Lys Asp Thr Tyr Asp Ala Leu His Met Gln
        355                 360                 365

Ala Leu Pro Pro Arg
    370

<210> SEQ ID NO 300
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 300

Thr Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
                20                  25                  30

Val Thr Leu
        35

<210> SEQ ID NO 301
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 301
acaaaaaaga agtattcatc cagtgtgcac gaccctaacg gtgaatacat gttcatgaga      60
gcagtgaaca cagccaaaaa atccagactc acagatgtga cccta                    105

<210> SEQ ID NO 302
<211> LENGTH: 69
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 302

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Phe Trp Leu
            35                  40                  45

Pro Ile Gly Cys Ala Ala Phe Val Val Val Cys Ile Leu Gly Cys Ile
        50                  55                  60

Leu Ile Cys Trp Leu
65

<210> SEQ ID NO 303
<211> LENGTH: 207
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 303
accacgacgc cagcgccgcg accaccaaca ccggcgccca ccatcgcgtc gcagcccctg    60
tccctgcgcc cagaggcgtg ccggccagcg gcggggggcg cagtgcacac gaggggggctg   120 gacttcgcct gtgatttctg gttacccata ggatgtgcag cctttgttgt agtctgcatt   180
ttgggatgca tacttatttg ttggctt                                       207

<210> SEQ ID NO 304
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 304

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 305
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 305
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 306
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306

Gly Val Ser Leu Pro Asp Tyr Gly Val Ser
1               5                   10

<210> SEQ ID NO 307
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Val Ile Trp Gly Ser Glu Thr Thr Tyr Tyr Asn Ser Ala Leu Lys Ser

-continued

<210> SEQ ID NO 308
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Val Ile Trp Gly Ser Glu Thr Thr Tyr Tyr Ser Ser Ser Leu Lys Ser
1               5                   10                  15

<210> SEQ ID NO 309
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Val Ile Trp Gly Ser Glu Thr Thr Tyr Tyr Gln Ser Ser Leu Lys Ser
1               5                   10                  15

<210> SEQ ID NO 310
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Val Ile Trp Gly Ser Glu Thr Thr Tyr Tyr Asn Ser Ser Leu Lys Ser
1               5                   10                  15

<210> SEQ ID NO 311
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Arg Ala Ser Gln Asp Ile Ser Lys Tyr Leu Asn
1               5                   10

<210> SEQ ID NO 312
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

His Thr Ser Arg Leu His Ser
1               5

<210> SEQ ID NO 313

```
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(40)
<223> OTHER INFORMATION: /note="This sequence may encompass 1-10 'Gly
      Gly Gly Ser' repeating units"

<400> SEQUENCE: 313

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
            35                  40

<210> SEQ ID NO 314
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Arg Gly Asp Ser
1
```